United States Patent
Zhang et al.

(10) Patent No.: US 12,281,301 B2
(45) Date of Patent: Apr. 22, 2025

(54) SEQUENCING-BASED PROTEOMICS

(71) Applicants: THE BROAD INSTITUTE, INC., Cambridge, MA (US); MASSACHUSETTS INSTITUTE OF TECHNOLOGY, Cambridge, MA (US)

(72) Inventors: Feng Zhang, Cambridge, MA (US); Jonathan Leo Schmid-Burgk, Cambridge, MA (US); Veit Hornung, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1069 days.

(21) Appl. No.: 17/048,369

(22) PCT Filed: Apr. 26, 2019

(86) PCT No.: PCT/US2019/029488
§ 371 (c)(1),
(2) Date: Oct. 16, 2020

(87) PCT Pub. No.: WO2019/210268
PCT Pub. Date: Oct. 31, 2019

(65) Prior Publication Data
US 2021/0147831 A1    May 20, 2021

Related U.S. Application Data

(60) Provisional application No. 62/663,712, filed on Apr. 27, 2018, provisional application No. 62/751,314, filed on Oct. 26, 2018.

(51) Int. Cl.
C40B 30/04 (2006.01)
C12N 9/22 (2006.01)
(Continued)

(52) U.S. Cl.
CPC .......... *C12N 15/1065* (2013.01); *C12N 9/22* (2013.01); *C12N 15/65* (2013.01); *C12N 2310/20* (2017.05)

(58) Field of Classification Search
None
See application file for complete search history.

(56) References Cited

FOREIGN PATENT DOCUMENTS

JP    2018-042503 A    3/2018
WO    2016/149422 A1    9/2016

OTHER PUBLICATIONS

Roberts et al., Systematic Gene-Tagging Using CRISPR/Cas9 in Human Stem Cells to Illuminate Cell Organization, 2017, Molecular Biology of the Cell, vol. 28, 2854-2874 (Year: 2017).*

(Continued)

*Primary Examiner* — Christian C Boesen
(74) *Attorney, Agent, or Firm* — F. Brent Nix, Esq.; Johnson, Marcou, Isaacs & Nix, LLC; Erin M. Daly, Esq.

(57) ABSTRACT

The invention provides a cell library for use in detecting protein expression comprising a plurality of cells, wherein each cell comprises a polynucleotide sequence encoding a detectable marker integrated into the genome of the cell in frame with a protein coding gene selected from a set of target genes, wherein the library comprises more than one cell tagged at each target gene, as well as a cell library for use in detecting protein interactions between a protein of interest and a set of target proteins and a cell library for use in detecting protein modifications. The invention also provides methods of constructing a cell library for use in proteomics, as well as methods for sequencing integration sites of a (Continued)

donor sequence inserted into the genome of a cell. Also provided are systems for analysis of proteins in a cell and kits comprising vectors for tagging a population of cells and for performing proteomics studies.

17 Claims, 75 Drawing Sheets

Specification includes a Sequence Listing.

(51) Int. Cl.
    *C12N 15/10*     (2006.01)
    *C12N 15/65*     (2006.01)

(56) References Cited

OTHER PUBLICATIONS

"International Preliminary Report on Patentability issued in International Application No. PCT/US2019/029488", mailed on Nov. 5, 2020, 17 pages.
"International Search Report and Written Opinion issued in International Application No. PCT/US2019/029488", mailed on Mar. 25, 2020, 28 pages.
"Invitation to Pay Additional Fees issued in International Application No. PCT/US2019/029488", mailed on Jan. 31, 2020, 13 pages.
Auer, et al., "Highly Efficient CRISPR/Cas9-Mediated Knock-in In Zebrafish by Homology-Independent DNA Repair", Genome Research, vol. 24, Oct. 31, 2013, 142-153.
Cohen, et al., "Dynamic Proteomics of Individual Cancer Cells in Response to a Drug", Science, vol. 322, Dec. 5, 2008, 1511-1516.
Cristea, et al., "In Vivo Cleavage of Transgene Donors Promotes Nuclease-Mediated Targeted Integration", Biotechnology and Bioengineering, vol. 110, No. 3, Mar. 2013, 871-880.
Dewari, et al., "An Efficient and Scalable Pipeline for Epitope Tagging in Mammalian Stem Cells Using Cas9 Ribonucleoprotein", eLife, vol. 7, No. e35069, Apr. 11, 2018, 29 pages.
Dixon, et al., "NanoLuc Complementation Reporter Optimized for Accurate Measurement of Protein Interactions in Cells", ACS Chemical Biology, vol. 11, 2016, 400-408.
Feldman, et al., "Pooled Optical Screens in Human Cells", bioRxiv, Retrieved via: http://dx.doi.org/10.1101/383943, Aug. 2, 2018, 23 pages.
Harikumar, et al., "An Endogenously Tagged Fluorescent Fusion Protein Library in Mouse Embryonic Stem Cells", Stem Cell Reports, vol. 9, Oct. 10, 2017, 1304-1314.
Huh, et al., "Global Analysis of Protein Localization in Budding Yeast", Nature, vol. 425, Oct. 16, 2003, 686-691.
Lackner, et al., "A Generic Strategy for CRISPR-Cas9-Mediated Gene Tagging", Nature Communications, vol. 6, No. 10237, Dec. 17, 2015, 7 pages.
Leonetti, et al., "A Scalable Strategy for High-Throughput GFP Tagging of Endogenous Human Proteins", Proceedings of the National Academy of Sciences, vol. 113, No. 25, Jun. 6, 2016, E3501-E3508.
Maresca, et al., "Obligate Ligation-Gated Recombination (ObLiGaRe): Custom-designed Nuclease-mediated Targeted Integration through Nonhomologous End Joining", Genome Research, vol. 23, 2013, 539-546.
Roberts, et al., "Systematic Gene Tagging Using CRISPR/Cas9 in Human Stem Cells to Illuminate Cell Organization", Molecular Biology of the Cell, vol. 28, Oct. 15, 2017, 2854-2874.
Schmid-Burgk, et al., "CRISpaint Allows Modular Base-Specific Gene Tagging Using a Ligase-4-Dependent Mechanism", Nature Communications, vol. 7, No. 12338, Jul. 28, 2016, 12 pages.
Schwinn, et al., "CRISPR-Mediated Tagging of Endogenous Proteins with a Luminescent Peptide", ACS Chemical Biology, vol. 13, 2018, 467-474.
Sigal, et al., "Generation of a Fluorescently Labeled Endogenous Protein Library in Living Human Cells", Nature Protocols, vol. 2, No. 6, 2007, 1515-1527.
Tsai, et al., "Guide-seq Enables Genome-wide Profiling of Off-target Cleavage by Crispr-cas Nucleases", Nature Biotechnology, vol. 33, No. 2, Feb. 2015, 187-197.

* cited by examiner

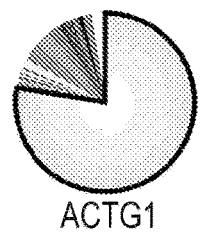
ACTG1
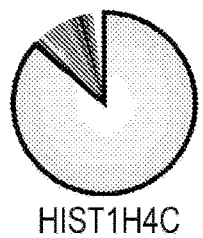
HIST1H4C
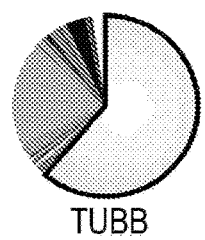
TUBB
☐ mNeon seamless integration  ▨ Frame +0  ▨ Frame +1  ■ Frame +2
FIG. 4

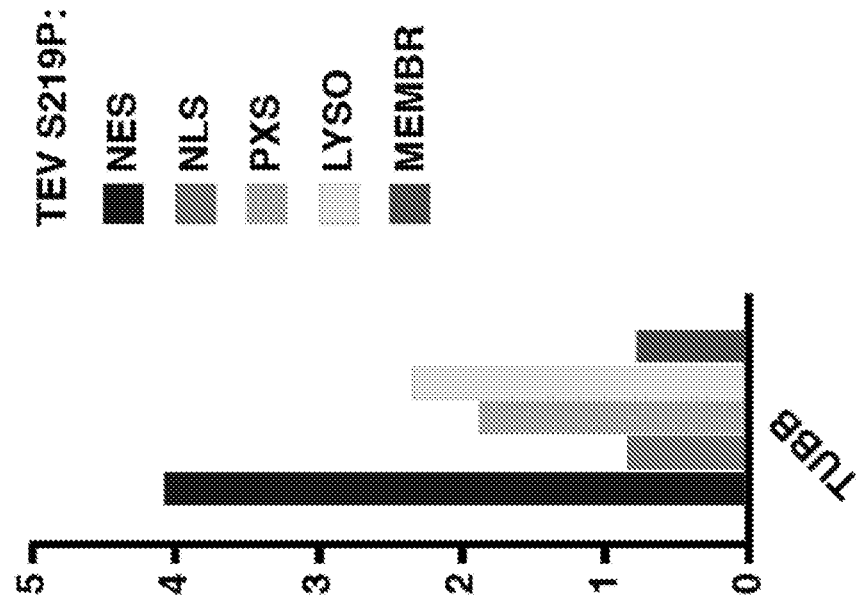
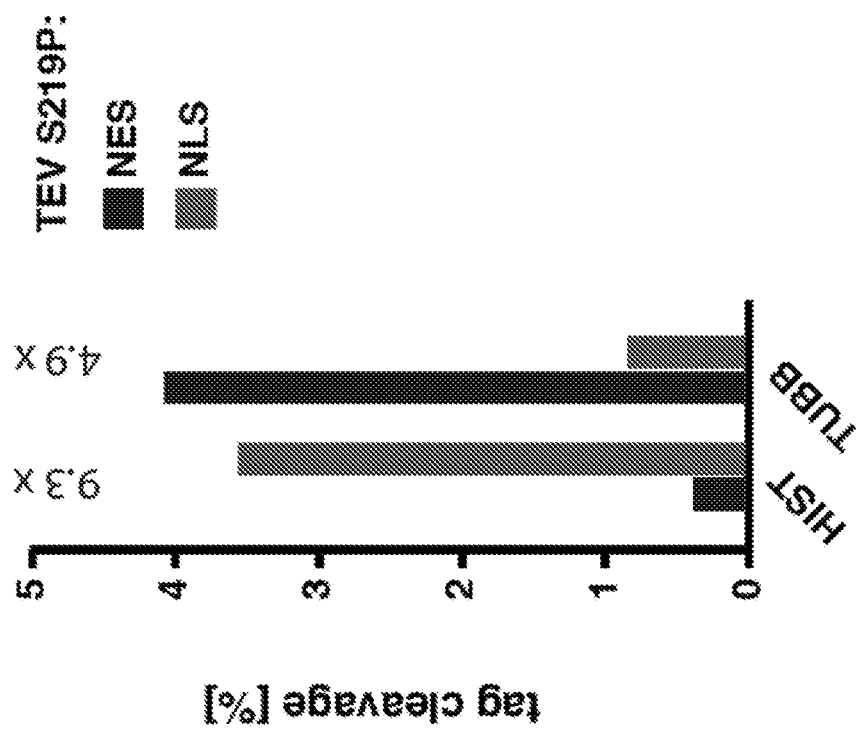
FIG. 16

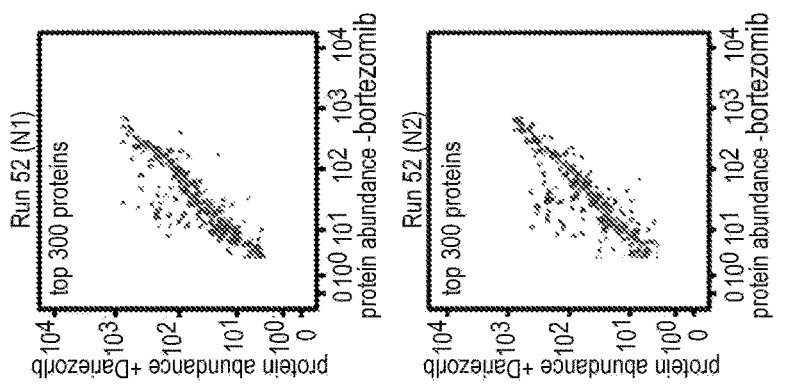
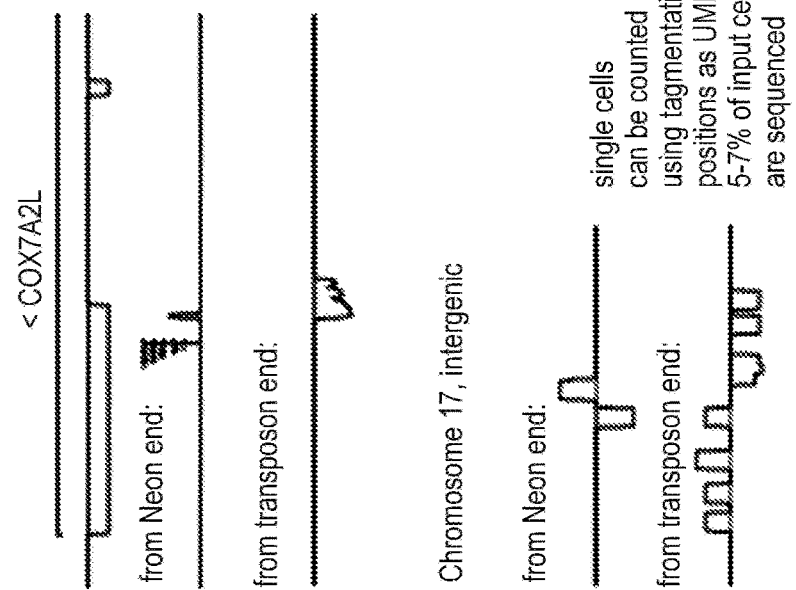
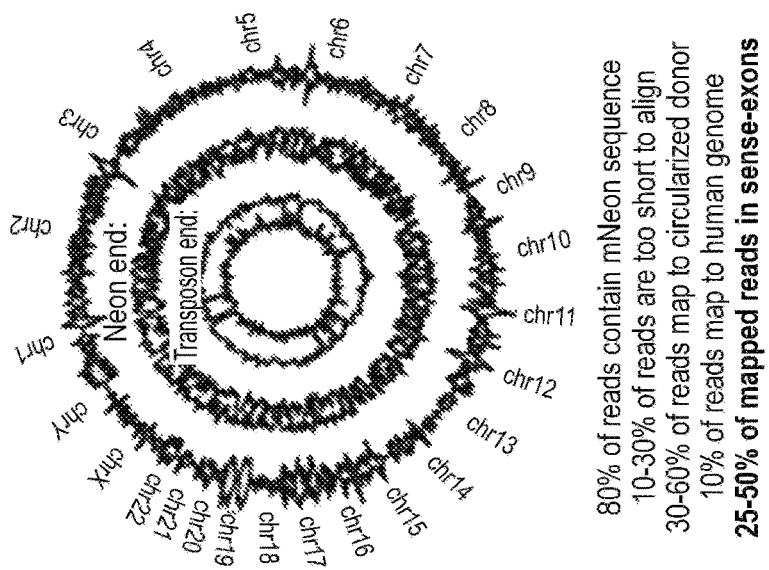
FIG. 20

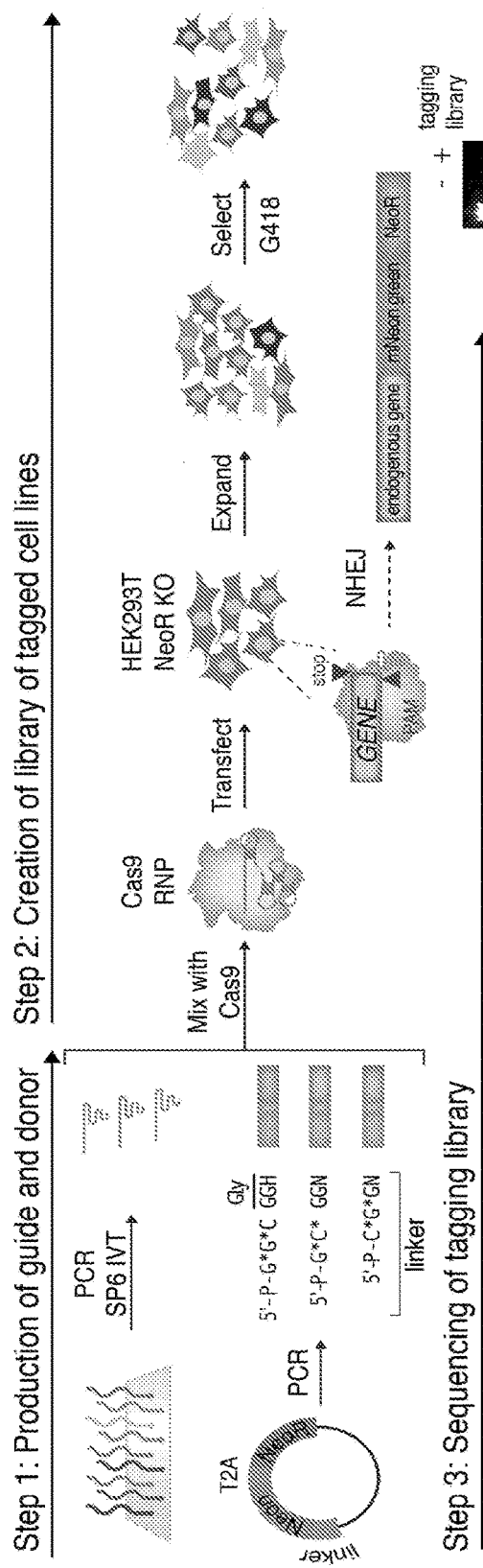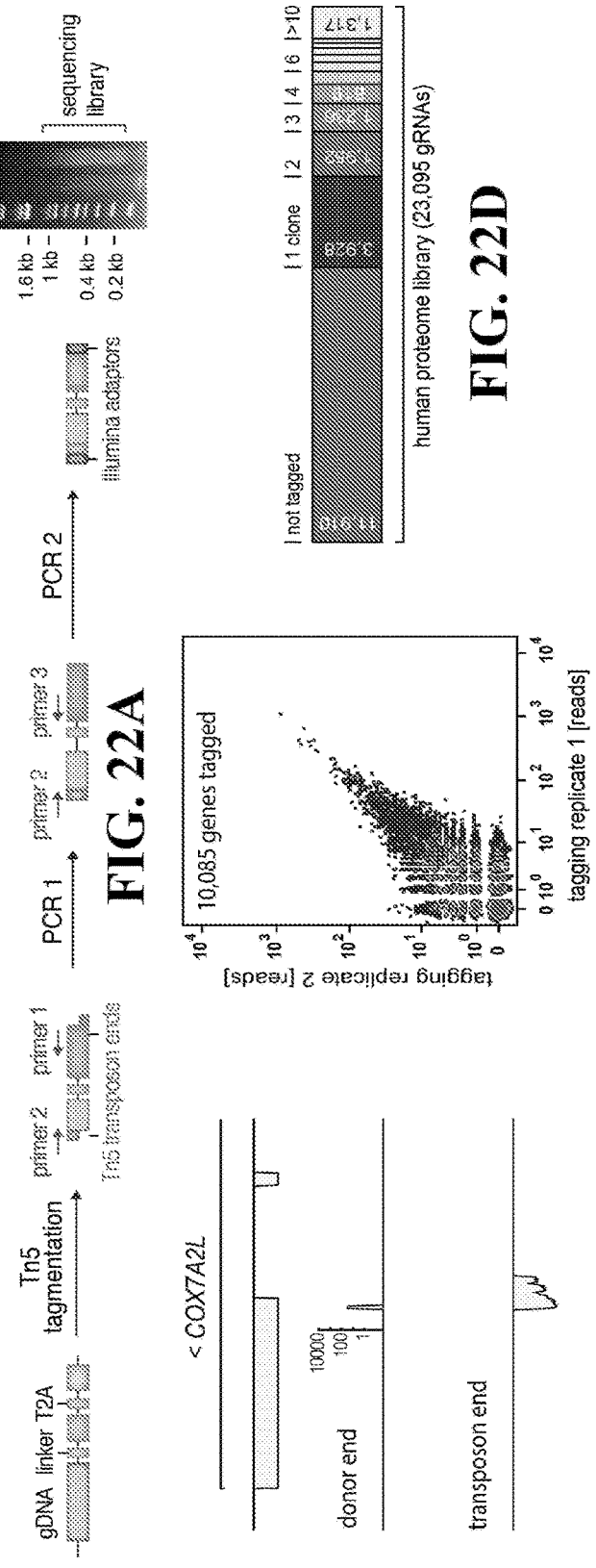
FIG. 22A
FIG. 22B
FIG. 22C
FIG. 22D

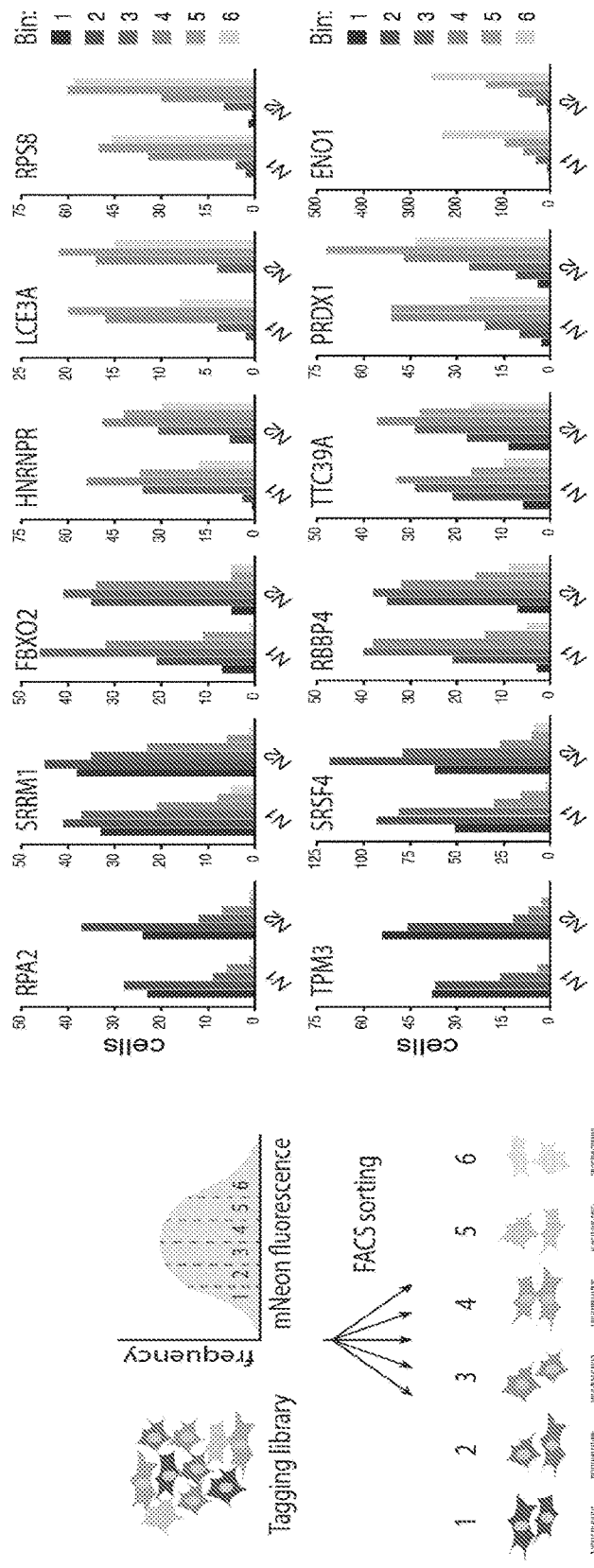
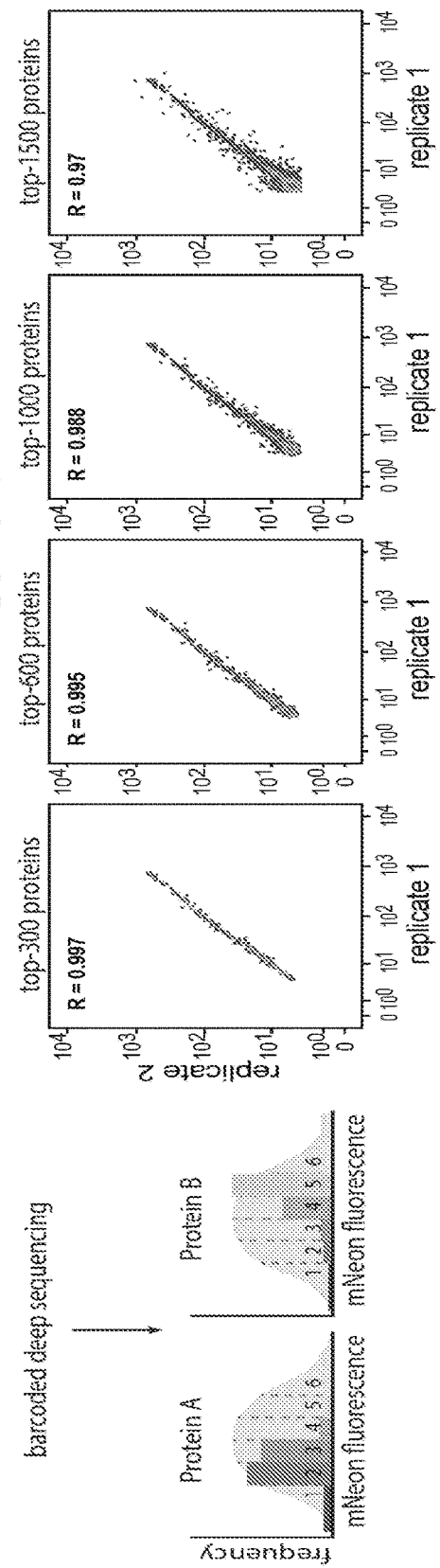
FIG. 23B
FIG. 23C
FIG. 23A

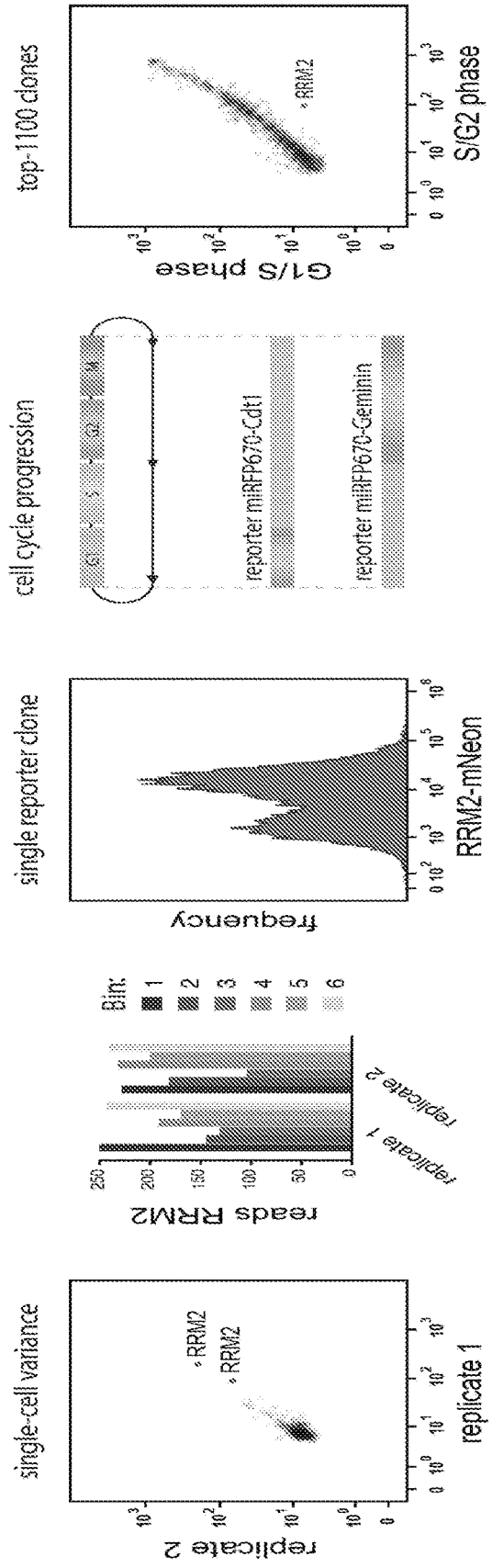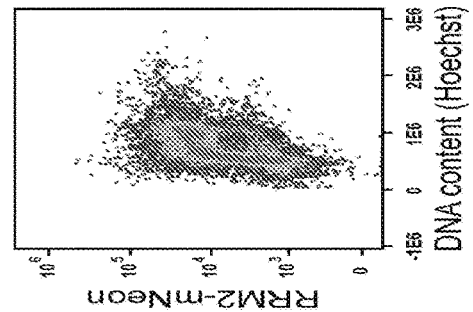
FIG. 23H
FIG. 23G
FIG. 23F
FIG. 23E
FIG. 23D
FIG. 23J
FIG. 23I

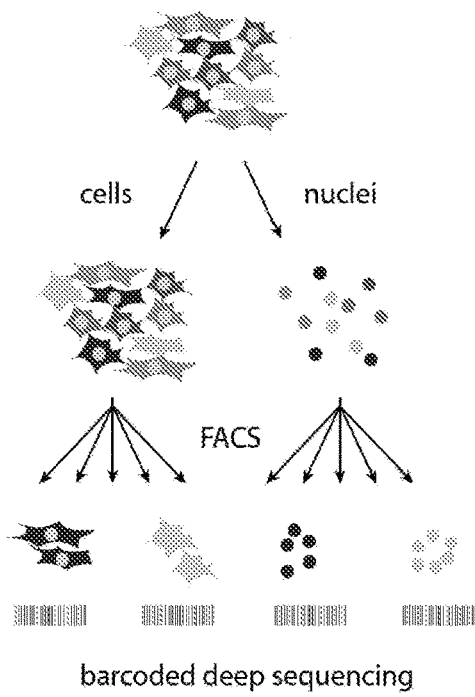

FIG. 25A

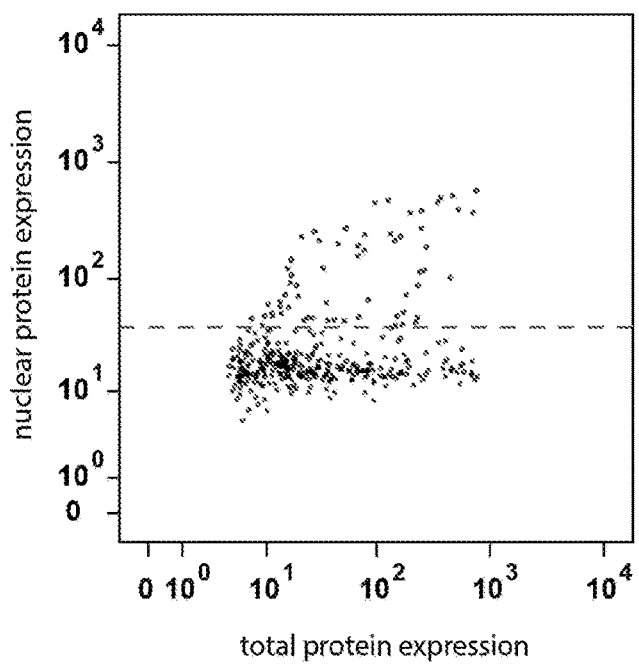

FIG. 25B

| Protein | Confocal | Literature | Protein | Confocal | Literature |
|---|---|---|---|---|---|
| ADAR | Nuclear | Nuclear/Cyto | RPS17 | Nuclear/Cyto | Nuclear/Cyto |
| BRD2 | n/d | Nuclear/Cyto | RPS4X | Nuclear/Cyto | Cytoplasmic |
| BRIX1 | n/d | Nuclear | RPS5 | n/d | Nuclear/Cyto |
| CCER1 | n/d | n/d | RPS8 | Nuclear/Cyto | Nuclear/Cyto |
| CDV3 | n/d | Nuclear/Cyto | SF3B5 | n/d | Nuclear |
| CHERP | Nuclear | Nuclear/Cyto | SNRNP200 | n/d | Nuclear |
| DDX39B | n/d | Nuclear | SNRNP70 | Nuclear | Nuclear |
| DHX15 | n/d | Nuclear | SNRPB | n/d | Nuclear |
| DHX9 | Nuclear | Nuclear/Cyto | SNRPD3 | n/d | Nuclear/Cyto |
| EIF3A | n/d | Nuclear/Cyto | SNRPF | n/d | Nuclear/Cyto |
| H2AFZ | n/d | Nuclear | SNRPG | n/d | Nuclear |
| HNRNPR | Nuclear | Nuclear | SOX9 | n/d | Nuclear |
| HOXD13 | n/d | Nuclear | SRRM1 | n/d | Nuclear |
| IFITM3 | n/d | Cytoplasmic | SRRM2 | n/d | Nuclear |
| ILF3 | n/d | Nuclear/Cyto | SRSF2 | n/d | Nuclear/Cyto |
| MATR3 | Nuclear | Nuclear | SRSF3 | n/d | Nuclear |
| MFAP1 | n/d | Nuclear/Cyto | SRSF4 | n/d | Nuclear |
| MYBBP1A | n/d | Nuclear | SRSF5 | Nuclear | Nuclear |
| NCL | Nuclear | Nuclear | SRSF6 | Nuclear | Nuclear |
| NOP56 | Nuclear | Nuclear | SRSF7 | n/d | Nuclear |
| PARP1 | n/d | Nuclear | SSRP1 | n/d | Nuclear/Cyto |
| PMPCA | Nuclear/Cyto* | Mitochondrial | STAG2 | n/d | Nuclear/Cyto |
| PNN | n/d | Nuclear | SYNCRIP | n/d | Nuclear/Cyto |
| POLR1C | n/d | Nuclear | TRA2B | n/d | Nuclear |
| PRPF40A | n/d | Nuclear | TYMS | n/d | Nuclear |
| RACK1 | n/d | Nuclear/Cyto | U2SURP | n/d | Nuclear |
| RBBP4 | Nuclear/Cyto | Nuclear | WDR3 | n/d | Nuclear |
| RBM39 | n/d | Nuclear | WDR43 | n/d | Nuclear |
| RNPS1 | n/d | Nuclear | WNT8 | n/d | Extracellular |
| RPL10A | n/d | Nuclear/Cyto | ZC3H19 | n/d | Nuclear |
| RPL3 | Nuclear/Cyto | Nuclear/Cyto | ZSCAN16 | n/d | Nuclear |

*Passenger tag present in clone

FIG. 25C

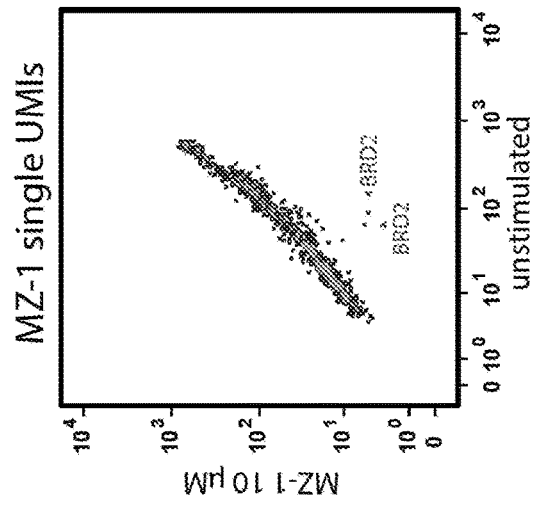
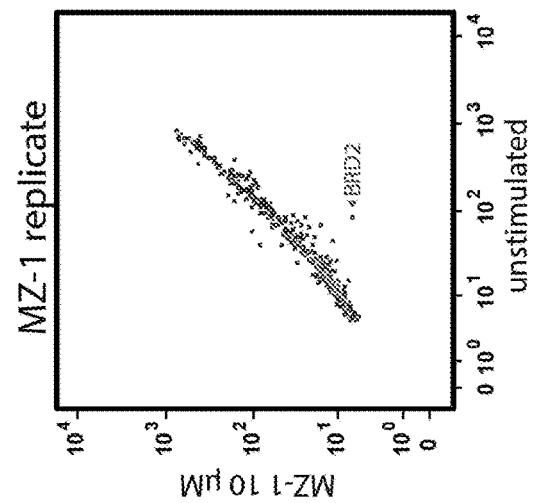
FIG. 31A
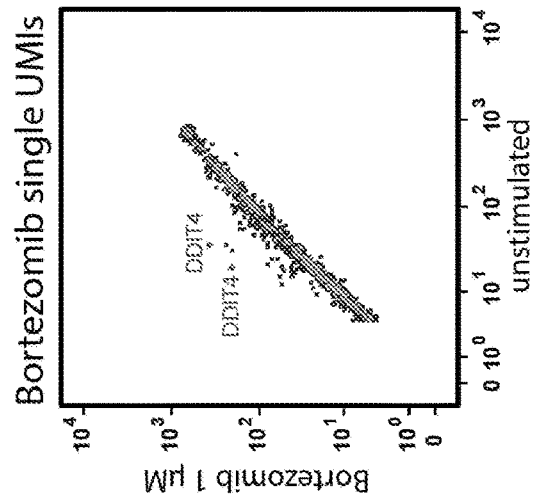
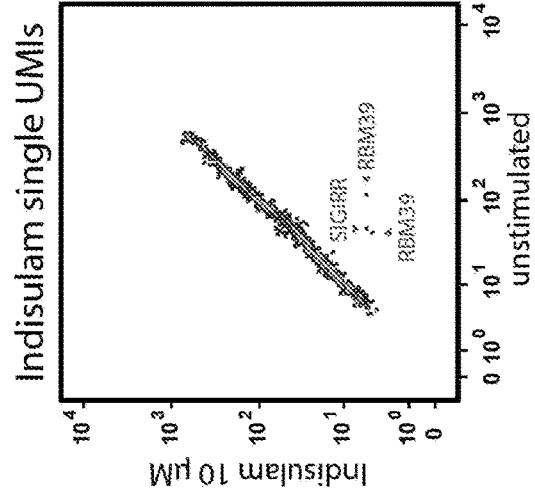
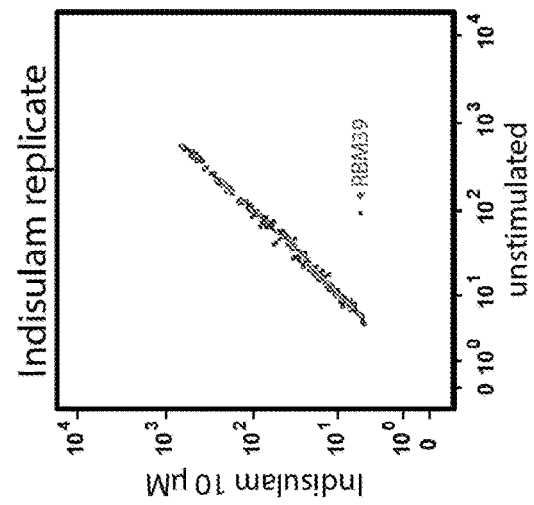
FIG. 31B

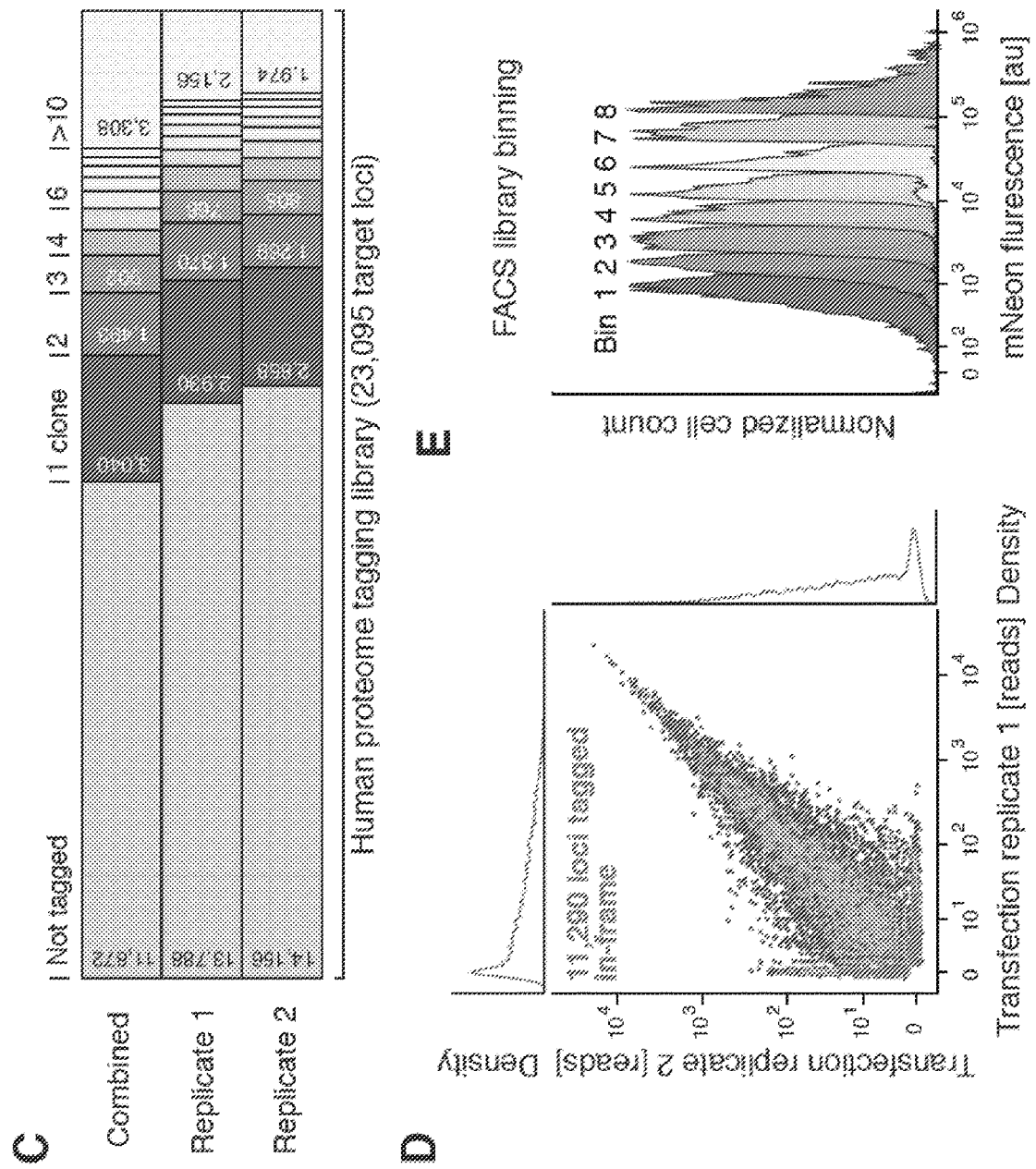
FIG. 32C-E

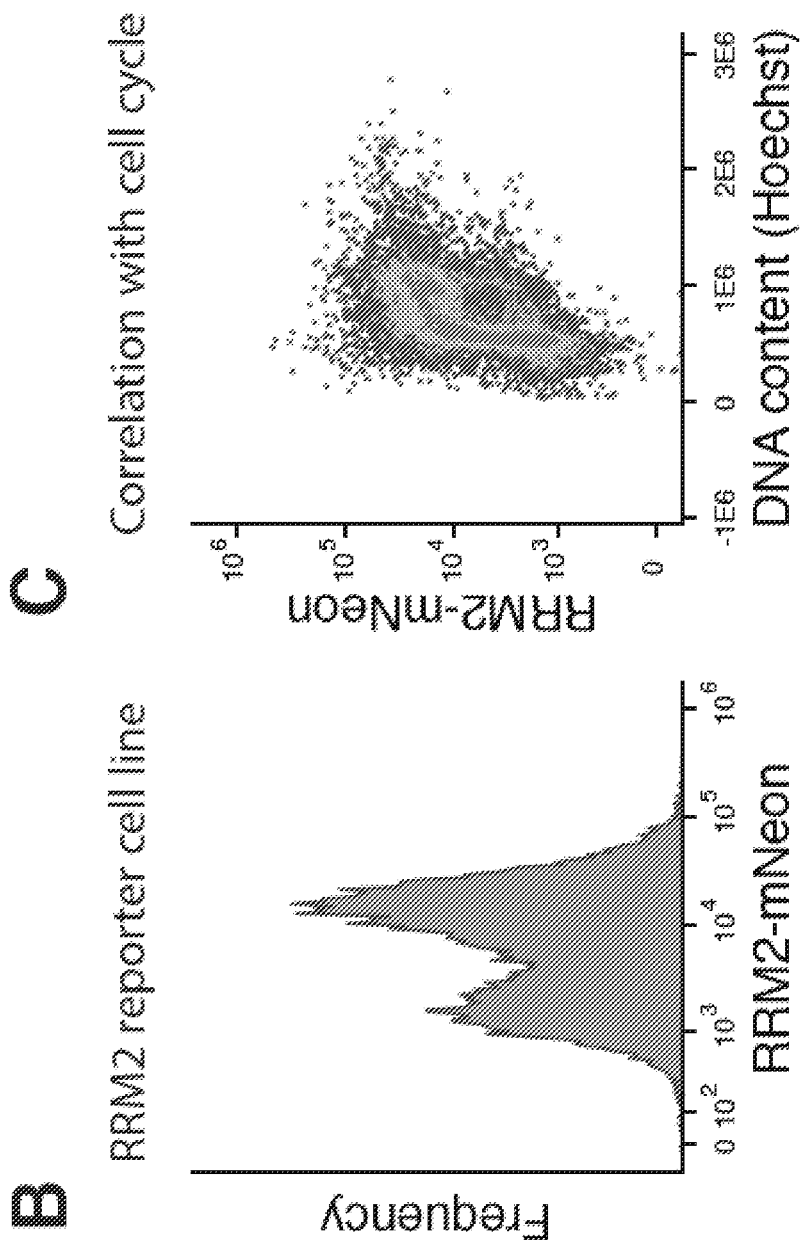
FIG. 33B-C

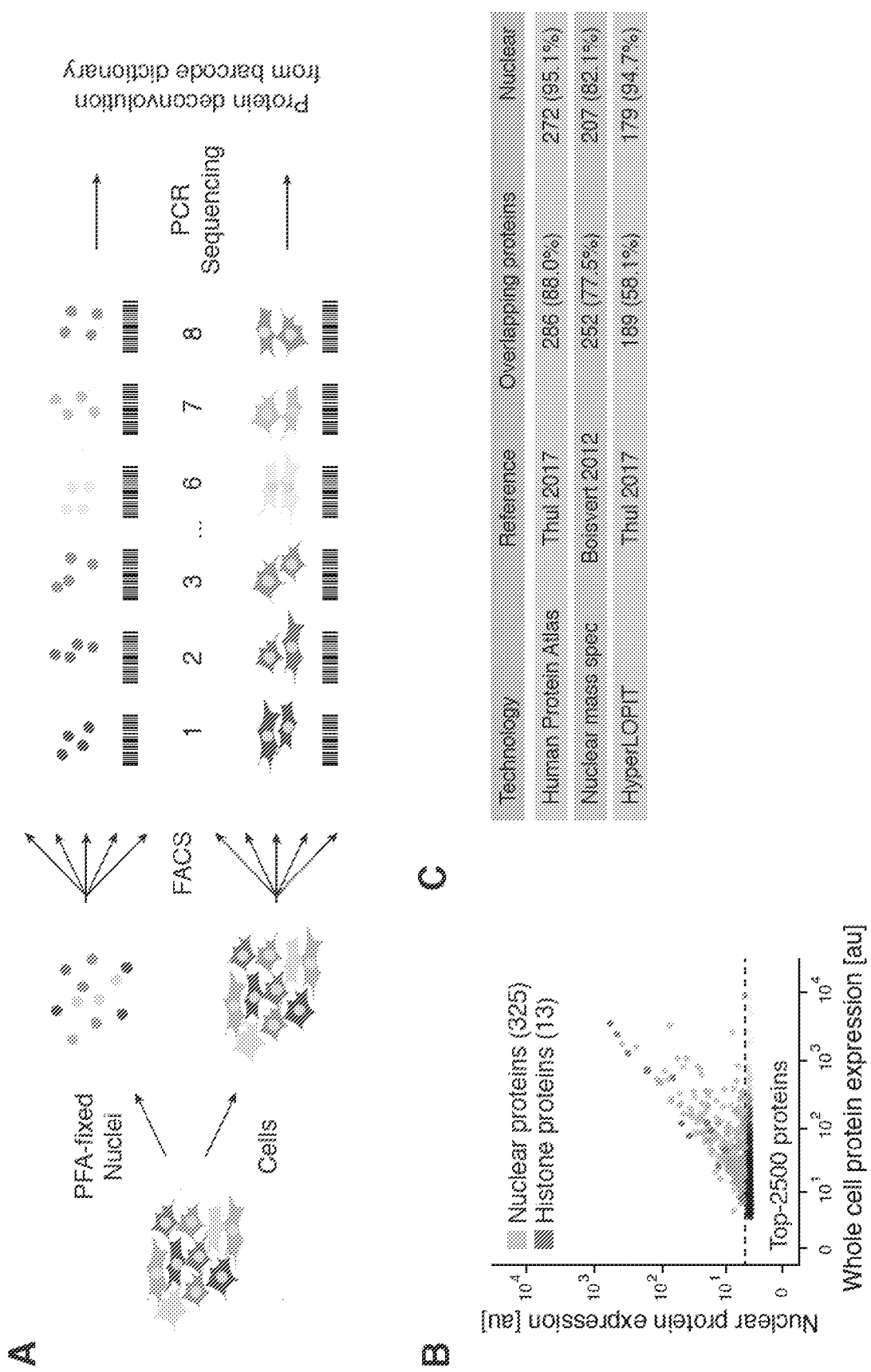
FIG. 34A-C

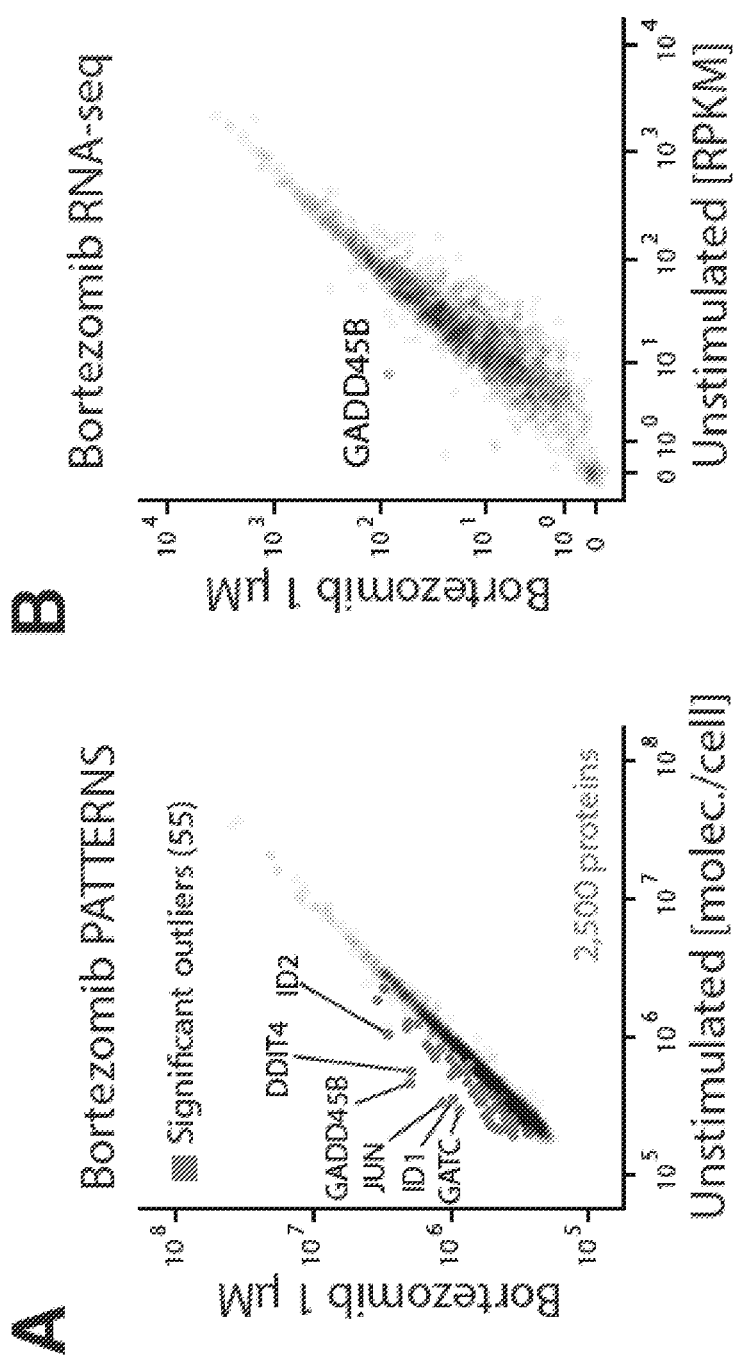
FIG. 35A-B

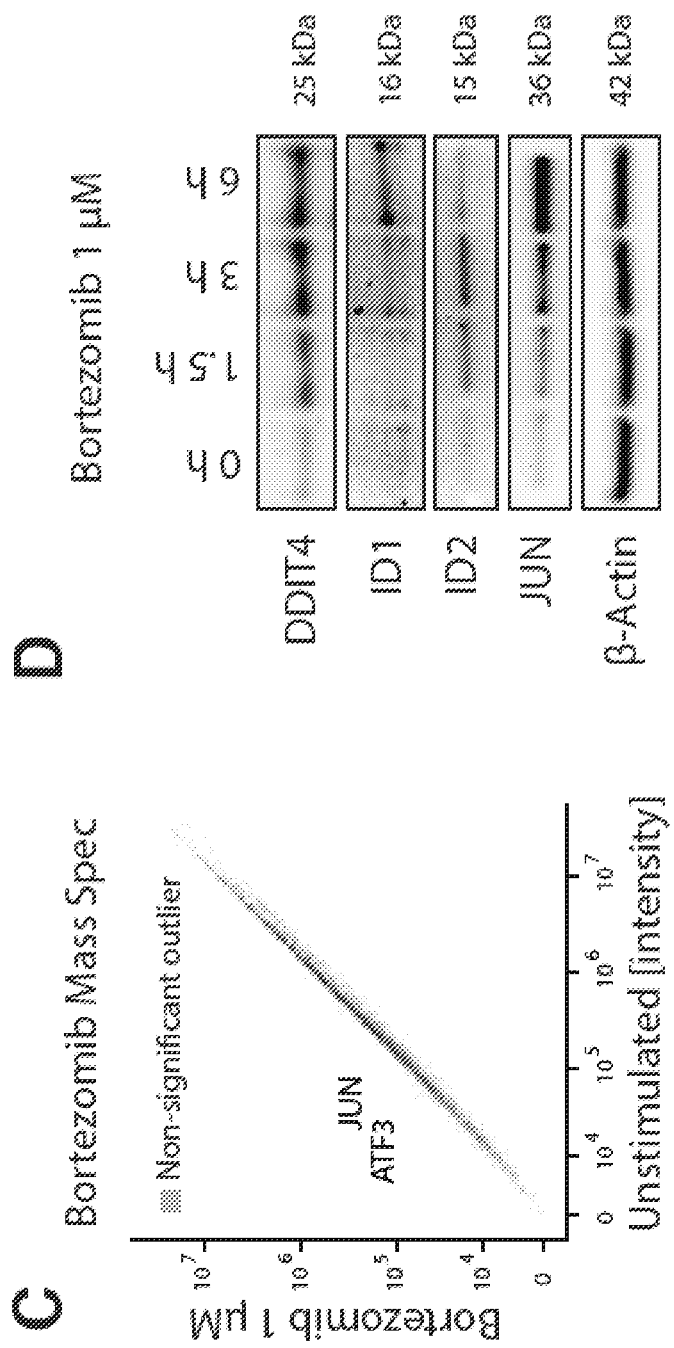
FIG. 35C-D

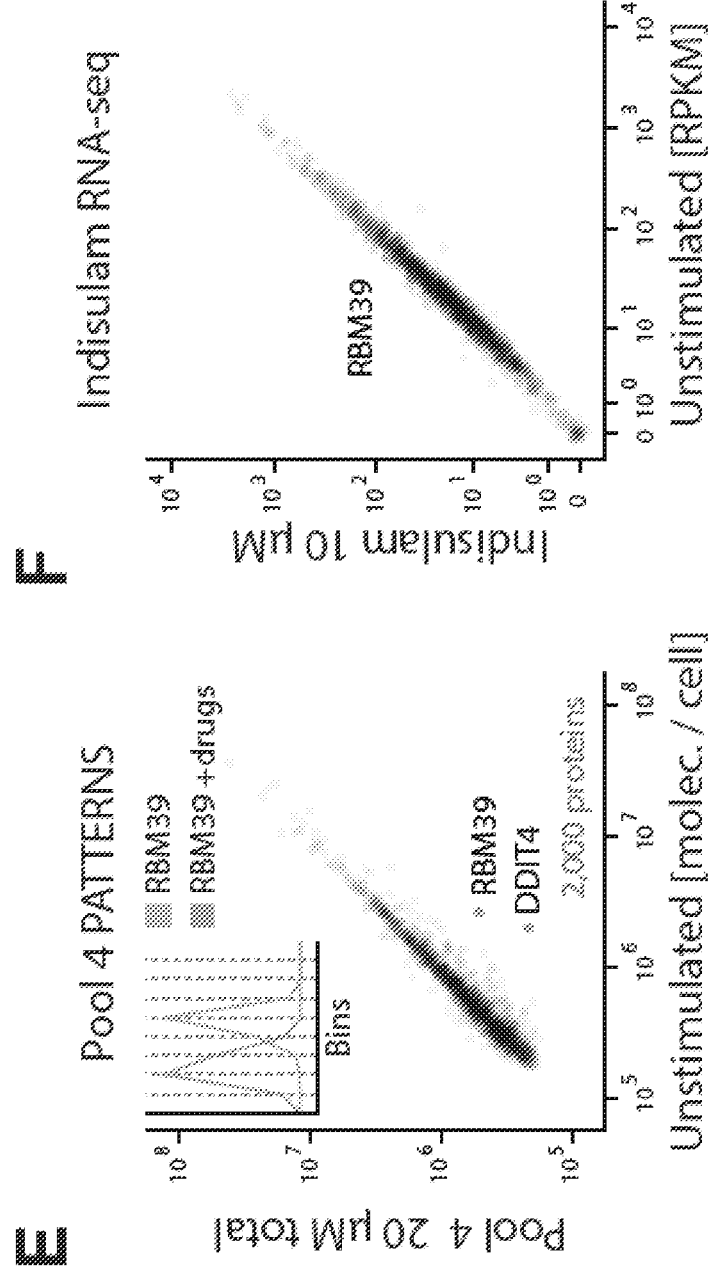
FIG. 35E-F

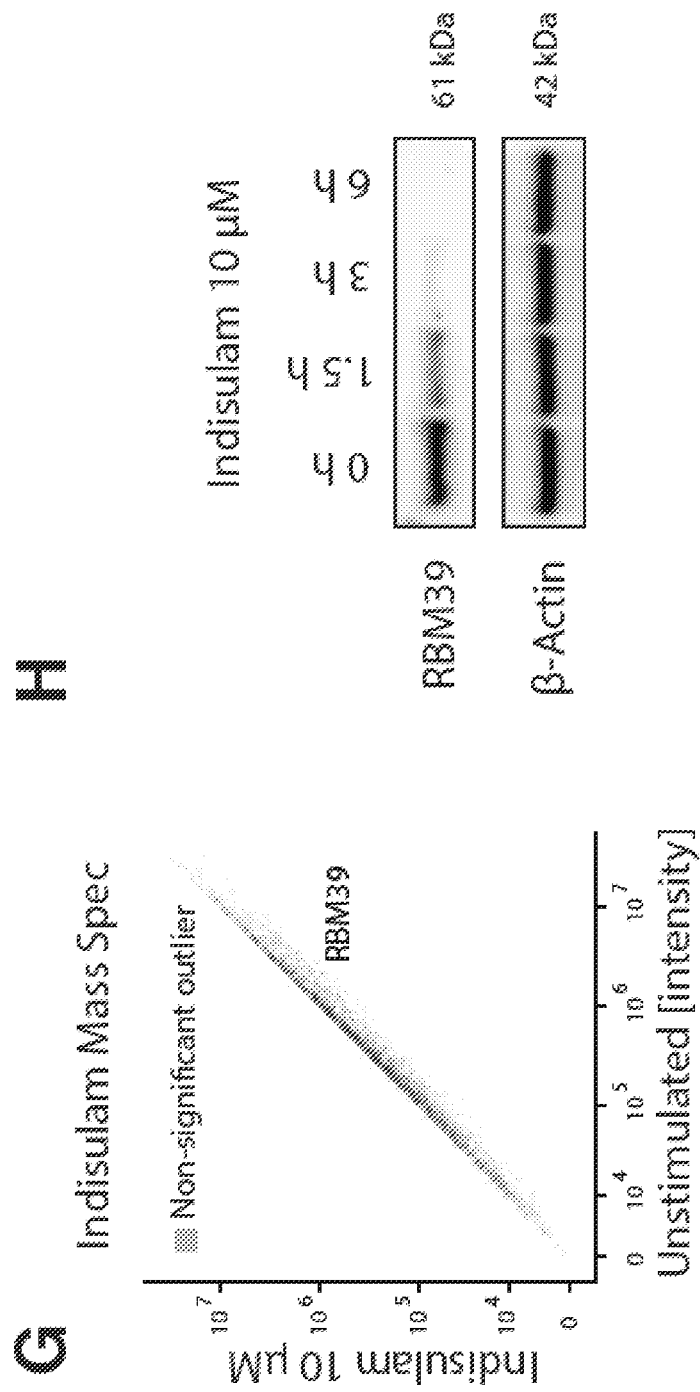
FIG. 35G-H

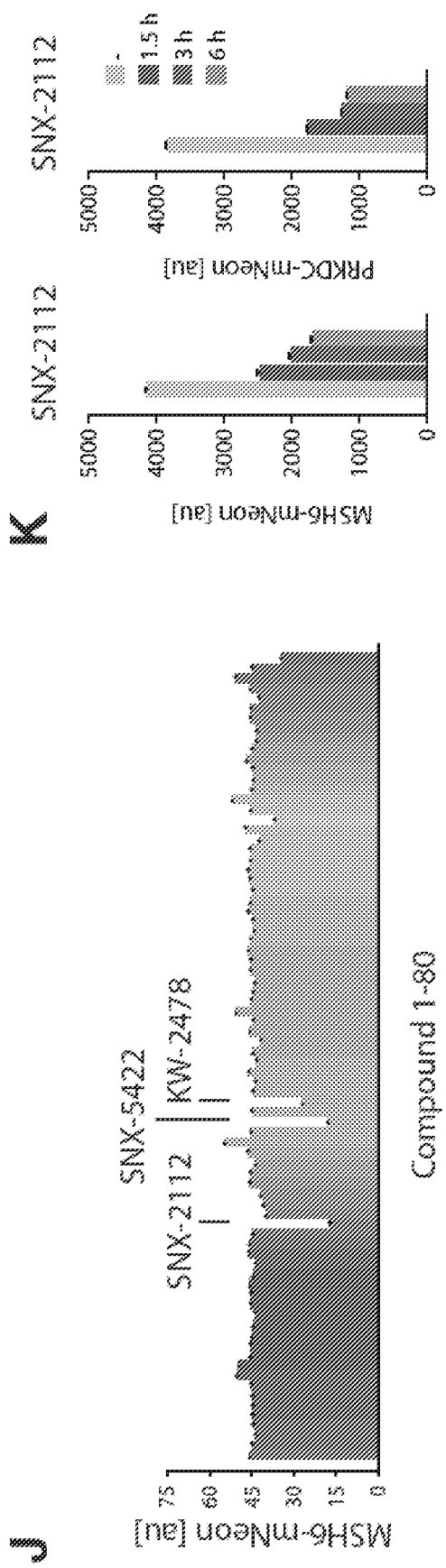
FIG. 35J-K

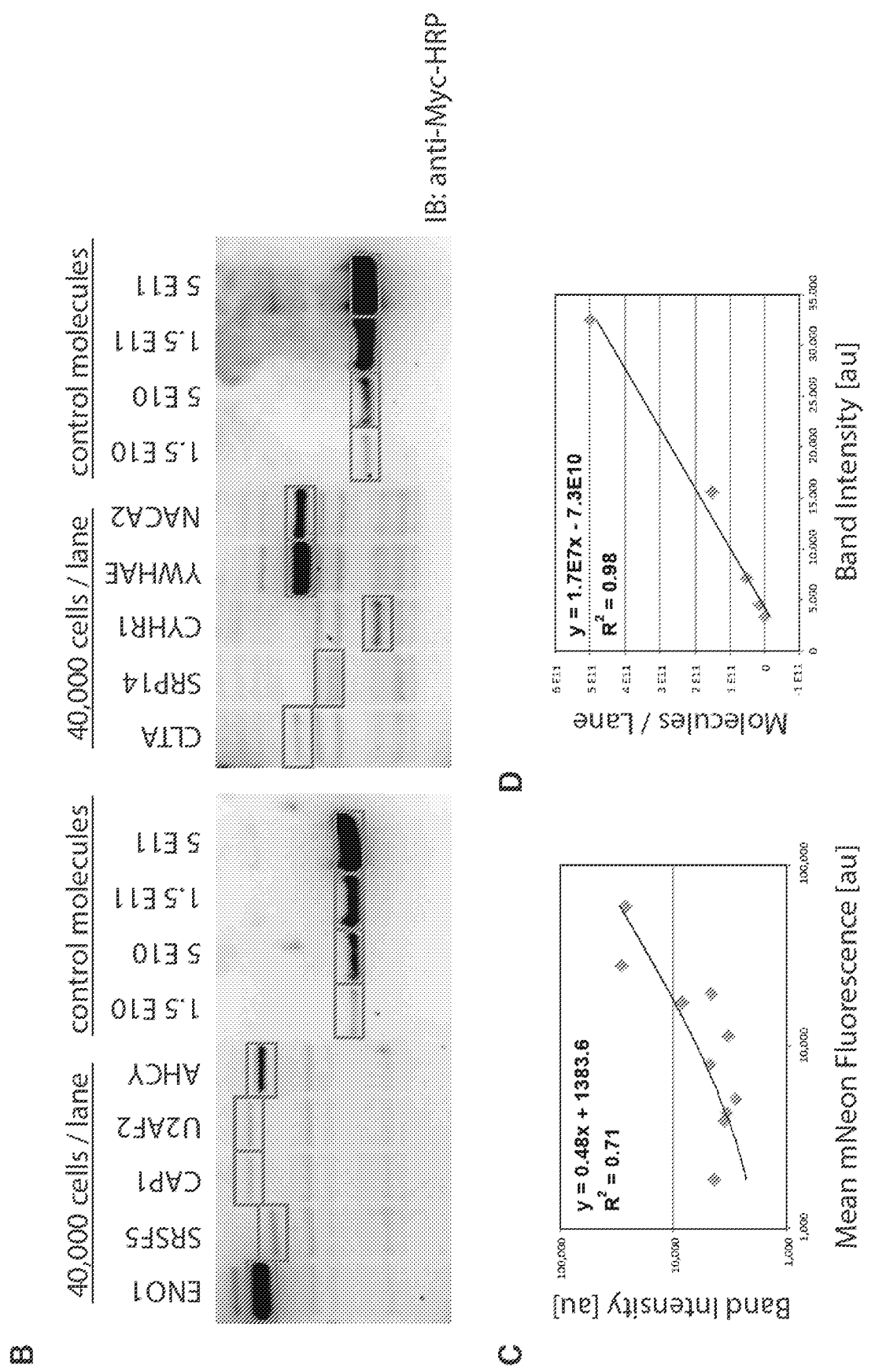
FIG. 37B-D

Estimated Molecules Per Cell = 203.8 * (Mean mNeon Fluorescence)

| Sorted Bin | Mean Fluorescence [au] | Est. Molecules/Cell |
|---|---|---|
| Bin 1 | 852.9 | 173,818 |
| Bin 2 | 1,859 | 378,820 |
| Bin 3 | 3,831 | 780,787 |
| Bin 4 | 7,598 | 1,548,533 |
| Bin 5 | 15,261 | 3,110,267 |
| Bin 6 | 30,380 | 6,191,443 |
| Bin 7 | 76,148 | 15,518,993 |
| Bin 8 | 194,285 | 39,595,198 |

FIG. 37E-F

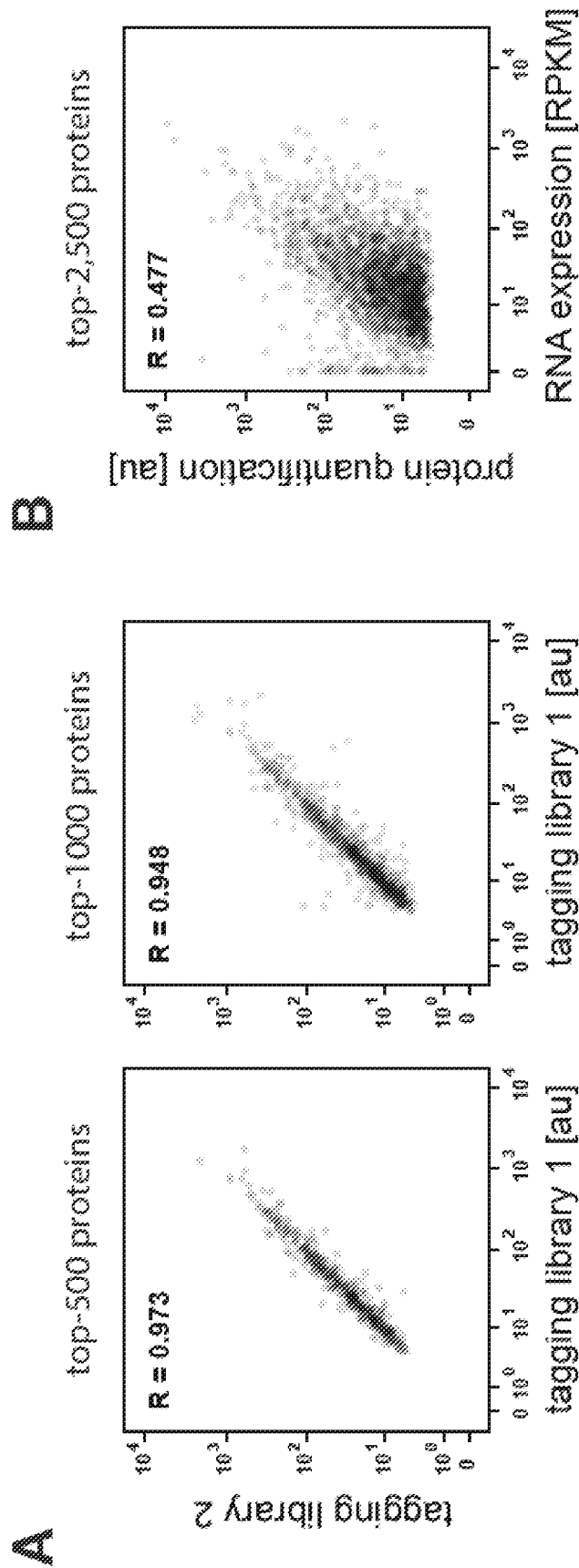
FIG. 38A-B

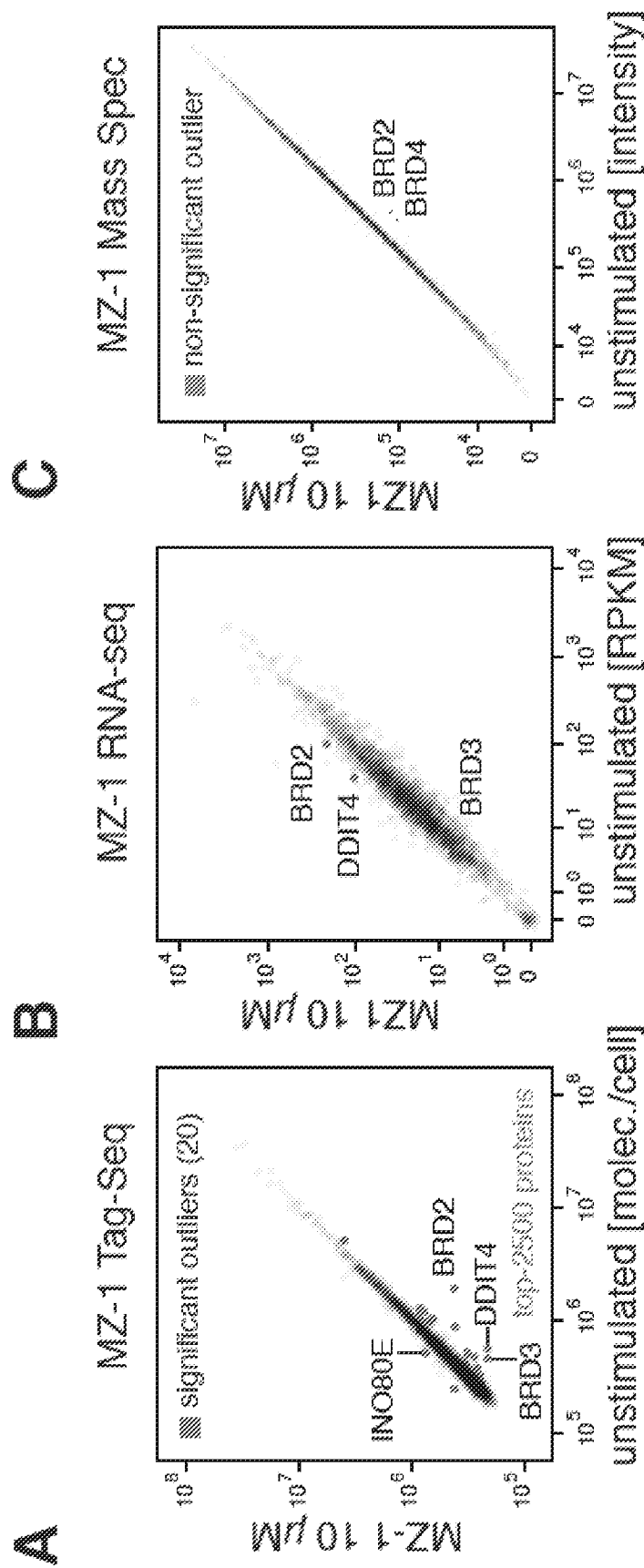
FIG. 39A-C

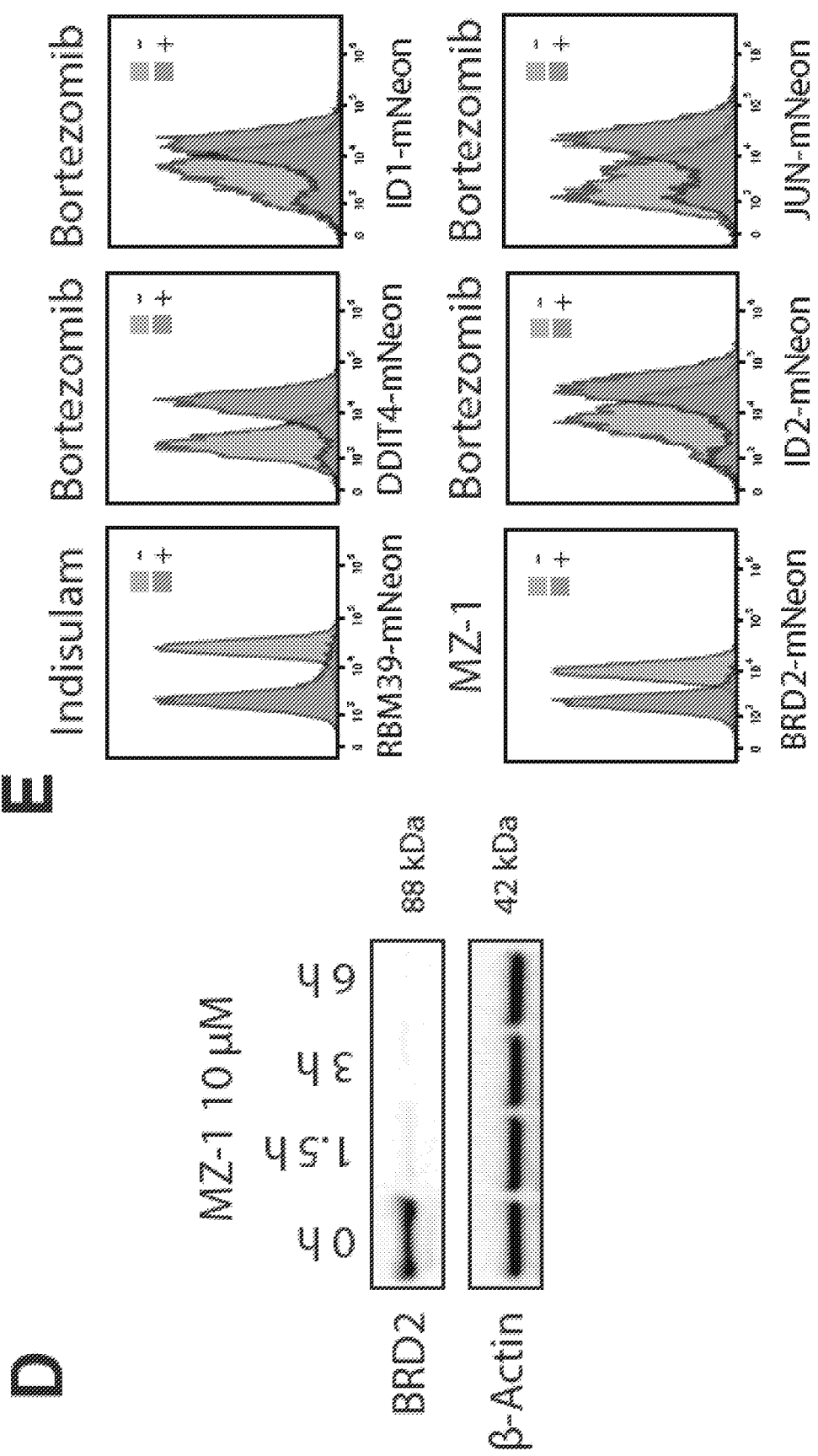
FIG. 39D-E

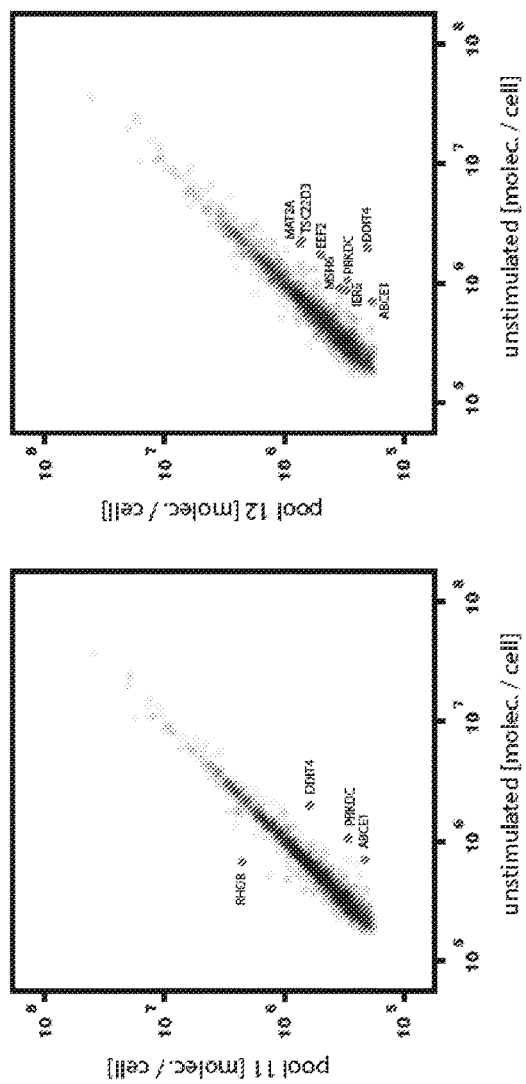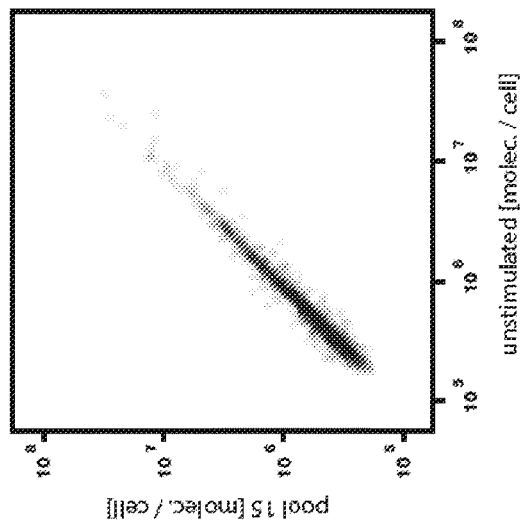
FIG. 41 continued

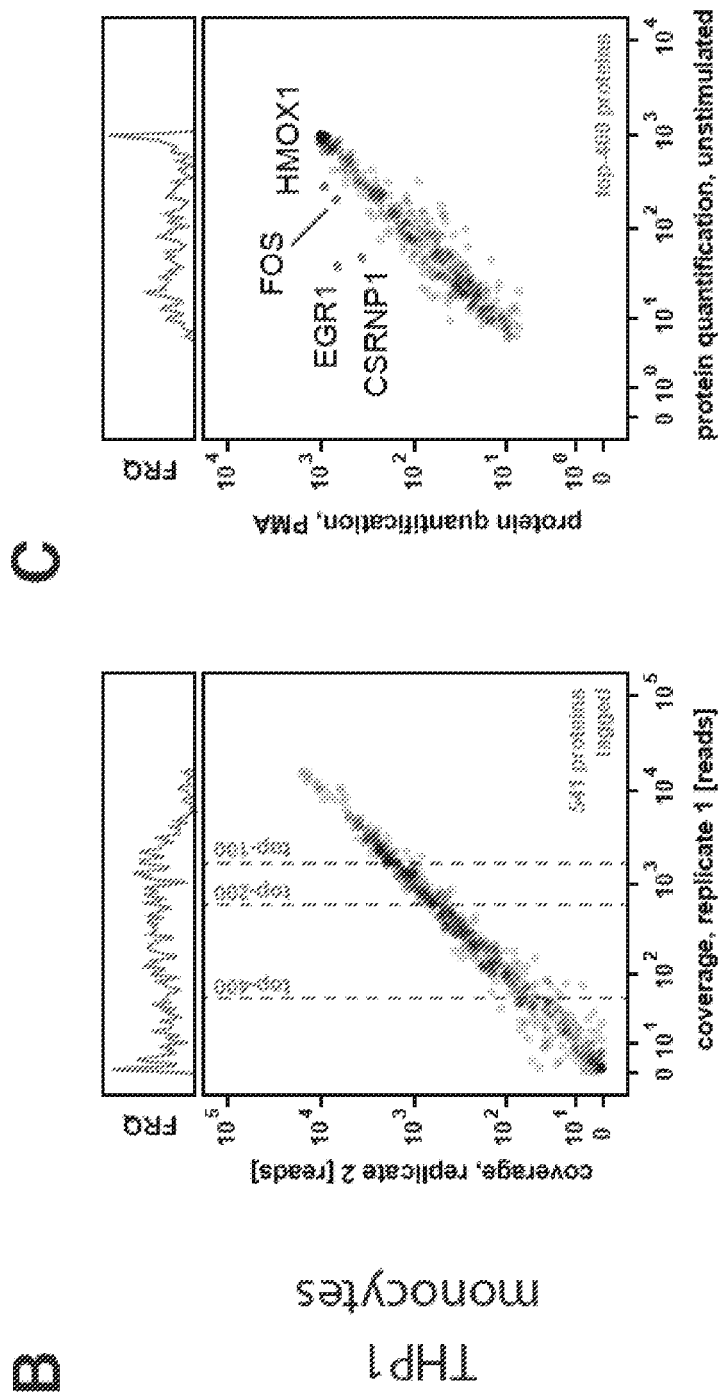
FIG. 42B-C

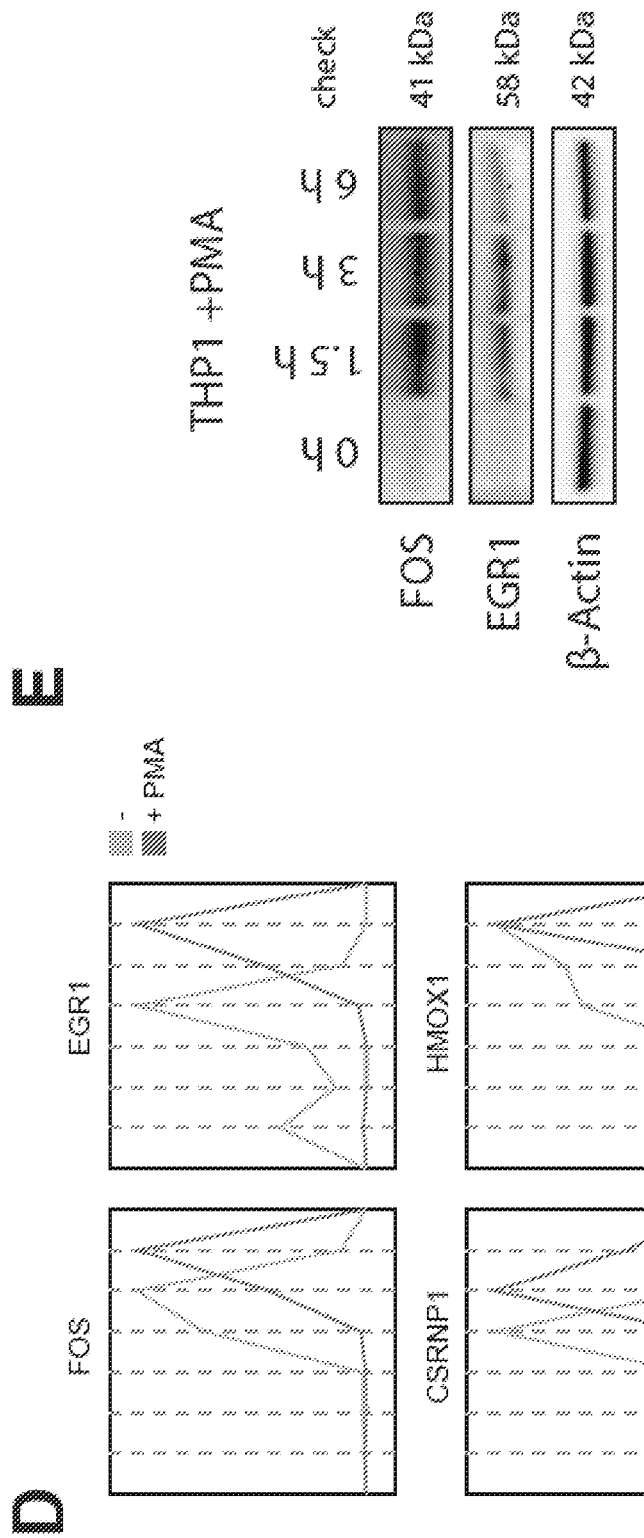
FIG. 42D-E

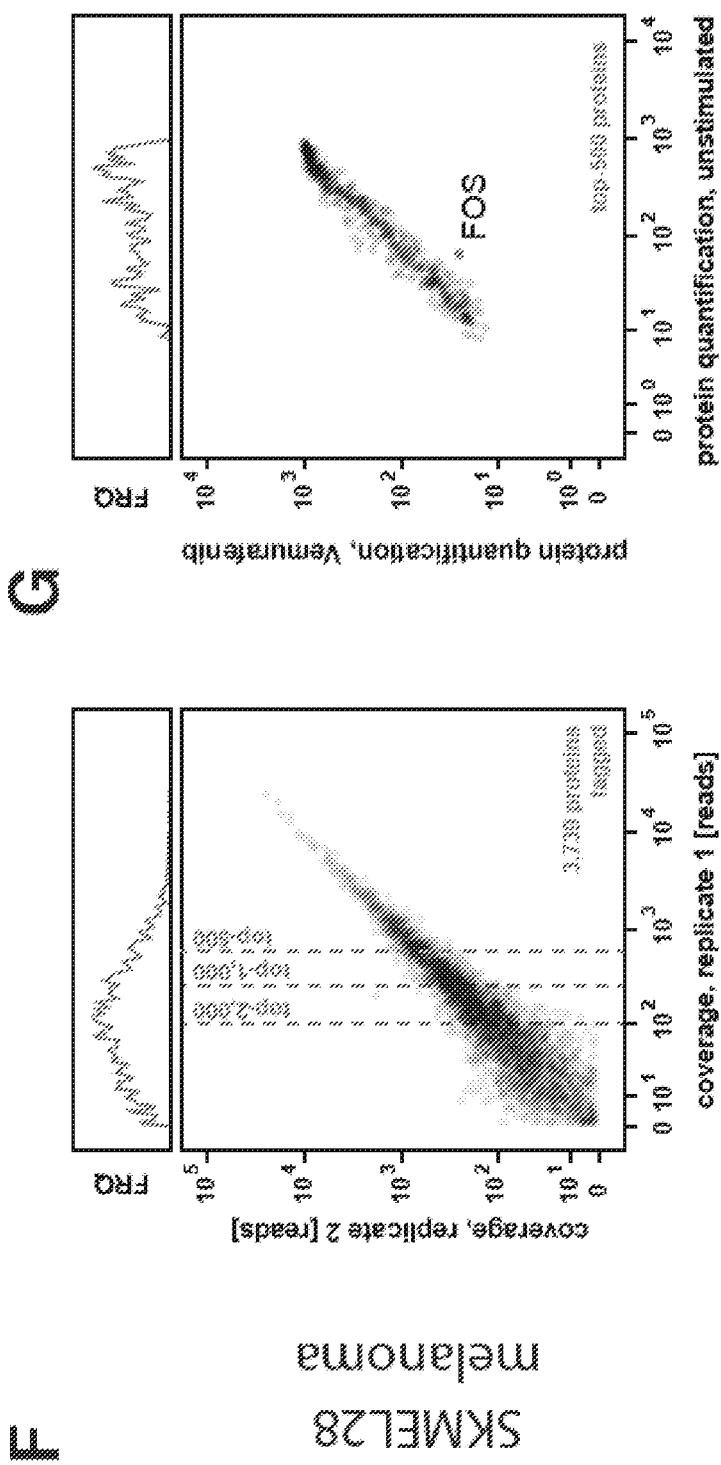
FIG. 42F-G

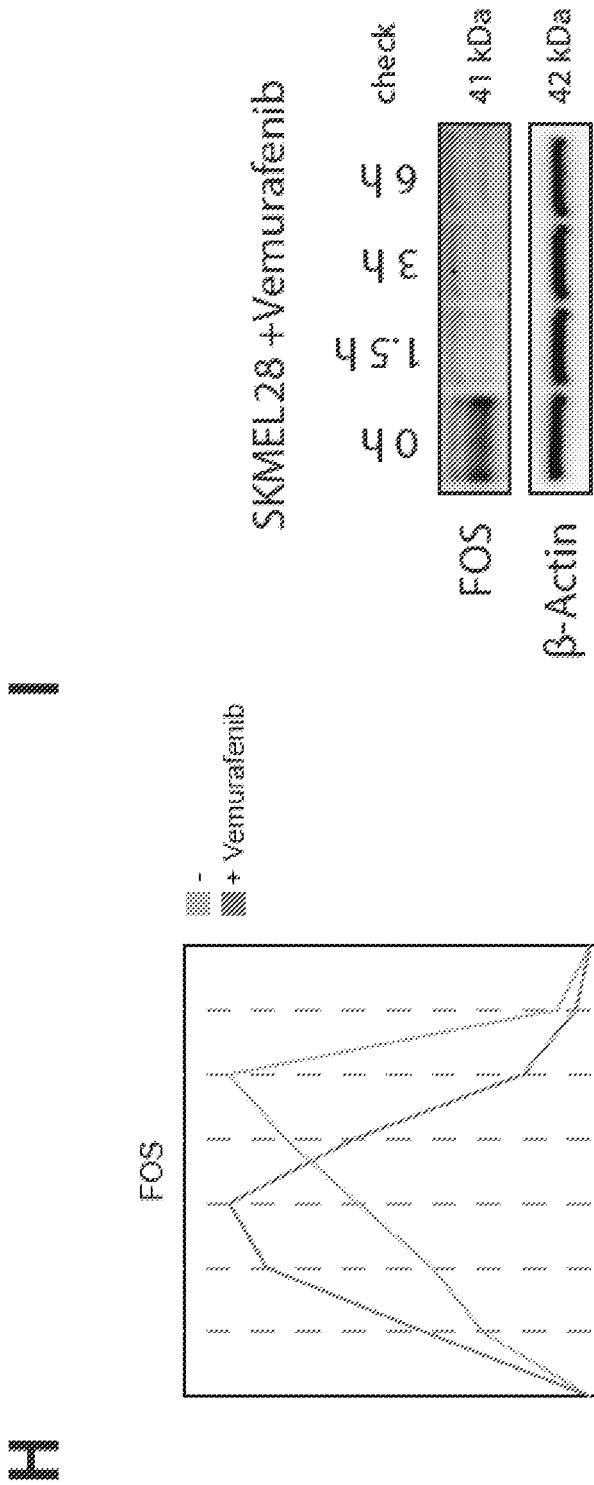
FIG. 42H-I

SEQUENCING-BASED PROTEOMICS

CROSS-REFERENCE TO RELATED APPLICATIONS

This application is a national stage entry of International Application No. PCT/US2019/029488 filed Apr. 26, 2019, which claims the benefit of U.S. Provisional Application Nos. 62/663,712, filed Apr. 27, 2018 and 62/751,314, filed Oct. 26, 2018. The entire contents of the above-identified applications are hereby fully incorporated herein by reference.

STATEMENT REGARDING FEDERALLY SPONSORED RESEARCH

This invention was made with government support under grant Nos. HL141201, HG009761, MH100706 and MH110049 awarded by the National Institutes of Health. The government has certain rights in the invention.

REFERENCE TO AN ELECTRONIC SEQUENCE LISTING

The contents of the electronic sequence listing (BROD_2090WP_ST25.txt"; Size is 13,257,876 bytes and it was created on Apr. 23, 2019) is herein incorporated by reference in its entirety.

TECHNICAL FIELD

The subject matter disclosed herein is generally directed to proteomics. More specifically, the invention is directed to methods for quantification and localization of proteins expressed in a cell.

BACKGROUND

Large-scale RNA sequencing or gene perturbation screens are currently used to identify novel candidate genes involved in biological processes, followed by classical biochemistry to validate single hits at the protein level. Standard validation methods known in the art, such as western blot, co-immunoprecipitation, or immunofluorescence microscopy, are laborious and rely on high-quality antibodies against the protein in question. Thus, a rapid, unbiased technology to assess protein abundance, localization, modification, and interaction on a proteome-wide scale would be very beneficial.

The present invention, therefore, provides such an approach, leveraging the power of deep sequencing in combination with the CRISPR/Cas9 system to create a sequencing-based proteomics method. Through the methods of the invention, answers to fundamentally important biological questions, particularly relating to innate immune signaling, cell cycle biology, and cellular drug response on the systems level, may be obtained. Sequencing-based proteomics provides a tractable, high-throughput method to access information stored at the protein level in cells, and to uncover unknown pathways or potential drug targets, which otherwise would require extensive research on single protein components.

SUMMARY

In one aspect, the invention provides a cell library for use in detecting the distribution of protein levels in single cells comprising a plurality of cells, wherein each cell comprises a polynucleotide sequence encoding a detectable marker integrated into the genome of the cell in frame with a protein coding gene selected from a set of target genes, wherein the library comprises more than one cell tagged at each target gene, whereby each gene in the set of genes is tagged with a detectable marker in single cells of the library. Thus, each cell expresses a fusion protein between the target gene and the detectable marker that is under control of the endogenous target gene locus. In certain embodiments, the detectable marker is a gene encoding for a fluorescent protein, or a protease, or an epitope, or an enzyme. In certain embodiments, the polynucleotide sequence further comprises a codon-neutral unique molecular identifier (UMI) sequence or a non-coding UMI after the detectable marker coding sequence, preferably, wherein the library is sequence-verified, such that each UMI identifies a tagged target gene (e.g., the polynucleotide sequence encoding a detectable marker further contains randomized bases that allow counting of independent integration events into the same genomic locus and identification of the tagged gene). The UMI may be integrated into the sequence of the detectable marker.

In certain embodiments, the polynucleotide sequence further encodes a selectable marker expressed as a separate protein. In certain embodiments, the sequence encoding the selectable marker is separated from the sequence encoding the fusion protein by an internal ribosome entry site (IRES) or a 2A peptide. In certain embodiments, the sequence encoding the selectable marker is operably linked to a separate regulatory element. In one embodiment, the selectable marker is an antibiotic resistance gene. In yet another embodiment, the selectable marker encodes for an enzyme that regulates expression of another selectable marker, (e.g., cre recombinase turning on or off a loxP-flanked reporter).

In certain embodiments, the polynucleotide sequence encoding a detectable marker further comprises a sequence encoding a protease cleavage site and a cleavable marker, wherein the sequence is in frame with the detectable marker sequence. Thus, the polynucleotide sequence is arranged such that the fusion protein expresses both the detectable marker and cleavable marker. Upon the fusion protein coming into contact with a protease specific for the cleavage site, cleavage of the fusion protein results in loss of only the cleavable marker from the fusion protein (see, e.g., FIG. 13 where the cleavable marker is a MYC epitope). In certain embodiments, the cleavable marker is a gene encoding for an epitope, or a protease, or a fluorescent protein, or an enzyme. In preferred embodiments, the cleavable marker is an epitope. As used herein, the term "cleavable marker" refers to any additional marker that can be cleaved from the fusion protein. In certain embodiments, the "cleavable marker" is only cleavable because it is outside of the protease cleavage site. The cleavable marker can be cleaved from the fusion protein, but is not cleaved per se. The marker should be different from the detectable marker.

In certain embodiments, a recombinant protease localized to a cellular compartment can be introduced to the library of cells at a time point where detection of protein expression for tagged proteins is desired. In certain embodiments, each cell is configured for expression of a recombinant protease localized to a cellular compartment. The cellular compartment may include, but is not limited to nuclear, cytoplasmic, mitochondrial, peroxisomal, endoplasmic reticulum (ER), golgi, lysosomal, membrane, or cytoskeleton compartments. Thus, localization of tagged proteins can be determined by detection of cleaved fusion proteins. The protease may comprise at least one nuclear export signal, nuclear localization signal, peroxisome localization signal, ER localization signal, golgi localization signal, lysosome localization signal, or mitochondrial localization signal.

In certain embodiments, the polynucleotide sequence encoding a detectable marker further comprises a T7 RNA polymerase promoter. In another embodiment, the polynucleotide sequence encoding a detectable marker further encodes for a linker peptide. The linker peptide may be any linker known in the art (e.g., gly-ser linker). The linker peptide may be between the detectable marker and tagged gene, between the detectable marker and cleavage site, between the cleavage site and cleavable marker, or between the cleavable marker and the selectable marker. In another embodiment, each cell comprises a sequence encoding a guide sequence specific for the tagged target gene, whereby detection of the sequence indicates the tagged target gene. In other embodiments, the library comprises eukaryotic cells, or the eukaryotic cells are mammalian, insect, yeast, or plant cells. In another embodiment, the cells of the library were generated from cells configured to express a CRISPR enzyme. In another embodiment, the CRISPR enzyme is inducible or transiently delivered as a protein. In another embodiment, the cells of the library were generated from cells obtained from a transgenic animal configured to express a CRISPR enzyme.

In another aspect, the present invention provides for a cell library for use in detecting protein interactions between a protein of interest and a set of target proteins, said library comprising a plurality of cells, wherein each cell comprises a first polynucleotide sequence encoding a first complementary protein integrated into the genome of the cell in frame with the protein of interest or comprises a first polynucleotide sequence encoding a fusion protein of the first complementary protein and protein of interest, wherein each cell comprises a second polynucleotide sequence encoding a second complementary protein integrated into the genome of the cell in frame with a protein coding gene selected from a set of target genes, wherein the library comprises more than one cell tagged at the protein of interest and a target gene and wherein an interaction between the protein of interest and a target gene can be detected with a detectable marker, whereby each gene in the set of target genes is tagged with a second complementary protein in single cells of the library. As used herein, "complementary protein" refers to a protein that complements another complementary protein, such that the complementary proteins create a functional or detectable unit (e.g, split fluorescent marker, split enzyme, epitopes binding, oligonucleotide linked antibodies, inactive marker and activating enzyme, protease and protease-cleavable epitope, FRET pair of fluorescent proteins). In certain embodiments, the second polynucleotide sequence further comprises a codon-neutral unique molecular identifier (UMI) sequence or a non-coding UMI after the detectable marker coding sequence, preferably, wherein the library is sequence-verified, such that each UMI identifies a tagged target gene. In certain embodiments, the first and second complementary proteins may comprise protein complementary assay (PCA) fragments; or one of the first or second complementary proteins may comprise a permuted inactive reporter and the other complementary protein comprises TEV; or the first and second complementary proteins may comprise a different epitope tag; or one of the first or second complementary proteins comprises one or more TEV cleavage sites followed by one or more epitopes and the other complementary protein comprises TEV. In certain embodiments, interactions may be detected by proximity ligation using oligo linked affinity ligands specific for the epitope tags (e.g., antibodies). In certain embodiments, the TEV cleavage site might be mutated to slow down cleavage in order to make cleavage more specific. The ligation products may be detected using a detectable probe as described herein. The PCA fragments may comprise split fluorescent protein fragments or split TEV fragments. In other embodiments, the first polynucleotide sequence may encode an epitope for use in a proximity ligation assay, or a recognition site for measurement of interaction by TEV cleavage of nearby target sites. In one embodiment, the second polynucleotide sequence comprises a selectable marker operably linked to a separate regulatory element; or wherein the polynucleotide sequence comprises an IRES or a 2A peptide, whereby the selectable marker is expressed as a separate protein. In another embodiment, the selectable marker is an antibiotic resistance gene. In another embodiment, the second polynucleotide sequence comprises a T7 RNA polymerase promoter. In another embodiment, each cell comprises a sequence encoding a guide sequence specific for the tagged target gene, whereby detection of the sequence indicates the tagged target gene. In other embodiments, the library comprises eukaryotic cells, such as mammalian, insect, yeast, or plant cells. In another embodiment, the cells of the library were generated from cells configured to express a CRISPR enzyme. In another embodiment, the CRISPR enzyme is inducible or transiently delivered as a protein. In another embodiment, the cells of the library were generated from cells obtained from a transgenic animal configured to express a CRISPR enzyme.

In another aspect, the present invention provides for a cell library for use in detecting protein modifications comprising a plurality of cells, wherein each cell stably expresses a fusion protein comprising a protein modification binding protein fused to a first complementary protein, wherein each cell comprises a polynucleotide sequence encoding a second complementary protein integrated into the genome of the cell in frame with a protein coding gene selected from a set of target genes, wherein the library comprises more than one cell tagged at each target gene and wherein binding of a protein modification binding protein to a target gene can be detected with a detectable marker, whereby each gene in the set of target genes is tagged with a second complementary protein in single cells of the library. The complementary proteins may include, e.g, a split fluorescent marker, split enzyme, epitopes binding, oligonucleotide linked antibodies, inactive marker and activating enzyme, protease and protease-cleavable epitope, or FRET pair of fluorescent proteins. In certain embodiments, the polynucleotide sequence further comprises a codon-neutral unique molecular identifier (UMI) sequence or a non-coding UMI after the detectable marker coding sequence, preferably, wherein the library is sequence-verified, such that each UMI identifies a tagged target gene. In certain embodiments, the first and second complementary proteins may comprise protein complementary assay (PCA) fragments; or one of the first or second complementary proteins may comprise a permuted inactive reporter and the other complementary protein comprises TEV; or the first and second complementary proteins may comprise a different epitope tag; or one of the first or second complementary proteins comprises one or more TEV cleavage sites followed by one or more epitopes and the other complementary protein comprises TEV. In certain embodiments, interactions may be detected by proximity ligation using oligo linked affinity ligands specific for the epitope tags (e.g., antibodies). In certain embodiments, the TEV cleavage site might be mutated to slow down cleavage in order to make cleavage more specific. The ligation products may be detected using a detectable probe as described herein. The PCA fragments may comprise split fluorescent protein fragments or split TEV fragments. In other embodiments, the first polynucleotide sequence may encode an epitope for use in a proximity ligation assay, or a recognition site for measurement of interaction by TEV cleavage of nearby target sites. In one embodiment, the polynucleotide sequence comprises a selectable marker operably linked to a separate regulatory element; or wherein the polynucleotide sequence comprises an IRES or a 2A peptide, whereby the selectable marker is expressed as a separate protein. In another embodiment, the selectable marker is an antibiotic resistance gene. In another embodiment, the polynucleotide sequence comprises a T7 RNA polymerase promoter. In another embodiment, each cell comprises a sequence encoding a guide sequence specific for the tagged target gene, whereby detection of the sequence indicates the tagged target gene. In another embodiment, the library comprises eukaryotic cells, such as mammalian, insect, yeast, or plant cells. In another embodiment, the cells of the library were generated from cells configured to express a CRISPR enzyme. In another embodiment, the CRISPR enzyme is inducible or transiently delivered as a protein. In another embodiment, the cells of the library were generated from cells obtained from a transgenic animal configured to express a CRISPR enzyme.

In any embodiment described herein, the tagged protein may be tagged at the N-terminus or C-terminus depending on the protein to be tagged. For example, a membrane protein may be advantageously tagged on an extracellular or intracellular domain. In any embodiment described herein, the detectable marker comprises a fluorescent protein or an epitope tag. The epitope tag may be detected by binding of a fluorescently tagged antibody or any binding molecule (e.g., aptamer).

In another aspect, the invention provides for a scalable method of constructing a cell library for use in proteomics comprising: introducing to a population of cells configured for expression of a CRISPR enzyme a plurality of polynucleotide sequences, wherein each cell receives one or more polynucleotide sequences comprising: a first guide sequence or a polynucleotide sequence configured for expression of the guide, wherein the first guide sequence is sequence specific for a target sequence in a protein coding gene selected from a set of target genes, a donor polynucleotide sequence comprising a CRISPR target site and a sequence encoding a detectable marker, preferably, comprising a codon-neutral unique molecular identifier (UMI) sequence or a non-coding UMI after the detectable marker coding sequence, and a second guide sequence or a polynucleotide sequence configured for expression of the guide sequence, wherein the second guide sequence is specific for the CRISPR target site, wherein the target sequence and target site are cleaved by the CRISPR enzyme such that the donor polynucleotide sequence is integrated in frame into the target sequence in the protein coding gene by NHEJ; and selecting for cells comprising the donor polynucleotide sequence integrated in frame into a target sequence in a protein coding gene from the set of target genes, whereby the cell library comprises cells singly tagged at every target gene. The CRISPR enzyme may be inducible or transiently provided as a protein. In certain embodiments, the cells are obtained from a transgenic animal configured to express a CRISPR enzyme.

In another aspect, the present invention provides for a scalable method of constructing a cell library for use in proteomics comprising: introducing to a population of cells configured for expression of a CRISPR enzyme a plurality of polynucleotide sequences, wherein each cell receives one or more polynucleotide sequences comprising: a guide sequence or a polynucleotide sequence configured for expression of the guide sequence specific for a target sequence in a protein coding gene selected from a set of target genes, and a donor polynucleotide sequence encoding a detectable marker gene; and selecting for cells comprising the donor polynucleotide sequence integrated in frame into a target sequence in a protein coding gene from the set of target genes, whereby the cell library comprises cells singly tagged at every target gene. The CRISPR enzyme may be inducible or transiently delivered as a protein. In certain embodiments, the cells are obtained from a transgenic animal configured to express a CRISPR enzyme.

In another aspect, the present invention provides for a scalable method of constructing a cell library for use in proteomics comprising: introducing to a population of cells a plurality of polynucleotide sequences, wherein each cell receives one or more polynucleotide sequences comprising: a polynucleotide sequence configured for expression of a CRISPR enzyme, a guide sequence or a polynucleotide sequence configured for expression of the guide sequence specific for a target sequence in a protein coding gene selected from a set of target genes, a donor polynucleotide sequence encoding a detectable marker gene; and selecting for cells comprising the donor polynucleotide sequence integrated in frame into a target sequence in a protein coding gene from the set of target genes, whereby the cell library comprises cells singly tagged at every target gene.

In another aspect, the present invention provides for a scalable method of constructing a cell library for use in proteomics comprising: introducing to a population of cells a plurality of ribonucleoprotein complexes (RNP) comprising a CRISPR enzyme and a plurality of polynucleotide sequences, wherein each cell receives one or more polynucleotide sequences comprising: a guide sequence specific for a target sequence in a protein coding gene selected from a set of target genes, a donor polynucleotide sequence encoding a detectable marker gene; and selecting for cells comprising the donor polynucleotide sequence integrated in frame into a target sequence in a protein coding gene from the set of target genes, whereby the cell library comprises cells singly tagged at every target gene.

In certain embodiments, the one or more of the polynucleotide sequences are introduced by one or more vectors. In certain embodiments, the donor polynucleotide sequence comprises a codon-neutral unique molecular identifier (UMI) sequence or a non-coding UMI after the detectable marker coding sequence.

In certain embodiments, the donor polynucleotide sequence is a PCR product. The PCR product may comprise a phosphorylation modification on each 5' end. The PCR product may comprise one or more PTO modifications, preferably, one, two, three, or more PTO modifications on each 5' end. In certain embodiments, the PCR product is 5' phosphorylated and protected by two PTO modifications at both 5' termini.

In certain embodiments, the PCR product may be obtained by amplifying a template with primer pairs comprising codon neutral unique molecular identifiers (UMI). The primers may further comprise a 5' phosphorylation modification or PTO modifications.

In certain embodiments, selecting cells comprises sorting for the 0.05-50% most positive cells for the detectable marker. In one embodiment, selecting cells comprises sorting for the 1% most positive cells for the detectable marker.

In certain embodiments, the donor polynucleotide sequence may further comprise a selectable marker gene operably linked to a separate regulatory element and selecting comprises selecting cells comprising the selectable marker. The selectable marker may be an antibiotic resistance gene and selecting comprises treating the cells with an antibiotic.

In certain embodiments, the donor polynucleotide sequence further comprises a sequence encoding a protease cleavage site and a cleavable marker, wherein the sequence is in frame with the detectable marker sequence. In certain embodiments, each cell may be configured for expression of a recombinant protease specific for the protease cleavage site and localized to a cellular compartment. The cellular compartment may include, but is not limited to nuclear, cytoplasmic, mitochondrial, peroxisomal, endoplasmic reticulum (ER), golgi, lysosomal, membrane, or cytoskeleton compartments. The recombinant protease may be induced or delivered after library generation. The protease may comprise at least one nuclear export signal, nuclear localization signal, peroxisome localization signal, ER localization signal, golgi localization signal, lysosome localization signal, or mitochondrial localization signal. In some specific embodiments, the expression of a localized protease, for example including, but not limited to, TEV protease, is induced or introduced (e.g., transfection) after generating the library, such that the library is split into sub-pools and the protease is either induced or transfected with a TEV plasmid or another protease.

In certain embodiments, the donor polynucleotide sequence further comprises a T7 RNA polymerase promoter.

In certain embodiments, the guide sequences of the present invention may be synthesized, generated by in vitro transcription or expressed from a vector as described herein.

In another embodiment, the population of cells comprises eukaryotic cells, such as mammalian, insect, yeast, or plant cells. In another embodiment, the CRISPR enzyme is inducible. In another embodiment, the method comprises maintaining the library of cells.

In another aspect, the invention provides a method of determining the distribution of protein levels in a population of cells, said method comprising: sorting a library of cells according to any of claims 1 to 15 into at least two groups based on expression of the detectable marker in each cell; and nucleic acid sequencing of the cells in each group, wherein the tagged target genes in each group are determined. In certain embodiments, the sequencing comprises PCR amplification of the UMIs with primers specific to the polynucleotide sequence encoding a detectable marker, optionally, a nested PCR, and sequencing the PCR products (e.g., lyse cells with proteinase K, heat inactivate, pipet into PCR reaction with primers PATTERNS-seq-fwd/rev). In one embodiment, the sequencing comprises transcription of the tagged gene by T7 polymerase, cDNA production, and sequencing of the cDNA. In another embodiment, the sequencing comprises tagmentation with Tn5, optional linear amplification (LAM), PCR amplification, optionally, nested PCR, and sequencing of the amplified DNA. In certain embodiments, a hyperactive Tn5 is used (see, e.g., Picelli et al., Tn5 transposase and tagmentation procedures for massively scaled sequencing projects, Genome Res. 2014. 24:2033-2040). In another embodiment, the sequencing comprises PCR amplification of a genomically integrated guide expression cassette. In another embodiment, the expression level of a tagged target protein is determined by fitting a distribution to the representation of that target gene in the plurality of sorted and sequenced expression bins, wherein the distribution can be a normal, log-normal, or other defined distribution. In another embodiment, the library of cells is treated with a perturbation prior to determining expression of proteins. In another embodiment, the perturbation comprises a small molecule, protein, RNAi, CRISPR system, TALE system, Zn finger system, meganuclease, pathogen, allergen, recombinant virus, temperature, salt, lipid, biomolecule, a pool of any perturbation thereof, or any combination thereof. In another embodiment, the localization of proteins is determined by further sorting the cells based on cleavage of the cleavable marker by the protease localized to a cellular compartment; or wherein the localization of proteins is determined by comparing the distribution of protein levels of tagged genes between sorted cells and sorted nuclei obtained from the library, optionally, the nuclei are fixed (e.g., with paraformaldehyde (PFA), formaldehyde, or glutaraldehyde).

In another aspect, the invention provides a method of determining protein interactions in a population of cells, said method comprising: sorting a library of cells into at least two groups based on the signal of the detectable marker in each cell (i.e., the detectable marker is interaction dependent); and nucleic acid sequencing of the cells in each group, wherein the tagged target genes in each group are determined, wherein the library of cell comprises a plurality of cells wherein each cell comprises a first polynucleotide sequence encoding a first complementary protein integrated into the genome of the cell in frame with the protein of interest or comprises a first polynuycleotide sequence encoding a fusion protein of the first complementary protein and protein of interest, wherein each cell comprises a second polynucleotide sequence encoding a second complementary protein integrated into the genome of the cell in a frame with a protein coding gene selected from a set of target genes, wherein the library comprises more than one cell tagged at a target gene, whereby an interaction between the protein of interest and a target gene can be detected with a detectable marker. The signal of the detectable marker is dependent upon interaction of a target gene with a gene of interest, such that complementation can occur. In certain embodiments, the sequencing comprises PCR amplification of the UMIs with primers specific to the polynucleotide sequence encoding a detectable marker, optionally, a nested PCR, and sequencing the PCR products. In one embodiment, the sequencing comprises transcription of the tagged gene by T7 polymerase, cDNA production, and sequencing of the cDNA. In another embodiment, the sequencing comprises tagmentation with Tn5, optional LAM, PCR amplification, optionally, nested PCR, and sequencing of the amplified DNA. In another embodiment, the sequencing comprises PCR amplification of a genomically integrated guide expression cassette. In another embodiment, the expression level of a tagged target protein is determined by fitting a distribution to the representation of that target gene in the plurality of sorted and sequenced expression bins, wherein the distribution can be a normal, log-normal, or other defined distribution. In another embodiment, the library of cells is treated with a perturbation prior to determining protein interactions. In another embodiment, the perturbation comprises a small molecule, protein, RNAi, CRISPR system, TALE system, Zn finger system, meganuclease, pathogen, allergen, recombinant virus, temperature, salt, lipid, biomolecule, a pool of any perturbation thereof, or any combination thereof.

In another aspect, the present invention provides for a method of determining protein modifications in a population of cells, said method comprising: sorting a library of cells into at least two groups based on the signal of the detectable marker in each cell; and nucleic acid sequencing of the cells in each group, wherein the tagged target genes in each group are determined, wherein the library of cell comprises a plurality of cells, wherein each cell stably expresses a fusion protein comprising a protein modification binding protein fused to a first complementary protein, wherein each cell comprises a polynucleotide sequence encoding a second complementary protein integrated into the genome of the cell in a frame with a protein coding gene selected from a set of target genes, wherein the library comprises more than one cell tagged at a target gene and wherein binding of a protein modification binding protein to a target gene protien can be detected with a detectable marker. The invention provides a method of determining protein modifications in a population of cells, said method comprising: sorting a library of cells into at least two groups based on the signal of the fluorescent marker in each cell; and sequencing each group, wherein the tagged target genes in each group are determined, wherein the library of cells comprises a plurality of cells, wherein each cell stably expresses a fusion protein comprising a protein modification binding protein fused to a first complementary protein, wherein each cell comprises a polynucleotide sequence encoding a second complementary protein integrated into the genome of the cell in frame with a protein coding gene selected from a set of target genes, wherein the library comprises more than one cell tagged at each target gene and wherein binding of a protein modification binding protein to a target gene protein can be detected with a detactable marker. In certain embodiments, the sequencing comprises PCR amplification of the UMIs with primers specific to the polynucleotide sequence encoding a detectable marker, optionally, a nested PCR, and sequencing the PCR products. In one embodiment, the sequencing comprises transcription of the tagged gene by T7 polymerase, cDNA production, and sequencing of the cDNA. In another embodiment, the sequencing comprises tagmentation with Tn5, optional LAM, PCR amplification, optionally, nested PCR, and sequencing of the amplified DNA. In another embodiment, the sequencing comprises PCR amplification of a genomically integrated guide expression cassette. In another embodiment, the expression level of a tagged target protein is determined by fitting a distribution to the representation of that target gene in the plurality of sorted and sequenced expression bins, wherein the distribution can be a normal, log-normal, or other defined distribution. In another embodiment, the library of cells is treated with a perturbation prior to determining protein modifications. In another embodiment, the perturbation comprises a small molecule, protein, RNAi, CRISPR system, TALE system, Zn finger system, meganuclease, pathogen, allergen, recombinant virus, temperature, salt, lipid, biomolecule, a pool of any perturbation thereof, or any combination thereof.

In another aspect, the invention provides a method for sequencing integration sites of a donor sequence inserted into the genome of a cell comprising: lysing cells with proteinase K, wherein the proteinase K is not heat inactivated; performing tagmentation of genomic DNA with Tn5 loaded with adaptors, wherein the adaptors comprise a priming site; performing linear amplification with a first primer specific for the donor sequence; performing PCR with a second primer specific for the donor sequence downstream of the first primer and a reverse primer specific for the adaptor priming site; and constructing and sequencing a sequencing library from the PCR products. In another aspect, the invention provides a method for sequencing integration sites of a donor sequence inserted into the genome of a cell comprising: lysing cells with proteinase K, wherein the proteinase K is not heat inactivated; performing tagmentation of genomic DNA with Tn5 loaded with adaptors, wherein the adaptors comprise a priming site; performing a PCR with a first primer specific for the donor sequence and a second primer specific for the adaptor priming site; optionally, performing a second nested PCR using the product of the first PCR as a template; and sequencing the PCR products. In certain embodiments, detergent may be used when lysing the cells (e.g., Triton X-100, NP-40). In certain embodiments, the Tn5 is a hyperactive Tn5. In certain embodiments, the method further comprises purifying the sample using a silica column, beads, or detaching Tn5 by adding SDS. In certain embodiments, the method further comprises heat-denaturing the sample.

In another aspect, the present invention provides for a scalable system for analysis of proteins in a cell comprising: a universal donor construct; a cell population configured for expression of a CRISPR system; and sequencing reagents, wherein the system provides for a population of cells tagged with the donor construct at one or more integration sites and wherein the system can determine the site of integration. The CRISPR system may be delivered to the cell on one or more vectors. The CRISPR system may be delivered to the cell as a ribonucleic acid complex (RNP). The CRISPR system may be stably expressed by the cell population. The donor construct may comprise a nucleotide sequence encoding a detectable marker and a selectable marker. The donor construct may further comprise a nucleotide sequence encoding a T7 promoter. The donor construct may further comprise a nucleotide sequence encoding an epitope tag. The donor construct may further comprise a nucleotide sequence encoding a protease cleavage site and a cleavable epitope tag. The system may further comprise a protease specific for the protease cleavage site localized to a cellular compartment. The donor construct may further comprise a codon-neutral unique molecular identifier (UMI) sequence.

In another aspect, the present invention provides for a donor construct for tagging a target gene in a cell comprising a nucleotide sequence encoding: a CRISPR target site, a detectable marker, a resistance gene, and a codon-neutral unique molecular identifier (UMI) sequence. In certain embodiments, the donor construct further comprises a protease cleavage site and a cleavable epitope tag (i.e, an epitope tag outside of the protease cleavage site). In certain embodiments, the donor construct further comprises a T7 promoter. In certain embodiments, the donor construct is a plasmid, vector, PCR product, or synthesized polynucleotide sequence. The plasmid may be linearized (e.g., using CRISPR in the cell). The vector may be a viral vector that produces a DNA donor template by replication of the viral vector (e.g., AAV).

In another aspect, the present invention provides for a plurality of donor constructs.

In another aspect, the invention provides for a kit comprising vectors for tagging a population of cells; or a kit comprising a library of tagged cells, reagents and protocols for sorting cells and sequencing tag integration sites. Thus, a user could stimulate or perturb the library of cells, sort and sequence as described herein.

In certain embodiments, the library according to any embodiments herein, comprises a sequence encoding a detectable marker and a sequence encoding a protease, wherein the sequence is in frame with the detectable marker sequence. The library of cells may be configured for expression of a reporter gene localized to a cellular compartment described herein, wherein said reporter comprises a cleavage site for the protease and cleavage results in a detectable signal.

In certain embodiments, the system according to any embodiment herein, comprises a donor construct comprising a nucleotide sequence encoding a protease in frame with a detectable marker. In certain embodiments, the system further comprises one or more reporter constructs configured for expression of a reporter gene comprising a localization signal for a cellular compartment, wherein said reporter comprises a cleavage site for the protease and cleavage results in a detectable signal.

In another aspect, the invention provides for a method of determining the localization of a target protein comprising: a) tagging a population of cells with the donor constructs to obtain a library of cells tagged at one or more target proteins; b) introducing one or more of the reporter constructs to the library of cells; c) sorting the cells based on the signal of the reporter gene; and d) identifying the tagged target proteins.

In certain embodiments, the methods of determining the distribution of protein levels may be used for identifying cell cycle regulated proteins. Cell cycle regulated proteins may be distributed in single cells in different sorted bins.

In certain embodiments, the methods of determining the distribution of protein levels, protein interactions and protein modifications may be used for identifying or confirming drug targets that are not regulated at the transcript level. For example, drugs with unknown targets can be administered to the library of cells and changes in protein levels, protein interactions, or protein modifications can indicate an unknown target for the drug.

In certain embodiments, the methods of determining the distribution of protein levels, protein interactions and protein modifications may further comprise transferring the library to an in vivo model (e.g., nude mouse) and recovering the cells before the step of sorting. In certain embodiments, drugs are screened in vivo and the protein distribution levels are determined in the recovered cells.

In certain embodiments, the CRISPR enzyme or CRISPR system according to any embodiment herein comprises Cas9 or Cas12.

In another aspect, the invention provides for a scalable method of constructing a cell library for use in proteomics comprising: a) introducing to a population of cells a plurality of polynucleotide sequences, wherein each cell receives one or more polynucleotide sequences comprising: i) a polynucleotide sequence configured for expression of a nuclease system specific for a target sequence in a protein coding gene selected from a set of target genes, and ii) a donor polynucleotide sequence encoding a detectable marker gene; and b) selecting for cells comprising the donor polynucleotide sequence integrated in frame into a target sequence in a protein coding gene from the set of target genes, whereby the cell library comprises cells singly tagged at every target gene. In certain embodiments, the nuclease system comprises a CRISPR system, TALEN system, Zn finger system, or meganuclease system. In certain embodiments, the donor polynucleotide sequence comprises a codon-neutral unique molecular identifier (UMI) sequence or a non-coding UMI after the detectable marker coding sequence.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 4—Shows mNeon integration events using primer pairs upstream of the targeting region and within the mNeon gene. Shown are representative results of tagged ACTG1, HIST1H4C, and TUBB genes.

FIG. 16—Shows bar graphs depicting that the TEV S219P mutant allows localization-dependent cleavage.

FIG. 20—Shows results of deep sequencing, demonstrating that 80% of reads contain mNeon marker sequence (left); single cells can be counted using the tagmentation positions as UMIs (middle); Right side shows protein abundance estimation for independent proteins following FACS sorting and sequencing with and without Bortezomib.

FIG. 22A-FIG. 22E—Large-scale tagging of protein-coding genes. FIG. 22A shows a schematic representation of the generation of pooled RNP complexes starting from an oligo array template (Step 1), pooled NHEJ-mediated gene tagging leading to in-frame integration of an mNeonGreen-2A-NeoR cassette into a plurality of genes (Step 2), and Tagmentation-based Tag Integration Site Sequencing (TTISS, Step 3). FIG. 22B shows representative results of TTISS data aligned to the human genome. Scale denotes number of reads aligned. FIG. 22C shows the per-gene coverage of two replicate experiments of genome-scale gene tagging measured by TTISS. FIG. 22D shows the distribution of independent clone counts per target locus in the tagging library as determined from silent UMI sequences. FIG. 22E shows representative confocal microscopic images and TTISS sequencing results of single-cell clones grown out of a polyclonal library of tagged cells. Scale-bars, 20 μm.

FIG. 23A-FIG. 23J—Large-scale protein quantification by sequencing. FIG. 23A shows a schematic representation of Sequencing-Based Proteomics (SBP)-based protein quantification. A library of cells expressing fluorescently tagged proteins is sorted into expression bins. Sequencing the tag integration sites in each bin allows to assess the distribution of protein expression among single cells. FIG. 23B shows representative histograms of protein expression levels in single cells quantified by SBP. N1, N2 denote biological replicates from the sorting stage. FIG. 23C shows the correlation of mean protein expression measurements obtained by SBP among replicates at different protein representation cutoffs. R denotes Pearson correlation coefficients. FIG. 23D shows single-cell variance of protein expression measurements obtained by SBP. FIG. 23E shows the representation of RRM2 in sorted bins among two SBP replicates. FIG. 23F shows the distribution of single-cell RRM2 expression levels in a clonal tagged cell line measured by FACS. FIG. 23G shows a schematic representation of transiently expressed cell-cycle reporters used for identifying cell-cycle regulated proteins. FIG. 23H shows mean protein expression measurements obtained by SBP from cell-cycle phase enriched cells. FIG. 23I shows validation of predicted cell-cycle regulated RRM2 expression by FACS analysis after Hoechst DNA staining. FIG. 23J shows validation of predicted cell-cycle regulated RRM2 expression using immuno-blotting of synchronized cells released for the denoted amounts of time after double-Thymidine block (left panel), or cells enriched for cell-cycle phases using FACS sorting on PI signal (right panel).

FIG. 24A shows the mean protein expression measurements obtained by SBP from drug-treated versus untreated control cells. Significant outlier proteins are denoted as dots, and non-significant outliers are marked (See Methods). FIG. 24B shows the mean transcript expression measurements obtained by RNA-sequencing from drug-treated versus untreated control cells. The selection of genes shown is matched to the proteins quantified in (A) using SBP. Outliers from SBP protein quantification are marked in colored circles. FIG. 24C shows the relative protein expression measurements obtained by TMT labeling whole proteome mass spectrometry from drug-treated versus untreated control cells. Non-significant outliers are marked. Replicates were combined for plotting by summation of raw reporter intensities. FIG. 24D shows validation of predicted drug-regulated proteins using immuno-blotting of cells at indicated time points after drug treatment. FIG. 24E shows validation of predicted drug-regulated proteins using indicated clonal mNeon-tagged reporter cell lines stimulated for six hours and analyzed by FACS. Actinomycin D (ActD) or Cycloheximide was applied one hour before drug stimulation.

FIG. 25A-FIG. 25C—SBP-mediated protein localization measurement. FIG. 25A shows a schematic of SBP-mediated protein localization assessment. FIG. 25B shows protein quantification results from whole cells (X-axis) versus purified nuclei (Y-axis). The dashed line indicates the cutoff of nuclear localization calling for downstream validation. FIG. 25C shows validation of SBP nuclear localization prediction based on literature consensus.

FIG. 26A shows a schematic of the NHEJ-mediated tagging process. A protein-coding gene is cleaved using Cas9 at the PAM motif closest to the stop codon. Either a PCR product is inserted in-frame, or a donor plasmid is co-linearized in the cell using Cas9 to be inserted in-frame. Cas9 and the gRNA are either expressed from a plasmid, or delivered using pre-assembled RNP complexes. FIG. 26B shows that the endogenous TUBB gene was tagged in-frame with mNeonGreen using indicated Cas9 delivery method and type of donor DNA. mNeon-positive cells were quantized over the course of two weeks using FACS. FIG. 26C shows that the endogenous TUBB gene was tagged in-frame with each of six indicated fluorescent proteins using RNP delivery, and cells were expanded under Puromycin selection for one week. Brightness over autofluorescence was assessed by FACS using indicated filter sets. Grey histograms indicate tagged cells, while black histograms indicate untransfected control cells. FIG. 26D shows that 22 protein-coding genes were tagged with mNeon coupled to each of three different resistance genes. Cells were expanded for 10 days under selection pressure with the corresponding antibiotics indicated, and the number of surviving cells was quantified using FACS.

The dashed line indicates a log-normal distribution fitted by calculating the mean and variance of log-transformed expression values. KLdiv indicates the Kullback-Leibler divergence for each fit, and values higher than 0.2 are marked to highlight clones diverging from a log-normal distribution. The same clones shown in FIG. 28 were trypsinized and analyzed using FACS.

Figure 30A:
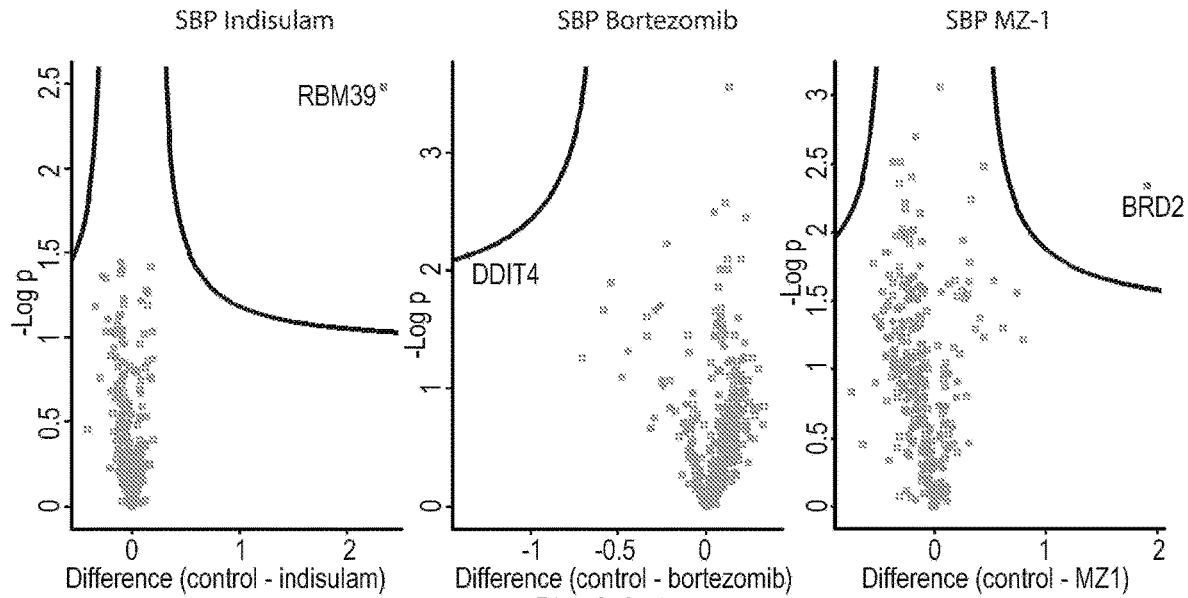
Figure 30B:
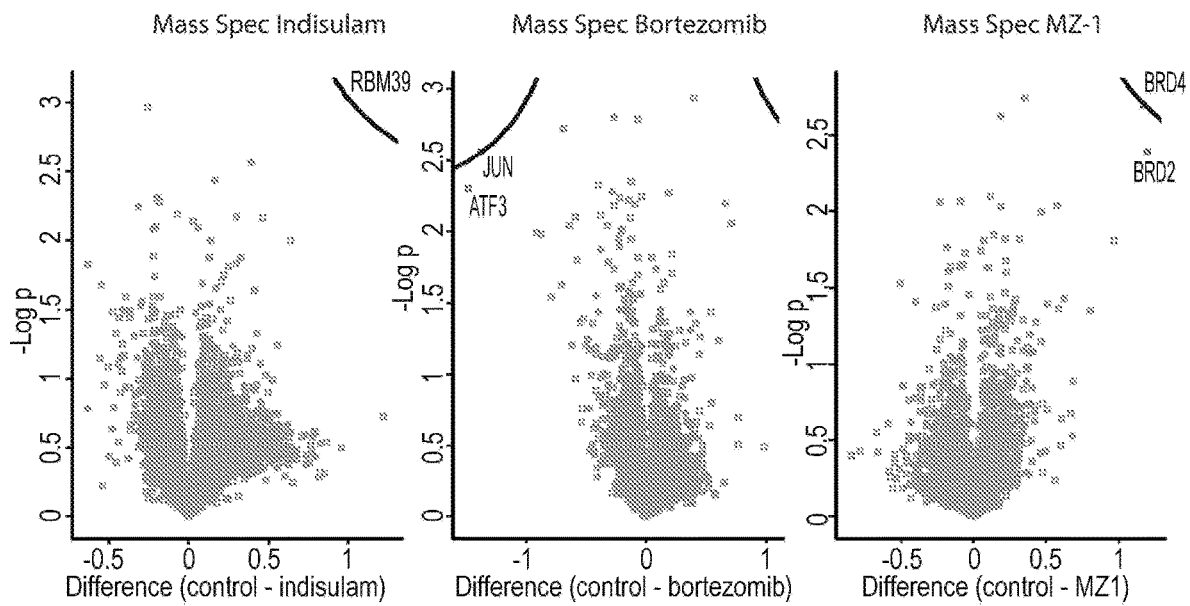

FIG. 30A-FIG. 30B—Statistical analysis of quantitative proteomics data. FIG. 30A shows SBP protein quantification data from two replicate screens that were median-subtracted and tested for drug regulated proteins (see Methods). The mean difference between conditions is plotted on the x-axis versus the −log P value on the y-axis. The two outliers RBM39 and BRD2 were identified to be statistically significant, as they are located above the black line indicating the significance threshold at an FDR of 5%. FIG. 30B shows TMT mass spectrometry protein quantification data that was filtered for missing values, log-2-transformed, median-subtracted, and tested for drug regulated proteins (see Methods). No outliers were identified to be statistically significant.

Figure 24A:
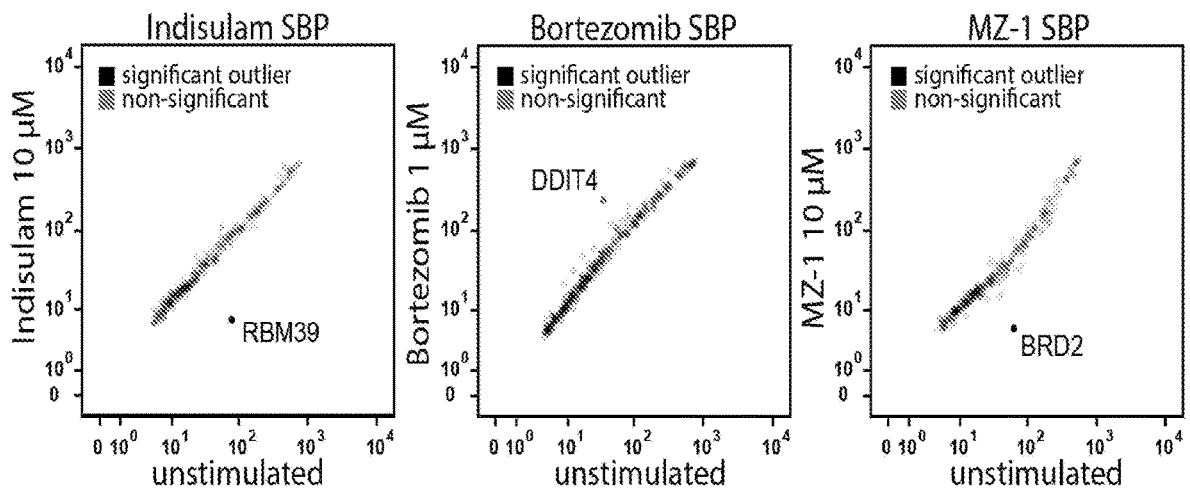
FIG. 24A-FIG. 24E—Unbiased drug target identification by SBP.

FIG. 31A-FIG. 31B—SBP single-UMI screening results and independent replicate screening results. FIG. 31A shows the drug responses of individual clones in the tagging library plotted after UMI-based analysis of the SBP screen presented in FIG. 24a. Of note, all hits are represented by two independent UMI clones, and one additional hit (SIGIRR (SEQ ID NO: 69339)) was found to be represented by a single UMI, but could not be validated (data not shown). FIG. 31B shows mean protein expression measurements obtained by SBP from drug-treated versus untreated control cells as an independent biological replicate employing the same screening conditions as in FIG. 24a.

Figure 32A:
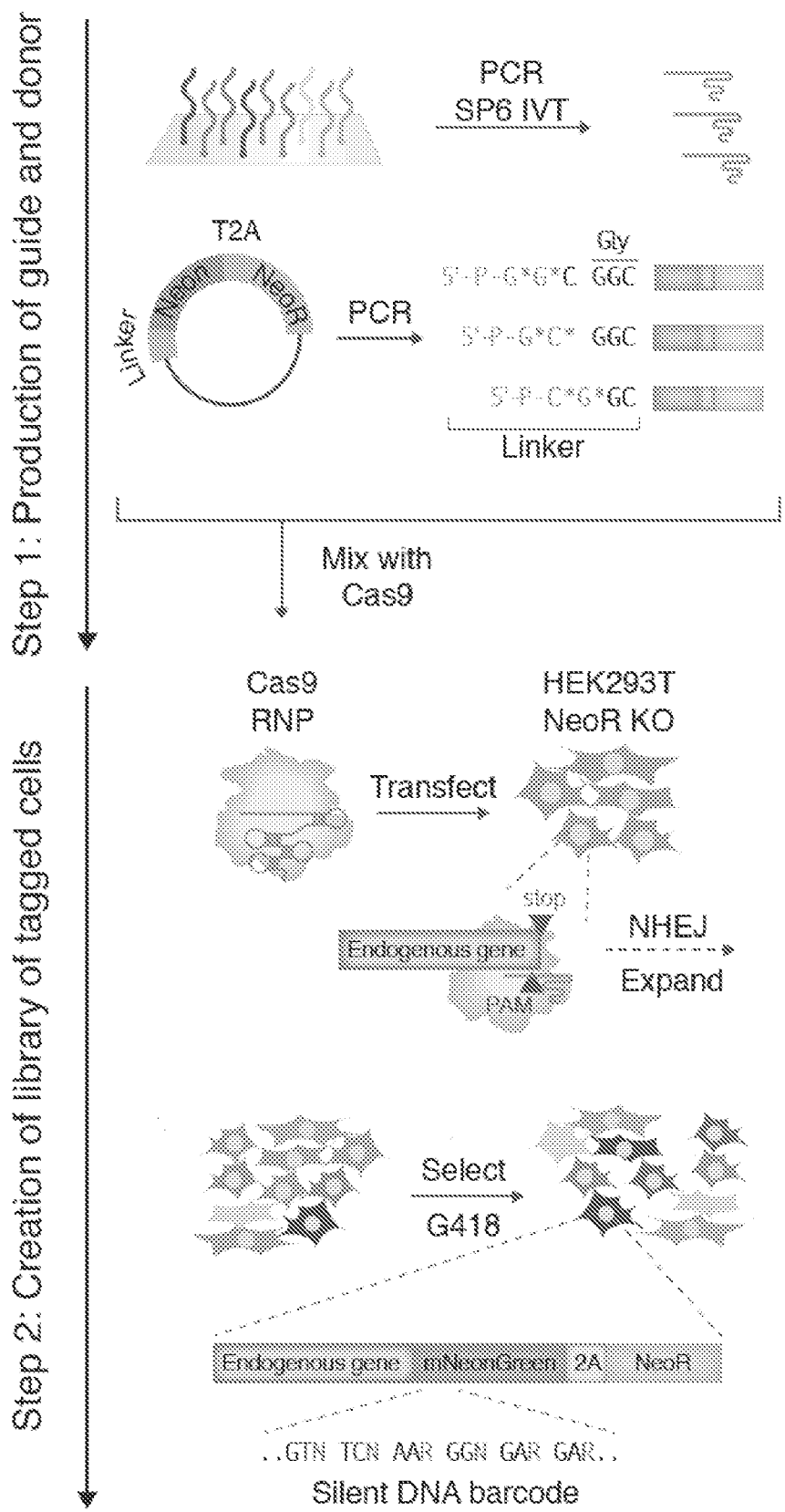
Figure 32A:
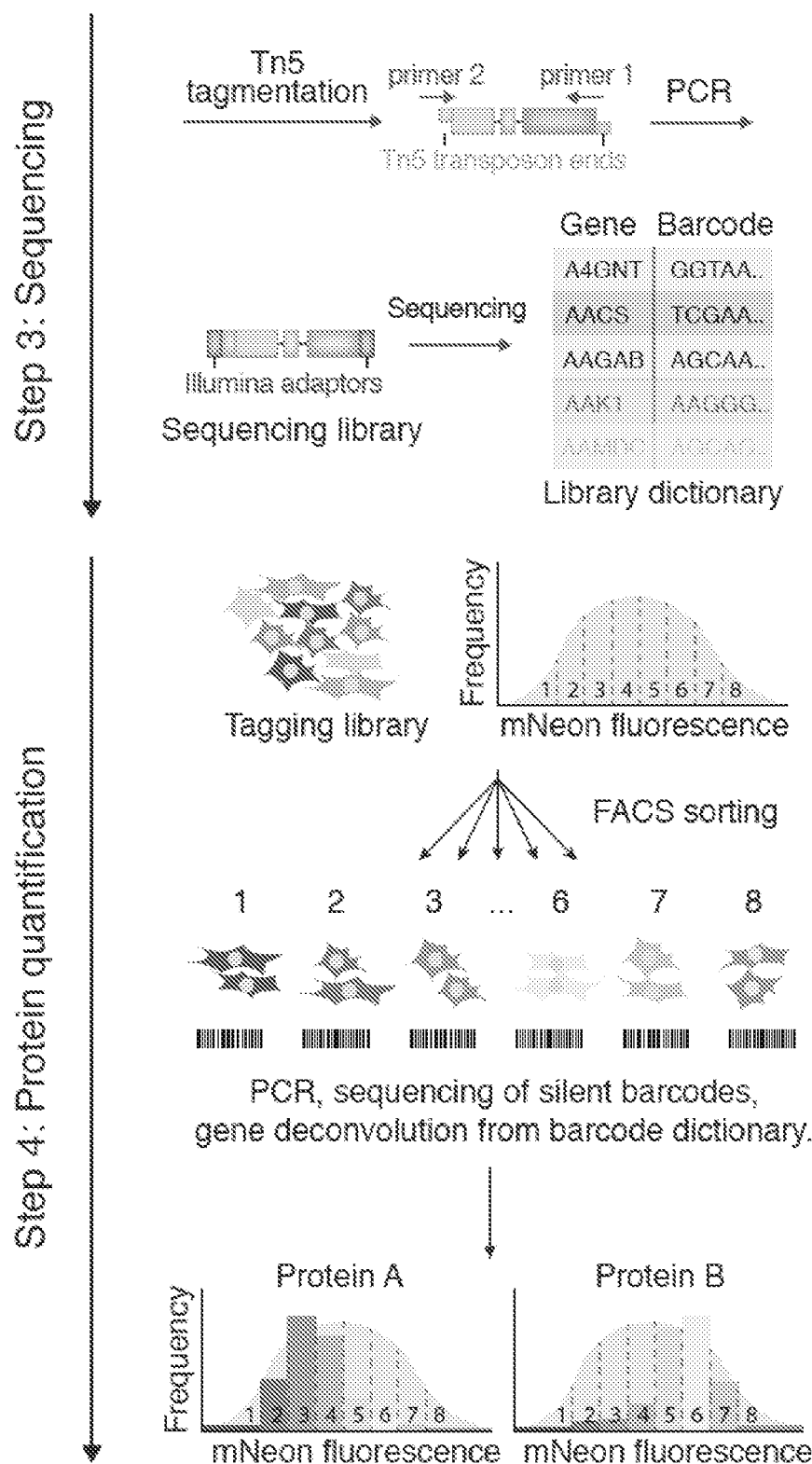
Figure 32B:
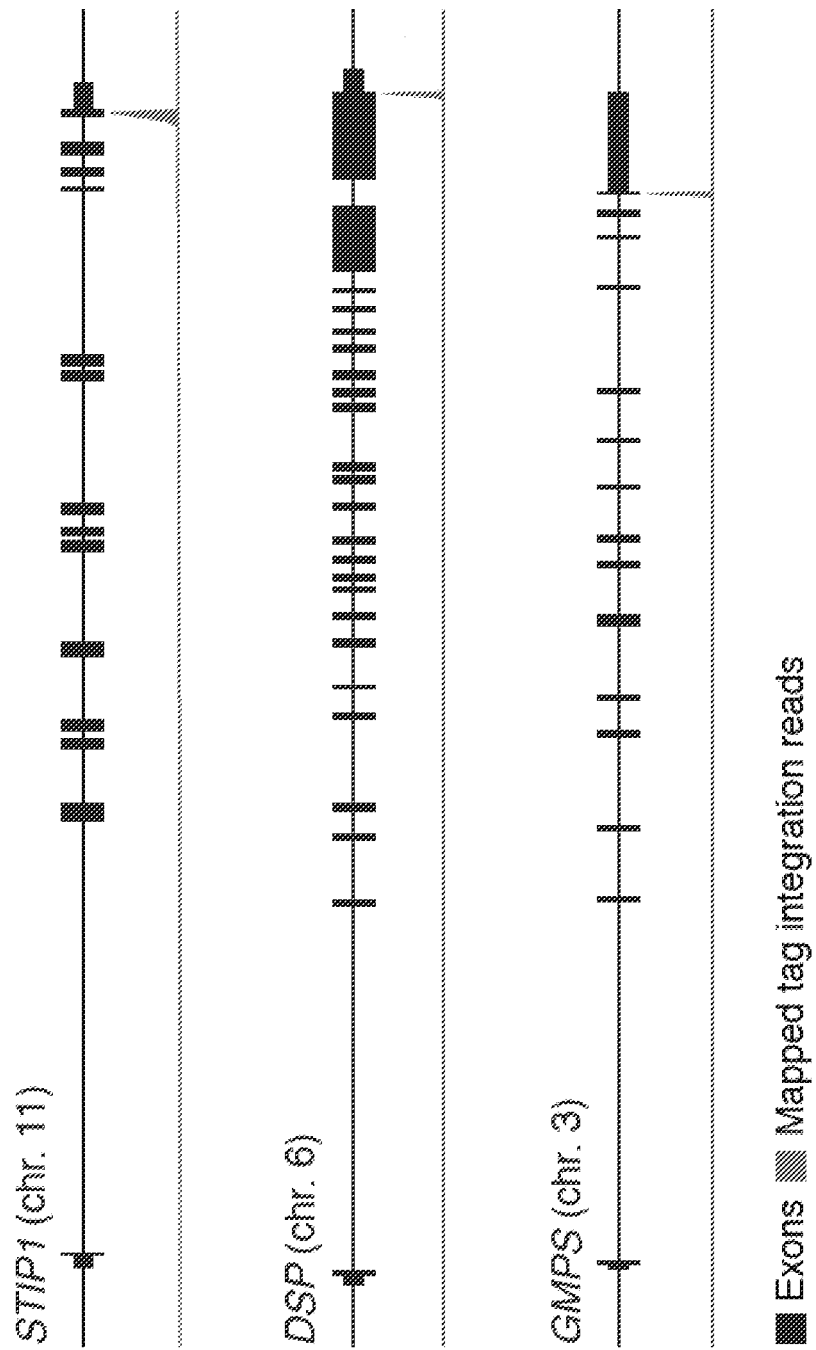
Figure 32F:
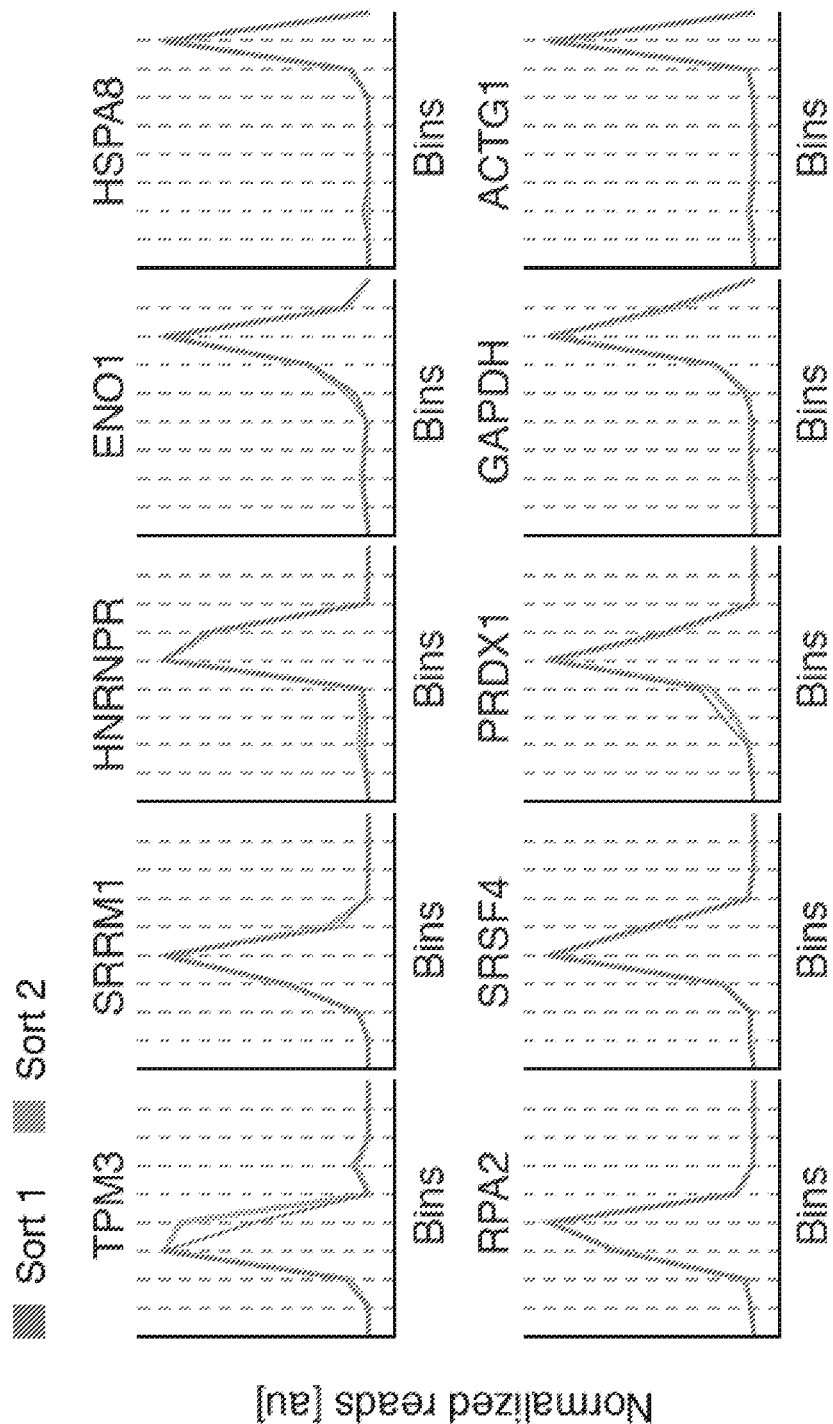
Figure 32G:
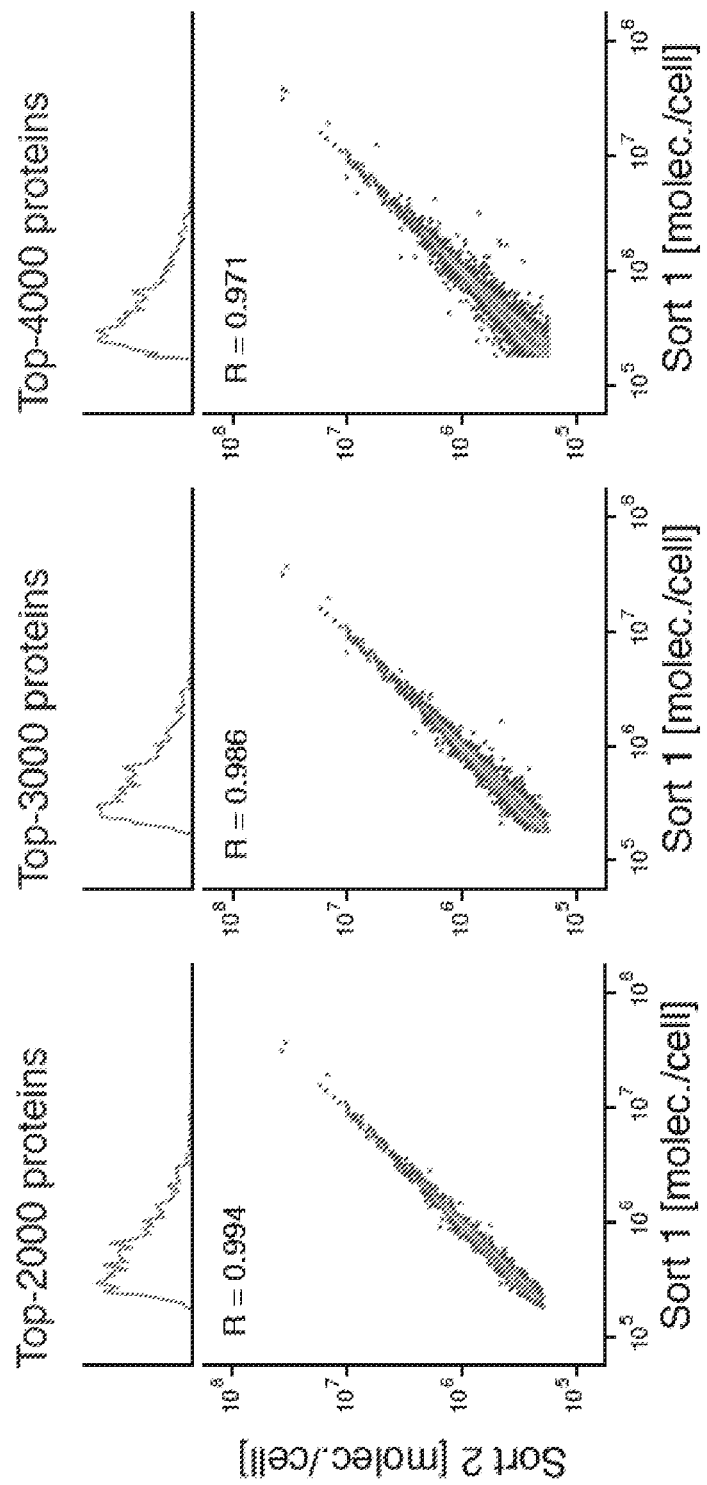

FIG. 32A-FIG. 32G—PATTERNS allows large-scale tagging of protein-coding genes and quantification of protein abundance. FIG. 32A shows PATTERNS workflow. Schematic representation of the generation of pooled RNP complexes starting from an oligo array template (Step 1), pooled NHEJ-mediated gene tagging leading to in-frame integration of an mNeonGreen-2A-NeoR cassette bearing a silent barcode (SEQ ID NO:69340) into a plurality of genes (Step 2), Tagmentation-based Tag Integration Site Sequencing (TTISS) to create a barcode dictionary (Step 3), and protein quantification through FACS sorting into eight bins and subsequent sequencing of silent barcodes in each bin (Step 4). A library of cells expressing fluorescently tagged endogenous proteins is sorted into eight expression bins. Quantitatively sequencing silent tag-specific barcodes in each bin allows inferring distributions of protein expression among single cells. FIG. 32B Examples of tag insertion densities in four protein-coding genes. TTISS read coverage is shown. FIG. 32C Breakdown of targeted protein-coding loci represented in the combined library of tagged cells. FIG. 32D Per-gene coverage in two replicate tagging libraries as measured by TTISS. FIG. 32E Empirical fluorescence distribution after FACS sorting the library of tagged cells and binning into 8 bins. FIG. 32F Representative protein abundance distributions from two library sorting replicates. FIG. 32G Correlation of measured mean protein levels between screening replicates for different protein representation cutoffs. R denotes Pearson correlation coefficient.

Figure 33A:
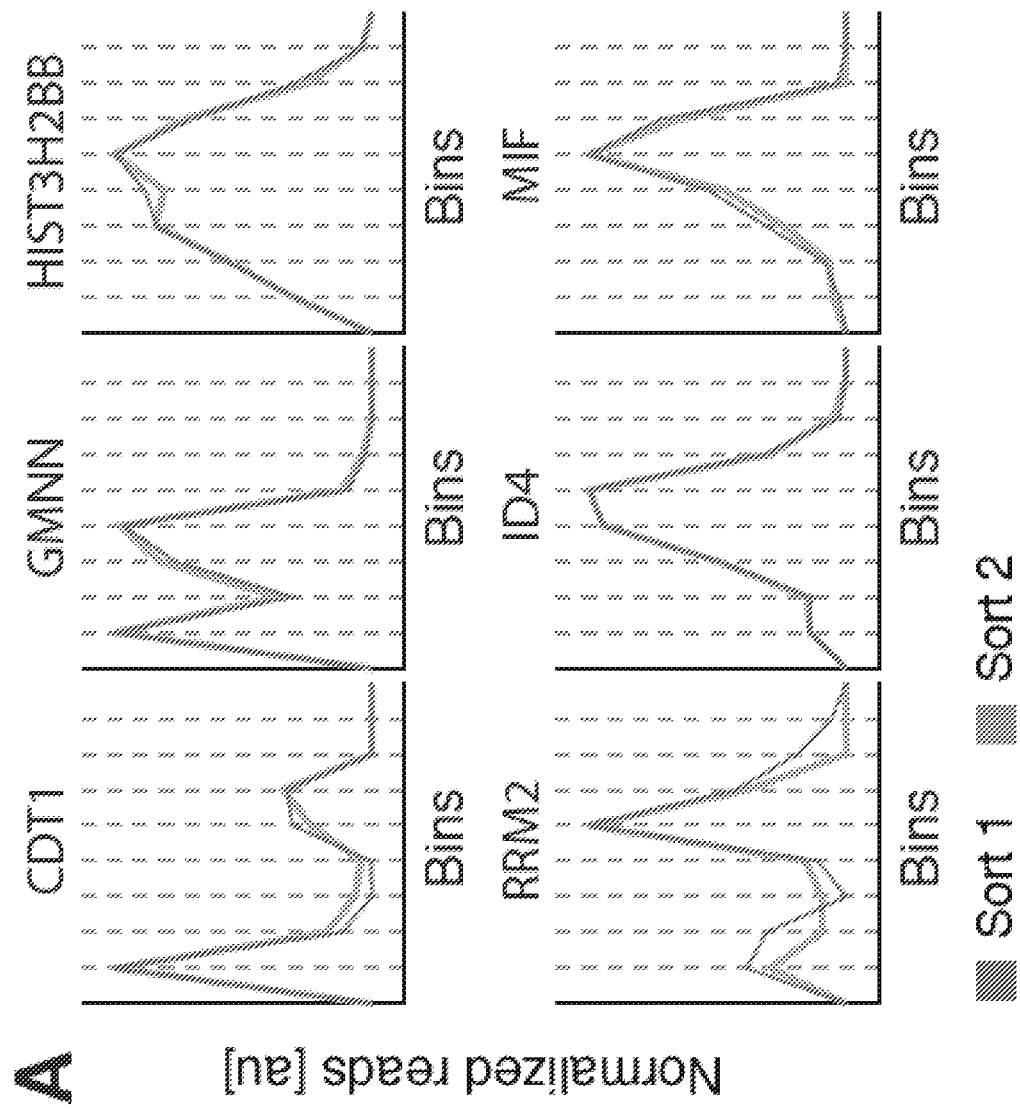
Figure 33D:
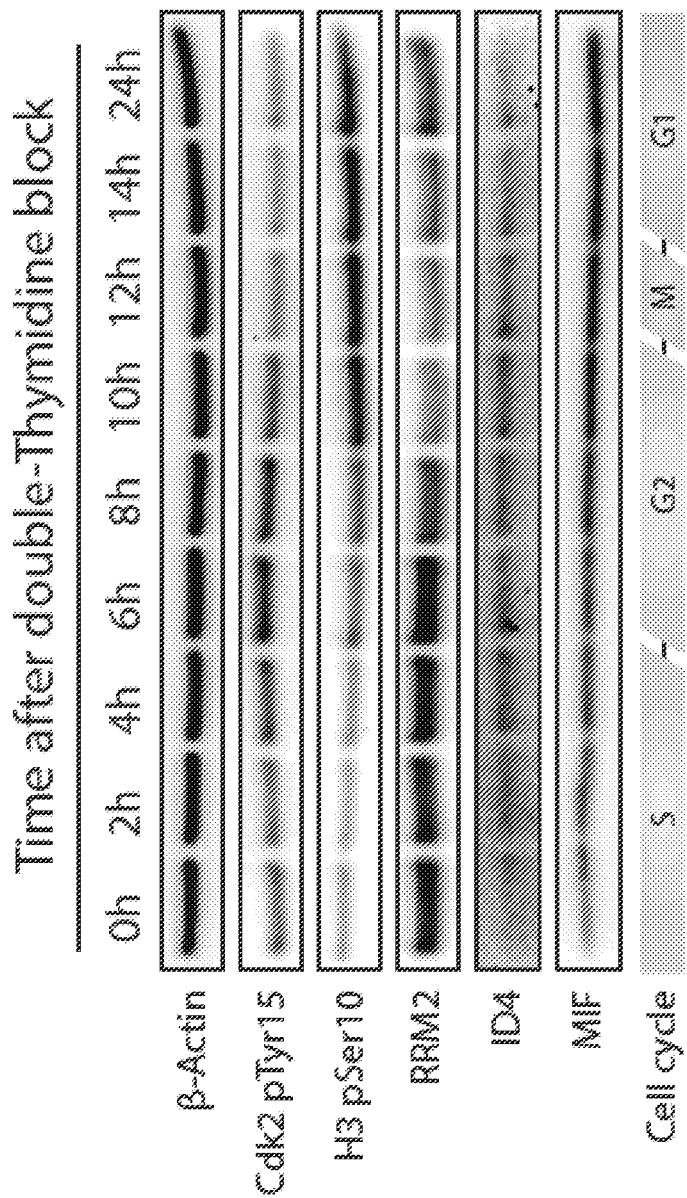

FIG. 33A-FIG. 33D—PATTERNS can be used to obtain single-cell distributions of protein abundance. FIG. 33A Examples of single-cell protein abundance distributions with broadened or bifurcated shape in two screening replicates. FIG. 33B Validation of bifurcated RRM2 abundance distribution measured in a tagged cell line by FACS. FIG. 33C Correlation of RRM2 levels with DNA content (Hoechst) validates RRM2 as a cell cycle-regulated protein. FIG. 33D Assessment of cell-cycle regulation of RRM2, ID4, and MIF by immuno-blotting of cells released for denoted amounts of time after double-Thymidine block.

Figure 34D:
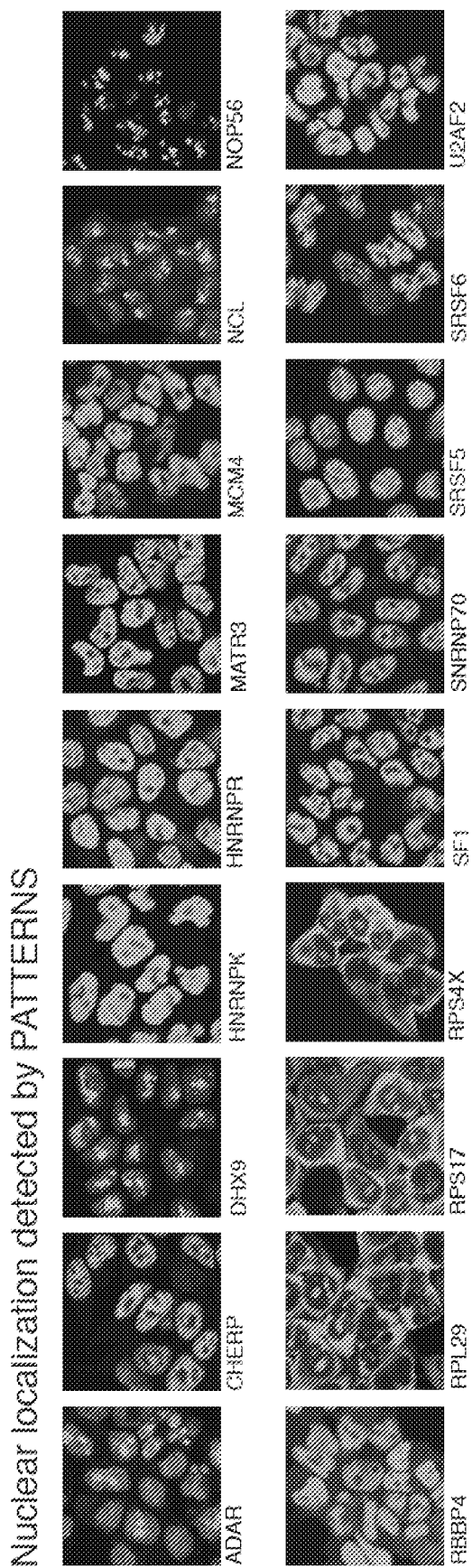
Figure 34E:
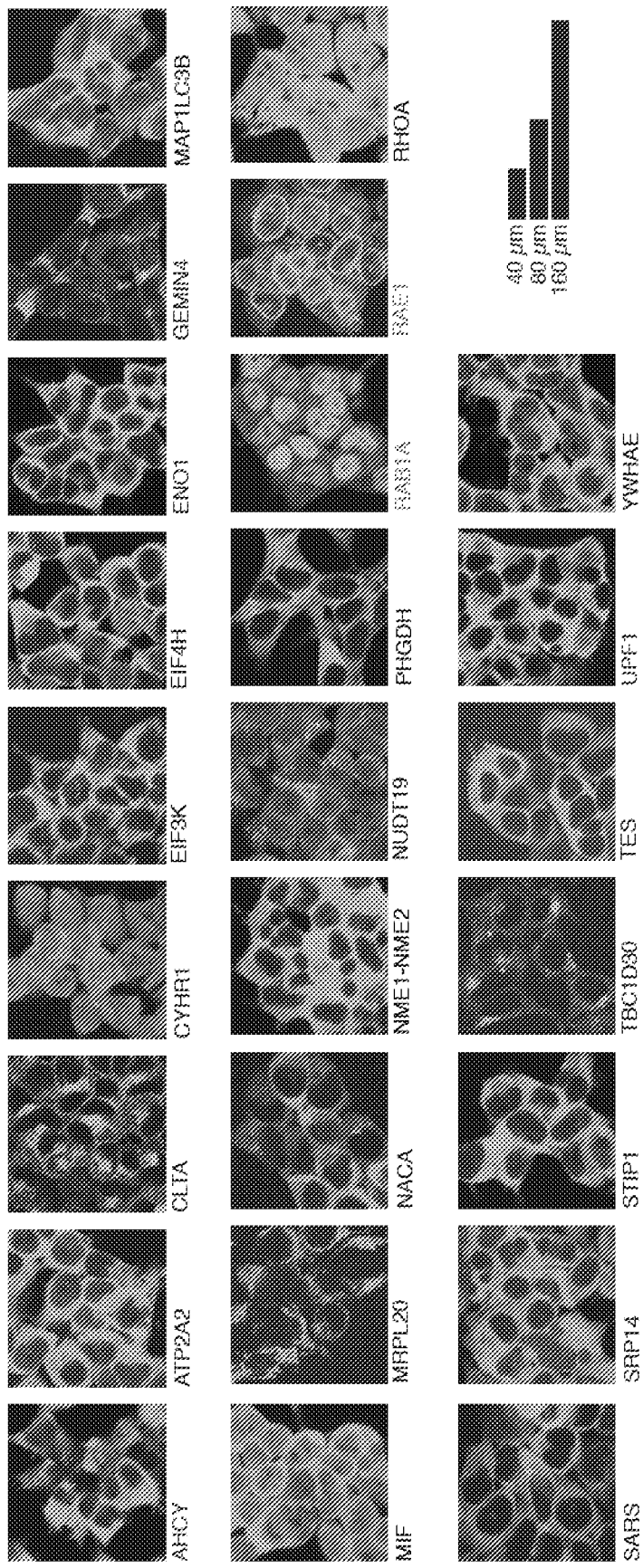

FIG. 34A-FIG. 34E—PATTERNS-mediated protein localization determination. FIG. 34A Schematic of PATTERNS-mediated protein localization assessment. FIG. 34B Protein quantification results from whole cells (X-axis) versus purified nuclei (Y-axis). The dashed line indicates the cutoff for nuclear localization calling. Histone proteins are marked. FIG. 34C Agreement between nuclear localization prediction methods based on PATTERNS and three published datasets using three different methods for nuclear protein localization detection. FIG. 34D, E Validation of nuclear (D) and non-nuclear (E) localization predictions by confocal microscopy of 43 clonal cell lines in which indicated proteins are tagged with mNeonGreen. The scale bars in (E) apply to both panels (D) and (E).

Figure 35I:
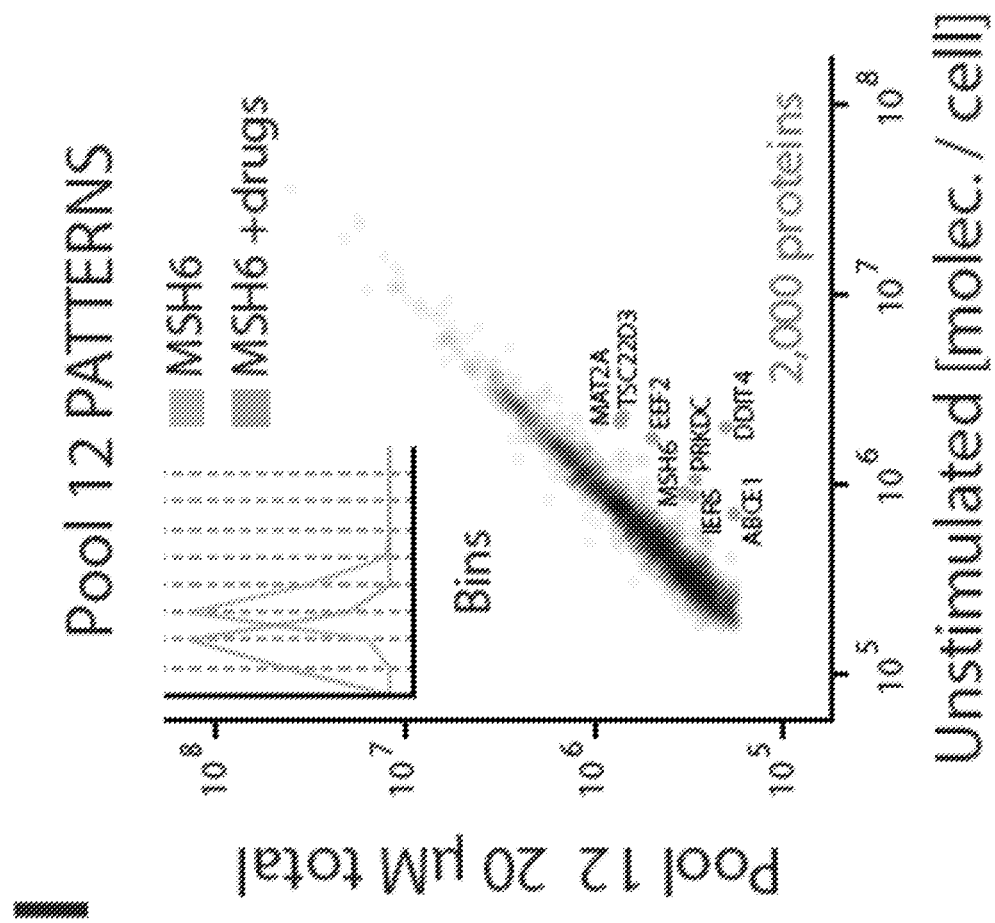

FIG. 35A-FIG. 35K—Unbiased drug target identification by PATTERNS. FIG. 35A Mean protein level measurements obtained by PATTERNS from Bortezomib-treated versus untreated control cells. Significant outlier proteins are denoted as dots; non-significant outliers are marked (See Methods). FIG. 35B Mean transcript expression measurements obtained by RNA-sequencing from Bortezomib-treated versus untreated control cells. The selection of genes shown is matched to the proteins quantified in (A) using PATTERNS. FIG. 35C Relative protein abundance measurements obtained by TMT labeling whole proteome mass spectrometry from Bortezomib-treated versus untreated control cells. Non-significant outliers are marked. Two TMT labelling replicate samples were combined for plotting by summation of raw reporter intensities. FIG. 35D Validation of predicted Bortezomib-regulated proteins using immuno-blotting of cells at indicated time points after drug treatment. FIG. 35E Quantification of proteins using PATTERNS upon application of a pool of 80 compounds at 20 µM total concentration for 6 h. Inset depicts single-cell protein abundance distribution of RBM39 with or without drug stimulation. FIG. 35F Mean transcript expression measurements obtained by RNA-sequencing from Indisulam-treated versus untreated control cells. The selection of genes shown is matched to the proteins quantified in (E) using PATTERNS. FIG. 35G Relative protein abundance measurements obtained by TMT labeling whole proteome mass spectrometry from Indisulam-treated versus untreated control cells. Non-significant outliers are marked. Two TMT labelling replicate samples were combined for plotting by summation of raw reporter intensities. FIG. 35H Validation of a predicted Indisulam-regulated protein using immunoblotting of cells at indicated time points after drug treatment. FIG. 35I Quantification of proteins using PATTERNS upon application of a second pool of 80 compounds at 20 µM total concentration for 6 h. Inset depicts single-cell protein abundance distribution of MSH6 with or without drug stimulation. FIG. 35J MSH6-mNeonGreen expression after application of single compounds at 125 nM for 6 h. Three hit compounds are annotated by name, all of which are known to target human Hsp90. FIG. 35K MSH6-mNeonGreen (left panel) and PRKDC-mNeonGreen (right panel) expression in single reporter cells at indicated time points after application of hit compound SNX-2112 at 125 nM.

Figure 36:
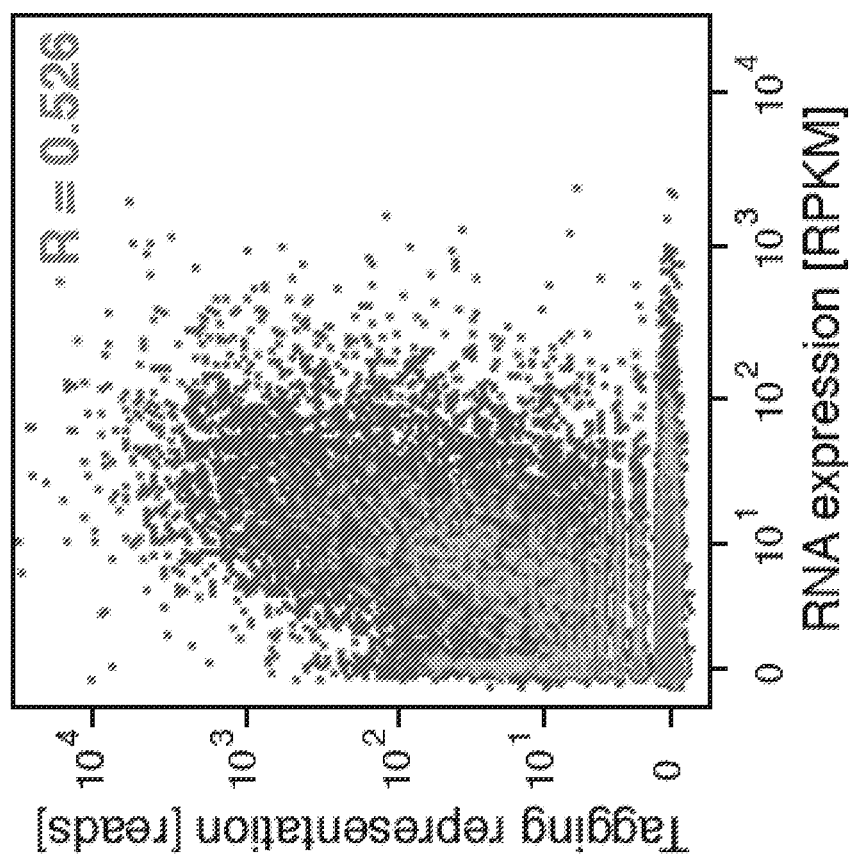

FIG. 36—Tagging library representation. Correlation of tagging library representation with RNA-seq gene expression data. Pearson R is denoted.

Figure 37A:
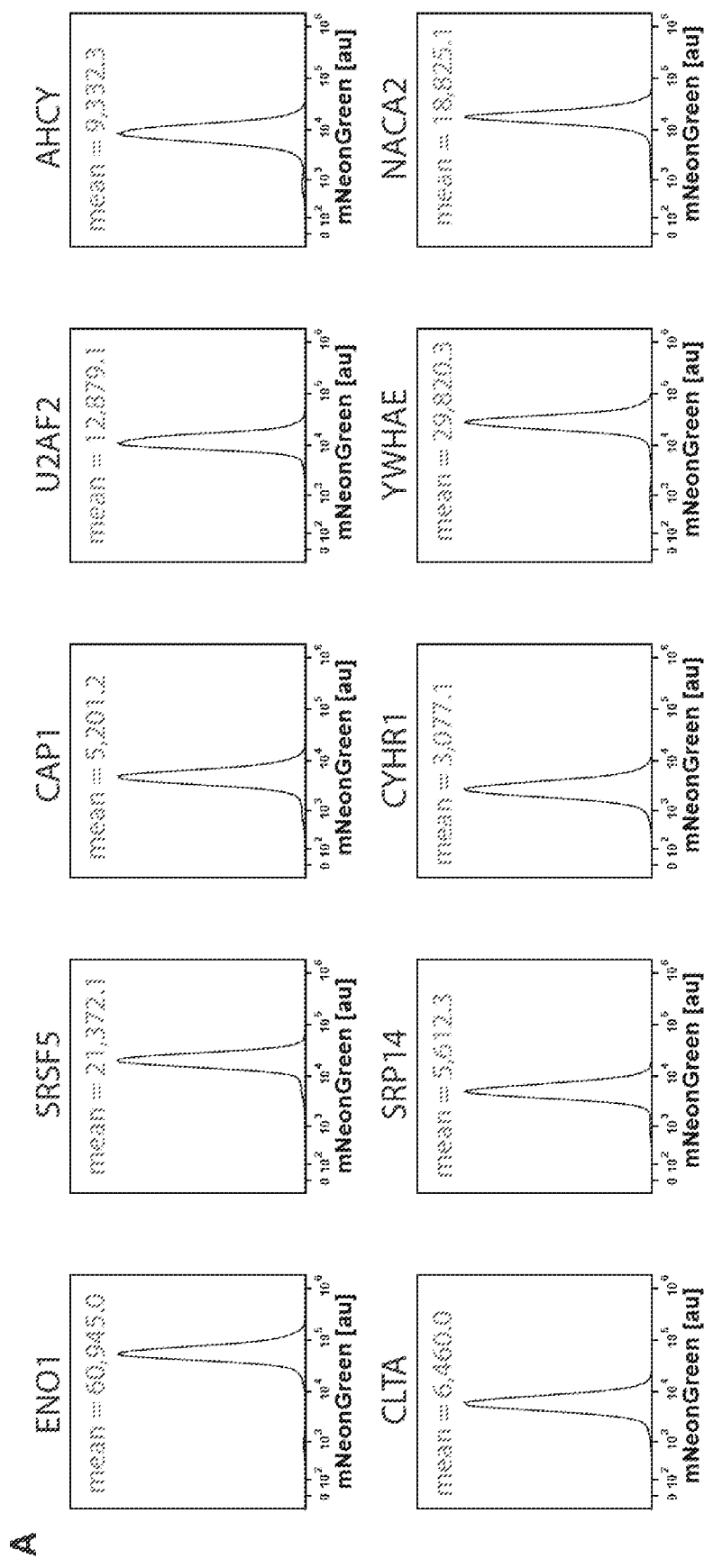

FIG. 37A-FIG. 37F—Absolute gauging of protein levels for FACS-sorted bins. FIG. 37A FACS histograms for ten mNeonGreen-myc-tagged cell lines used for gauging. FIG. 37B Immunoblotting results from defined cell numbers of tagged cell lines along with a defined myc-tagged protein standard. FIG. 37C Linear regression between mean florescence intensity of endogenously tagged proteins measured by FACS and band intensity quantification from blots shown in (B). FIG. 37D Linear regression between protein standard band intensity quantification from blots shown in (B) and absolute loaded molecule numbers. FIG. 37E Combined estimated relationship between mean fluorescence measured by FACS and the number of tagged protein molecules per cell. Note that the combined formula relies on an assumed proportionality of mean fluorescence measured by FACS and fluorescent protein abundance. FIG. 37F Estimation of the average number of mNeonGreen molecules per cell among bins of cells that were FACS-sorted for Tag-Seq proteome analysis, and re-analyzed using the same FACS analyzer as in (A). Fluorescent standard beads were included as controls in both runs to ensure reproducible sensitivity of the FACS analyzer (not shown).

Figure 38C:
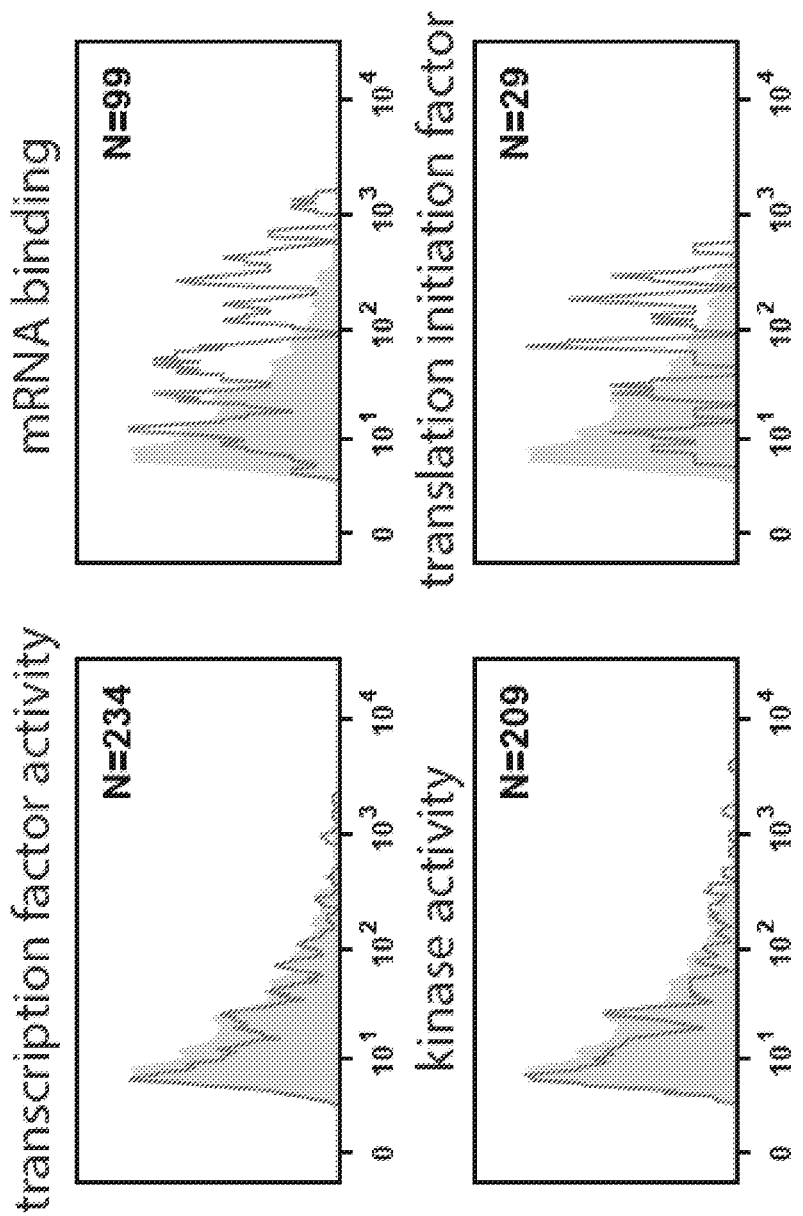

FIG. 38A-FIG. 38C—Additional protein quantification. FIG. 38A Correlation of measured mean protein expression levels between independent tagging libraries for different protein representation cutoffs. R denotes Pearson correlation coefficient. FIG. 38B Correlation of measured mean protein expression levels to RNA-seq gene expression data. FIG. 38C Comparison of protein abundance distributions of four protein families by GO molecular function annotation. Grey histograms denote the abundance distribution of all proteins covered.

Figure 39F:
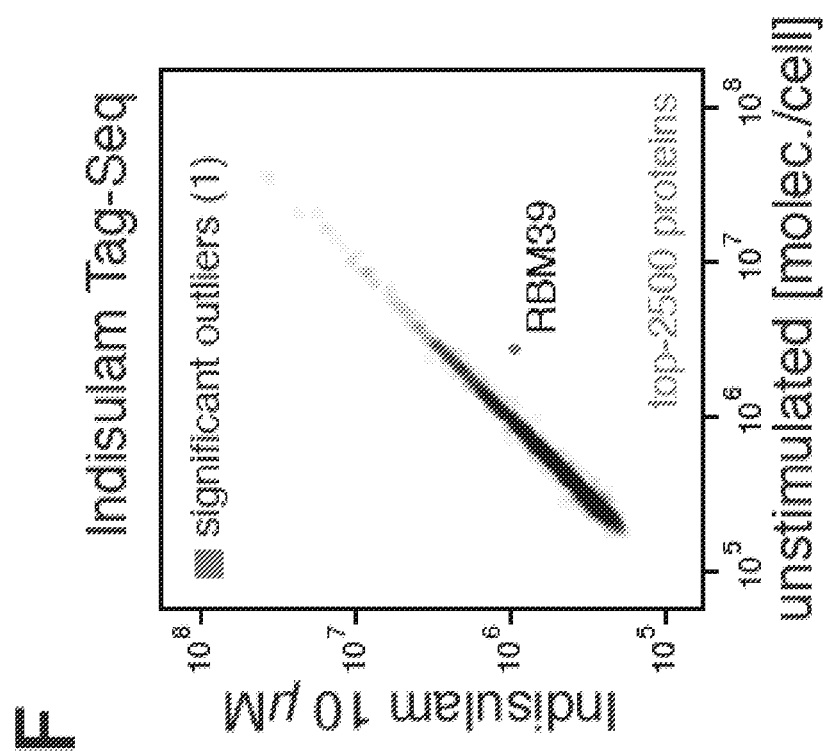

FIG. 39A-FIG. 39F—Additional drug screening results. FIG. 39A Mean protein expression measurements obtained by Tag-Seq from drug-treated versus untreated control cells. Significant outlier proteins are denoted as dots, non-significant outliers are marked (See Methods). FIG. 39B Mean transcript expression measurements obtained by RNA-sequencing from drug-treated versus untreated control cells. The selection of genes shown is matched to the proteins quantified in (A) using Tag-Seq. Outliers from Tag-Seq protein quantification are marked as colored dots. FIG. 39C Relative protein expression measurements obtained by TMT labeling whole proteome mass spectrometry from drug-treated versus untreated control cells. Non-significant outliers are marked. Replicates were combined for plotting by summation of raw reporter intensities. FIG. 39D Validation of predicted drug-regulated proteins using immuno-blotting of cells at indicated time points after drug treatment. FIG. 39E Validation of predicted drug-regulated proteins using indicated clonal mNeon-tagged reporter cell lines stimulated for six hours and analyzed by FACS. FIG. 39F Treatment of tagged library with Indisulam alone and then performing PATTERNS.

Figure 40A:
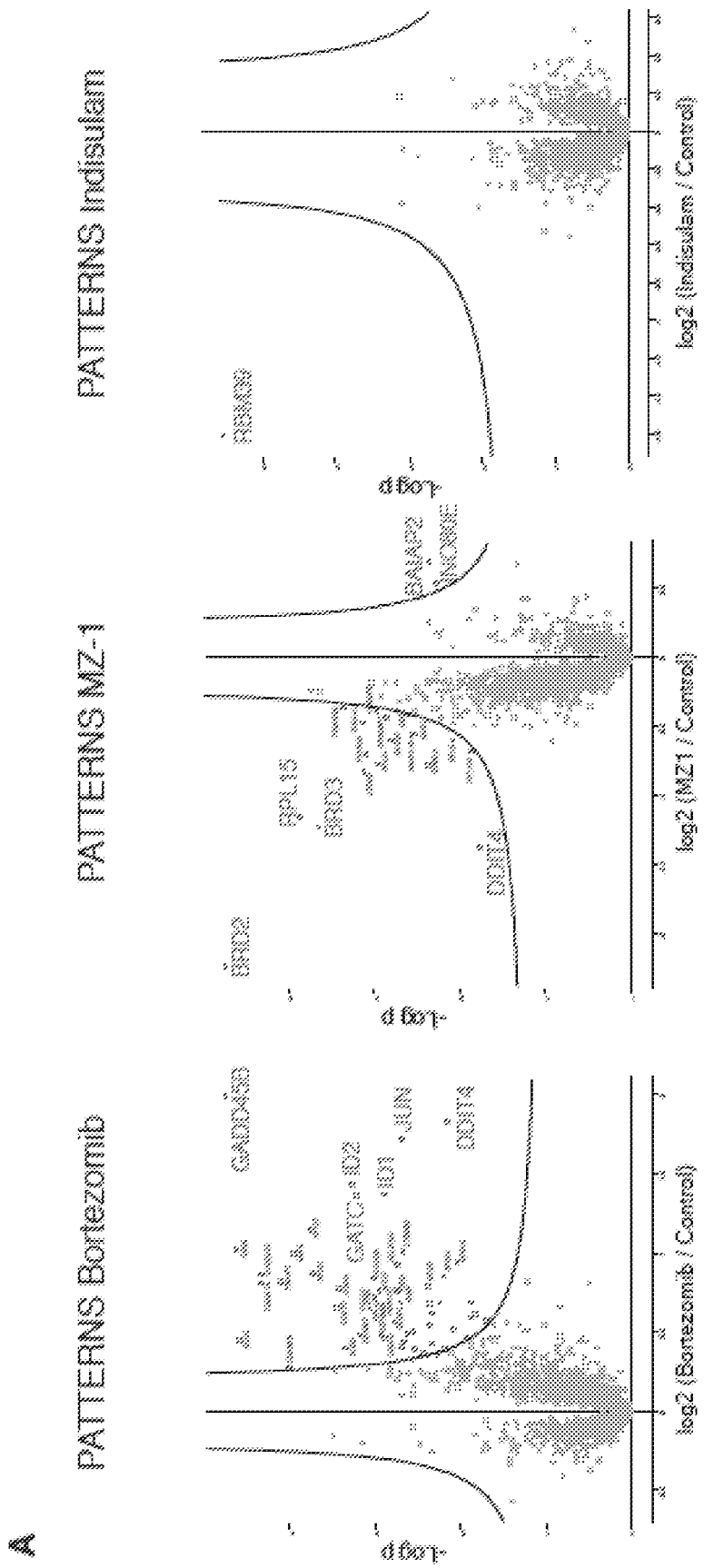
Figure 40B:
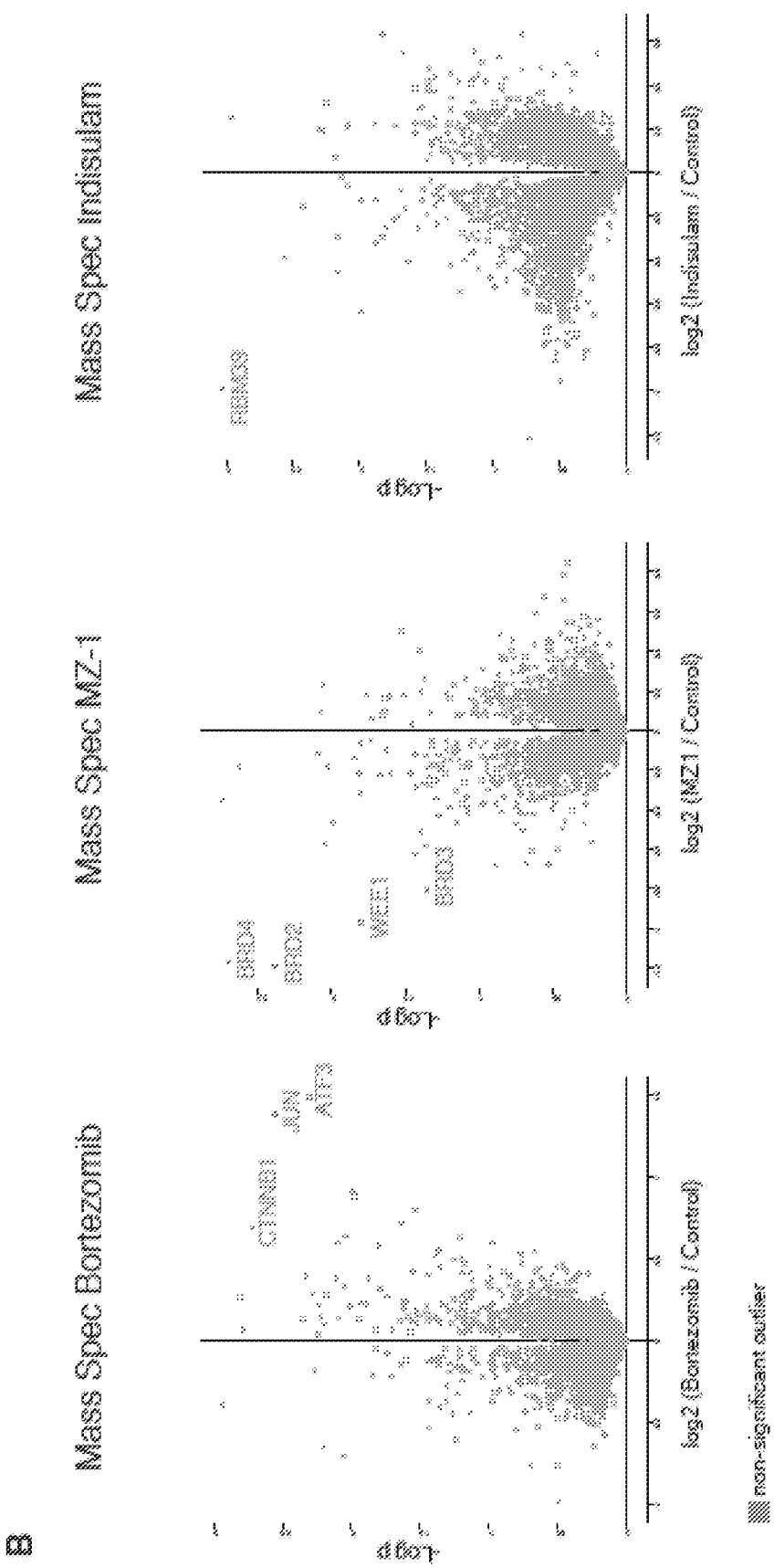

FIG. 40A-FIG. 40B—Statistical analysis of quantitative proteomics data. FIG. 40A shows Tag-seq (SBP) protein quantification data from two replicate screens that were median-subtracted and tested for drug regulated proteins (see Methods). The mean difference between conditions is plotted on the x-axis versus the −log P value on the y-axis. The two outliers RBM39 and BRD2 were identified to be statistically significant, as they are located above the black line indicating the significance threshold at an FDR of 5%. FIG. 40B shows TMT mass spectrometry protein quantification data that was filtered for missing values, log-2-transformed, median-subtracted, and tested for drug regulated proteins (see Methods). No outliers were identified to be statistically significant.

Figure 41:
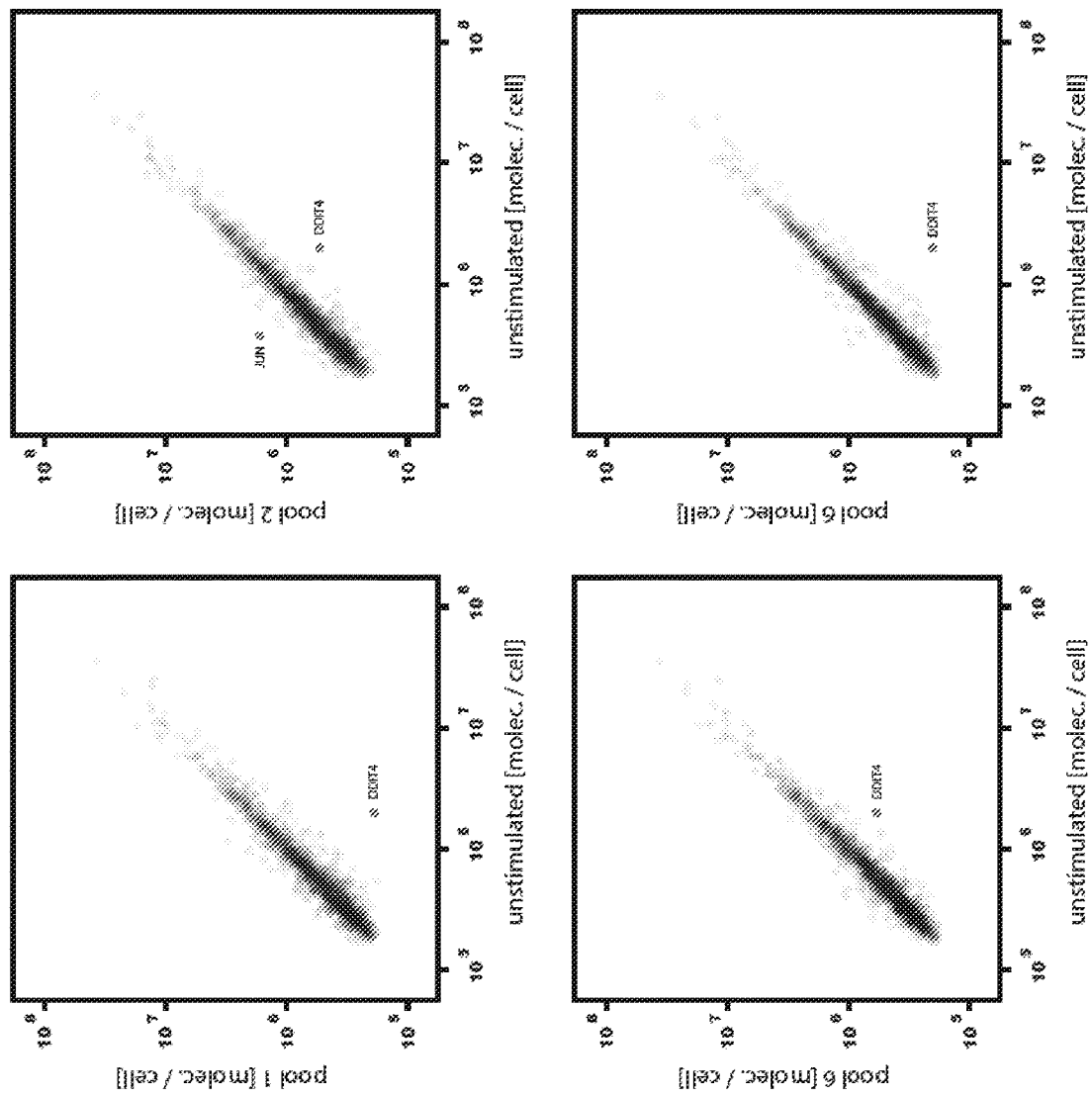
Figure 41:
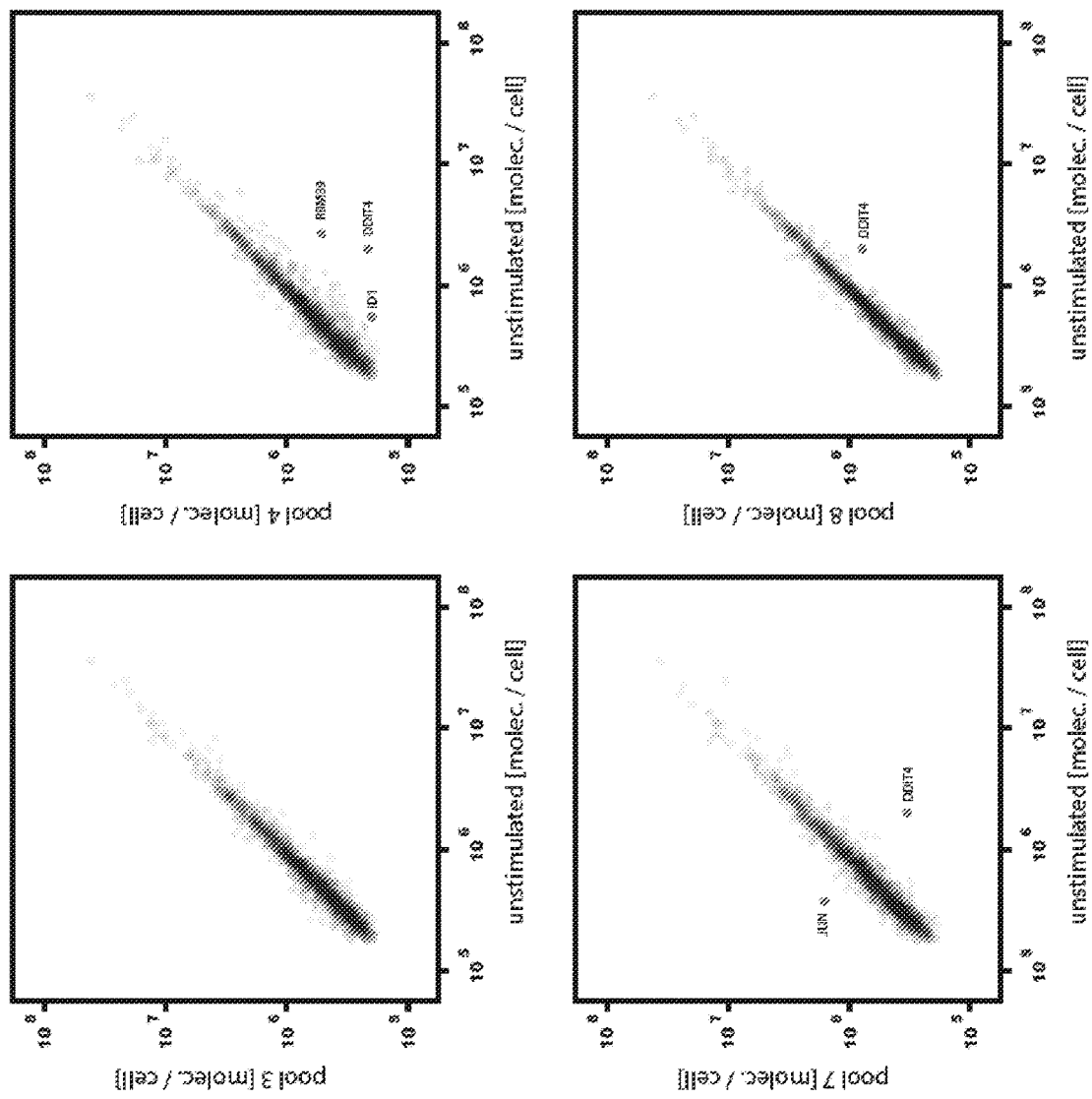
Figure 41:
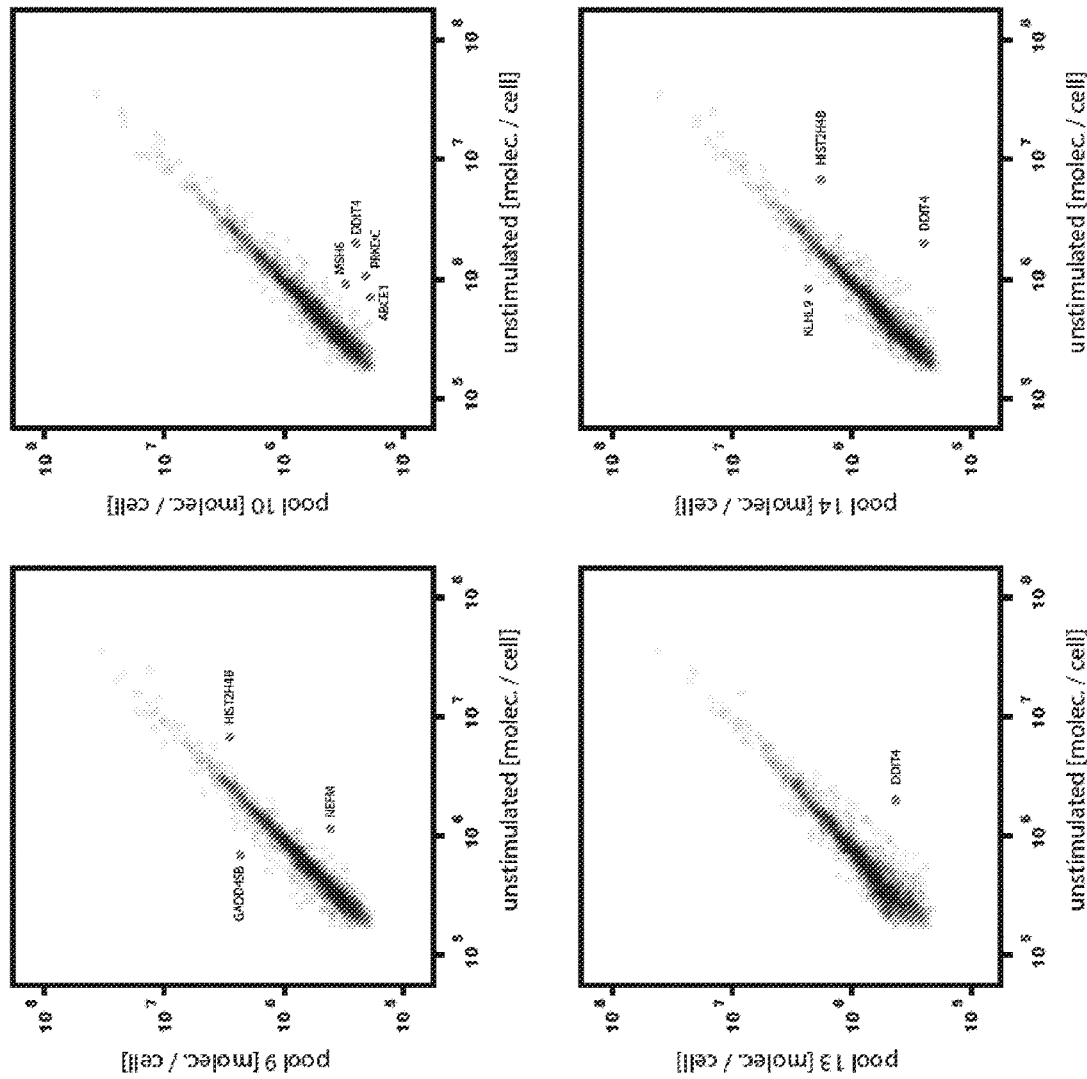

FIG. 41—Raw results from pooled drug screening. Tag-Seq proteome quantification upon application of 22 independent pools of up to 80 compounds each at 10 μM total concentration per pool for 6 h. Outlier proteins are marked.

FIG. 42A-FIG. 42I—Employing Tag-Seq in additional cell lines. FIG. 39A Seven cell lines were electroporated with Cas9 RNPs targeting the human TUBB gene locus and an mNeonGreen-NeoR donor DNA (see Materials and Methods section for details). Cells were expanded for ten days in G418-containing media and analyzed by FACS. Percentages indicate the fraction of cells whose green fluorescence exceeded the threshold indicated by the dashed line. FIG. 39B Representation of tagged genes in a polyclonal THP1 monocyte tagging library. FIG. 39C Quantification of 400 proteins in THP-1 monocytes with or without PMA stimulation. FIG. 39D Single-cell distributions of PMA-regulated proteins. FIG. 39E Western blot validation of predicted regulated proteins in (C). FIG. 39F Representation of tagged genes in a polyclonal SKMEL28 melanoma cell tagging library. FIG. 39G Quantification of 500 proteins in melanoma cells with or without Vemurafenib treatment. FIG. 39H Single-cell distributions of Vemurafenib-regulated proteins. FIG. 39I Western blot validation of predicted regulated proteins in (G).

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R.I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology $2^{nd}$ ed., J. Wiley & Sons (New York, N.Y. 1994), March, Advanced Organic Chemistry Reactions, Mechanisms and Structure $4^{th}$ ed., John Wiley & Sons (New York, N.Y. 1992); and Marten H. Hofker and Jan van Deursen, Transgenic Mouse Methods and Protocols, $2^{nd}$ edition (2011)

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Many known cellular signaling pathways process information by modulating protein abundance, localization, or post-translational modifications (Liu, Y., Beyer, A. & Aebersold, R. On the Dependency of Cellular Protein Levels on mRNA Abundance. Cell 165, 535-550, doi: 10.1016/j.cell.2016.03.014 (2016); and Payne, S. H. The utility of protein and mRNA correlation. Trends Biochem Sci 40, 1-3, doi: 10.1016/j.tibs.2014.10.010 (2015)), but our ability to assess these changes in a high-throughput manner is hampered by the lack of a scalable method for monitoring a large number of proteins. Current methods for large-scale protein analysis largely rely on either affinity reagents like antibodies or aptamers, tagged protein overexpression, or mass spectrometry. However, high-quality affinity reagents do not exist for all human proteins and are expensive to validate (Egelhofer, T. A. et al. An assessment of histone-modification antibody quality. Nat Struct Mol Biol 18, 91-93, doi: 10.1038/nsmb. 1972 (2011); and Meliopoulos, V. A. & Schultz-Cherry, S. Although it's painful: The importance of stringent antibody validation. PLOS Pathog 14, e1006701, doi: 10.1371/journal.ppat.1006701 (2018)), tagged overexpression is prone to cause artifacts, and mass spectrometry is technically challenging and has limited sensitivity (Aebersold, R. & Mann, M. Mass-spectrometric exploration of proteome structure and function. Nature 537, 347-355, doi: 10.1038/nature19949 (2016)). Early studies in yeast and mammals have shown the value of a genome-scale library of GFP strains as a transformative resource that yields key biological insights (Huh, W. K. et al. Global analysis of protein localization in budding yeast. Nature 425, 686-691, doi: 10.1038/nature02026 (2003); and Cohen, A. A. et al. Dynamic proteomics of individual cancer cells in response to a drug. Science 322, 1511-1516, doi: 10.1126/science.1160165 (2008)), but those strains could not be studied in a pooled setting, requiring individual cultures and microscopy for detection. A refined understanding of molecular phenotypes requires scalable and quantitative methods for directly monitoring dynamic changes in protein abundance and localization.

At present, studying cellular signaling pathways at the systems level broadly relies on high-throughput gene transcription measurements by RNA sequencing. However, despite the fact that most cellular signaling pathways store and process information at the protein level by modulating protein abundance, localization, or post-translational modifications, currently no method exists for monitoring these important parameters in living cells at a proteome-wide scale.

To address these challenges, Applicants developed a Sequencing-Based Protein analysis method for mammalian cells (FIG. 22a, FIG. 32a), which combines polyclonal CRISPR-assisted gene tagging, FACS-mediated binning of tagged cells into expression levels, and efficient tag integration sequencing to enable large-scale proteomics. As used herein, "Sequencing-Based Protein analysis" (SBP) is also referred to as "PATTERNS" and "Tag-Seq" and the terms are used interchangeably. Here Applicants describe PATTERNS (Proteome Analysis Through Tagging Endogenous pRoteiNs and Sequencing), a novel approach to analyzing protein dynamics. Using CRISPR-mediated NHEJ, Applicants integrated fluorescent barcoded tags into protein-coding genes to create a library of human cells containing more than 11,000 endogenously tagged proteins. Applicants then used this library to develop a sequencing-based proteomics method (PATTERNS) that combines the scalability of flow cytometry and next-generation DNA sequencing to dynamically monitor the levels, single-cell distributions, and localizations of up to 4,000 proteins. Applicants show that PATTERNS successfully identifies cell-cycle regulated proteins and distinguishes between nuclear and non-nuclear localization of tagged proteins. Additionally, Applicants applied PATTERNS in multiple human cell lines to discover small-molecule drug targets that are not regulated at the transcript level. PATTERNS is an accessible protein analysis approach that offers a novel approach to studying proteome dynamics.

The sequence based proteomics approach described herein provides a main advantage of scalability in that any number of target genes can be used. The approach can also be used with any tagged library of cells. For example, a cell library where a set of target genes are tagged with a fluorescent maker.

Specific embodiments disclosed herein provide methods for quantification and localization of proteins in a cell, identification of protein interactions in a cell and identification of protein modifications in a cell, particularly a human cell. The methods described herein for sequencing-based proteomics utilize the CRISPR system to tag endogenous genes, along with deep DNA sequencing as an alternative to mass spectrometry, the current standard for analysis of the proteome. In certain embodiments, the present invention utilizes a genome-wide CRISPR guide sequence library to integrate sequences encoding a detectable marker (e.g., a fluorescent tag) into all endogenous protein-coding genes in a particular cell or cell type. Due to stochastic delivery of the target-specific guide sequences, most cells will have only one random gene tagged, but every gene will be covered by many independent single cells. The resulting library of protein-tagged cells can be FACS-sorted into bins according to expression levels of the reporters used, and the identity is then decoded by barcoded deep-sequencing. In other words, single cells are tagged at single endogenous genes and a library of cells is generated where each gene is tagged in a plurality of single cells in a population of cells. The population of cells can then be used for determining protein levels by sorting cells based on levels of the detectable marker and providing a sequencing readout of tagged genes. The sequencing-based proteomics (SBP) approach allows for rapid, global measurements of protein expression. The sequencing-based proteomics (SBP) approach can also be used to compare changes in protein levels, protein interactions or protein modifications as a result of a perturbation (e.g., chemical, genetic, or pathogens). Mean protein levels for a library can be determined before perturbation by sorting the library and sequencing. Changes in protein levels can then be determined in response to a perturbation. In certain embodiments, a tagged library can be introduced to an in vivo model and changes in protein levels can be determined by sorting and sequencing recovered cells. In certain embodiments, tagged libraries can be used to monitor protein levels over time by detecting expression of the tagged proteins in live cells. In certain embodiments, tagged cells can be binned and resorted to assess noise distribution per protein in live cells over time.

In an exemplary embodiment, the present invention can be used for exploring innate immune signaling by stimulating cells with pathogen-associated molecules and then subjecting them to proteomic analysis to generate a map of the relevant signaling pathways. In another exemplary embodiment, the present invention can be used for exploring differentiation programs by stimulating cells to differentiate and then subjecting them to proteomic analysis to generate a map of the relevant signaling pathways. Similarly, sequencing-based proteomics can be used to record proteome fingerprints of an array of drugs, which may provide new insight into their mechanisms of action. These methods may be used to better understand the fundamental role of the proteome in human health and disease.

The technology can also be extended to assess protein localization, modification, or protein-protein interactions on a proteome-wide scale by employing tags with localization- or interaction-dependent properties. The methods of the invention can thus be applied for analysis of immune signaling (e.g., innate and adaptive immune signaling), cell cycle biology, differentiation programs, and drug responses. In comparison to the well-established high-throughput mRNA sequencing, the SBP technology is expected to require lower sequencing depth, since read numbers per gene do not correlate with gene expression. The unique advantages of SBP will enable the analysis of high numbers of experimental conditions in parallel using currently available sequencing power.

Another advantage of the technology is that it does not only measure the average expression of a given protein in a population of cells, but it also reveals the distribution of protein expression among individual cells in a population; instead of mean expression obtained for each protein. This information could yield important insights into the mechanisms of signal processing in populations of cells. The methods also provide for routine quantification of 2000-4000 proteins, and semi-absolute quantification (estimated number of molecules per cell). The methods are also applicable to diverse cell lines.

Donor Constructs

In certain embodiments, a donor construct is integrated into a host cell genome to obtain a cell tagged at an endogenous gene. In certain embodiments, a donor construct is a polynucleotide sequence that can be used to integrate a detectable marker gene into an endogenous protein coding gene resulting in a fusion protein between the endogenous protein coding sequence and the detectable marker, such that the fusion protein is under the control of the endogenous regulatory sequences. Thus, tagged proteins are not overexpressed.

In certain embodiments, the donor construct comprises a nucleotide sequence encoding a detectable marker and, optionally, any one or more of a CRISPR target site, a codon-neutral unique molecular identifier (UMI) sequence, a selectable marker (e.g., resistance gene) operably linked to a regulatory sequence, a T7 promoter and, a protease cleavable marker or a protease.

CRISPaint (CRISPR-assisted insertion tagging) has been previously developed and allows precise and efficient integration of large heterologous DNA cassettes into eukaryotic genomes (Schmid-Burgk J L, et al., CRISPaint allows modular base-specific gene tagging using a ligase-4-dependent mechanism. Nat Commun. 2016 Jul. 28; 7:12338. doi: 10.1038/ncomms12338). In certain embodiments, the donor construct comprises a universal donor DNA as described and, optionally, is provided as minicircle DNA. In certain embodiments, a CRISPR-Cas9 system is used to introduce a double-strand break (DSB) at a user-defined genomic location and the universal donor is cleaved simultaneously to be integrated at the genomic DSB.

In some embodiments, the CRISPR system as described herein is used to integrate a polynucleotide sequence encoding a detectable marker. In certain embodiments, integration is by NHEJ, wherein CRISPR is used to cleave a donor construct and genomic target site and the genomic target site is repaired with the donor construct integrated.

In certain embodiments, the donor construct may comprise a nucleotide sequence encoding a CRISPR target site. The CRISPR target site may be a frame selector site, whereby cleaving with different frame selector guide sequences can select the proper frame for integration in frame with an endogenous protein coding sequence. Thus, processing the donor construct at three possible positions allows flexible reading-frame selection.

In certain embodiments, cells tagged with the donor construct are selected by measuring the detectable marker. The detectable marker may be used to detect expression from the endogenous protein coding locus. The detectable marker may also be used to select for tagged cells. In one embodiment, the most positive cells for the detectable marker are selected. In one embodiment, the top 0.5-5% expressing cells are selected. In certain embodiments, the top 0.5, 1, 2, 3, 4, 5, 6, 7, 8, 9, 10, up to 50% are selected. In certain embodiments, cells tagged with the donor construct are selected by selecting for the selectable marker. The selectable marker may be a resistance gene (e.g., selecting by contacting the cells with an antibiotic).

In certain embodiments, the donor construct may comprise a barcode sequence. The barcode sequence may be a unique molecular identifier (UMI). In certain embodiments, the present invention provides for a plurality of donor constructs each comprising a detectable marker and a codon-neutral UMI. Each donor construct may include a different UMI. The UMI can allow counting of every tagging event, as each donor construct will have a different UMI. In certain embodiments, if a population of cells is tagged at a number of endogenous genes with donor constructs including a UMI it is possible to count how many times each of the genes is tagged in different cells of the population. In certain embodiments, this information can be used to obtain more reliable protein expression data, ensuring independent tagging events in order to avoid clonal bias. In preferred embodiments, the UMI indicates the number of cells tagged at a target exhibiting a certain level of expression. In certain embodiments, a cut off may be chosen, such that the expression of a target is only considered if the expression is determined for a target in more than one cell. For example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or more than 100 tagged cells.

Nucleic acid barcode, barcode, unique molecular identifier, or UMI refer to a short sequence of nucleotides (for example, DNA or RNA) that is used as an identifier for an associated molecule, such as a target molecule and/or target nucleic acid. A UMI is a type of barcode sequence and thus, barcode and UMI can be used interchangeably. A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. In the present examples, silent UMIs having 9 and 14 bases are disclosed. In certain embodiments, longer silent DNA barcoding makes the method more scalable, fast, accessible, cheap, and reproducible e.g., 14 or more bases).

In certain embodiments, the UMI can be used to identify the tagged gene. A barcode dictionary can be generated for the library of tagged cells ("library") by sequencing the library and determining the UMI associated with each integration site. In certain embodiments, each tagging event is identified by a unique UMI and the identity of the tagged gene in each FACS sorted bin can be identified by sequencing the UMI's only. As used herein, barcode dictionary refers to a listing of all of the UMIs in a library and the tagged gene associated with each barcode. In the case of the same gene tagged in different cells in a library, multiple barcodes will correspond to a tagged gene. The presence of UMIs associated with the same tagged gene in different cells but sequenced in different bins can be used to determine differential expression of the gene in different single cells. For example, the same gene may be differentially expressed in different cells because the gene is a cell-cycle regulated gene, as discussed further herein.

The term "unique molecular identifiers" (UMI) generally refers to a sequencing linker or a subtype of nucleic acid barcode used in a method that uses molecular tags to detect and quantify unique amplified products. In certain embodiments, the UMI or barcode used in the present invention refers to a different UMI for each donor construct, such that each UMI is associated with a tagging event at a target gene in a single cell.

Unique molecular identifiers are a subtype of nucleic acid barcode that can be used, for example, to normalize samples for variable amplification efficiency. In certain embodiments, an UMI with a random sequence of between 4 and 20 base pairs is added to a template (e.g., donor construct), which is amplified and sequenced. In preferred embodiments, the UMI is added to the 5' end of the template. Sequencing allows for high resolution reads, enabling accurate detection of true variants (e.g., true tagging event). As used herein, a "true tagging event" will be present in every amplified product originating from the original clone as identified by aligning all products with a UMI. Each clone amplified will have a different random UMI that will indicate that the amplified product originated from that clone (i.e., each represents a tagging event). Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI's are designed such that assignment to the original can take place despite up to 4-7 errors during amplification or sequencing.

In certain embodiments, the donor constructs comprise a codon-neutral UMI (e.g., a silent DNA barcode). In certain embodiments, the UMI of the present invention is codon-neutral. A codon neutral UMI allows for each donor construct to have a unique barcode nucleotide sequence, but express the same amino acid sequence for the integrated donor sequence. The UMI may include 3, 4, 5, 6, 7, 8, 9, 10, 11, 12, 13, 14, 15, 16, 17, 18, 19, 20 or more random nucleotide bases. In certain embodiments, the random bases are included in the third base of each codon (i.e., wobble base pair). An example of codon neutral UMI is incorporation of 9 codon-neutral random bases into the forward primer of the donor. An example forward primer for a mNeon donor (H and N stand for random bases):/5phos/ G*G*C GGH TCN GGN GGN AGY GGN GGN GGN TCN GTGAGCAAGGGCGAGGAGGATAAC (SEQ ID NO:69332). In certain embodiments, software can be used that counts tagging events, while ignoring sequencing errors or uneven cellular expansion events that look like individual tagging events. In certain embodiments, the codon-neutral UMI is inserted in the sequence of the detectable marker.

In certain embodiments, target molecules and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more).

In certain embodiments, the T7 promoter may be used for T7 polymerase extension for determining integration site of the donor construct and/or identification of a UMI.

In certain embodiments, the donor construct includes a protease cleavage site and a cleavable epitope tag that can be used to determine localization if a localization specific protease is expressed. The protease cleavage site and cleavable epitope tag is encoded in frame with the fusion protein. The cleavable epitope tag and protease cleavage site may be used to determine localization of the protein fusion protein by co-expressing proteases specifically localized to a region of the cell (e.g., nuclear, cytoplasmic, mitochondrial, peroxisomal, ER, golgi, lysosomal, membrane, or cytoskeleton). In certain embodiments, the donor construct includes a protease that can be used to determine localization if a localization specific protease reporter construct is expressed. The protease is encoded in frame with the fusion protein. The protein protease fusion protein can be used to determine localization by co-expressing cleavable reporter proteins specifically localized to a region of the cell (e.g., nuclear, cytoplasmic, mitochondrial, peroxisomal, ER, golgi, lysosomal, membrane, or cytoskeleton). The cleavable reporter protein provides a detectable marker upon cleavage.

In certain embodiments, the donor construct may comprise the detectable marker and any combination of the above elements. For example, the donor construct may comprise a detectable marker and any of a selectable marker, UMI, T7 promoter, CRISPR target site, and protease cleavage site and epitope tag or protease.

In certain embodiments, the donor construct is obtained by PCR amplification of a template DNA molecule using 5' forward primers each comprising a codon neutral UMI. Each primer can include a different codon neutral UMI, while the rest of the primer sequence is the same. Applicants generated donor sequences by performing three separate PCRs using primers Donor-mNeon-UMI-PTO-fwd +0/+1/+2 and Donor-NeoR-PTO-rev (Table 1) and template plasmid pCRISPaint-mNeon-T2A-NeoR (Schmid-Burgk J L, et al., CRISPaint allows modular base-specific gene tagging using a ligase-4-dependent mechanism. Nat Commun. 2016 Jul. 28; 7:12338. doi: 10.1038/ncomms12338). In certain embodiments, the donor construct is modified to increase stability or to increase efficiency of integration into a genomic locus. In certain embodiments, the donor construct is modified by a 5' and/or 3' phosphorylation modification. In certain embodiments, the donor construct is modified by one or more internal or terminal PTO modifications. Phosphorothioate (PTO) modifications are used to generate nuclease resistant oligonucleotides. In PTO oligonucleotides, a non-bridging oxygen is replaced by a sulfur atom. Therefore, PTOs are also known as "S-oligos". Phosphorothioate can be introduced to an oligonucleotide at 5'- or 3'-end to inhibits exonuclease degradation and internally to limit the attack by endonucleases. In certain embodiments, the donor construct is obtained using PCR amplification and 5' phosphorylation is introduced using 5' phosphorylated primers.

In certain embodiments, the donor construct is a plasmid, vector, PCR product, viral genome, or synthesized polynucleotide sequence. The donor construct may be a plasmid and the plasmid may be cut to form the linear donor construct. The donor may be linearized with a restriction enzyme or a CRISPR system. The donor construct may be linearized in vitro. The donor construct plasmid may be introduced into a cell according to any method described herein (e.g., transfection) and linearized inside the cell to be tagged (e.g., CRISPR). The donor construct may be introduced by a vector. For example, replication of a recombinant adeno associated virus (AAV) can be used to generate a DNA donor construct. The donor construct may also be a PCR product amplified from a template DNA molecule. The donor construct may also be a synthesized polynucleotide sequence. The synthesized polynucleotide sequence can be amplified by PCR to generate the donor construct.

The term "vector" generally denotes a tool that allows or facilitates the transfer of an entity from one environment to another. More particularly, the term "vector" as used throughout this specification refers to nucleic acid molecules to which nucleic acid fragments may be inserted and cloned, i.e., propagated. Hence, a vector is typically a replicon, into which another nucleic acid segment may be inserted, such as to bring about the replication of the inserted segment in a defined host cell or vehicle organism.

A vector thus typically contains an origin of replication and other entities necessary for replication and/or maintenance in a host cell. A vector may typically contain one or more unique restriction sites allowing for insertion of nucleic acid fragments. A vector may also preferably contain a selection marker, such as, e.g., an antibiotic resistance gene or auxotrophic gene (e.g., URA3, which encodes an enzyme necessary for uracil biosynthesis or TRP1, which encodes an enzyme required for tryptophan biosynthesis), to allow selection of recipient cells that contain the vector. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art.

Expression vectors are generally configured to allow for and/or effect the expression of nucleic acids (e.g., CRISPR system) introduced thereto in a desired expression system, e.g., in vitro, in a host cell, host organ and/or host organism. For example, expression vectors may advantageously comprise suitable regulatory sequences.

Vectors may include, without limitation, plasmids (which refer to circular double stranded DNA loops which, in their vector form are not bound to the chromosome), episomes, phagemids, bacteriophages, bacteriophage-derived vectors, bacterial artificial chromosomes (BAC), yeast artificial chromosomes (YAC), P1-derived artificial chromosomes (PAC), transposons, cosmids, linear nucleic acids, viral vectors, etc., as appropriate. A vector can be a DNA or RNA vector. A vector can be a self-replicating extrachromosomal vector or a vector which integrates into a host genome, hence, vectors can be autonomous or integrative.

The term "viral vectors" refers to the use as viruses, or virus-associated vectors as carriers of the nucleic acid construct into the cell. Constructs may be integrated and packaged into non-replicating, defective viral genomes like adenovirus, adeno-associated virus (AAV), or herpes simplex virus (HSV) or others, including retroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g., EPV and EBV vectors.

Methods for introducing nucleic acids, including vectors, expression cassettes, expression vectors, and RNPs into cells (transfection or transformation) are known to the person skilled in the art, and may include calcium phosphate co-precipitation, electroporation, micro-injection, protoplast fusion, lipofection, exosome-mediated transfection, transfection employing polyamine transfection reagents, bombardment of cells by nucleic acid-coated tungsten micro projectiles, viral particle delivery, etc.

Detectable Markers

In certain embodiments, the detectable marker is a fluorescent protein such as green fluorescent protein (GFP), enhanced green fluorescent protein (EGFP), red fluorescent protein (RFP), blue fluorescent protein (BFP), cyan fluorescent protein (CFP), yellow fluorescent protein (YFP), miRFP (e.g., miRFP670, see, Shcherbakova, et al., Nat Commun. 2016; 7: 12405), mCherry, tdTomato, DsRed-Monomer, DsRed-Express, DSRed-Express2, DsRed2, AsRed2, mStrawberry, mPlum, mRaspberry, HcRed1, E2-Crimson, mOrange, mOrange2, mBanana, ZsYellow1, TagBFP, mTagBFP2, Azurite, EBFP2, mKalama1, Sirius, Sapphire, T-Sapphire, ECFP, Cerulean, SCFP3A, mTurquoise, mTurquoise2, monomelic Midoriishi-Cyan, TagCFP, niTFP1, Emerald, Superfolder GFP, Monomeric Azami Green, TagGFP2, mUKG, mWasabi, Clover, mNeonGreen, Citrine, Venus, SYFP2, TagYFP, Monomeric Kusabira-Orange, mKOK, mK02, mTangerine, mApple, mRuby, mRuby2, HcRed-Tandem, mKate2, mNeptune, NiFP, mkeima Red, LSS-mKate1, LSS-mkate2, mBeRFP, PA-GFP, PAmCherry 1, PATagRFP, TagRFP6457, IFP1.2, iRFP, Kaede (green), Kaede (red), KikGR1 (green), KikGR1 (red), PS-CFP2, mEos2 (green), mEos2 (red), mEos3.2 (green), mEos3.2 (red), PSmOrange, Dronpa, Dendra2, Timer, AmCyan1, or a combination thereof. In certain embodiments, the detectable marker is a cell surface marker. In other instances, the cell surface marker is a marker not normally expressed on the cells, such as a truncated nerve growth factor receptor (tNGFR), a truncated epidermal growth factor receptor (tEGFR), CD8, truncated CD8, CD19, truncated CD19, a variant thereof, a fragment thereof, a derivative thereof, or a combination thereof. In certain embodiments, the detectable marker is an epitope tag. An epitope tag may include, but is not limited to, Flag, CBP, GST, HA, HBH, MBP, Myc, polyHis, S-tag, SUMO, TAP, TRX, SpyTag, StrepTag, Ollas, or V5.

In certain embodiments, the signal of the detectable marker may be detected or enhanced by using a fluorescently labeled antibody, antibody fragment, nanobody, or aptamer. The binding agent may be specific to the detectable marker.

Selectable Markers

In some embodiments, the polynucleotide sequence may further comprise a selectable marker that is expressed as a separate protein from the tagged target gene, detectable marker fusion protein. The selectable marker may be operably linked to a separate regulatory element, or separated from the fusion protein sequence by an IRES or ribosomal skipping site.

In certain embodiments, the detectable marker is separated from the marker gene by a ribosomal skipping site. Ribosomal 'skipping' refers to generating more than one protein during translation where a specific sequence in the nascent peptide chain prevents the ribosome from creating the peptide bond with the next proline. Translation continues and gives rise to a second chain. This mechanism results in apparent co-translational cleavage of the polyprotein. This process is induced by a '2A-like', or CHYSEL (cis-acting hydrolase element) sequence. In other words, a normal peptide bond is impaired at the site, resulting in two discontinuous protein fragments from one translation event. 2A peptides are 18-22 amino-acid (aa)-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (thosea asigna virus 2A) were also identified. (see, e.g., Liu et al., Systematic comparison of 2A peptides for cloning multi-genes in a polycistronic vector. Sci Rep. 2017; 7:2193).

Selectable markers are known in the art and enable screening for targeted integrations, i.e., a protein present in the cell and to which a tag is attached. A selectable marker useful in accordance with the invention may be any selectable marker appropriate for use in a eukaryotic cell, such as a mammalian cell, or more specifically a human cell. One of skill in the art will understand and be able to identify and use selectable markers in accordance with the invention. Suitable selection genes for use in mammalian cell expression include, but are not limited to, genes enabling for nutritional selection, such as the thymidine kinase gene (TK), glutamine synthetase gene (GS), tryptophan synthase gene (trpB) or histidinol dehydrogenase gene (hisD). Further, selection markers are antimetabolite resistance genes conferring drug resistance, such as the dihydrofolate reductase gene (dhfr) which can be selected for with hypoxanthine and thymidine deficient medium and further selected for with methotrexate, the xanthine-guanine phosphoribosyltransferase gene (gpt), which can be selected for with mycophenolic acid, the neomycin phosphotransferase gene (neo) which can be selected for with G418 in eukaryotic cell and neomycin or kanamycin in prokaryotic cells, the hygromycin B phosphotransferase (hyg, hph, hpt) gene which can be selected for with hygromycin, the puromycin N-acetyltransferase gene (pac) which can be selected with puromycin or the Blasticidin S deaminase gene (Bsd) which can be selected with blasticidin. In preferred embodiments, Bsd is used to select for tagged cells as tagging is improved as compared to selection with puro and hygro. Finally, genes encoding proteins that enables sorting e.g. by flow cytometry can also be used as selection markers, such as green fluorescent protein (GFP) (or any fluorescent protein discussed for detectable markers), the nerve growth factor receptor (NGFR) or other membrane proteins, or beta-galactosidase (LacZ).

Cell Libraries

In some embodiments, the invention provides cell libraries for use in detecting protein expression. Such libraries may comprise a plurality of cells, wherein each cell comprises a polynucleotide sequence that encodes a detectable marker integrated into the genome of the cell. The polynucleotide sequence may be integrated into the genome of the host cell in-frame with a protein coding gene. In certain embodiments, the library of tagged cells is sequenced prior to performing sequence based proteomics, such that each UMI or barcode can be associated with a target gene in the library. Thus, the library of tagged cells is sequenced verified and a barcode dictionary for the library is obtained. In certain embodiments, the library is used for proteomic experiments and barcodes can be identified for each sorted bin. Thus, the identity of each protein expressed in a single cell in each sorted bin can be identified by sequencing of the barcode. The level of expression is determined by the sorting and not by the number of UMI.

The protein coding gene may be selected from a set of target genes (see, e.g., Table 2). As described herein, the library comprises more than one cell tagged at each target gene, whereby each gene in the set of genes is tagged with a detectable marker in single cells of the library. In other words, while each cell contains only one tagged gene, multiple cells may have the same gene tagged, therefore each gene may be represented more than once in the library. Some specific embodiments provide for tagging of all protein coding genes at one time. Such a cell library enables identification and/or assessment or quantification of one or more proteins in a cell or cell type. In some embodiments, such a cell library identifies and/or assesses all proteins encoded by a particular cell or cell type. The set of target genes may comprise every protein coding gene in a cell (e.g., genome wide). The set of target genes may represent a specific pathway or gene signature, such that factors (e.g., drugs, pathogens, cytokines, time, interaction with microenvironment) that modulate the specific pathway or signature may be determined.

As described herein, a target gene may be any gene of interest or any gene for which expression analysis is desired. For example, a target gene as described herein may be a protein coding gene (e.g. every protein coding gene in a genome or a subset of protein coding genes of interest). In some embodiments, a target gene may be a gene that is to be down-regulated. In some embodiments, a target gene may be a gene that is to be up-regulated. One of skill in the art will understand the meaning of a target gene as presently claimed.

In some embodiments, the invention provides a library as herein discussed, wherein the targeting is of about 100 or more genes, or the targeting may be of about 1000 or more genes, or the targeting may be of about 20,000 or more genes. In some specific embodiments, the invention provides a library as herein discussed, wherein the targeting is of the entire proteome, or the entire collection of proteins or gene products of the cell or of a particular cell type. In some embodiments, the invention provides a cell library wherein every protein of an organism is represented at least once in the library. In other embodiments, every protein may be represented one time in a single cell, and represented multiple times in the library. In some embodiments, every target gene is tagged at more than one independent insertion position. In some embodiments, a library as described herein may contain a panel of target sequences focused on a relevant or desirable pathway. For example, a relevant or desirable pathway may be a biological pathway, such as an immune pathway or a cell division pathway. Other embodiments provide a cell library containing all proteins of any pathway of interest, as appropriate for the particular use or application.

In certain embodiments, each cell may comprise a sequence encoding a guide sequence specific for the tagged target gene, whereby detection of the sequence indicates the tagged target gene. A guide sequence may be generated or designed for any or all proteins in the proteome. In other embodiments, a barcode associated with a specific guide sequence is expressed in each cell. In certain embodiments, the barcode is expressed as a polyadenylated transcript. In certain embodiments, the transcript is expressed from the same construct as the guide sequence, whereby expression of the guide sequence correlates to expression of the barcode transcript. The barcodes may be determined by RNA sequencing of sorted cells and therefore can be associated with a target gene expression level. Barcoded transcripts for determining guide sequences introduced into a cell have been described (see, e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). In this way, tagging of every protein in the proteome of a cell or cell type as described herein will enable sequencing and subsequent identification of every protein, along with detection of the expression levels of all proteins.

In other embodiments, a library as described herein may comprise eukaryotic cells, such as mammalian, insect, yeast, plant, or synthetic cells. Any particular cell type may be used as desired or as appropriate for the particular application. In some embodiments, any cell type may include, but is not limited to, cells from any area, organ, muscle, tissue, or the like. In some embodiments, the cells of a library as described herein may be configured to express a CRISPR enzyme (e.g., cells stably expressing a transgene, cells from a CRISPR transgenic animal). The CRISPR enzyme may be part of the CRISPR system and may be introduced into the cell of the library by any means available and/or known in the art. CRISPR enzymes or systems as described herein may, in some embodiments, be introduced into a cell or cells in active form (i.e. as a ribonucleoprotein complex (RNP)), or may be introduced in a form that requires expression of the necessary components, such as on an expression vector. In other embodiments, a CRISPR enzyme as described herein may be inducible. In another embodiment, the cells were obtained from a transgenic animal configured to express a CRISPR enzyme.

In some embodiments, a cell suitable for construction of a library as described herein may be a cell having in its genome a nucleic acid construct encoding a CRISPR system as described herein. The CRISPR system may be incorporated into the cell from a construct comprising a nucleic acid encoding the CRISPR system. In such cases, the CRISPR system may be delivered and/or present on one construct and a guide sequence targeting the CRISPR system to a particular nucleic acid target may be delivered and/or present on a second construct. In some embodiments, the Cas nuclease and guide sequence may be operably linked and thus delivered together on a single construct.

In another aspect, the invention provides a cell library for use in detecting protein interactions between a protein of interest and a set of target proteins, said library comprising a plurality of cells, wherein each cell comprises a first polynucleotide sequence encoding a first complementary protein integrated into the genome of the cell in frame with the protein of interest, wherein each cell comprises a second polynucleotide sequence encoding a second complementary protein integrated into the genome of the cell in frame with a protein coding gene selected from a set of target genes, wherein the library comprises more than one cell tagged at each target gene, whereby each gene in the set of genes is tagged with a second complementary protein in single cells of the library. In certain embodiments, the first and second polynucleotide sequence may encode an epitope for use in a proximity ligation assay, a recognition site for measurement of interaction by TEV cleavage of nearby target sites or a protein complementation assay fragment as described herein. In one embodiment, the second polynucleotide sequence comprises a selectable marker operably linked to a separate regulatory element. In another embodiment, the selectable marker may be an antibiotic resistance gene as described herein. In another embodiment, the second polynucleotide sequence may comprise a T7 RNA polymerase promoter. In another embodiment, each cell comprises a sequence encoding a guide sequence specific for the tagged target gene, whereby detection of the sequence indicates the tagged target gene. In other embodiments, the library comprises eukaryotic cells, such as mammalian, insect, yeast, or plant cells. In other embodiments, the cells are configured to express a CRISPR enzyme, or the CRISPR enzyme is inducible. In another embodiment, the cells were obtained from a transgenic animal configured to express a CRISPR enzyme.

In another aspect, the invention provides a cell library for use in detecting protein modifications comprising a plurality of cells, wherein each cell stably expresses a fusion protein comprising a protein modification binding protein fused to a first complementary protein, wherein each cell comprises a polynucleotide sequence encoding a second complementary protein integrated into the genome of the cell in frame with a protein coding gene selected from a set of target genes, wherein the library comprises more than one cell tagged at each target gene, whereby each gene in the set of genes is tagged with a second complementary protein in single cells of the library. In other embodiments, the first and second polynucleotide sequence may encode an epitope for use in a proximity ligation assay, a recognition site for measurement of interaction by TEV cleavage of nearby target sites or a protein complementation assay fragment as described herein. In one embodiment, the polynucleotide sequence comprises a selectable marker operably linked to a separate regulatory element. In another embodiment, the selectable marker is an antibiotic resistance gene. In another embodiment, the polynucleotide sequence comprises a T7 RNA polymerase promoter. In another embodiment, each cell comprises a sequence encoding a guide sequence specific for the tagged target gene, whereby detection of the sequence indicates the tagged target gene. In another embodiment, the library comprises eukaryotic cells, such as mammalian, insect, yeast, or plant cells. In other embodiments, the cells are configured to express a CRISPR enzyme, or the CRISPR enzyme is inducible. In another embodiment, the cells were obtained from a transgenic animal configured to express a CRISPR enzyme.

In certain embodiments, the cell libraries may be monitored in live cells using live cell microscopy. In certain embodiments, cell libraries are analyzed using in situ sequencing of barcodes. In certain embodiments, live cells expressing a detectable marker are monitored and a video of the changes in expression of the detectable marker are recorded. In certain embodiments, phenotypic changes in cell morphology are also observed. The tagged genes in the cells may then be identified using in situ sequencing of barcodes. Methods of in situ sequencing are known in the art (see, e.g., Feldman, D. et al. Pooled optical screens in human cells. bioRxiv, doi: 10.1101/383943 (2018)). Other spatial organization methods applicable to the present invention include, but are not limited to, Rodriques et al., Slide-seq: A scalable technology for measuring genome-wide expression at high spatial resolution, Science 29 Mar. 2019: Vol. 363, Issue 6434, pp. 1463-1467; WO 2015/058052 "Spatial and Cellular Mapping of Biomolecules in situ by High-Throughput Sequencing"; and WO 2017/044893 "DNA Microscopy."

In certain embodiments, a cell library may be transferred to an in vivo organism and the recovered cells may be sorted and sequenced to determine protein levels, localization, interaction and modification. Typical mouse models include immunocompromised mouse models (e.g., nude mice). Cell libraries may be generated in tumor cells or immune cells and transferred to a mouse. Protein changes in response to treatment may be determined.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Th$\alpha\beta$, $CD4^+$, $CD8^+$, effector Th, memory Th, regulatory Th, $CD4^+/CD8^+$ thymocytes, CD4–/CD8– thymocytes, $\gamma\delta$ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

Protein Localization

In certain embodiments, the sequence encoding a detectable marker as described herein may further comprise a sequence encoding a protease cleavage site and a cleavable marker, wherein the sequence is in frame with the detectable marker sequence and upon cleavage at the protease cleavage site the cleavable marker is removed from the fusion protein. As used herein, a protease refers to a proteolytic enzyme that hydrolyses peptide bonds. Proteases bind to cleavage sites and hydrolyze peptide bonds to break down proteins. A protease in accordance with the invention may be any protease appropriate for the particular application, such as including, but not limited to TEV protease, thrombin, Rhinovirus protease, a SARS protease, caspases, engineered proteases, or any other protease that may provide similar activity or produce similar results. In certain embodiments, the cleavable marker is an epitope tag, such that the epitope can no longer be detected in tagged cells after removal of the epitope by cleavage at the protease site. An epitope tag may include, but is not limited to, Flag, CBP, GST, HA, HBH, MBP, Myc, polyHis, S-tag, SUMO, TAP, TRX, SpyTag, StrepTag, Ollas, or V5.

In some embodiments, localization of an expressed protein or expression product may be beneficial for methods as described herein. For example, in accordance with the invention, each cell of a library as described herein may be configured for expression of a recombinant protease or a protease reporter localized to a cellular compartment. The protease or reporter may be expressed or inducibly expressed by the cells or the protease or reporter may be introduced when detection of tagged proteins is desired. The protease or reporter may comprise any localization signal known in the art (see, e.g., Negi et al., LocSigDB: a database of protein localization signals. Database (Oxford). 2015; 2015: bav003. Published online 2015 Feb. 27. doi: 10.1093/database/bav003; and genome.unmc.edu/LocSigDB/) (e.g., nuclear export signal, nuclear localization signal, peroxisome localization signal, ER localization signal, golgi localization signal, lysosome localization signal, or mitochondrial localization signal). LocSigDB comprises sorting signal information for 533 distinct experimentally validated signals, along with the proteins that harbor them for eight distinct subcellular locations. In certain embodiments, one of ordinary skill in the art would know that more than one localization signal may be used. For example, two nuclear localization signals may be used to improve localization to the nucleus.

In certain embodiments, the sequence encoding a detectable marker as described herein may further comprise a sequence encoding a protease instead of the cleavable marker. In this case, the donor construct does not include a protease cleavage site and the fusion protein comprises the gene of interest, the detectable marker and the protease. To determine the localization of the fusion protein reporter constructs that will generate a detectable signal after cleavage by the protease are induced or introduced to the cells before determining protein localization. The reporter constructs can include any localization signal peptide as described herein. In certain embodiments, TEV is very active, such that low target expression of a fusion protein and overexpressed reporter may be easier to detect.

In certain embodiments, localization of tagged proteins is determined by isolating nuclei. The nuclei can be sorted by FACS based on expression of the detectable marker and nuclear protein expression can be compared to total protein expression determined by sorting whole cells. In certain embodiments, localization of tagged proteins is determined by fixing cells (e.g., paraformaldehyde (PFA)) in the library and isolating PFA-fixed nuclei. The PFA-fixed nuclei can be sorted by FACS based on expression of the detectable marker and nuclear protein expression can be compared to total protein expression determined by sorting whole cells. Methods of isolating nuclei is known in the art (see, e.g., Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14 (10): 955-958; and International patent application number PCT/US2016/059239, published as WO2017164936 on Sep. 28, 2017).

In some embodiments, localization of proteins may be determined by sorting the cells of a library as described herein. Sorting may be based on any appropriate means, such as including, but not limited to size, abundance, presence of a particular marker, such as a fluorescent marker, or other appropriate marker as described herein. In some embodiments, sorting may be based on cleavage of a cleavable marker as described herein. Cleavage may be performed by a protease, such as a TEV protease, as described herein. In some embodiments, a protease to be used for cleavage of a protein as described herein may be localized to a cellular compartment. Localization of a protease may be accomplished with the use or inclusion of a localization signal or tag, for example a nuclear localization signal or tag, or a nuclear export signal or tag. Localization of a protease as described herein may enable quantification of a particular protein or a collection of proteins, or the abundance thereof, from a particular cellular compartment in a cell. In some embodiments, quantification of a particular protein may be desired from a particular tissue type, or a particular cell type, or a particular species, or a particular cell process. The invention is not intended to be limited to a particular application or cell type, and such applications as described herein are all intended to be encompassed within the scope of the present invention.

Constructing Cell Libraries for Analysis of Proteins

In some embodiments, the invention provides methods of constructing a cell library for use in proteomics comprising introducing to a population of cells configured for expression of a CRISPR enzyme a plurality of vectors, wherein each cell receives one or more vectors. In some embodiments, a vector as described herein may comprise a polynucleotide sequence configured for expression of a guide sequence specific for a target sequence in a protein coding gene. In some other embodiments, the protein coding gene is selected from a set of target genes. As described herein, a target gene may be any gene of interest or any gene for which expression analysis is desired. In other embodiments, a target gene may be a gene that is to be downregulated or upregulated. Applicants constructed cell libraries using 23,095 single guide RNAs targeting a set of target genes (Table 2). The single guide RNAs were generated using DNA oligonucleotides (SEQ ID NOs: 46191-69285) as described further herein (methods).

In some embodiments, a polynucleotide sequence as described herein may comprise a CRISPR target site and a sequence encoding a detectable marker, and a polynucleotide sequence configured for expression of a guide sequence specific for the CRISPR target site, wherein the target sequence and target site are cleaved by the CRISPR enzyme such that the sequence encoding a detectable marker is integrated in-frame into the target sequence in the protein coding gene by non-homologous end joining (NHEJ). In some embodiments, a method as described herein may further comprise selecting for cells comprising the polynucleotide sequence encoding a detectable marker integrated in the target sequence in the protein coding gene, whereby the cell library comprises cells singly tagged at every target gene. Selecting as described herein may comprise any selection agent appropriate for the particular application. For example, puromycin selection may be employed in accordance with the invention, or any other selection agent, including, but not limited to, an antibiotic. Such a selection agent may be employed in the form of a selectable marker provided to the cells on a vector or other appropriate vehicle or delivery system. Antibiotic resistance genes may be introduced into a vector along with other elements as described herein, such as FLAG tag sequences, one or more CRISPR-Cas9 system genes, polynucleotides encoding a detectable marker as described herein. In one embodiment, the CRISPR enzyme may be inducible. In another embodiment, the cells were obtained from a transgenic animal configured to express a CRISPR enzyme.

In another aspect, the invention provides a method of constructing a cell library for use in proteomics comprising: introducing to a population of cells configured for expression of a CRISPR enzyme a plurality of vectors, wherein each cell receives one or more vectors comprising: a polynucleotide sequence configured for expression of a guide sequence specific for a target sequence in a protein coding gene selected from a set of target genes, a PCR product comprising a marker gene and a resistance gene; and selecting for cells comprising the polynucleotide sequence encoding a detectable marker integrated in the target sequence in the protein coding gene, whereby the cell library comprises cells singly tagged at every target gene. In some embodiments, the PCR product comprises a phosphorylation modification on 5' end, or comprises one or more PTO modifications (e.g., 5' end, 3' end, or internal). In another embodiment, the CRISPR enzyme is delivered to the population of cells transiently as a protein (e.g., RNP).

In another aspect, the invention provides a method of constructing a cell library for use in proteomics comprising: introducing to a population of cells a plurality of vectors, wherein each cell receives one or more vectors comprising: a polynucleotide sequence configured for expression of a CRISPR enzyme, a polynucleotide sequence configured for expression of a random guide sequence from the library, wherein the guide sequence is specific for a target sequence in a protein coding gene selected from a set of target genes, a PCR product comprising a marker gene and a resistance gene; and selecting for cells comprising the polynucleotide sequence encoding a detectable marker integrated in the target sequence in the protein coding gene, whereby the cell library comprises cells singly tagged at every target gene. In one embodiment, the sequence encoding a detectable marker further comprises a selectable marker gene operably linked to a separate regulatory element and selecting comprises selecting cells comprising the selectable marker. In another embodiment, the selectable marker is an antibiotic resistance gene and selecting comprises treating the cells with an antibiotic. In another embodiment, the sequence encoding a fluorescent marker further comprises a sequence encoding a protease cleavage site and a cleavable marker gene, wherein the sequence is in frame with the fluorescent marker sequence.

In some embodiments, each cell of a library as described herein may be configured for expression of a recombinant protease or reporter localized to a cellular compartment. For example, a protease useful for the invention as described herein may be a TEV protease from the Tobacco Etch Virus. One of skill in the art will recognize that any protease may be used for the methods as described herein, as long as the activity is in accordance with the particular application. In some embodiments, a protease appropriate for use with the invention may be any protease that has sequence specificity and is capable of controlled cleavage of a protein, such as a fusion protein, as described herein. Such a protease may be used in vitro or in vivo, and may be combined with other elements as described herein. A protease may have a localization signal, such as a nuclear localization signal (NLS) or a nuclear export signal (NES). Other localization signals are described herein (e.g., for nuclear, cytoplasmic, mitochondrial, peroxisomal, endoplasmic reticulum (ER), golgi, lysosomal, membrane, or cytoskeleton compartments). In certain embodiments, a protease mutant is used that inhibits auto-cleavage. The TEV mutants 219S and 219P for example inhibit auto-cleavage.

In some embodiments, the expression of localized TEV protease may be induced after generating a library as described herein. For example, the library may be split into sub-pools and transfected with a protease. For example, a TEV-NLS plasmid may be introduced into a library as described herein. In some embodiments, the protease may comprise at least one localization signal as described herein, in order to localize the activity of the desired protease.

In some embodiments, a polynucleotide sequence encoding a detectable marker as described herein may further comprise a T7 RNA polymerase promoter, or any other promoter appropriate for the particular application. Promoters are well known in the art, and one of skill will be able to select an appropriate promoter useful in accordance with the invention. Not being bound by a theory addition of a T7 promoter may be used to identify integration sites by sequencing. Methods of integration site sequencing are described herein.

In some embodiments, a population of cells as described herein may comprise any type of cells desired for the particular application. For example, in some embodiments, eukaryotic cells may be used to generate a cell library as described herein. Eukaryotic cells may be mammalian cells, insect cells, yeast cells, or plant cells, however any desirable cell type may be used as appropriate with the invention. In accordance with the invention, a cell to be used with the methods as described herein will be transformable using any appropriate methods, which will be recognized by one of skill in the art.

In some embodiments, a CRISPR enzyme as described herein may be inducible. In other words, a cell may be transformed with a functional or active CRISPR system, or the components or elements thereof, or cell may be provided or transformed or transduced with one or more polynucleotides encoding one or more elements of a CRISPR system as described herein. In certain embodiments, the CRISPR system is operably linked or under control of an inducible expression system (e.g., Tet on or Tet off systems).

In some embodiments, a method of producing a cell library as described herein may comprise a step of maintaining the library of cells. For example, as known in the art, appropriate media and/or nutrient additives, components such as antibiotics, vitamins, or the like, may be needed in order to maintain a cell library, and such steps may be used as appropriate in order to maintain a library in accordance with the invention. In some embodiments, media changes may be required to maintain cells, or cells may be frozen in appropriate buffers or solutions to maintain cell integrity. In some embodiments, storage or culture conditions may be altered or optimized as needed for the particular cell type or application. In some embodiments, a cell library as described herein may be copied as necessary for the particular application using methods known in the art. In certain embodiments, aliquots of a library may be frozen as is known in the art (e.g., frozen in liquid nitrogen). Not being bound by a theory, aliquots of the tagged library may be thawed and used in future experiments.

In certain embodiments, a method of tagging genes in cells uses a generic donor template that can be integrated at any target locus in the genome of a cell using homology independent based repair mechanisms. In certain embodiments, gene tagging uses a CRISPR system. In certain embodiments, gene tagging uses a system that alleviates the need for homology templates. Previous reports using zinc-finger nucleases, TALE effector nucleases or CRISPR-Cas9 technology have shown that plasmids containing an endonuclease cleavage site can be integrated in a homology-independent manner and any of these methods may be used for constructing the library of the present invention (see, e.g., Lackner, D. H. et al. A generic strategy for CRISPR-Cas9-mediated gene tagging. Nat. Commun. 6:10237 doi: 10.1038/ncomms10237 (2015); Auer, et al., Highly efficient CRISPR/Cas9-mediated knock-in in zebrafish by homology-independent DNA repair. Genome Res. 24, 142-153 (2014); Maresca, et al., Obligate ligation-gated recombination (ObLiGaRe): custom-designed nuclease-mediated targeted integration through nonhomologous end joining. Genome Res. 23, 539-546 (2013); and Cristea, S. et al., In vivo cleavage of transgene donors promotes nuclease-mediated targeted integration. Biotechnol. Bioeng. 110, 871-880 (2013)).

Furthermore, tagging of cells can use any method of tagging, including, but not limited to any homology based tagging or using any DNA targeting nuclease system, such as a CRISPR system, TALE system, Zn-finger nuclease system or meganucleases. DNA targeting proteins are described further herein. In certain embodiments, a library of cells is randomly tagged and clones expressing a protein of interest fusion protein can be selected for.

Cell Lines

In certain embodiments, the population of cells is derived from cells taken from a subject, such as a cell line. A wide variety of cell lines for tissue culture models are known in the art. Examples of cell lines include, but are not limited to, HT115, RPE1, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CIR, Rat6, CVI, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr–/–, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/ARI, EMT6/AR10.0, FM3, H1299, H69, HB54, HB55, HCA2, HEK-293, HeLa, Hepalc1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

Determining the Expression of Proteins

In another aspect, the invention provides a method of determining the distribution of protein levels or the expression of proteins in a population of cells. In some embodiments, such a method may comprise sorting a library of cells as described herein into at least two groups based on expression of a detectable marker in each cell as described herein. In some embodiments, nucleic acid sequencing may be performed for and/or of cells in each group, wherein the tagged target genes or tagged genes of interest in each group may be determined or evaluated. In some embodiments, evaluation as described herein may refer to analysis of protein expression or abundance. In some embodiments, sequencing as described herein may comprise transcription of a tagged gene using a polymerase appropriate for the particular application. For example, in some embodiments, a T7 polymerase may be used, or any other polymerase appropriate. Polymerases are well known and available in the art. In some embodiments, DNA replication or amplification with a T7 or other polymerase may be followed by production of cDNA using, for example, reverse transcription or other appropriate methods. Sequencing of the cDNA may then be performed. Any appropriate amplification and/or sequencing methods known in the art may be used in accordance with the invention.

In some embodiments, sequencing as described herein may comprise tagmentation using a transposase, such as a Tn5 transposase. Use of transposases is well known in the art and one of skill would be able to perform such methods. In some embodiments, linear amplification may be performed for applications in which deep sequencing is to be performed. Such methods may be appropriate or beneficial for template sequences that are present in low numbers. In some embodiments, PCR amplification and sequencing of the amplified DNA may be performed. Such methods are well known in the art.

Determining Protein Interactions

In some embodiments, the invention provides methods of determining protein interactions in a population of cells. Such a method may comprise sorting a library of cells as described herein into at least two groups. Sorting may be based on any desired criteria, including, but not limited to, a signal of a detectable marker in each cell as described herein (the detectable signal is dependent upon two proteins being in proximity such that the complementation proteins interact). In certain embodiments, the general method comprises 1) make a tagging library with a complementation protein fused to target genes, 2) introduce or express a bait protein of interest fused with a complementation protein (e.g., TEV or another interaction-dependent tag) and 3) sort the cells in which an interaction took place. Such detectable markers (complementation pairs) may be introduced into the cell using any means as described herein, and may be introduced on a vector or other appropriate vehicle or delivery system. In some embodiments, the delivery system may be a CRISPR system, as described herein. Nucleic acid sequencing may be performed on cells in each of the groups. In some embodiments, the tagged target genes in each group are determined. In one embodiment, the sequencing comprises transcription of the tagged gene by T7 polymerase, cDNA production, and sequencing of the cDNA. In another embodiment, the sequencing comprises tagmentation with Tn5, optional LAM, PCR amplification, and sequencing of the amplified DNA. In some embodiments, the library of cells may be treated with a perturbation prior to determining protein interactions as described herein. In some embodiments, the perturbation may comprise a small molecule, protein, RNAi, CRISPR system, pathogen, allergen, recombinant virus, temperature, salt, lipid, or biomolecule.

Determining Protein Modifications

In another aspect, the invention provides a method of determining protein modifications in a population of cells. In some embodiments, the method comprises sorting a library of cells as described herein into at least two groups based on the signal of the detectable marker in each cell as described herein (the detectable signal is dependent upon the modification binding protein binding to a target protein such that the complementation proteins interact). In certain embodiments, the general method comprises 1) make a tagging library with a complementation protein fused to target genes, 2) introduce or express a modification binding protein fused with a complementation protein (e.g., TEV or another interaction-dependent tag) and 3) sort the cells in which the modification is detected on a target protein. Sequencing may be performed for or on each group, wherein the tagged target genes in each group are determined. In some embodiments, the sequencing may comprise transcription of the tagged gene by T7 polymerase, cDNA production, and sequencing of the cDNA as described herein. In other embodiments, sequencing may comprise tagmentation with Tn5, PCR amplification, and sequencing of the amplified DNA as described herein. In other embodiments, the library of cells may be treated with a perturbation prior to determining protein modifications. In another embodiment, the perturbation comprises a small molecule, protein, RNAi, CRISPR system, pathogen, allergen, or biomolecule.

Complementation Systems

In certain embodiments, protein interactions and protein modifications are detected using a population of cells described herein. In certain embodiments, protein interactions and protein modifications are detected by using tagged proteins or fusion proteins that together form a protein complementation assay (PCA) (see, e.g., Rebois, R. V., et al., *Methods,* 2008. 45(3): p. 214-8). PCA is a method for the identification of protein-protein interactions in biological systems. In the PCA, the proteins of interest ("Bait" and "Prey") are each covalently linked to incomplete fragments of a third protein (e.g. a fluorescent protein), which acts as a "reporter". Interaction between the "bait" and the "prey" proteins brings the fragments of the "reporter" protein in close enough proximity to allow them to form a functional reporter protein whose activity can be measured. This principle can be applied to many different "reporter" proteins. Any protein that can be split into two parts and reconstituted non-covalently may be used in a PCA. The two parts are brought together by two interacting proteins fused to them ("bait" and "prey"). Usually enzymes which confer resistance to antibiotics, such as Dihydrofolate reductase or Beta-lactamase, or proteins that give colorimetric or fluorescent signals are used as reporters. When fluorescent proteins are reconstituted, the PCA is called Bimolecular fluorescence complementation assay. The most popular PCAs utilize split versions of the following proteins: Dihydrofolate reductase (DHFR), Beta-lactamase, Yeast Gal4 (as in the classical yeast two-hybrid system), Luciferase, Split TEV (Tobacco etch virus protease), Ubiquitin, GFP (split-GFP), LacZ (beta-galactosidase). In an embodiment, the reporter protein is TEV and the biosensor comprises a split version of TEV, i.e. two fragments/portions of TEV that can generate a functional TEV when the two fragments/portions are brought in close enough proximity. The active TEV can then generate a detectable signal by measurement of cleavage of nearby target sites. Functional reconstitution of TEV protease fragments can be monitored with 'proteolysis-only' reporters, which can be previously silent fluorescent and luminescent reporter proteins. Additionally, proteolytically cleavable inactive transcription factors can be combined with any downstream reporter gene of choice to yield 'transcription-coupled' reporter systems (see, e.g., Wehr et al., Nat Methods. 2006 December; 3 (12): 985-93).

Proximity ligation assays allow protein interactions to be detected using a nucleic acid readout (e.g., sequencing or PCR). Proximity ligation assays using epitope tags has been described (see, e.g., Gajadhar and Guha, A proximity ligation assay using transiently transfected, epitope-tagged proteins: application for in situ detection of dimerized receptor tyrosine kinases. Biotechniques. 2010 February; 48 (2): 145-52). In certain example embodiments, the constructs disclosed herein may further encode an epitope tag for use in detecting interactions or modifications by proximity ligation assays. Not being bound by a theory, epitope tags provides high sensitivity and specificity in detection by specific antigen binding molecules (e.g., antibodies, aptamers). In other words, epitope tags provide epitopes that can be bound strongly and specifically without non-specific binding. An epitope tag may include, but is not limited to, Flag, CBP, GST, HA, HBH, MBP, Myc, polyHis, S-tag, SUMO, TAP, TRX, SpyTag, StrepTag, Ollas, or V5. In certain embodiments, the proximity ligation assays used in the present invention utilize oligonucleotide linked antibodies specific for a first and second epitope as described herein. In certain embodiments, the antibodies bind to their epitope and if both antibodies are in proximity the oligonucleotides linked to each antibody can be ligated. In one embodiment, detection of the ligated product by sequencing or PCR indicates an interaction. In one embodiment, detection of the ligated product by use of a fluorescent probe or molecular beacon indicates an interaction. Detection of DNA using molecular probes or molecular beacons and sorting cells has been described (see, e.g., U.S. Pat. No. 6,692,965 and international publication number WO2005079462). In a preferred embodiment, molecular beacons are used to select for cells wherein a ligation product is generated. In certain embodiments, cells are fixed and permeabilized. The cells are then incubated with epitope specific oligonucleotide linked antibodies under conditions where ligation can occur. In certain embodiments, ligase is added to the cells. The fixed cells may then be incubated with a probe or molecular beacon. Cells may be sorted into groups based on the intensity of the signal and the tagged targets can be identified by sequencing.

In certain embodiments, the complementation system comprises a permuted inactive reporter (see, e.g., WO2007120522A3; and Eishingdrelo et al., A Cell-Based Protein-Protein Interaction Method Using a Permuted Luciferase Reporter. Current Chemical Genomics, 2011, 5, 122-128). In one embodiment, the assay design consists of two components: an inactive permuted reporter (e.g., luciferase) containing a Tobacco Etch Virus (TEV) protease cleavage sequence fused to one protein and the protease TEV fused to the second protein. Upon interaction between the proteins, the inactive permuted reporter (e.g., luciferase) is cleaved and the active reporter is reconstituted.

In certain embodiments, protein modification is detected by a complementation assay as described herein, wherein one of the complementation proteins comprises a protein modification binding protein or fragment thereof (e.g., a domain). Protein modification proteins may include any protein domain capable of binding to and/or distinguishing modified proteins. Modifications may include, but are not limited to phosphorylation, acetylation, methylation or ubiquitination. In an exemplary embodiment, domains capable of binding to phosphorylated tyrosine include SH2 domains. The SH2 (Src Homology 2) domain is a structurally conserved protein domain contained within the Src oncoprotein and in many other intracellular signal-transducing proteins. SH2 domains allow proteins containing those domains to dock to phosphorylated tyrosine residues on other proteins. SH2 domains are commonly found in adaptor proteins that aid in the signal transduction of receptor tyrosine kinase pathways. Phosphorylation of tyrosine residues in a protein occurs during signal transduction and is carried out by tyrosine kinases. In this way, phosphorylation of a substrate by tyrosine kinases acts as a switch to trigger binding to an SH2 domain-containing protein. Many tyrosine containing short linear motifs that bind to SH2 domains are conserved across a wide variety of higher Eukaryotes. In another exemplary embodiment, domains capable of binding methylated lysine include chromodomains. A chromodomain (chromatin organization modifier) is a protein structural domain of about 40-50 amino acid residues commonly found in proteins associated with the remodeling and manipulation of chromatin. Chromodomain-containing proteins bind methylated histones. In another exemplary embodiment, domains capable of binding acetylated lysine include bromodomains. A bromodomain is an approximately 110 amino acid protein domain that recognizes acetylated lysine residues, such as those on the N-terminal tails of histones. Bromodomains, as the "readers" of lysine acetylation, are responsible in transducing the signal carried by acetylated lysine residues and translating it into various normal or abnormal phenotypes. Their affinity is higher for regions where multiple acetylation sites exist in proximity. This recognition is often a prerequisite for protein-histone association and chromatin remodeling. The domain itself adopts an all-α protein fold, a bundle of four alpha helices each separated by loop regions of variable lengths that form a hydrophobic pocket that recognizes the acetyl lysine.

Sequencing of Integration Sites

In some embodiments, the invention provides a method for sequencing integration sites of a donor sequence inserted into the genome of a cell. In some embodiments, such a method may comprise lysing cells with proteinase K, detergent (e.g., Triton-X100) or another agent as appropriate. In some embodiments, the proteinase K may not be heat inactivated. In some embodiments, tagmentation may be performed on genomic DNA with a transposase such as Tn5 as described herein. In some embodiments, the transposase may be loaded with adaptors, and the adaptors may comprise a priming site. Linear amplification may be performed as described herein with a first primer specific for the donor sequence. PCR may be performed as described herein with a second primer specific for the donor sequence downstream of the first primer and a reverse primer specific for the adaptor priming site. Such a method may also comprise a step of constructing and sequencing a sequencing library as described herein. In some embodiments, kits are provided, comprising materials for tagging a population of cells according to the methods described herein.

Systems for Analysis of Proteins

In some embodiments, the invention provides a system for analysis of proteins. Such a system may comprise a universal donor construct. In some embodiments, a system as described herein may also comprise a cell population stably expressing a CRISPR system. In some embodiments, a system may comprise a construct for delivery of a CRISPR system to a cell as described herein. In further embodiments, a system may also comprise sequencing reagents.

The CRISPR system may be delivered to the cell on one or more vectors. The CRISPR system may be delivered to the cell as a ribonucleoprotein complex (RNP). The RNP complex may comprise recombinant CRISPR enzyme, guide sequences, and the donor construct. The RNP complexes may be delivered to a population of cells by transfection.

The donor construct may comprise a nucleotide sequence encoding a detectable marker and a selectable marker. The donor construct may further comprise a nucleotide sequence encoding a T7 promoter. The donor construct may further comprise a nucleotide sequence encoding an epitope tag. The donor construct may further comprise a nucleotide sequence encoding a protease cleavage site and an epitope tag. The system may further comprise a protease specific for the protease cleavage site localized to a cellular compartment. The system may comprise a donor construct for tagging a target gene in a cell comprising a nucleotide sequence encoding: a detectable marker, a resistance gene, a protease cleavage site and an epitope tag.

In accordance with the invention, a system may comprise one or more constructs for determining integration sites as described herein, indicating the location in the genome into which a nucleic acid encoding a detectable label was inserted. The constructs may comprise a T7 promoter.

Proteomics Analysis and Perturbation

In some embodiments, a cell library as described herein may be treated with a perturbation or agent prior to determining protein levels, protein interactions, or protein modifications. As used herein, a perturbation may refer to treatment with a small molecule, protein, RNAi, CRISPR system, TALE system, Zn finger system, meganuclease, pathogen, allergen, biomolecule, or environmental stress. Such methods may be performed in any manner appropriate for the particular application. The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein (see, e.g., Table 3).

The methods of proteomic analysis can be utilized for evaluating environmental stress and/or state, for screening of chemical libraries, and to screen or identify structural, syntenic, genomic, and/or organism and species variations. For example, a library of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, the library can be subjected to analysis, for example at various time points, and compared to a control, such as a mean protein level. By exposing a tagged cell library to different members of the chemical libraries, and performing the methods described herein, different members of a chemical library can be screened for their effect on proteins simultaneously in a relatively short amount of time, for example using a high throughput method.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, the present invention can be used to determine drug targets that are not regulated at the transcript level. For example, drugs that affect protein levels, modifications and interactions post transcription. In certain embodiments, a drug may not affect RNA levels, but affect protein levels, protein localization, protein interactions, or protein modifications.

The current invention comprehends the use of CRISPR technology for perturbation of cells to determine the effect of a perturbation on protein expression. In one embodiment, a library of tagged cells as described herein is perturbed at a single locus and the changes in protein expression is determined for the perturbed or other targets. In one embodiment, a library of tagged cells as described herein is perturbed at multiple loci in each cell of the population of cells and the changes in protein expression is determined for a combination of perturbed and other targets. Genes or loci targeted for perturbation may be selected by one skilled in the art based on knowledge of cellular pathways and cellular networks. The target may be a novel target. The novel target may be within a gene signature associated with a specific phenotype. One skilled in the art can apply the present invention to any target or combination of targets of interest. The current method provides for a standard predictable method of determining changes in protein expression for any perturbed target or combination of targets.

In certain embodiments, a CRISPR system is used to create an INDEL at a target gene. In other embodiments, epigenetic perturbation is performed by applying CRISPRa/i/x technology (see, e.g., Konermann et al. "Genome-scale transcriptional activation by an engineered CRISPR-Cas9 complex" Nature. 2014 Dec. 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353 (6305); Yang et al., 2016, Engineering and optimizing deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide sequence is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with the present invention, including alternative editors such as CRISPR/Cpf1. In certain embodiments, Cpf1 is the CRISPR enzyme for introducing perturbations. Not being bound by a theory, Cpf1 does not require TracrRNA and is a smaller enzyme, thus allowing higher combinatorial perturbations to be tested.

In some embodiments, the invention provides a library of non-naturally occurring or engineered compositions contained within a plurality of cells, each cell comprising a polynucleotide sequence encoding a detectable marker integrated into the genome of the cell in-frame with a protein coding gene selected from a set of target genes, wherein the library comprises more than one cell tagged at each target gene, whereby each gene in the set of genes is tagged with a detectable marker in single cells of the library.

In some embodiments, the cells of a library as described herein may comprise a RNA targeting or DNA targeting CRISPR guide sequence comprising a guide sequence capable of hybridizing to a target RNA sequence of interest in a cell, an RNA targeting enzyme, wherein the RNA targeting enzyme comprises at least one mutation, such that the RNA targeting enzyme has no more than 5% of the nuclease activity of the RNA targeting enzyme not having the at least one mutation, wherein the gRNA is modified by the insertion of distinct RNA sequence(s) that bind to one or more adaptor proteins, and wherein the adaptor protein is associated with one or more functional domains, wherein the composition comprises one or more or two or more adaptor proteins, wherein the each protein is associated with one or more functional domains, and wherein the gRNAs comprise a genome wide library comprising a plurality of RNA targeting guide sequences.

In some embodiments, the invention provides a library as described herein, wherein the RNA targeting enzyme has a diminished nuclease activity of at least 97%, or 100% as compared with the RNA targeting enzyme not having the at least one mutation. In other embodiments, the invention provides a library as herein-discussed, wherein the adaptor protein is a fusion protein comprising the functional domain. Other embodiments provide a library as herein discussed, wherein the gRNA is not modified by the insertion of distinct RNA sequence(s) that bind to the one or two or more adaptor proteins. Some embodiments provide a library as herein discussed, wherein the one or two or more functional domains are associated with the RNA targeting enzyme. In other embodiments, the invention provides a library as herein discussed, wherein the cell population of cells is a population of eukaryotic cells. A eukaryotic cell in accordance with the invention may be a mammalian cell, a plant cell, or a yeast cell. The mammalian cell may be a human cell. Some embodiments of the invention may also provide a cell library comprising a population of embryonic stem (ES) cells.

In one aspect, the invention provides a method of generating a model eukaryotic cell comprising a gene with modified expression. Such a cell may be used for a cell library as described herein. A gene with modified expression may be a disease-causing gene, or a gene that contributes to a disease. As used herein, a disease gene is any gene associated an increase in the risk of having or developing a disease. In some embodiments, such a method may comprise (a) introducing one or more vectors encoding the components of the system described herein above into a eukaryotic cell, and (b) allowing a CRISPR complex to bind to a target polynucleotide so as to modify expression of a gene, thereby generating a model eukaryotic cell comprising modified gene expression.

The structural information provided herein allows for interrogation of guide sequence interaction with the target RNA and the RNA targeting enzyme permitting engineering or alteration of guide sequence structure to optimize functionality of the entire RNA targeting CRISPR-Cas system. For example, a guide sequence may be extended, without colliding with the RNA targeting protein by the insertion of adaptor proteins that can bind to RNA or DNA. These adaptor proteins can further recruit effector proteins or fusions that comprise one or more functional domains.

In some embodiments, the above elements may be comprised in a single composition or may be comprised in individual compositions. These compositions may advantageously be applied to a host cell or organism to elicit a functional effect at the genomic level.

One of skill in the art will understand that modifications to the guide sequence that allow for binding of the adapter+functional domain but not proper positioning of the adapter +functional domain (e.g., due to steric hindrance within the three-dimensional structure of the CRISPR complex) are modifications which are not intended. The one or more modified guide sequences may be modified by introduction of one or more distinct RNA sequences located 5' of the direct repeat, within the direct repeat, or located 3' of the guide sequence.

The modified guide sequence, the inactivated RNA targeting enzyme (with or without functional domains), and the binding protein with one or more functional domains, may each individually be comprised in a composition and administered to a host cell or organism individually or collectively. Alternatively, these components may be provided in a single composition for administration. Administration to a host cell or organism may be performed via viral vectors known in the art or described herein for delivery to a host (e.g., lentiviral vector, adenoviral vector, AAV vector, or the like). As explained herein, use of different selection markers (e.g., for lentiviral gRNA selection) and concentration of gRNA (e.g., dependent on whether multiple gRNAs are used) may be advantageous for eliciting an improved effect.

Using the provided compositions, one of skill in the art can advantageously and specifically target single or multiple loci with the same or different functional domains to elicit one or more genomic events. The compositions may be applied in a wide variety of methods for screening in libraries in cells and functional modeling in vivo (e.g., gene activation of lincRNA and identification of function; gain-of-function modeling; loss-of-function modeling; and/or the use the compositions of the invention to establish cell lines and transgenic animals for optimization and screening purposes).

The current invention comprehends the use of the compositions of the current invention to establish and utilize conditional or inducible CRISPR RNA targeting events. (see, e.g., Platt et al., ('ell (2014), dx.doi.org/10.1016/j.cell.2014.09.014, or PCT patent publications cited herein, such as WO 2014/093622 (PCT/US2013/074667). For example, a target cell as described herein may comprise an RNA targeting CRISPR enzyme conditionally or inducibly (e.g., in the form of Cre-dependent constructs) and/or the adapter protein conditionally or inducibly and, on expression of a vector introduced into the target cell, the vector expresses that which induces or gives rise to the condition of a RNA targeting enzyme expression and/or adaptor expression in the target cell. By applying the teachings and compositions of the current invention with the known method of creating a CRISPR complex, inducible gene expression affected by functional domains are also an aspect of the current invention. Alternatively, the adaptor protein may be provided as a conditional or inducible element with a conditional or inducible RNA targeting enzyme to provide an effective model for screening purposes, which advantageously only requires minimal design and administration of specific gRNAs for a broad number of applications.

Nuclease Systems

As described herein, the present invention provides cell libraries for use in detecting protein expression, protein localization, or for use in detecting protein interactions between a protein of interest and a set of target proteins, or for use in detecting protein modifications, along with methods and kits for constructing such libraries, and methods for determining the expression of proteins, protein localizations, protein interactions, or protein modifications in a population of cells, and methods for sequencing integration sites of a donor sequence inserted into the genome of a cell, wherein the cells of such libraries are configured to express a nuclease system, preferably a CRISPR system, more preferably Cas9 or Cas12. The integration system as described herein is based on non-homologous end joining repair at a target locus cut using a DNA targeting nuclease. Perturbation of cells in a library may also utilize a nuclease system described herein. In certain embodiments, the nuclease system may comprise a CRISPR system, a zinc finger nuclease system, a TALEN, or a meganuclease.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein His A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159 (2): 440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that an RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106 (1): 23-24; and P A Carr and G M Church, 2009, Nature Biotechnology 27 (12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl (cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33 (9): 985-9, doi: 10.1038/nbt.3290, published online 29 Jun. 2015 Ragdarm et al., 0215, *PNAS, E*7110-E7111; Allerson et al., *J. Med. Chem.* 2005, 48:901-904; Bramsen et al., *Front. Genet.*, 2012, 3:154; Deng et al., *PNAS,* 2015, 112:11870-11875; Sharma et al., *MedChemComm.,* 2014, 5:1454-1471; Hendel et al., *Nat. Biotechnol.* (2015) 33 (9): 985-989; Li et al., *Nature Biomedical Engineering,* 2017, 1, 0066 DOI: 10.1038/s41551-017-0066). In some embodiments, 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in 5'-handle of the stem-loop regions. Chemical modification in 5'-handle of the stem-loop region of a guide may abolish its function (see Li, et al., *Nature Biomedical Engineering,* 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either 3' or 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at 5' and/or 3' end of the guide are chemically modified with 2'-O-methyl (M), 2'-O-methyl 3' phosphorothioate (MS), S-constrained ethyl (cEt), or 2'-O-methyl 3' thioPACE (MSP). Such modification can enhance genome editing efficiency (see Hendel et al., *Nat. Biotechnol.* (2015) 33 (9): 985-989). In certain embodiments, all of the phosphodiester bonds of a guide are substituted with phosphorothioates (PS) for enhancing levels of gene disruption. In certain embodiments, more than five nucleotides at 5' and/or 3' end of the guide are chemically modified with 2'-O-Me, 2'-F or S-constrained ethyl (cEt). Such chemically modified guide can mediate enhanced levels of gene disruption (see Ragdarm et al., 0215, *PNAS, E*7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6: e25312, DOI: 10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (melΨ), 5-methoxyuridine (5moU), inosine, 7-methylguanosine, 2'-O-methyl 3'phosphorothioate (MS), S-constrained ethyl (cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in 3'-terminus are chemically modified. In certain embodiments, none of the nucleotides in 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in 3'-terminus are replaced with 2'-fluoro analogues. In a specific embodiment, 1, 2, 3, 4, 5, 6, 7, 8, 9 or 10 nucleotides in 3'-terminus are replaced with 2'-O-methyl (M) analogs.

In some embodiments, the loop of 5'-handle of the guide is modified. In some embodiments, the loop of 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120:11820-11821; Scaringe, Methods Enzymol. (2000) 317:3-18) or 2'-thionocarbamate (2'-TC) chemistry (Dellinger et al., J. Am. Chem. Soc. (2011) 133:11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of th guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y base pairing sequence (e.g., as to length) is tolerated, so long as the secondary structure of the entire guide molecule is preserved. In one aspect, the loop that connects the stem made of X:Y base pairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer base pairs are also contemplated. In one aspect, non-Watson Crick base pairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155 (7): 1479-1491). In particular embodiments the stem of the stemloop is extended by at least 1, 2, 3, 4, 5 or more complementary base pairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a base pair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561): 481-5. doi: 10.1038/nature 14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm$^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/1Apr. 3, 1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 k Volts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 k Volts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu·s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm$^2$ to about 100 W/cm$^2$. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm up to 1 kW/cm$^2$ (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm−2. Even more preferably, the exposure to an ultrasound energy source is at a power density of from about 1 to about 15 Wcm−2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm−2 to about 10 Wcm−2 with a frequency ranging from about 0.015 to about 10 MHZ (see WO 98/52609). However, alternatives are also possible, for example, exposure to an ultrasound energy source at an acoustic power density of above 100 Wcm−2, but for reduced periods of time, for example, 1000 Wcm−2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm−2 or 1.25 Wcm−2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched base pairs at 3' end. In particular embodiments of the invention, additional sequences comprising an extented length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

The present invention may also use a Cas12 CRISPR enzyme. Cas12 enzymes include Cas12a (Cpf1), Cas12b (C2cl), and Cas12c (C2c3), described further herein.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339 (6121): 819-23 (2013);

RNA-guided editing of bacterial genomes using CRISPR-Cas systems. Jiang W., Bikard D., Cox D., Zhang F, Marraffini LA. Nat Biotechnol March; 31 (3): 233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153 (4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500 (7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674 (13) 01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, T J., Marraffini, L A., Bao, G., & Zhang, F. Nat Biotechnol doi: 10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8 (11): 2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156 (5): 935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159 (2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157 (6): 1262-78 (2014);

Genetic screens in human cells using the CRISPR-Cas9 system, Wang T, Wei J J, Sabatini D M, Lander E S., Science. January 3; 343 (6166): 80-84. doi: 10.1126/science. 1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32 (12): 1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33 (1): 102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517 (7536): 583-8 (2015);

A split-Cas9 architecture for inducible genome editing and transcription modulation, Zetsche B, Volz S E, Zhang F., (published online 2 Feb. 2015) Nat Biotechnol. February; 33 (2): 139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260 Mar. 12, 2015 (multiplex screen in mouse); and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546): 186-91 (2015);

A Shalem et al., "High-throughput functional genomics using CRISPR-Cas9," Nature Reviews Genetics 16, 299-311 (May 2015);

Xu et al., "Sequence determinants of improved CRISPR sgRNA design," Genome Research 25, 1147-1157 (August 2015);

Parnas et al., "A Genome-wide CRISPR Screen in Primary Immune Cells to Dissect Regulatory Networks," Cell 162, 675-686 (Jul. 30, 2015);

Ramanan et al., "CRISPR-Cas9 cleavage of viral DNA efficiently suppresses hepatitis B virus," Scientific Reports 5:10833. doi: 10.1038/srep10833 (Jun. 2, 2015);

Nishimasu et al., "Crystal Structure of *Staphylococcus aureus* Cas9," Cell 162, 1113-1126 (Aug. 27, 2015);

A BCL11A enhancer dissection by Cas9-mediated in situ saturating mutagenesis, Canver et al., Nature 527 (7577): 192-7 (Nov. 12, 2015) doi: 10.1038/nature15521. Epub 2015 Sep. 16.;

*Cpf1 Is a Single RNA-Guided Endonuclease of a Class 2 CRISPR-Cas System*, Zetsche et al., Cell 163, 759-71 (Sep. 25, 2015);

*Discovery and Functional Characterization of Diverse Class 2 CRISPR-Cas Systems*, Shmakov et al., Molecular Cell, 60 (3), 385-397 doi: 10.1016/j.molcel.2015.10.008 Epub Oct. 22, 2015;

*Rationally engineered Cas9 nucleases with improved specificity*, Slaymaker et al., Science 2016 Jan. 1 351 (6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016);

Cox et al., "RNA editing with CRISPR-Cas13," Science. 2017 Nov. 24; 358 (6366): 1019-1027. doi: 10.1126/science.aaq0180. Epub 2017 Oct. 25;

Gaudelli et al. "Programmable base editing of A-T to G-C in genomic DNA without DNA cleavage" Nature 464 (551); 464-471 (2017);

Strecker et al., "Engineering of CRISPR-Cas12b for human genome editing," Nature Communications volume 10, Article number: 212 (2019).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA: Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

A Konermann et al. (2013) addressed the need in the art for versatile and robust technologies that enable optical and chemical modulation of DNA-binding domains based CRISPR Cas9 enzyme and also Transcriptional Activator Like Effectors.

A Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293 FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA: DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

A Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

A Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

A Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

A Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32 (6): 569-77 (2014), relates to dimeric RNA-guided FokI Nucleases that recognize extended sequences and can edit endogenous genes with high efficiencies in human cells.

Also, Harrington et al. "Programmed DNA destruction by miniature CRISPR-Cas14 enzymes" Science 2018 doi: 10/1126/science.aav4293, relates to Cas14.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17-Jun.-2015, PROTECTED GUIDE RNAS (PGRNAS); U.S. application 62/091,455, filed, 12-Dec.-2014, PROTECTED GUIDE RNAS (PGRNAS); U.S. application 62/096,708, 24-Dec.-2014, PROTECTED GUIDE RNAS (PGRNAS); U.S. applications 62/091,462, 12-Dec.-2014, 62/096,324, 23-Dec.-2014, 62/180,681, 17 Jun. 2015, and 62/237,496, 5 Oct. 2015, DEAD GUIDES FOR CRISPR TRANSCRIPTION FACTORS; U.S. application 62/091, 456, 12-Dec.-2014 and 62/180,692, 17-Jun.-2015, ESCORTED AND FUNCTIONALIZED GUIDES FOR CRISPR-CAS SYSTEMS; U.S. application 62/091,461, 12-Dec.-2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19-Dec.-2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24-Dec.-2014, ENGINEERING OF SYSTEMS, METHODS AND OPTIMIZED ENZYME AND GUIDE SCAFFOLDS FOR SEQUENCE MANIPULATION; U.S. application 62/098,059, 30-Dec.-2014, 62/181,641, 18 Jun. 2015, and 62/181,667, 18 Jun. 2015, RNA-TARGETING SYSTEM; U.S. application 62/096,656, 24-Dec.-2014 and 62/181,151, 17 Jun. 2015, CRISPR HAVING OR ASSOCIATED WITH DESTABILIZATION DOMAINS; U.S. application 62/096,697, 24-Dec.-2014, CRISPR HAVING OR ASSOCIATED WITH AAV; U.S. application 62/098,158, 30-Dec.-2014, ENGINEERED CRISPR COMPLEX INSERTIONAL TARGETING SYSTEMS; U.S. application 62/151,052, 22-Apr.-2015, CELLULAR TARGETING FOR EXTRACELLULAR EXOSOMAL REPORTING; U.S. application 62/054,490, 24-Sep.-14, DELIVERY, USE AND THERAPEUTIC APPLICATIONS OF THE CRISPR- CAS SYSTEMS AND COMPOSITIONS FOR TARGETING DISORDERS AND DISEASES USING PARTICLE DELIVERY COMPONENTS; US application 61/939,154, 12-F EB-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25-Sep.-14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4-Dec.-2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24-Sep.-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23-Oct.-2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24-Sep.-14 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24-Sep.-14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25-Sep.-14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25-Sep.-14, MULTIFUNCTIONAL-CRISPR COMPLEXES AND/OR OPTIMIZED ENZYME LINKED FUNCTIONAL-CRISPR COMPLEXES; U.S. application 62/087,475, 4-Dec.-2014 and 62/181,690, 18 Jun. 2015, FUNCTIONAL SCREENING WITH OPTIMIZED FUNCTIONAL CRISPR-CAS SYSTEMS; U.S. application 62/055,487, 25-Sep.-14, FUNCTIONAL SCREENING WITH OPTIMIZED FUNCTIONAL CRISPR-CAS SYSTEMS; U.S. application 62/087,546, 4-Dec.-14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30-Dec.-2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19-Aug.-2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5-Aug.-2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15-Aug.-2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24 (6): 1012-9), Paix et al. (2015, Genetics 204 (1): 47-54), Chu et al. (2016, BMC Biotechnol. 16:4), and Wang et al. (2013, Cell. 9; 153 (4): 910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39: e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35) z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514; 8,133,697; 8,021,867; 8,119,361; 8,119,381; 8,124, 369; and 8,129,134, which are specifically incorporated by reference.

The invention is further described in the following examples, which do not limit the scope of the invention described in the claims.

EXAMPLES

Example 1—Sequencing-Based Proteomics (SBP)

At present, studying cellular signaling pathways at the systems level broadly relies on high-throughput gene transcription measurements by RNA sequencing. However, despite the fact that most cellular signaling pathways store and process information at the protein level by modulating protein abundance, localization, or post-translational modifications, currently no method exists for monitoring these important parameters in living cells at a proteome-wide scale.

A high-throughput method for studying proteomics was developed, based on CRISPR/Cas9 and DNA sequencing. This technology employs a genome-wide CRISPR/Cas9 gRNA library for integrating sequences encoding fluorescent tags into endogenous protein-coding genes. Quantification and localization of proteins at high-throughput is based on tagging protein-coding genes with a marker gene at high-throughput using Cas9 and non-homologous end joining (NHEJ) (FIGS. 1-4, see, also Schmid-Burgk J L, et al., CRISPaint allows modular base-specific gene tagging using a ligase-4-dependent mechanism. Nat Commun. 2016 Jul. 28; 7:12338. doi: 10.1038/ncomms12338). The universal donor system utilizes guide sequences to target CRISPR/Cas9 to a genomic locus encoding a gene to be tagged. A universal donor construct is targeted for cleavage by a guide sequence capable of selecting the frame of the donor sequence. In this way, the donor sequence can be used for any target gene requiring insertion in a different frame. Upon expression of the donor system in a cell the genomic locus is repaired using the cleaved universal donor construct, frequently resulting in an in-frame insertion of a tag gene (e.g., detectable marker) at the C-terminus of a target gene. Due to stochastic delivery of the target-specific guide sequences, most cells will have only one random gene tagged, but every gene will be covered by many independent single cells. As shown in FIG. 4, integration fidelity is high as the reading frame of mNeonGreen fusions of three tagged genes, ACTG1, HIST1H4C and TUBB, is correct in the majority of cells, as denoted by the green pieces of the pie charts, as measured by deep sequencing.

Figure 1:
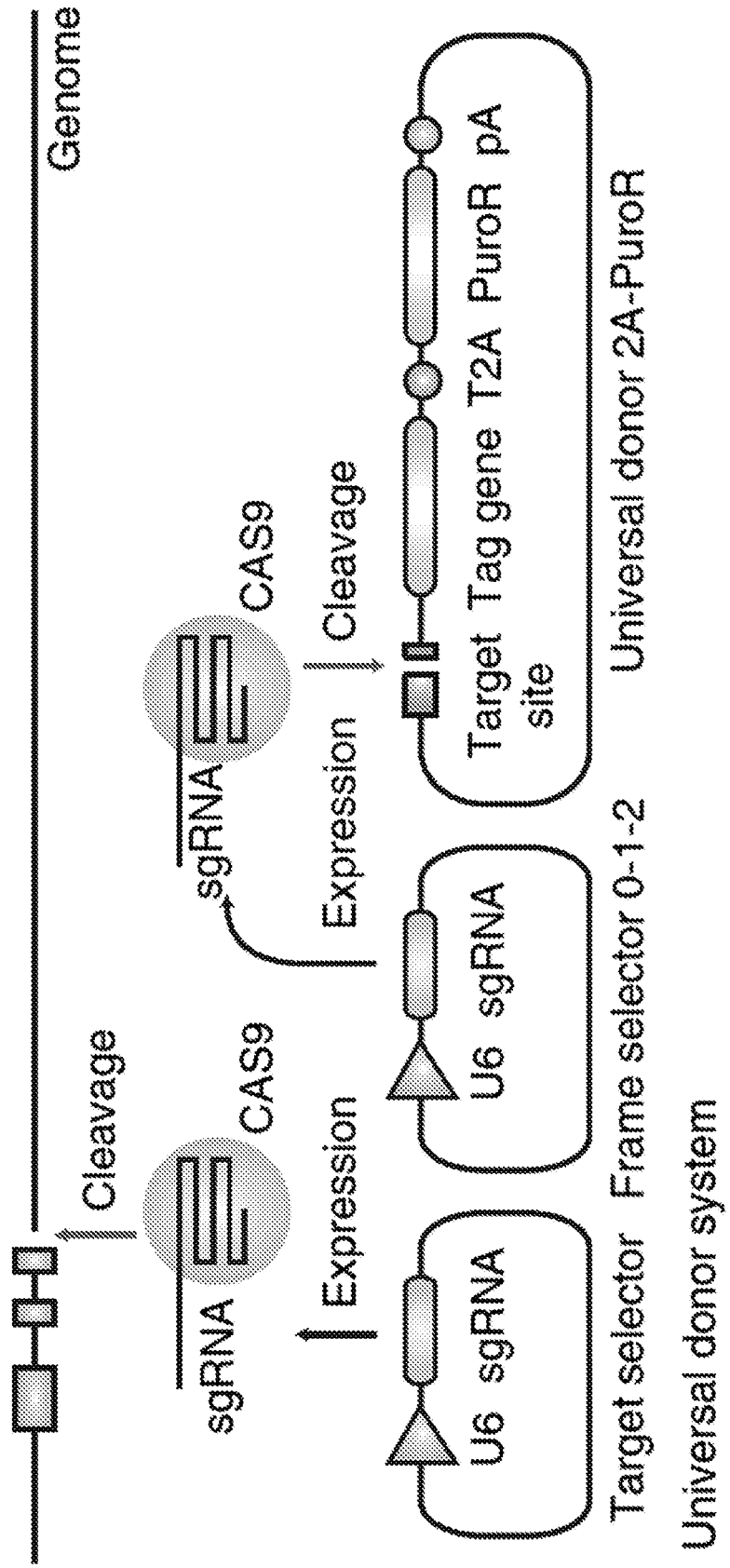
FIG. 1—Shows a schematic of non-homologous end joining (NHEJ)-based gene tagging of a target gene at its genomic locus with a donor sequence using a CRISPR system.
Figure 2:
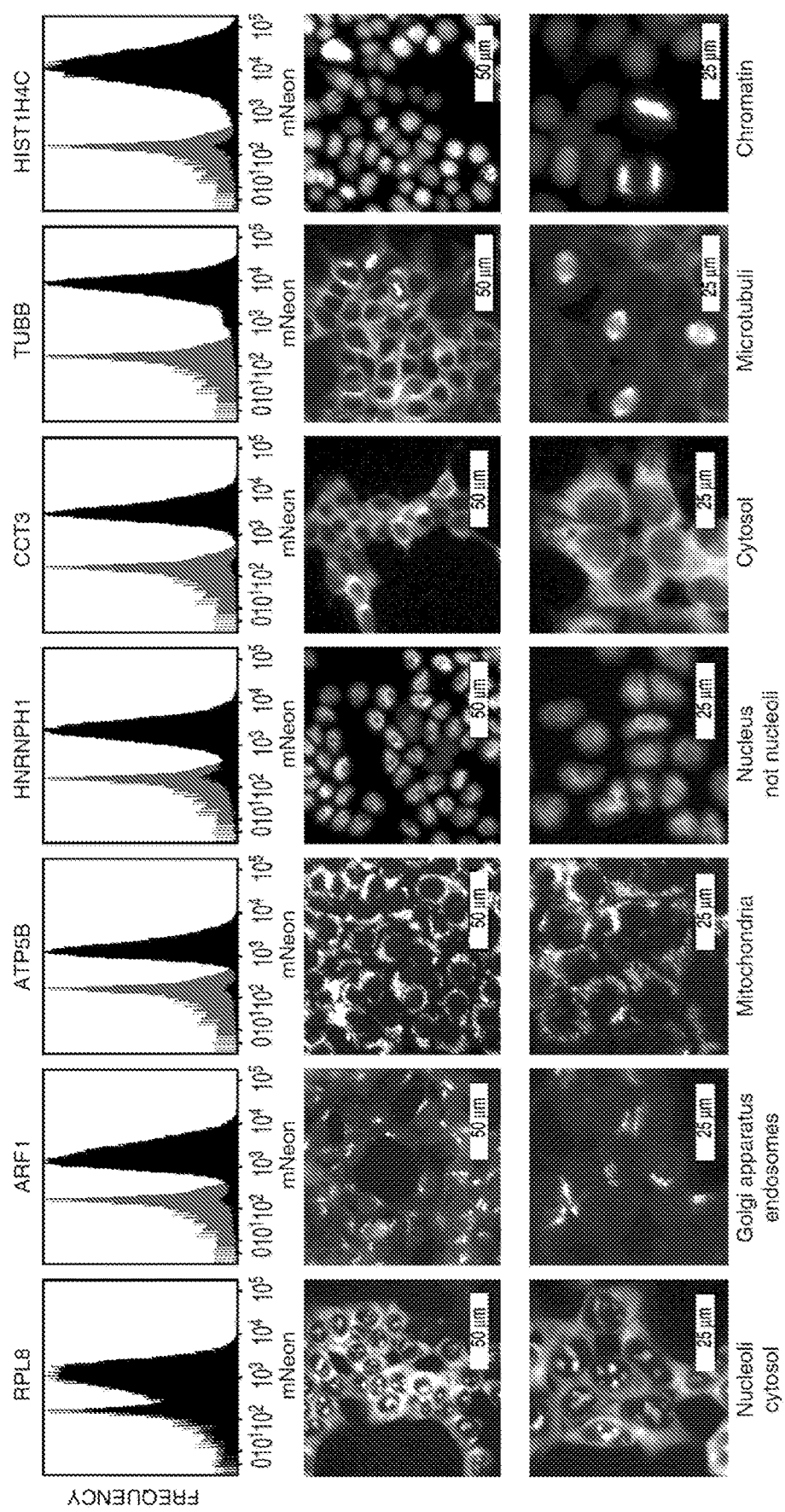
FIG. 2—Shows NHEJ-based gene tagging of genes representative of proteins localized to different cellular compartments and organelles with mNeon.
Figure 3:
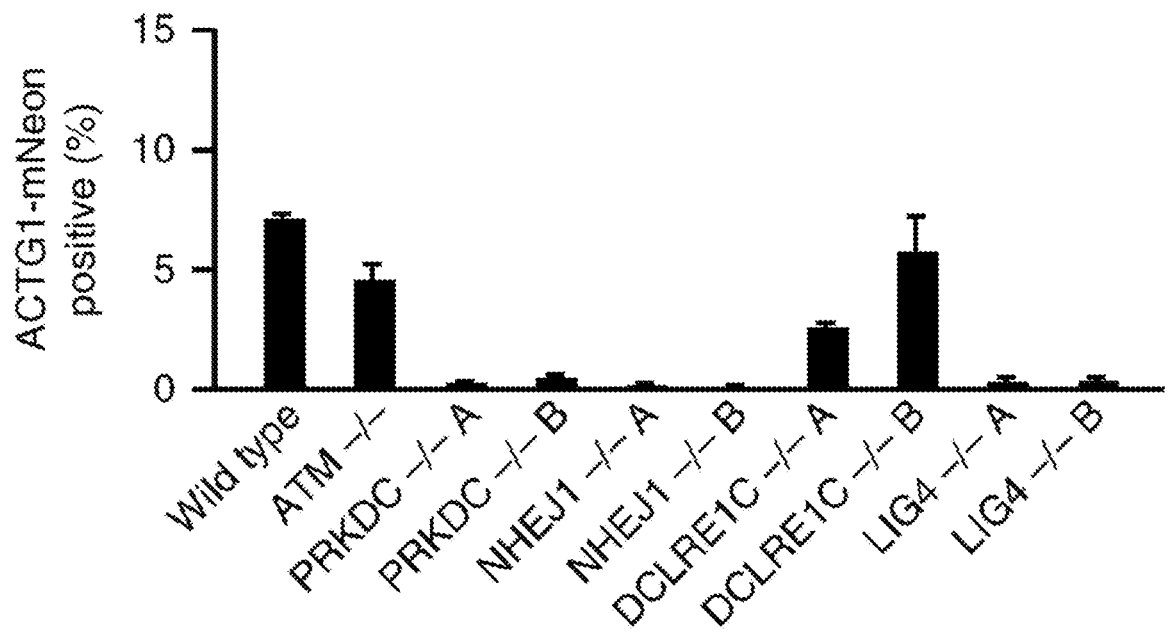
FIG. 3—Shows that tagging of genes is efficient and dependent on ligase IV. Image quantification of ACTG1-mNeon-positive cells. Shown are mean values+s.e.m. from three independent biological replicates.
Figure 5:
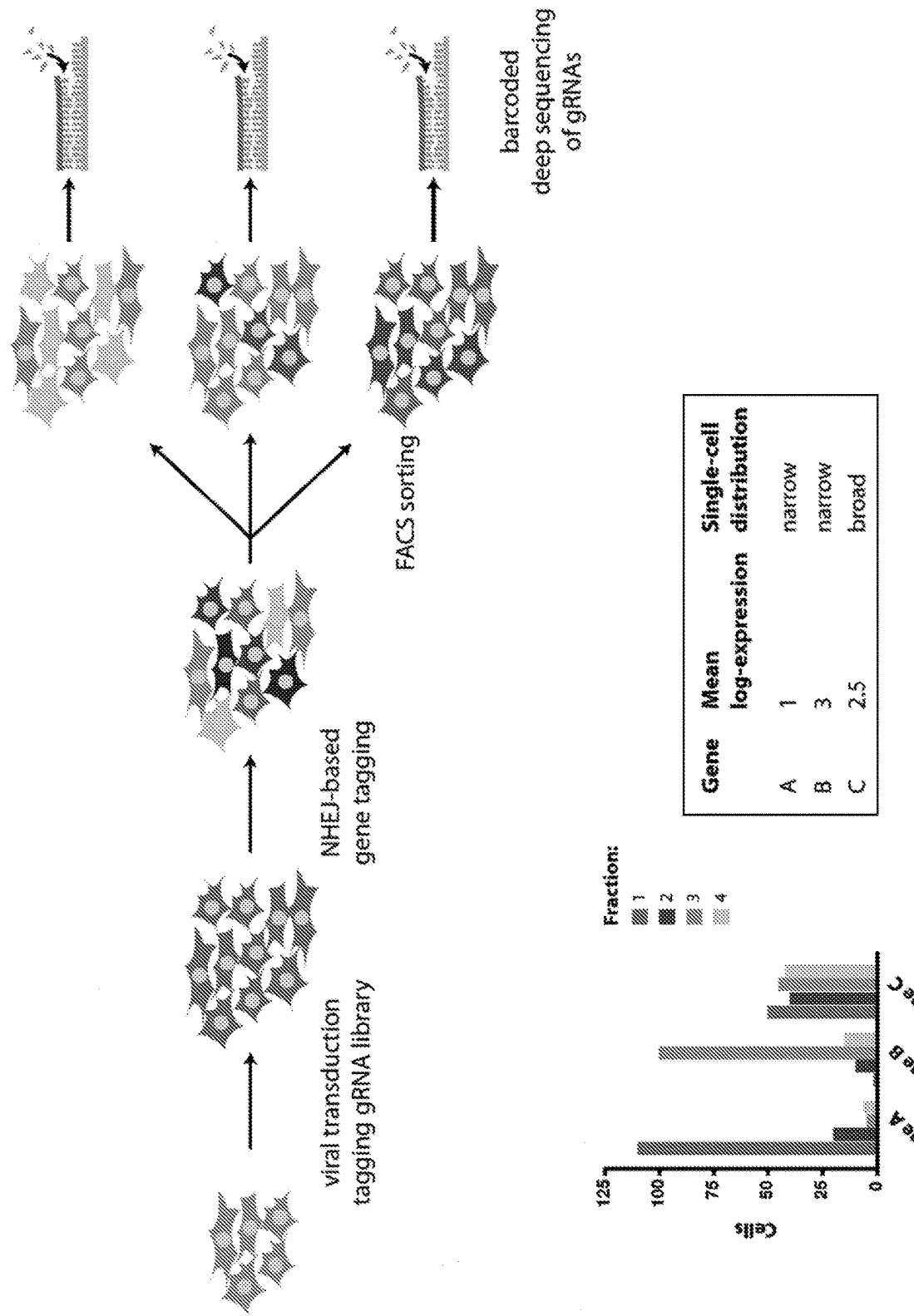
FIG. 5—Shows a schematic of sequencing-based proteomics, demonstrating the expression levels of genes A-C.

A summary of the method for sequencing-based proteomics comprising tagging and measuring gene expression is described (FIG. 5). As shown in FIG. 5, viral transduction of a population of cells is used to introduce a library of guide sequences targeting protein-coding genes A-C and the CRISPR-Cas9 system containing the universal donor system for tagging genes. The genes are tagged by NHEJ. After establishing and validating a library of cells with randomly tagged genes, the cells can be FACS-sorted into populations of distinct levels of fluorescent tag expression. The tags were fused with the endogenous proteins; therefore, the expression of the proteins should be highly correlated with the expression of the tagged proteins. Cells can then be sorted based on expression of the detectable marker and thus expression of genes A-C fused to the detectable marker. Biochemical methods like immunoblotting were used to verify the expression levels of the proteins. Each sorted population of cells was subsequently analyzed by deep sequencing of the guide sequences that were present in each cell. As these guide sequences contain information relating to which genes were tagged, sequencing enabled assignment of individual tagged genes to sorted expression levels. The sorted groups are sequenced to determine the guide sequences present in each group and thus determining the tagged genes in each group. In this example the cells are sorted into 4 groups. In certain embodiments, the cells may be sorted into 2, 3, 4, 5, 6, 7, 8, 9, 10, 11, 12, 13, 14, 15, 16 or more than 16 groups. Not being bound by a theory measurement of gene expression is more sensitive when cells are sorted into more groups. Cells in which gene A is tagged are present predominantly in population 1, thus gene A has low expression levels in the population of cells. Cells in which gene B was tagged predominantly reside in population 3 and thus gene B has higher expression than gene A. Cells in which gene C is tagged were present in all groups, thus the expression level of gene C is variable in the population. In certain embodiments, the population of cells can be used to compare treated and untreated cells to measure changes in gene expression.

Figure 6:
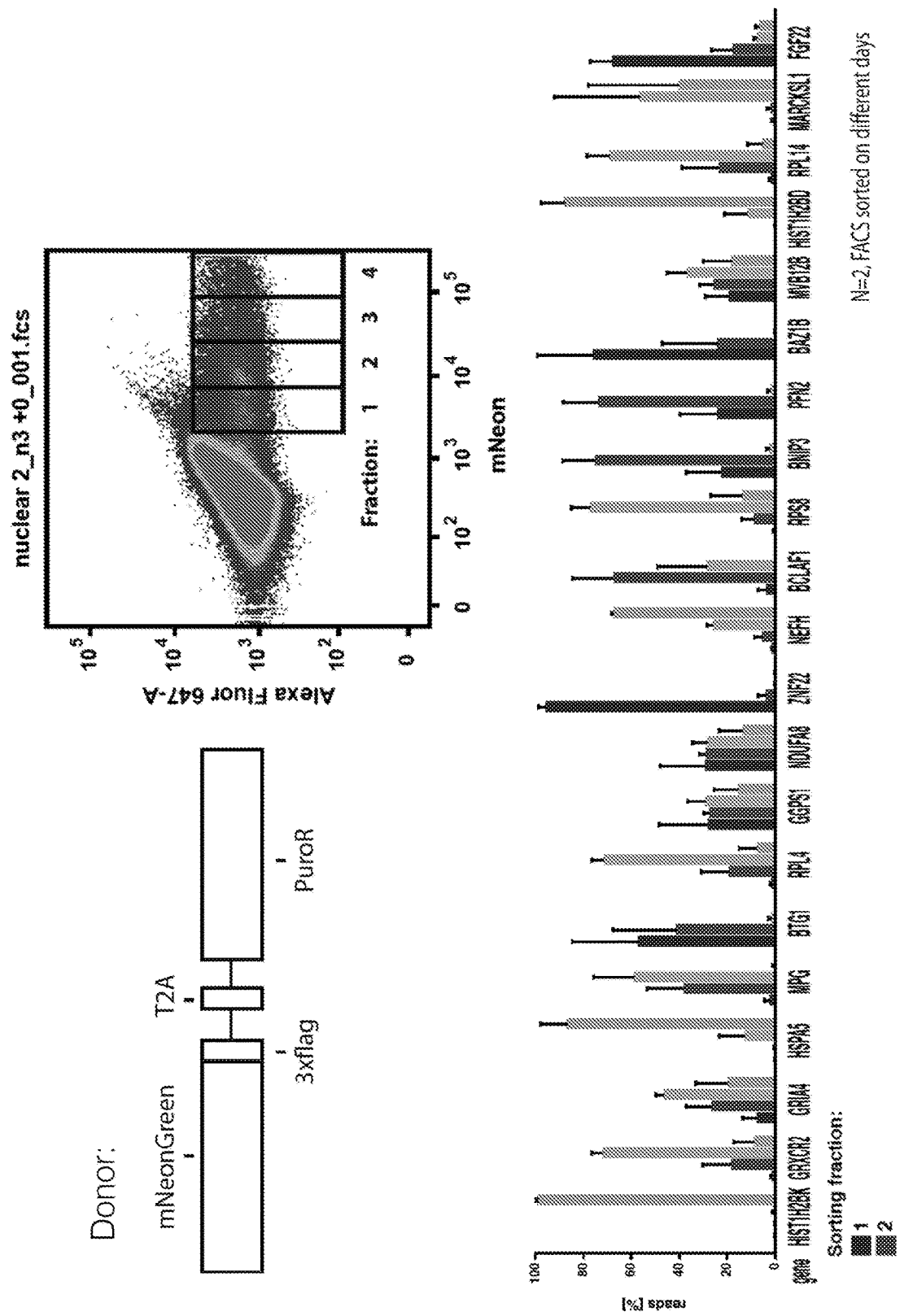
FIG. 6—Shows results of barcoded deep sequencing of the gRNAs when expressed proteins were FACS-sorted into 4 bins of expression levels. mNeonGreen was used as the marker on a tagging construct introduced into human cells.

As shown in FIG. 6, Applicants tagged and determined differential expression of a panel of genes using the methods described herein. Flow cytometry (i.e., FACS) was done to separate the cells into bins based on gene expression levels. Barcoded deep sequencing of the guide sequences was then performed to evaluate the abundance of each protein. mNeonGreen was used as the marker on the donor construct introduced into human cells (FIG. 6). The donor construct also included an epitope tag (3×flag) and a selectable marker (puromycin resistance gene) linked by a ribosomal stuttering site (T2A).

Example 2—Tagging Optimization

Figure 7:
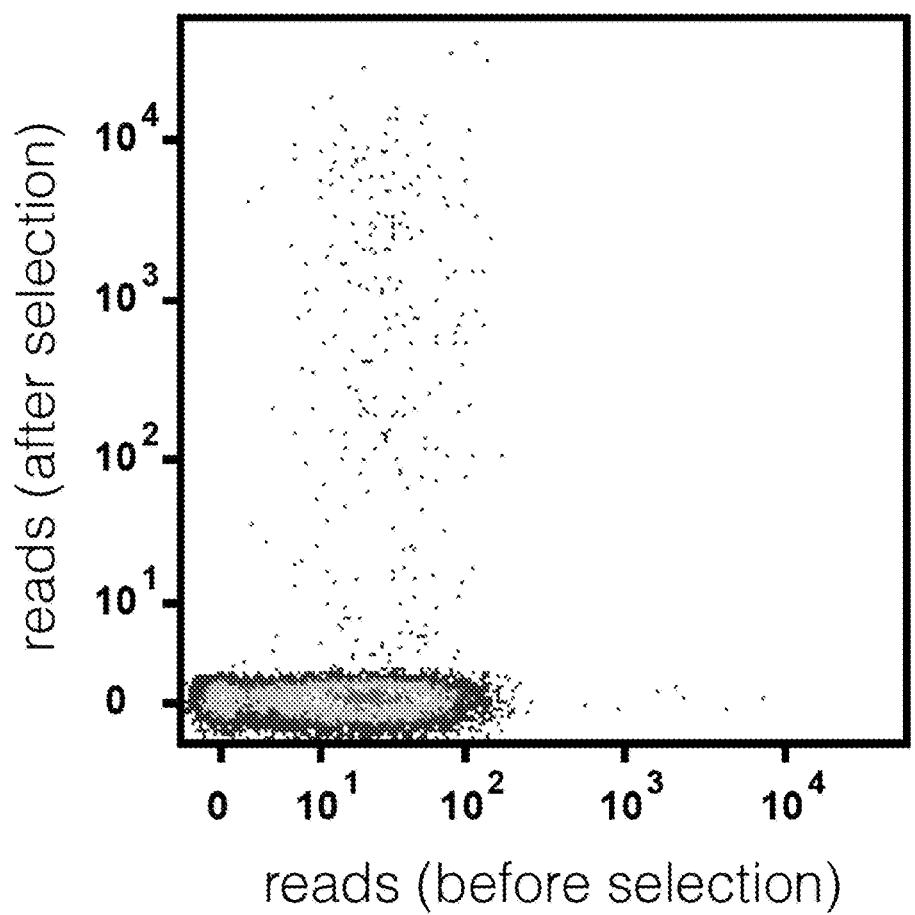
FIG. 7—Shows representation of tagged target gene library before and after selecting for selectable marker.
Figure 8:
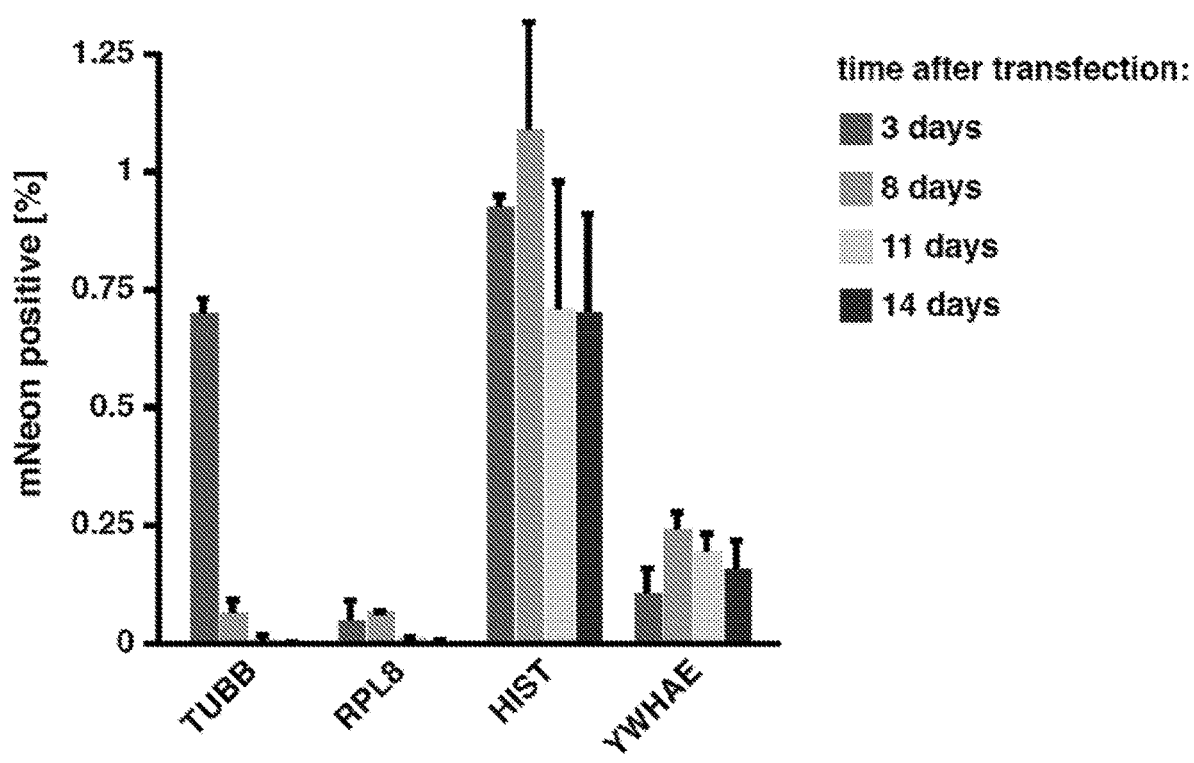
FIG. 8—Shows expression of mNeon tagged proteins over time after tagging.
Figure 9:
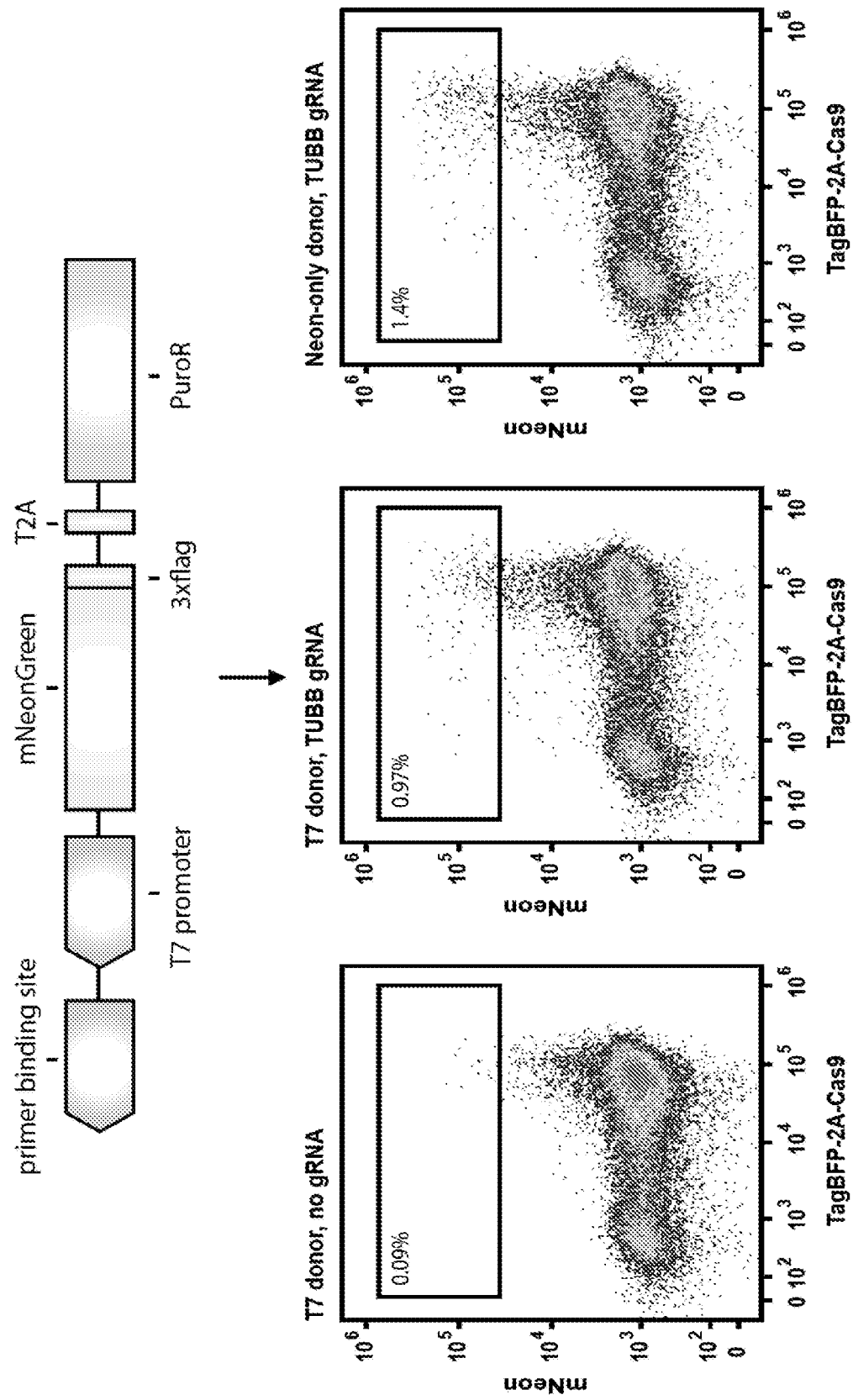
FIG. 9—Shows results testing the efficiency of tagging with a donor construct performed for no gRNA, as well as a gRNA targeting the TUBB gene with and without a T7 promoter.
Figure 10:
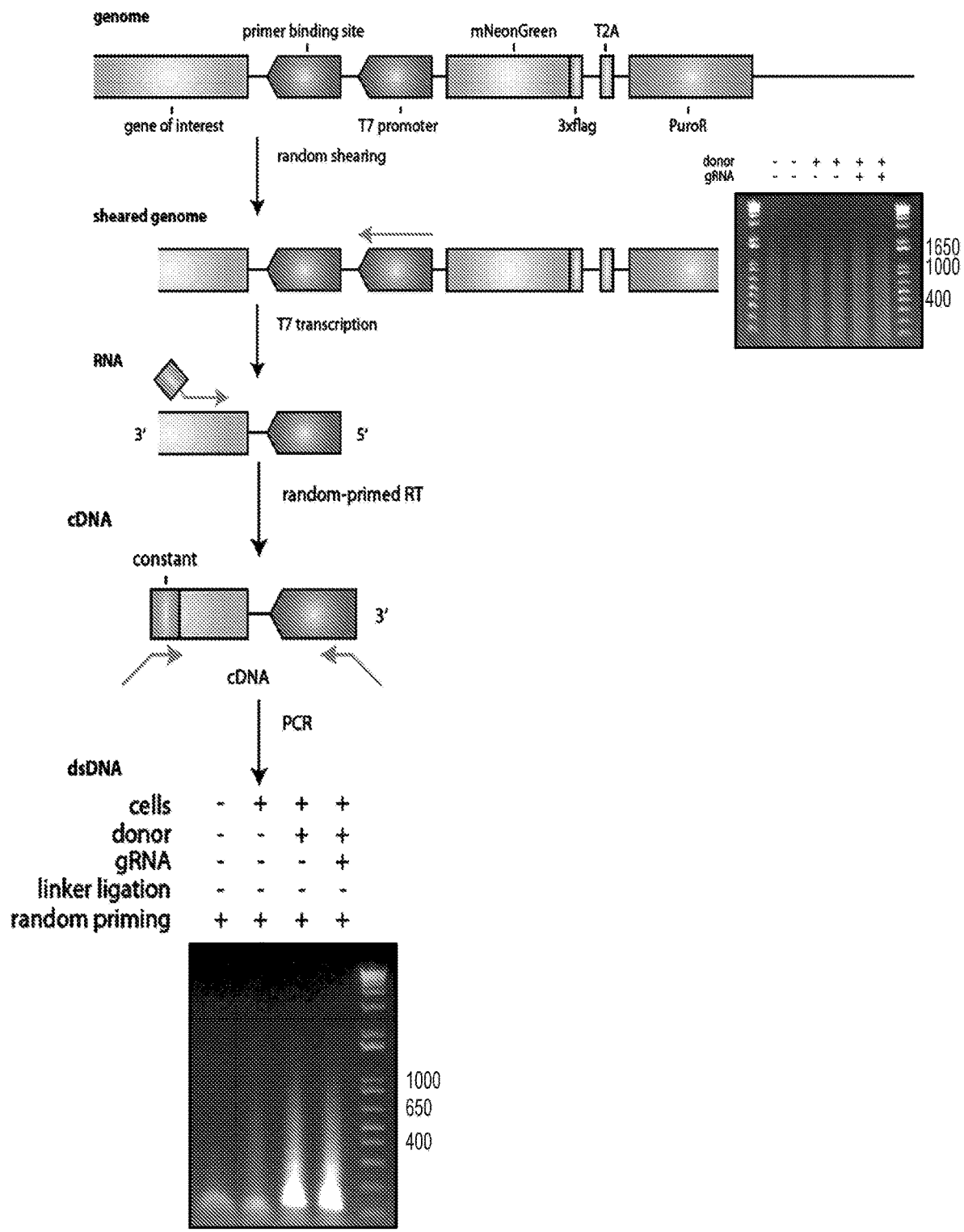
FIG. 10—Shows a step-by-step schematic demonstrating a method of integration site sequencing.
Figure 11:
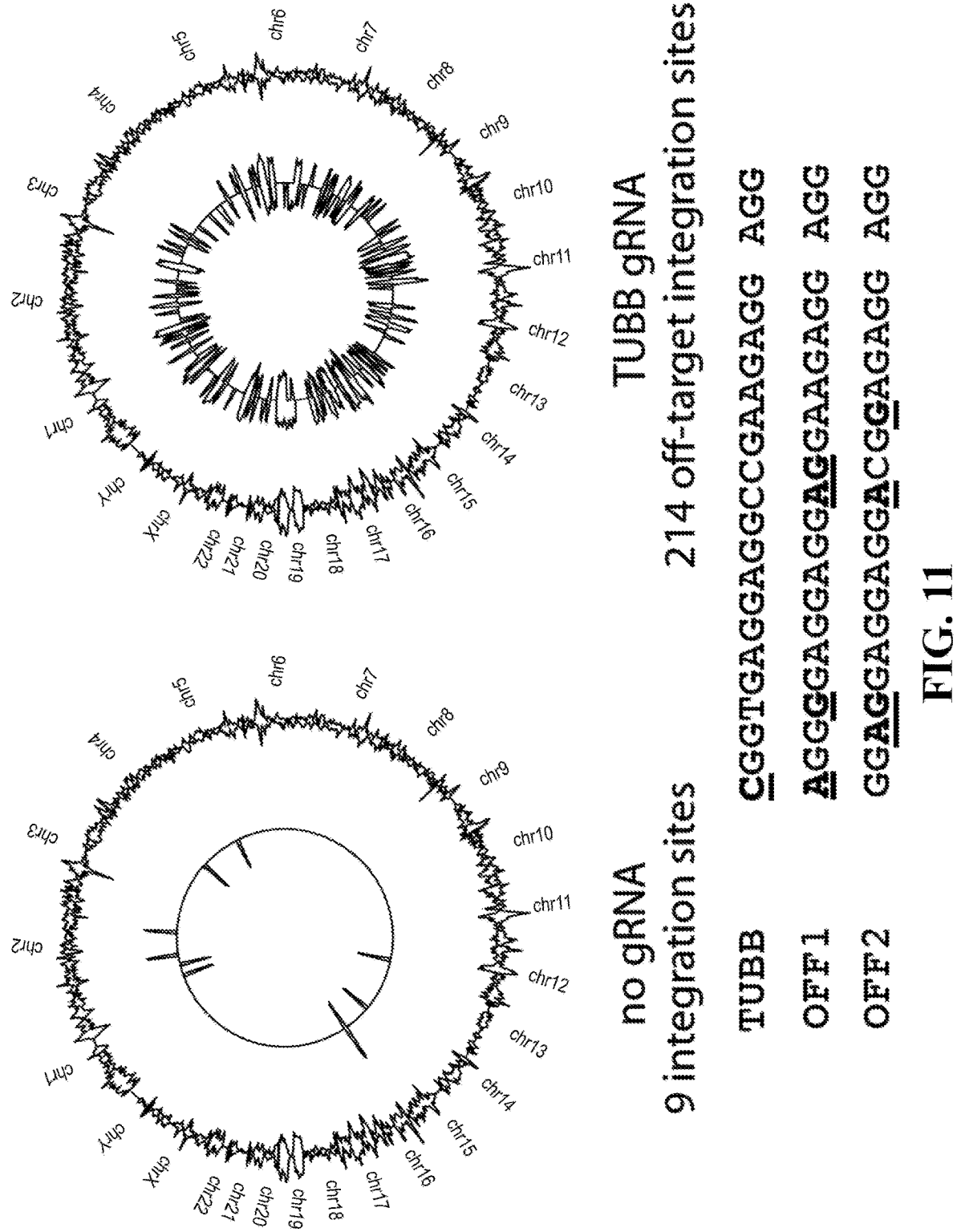
FIG. 11—Shows results of integration site sequencing performed after tagging experiments using spCas9 with no guide sequence or with TUBB guide sequence (SEQ ID NO: 69329). The donor was found at 9 integration sites when no gRNA was used, while the donor was found at 214 off-target integration sites when TUBB gRNA was used. Exemplary sequences of guide sequence targets and off target sequences (SEQ ID NO:69330 and 69331) upstream of PAM sequences is shown.
Figure 12:
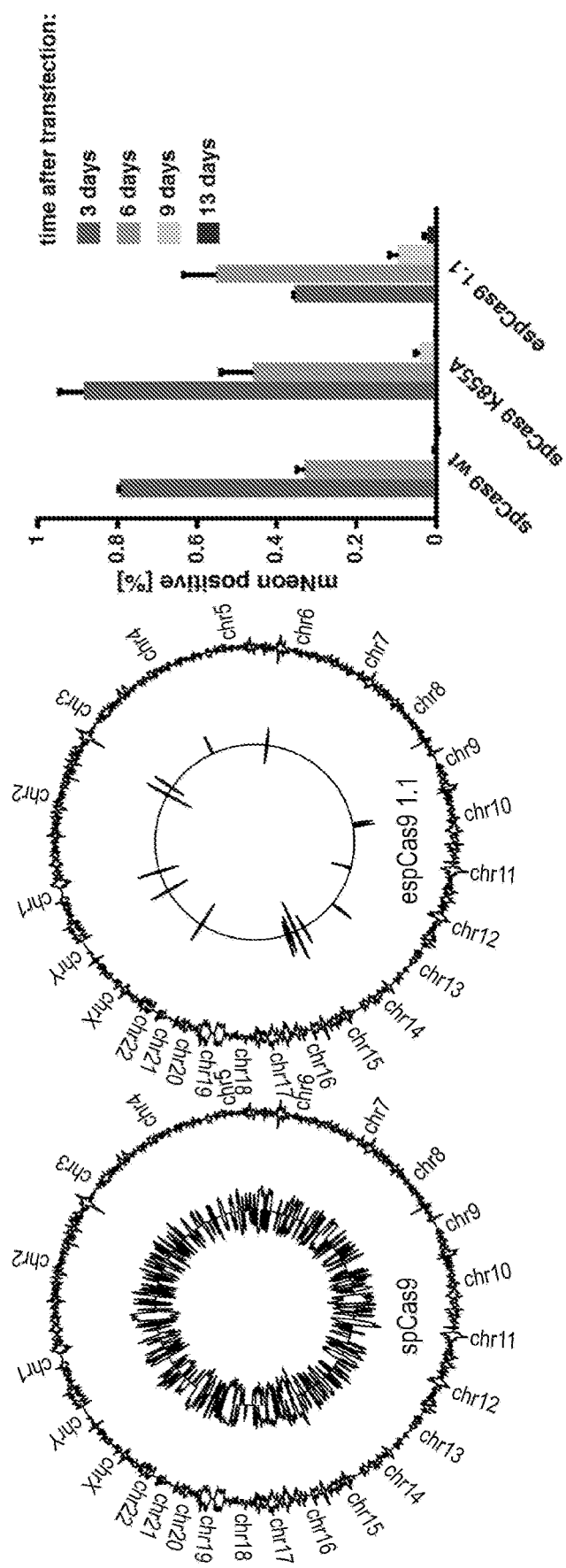
FIG. 12—Shows a comparison of integration site number and toxicity in tagging experiments using spCas9 and esp-Cas9 1.1.

Applicants performed experiments for determining the initial efficiency of tagging. FIG. 7 shows gRNA reads before and after selection. Applicants enriched for tagging by selection. Applicants transfected 15 million cells and greater than 200 genes were tagged. Applicants performed experiments to determine the cause of the low efficiency of tagging. Applicants hypothesized that there were differences in guide sequence tagging efficiency, general low tagging efficiency or low survival of tagged cells. FIG. 8 shows that 4 genes were tagged with different efficiencies and the tagged genes were lost over time. This suggested guide sequence specific toxicity after tagging. Tagging efficiency of a donor construct with and without a T7 promoter was performed for no guide sequence, as well as a guide sequence targeting the TUBB gene (FIG. 9). BFP was used to detect cells expressing Cas9. T7 did not affect the efficiency of tagging. Only about 1% of the cells were tagged in the TUBB gRNA cells. NHEJ was used to integrate the nucleic acid construct with the T7 promoter, encoding the mNeonGreen marker, a 3×FLAG site, T2A sequence, and a puromycin resistance selectable marker into the genome of the host cell. This construct allows for integration site sequencing using T7 transcription as shown in FIG. 10. Random shearing of the tagged genome was performed, followed by T7 transcription to generate RNA comprising the primer binding site and sequence correlated to the tagged gene of interest. Random-primed reverse transcription was performed to produce cDNA, followed by PCR to produce dsDNA. FIG. 11 shows 9 integration sites when no gRNA was used, while 214 off-target integration sites were found when TUBB gRNA was used. Also shown is the TUBB target site and PAM sequence, as well as exemplary off-target site sequences. The donor can be integrated in off-target sites upstream of a PAM sequence with a few mismatches. Applicants hypothesized that off-target integration can lead to toxicity. Applicants performed tagging with espCas9 1.1, which resulted in much fewer off-target integration sites as compared to spCas9. Applicants generated a library having 5000 tagged genes (FIG. 12). Applicants were also able to detect mNeonGreen positive cells after 13 days using espCas9 1.1.

Figure 21:
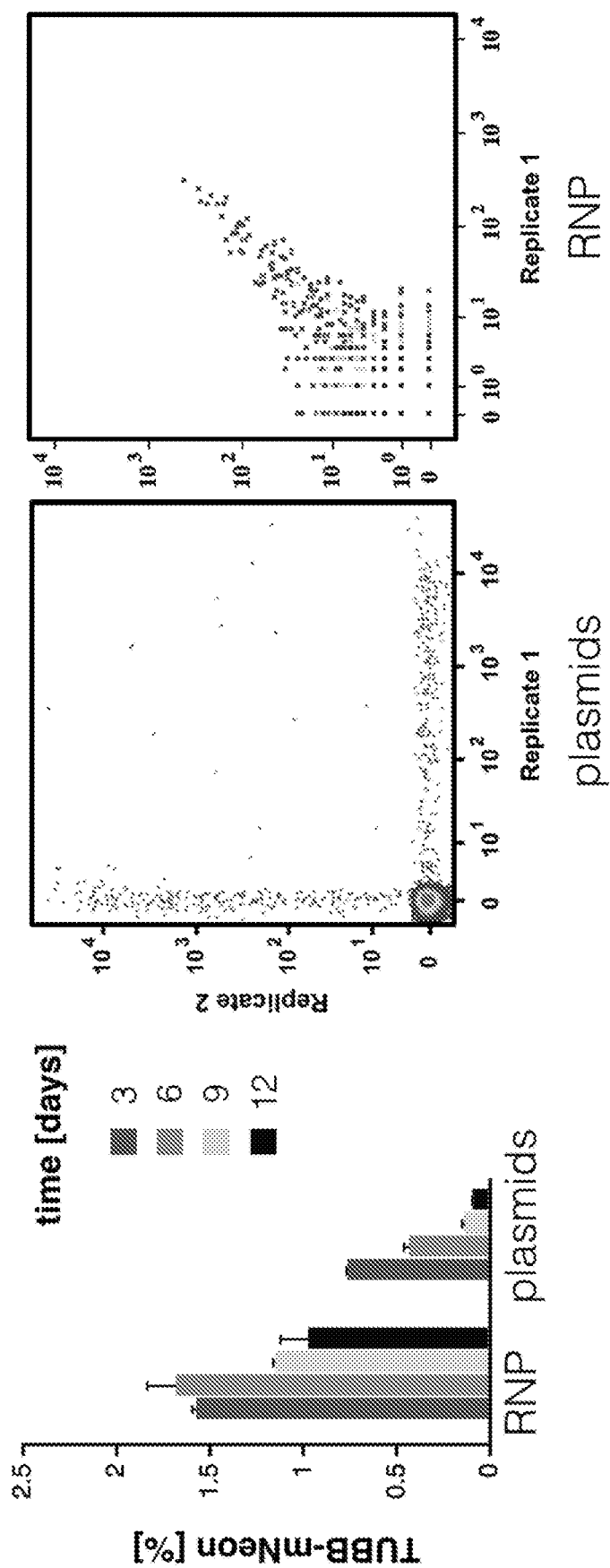
FIG. 21—Shows that RNP delivery gives rise to more efficient and more persistent tagging of an endogenous gene (left panel) and more reproducible gene representation in replicates of polyclonal tagging libraries (right panel).

Applicants have also determined that the CRISPR system may be delivered to the cell as a ribonucleoprotein complex (RNP). The RNP complex may comprise recombinant CRISPR enzyme, guide sequences (e.g., in vitro transcribed (IVT)), and the donor construct. The RNP complexes may be delivered to a population of cells by transfection. Applicants determined that tagging is less toxic by transfecting RNP complexes (Cas9+IVT-transcribed gRNA pool)+donor DNA (FIG. 21).

The transfection conditions for an optimized protocol are:
mix 1:
  25 µl Optimum
  100 ng Cas9-3×NLS (from IDT)
  10 ng gRNA pool (transcribed in vitro from a PCR-amplified oligo pool by T7)
  100 ng donor DNA
mix 2:
  25 µl Optimum
  0.5 µl Lipofectamine 2000 incubate each mix for 5 minutes, mix both mixes, incubate for 20 minutes
  add 7 µl per 96-well, each containing ca. 50,000 HEK293T cells plated the day before.

Example 3—Protein Localization Using SBP

Figure 13:
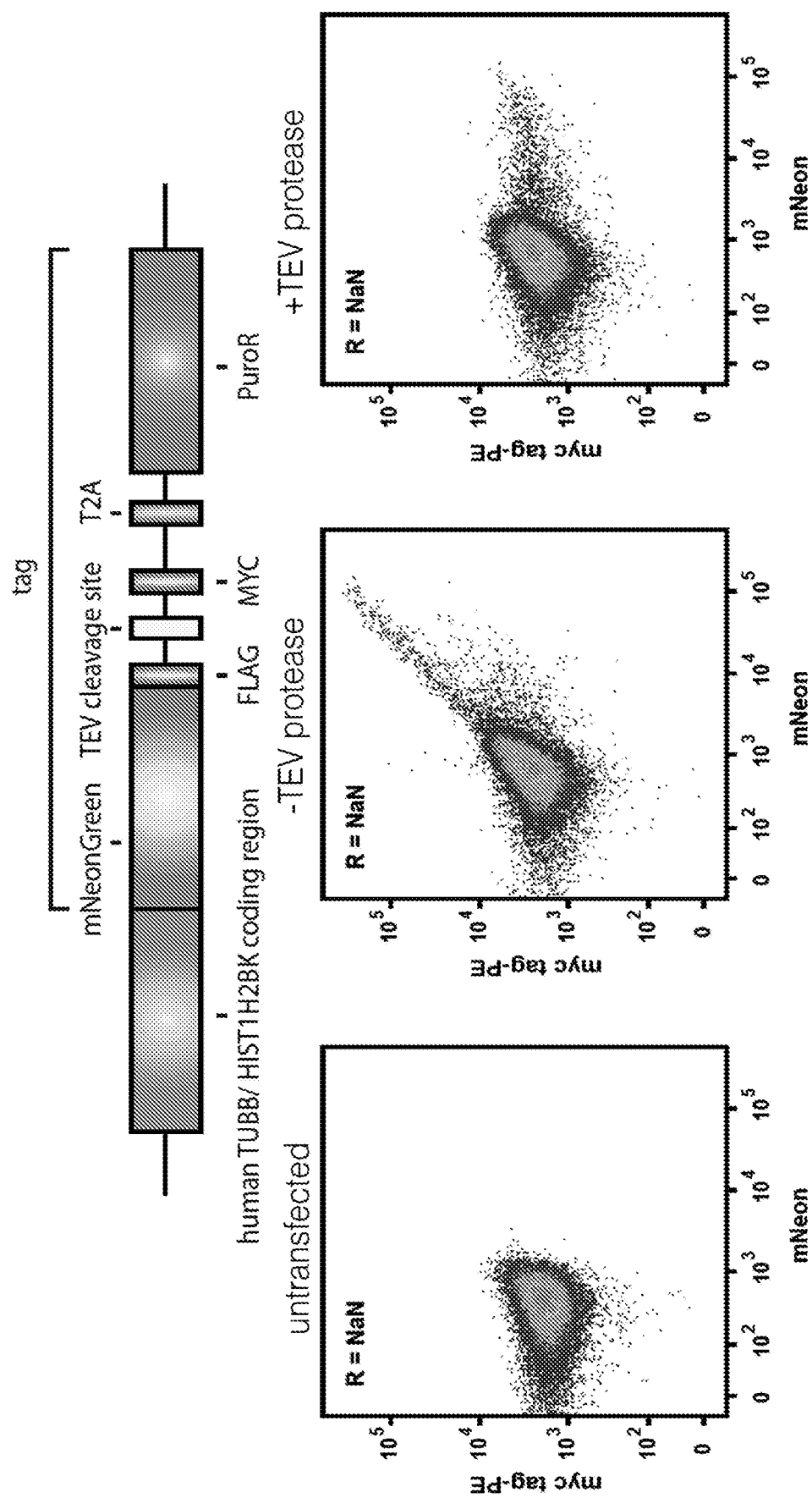
FIG. 13—Shows a protein localization reporter integrated into the TUBB gene and FACS analysis with and without TEV protease.
Figure 14:
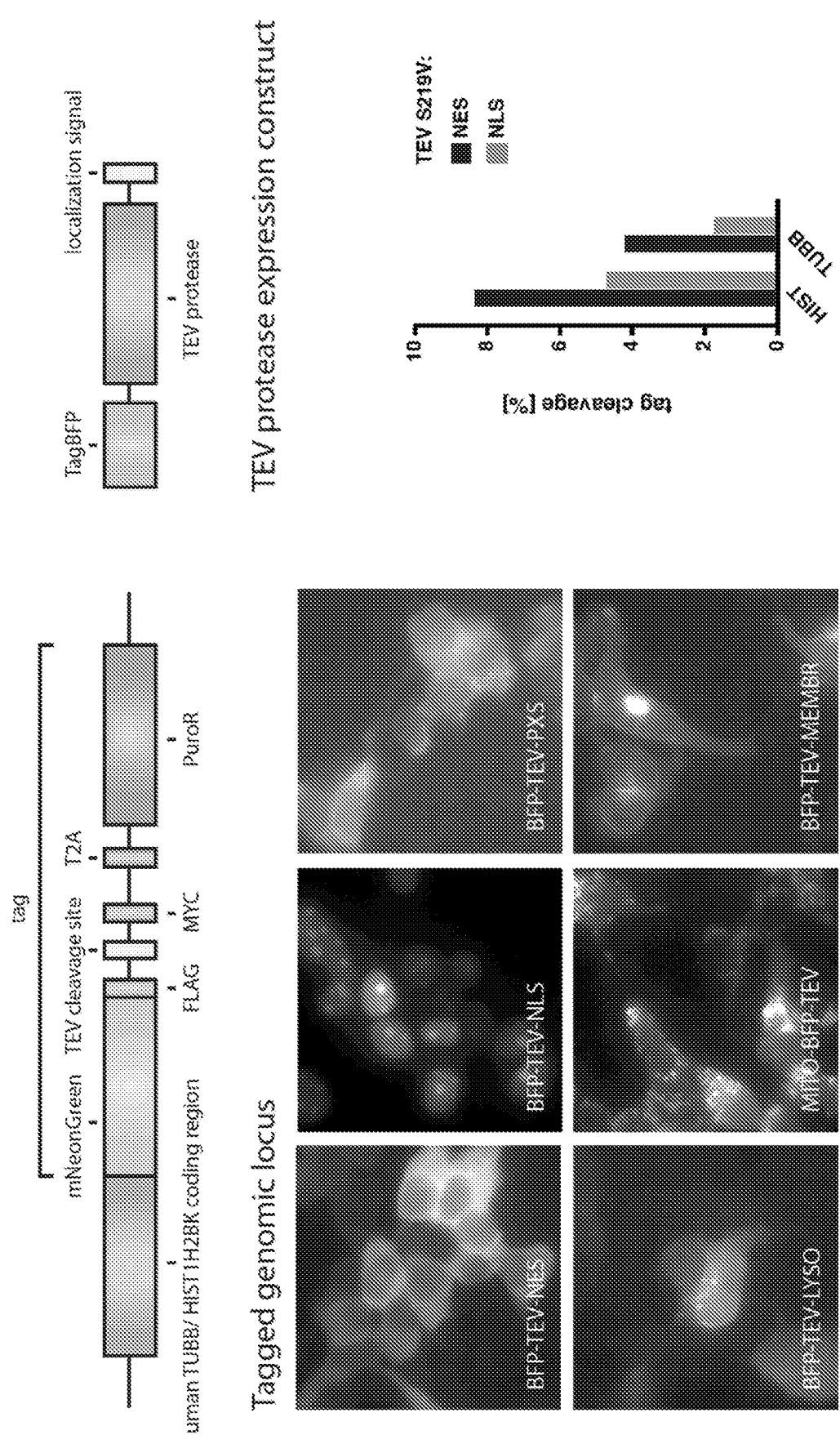
FIG. 14—Shows protein localization experiments using TEV protease expression constructs localized to organelles.
Figure 15:
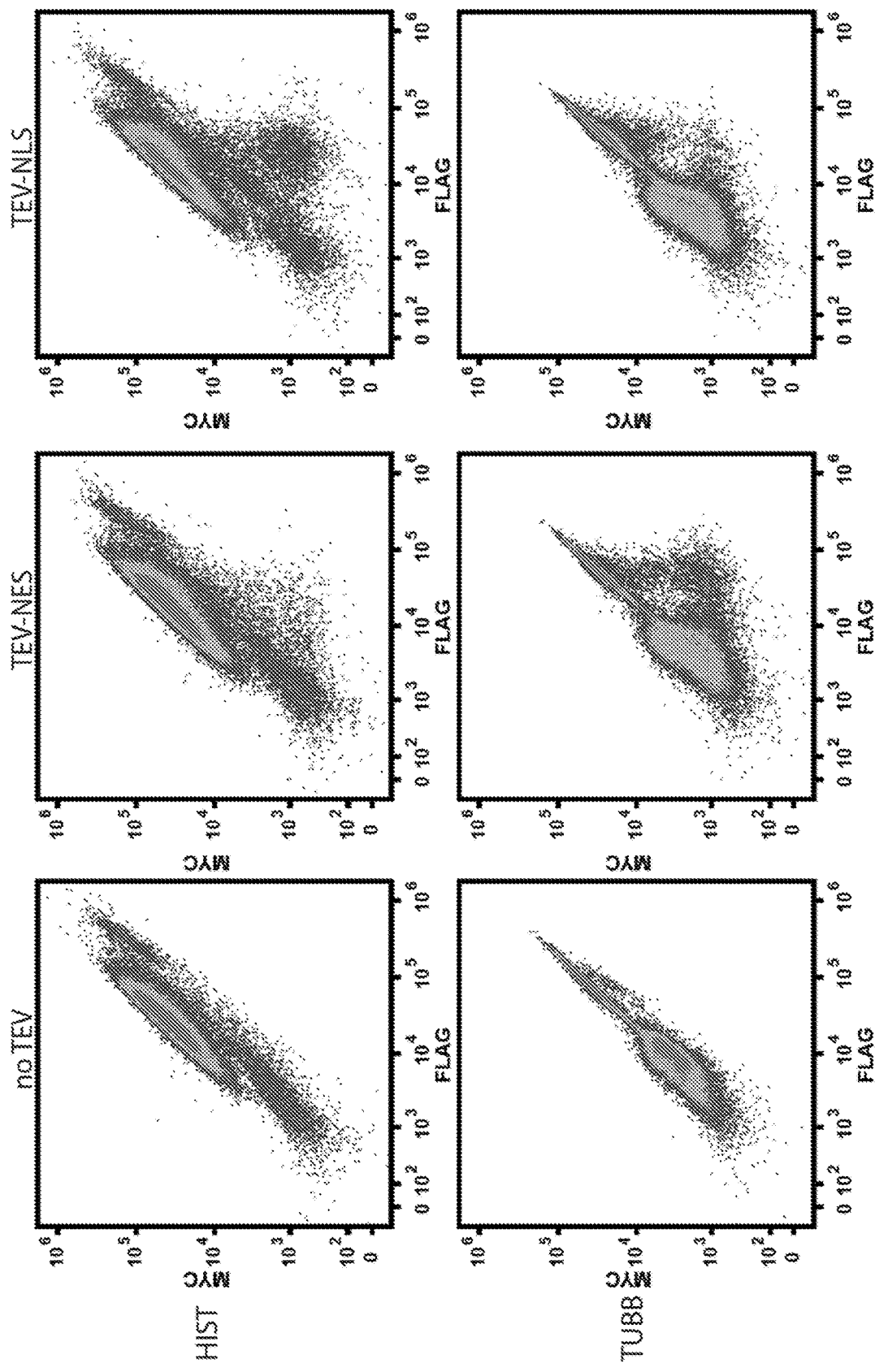
FIG. 15—Shows that the TEV S219P mutant allows localization-dependent cleavage by FACS.

As shown in FIG. 13, Applicants integrated a protein localization donor construct into human HEK 293T cells. The donor construct includes mNeonGreen and further includes a 3×flag epitope, a TEV cleavage site followed by a MYC epitope, all in frame with the target gene of interest (e.g., TUBB or HIST1H2BK). FACS analysis was performed with and without TEV protease. Without TEV protease, tagged cells are positive for myc and mNeonGreen. With TEV cells are positive for mNeon only. The TEV protease cleaved off the myc tag. Applicants hypothesized that protein localization could be determined by using a TEV protease localized to different cellular compartments. Different TEV mutants are more stable while maintaining wild-type catalytic proficiency. In one embodiment, Applicants use the TEV S219P mutant for localization-dependent cleavage (see, e.g., Kapust et al., Protein Engineering, 2001 vol. 14, No 12 pp. 993-1000). FIG. 14 shows protein localization experiments using TEV protease expression constructs localized to organelles. The TEV protease was labeled with BFP and included a localization signal. BFP was visualized in the correct location depending on the localization signal (e.g., nucleus, cytoplasm, lysosomes, nucleus, mitochondria, peroxisomes). Moreover, MYC tag cleavage is increased for TUBB using the TEV having a nuclear export signal as compared to TEV having a nuclear localization signal. FIG. 15 shows that the TEV S219P mutant allows localization-dependent cleavage by FACS. Applicants used a nuclear protein, HIST, and a cytoplasmic protein, TUBB, to show protein localization-dependent cleavage. Shown are FACS experiments using the non-cleavable FLAG tag and the cleavable MYC tag. For HIST the MYC tag is only cleaved efficiently when using a TEV having a NLS. For TUBB the MYC tag is only cleaved efficiently when using a TEV having a NES. FIG. 16 shows bar graphs depicting that the TEV S219P mutant allows localization-dependent cleavage. The left panel shows experiments similar to FIG. 19. The right panel shows that TUBB is mainly localized to the cytoplasm, as tag cleavage is highest when TEV includes a NES (also shown are experiments with nuclear localization signal (NLS), peroxisome localization signal (PXS), lysosome localization signal (LYSO), and membrane localization signal (MEMBR).

Example 4—Integration Site Sequencing Using Tagmentation

Figure 17:
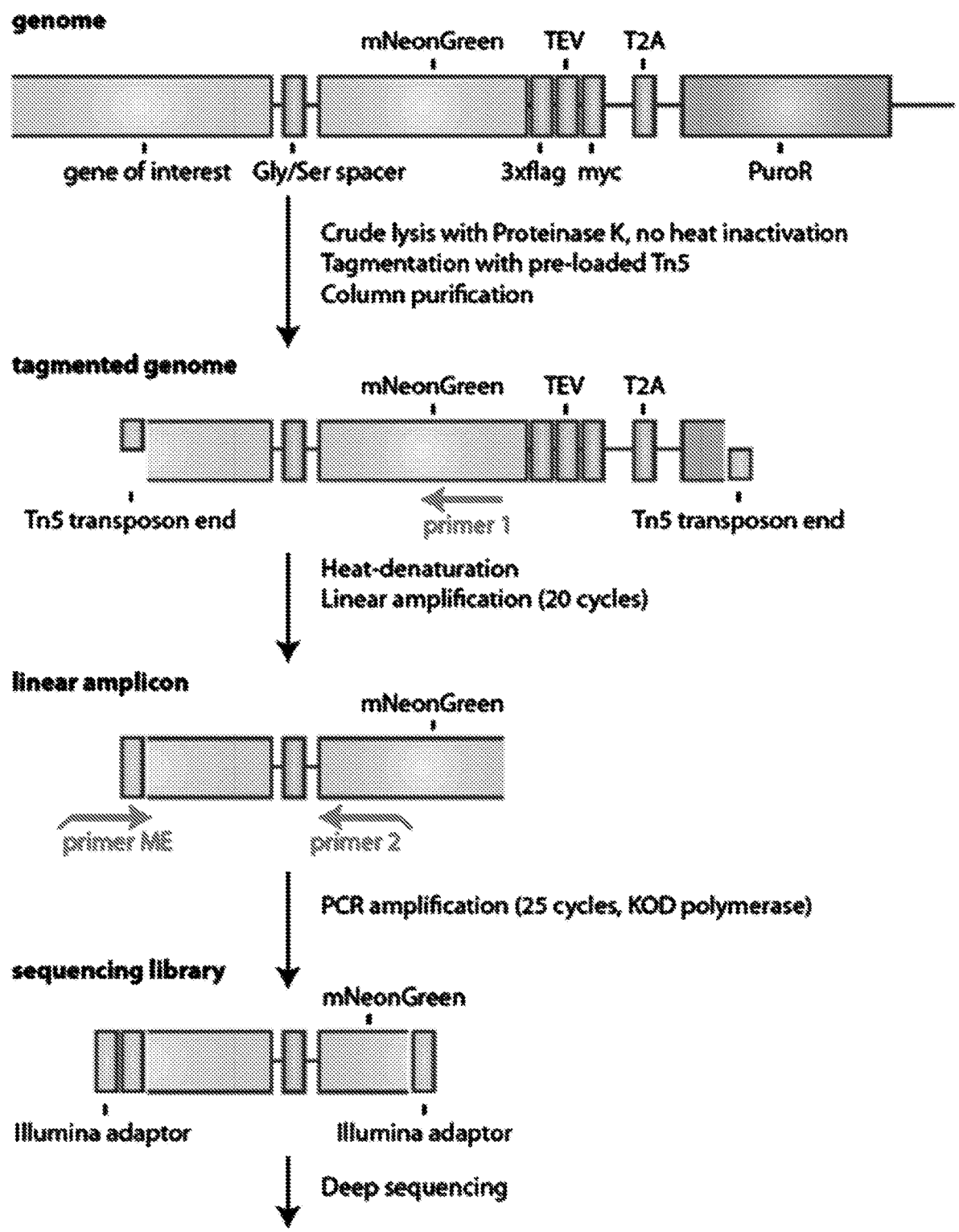
FIG. 17—Shows a schematic of a method for creating a sequencing library using tagmentation.
Figure 18:
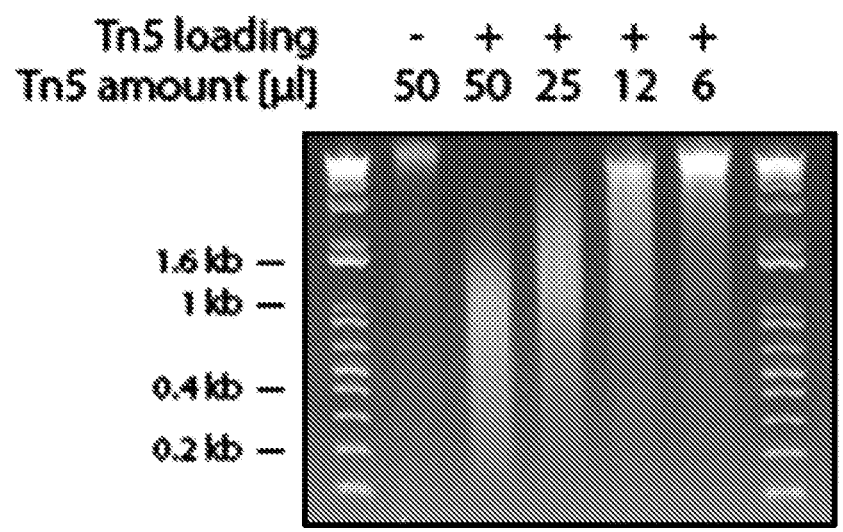
FIG. 18—Shows gel electrophoresis results of Tn5 tagmentation.
Figure 19:
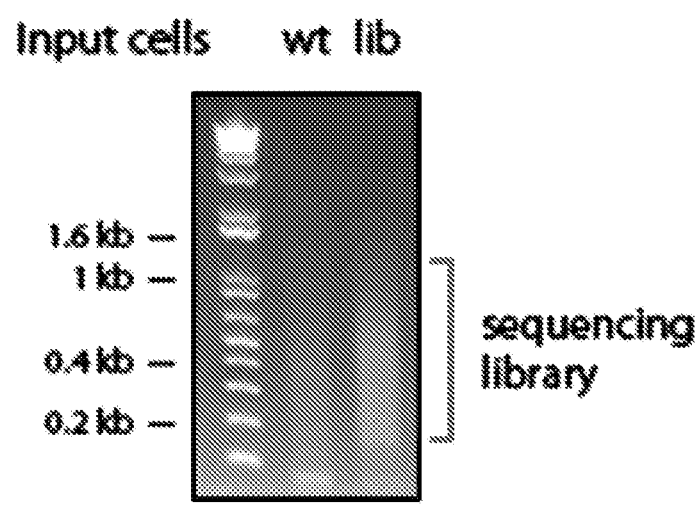
FIG. 19—Shows gel electrophoresis results of the PCR amplification to create a sequencing library with mNeon-Green marker.

FIG. 17 shows a summary of integration site sequencing using tagmentation (TagSeq). Sequencing tag integration sites was performed using Tn5-mediated tagmentation in a crude proteinase-K lysis buffer (FIG. 18). Linear amplification was then performed with tag-specific primers using a high-processivity polymerase (KOD). PCR amplification was then done using a high-processivity polymerase (KOD) and shifted primer (FIG. 19). Highly specific sequencing libraries were produced with >80% on-target reads (FIG. 20).

The tagmentation step in the TagSeq method fragments the genomic DNA and adds a constant sequence to the ends at the same time. The fragment size is controlled by the ratio of gDNA and loaded Tn5 transposase. However, Applicants found that there is a saturation of Tn5, yielding a fragment size of 100-300 bp, which is quite optimal for the TagSeq method. Therefore, Applicants can saturate any tagmentation reaction instead of calculating the optimal amount of Tn5 transposase.

Example 5—Other Exemplary Embodiments

In one exemplary embodiment, enrichment was performed on successfully tagged cells, followed by sorting of cells based on tag expression. Identification of tagged genes in each sorted bin was then performed. If desired, protein localization was measured by cleaving the tags in specific organelles using targeted TEV protease overexpression, which created a localization-dependent fluorescent signal after antibody staining. 390 proteins were able to be quantified in parallel, with TEV-dependent localization producing robust results for control genes.

In another embodiment, barcoding of cells can be performed using combinations of fluorescent proteins. LIC-based random assembly was done on three 2A-separated fluorescent proteins (FPs) chosen in a random fashion from a large set of FPs with distinct spectra. Optionally, a biological entity could be included in the plasmids linked to barcodes (e.g., a guide sequence cassette). Sequencing may be performed on the combinations of fluorescent proteins and the biological entity using long read sequencing (e.g., Oxford Nanopore Technologies, Pacific Biosciences). Lentivirus pools were then produced from fluorescent barcodes, and cells were infected with virus and expanded in culture. Cells were analyzed using spectral flow cytometry (Sony), multi-channel flow cytometry, or spectral microscopy. Barcodes were identified from combined fluorescent spectra. Transient expression of 19 random combinations of 12 FPs was distinguished in single cells after spectral FACS at a confidence level of 94%.

Example 6—Studying Systems Immunology Using SBP

The signaling pathways governing innate immunity in human cells at the systems level can be evaluated. Specifically, SBP technology can be used to generate an etiologic map of signaling components regulated at the protein level after activation of the immune receptors RIG-I, STING, TNFR, TLRs, as well as inflammasome receptors.

Initially, mapping of the signaling pathways downstream of RIG-I and TNER activation in HEK-293T cells can be done using SBP technology, since these cells are highly permissive to CRISPR/Cas9-mediated genome editing. Custom software can be developed that allows establishment of a detailed picture of how a population of immune-competent human cells reacts to synchronous immune-stimulation over time. Identified pathways can be validated using complementary biochemical methods like immunoblotting, immunofluorescence microscopy, and mass spectrometry.

In parallel, SBP can be employed in a myeloid cell line like THP-1, Seraphina-C/EBPα, or immortalized mouse macrophages. Optimizing the technology to work in these cells can allow mapping of the etiology of signaling components after TLR or inflammasome activation, which are non-functional in HEK-293T cells. These studies can contribute to a fuller understanding of the molecular signal processing network in specialized innate immune cells and can broadly translate into a better understanding of the mechanisms of clinically relevant chronic inflammation, allowing more precise interventions.

Example 7—Studying Cell Cycle Biology Using SBP

SBP technology relies on FACS, therefore it can be combined with additional fluorescent markers to enable the characterization of the proteome in specific subsets of cells or cell states. A three-color cell cycle reporter can be employed (Lister et al., (2008) Highly integrated single-base resolution maps of the epigenome in Arabidopsis. Cell 133 (3): 523-36), allowing differentiation of individual cell cycle phases at the time of sorting the tagged library. Changes in the proteome could thus be monitored over the course of the cell cycle in tumor cell lines. Combining these measurements with genetic perturbations of potential cell cycle regulators or with the application of anti-cancer drugs, unknown regulatory mechanisms that are relevant for the boundless cell division of cancer cells and drug resistance can be studied.

Example 8—Predicting the Mechanism of Action of Small-Molecule Drugs Using SBP

An established proteome-scale library of tagged cells can be expanded and reused ad libitum. Moreover, because all subsequent steps of the SBP method, namely sorting and sequencing, are easily scalable, the method could be applied to hundreds of conditions in parallel. As such, it is realistic to screen a panel of 384 drugs with known mechanisms of action for their effects on the proteome of human cells, thus establishing a database of drug proteome fingerprints. Subsequently, a set of chemicals with unknown function or mode of action can be tested using the same pipeline. By comparing the proteome fingerprints of the unknown drugs to the fingerprints of the known drugs, predictions can be made with regards to the function and mode of action of the second set of chemicals using a similar approach as described for transcriptome fingerprinting (Liu C, et al., (2015) Compound signature detection on LINCS L1000 big data. Mol Biosyst. 11 (3): 714-22). After confirming the validity of the method using control drugs not contained in the learning set, large libraries of chemicals could be screened in order to identify novel drug candidates regulating clinically relevant cellular processes like cell division or immune signaling.

Example 9—Detection of Protein Dynamics Through DNA Sequencing

Figure 26A:
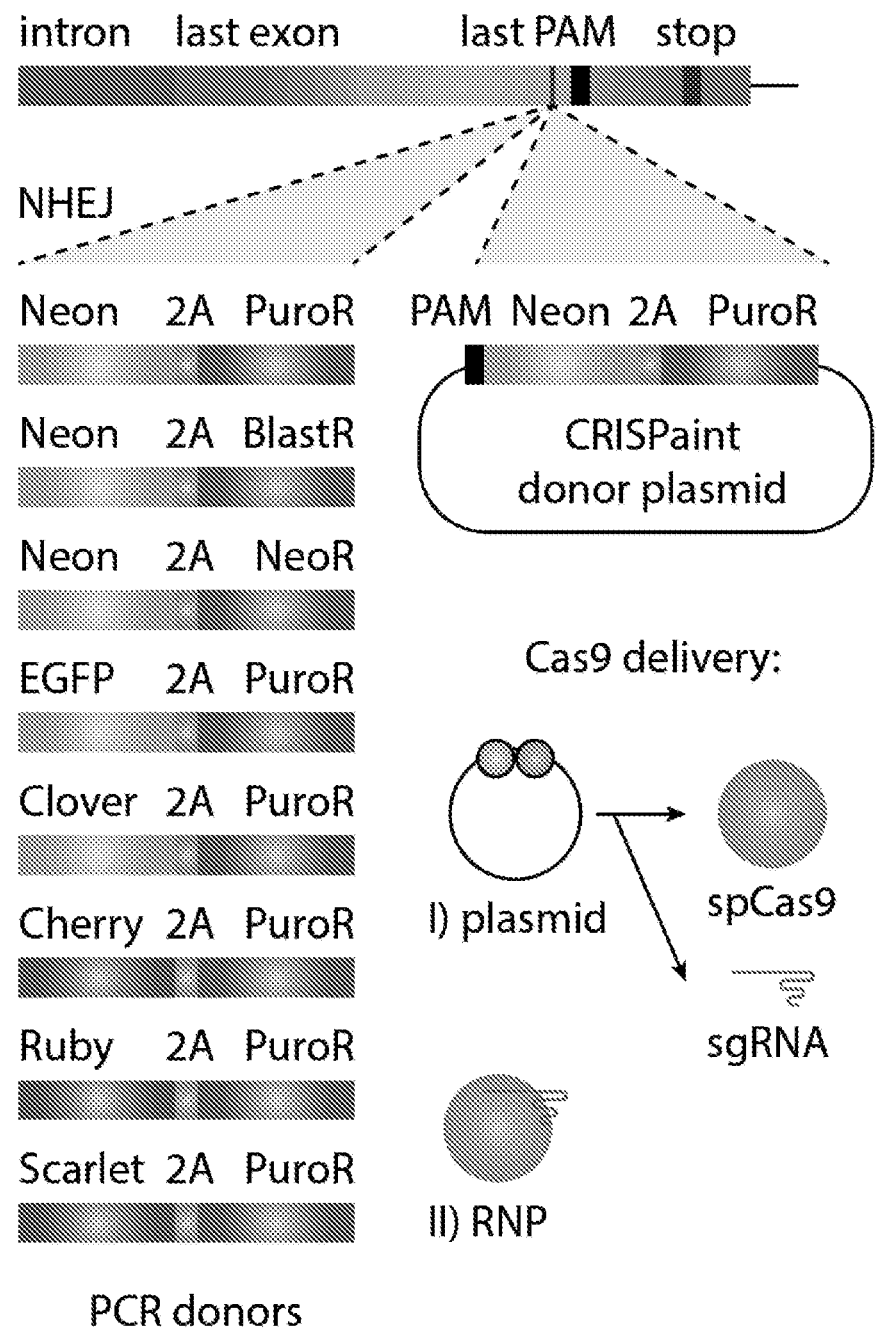
FIG. 26A-FIG. 26D—Optimization of NHEJ-mediated gene tagging.
Figures 26B, 26C, 26D:
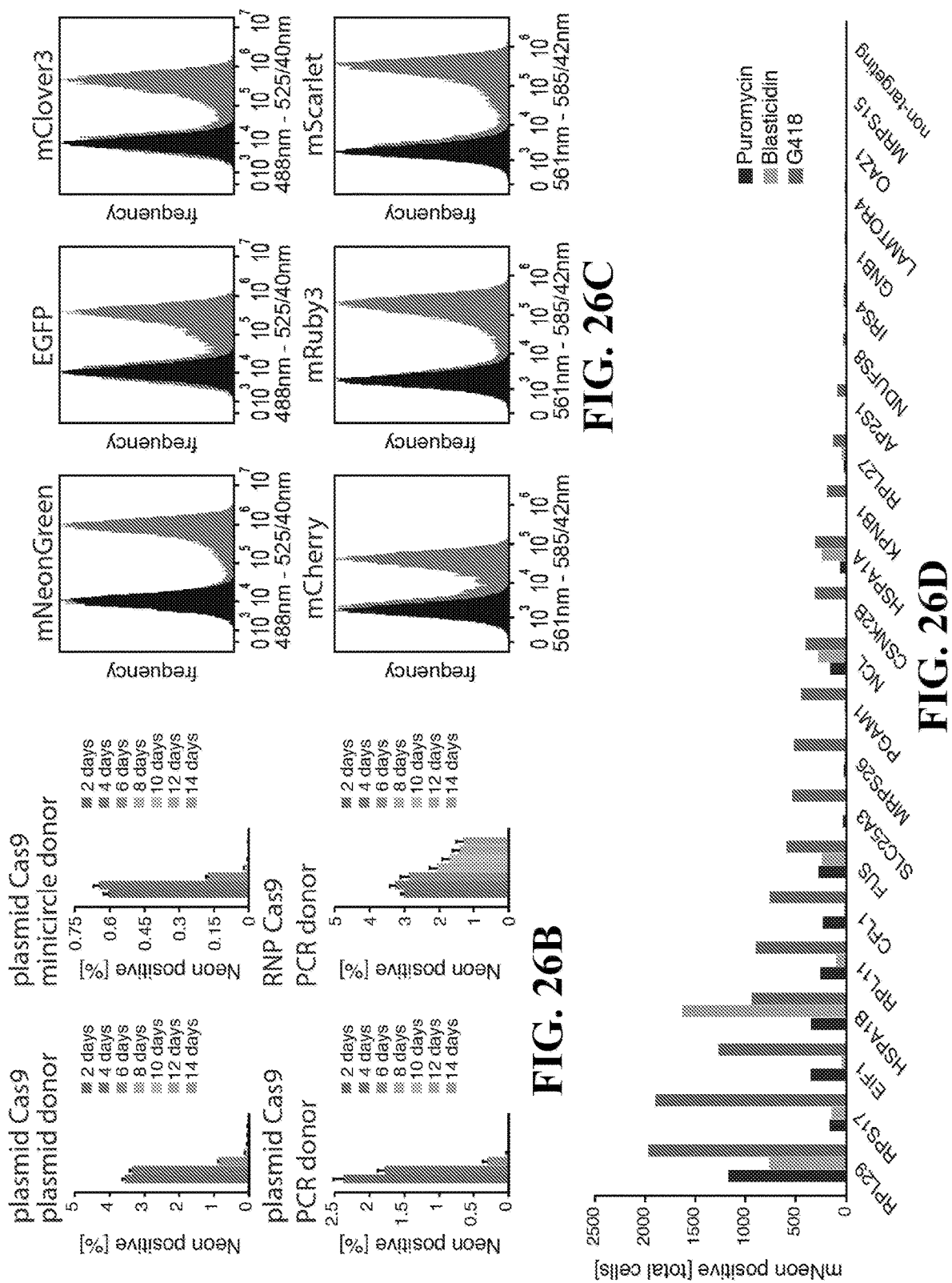

To generate a complex pooled library of human cells in which a large number of protein-coding genes is tagged with a fluorescent protein, Applicants took advantage of a previously established approach for efficient tagging of cell lines through Ligase-IV dependent tag insertion into protein-coding genes following targeted CRISPR-Cas9 cleavage (Schmid-Burgk, J. L., Honing, K., Ebert, T. S. & Hornung, V. CRISPaint allows modular base-specific gene tagging using a ligase-4-dependent mechanism. Nat Commun 7, 12338, doi: 10.1038/ncomms12338 (2016)). To parallelize this for library generation, Applicants performed several optimizations. First, comparing Cas9 and donor delivery strategies, Applicants found that RNP co-transfection with a phosphorothioate (PTO)-modified linear double-stranded DNA (dsDNA) donor yields the most sustainable gene tagging, whereas endogenous overexpression of Cas9 leads to rapid loss of tagged cells over the course of two weeks (FIG. 26a,b). Next, Applicants tagged endogenous Tubulin-beta with each of six fluorescent proteins and found that mNeonGreen and mScarlet provide the highest signal-to-noise ratios (FIG. 26c). To facilitate efficient enrichment of tagged cells for the generation of large tagging libraries, Applicants coupled an antibiotic resistance gene to the fluorescent tag using a 2A linker. However, when Applicants tested the commonly used Puromycin N-acetyl transferase as a resistance marker, the resulting library contained a limited number of highly expressed tagged genes (data not shown). Applicants therefore compared it to two other antibiotic selection markers for their ability to efficiently recover cells with an mNeonGreen-2A-resistance construct fused to each of 22 different endogenous genes in a HEK293T cell line in which the endogenous NeoR gene had been knocked out using CRISPR-Cas9. In this assay, G418 selection was superior to Puromycin and Blasticidin selection with respect to the number of tagged genes that could be efficiently recovered, indicating that Neomycin 3'-glycosyl phosphotransferase provides resistance at lower expression levels (Nakatake, Y. et al. Kinetics of drug selection systems in mouse embryonic stem cells. BMC Biotechnol 13, 64, doi: 10.1186/1472-6750-13-64 (2013)) (FIG. 26d).

Figure 22E:
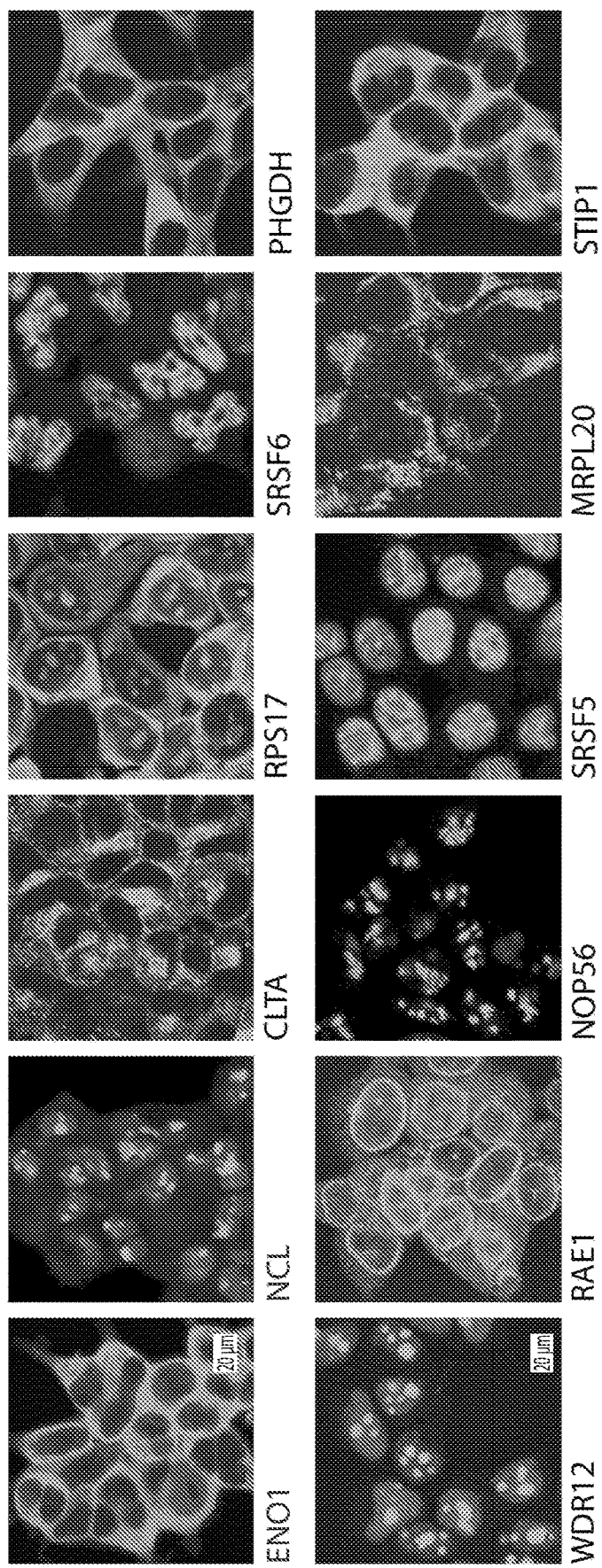
Figure 27:
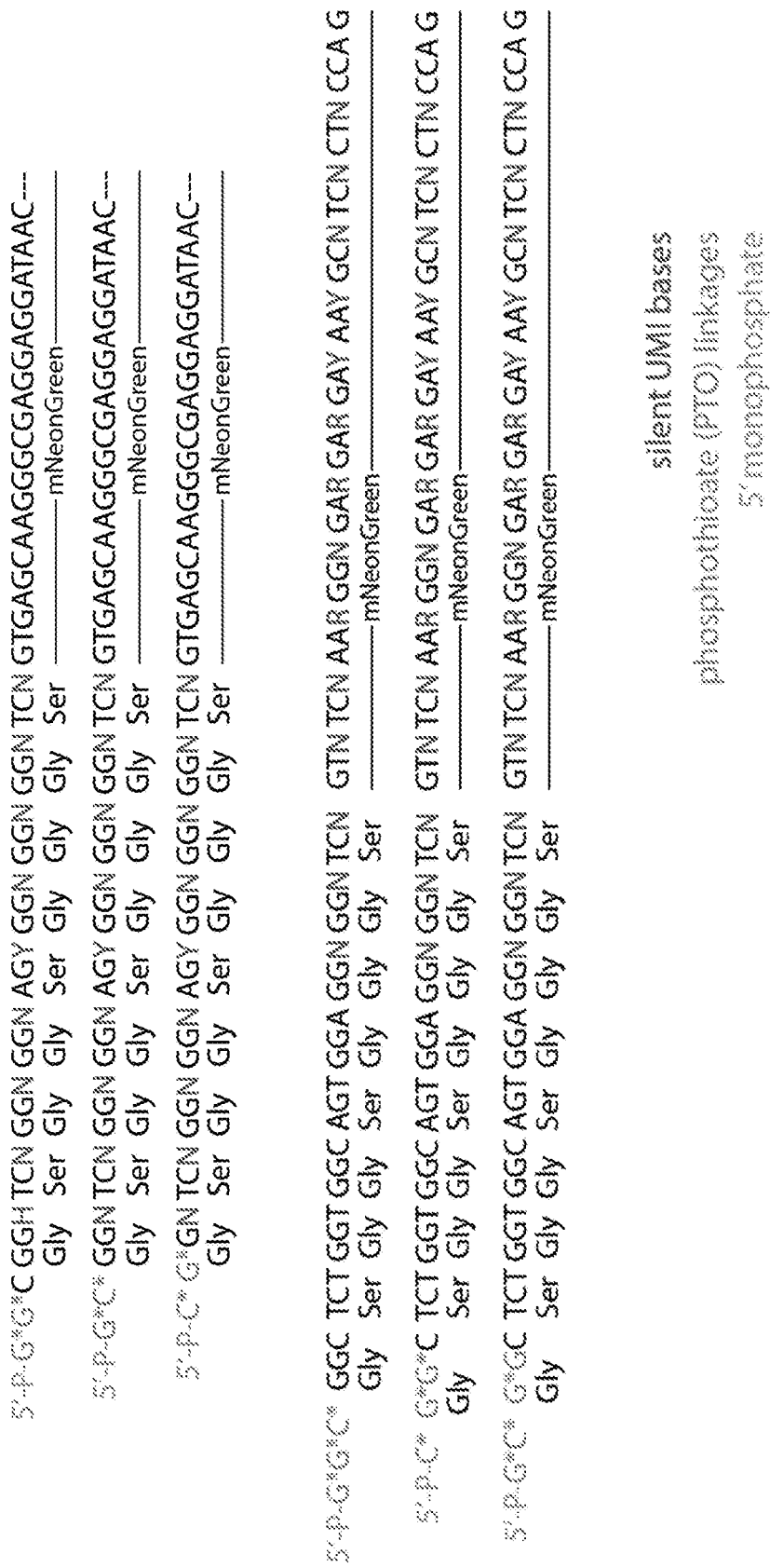
FIG. 27—Design of donor DNA for large-scale library tagging. Using modified PCR primers, the donor DNA is equipped with a 5' phosphate, two phosphorothioate-linkages on each 5' terminus, a Unique Molecular Identifier (UMI) of 9 or 14 degenerate bases incorporated without affecting the encoded amino acids (Silent Barcode), and three different 5' extensions in order to accommodate all three possible reading frames occurring among target genes. (SEQ ID NOs: 69332-69338).
Figure 28:
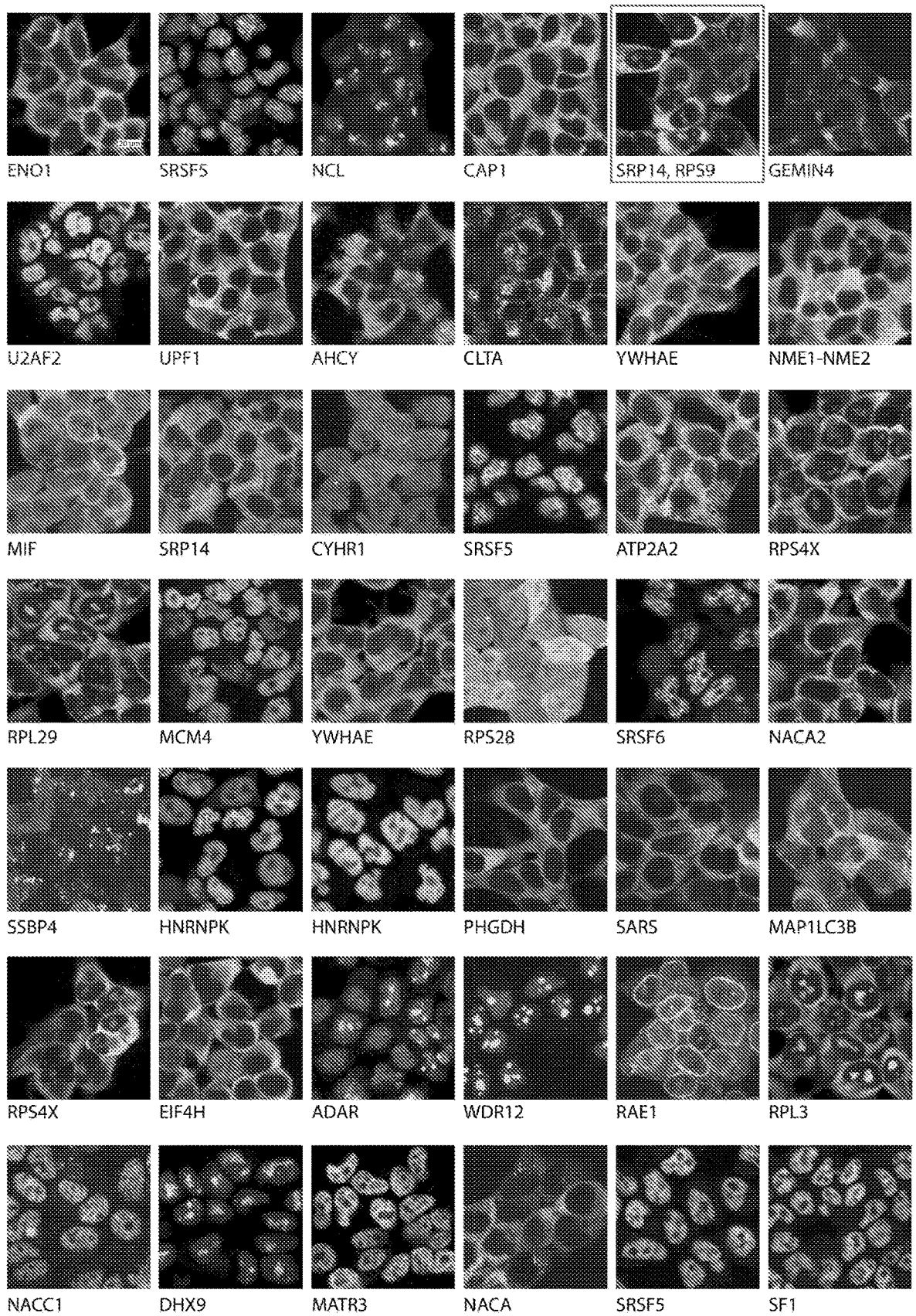
FIG. 28—Confocal microscopy images of library clones. The polyclonal tagging library was pre-sorted for mNeon expression and plated at limiting dilution conditions. After two weeks, clones were picked and duplicated, and one replicate was lysed and subjected to TTISS sequencing as described in the methods section. TTISS results are indicated as gene names below the images. Representative z-slice images from acquiring 1 μm-spaced confocal z-stacks are shown. Scale bar, 20 μm. Clones with two genes tagged are marked by a box.
Figure 28:
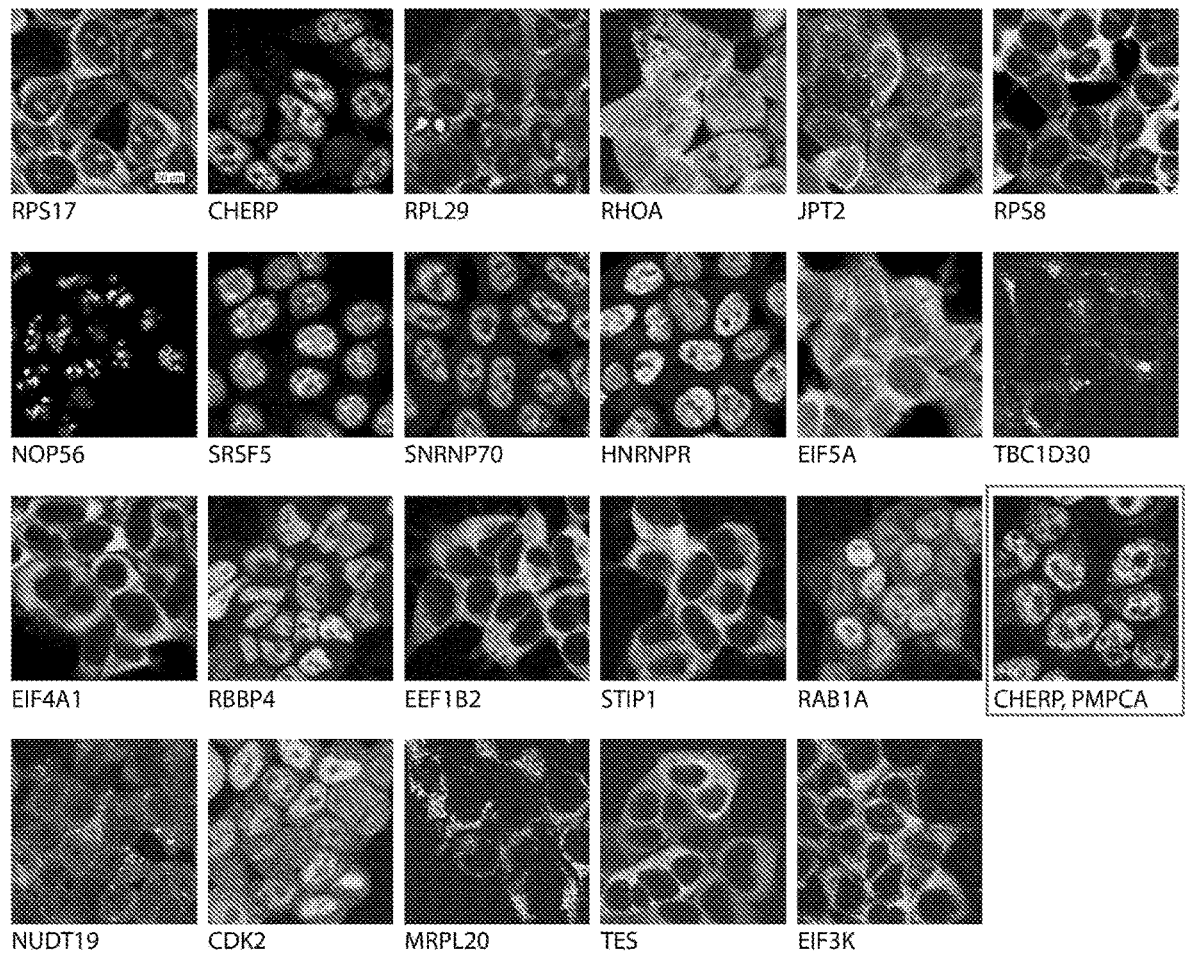

Next, Applicants applied the optimized NHEJ-based tagging protocol in a pooled fashion using a library of 23,095 sgRNAs spanning the human protein-coding genes (FIG. 22a). To verify successful tag integration in each protein-coding gene, Applicants developed a Tagmentation-based Tag Integration Site Sequencing (TTISS) method (FIG. 22a, bottom), which quantitatively identifies tag integration sites (FIG. 22b). TTISS determined that 10,085 protein-coding genes were successfully tagged in the polyclonal library (FIG. 22c). To assess individual tagging events, Applicants incorporated a Unique Molecular Identifier (UMI) in the donor by randomizing the third position of the codons in the linker (FIG. 22a and FIG. 27). Most successfully tagged genes are represented by at least two UMIs in the library, reflecting two independent tagging events (FIG. 22d). To confirm that most cells have only a single tagging event, Applicants expanded 96 single clones from the library of tagged cells by limiting dilution and both imaged them and analyzed them by TTISS (FIG. 22e, FIG. 28). Applicants observed single-gene in-frame tagging in 71/87 (81.6%) of successfully sequenced clones (9 clones could not be sequenced), and only three clones bearing two independent in-frame tag integrations (FIG. 28). The presence of these rare double-tagged clones may lead to artifacts in protein quantification due to passenger effects, where the expression of one tagged gene masks the expression of another, but because most (64.9%) tagged genes are represented multiple times in the library, such artifacts can be mitigated by UMI sequencing.

Figure 29:
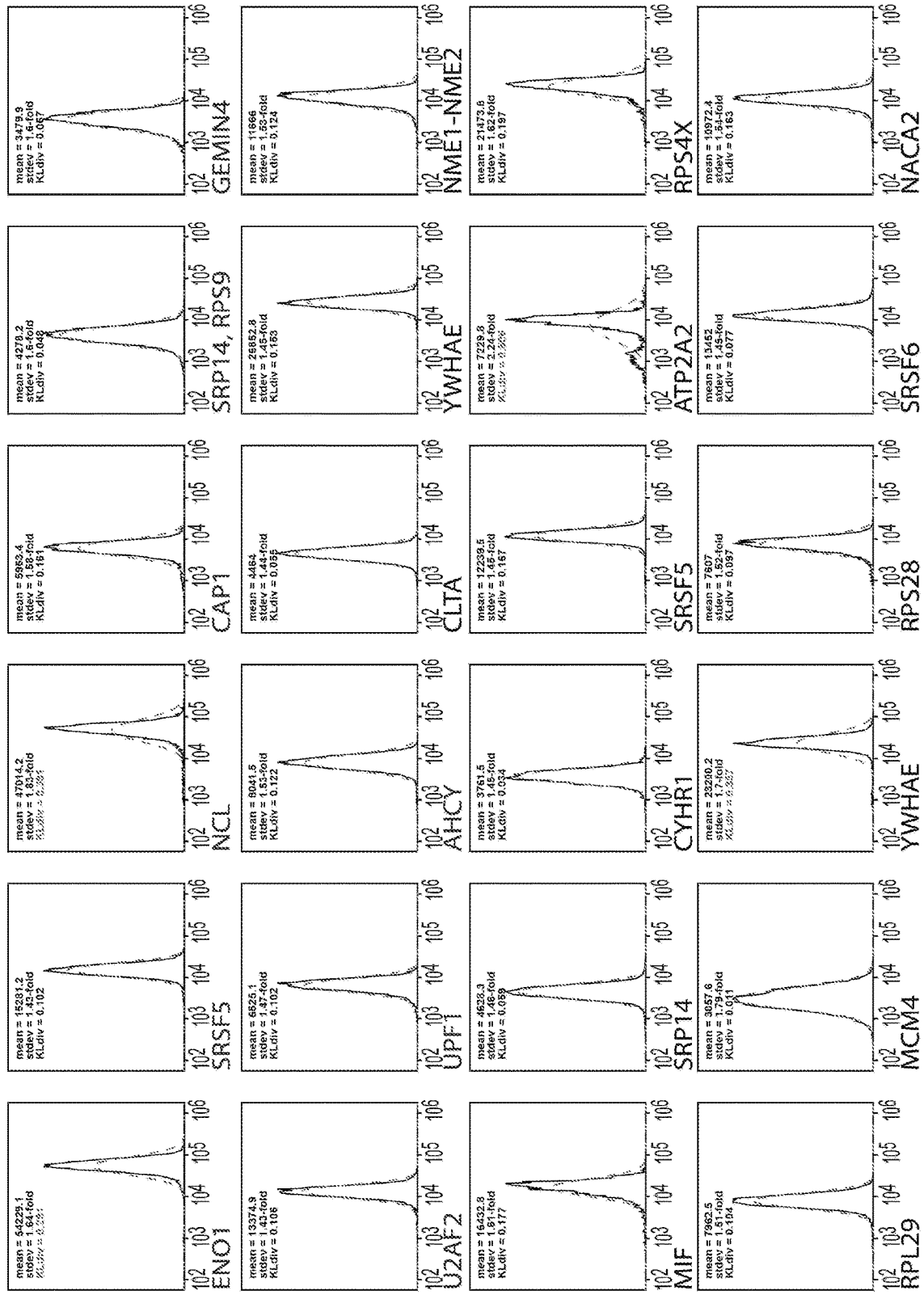
FIG. 29—FACS analysis of tagged clones. A random tagging library was pre-sorted for m Neon expression and plated at limiting dilution conditions. After two weeks, clones were picked and duplicated, and one replicate was lysed and subjected to Tagmentation-based Tag Integration Site Sequencing (TTISS) sequencing as described in the methods section. TTISS results are indicated as gene names below the plot. The same clones were analyzed using FACS. Shown are histograms of logarithmic fluorescence per cell.
Figure 29:
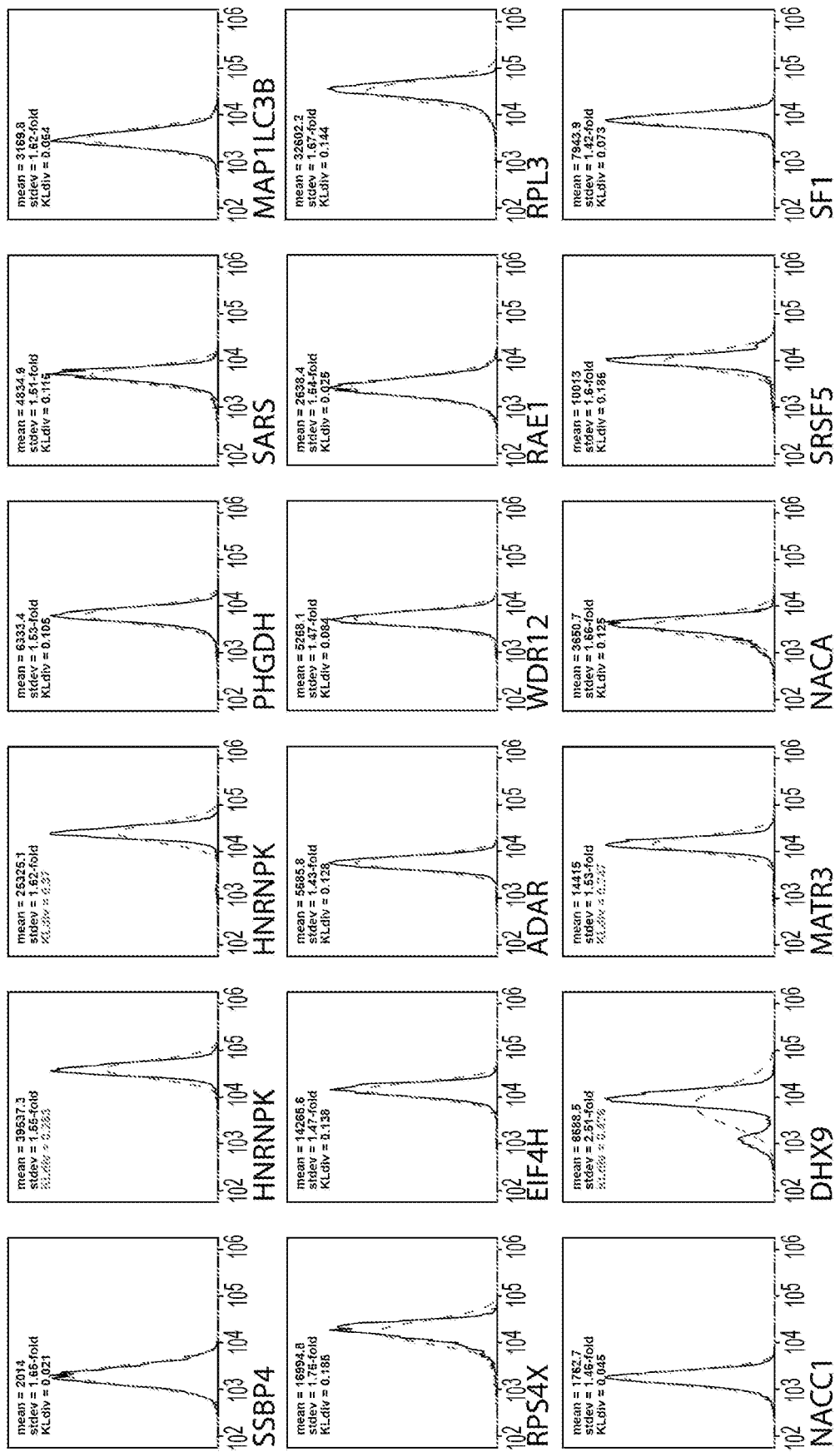
Figure 29:
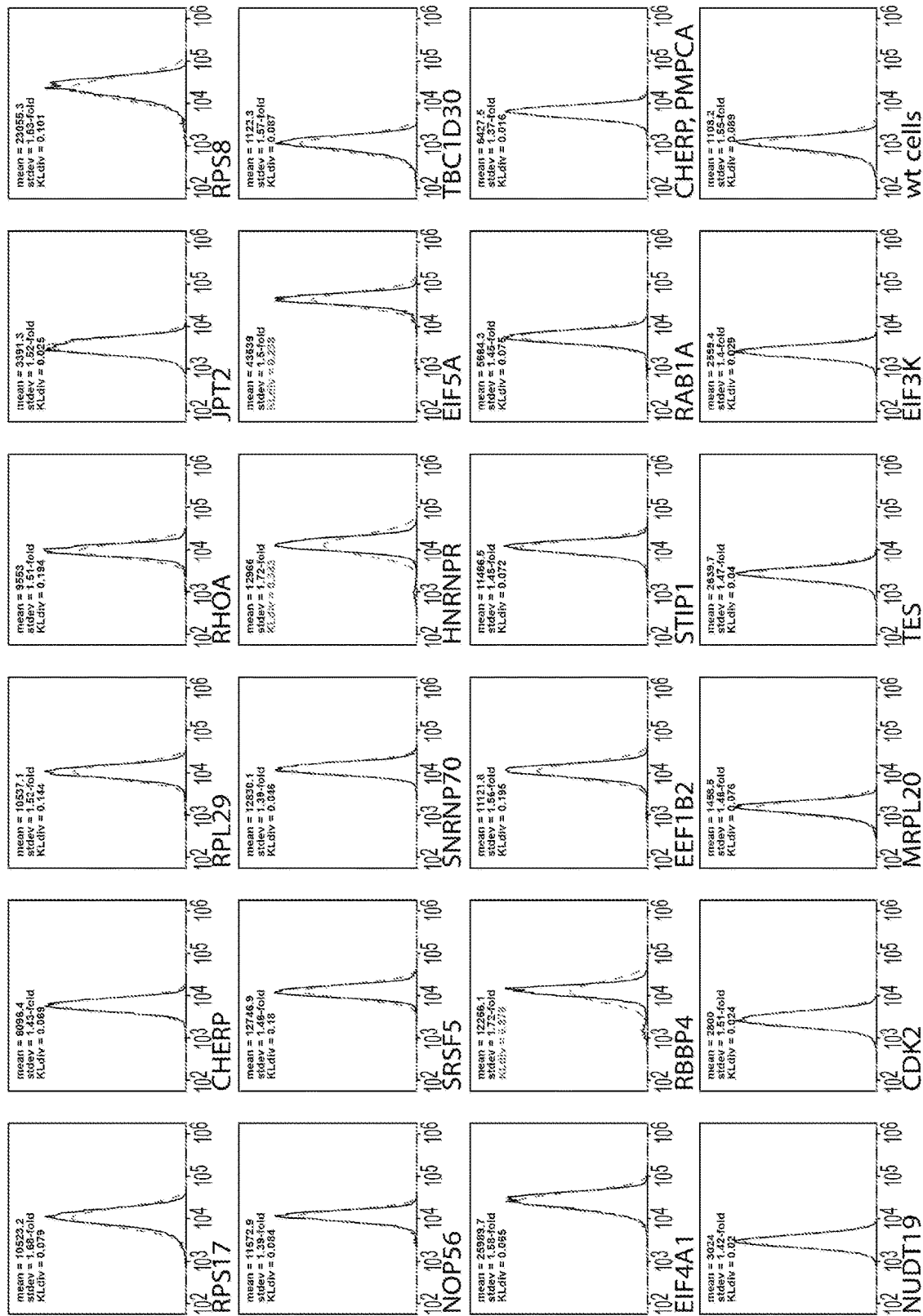

To quantify protein abundances at large scale, Applicants first confirmed that single-cell expression of most tagged proteins could be modeled by log-normal distributions (FIG. 29). When Applicants pre-enriched the library of tagged cells for detectable fluorescence, FACS-sorted it into six protein expression bins, and performed bin-wise TTISS (FIG. 23a), the distribution of individual proteins across the six bins was reproducible among sorting replicates (FIG. 23b). To quantify large numbers of proteins in the library, Applicants gated on protein representation based on the TTISS data with varying cut-offs and found that the estimated mean expression values were very highly correlated between replicates for up to 1,000 top represented proteins (FIG. 23c).

In contrast to mass-spectrometry, SBP measures the expression distribution of proteins among single cells, allowing us to identify proteins that are heterogeneously expressed across cells in a population, as well as to relate proteins to each other by the similarity of their distributions. For example, RRM2 was the most heterogeneously expressed protein in the library by its single cell expression variance (FIG. 23d, e), and Applicants confirmed its bi-modal expression using a clonal reporter cell line (FIG. 23f). Because the cells were not cell-cycle synchronized before FACS, Applicants hypothesized that this protein might be regulated in a cell-cycle dependent fashion, as has been observed for other proteins (Sakaue-Sawano, A. et al. Visualizing spatiotemporal dynamics of multicellular cell-cycle progression. Cell 132, 487-498, doi: 10.1016/j.cell.2007.12.033 (2008)). To test this hypothesis, Applicants combined SBP with two transiently expressed cell-cycle reporters (FIG. 23g) and gated cells in G1/S or S/G2 phase during FACS of the tagging libraries. Indeed, RRM2 was enriched in the S/G2 cell-cycle phase (FIG. 23h), and a clonal RRM2 reporter showed markedly reduced expression in cells with low DNA content (FIG. 23i). Applicants further validated this finding by quantifying RRM2 using western blotting of synchronized or cell-cycle phase enriched cells (FIG. 23j), confirming cell-cycle dependent protein regulation.

Figure 24B:
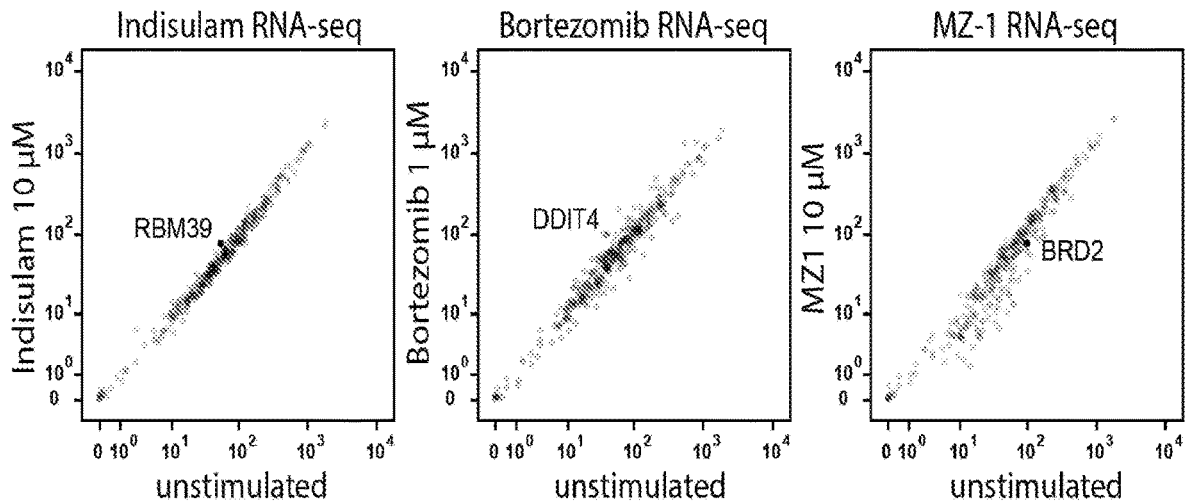
Figure 24C:
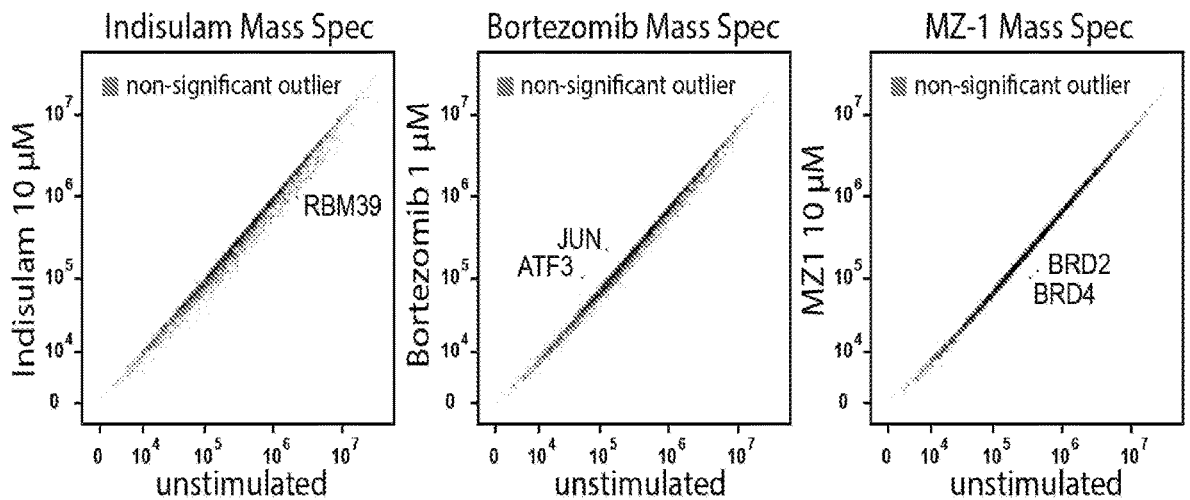
Figures 24D, 24E:
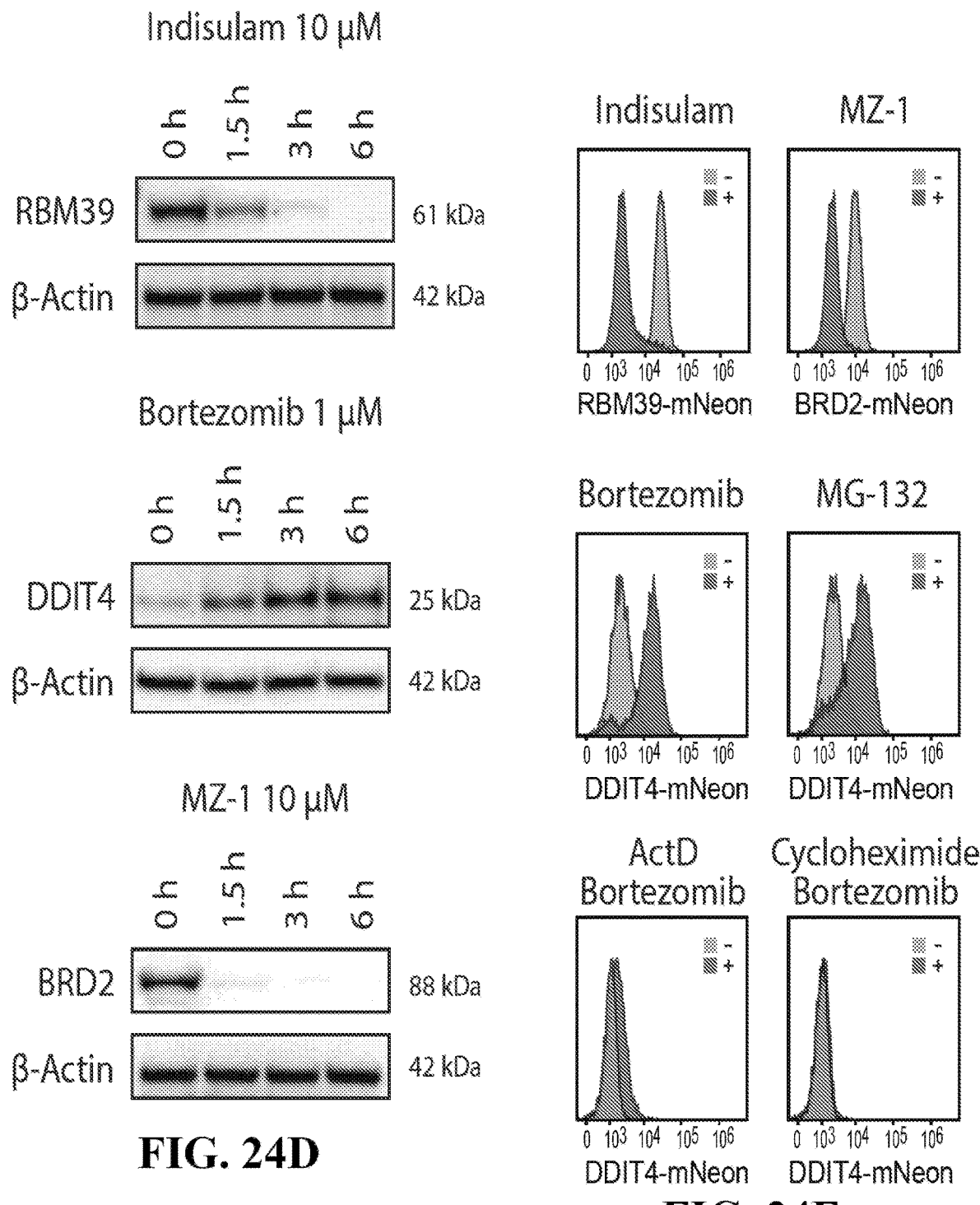

SBP can also help identify drug targets in a systematic manner, by highlighting proteins whose levels change following drug treatment, as many small-molecule drugs function by binding to and regulating cellular proteins. To this end, Applicants performed SBP using a tagging library stimulated with each of three drugs or DMSO as a control. Treatment with the first drug, Indisulam, which has shown anti-cancer activity in phase-II trials (Talbot, D. C. et al. A randomized phase II pharmacokinetic and pharmacodynamic study of indisulam as second-line therapy in patients with advanced non-small cell lung cancer. Clin Cancer Res 13, 1816-1822, doi: 10.1158/1078-0432.CCR-06-0249 (2007)), led to a highly specific depletion of the splicing factor RBM39 (FIG. 24a, left panel), which Applicants confirmed by western blot (FIG. 24d, top) and FACS of a clonal reporter cell line (FIG. 24e). Indeed, a recent study reported RBM39 degradation by Indisulam, which was discovered through studying resistance-conferring mutations in tumor cells (Han, T. et al. Anticancer sulfonamides target splicing by inducing RBM39 degradation via recruitment to DCAF15. Science 356, doi: 10.1126/science.aal3755 (2017)). Notably, SBP was highly specific: RBM39 was the only significantly depleted protein in two replicate runs (FIG. 30a, left), with a dramatically larger effect size than the next potentially depleted protein (−2.1 bins vs. −0.37 bins). This is in marked contrast to the effect at the RNA level, which showed no significant change in the level of RBM39 (FIG. 24b, left panel). In comparison, triplicate TMT-based whole proteome mass spectrometry also revealed RBM39 as a strong (2-fold down-regulated) but not statistically significant hit (FIG. 24c left, FIG. 30b, left).

Similarly, when cells were treated with another anticancer drug, the proteasome inhibitor Bortezomib, the topmost change by SBP was a strong increase (+1.6 bins) in the level of DDIT4 (FIG. 24a, middle), which, although not statistically significant in the SBP data, was confirmed by both western blot and FACS (FIG. 24d, middle, and FIG. 24e) and which is consistent with previous reports (Decaux, O. et al. Inhibition of mTORC1 activity by REDD1 induction in myeloma cells resistant to bortezomib cytotoxicity. Cancer Sci 101, 889-897, doi: 10.1111/j. 1349-7006.2009.01467.x (2010); and Barakat, D. J. et al. C/EBPbeta regulates sensitivity to bortezomib in prostate cancer cells by inducing REDD1 and autophagosome-lysosome fusion. Cancer Lett 375, 152-161, doi: 10.1016/j.canlet.2016.03.005 (2016)). Of note, Applicants also found DDIT4 to be regulated by MG-132, another proteasome inhibitor (FIG. 24e, middle right). Blocking transcription did not abolish DDIT4 up-regulation, whereas translation was required (FIG. 24e, bottom). Again, RNA-Seq could not identify DDIT4 as a target (FIG. 24b, middle), and quantitative mass spectrometry failed to quantify it, although two outliers were identified (ATF3 and JUN, neither of which are represented in the SBP library) (FIG. 24c, middle). Finally, SBP determined that the third drug, MZ-1, led to a significant decrease of its known degradation target BRD2 (Zengerle, M., Chan, K. H. & Ciulli, A. Selective Small Molecule Induced Degradation of the BET Bromodomain Protein BRD4. ACS Chem Biol 10, 1770-1777, doi: 10.1021/acschembio.5b00216 (2015)) (FIG. 24a, right, FIG. 30a, right), which Applicants confirmed by western blot and FACS (FIG. 24d, bottom, FIG. 24e). Although BRD2 could not be identified by RNA-Seq (FIG. 3b, right panel), it was a strong (2.3-fold down-regulated) albeit not statistically significant hit in mass spectrometry analysis, as was the related known target BRD4 (which is not represented in the SBP library) (FIG. 24c, FIG. 30b). All three of these proteins were tagged more than once in the library, and UMI sequencing confirmed that two or more independent clones showed altered protein levels (FIG. 31a). All regulated protein hits were observed in an independent replicate SBP screen (FIG. 31b).

Some cellular protein functions are regulated by protein localization, interaction, and/or modification. To demonstrate SBP's utility for such events, Applicants performed the same quantification protocol on purified nuclei from the cellular tagging library (FIG. 25a). Comparing the levels of protein in nuclei versus cells revealed a marked sub-population of predicted nuclear proteins (FIG. 25b), which matched literature reports for 58/61 clones (95.1%) and the confocal imaging of library clones for 16/16 (100%) of clones (FIG. 25c and FIG. 28).

SBP allows scalable and specific protein quantification and localization in single cells using commonly available laboratory equipment, providing a new tool for delineating the cellular responses induced by drugs, chemicals, endogenous signaling molecules, pathogens, irradiation, or specific genetic perturbations. SBP is scalable at all levels: cell libraries are generated by a pooled transfection approach, and screened in a pooled manner as well. Furthermore, the ability to seamlessly integrate SBP with additional fluorescence-based reporters for cellular states, such as cell cycle, offers a new approach for exploring the heterogeneity of populations of cells at the level of the proteome. SBP is specific and accurate, due to the redundancy of the library, which reduces false positives, a feature that could be further improved by scaling up the library complexity. Currently, uneven representation of genes in the library might be caused by a combination of gRNA-dependent IVT efficiency, gRNA-dependent Cas9 efficiency, gene expression allowing efficient G418 selection, and random sampling by starting with a limited number of cells.

SBP can be readily extended to other cell lines, and can thus generate diverse cell line resources. In some cases, it could also be applied in vivo, for example by generating a library ex vivo and transferring it into a mouse model, followed by cell isolation or by assays in situ (Feldman, D. et al. Pooled optical screens in human cells. bioRxiv, doi: 10.1101/383943 (2018)). An important enhancement would be to increase SBP's sensitivity, which is currently limited by fluorescence signal intensity over auto-fluorescence. This can be addressed by using a small epitope tag combined with antibody staining, which could also reduce possible impacts of tag addition to overall protein structure. Cas9 variants with engineered PAM recognition motifs matching the three stop codons TAG, TAA, and TGA would reduce the number of amino acids lost due to tagging to a maximum of one amino acid. Moreover, use of these PAM variants would expand the landscape of taggable proteins, which is currently restricted to ~94% of the human proteome because of the PAM requirement for targeting Cas9. By leveraging the power of next-generation sequencing, which has transformed our ability to monitor the genome and transcriptome, SBP opens the way for routine large-scale analysis of the proteome.

Example 10—Scalable Analysis of Proteome Dynamics Using Barcoded Gene Tagging

Cellular responses to the environment are ultimately defined by protein dynamics. Although RNA sequencing is a powerful tool that can be used as a proxy for understanding these dynamics, mapping the flow of information through cellular signaling pathways requires direct, scalable measurements of protein abundance, localization, and post-translational modification, which cannot be obtained through transcriptomics. To analyze these parameters, a number of methods have been developed based on either affinity reagents, tagged protein overexpression[1], or mass spectrometry [2]. However, high-quality validated antibodies or aptamers do not exist for all human proteins[3,4], tagged overexpression is inherently prone to causing artifacts, and whole-proteome mass spectrometry is technically challenging and has limited sensitivity[5]. In yeast, genome-scale protein tagging libraries have enabled powerful in-depth studies of the proteome[6,7], and there has been some progress toward systematically tagging genes in human cells lines[8-11], but the approaches that have been reported to date are low throughput and not amenable to pooled analyses, limiting their scalability. Applicants therefore sought to develop an approach that leveraged the accessibility of sequencing technology to directly readout protein dynamics to answer questions about protein stability, localization, and translation. To accomplish this, Applicants first generated a library of human cells containing thousands of protein-coding genes endogenously tagged with a fluorescent protein. In addition, each tag contains a silent identifier DNA sequence, which enables pooled screening approaches for downstream proteome analysis. By subjecting this library of tagged cells to FACS and sorting cells into bins ranging from low to high protein levels and then sequencing the silent identifiers in each bin, Applicants developed a scalable method, which Applicants call PATTERNS (Proteome Analysis Through Tagging Endogenous pRoteiNs and Sequencing), for assessing mammalian proteome dynamics in single cells.

To achieve the scalability needed for large-scale protein analysis, Applicants leveraged CRISPR-mediated NHEJ tagging to generate a polyclonal library of tagged HEK293T cells. Applicants adapted a Ligase-IV dependent approach[12,13] for pooled genome-scale library generation by optimizing the transfection of Cas9 RNPs loaded with a pool of guide RNAs spanning the human protein-coding genes and an mNeonGreen donor (FIGS. 32A and 26A-D). Applicants used 23,095 single guide RNAs (Table 2), each targeting as close as possible to the C-terminus given Cas9 PAM constraints, as it has been found that C-terminal tagging is generally less disruptive to protein expression and localization than N-terminal tagging[14]. The mNeonGreen donor also contains a silent random barcode within the coding sequence to allow efficient sequencing-based deconvolution of the library for downstream protein identification (FIG. 27). To assess successful tag integration, Applicants developed a tagmentation-based sequencing method (FIG. 32A) that efficiently identifies tag integration sites and their corresponding silent barcodes (FIG. 32B). Using this method, Applicants determined that among two library transfection replicates (FIG. 32C), the representation of tagged loci was highly correlated (FIG. 32D). In the combined library of cells, most tagged loci (72.9%) were represented by at least two independent tagging events (FIG. 32C). 11,290 out of 18,823 targeted protein-coding genes were successfully tagged, with an average loss of 5 amino acids per protein. Tagging frequencies weakly correlated with gene expression levels, as assessed by RNA-sequencing (FIG. 36B).

To develop PATTERNS, Applicants subjected the library of tagged cells to FACS, sorting cells into eight bins spaced equally based on fluorescence levels. Then Applicants sequenced the cells in each bin using the silent barcode to obtain a distribution of protein levels (FIG. 32A,E,F). Sorting the same library of cells twice gave highly reproducible distributions (FIG. 33F). Applicants used these distributions to obtain quantitative mean protein levels gauged by immunoblotting (FIG. 37). Although the majority of protein coding genes was successfully tagged in the library, the broad distribution of tagging efficiencies as well as technical limits imposed by FACS sorting could reduce the number of proteins reliably quantified by PATTERNS. To assess this, Applicants first ranked proteins by their representation in the library and then examined the correlation between the mean protein levels between two sorting replicates. Applicants found that PATTERNS could reproducibly quantify correlate up to 4,000 proteins (R=0.971) (FIG. 32G). Protein quantification results were also highly correlated for the overlapping top-1000 represented proteins between libraries of cells from two independent transfection replicates (FIG. 38A). Comparison of protein quantification results obtained with PATTERNS to RNA expression data showed poor correlation, as has been reported for other protein quantification data 15 (FIG. 38B).

A key advantage of PATTERNS is that it measures the distribution of protein levels in a population of single cells, allowing identification of proteins that are heterogeneously expressed. Applicants identified several proteins that clearly displayed broadened or bimodal distributions, suggesting these proteins are present at different levels in different cells (FIG. 33A). As the cell population was not synchronized, Applicants reasoned that proteins with bimodal distribution patterns may be cell-cycle regulated, and indeed, two of the identified hits, CDT1 and Geminin, are known cell-cycle regulated proteins employed as reporters in the two-color FUCCI system[16]. In addition to CDT1 and GMNN, RRM2 exhibited a bimodal abundance distribution, suggesting it is also cell-cycle regulated. Applicants validated this observation using an RRM2 reporter cell line, which recapitulated the bimodal abundance distribution and showed that RRM2 levels covary with cellular DNA content (FIG. 33B,C). Applicants synchronized cells and performed western blots on RRM2 as well as two additional heterogeneously expressed hits, ID4 and MIF, all three of which exhibited cell cycle-dependent fluctuations (FIG. 33D). Because fluorescence intensities can be normalized to absolute numbers of fluorophore molecules per cell, PATTERNS also allows comparisons between the relative abundance of groups of proteins (FIG. 37). For example, Applicants find mRNA binding proteins to be more abundant than transcription factors (FIG. 38C).

PATTERNS can also provide information about the localization of proteins, which has important ramifications for their function. Applicants performed PATTERNS on PFA-fixed purified nuclei to identify nuclear localized proteins in the library of tagged cells (FIG. 34A). Applicants detected 325 nuclear proteins (13% of all quantified proteins), including all represented histone proteins (FIG. 34B). Comparing the list of nuclear detected proteins to localization data based on antibody staining, nuclear mass spectrometry, and Hyper-LOPIT methods showed strong agreement (82-95%) for these 325 proteins (FIG. 34C). Applicants note however that very lowly expressed proteins may be missed by PATTERNS, in part due to loss of fluorescence during PFA fixation. To validate the localization results, Applicants imaged 43 tagged cell lines comprising a mix of nuclear and non-nuclear localized proteins and confirmed that PATTERNS correctly predicted the localization of 95% of the imaged proteins (FIG. 34D,E).

Applicants next applied PATTERNS to identify changes at the protein level in response to small molecules, a key goal of the pharmaceutical industry. Applicants first investigated the effects of the proteasome inhibitor Bortezomib, which is used to treat progressive multiple myeloma and has been reported to have a broad effect on the proteome 17 18. Applicants treated the library of tagged HEK293T cells with Bortezomib for 6 hours, and then FACS sorted and sequenced to identify proteins whose levels changed upon drug treatment. PATTERNS identified 55 proteins significantly affected by Bortezomib (FIG. 35A). Applicants confirmed four PATTERNS hits, DDIT4, ID1, ID2, and JUN, by western blot and FACS of reporter cell lines (FIG. 35D, and FIG. 39E, middle). DDIT4/REDD1 induction has been observed in response to various stresses (arsenic, hypoxia, heat shock, and DNA damage) and has been investigated as a resistance mechanism of cancer cells during Bortezomib treatment19,20. ID1 are ID2 are negative regulators of bHLH transcription factors21, which are known to be regulated by proteasomal degradation22. Similarly, the c-Jun oncoprotein is known to be destabilized due to proteasomal degradation23. Of the 55 PATTERNS hits, only GADD45B was regulated at the transcript level (FIG. 35B). Triplicate TMT-based whole proteome mass spectrometry revealed two upregulated proteins: JUN, which is among the top hits by PATTERNS, and ATF3, which is not represented in the library of tagged cells (FIG. 35C). Similarly, when Applicants applied PATTERNS to study MZ-1, a PROTAC drug that was designed to degrade BRD proteins 24, Applicants observed degradation of two BRD protein family members, BRD2 and BRD3, among 20 significantly affected proteins (FIG. 39A-E).

Applicants next took advantage of the scalability of PATTERNS to screen for small molecules that induce protein level changes in a high-throughput manner. To this end, Applicants stimulated the HEK293T library of tagged cells with 15 pools of small molecules, each containing 80 drug-like compounds (Table 3), for 6 hours. In Pool 4, PATTERNS identified two candidate proteins, RBM39 and DDIT4 (FIG. 35E). The level of DDIT4, which is a regulator of autophagy, was affected by Bortezomib as well as most of the drug pools, suggesting the change may be non-specific, and Applicants therefore focused only on RBM39 (FIG. 35A, 41). RBM39 was recently identified as the target of the anti-cancer drug Indisulam, which was found by screening cancer cell lines for drug resistance25. Indeed, treating the library of tagged cells with Indisulam alone and then performing PATTERNS showed specific depletion of RBM39 (FIG. 39F), which Applicants confirmed by western blot (FIG. 35H) and FACS of a clonal reporter cell line (FIG. 39E, top panel). Notably, PATTERNS was highly specific: after treatment with Indisulam, RBM39 was the only significantly depleted protein in two biological replicates (FIG. 40A, left). This is in marked contrast to the effect at the RNA level, which showed no significant change in the level of RBM39 (FIG. 35F). Whole proteome mass spectrometry also revealed RBM39 as a strong (2-fold down-regulated) but not statistically significant hit (FIG. 35G, FIG. 40B, left).

Treatment of the library of tagged cells with a second pool of small molecules, Pool 5, led to changes in several proteins, including MSH6 and PRKDC, which also co-appear in one other pool (FIG. 34I, FIG. 41). In contrast to RBM39, the compounds regulating MSH6 and PKRDC were not immediately evident from the published literature. Therefore, to identify the compounds responsible for the observed MSH6 protein level changes, Applicants generated a fluorescent MSH6 reporter cell line and assayed all single compounds from respective drug Pool 5 by FACS. Three Hsp90-inhibiting compounds were identified that led to downregulation of MSH6 (SNX2112, SNX-5422, and KW-2478) (FIG. 35J). Applicants investigated the kinetics of the reduction of MSH6 levels by treating cells with SNX2112, and Applicants saw a significant depletion in MSH6 levels in under two hours (FIG. 35K, left panel), which we also observed for PRKDC (FIG. 35K, right panel).

Figure 42A:
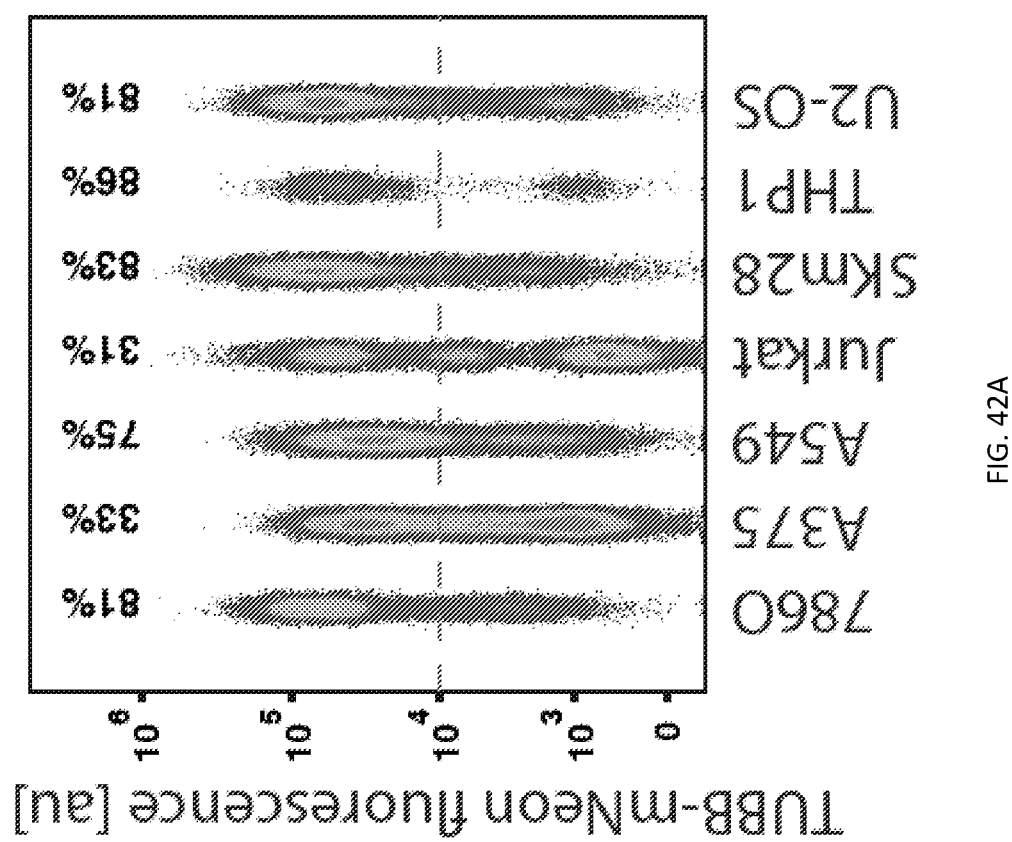

Finally, Applicants explored the feasibility of applying PATTERNS in other cells lines, which may be particularly useful for the identification of therapeutically-relevant proteins regulated by small molecules. Applicants therefore generated libraries of tagged cells in THP-1 monocytes and SKMEL28 melanoma cells by developing an electroporation protocol to achieve large-scale tagging in non-transfectable cell lines (FIG. 42A, B, F). Applicants then applied PATTERNS to these libraries of tagged cells to identify additional protein targets of small molecules. Treatment of tagged THP-1 monocytes for 6 hours with Phorbol 12-Myristate 13-Acetate (PMA) followed by PATTERNS revealed four proteins (out of 400 proteins represented in the THP-1 monocyte library) whose levels were altered by the treatment, including FOS and EGR1, which are known to be upregulated by PMA[26] (FIG. 42C-E). Similarly, PATTERNS-based quantification of 500 proteins in SKMEL28 melanoma cells revealed one protein downregulated after 6 hours of treatment with Vemurafenib (FIG. 42G-I). Together, these results demonstrate that scalable drug screening using PATTERNS in diverse cell types can provide a novel avenue to identification of specific protein degraders, which have the potential to greatly expand the range of targetable proteins[27].

PATTERNS allows quantification and localization of thousands of proteins in single cells using commonly available laboratory equipment, providing an accessible tool for delineating cellular responses at the protein level induced by chemicals, pathogens, or genetic perturbations. PATTERNS is scalable, rapid, and cost-efficient at all levels: cell libraries are generated and screened in a pooled fashion, while silent tag barcodes allow highly efficient library de-convolution using a simple PCR reaction and barcode sequencing. Furthermore, because most genes are tagged more than once during the library generation step, the resulting library of cells contains multiple clones with the same protein tagged, which creates a buffer against artifacts arising from cellular heterogeneity. Finally, PATTERNS provides information about how protein levels vary across individual cells, offering a new approach to understanding proteome dynamics at the single-cell level.

Currently, the sensitivity of PATTERNS is limited by fluorescence signal intensity over auto-fluorescence, which might be enhanced by using a small epitope tag combined with antibody staining. Such an approach could also reduce possible impacts on overall protein structure arising from addition of a fluorescent tag. Similarly, Cas9 variants with engineered PAM recognition motifs matching the three stop codons TAG, TAA, and TGA would reduce the number of amino acids lost due to tagging to a maximum of one amino acid. Moreover, use of these PAM variants would expand the landscape of taggable proteins through providing more flexibility to optimize guide design and by relaxing the PAM requirement currently restricting PATTERNS to ~94% of the human proteome.

Going forward, PATTERNS can be applied in a number of interesting ways. First, by overlaying PATTERNS data with transcriptomic data, such as in the drug screens, it is possible to rapidly distinguish between affects at the transcriptomic level from those that act on the level of protein stability and translation. Second, because a silent barcode identifier is incorporated into every tag, PATTERNS is compatible with multiplex in-situ barcode sequencing[28] and high-resolution microscopy, which will allow researchers to monitor thousands of proteins in live single cells in parallel. Third, in contrast to other proteomic approaches, cells can be subjected to PATTERNS multiple times, enabling monitoring of fluctuations in protein levels in single cells. Fourth, PATTERNS could be combined with a localization- or interaction-dependent fluorescent tag to enable large-scale studies of organellar protein localization or protein-protein interactions. By leveraging the power of next-generation sequencing, which has transformed our ability to monitor the genome and transcriptome, PATTERNS opens the way for routine large-scale analysis of proteome dynamics[19].

Example 11—Methods

Generation of sgRNA pools. DNA oligonucleotide pools with the sequence 5'-GCCAAGCATTTAGGTGACAC-TATAG-N20-GTTTCAGAGCTATGCTGGAAACAGC-3' were ordered from Twist Biosciences and resuspended in 30 µl of water (5 ng/µl), amplified using NEBNext polymerase (300 µl volume, 15 ng template, 8 cycles, Ta=65° C.) using primers SP6-fwd and gRNA-rev, and purified using a PCR purification column (Qiagen) (Sequences of genomic target site, adjacent mapping sequence, and oligonucleotide sequences are listed in Table 2 and SEQ ID NOs: 1-69285). 80 ng template product was used in a 20 µl IVT reaction (HiScribe SP6 kit, NEB) and incubated for 4 h at 37° C. RNA was purified using a PCR purification column (Qiagen), measured using a NanoDrop (Thermo) spectrometer, and re-annealed in 0.1× annealing buffer (IDT) by ramping from 95° C. to room temperature over 12 minutes.

Generation of donor DNA. Three separate PCRs were performed using NEBNext polymerase, with primers Donor-mNeon-UMI-PTO-fwd+0/+1/+2 and Donor-NeoR-PTO-rev (Table 1 and SEQ ID NOs: 69286-69328), template plasmid pCRISPaint-mNeon-T2A-NeoR (SEQ ID NO: 69341) for 30 cycles with Ta=65° C. PCR products were purified using 100 µl of PCR volume per PCR purification column (Qiagen). Typical yields were 5-10 µg DNA per column. Clean PCR products were verified using agarose gels and quantified using a NanoDrop spectrometer.

RNP-mediated gene tagging. 25,000 HEK293T NeoR-KO cells were plated per well in a 96-well plate. The next day, 100 ng SpCas9-3×NLS (IDT), 10 ng sgRNA, and 100 ng donor DNA were mixed with 25 µl OptiMEM (Thermo). In parallel, 0.5 µl Lipofectamine 2000 was mixed with 25 µl OptiMEM. After five minutes, both solutions were mixed and incubated for 20 minutes. 8 µl transfection mix were added per well in a 96-well plate. The cells were analyzed after two days of incubation. For the generation of complex tagging libraries, the protocol was scaled up linearly.

Library-scale RNP-mediated gene tagging. On day one, 18 million HEK293T NeoR-KO cells were plated per 15-cm dish into 32 dishes. On day two, 4 ml of scaled-up transfection mix (see above) were gently added per dish. On day seven, cells were trypsinized and re-plated in media containing 300 µg/ml G418 (Invivogen). The selection media was changed every 4-8 days. On day 25, the library was pre-enriched for detectable fluorescence by FACS sorting, gating on the top-30% mNeon-positive population. The library was expanded for a week and frozen for future use.

RNP-mediated gene tagging in other cell lines. Non-confluent cells were trypsinized and/or washed and adjusted to a density 2E7/ml in warm OptiMEM. 125 µl of cell suspension were mixed with 125 µl OptiMEM containing 2.5 µg donor DNA, 2.5 µg Cas9 protein, and 250 ng sgRNA. The mix was incubated for 15 minutes at room temperature, and transferred to a 4 mm electroporation cuvette (BioRad). Cells were electroporated on a Gene Pulser Xcell Electroporation System (BioRad) using the following settings: 265V, 975 µF, and 720 Ohm. Cells were recovered immediately in 5 ml of pre-warmed growth medium. For library generation in THP-1 and SKMEL28 cells, the above protocol was scaled up 10-fold.

Antibiotic selection. Puromycin was added to a final concentration of 3 µg/ml (4 days), Blasticidin was added to a final concentration of 15 µg/ml (4 days), or G418 was added to a final concentration of 300 µg/ml (7 days). Selection was carried out for 4 days. During G418 selection, cells were replated once every three days.

Transposition-based Tag Integration Site Sequencing (TTISS). 800,000 cells were resuspended in 80 µl direct lysis buffer (1 mM CaCl$_2$), 3 mM MgCl$_2$, 1 mM EDTA, 1% Triton X-100, 10 mM Tris pH 7.5, 0.2 mg/ml Proteinase K), lysed at 65° C. for 10 minutes, and kept on ice or frozen at −20° C. 25 µl 5×TAPS buffer (50 mM TAPS-NaOH pH 8.5, 25 mM MgCl$_2$), and 21 µl transposon-loaded Tn5 (16 mg/ml, produced as described in Picelli, S. et al. Tn5 transposase and tagmentation procedures for massively scaled sequencing projects. Genome Res 24, 2033-2040, doi: 10.1101/gr.177881.114 (2014), titrated batch-wise for optimal fragment sizes) were added, mixed well, and incubated at 55° C. for 10 minutes. The reaction was mixed with 625 µl buffer PB (Qiagen) and purified using a plasmid miniprep column (Qiagen). Typical yields were 15 µg per column. The tagmentation size distribution was verified on an agarose gel to range from 200 bp to 1 kb. All DNA from a single column was used as template in a 300 µl KOD extreme hot start PCR (Roche) with primers TTISS-mNeon-fwd1 and Tn5-Loading-R2 (Table 1), 12 cycles, Ta=60° C. 6 µl of PCR reaction was used as template in a secondary 50 µl KOD extreme hot start PCR with a unique combination of barcoded primers TTISS-mNeon-fwd2-D50× and TTISS-rev2-D70x(Table 1), 20 cycles, Ta=65° C. Barcoded PCRs were pooled on ice, purified using a PCR column (Qiagen), and run on an agarose gel. Products of 250 bp-1 kb were excised, purified using a gel purification kit (Qiagen), and re-purified using a PCR column (Qiagen). Samples were quantified using a NanoDrop spectrometer and sequenced using a NextSeq High Output kit (Illumina) with 30% PhiX spike-in and the following read settings: 120 cycles read 1, 25 cycles read 2, 8 cycles index 1, and 8 cycles index 2.

TTISS data analysis. For whole-genome tagging detection, 25 bp forward (fwd) reads and 25 bp reverse (rev) reads were mapped to the human genome sequence (hg38) using BrowserGenome.org while not allowing mismatches. For silent barcode dictionary generation, 25 bp fwd reads and 25 bp rev reads were mapped to 75 bp windows of the human genome sequence (hg38) upstream of all gRNA target sites of the library while not allowing mismatches, and hits were filtered to be in-frame with the annotated overlapping ORF (RefSeq). Silent barcode bases from successfully mapped reads were extracted and converted to a 28-bit hash value, which was stored in a table together with its target gene information. When quantifying unique library coverage, barcodes with a Hamming distance of 1 were collapsed in order to account for sequencing errors. All software was written as interactive web tools in JavaScript that is available online.

Alternatively, 22 bp forward (fwd) reads and 8 bp reverse (rev) reads were aligned to 1 kb windows of the human genomic sequence (hg38) upstream of gRNA target sites not allowing mismatches, and hits were filtered to be in-frame with the annotated ORF (RefSeq). For gRNA-wise protein quantification, counts per gRNA from six adjacent sorted bins were used to calculate the weighted mean bin and variance. For UMI-based evaluation, a dictionary of UMIs was created per sequencing run by calculating a 28-bit hash of nine UMI bases together with one constant donor base and 22 target bases from successfully aligned fwd reads using the same alignment parameters as for gRNA-wise protein quantification. The hash was used to count UMI occurrences and store UMI sequence/target information in an array with typically below 10 conflicts per run. UMIs were collapsed with an edit distance of 1 in order to account for sequencing errors. The UMI dictionary was used to count bin- and UMI-wise reads using the same hash function. Counts per UMI from six adjacent sorted bins were used to calculate the weighted mean bin and variance. All software was written as interactive web tools in JavaScript and will be available through GitHub.

Microscopy. Cells were seeded on glass bottom 96-well plates two days before imaging. The medium was changed to FluoroBrite DMEM (Thermo), and images were acquired using a Nikon Eclipse Ti spinning disc confocal microscope (CSU-W1, Yokogawa) using a 40× water immersion objective.

Analytical flow cytometry. For optional genomic DNA staining, 1/20 volume of Hoechst 33342 (10 mg/ml, Thermo) was added to live cells for 15 minutes at 37° C. Cells were washed in PBS, trypsinized, resuspended in media, and analyzed on a CytoFLEX (Beckman Coulter) in 96-well plate mode.

Nuclei preparation for FACS sorting. A 15-cm dish of cells were trypsinized, PBS washed, re-suspended in 2 ml hypotonic buffer and kept on ice for 20 minutes. Cells were fixed by re-suspending, adding 280 µl ice-cold PFA 4%, thoroughly mixing, and incubating on ice for exactly one minute. 100 µl 10% NP-40 were added, the suspension was vortexed for 10 seconds, and was kept on ice for 10 minutes. 600 µl 5% BSA in PBS were added, nuclei were spun down for 5 minutes at 200 g, and were re-suspended in PBS.

FACS sorting. Cells were trypsinized, washed in Fluoro-Brite DMEM Media (Thermo) and sorted using a Sony MA900 (where not denoted otherwise) or a MoFlo Astrios sorter (for THP-1 screens, THP-1 screens, SKMEL28 screens) using a 488 nm laser. Cells were collected in 1 ml growth medium and kept on ice until pelleting and lysis.

De-convolution of sorted libraries using Silent Barcode Sequencing. Cells or nuclei were spun down and re-suspended in at least 100 µl direct lysis buffer (1 mM CaCl$_2$, 3 mM MgCl$_2$, 1 mM EDTA, 1% Triton X-100, 10 mM Tris pH 7.5, 0.2 mg/ml Proteinase K) per 1 million cells/nuclei. Samples were heated to 65° C. for 10 minutes (except in the case of nucleI, which were heated for 1 h), and subsequently incubated at 95° C. for 15 minutes. 100 µl first PCR reactions were performed using NEBNext (NEB), 40 µl lysate per reaction, primers PATTERNS-seq-fwd and PATTERNS-seq-rev (Table 1), and cycling parameters: 16 cycles, 30 seconds elongation time, 65° C. annealing temperature. 25 µl secondary PCR reactions were performed using 4 µl first PCR reaction as a template, a unique Illumina-fwd-D50× and Illumina-rev-D70× barcode primer combination (Table 1) and equal cycling conditions. PCR products were pooled, purified, and sequenced as described above for TTISS sequencing (76-cycle single-end high-output NextSeq run with dual-indexing).

Analysis of Silent Barcode Sequencing data. Silent barcode bases were extracted from raw sequencing reads and were converted to a 28-bit integer value. Using a barcode lookup table, reads were collapsed into target loci, and a matrix of screening conditions vs. sorted bins was incremented for every successfully mapped read. Total read counts in every position of the matrix were normalized by the ratio of sorted cells (from control sort for simplification) divided by total reads with correctly mapped 10 bp reverse primer sequence, which helped to even out PCR saturation artifacts. For calculating mean protein levels, normalized barcode coverage across eight sorted bins is used to calculate a linearly weighted average of previously determined bin-wise protein levels, which can be relative quantitative (e.g., arbitrary fluorescence units from FACS re-analysis of sorted bins), or absolute estimated numbers of molecules per cell. All data were analyzed using a custom JavaScript-based analysis tool that is available online.

Immunoblotting. Cells were lysed in 6-well plates in 400 µl 2×LDS buffer (Thermo) supplemented with 2×Bolt reducing agent (Thermo), heated to 95° C. for 15 minutes, and cooled on ice. 9 µl lysate was loaded per lane of Bolt 4-12% Bis-Tris Plus gels (Thermo) and run at 100 V for 1:15 h. Blotting was performed using the iBlot PVDF kit (Thermo) and program P-3 for 4 minutes. After blocking for 1 h in TBST 5% BSA, primary antibodies were bound over night at 4° C. in TBST 5% BSA. After triple washing, HRP-conjugated secondary antibodies (Cell Signaling Technology) were bound at 1:5000 dilution in TBST 5% BSA for 1 h at room temperature. Blots were imaged using Pierce ECL (Thermo) on a Chemidoc luminescence imager (Biorad). Primary antibodies used were: RBM39 clone 4G8 (Novus Biologicals), DDIT4 clone EPR18716 (Abcam), BRD2 clone D89B4 (Cell Signaling Technology), RRM2 clone 1E1 (Sigma), HRP-coupled beta-Actin clone 13E5 (Cell Signaling Technology), and cell cycle antibody cocktail (ab136810, Abcam).

Cell cycle synchronization. 625,000 HEK293T cells were plated per 6-well plate in medium supplemented with 3.5 mM Thymidine (Sigma). After 19 h, cells were washed twice in PBS and grown in medium for 9 h. Then, the medium was changed back to 3.5 mM Thymidine for 15 h, cells were washed twice in PBS, and cells were grown in medium. Western blot lysates were obtained every two hours after washing individual wells with PBS and kept frozen at −20° C.

RNA-seq. Whole-cell RNA was purified using an RNeasy Plus Mini Kit (Qiagen). Poly (A) mRNA was enriched using the Poly(A) mRNA Magnetic Isolation Module (NEB). Sequencing libraries were prepared using the NEBNext Ultra II Directional RNA Library Prep kit (NEB), quantified using a NanoDrop (Thermo), and sequenced on the NextSeq sequencer (Illumina). Reads were aligned to the human genome and gene expression was quantified using the online tool BrowserGenome.org (Schmid-Burgk, J. L. & Hornung, V. BrowserGenome.org: web-based RNA-seq data analysis and visualization. Nat Methods 12, 1001, doi: 10.1038/nmeth.3615 (2015)).

Mass spectrometry. Cells were grown and stimulated in 10 cm dishes, washed three times in cold PBS, and scraped into 1 ml 8 M urea in water per dish. Protein content of the lysates was quantified using Pierce 660 reagent and a NanoDrop spectrometer. Samples were reduced, iodoacetamide alkylated, digested with Trypsin, labeled with 10-plex TMT (VWR cat no PI90110), and combined. After SPE clean-up and volume reduction by SpeedVac, the combined sample was run on a C18 reverse phase LC using a pH 10 A buffer, and eight fractions were collected. The volume was reduced to 20 µl by SpeedVac. Each fraction was run on an EASY nLC HPLC attached to a Thermo QE-HFX mass spectrometer in nanospray configuration using a 90 minutes acquisition time. Proteins were quantified using the MaxQuant software package.

Statistical analysis. Mass spectrometry reporter intensity data were imported into Perseus software, log-2-transformed, and filtered for missing values as well as reverse peptides or potential contaminants. Data were median-subtracted and significant outliers were determined by performing two-sided unpaired t-tests, correcting for multiple testing using an FDR=5% and s0=0.1, performing 250 randomizations. PATTERNS mean protein level bin data were processed in the same way except without the filtering and normalization steps. Volcano plots were generated using the Perseus software, and all other plots were created using custom code.

Tables:

TABLE 1

Primers

| Primer name | SEQ ID NO: | Sequence |
|---|---|---|
| Donor-mNeon-PTO-fwd +0 | 69286 | /5phos/G*G*C* GGC TCT GGT GGC AGT GGA GGN GGN TCN GTN TCN AAR GGN GAR GAR GAY AAY GCN TCN CTN CCA G |
| Donor-mNeon-PTO-fwd +1 | 69287 | /5phos/C* G*G*C TCT GGT GGC AGT GGA GGN GGN TCN GTN TCN AAR GGN GAR GAR GAY AAY GCN TCN CTN CCA G |
| Donor-mNeon-PTO-fwd +2 | 69288 | /5phos/G*C* G*GC TCT GGT GGC AGT GGA GGN GGN TCN GTN TCN AAR GGN GAR GAR GAY AAY GCN TCN CTN CCA G |
| Donor-NeoR-PTO-rev | 69289 | /5phos/T*T*A TCAGAAGAACTCGTCAAGAAGGC |
| Tn5-Loading-R2 | 69290 | GTCTCGTGGGCTCGG AGATGTGTATAAGAGACAG |
| Tn5-loading-ME | 69291 | /5Phos/CTGTCTCTTATACA/3ddC/ |
| TTISS-mNeon-fwd1 | 69292 | CCGTTGATGGAGCCAAAGATGTG |
| TTISS-mNeon-fwd2-D501 | 69293 | AATGATACGGCGACCACCGAGATCTACACTATAGCCTACACTCTTTCCCTACACGAC Gctcttccgatct ATGTGTAACTCATGTGTCGCTGG |
| TTISS-nn Neon-fwd2-D502 | 69294 | AATGATACGGCGACCACCGAGATCTACACATAGAGGCACACTCTTTCCCTACACGAC Gctcttccgatct ATGTGTAACTCATGTGTCGCTGG |
| TTISS-rev2-D701 | 69295 | CAAGCAGAAGACGGCATACGAGATCGAGTAAT GTCTCGTGGGCTCGGAGATGTGT |
| TTISS-rev2-D702 | 69296 | CAAGCAGAAGACGGCATACGAGATTCTCCGGA GTCTCGTGGGCTCGGAGATGTGT |
| TTISS-rev2-D703 | 69297 | CAAGCAGAAGACGGCATACGAGATAATGAGCG GTCTCGTGGGCTCGGAGATGTGT |

TABLE 1-continued

Primers

| Primer name | SEQ ID NO: | Sequence |
|---|---|---|
| TTISS-rev2-D704 | 69298 | CAAGCAGAAGACGGCATACGAGATGGAATCTC GTCTCGTGGGCTCGGAGATGTGT |
| TTISS-rev2-D705 | 69299 | CAAGCAGAAGACGGCATACGAGATTTCTGAAT GTCTCGTGGGCTCGGAGATGTGT |
| TTISS-rev2-D706 | 69300 | CAAGCAGAAGACGGCATACGAGATACGAATTC GTCTCGTGGGCTCGGAGATGTGT |
| TTISS-rev2-D707 | 69301 | CAAGCAGAAGACGGCATACGAGATAGCTTCAG GTCTCGTGGGCTCGGAGATGTGT |
| TTISS-rev2-D708 | 69302 | CAAGCAGAAGACGGCATACGAGATGCGCATTA GTCTCGTGGGCTCGGAGATGTGT |
| TTISS-rev2-D709 | 69303 | CAAGCAGAAGACGGCATACGAGATCATAGCCG GTCTCGTGGGCTCGGAGATGTGT |
| TTISS-rev2-D710 | 69304 | CAAGCAGAAGACGGCATACGAGATTTCGCGGA GTCTCGTGGGCTCGGAGATGTGT |
| TTISS-rev2-D711 | 69305 | CAAGCAGAAGACGGCATACGAGATGCGCGAGA GTCTCGTGGGCTCGGAGATGTGT |
| TTISS-rev2-D712 | 69306 | CAAGCAGAAGACGGCATACGAGATCTATCGCT GTCTCGTGGGCTCGGAGATGTGT |
| PATTERNS-seq-fwd | 69307 | ACACTCTTTCCCTACACGACGCTCTTCCGATCT GATGTGTAACTCATGTGTCGCTG |
| PATTERNS-seq-rev | 69308 | TGACTGGAGTTCAGACGTGTGCTCTTCCGATCTCGGCTCTGGTGGCAGTGGAGG |
| Illumina-fwd-D501 | 69309 | AATGATACGGCGACCACCGAGATCTACACTATAGCCTACACTCTTTCCCTACACGACGCT |
| Illumina-fwd-D502 | 69310 | AATGATACGGCGACCACCGAGATCTACACATAGAGGCACACTCTTTCCCTACACGACGCT |
| Illumina-fwd-D503 | 69311 | AATGATACGGCGACCACCGAGATCTACACCCTATCCTACACTCTTTCCCTACACGACGCT |
| Illumina-fwd-D504 | 69312 | AATGATACGGCGACCACCGAGATCTACACGGCTCTGAACACTCTTTCCCTACACGACGCT |
| Illumina-fwd-D505 | 69313 | AATGATACGGCGACCACCGAGATCTACACAGGCGAAGACACTCTTTCCCTACACGACGCT |
| Illumina-fwd-D506 | 69314 | AATGATACGGCGACCACCGAGATCTACACTAATCTTAACACTCTTTCCCTACACGACGCT |
| Illumina-fwd-D507 | 69315 | AATGATACGGCGACCACCGAGATCTACACCAGGACGTACACTCTTTCCCTACACGACGCT |
| Illumina-fwd-D508 | 69316 | AATGATACGGCGACCACCGAGATCTACACGTACTGACACACTCTTTCCCTACACGACGCT |
| Illumina-rev-D701 | 69317 | CAAGCAGAAGACGGCATACGAGATCGAGTAATGTGACTGGAGTTCAGACGTGTGCT |
| Illumina-rev-D702 | 69318 | CAAGCAGAAGACGGCATACGAGATTCTCCGGAGTGACTGGAGTTCAGACGTGTGCT |
| Illumina-rev-D703 | 69319 | CAAGCAGAAGACGGCATACGAGATAATGAGCGGTGACTGGAGTTCAGACGTGTGCT |
| Illumina-rev-D704 | 69320 | CAAGCAGAAGACGGCATACGAGATGGAATCTCGTGACTGGAGTTCAGACGTGTGCT |
| Illumina-rev-D705 | 69321 | CAAGCAGAAGACGGCATACGAGATTTCTGAATGTGACTGGAGTTCAGACGTGTGCT |
| Illumina-rev-D706 | 69322 | CAAGCAGAAGACGGCATACGAGATACGAATTCGTGACTGGAGTTCAGACGTGTGCT |
| Illumina-rev-D707 | 69323 | CAAGCAGAAGACGGCATACGAGATAGCTTCAGGTGACTGGAGTTCAGACGTGTGCT |
| Illumina-rev-D708 | 69324 | CAAGCAGAAGACGGCATACGAGATGCGCATTAGTGACTGGAGTTCAGACGTGTGCT |
| Illumina-rev-D709 | 69325 | CAAGCAGAAGACGGCATACGAGATCATAGCCGGTGACTGGAGTTCAGACGTGTGCT |

TABLE 1-continued

Primers

| Primer name | SEQ ID NO: | Sequence |
|---|---|---|
| Illumina-rev-D710 | 69326 | CAAGCAGAAGACGGCATACGAGATTTCGCGGAGTGACTGGAGTTCAGACGTGTGCT |
| Illumina-rev-D711 | 69327 | CAAGCAGAAGACGGCATACGAGATGCGCGAGAGTGACTGGAGTTCAGACGTGTGCT |
| Illumina-rev-D712 | 69328 | CAAGCAGAAGACGGCATACGAGATCTATCGCTGTGACTGGAGTTCAGACGTGTGCT |

TABLE 2

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| A*01:01:01:01 | 1 | 23096 | 46191 |
| A*03:01:0:01 | 2 | 23097 | 46192 |
| A1BG | 3 | 23098 | 46193 |
| A1CF | 4 | 23099 | 46194 |
| A2M | 5 | 23100 | 46195 |
| A2ML1 | 6 | 23101 | 46196 |
| A3GALT2 | 7 | 23102 | 46197 |
| A4GALT | 8 | 23103 | 46198 |
| A4GNT | 9 | 23104 | 46199 |
| AAAS | 10 | 23105 | 46200 |
| AACS | 11 | 23106 | 46201 |
| AACS | 12 | 23107 | 46202 |
| AADAC | 13 | 23108 | 46203 |
| AADACL2 | 14 | 23109 | 46204 |
| AADACL3 | 15 | 23110 | 46205 |
| AADACL4 | 16 | 23111 | 46206 |
| AADAT | 17 | 23112 | 46207 |
| AAED1 | 18 | 23113 | 46208 |
| AAGAB | 19 | 23114 | 46209 |
| AAK1 | 20 | 23115 | 46210 |
| AAMDC | 21 | 23116 | 46211 |
| AAMDC | 22 | 23117 | 46212 |
| AAMDC | 23 | 23118 | 46213 |
| AAMP | 24 | 23119 | 46214 |
| AANAT | 25 | 23120 | 46215 |
| AAR2 | 26 | 23121 | 46216 |
| AARD | 27 | 23122 | 46217 |
| AARS | 28 | 23123 | 46218 |
| AARS2 | 29 | 23124 | 46219 |
| AARSD1 | 30 | 23125 | 46220 |
| AASDH | 31 | 23126 | 46221 |
| AASDH | 32 | 23127 | 46222 |
| AASDH | 33 | 23128 | 46223 |
| AASDHPPT | 34 | 23129 | 46224 |
| AASS | 35 | 23130 | 46225 |
| AATF | 36 | 23131 | 46226 |
| AATK | 37 | 23132 | 46227 |
| ABAT | 38 | 23133 | 46228 |
| ABCA1 | 39 | 23134 | 46229 |
| ABCA10 | 40 | 23135 | 46230 |
| ABCA12 | 41 | 23136 | 46231 |
| ABCA13 | 42 | 23137 | 46232 |
| ABCA2 | 43 | 23138 | 46233 |
| ABCA3 | 44 | 23139 | 46234 |
| ABCA4 | 45 | 23140 | 46235 |
| ABCA5 | 46 | 23141 | 46236 |
| ABCA6 | 47 | 23142 | 46237 |
| ABCA7 | 48 | 23143 | 46238 |
| ABCA8 | 49 | 23144 | 46239 |
| ABCA9 | 50 | 23145 | 46240 |
| ABCB1 | 51 | 23146 | 46241 |
| ABCB10 | 52 | 23147 | 46242 |
| ABCB11 | 53 | 23148 | 46243 |
| ABCB4 | 54 | 23149 | 46244 |
| ABCB5 | 55 | 23150 | 46245 |
| ABCB5 | 56 | 23151 | 46246 |
| ABCB5 | 57 | 23152 | 46247 |
| ABCB6 | 58 | 23153 | 46248 |
| ABCB7 | 59 | 23154 | 46249 |
| ABCB8 | 60 | 23155 | 46250 |
| ABCB9 | 61 | 23156 | 46251 |
| ABCB9 | 62 | 23157 | 46252 |
| ABCC1 | 63 | 23158 | 46253 |
| ABCC10 | 64 | 23159 | 46254 |
| ABCC11 | 65 | 23160 | 46255 |
| ABCC12 | 66 | 23161 | 46256 |
| ABCC2 | 67 | 23162 | 46257 |
| ABCC3 | 68 | 23163 | 46258 |
| ABCC3 | 69 | 23164 | 46259 |
| ABCC4 | 70 | 23165 | 46260 |
| ABCC4 | 71 | 23166 | 46261 |
| ABCC5 | 72 | 23167 | 46262 |
| ABCC5 | 73 | 23168 | 46263 |
| ABCC6 | 74 | 23169 | 46264 |
| ABCC6 | 75 | 23170 | 46265 |
| ABCC8 | 76 | 23171 | 46266 |
| ABCC9 | 77 | 23172 | 46267 |
| ABCC9 | 78 | 23173 | 46268 |
| ABCD1 | 79 | 23174 | 46269 |
| ABCD2 | 80 | 23175 | 46270 |
| ABCD3 | 81 | 23176 | 46271 |
| ABCD3 | 82 | 23177 | 46272 |
| ABCD4 | 83 | 23178 | 46273 |
| ABCD4 | 84 | 23179 | 46274 |
| ABCD4 | 85 | 23180 | 46275 |
| ABCE1 | 86 | 23181 | 46276 |
| ABCF1 | 87 | 23182 | 46277 |
| ABCF2 | 88 | 23183 | 46278 |
| ABCF2 | 89 | 23184 | 46279 |
| ABCF3 | 90 | 23185 | 46280 |
| ABCG1 | 91 | 23186 | 46281 |
| ABCG2 | 92 | 23187 | 46282 |
| ABCG2 | 93 | 23188 | 46283 |
| ABCG4 | 94 | 23189 | 46284 |
| ABCG5 | 95 | 23190 | 46285 |
| ABCG8 | 96 | 23191 | 46286 |
| ABHD1 | 97 | 23192 | 46287 |
| ABHD10 | 98 | 23193 | 46288 |
| ABHD10 | 99 | 23194 | 46289 |
| ABHD11 | 100 | 23195 | 46290 |
| ABHD11 | 101 | 23196 | 46291 |
| ABHD11 | 102 | 23197 | 46292 |
| ABHD12 | 103 | 23198 | 46293 |
| ABHD12 | 104 | 23199 | 46294 |
| ABHD12B | 105 | 23200 | 46295 |
| ABHD13 | 106 | 23201 | 46296 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ABHD14A | 107 | 23202 | 46297 |
| ABHD14B | 108 | 23203 | 46298 |
| ABHD15 | 109 | 23204 | 46299 |
| ABHD16A | 110 | 23205 | 46300 |
| ABHD16B | 111 | 23206 | 46301 |
| ABHD17A | 112 | 23207 | 46302 |
| ABHD17B | 113 | 23208 | 46303 |
| ABHD17C | 114 | 23209 | 46304 |
| ABHD18 | 115 | 23210 | 46305 |
| ABHD2 | 116 | 23211 | 46306 |
| ABHD3 | 117 | 23212 | 46307 |
| ABHD4 | 118 | 23213 | 46308 |
| ABHD5 | 119 | 23214 | 46309 |
| ABHD6 | 120 | 23215 | 46310 |
| ABHD8 | 121 | 23216 | 46311 |
| ABI1 | 122 | 23217 | 46312 |
| ABI2 | 123 | 23218 | 46313 |
| ABI3 | 124 | 23219 | 46314 |
| ABI3BP | 125 | 23220 | 46315 |
| ABL1 | 126 | 23221 | 46316 |
| ABL2 | 127 | 23222 | 46317 |
| ABL2 | 128 | 23223 | 46318 |
| ABLIM1 | 129 | 23224 | 46319 |
| ABLIM2 | 130 | 23225 | 46320 |
| ABLIM2 | 131 | 23226 | 46321 |
| ABLIM3 | 132 | 23227 | 46322 |
| ABLIM3 | 133 | 23228 | 46323 |
| ABO | 134 | 23229 | 46324 |
| ABR | 135 | 23230 | 46325 |
| ABR | 136 | 23231 | 46326 |
| ABRA | 137 | 23232 | 46327 |
| ABRACL | 138 | 23233 | 46328 |
| ABRAXAS1 | 139 | 23234 | 46329 |
| ABRAXAS2 | 140 | 23235 | 46330 |
| ABT1 | 141 | 23236 | 46331 |
| ABTB1 | 142 | 23237 | 46332 |
| ABTB2 | 143 | 23238 | 46333 |
| ACAA1 | 144 | 23239 | 46334 |
| ACAA2 | 145 | 23240 | 46335 |
| ACACA | 146 | 23241 | 46336 |
| ACACB | 147 | 23242 | 46337 |
| ACAD10 | 148 | 23243 | 46338 |
| ACAD11 | 149 | 23244 | 46339 |
| ACAD8 | 150 | 23245 | 46340 |
| ACAD9 | 151 | 23246 | 46341 |
| ACADL | 152 | 23247 | 46342 |
| ACADM | 153 | 23248 | 46343 |
| ACADS | 154 | 23249 | 46344 |
| ACADSB | 155 | 23250 | 46345 |
| ACADVL | 156 | 23251 | 46346 |
| ACAN | 157 | 23252 | 46347 |
| ACAP1 | 158 | 23253 | 46348 |
| ACAP2 | 159 | 23254 | 46349 |
| ACAP3 | 160 | 23255 | 46350 |
| ACAT1 | 161 | 23256 | 46351 |
| ACAT2 | 162 | 23257 | 46352 |
| ACBD3 | 163 | 23258 | 46353 |
| ACBD4 | 164 | 23259 | 46354 |
| ACBD4 | 165 | 23260 | 46355 |
| ACBD4 | 166 | 23261 | 46356 |
| ACBD5 | 167 | 23262 | 46357 |
| ACBD5 | 168 | 23263 | 46358 |
| ACBD6 | 169 | 23264 | 46359 |
| ACBD7 | 170 | 23265 | 46360 |
| ACCS | 171 | 23266 | 46361 |
| ACCSL | 172 | 23267 | 46362 |
| ACD | 173 | 23268 | 46363 |
| ACE | 174 | 23269 | 46364 |
| ACE2 | 175 | 23270 | 46365 |
| ACER1 | 176 | 23271 | 46366 |
| ACER2 | 177 | 23272 | 46367 |
| ACER3 | 178 | 23273 | 46368 |
| ACER3 | 179 | 23274 | 46369 |
| ACHE | 180 | 23275 | 46370 |
| ACHE | 181 | 23276 | 46371 |
| ACIN1 | 182 | 23277 | 46372 |
| ACKR1 | 183 | 23278 | 46373 |
| ACKR2 | 184 | 23279 | 46374 |
| ACKR3 | 185 | 23280 | 46375 |
| ACKR4 | 186 | 23281 | 46376 |
| ACLY | 187 | 23282 | 46377 |
| ACMSD | 188 | 23283 | 46378 |
| ACO1 | 189 | 23284 | 46379 |
| ACO2 | 190 | 23285 | 46380 |
| ACOD1 | 191 | 23286 | 46381 |
| ACOT11 | 192 | 23287 | 46382 |
| ACOT11 | 193 | 23288 | 46383 |
| ACOT12 | 194 | 23289 | 46384 |
| ACOT13 | 195 | 23290 | 46385 |
| ACOT2 | 196 | 23291 | 46386 |
| ACOT4 | 197 | 23292 | 46387 |
| ACOT6 | 198 | 23293 | 46388 |
| ACOT7 | 199 | 23294 | 46389 |
| ACOT8 | 200 | 23295 | 46390 |
| ACOT9 | 201 | 23296 | 46391 |
| ACOX1 | 202 | 23297 | 46392 |
| ACOX2 | 203 | 23298 | 46393 |
| ACOX3 | 204 | 23299 | 46394 |
| ACOX3 | 205 | 23300 | 46395 |
| ACOXL | 206 | 23301 | 46396 |
| ACP1 | 207 | 23302 | 46397 |
| ACP1 | 208 | 23303 | 46398 |
| ACP2 | 209 | 23304 | 46399 |
| ACP4 | 210 | 23305 | 46400 |
| ACP5 | 211 | 23306 | 46401 |
| ACP6 | 212 | 23307 | 46402 |
| ACP6 | 213 | 23308 | 46403 |
| ACP7 | 214 | 23309 | 46404 |
| ACPP | 215 | 23310 | 46405 |
| ACPP | 216 | 23311 | 46406 |
| ACR | 217 | 23312 | 46407 |
| ACRBP | 218 | 23313 | 46408 |
| ACRV1 | 219 | 23314 | 46409 |
| ACSBG1 | 220 | 23315 | 46410 |
| ACSBG2 | 221 | 23316 | 46411 |
| ACSF2 | 222 | 23317 | 46412 |
| ACSF3 | 223 | 23318 | 46413 |
| ACSL1 | 224 | 23319 | 46414 |
| ACSL3 | 225 | 23320 | 46415 |
| ACSL4 | 226 | 23321 | 46416 |
| ACSL5 | 227 | 23322 | 46417 |
| ACSL6 | 228 | 23323 | 46418 |
| ACSM1 | 229 | 23324 | 46419 |
| ACSM2A | 230 | 23325 | 46420 |
| ACSM2B | 231 | 23326 | 46421 |
| ACSM3 | 232 | 23327 | 46422 |
| ACSM3 | 233 | 23328 | 46423 |
| ACSM4 | 234 | 23329 | 46424 |
| ACSM5 | 235 | 23330 | 46425 |
| ACSM5 | 236 | 23331 | 46426 |
| ACSM5 | 237 | 23332 | 46427 |
| ACSM6 | 238 | 23333 | 46428 |
| ACSS1 | 239 | 23334 | 46429 |
| ACSS1 | 240 | 23335 | 46430 |
| ACSS2 | 241 | 23336 | 46431 |
| ACSS3 | 242 | 23337 | 46432 |
| ACTA1 | 243 | 23338 | 46433 |
| ACTA2 | 244 | 23339 | 46434 |
| ACTB | 245 | 23340 | 46435 |
| ACTBL2 | 246 | 23341 | 46436 |
| ACTC1 | 247 | 23342 | 46437 |
| ACTG1 | 248 | 23343 | 46438 |
| ACTG2 | 249 | 23344 | 46439 |
| ACTL10 | 250 | 23345 | 46440 |
| ACTL6A | 251 | 23346 | 46441 |
| ACTL6B | 252 | 23347 | 46442 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ACTL7A | 253 | 23348 | 46443 |
| ACTL7B | 254 | 23349 | 46444 |
| ACTL8 | 255 | 23350 | 46445 |
| ACTL9 | 256 | 23351 | 46446 |
| ACTN1 | 257 | 23352 | 46447 |
| ACTN2 | 258 | 23353 | 46448 |
| ACTN3 | 259 | 23354 | 46449 |
| ACTN4 | 260 | 23355 | 46450 |
| ACTR10 | 261 | 23356 | 46451 |
| ACTR1A | 262 | 23357 | 46452 |
| ACTR1B | 263 | 23358 | 46453 |
| ACTR2 | 264 | 23359 | 46454 |
| ACTR3 | 265 | 23360 | 46455 |
| ACTR3B | 266 | 23361 | 46456 |
| ACTR3C | 267 | 23362 | 46457 |
| ACTR3C | 268 | 23363 | 46458 |
| ACTR3C | 269 | 23364 | 46459 |
| ACTR5 | 270 | 23365 | 46460 |
| ACTR6 | 271 | 23366 | 46461 |
| ACTR8 | 272 | 23367 | 46462 |
| ACTRT1 | 273 | 23368 | 46463 |
| ACTRT2 | 274 | 23369 | 46464 |
| ACTRT3 | 275 | 23370 | 46465 |
| ACVR1 | 276 | 23371 | 46466 |
| ACVR1B | 277 | 23372 | 46467 |
| ACVR1C | 278 | 23373 | 46468 |
| ACVR2A | 279 | 23374 | 46469 |
| ACVR2B | 280 | 23375 | 46470 |
| ACVRL1 | 281 | 23376 | 46471 |
| ACY1 | 282 | 23377 | 46472 |
| ACY3 | 283 | 23378 | 46473 |
| ACYP1 | 284 | 23379 | 46474 |
| ACYP2 | 285 | 23380 | 46475 |
| ACYP2 | 286 | 23381 | 46476 |
| ACYP2 | 287 | 23382 | 46477 |
| ADA | 288 | 23383 | 46478 |
| ADA2 | 289 | 23384 | 46479 |
| ADAD1 | 290 | 23385 | 46480 |
| ADAD2 | 291 | 23386 | 46481 |
| ADAL | 292 | 23387 | 46482 |
| ADAL | 293 | 23388 | 46483 |
| ADAM10 | 294 | 23389 | 46484 |
| ADAM11 | 295 | 23390 | 46485 |
| ADAM12 | 296 | 23391 | 46486 |
| ADAM12 | 297 | 23392 | 46487 |
| ADAM15 | 298 | 23393 | 46488 |
| ADAM15 | 299 | 23394 | 46489 |
| ADAM15 | 300 | 23395 | 46490 |
| ADAM17 | 301 | 23396 | 46491 |
| ADAM18 | 302 | 23397 | 46492 |
| ADAM18 | 303 | 23398 | 46493 |
| ADAM19 | 304 | 23399 | 46494 |
| ADAM2 | 305 | 23400 | 46495 |
| ADAM20 | 306 | 23401 | 46496 |
| ADAM21 | 307 | 23402 | 46497 |
| ADAM22 | 308 | 23403 | 46498 |
| ADAM22 | 309 | 23404 | 46499 |
| ADAM22 | 310 | 23405 | 46500 |
| ADAM23 | 311 | 23406 | 46501 |
| ADAM28 | 312 | 23407 | 46502 |
| ADAM28 | 313 | 23408 | 46503 |
| ADAM29 | 314 | 23409 | 46504 |
| ADAM30 | 315 | 23410 | 46505 |
| ADAM32 | 316 | 23411 | 46506 |
| ADAM33 | 317 | 23412 | 46507 |
| ADAM7 | 318 | 23413 | 46508 |
| ADAM8 | 319 | 23414 | 46509 |
| ADAM8 | 320 | 23415 | 46510 |
| ADAM9 | 321 | 23416 | 46511 |
| ADAMDEC1 | 322 | 23417 | 46512 |
| ADAMTS1 | 323 | 23418 | 46513 |
| ADAMTS10 | 324 | 23419 | 46514 |
| ADAMTS12 | 325 | 23420 | 46515 |
| ADAMTS12 | 326 | 23421 | 46516 |
| ADAMTS13 | 327 | 23422 | 46517 |
| ADAMTS14 | 328 | 23423 | 46518 |
| ADAMTS15 | 329 | 23424 | 46519 |
| ADAMTS16 | 330 | 23425 | 46520 |
| ADAMTS17 | 331 | 23426 | 46521 |
| ADAMTS18 | 332 | 23427 | 46522 |
| ADAMTS19 | 333 | 23428 | 46523 |
| ADAMTS2 | 334 | 23429 | 46524 |
| ADAMTS2 | 335 | 23430 | 46525 |
| ADAMTS20 | 336 | 23431 | 46526 |
| ADAMTS3 | 337 | 23432 | 46527 |
| ADAMTS4 | 338 | 23433 | 46528 |
| ADAMTS4 | 339 | 23434 | 46529 |
| ADAMTS5 | 340 | 23435 | 46530 |
| ADAMTS6 | 341 | 23436 | 46531 |
| ADAMTS7 | 342 | 23437 | 46532 |
| ADAMTS8 | 343 | 23438 | 46533 |
| ADAMTS9 | 344 | 23439 | 46534 |
| ADAMTSL1 | 345 | 23440 | 46535 |
| ADAMTSL1 | 346 | 23441 | 46536 |
| ADAMTSL2 | 347 | 23442 | 46537 |
| ADAMTSL3 | 348 | 23443 | 46538 |
| ADAMTSL3 | 349 | 23444 | 46539 |
| ADAMTSL4 | 350 | 23445 | 46540 |
| ADAMTSL4 | 351 | 23446 | 46541 |
| ADAMTSL5 | 352 | 23447 | 46542 |
| ADAP1 | 353 | 23448 | 46543 |
| ADAP2 | 354 | 23449 | 46544 |
| ADAR | 355 | 23450 | 46545 |
| ADARB1 | 356 | 23451 | 46546 |
| ADARB1 | 357 | 23452 | 46547 |
| ADARB1 | 358 | 23453 | 46548 |
| ADARB2 | 359 | 23454 | 46549 |
| ADAT1 | 360 | 23455 | 46550 |
| ADAT2 | 361 | 23456 | 46551 |
| ADAT3 | 362 | 23457 | 46552 |
| ADCK1 | 363 | 23458 | 46553 |
| ADCK2 | 364 | 23459 | 46554 |
| ADCK5 | 365 | 23460 | 46555 |
| ADCY1 | 366 | 23461 | 46556 |
| ADCY1 | 367 | 23462 | 46557 |
| ADCY10 | 368 | 23463 | 46558 |
| ADCY2 | 369 | 23464 | 46559 |
| ADCY3 | 370 | 23465 | 46560 |
| ADCY4 | 371 | 23466 | 46561 |
| ADCY5 | 372 | 23467 | 46562 |
| ADCY6 | 373 | 23468 | 46563 |
| ADCY7 | 374 | 23469 | 46564 |
| ADCY7 | 375 | 23470 | 46565 |
| ADCY8 | 376 | 23471 | 46566 |
| ADCY9 | 377 | 23472 | 46567 |
| ADCYAP1 | 378 | 23473 | 46568 |
| ADCYAP1R1 | 379 | 23474 | 46569 |
| ADD1 | 380 | 23475 | 46570 |
| ADD1 | 381 | 23476 | 46571 |
| ADD2 | 382 | 23477 | 46572 |
| ADD2 | 383 | 23478 | 46573 |
| ADD2 | 384 | 23479 | 46574 |
| ADD3 | 385 | 23480 | 46575 |
| ADGB | 386 | 23481 | 46576 |
| ADGRA1 | 387 | 23482 | 46577 |
| ADGRA2 | 388 | 23483 | 46578 |
| ADGRA3 | 389 | 23484 | 46579 |
| ADGRB1 | 390 | 23485 | 46580 |
| ADGRB2 | 391 | 23486 | 46581 |
| ADGRB3 | 392 | 23487 | 46582 |
| ADGRD1 | 393 | 23488 | 46583 |
| ADGRE1 | 394 | 23489 | 46584 |
| ADGRE2 | 395 | 23490 | 46585 |
| ADGRE3 | 396 | 23491 | 46586 |
| ADGRE5 | 397 | 23492 | 46587 |
| ADGRF1 | 398 | 23493 | 46588 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ADGRF1 | 399 | 23494 | 46589 |
| ADGRF2 | 400 | 23495 | 46590 |
| ADGRF3 | 401 | 23496 | 46591 |
| ADGRF3 | 402 | 23497 | 46592 |
| ADGRF3 | 403 | 23498 | 46593 |
| ADGRF4 | 404 | 23499 | 46594 |
| ADGRF5 | 405 | 23500 | 46595 |
| ADGRG1 | 406 | 23501 | 46596 |
| ADGRG2 | 407 | 23502 | 46597 |
| ADGRG3 | 408 | 23503 | 46598 |
| ADGRG4 | 409 | 23504 | 46599 |
| ADGRG5 | 410 | 23505 | 46600 |
| ADGRG5 | 411 | 23506 | 46601 |
| ADGRG6 | 412 | 23507 | 46602 |
| ADGRG6 | 413 | 23508 | 46603 |
| ADGRG7 | 414 | 23509 | 46604 |
| ADGRL1 | 415 | 23510 | 46605 |
| ADGRL2 | 416 | 23511 | 46606 |
| ADGRL2 | 417 | 23512 | 46607 |
| ADGRL2 | 418 | 23513 | 46608 |
| ADGRL2 | 419 | 23514 | 46609 |
| ADGRL3 | 420 | 23515 | 46610 |
| ADGRL3 | 421 | 23516 | 46611 |
| ADGRL4 | 422 | 23517 | 46612 |
| ADGRV1 | 423 | 23518 | 46613 |
| ADH1A | 424 | 23519 | 46614 |
| ADH1B | 425 | 23520 | 46615 |
| ADH1C | 426 | 23521 | 46616 |
| ADH4 | 427 | 23522 | 46617 |
| ADH5 | 428 | 23523 | 46618 |
| ADH6 | 429 | 23524 | 46619 |
| ADH7 | 430 | 23525 | 46620 |
| ADHFE1 | 431 | 23526 | 46621 |
| ADI1 | 432 | 23527 | 46622 |
| ADIG | 433 | 23528 | 46623 |
| ADIPOQ | 434 | 23529 | 46624 |
| ADIPOR1 | 435 | 23530 | 46625 |
| ADIPOR2 | 436 | 23531 | 46626 |
| ADIRF | 437 | 23532 | 46627 |
| ADK | 438 | 23533 | 46628 |
| ADM | 439 | 23534 | 46629 |
| ADM2 | 440 | 23535 | 46630 |
| ADM5 | 441 | 23536 | 46631 |
| ADNP | 442 | 23537 | 46632 |
| ADNP2 | 443 | 23538 | 46633 |
| ADO | 444 | 23539 | 46634 |
| ADORA1 | 445 | 23540 | 46635 |
| ADORA2A | 446 | 23541 | 46636 |
| ADORA2B | 447 | 23542 | 46637 |
| ADORA3 | 448 | 23543 | 46638 |
| ADPGK | 449 | 23544 | 46639 |
| ADPRH | 450 | 23545 | 46640 |
| ADPRHL1 | 451 | 23546 | 46641 |
| ADPRHL2 | 452 | 23547 | 46642 |
| ADPRM | 453 | 23548 | 46643 |
| ADRA1A | 454 | 23549 | 46644 |
| ADRA1A | 455 | 23550 | 46645 |
| ADRA1A | 456 | 23551 | 46646 |
| ADRA1A | 457 | 23552 | 46647 |
| ADRA1A | 458 | 23553 | 46648 |
| ADRA1A | 459 | 23554 | 46649 |
| ADRA1B | 460 | 23555 | 46650 |
| ADRA1D | 461 | 23556 | 46651 |
| ADRA2A | 462 | 23557 | 46652 |
| ADRA2B | 463 | 23558 | 46653 |
| ADRA2C | 464 | 23559 | 46654 |
| ADRB1 | 465 | 23560 | 46655 |
| ADRB2 | 466 | 23561 | 46656 |
| ADRB3 | 467 | 23562 | 46657 |
| ADRM1 | 468 | 23563 | 46658 |
| ADSL | 469 | 23564 | 46659 |
| ADSS | 470 | 23565 | 46660 |
| ADSSL1 | 471 | 23566 | 46661 |
| ADTRP | 472 | 23567 | 46662 |
| AEBP1 | 473 | 23568 | 46663 |
| AEBP2 | 474 | 23569 | 46664 |
| AEBP2 | 475 | 23570 | 46665 |
| AEN | 476 | 23571 | 46666 |
| AES | 477 | 23572 | 46667 |
| AFAP1 | 478 | 23573 | 46668 |
| AFAP1L1 | 479 | 23574 | 46669 |
| AFAP1L1 | 480 | 23575 | 46670 |
| AFAP1L2 | 481 | 23576 | 46671 |
| AFDN | 482 | 23577 | 46672 |
| AFDN | 483 | 23578 | 46673 |
| AFF1 | 484 | 23579 | 46674 |
| AFF2 | 485 | 23580 | 46675 |
| AFF3 | 486 | 23581 | 46676 |
| AFF4 | 487 | 23582 | 46677 |
| AFG1L | 488 | 23583 | 46678 |
| AFG3L2 | 489 | 23584 | 46679 |
| AFM | 490 | 23585 | 46680 |
| AFMID | 491 | 23586 | 46681 |
| AFP | 492 | 23587 | 46682 |
| AFTPH | 493 | 23588 | 46683 |
| AGA | 494 | 23589 | 46684 |
| AGAP1 | 495 | 23590 | 46685 |
| AGAP1 | 496 | 23591 | 46686 |
| AGAP11 | 497 | 23592 | 46687 |
| AGAP2 | 498 | 23593 | 46688 |
| AGAP3 | 499 | 23594 | 46689 |
| AGAP3 | 500 | 23595 | 46690 |
| AGAP4 | 501 | 23596 | 46691 |
| AGAP6 | 502 | 23597 | 46692 |
| AGAP9 | 503 | 23598 | 46693 |
| AGBL1 | 504 | 23599 | 46694 |
| AGBL2 | 505 | 23600 | 46695 |
| AGBL3 | 506 | 23601 | 46696 |
| AGBL3 | 507 | 23602 | 46697 |
| AGBL4 | 508 | 23603 | 46698 |
| AGBL5 | 509 | 23604 | 46699 |
| AGBL5 | 510 | 23605 | 46700 |
| AGER | 511 | 23606 | 46701 |
| AGER | 512 | 23607 | 46702 |
| AGER | 513 | 23608 | 46703 |
| AGER | 514 | 23609 | 46704 |
| AGFG1 | 515 | 23610 | 46705 |
| AGFG2 | 516 | 23611 | 46706 |
| AGGF1 | 517 | 23612 | 46707 |
| AGK | 518 | 23613 | 46708 |
| AGL | 519 | 23614 | 46709 |
| AGMAT | 520 | 23615 | 46710 |
| AGMO | 521 | 23616 | 46711 |
| AGO1 | 522 | 23617 | 46712 |
| AGO2 | 523 | 23618 | 46713 |
| AGO3 | 524 | 23619 | 46714 |
| AGO4 | 525 | 23620 | 46715 |
| AGPAT1 | 526 | 23621 | 46716 |
| AGPAT2 | 527 | 23622 | 46717 |
| AGPAT3 | 528 | 23623 | 46718 |
| AGPAT4 | 529 | 23624 | 46719 |
| AGPAT5 | 530 | 23625 | 46720 |
| AGPS | 531 | 23626 | 46721 |
| AGR2 | 532 | 23627 | 46722 |
| AGR3 | 533 | 23628 | 46723 |
| AGRN | 534 | 23629 | 46724 |
| AGRP | 535 | 23630 | 46725 |
| AGT | 536 | 23631 | 46726 |
| AGTPBP1 | 537 | 23632 | 46727 |
| AGTR1 | 538 | 23633 | 46728 |
| AGTR2 | 539 | 23634 | 46729 |
| AGTRAP | 540 | 23635 | 46730 |
| AGTRAP | 541 | 23636 | 46731 |
| AGTRAP | 542 | 23637 | 46732 |
| AGXT | 543 | 23638 | 46733 |
| AGXT2 | 544 | 23639 | 46734 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| AHCTF1 | 545 | 23640 | 46735 |
| AHCTF1 | 546 | 23641 | 46736 |
| AHCY | 547 | 23642 | 46737 |
| AHCYL1 | 548 | 23643 | 46738 |
| AHCYL2 | 549 | 23644 | 46739 |
| AHDC1 | 550 | 23645 | 46740 |
| AHI1 | 551 | 23646 | 46741 |
| AHI1 | 552 | 23647 | 46742 |
| AHI1 | 553 | 23648 | 46743 |
| AHNAK | 554 | 23649 | 46744 |
| AHNAK | 555 | 23650 | 46745 |
| AHNAK2 | 556 | 23651 | 46746 |
| AHR | 557 | 23652 | 46747 |
| AHRR | 558 | 23653 | 46748 |
| AHSA1 | 559 | 23654 | 46749 |
| AHSA2 | 560 | 23655 | 46750 |
| AHSA2 | 561 | 23656 | 46751 |
| AHSG | 562 | 23657 | 46752 |
| AHSP | 563 | 23658 | 46753 |
| AICDA | 564 | 23659 | 46754 |
| AIDA | 565 | 23660 | 46755 |
| AIF1 | 566 | 23661 | 46756 |
| AIF1L | 567 | 23662 | 46757 |
| AIF1L | 568 | 23663 | 46758 |
| AIFM1 | 569 | 23664 | 46759 |
| AIFM1 | 570 | 23665 | 46760 |
| AIFM2 | 571 | 23666 | 46761 |
| AIFM3 | 572 | 23667 | 46762 |
| AIG1 | 573 | 23668 | 46763 |
| AIG1 | 574 | 23669 | 46764 |
| AIM2 | 575 | 23670 | 46765 |
| AIMP1 | 576 | 23671 | 46766 |
| AIMP2 | 577 | 23672 | 46767 |
| AIP | 578 | 23673 | 46768 |
| AIP | 579 | 23674 | 46769 |
| AIPL1 | 580 | 23675 | 46770 |
| AIPL1 | 581 | 23676 | 46771 |
| AIRE | 582 | 23677 | 46772 |
| AJAP1 | 583 | 23678 | 46773 |
| AJUBA | 584 | 23679 | 46774 |
| AJUBA | 585 | 23680 | 46775 |
| AJUBA | 586 | 23681 | 46776 |
| AK1 | 587 | 23682 | 46777 |
| AK2 | 588 | 23683 | 46778 |
| AK2 | 589 | 23684 | 46779 |
| AK2 | 590 | 23685 | 46780 |
| AK2 | 591 | 23686 | 46781 |
| AK3 | 592 | 23687 | 46782 |
| AK4 | 593 | 23688 | 46783 |
| AK5 | 594 | 23689 | 46784 |
| AK6 | 595 | 23690 | 46785 |
| AK7 | 596 | 23691 | 46786 |
| AK7 | 597 | 23692 | 46787 |
| AK8 | 598 | 23693 | 46788 |
| AK9 | 599 | 23694 | 46789 |
| AK9 | 600 | 23695 | 46790 |
| AKAIN1 | 601 | 23696 | 46791 |
| AKAIN1 | 602 | 23697 | 46792 |
| AKAP1 | 603 | 23698 | 46793 |
| AKAP10 | 604 | 23699 | 46794 |
| AKAP11 | 605 | 23700 | 46795 |
| AKAP12 | 606 | 23701 | 46796 |
| AKAP13 | 607 | 23702 | 46797 |
| AKAP14 | 608 | 23703 | 46798 |
| AKAP14 | 609 | 23704 | 46799 |
| AKAP17A | 610 | 23705 | 46800 |
| AKAP3 | 611 | 23706 | 46801 |
| AKAP4 | 612 | 23707 | 46802 |
| AKAP5 | 613 | 23708 | 46803 |
| AKAP6 | 614 | 23709 | 46804 |
| AKAP7 | 615 | 23710 | 46805 |
| AKAP8 | 616 | 23711 | 46806 |
| AKAP8L | 617 | 23712 | 46807 |
| AKAP9 | 618 | 23713 | 46808 |
| AKIP1 | 619 | 23714 | 46809 |
| AKIRIN1 | 620 | 23715 | 46810 |
| AKIRIN2 | 621 | 23716 | 46811 |
| AKNA | 622 | 23717 | 46812 |
| AKNAD1 | 623 | 23718 | 46813 |
| AKR1A1 | 624 | 23719 | 46814 |
| AKR1B1 | 625 | 23720 | 46815 |
| AKR1B10 | 626 | 23721 | 46816 |
| AKR1B15 | 627 | 23722 | 46817 |
| AKR1C2 | 628 | 23723 | 46818 |
| AKR1C2 | 629 | 23724 | 46819 |
| AKR1C3 | 630 | 23725 | 46820 |
| AKR1C3 | 631 | 23726 | 46821 |
| AKR1C4 | 632 | 23727 | 46822 |
| AKR1D1 | 633 | 23728 | 46823 |
| AKR1D1 | 634 | 23729 | 46824 |
| AKR1E2 | 635 | 23730 | 46825 |
| AKR7A2 | 636 | 23731 | 46826 |
| AKR7A3 | 637 | 23732 | 46827 |
| AKR7L | 638 | 23733 | 46828 |
| AKT1 | 639 | 23734 | 46829 |
| AKT1S1 | 640 | 23735 | 46830 |
| AKT2 | 641 | 23736 | 46831 |
| AKT3 | 642 | 23737 | 46832 |
| AKT3 | 643 | 23738 | 46833 |
| AKTIP | 644 | 23739 | 46834 |
| ALAD | 645 | 23740 | 46835 |
| ALAS1 | 646 | 23741 | 46836 |
| ALAS2 | 647 | 23742 | 46837 |
| ALB | 648 | 23743 | 46838 |
| ALCAM | 649 | 23744 | 46839 |
| ALCAM | 650 | 23745 | 46840 |
| ALCAM | 651 | 23746 | 46841 |
| ALDH16A1 | 652 | 23747 | 46842 |
| ALDH18A1 | 653 | 23748 | 46843 |
| ALDH1A1 | 654 | 23749 | 46844 |
| ALDH1A2 | 655 | 23750 | 46845 |
| ALDH1A3 | 656 | 23751 | 46846 |
| ALDH1B1 | 657 | 23752 | 46847 |
| ALDH1L1 | 658 | 23753 | 46848 |
| ALDH1L2 | 659 | 23754 | 46849 |
| ALDH2 | 660 | 23755 | 46850 |
| ALDH3A1 | 661 | 23756 | 46851 |
| ALDH3A2 | 662 | 23757 | 46852 |
| ALDH3A2 | 663 | 23758 | 46853 |
| ALDH3B1 | 664 | 23759 | 46854 |
| ALDH3B2 | 665 | 23760 | 46855 |
| ALDH4A1 | 666 | 23761 | 46856 |
| ALDH5A1 | 667 | 23762 | 46857 |
| ALDH6A1 | 668 | 23763 | 46858 |
| ALDH7A1 | 669 | 23764 | 46859 |
| ALDH8A1 | 670 | 23765 | 46860 |
| ALDH9A1 | 671 | 23766 | 46861 |
| ALDOA | 672 | 23767 | 46862 |
| ALDOB | 673 | 23768 | 46863 |
| ALDOC | 674 | 23769 | 46864 |
| ALG1 | 675 | 23770 | 46865 |
| ALG10 | 676 | 23771 | 46866 |
| ALG10B | 677 | 23772 | 46867 |
| ALG11 | 678 | 23773 | 46868 |
| ALG12 | 679 | 23774 | 46869 |
| ALG13 | 680 | 23775 | 46870 |
| ALG13 | 681 | 23776 | 46871 |
| ALG13 | 682 | 23777 | 46872 |
| ALG14 | 683 | 23778 | 46873 |
| ALG14 | 684 | 23779 | 46874 |
| ALG1L | 685 | 23780 | 46875 |
| ALG1L2 | 686 | 23781 | 46876 |
| ALG2 | 687 | 23782 | 46877 |
| ALG3 | 688 | 23783 | 46878 |
| ALG5 | 689 | 23784 | 46879 |
| ALG6 | 690 | 23785 | 46880 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ALG8 | 691 | 23786 | 46881 |
| ALG8 | 692 | 23787 | 46882 |
| ALG9 | 693 | 23788 | 46883 |
| ALG9 | 694 | 23789 | 46884 |
| ALG9 | 695 | 23790 | 46885 |
| ALG9 | 696 | 23791 | 46886 |
| ALK | 697 | 23792 | 46887 |
| ALKAL1 | 698 | 23793 | 46888 |
| ALKAL2 | 699 | 23794 | 46889 |
| ALKBH1 | 700 | 23795 | 46890 |
| ALKBH2 | 701 | 23796 | 46891 |
| ALKBH2 | 702 | 23797 | 46892 |
| ALKBH3 | 703 | 23798 | 46893 |
| ALKBH4 | 704 | 23799 | 46894 |
| ALKBH5 | 705 | 23800 | 46895 |
| ALKBH6 | 706 | 23801 | 46896 |
| ALKBH6 | 707 | 23802 | 46897 |
| ALKBH7 | 708 | 23803 | 46898 |
| ALKBH8 | 709 | 23804 | 46899 |
| ALLC | 710 | 23805 | 46900 |
| ALMS1 | 711 | 23806 | 46901 |
| ALOX12 | 712 | 23807 | 46902 |
| ALOX12B | 713 | 23808 | 46903 |
| ALOX15 | 714 | 23809 | 46904 |
| ALOX15B | 715 | 23810 | 46905 |
| ALOX5 | 716 | 23811 | 46906 |
| ALOX5AP | 717 | 23812 | 46907 |
| ALOXE3 | 718 | 23813 | 46908 |
| ALPI | 719 | 23814 | 46909 |
| ALPK1 | 720 | 23815 | 46910 |
| ALPK2 | 721 | 23816 | 46911 |
| ALPK3 | 722 | 23817 | 46912 |
| ALPL | 723 | 23818 | 46913 |
| ALPP | 724 | 23819 | 46914 |
| ALS2 | 725 | 23820 | 46915 |
| ALS2 | 726 | 23821 | 46916 |
| ALS2CL | 727 | 23822 | 46917 |
| ALS2CR12 alternate allele | 728 | 23823 | 46918 |
| | 729 | 23824 | 46919 |
| ALX1 | 730 | 23825 | 46920 |
| ALX3 | 731 | 23826 | 46921 |
| ALX4 | 732 | 23827 | 46922 |
| ALYREF | 733 | 23828 | 46923 |
| AMACR | 734 | 23829 | 46924 |
| AMACR | 735 | 23830 | 46925 |
| AMACR | 736 | 23831 | 46926 |
| AMBN | 737 | 23832 | 46927 |
| AMBP | 738 | 23833 | 46928 |
| AMBRA1 | 739 | 23834 | 46929 |
| AMD1 | 740 | 23835 | 46930 |
| AMDHD1 | 741 | 23836 | 46931 |
| AMDHD2 | 742 | 23837 | 46932 |
| AMDHD2 | 743 | 23838 | 46933 |
| AMELX | 744 | 23839 | 46934 |
| AMELY | 745 | 23840 | 46935 |
| AMER1 | 746 | 23841 | 46936 |
| AMER2 | 747 | 23842 | 46937 |
| AMER3 | 748 | 23843 | 46938 |
| AMFR | 749 | 23844 | 46939 |
| AMH | 750 | 23845 | 46940 |
| AMHR2 | 751 | 23846 | 46941 |
| AMHR2 | 752 | 23847 | 46942 |
| AMIGO1 | 753 | 23848 | 46943 |
| AMIGO2 | 754 | 23849 | 46944 |
| AMIGO3 | 755 | 23850 | 46945 |
| AMMECR1 | 756 | 23851 | 46946 |
| AMMECR1L | 757 | 23852 | 46947 |
| AMN | 758 | 23853 | 46948 |
| AMN1 | 759 | 23854 | 46949 |
| AMOT | 760 | 23855 | 46950 |
| AMOTL1 | 761 | 23856 | 46951 |
| AMOTL2 | 762 | 23857 | 46952 |
| AMPD1 | 763 | 23858 | 46953 |
| AMPD2 | 764 | 23859 | 46954 |
| AMPD3 | 765 | 23860 | 46955 |
| AMPH | 766 | 23861 | 46956 |
| AMT | 767 | 23862 | 46957 |
| AMT | 768 | 23863 | 46958 |
| AMTN | 769 | 23864 | 46959 |
| AMY1A | 770 | 23865 | 46960 |
| AMY2A | 771 | 23866 | 46961 |
| AMY2B | 772 | 23867 | 46962 |
| AMZ1 | 773 | 23868 | 46963 |
| AMZ1 | 774 | 23869 | 46964 |
| AMZ1 | 775 | 23870 | 46965 |
| AMZ2 | 776 | 23871 | 46966 |
| ANAPC1 | 777 | 23872 | 46967 |
| ANAPC10 | 778 | 23873 | 46968 |
| ANAPC10 | 779 | 23874 | 46969 |
| ANAPC10 | 780 | 23875 | 46970 |
| ANAPC11 | 781 | 23876 | 46971 |
| ANAPC11 | 782 | 23877 | 46972 |
| ANAPC13 | 783 | 23878 | 46973 |
| ANAPC13 | 784 | 23879 | 46974 |
| ANAPC13 | 785 | 23880 | 46975 |
| ANAPC15 | 786 | 23881 | 46976 |
| ANAPC15 | 787 | 23882 | 46977 |
| ANAPC16 | 788 | 23883 | 46978 |
| ANAPC2 | 789 | 23884 | 46979 |
| ANAPC4 | 790 | 23885 | 46980 |
| ANAPC5 | 791 | 23886 | 46981 |
| ANAPC7 | 792 | 23887 | 46982 |
| ANAPC7 | 793 | 23888 | 46983 |
| ANG | 794 | 23889 | 46984 |
| ANG | 795 | 23890 | 46985 |
| ANGEL1 | 796 | 23891 | 46986 |
| ANGEL2 | 797 | 23892 | 46987 |
| ANGPT1 | 798 | 23893 | 46988 |
| ANGPT2 | 799 | 23894 | 46989 |
| ANGPT4 | 800 | 23895 | 46990 |
| ANGPT4 | 801 | 23896 | 46991 |
| ANGPTL1 | 802 | 23897 | 46992 |
| ANGPTL2 | 803 | 23898 | 46993 |
| ANGPTL3 | 804 | 23899 | 46994 |
| ANGPTL4 | 805 | 23900 | 46995 |
| ANGPTL5 | 806 | 23901 | 46996 |
| ANGPTL6 | 807 | 23902 | 46997 |
| ANGPTL7 | 808 | 23903 | 46998 |
| ANGPTL8 | 809 | 23904 | 46999 |
| ANHX | 810 | 23905 | 47000 |
| ANK1 | 811 | 23906 | 47001 |
| ANK1 | 812 | 23907 | 47002 |
| ANK2 | 813 | 23908 | 47003 |
| ANK2 | 814 | 23909 | 47004 |
| ANK2 | 815 | 23910 | 47005 |
| ANK3 | 816 | 23911 | 47006 |
| ANKAR | 817 | 23912 | 47007 |
| ANKDD1A | 818 | 23913 | 47008 |
| ANKDD1B | 819 | 23914 | 47009 |
| ANKEF1 | 820 | 23915 | 47010 |
| ANKFN1 | 821 | 23916 | 47011 |
| ANKFY1 | 822 | 23917 | 47012 |
| ANKH | 823 | 23918 | 47013 |
| ANKHD1 | 824 | 23919 | 47014 |
| ANKHD1 | 825 | 23920 | 47015 |
| ANKHD1-EIF4EBP3 | 826 | 23921 | 47016 |
| ANKIB1 | 827 | 23922 | 47017 |
| ANKK1 | 828 | 23923 | 47018 |
| ANKLE1 | 829 | 23924 | 47019 |
| ANKLE1 | 830 | 23925 | 47020 |
| ANKLE2 | 831 | 23926 | 47021 |
| ANKMY1 | 832 | 23927 | 47022 |
| ANKMY2 | 833 | 23928 | 47023 |
| ANKRA2 | 834 | 23929 | 47024 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ANKRD1 | 835 | 23930 | 47025 |
| ANKRD10 | 836 | 23931 | 47026 |
| ANKRD10 | 837 | 23932 | 47027 |
| ANKRD11 | 838 | 23933 | 47028 |
| ANKRD12 | 839 | 23934 | 47029 |
| ANKRD13A | 840 | 23935 | 47030 |
| ANKRD13B | 841 | 23936 | 47031 |
| ANKRD13C | 842 | 23937 | 47032 |
| ANKRD13D | 843 | 23938 | 47033 |
| ANKRD16 | 844 | 23939 | 47034 |
| ANKRD16 | 845 | 23940 | 47035 |
| ANKRD17 | 846 | 23941 | 47036 |
| ANKRD18A | 847 | 23942 | 47037 |
| ANKRD18B | 848 | 23943 | 47038 |
| ANKRD2 | 849 | 23944 | 47039 |
| ANKRD20A3 | 850 | 23945 | 47040 |
| ANKRD20A4 | 851 | 23946 | 47041 |
| ANKRD22 | 852 | 23947 | 47042 |
| ANKRD23 | 853 | 23948 | 47043 |
| ANKRD24 | 854 | 23949 | 47044 |
| ANKRD26 | 855 | 23950 | 47045 |
| ANKRD27 | 856 | 23951 | 47046 |
| ANKRD28 | 857 | 23952 | 47047 |
| ANKRD28 | 858 | 23953 | 47048 |
| ANKRD29 | 859 | 23954 | 47049 |
| ANKRD30A | 860 | 23955 | 47050 |
| ANKRD30B | 861 | 23956 | 47051 |
| ANKRD31 | 862 | 23957 | 47052 |
| ANKRD33 | 863 | 23958 | 47053 |
| ANKRD33 | 864 | 23959 | 47054 |
| ANKRD33B | 865 | 23960 | 47055 |
| ANKRD34A | 866 | 23961 | 47056 |
| ANKRD34B | 867 | 23962 | 47057 |
| ANKRD34C | 868 | 23963 | 47058 |
| ANKRD35 | 869 | 23964 | 47059 |
| ANKRD36B | 870 | 23965 | 47060 |
| ANKRD36B | 871 | 23966 | 47061 |
| ANKRD36C | 872 | 23967 | 47062 |
| ANKRD37 | 873 | 23968 | 47063 |
| ANKRD39 | 874 | 23969 | 47064 |
| ANKRD40 | 875 | 23970 | 47065 |
| ANKRD42 | 876 | 23971 | 47066 |
| ANKRD42 | 877 | 23972 | 47067 |
| ANKRD42 | 878 | 23973 | 47068 |
| ANKRD42 | 879 | 23974 | 47069 |
| ANKRD42 | 880 | 23975 | 47070 |
| ANKRD42 | 881 | 23976 | 47071 |
| ANKRD44 | 882 | 23977 | 47072 |
| ANKRD44 | 883 | 23978 | 47073 |
| ANKRD45 | 884 | 23979 | 47074 |
| ANKRD46 | 885 | 23980 | 47075 |
| ANKRD46 | 886 | 23981 | 47076 |
| ANKRD49 | 887 | 23982 | 47077 |
| ANKRD50 | 888 | 23983 | 47078 |
| ANKRD52 | 889 | 23984 | 47079 |
| ANKRD53 | 890 | 23985 | 47080 |
| ANKRD53 | 891 | 23986 | 47081 |
| ANKRD54 | 892 | 23987 | 47082 |
| ANKRD55 | 893 | 23988 | 47083 |
| ANKRD6 | 894 | 23989 | 47084 |
| ANKRD60 | 895 | 23990 | 47085 |
| ANKRD61 | 896 | 23991 | 47086 |
| ANKRD62 | 897 | 23992 | 47087 |
| ANKRD63 | 898 | 23993 | 47088 |
| ANKRD65 | 899 | 23994 | 47089 |
| ANKRD65 | 900 | 23995 | 47090 |
| ANKRD66 | 901 | 23996 | 47091 |
| ANKRD7 | 902 | 23997 | 47092 |
| ANKRD9 | 903 | 23998 | 47093 |
| ANKS1A | 904 | 23999 | 47094 |
| ANKS1B | 905 | 24000 | 47095 |
| ANKS1B | 906 | 24001 | 47096 |
| ANKS1B | 907 | 24002 | 47097 |
| ANKS3 | 908 | 24003 | 47098 |
| ANKS4B | 909 | 24004 | 47099 |
| ANKS6 | 910 | 24005 | 47100 |
| ANKUB1 | 911 | 24006 | 47101 |
| ANKUB1 | 912 | 24007 | 47102 |
| ANKZF1 | 913 | 24008 | 47103 |
| ANLN | 914 | 24009 | 47104 |
| ANO1 | 915 | 24010 | 47105 |
| ANO10 | 916 | 24011 | 47106 |
| ANO10 | 917 | 24012 | 47107 |
| ANO2 | 918 | 24013 | 47108 |
| ANO3 | 919 | 24014 | 47109 |
| ANO4 | 920 | 24015 | 47110 |
| ANO5 | 921 | 24016 | 47111 |
| ANO6 | 922 | 24017 | 47112 |
| ANO6 | 923 | 24018 | 47113 |
| ANO7 | 924 | 24019 | 47114 |
| ANO7 | 925 | 24020 | 47115 |
| ANO8 | 926 | 24021 | 47116 |
| ANO9 | 927 | 24022 | 47117 |
| ANOS1 | 928 | 24023 | 47118 |
| ANP32A | 929 | 24024 | 47119 |
| ANP32B | 930 | 24025 | 47120 |
| ANP32C | 931 | 24026 | 47121 |
| ANP32D | 932 | 24027 | 47122 |
| ANP32E | 933 | 24028 | 47123 |
| ANP32E | 934 | 24029 | 47124 |
| ANPEP | 935 | 24030 | 47125 |
| ANTXR1 | 936 | 24031 | 47126 |
| ANTXR1 | 937 | 24032 | 47127 |
| ANTXR1 | 938 | 24033 | 47128 |
| ANTXR2 | 939 | 24034 | 47129 |
| ANTXR2 | 940 | 24035 | 47130 |
| ANTXRL | 941 | 24036 | 47131 |
| ANXA1 | 942 | 24037 | 47132 |
| ANXA10 | 943 | 24038 | 47133 |
| ANXA11 | 944 | 24039 | 47134 |
| ANXA13 | 945 | 24040 | 47135 |
| ANXA2 | 946 | 24041 | 47136 |
| ANXA2R | 947 | 24042 | 47137 |
| ANXA3 | 948 | 24043 | 47138 |
| ANXA4 | 949 | 24044 | 47139 |
| ANXA5 | 950 | 24045 | 47140 |
| ANXA6 | 951 | 24046 | 47141 |
| ANXA7 | 952 | 24047 | 47142 |
| ANXA8 | 953 | 24048 | 47143 |
| ANXA9 | 954 | 24049 | 47144 |
| AOAH | 955 | 24050 | 47145 |
| AOAH | 956 | 24051 | 47146 |
| AOC1 | 957 | 24052 | 47147 |
| AOC2 | 958 | 24053 | 47148 |
| AOC3 | 959 | 24054 | 47149 |
| AOC3 | 960 | 24055 | 47150 |
| AOX1 | 961 | 24056 | 47151 |
| AP1AR | 962 | 24057 | 47152 |
| AP1B1 | 963 | 24058 | 47153 |
| AP1G1 | 964 | 24059 | 47154 |
| AP1G2 | 965 | 24060 | 47155 |
| AP1M1 | 966 | 24061 | 47156 |
| AP1M2 | 967 | 24062 | 47157 |
| AP1S1 | 968 | 24063 | 47158 |
| AP1S2 | 969 | 24064 | 47159 |
| AP1S3 | 970 | 24065 | 47160 |
| AP2A1 | 971 | 24066 | 47161 |
| AP2A2 | 972 | 24067 | 47162 |
| AP2B1 | 973 | 24068 | 47163 |
| AP2M1 | 974 | 24069 | 47164 |
| AP2S1 | 975 | 24070 | 47165 |
| AP3B1 | 976 | 24071 | 47166 |
| AP3B2 | 977 | 24072 | 47167 |
| AP3B2 | 978 | 24073 | 47168 |
| AP3D1 | 979 | 24074 | 47169 |
| AP3M1 | 980 | 24075 | 47170 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| AP3M2 | 981 | 24076 | 47171 |
| AP3S1 | 982 | 24077 | 47172 |
| AP3S1 | 983 | 24078 | 47173 |
| AP3S2 | 984 | 24079 | 47174 |
| AP4B1 | 985 | 24080 | 47175 |
| AP4E1 | 986 | 24081 | 47176 |
| AP4M1 | 987 | 24082 | 47177 |
| AP4S1 | 988 | 24083 | 47178 |
| AP4S1 | 989 | 24084 | 47179 |
| AP4S1 | 990 | 24085 | 47180 |
| AP5B1 | 991 | 24086 | 47181 |
| AP5M1 | 992 | 24087 | 47182 |
| AP5S1 | 993 | 24088 | 47183 |
| AP5Z1 | 994 | 24089 | 47184 |
| APAF1 | 995 | 24090 | 47185 |
| APAF1 | 996 | 24091 | 47186 |
| APBA1 | 997 | 24092 | 47187 |
| APBA2 | 998 | 24093 | 47188 |
| APBA2 | 999 | 24094 | 47189 |
| APBA3 | 1000 | 24095 | 47190 |
| APBB1 | 1001 | 24096 | 47191 |
| APBB1IP | 1002 | 24097 | 47192 |
| APBB2 | 1003 | 24098 | 47193 |
| APBB3 | 1004 | 24099 | 47194 |
| APC | 1005 | 24100 | 47195 |
| APC2 | 1006 | 24101 | 47196 |
| APCDD1 | 1007 | 24102 | 47197 |
| APCDD1L | 1008 | 24103 | 47198 |
| APCS | 1009 | 24104 | 47199 |
| APEH | 1010 | 24105 | 47200 |
| APELA | 1011 | 24106 | 47201 |
| APEX1 | 1012 | 24107 | 47202 |
| APEX2 | 1013 | 24108 | 47203 |
| APH1A | 1014 | 24109 | 47204 |
| APH1A | 1015 | 24110 | 47205 |
| APH1B | 1016 | 24111 | 47206 |
| API5 | 1017 | 24112 | 47207 |
| API5 | 1018 | 24113 | 47208 |
| APIP | 1019 | 24114 | 47209 |
| APLF | 1020 | 24115 | 47210 |
| APLN | 1021 | 24116 | 47211 |
| APLNR | 1022 | 24117 | 47212 |
| APLP1 | 1023 | 24118 | 47213 |
| APLP2 | 1024 | 24119 | 47214 |
| APMAP | 1025 | 24120 | 47215 |
| APOA1 | 1026 | 24121 | 47216 |
| APOA2 | 1027 | 24122 | 47217 |
| APOA4 | 1028 | 24123 | 47218 |
| APOA5 | 1029 | 24124 | 47219 |
| APOB | 1030 | 24125 | 47220 |
| APOBEC1 | 1031 | 24126 | 47221 |
| APOBEC2 | 1032 | 24127 | 47222 |
| APOBEC3B | 1033 | 24128 | 47223 |
| APOBEC3D | 1034 | 24129 | 47224 |
| APOBEC3F | 1035 | 24130 | 47225 |
| APOBEC3F | 1036 | 24131 | 47226 |
| APOBEC3G | 1037 | 24132 | 47227 |
| APOBEC3G | 1038 | 24133 | 47228 |
| APOBEC3G | 1039 | 24134 | 47229 |
| APOBEC3H | 1040 | 24135 | 47230 |
| APOBEC3H | 1041 | 24136 | 47231 |
| APOBEC4 | 1042 | 24137 | 47232 |
| APOBR | 1043 | 24138 | 47233 |
| APOC1 | 1044 | 24139 | 47234 |
| APOC2 | 1045 | 24140 | 47235 |
| APOC3 | 1046 | 24141 | 47236 |
| APOC4 | 1047 | 24142 | 47237 |
| APOD | 1048 | 24143 | 47238 |
| APOE | 1049 | 24144 | 47239 |
| APOF | 1050 | 24145 | 47240 |
| APOH | 1051 | 24146 | 47241 |
| APOL1 | 1052 | 24147 | 47242 |
| APOL2 | 1053 | 24148 | 47243 |
| APOL3 | 1054 | 24149 | 47244 |
| APOL4 | 1055 | 24150 | 47245 |
| APOL5 | 1056 | 24151 | 47246 |
| APOL6 | 1057 | 24152 | 47247 |
| APOLD1 | 1058 | 24153 | 47248 |
| APOM | 1059 | 24154 | 47249 |
| APOO | 1060 | 24155 | 47250 |
| APOOL | 1061 | 24156 | 47251 |
| APOPT1 | 1062 | 24157 | 47252 |
| APOPT1 | 1063 | 24158 | 47253 |
| APOPT1 | 1064 | 24159 | 47254 |
| APOPT1 | 1065 | 24160 | 47255 |
| APP | 1066 | 24161 | 47256 |
| APPBP2 | 1067 | 24162 | 47257 |
| APPL1 | 1068 | 24163 | 47258 |
| APPL2 | 1069 | 24164 | 47259 |
| APRT | 1070 | 24165 | 47260 |
| APRT | 1071 | 24166 | 47261 |
| APTX | 1072 | 24167 | 47262 |
| APTX | 1073 | 24168 | 47263 |
| AQP1 | 1074 | 24169 | 47264 |
| AQP1 | 1075 | 24170 | 47265 |
| AQP10 | 1076 | 24171 | 47266 |
| AQP11 | 1077 | 24172 | 47267 |
| AQP12A | 1078 | 24173 | 47268 |
| AQP2 | 1079 | 24174 | 47269 |
| AQP3 | 1080 | 24175 | 47270 |
| AQP3 | 1081 | 24176 | 47271 |
| AQP4 | 1082 | 24177 | 47272 |
| AQP5 | 1083 | 24178 | 47273 |
| AQP6 | 1084 | 24179 | 47274 |
| AQP7 | 1085 | 24180 | 47275 |
| AQP7 | 1086 | 24181 | 47276 |
| AQP7 | 1087 | 24182 | 47277 |
| AQP8 | 1088 | 24183 | 47278 |
| AQP9 | 1089 | 24184 | 47279 |
| AQP9 | 1090 | 24185 | 47280 |
| AQR | 1091 | 24186 | 47281 |
| AR | 1092 | 24187 | 47282 |
| AR | 1093 | 24188 | 47283 |
| AR | 1094 | 24189 | 47284 |
| AR | 1095 | 24190 | 47285 |
| AR | 1096 | 24191 | 47286 |
| ARAF | 1097 | 24192 | 47287 |
| ARAF | 1098 | 24193 | 47288 |
| ARAP1 | 1099 | 24194 | 47289 |
| ARAP2 | 1100 | 24195 | 47290 |
| ARAP3 | 1101 | 24196 | 47291 |
| ARC | 1102 | 24197 | 47292 |
| ARCN1 | 1103 | 24198 | 47293 |
| AREG | 1104 | 24199 | 47294 |
| AREL1 | 1105 | 24200 | 47295 |
| ARF1 | 1106 | 24201 | 47296 |
| ARF3 | 1107 | 24202 | 47297 |
| ARF4 | 1108 | 24203 | 47298 |
| ARF5 | 1109 | 24204 | 47299 |
| ARF6 | 1110 | 24205 | 47300 |
| ARFGAP1 | 1111 | 24206 | 47301 |
| ARFGAP1 | 1112 | 24207 | 47302 |
| ARFGAP2 | 1113 | 24208 | 47303 |
| ARFGAP3 | 1114 | 24209 | 47304 |
| ARFGEF1 | 1115 | 24210 | 47305 |
| ARFGEF2 | 1116 | 24211 | 47306 |
| ARFGEF3 | 1117 | 24212 | 47307 |
| ARFIP1 | 1118 | 24213 | 47308 |
| ARFIP2 | 1119 | 24214 | 47309 |
| ARFRP1 | 1120 | 24215 | 47310 |
| ARFRP1 | 1121 | 24216 | 47311 |
| ARFRP1 | 1122 | 24217 | 47312 |
| ARG1 | 1123 | 24218 | 47313 |
| ARG2 | 1124 | 24219 | 47314 |
| ARGFX | 1125 | 24220 | 47315 |
| ARGLU1 | 1126 | 24221 | 47316 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ARHGAP1 | 1127 | 24222 | 47317 |
| ARHGAP10 | 1128 | 24223 | 47318 |
| ARHGAP11A | 1129 | 24224 | 47319 |
| ARHGAP11A | 1130 | 24225 | 47320 |
| ARHGAP11B | 1131 | 24226 | 47321 |
| ARHGAP12 | 1132 | 24227 | 47322 |
| ARHGAP15 | 1133 | 24228 | 47323 |
| ARHGAP17 | 1134 | 24229 | 47324 |
| ARHGAP18 | 1135 | 24230 | 47325 |
| ARHGAP19 | 1136 | 24231 | 47326 |
| ARHGAP20 | 1137 | 24232 | 47327 |
| ARHGAP21 | 1138 | 24233 | 47328 |
| ARHGAP22 | 1139 | 24234 | 47329 |
| ARHGAP22 | 1140 | 24235 | 47330 |
| ARHGAP23 | 1141 | 24236 | 47331 |
| ARHGAP24 | 1142 | 24237 | 47332 |
| ARHGAP25 | 1143 | 24238 | 47333 |
| ARHGAP26 | 1144 | 24239 | 47334 |
| ARHGAP27 | 1145 | 24240 | 47335 |
| ARHGAP27 | 1146 | 24241 | 47336 |
| ARHGAP28 | 1147 | 24242 | 47337 |
| ARHGAP29 | 1148 | 24243 | 47338 |
| ARHGAP30 | 1149 | 24244 | 47339 |
| ARHGAP31 | 1150 | 24245 | 47340 |
| ARHGAP32 | 1151 | 24246 | 47341 |
| ARHGAP33 | 1152 | 24247 | 47342 |
| ARHGAP35 | 1153 | 24248 | 47343 |
| ARHGAP36 | 1154 | 24249 | 47344 |
| ARHGAP39 | 1155 | 24250 | 47345 |
| ARHGAP4 | 1156 | 24251 | 47346 |
| ARHGAP40 | 1157 | 24252 | 47347 |
| ARHGAP42 | 1158 | 24253 | 47348 |
| ARHGAP44 | 1159 | 24254 | 47349 |
| ARHGAP44 | 1160 | 24255 | 47350 |
| ARHGAP45 | 1161 | 24256 | 47351 |
| ARHGAP5 | 1162 | 24257 | 47352 |
| ARHGAP6 | 1163 | 24258 | 47353 |
| ARHGAP6 | 1164 | 24259 | 47354 |
| ARHGAP8 | 1165 | 24260 | 47355 |
| ARHGAP8 | 1166 | 24261 | 47356 |
| ARHGAP9 | 1167 | 24262 | 47357 |
| ARHGAP9 | 1168 | 24263 | 47358 |
| ARHGDIA | 1169 | 24264 | 47359 |
| ARHGDIA | 1170 | 24265 | 47360 |
| ARHGDIA | 1171 | 24266 | 47361 |
| ARHGDIB | 1172 | 24267 | 47362 |
| ARHGDIG | 1173 | 24268 | 47363 |
| ARHGEF1 | 1174 | 24269 | 47364 |
| ARHGEF10 | 1175 | 24270 | 47365 |
| ARHGEF10L | 1176 | 24271 | 47366 |
| ARHGEF11 | 1177 | 24272 | 47367 |
| ARHGEF12 | 1178 | 24273 | 47368 |
| ARHGEF15 | 1179 | 24274 | 47369 |
| ARHGEF16 | 1180 | 24275 | 47370 |
| ARHGEF17 | 1181 | 24276 | 47371 |
| ARHGEF18 | 1182 | 24277 | 47372 |
| ARHGEF19 | 1183 | 24278 | 47373 |
| ARHGEF2 | 1184 | 24279 | 47374 |
| ARHGEF25 | 1185 | 24280 | 47375 |
| ARHGEF26 | 1186 | 24281 | 47376 |
| ARHGEF26 | 1187 | 24282 | 47377 |
| ARHGEF28 | 1188 | 24283 | 47378 |
| ARHGEF3 | 1189 | 24284 | 47379 |
| ARHGEF33 | 1190 | 24285 | 47380 |
| ARHGEF35 | 1191 | 24286 | 47381 |
| ARHGEF37 | 1192 | 24287 | 47382 |
| ARHGEF38 | 1193 | 24288 | 47383 |
| ARHGEF38 | 1194 | 24289 | 47384 |
| ARHGEF39 | 1195 | 24290 | 47385 |
| ARHGEF4 | 1196 | 24291 | 47386 |
| ARHGEF4 | 1197 | 24292 | 47387 |
| ARHGEF40 | 1198 | 24293 | 47388 |
| ARHGEF5 | 1199 | 24294 | 47389 |
| ARHGEF6 | 1200 | 24295 | 47390 |
| ARHGEF7 | 1201 | 24296 | 47391 |
| ARHGEF7 | 1202 | 24297 | 47392 |
| ARHGEF9 | 1203 | 24298 | 47393 |
| ARID1A | 1204 | 24299 | 47394 |
| ARID1B | 1205 | 24300 | 47395 |
| ARID2 | 1206 | 24301 | 47396 |
| ARID2 | 1207 | 24302 | 47397 |
| ARID3A | 1208 | 24303 | 47398 |
| ARID3B | 1209 | 24304 | 47399 |
| ARID3C | 1210 | 24305 | 47400 |
| ARID4A | 1211 | 24306 | 47401 |
| ARID4B | 1212 | 24307 | 47402 |
| ARID5A | 1213 | 24308 | 47403 |
| ARID5B | 1214 | 24309 | 47404 |
| ARIH1 | 1215 | 24310 | 47405 |
| ARIH2 | 1216 | 24311 | 47406 |
| ARIH2 | 1217 | 24312 | 47407 |
| ARIH2 | 1218 | 24313 | 47408 |
| ARIH2OS | 1219 | 24314 | 47409 |
| ARL1 | 1220 | 24315 | 47410 |
| ARL10 | 1221 | 24316 | 47411 |
| ARL10 | 1222 | 24317 | 47412 |
| ARL11 | 1223 | 24318 | 47413 |
| ARL13A | 1224 | 24319 | 47414 |
| ARL13B | 1225 | 24320 | 47415 |
| ARL14 | 1226 | 24321 | 47416 |
| ARL14EP | 1227 | 24322 | 47417 |
| ARL14EPL | 1228 | 24323 | 47418 |
| ARL15 | 1229 | 24324 | 47419 |
| ARL16 | 1230 | 24325 | 47420 |
| ARL17A | 1231 | 24326 | 47421 |
| ARL17A | 1232 | 24327 | 47422 |
| ARL17A | 1233 | 24328 | 47423 |
| ARL17A | 1234 | 24329 | 47424 |
| ARL17A | 1235 | 24330 | 47425 |
| ARL17B | 1236 | 24331 | 47426 |
| ARL2 | 1237 | 24332 | 47427 |
| ARL2BP | 1238 | 24333 | 47428 |
| ARL3 | 1239 | 24334 | 47429 |
| ARL4A | 1240 | 24335 | 47430 |
| ARL4C | 1241 | 24336 | 47431 |
| ARL4D | 1242 | 24337 | 47432 |
| ARL5A | 1243 | 24338 | 47433 |
| ARL5B | 1244 | 24339 | 47434 |
| ARL5C | 1245 | 24340 | 47435 |
| ARL6 | 1246 | 24341 | 47436 |
| ARL6 | 1247 | 24342 | 47437 |
| ARL6IP1 | 1248 | 24343 | 47438 |
| ARL6IP4 | 1249 | 24344 | 47439 |
| ARL6IP4 | 1250 | 24345 | 47440 |
| ARL6IP5 | 1251 | 24346 | 47441 |
| ARL6IP6 | 1252 | 24347 | 47442 |
| ARL8A | 1253 | 24348 | 47443 |
| ARL8A | 1254 | 24349 | 47444 |
| ARL8B | 1255 | 24350 | 47445 |
| ARL9 | 1256 | 24351 | 47446 |
| ARMC1 | 1257 | 24352 | 47447 |
| ARMC10 | 1258 | 24353 | 47448 |
| ARMC12 | 1259 | 24354 | 47449 |
| ARMC2 | 1260 | 24355 | 47450 |
| ARMC3 | 1261 | 24356 | 47451 |
| ARMC3 | 1262 | 24357 | 47452 |
| ARMC4 | 1263 | 24358 | 47453 |
| ARMC5 | 1264 | 24359 | 47454 |
| ARMC5 | 1265 | 24360 | 47455 |
| ARMC6 | 1266 | 24361 | 47456 |
| ARMC7 | 1267 | 24362 | 47457 |
| ARMC7 | 1268 | 24363 | 47458 |
| ARMC7 | 1269 | 24364 | 47459 |
| ARMC7 | 1270 | 24365 | 47460 |
| ARMC8 | 1271 | 24366 | 47461 |
| ARMC8 | 1272 | 24367 | 47462 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ARMC9 | 1273 | 24368 | 47463 |
| ARMC9 | 1274 | 24369 | 47464 |
| ARMCX1 | 1275 | 24370 | 47465 |
| ARMCX2 | 1276 | 24371 | 47466 |
| ARMCX3 | 1277 | 24372 | 47467 |
| ARMCX4 | 1278 | 24373 | 47468 |
| ARMCX5 | 1279 | 24374 | 47469 |
| ARMCX6 | 1280 | 24375 | 47470 |
| ARMS2 | 1281 | 24376 | 47471 |
| ARMT1 | 1282 | 24377 | 47472 |
| ARNT | 1283 | 24378 | 47473 |
| ARNT2 | 1284 | 24379 | 47474 |
| ARNTL | 1285 | 24380 | 47475 |
| ARNTL2 | 1286 | 24381 | 47476 |
| ARNTL2 | 1287 | 24382 | 47477 |
| ARPC1A | 1288 | 24383 | 47478 |
| ARPC1B | 1289 | 24384 | 47479 |
| ARPC2 | 1290 | 24385 | 47480 |
| ARPC3 | 1291 | 24386 | 47481 |
| ARPC4 | 1292 | 24387 | 47482 |
| ARPC4 | 1293 | 24388 | 47483 |
| ARPC4-TTLL3 | 1294 | 24389 | 47484 |
| ARPC5 | 1295 | 24390 | 47485 |
| ARPC5L | 1296 | 24391 | 47486 |
| ARPIN | 1297 | 24392 | 47487 |
| ARPIN | 1298 | 24393 | 47488 |
| ARPP19 | 1299 | 24394 | 47489 |
| ARPP21 | 1300 | 24395 | 47490 |
| ARPP21 | 1301 | 24396 | 47491 |
| ARPP21 | 1302 | 24397 | 47492 |
| ARR3 | 1303 | 24398 | 47493 |
| ARRB1 | 1304 | 24399 | 47494 |
| ARRB2 | 1305 | 24400 | 47495 |
| ARRB2 | 1306 | 24401 | 47496 |
| ARRDC1 | 1307 | 24402 | 47497 |
| ARRDC1 | 1308 | 24403 | 47498 |
| ARRDC2 | 1309 | 24404 | 47499 |
| ARRDC3 | 1310 | 24405 | 47500 |
| ARRDC4 | 1311 | 24406 | 47501 |
| ARRDC5 | 1312 | 24407 | 47502 |
| ARSA | 1313 | 24408 | 47503 |
| ARSB | 1314 | 24409 | 47504 |
| ARSB | 1315 | 24410 | 47505 |
| ARSD | 1316 | 24411 | 47506 |
| ARSD | 1317 | 24412 | 47507 |
| ARSE | 1318 | 24413 | 47508 |
| ARSF | 1319 | 24414 | 47509 |
| ARSG | 1320 | 24415 | 47510 |
| ARSG | 1321 | 24416 | 47511 |
| ARSH | 1322 | 24417 | 47512 |
| ARSI | 1323 | 24418 | 47513 |
| ARSJ | 1324 | 24419 | 47514 |
| ARSJ | 1325 | 24420 | 47515 |
| ARSK | 1326 | 24421 | 47516 |
| ART1 | 1327 | 24422 | 47517 |
| ART3 | 1328 | 24423 | 47518 |
| ART4 | 1329 | 24424 | 47519 |
| ART5 | 1330 | 24425 | 47520 |
| ART5 | 1331 | 24426 | 47521 |
| ARTN | 1332 | 24427 | 47522 |
| ARV1 | 1333 | 24428 | 47523 |
| ARVCF | 1334 | 24429 | 47524 |
| ARX | 1335 | 24430 | 47525 |
| AS3MT | 1336 | 24431 | 47526 |
| ASAH1 | 1337 | 24432 | 47527 |
| ASAH2 | 1338 | 24433 | 47528 |
| ASAP1 | 1339 | 24434 | 47529 |
| ASAP2 | 1340 | 24435 | 47530 |
| ASAP3 | 1341 | 24436 | 47531 |
| ASB1 | 1342 | 24437 | 47532 |
| ASB10 | 1343 | 24438 | 47533 |
| ASB11 | 1344 | 24439 | 47534 |
| ASB12 | 1345 | 24440 | 47535 |
| ASB13 | 1346 | 24441 | 47536 |
| ASB14 | 1347 | 24442 | 47537 |
| ASB15 | 1348 | 24443 | 47538 |
| ASB16 | 1349 | 24444 | 47539 |
| ASB17 | 1350 | 24445 | 47540 |
| ASB18 | 1351 | 24446 | 47541 |
| ASB2 | 1352 | 24447 | 47542 |
| ASB3 | 1353 | 24448 | 47543 |
| ASB4 | 1354 | 24449 | 47544 |
| ASB4 | 1355 | 24450 | 47545 |
| ASB5 | 1356 | 24451 | 47546 |
| ASB6 | 1357 | 24452 | 47547 |
| ASB6 | 1358 | 24453 | 47548 |
| ASB7 | 1359 | 24454 | 47549 |
| ASB7 | 1360 | 24455 | 47550 |
| ASB8 | 1361 | 24456 | 47551 |
| ASB9 | 1362 | 24457 | 47552 |
| ASB9 | 1363 | 24458 | 47553 |
| ASCC1 | 1364 | 24459 | 47554 |
| ASCC1 | 1365 | 24460 | 47555 |
| ASCC2 | 1366 | 24461 | 47556 |
| ASCC3 | 1367 | 24462 | 47557 |
| ASCC3 | 1368 | 24463 | 47558 |
| ASCC3 | 1369 | 24464 | 47559 |
| ASCL1 | 1370 | 24465 | 47560 |
| ASCL2 | 1371 | 24466 | 47561 |
| ASCL3 | 1372 | 24467 | 47562 |
| ASCL4 | 1373 | 24468 | 47563 |
| ASCL5 | 1374 | 24469 | 47564 |
| ASDURF | 1375 | 24470 | 47565 |
| ASF1A | 1376 | 24471 | 47566 |
| ASF1B | 1377 | 24472 | 47567 |
| ASGR1 | 1378 | 24473 | 47568 |
| ASGR2 | 1379 | 24474 | 47569 |
| ASH1L | 1380 | 24475 | 47570 |
| ASH2L | 1381 | 24476 | 47571 |
| ASIC1 | 1382 | 24477 | 47572 |
| ASIC2 | 1383 | 24478 | 47573 |
| ASIC3 | 1384 | 24479 | 47574 |
| ASIC3 | 1385 | 24480 | 47575 |
| ASIC3 | 1386 | 24481 | 47576 |
| ASIC4 | 1387 | 24482 | 47577 |
| ASIC5 | 1388 | 24483 | 47578 |
| ASIP | 1389 | 24484 | 47579 |
| ASL | 1390 | 24485 | 47580 |
| ASMT | 1391 | 24486 | 47581 |
| ASMTL | 1392 | 24487 | 47582 |
| ASNA1 | 1393 | 24488 | 47583 |
| ASNS | 1394 | 24489 | 47584 |
| ASNSD1 | 1395 | 24490 | 47585 |
| ASPA | 1396 | 24491 | 47586 |
| ASPDH | 1397 | 24492 | 47587 |
| ASPG | 1398 | 24493 | 47588 |
| ASPH | 1399 | 24494 | 47589 |
| ASPH | 1400 | 24495 | 47590 |
| ASPH | 1401 | 24496 | 47591 |
| ASPH | 1402 | 24497 | 47592 |
| ASPHD1 | 1403 | 24498 | 47593 |
| ASPHD2 | 1404 | 24499 | 47594 |
| ASPM | 1405 | 24500 | 47595 |
| ASPN | 1406 | 24501 | 47596 |
| ASPN | 1407 | 24502 | 47597 |
| ASPRV1 | 1408 | 24503 | 47598 |
| ASPSCR1 | 1409 | 24504 | 47599 |
| ASRGL1 | 1410 | 24505 | 47600 |
| ASS1 | 1411 | 24506 | 47601 |
| ASTE1 | 1412 | 24507 | 47602 |
| ASTL | 1413 | 24508 | 47603 |
| ASTN1 | 1414 | 24509 | 47604 |
| ASTN1 | 1415 | 24510 | 47605 |
| ASTN1 | 1416 | 24511 | 47606 |
| ASTN2 | 1417 | 24512 | 47607 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ASTN2 | 1418 | 24513 | 47608 |
| ASTN2 | 1419 | 24514 | 47609 |
| ASTN2 | 1420 | 24515 | 47610 |
| ASTN2 | 1421 | 24516 | 47611 |
| ASXL1 | 1422 | 24517 | 47612 |
| ASXL1 | 1423 | 24518 | 47613 |
| ASXL2 | 1424 | 24519 | 47614 |
| ASXL3 | 1425 | 24520 | 47615 |
| ASZ1 | 1426 | 24521 | 47616 |
| ATAD1 | 1427 | 24522 | 47617 |
| ATAD2 | 1428 | 24523 | 47618 |
| ATAD2B | 1429 | 24524 | 47619 |
| ATAD3A | 1430 | 24525 | 47620 |
| ATAD3B | 1431 | 24526 | 47621 |
| ATAD3C | 1432 | 24527 | 47622 |
| ATAD5 | 1433 | 24528 | 47623 |
| ATAT1 | 1434 | 24529 | 47624 |
| ATAT1 | 1435 | 24530 | 47625 |
| ATAT1 | 1436 | 24531 | 47626 |
| ATCAY | 1437 | 24532 | 47627 |
| ATE1 | 1438 | 24533 | 47628 |
| ATF1 | 1439 | 24534 | 47629 |
| ATF2 | 1440 | 24535 | 47630 |
| ATF2 | 1441 | 24536 | 47631 |
| ATF2 | 1442 | 24537 | 47632 |
| ATF3 | 1443 | 24538 | 47633 |
| ATF3 | 1444 | 24539 | 47634 |
| ATF4 | 1445 | 24540 | 47635 |
| ATF5 | 1446 | 24541 | 47636 |
| ATF6 | 1447 | 24542 | 47637 |
| ATF6B | 1448 | 24543 | 47638 |
| ATF7 | 1449 | 24544 | 47639 |
| ATF7 | 1450 | 24545 | 47640 |
| ATF7IP | 1451 | 24546 | 47641 |
| ATF7IP | 1452 | 24547 | 47642 |
| ATF7IP2 | 1453 | 24548 | 47643 |
| ATF7IP2 | 1454 | 24549 | 47644 |
| ATG10 | 1455 | 24550 | 47645 |
| ATG101 | 1456 | 24551 | 47646 |
| ATG12 | 1457 | 24552 | 47647 |
| ATG12 | 1458 | 24553 | 47648 |
| ATG13 | 1459 | 24554 | 47649 |
| ATG14 | 1460 | 24555 | 47650 |
| ATG16L1 | 1461 | 24556 | 47651 |
| ATG16L2 | 1462 | 24557 | 47652 |
| ATG2A | 1463 | 24558 | 47653 |
| ATG2B | 1464 | 24559 | 47654 |
| ATG3 | 1465 | 24560 | 47655 |
| ATG3 | 1466 | 24561 | 47656 |
| ATG4A | 1467 | 24562 | 47657 |
| ATG4B | 1468 | 24563 | 47658 |
| ATG4B | 1469 | 24564 | 47659 |
| ATG4C | 1470 | 24565 | 47660 |
| ATG4D | 1471 | 24566 | 47661 |
| ATG5 | 1472 | 24567 | 47662 |
| ATG5 | 1473 | 24568 | 47663 |
| ATG7 | 1474 | 24569 | 47664 |
| ATG7 | 1475 | 24570 | 47665 |
| ATG9A | 1476 | 24571 | 47666 |
| ATG9B | 1477 | 24572 | 47667 |
| ATIC | 1478 | 24573 | 47668 |
| ATL1 | 1479 | 24574 | 47669 |
| ATL2 | 1480 | 24575 | 47670 |
| ATL2 | 1481 | 24576 | 47671 |
| ATL3 | 1482 | 24577 | 47672 |
| ATM | 1483 | 24578 | 47673 |
| ATM | 1484 | 24579 | 47674 |
| ATMIN | 1485 | 24580 | 47675 |
| ATN1 | 1486 | 24581 | 47676 |
| ATOH1 | 1487 | 24582 | 47677 |
| ATOH7 | 1488 | 24583 | 47678 |
| ATOH8 | 1489 | 24584 | 47679 |
| ATOX1 | 1490 | 24585 | 47680 |
| ATP10A | 1491 | 24586 | 47681 |
| ATP10B | 1492 | 24587 | 47682 |
| ATP10D | 1493 | 24588 | 47683 |
| ATP11A | 1494 | 24589 | 47684 |
| ATP11A | 1495 | 24590 | 47685 |
| ATP11AUN | 1496 | 24591 | 47686 |
| ATP11B | 1497 | 24592 | 47687 |
| ATP11C | 1498 | 24593 | 47688 |
| ATP11C | 1499 | 24594 | 47689 |
| ATP11C | 1500 | 24595 | 47690 |
| ATP12A | 1501 | 24596 | 47691 |
| ATP13A1 | 1502 | 24597 | 47692 |
| ATP13A2 | 1503 | 24598 | 47693 |
| ATP13A2 | 1504 | 24599 | 47694 |
| ATP13A3 | 1505 | 24600 | 47695 |
| ATP13A4 | 1506 | 24601 | 47696 |
| ATP13A5 | 1507 | 24602 | 47697 |
| ATP1A1 | 1508 | 24603 | 47698 |
| ATP1A2 | 1509 | 24604 | 47699 |
| ATP1A3 | 1510 | 24605 | 47700 |
| ATP1A4 | 1511 | 24606 | 47701 |
| ATP1B1 | 1512 | 24607 | 47702 |
| ATP1B2 | 1513 | 24608 | 47703 |
| ATP1B3 | 1514 | 24609 | 47704 |
| ATP1B4 | 1515 | 24610 | 47705 |
| ATP23 | 1516 | 24611 | 47706 |
| ATP23 | 1517 | 24612 | 47707 |
| ATP2A1 | 1518 | 24613 | 47708 |
| ATP2A1 | 1519 | 24614 | 47709 |
| ATP2A2 | 1520 | 24615 | 47710 |
| ATP2A2 | 1521 | 24616 | 47711 |
| ATP2A3 | 1522 | 24617 | 47712 |
| ATP2A3 | 1523 | 24618 | 47713 |
| ATP2A3 | 1524 | 24619 | 47714 |
| ATP2A3 | 1525 | 24620 | 47715 |
| ATP2B1 | 1526 | 24621 | 47716 |
| ATP2B1 | 1527 | 24622 | 47717 |
| ATP2B2 | 1528 | 24623 | 47718 |
| ATP2B2 | 1529 | 24624 | 47719 |
| ATP2B3 | 1530 | 24625 | 47720 |
| ATP2B3 | 1531 | 24626 | 47721 |
| ATP2B4 | 1532 | 24627 | 47722 |
| ATP2B4 | 1533 | 24628 | 47723 |
| ATP2C1 | 1534 | 24629 | 47724 |
| ATP2C1 | 1535 | 24630 | 47725 |
| ATP2C1 | 1536 | 24631 | 47726 |
| ATP2C2 | 1537 | 24632 | 47727 |
| ATP4A | 1538 | 24633 | 47728 |
| ATP4B | 1539 | 24634 | 47729 |
| ATP5A1 | 1540 | 24635 | 47730 |
| ATP5B | 1541 | 24636 | 47731 |
| ATP5C1 | 1542 | 24637 | 47732 |
| ATP5D | 1543 | 24638 | 47733 |
| ATP5D | 1544 | 24639 | 47734 |
| ATP5E | 1545 | 24640 | 47735 |
| ATP5F1 | 1546 | 24641 | 47736 |
| ATP5G1 | 1547 | 24642 | 47737 |
| ATP5G2 | 1548 | 24643 | 47738 |
| ATP5G3 | 1549 | 24644 | 47739 |
| ATP5G3 | 1550 | 24645 | 47740 |
| ATP5H | 1551 | 24646 | 47741 |
| ATP5I | 1552 | 24647 | 47742 |
| ATP5J | 1553 | 24648 | 47743 |
| ATP5J2 | 1554 | 24649 | 47744 |
| ATP5L | 1555 | 24650 | 47745 |
| ATP5L2 | 1556 | 24651 | 47746 |
| ATP5O | 1557 | 24652 | 47747 |
| ATP5S | 1558 | 24653 | 47748 |
| ATP5S | 1559 | 24654 | 47749 |
| ATP5S | 1560 | 24655 | 47750 |
| ATP6AP1 | 1561 | 24656 | 47751 |
| ATP6AP1L | 1562 | 24657 | 47752 |
| ATP6AP2 | 1563 | 24658 | 47753 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ATP6V0A1 | 1564 | 24659 | 47754 |
| ATP6V0A2 | 1565 | 24660 | 47755 |
| ATP6V0A4 | 1566 | 24661 | 47756 |
| ATP6V0B | 1567 | 24662 | 47757 |
| ATP6V0B | 1568 | 24663 | 47758 |
| ATP6V0C | 1569 | 24664 | 47759 |
| ATP6V0D1 | 1570 | 24665 | 47760 |
| ATP6V0D2 | 1571 | 24666 | 47761 |
| ATP6V0E1 | 1572 | 24667 | 47762 |
| ATP6V0E2 | 1573 | 24668 | 47763 |
| ATP6V0E2 | 1574 | 24669 | 47764 |
| ATP6V1A | 1575 | 24670 | 47765 |
| ATP6V1B1 | 1576 | 24671 | 47766 |
| ATPSV1B2 | 1577 | 24672 | 47767 |
| ATPSV1C1 | 1578 | 24673 | 47768 |
| ATP6V1C2 | 1579 | 24674 | 47769 |
| ATP6V1D | 1580 | 24675 | 47770 |
| ATP6V1E1 | 1581 | 24676 | 47771 |
| ATP6V1E2 | 1582 | 24677 | 47772 |
| ATP6V1F | 1583 | 24678 | 47773 |
| ATP6V1G1 | 1584 | 24679 | 47774 |
| ATP6V1G2 | 1585 | 24680 | 47775 |
| ATP6V1G3 | 1586 | 24681 | 47776 |
| ATP6V1H | 1587 | 24682 | 47777 |
| ATP7A | 1588 | 24683 | 47778 |
| ATP7B | 1589 | 24684 | 47779 |
| ATP8A1 | 1590 | 24685 | 47780 |
| ATP8A2 | 1591 | 24686 | 47781 |
| ATP8B1 | 1592 | 24687 | 47782 |
| ATP8B2 | 1593 | 24688 | 47783 |
| ATP8B2 | 1594 | 24689 | 47784 |
| ATP8B3 | 1595 | 24690 | 47785 |
| ATP8B4 | 1596 | 24691 | 47786 |
| ATP9A | 1597 | 24692 | 47787 |
| ATP9B | 1598 | 24693 | 47788 |
| ATPAF1 | 1599 | 24694 | 47789 |
| ATPAF2 | 1600 | 24695 | 47790 |
| ATPIF1 | 1601 | 24696 | 47791 |
| ATPIF1 | 1602 | 24697 | 47792 |
| ATR | 1603 | 24698 | 47793 |
| ATRAID | 1604 | 24699 | 47794 |
| ATRIP | 1605 | 24700 | 47795 |
| ATRN | 1606 | 24701 | 47796 |
| ATRN | 1607 | 24702 | 47797 |
| ATRN | 1608 | 24703 | 47798 |
| ATRNL1 | 1609 | 24704 | 47799 |
| ATRNL1 | 1610 | 24705 | 47800 |
| ATRX | 1611 | 24706 | 47801 |
| ATXN1 | 1612 | 24707 | 47802 |
| ATXN10 | 1613 | 24708 | 47803 |
| ATXN1L | 1614 | 24709 | 47804 |
| ATXN2 | 1615 | 24710 | 47805 |
| ATXN2L | 1616 | 24711 | 47806 |
| ATXN2L | 1617 | 24712 | 47807 |
| ATXN2L | 1618 | 24713 | 47808 |
| ATXN2L | 1619 | 24714 | 47809 |
| ATXN3 | 1620 | 24715 | 47810 |
| ATXN3 | 1621 | 24716 | 47811 |
| ATXN3 | 1622 | 24717 | 47812 |
| ATXN3L | 1623 | 24718 | 47813 |
| ATXN7 | 1624 | 24719 | 47814 |
| ATXN7 | 1625 | 24720 | 47815 |
| ATXN7L1 | 1626 | 24721 | 47816 |
| ATXN7L1 | 1627 | 24722 | 47817 |
| ATXN7L1 | 1628 | 24723 | 47818 |
| ATXN7L2 | 1629 | 24724 | 47819 |
| ATXN7L2 | 1630 | 24725 | 47820 |
| ATXN7L3 | 1631 | 24726 | 47821 |
| ATXN7L3B | 1632 | 24727 | 47822 |
| AUH | 1633 | 24728 | 47823 |
| AUNIP | 1634 | 24729 | 47824 |
| AUNIP | 1635 | 24730 | 47825 |
| AUP1 | 1636 | 24731 | 47826 |
| AURKA | 1637 | 24732 | 47827 |
| AURKAIP1 | 1638 | 24733 | 47828 |
| AURKB | 1639 | 24734 | 47829 |
| AURKB | 1640 | 24735 | 47830 |
| AURKC | 1641 | 24736 | 47831 |
| AUTS2 | 1642 | 24737 | 47832 |
| AUTS2 | 1643 | 24738 | 47833 |
| AVEN | 1644 | 24739 | 47834 |
| AVIL | 1645 | 24740 | 47835 |
| AVL9 | 1646 | 24741 | 47836 |
| AVP | 1647 | 24742 | 47837 |
| AVPI1 | 1648 | 24743 | 47838 |
| AVPR1A | 1649 | 24744 | 47839 |
| AVPR1B | 1650 | 24745 | 47840 |
| AVPR2 | 1651 | 24746 | 47841 |
| AVPR2 | 1652 | 24747 | 47842 |
| AWAT1 | 1653 | 24748 | 47843 |
| AWAT2 | 1654 | 24749 | 47844 |
| AXDND1 | 1655 | 24750 | 47845 |
| AXIN1 | 1656 | 24751 | 47846 |
| AXIN2 | 1657 | 24752 | 47847 |
| AXL | 1658 | 24753 | 47848 |
| AZGP1 | 1659 | 24754 | 47849 |
| AZI2 | 1660 | 24755 | 47850 |
| AZI2 | 1661 | 24756 | 47851 |
| AZI2 | 1662 | 24757 | 47852 |
| AZIN1 | 1663 | 24758 | 47853 |
| AZIN1 | 1664 | 24759 | 47854 |
| AZIN2 | 1665 | 24760 | 47855 |
| AZIN2 | 1666 | 24761 | 47856 |
| AZU1 | 1667 | 24762 | 47857 |
| B2M | 1668 | 24763 | 47858 |
| B3GALNT1 | 1669 | 24764 | 47859 |
| B3GALNT2 | 1670 | 24765 | 47860 |
| B3GALNT2 | 1671 | 24766 | 47861 |
| B3GALT1 | 1672 | 24767 | 47862 |
| B3GALT2 | 1673 | 24768 | 47863 |
| B3GALT4 | 1674 | 24769 | 47864 |
| B3GALT5 | 1675 | 24770 | 47865 |
| B3GALT6 | 1676 | 24771 | 47866 |
| B3GAT1 | 1677 | 24772 | 47867 |
| B3GAT2 | 1678 | 24773 | 47868 |
| B3GAT3 | 1679 | 24774 | 47869 |
| B3GAT3 | 1680 | 24775 | 47870 |
| B3GLCT | 1681 | 24776 | 47871 |
| B3GNT2 | 1682 | 24777 | 47872 |
| B3GNT3 | 1683 | 24778 | 47873 |
| B3GNT4 | 1684 | 24779 | 47874 |
| B3GNT5 | 1685 | 24780 | 47875 |
| B3GNT6 | 1686 | 24781 | 47876 |
| B3GNT7 | 1687 | 24782 | 47877 |
| B3GNT8 | 1688 | 24783 | 47878 |
| B3GNT9 | 1689 | 24784 | 47879 |
| B3GNTL1 | 1690 | 24785 | 47880 |
| B4GALNT1 | 1691 | 24786 | 47881 |
| B4GALNT1 | 1692 | 24787 | 47882 |
| B4GALNT2 | 1693 | 24788 | 47883 |
| B4GALNT3 | 1694 | 24789 | 47884 |
| B4GALNT4 | 1695 | 24790 | 47885 |
| B4GALT1 | 1696 | 24791 | 47886 |
| B4GALT2 | 1697 | 24792 | 47887 |
| B4GALT3 | 1698 | 24793 | 47888 |
| B4GALT4 | 1699 | 24794 | 47889 |
| B4GALT5 | 1700 | 24795 | 47890 |
| B4GALT6 | 1701 | 24796 | 47891 |
| B4GALT7 | 1702 | 24797 | 47892 |
| B4GAT1 | 1703 | 24798 | 47893 |
| B9D1 | 1704 | 24799 | 47894 |
| B9D1 | 1705 | 24800 | 47895 |
| B9D1 | 1706 | 24801 | 47896 |
| B9D1 | 1707 | 24802 | 47897 |
| B9D1 | 1708 | 24803 | 47898 |
| B9D1 | 1709 | 24804 | 47899 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| B9D2 | 1710 | 24805 | 47900 |
| BAALC | 1711 | 24806 | 47901 |
| BAAT | 1712 | 24807 | 47902 |
| BABAM1 | 1713 | 24808 | 47903 |
| BABAM2 | 1714 | 24809 | 47904 |
| BABAM2 | 1715 | 24810 | 47905 |
| BABAM2 | 1716 | 24811 | 47906 |
| BABAM2 | 1717 | 24812 | 47907 |
| BACE1 | 1718 | 24813 | 47908 |
| BACE2 | 1719 | 24814 | 47909 |
| BACE2 | 1720 | 24815 | 47910 |
| BACH1 | 1721 | 24816 | 47911 |
| BACH2 | 1722 | 24817 | 47912 |
| BAD | 1723 | 24818 | 47913 |
| BAG1 | 1724 | 24819 | 47914 |
| BAG2 | 1725 | 24820 | 47915 |
| BAG3 | 1726 | 24821 | 47916 |
| BAG4 | 1727 | 24822 | 47917 |
| BAG5 | 1728 | 24823 | 47918 |
| BAG6 | 1729 | 24824 | 47919 |
| BAGE | 1730 | 24825 | 47920 |
| BAGE2 | 1731 | 24826 | 47921 |
| BAGE4 | 1732 | 24827 | 47922 |
| BAGE5 | 1733 | 24828 | 47923 |
| BAHCC1 | 1734 | 24829 | 47924 |
| BAHD1 | 1735 | 24830 | 47925 |
| BAIAP2 | 1736 | 24831 | 47926 |
| BAIAP2 | 1737 | 24832 | 47927 |
| BAIAP2 | 1738 | 24833 | 47928 |
| BAIAP2 | 1739 | 24834 | 47929 |
| BAIAP2L1 | 1740 | 24835 | 47930 |
| BAIAP2L2 | 1741 | 24836 | 47931 |
| BAIAP3 | 1742 | 24837 | 47932 |
| BAK1 | 1743 | 24838 | 47933 |
| BAMBI | 1744 | 24839 | 47934 |
| BANF1 | 1745 | 24840 | 47935 |
| BANF2 | 1746 | 24841 | 47936 |
| BANK1 | 1747 | 24842 | 47937 |
| BANP | 1748 | 24843 | 47938 |
| BAP1 | 1749 | 24844 | 47939 |
| BARD1 | 1750 | 24845 | 47940 |
| BARHL1 | 1751 | 24846 | 47941 |
| BARHL2 | 1752 | 24847 | 47942 |
| BARX1 | 1753 | 24848 | 47943 |
| BARX2 | 1754 | 24849 | 47944 |
| BASP1 | 1755 | 24850 | 47945 |
| BATF | 1756 | 24851 | 47946 |
| BATF2 | 1757 | 24852 | 47947 |
| BATF2 | 1758 | 24853 | 47948 |
| BATF3 | 1759 | 24854 | 47949 |
| BAX | 1760 | 24855 | 47950 |
| BAX | 1761 | 24856 | 47951 |
| BAX | 1762 | 24857 | 47952 |
| BAZ1A | 1763 | 24858 | 47953 |
| BAZ1B | 1764 | 24859 | 47954 |
| BAZ2A | 1765 | 24860 | 47955 |
| BAZ2B | 1766 | 24861 | 47956 |
| BBC3 | 1767 | 24862 | 47957 |
| BBC3 | 1768 | 24863 | 47958 |
| BBIP1 | 1769 | 24864 | 47959 |
| BBIP1 | 1770 | 24865 | 47960 |
| BBOF1 | 1771 | 24866 | 47961 |
| BBOX1 | 1772 | 24867 | 47962 |
| BBS1 | 1773 | 24868 | 47963 |
| BBS10 | 1774 | 24869 | 47964 |
| BBS12 | 1775 | 24870 | 47965 |
| BBS2 | 1776 | 24871 | 47966 |
| BBS4 | 1777 | 24872 | 47967 |
| BBS5 | 1778 | 24873 | 47968 |
| BBS7 | 1779 | 24874 | 47969 |
| BBS7 | 1780 | 24875 | 47970 |
| BBS9 | 1781 | 24876 | 47971 |
| BBS9 | 1782 | 24877 | 47972 |
| BBX | 1783 | 24878 | 47973 |
| BBX | 1784 | 24879 | 47974 |
| BCAM | 1785 | 24880 | 47975 |
| BCAM | 1786 | 24881 | 47976 |
| BCAN | 1787 | 24882 | 47977 |
| BCAN | 1788 | 24883 | 47978 |
| BCAP29 | 1789 | 24884 | 47979 |
| BCAP29 | 1790 | 24885 | 47980 |
| BCAP31 | 1791 | 24886 | 47981 |
| BCAR1 | 1792 | 24887 | 47982 |
| BCAR3 | 1793 | 24888 | 47983 |
| BCAS1 | 1794 | 24889 | 47984 |
| BCAS2 | 1795 | 24890 | 47985 |
| BCAS3 | 1796 | 24891 | 47986 |
| BCAS3 | 1797 | 24892 | 47987 |
| BCAS4 | 1798 | 24893 | 47988 |
| BCAS4 | 1799 | 24894 | 47989 |
| BCAT1 | 1800 | 24895 | 47990 |
| BCAT2 | 1801 | 24896 | 47991 |
| BCCIP | 1802 | 24897 | 47992 |
| BCCIP | 1803 | 24898 | 47993 |
| BCCIP | 1804 | 24899 | 47994 |
| BCDIN3D | 1805 | 24900 | 47995 |
| BCHE | 1806 | 24901 | 47996 |
| BCKDHA | 1807 | 24902 | 47997 |
| BCKDHB | 1808 | 24903 | 47998 |
| BCKDK | 1809 | 24904 | 47999 |
| BCKDK | 1810 | 24905 | 48000 |
| BCL10 | 1811 | 24906 | 48001 |
| BCL11A | 1812 | 24907 | 48002 |
| BCL11A | 1813 | 24908 | 48003 |
| BCL11B | 1814 | 24909 | 48004 |
| BCL2 | 1815 | 24910 | 48005 |
| BCL2 | 1816 | 24911 | 48006 |
| BCL2A1 | 1817 | 24912 | 48007 |
| BCL2A1 | 1818 | 24913 | 48008 |
| BCL2L1 | 1819 | 24914 | 48009 |
| BCL2L1 | 1820 | 24915 | 48010 |
| BCL2L10 | 1821 | 24916 | 48011 |
| BCL2L10 | 1822 | 24917 | 48012 |
| BCL2L11 | 1823 | 24918 | 48013 |
| BCL2L11 | 1824 | 24919 | 48014 |
| BCL2L11 | 1825 | 24920 | 48015 |
| BCL2L11 | 1826 | 24921 | 48016 |
| BCL2L11 | 1827 | 24922 | 48017 |
| BCL2L11 | 1828 | 24923 | 48018 |
| BCL2L11 | 1829 | 24924 | 48019 |
| BCL2L11 | 1830 | 24925 | 48020 |
| BCL2L12 | 1831 | 24926 | 48021 |
| BCL2L12 | 1832 | 24927 | 48022 |
| BCL2L13 | 1833 | 24928 | 48023 |
| BCL2L14 | 1834 | 24929 | 48024 |
| BCL2L14 | 1835 | 24930 | 48025 |
| BCL2L15 | 1836 | 24931 | 48026 |
| BCL2L2 | 1837 | 24932 | 48027 |
| BCL3 | 1838 | 24933 | 48028 |
| BCL6 | 1839 | 24934 | 48029 |
| BCL6B | 1840 | 24935 | 48030 |
| BCL7A | 1841 | 24936 | 48031 |
| BCL7B | 1842 | 24937 | 48032 |
| BCL7C | 1843 | 24938 | 48033 |
| BCL7C | 1844 | 24939 | 48034 |
| BCL9 | 1845 | 24940 | 48035 |
| BCL9L | 1846 | 24941 | 48036 |
| BCLAF1 | 1847 | 24942 | 48037 |
| BCLAF3 | 1848 | 24943 | 48038 |
| BCO1 | 1849 | 24944 | 48039 |
| BCO2 | 1850 | 24945 | 48040 |
| BCOR | 1851 | 24946 | 48041 |
| BCORL1 | 1852 | 24947 | 48042 |
| BCR | 1853 | 24948 | 48043 |
| BCS1L | 1854 | 24949 | 48044 |
| BDH1 | 1855 | 24950 | 48045 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| BDH2 | 1856 | 24951 | 48046 |
| BDKRB1 | 1857 | 24952 | 48047 |
| BDKRB2 | 1858 | 24953 | 48048 |
| BDNF | 1859 | 24954 | 48049 |
| BDP1 | 1860 | 24955 | 48050 |
| BEAN1 | 1861 | 24956 | 48051 |
| BEAN1 | 1862 | 24957 | 48052 |
| BECN1 | 1863 | 24958 | 48053 |
| BECN1 | 1864 | 24959 | 48054 |
| BECN2 | 1865 | 24960 | 48055 |
| BEGAIN | 1866 | 24961 | 48056 |
| BEND2 | 1867 | 24962 | 48057 |
| BEND2 | 1868 | 24963 | 48058 |
| BEND3 | 1869 | 24964 | 48059 |
| BEND4 | 1870 | 24965 | 48060 |
| BEND4 | 1871 | 24966 | 48061 |
| BEND5 | 1872 | 24967 | 48062 |
| BEND6 | 1873 | 24968 | 48063 |
| BEND6 | 1874 | 24969 | 48064 |
| BEND7 | 1875 | 24970 | 48065 |
| BEND7 | 1876 | 24971 | 48066 |
| BEST1 | 1877 | 24972 | 48067 |
| BEST1 | 1878 | 24973 | 48068 |
| BEST2 | 1879 | 24974 | 48069 |
| BEST3 | 1880 | 24975 | 48070 |
| BEST3 | 1881 | 24976 | 48071 |
| BEST3 | 1882 | 24977 | 48072 |
| BEST4 | 1883 | 24978 | 48073 |
| BET1 | 1884 | 24979 | 48074 |
| BET1 | 1885 | 24980 | 48075 |
| BET1L | 1886 | 24981 | 48076 |
| BEX2 | 1887 | 24982 | 48077 |
| BEX3 | 1888 | 24983 | 48078 |
| BEX4 | 1889 | 24984 | 48079 |
| BEX5 | 1890 | 24985 | 48080 |
| BFAR | 1891 | 24986 | 48081 |
| BFSP1 | 1892 | 24987 | 48082 |
| BFSP2 | 1893 | 24988 | 48083 |
| BGLAP | 1894 | 24989 | 48084 |
| BGN | 1895 | 24990 | 48085 |
| BHLHA15 | 1896 | 24991 | 48086 |
| BHLHA9 | 1897 | 24992 | 48087 |
| BHLHB9 | 1898 | 24993 | 48088 |
| BHLHE22 | 1899 | 24994 | 48089 |
| BHLHE23 | 1900 | 24995 | 48090 |
| BHLHE40 | 1901 | 24996 | 48091 |
| BHLHE41 | 1902 | 24997 | 48092 |
| BHMG1 | 1903 | 24998 | 48093 |
| BHMT | 1904 | 24999 | 48094 |
| BHMT2 | 1905 | 25000 | 48095 |
| BICC1 | 1906 | 25001 | 48096 |
| BICD1 | 1907 | 25002 | 48097 |
| BICD1 | 1908 | 25003 | 48098 |
| BICD2 | 1909 | 25004 | 48099 |
| BICD2 | 1910 | 25005 | 48100 |
| BICDL1 | 1911 | 25006 | 48101 |
| BICDL2 | 1912 | 25007 | 48102 |
| BICRA | 1913 | 25008 | 48103 |
| BICRAL | 1914 | 25009 | 48104 |
| BID | 1915 | 25010 | 48105 |
| BIK | 1916 | 25011 | 48106 |
| BIN1 | 1917 | 25012 | 48107 |
| BIN2 | 1918 | 25013 | 48108 |
| BIN3 | 1919 | 25014 | 48109 |
| BIRC2 | 1920 | 25015 | 48110 |
| BIRC3 | 1921 | 25016 | 48111 |
| BIRC5 | 1922 | 25017 | 48112 |
| BIRC5 | 1923 | 25018 | 48113 |
| BIRC6 | 1924 | 25019 | 48114 |
| BIRC7 | 1925 | 25020 | 48115 |
| BIRC8 | 1926 | 25021 | 48116 |
| BIVM | 1927 | 25022 | 48117 |
| BLCAP | 1928 | 25023 | 48118 |
| BUD | 1929 | 25024 | 48119 |
| BLK | 1930 | 25025 | 48120 |
| BLM | 1931 | 25026 | 48121 |
| BLMH | 1932 | 25027 | 48122 |
| BLNK | 1933 | 25028 | 48123 |
| BLOC1S1 | 1934 | 25029 | 48124 |
| BLOC1S2 | 1935 | 25030 | 48125 |
| BLOC1S3 | 1936 | 25031 | 48126 |
| BLOC1S4 | 1937 | 25032 | 48127 |
| BLOC1S5 | 1938 | 25033 | 48128 |
| BLOC1S5 | 1939 | 25034 | 48129 |
| BLOC1S6 | 1940 | 25035 | 48130 |
| BLOC1S6 | 1941 | 25036 | 48131 |
| BLVRA | 1942 | 25037 | 48132 |
| BLVRB | 1943 | 25038 | 48133 |
| BLZF1 | 1944 | 25039 | 48134 |
| BLZF1 | 1945 | 25040 | 48135 |
| BMF | 1946 | 25041 | 48136 |
| BMF | 1947 | 25042 | 48137 |
| BMI1 | 1948 | 25043 | 48138 |
| BMP1 | 1949 | 25044 | 48139 |
| BMP1 | 1950 | 25045 | 48140 |
| BMP10 | 1951 | 25046 | 48141 |
| BMP15 | 1952 | 25047 | 48142 |
| BMP2 | 1953 | 25048 | 48143 |
| BMP2K | 1954 | 25049 | 48144 |
| BMP2K | 1955 | 25050 | 48145 |
| BMP3 | 1956 | 25051 | 48146 |
| BMP4 | 1957 | 25052 | 48147 |
| BMP5 | 1958 | 25053 | 48148 |
| BMP5 | 1959 | 25054 | 48149 |
| BMP6 | 1960 | 25055 | 48150 |
| BMP7 | 1961 | 25056 | 48151 |
| BMP8A | 1962 | 25057 | 48152 |
| BMP8B | 1963 | 25058 | 48153 |
| BMPER | 1964 | 25059 | 48154 |
| BMPR1A | 1965 | 25060 | 48155 |
| BMPR1B | 1966 | 25061 | 48156 |
| BMPR2 | 1967 | 25062 | 48157 |
| BMS1 | 1968 | 25063 | 48158 |
| BMT2 | 1969 | 25064 | 48159 |
| BMX | 1970 | 25065 | 48160 |
| BNC1 | 1971 | 25066 | 48161 |
| BNC2 | 1972 | 25067 | 48162 |
| BNC2 | 1973 | 25068 | 48163 |
| BNIP1 | 1974 | 25069 | 48164 |
| BNIP2 | 1975 | 25070 | 48165 |
| BNIP3 | 1976 | 25071 | 48166 |
| BNIP3L | 1977 | 25072 | 48167 |
| BNIPL | 1978 | 25073 | 48168 |
| BOC | 1979 | 25074 | 48169 |
| BOC | 1980 | 25075 | 48170 |
| BOD1 | 1981 | 25076 | 48171 |
| BOD1L1 | 1982 | 25077 | 48172 |
| BOD1L2 | 1983 | 25078 | 48173 |
| BOK | 1984 | 25079 | 48174 |
| BOLA1 | 1985 | 25080 | 48175 |
| BOLA2 | 1986 | 25081 | 48176 |
| BOLA2 | 1987 | 25082 | 48177 |
| BOLA2-SMG1P6 | 1988 | 25083 | 48178 |
| BOLA3 | 1989 | 25084 | 48179 |
| BOLA3 | 1990 | 25085 | 48180 |
| BOLL | 1991 | 25086 | 48181 |
| BOLL | 1992 | 25087 | 48182 |
| BOP1 | 1993 | 25088 | 48183 |
| BORA | 1994 | 25089 | 48184 |
| BORCS5 | 1995 | 25090 | 48185 |
| BORCS6 | 1996 | 25091 | 48186 |
| BORCS7 | 1997 | 25092 | 48187 |
| BORCS8 | 1998 | 25093 | 48188 |
| BORCS8 | 1999 | 25094 | 48189 |
| BORCS8- | 2000 | 25095 | 48190 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MEF2B | | | |
| BPGM | 2001 | 25096 | 48191 |
| BPHL | 2002 | 25097 | 48192 |
| BPI | 2003 | 25098 | 48193 |
| BPIFA1 | 2004 | 25099 | 48194 |
| BPIFA2 | 2005 | 25100 | 48195 |
| BPIFA3 | 2006 | 25101 | 48196 |
| BPIFB1 | 2007 | 25102 | 48197 |
| BPIFB2 | 2008 | 25103 | 48198 |
| BPIFB3 | 2009 | 25104 | 48199 |
| BPIFB4 | 2010 | 25105 | 48200 |
| BPIFB6 | 2011 | 25106 | 48201 |
| BPIFC | 2012 | 25107 | 48202 |
| BPNT1 | 2013 | 25108 | 48203 |
| BPTF | 2014 | 25109 | 48204 |
| BPY2 | 2015 | 25110 | 48205 |
| BRAF | 2016 | 25111 | 48206 |
| BRAP | 2017 | 25112 | 48207 |
| BRAT1 | 2018 | 25113 | 48208 |
| BRCA1 | 2019 | 25114 | 48209 |
| BRCA1 | 2020 | 25115 | 48210 |
| BRCA2 | 2021 | 25116 | 48211 |
| BRCC3 | 2022 | 25117 | 48212 |
| BRD1 | 2023 | 25118 | 48213 |
| BRD2 | 2024 | 25119 | 48214 |
| BRD3 | 2025 | 25120 | 48215 |
| BRD4 | 2026 | 25121 | 48216 |
| BRD4 | 2027 | 25122 | 48217 |
| BRD4 | 2028 | 25123 | 48218 |
| BRD7 | 2029 | 25124 | 48219 |
| BRD8 | 2030 | 25125 | 48220 |
| BRD8 | 2031 | 25126 | 48221 |
| BRD9 | 2032 | 25127 | 48222 |
| BRDT | 2033 | 25128 | 48223 |
| BRF1 | 2034 | 25129 | 48224 |
| BRF1 | 2035 | 25130 | 48225 |
| BRF2 | 2036 | 25131 | 48226 |
| BRI3 | 2037 | 25132 | 48227 |
| BRI3 | 2038 | 25133 | 48228 |
| BRI3BP | 2039 | 25134 | 48229 |
| BRICD5 | 2040 | 25135 | 48230 |
| BRINP1 | 2041 | 25136 | 48231 |
| BRINP2 | 2042 | 25137 | 48232 |
| BRINP3 | 2043 | 25138 | 48233 |
| BRIP1 | 2044 | 25139 | 48234 |
| BRIX1 | 2045 | 25140 | 48235 |
| BRK1 | 2046 | 25141 | 48236 |
| BRMS1 | 2047 | 25142 | 48237 |
| BRMS1 | 2048 | 25143 | 48238 |
| BRMS1L | 2049 | 25144 | 48239 |
| BROX | 2050 | 25145 | 48240 |
| BROX | 2051 | 25146 | 48241 |
| BRPF1 | 2052 | 25147 | 48242 |
| BRPF3 | 2053 | 25148 | 48243 |
| BRS3 | 2054 | 25149 | 48244 |
| BRSK1 | 2055 | 25150 | 48245 |
| BRSK2 | 2056 | 25151 | 48246 |
| BRSK2 | 2057 | 25152 | 48247 |
| BRSK2 | 2058 | 25153 | 48248 |
| BRWD1 | 2059 | 25154 | 48249 |
| BRWD1 | 2060 | 25155 | 48250 |
| BRWD1 | 2061 | 25156 | 48251 |
| BRWD3 | 2062 | 25157 | 48252 |
| BSCL2 | 2063 | 25158 | 48253 |
| BSCL2 | 2064 | 25159 | 48254 |
| BSDC1 | 2065 | 25160 | 48255 |
| BSDC1 | 2066 | 25161 | 48256 |
| BSG | 2067 | 25162 | 48257 |
| BSN | 2068 | 25163 | 48258 |
| BSND | 2069 | 25164 | 48259 |
| BSPH1 | 2070 | 25165 | 48260 |
| BSPRY | 2071 | 25166 | 48261 |
| BSPRY | 2072 | 25167 | 48262 |
| BST1 | 2073 | 25168 | 48263 |
| BST2 | 2074 | 25169 | 48264 |
| BSX | 2075 | 25170 | 48265 |
| BTAF1 | 2076 | 25171 | 48266 |
| BTBD1 | 2077 | 25172 | 48267 |
| BTBD1 | 2078 | 25173 | 48268 |
| BTBD10 | 2079 | 25174 | 48269 |
| BTBD11 | 2080 | 25175 | 48270 |
| BTBD16 | 2081 | 25176 | 48271 |
| BTBD17 | 2082 | 25177 | 48272 |
| BTBD18 | 2083 | 25178 | 48273 |
| BTBD19 | 2084 | 25179 | 48274 |
| BTBD2 | 2085 | 25180 | 48275 |
| BTBD3 | 2086 | 25181 | 48276 |
| BTBD6 | 2087 | 25182 | 48277 |
| BTBD7 | 2088 | 25183 | 48278 |
| BTBD7 | 2089 | 25184 | 48279 |
| BTBD8 | 2090 | 25185 | 48280 |
| BTBD9 | 2091 | 25186 | 48281 |
| BTC | 2092 | 25187 | 48282 |
| BTD | 2093 | 25188 | 48283 |
| BTD | 2094 | 25189 | 48284 |
| BTF3 | 2095 | 25190 | 48285 |
| BTF3L4 | 2096 | 25191 | 48286 |
| BTG1 | 2097 | 25192 | 48287 |
| BTG2 | 2098 | 25193 | 48288 |
| BTG3 | 2099 | 25194 | 48289 |
| BTG4 | 2100 | 25195 | 48290 |
| BTK | 2101 | 25196 | 48291 |
| BTLA | 2102 | 25197 | 48292 |
| BTN1A1 | 2103 | 25198 | 48293 |
| BTN2A1 | 2104 | 25199 | 48294 |
| BTN2A1 | 2105 | 25200 | 48295 |
| BTN2A1 | 2106 | 25201 | 48296 |
| BTN2A2 | 2107 | 25202 | 48297 |
| BTN2A2 | 2108 | 25203 | 48298 |
| BTN3A1 | 2109 | 25204 | 48299 |
| BTN3A1 | 2110 | 25205 | 48300 |
| BTN3A1 | 2111 | 25206 | 48301 |
| BTN3A2 | 2112 | 25207 | 48302 |
| BTN3A3 | 2113 | 25208 | 48303 |
| BTNL10 | 2114 | 25209 | 48304 |
| BTNL2 | 2115 | 25210 | 48305 |
| BTNL3 | 2116 | 25211 | 48306 |
| BTNL8 | 2117 | 25212 | 48307 |
| BTNL8 | 2118 | 25213 | 48308 |
| BTNL9 | 2119 | 25214 | 48309 |
| BTNL9 | 2120 | 25215 | 48310 |
| BTRC | 2121 | 25216 | 48311 |
| BUB1 | 2122 | 25217 | 48312 |
| BUB1B | 2123 | 25218 | 48313 |
| BUB3 | 2124 | 25219 | 48314 |
| BUB3 | 2125 | 25220 | 48315 |
| BUD13 | 2126 | 25221 | 48316 |
| BUD23 | 2127 | 25222 | 48317 |
| BUD31 | 2128 | 25223 | 48318 |
| BVES | 2129 | 25224 | 48319 |
| BYSL | 2130 | 25225 | 48320 |
| BZW1 | 2131 | 25226 | 48321 |
| BZW2 | 2132 | 25227 | 48322 |
| C10orf10 | 2133 | 25228 | 48323 |
| C10orf105 | 2134 | 25229 | 48324 |
| C10orf111 | 2135 | 25230 | 48325 |
| C10orf113 | 2136 | 25231 | 48326 |
| C10orf113 | 2137 | 25232 | 48327 |
| C10orf120 | 2138 | 25233 | 48328 |
| C10orf126 | 2139 | 25234 | 48329 |
| C10orf128 | 2140 | 25235 | 48330 |
| C10orf128 | 2141 | 25236 | 48331 |
| C10orf128 | 2142 | 25237 | 48332 |
| C10orf128 | 2143 | 25238 | 48333 |
| C10orf128 | 2144 | 25239 | 48334 |
| C10orf128 | 2145 | 25240 | 48335 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| C10orf142 | 2146 | 25241 | 48336 |
| C10orf25 | 2147 | 25242 | 48337 |
| C10orf53 | 2148 | 25243 | 48338 |
| C10orf53 | 2149 | 25244 | 48339 |
| C10orf55 | 2150 | 25245 | 48340 |
| C10orf62 | 2151 | 25246 | 48341 |
| C10orf67 | 2152 | 25247 | 48342 |
| C10orf67 | 2153 | 25248 | 48343 |
| C10orf71 | 2154 | 25249 | 48344 |
| C10orf76 | 2155 | 25250 | 48345 |
| C10orf82 | 2156 | 25251 | 48346 |
| C10orf82 | 2157 | 25252 | 48347 |
| C10orf88 | 2158 | 25253 | 48348 |
| C10orf90 | 2159 | 25254 | 48349 |
| C10orf90 | 2160 | 25255 | 48350 |
| C10orf91 | 2161 | 25256 | 48351 |
| C10orf95 | 2162 | 25257 | 48352 |
| C10orf99 | 2163 | 25258 | 48353 |
| C11orf1 | 2164 | 25259 | 48354 |
| C11orf16 | 2165 | 25260 | 48355 |
| C11orf21 | 2166 | 25261 | 48356 |
| C11orf24 | 2167 | 25262 | 48357 |
| C11orf40 | 2168 | 25263 | 48358 |
| C11orf42 | 2169 | 25264 | 48359 |
| C11orf44 | 2170 | 25265 | 48360 |
| C11orf45 | 2171 | 25266 | 48361 |
| C11orf49 | 2172 | 25267 | 48362 |
| C11orf49 | 2173 | 25268 | 48363 |
| C11orf49 | 2174 | 25269 | 48364 |
| C11orf52 | 2175 | 25270 | 48365 |
| C11orf53 | 2176 | 25271 | 48366 |
| C11orf54 | 2177 | 25272 | 48367 |
| C11orf57 | 2178 | 25273 | 48368 |
| C11orf58 | 2179 | 25274 | 48369 |
| C11orf63 | 2180 | 25275 | 48370 |
| C11orf63 | 2181 | 25276 | 48371 |
| C11orf65 | 2182 | 25277 | 48372 |
| C11orf65 | 2183 | 25278 | 48373 |
| C11orf65 | 2184 | 25279 | 48374 |
| C11orf68 | 2185 | 25280 | 48375 |
| C11orf70 | 2186 | 25281 | 48376 |
| C11orf70 | 2187 | 25282 | 48377 |
| C11orf71 | 2188 | 25283 | 48378 |
| C11orf71 | 2189 | 25284 | 48379 |
| C11orf74 | 2190 | 25285 | 48380 |
| C11orf80 | 2191 | 25286 | 48381 |
| C11orf84 | 2192 | 25287 | 48382 |
| C11orf86 | 2193 | 25288 | 48383 |
| C11orf87 | 2194 | 25289 | 48384 |
| C11orf88 | 2195 | 25290 | 48385 |
| C11orf91 | 2196 | 25291 | 48386 |
| C11orf94 | 2197 | 25292 | 48387 |
| C11orf95 | 2198 | 25293 | 48388 |
| C11orf96 | 2199 | 25294 | 48389 |
| C11orf97 | 2200 | 25295 | 48390 |
| C11orf98 | 2201 | 25296 | 48391 |
| C12orf10 | 2202 | 25297 | 48392 |
| C12orf29 | 2203 | 25298 | 48393 |
| C12orf4 | 2204 | 25299 | 48394 |
| C12orf40 | 2205 | 25300 | 48395 |
| C12orf40 | 2206 | 25301 | 48396 |
| C12orf42 | 2207 | 25302 | 48397 |
| C12orf43 | 2208 | 25303 | 48398 |
| C12orf45 | 2209 | 25304 | 48399 |
| C12orf49 | 2210 | 25305 | 48400 |
| C12orf49 | 2211 | 25306 | 48401 |
| C12orf50 | 2212 | 25307 | 48402 |
| C12orf54 | 2213 | 25308 | 48403 |
| C12orf56 | 2214 | 25309 | 48404 |
| C12orf57 | 2215 | 25310 | 48405 |
| C12orf60 | 2216 | 25311 | 48406 |
| C12orf65 | 2217 | 25312 | 48407 |
| C12orf66 | 2218 | 25313 | 48408 |
| C12orf66 | 2219 | 25314 | 48409 |
| C12orf71 | 2220 | 25315 | 48410 |
| C12orf73 | 2221 | 25316 | 48411 |
| C12orf74 | 2222 | 25317 | 48412 |
| C12orf74 | 2223 | 25318 | 48413 |
| C12orf75 | 2224 | 25319 | 48414 |
| C12orf76 | 2225 | 25320 | 48415 |
| C12orf77 | 2226 | 25321 | 48416 |
| C12orf80 | 2227 | 25322 | 48417 |
| C13orf42 | 2228 | 25323 | 48418 |
| C14orf119 | 2229 | 25324 | 48419 |
| C14orf132 | 2230 | 25325 | 48420 |
| C14orf132 | 2231 | 25326 | 48421 |
| C14orf166 | 2232 | 25327 | 48422 |
| C14orf177 | 2233 | 25328 | 48423 |
| C14orf178 | 2234 | 25329 | 48424 |
| C14orf180 | 2235 | 25330 | 48425 |
| C14orf180 | 2236 | 25331 | 48426 |
| C14orf2 | 2237 | 25332 | 48427 |
| C14orf28 | 2238 | 25333 | 48428 |
| C14orf37 | 2239 | 25334 | 48429 |
| C14orf37 | 2240 | 25335 | 48430 |
| C14orf39 | 2241 | 25336 | 48431 |
| C14orf93 | 2242 | 25337 | 48432 |
| C15orf32 | 2243 | 25338 | 48433 |
| C15orf32 | 2244 | 25339 | 48434 |
| C15orf39 | 2245 | 25340 | 48435 |
| C15orf40 | 2246 | 25341 | 48436 |
| C15orf40 | 2247 | 25342 | 48437 |
| C15orf40 | 2248 | 25343 | 48438 |
| C15orf40 | 2249 | 25344 | 48439 |
| C15orf40 | 2250 | 25345 | 48440 |
| C15orf41 | 2251 | 25346 | 48441 |
| C15orf41 | 2252 | 25347 | 48442 |
| C15orf41 | 2253 | 25348 | 48443 |
| C15orf48 | 2254 | 25349 | 48444 |
| C15orf52 | 2255 | 25350 | 48445 |
| C15orf53 | 2256 | 25351 | 48446 |
| C15orf56 | 2257 | 25352 | 48447 |
| C15orf59 | 2258 | 25353 | 48448 |
| C15orf61 | 2259 | 25354 | 48449 |
| C15orf62 | 2260 | 25355 | 48450 |
| C15orf65 | 2261 | 25356 | 48451 |
| C16orf45 | 2262 | 25357 | 48452 |
| C16orf46 | 2263 | 25358 | 48453 |
| C16orf46 | 2264 | 25359 | 48454 |
| C16orf47 | 2265 | 25360 | 48455 |
| C16orf52 | 2266 | 25361 | 48456 |
| C16orf54 | 2267 | 25362 | 48457 |
| C16orf58 | 2268 | 25363 | 48458 |
| C16orf62 | 2269 | 25364 | 48459 |
| C16orf70 | 2270 | 25365 | 48460 |
| C16orf71 | 2271 | 25366 | 48461 |
| C16orf72 | 2272 | 25367 | 48462 |
| C16orf74 | 2273 | 25368 | 48463 |
| C16orf78 | 2274 | 25369 | 48464 |
| C16orf82 | 2275 | 25370 | 48465 |
| C16orf86 | 2276 | 25371 | 48466 |
| C16orf87 | 2277 | 25372 | 48467 |
| C16orf87 | 2278 | 25373 | 48468 |
| C16orf89 | 2279 | 25374 | 48469 |
| C16orf89 | 2280 | 25375 | 48470 |
| C16orf90 | 2281 | 25376 | 48471 |
| C16orf91 | 2282 | 25377 | 48472 |
| C16orf92 | 2283 | 25378 | 48473 |
| C16orf92 | 2284 | 25379 | 48474 |
| C16orf95 | 2285 | 25380 | 48475 |
| C16orf95 | 2286 | 25381 | 48476 |
| C16orf96 | 2287 | 25382 | 48477 |
| C16orf97 | 2288 | 25383 | 48478 |
| C17orf100 | 2289 | 25384 | 48479 |
| C17orf102 | 2290 | 25385 | 48480 |
| C17orf105 | 2291 | 25386 | 48481 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| C17orf105 | 2292 | 25387 | 48482 |
| C17orf107 | 2293 | 25388 | 48483 |
| C17orf112 | 2294 | 25389 | 48484 |
| C17orf47 | 2295 | 25390 | 48485 |
| C17orf49 | 2296 | 25391 | 48486 |
| C17orf49 | 2297 | 25392 | 48487 |
| C17orf50 | 2298 | 25393 | 48488 |
| C17orf51 | 2299 | 25394 | 48489 |
| C17orf53 | 2300 | 25395 | 48490 |
| C17orf53 | 2301 | 25396 | 48491 |
| C17orf58 | 2302 | 25397 | 48492 |
| C17orf58 | 2303 | 25398 | 48493 |
| C17orf62 | 2304 | 25399 | 48494 |
| C17orf64 | 2305 | 25400 | 48495 |
| C17orf67 | 2306 | 25401 | 48496 |
| C17orf75 | 2307 | 25402 | 48497 |
| C17orf77 | 2308 | 25403 | 48498 |
| C17orf78 | 2309 | 25404 | 48499 |
| C17orf78 | 2310 | 25405 | 48500 |
| C17orf80 | 2311 | 25406 | 48501 |
| C17orf80 | 2312 | 25407 | 48502 |
| C17orf82 | 2313 | 25408 | 48503 |
| C17orf97 | 2314 | 25409 | 48504 |
| C17orf98 | 2315 | 25410 | 48505 |
| C17orf99 | 2316 | 25411 | 48506 |
| C18orf12 | 2317 | 25412 | 48507 |
| C18orf21 | 2318 | 25413 | 48508 |
| C18orf21 | 2319 | 25414 | 48509 |
| C18orf25 | 2320 | 25415 | 48510 |
| C18orf32 | 2321 | 25416 | 48511 |
| C18orf54 | 2322 | 25417 | 48512 |
| C18orf63 | 2323 | 25418 | 48513 |
| C18orf65 | 2324 | 25419 | 48514 |
| C18orf8 | 2325 | 25420 | 48515 |
| C19orf12 | 2326 | 25421 | 48516 |
| C19orf12 | 2327 | 25422 | 48517 |
| C19orf12 | 2328 | 25423 | 48518 |
| C19orf18 | 2329 | 25424 | 48519 |
| C19orf24 | 2330 | 25425 | 48520 |
| C19orf25 | 2331 | 25426 | 48521 |
| C19orf33 | 2332 | 25427 | 48522 |
| C19orf33 | 2333 | 25428 | 48523 |
| C19orf38 | 2334 | 25429 | 48524 |
| C19orf44 | 2335 | 25430 | 48525 |
| C19orf47 | 2336 | 25431 | 48526 |
| C19orf48 | 2337 | 25432 | 48527 |
| C19orf53 | 2338 | 25433 | 48528 |
| C19orf54 | 2339 | 25434 | 48529 |
| C19orf54 | 2340 | 25435 | 48530 |
| C19orf54 | 2341 | 25436 | 48531 |
| C19orf57 | 2342 | 25437 | 48532 |
| C19orf66 | 2343 | 25438 | 48533 |
| C19orf67 | 2344 | 25439 | 48534 |
| C19orf70 | 2345 | 25440 | 48535 |
| C19orf71 | 2346 | 25441 | 48536 |
| C19orf73 | 2347 | 25442 | 48537 |
| C19orf81 | 2348 | 25443 | 48538 |
| C19orf84 | 2349 | 25444 | 48539 |
| C1D | 2350 | 25445 | 48540 |
| C1GALT1 | 2351 | 25446 | 48541 |
| C1GALT1C1 | 2352 | 25447 | 48542 |
| C1GALT1C1L | 2353 | 25448 | 48543 |
| C1orf100 | 2354 | 25449 | 48544 |
| C1orf100 | 2355 | 25450 | 48545 |
| C1orf105 | 2356 | 25451 | 48546 |
| C1orf106 | 2357 | 25452 | 48547 |
| C1orf109 | 2358 | 25453 | 48548 |
| C1orf109 | 2359 | 25454 | 48549 |
| C1orf112 | 2360 | 25455 | 48550 |
| C1orf112 | 2361 | 25456 | 48551 |
| C1orf112 | 2362 | 25457 | 48552 |
| C1orf115 | 2363 | 25458 | 48553 |
| C1orf116 | 2364 | 25459 | 48554 |
| C1orf122 | 2365 | 25460 | 48555 |
| C1orf122 | 2366 | 25461 | 48556 |
| C1orf123 | 2367 | 25462 | 48557 |
| C1orf127 | 2368 | 25463 | 48558 |
| C1orf131 | 2369 | 25464 | 48559 |
| C1orf137 | 2370 | 25465 | 48560 |
| C1orf141 | 2371 | 25466 | 48561 |
| C1orf141 | 2372 | 25467 | 48562 |
| C1orf146 | 2373 | 25468 | 48563 |
| C1orf158 | 2374 | 25469 | 48564 |
| C1orf159 | 2375 | 25470 | 48565 |
| C1orf162 | 2376 | 25471 | 48566 |
| C1orf167 | 2377 | 25472 | 48567 |
| C1orf174 | 2378 | 25473 | 48568 |
| C1orf185 | 2379 | 25474 | 48569 |
| C1orf186 | 2380 | 25475 | 48570 |
| C1orf189 | 2381 | 25476 | 48571 |
| C1orf194 | 2382 | 25477 | 48572 |
| C1orf195 | 2383 | 25478 | 48573 |
| C1orf195 | 2384 | 25479 | 48574 |
| C1orf198 | 2385 | 25480 | 48575 |
| C1orf21 | 2386 | 25481 | 48576 |
| C1orf210 | 2387 | 25482 | 48577 |
| C1orf216 | 2388 | 25483 | 48578 |
| C1orf226 | 2389 | 25484 | 48579 |
| C1orf228 | 2390 | 25485 | 48580 |
| C1orf229 | 2391 | 25486 | 48581 |
| C1orf27 | 2392 | 25487 | 48582 |
| C1orf35 | 2393 | 25488 | 48583 |
| C1orf43 | 2394 | 25489 | 48584 |
| C1orf43 | 2395 | 25490 | 48585 |
| C1orf43 | 2396 | 25491 | 48586 |
| C1orf50 | 2397 | 25492 | 48587 |
| C1orf52 | 2398 | 25493 | 48588 |
| C1orf53 | 2399 | 25494 | 48589 |
| C1orf54 | 2400 | 25495 | 48590 |
| C1orf54 | 2401 | 25496 | 48591 |
| C1orf56 | 2402 | 25497 | 48592 |
| C1orf61 | 2403 | 25498 | 48593 |
| C1orf61 | 2404 | 25499 | 48594 |
| C1orf61 | 2405 | 25500 | 48595 |
| C1orf68 | 2406 | 25501 | 48596 |
| C1orf74 | 2407 | 25502 | 48597 |
| C1orf87 | 2408 | 25503 | 48598 |
| C1orf94 | 2409 | 25504 | 48599 |
| C1QA | 2410 | 25505 | 48600 |
| C1QB | 2411 | 25506 | 48601 |
| C1QBP | 2412 | 25507 | 48602 |
| C1QC | 2413 | 25508 | 48603 |
| C1QL1 | 2414 | 25509 | 48604 |
| C1QL2 | 2415 | 25510 | 48605 |
| C1QL3 | 2416 | 25511 | 48606 |
| C1QL4 | 2417 | 25512 | 48607 |
| C1QTNF1 | 2418 | 25513 | 48608 |
| C1QTNF12 | 2419 | 25514 | 48609 |
| C1QTNF2 | 2420 | 25515 | 48610 |
| C1QTNF3 | 2421 | 25516 | 48611 |
| C1QTNF4 | 2422 | 25517 | 48612 |
| C1QTNF5 | 2423 | 25518 | 48613 |
| C1QTNF5 | 2424 | 25519 | 48614 |
| C1QTNF6 | 2425 | 25520 | 48615 |
| C1QTNF7 | 2426 | 25521 | 48616 |
| C1QTNF8 | 2427 | 25522 | 48617 |
| C1QTNF9 | 2428 | 25523 | 48618 |
| C1QTNF9B | 2429 | 25524 | 48619 |
| C1R | 2430 | 25525 | 48620 |
| C1RL | 2431 | 25526 | 48621 |
| C1RL | 2432 | 25527 | 48622 |
| C1RL | 2433 | 25528 | 48623 |
| C1S | 2434 | 25529 | 48624 |
| C2 | 2435 | 25530 | 48625 |
| C2 | 2436 | 25531 | 48626 |
| C20orf141 | 2437 | 25532 | 48627 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| C20orf144 | 2438 | 25533 | 48628 |
| C20orf173 | 2439 | 25534 | 48629 |
| C20orf194 | 2440 | 25535 | 48630 |
| C20orf196 | 2441 | 25536 | 48631 |
| C20orf196 | 2442 | 25537 | 48632 |
| C20orf197 | 2443 | 25538 | 48633 |
| C20orf197 | 2444 | 25539 | 48634 |
| C20orf202 | 2445 | 25540 | 48635 |
| C20orf203 | 2446 | 25541 | 48636 |
| C20orf204 | 2447 | 25542 | 48637 |
| C20orf24 | 2448 | 25543 | 48638 |
| C20orf24 | 2449 | 25544 | 48639 |
| C20orf24 | 2450 | 25545 | 48640 |
| C20orf27 | 2451 | 25546 | 48641 |
| C20orf78 | 2452 | 25547 | 48642 |
| C20orf85 | 2453 | 25548 | 48643 |
| C20orf96 | 2454 | 25549 | 48644 |
| C21orf140 | 2455 | 25550 | 48645 |
| C21orf2 | 2456 | 25551 | 48646 |
| C21orf33 | 2457 | 25552 | 48647 |
| C21orf33 | 2458 | 25553 | 48648 |
| C21orf33 | 2459 | 25554 | 48649 |
| C21orf58 | 2460 | 25555 | 48650 |
| C21orf58 | 2461 | 25556 | 48651 |
| C21orf59 | 2462 | 25557 | 48652 |
| C21orf59 | 2463 | 25558 | 48653 |
| C21orf59 | 2464 | 25559 | 48654 |
| C21orf59 | 2465 | 25560 | 48655 |
| C21orf62 | 2466 | 25561 | 48656 |
| C21orf91 | 2467 | 25562 | 48657 |
| C21orf91 | 2468 | 25563 | 48658 |
| C22orf15 | 2469 | 25564 | 48659 |
| C22orf23 | 2470 | 25565 | 48660 |
| C22orf24 | 2471 | 25566 | 48661 |
| C22orf24 | 2472 | 25567 | 48662 |
| C22orf31 | 2473 | 25568 | 48663 |
| C22orf34 | 2474 | 25569 | 48664 |
| C22orf39 | 2475 | 25570 | 48665 |
| C22orf39 | 2476 | 25571 | 48666 |
| C22orf42 | 2477 | 25572 | 48667 |
| C22orf46 | 2478 | 25573 | 48668 |
| C2CD2 | 2479 | 25574 | 48669 |
| C2CD2L | 2480 | 25575 | 48670 |
| C2CD3 | 2481 | 25576 | 48671 |
| C2CD3 | 2482 | 25577 | 48672 |
| C2CD4A | 2483 | 25578 | 48673 |
| C2CD4C | 2484 | 25579 | 48674 |
| C2CD4D | 2485 | 25580 | 48675 |
| C2CD5 | 2486 | 25581 | 48676 |
| C2CD6 | 2487 | 25582 | 48677 |
| C2CD6 | 2488 | 25583 | 48678 |
| C2CD6 | 2489 | 25584 | 48679 |
| C2orf15 | 2490 | 25585 | 48680 |
| C2orf16 | 2491 | 25586 | 48681 |
| C2orf27B | 2492 | 25587 | 48682 |
| C2orf40 | 2493 | 25588 | 48683 |
| C2orf42 | 2494 | 25589 | 48684 |
| C2orf48 | 2495 | 25590 | 48685 |
| C2orf49 | 2496 | 25591 | 48686 |
| C2orf50 | 2497 | 25592 | 48687 |
| C2orf54 | 2498 | 25593 | 48688 |
| C2orf66 | 2499 | 25594 | 48689 |
| C2orf68 | 2500 | 25595 | 48690 |
| C2orf69 | 2501 | 25596 | 48691 |
| C2orf70 | 2502 | 25597 | 48692 |
| C2orf71 | 2503 | 25598 | 48693 |
| C2orf72 | 2504 | 25599 | 48694 |
| C2orf73 | 2505 | 25600 | 48695 |
| C2orf74 | 2506 | 25601 | 48696 |
| C2orf76 | 2507 | 25602 | 48697 |
| C2orf78 | 2508 | 25603 | 48698 |
| C2orf80 | 2509 | 25604 | 48699 |
| C2orf81 | 2510 | 25605 | 48700 |
| C2orf82 | 2511 | 25606 | 48701 |
| C2orf83 | 2512 | 25607 | 48702 |
| C2orf83 | 2513 | 25608 | 48703 |
| C2orf88 | 2514 | 25609 | 48704 |
| C2orf91 | 2515 | 25610 | 48705 |
| C3 | 2516 | 25611 | 48706 |
| C3AR1 | 2517 | 25612 | 48707 |
| C3orf14 | 2518 | 25613 | 48708 |
| C3orf14 | 2519 | 25614 | 48709 |
| C3orf18 | 2520 | 25615 | 48710 |
| C3orf18 | 2521 | 25616 | 48711 |
| C3orf20 | 2522 | 25617 | 48712 |
| C3orf22 | 2523 | 25618 | 48713 |
| C3orf30 | 2524 | 25619 | 48714 |
| C3orf33 | 2525 | 25620 | 48715 |
| C3orf35 | 2526 | 25621 | 48716 |
| C3orf35 | 2527 | 25622 | 48717 |
| C3orf36 | 2528 | 25623 | 48718 |
| C3orf38 | 2529 | 25624 | 48719 |
| C3orf52 | 2530 | 25625 | 48720 |
| C3orf52 | 2531 | 25626 | 48721 |
| C3orf56 | 2532 | 25627 | 48722 |
| C3orf58 | 2533 | 25628 | 48723 |
| C3orf62 | 2534 | 25629 | 48724 |
| C3orf67 | 2535 | 25630 | 48725 |
| C3orf67 | 2536 | 25631 | 48726 |
| C3orf67 | 2537 | 25632 | 48727 |
| C3orf67 | 2538 | 25633 | 48728 |
| C3orf70 | 2539 | 25634 | 48729 |
| C3orf79 | 2540 | 25635 | 48730 |
| C3orf80 | 2541 | 25636 | 48731 |
| C3orf84 | 2542 | 25637 | 48732 |
| C3orf85 | 2543 | 25638 | 48733 |
| C3orf85 | 2544 | 25639 | 48734 |
| C4A | 2545 | 25640 | 48735 |
| C4BPA | 2546 | 25641 | 48736 |
| C4BPB | 2547 | 25642 | 48737 |
| C4orf17 | 2548 | 25643 | 48738 |
| C4orf19 | 2549 | 25644 | 48739 |
| C4orf22 | 2550 | 25645 | 48740 |
| C4orf3 | 2551 | 25646 | 48741 |
| C4orf33 | 2552 | 25647 | 48742 |
| C4orf36 | 2553 | 25648 | 48743 |
| C4orf45 | 2554 | 25649 | 48744 |
| C4orf46 | 2555 | 25650 | 48745 |
| C4orf47 | 2556 | 25651 | 48746 |
| C4orf48 | 2557 | 25652 | 48747 |
| C4orf51 | 2558 | 25653 | 48748 |
| C5 | 2559 | 25654 | 48749 |
| C5 | 2560 | 25655 | 48750 |
| C5AR1 | 2561 | 25656 | 48751 |
| C5AR2 | 2562 | 25657 | 48752 |
| C5orf15 | 2563 | 25658 | 48753 |
| C5orf22 | 2564 | 25659 | 48754 |
| C5orf24 | 2565 | 25660 | 48755 |
| C5orf24 | 2566 | 25661 | 48756 |
| C5orf30 | 2567 | 25662 | 48757 |
| C5orf34 | 2568 | 25663 | 48758 |
| C5orf38 | 2569 | 25664 | 48759 |
| C5orf38 | 2570 | 25665 | 48760 |
| C5orf38 | 2571 | 25666 | 48761 |
| C5orf38 | 2572 | 25667 | 48762 |
| C5orf42 | 2573 | 25668 | 48763 |
| C5orf46 | 2574 | 25669 | 48764 |
| C5orf47 | 2575 | 25670 | 48765 |
| C5orf49 | 2576 | 25671 | 48766 |
| C5orf51 | 2577 | 25672 | 48767 |
| C5orf52 | 2578 | 25673 | 48768 |
| C5orf58 | 2579 | 25674 | 48769 |
| C5orf58 | 2580 | 25675 | 48770 |
| C5orf60 | 2581 | 25676 | 48771 |
| C5orf63 | 2582 | 25677 | 48772 |
| C5orf63 | 2583 | 25678 | 48773 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| C5orf64 | 2584 | 25679 | 48774 |
| C5orf66 | 2585 | 25680 | 48775 |
| C5orf67 | 2586 | 25681 | 48776 |
| C6 | 2587 | 25682 | 48777 |
| C6orf10 | 2588 | 25683 | 48778 |
| C6orf106 | 2589 | 25684 | 48779 |
| C6orf118 | 2590 | 25685 | 48780 |
| C6orf120 | 2591 | 25686 | 48781 |
| C6orf132 | 2592 | 25687 | 48782 |
| C6orf136 | 2593 | 25688 | 48783 |
| C6orf141 | 2594 | 25689 | 48784 |
| C6orf15 | 2595 | 25690 | 48785 |
| C6orf163 | 2596 | 25691 | 48786 |
| C6orf183 | 2597 | 25692 | 48787 |
| C6orf201 | 2598 | 25693 | 48788 |
| C6orf203 | 2599 | 25694 | 48789 |
| C6orf222 | 2600 | 25695 | 48790 |
| C6orf223 | 2601 | 25696 | 48791 |
| C6orf223 | 2602 | 25697 | 48792 |
| C6orf226 | 2603 | 25698 | 48793 |
| C6orf229 | 2604 | 25699 | 48794 |
| C6orf47 | 2605 | 25700 | 48795 |
| C6orf48 | 2606 | 25701 | 48796 |
| C6orf48 | 2607 | 25702 | 48797 |
| C6orf52 | 2608 | 25703 | 48798 |
| C6orf58 | 2609 | 25704 | 48799 |
| C6orf62 | 2610 | 25705 | 48800 |
| C6orf89 | 2611 | 25706 | 48801 |
| C6orf99 | 2612 | 25707 | 48802 |
| C7 | 2613 | 25708 | 48803 |
| C7orf25 | 2614 | 25709 | 48804 |
| C7orf26 | 2615 | 25710 | 48805 |
| C7orf31 | 2616 | 25711 | 48806 |
| C7orf33 | 2617 | 25712 | 48807 |
| C7orf43 | 2618 | 25713 | 48808 |
| C7orf49 | 2619 | 25714 | 48809 |
| C7orf49 | 2620 | 25715 | 48810 |
| C7orf50 | 2621 | 25716 | 48811 |
| C7orf50 | 2622 | 25717 | 48812 |
| C7orf50 | 2623 | 25718 | 48813 |
| C7orf57 | 2624 | 25719 | 48814 |
| C7orf61 | 2625 | 25720 | 48815 |
| C7orf65 | 2626 | 25721 | 48816 |
| C7orf66 | 2627 | 25722 | 48817 |
| C7orf69 | 2628 | 25723 | 48818 |
| C7orf71 | 2629 | 25724 | 48819 |
| C7orf77 | 2630 | 25725 | 48820 |
| C8A | 2631 | 25726 | 48821 |
| C8B | 2632 | 25727 | 48822 |
| C8G | 2633 | 25728 | 48823 |
| C8orf31 | 2634 | 25729 | 48824 |
| C8orf33 | 2635 | 25730 | 48825 |
| C8orf34 | 2636 | 25731 | 48826 |
| C8orf34 | 2637 | 25732 | 48827 |
| C8orf37 | 2638 | 25733 | 48828 |
| C8orf44 | 2639 | 25734 | 48829 |
| C8orf46 | 2640 | 25735 | 48830 |
| C8orf48 | 2641 | 25736 | 48831 |
| C8orf58 | 2642 | 25737 | 48832 |
| C8orf58 | 2643 | 25738 | 48833 |
| C8orf59 | 2644 | 25739 | 48834 |
| C8orf74 | 2645 | 25740 | 48835 |
| C8orf76 | 2646 | 25741 | 48836 |
| C8orf82 | 2647 | 25742 | 48837 |
| C8orf86 | 2648 | 25743 | 48838 |
| C8orf86 | 2649 | 25744 | 48839 |
| C8orf87 | 2650 | 25745 | 48840 |
| C8orf88 | 2651 | 25746 | 48841 |
| C8orf89 | 2652 | 25747 | 48842 |
| C9 | 2653 | 25748 | 48843 |
| C9orf106 | 2654 | 25749 | 48844 |
| C9orf116 | 2655 | 25750 | 48845 |
| C9orf116 | 2656 | 25751 | 48846 |
| C9orf129 | 2657 | 25752 | 48847 |
| C9orf131 | 2658 | 25753 | 48848 |
| C9orf135 | 2659 | 25754 | 48849 |
| C9orf135 | 2660 | 25755 | 48850 |
| C9orf135 | 2661 | 25756 | 48851 |
| C9orf139 | 2662 | 25757 | 48852 |
| C9orf147 | 2663 | 25758 | 48853 |
| C9orf152 | 2664 | 25759 | 48854 |
| C9orf153 | 2665 | 25760 | 48855 |
| C9orf16 | 2666 | 25761 | 48856 |
| C9orf163 | 2667 | 25762 | 48857 |
| C9orf170 | 2668 | 25763 | 48858 |
| C9orf172 | 2669 | 25764 | 48859 |
| C9orf24 | 2670 | 25765 | 48860 |
| C9orf24 | 2671 | 25766 | 48861 |
| C9orf24 | 2672 | 25767 | 48862 |
| C9orf3 | 2673 | 25768 | 48863 |
| C9orf3 | 2674 | 25769 | 48864 |
| C9orf40 | 2675 | 25770 | 48865 |
| C9orf43 | 2676 | 25771 | 48866 |
| C9orf47 | 2677 | 25772 | 48867 |
| C9orf50 | 2678 | 25773 | 48868 |
| C9orf57 | 2679 | 25774 | 48869 |
| C9orf62 | 2680 | 25775 | 48870 |
| C9orf64 | 2681 | 25776 | 48871 |
| C9orf66 | 2682 | 25777 | 48872 |
| C9orf72 | 2683 | 25778 | 48873 |
| C9orf72 | 2684 | 25779 | 48874 |
| C9orf78 | 2685 | 25780 | 48875 |
| C9orf84 | 2686 | 25781 | 48876 |
| C9orf85 | 2687 | 25782 | 48877 |
| C9orf92 | 2688 | 25783 | 48878 |
| CA1 | 2689 | 25784 | 48879 |
| CA10 | 2690 | 25785 | 48880 |
| CA11 | 2691 | 25786 | 48881 |
| CA12 | 2692 | 25787 | 48882 |
| CA13 | 2693 | 25788 | 48883 |
| CA14 | 2694 | 25789 | 48884 |
| CA2 | 2695 | 25790 | 48885 |
| CA3 | 2696 | 25791 | 48886 |
| CA4 | 2697 | 25792 | 48887 |
| CA5A | 2698 | 25793 | 48888 |
| CA5B | 2699 | 25794 | 48889 |
| CA6 | 2700 | 25795 | 48890 |
| CA6 | 2701 | 25796 | 48891 |
| CA7 | 2702 | 25797 | 48892 |
| CA8 | 2703 | 25798 | 48893 |
| CA8 | 2704 | 25799 | 48894 |
| CA9 | 2705 | 25800 | 48895 |
| CAAP1 | 2706 | 25801 | 48896 |
| CAB39 | 2707 | 25802 | 48897 |
| CAB39L | 2708 | 25803 | 48898 |
| CABCOCO1 | 2709 | 25804 | 48899 |
| CABIN1 | 2710 | 25805 | 48900 |
| CABLES1 | 2711 | 25806 | 48901 |
| CABLES2 | 2712 | 25807 | 48902 |
| CABP1 | 2713 | 25808 | 48903 |
| CABP2 | 2714 | 25809 | 48904 |
| CABP4 | 2715 | 25810 | 48905 |
| CABP5 | 2716 | 25811 | 48906 |
| CABP7 | 2717 | 25812 | 48907 |
| CABS1 | 2718 | 25813 | 48908 |
| CABYR | 2719 | 25814 | 48909 |
| CABYR | 2720 | 25815 | 48910 |
| CACFD1 | 2721 | 25816 | 48911 |
| CACFD1 | 2722 | 25817 | 48912 |
| CACHD1 | 2723 | 25818 | 48913 |
| CACNA1A | 2724 | 25819 | 48914 |
| CACNA1A | 2725 | 25820 | 48915 |
| CACNA1B | 2726 | 25821 | 48916 |
| CACNA1B | 2727 | 25822 | 48917 |
| CACNA1C | 2728 | 25823 | 48918 |
| CACNA1D | 2729 | 25824 | 48919 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CACNA1E | 2730 | 25825 | 48920 |
| CACNA1F | 2731 | 25826 | 48921 |
| CACNA1G | 2732 | 25827 | 48922 |
| CACNA1H | 2733 | 25828 | 48923 |
| CACNA1I | 2734 | 25829 | 48924 |
| CACNA1S | 2735 | 25830 | 48925 |
| CACNA2D1 | 2736 | 25831 | 48926 |
| CACNA2D1 | 2737 | 25832 | 48927 |
| CACNA2D2 | 2738 | 25833 | 48928 |
| CACNA2D3 | 2739 | 25834 | 48929 |
| CACNA2D4 | 2740 | 25835 | 48930 |
| CACNB1 | 2741 | 25836 | 48931 |
| CACNB1 | 2742 | 25837 | 48932 |
| CACNB2 | 2743 | 25838 | 48933 |
| CACNB3 | 2744 | 25839 | 48934 |
| CACNB4 | 2745 | 25840 | 48935 |
| CACNG1 | 2746 | 25841 | 48936 |
| CACNG2 | 2747 | 25842 | 48937 |
| CACNG3 | 2748 | 25843 | 48938 |
| CACNG4 | 2749 | 25844 | 48939 |
| CACNG5 | 2750 | 25845 | 48940 |
| CACNG6 | 2751 | 25846 | 48941 |
| CACNG7 | 2752 | 25847 | 48942 |
| CACNG8 | 2753 | 25848 | 48943 |
| CACTIN | 2754 | 25849 | 48944 |
| CACUL1 | 2755 | 25850 | 48945 |
| CACYBP | 2756 | 25851 | 48946 |
| CAD | 2757 | 25852 | 48947 |
| CADM1 | 2758 | 25853 | 48948 |
| CADM2 | 2759 | 25854 | 48949 |
| CADM3 | 2760 | 25855 | 48950 |
| CADM4 | 2761 | 25856 | 48951 |
| CADPS | 2762 | 25857 | 48952 |
| CADPS2 | 2763 | 25858 | 48953 |
| CAGE1 | 2764 | 25859 | 48954 |
| CAGE1 | 2765 | 25860 | 48955 |
| CALB1 | 2766 | 25861 | 48956 |
| CALB2 | 2767 | 25862 | 48957 |
| CALB2 | 2768 | 25863 | 48958 |
| CALCA | 2769 | 25864 | 48959 |
| CALCA | 2770 | 25865 | 48960 |
| CALCB | 2771 | 25866 | 48961 |
| CALCOCO1 | 2772 | 25867 | 48962 |
| CALCOCO2 | 2773 | 25868 | 48963 |
| CALCR | 2774 | 25869 | 48964 |
| CALCRL | 2775 | 25870 | 48965 |
| CALD1 | 2776 | 25871 | 48966 |
| CALHM1 | 2777 | 25872 | 48967 |
| CALHM2 | 2778 | 25873 | 48968 |
| CALHM3 | 2779 | 25874 | 48969 |
| CALHM4 | 2780 | 25875 | 48970 |
| CALHM5 | 2781 | 25876 | 48971 |
| CALHM6 | 2782 | 25877 | 48972 |
| CALM1 | 2783 | 25878 | 48973 |
| CALM2 | 2784 | 25879 | 48974 |
| CALM3 | 2785 | 25880 | 48975 |
| CALML3 | 2786 | 25881 | 48976 |
| CALML4 | 2787 | 25882 | 48977 |
| CALML5 | 2788 | 25883 | 48978 |
| CALML6 | 2789 | 25884 | 48979 |
| CALN1 | 2790 | 25885 | 48980 |
| CALR | 2791 | 25886 | 48981 |
| CALR3 | 2792 | 25887 | 48982 |
| CALU | 2793 | 25888 | 48983 |
| CALU | 2794 | 25889 | 48984 |
| CALY | 2795 | 25890 | 48985 |
| CAMK1 | 2796 | 25891 | 48986 |
| CAMK1D | 2797 | 25892 | 48987 |
| CAMK1D | 2798 | 25893 | 48988 |
| CAMK1G | 2799 | 25894 | 48989 |
| CAMK2A | 2800 | 25895 | 48990 |
| CAMK2B | 2801 | 25896 | 48991 |
| CAMK2D | 2802 | 25897 | 48992 |
| CAMK2D | 2803 | 25898 | 48993 |
| CAMK2D | 2804 | 25899 | 48994 |
| CAMK2D | 2805 | 25900 | 48995 |
| CAMK2G | 2806 | 25901 | 48996 |
| CAMK2G | 2807 | 25902 | 48997 |
| CAMK2N1 | 2808 | 25903 | 48998 |
| CAMK2N2 | 2809 | 25904 | 48999 |
| CAMK4 | 2810 | 25905 | 49000 |
| CAMKK1 | 2811 | 25906 | 49001 |
| CAMKK1 | 2812 | 25907 | 49002 |
| CAMKK2 | 2813 | 25908 | 49003 |
| CAMKK2 | 2814 | 25909 | 49004 |
| CAMKK2 | 2815 | 25910 | 49005 |
| CAMKK2 | 2816 | 25911 | 49006 |
| CAMKMT | 2817 | 25912 | 49007 |
| CAMKV | 2818 | 25913 | 49008 |
| CAMLG | 2819 | 25914 | 49009 |
| CAMP | 2820 | 25915 | 49010 |
| CAMSAP1 | 2821 | 25916 | 49011 |
| CAMSAP2 | 2822 | 25917 | 49012 |
| CAMSAP3 | 2823 | 25918 | 49013 |
| CAMTA1 | 2824 | 25919 | 49014 |
| CAMTA1 | 2825 | 25920 | 49015 |
| CAMTA1 | 2826 | 25921 | 49016 |
| CAMTA1 | 2827 | 25922 | 49017 |
| CAMTA1 | 2828 | 25923 | 49018 |
| CAMTA2 | 2829 | 25924 | 49019 |
| CAMTA2 | 2830 | 25925 | 49020 |
| CAND1 | 2831 | 25926 | 49021 |
| CAND2 | 2832 | 25927 | 49022 |
| CANT1 | 2833 | 25928 | 49023 |
| CANX | 2834 | 25929 | 49024 |
| CAP1 | 2835 | 25930 | 49025 |
| CAP2 | 2836 | 25931 | 49026 |
| CAPG | 2837 | 25932 | 49027 |
| CAPN1 | 2838 | 25933 | 49028 |
| CAPN10 | 2839 | 25934 | 49029 |
| CAPN11 | 2840 | 25935 | 49030 |
| CAPN12 | 2841 | 25936 | 49031 |
| CAPN13 | 2842 | 25937 | 49032 |
| CAPN14 | 2843 | 25938 | 49033 |
| CAPN15 | 2844 | 25939 | 49034 |
| CAPN2 | 2845 | 25940 | 49035 |
| CAPN3 | 2846 | 25941 | 49036 |
| CAPN5 | 2847 | 25942 | 49037 |
| CAPN6 | 2848 | 25943 | 49038 |
| CAPN7 | 2849 | 25944 | 49039 |
| CAPN8 | 2850 | 25945 | 49040 |
| CAPN9 | 2851 | 25946 | 49041 |
| CAPNS1 | 2852 | 25947 | 49042 |
| CAPNS2 | 2853 | 25948 | 49043 |
| CAPRIN1 | 2854 | 25949 | 49044 |
| CAPRIN1 | 2855 | 25950 | 49045 |
| CAPRIN2 | 2856 | 25951 | 49046 |
| CAPRIN2 | 2857 | 25952 | 49047 |
| CAPS | 2858 | 25953 | 49048 |
| CAPS2 | 2859 | 25954 | 49049 |
| CAPS2 | 2860 | 25955 | 49050 |
| CAPSL | 2861 | 25956 | 49051 |
| CAPZA1 | 2862 | 25957 | 49052 |
| CAPZA2 | 2863 | 25958 | 49053 |
| CAPZA3 | 2864 | 25959 | 49054 |
| CAPZB | 2865 | 25960 | 49055 |
| CAPZB | 2866 | 25961 | 49056 |
| CAPZB | 2867 | 25962 | 49057 |
| CAPZB | 2868 | 25963 | 49058 |
| CARD10 | 2869 | 25964 | 49059 |
| CARD11 | 2870 | 25965 | 49060 |
| CARD14 | 2871 | 25966 | 49061 |
| CARD14 | 2872 | 25967 | 49062 |
| CARD14 | 2873 | 25968 | 49063 |
| CARD16 | 2874 | 25969 | 49064 |
| CARD16 | 2875 | 25970 | 49065 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CARD17 | 2876 | 25971 | 49066 |
| CARD18 | 2877 | 25972 | 49067 |
| CARD19 | 2878 | 25973 | 49068 |
| CARD19 | 2879 | 25974 | 49069 |
| CARD6 | 2880 | 25975 | 49070 |
| CARD8 | 2881 | 25976 | 49071 |
| CARD8 | 2882 | 25977 | 49072 |
| CARD8 | 2883 | 25978 | 49073 |
| CARD8 | 2884 | 25979 | 49074 |
| CARD9 | 2885 | 25980 | 49075 |
| CARD9 | 2886 | 25981 | 49076 |
| CARF | 2887 | 25982 | 49077 |
| CARF | 2888 | 25983 | 49078 |
| CARHSP1 | 2889 | 25984 | 49079 |
| CARHSP1 | 2890 | 25985 | 49080 |
| CARM1 | 2891 | 25986 | 49081 |
| CARMIL1 | 2892 | 25987 | 49082 |
| CARMIL2 | 2893 | 25988 | 49083 |
| CARMIL3 | 2894 | 25989 | 49084 |
| CARNMT1 | 2895 | 25990 | 49085 |
| CARNS1 | 2896 | 25991 | 49086 |
| CARS | 2897 | 25992 | 49087 |
| CARS | 2898 | 25993 | 49088 |
| CARS2 | 2899 | 25994 | 49089 |
| CARS2 | 2900 | 25995 | 49090 |
| CARTPT | 2901 | 25996 | 49091 |
| CASC1 | 2902 | 25997 | 49092 |
| CASC1 | 2903 | 25998 | 49093 |
| CASC10 | 2904 | 25999 | 49094 |
| CASC3 | 2905 | 26000 | 49095 |
| CASC4 | 2906 | 26001 | 49096 |
| CASD1 | 2907 | 26002 | 49097 |
| CASK | 2908 | 26003 | 49098 |
| CASKIN1 | 2909 | 26004 | 49099 |
| CASKIN2 | 2910 | 26005 | 49100 |
| CASP1 | 2911 | 26006 | 49101 |
| CASP10 | 2912 | 26007 | 49102 |
| CASP10 | 2913 | 26008 | 49103 |
| CASP10 | 2914 | 26009 | 49104 |
| CASP10 | 2915 | 26010 | 49105 |
| CASP12 | 2916 | 26011 | 49106 |
| CASP14 | 2917 | 26012 | 49107 |
| CASP2 | 2918 | 26013 | 49108 |
| CASP2 | 2919 | 26014 | 49109 |
| CASP3 | 2920 | 26015 | 49110 |
| CASP4 | 2921 | 26016 | 49111 |
| CASP5 | 2922 | 26017 | 49112 |
| CASP6 | 2923 | 26018 | 49113 |
| CASP7 | 2924 | 26019 | 49114 |
| CASP7 | 2925 | 26020 | 49115 |
| CASP8 | 2926 | 26021 | 49116 |
| CASP8 | 2927 | 26022 | 49117 |
| CASP8AP2 | 2928 | 26023 | 49118 |
| CASP9 | 2929 | 26024 | 49119 |
| CASQ1 | 2930 | 26025 | 49120 |
| CASQ2 | 2931 | 26026 | 49121 |
| CASR | 2932 | 26027 | 49122 |
| CASS4 | 2933 | 26028 | 49123 |
| CAST | 2934 | 26029 | 49124 |
| CASTOR1 | 2935 | 26030 | 49125 |
| CASTOR2 | 2936 | 26031 | 49126 |
| CASZ1 | 2937 | 26032 | 49127 |
| CASZ1 | 2938 | 26033 | 49128 |
| CAT | 2939 | 26034 | 49129 |
| CATIP | 2940 | 26035 | 49130 |
| CATSPER1 | 2941 | 26036 | 49131 |
| CATSPER2 | 2942 | 26037 | 49132 |
| CATSPER3 | 2943 | 26038 | 49133 |
| CATSPER4 | 2944 | 26039 | 49134 |
| CATSPERB | 2945 | 26040 | 49135 |
| CATSPERD | 2946 | 26041 | 49136 |
| CATSPERE | 2947 | 26042 | 49137 |
| CATSPERE | 2948 | 26043 | 49138 |
| CATSPERG | 2949 | 26044 | 49139 |
| CATSPERZ | 2950 | 26045 | 49140 |
| CAV1 | 2951 | 26046 | 49141 |
| CAV2 | 2952 | 26047 | 49142 |
| CAV2 | 2953 | 26048 | 49143 |
| CAV3 | 2954 | 26049 | 49144 |
| CAVIN1 | 2955 | 26050 | 49145 |
| CAVIN2 | 2956 | 26051 | 49146 |
| CAVIN3 | 2957 | 26052 | 49147 |
| CAVIN4 | 2958 | 26053 | 49148 |
| CBARP | 2959 | 26054 | 49149 |
| CBFA2T2 | 2960 | 26055 | 49150 |
| CBFA2T3 | 2961 | 26056 | 49151 |
| CBFB | 2962 | 26057 | 49152 |
| CBFB | 2963 | 26058 | 49153 |
| CBL | 2964 | 26059 | 49154 |
| CBLB | 2965 | 26060 | 49155 |
| CBLC | 2966 | 26061 | 49156 |
| CBLL1 | 2967 | 26062 | 49157 |
| CBLN1 | 2968 | 26063 | 49158 |
| CBLN2 | 2969 | 26064 | 49159 |
| CBLN3 | 2970 | 26065 | 49160 |
| CBLN4 | 2971 | 26066 | 49161 |
| CBR1 | 2972 | 26067 | 49162 |
| CBR3 | 2973 | 26068 | 49163 |
| CBR4 | 2974 | 26069 | 49164 |
| CBSL | 2975 | 26070 | 49165 |
| CBWD2 | 2976 | 26071 | 49166 |
| CBWD5 | 2977 | 26072 | 49167 |
| CBWD5 | 2978 | 26073 | 49168 |
| CBX1 | 2979 | 26074 | 49169 |
| CBX2 | 2980 | 26075 | 49170 |
| CBX2 | 2981 | 26076 | 49171 |
| CBX3 | 2982 | 26077 | 49172 |
| CBX4 | 2983 | 26078 | 49173 |
| CBX5 | 2984 | 26079 | 49174 |
| CBX6 | 2985 | 26080 | 49175 |
| CBX7 | 2986 | 26081 | 49176 |
| CBX8 | 2987 | 26082 | 49177 |
| CBY1 | 2988 | 26083 | 49178 |
| CBY3 | 2989 | 26084 | 49179 |
| CC2D1A | 2990 | 26085 | 49180 |
| CC2D1B | 2991 | 26086 | 49181 |
| CC2D1B | 2992 | 26087 | 49182 |
| CC2D2A | 2993 | 26088 | 49183 |
| CC2D2A | 2994 | 26089 | 49184 |
| CC2D2A | 2995 | 26090 | 49185 |
| CC2D2B | 2996 | 26091 | 49186 |
| CC2D2B | 2997 | 26092 | 49187 |
| CCAR1 | 2998 | 26093 | 49188 |
| CCAR2 | 2999 | 26094 | 49189 |
| CCBE1 | 3000 | 26095 | 49190 |
| CCDC102A | 3001 | 26096 | 49191 |
| CCDC102B | 3002 | 26097 | 49192 |
| CCDC103 | 3003 | 26098 | 49193 |
| CCDC103 | 3004 | 26099 | 49194 |
| CCDC103 | 3005 | 26100 | 49195 |
| CCDC105 | 3006 | 26101 | 49196 |
| CCDC106 | 3007 | 26102 | 49197 |
| CCDC107 | 3008 | 26103 | 49198 |
| CCDC107 | 3009 | 26104 | 49199 |
| CCDC107 | 3010 | 26105 | 49200 |
| CCDC110 | 3011 | 26106 | 49201 |
| CCDC112 | 3012 | 26107 | 49202 |
| CCDC113 | 3013 | 26108 | 49203 |
| CCDC114 | 3014 | 26109 | 49204 |
| CCDC115 | 3015 | 26110 | 49205 |
| CCDC116 | 3016 | 26111 | 49206 |
| CCDC116 | 3017 | 26112 | 49207 |
| CCDC117 | 3018 | 26113 | 49208 |
| CCDC12 | 3019 | 26114 | 49209 |
| CCDC120 | 3020 | 26115 | 49210 |
| CCDC120 | 3021 | 26116 | 49211 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CCDC121 | 3022 | 26117 | 49212 |
| CCDC122 | 3023 | 26118 | 49213 |
| CCDC124 | 3024 | 26119 | 49214 |
| CCDC125 | 3025 | 26120 | 49215 |
| CCDC125 | 3026 | 26121 | 49216 |
| CCDC126 | 3027 | 26122 | 49217 |
| CCDC127 | 3028 | 26123 | 49218 |
| CCDC129 | 3029 | 26124 | 49219 |
| CCDC129 | 3030 | 26125 | 49220 |
| CCDC13 | 3031 | 26126 | 49221 |
| CCDC130 | 3032 | 26127 | 49222 |
| CCDC134 | 3033 | 26128 | 49223 |
| CCDC136 | 3034 | 26129 | 49224 |
| CCDC137 | 3035 | 26130 | 49225 |
| CCDC138 | 3036 | 26131 | 49226 |
| CCDC138 | 3037 | 26132 | 49227 |
| CCDC138 | 3038 | 26133 | 49228 |
| CCDC138 | 3039 | 26134 | 49229 |
| CCDC14 | 3040 | 26135 | 49230 |
| CCDC140 | 3041 | 26136 | 49231 |
| CCDC141 | 3042 | 26137 | 49232 |
| CCDC141 | 3043 | 26138 | 49233 |
| CCDC142 | 3044 | 26139 | 49234 |
| CCDC144A | 3045 | 26140 | 49235 |
| CCDC144NL | 3046 | 26141 | 49236 |
| CCDC146 | 3047 | 26142 | 49237 |
| CCDC148 | 3048 | 26143 | 49238 |
| CCDC148 | 3049 | 26144 | 49239 |
| CCDC149 | 3050 | 26145 | 49240 |
| CCDC15 | 3051 | 26146 | 49241 |
| CCDC150 | 3052 | 26147 | 49242 |
| CCDC151 | 3053 | 26148 | 49243 |
| CCDC152 | 3054 | 26149 | 49244 |
| CCDC153 | 3055 | 26150 | 49245 |
| CCDC154 | 3056 | 26151 | 49246 |
| CCDC155 | 3057 | 26152 | 49247 |
| CCDC157 | 3058 | 26153 | 49248 |
| CCDC157 | 3059 | 26154 | 49249 |
| CCDC158 | 3060 | 26155 | 49250 |
| CCDC159 | 3061 | 26156 | 49251 |
| CCDC160 | 3062 | 26157 | 49252 |
| CCDC166 | 3063 | 26158 | 49253 |
| CCDC167 | 3064 | 26159 | 49254 |
| CCDC168 | 3065 | 26160 | 49255 |
| CCDC169 | 3066 | 26161 | 49256 |
| CCDC169 | 3067 | 26162 | 49257 |
| CCDC17 | 3068 | 26163 | 49258 |
| CCDC170 | 3069 | 26164 | 49259 |
| CCDC171 | 3070 | 26165 | 49260 |
| CCDC172 | 3071 | 26166 | 49261 |
| CCDC173 | 3072 | 26167 | 49262 |
| CCDC174 | 3073 | 26168 | 49263 |
| CCDC175 | 3074 | 26169 | 49264 |
| CCDC177 | 3075 | 26170 | 49265 |
| CCDC178 | 3076 | 26171 | 49266 |
| CCDC179 | 3077 | 26172 | 49267 |
| CCDC18 | 3078 | 26173 | 49268 |
| CCDC18 | 3079 | 26174 | 49269 |
| CCDC180 | 3080 | 26175 | 49270 |
| CCDC180 | 3081 | 26176 | 49271 |
| CCDC181 | 3082 | 26177 | 49272 |
| CCDC182 | 3083 | 26178 | 49273 |
| CCDC183 | 3084 | 26179 | 49274 |
| CCDC184 | 3085 | 26180 | 49275 |
| CCDC185 | 3086 | 26181 | 49276 |
| CCDC186 | 3087 | 26182 | 49277 |
| CCDC186 | 3088 | 26183 | 49278 |
| CCDC187 | 3089 | 26184 | 49279 |
| CCDC188 | 3090 | 26185 | 49280 |
| CCDC189 | 3091 | 26186 | 49281 |
| CCDC189 | 3092 | 26187 | 49282 |
| CCDC190 | 3093 | 26188 | 49283 |
| CCDC191 | 3094 | 26189 | 49284 |
| CCDC192 | 3095 | 26190 | 49285 |
| CCDC196 | 3096 | 26191 | 49286 |
| CCDC197 | 3097 | 26192 | 49287 |
| CCDC198 | 3098 | 26193 | 49288 |
| CCDC198 | 3099 | 26194 | 49289 |
| CCDC22 | 3100 | 26195 | 49290 |
| CCDC24 | 3101 | 26196 | 49291 |
| CCDC24 | 3102 | 26197 | 49292 |
| CCDC25 | 3103 | 26198 | 49293 |
| CCDC25 | 3104 | 26199 | 49294 |
| CCDC27 | 3105 | 26200 | 49295 |
| CCDC28A | 3106 | 26201 | 49296 |
| CCDC28B | 3107 | 26202 | 49297 |
| CCDC28B | 3108 | 26203 | 49298 |
| CCDC3 | 3109 | 26204 | 49299 |
| CCDC30 | 3110 | 26205 | 49300 |
| CCDC32 | 3111 | 26206 | 49301 |
| CCDC32 | 3112 | 26207 | 49302 |
| CCDC33 | 3113 | 26208 | 49303 |
| CCDC33 | 3114 | 26209 | 49304 |
| CCDC34 | 3115 | 26210 | 49305 |
| CCDC34 | 3116 | 26211 | 49306 |
| CCDC36 | 3117 | 26212 | 49307 |
| CCDC38 | 3118 | 26213 | 49308 |
| CCDC39 | 3119 | 26214 | 49309 |
| CCDC40 | 3120 | 26215 | 49310 |
| CCDC40 | 3121 | 26216 | 49311 |
| CCDC40 | 3122 | 26217 | 49312 |
| CCDC42 | 3123 | 26218 | 49313 |
| CCDC43 | 3124 | 26219 | 49314 |
| CCDC43 | 3125 | 26220 | 49315 |
| CCDC47 | 3126 | 26221 | 49316 |
| CCDC50 | 3127 | 26222 | 49317 |
| CCDC51 | 3128 | 26223 | 49318 |
| CCDC54 | 3129 | 26224 | 49319 |
| CCDC57 | 3130 | 26225 | 49320 |
| CCDC57 | 3131 | 26226 | 49321 |
| CCDC58 | 3132 | 26227 | 49322 |
| CCDC59 | 3133 | 26228 | 49323 |
| CCDC6 | 3134 | 26229 | 49324 |
| CCDC60 | 3135 | 26230 | 49325 |
| CCDC61 | 3136 | 26231 | 49326 |
| CCDC62 | 3137 | 26232 | 49327 |
| CCDC63 | 3138 | 26233 | 49328 |
| CCDC65 | 3139 | 26234 | 49329 |
| CCDC66 | 3140 | 26235 | 49330 |
| CCDC68 | 3141 | 26236 | 49331 |
| CCDC69 | 3142 | 26237 | 49332 |
| CCDC7 | 3143 | 26238 | 49333 |
| CCDC7 | 3144 | 26239 | 49334 |
| CCDC70 | 3145 | 26240 | 49335 |
| CCDC71 | 3146 | 26241 | 49336 |
| CCDC71L | 3147 | 26242 | 49337 |
| CCDC73 | 3148 | 26243 | 49338 |
| CCDC74A | 3149 | 26244 | 49339 |
| CCDC74A | 3150 | 26245 | 49340 |
| CCDC74B | 3151 | 26246 | 49341 |
| CCDC77 | 3152 | 26247 | 49342 |
| CCDC78 | 3153 | 26248 | 49343 |
| CCDC8 | 3154 | 26249 | 49344 |
| CCDC80 | 3155 | 26250 | 49345 |
| CCDC81 | 3156 | 26251 | 49346 |
| CCDC82 | 3157 | 26252 | 49347 |
| CCDC82 | 3158 | 26253 | 49348 |
| CCDC83 | 3159 | 26254 | 49349 |
| CCDC84 | 3160 | 26255 | 49350 |
| CCDC85A | 3161 | 26256 | 49351 |
| CCDC85A | 3162 | 26257 | 49352 |
| CCDC85B | 3163 | 26258 | 49353 |
| CCDC85C | 3164 | 26259 | 49354 |
| CCDC86 | 3165 | 26260 | 49355 |
| CCDC87 | 3166 | 26261 | 49356 |
| CCDC88A | 3167 | 26262 | 49357 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CCDC88B | 3168 | 26263 | 49358 |
| CCDC88C | 3169 | 26264 | 49359 |
| CCDC89 | 3170 | 26265 | 49360 |
| CCDC9 | 3171 | 26266 | 49361 |
| CCDC90B | 3172 | 26267 | 49362 |
| CCDC91 | 3173 | 26268 | 49363 |
| CCDC92 | 3174 | 26269 | 49364 |
| CCDC93 | 3175 | 26270 | 49365 |
| CCDC94 | 3176 | 26271 | 49366 |
| CCDC96 | 3177 | 26272 | 49367 |
| CCDC97 | 3178 | 26273 | 49368 |
| CCER1 | 3179 | 26274 | 49369 |
| CCER2 | 3180 | 26275 | 49370 |
| CCHCR1 | 3181 | 26276 | 49371 |
| CCIN | 3182 | 26277 | 49372 |
| CCK | 3183 | 26278 | 49373 |
| CCKAR | 3184 | 26279 | 49374 |
| CCKBR | 3185 | 26280 | 49375 |
| CCL1 | 3186 | 26281 | 49376 |
| CCL11 | 3187 | 26282 | 49377 |
| CCL13 | 3188 | 26283 | 49378 |
| CCL14 | 3189 | 26284 | 49379 |
| CCL15 | 3190 | 26285 | 49380 |
| CCL16 | 3191 | 26286 | 49381 |
| CCL17 | 3192 | 26287 | 49382 |
| CCL18 | 3193 | 26288 | 49383 |
| CCL19 | 3194 | 26289 | 49384 |
| CCL2 | 3195 | 26290 | 49385 |
| CCL20 | 3196 | 26291 | 49386 |
| CCL21 | 3197 | 26292 | 49387 |
| CCL22 | 3198 | 26293 | 49388 |
| CCL23 | 3199 | 26294 | 49389 |
| CCL24 | 3200 | 26295 | 49390 |
| CCL25 | 3201 | 26296 | 49391 |
| CCL26 | 3202 | 26297 | 49392 |
| CCL27 | 3203 | 26298 | 49393 |
| CCL28 | 3204 | 26299 | 49394 |
| CCL3L3 | 3205 | 26300 | 49395 |
| CCL4 | 3206 | 26301 | 49396 |
| CCL4L2 | 3207 | 26302 | 49397 |
| CCL4L2 | 3208 | 26303 | 49398 |
| CCL4L2 | 3209 | 26304 | 49399 |
| CCL4L2 | 3210 | 26305 | 49400 |
| CCL5 | 3211 | 26306 | 49401 |
| CCL5 | 3212 | 26307 | 49402 |
| CCL7 | 3213 | 26308 | 49403 |
| CCL8 | 3214 | 26309 | 49404 |
| COM2 | 3215 | 26310 | 49405 |
| CCM2L | 3216 | 26311 | 49406 |
| CCNA1 | 3217 | 26312 | 49407 |
| CCNA2 | 3218 | 26313 | 49408 |
| CCNB1 | 3219 | 26314 | 49409 |
| CCNB1IP1 | 3220 | 26315 | 49410 |
| CCNB2 | 3221 | 26316 | 49411 |
| CCNB3 | 3222 | 26317 | 49412 |
| CCNC | 3223 | 26318 | 49413 |
| CCND1 | 3224 | 26319 | 49414 |
| CCND2 | 3225 | 26320 | 49415 |
| CCND3 | 3226 | 26321 | 49416 |
| CCNDBP1 | 3227 | 26322 | 49417 |
| CCNE1 | 3228 | 26323 | 49418 |
| CCNE2 | 3229 | 26324 | 49419 |
| CCNF | 3230 | 26325 | 49420 |
| CCNG1 | 3231 | 26326 | 49421 |
| CCNG2 | 3232 | 26327 | 49422 |
| CCNH | 3233 | 26328 | 49423 |
| CCNI | 3234 | 26329 | 49424 |
| CCNI | 3235 | 26330 | 49425 |
| CCNI2 | 3236 | 26331 | 49426 |
| CCNJ | 3237 | 26332 | 49427 |
| CCNJL | 3238 | 26333 | 49428 |
| CCNK | 3239 | 26334 | 49429 |
| CCNL1 | 3240 | 26335 | 49430 |
| CCNL1 | 3241 | 26336 | 49431 |
| CCNL2 | 3242 | 26337 | 49432 |
| CCNL2 | 3243 | 26338 | 49433 |
| CCNO | 3244 | 26339 | 49434 |
| CCNQ | 3245 | 26340 | 49435 |
| CCNT1 | 3246 | 26341 | 49436 |
| CCNT2 | 3247 | 26342 | 49437 |
| CCNT2 | 3248 | 26343 | 49438 |
| CCNY | 3249 | 26344 | 49439 |
| CCNYL1 | 3250 | 26345 | 49440 |
| CCP110 | 3251 | 26346 | 49441 |
| CCPG1 | 3252 | 26347 | 49442 |
| CCPG1 | 3253 | 26348 | 49443 |
| CCR1 | 3254 | 26349 | 49444 |
| CCR10 | 3255 | 26350 | 49445 |
| CCR2 | 3256 | 26351 | 49446 |
| CCR2 | 3257 | 26352 | 49447 |
| CCR3 | 3258 | 26353 | 49448 |
| CCR4 | 3259 | 26354 | 49449 |
| CCR5 | 3260 | 26355 | 49450 |
| CCR6 | 3261 | 26356 | 49451 |
| CCR7 | 3262 | 26357 | 49452 |
| CCR8 | 3263 | 26358 | 49453 |
| CCR9 | 3264 | 26359 | 49454 |
| CCRL2 | 3265 | 26360 | 49455 |
| CCS | 3266 | 26361 | 49456 |
| CCSAP | 3267 | 26362 | 49457 |
| CCSER1 | 3268 | 26363 | 49458 |
| CCSER1 | 3269 | 26364 | 49459 |
| CCSER2 | 3270 | 26365 | 49460 |
| CCSER2 | 3271 | 26366 | 49461 |
| CCSER2 | 3272 | 26367 | 49462 |
| CCSER2 | 3273 | 26368 | 49463 |
| CCT2 | 3274 | 26369 | 49464 |
| CCT3 | 3275 | 26370 | 49465 |
| CCT4 | 3276 | 26371 | 49466 |
| CCT5 | 3277 | 26372 | 49467 |
| CCT6A | 3278 | 26373 | 49468 |
| CCT6B | 3279 | 26374 | 49469 |
| CCT7 | 3280 | 26375 | 49470 |
| CCT8 | 3281 | 26376 | 49471 |
| CCT8L2 | 3282 | 26377 | 49472 |
| CCZ1B | 3283 | 26378 | 49473 |
| CD101 | 3284 | 26379 | 49474 |
| CD109 | 3285 | 26380 | 49475 |
| CD14 | 3286 | 26381 | 49476 |
| CD151 | 3287 | 26382 | 49477 |
| CD160 | 3288 | 26383 | 49478 |
| CD163 | 3289 | 26384 | 49479 |
| CD163 | 3290 | 26385 | 49480 |
| CD163L1 | 3291 | 26386 | 49481 |
| CD164 | 3292 | 26387 | 49482 |
| CD164 | 3293 | 26388 | 49483 |
| CD164L2 | 3294 | 26389 | 49484 |
| CD164L2 | 3295 | 26390 | 49485 |
| CD177 | 3296 | 26391 | 49486 |
| CD180 | 3297 | 26392 | 49487 |
| CD19 | 3298 | 26393 | 49488 |
| CD1A | 3299 | 26394 | 49489 |
| CD1B | 3300 | 26395 | 49490 |
| CD1C | 3301 | 26396 | 49491 |
| CD1D | 3302 | 26397 | 49492 |
| CD1E | 3303 | 26398 | 49493 |
| CD1E | 3304 | 26399 | 49494 |
| CD2 | 3305 | 26400 | 49495 |
| CD200 | 3306 | 26401 | 49496 |
| CD200R1 | 3307 | 26402 | 49497 |
| CD200R1 | 3308 | 26403 | 49498 |
| CD200R1L | 3309 | 26404 | 49499 |
| CD207 | 3310 | 26405 | 49500 |
| CD209 | 3311 | 26406 | 49501 |
| CD22 | 3312 | 26407 | 49502 |
| CD22 | 3313 | 26408 | 49503 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CD226 | 3314 | 26409 | 49504 |
| CD24 | 3315 | 26410 | 49505 |
| CD24 | 3316 | 26411 | 49506 |
| CD244 | 3317 | 26412 | 49507 |
| CD247 | 3318 | 26413 | 49508 |
| CD248 | 3319 | 26414 | 49509 |
| CD27 | 3320 | 26415 | 49510 |
| CD274 | 3321 | 26416 | 49511 |
| CD274 | 3322 | 26417 | 49512 |
| CD276 | 3323 | 26418 | 49513 |
| CD28 | 3324 | 26419 | 49514 |
| CD2AP | 3325 | 26420 | 49515 |
| CD2BP2 | 3326 | 26421 | 49516 |
| CD300A | 3327 | 26422 | 49517 |
| CD300C | 3328 | 26423 | 49518 |
| CD300E | 3329 | 26424 | 49519 |
| CD300H | 3330 | 26425 | 49520 |
| CD300LB | 3331 | 26426 | 49521 |
| CD300LD | 3332 | 26427 | 49522 |
| CD300LF | 3333 | 26428 | 49523 |
| CD300LF | 3334 | 26429 | 49524 |
| CD300LG | 3335 | 26430 | 49525 |
| CD300LG | 3336 | 26431 | 49526 |
| CD300LG | 3337 | 26432 | 49527 |
| CD302 | 3338 | 26433 | 49528 |
| CD320 | 3339 | 26434 | 49529 |
| CD33 | 3340 | 26435 | 49530 |
| CD33 | 3341 | 26436 | 49531 |
| CD34 | 3342 | 26437 | 49532 |
| CD34 | 3343 | 26438 | 49533 |
| CD36 | 3344 | 26439 | 49534 |
| CD37 | 3345 | 26440 | 49535 |
| CD38 | 3346 | 26441 | 49536 |
| CD3D | 3347 | 26442 | 49537 |
| CD3E | 3348 | 26443 | 49538 |
| CD3EAP | 3349 | 26444 | 49539 |
| CD3G | 3350 | 26445 | 49540 |
| CD4 | 3351 | 26446 | 49541 |
| CD40 | 3352 | 26447 | 49542 |
| CD40 | 3353 | 26448 | 49543 |
| CD40LG | 3354 | 26449 | 49544 |
| CD44 | 3355 | 26450 | 49545 |
| CD44 | 3356 | 26451 | 49546 |
| CD44 | 3357 | 26452 | 49547 |
| CD46 | 3358 | 26453 | 49548 |
| CD46 | 3359 | 26454 | 49549 |
| CD47 | 3360 | 26455 | 49550 |
| CD48 | 3361 | 26456 | 49551 |
| CD48 | 3362 | 26457 | 49552 |
| CD5 | 3363 | 26458 | 49553 |
| CD52 | 3364 | 26459 | 49554 |
| CD53 | 3365 | 26460 | 49555 |
| CD55 | 3366 | 26461 | 49556 |
| CD55 | 3367 | 26462 | 49557 |
| CD55 | 3368 | 26463 | 49558 |
| CD58 | 3369 | 26464 | 49559 |
| CD58 | 3370 | 26465 | 49560 |
| CD59 | 3371 | 26466 | 49561 |
| CD5L | 3372 | 26467 | 49562 |
| CD5L | 3373 | 26468 | 49563 |
| CD6 | 3374 | 26469 | 49564 |
| CD63 | 3375 | 26470 | 49565 |
| CD68 | 3376 | 26471 | 49566 |
| CD69 | 3377 | 26472 | 49567 |
| CD7 | 3378 | 26473 | 49568 |
| CD70 | 3379 | 26474 | 49569 |
| CD70 | 3380 | 26475 | 49570 |
| CD72 | 3381 | 26476 | 49571 |
| CD74 | 3382 | 26477 | 49572 |
| CD74 | 3383 | 26478 | 49573 |
| CD79A | 3384 | 26479 | 49574 |
| CD79B | 3385 | 26480 | 49575 |
| CD80 | 3386 | 26481 | 49576 |
| CD81 | 3387 | 26482 | 49577 |
| CD82 | 3388 | 26483 | 49578 |
| CD83 | 3389 | 26484 | 49579 |
| CD84 | 3390 | 26485 | 49580 |
| CD84 | 3391 | 26486 | 49581 |
| CD86 | 3392 | 26487 | 49582 |
| CD8A | 3393 | 26488 | 49583 |
| CD8A | 3394 | 26489 | 49584 |
| CD8A | 3395 | 26490 | 49585 |
| CD8B | 3396 | 26491 | 49586 |
| CD8B | 3397 | 26492 | 49587 |
| CD8B | 3398 | 26493 | 49588 |
| CD8B | 3399 | 26494 | 49589 |
| CD9 | 3400 | 26495 | 49590 |
| CD93 | 3401 | 26496 | 49591 |
| CD96 | 3402 | 26497 | 49592 |
| CD96 | 3403 | 26498 | 49593 |
| CD99 | 3404 | 26499 | 49594 |
| CD99 | 3405 | 26500 | 49595 |
| CD99L2 | 3406 | 26501 | 49596 |
| CDA | 3407 | 26502 | 49597 |
| CDADC1 | 3408 | 26503 | 49598 |
| CDADC1 | 3409 | 26504 | 49599 |
| CDAN1 | 3410 | 26505 | 49600 |
| CDC123 | 3411 | 26506 | 49601 |
| CDC14A | 3412 | 26507 | 49602 |
| CDC14A | 3413 | 26508 | 49603 |
| CDC14A | 3414 | 26509 | 49604 |
| CDC14A | 3415 | 26510 | 49605 |
| CDC14B | 3416 | 26511 | 49606 |
| CDC14B | 3417 | 26512 | 49607 |
| CDC14B | 3418 | 26513 | 49608 |
| CDC16 | 3419 | 26514 | 49609 |
| CDC20 | 3420 | 26515 | 49610 |
| CDC20B | 3421 | 26516 | 49611 |
| CDC23 | 3422 | 26517 | 49612 |
| CDC25A | 3423 | 26518 | 49613 |
| CDC25B | 3424 | 26519 | 49614 |
| CDC25C | 3425 | 26520 | 49615 |
| CDC26 | 3426 | 26521 | 49616 |
| CDC27 | 3427 | 26522 | 49617 |
| CDC27 | 3428 | 26523 | 49618 |
| CDC34 | 3429 | 26524 | 49619 |
| CDC37 | 3430 | 26525 | 49620 |
| CDC37L1 | 3431 | 26526 | 49621 |
| CDC40 | 3432 | 26527 | 49622 |
| CDC42 | 3433 | 26528 | 49623 |
| CDC42 | 3434 | 26529 | 49624 |
| CDC42BPA | 3435 | 26530 | 49625 |
| CDC42BPB | 3436 | 26531 | 49626 |
| CDC42BPG | 3437 | 26532 | 49627 |
| CDC42EP1 | 3438 | 26533 | 49628 |
| CDC42EP2 | 3439 | 26534 | 49629 |
| CDC42EP3 | 3440 | 26535 | 49630 |
| CDC42EP4 | 3441 | 26536 | 49631 |
| CDC42EP5 | 3442 | 26537 | 49632 |
| CDC42SE1 | 3443 | 26538 | 49633 |
| CDC42SE2 | 3444 | 26539 | 49634 |
| CDC45 | 3445 | 26540 | 49635 |
| CDC5L | 3446 | 26541 | 49636 |
| CDC6 | 3447 | 26542 | 49637 |
| CDC7 | 3448 | 26543 | 49638 |
| CDC73 | 3449 | 26544 | 49639 |
| CDCA2 | 3450 | 26545 | 49640 |
| CDCA2 | 3451 | 26546 | 49641 |
| CDCA3 | 3452 | 26547 | 49642 |
| CDCA3 | 3453 | 26548 | 49643 |
| CDCA3 | 3454 | 26549 | 49644 |
| CDCA4 | 3455 | 26550 | 49645 |
| CDCA5 | 3456 | 26551 | 49646 |
| CDCA7 | 3457 | 26552 | 49647 |
| CDCA7L | 3458 | 26553 | 49648 |
| CDCA8 | 3459 | 26554 | 49649 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CDCP1 | 3460 | 26555 | 49650 |
| CDCP1 | 3461 | 26556 | 49651 |
| CDCP2 | 3462 | 26557 | 49652 |
| CDCP2 | 3463 | 26558 | 49653 |
| CDH1 | 3464 | 26559 | 49654 |
| CDH1 | 3465 | 26560 | 49655 |
| CDH1 | 3466 | 26561 | 49656 |
| CDH10 | 3467 | 26562 | 49657 |
| CDH10 | 3468 | 26563 | 49658 |
| CDH11 | 3469 | 26564 | 49659 |
| CDH11 | 3470 | 26565 | 49660 |
| CDH12 | 3471 | 26566 | 49661 |
| CDH13 | 3472 | 26567 | 49662 |
| CDH13 | 3473 | 26568 | 49663 |
| CDH13 | 3474 | 26569 | 49664 |
| CDH15 | 3475 | 26570 | 49665 |
| CDH16 | 3476 | 26571 | 49666 |
| CDH17 | 3477 | 26572 | 49667 |
| CDH18 | 3478 | 26573 | 49668 |
| CDH18 | 3479 | 26574 | 49669 |
| CDH19 | 3480 | 26575 | 49670 |
| CDH19 | 3481 | 26576 | 49671 |
| CDH2 | 3482 | 26577 | 49672 |
| CDH20 | 3483 | 26578 | 49673 |
| CDH22 | 3484 | 26579 | 49674 |
| CDH23 | 3485 | 26580 | 49675 |
| CDH23 | 3486 | 26581 | 49676 |
| CDH23 | 3487 | 26582 | 49677 |
| CDH23 | 3488 | 26583 | 49678 |
| CDH23 | 3489 | 26584 | 49679 |
| CDH24 | 3490 | 26585 | 49680 |
| CDH26 | 3491 | 26586 | 49681 |
| CDH3 | 3492 | 26587 | 49682 |
| CDH3 | 3493 | 26588 | 49683 |
| CDH4 | 3494 | 26589 | 49684 |
| CDH5 | 3495 | 26590 | 49685 |
| CDH6 | 3496 | 26591 | 49686 |
| CDH7 | 3497 | 26592 | 49687 |
| CDH7 | 3498 | 26593 | 49688 |
| CDH8 | 3499 | 26594 | 49689 |
| CDH9 | 3500 | 26595 | 49690 |
| CDHR1 | 3501 | 26596 | 49691 |
| CDHR1 | 3502 | 26597 | 49692 |
| CDHR2 | 3503 | 26598 | 49693 |
| CDHR3 | 3504 | 26599 | 49694 |
| CDHR4 | 3505 | 26600 | 49695 |
| CDHR5 | 3506 | 26601 | 49696 |
| CDIP1 | 3507 | 26602 | 49697 |
| CDIPT | 3508 | 26603 | 49698 |
| CDK1 | 3509 | 26604 | 49699 |
| CDK1 | 3510 | 26605 | 49700 |
| CDK10 | 3511 | 26606 | 49701 |
| CDK10 | 3512 | 26607 | 49702 |
| CDK11B | 3513 | 26608 | 49703 |
| CDK12 | 3514 | 26609 | 49704 |
| CDK13 | 3515 | 26610 | 49705 |
| CDK14 | 3516 | 26611 | 49706 |
| CDK15 | 3517 | 26612 | 49707 |
| CDK15 | 3518 | 26613 | 49708 |
| CDK16 | 3519 | 26614 | 49709 |
| CDK17 | 3520 | 26615 | 49710 |
| CDK17 | 3521 | 26616 | 49711 |
| CDK18 | 3522 | 26617 | 49712 |
| CDK19 | 3523 | 26618 | 49713 |
| CDK2 | 3524 | 26619 | 49714 |
| CDK20 | 3525 | 26620 | 49715 |
| CDK20 | 3526 | 26621 | 49716 |
| CDK2AP1 | 3527 | 26622 | 49717 |
| CDK2AP2 | 3528 | 26623 | 49718 |
| CDK2AP2 | 3529 | 26624 | 49719 |
| CDK3 | 3530 | 26625 | 49720 |
| CDK4 | 3531 | 26626 | 49721 |
| CDK5 | 3532 | 26627 | 49722 |
| CDK5R1 | 3533 | 26628 | 49723 |
| CDK5R2 | 3534 | 26629 | 49724 |
| CDK5RAP1 | 3535 | 26630 | 49725 |
| CDK5RAP2 | 3536 | 26631 | 49726 |
| CDK5RAP3 | 3537 | 26632 | 49727 |
| CDK5RAP3 | 3538 | 26633 | 49728 |
| CDK6 | 3539 | 26634 | 49729 |
| CDK7 | 3540 | 26635 | 49730 |
| CDK8 | 3541 | 26636 | 49731 |
| CDK9 | 3542 | 26637 | 49732 |
| CDKAL1 | 3543 | 26638 | 49733 |
| CDKL1 | 3544 | 26639 | 49734 |
| CDKL1 | 3545 | 26640 | 49735 |
| CDKL2 | 3546 | 26641 | 49736 |
| CDKL3 | 3547 | 26642 | 49737 |
| CDKL3 | 3548 | 26643 | 49738 |
| CDKL3 | 3549 | 26644 | 49739 |
| CDKL4 | 3550 | 26645 | 49740 |
| CDKL4 | 3551 | 26646 | 49741 |
| CDKL5 | 3552 | 26647 | 49742 |
| CDKL5 | 3553 | 26648 | 49743 |
| CDKN1A | 3554 | 26649 | 49744 |
| CDKN1B | 3555 | 26650 | 49745 |
| CDKN1C | 3556 | 26651 | 49746 |
| CDKN2A | 3557 | 26652 | 49747 |
| CDKN2A | 3558 | 26653 | 49748 |
| CDKN2A | 3559 | 26654 | 49749 |
| CDKN2A | 3560 | 26655 | 49750 |
| CDKN2AIP | 3561 | 26656 | 49751 |
| CDKN2AIPNL | 3562 | 26657 | 49752 |
| CDKN2B | 3563 | 26658 | 49753 |
| CDKN2C | 3564 | 26659 | 49754 |
| CDKN2C | 3565 | 26660 | 49755 |
| CDKN2D | 3566 | 26661 | 49756 |
| CDKN3 | 3567 | 26662 | 49757 |
| CDKN3 | 3568 | 26663 | 49758 |
| CDNF | 3569 | 26664 | 49759 |
| CDO1 | 3570 | 26665 | 49760 |
| CDON | 3571 | 26666 | 49761 |
| CDPF1 | 3572 | 26667 | 49762 |
| CDR1 | 3573 | 26668 | 49763 |
| CDR2 | 3574 | 26669 | 49764 |
| CDR2L | 3575 | 26670 | 49765 |
| CDRT1 | 3576 | 26671 | 49766 |
| CDRT1 | 3577 | 26672 | 49767 |
| CDRT15 | 3578 | 26673 | 49768 |
| CDRT15L2 | 3579 | 26674 | 49769 |
| CDRT4 | 3580 | 26675 | 49770 |
| CDS1 | 3581 | 26676 | 49771 |
| CDS2 | 3582 | 26677 | 49772 |
| CDSN | 3583 | 26678 | 49773 |
| CDT1 | 3584 | 26679 | 49774 |
| CDV3 | 3585 | 26680 | 49775 |
| CDV3 | 3586 | 26681 | 49776 |
| CDX1 | 3587 | 26682 | 49777 |
| CDX2 | 3588 | 26683 | 49778 |
| CDX4 | 3589 | 26684 | 49779 |
| CDY1 | 3590 | 26685 | 49780 |
| CDY2A | 3591 | 26686 | 49781 |
| CDYL | 3592 | 26687 | 49782 |
| CDYL2 | 3593 | 26688 | 49783 |
| CEACAM1 | 3594 | 26689 | 49784 |
| CEACAM1 | 3595 | 26690 | 49785 |
| CEACAM16 | 3596 | 26691 | 49786 |
| CEACAM18 | 3597 | 26692 | 49787 |
| CEACAM19 | 3598 | 26693 | 49788 |
| CEACAM20 | 3599 | 26694 | 49789 |
| CEACAM21 | 3600 | 26695 | 49790 |
| CEACAM21 | 3601 | 26696 | 49791 |
| CEACAM3 | 3602 | 26697 | 49792 |
| CEACAM3 | 3603 | 26698 | 49793 |
| CEACAM4 | 3604 | 26699 | 49794 |
| CEACAM5 | 3605 | 26700 | 49795 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CEACAM6 | 3606 | 26701 | 49796 |
| CEACAM7 | 3607 | 26702 | 49797 |
| CEACAM8 | 3608 | 26703 | 49798 |
| CEBPA | 3609 | 26704 | 49799 |
| CEBPB | 3610 | 26705 | 49800 |
| CEBPD | 3611 | 26706 | 49801 |
| CEBPE | 3612 | 26707 | 49802 |
| CEBPG | 3613 | 26708 | 49803 |
| CEBPZ | 3614 | 26709 | 49804 |
| CEBPZOS | 3615 | 26710 | 49805 |
| CEBPZOS | 3616 | 26711 | 49806 |
| CECR2 | 3617 | 26712 | 49807 |
| CEL | 3618 | 26713 | 49808 |
| CELA1 | 3619 | 26714 | 49809 |
| CELA2A | 3620 | 26715 | 49810 |
| CELA2B | 3621 | 26716 | 49811 |
| CELA3A | 3622 | 26717 | 49812 |
| CELF1 | 3623 | 26718 | 49813 |
| CELF2 | 3624 | 26719 | 49814 |
| CELF3 | 3625 | 26720 | 49815 |
| CELF4 | 3626 | 26721 | 49816 |
| CELF4 | 3627 | 26722 | 49817 |
| CELF4 | 3628 | 26723 | 49818 |
| CELF4 | 3629 | 26724 | 49819 |
| CELF5 | 3630 | 26725 | 49820 |
| CELF5 | 3631 | 26726 | 49821 |
| CELF6 | 3632 | 26727 | 49822 |
| CELSR1 | 3633 | 26728 | 49823 |
| CELSR2 | 3634 | 26729 | 49824 |
| CELSR3 | 3635 | 26730 | 49825 |
| CEMIP | 3636 | 26731 | 49826 |
| CEMP1 | 3637 | 26732 | 49827 |
| CEND1 | 3638 | 26733 | 49828 |
| CENPA | 3639 | 26734 | 49829 |
| CENPB | 3640 | 26735 | 49830 |
| CENPBD1 | 3641 | 26736 | 49831 |
| CENPC | 3642 | 26737 | 49832 |
| CENPE | 3643 | 26738 | 49833 |
| CENPF | 3644 | 26739 | 49834 |
| CENPH | 3645 | 26740 | 49835 |
| CENPI | 3646 | 26741 | 49836 |
| CENPI | 3647 | 26742 | 49837 |
| CENPJ | 3648 | 26743 | 49838 |
| CENPK | 3649 | 26744 | 49839 |
| CENPK | 3650 | 26745 | 49840 |
| CENPL | 3651 | 26746 | 49841 |
| CENPM | 3652 | 26747 | 49842 |
| CENPM | 3653 | 26748 | 49843 |
| CENPM | 3654 | 26749 | 49844 |
| CENPM | 3655 | 26750 | 49845 |
| CENPM | 3656 | 26751 | 49846 |
| CENPN | 3657 | 26752 | 49847 |
| CENPN | 3658 | 26753 | 49848 |
| CENPN | 3659 | 26754 | 49849 |
| CENPO | 3660 | 26755 | 49850 |
| CENPP | 3661 | 26756 | 49851 |
| CENPP | 3662 | 26757 | 49852 |
| CENPQ | 3663 | 26758 | 49853 |
| CENPS | 3664 | 26759 | 49854 |
| CENPS-CORT | 3665 | 26760 | 49855 |
| CENPT | 3666 | 26761 | 49856 |
| CENPU | 3667 | 26762 | 49857 |
| CENPV | 3668 | 26763 | 49858 |
| CENPW | 3669 | 26764 | 49859 |
| CENPX | 3670 | 26765 | 49860 |
| CENPX | 3671 | 26766 | 49861 |
| CEP104 | 3672 | 26767 | 49862 |
| CEP112 | 3673 | 26768 | 49863 |
| CEP120 | 3674 | 26769 | 49864 |
| CEP126 | 3675 | 26770 | 49865 |
| CEP128 | 3676 | 26771 | 49866 |
| CEP131 | 3677 | 26772 | 49867 |
| CEP135 | 3678 | 26773 | 49868 |
| CEP152 | 3679 | 26774 | 49869 |
| CEP162 | 3680 | 26775 | 49870 |
| CEP164 | 3681 | 26776 | 49871 |
| CEP170 | 3682 | 26777 | 49872 |
| CEP170B | 3683 | 26778 | 49873 |
| CEP19 | 3684 | 26779 | 49874 |
| CEP192 | 3685 | 26780 | 49875 |
| CEP250 | 3686 | 26781 | 49876 |
| CEP290 | 3687 | 26782 | 49877 |
| CEP295 | 3688 | 26783 | 49878 |
| CEP295NL | 3689 | 26784 | 49879 |
| CEP350 | 3690 | 26785 | 49880 |
| CEP41 | 3691 | 26786 | 49881 |
| CEP41 | 3692 | 26787 | 49882 |
| CEP44 | 3693 | 26788 | 49883 |
| CEP44 | 3694 | 26789 | 49884 |
| CEP55 | 3695 | 26790 | 49885 |
| CEP57 | 3696 | 26791 | 49886 |
| CEP57L1 | 3697 | 26792 | 49887 |
| CEP57L1 | 3698 | 26793 | 49888 |
| CEP57L1 | 3699 | 26794 | 49889 |
| CEP63 | 3700 | 26795 | 49890 |
| CEP63 | 3701 | 26796 | 49891 |
| CEP68 | 3702 | 26797 | 49892 |
| CEP70 | 3703 | 26798 | 49893 |
| CEP70 | 3704 | 26799 | 49894 |
| CEP70 | 3705 | 26800 | 49895 |
| CEP70 | 3706 | 26801 | 49896 |
| CEP72 | 3707 | 26802 | 49897 |
| CEP76 | 3708 | 26803 | 49898 |
| CEP78 | 3709 | 26804 | 49899 |
| CEP78 | 3710 | 26805 | 49900 |
| CEP83 | 3711 | 26806 | 49901 |
| CEP83 | 3712 | 26807 | 49902 |
| CEP85 | 3713 | 26808 | 49903 |
| CEP85L | 3714 | 26809 | 49904 |
| CEP85L | 3715 | 26810 | 49905 |
| CEP89 | 3716 | 26811 | 49906 |
| CEP95 | 3717 | 26812 | 49907 |
| CEP97 | 3718 | 26813 | 49908 |
| CEPT1 | 3719 | 26814 | 49909 |
| CER1 | 3720 | 26815 | 49910 |
| CERCAM | 3721 | 26816 | 49911 |
| CERK | 3722 | 26817 | 49912 |
| CERKL | 3723 | 26818 | 49913 |
| CERS1 | 3724 | 26819 | 49914 |
| CERS1 | 3725 | 26820 | 49915 |
| CERS2 | 3726 | 26821 | 49916 |
| CERS3 | 3727 | 26822 | 49917 |
| CERS4 | 3728 | 26823 | 49918 |
| CERS5 | 3729 | 26824 | 49919 |
| CERS5 | 3730 | 26825 | 49920 |
| CERS5 | 3731 | 26826 | 49921 |
| CERS6 | 3732 | 26827 | 49922 |
| CES1 | 3733 | 26828 | 49923 |
| CES2 | 3734 | 26829 | 49924 |
| CES3 | 3735 | 26830 | 49925 |
| CES4A | 3736 | 26831 | 49926 |
| CES4A | 3737 | 26832 | 49927 |
| CES5A | 3738 | 26833 | 49928 |
| CETN1 | 3739 | 26834 | 49929 |
| CETN2 | 3740 | 26835 | 49930 |
| CETN3 | 3741 | 26836 | 49931 |
| CETP | 3742 | 26837 | 49932 |
| CFAP100 | 3743 | 26838 | 49933 |
| CFAP126 | 3744 | 26839 | 49934 |
| CFAP157 | 3745 | 26840 | 49935 |
| CFAP161 | 3746 | 26841 | 49936 |
| CFAP161 | 3747 | 26842 | 49937 |
| CFAP20 | 3748 | 26843 | 49938 |
| CFAP206 | 3749 | 26844 | 49939 |
| CFAP221 | 3750 | 26845 | 49940 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CFAP36 | 3751 | 26846 | 49941 |
| CFAP43 | 3752 | 26847 | 49942 |
| CFAP44 | 3753 | 26848 | 49943 |
| CFAP44 | 3754 | 26849 | 49944 |
| CFAP45 | 3755 | 26850 | 49945 |
| CFAP46 | 3756 | 26851 | 49946 |
| CFAP47 | 3757 | 26852 | 49947 |
| CFAP47 | 3758 | 26853 | 49948 |
| CFAP52 | 3759 | 26854 | 49949 |
| CFAP53 | 3760 | 26855 | 49950 |
| CFAP54 | 3761 | 26856 | 49951 |
| CFAP57 | 3762 | 26857 | 49952 |
| CFAP57 | 3763 | 26858 | 49953 |
| CFAP58 | 3764 | 26859 | 49954 |
| CFAP61 | 3765 | 26860 | 49955 |
| CFAP61 | 3766 | 26861 | 49956 |
| CFAP65 | 3767 | 26862 | 49957 |
| CFAP65 | 3768 | 26863 | 49958 |
| CFAP65 | 3769 | 26864 | 49959 |
| CFAP69 | 3770 | 26865 | 49960 |
| CFAP70 | 3771 | 26866 | 49961 |
| CFAP73 | 3772 | 26867 | 49962 |
| CFAP74 | 3773 | 26868 | 49963 |
| CFAP77 | 3774 | 26869 | 49964 |
| CFAP97 | 3775 | 26870 | 49965 |
| CFAP97 | 3776 | 26871 | 49966 |
| CFAP99 | 3777 | 26872 | 49967 |
| CFB | 3778 | 26873 | 49968 |
| CFC1 | 3779 | 26874 | 49969 |
| CFD | 3780 | 26875 | 49970 |
| CFDP1 | 3781 | 26876 | 49971 |
| CFH | 3782 | 26877 | 49972 |
| CFH | 3783 | 26878 | 49973 |
| CFHR2 | 3784 | 26879 | 49974 |
| CFHR3 | 3785 | 26880 | 49975 |
| CFHR5 | 3786 | 26881 | 49976 |
| CFI | 3787 | 26882 | 49977 |
| CFL1 | 3788 | 26883 | 49978 |
| CFL2 | 3789 | 26884 | 49979 |
| CFLAR | 3790 | 26885 | 49980 |
| CFLAR | 3791 | 26886 | 49981 |
| CFLAR | 3792 | 26887 | 49982 |
| CFLAR | 3793 | 26888 | 49983 |
| CFP | 3794 | 26889 | 49984 |
| CFTR | 3795 | 26890 | 49985 |
| CGA | 3796 | 26891 | 49986 |
| CGB1 | 3797 | 26892 | 49987 |
| CGB2 | 3798 | 26893 | 49988 |
| CGGBP1 | 3799 | 26894 | 49989 |
| CGN | 3800 | 26895 | 49990 |
| CGNL1 | 3801 | 26896 | 49991 |
| CGREF1 | 3802 | 26897 | 49992 |
| CGREF1 | 3803 | 26898 | 49993 |
| CGREF1 | 3804 | 26899 | 49994 |
| CGRRF1 | 3805 | 26900 | 49995 |
| CH25H | 3806 | 26901 | 49996 |
| CHAC1 | 3807 | 26902 | 49997 |
| CHAC2 | 3808 | 26903 | 49998 |
| CHAD | 3809 | 26904 | 49999 |
| CHADL | 3810 | 26905 | 50000 |
| CHAF1A | 3811 | 26906 | 50001 |
| CHAF1B | 3812 | 26907 | 50002 |
| CHAMP1 | 3813 | 26908 | 50003 |
| CHAT | 3814 | 26909 | 50004 |
| CHCHD1 | 3815 | 26910 | 50005 |
| CHCHD10 | 3816 | 26911 | 50006 |
| CHCHD2 | 3817 | 26912 | 50007 |
| CHCHD2 | 3818 | 26913 | 50008 |
| CHCHD3 | 3819 | 26914 | 50009 |
| CHCHD3 | 3820 | 26915 | 50010 |
| CHCHD4 | 3821 | 26916 | 50011 |
| CHCHD5 | 3822 | 26917 | 50012 |
| CHCHD6 | 3823 | 26918 | 50013 |
| CHCHD7 | 3824 | 26919 | 50014 |
| CHCHD7 | 3825 | 26920 | 50015 |
| CHCHD7 | 3826 | 26921 | 50016 |
| CHCHD7 | 3827 | 26922 | 50017 |
| CHD1 | 3828 | 26923 | 50018 |
| CHD1L | 3829 | 26924 | 50019 |
| CHD2 | 3830 | 26925 | 50020 |
| CHD2 | 3831 | 26926 | 50021 |
| CHD3 | 3832 | 26927 | 50022 |
| CHD4 | 3833 | 26928 | 50023 |
| CHD5 | 3834 | 26929 | 50024 |
| CHD6 | 3835 | 26930 | 50025 |
| CHD7 | 3836 | 26931 | 50026 |
| CHD8 | 3837 | 26932 | 50027 |
| CHD9 | 3838 | 26933 | 50028 |
| CHDH | 3839 | 26934 | 50029 |
| CHEK1 | 3840 | 26935 | 50030 |
| CHEK2 | 3841 | 26936 | 50031 |
| CHERP | 3842 | 26937 | 50032 |
| CHFR | 3843 | 26938 | 50033 |
| CHGA | 3844 | 26939 | 50034 |
| CHGB | 3845 | 26940 | 50035 |
| CHI3L1 | 3846 | 26941 | 50036 |
| CHI3L2 | 3847 | 26942 | 50037 |
| CHIA | 3848 | 26943 | 50038 |
| CHIC1 | 3849 | 26944 | 50039 |
| CHIC2 | 3850 | 26945 | 50040 |
| CHID1 | 3851 | 26946 | 50041 |
| CHIT1 | 3852 | 26947 | 50042 |
| CHKA | 3853 | 26948 | 50043 |
| CHKB | 3854 | 26949 | 50044 |
| CHL1 | 3855 | 26950 | 50045 |
| CHM | 3856 | 26951 | 50046 |
| CHM | 3857 | 26952 | 50047 |
| CHML | 3858 | 26953 | 50048 |
| CHMP1A | 3859 | 26954 | 50049 |
| CHMP1A | 3860 | 26955 | 50050 |
| CHMP1B | 3861 | 26956 | 50051 |
| CHMP2A | 3862 | 26957 | 50052 |
| CHMP2B | 3863 | 26958 | 50053 |
| CHMP3 | 3864 | 26959 | 50054 |
| CHMP4A | 3865 | 26960 | 50055 |
| CHMP4B | 3866 | 26961 | 50056 |
| CHMP4C | 3867 | 26962 | 50057 |
| CHMP5 | 3868 | 26963 | 50058 |
| CHMP5 | 3869 | 26964 | 50059 |
| CHMP6 | 3870 | 26965 | 50060 |
| CHMP7 | 3871 | 26966 | 50061 |
| CHN1 | 3872 | 26967 | 50062 |
| CHN2 | 3873 | 26968 | 50063 |
| CHN2 | 3874 | 26969 | 50064 |
| CHODL | 3875 | 26970 | 50065 |
| CHODL | 3876 | 26971 | 50066 |
| CHORDC1 | 3877 | 26972 | 50067 |
| CHP1 | 3878 | 26973 | 50068 |
| CHP2 | 3879 | 26974 | 50069 |
| CHPF | 3880 | 26975 | 50070 |
| CHPF2 | 3881 | 26976 | 50071 |
| CHPT1 | 3882 | 26977 | 50072 |
| CHRAC1 | 3883 | 26978 | 50073 |
| CHRD | 3884 | 26979 | 50074 |
| CHRDL1 | 3885 | 26980 | 50075 |
| CHRDL2 | 3886 | 26981 | 50076 |
| CHRM1 | 3887 | 26982 | 50077 |
| CHRM2 | 3888 | 26983 | 50078 |
| CHRM3 | 3889 | 26984 | 50079 |
| CHRM4 | 3890 | 26985 | 50080 |
| CHRM5 | 3891 | 26986 | 50081 |
| CHRNA1 | 3892 | 26987 | 50082 |
| CHRNA10 | 3893 | 26988 | 50083 |
| CHRNA2 | 3894 | 26989 | 50084 |
| CHRNA3 | 3895 | 26990 | 50085 |
| CHRNA3 | 3896 | 26991 | 50086 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CHRNA4 | 3897 | 26992 | 50087 |
| CHRNA5 | 3898 | 26993 | 50088 |
| CHRNA5 | 3899 | 26994 | 50089 |
| CHRNA6 | 3900 | 26995 | 50090 |
| CHRNA7 | 3901 | 26996 | 50091 |
| CHRNA9 | 3902 | 26997 | 50092 |
| CHRNB1 | 3903 | 26998 | 50093 |
| CHRNB2 | 3904 | 26999 | 50094 |
| CHRNB3 | 3905 | 27000 | 50095 |
| CHRNB4 | 3906 | 27001 | 50096 |
| CHRNB4 | 3907 | 27002 | 50097 |
| CHRND | 3908 | 27003 | 50098 |
| CHRNE | 3909 | 27004 | 50099 |
| CHRNG | 3910 | 27005 | 50100 |
| CHST1 | 3911 | 27006 | 50101 |
| CHST10 | 3912 | 27007 | 50102 |
| CHST11 | 3913 | 27008 | 50103 |
| CHST12 | 3914 | 27009 | 50104 |
| CHST13 | 3915 | 27010 | 50105 |
| CHST14 | 3916 | 27011 | 50106 |
| CHST15 | 3917 | 27012 | 50107 |
| CHST15 | 3918 | 27013 | 50108 |
| CHST2 | 3919 | 27014 | 50109 |
| CHST3 | 3920 | 27015 | 50110 |
| CHST4 | 3921 | 27016 | 50111 |
| CHST5 | 3922 | 27017 | 50112 |
| CHST6 | 3923 | 27018 | 50113 |
| CHST7 | 3924 | 27019 | 50114 |
| CHST8 | 3925 | 27020 | 50115 |
| CHST9 | 3926 | 27021 | 50116 |
| CHSY1 | 3927 | 27022 | 50117 |
| CHSY3 | 3928 | 27023 | 50118 |
| CHTF18 | 3929 | 27024 | 50119 |
| CHTF8 | 3930 | 27025 | 50120 |
| CHTOP | 3931 | 27026 | 50121 |
| CHTOP | 3932 | 27027 | 50122 |
| CHUK | 3933 | 27028 | 50123 |
| CHUK | 3934 | 27029 | 50124 |
| CHURC1 | 3935 | 27030 | 50125 |
| CHURC1 | 3936 | 27031 | 50126 |
| CHURC1-FNTB | 3937 | 27032 | 50127 |
| CIAO1 | 3938 | 27033 | 50128 |
| CIAPIN1 | 3939 | 27034 | 50129 |
| CIAPIN1 | 3940 | 27035 | 50130 |
| CIART | 3941 | 27036 | 50131 |
| CIB1 | 3942 | 27037 | 50132 |
| CIB2 | 3943 | 27038 | 50133 |
| CIB3 | 3944 | 27039 | 50134 |
| CIB4 | 3945 | 27040 | 50135 |
| CIC | 3946 | 27041 | 50136 |
| CIDEA | 3947 | 27042 | 50137 |
| CIDEB | 3948 | 27043 | 50138 |
| CIDEC | 3949 | 27044 | 50139 |
| CIITA | 3950 | 27045 | 50140 |
| CILP | 3951 | 27046 | 50141 |
| CILP2 | 3952 | 27047 | 50142 |
| CINP | 3953 | 27048 | 50143 |
| CINP | 3954 | 27049 | 50144 |
| CIP2A | 3955 | 27050 | 50145 |
| CIPC | 3956 | 27051 | 50146 |
| CIR1 | 3957 | 27052 | 50147 |
| CIRBP | 3958 | 27053 | 50148 |
| CIRBP | 3959 | 27054 | 50149 |
| CIRBP | 3960 | 27055 | 50150 |
| CISD1 | 3961 | 27056 | 50151 |
| CISD2 | 3962 | 27057 | 50152 |
| CISD3 | 3963 | 27058 | 50153 |
| CISH | 3964 | 27059 | 50154 |
| CIT | 3965 | 27060 | 50155 |
| CITED1 | 3966 | 27061 | 50156 |
| CITED2 | 3967 | 27062 | 50157 |
| CITED4 | 3968 | 27063 | 50158 |
| CIZ1 | 3969 | 27064 | 50159 |
| CKAP2 | 3970 | 27065 | 50160 |
| CKAP2 | 3971 | 27066 | 50161 |
| CKAP2L | 3972 | 27067 | 50162 |
| CKAP4 | 3973 | 27068 | 50163 |
| CKAP5 | 3974 | 27069 | 50164 |
| CKB | 3975 | 27070 | 50165 |
| CKLF | 3976 | 27071 | 50166 |
| CKLF | 3977 | 27072 | 50167 |
| CKM | 3978 | 27073 | 50168 |
| CKMT1A | 3979 | 27074 | 50169 |
| CKMT2 | 3980 | 27075 | 50170 |
| CKS1B | 3981 | 27076 | 50171 |
| CKS2 | 3982 | 27077 | 50172 |
| CLASP1 | 3983 | 27078 | 50173 |
| CLASP2 | 3984 | 27079 | 50174 |
| CLASRP | 3985 | 27080 | 50175 |
| CLBA1 | 3986 | 27081 | 50176 |
| CLC | 3987 | 27082 | 50177 |
| CLCA1 | 3988 | 27083 | 50178 |
| CLCA2 | 3989 | 27084 | 50179 |
| CLCA4 | 3990 | 27085 | 50180 |
| CLCC1 | 3991 | 27086 | 50181 |
| CLCF1 | 3992 | 27087 | 50182 |
| CLCN1 | 3993 | 27088 | 50183 |
| CLCN2 | 3994 | 27089 | 50184 |
| CLCN3 | 3995 | 27090 | 50185 |
| CLCN3 | 3996 | 27091 | 50186 |
| CLCN4 | 3997 | 27092 | 50187 |
| CLCN5 | 3998 | 27093 | 50188 |
| CLCN5 | 3999 | 27094 | 50189 |
| CLCN6 | 4000 | 27095 | 50190 |
| CLCN7 | 4001 | 27096 | 50191 |
| CLCNKA | 4002 | 27097 | 50192 |
| CLCNKB | 4003 | 27098 | 50193 |
| CLDN1 | 4004 | 27099 | 50194 |
| CLDN10 | 4005 | 27100 | 50195 |
| CLDN11 | 4006 | 27101 | 50196 |
| CLDN12 | 4007 | 27102 | 50197 |
| CLDN14 | 4008 | 27103 | 50198 |
| CLDN15 | 4009 | 27104 | 50199 |
| CLDN16 | 4010 | 27105 | 50200 |
| CLDN17 | 4011 | 27106 | 50201 |
| CLDN18 | 4012 | 27107 | 50202 |
| CLDN19 | 4013 | 27108 | 50203 |
| CLDN19 | 4014 | 27109 | 50204 |
| CLDN19 | 4015 | 27110 | 50205 |
| CLDN2 | 4016 | 27111 | 50206 |
| CLDN20 | 4017 | 27112 | 50207 |
| CLDN22 | 4018 | 27113 | 50208 |
| CLDN23 | 4019 | 27114 | 50209 |
| CLDN24 | 4020 | 27115 | 50210 |
| CLDN25 | 4021 | 27116 | 50211 |
| CLDN3 | 4022 | 27117 | 50212 |
| CLDN34 | 4023 | 27118 | 50213 |
| CLDN4 | 4024 | 27119 | 50214 |
| CLDN5 | 4025 | 27120 | 50215 |
| CLDN6 | 4026 | 27121 | 50216 |
| CLDN7 | 4027 | 27122 | 50217 |
| CLDN7 | 4028 | 27123 | 50218 |
| CLDN8 | 4029 | 27124 | 50219 |
| CLDN9 | 4030 | 27125 | 50220 |
| CLDND1 | 4031 | 27126 | 50221 |
| CLDND2 | 4032 | 27127 | 50222 |
| CLEC10A | 4033 | 27128 | 50223 |
| CLEC11A | 4034 | 27129 | 50224 |
| CLEC12A | 4035 | 27130 | 50225 |
| CLEC12A | 4036 | 27131 | 50226 |
| CLEC12B | 4037 | 27132 | 50227 |
| CLEC12B | 4038 | 27133 | 50228 |
| CLEC14A | 4039 | 27134 | 50229 |
| CLEC16A | 4040 | 27135 | 50230 |
| CLEC16A | 4041 | 27136 | 50231 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CLEC17A | 4042 | 27137 | 50232 |
| CLEC17A | 4043 | 27138 | 50233 |
| CLEC18C | 4044 | 27139 | 50234 |
| CLEC19A | 4045 | 27140 | 50235 |
| CLEC1A | 4046 | 27141 | 50236 |
| CLEC1B | 4047 | 27142 | 50237 |
| CLEC2A | 4048 | 27143 | 50238 |
| CLEC2A | 4049 | 27144 | 50239 |
| CLEC2B | 4050 | 27145 | 50240 |
| CLEC2L | 4051 | 27146 | 50241 |
| CLEC3A | 4052 | 27147 | 50242 |
| CLEC3B | 4053 | 27148 | 50243 |
| CLEC4A | 4054 | 27149 | 50244 |
| CLEC4C | 4055 | 27150 | 50245 |
| CLEC4D | 4056 | 27151 | 50246 |
| CLEC4E | 4057 | 27152 | 50247 |
| CLEC4F | 4058 | 27153 | 50248 |
| CLEC4F | 4059 | 27154 | 50249 |
| CLEC4F | 4060 | 27155 | 50250 |
| CLEC4G | 4061 | 27156 | 50251 |
| CLEC4M | 4062 | 27157 | 50252 |
| CLEC4M | 4063 | 27158 | 50253 |
| CLEC5A | 4064 | 27159 | 50254 |
| CLEC6A | 4065 | 27160 | 50255 |
| CLEC7A | 4066 | 27161 | 50256 |
| CLEC7A | 4067 | 27162 | 50257 |
| CLEC7A | 4068 | 27163 | 50258 |
| CLEC9A | 4069 | 27164 | 50259 |
| CLECL1 | 4070 | 27165 | 50260 |
| CLGN | 4071 | 27166 | 50261 |
| CLHC1 | 4072 | 27167 | 50262 |
| CLIC1 | 4073 | 27168 | 50263 |
| CLIC2 | 4074 | 27169 | 50264 |
| CLIC3 | 4075 | 27170 | 50265 |
| CLIC4 | 4076 | 27171 | 50266 |
| CLIC5 | 4077 | 27172 | 50267 |
| CLIC5 | 4078 | 27173 | 50268 |
| CLIC6 | 4079 | 27174 | 50269 |
| CLINT1 | 4080 | 27175 | 50270 |
| CLIP1 | 4081 | 27176 | 50271 |
| CLIP2 | 4082 | 27177 | 50272 |
| CLIP3 | 4083 | 27178 | 50273 |
| CLIP4 | 4084 | 27179 | 50274 |
| CLIP4 | 4085 | 27180 | 50275 |
| CLK1 | 4086 | 27181 | 50276 |
| CLK2 | 4087 | 27182 | 50277 |
| CLK3 | 4088 | 27183 | 50278 |
| CLK4 | 4089 | 27184 | 50279 |
| CLLU1OS | 4090 | 27185 | 50280 |
| CLMN | 4091 | 27186 | 50281 |
| CLMP | 4092 | 27187 | 50282 |
| CLN3 | 4093 | 27188 | 50283 |
| CLN5 | 4094 | 27189 | 50284 |
| CLN6 | 4095 | 27190 | 50285 |
| CLN8 | 4096 | 27191 | 50286 |
| CLNK | 4097 | 27192 | 50287 |
| CLNS1A | 4098 | 27193 | 50288 |
| CLOCK | 4099 | 27194 | 50289 |
| CLP1 | 4100 | 27195 | 50290 |
| CLPB | 4101 | 27196 | 50291 |
| CLPP | 4102 | 27197 | 50292 |
| CLPS | 4103 | 27198 | 50293 |
| CLPSL1 | 4104 | 27199 | 50294 |
| CLPSL1 | 4105 | 27200 | 50295 |
| CLPSL2 | 4106 | 27201 | 50296 |
| CLPSL2 | 4107 | 27202 | 50297 |
| CLPTM1 | 4108 | 27203 | 50298 |
| CLPTM1L | 4109 | 27204 | 50299 |
| CLPX | 4110 | 27205 | 50300 |
| CLRN1 | 4111 | 27206 | 50301 |
| CLRN1 | 4112 | 27207 | 50302 |
| CLRN1 | 4113 | 27208 | 50303 |
| CLRN2 | 4114 | 27209 | 50304 |
| CLRN3 | 4115 | 27210 | 50305 |
| CLSPN | 4116 | 27211 | 50306 |
| CLSPN | 4117 | 27212 | 50307 |
| CLSTN1 | 4118 | 27213 | 50308 |
| CLSTN2 | 4119 | 27214 | 50309 |
| CLSTN3 | 4120 | 27215 | 50310 |
| CLTA | 4121 | 27216 | 50311 |
| CLTA | 4122 | 27217 | 50312 |
| CLTB | 4123 | 27218 | 50313 |
| CLTC | 4124 | 27219 | 50314 |
| CLTCL1 | 4125 | 27220 | 50315 |
| CLU | 4126 | 27221 | 50316 |
| CLUAP1 | 4127 | 27222 | 50317 |
| CLUH | 4128 | 27223 | 50318 |
| CLUL1 | 4129 | 27224 | 50319 |
| CLVS1 | 4130 | 27225 | 50320 |
| CLVS2 | 4131 | 27226 | 50321 |
| CLYBL | 4132 | 27227 | 50322 |
| CMA1 | 4133 | 27228 | 50323 |
| CMAS | 4134 | 27229 | 50324 |
| CMBL | 4135 | 27230 | 50325 |
| CMC1 | 4136 | 27231 | 50326 |
| CMC2 | 4137 | 27232 | 50327 |
| CMC4 | 4138 | 27233 | 50328 |
| CMIP | 4139 | 27234 | 50329 |
| CMKLR1 | 4140 | 27235 | 50330 |
| CMPK1 | 4141 | 27236 | 50331 |
| CMPK2 | 4142 | 27237 | 50332 |
| CMPK2 | 4143 | 27238 | 50333 |
| CMPK2 | 4144 | 27239 | 50334 |
| CMSS1 | 4145 | 27240 | 50335 |
| CMTM1 | 4146 | 27241 | 50336 |
| CMTM1 | 4147 | 27242 | 50337 |
| CMTM2 | 4148 | 27243 | 50338 |
| CMTM3 | 4149 | 27244 | 50339 |
| CMTM4 | 4150 | 27245 | 50340 |
| CMTM4 | 4151 | 27246 | 50341 |
| CMTM5 | 4152 | 27247 | 50342 |
| CMTM6 | 4153 | 27248 | 50343 |
| CMTM7 | 4154 | 27249 | 50344 |
| CMTM8 | 4155 | 27250 | 50345 |
| CMTR1 | 4156 | 27251 | 50346 |
| CMTR2 | 4157 | 27252 | 50347 |
| CMYA5 | 4158 | 27253 | 50348 |
| CNBD1 | 4159 | 27254 | 50349 |
| CNBD2 | 4160 | 27255 | 50350 |
| CNBD2 | 4161 | 27256 | 50351 |
| CNBD2 | 4162 | 27257 | 50352 |
| CNBP | 4163 | 27258 | 50353 |
| CNDP1 | 4164 | 27259 | 50354 |
| CNDP2 | 4165 | 27260 | 50355 |
| CNEP1R1 | 4166 | 27261 | 50356 |
| CNFN | 4167 | 27262 | 50357 |
| CNGA1 | 4168 | 27263 | 50358 |
| CNGA2 | 4169 | 27264 | 50359 |
| CNGA3 | 4170 | 27265 | 50360 |
| CNGA4 | 4171 | 27266 | 50361 |
| CNGB1 | 4172 | 27267 | 50362 |
| CNGB1 | 4173 | 27268 | 50363 |
| CNGB3 | 4174 | 27269 | 50364 |
| CNIH1 | 4175 | 27270 | 50365 |
| CNIH2 | 4176 | 27271 | 50366 |
| CNIH3 | 4177 | 27272 | 50367 |
| CNIH4 | 4178 | 27273 | 50368 |
| CNIH4 | 4179 | 27274 | 50369 |
| CNIH4 | 4180 | 27275 | 50370 |
| CNKSR1 | 4181 | 27276 | 50371 |
| CNKSR2 | 4182 | 27277 | 50372 |
| CNKSR2 | 4183 | 27278 | 50373 |
| CNKSR3 | 4184 | 27279 | 50374 |
| CNMD | 4185 | 27280 | 50375 |
| CNN1 | 4186 | 27281 | 50376 |
| CNN2 | 4187 | 27282 | 50377 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CNN3 | 4188 | 27283 | 50378 |
| CNNM1 | 4189 | 27284 | 50379 |
| CNNM2 | 4190 | 27285 | 50380 |
| CNNM2 | 4191 | 27286 | 50381 |
| CNNM3 | 4192 | 27287 | 50382 |
| CNNM4 | 4193 | 27288 | 50383 |
| CNOT1 | 4194 | 27289 | 50384 |
| CNOT1 | 4195 | 27290 | 50385 |
| CNOT10 | 4196 | 27291 | 50386 |
| CNOT11 | 4197 | 27292 | 50387 |
| CNOT2 | 4198 | 27293 | 50388 |
| CNOT3 | 4199 | 27294 | 50389 |
| CNOT4 | 4200 | 27295 | 50390 |
| CNOT4 | 4201 | 27296 | 50391 |
| CNOT6 | 4202 | 27297 | 50392 |
| CNOT6L | 4203 | 27298 | 50393 |
| CNOT7 | 4204 | 27299 | 50394 |
| CNOT7 | 4205 | 27300 | 50395 |
| CNOT8 | 4206 | 27301 | 50396 |
| CNOT9 | 4207 | 27302 | 50397 |
| CNOT9 | 4208 | 27303 | 50398 |
| CNP | 4209 | 27304 | 50399 |
| CNPPD1 | 4210 | 27305 | 50400 |
| CNPY1 | 4211 | 27306 | 50401 |
| CNPY2 | 4212 | 27307 | 50402 |
| CNPY2 | 4213 | 27308 | 50403 |
| CNPY3 | 4214 | 27309 | 50404 |
| CNPY3 | 4215 | 27310 | 50405 |
| CNPY3 | 4216 | 27311 | 50406 |
| CNPY4 | 4217 | 27312 | 50407 |
| CNR1 | 4218 | 27313 | 50408 |
| CNR2 | 4219 | 27314 | 50409 |
| CNRIP1 | 4220 | 27315 | 50410 |
| CNRIP1 | 4221 | 27316 | 50411 |
| CNST | 4222 | 27317 | 50412 |
| CNST | 4223 | 27318 | 50413 |
| CNTD1 | 4224 | 27319 | 50414 |
| CNTD2 | 4225 | 27320 | 50415 |
| CNTF | 4226 | 27321 | 50416 |
| CNTFR | 4227 | 27322 | 50417 |
| CNTLN | 4228 | 27323 | 50418 |
| CNTLN | 4229 | 27324 | 50419 |
| CNTLN | 4230 | 27325 | 50420 |
| CNTN1 | 4231 | 27326 | 50421 |
| CNTN1 | 4232 | 27327 | 50422 |
| CNTN2 | 4233 | 27328 | 50423 |
| CNTN3 | 4234 | 27329 | 50424 |
| CNTN4 | 4235 | 27330 | 50425 |
| CNTN5 | 4236 | 27331 | 50426 |
| CNTN5 | 4237 | 27332 | 50427 |
| CNTN6 | 4238 | 27333 | 50428 |
| CNTNAP1 | 4239 | 27334 | 50429 |
| CNTNAP2 | 4240 | 27335 | 50430 |
| CNTNAP3 | 4241 | 27336 | 50431 |
| CNTNAP4 | 4242 | 27337 | 50432 |
| CNTNAP5 | 4243 | 27338 | 50433 |
| CNTRL | 4244 | 27339 | 50434 |
| CNTROB | 4245 | 27340 | 50435 |
| CNTROB | 4246 | 27341 | 50436 |
| COA1 | 4247 | 27342 | 50437 |
| COA1 | 4248 | 27343 | 50438 |
| COA3 | 4249 | 27344 | 50439 |
| COA4 | 4250 | 27345 | 50440 |
| COA5 | 4251 | 27346 | 50441 |
| COA6 | 4252 | 27347 | 50442 |
| COA7 | 4253 | 27348 | 50443 |
| COASY | 4254 | 27349 | 50444 |
| COBL | 4255 | 27350 | 50445 |
| COBL | 4256 | 27351 | 50446 |
| COBL | 4257 | 27352 | 50447 |
| COBLL1 | 4258 | 27353 | 50448 |
| COCH | 4259 | 27354 | 50449 |
| COG1 | 4260 | 27355 | 50450 |
| COG2 | 4261 | 27356 | 50451 |
| COG3 | 4262 | 27357 | 50452 |
| COG4 | 4263 | 27358 | 50453 |
| COG5 | 4264 | 27359 | 50454 |
| COG5 | 4265 | 27360 | 50455 |
| COG6 | 4266 | 27361 | 50456 |
| COG6 | 4267 | 27362 | 50457 |
| COG7 | 4268 | 27363 | 50458 |
| COG8 | 4269 | 27364 | 50459 |
| COIL | 4270 | 27365 | 50460 |
| COL10A1 | 4271 | 27366 | 50461 |
| COL11A1 | 4272 | 27367 | 50462 |
| COL11A2 | 4273 | 27368 | 50463 |
| COL11A2 | 4274 | 27369 | 50464 |
| COL12A1 | 4275 | 27370 | 50465 |
| COL13A1 | 4276 | 27371 | 50466 |
| COL14A1 | 4277 | 27372 | 50467 |
| COL15A1 | 4278 | 27373 | 50468 |
| COL16A1 | 4279 | 27374 | 50469 |
| COL17A1 | 4280 | 27375 | 50470 |
| COL18A1 | 4281 | 27376 | 50471 |
| COL19A1 | 4282 | 27377 | 50472 |
| COL1A1 | 4283 | 27378 | 50473 |
| COL1A2 | 4284 | 27379 | 50474 |
| COL20A1 | 4285 | 27380 | 50475 |
| COL21A1 | 4286 | 27381 | 50476 |
| COL22A1 | 4287 | 27382 | 50477 |
| COL23A1 | 4288 | 27383 | 50478 |
| COL24A1 | 4289 | 27384 | 50479 |
| COL25A1 | 4290 | 27385 | 50480 |
| COL25A1 | 4291 | 27386 | 50481 |
| COL26A1 | 4292 | 27387 | 50482 |
| COL27A1 | 4293 | 27388 | 50483 |
| COL28A1 | 4294 | 27389 | 50484 |
| COL2A1 | 4295 | 27390 | 50485 |
| COL3A1 | 4296 | 27391 | 50486 |
| COL4A1 | 4297 | 27392 | 50487 |
| COL4A1 | 4298 | 27393 | 50488 |
| COL4A2 | 4299 | 27394 | 50489 |
| COL4A2-AS2 | 4300 | 27395 | 50490 |
| COL4A3 | 4301 | 27396 | 50491 |
| COL4A3BP | 4302 | 27397 | 50492 |
| COL4A4 | 4303 | 27398 | 50493 |
| COL4A5 | 4304 | 27399 | 50494 |
| COL4A6 | 4305 | 27400 | 50495 |
| COL5A1 | 4306 | 27401 | 50496 |
| COL5A2 | 4307 | 27402 | 50497 |
| COL5A3 | 4308 | 27403 | 50498 |
| COL6A1 | 4309 | 27404 | 50499 |
| COL6A2 | 4310 | 27405 | 50500 |
| COL6A2 | 4311 | 27406 | 50501 |
| COL6A2 | 4312 | 27407 | 50502 |
| COL6A3 | 4313 | 27408 | 50503 |
| COL6A3 | 4314 | 27409 | 50504 |
| COL6A5 | 4315 | 27410 | 50505 |
| COL6A5 | 4316 | 27411 | 50506 |
| COL6A6 | 4317 | 27412 | 50507 |
| COL7A1 | 4318 | 27413 | 50508 |
| COL8A1 | 4319 | 27414 | 50509 |
| COL8A2 | 4320 | 27415 | 50510 |
| COL9A1 | 4321 | 27416 | 50511 |
| COL9A2 | 4322 | 27417 | 50512 |
| COL9A3 | 4323 | 27418 | 50513 |
| COLCA1 | 4324 | 27419 | 50514 |
| COLCA2 | 4325 | 27420 | 50515 |
| COLEC10 | 4326 | 27421 | 50516 |
| COLEC11 | 4327 | 27422 | 50517 |
| COLEC12 | 4328 | 27423 | 50518 |
| COLGALT1 | 4329 | 27424 | 50519 |
| COLGALT2 | 4330 | 27425 | 50520 |
| COLGALT2 | 4331 | 27426 | 50521 |
| COLQ | 4332 | 27427 | 50522 |
| COMMD1 | 4333 | 27428 | 50523 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| COMMD10 | 4334 | 27429 | 50524 |
| COMMD2 | 4335 | 27430 | 50525 |
| COMMD3 | 4336 | 27431 | 50526 |
| COMMD4 | 4337 | 27432 | 50527 |
| COMMD5 | 4338 | 27433 | 50528 |
| COMMD6 | 4339 | 27434 | 50529 |
| COMMD7 | 4340 | 27435 | 50530 |
| COMMD8 | 4341 | 27436 | 50531 |
| COMMD9 | 4342 | 27437 | 50532 |
| COMP | 4343 | 27438 | 50533 |
| COMT | 4344 | 27439 | 50534 |
| COMTD1 | 4345 | 27440 | 50535 |
| COPA | 4346 | 27441 | 50536 |
| COPB1 | 4347 | 27442 | 50537 |
| COPB2 | 4348 | 27443 | 50538 |
| COPE | 4349 | 27444 | 50539 |
| COPG1 | 4350 | 27445 | 50540 |
| COPG2 | 4351 | 27446 | 50541 |
| COPG2 | 4352 | 27447 | 50542 |
| COPRS | 4353 | 27448 | 50543 |
| COPS2 | 4354 | 27449 | 50544 |
| COPS3 | 4355 | 27450 | 50545 |
| COPS4 | 4356 | 27451 | 50546 |
| COPS4 | 4357 | 27452 | 50547 |
| COPS4 | 4358 | 27453 | 50548 |
| COPS5 | 4359 | 27454 | 50549 |
| COPS6 | 4360 | 27455 | 50550 |
| COPS7A | 4361 | 27456 | 50551 |
| COPS7B | 4362 | 27457 | 50552 |
| COPS7B | 4363 | 27458 | 50553 |
| COPS8 | 4364 | 27459 | 50554 |
| COPS9 | 4365 | 27460 | 50555 |
| COPS9 | 4366 | 27461 | 50556 |
| COPZ1 | 4367 | 27462 | 50557 |
| COPZ2 | 4368 | 27463 | 50558 |
| COQ10A | 4369 | 27464 | 50559 |
| COQ10B | 4370 | 27465 | 50560 |
| COQ2 | 4371 | 27466 | 50561 |
| COQ3 | 4372 | 27467 | 50562 |
| COQ4 | 4373 | 27468 | 50563 |
| COQ4 | 4374 | 27469 | 50564 |
| COQ5 | 4375 | 27470 | 50565 |
| COQ6 | 4376 | 27471 | 50566 |
| COQ7 | 4377 | 27472 | 50567 |
| COQ8A | 4378 | 27473 | 50568 |
| COQ8B | 4379 | 27474 | 50569 |
| COQ9 | 4380 | 27475 | 50570 |
| CORIN | 4381 | 27476 | 50571 |
| CORIN | 4382 | 27477 | 50572 |
| CORO1A | 4383 | 27478 | 50573 |
| CORO1B | 4384 | 27479 | 50574 |
| CORO1C | 4385 | 27480 | 50575 |
| CORO2A | 4386 | 27481 | 50576 |
| CORO2B | 4387 | 27482 | 50577 |
| CORO6 | 4388 | 27483 | 50578 |
| CORO7 | 4389 | 27484 | 50579 |
| CORT | 4390 | 27485 | 50580 |
| COTL1 | 4391 | 27486 | 50581 |
| COX10 | 4392 | 27487 | 50582 |
| COX11 | 4393 | 27488 | 50583 |
| COX11 | 4394 | 27489 | 50584 |
| COX11 | 4395 | 27490 | 50585 |
| COX11 | 4396 | 27491 | 50586 |
| COX14 | 4397 | 27492 | 50587 |
| COX14 | 4398 | 27493 | 50588 |
| COX15 | 4399 | 27494 | 50589 |
| COX15 | 4400 | 27495 | 50590 |
| COX15 | 4401 | 27496 | 50591 |
| COX15 | 4402 | 27497 | 50592 |
| COX16 | 4403 | 27498 | 50593 |
| COX17 | 4404 | 27499 | 50594 |
| COX18 | 4405 | 27500 | 50595 |
| COX19 | 4406 | 27501 | 50596 |
| COX20 | 4407 | 27502 | 50597 |
| COX20 | 4408 | 27503 | 50598 |
| COX4I1 | 4409 | 27504 | 50599 |
| COX4I1 | 4410 | 27505 | 50600 |
| COX4I1 | 4411 | 27506 | 50601 |
| COX4I1 | 4412 | 27507 | 50602 |
| COX4I2 | 4413 | 27508 | 50603 |
| COX5A | 4414 | 27509 | 50604 |
| COX5B | 4415 | 27510 | 50605 |
| COX6A1 | 4416 | 27511 | 50606 |
| COX6A2 | 4417 | 27512 | 50607 |
| COX6B1 | 4418 | 27513 | 50608 |
| COX6B2 | 4419 | 27514 | 50609 |
| COX6C | 4420 | 27515 | 50610 |
| COX7A1 | 4421 | 27516 | 50611 |
| COX7A2 | 4422 | 27517 | 50612 |
| COX7A2L | 4423 | 27518 | 50613 |
| COX7A2L | 4424 | 27519 | 50614 |
| COX7A2L | 4425 | 27520 | 50615 |
| COX7B | 4426 | 27521 | 50616 |
| COX7B2 | 4427 | 27522 | 50617 |
| COX7C | 4428 | 27523 | 50618 |
| COX8A | 4429 | 27524 | 50619 |
| COX8C | 4430 | 27525 | 50620 |
| CP | 4431 | 27526 | 50621 |
| CPA1 | 4432 | 27527 | 50622 |
| CPA2 | 4433 | 27528 | 50623 |
| CPA3 | 4434 | 27529 | 50624 |
| CPA4 | 4435 | 27530 | 50625 |
| CPA5 | 4436 | 27531 | 50626 |
| CPA5 | 4437 | 27532 | 50627 |
| CPA6 | 4438 | 27533 | 50628 |
| CPAMD8 | 4439 | 27534 | 50629 |
| CPB1 | 4440 | 27535 | 50630 |
| CPB2 | 4441 | 27536 | 50631 |
| CPD | 4442 | 27537 | 50632 |
| CPE | 4443 | 27538 | 50633 |
| CPEB1 | 4444 | 27539 | 50634 |
| CPEB2 | 4445 | 27540 | 50635 |
| CPEB3 | 4446 | 27541 | 50636 |
| CPEB4 | 4447 | 27542 | 50637 |
| CPED1 | 4448 | 27543 | 50638 |
| CPED1 | 4449 | 27544 | 50639 |
| CPLX1 | 4450 | 27545 | 50640 |
| CPLX2 | 4451 | 27546 | 50641 |
| CPLX3 | 4452 | 27547 | 50642 |
| CPLX4 | 4453 | 27548 | 50643 |
| CPM | 4454 | 27549 | 50644 |
| CPN1 | 4455 | 27550 | 50645 |
| CPN2 | 4456 | 27551 | 50646 |
| CPNE1 | 4457 | 27552 | 50647 |
| CPNE2 | 4458 | 27553 | 50648 |
| CPNE3 | 4459 | 27554 | 50649 |
| CPNE4 | 4460 | 27555 | 50650 |
| CPNE5 | 4461 | 27556 | 50651 |
| CPNE5 | 4462 | 27557 | 50652 |
| CPNE6 | 4463 | 27558 | 50653 |
| CPNE7 | 4464 | 27559 | 50654 |
| CPNE8 | 4465 | 27560 | 50655 |
| CPNE9 | 4466 | 27561 | 50656 |
| CPNE9 | 4467 | 27562 | 50657 |
| CPO | 4468 | 27563 | 50658 |
| CPOX | 4469 | 27564 | 50659 |
| CPPED1 | 4470 | 27565 | 50660 |
| CPQ | 4471 | 27566 | 50661 |
| CPS1 | 4472 | 27567 | 50662 |
| CPSF1 | 4473 | 27568 | 50663 |
| CPSF2 | 4474 | 27569 | 50664 |
| CPSF3 | 4475 | 27570 | 50665 |
| CPSF4 | 4476 | 27571 | 50666 |
| CPSF4 | 4477 | 27572 | 50667 |
| CPSF4L | 4478 | 27573 | 50668 |
| CPSF6 | 4479 | 27574 | 50669 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CPSF7 | 4480 | 27575 | 50670 |
| CPT1A | 4481 | 27576 | 50671 |
| CPT1A | 4482 | 27577 | 50672 |
| CPT1B | 4483 | 27578 | 50673 |
| CPT1B | 4484 | 27579 | 50674 |
| CPT1C | 4485 | 27580 | 50675 |
| CPT2 | 4486 | 27581 | 50676 |
| CPTP | 4487 | 27582 | 50677 |
| CPVL | 4488 | 27583 | 50678 |
| CPXCR1 | 4489 | 27584 | 50679 |
| CPXM1 | 4490 | 27585 | 50680 |
| CPXM2 | 4491 | 27586 | 50681 |
| CPZ | 4492 | 27587 | 50682 |
| CR1 | 4493 | 27588 | 50683 |
| CR1L | 4494 | 27589 | 50684 |
| CR2 | 4495 | 27590 | 50685 |
| CRABP1 | 4496 | 27591 | 50686 |
| CRABP2 | 4497 | 27592 | 50687 |
| CRACR2A | 4498 | 27593 | 50688 |
| CRACR2A | 4499 | 27594 | 50689 |
| CRACR2B | 4500 | 27595 | 50690 |
| CRACR2B | 4501 | 27596 | 50691 |
| CRADD | 4502 | 27597 | 50692 |
| CRADD | 4503 | 27598 | 50693 |
| CRADD | 4504 | 27599 | 50694 |
| CRADD | 4505 | 27600 | 50695 |
| CRAMP1 | 4506 | 27601 | 50696 |
| CRAT | 4507 | 27602 | 50697 |
| CRB1 | 4508 | 27603 | 50698 |
| CRB2 | 4509 | 27604 | 50699 |
| CRB3 | 4510 | 27605 | 50700 |
| CRB3 | 4511 | 27606 | 50701 |
| CRBN | 4512 | 27607 | 50702 |
| CRCP | 4513 | 27608 | 50703 |
| CRCP | 4514 | 27609 | 50704 |
| CRCT1 | 4515 | 27610 | 50705 |
| CREB1 | 4516 | 27611 | 50706 |
| CREB1 | 4517 | 27612 | 50707 |
| CREB3 | 4518 | 27613 | 50708 |
| CREB3L1 | 4519 | 27614 | 50709 |
| CREB3L2 | 4520 | 27615 | 50710 |
| CREB3L2 | 4521 | 27616 | 50711 |
| CREB3L3 | 4522 | 27617 | 50712 |
| CREB3L3 | 4523 | 27618 | 50713 |
| CREB3L4 | 4524 | 27619 | 50714 |
| CREB5 | 4525 | 27620 | 50715 |
| CREBBP | 4526 | 27621 | 50716 |
| CREBL2 | 4527 | 27622 | 50717 |
| CREBRF | 4528 | 27623 | 50718 |
| CREBRF | 4529 | 27624 | 50719 |
| CREBZF | 4530 | 27625 | 50720 |
| CREG1 | 4531 | 27626 | 50721 |
| CREG2 | 4532 | 27627 | 50722 |
| CRELD1 | 4533 | 27628 | 50723 |
| CRELD1 | 4534 | 27629 | 50724 |
| CRELD2 | 4535 | 27630 | 50725 |
| CREM | 4536 | 27631 | 50726 |
| CREM | 4537 | 27632 | 50727 |
| CREM | 4538 | 27633 | 50728 |
| CREM | 4539 | 27634 | 50729 |
| CRH | 4540 | 27635 | 50730 |
| CRHBP | 4541 | 27636 | 50731 |
| CRHR1 | 4542 | 27637 | 50732 |
| CRHR2 | 4543 | 27638 | 50733 |
| CRHR2 | 4544 | 27639 | 50734 |
| CRIM1 | 4545 | 27640 | 50735 |
| CRIP1 | 4546 | 27641 | 50736 |
| CRIP2 | 4547 | 27642 | 50737 |
| CRIP3 | 4548 | 27643 | 50738 |
| CRIPAK | 4549 | 27644 | 50739 |
| CRIPT | 4550 | 27645 | 50740 |
| CRISP1 | 4551 | 27646 | 50741 |
| CRISP1 | 4552 | 27647 | 50742 |
| CRISP2 | 4553 | 27648 | 50743 |
| CRISP3 | 4554 | 27649 | 50744 |
| CRISPLD1 | 4555 | 27650 | 50745 |
| CRISPLD2 | 4556 | 27651 | 50746 |
| CRK | 4557 | 27652 | 50747 |
| CRK | 4558 | 27653 | 50748 |
| CRKL | 4559 | 27654 | 50749 |
| CRLF1 | 4560 | 27655 | 50750 |
| CRLF2 | 4561 | 27656 | 50751 |
| CRLF3 | 4562 | 27657 | 50752 |
| CRLS1 | 4563 | 27658 | 50753 |
| CRMP1 | 4564 | 27659 | 50754 |
| CRNDE | 4565 | 27660 | 50755 |
| CRNKL1 | 4566 | 27661 | 50756 |
| CRNN | 4567 | 27662 | 50757 |
| CROCC | 4568 | 27663 | 50758 |
| CROCC2 | 4569 | 27664 | 50759 |
| CROT | 4570 | 27665 | 50760 |
| CROT | 4571 | 27666 | 50761 |
| CRP | 4572 | 27667 | 50762 |
| CRTAC1 | 4573 | 27668 | 50763 |
| CRTAC1 | 4574 | 27669 | 50764 |
| CRTAM | 4575 | 27670 | 50765 |
| CRTAP | 4576 | 27671 | 50766 |
| CRTC1 | 4577 | 27672 | 50767 |
| CRTC2 | 4578 | 27673 | 50768 |
| CRTC3 | 4579 | 27674 | 50769 |
| CRX | 4580 | 27675 | 50770 |
| CRY1 | 4581 | 27676 | 50771 |
| CRY2 | 4582 | 27677 | 50772 |
| CRYAB | 4583 | 27678 | 50773 |
| CRYBA1 | 4584 | 27679 | 50774 |
| CRYBA2 | 4585 | 27680 | 50775 |
| CRYBA4 | 4586 | 27681 | 50776 |
| CRYBB1 | 4587 | 27682 | 50777 |
| CRYBB2 | 4588 | 27683 | 50778 |
| CRYBB3 | 4589 | 27684 | 50779 |
| CRYBG1 | 4590 | 27685 | 50780 |
| CRYBG2 | 4591 | 27686 | 50781 |
| CRYBG3 | 4592 | 27687 | 50782 |
| CRYGA | 4593 | 27688 | 50783 |
| CRYGB | 4594 | 27689 | 50784 |
| CRYGC | 4595 | 27690 | 50785 |
| CRYGD | 4596 | 27691 | 50786 |
| CRYGN | 4597 | 27692 | 50787 |
| CRYGN | 4598 | 27693 | 50788 |
| CRYGS | 4599 | 27694 | 50789 |
| CRYL1 | 4600 | 27695 | 50790 |
| CRYM | 4601 | 27696 | 50791 |
| CRYZ | 4602 | 27697 | 50792 |
| CRYZL1 | 4603 | 27698 | 50793 |
| CS | 4604 | 27699 | 50794 |
| CSAD | 4605 | 27700 | 50795 |
| CSAG3 | 4606 | 27701 | 50796 |
| CSDC2 | 4607 | 27702 | 50797 |
| CSDE1 | 4608 | 27703 | 50798 |
| CSE1L | 4609 | 27704 | 50799 |
| CSF1 | 4610 | 27705 | 50800 |
| CSF1R | 4611 | 27706 | 50801 |
| CSF2 | 4612 | 27707 | 50802 |
| CSF2RA | 4613 | 27708 | 50803 |
| CSF2RA | 4614 | 27709 | 50804 |
| CSF2RA | 4615 | 27710 | 50805 |
| CSF2RA | 4616 | 27711 | 50806 |
| CSF2RB | 4617 | 27712 | 50807 |
| CSF3 | 4618 | 27713 | 50808 |
| CSF3R | 4619 | 27714 | 50809 |
| CSF3R | 4620 | 27715 | 50810 |
| CSGALNACT1 | 4621 | 27716 | 50811 |
| CSGALNACT2 | 4622 | 27717 | 50812 |
| CSGALNACT2 | 4623 | 27718 | 50813 |
| CSGALNACT2 | 4624 | 27719 | 50814 |
| CSH1 | 4625 | 27720 | 50815 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CSH2 | 4626 | 27721 | 50816 |
| CSH2 | 4627 | 27722 | 50817 |
| CSHL1 | 4628 | 27723 | 50818 |
| CSK | 4629 | 27724 | 50819 |
| CSMD1 | 4630 | 27725 | 50820 |
| CSMD2 | 4631 | 27726 | 50821 |
| CSMD3 | 4632 | 27727 | 50822 |
| CSN1S1 | 4633 | 27728 | 50823 |
| CSN2 | 4634 | 27729 | 50824 |
| CSN3 | 4635 | 27730 | 50825 |
| CSNK1A1 | 4636 | 27731 | 50826 |
| CSNK1A1 | 4637 | 27732 | 50827 |
| CSNK1A1L | 4638 | 27733 | 50828 |
| CSNK1D | 4639 | 27734 | 50829 |
| CSNK1D | 4640 | 27735 | 50830 |
| CSNK1E | 4641 | 27736 | 50831 |
| CSNK1G1 | 4642 | 27737 | 50832 |
| CSNK1G1 | 4643 | 27738 | 50833 |
| CSNK1G2 | 4644 | 27739 | 50834 |
| CSNK1G3 | 4645 | 27740 | 50835 |
| CSNK2A1 | 4646 | 27741 | 50836 |
| CSNK2A2 | 4647 | 27742 | 50837 |
| CSNK2A3 | 4648 | 27743 | 50838 |
| CSNK2B | 4649 | 27744 | 50839 |
| CSPG4 | 4650 | 27745 | 50840 |
| CSPG5 | 4651 | 27746 | 50841 |
| CSPG5 | 4652 | 27747 | 50842 |
| CSPP1 | 4653 | 27748 | 50843 |
| CSRNP1 | 4654 | 27749 | 50844 |
| CSRNP2 | 4655 | 27750 | 50845 |
| CSRNP3 | 4656 | 27751 | 50846 |
| CSRP1 | 4657 | 27752 | 50847 |
| CSRP1 | 4658 | 27753 | 50848 |
| CSRP2 | 4659 | 27754 | 50849 |
| CSRP3 | 4660 | 27755 | 50850 |
| CST1 | 4661 | 27756 | 50851 |
| CST11 | 4662 | 27757 | 50852 |
| CST2 | 4663 | 27758 | 50853 |
| CST3 | 4664 | 27759 | 50854 |
| CST4 | 4665 | 27760 | 50855 |
| CST5 | 4666 | 27761 | 50856 |
| CST6 | 4667 | 27762 | 50857 |
| CST7 | 4668 | 27763 | 50858 |
| CST8 | 4669 | 27764 | 50859 |
| CST9 | 4670 | 27765 | 50860 |
| CST9L | 4671 | 27766 | 50861 |
| CSTA | 4672 | 27767 | 50862 |
| CSTB | 4673 | 27768 | 50863 |
| CSTF1 | 4674 | 27769 | 50864 |
| CSTF2 | 4675 | 27770 | 50865 |
| CSTF2T | 4676 | 27771 | 50866 |
| CSTF3 | 4677 | 27772 | 50867 |
| CSTF3 | 4678 | 27773 | 50868 |
| CSTF3 | 4679 | 27774 | 50869 |
| CSTL1 | 4680 | 27775 | 50870 |
| CT45A3 | 4681 | 27776 | 50871 |
| CT47A1 | 4682 | 27777 | 50872 |
| CT47B1 | 4683 | 27778 | 50873 |
| CT55 | 4684 | 27779 | 50874 |
| CT55 | 4685 | 27780 | 50875 |
| CT62 | 4686 | 27781 | 50876 |
| CT83 | 4687 | 27782 | 50877 |
| CTAG1B | 4688 | 27783 | 50878 |
| CTAG2 | 4689 | 27784 | 50879 |
| CTAG2 | 4690 | 27785 | 50880 |
| CTAGE1 | 4691 | 27786 | 50881 |
| CTAGE15 | 4692 | 27787 | 50882 |
| CTAGE8 | 4693 | 27788 | 50883 |
| CTBP1 | 4694 | 27789 | 50884 |
| CTBP2 | 4695 | 27790 | 50885 |
| CTBS | 4696 | 27791 | 50886 |
| CTC1 | 4697 | 27792 | 50887 |
| CTCF | 4698 | 27793 | 50888 |
| CTCFL | 4699 | 27794 | 50889 |
| CTCFL | 4700 | 27795 | 50890 |
| CTCFL | 4701 | 27796 | 50891 |
| CTCFL | 4702 | 27797 | 50892 |
| CTCFL | 4703 | 27798 | 50893 |
| CTCFL | 4704 | 27799 | 50894 |
| CTCFL | 4705 | 27800 | 50895 |
| CTDNEP1 | 4706 | 27801 | 50896 |
| CTDP1 | 4707 | 27802 | 50897 |
| CTDP1 | 4708 | 27803 | 50898 |
| CTDP1 | 4709 | 27804 | 50899 |
| CTDSP1 | 4710 | 27805 | 50900 |
| CTDSP2 | 4711 | 27806 | 50901 |
| CTDSPL | 4712 | 27807 | 50902 |
| CTDSPL2 | 4713 | 27808 | 50903 |
| CTF1 | 4714 | 27809 | 50904 |
| CTGF | 4715 | 27810 | 50905 |
| CTH | 4716 | 27811 | 50906 |
| CTHRC1 | 4717 | 27812 | 50907 |
| CTIF | 4718 | 27813 | 50908 |
| CTLA4 | 4719 | 27814 | 50909 |
| CTNNA1 | 4720 | 27815 | 50910 |
| CTNNA1 | 4721 | 27816 | 50911 |
| CTNNA2 | 4722 | 27817 | 50912 |
| CTNNA3 | 4723 | 27818 | 50913 |
| CTNNA3 | 4724 | 27819 | 50914 |
| CTNNAL1 | 4725 | 27820 | 50915 |
| CTNNAL1 | 4726 | 27821 | 50916 |
| CTNNB1 | 4727 | 27822 | 50917 |
| CTNNBIP1 | 4728 | 27823 | 50918 |
| CTNNBL1 | 4729 | 27824 | 50919 |
| CTNND1 | 4730 | 27825 | 50920 |
| CTNND1 | 4731 | 27826 | 50921 |
| CTNND2 | 4732 | 27827 | 50922 |
| CTNS | 4733 | 27828 | 50923 |
| CTNS | 4734 | 27829 | 50924 |
| CTPS1 | 4735 | 27830 | 50925 |
| CTPS2 | 4736 | 27831 | 50926 |
| CTR9 | 4737 | 27832 | 50927 |
| CTRB1 | 4738 | 27833 | 50928 |
| CTRB1 | 4739 | 27834 | 50929 |
| CTRB2 | 4740 | 27835 | 50930 |
| CTRC | 4741 | 27836 | 50931 |
| CTRL | 4742 | 27837 | 50932 |
| CTSA | 4743 | 27838 | 50933 |
| CTSB | 4744 | 27839 | 50934 |
| CTSC | 4745 | 27840 | 50935 |
| CTSC | 4746 | 27841 | 50936 |
| CTSC | 4747 | 27842 | 50937 |
| CTSD | 4748 | 27843 | 50938 |
| CTSE | 4749 | 27844 | 50939 |
| CTSE | 4750 | 27845 | 50940 |
| CTSF | 4751 | 27846 | 50941 |
| CTSG | 4752 | 27847 | 50942 |
| CTSH | 4753 | 27848 | 50943 |
| CTSK | 4754 | 27849 | 50944 |
| CTSL | 4755 | 27850 | 50945 |
| CTSO | 4756 | 27851 | 50946 |
| CTSS | 4757 | 27852 | 50947 |
| CTSV | 4758 | 27853 | 50948 |
| CTSW | 4759 | 27854 | 50949 |
| CTSZ | 4760 | 27855 | 50950 |
| CTTN | 4761 | 27856 | 50951 |
| CTTN | 4762 | 27857 | 50952 |
| CTTNBP2 | 4763 | 27858 | 50953 |
| CTTNBP2NL | 4764 | 27859 | 50954 |
| CTU1 | 4765 | 27860 | 50955 |
| CTU2 | 4766 | 27861 | 50956 |
| CTU2 | 4767 | 27862 | 50957 |
| CTXN1 | 4768 | 27863 | 50958 |
| CTXN2 | 4769 | 27864 | 50959 |
| CTXN3 | 4770 | 27865 | 50960 |
| CTXND1 | 4771 | 27866 | 50961 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CUBN | 4772 | 27867 | 50962 |
| CUEDC1 | 4773 | 27868 | 50963 |
| CUEDC2 | 4774 | 27869 | 50964 |
| CUL1 | 4775 | 27870 | 50965 |
| CUL2 | 4776 | 27871 | 50966 |
| CUL3 | 4777 | 27872 | 50967 |
| CUL4A | 4778 | 27873 | 50968 |
| CUL4B | 4779 | 27874 | 50969 |
| CUL5 | 4780 | 27875 | 50970 |
| CUL7 | 4781 | 27876 | 50971 |
| CUL9 | 4782 | 27877 | 50972 |
| CUTA | 4783 | 27878 | 50973 |
| CUTC | 4784 | 27879 | 50974 |
| CUX1 | 4785 | 27880 | 50975 |
| CUX1 | 4786 | 27881 | 50976 |
| CUX2 | 4787 | 27882 | 50977 |
| CUZD1 | 4788 | 27883 | 50978 |
| CWC15 | 4789 | 27884 | 50979 |
| CWC22 | 4790 | 27885 | 50980 |
| CWC25 | 4791 | 27886 | 50981 |
| CWC27 | 4792 | 27887 | 50982 |
| CWC27 | 4793 | 27888 | 50983 |
| CWC27 | 4794 | 27889 | 50984 |
| CWC27 | 4795 | 27890 | 50985 |
| CWF19L1 | 4796 | 27891 | 50986 |
| CWF19L2 | 4797 | 27892 | 50987 |
| CWH43 | 4798 | 27893 | 50988 |
| CX3CL1 | 4799 | 27894 | 50989 |
| CX3CR1 | 4800 | 27895 | 50990 |
| CXADR | 4801 | 27896 | 50991 |
| CXADR | 4802 | 27897 | 50992 |
| CXADR | 4803 | 27898 | 50993 |
| CXADR | 4804 | 27899 | 50994 |
| CXCL1 | 4805 | 27900 | 50995 |
| CXCL10 | 4806 | 27901 | 50996 |
| CXCL11 | 4807 | 27902 | 50997 |
| CXCL11 | 4808 | 27903 | 50998 |
| CXCL12 | 4809 | 27904 | 50999 |
| CXCL12 | 4810 | 27905 | 51000 |
| CXCL12 | 4811 | 27906 | 51001 |
| CXCL12 | 4812 | 27907 | 51002 |
| CXCL12 | 4813 | 27908 | 51003 |
| CXCL13 | 4814 | 27909 | 51004 |
| CXCL14 | 4815 | 27910 | 51005 |
| CXCL16 | 4816 | 27911 | 51006 |
| CXCL17 | 4817 | 27912 | 51007 |
| CXCL2 | 4818 | 27913 | 51008 |
| CXCL3 | 4819 | 27914 | 51009 |
| CXCL5 | 4820 | 27915 | 51010 |
| CXCL8 | 4821 | 27916 | 51011 |
| CXCL9 | 4822 | 27917 | 51012 |
| CXCR1 | 4823 | 27918 | 51013 |
| CXCR2 | 4824 | 27919 | 51014 |
| CXCR3 | 4825 | 27920 | 51015 |
| CXCR4 | 4826 | 27921 | 51016 |
| CXCR5 | 4827 | 27922 | 51017 |
| CXCR6 | 4828 | 27923 | 51018 |
| CXorf21 | 4829 | 27924 | 51019 |
| CXorf36 | 4830 | 27925 | 51020 |
| CXorf36 | 4831 | 27926 | 51021 |
| CXorf38 | 4832 | 27927 | 51022 |
| CXorf38 | 4833 | 27928 | 51023 |
| CXorf40A | 4834 | 27929 | 51024 |
| CXorf40A | 4835 | 27930 | 51025 |
| CXorf40A | 4836 | 27931 | 51026 |
| CXorf49 | 4837 | 27932 | 51027 |
| CXorf51A | 4838 | 27933 | 51028 |
| CXorf56 | 4839 | 27934 | 51029 |
| CXorf57 | 4840 | 27935 | 51030 |
| CXorf58 | 4841 | 27936 | 51031 |
| CXorf65 | 4842 | 27937 | 51032 |
| CXorf66 | 4843 | 27938 | 51033 |
| CXorf67 | 4844 | 27939 | 51034 |
| CXXC1 | 4845 | 27940 | 51035 |
| CXXC4 | 4846 | 27941 | 51036 |
| CXXC5 | 4847 | 27942 | 51037 |
| CYB561 | 4848 | 27943 | 51038 |
| CYB561A3 | 4849 | 27944 | 51039 |
| CYB561A3 | 4850 | 27945 | 51040 |
| CYB561D1 | 4851 | 27946 | 51041 |
| CYB561D2 | 4852 | 27947 | 51042 |
| CYB5A | 4853 | 27948 | 51043 |
| CYB5A | 4854 | 27949 | 51044 |
| CYB5B | 4855 | 27950 | 51045 |
| CYB5D1 | 4856 | 27951 | 51046 |
| CYB5D1 | 4857 | 27952 | 51047 |
| CYB5D2 | 4858 | 27953 | 51048 |
| CYB5R1 | 4859 | 27954 | 51049 |
| CYB5R2 | 4860 | 27955 | 51050 |
| CYB5R2 | 4861 | 27956 | 51051 |
| CYB5R3 | 4862 | 27957 | 51052 |
| CYB5R4 | 4863 | 27958 | 51053 |
| CYB5RL | 4864 | 27959 | 51054 |
| CYB5RL | 4865 | 27960 | 51055 |
| CYBA | 4866 | 27961 | 51056 |
| CYBB | 4867 | 27962 | 51057 |
| CYBRD1 | 4868 | 27963 | 51058 |
| CYBRD1 | 4869 | 27964 | 51059 |
| CYC1 | 4870 | 27965 | 51060 |
| CYCS | 4871 | 27966 | 51061 |
| CYFIP1 | 4872 | 27967 | 51062 |
| CYFIP2 | 4873 | 27968 | 51063 |
| CYGB | 4874 | 27969 | 51064 |
| CYHR1 | 4875 | 27970 | 51065 |
| CYHR1 | 4876 | 27971 | 51066 |
| CYLC1 | 4877 | 27972 | 51067 |
| CYLC2 | 4878 | 27973 | 51068 |
| CYLD | 4879 | 27974 | 51069 |
| CYP11A1 | 4880 | 27975 | 51070 |
| CYP11B1 | 4881 | 27976 | 51071 |
| CYP11B2 | 4882 | 27977 | 51072 |
| CYP17A1 | 4883 | 27978 | 51073 |
| CYP19A1 | 4884 | 27979 | 51074 |
| CYP1A1 | 4885 | 27980 | 51075 |
| CYP1A2 | 4886 | 27981 | 51076 |
| CYP1B1 | 4887 | 27982 | 51077 |
| CYP20A1 | 4888 | 27983 | 51078 |
| CYP21A2 | 4889 | 27984 | 51079 |
| CYP24A1 | 4890 | 27985 | 51080 |
| CYP26A1 | 4891 | 27986 | 51081 |
| CYP26B1 | 4892 | 27987 | 51082 |
| CYP26C1 | 4893 | 27988 | 51083 |
| CYP27A1 | 4894 | 27989 | 51084 |
| CYP27B1 | 4895 | 27990 | 51085 |
| CYP27C1 | 4896 | 27991 | 51086 |
| CYP2A13 | 4897 | 27992 | 51087 |
| CYP2A7 | 4898 | 27993 | 51088 |
| CYP2B6 | 4899 | 27994 | 51089 |
| CYP2C18 | 4900 | 27995 | 51090 |
| CYP2C19 | 4901 | 27996 | 51091 |
| CYP2C8 | 4902 | 27997 | 51092 |
| CYP2C9 | 4903 | 27998 | 51093 |
| CYP2D6 | 4904 | 27999 | 51094 |
| CYP2E1 | 4905 | 28000 | 51095 |
| CYP2F1 | 4906 | 28001 | 51096 |
| CYP2J2 | 4907 | 28002 | 51097 |
| CYP2R1 | 4908 | 28003 | 51098 |
| CYP2S1 | 4909 | 28004 | 51099 |
| CYP2U1 | 4910 | 28005 | 51100 |
| CYP2W1 | 4911 | 28006 | 51101 |
| CYP39A1 | 4912 | 28007 | 51102 |
| CYP3A4 | 4913 | 28008 | 51103 |
| CYP3A43 | 4914 | 28009 | 51104 |
| CYP3A43 | 4915 | 28010 | 51105 |
| CYP3A5 | 4916 | 28011 | 51106 |
| CYP3A5 | 4917 | 28012 | 51107 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| CYP3A7 | 4918 | 28013 | 51108 |
| CYP3A7-CYP3A51P | 4919 | 28014 | 51109 |
| CYP46A1 | 4920 | 28015 | 51110 |
| CYP4A11 | 4921 | 28016 | 51111 |
| CYP4A22 | 4922 | 28017 | 51112 |
| CYP4B1 | 4923 | 28018 | 51113 |
| CYP4F11 | 4924 | 28019 | 51114 |
| CYP4F12 | 4925 | 28020 | 51115 |
| CYP4F2 | 4926 | 28021 | 51116 |
| CYP4F22 | 4927 | 28022 | 51117 |
| CYP4F8 | 4928 | 28023 | 51118 |
| CYP4V2 | 4929 | 28024 | 51119 |
| CYP4X1 | 4930 | 28025 | 51120 |
| CYP4Z1 | 4931 | 28026 | 51121 |
| CYP51A1 | 4932 | 28027 | 51122 |
| CYP7A1 | 4933 | 28028 | 51123 |
| CYP7B1 | 4934 | 28029 | 51124 |
| CYP7B1 | 4935 | 28030 | 51125 |
| CYP8B1 | 4936 | 28031 | 51126 |
| CYR61 | 4937 | 28032 | 51127 |
| CYS1 | 4938 | 28033 | 51128 |
| CYSLTR1 | 4939 | 28034 | 51129 |
| CYSLTR2 | 4940 | 28035 | 51130 |
| CYSRT1 | 4941 | 28036 | 51131 |
| CYSTM1 | 4942 | 28037 | 51132 |
| CYTH1 | 4943 | 28038 | 51133 |
| CYTH2 | 4944 | 28039 | 51134 |
| CYTH3 | 4945 | 28040 | 51135 |
| CYTH4 | 4946 | 28041 | 51136 |
| CYTIP | 4947 | 28042 | 51137 |
| CYTL1 | 4948 | 28043 | 51138 |
| CYYR1 | 4949 | 28044 | 51139 |
| D2HGDH | 4950 | 28045 | 51140 |
| DAAM1 | 4951 | 28046 | 51141 |
| DAAM2 | 4952 | 28047 | 51142 |
| DAB1 | 4953 | 28048 | 51143 |
| DAB1 | 4954 | 28049 | 51144 |
| DAB2 | 4955 | 28050 | 51145 |
| DAB2IP | 4956 | 28051 | 51146 |
| DAB2IP | 4957 | 28052 | 51147 |
| DACH1 | 4958 | 28053 | 51148 |
| DACH2 | 4959 | 28054 | 51149 |
| DACH2 | 4960 | 28055 | 51150 |
| DACT1 | 4961 | 28056 | 51151 |
| DACT2 | 4962 | 28057 | 51152 |
| DACT2 | 4963 | 28058 | 51153 |
| DACT3 | 4964 | 28059 | 51154 |
| DAD1 | 4965 | 28060 | 51155 |
| DAG1 | 4966 | 28061 | 51156 |
| DAGLA | 4967 | 28062 | 51157 |
| DAGLB | 4968 | 28063 | 51158 |
| DALRD3 | 4969 | 28064 | 51159 |
| DALRD3 | 4970 | 28065 | 51160 |
| DAND5 | 4971 | 28066 | 51161 |
| DAO | 4972 | 28067 | 51162 |
| DAOA | 4973 | 28068 | 51163 |
| DAP | 4974 | 28069 | 51164 |
| DAP3 | 4975 | 28070 | 51165 |
| DAPK1 | 4976 | 28071 | 51166 |
| DAPK2 | 4977 | 28072 | 51167 |
| DAPK3 | 4978 | 28073 | 51168 |
| DAPL1 | 4979 | 28074 | 51169 |
| DAPP1 | 4980 | 28075 | 51170 |
| DAPP1 | 4981 | 28076 | 51171 |
| DARS | 4982 | 28077 | 51172 |
| DARS2 | 4983 | 28078 | 51173 |
| DAW1 | 4984 | 28079 | 51174 |
| DAXX | 4985 | 28080 | 51175 |
| DAZ1 | 4986 | 28081 | 51176 |
| DAZAP1 | 4987 | 28082 | 51177 |
| DAZAP1 | 4988 | 28083 | 51178 |
| DAZAP2 | 4989 | 28084 | 51179 |
| DAZAP2 | 4990 | 28085 | 51180 |
| DAZAP2 | 4991 | 28086 | 51181 |
| DAZL | 4992 | 28087 | 51182 |
| DBF4 | 4993 | 28088 | 51183 |
| DBF4B | 4994 | 28089 | 51184 |
| DBF4B | 4995 | 28090 | 51185 |
| DBH | 4996 | 28091 | 51186 |
| DBI | 4997 | 28092 | 51187 |
| DBI | 4998 | 28093 | 51188 |
| DBN1 | 4999 | 28094 | 51189 |
| DBNDD1 | 5000 | 28095 | 51190 |
| DBNDD1 | 5001 | 28096 | 51191 |
| DBNDD2 | 5002 | 28097 | 51192 |
| DBNDD2 | 5003 | 28098 | 51193 |
| DBNL | 5004 | 28099 | 51194 |
| DBP | 5005 | 28100 | 51195 |
| DBR1 | 5006 | 28101 | 51196 |
| DBT | 5007 | 28102 | 51197 |
| DBX1 | 5008 | 28103 | 51198 |
| DBX2 | 5009 | 28104 | 51199 |
| DCAF1 | 5010 | 28105 | 51200 |
| DCAF10 | 5011 | 28106 | 51201 |
| DCAF11 | 5012 | 28107 | 51202 |
| DCAF12 | 5013 | 28108 | 51203 |
| DCAF12L1 | 5014 | 28109 | 51204 |
| DCAF12L2 | 5015 | 28110 | 51205 |
| DCAF13 | 5016 | 28111 | 51206 |
| DCAF15 | 5017 | 28112 | 51207 |
| DCAF16 | 5018 | 28113 | 51208 |
| DCAF17 | 5019 | 28114 | 51209 |
| DCAF4 | 5020 | 28115 | 51210 |
| DCAF4 | 5021 | 28116 | 51211 |
| DCAF4L1 | 5022 | 28117 | 51212 |
| DCAF4L2 | 5023 | 28118 | 51213 |
| DCAF5 | 5024 | 28119 | 51214 |
| DCAF5 | 5025 | 28120 | 51215 |
| DCAF6 | 5026 | 28121 | 51216 |
| DCAF7 | 5027 | 28122 | 51217 |
| DCAF8 | 5028 | 28123 | 51218 |
| DCAF8L1 | 5029 | 28124 | 51219 |
| DCAF8L2 | 5030 | 28125 | 51220 |
| DCAKD | 5031 | 28126 | 51221 |
| DCANP1 | 5032 | 28127 | 51222 |
| DCBLD1 | 5033 | 28128 | 51223 |
| DCBLD2 | 5034 | 28129 | 51224 |
| DCC | 5035 | 28130 | 51225 |
| DCD | 5036 | 28131 | 51226 |
| DCD | 5037 | 28132 | 51227 |
| DCDC1 | 5038 | 28133 | 51228 |
| DCDC1 | 5039 | 28134 | 51229 |
| DCDC2 | 5040 | 28135 | 51230 |
| DCDC2B | 5041 | 28136 | 51231 |
| DCDC2C | 5042 | 28137 | 51232 |
| DCHS1 | 5043 | 28138 | 51233 |
| DCHS2 | 5044 | 28139 | 51234 |
| DCHS2 | 5045 | 28140 | 51235 |
| DCK | 5046 | 28141 | 51236 |
| DCLK1 | 5047 | 28142 | 51237 |
| DCLK1 | 5048 | 28143 | 51238 |
| DCLK1 | 5049 | 28144 | 51239 |
| DCLK2 | 5050 | 28145 | 51240 |
| DCLK3 | 5051 | 28146 | 51241 |
| DCLRE1A | 5052 | 28147 | 51242 |
| DCLRE1B | 5053 | 28148 | 51243 |
| DCLRE1C | 5054 | 28149 | 51244 |
| DCLRE1C | 5055 | 28150 | 51245 |
| DCN | 5056 | 28151 | 51246 |
| DCN | 5057 | 28152 | 51247 |
| DCP1A | 5058 | 28153 | 51248 |
| DCP1B | 5059 | 28154 | 51249 |
| DCP1B | 5060 | 28155 | 51250 |
| DCP2 | 5061 | 28156 | 51251 |
| DCPS | 5062 | 28157 | 51252 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| DCST1 | 5063 | 28158 | 51253 |
| DCST2 | 5064 | 28159 | 51254 |
| DCSTAMP | 5065 | 28160 | 51255 |
| DCSTAMP | 5066 | 28161 | 51256 |
| DCT | 5067 | 28162 | 51257 |
| DCTD | 5068 | 28163 | 51258 |
| DCTN1 | 5069 | 28164 | 51259 |
| DCTN2 | 5070 | 28165 | 51260 |
| DCTN3 | 5071 | 28166 | 51261 |
| DCTN3 | 5072 | 28167 | 51262 |
| DCTN4 | 5073 | 28168 | 51263 |
| DCTN5 | 5074 | 28169 | 51264 |
| DCTN5 | 5075 | 28170 | 51265 |
| DCTN5 | 5076 | 28171 | 51266 |
| DCTN6 | 5077 | 28172 | 51267 |
| DCTPP1 | 5078 | 28173 | 51268 |
| DCUN1D1 | 5079 | 28174 | 51269 |
| DCUN1D2 | 5080 | 28175 | 51270 |
| DCUN1D3 | 5081 | 28176 | 51271 |
| DCUN1D4 | 5082 | 28177 | 51272 |
| DCUN1D5 | 5083 | 28178 | 51273 |
| DCX | 5084 | 28179 | 51274 |
| DCXR | 5085 | 28180 | 51275 |
| DDA1 | 5086 | 28181 | 51276 |
| DDAH1 | 5087 | 28182 | 51277 |
| DDAH2 | 5088 | 28183 | 51278 |
| DDB1 | 5089 | 28184 | 51279 |
| DDB2 | 5090 | 28185 | 51280 |
| DDC | 5091 | 28186 | 51281 |
| DDC | 5092 | 28187 | 51282 |
| DDHD1 | 5093 | 28188 | 51283 |
| DDHD2 | 5094 | 28189 | 51284 |
| DDHD2 | 5095 | 28190 | 51285 |
| DDI1 | 5096 | 28191 | 51286 |
| DDI2 | 5097 | 28192 | 51287 |
| DDIAS | 5098 | 28193 | 51288 |
| DDIT3 | 5099 | 28194 | 51289 |
| DDIT4 | 5100 | 28195 | 51290 |
| DDIT4L | 5101 | 28196 | 51291 |
| DDN | 5102 | 28197 | 51292 |
| DDO | 5103 | 28198 | 51293 |
| DDOST | 5104 | 28199 | 51294 |
| DDR1 | 5105 | 28200 | 51295 |
| DDR1 | 5106 | 28201 | 51296 |
| DDR2 | 5107 | 28202 | 51297 |
| DDRGK1 | 5108 | 28203 | 51298 |
| DDT | 5109 | 28204 | 51299 |
| DDTL | 5110 | 28205 | 51300 |
| DDX1 | 5111 | 28206 | 51301 |
| DDX10 | 5112 | 28207 | 51302 |
| DDX11 | 5113 | 28208 | 51303 |
| DDX11 | 5114 | 28209 | 51304 |
| DDX17 | 5115 | 28210 | 51305 |
| DDX18 | 5116 | 28211 | 51306 |
| DDX19B | 5117 | 28212 | 51307 |
| DDX20 | 5118 | 28213 | 51308 |
| DDX21 | 5119 | 28214 | 51309 |
| DDX23 | 5120 | 28215 | 51310 |
| DDX24 | 5121 | 28216 | 51311 |
| DDX25 | 5122 | 28217 | 51312 |
| DDX27 | 5123 | 28218 | 51313 |
| DDX28 | 5124 | 28219 | 51314 |
| DDX31 | 5125 | 28220 | 51315 |
| DDX31 | 5126 | 28221 | 51316 |
| DDX31 | 5127 | 28222 | 51317 |
| DDX39A | 5128 | 28223 | 51318 |
| DDX39B | 5129 | 28224 | 51319 |
| DDX3Y | 5130 | 28225 | 51320 |
| DDX4 | 5131 | 28226 | 51321 |
| DDX41 | 5132 | 28227 | 51322 |
| DDX42 | 5133 | 28228 | 51323 |
| DDX43 | 5134 | 28229 | 51324 |
| DDX46 | 5135 | 28230 | 51325 |
| DDX47 | 5136 | 28231 | 51326 |
| DDX49 | 5137 | 28232 | 51327 |
| DDX5 | 5138 | 28233 | 51328 |
| DDX50 | 5139 | 28234 | 51329 |
| DDX51 | 5140 | 28235 | 51330 |
| DDX52 | 5141 | 28236 | 51331 |
| DDX53 | 5142 | 28237 | 51332 |
| DDX54 | 5143 | 28238 | 51333 |
| DDX55 | 5144 | 28239 | 51334 |
| DDX56 | 5145 | 28240 | 51335 |
| DDX58 | 5146 | 28241 | 51336 |
| DDX59 | 5147 | 28242 | 51337 |
| DDX59 | 5148 | 28243 | 51338 |
| DDX59 | 5149 | 28244 | 51339 |
| DDX6 | 5150 | 28245 | 51340 |
| DDX60 | 5151 | 28246 | 51341 |
| DDX60L | 5152 | 28247 | 51342 |
| DDX60L | 5153 | 28248 | 51343 |
| DEAF1 | 5154 | 28249 | 51344 |
| DEC1 | 5155 | 28250 | 51345 |
| DECR1 | 5156 | 28251 | 51346 |
| DECR2 | 5157 | 28252 | 51347 |
| DEDD | 5158 | 28253 | 51348 |
| DEDD2 | 5159 | 28254 | 51349 |
| DEF6 | 5160 | 28255 | 51350 |
| DEF8 | 5161 | 28256 | 51351 |
| DEF8 | 5162 | 28257 | 51352 |
| DEFA1 | 5163 | 28258 | 51353 |
| DEFA4 | 5164 | 28259 | 51354 |
| DEFA5 | 5165 | 28260 | 51355 |
| DEFA6 | 5166 | 28261 | 51356 |
| DEFB1 | 5167 | 28262 | 51357 |
| DEFB103B | 5168 | 28263 | 51358 |
| DEFB104A | 5169 | 28264 | 51359 |
| DEFB105A | 5170 | 28265 | 51360 |
| DEFB106A | 5171 | 28266 | 51361 |
| DEFB107A | 5172 | 28267 | 51362 |
| DEFB108B | 5173 | 28268 | 51363 |
| DEFB110 | 5174 | 28269 | 51364 |
| DEFB110 | 5175 | 28270 | 51365 |
| DEFB112 | 5176 | 28271 | 51366 |
| DEFB113 | 5177 | 28272 | 51367 |
| DEFB114 | 5178 | 28273 | 51368 |
| DEFB115 | 5179 | 28274 | 51369 |
| DEFB116 | 5180 | 28275 | 51370 |
| DEFB118 | 5181 | 28276 | 51371 |
| DEFB119 | 5182 | 28277 | 51372 |
| DEFB119 | 5183 | 28278 | 51373 |
| DEFB121 | 5184 | 28279 | 51374 |
| DEFB123 | 5185 | 28280 | 51375 |
| DEFB124 | 5186 | 28281 | 51376 |
| DEFB125 | 5187 | 28282 | 51377 |
| DEFB126 | 5188 | 28283 | 51378 |
| DEFB127 | 5189 | 28284 | 51379 |
| DEFB128 | 5190 | 28285 | 51380 |
| DEFB129 | 5191 | 28286 | 51381 |
| DEFB130B | 5192 | 28287 | 51382 |
| DEFB131A | 5193 | 28288 | 51383 |
| DEFB131B | 5194 | 28289 | 51384 |
| DEFB132 | 5195 | 28290 | 51385 |
| DEFB133 | 5196 | 28291 | 51386 |
| DEFB134 | 5197 | 28292 | 51387 |
| DEFB135 | 5198 | 28293 | 51388 |
| DEFB136 | 5199 | 28294 | 51389 |
| DEFB4A | 5200 | 28295 | 51390 |
| DEGS1 | 5201 | 28296 | 51391 |
| DEGS1 | 5202 | 28297 | 51392 |
| DEGS2 | 5203 | 28298 | 51393 |
| DEK | 5204 | 28299 | 51394 |
| DENND1A | 5205 | 28300 | 51395 |
| DENND1A | 5206 | 28301 | 51396 |
| DENND1A | 5207 | 28302 | 51397 |
| DENND1B | 5208 | 28303 | 51398 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| DENND1B | 5209 | 28304 | 51399 |
| DENND1B | 5210 | 28305 | 51400 |
| DENND1C | 5211 | 28306 | 51401 |
| DENND2A | 5212 | 28307 | 51402 |
| DENND2A | 5213 | 28308 | 51403 |
| DENND2C | 5214 | 28309 | 51404 |
| DENND2D | 5215 | 28310 | 51405 |
| DENND3 | 5216 | 28311 | 51406 |
| DENND3 | 5217 | 28312 | 51407 |
| DENND4A | 5218 | 28313 | 51408 |
| DENND4B | 5219 | 28314 | 51409 |
| DENND4C | 5220 | 28315 | 51410 |
| DENND5A | 5221 | 28316 | 51411 |
| DENND5A | 5222 | 28317 | 51412 |
| DENND5B | 5223 | 28318 | 51413 |
| DENND6A | 5224 | 28319 | 51414 |
| DENND6B | 5225 | 28320 | 51415 |
| DENR | 5226 | 28321 | 51416 |
| DEPDC1 | 5227 | 28322 | 51417 |
| DEPDC1B | 5228 | 28323 | 51418 |
| DEPDC4 | 5229 | 28324 | 51419 |
| DEPDC4 | 5230 | 28325 | 51420 |
| DEPDC4 | 5231 | 28326 | 51421 |
| DEPDC5 | 5232 | 28327 | 51422 |
| DEPDC5 | 5233 | 28328 | 51423 |
| DEPDC7 | 5234 | 28329 | 51424 |
| DEPTOR | 5235 | 28330 | 51425 |
| DERA | 5236 | 28331 | 51426 |
| DERL1 | 5237 | 28332 | 51427 |
| DERL2 | 5238 | 28333 | 51428 |
| DERL2 | 5239 | 28334 | 51429 |
| DERL3 | 5240 | 28335 | 51430 |
| DERL3 | 5241 | 28336 | 51431 |
| DERL3 | 5242 | 28337 | 51432 |
| DES | 5243 | 28338 | 51433 |
| DESI1 | 5244 | 28339 | 51434 |
| DESI2 | 5245 | 28340 | 51435 |
| DET1 | 5246 | 28341 | 51436 |
| DEUP1 | 5247 | 28342 | 51437 |
| DEXI | 5248 | 28343 | 51438 |
| DFFA | 5249 | 28344 | 51439 |
| DFFA | 5250 | 28345 | 51440 |
| DFFB | 5251 | 28346 | 51441 |
| DFNA5 | 5252 | 28347 | 51442 |
| DGAT1 | 5253 | 28348 | 51443 |
| DGAT2 | 5254 | 28349 | 51444 |
| DGAT2L6 | 5255 | 28350 | 51445 |
| DGCR2 | 5256 | 28351 | 51446 |
| DGCR6L | 5257 | 28352 | 51447 |
| DGCR8 | 5258 | 28353 | 51448 |
| DGKA | 5259 | 28354 | 51449 |
| DGKB | 5260 | 28355 | 51450 |
| DGKB | 5261 | 28356 | 51451 |
| DGKD | 5262 | 28357 | 51452 |
| DGKE | 5263 | 28358 | 51453 |
| DGKG | 5264 | 28359 | 51454 |
| DGKH | 5265 | 28360 | 51455 |
| DGKH | 5266 | 28361 | 51456 |
| DGKI | 5267 | 28362 | 51457 |
| DGKK | 5268 | 28363 | 51458 |
| DGKQ | 5269 | 28364 | 51459 |
| DGKZ | 5270 | 28365 | 51460 |
| DGLUCY | 5271 | 28366 | 51461 |
| DGLUCY | 5272 | 28367 | 51462 |
| DGUOK | 5273 | 28368 | 51463 |
| DHCR24 | 5274 | 28369 | 51464 |
| DHCR7 | 5275 | 28370 | 51465 |
| DHDDS | 5276 | 28371 | 51466 |
| DHDH | 5277 | 28372 | 51467 |
| DHFR | 5278 | 28373 | 51468 |
| DHFR | 5279 | 28374 | 51469 |
| DHFR | 5280 | 28375 | 51470 |
| DHFR2 | 5281 | 28376 | 51471 |
| DHH | 5282 | 28377 | 51472 |
| DHODH | 5283 | 28378 | 51473 |
| DHPS | 5284 | 28379 | 51474 |
| DHRS1 | 5285 | 28380 | 51475 |
| DHRS11 | 5286 | 28381 | 51476 |
| DHRS12 | 5287 | 28382 | 51477 |
| DHRS12 | 5288 | 28383 | 51478 |
| DHRS12 | 5289 | 28384 | 51479 |
| DHRS13 | 5290 | 28385 | 51480 |
| DHRS2 | 5291 | 28386 | 51481 |
| DHRS2 | 5292 | 28387 | 51482 |
| DHRS2 | 5293 | 28388 | 51483 |
| DHRS3 | 5294 | 28389 | 51484 |
| DHRS4 | 5295 | 28390 | 51485 |
| DHRS4 | 5296 | 28391 | 51486 |
| DHRS4L1 | 5297 | 28392 | 51487 |
| DHRS4L2 | 5298 | 28393 | 51488 |
| DHRS4L2 | 5299 | 28394 | 51489 |
| DHRS7 | 5300 | 28395 | 51490 |
| DHRS7B | 5301 | 28396 | 51491 |
| DHRS7C | 5302 | 28397 | 51492 |
| DHRS9 | 5303 | 28398 | 51493 |
| DHRSX | 5304 | 28399 | 51494 |
| DHTKD1 | 5305 | 28400 | 51495 |
| DHX15 | 5306 | 28401 | 51496 |
| DHX16 | 5307 | 28402 | 51497 |
| DHX29 | 5308 | 28403 | 51498 |
| DHX30 | 5309 | 28404 | 51499 |
| DHX32 | 5310 | 28405 | 51500 |
| DHX33 | 5311 | 28406 | 51501 |
| DHX34 | 5312 | 28407 | 51502 |
| DHX35 | 5313 | 28408 | 51503 |
| DHX36 | 5314 | 28409 | 51504 |
| DHX37 | 5315 | 28410 | 51505 |
| DHX38 | 5316 | 28411 | 51506 |
| DHX40 | 5317 | 28412 | 51507 |
| DHX57 | 5318 | 28413 | 51508 |
| DHX58 | 5319 | 28414 | 51509 |
| DHX8 | 5320 | 28415 | 51510 |
| DHX8 | 5321 | 28416 | 51511 |
| DHX8 | 5322 | 28417 | 51512 |
| DHX8 | 5323 | 28418 | 51513 |
| DHX9 | 5324 | 28419 | 51514 |
| DIABLO | 5325 | 28420 | 51515 |
| DIAPH1 | 5326 | 28421 | 51516 |
| DIAPH1 | 5327 | 28422 | 51517 |
| DIAPH2 | 5328 | 28423 | 51518 |
| DIAPH2 | 5329 | 28424 | 51519 |
| DIAPH3 | 5330 | 28425 | 51520 |
| DIAPH3 | 5331 | 28426 | 51521 |
| DIAPH3 | 5332 | 28427 | 51522 |
| DICER1 | 5333 | 28428 | 51523 |
| DICER1 | 5334 | 28429 | 51524 |
| DIDO1 | 5335 | 28430 | 51525 |
| DIDO1 | 5336 | 28431 | 51526 |
| DIDO1 | 5337 | 28432 | 51527 |
| DIEXF | 5338 | 28433 | 51528 |
| DIMT1 | 5339 | 28434 | 51529 |
| DIMT1 | 5340 | 28435 | 51530 |
| DIO1 | 5341 | 28436 | 51531 |
| DIO1 | 5342 | 28437 | 51532 |
| DIO1 | 5343 | 28438 | 51533 |
| DIO2 | 5344 | 28439 | 51534 |
| DIO3 | 5345 | 28440 | 51535 |
| DIP2A | 5346 | 28441 | 51536 |
| DIP2A | 5347 | 28442 | 51537 |
| DIP2A | 5348 | 28443 | 51538 |
| DIP2A | 5349 | 28444 | 51539 |
| DIP2B | 5350 | 28445 | 51540 |
| DIP2C | 5351 | 28446 | 51541 |
| DIRAS1 | 5352 | 28447 | 51542 |
| DIRAS2 | 5353 | 28448 | 51543 |
| DIRAS3 | 5354 | 28449 | 51544 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| DIRC1 | 5355 | 28450 | 51545 |
| DIRC2 | 5356 | 28451 | 51546 |
| DIS3 | 5357 | 28452 | 51547 |
| DIS3L | 5358 | 28453 | 51548 |
| DIS3L2 | 5359 | 28454 | 51549 |
| DIS3L2 | 5360 | 28455 | 51550 |
| DIS3L2 | 5361 | 28456 | 51551 |
| DISC1 | 5362 | 28457 | 51552 |
| DISC1 | 5363 | 28458 | 51553 |
| DISC1 | 5364 | 28459 | 51554 |
| DISC1 | 5365 | 28460 | 51555 |
| DISC1 | 5366 | 28461 | 51556 |
| DISC1 | 5367 | 28462 | 51557 |
| DISC1 | 5368 | 28463 | 51558 |
| DISC1 | 5369 | 28464 | 51559 |
| DISC1 | 5370 | 28465 | 51560 |
| DISC1 | 5371 | 28466 | 51561 |
| DISC1 | 5372 | 28467 | 51562 |
| DISC1 | 5373 | 28468 | 51563 |
| DISC1 | 5374 | 28469 | 51564 |
| DISC1 | 5375 | 28470 | 51565 |
| DISC1 | 5376 | 28471 | 51566 |
| DISC1 | 5377 | 28472 | 51567 |
| DISP1 | 5378 | 28473 | 51568 |
| DISP2 | 5379 | 28474 | 51569 |
| DISP3 | 5380 | 28475 | 51570 |
| DIXDC1 | 5381 | 28476 | 51571 |
| DIXDC1 | 5382 | 28477 | 51572 |
| DKC1 | 5383 | 28478 | 51573 |
| DKC1 | 5384 | 28479 | 51574 |
| DKK1 | 5385 | 28480 | 51575 |
| DKK2 | 5386 | 28481 | 51576 |
| DKK3 | 5387 | 28482 | 51577 |
| DKK4 | 5388 | 28483 | 51578 |
| DKKL1 | 5389 | 28484 | 51579 |
| DLAT | 5390 | 28485 | 51580 |
| DLC1 | 5391 | 28486 | 51581 |
| DLC1 | 5392 | 28487 | 51582 |
| DLD | 5393 | 28488 | 51583 |
| DLEC1 | 5394 | 28489 | 51584 |
| DLEC1 | 5395 | 28490 | 51585 |
| DLEU7 | 5396 | 28491 | 51586 |
| DLEU7 | 5397 | 28492 | 51587 |
| DLG1 | 5398 | 28493 | 51588 |
| DLG2 | 5399 | 28494 | 51589 |
| DLG3 | 5400 | 28495 | 51590 |
| DLG4 | 5401 | 28496 | 51591 |
| DLG5 | 5402 | 28497 | 51592 |
| DLGAP1 | 5403 | 28498 | 51593 |
| DLGAP1 | 5404 | 28499 | 51594 |
| DLGAP2 | 5405 | 28500 | 51595 |
| DLGAP3 | 5406 | 28501 | 51596 |
| DLGAP4 | 5407 | 28502 | 51597 |
| DLGAP5 | 5408 | 28503 | 51598 |
| DLGAP5 | 5409 | 28504 | 51599 |
| DLK1 | 5410 | 28505 | 51600 |
| DLK2 | 5411 | 28506 | 51601 |
| DLL1 | 5412 | 28507 | 51602 |
| DLL3 | 5413 | 28508 | 51603 |
| DLL3 | 5414 | 28509 | 51604 |
| DLL4 | 5415 | 28510 | 51605 |
| DLST | 5416 | 28511 | 51606 |
| DLST | 5417 | 28512 | 51607 |
| DLX1 | 5418 | 28513 | 51608 |
| DLX1 | 5419 | 28514 | 51609 |
| DLX2 | 5420 | 28515 | 51610 |
| DLX3 | 5421 | 28516 | 51611 |
| DLX4 | 5422 | 28517 | 51612 |
| DLX5 | 5423 | 28518 | 51613 |
| DLX6 | 5424 | 28519 | 51614 |
| DMAC1 | 5425 | 28520 | 51615 |
| DMAC1 | 5426 | 28521 | 51616 |
| DMAC2 | 5427 | 28522 | 51617 |
| DMAC2 | 5428 | 28523 | 51618 |
| DMAC2 | 5429 | 28524 | 51619 |
| DMAP1 | 5430 | 28525 | 51620 |
| DMBT1 | 5431 | 28526 | 51621 |
| DMBX1 | 5432 | 28527 | 51622 |
| DMC1 | 5433 | 28528 | 51623 |
| DMD | 5434 | 28529 | 51624 |
| DMD | 5435 | 28530 | 51625 |
| DMD | 5436 | 28531 | 51626 |
| DMGDH | 5437 | 28532 | 51627 |
| DMKN | 5438 | 28533 | 51628 |
| DMKN | 5439 | 28534 | 51629 |
| DMP1 | 5440 | 28535 | 51630 |
| DMPK | 5441 | 28536 | 51631 |
| DMPK | 5442 | 28537 | 51632 |
| DMPK | 5443 | 28538 | 51633 |
| DMRT1 | 5444 | 28539 | 51634 |
| DMRT2 | 5445 | 28540 | 51635 |
| DMRT3 | 5446 | 28541 | 51636 |
| DMRTA1 | 5447 | 28542 | 51637 |
| DMRTA2 | 5448 | 28543 | 51638 |
| DMRTB1 | 5449 | 28544 | 51639 |
| DMRTC1 | 5450 | 28545 | 51640 |
| DMRTC2 | 5451 | 28546 | 51641 |
| DMTF1 | 5452 | 28547 | 51642 |
| DMTN | 5453 | 28548 | 51643 |
| DMWD | 5454 | 28549 | 51644 |
| DMXL1 | 5455 | 28550 | 51645 |
| DMXL2 | 5456 | 28551 | 51646 |
| DNA2 | 5457 | 28552 | 51647 |
| DNAAF1 | 5458 | 28553 | 51648 |
| DNAAF2 | 5459 | 28554 | 51649 |
| DNAAF3 | 5460 | 28555 | 51650 |
| DNAAF4 | 5461 | 28556 | 51651 |
| DNAAF4 | 5462 | 28557 | 51652 |
| DNAAF5 | 5463 | 28558 | 51653 |
| DNAH1 | 5464 | 28559 | 51654 |
| DNAH10 | 5465 | 28560 | 51655 |
| DNAH11 | 5466 | 28561 | 51656 |
| DNAH12 | 5467 | 28562 | 51657 |
| DNAH12 | 5468 | 28563 | 51658 |
| DNAH14 | 5469 | 28564 | 51659 |
| DNAH14 | 5470 | 28565 | 51660 |
| DNAH14 | 5471 | 28566 | 51661 |
| DNAH14 | 5472 | 28567 | 51662 |
| DNAH17 | 5473 | 28568 | 51663 |
| DNAH2 | 5474 | 28569 | 51664 |
| DNAH2 | 5475 | 28570 | 51665 |
| DNAH3 | 5476 | 28571 | 51666 |
| DNAH5 | 5477 | 28572 | 51667 |
| DNAH6 | 5478 | 28573 | 51668 |
| DNAH7 | 5479 | 28574 | 51669 |
| DNAH8 | 5480 | 28575 | 51670 |
| DNAH9 | 5481 | 28576 | 51671 |
| DNAI1 | 5482 | 28577 | 51672 |
| DNAI2 | 5483 | 28578 | 51673 |
| DNAJA1 | 5484 | 28579 | 51674 |
| DNAJA2 | 5485 | 28580 | 51675 |
| DNAJA3 | 5486 | 28581 | 51676 |
| DNAJA3 | 5487 | 28582 | 51677 |
| DNAJA4 | 5488 | 28583 | 51678 |
| DNAJB1 | 5489 | 28584 | 51679 |
| DNAJB11 | 5490 | 28585 | 51680 |
| DNAJB12 | 5491 | 28586 | 51681 |
| DNAJB13 | 5492 | 28587 | 51682 |
| DNAJB14 | 5493 | 28588 | 51683 |
| DNAJB14 | 5494 | 28589 | 51684 |
| DNAJB2 | 5495 | 28590 | 51685 |
| DNAJB2 | 5496 | 28591 | 51686 |
| DNAJB3 | 5497 | 28592 | 51687 |
| DNAJB4 | 5498 | 28593 | 51688 |
| DNAJB5 | 5499 | 28594 | 51689 |
| DNAJB6 | 5500 | 28595 | 51690 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| DNAJB6 | 5501 | 28596 | 51691 |
| DNAJB7 | 5502 | 28597 | 51692 |
| DNAJB8 | 5503 | 28598 | 51693 |
| DNAJB9 | 5504 | 28599 | 51694 |
| DNAJC1 | 5505 | 28600 | 51695 |
| DNAJC10 | 5506 | 28601 | 51696 |
| DNAJC11 | 5507 | 28602 | 51697 |
| DNAJC12 | 5508 | 28603 | 51698 |
| DNAJC12 | 5509 | 28604 | 51699 |
| DNAJC13 | 5510 | 28605 | 51700 |
| DNAJC14 | 5511 | 28606 | 51701 |
| DNAJC15 | 5512 | 28607 | 51702 |
| DNAJC16 | 5513 | 28608 | 51703 |
| DNAJC17 | 5514 | 28609 | 51704 |
| DNAJC18 | 5515 | 28610 | 51705 |
| DNAJC19 | 5516 | 28611 | 51706 |
| DNAJC2 | 5517 | 28612 | 51707 |
| DNAJC21 | 5518 | 28613 | 51708 |
| DNAJC22 | 5519 | 28614 | 51709 |
| DNAJC24 | 5520 | 28615 | 51710 |
| DNAJC25 | 5521 | 28616 | 51711 |
| DNAJC27 | 5522 | 28617 | 51712 |
| DNAJC27 | 5523 | 28618 | 51713 |
| DNAJC28 | 5524 | 28619 | 51714 |
| DNAJC3 | 5525 | 28620 | 51715 |
| DNAJC30 | 5526 | 28621 | 51716 |
| DNAJC4 | 5527 | 28622 | 51717 |
| DNAJC4 | 5528 | 28623 | 51718 |
| DNAJC5 | 5529 | 28624 | 51719 |
| DNAJC5B | 5530 | 28625 | 51720 |
| DNAJC5G | 5531 | 28626 | 51721 |
| DNAJC6 | 5532 | 28627 | 51722 |
| DNAJC7 | 5533 | 28628 | 51723 |
| DNAJC8 | 5534 | 28629 | 51724 |
| DNAJC9 | 5535 | 28630 | 51725 |
| DNAL1 | 5536 | 28631 | 51726 |
| DNAL4 | 5537 | 28632 | 51727 |
| DNALI1 | 5538 | 28633 | 51728 |
| DNASE1 | 5539 | 28634 | 51729 |
| DNASE1L1 | 5540 | 28635 | 51730 |
| DNASE1L2 | 5541 | 28636 | 51731 |
| DNASE1L3 | 5542 | 28637 | 51732 |
| DNASE2 | 5543 | 28638 | 51733 |
| DNASE2B | 5544 | 28639 | 51734 |
| DND1 | 5545 | 28640 | 51735 |
| DNER | 5546 | 28641 | 51736 |
| DNHD1 | 5547 | 28642 | 51737 |
| DNHD1 | 5548 | 28643 | 51738 |
| DNLZ | 5549 | 28644 | 51739 |
| DNM1 | 5550 | 28645 | 51740 |
| DNM1 | 5551 | 28646 | 51741 |
| DNM1 | 5552 | 28647 | 51742 |
| DNM1L | 5553 | 28648 | 51743 |
| DNM2 | 5554 | 28649 | 51744 |
| DNM3 | 5555 | 28650 | 51745 |
| DNM3 | 5556 | 28651 | 51746 |
| DNM3 | 5557 | 28652 | 51747 |
| DNMBP | 5558 | 28653 | 51748 |
| DNMT1 | 5559 | 28654 | 51749 |
| DNMT3A | 5560 | 28655 | 51750 |
| DNMT3A | 5561 | 28656 | 51751 |
| DNMT3B | 5562 | 28657 | 51752 |
| DNMT3L | 5563 | 28658 | 51753 |
| DNPEP | 5564 | 28659 | 51754 |
| DNPH1 | 5565 | 28660 | 51755 |
| DNPH1 | 5566 | 28661 | 51756 |
| DNTT | 5567 | 28662 | 51757 |
| DNTTIP1 | 5568 | 28663 | 51758 |
| DNTTIP2 | 5569 | 28664 | 51759 |
| DOC2A | 5570 | 28665 | 51760 |
| DOC2B | 5571 | 28666 | 51761 |
| DOCK1 | 5572 | 28667 | 51762 |
| DOCK10 | 5573 | 28668 | 51763 |
| DOCK11 | 5574 | 28669 | 51764 |
| DOCK2 | 5575 | 28670 | 51765 |
| DOCK3 | 5576 | 28671 | 51766 |
| DOCK4 | 5577 | 28672 | 51767 |
| DOCK5 | 5578 | 28673 | 51768 |
| DOCK5 | 5579 | 28674 | 51769 |
| DOCK6 | 5580 | 28675 | 51770 |
| DOCK7 | 5581 | 28676 | 51771 |
| DOCK7 | 5582 | 28677 | 51772 |
| DOCK8 | 5583 | 28678 | 51773 |
| DOCK9 | 5584 | 28679 | 51774 |
| DOCK9 | 5585 | 28680 | 51775 |
| DOHH | 5586 | 28681 | 51776 |
| DOK1 | 5587 | 28682 | 51777 |
| DOK2 | 5588 | 28683 | 51778 |
| DOK3 | 5589 | 28684 | 51779 |
| DOK3 | 5590 | 28685 | 51780 |
| DOK4 | 5591 | 28686 | 51781 |
| DOK5 | 5592 | 28687 | 51782 |
| DOK5 | 5593 | 28688 | 51783 |
| DOK6 | 5594 | 28689 | 51784 |
| DOK7 | 5595 | 28690 | 51785 |
| DOK7 | 5596 | 28691 | 51786 |
| DOK7 | 5597 | 28692 | 51787 |
| DOLK | 5598 | 28693 | 51788 |
| DOLPP1 | 5599 | 28694 | 51789 |
| DONSON | 5600 | 28695 | 51790 |
| DOPEY1 | 5601 | 28696 | 51791 |
| DOPEY2 | 5602 | 28697 | 51792 |
| DOT1L | 5603 | 28698 | 51793 |
| DPAGT1 | 5604 | 28699 | 51794 |
| DPCD | 5605 | 28700 | 51795 |
| DPCD | 5606 | 28701 | 51796 |
| DPCD | 5607 | 28702 | 51797 |
| DPCD | 5608 | 28703 | 51798 |
| DPCR1 | 5609 | 28704 | 51799 |
| DPEP1 | 5610 | 28705 | 51800 |
| DPEP2 | 5611 | 28706 | 51801 |
| DPEP3 | 5612 | 28707 | 51802 |
| DPF1 | 5613 | 28708 | 51803 |
| DPF2 | 5614 | 28709 | 51804 |
| DPF3 | 5615 | 28710 | 51805 |
| DPF3 | 5616 | 28711 | 51806 |
| DPH1 | 5617 | 28712 | 51807 |
| DPH2 | 5618 | 28713 | 51808 |
| DPH3 | 5619 | 28714 | 51809 |
| DPH3 | 5620 | 28715 | 51810 |
| DPH3P1 | 5621 | 28716 | 51811 |
| DPH5 | 5622 | 28717 | 51812 |
| DPH6 | 5623 | 28718 | 51813 |
| DPH6 | 5624 | 28719 | 51814 |
| DPH7 | 5625 | 28720 | 51815 |
| DPH7 | 5626 | 28721 | 51816 |
| DPH7 | 5627 | 28722 | 51817 |
| DPM1 | 5628 | 28723 | 51818 |
| DPM2 | 5629 | 28724 | 51819 |
| DPM3 | 5630 | 28725 | 51820 |
| DPP10 | 5631 | 28726 | 51821 |
| DPP10 | 5632 | 28727 | 51822 |
| DPP3 | 5633 | 28728 | 51823 |
| DPP4 | 5634 | 28729 | 51824 |
| DPP6 | 5635 | 28730 | 51825 |
| DPP6 | 5636 | 28731 | 51826 |
| DPP7 | 5637 | 28732 | 51827 |
| DPP8 | 5638 | 28733 | 51828 |
| DPP9 | 5639 | 28734 | 51829 |
| DPP9-AS1 | 5640 | 28735 | 51830 |
| DPPA2 | 5641 | 28736 | 51831 |
| DPPA3 | 5642 | 28737 | 51832 |
| DPPA4 | 5643 | 28738 | 51833 |
| DPPA4 | 5644 | 28739 | 51834 |
| DPPA5 | 5645 | 28740 | 51835 |
| DPRX | 5646 | 28741 | 51836 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| DPT | 5647 | 28742 | 51837 |
| DPY19L1 | 5648 | 28743 | 51838 |
| DPY19L2 | 5649 | 28744 | 51839 |
| DPY19L3 | 5650 | 28745 | 51840 |
| DPY19L4 | 5651 | 28746 | 51841 |
| DPY30 | 5652 | 28747 | 51842 |
| DPY30 | 5653 | 28748 | 51843 |
| DPYD | 5654 | 28749 | 51844 |
| DPYD | 5655 | 28750 | 51845 |
| DPYS | 5656 | 28751 | 51846 |
| DPYSL2 | 5657 | 28752 | 51847 |
| DPYSL3 | 5658 | 28753 | 51848 |
| DPYSL4 | 5659 | 28754 | 51849 |
| DPYSL5 | 5660 | 28755 | 51850 |
| DQX1 | 5661 | 28756 | 51851 |
| DR1 | 5662 | 28757 | 51852 |
| DRAM1 | 5663 | 28758 | 51853 |
| DRAM2 | 5664 | 28759 | 51854 |
| DRAP1 | 5665 | 28760 | 51855 |
| DRAXIN | 5666 | 28761 | 51856 |
| DRC1 | 5667 | 28762 | 51857 |
| DRC3 | 5668 | 28763 | 51858 |
| DRC3 | 5669 | 28764 | 51859 |
| DRC7 | 5670 | 28765 | 51860 |
| DRD1 | 5671 | 28766 | 51861 |
| DRD2 | 5672 | 28767 | 51862 |
| DRD3 | 5673 | 28768 | 51863 |
| DRD4 | 5674 | 28769 | 51864 |
| DRD5 | 5675 | 28770 | 51865 |
| DRG1 | 5676 | 28771 | 51866 |
| DRG2 | 5677 | 28772 | 51867 |
| DRG2 | 5678 | 28773 | 51868 |
| DRGX | 5679 | 28774 | 51869 |
| DRICH1 | 5680 | 28775 | 51870 |
| DROSHA | 5681 | 28776 | 51871 |
| DRP2 | 5682 | 28777 | 51872 |
| DSC1 | 5683 | 28778 | 51873 |
| DSC1 | 5684 | 28779 | 51874 |
| DSC2 | 5685 | 28780 | 51875 |
| DSC3 | 5686 | 28781 | 51876 |
| DSC3 | 5687 | 28782 | 51877 |
| DSCAM | 5688 | 28783 | 51878 |
| DSCAML1 | 5689 | 28784 | 51879 |
| DSCC1 | 5690 | 28785 | 51880 |
| DSCR3 | 5691 | 28786 | 51881 |
| DSE | 5692 | 28787 | 51882 |
| DSEL | 5693 | 28788 | 51883 |
| DSG1 | 5694 | 28789 | 51884 |
| DSG2 | 5695 | 28790 | 51885 |
| DSG3 | 5696 | 28791 | 51886 |
| DSG4 | 5697 | 28792 | 51887 |
| DSN1 | 5698 | 28793 | 51888 |
| DSP | 5699 | 28794 | 51889 |
| DSPP | 5700 | 28795 | 51890 |
| DST | 5701 | 28796 | 51891 |
| DST | 5702 | 28797 | 51892 |
| DSTN | 5703 | 28798 | 51893 |
| DSTYK | 5704 | 28799 | 51894 |
| DTD1 | 5705 | 28800 | 51895 |
| DTD1 | 5706 | 28801 | 51896 |
| DTD2 | 5707 | 28802 | 51897 |
| DTHD1 | 5708 | 28803 | 51898 |
| DTL | 5709 | 28804 | 51899 |
| DTNA | 5710 | 28805 | 51900 |
| DTNA | 5711 | 28806 | 51901 |
| DTNA | 5712 | 28807 | 51902 |
| DTNA | 5713 | 28808 | 51903 |
| DTNB | 5714 | 28809 | 51904 |
| DTNB | 5715 | 28810 | 51905 |
| DTNB | 5716 | 28811 | 51906 |
| DTNB | 5717 | 28812 | 51907 |
| DTNB | 5718 | 28813 | 51908 |
| DTNB | 5719 | 28814 | 51909 |
| DTNB | 5720 | 28815 | 51910 |
| DTNB | 5721 | 28816 | 51911 |
| DTNB | 5722 | 28817 | 51912 |
| DTNBP1 | 5723 | 28818 | 51913 |
| DTNBP1 | 5724 | 28819 | 51914 |
| DTWD1 | 5725 | 28820 | 51915 |
| DTWD2 | 5726 | 28821 | 51916 |
| DTX1 | 5727 | 28822 | 51917 |
| DTX2 | 5728 | 28823 | 51918 |
| DTX3 | 5729 | 28824 | 51919 |
| DTX3L | 5730 | 28825 | 51920 |
| DTX4 | 5731 | 28826 | 51921 |
| DTYMK | 5732 | 28827 | 51922 |
| DTYMK | 5733 | 28828 | 51923 |
| DUOX1 | 5734 | 28829 | 51924 |
| DUOX2 | 5735 | 28830 | 51925 |
| DUOXA1 | 5736 | 28831 | 51926 |
| DUOXA1 | 5737 | 28832 | 51927 |
| DUOXA2 | 5738 | 28833 | 51928 |
| DUPD1 | 5739 | 28834 | 51929 |
| DUS1L | 5740 | 28835 | 51930 |
| DUS2 | 5741 | 28836 | 51931 |
| DUS3L | 5742 | 28837 | 51932 |
| DUS4L | 5743 | 28838 | 51933 |
| DUSP1 | 5744 | 28839 | 51934 |
| DUSP10 | 5745 | 28840 | 51935 |
| DUSP11 | 5746 | 28841 | 51936 |
| DUSP12 | 5747 | 28842 | 51937 |
| DUSP13 | 5748 | 28843 | 51938 |
| DUSP14 | 5749 | 28844 | 51939 |
| DUSP15 | 5750 | 28845 | 51940 |
| DUSP15 | 5751 | 28846 | 51941 |
| DUSP16 | 5752 | 28847 | 51942 |
| DUSP18 | 5753 | 28848 | 51943 |
| DUSP19 | 5754 | 28849 | 51944 |
| DUSP19 | 5755 | 28850 | 51945 |
| DUSP2 | 5756 | 28851 | 51946 |
| DUSP21 | 5757 | 28852 | 51947 |
| DUSP22 | 5758 | 28853 | 51948 |
| DUSP22 | 5759 | 28854 | 51949 |
| DUSP23 | 5760 | 28855 | 51950 |
| DUSP26 | 5761 | 28856 | 51951 |
| DUSP27 | 5762 | 28857 | 51952 |
| DUSP28 | 5763 | 28858 | 51953 |
| DUSP3 | 5764 | 28859 | 51954 |
| DUSP4 | 5765 | 28860 | 51955 |
| DUSP5 | 5766 | 28861 | 51956 |
| DUSP6 | 5767 | 28862 | 51957 |
| DUSP7 | 5768 | 28863 | 51958 |
| DUSP8 | 5769 | 28864 | 51959 |
| DUSP9 | 5770 | 28865 | 51960 |
| DUT | 5771 | 28866 | 51961 |
| DUX1 | 5772 | 28867 | 51962 |
| DUX4 | 5773 | 28868 | 51963 |
| DUXA | 5774 | 28869 | 51964 |
| DUXB | 5775 | 28870 | 51965 |
| DVL1 | 5776 | 28871 | 51966 |
| DVL2 | 5777 | 28872 | 51967 |
| DVL3 | 5778 | 28873 | 51968 |
| DWORF | 5779 | 28874 | 51969 |
| DXO | 5780 | 28875 | 51970 |
| DYDC1 | 5781 | 28876 | 51971 |
| DYDC2 | 5782 | 28877 | 51972 |
| DYM | 5783 | 28878 | 51973 |
| DYNAP | 5784 | 28879 | 51974 |
| DYNC1H1 | 5785 | 28880 | 51975 |
| DYNC1I1 | 5786 | 28881 | 51976 |
| DYNC1I1 | 5787 | 28882 | 51977 |
| DYNC1I2 | 5788 | 28883 | 51978 |
| DYNC1LI1 | 5789 | 28884 | 51979 |
| DYNC1LI2 | 5790 | 28885 | 51980 |
| DYNC2H1 | 5791 | 28886 | 51981 |
| DYNC2LI1 | 5792 | 28887 | 51982 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| DYNC2LI1 | 5793 | 28888 | 51983 |
| DYNC2LI1 | 5794 | 28889 | 51984 |
| DYNLL1 | 5795 | 28890 | 51985 |
| DYNLL2 | 5796 | 28891 | 51986 |
| DYNLRB1 | 5797 | 28892 | 51987 |
| DYNLRB1 | 5798 | 28893 | 51988 |
| DYNLRB1 | 5799 | 28894 | 51989 |
| DYNLRB2 | 5800 | 28895 | 51990 |
| DYNLT1 | 5801 | 28896 | 51991 |
| DYNLT1 | 5802 | 28897 | 51992 |
| DYNLT3 | 5803 | 28898 | 51993 |
| DYRK1A | 5804 | 28899 | 51994 |
| DYRK1A | 5805 | 28900 | 51995 |
| DYRK1A | 5806 | 28901 | 51996 |
| DYRK1B | 5807 | 28902 | 51997 |
| DYRK2 | 5808 | 28903 | 51998 |
| DYRK3 | 5809 | 28904 | 51999 |
| DYRK4 | 5810 | 28905 | 52000 |
| DYSF | 5811 | 28906 | 52001 |
| DYTN | 5812 | 28907 | 52002 |
| DZANK1 | 5813 | 28908 | 52003 |
| DZIP1 | 5814 | 28909 | 52004 |
| DZIP1L | 5815 | 28910 | 52005 |
| DZIP1L | 5816 | 28911 | 52006 |
| DZIP3 | 5817 | 28912 | 52007 |
| E2F1 | 5818 | 28913 | 52008 |
| E2F2 | 5819 | 28914 | 52009 |
| E2F3 | 5820 | 28915 | 52010 |
| E2F4 | 5821 | 28916 | 52011 |
| E2F5 | 5822 | 28917 | 52012 |
| E2F6 | 5823 | 28918 | 52013 |
| E2F7 | 5824 | 28919 | 52014 |
| E2F8 | 5825 | 28920 | 52015 |
| E4F1 | 5826 | 28921 | 52016 |
| E4F1 | 5827 | 28922 | 52017 |
| EAF1 | 5828 | 28923 | 52018 |
| EAF2 | 5829 | 28924 | 52019 |
| EAPP | 5830 | 28925 | 52020 |
| EAPP | 5831 | 28926 | 52021 |
| EARS2 | 5832 | 28927 | 52022 |
| EARS2 | 5833 | 28928 | 52023 |
| EBAG9 | 5834 | 28929 | 52024 |
| EBF1 | 5835 | 28930 | 52025 |
| EBF1 | 5836 | 28931 | 52026 |
| EBF2 | 5837 | 28932 | 52027 |
| EBF3 | 5838 | 28933 | 52028 |
| EBF4 | 5839 | 28934 | 52029 |
| EBI3 | 5840 | 28935 | 52030 |
| EBLN1 | 5841 | 28936 | 52031 |
| EBLN2 | 5842 | 28937 | 52032 |
| EBNA1BP2 | 5843 | 28938 | 52033 |
| EBP | 5844 | 28939 | 52034 |
| EBPL | 5845 | 28940 | 52035 |
| EBPL | 5846 | 28941 | 52036 |
| ECD | 5847 | 28942 | 52037 |
| ECE1 | 5848 | 28943 | 52038 |
| ECEL1 | 5849 | 28944 | 52039 |
| ECH1 | 5850 | 28945 | 52040 |
| ECHDC1 | 5851 | 28946 | 52041 |
| ECHDC1 | 5852 | 28947 | 52042 |
| ECHDC2 | 5853 | 28948 | 52043 |
| ECHDC3 | 5854 | 28949 | 52044 |
| ECHS1 | 5855 | 28950 | 52045 |
| ECI1 | 5856 | 28951 | 52046 |
| ECI2 | 5857 | 28952 | 52047 |
| ECM1 | 5858 | 28953 | 52048 |
| ECM2 | 5859 | 28954 | 52049 |
| ECM2 | 5860 | 28955 | 52050 |
| ECSCR | 5861 | 28956 | 52051 |
| ECSCR | 5862 | 28957 | 52052 |
| ECSIT | 5863 | 28958 | 52053 |
| ECSIT | 5864 | 28959 | 52054 |
| ECSIT | 5865 | 28960 | 52055 |
| ECT2 | 5866 | 28961 | 52056 |
| ECT2 | 5867 | 28962 | 52057 |
| ECT2L | 5868 | 28963 | 52058 |
| EDA | 5869 | 28964 | 52059 |
| EDA | 5870 | 28965 | 52060 |
| EDA | 5871 | 28966 | 52061 |
| EDA2R | 5872 | 28967 | 52062 |
| EDA2R | 5873 | 28968 | 52063 |
| EDAR | 5874 | 28969 | 52064 |
| EDARADD | 5875 | 28970 | 52065 |
| EDC3 | 5876 | 28971 | 52066 |
| EDC4 | 5877 | 28972 | 52067 |
| EDDM3A | 5878 | 28973 | 52068 |
| EDDM3B | 5879 | 28974 | 52069 |
| EDEM1 | 5880 | 28975 | 52070 |
| EDEM2 | 5881 | 28976 | 52071 |
| EDEM3 | 5882 | 28977 | 52072 |
| EDF1 | 5883 | 28978 | 52073 |
| EDF1 | 5884 | 28979 | 52074 |
| EDF1 | 5885 | 28980 | 52075 |
| EDIL3 | 5886 | 28981 | 52076 |
| EDN1 | 5887 | 28982 | 52077 |
| EDN2 | 5888 | 28983 | 52078 |
| EDN3 | 5889 | 28984 | 52079 |
| EDN3 | 5890 | 28985 | 52080 |
| EDNRA | 5891 | 28986 | 52081 |
| EDNRB | 5892 | 28987 | 52082 |
| EDNRB | 5893 | 28988 | 52083 |
| EDRF1 | 5894 | 28989 | 52084 |
| EEA1 | 5895 | 28990 | 52085 |
| EED | 5896 | 28991 | 52086 |
| EEF1A1 | 5897 | 28992 | 52087 |
| EEF1A2 | 5898 | 28993 | 52088 |
| EEF1AKMT1 | 5899 | 28994 | 52089 |
| EEF1AKMT2 | 5900 | 28995 | 52090 |
| EEF1AKMT2 | 5901 | 28996 | 52091 |
| EEF1AKMT3 | 5902 | 28997 | 52092 |
| EEF1AKMT3 | 5903 | 28998 | 52093 |
| EEF1AKMT4 | 5904 | 28999 | 52094 |
| EEF1AKMT4-ECE2 | 5905 | 29000 | 52095 |
| EEF1B2 | 5906 | 29001 | 52096 |
| EEF1D | 5907 | 29002 | 52097 |
| EEF1E1 | 5908 | 29003 | 52098 |
| EEF1E1 | 5909 | 29004 | 52099 |
| EEF1G | 5910 | 29005 | 52100 |
| EEF2 | 5911 | 29006 | 52101 |
| EEF2K | 5912 | 29007 | 52102 |
| EEF2KMT | 5913 | 29008 | 52103 |
| EEFSEC | 5914 | 29009 | 52104 |
| EEPD1 | 5915 | 29010 | 52105 |
| EFCAB1 | 5916 | 29011 | 52106 |
| EFCAB11 | 5917 | 29012 | 52107 |
| EFCAB11 | 5918 | 29013 | 52108 |
| EFCAB12 | 5919 | 29014 | 52109 |
| EFCAB13 | 5920 | 29015 | 52110 |
| EFCAB13 | 5921 | 29016 | 52111 |
| EFCAB14 | 5922 | 29017 | 52112 |
| EFCAB2 | 5923 | 29018 | 52113 |
| EFCAB2 | 5924 | 29019 | 52114 |
| EFCAB3 | 5925 | 29020 | 52115 |
| EFCAB5 | 5926 | 29021 | 52116 |
| EFCAB5 | 5927 | 29022 | 52117 |
| EFCAB6 | 5928 | 29023 | 52118 |
| EFCAB7 | 5929 | 29024 | 52119 |
| EFCAB8 | 5930 | 29025 | 52120 |
| EFCAB9 | 5931 | 29026 | 52121 |
| EFCC1 | 5932 | 29027 | 52122 |
| EFEMP1 | 5933 | 29028 | 52123 |
| EFEMP2 | 5934 | 29029 | 52124 |
| EFHB | 5935 | 29030 | 52125 |
| EFHC1 | 5936 | 29031 | 52126 |
| EFHC2 | 5937 | 29032 | 52127 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| EFHD1 | 5938 | 29033 | 52128 |
| EFHD2 | 5939 | 29034 | 52129 |
| EFL1 | 5940 | 29035 | 52130 |
| EFNA1 | 5941 | 29036 | 52131 |
| EFNA2 | 5942 | 29037 | 52132 |
| EFNA3 | 5943 | 29038 | 52133 |
| EFNA4 | 5944 | 29039 | 52134 |
| EFNA4 | 5945 | 29040 | 52135 |
| EFNA4 | 5946 | 29041 | 52136 |
| EFNA5 | 5947 | 29042 | 52137 |
| EFNB1 | 5948 | 29043 | 52138 |
| EFNB2 | 5949 | 29044 | 52139 |
| EFNB3 | 5950 | 29045 | 52140 |
| EFR3A | 5951 | 29046 | 52141 |
| EFR3B | 5952 | 29047 | 52142 |
| EFS | 5953 | 29048 | 52143 |
| EFTUD2 | 5954 | 29049 | 52144 |
| EGF | 5955 | 29050 | 52145 |
| EGFL6 | 5956 | 29051 | 52146 |
| EGFL7 | 5957 | 29052 | 52147 |
| EGFL8 | 5958 | 29053 | 52148 |
| EGFLAM | 5959 | 29054 | 52149 |
| EGFR | 5960 | 29055 | 52150 |
| EGFR | 5961 | 29056 | 52151 |
| EGFR | 5962 | 29057 | 52152 |
| EGFR | 5963 | 29058 | 52153 |
| EGFR | 5964 | 29059 | 52154 |
| EGLN1 | 5965 | 29060 | 52155 |
| EGLN2 | 5966 | 29061 | 52156 |
| EGLN3 | 5967 | 29062 | 52157 |
| EGR1 | 5968 | 29063 | 52158 |
| EGR2 | 5969 | 29064 | 52159 |
| EGR3 | 5970 | 29065 | 52160 |
| EGR4 | 5971 | 29066 | 52161 |
| EHBP1 | 5972 | 29067 | 52162 |
| EHBP1L1 | 5973 | 29068 | 52163 |
| EHD1 | 5974 | 29069 | 52164 |
| EHD2 | 5975 | 29070 | 52165 |
| EHD3 | 5976 | 29071 | 52166 |
| EHD4 | 5977 | 29072 | 52167 |
| EHF | 5978 | 29073 | 52168 |
| EHHADH | 5979 | 29074 | 52169 |
| EHMT1 | 5980 | 29075 | 52170 |
| EHMT1 | 5981 | 29076 | 52171 |
| EHMT1 | 5982 | 29077 | 52172 |
| EHMT2 | 5983 | 29078 | 52173 |
| EI24 | 5984 | 29079 | 52174 |
| EI24 | 5985 | 29080 | 52175 |
| EID1 | 5986 | 29081 | 52176 |
| EID2 | 5987 | 29082 | 52177 |
| EID2B | 5988 | 29083 | 52178 |
| EID3 | 5989 | 29084 | 52179 |
| EIF1 | 5990 | 29085 | 52180 |
| EIF1AD | 5991 | 29086 | 52181 |
| EIF1AX | 5992 | 29087 | 52182 |
| EIF1AY | 5993 | 29088 | 52183 |
| EIF1B | 5994 | 29089 | 52184 |
| EIF2A | 5995 | 29090 | 52185 |
| EIF2AK1 | 5996 | 29091 | 52186 |
| EIF2AK2 | 5997 | 29092 | 52187 |
| EIF2AK3 | 5998 | 29093 | 52188 |
| EIF2AK4 | 5999 | 29094 | 52189 |
| EIF2B1 | 6000 | 29095 | 52190 |
| EIF2B2 | 6001 | 29096 | 52191 |
| EIF2B3 | 6002 | 29097 | 52192 |
| EIF2B3 | 6003 | 29098 | 52193 |
| EIF2B3 | 6004 | 29099 | 52194 |
| EIF2B4 | 6005 | 29100 | 52195 |
| EIF2B5 | 6006 | 29101 | 52196 |
| EIF2D | 6007 | 29102 | 52197 |
| EIF2S1 | 6008 | 29103 | 52198 |
| EIF2S2 | 6009 | 29104 | 52199 |
| EIF2S3 | 6010 | 29105 | 52200 |
| EIF3A | 6011 | 29106 | 52201 |
| EIF3B | 6012 | 29107 | 52202 |
| EIF3C | 6013 | 29108 | 52203 |
| EIF3D | 6014 | 29109 | 52204 |
| EIF3E | 6015 | 29110 | 52205 |
| EIF3F | 6016 | 29111 | 52206 |
| EIF3G | 6017 | 29112 | 52207 |
| EIF3H | 6018 | 29113 | 52208 |
| EIF3I | 6019 | 29114 | 52209 |
| EIF3J | 6020 | 29115 | 52210 |
| EIF3K | 6021 | 29116 | 52211 |
| EIF3L | 6022 | 29117 | 52212 |
| EIF3M | 6023 | 29118 | 52213 |
| EIF4A1 | 6024 | 29119 | 52214 |
| EIF4A1 | 6025 | 29120 | 52215 |
| EIF4A2 | 6026 | 29121 | 52216 |
| EIF4A3 | 6027 | 29122 | 52217 |
| EIF4B | 6028 | 29123 | 52218 |
| EIF4E | 6029 | 29124 | 52219 |
| EIF4E1B | 6030 | 29125 | 52220 |
| EIF4E2 | 6031 | 29126 | 52221 |
| EIF4E2 | 6032 | 29127 | 52222 |
| EIF4E2 | 6033 | 29128 | 52223 |
| EIF4E3 | 6034 | 29129 | 52224 |
| EIF4EBP1 | 6035 | 29130 | 52225 |
| EIF4EBP2 | 6036 | 29131 | 52226 |
| EIF4ENIF1 | 6037 | 29132 | 52227 |
| EIF4G1 | 6038 | 29133 | 52228 |
| EIF4G2 | 6039 | 29134 | 52229 |
| EIF4G3 | 6040 | 29135 | 52230 |
| EIF4G3 | 6041 | 29136 | 52231 |
| EIF4H | 6042 | 29137 | 52232 |
| EIF5 | 6043 | 29138 | 52233 |
| EIF5A | 6044 | 29139 | 52234 |
| EIF5A2 | 6045 | 29140 | 52235 |
| EIF5B | 6046 | 29141 | 52236 |
| EIF6 | 6047 | 29142 | 52237 |
| EIPR1 | 6048 | 29143 | 52238 |
| ELAC1 | 6049 | 29144 | 52239 |
| ELAC2 | 6050 | 29145 | 52240 |
| ELANE | 6051 | 29146 | 52241 |
| ELAVL1 | 6052 | 29147 | 52242 |
| ELAVL2 | 6053 | 29148 | 52243 |
| ELAVL3 | 6054 | 29149 | 52244 |
| ELAVL4 | 6055 | 29150 | 52245 |
| ELAVL4 | 6056 | 29151 | 52246 |
| ELF1 | 6057 | 29152 | 52247 |
| ELF2 | 6058 | 29153 | 52248 |
| ELF3 | 6059 | 29154 | 52249 |
| ELF4 | 6060 | 29155 | 52250 |
| ELF5 | 6061 | 29156 | 52251 |
| ELFN1 | 6062 | 29157 | 52252 |
| ELFN2 | 6063 | 29158 | 52253 |
| ELK1 | 6064 | 29159 | 52254 |
| ELK1 | 6065 | 29160 | 52255 |
| ELK3 | 6066 | 29161 | 52256 |
| ELK4 | 6067 | 29162 | 52257 |
| ELK4 | 6068 | 29163 | 52258 |
| ELL | 6069 | 29164 | 52259 |
| ELL2 | 6070 | 29165 | 52260 |
| ELL3 | 6071 | 29166 | 52261 |
| ELMO1 | 6072 | 29167 | 52262 |
| ELMO2 | 6073 | 29168 | 52263 |
| ELMO3 | 6074 | 29169 | 52264 |
| ELMOD1 | 6075 | 29170 | 52265 |
| ELMOD2 | 6076 | 29171 | 52266 |
| ELMOD3 | 6077 | 29172 | 52267 |
| ELMSAN1 | 6078 | 29173 | 52268 |
| ELN | 6079 | 29174 | 52269 |
| ELOA | 6080 | 29175 | 52270 |
| ELOA2 | 6081 | 29176 | 52271 |
| ELOA3C | 6082 | 29177 | 52272 |
| ELOB | 6083 | 29178 | 52273 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ELOB | 6084 | 29179 | 52274 |
| ELOC | 6085 | 29180 | 52275 |
| ELOF1 | 6086 | 29181 | 52276 |
| ELOVL1 | 6087 | 29182 | 52277 |
| ELOVL2 | 6088 | 29183 | 52278 |
| ELOVL3 | 6089 | 29184 | 52279 |
| ELOVL4 | 6090 | 29185 | 52280 |
| ELOVL5 | 6091 | 29186 | 52281 |
| ELOVL5 | 6092 | 29187 | 52282 |
| ELOVL6 | 6093 | 29188 | 52283 |
| ELOVL7 | 6094 | 29189 | 52284 |
| ELP1 | 6095 | 29190 | 52285 |
| ELP2 | 6096 | 29191 | 52286 |
| ELP3 | 6097 | 29192 | 52287 |
| ELP4 | 6098 | 29193 | 52288 |
| ELP4 | 6099 | 29194 | 52289 |
| ELP4 | 6100 | 29195 | 52290 |
| ELP5 | 6101 | 29196 | 52291 |
| ELP5 | 6102 | 29197 | 52292 |
| ELP6 | 6103 | 29198 | 52293 |
| ELSPBP1 | 6104 | 29199 | 52294 |
| EMB | 6105 | 29200 | 52295 |
| EMC1 | 6106 | 29201 | 52296 |
| EMC10 | 6107 | 29202 | 52297 |
| EMC10 | 6108 | 29203 | 52298 |
| EMC2 | 6109 | 29204 | 52299 |
| EMC2 | 6110 | 29205 | 52300 |
| EMC3 | 6111 | 29206 | 52301 |
| EMC4 | 6112 | 29207 | 52302 |
| EMC4 | 6113 | 29208 | 52303 |
| EMC6 | 6114 | 29209 | 52304 |
| EMC7 | 6115 | 29210 | 52305 |
| EMC8 | 6116 | 29211 | 52306 |
| EMC8 | 6117 | 29212 | 52307 |
| EMC9 | 6118 | 29213 | 52308 |
| EMCN | 6119 | 29214 | 52309 |
| EMD | 6120 | 29215 | 52310 |
| EME1 | 6121 | 29216 | 52311 |
| EME2 | 6122 | 29217 | 52312 |
| EMG1 | 6123 | 29218 | 52313 |
| EMID1 | 6124 | 29219 | 52314 |
| EMILIN1 | 6125 | 29220 | 52315 |
| EMILIN2 | 6126 | 29221 | 52316 |
| EMILIN3 | 6127 | 29222 | 52317 |
| EML1 | 6128 | 29223 | 52318 |
| EML2 | 6129 | 29224 | 52319 |
| EML3 | 6130 | 29225 | 52320 |
| EML3 | 6131 | 29226 | 52321 |
| EML4 | 6132 | 29227 | 52322 |
| EML5 | 6133 | 29228 | 52323 |
| EML6 | 6134 | 29229 | 52324 |
| EMP1 | 6135 | 29230 | 52325 |
| EMP2 | 6136 | 29231 | 52326 |
| EMP3 | 6137 | 29232 | 52327 |
| EMSY | 6138 | 29233 | 52328 |
| EMX1 | 6139 | 29234 | 52329 |
| EMX2 | 6140 | 29235 | 52330 |
| EMX2 | 6141 | 29236 | 52331 |
| EN1 | 6142 | 29237 | 52332 |
| EN2 | 6143 | 29238 | 52333 |
| ENAH | 6144 | 29239 | 52334 |
| ENAM | 6145 | 29240 | 52335 |
| ENC1 | 6146 | 29241 | 52336 |
| ENDOD1 | 6147 | 29242 | 52337 |
| ENDOG | 6148 | 29243 | 52338 |
| ENDOU | 6149 | 29244 | 52339 |
| ENDOV | 6150 | 29245 | 52340 |
| ENDOV | 6151 | 29246 | 52341 |
| ENDOV | 6152 | 29247 | 52342 |
| ENG | 6153 | 29248 | 52343 |
| ENG | 6154 | 29249 | 52344 |
| ENGASE | 6155 | 29250 | 52345 |
| ENHO | 6156 | 29251 | 52346 |
| ENKD1 | 6157 | 29252 | 52347 |
| ENKUR | 6158 | 29253 | 52348 |
| ENO1 | 6159 | 29254 | 52349 |
| ENO2 | 6160 | 29255 | 52350 |
| ENO3 | 6161 | 29256 | 52351 |
| ENO4 | 6162 | 29257 | 52352 |
| ENOPH1 | 6163 | 29258 | 52353 |
| ENOSF1 | 6164 | 29259 | 52354 |
| ENOX1 | 6165 | 29260 | 52355 |
| ENOX2 | 6166 | 29261 | 52356 |
| ENPEP | 6167 | 29262 | 52357 |
| ENPP1 | 6168 | 29263 | 52358 |
| ENPP2 | 6169 | 29264 | 52359 |
| ENPP3 | 6170 | 29265 | 52360 |
| ENPP4 | 6171 | 29266 | 52361 |
| ENPP5 | 6172 | 29267 | 52362 |
| ENPP6 | 6173 | 29268 | 52363 |
| ENPP7 | 6174 | 29269 | 52364 |
| ENSA | 6175 | 29270 | 52365 |
| ENSA | 6176 | 29271 | 52366 |
| ENSA | 6177 | 29272 | 52367 |
| ENTHD1 | 6178 | 29273 | 52368 |
| ENTPD1 | 6179 | 29274 | 52369 |
| ENTPD1 | 6180 | 29275 | 52370 |
| ENTPD2 | 6181 | 29276 | 52371 |
| ENTPD3 | 6182 | 29277 | 52372 |
| ENTPD3 | 6183 | 29278 | 52373 |
| ENTPD4 | 6184 | 29279 | 52374 |
| ENTPD5 | 6185 | 29280 | 52375 |
| ENTPD5 | 6186 | 29281 | 52376 |
| ENTPD5 | 6187 | 29282 | 52377 |
| ENTPD6 | 6188 | 29283 | 52378 |
| ENTPD6 | 6189 | 29284 | 52379 |
| ENTPD7 | 6190 | 29285 | 52380 |
| ENTPD8 | 6191 | 29286 | 52381 |
| ENY2 | 6192 | 29287 | 52382 |
| EOGT | 6193 | 29288 | 52383 |
| EOMES | 6194 | 29289 | 52384 |
| EP300 | 6195 | 29290 | 52385 |
| EP400 | 6196 | 29291 | 52386 |
| EPAS1 | 6197 | 29292 | 52387 |
| EPB41 | 6198 | 29293 | 52388 |
| EPB41 | 6199 | 29294 | 52389 |
| EPB41L1 | 6200 | 29295 | 52390 |
| EPB41L2 | 6201 | 29296 | 52391 |
| EPB41L3 | 6202 | 29297 | 52392 |
| EPB41L3 | 6203 | 29298 | 52393 |
| EPB41L4A | 6204 | 29299 | 52394 |
| EPB41L4A | 6205 | 29300 | 52395 |
| EPB41L4A | 6206 | 29301 | 52396 |
| EPB41L4B | 6207 | 29302 | 52397 |
| EPB41L4B | 6208 | 29303 | 52398 |
| EPB41L5 | 6209 | 29304 | 52399 |
| EPB41L5 | 6210 | 29305 | 52400 |
| EPB41L5 | 6211 | 29306 | 52401 |
| EPB42 | 6212 | 29307 | 52402 |
| EPC1 | 6213 | 29308 | 52403 |
| EPC2 | 6214 | 29309 | 52404 |
| EPCAM | 6215 | 29310 | 52405 |
| EPDR1 | 6216 | 29311 | 52406 |
| EPDR1 | 6217 | 29312 | 52407 |
| EPG5 | 6218 | 29313 | 52408 |
| EPGN | 6219 | 29314 | 52409 |
| EPHA1 | 6220 | 29315 | 52410 |
| EPHA10 | 6221 | 29316 | 52411 |
| EPHA10 | 6222 | 29317 | 52412 |
| EPHA2 | 6223 | 29318 | 52413 |
| EPHA3 | 6224 | 29319 | 52414 |
| EPHA3 | 6225 | 29320 | 52415 |
| EPHA4 | 6226 | 29321 | 52416 |
| EPHA5 | 6227 | 29322 | 52417 |
| EPHA5 | 6228 | 29323 | 52418 |
| EPHA6 | 6229 | 29324 | 52419 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| EPHA6 | 6230 | 29325 | 52420 |
| EPHA6 | 6231 | 29326 | 52421 |
| EPHA7 | 6232 | 29327 | 52422 |
| EPHA7 | 6233 | 29328 | 52423 |
| EPHA8 | 6234 | 29329 | 52424 |
| EPHA8 | 6235 | 29330 | 52425 |
| EPHB1 | 6236 | 29331 | 52426 |
| EPHB2 | 6237 | 29332 | 52427 |
| EPHB2 | 6238 | 29333 | 52428 |
| EPHB3 | 6239 | 29334 | 52429 |
| EPHB4 | 6240 | 29335 | 52430 |
| EPHB6 | 6241 | 29336 | 52431 |
| EPHX1 | 6242 | 29337 | 52432 |
| EPHX2 | 6243 | 29338 | 52433 |
| EPHX3 | 6244 | 29339 | 52434 |
| EPHX4 | 6245 | 29340 | 52435 |
| EPM2A | 6246 | 29341 | 52436 |
| EPM2A | 6247 | 29342 | 52437 |
| EPM2AIP1 | 6248 | 29343 | 52438 |
| EPN1 | 6249 | 29344 | 52439 |
| EPN2 | 6250 | 29345 | 52440 |
| EPN3 | 6251 | 29346 | 52441 |
| EPO | 6252 | 29347 | 52442 |
| EPOP | 6253 | 29348 | 52443 |
| EPOR | 6254 | 29349 | 52444 |
| EPPIN | 6255 | 29350 | 52445 |
| EPPIN | 6256 | 29351 | 52446 |
| EPPIN-WFDC6 | 6257 | 29352 | 52447 |
| EPPK1 | 6258 | 29353 | 52448 |
| EPRS | 6259 | 29354 | 52449 |
| EPS15 | 6260 | 29355 | 52450 |
| EPS15L1 | 6261 | 29356 | 52451 |
| EPS15L1 | 6262 | 29357 | 52452 |
| EPS15L1 | 6263 | 29358 | 52453 |
| EPS15L1 | 6264 | 29359 | 52454 |
| EPS8 | 6265 | 29360 | 52455 |
| EPS8L1 | 6266 | 29361 | 52456 |
| EPS8L2 | 6267 | 29362 | 52457 |
| EPS8L3 | 6268 | 29363 | 52458 |
| EPSTI1 | 6269 | 29364 | 52459 |
| EPSTI1 | 6270 | 29365 | 52460 |
| EPX | 6271 | 29366 | 52461 |
| EPYC | 6272 | 29367 | 52462 |
| EQTN | 6273 | 29368 | 52463 |
| ERAL1 | 6274 | 29369 | 52464 |
| ERAP1 | 6275 | 29370 | 52465 |
| ERAP1 | 6276 | 29371 | 52466 |
| ERAP2 | 6277 | 29372 | 52467 |
| ERAP2 | 6278 | 29373 | 52468 |
| ERAS | 6279 | 29374 | 52469 |
| ERBB2 | 6280 | 29375 | 52470 |
| ERBB2 | 6281 | 29376 | 52471 |
| ERBB2 | 6282 | 29377 | 52472 |
| ERBB3 | 6283 | 29378 | 52473 |
| ERBB3 | 6284 | 29379 | 52474 |
| ERBB4 | 6285 | 29380 | 52475 |
| ERBIN | 6286 | 29381 | 52476 |
| ERC1 | 6287 | 29382 | 52477 |
| ERC1 | 6288 | 29383 | 52478 |
| ERC2 | 6289 | 29384 | 52479 |
| ERCC1 | 6290 | 29385 | 52480 |
| ERCC1 | 6291 | 29386 | 52481 |
| ERCC2 | 6292 | 29387 | 52482 |
| ERCC2 | 6293 | 29388 | 52483 |
| ERCC3 | 6294 | 29389 | 52484 |
| ERCC4 | 6295 | 29390 | 52485 |
| ERCC5 | 6296 | 29391 | 52486 |
| ERCC6 | 6297 | 29392 | 52487 |
| ERCC6L | 6298 | 29393 | 52488 |
| ERCC6L2 | 6299 | 29394 | 52489 |
| ERCC6L2 | 6300 | 29395 | 52490 |
| ERCC8 | 6301 | 29396 | 52491 |
| ERCC8 | 6302 | 29397 | 52492 |
| EREG | 6303 | 29398 | 52493 |
| ERF | 6304 | 29399 | 52494 |
| ERFE | 6305 | 29400 | 52495 |
| ERG | 6306 | 29401 | 52496 |
| ERG | 6307 | 29402 | 52497 |
| ERG | 6308 | 29403 | 52498 |
| ERG28 | 6309 | 29404 | 52499 |
| ERGIC1 | 6310 | 29405 | 52500 |
| ERGIC2 | 6311 | 29406 | 52501 |
| ERGIC3 | 6312 | 29407 | 52502 |
| ERH | 6313 | 29408 | 52503 |
| ERI1 | 6314 | 29409 | 52504 |
| ERI2 | 6315 | 29410 | 52505 |
| ERI2 | 6316 | 29411 | 52506 |
| ERI3 | 6317 | 29412 | 52507 |
| ERI3 | 6318 | 29413 | 52508 |
| ERICH1 | 6319 | 29414 | 52509 |
| ERICH1 | 6320 | 29415 | 52510 |
| ERICH2 | 6321 | 29416 | 52511 |
| ERICH2 | 6322 | 29417 | 52512 |
| ERICH3 | 6323 | 29418 | 52513 |
| ERICH4 | 6324 | 29419 | 52514 |
| ERICH5 | 6325 | 29420 | 52515 |
| ERICH6 | 6326 | 29421 | 52516 |
| ERICH6B | 6327 | 29422 | 52517 |
| ERLEC1 | 6328 | 29423 | 52518 |
| ERLIN1 | 6329 | 29424 | 52519 |
| ERLIN2 | 6330 | 29425 | 52520 |
| ERLIN2 | 6331 | 29426 | 52521 |
| ERMAP | 6332 | 29427 | 52522 |
| ERMARD | 6333 | 29428 | 52523 |
| ERMN | 6334 | 29429 | 52524 |
| ERMP1 | 6335 | 29430 | 52525 |
| ERN1 | 6336 | 29431 | 52526 |
| ERN2 | 6337 | 29432 | 52527 |
| ERO1A | 6338 | 29433 | 52528 |
| ERO1B | 6339 | 29434 | 52529 |
| ERP27 | 6340 | 29435 | 52530 |
| ERP29 | 6341 | 29436 | 52531 |
| ERP44 | 6342 | 29437 | 52532 |
| ERRFI1 | 6343 | 29438 | 52533 |
| ERV3-1 | 6344 | 29439 | 52534 |
| ERVFRD-1 | 6345 | 29440 | 52535 |
| ERVH48-1 | 6346 | 29441 | 52536 |
| ERVMER34-1 | 6347 | 29442 | 52537 |
| ERW-1 | 6348 | 29443 | 52538 |
| ERW-2 | 6349 | 29444 | 52539 |
| ERVW-1 | 6350 | 29445 | 52540 |
| ESAM | 6351 | 29446 | 52541 |
| ESCO1 | 6352 | 29447 | 52542 |
| ESCO2 | 6353 | 29448 | 52543 |
| ESD | 6354 | 29449 | 52544 |
| ESF1 | 6355 | 29450 | 52545 |
| ESM1 | 6356 | 29451 | 52546 |
| ESPL1 | 6357 | 29452 | 52547 |
| ESPN | 6358 | 29453 | 52548 |
| ESPNL | 6359 | 29454 | 52549 |
| ESR1 | 6360 | 29455 | 52550 |
| ESR1 | 6361 | 29456 | 52551 |
| ESR2 | 6362 | 29457 | 52552 |
| ESR2 | 6363 | 29458 | 52553 |
| ESR2 | 6364 | 29459 | 52554 |
| ESR2 | 6365 | 29460 | 52555 |
| ESRP1 | 6366 | 29461 | 52556 |
| ESRP1 | 6367 | 29462 | 52557 |
| ESRP1 | 6368 | 29463 | 52558 |
| ESRP2 | 6369 | 29464 | 52559 |
| ESRRA | 6370 | 29465 | 52560 |
| ESRRB | 6371 | 29466 | 52561 |
| ESRRG | 6372 | 29467 | 52562 |
| ESS2 | 6373 | 29468 | 52563 |
| ESX1 | 6374 | 29469 | 52564 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ESYT1 | 6375 | 29470 | 52565 |
| ESYT2 | 6376 | 29471 | 52566 |
| ESYT3 | 6377 | 29472 | 52567 |
| ESYT3 | 6378 | 29473 | 52568 |
| ETAA1 | 6379 | 29474 | 52569 |
| ETF1 | 6380 | 29475 | 52570 |
| ETFA | 6381 | 29476 | 52571 |
| ETFB | 6382 | 29477 | 52572 |
| ETFBKMT | 6383 | 29478 | 52573 |
| ETFDH | 6384 | 29479 | 52574 |
| ETFRF1 | 6385 | 29480 | 52575 |
| ETHE1 | 6386 | 29481 | 52576 |
| ETNK1 | 6387 | 29482 | 52577 |
| ETNK1 | 6388 | 29483 | 52578 |
| ETNK2 | 6389 | 29484 | 52579 |
| ETNK2 | 6390 | 29485 | 52580 |
| ETNPPL | 6391 | 29486 | 52581 |
| ETS1 | 6392 | 29487 | 52582 |
| ETS2 | 6393 | 29488 | 52583 |
| ETV1 | 6394 | 29489 | 52584 |
| ETV2 | 6395 | 29490 | 52585 |
| ETV3 | 6396 | 29491 | 52586 |
| ETV3 | 6397 | 29492 | 52587 |
| ETV3L | 6398 | 29493 | 52588 |
| ETV4 | 6399 | 29494 | 52589 |
| ETV5 | 6400 | 29495 | 52590 |
| ETV6 | 6401 | 29496 | 52591 |
| ETV7 | 6402 | 29497 | 52592 |
| ETV7 | 6403 | 29498 | 52593 |
| EVA1A | 6404 | 29499 | 52594 |
| EVA1B | 6405 | 29500 | 52595 |
| EVA1C | 6406 | 29501 | 52596 |
| EVC | 6407 | 29502 | 52597 |
| EVC | 6408 | 29503 | 52598 |
| EVC2 | 6409 | 29504 | 52599 |
| EVI2A | 6410 | 29505 | 52600 |
| EVI2B | 6411 | 29506 | 52601 |
| EVI5 | 6412 | 29507 | 52602 |
| EVI5 | 6413 | 29508 | 52603 |
| EVI5L | 6414 | 29509 | 52604 |
| EVL | 6415 | 29510 | 52605 |
| EVPL | 6416 | 29511 | 52606 |
| EVPLL | 6417 | 29512 | 52607 |
| EVX1 | 6418 | 29513 | 52608 |
| EVX2 | 6419 | 29514 | 52609 |
| EWSR1 | 6420 | 29515 | 52610 |
| EWSR1 | 6421 | 29516 | 52611 |
| EXD1 | 6422 | 29517 | 52612 |
| EXD2 | 6423 | 29518 | 52613 |
| EXD3 | 6424 | 29519 | 52614 |
| EXD3 | 6425 | 29520 | 52615 |
| EXO1 | 6426 | 29521 | 52616 |
| EXO1 | 6427 | 29522 | 52617 |
| EXO5 | 6428 | 29523 | 52618 |
| EXOC1 | 6429 | 29524 | 52619 |
| EXOC1L | 6430 | 29525 | 52620 |
| EXOC2 | 6431 | 29526 | 52621 |
| EXOC3 | 6432 | 29527 | 52622 |
| EXOC3L1 | 6433 | 29528 | 52623 |
| EXOC3L2 | 6434 | 29529 | 52624 |
| EXOC3L4 | 6435 | 29530 | 52625 |
| EXOC4 | 6436 | 29531 | 52626 |
| EXOC4 | 6437 | 29532 | 52627 |
| EXOC5 | 6438 | 29533 | 52628 |
| EXOC6 | 6439 | 29534 | 52629 |
| EXOC6B | 6440 | 29535 | 52630 |
| EXOC6B | 6441 | 29536 | 52631 |
| EXOC7 | 6442 | 29537 | 52632 |
| EXOC7 | 6443 | 29538 | 52633 |
| EXOC8 | 6444 | 29539 | 52634 |
| EXOG | 6445 | 29540 | 52635 |
| EXOSC1 | 6446 | 29541 | 52636 |
| EXOSC1 | 6447 | 29542 | 52637 |
| EXOSC10 | 6448 | 29543 | 52638 |
| EXOSC2 | 6449 | 29544 | 52639 |
| EXOSC3 | 6450 | 29545 | 52640 |
| EXOSC3 | 6451 | 29546 | 52641 |
| EXOSC4 | 6452 | 29547 | 52642 |
| EXOSC5 | 6453 | 29548 | 52643 |
| EXOSC6 | 6454 | 29549 | 52644 |
| EXOSC7 | 6455 | 29550 | 52645 |
| EXOSC8 | 6456 | 29551 | 52646 |
| EXOSC9 | 6457 | 29552 | 52647 |
| EXPH5 | 6458 | 29553 | 52648 |
| EXT1 | 6459 | 29554 | 52649 |
| EXT2 | 6460 | 29555 | 52650 |
| EXTL1 | 6461 | 29556 | 52651 |
| EXTL2 | 6462 | 29557 | 52652 |
| EXTL3 | 6463 | 29558 | 52653 |
| EYA1 | 6464 | 29559 | 52654 |
| EYA2 | 6465 | 29560 | 52655 |
| EYA3 | 6466 | 29561 | 52656 |
| EYA3 | 6467 | 29562 | 52657 |
| EYA4 | 6468 | 29563 | 52658 |
| EYS | 6469 | 29564 | 52659 |
| EYS | 6470 | 29565 | 52660 |
| EYS | 6471 | 29566 | 52661 |
| EZH1 | 6472 | 29567 | 52662 |
| EZH2 | 6473 | 29568 | 52663 |
| EZR | 6474 | 29569 | 52664 |
| F10 | 6475 | 29570 | 52665 |
| F10 | 6476 | 29571 | 52666 |
| F11 | 6477 | 29572 | 52667 |
| F11R | 6478 | 29573 | 52668 |
| F12 | 6479 | 29574 | 52669 |
| F13A1 | 6480 | 29575 | 52670 |
| F13B | 6481 | 29576 | 52671 |
| F2 | 6482 | 29577 | 52672 |
| F2R | 6483 | 29578 | 52673 |
| F2RL1 | 6484 | 29579 | 52674 |
| F2RL2 | 6485 | 29580 | 52675 |
| F2RL3 | 6486 | 29581 | 52676 |
| F3 | 6487 | 29582 | 52677 |
| F3 | 6488 | 29583 | 52678 |
| F5 | 6489 | 29584 | 52679 |
| F7 | 6490 | 29585 | 52680 |
| F8 | 6491 | 29586 | 52681 |
| F8A3 | 6492 | 29587 | 52682 |
| F9 | 6493 | 29588 | 52683 |
| FA2H | 6494 | 29589 | 52684 |
| FAAH | 6495 | 29590 | 52685 |
| FAAH2 | 6496 | 29591 | 52686 |
| FAAP100 | 6497 | 29592 | 52687 |
| FAAP20 | 6498 | 29593 | 52688 |
| FAAP20 | 6499 | 29594 | 52689 |
| FAAP20 | 6500 | 29595 | 52690 |
| FAAP20 | 6501 | 29596 | 52691 |
| FAAP20 | 6502 | 29597 | 52692 |
| FAAP20 | 6503 | 29598 | 52693 |
| FAAP20 | 6504 | 29599 | 52694 |
| FAAP24 | 6505 | 29600 | 52695 |
| FABP1 | 6506 | 29601 | 52696 |
| FABP12 | 6507 | 29602 | 52697 |
| FABP2 | 6508 | 29603 | 52698 |
| FABP3 | 6509 | 29604 | 52699 |
| FABP4 | 6510 | 29605 | 52700 |
| FABP5 | 6511 | 29606 | 52701 |
| FABP6 | 6512 | 29607 | 52702 |
| FABP7 | 6513 | 29608 | 52703 |
| FABP7 | 6514 | 29609 | 52704 |
| FABP9 | 6515 | 29610 | 52705 |
| FADD | 6516 | 29611 | 52706 |
| FADS1 | 6517 | 29612 | 52707 |
| FADS2 | 6518 | 29613 | 52708 |
| FADS3 | 6519 | 29614 | 52709 |
| FADS6 | 6520 | 29615 | 52710 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| FAF1 | 6521 | 29616 | 52711 |
| FAF2 | 6522 | 29617 | 52712 |
| FAH | 6523 | 29618 | 52713 |
| FAHD1 | 6524 | 29619 | 52714 |
| FAHD1 | 6525 | 29620 | 52715 |
| FAHD1 | 6526 | 29621 | 52716 |
| FAHD2B | 6527 | 29622 | 52717 |
| FAHD2B | 6528 | 29623 | 52718 |
| FAIM | 6529 | 29624 | 52719 |
| FAIM2 | 6530 | 29625 | 52720 |
| FAM102A | 6531 | 29626 | 52721 |
| FAM102B | 6532 | 29627 | 52722 |
| FAM103A1 | 6533 | 29628 | 52723 |
| FAM104A | 6534 | 29629 | 52724 |
| FAM104A | 6535 | 29630 | 52725 |
| FAM104B | 6536 | 29631 | 52726 |
| FAM104B | 6537 | 29632 | 52727 |
| FAM104B | 6538 | 29633 | 52728 |
| FAM105A | 6539 | 29634 | 52729 |
| FAM106CP | 6540 | 29635 | 52730 |
| FAM107A | 6541 | 29636 | 52731 |
| FAM107B | 6542 | 29637 | 52732 |
| FAM107B | 6543 | 29638 | 52733 |
| FAM109A | 6544 | 29639 | 52734 |
| FAM109B | 6545 | 29640 | 52735 |
| FAM110A | 6546 | 29641 | 52736 |
| FAM110B | 6547 | 29642 | 52737 |
| FAM110C | 6548 | 29643 | 52738 |
| FAM110D | 6549 | 29644 | 52739 |
| FAM111A | 6550 | 29645 | 52740 |
| FAM111B | 6551 | 29646 | 52741 |
| FAM114A1 | 6552 | 29647 | 52742 |
| FAM114A1 | 6553 | 29648 | 52743 |
| FAM114A1 | 6554 | 29649 | 52744 |
| FAM114A2 | 6555 | 29650 | 52745 |
| FAM117A | 6556 | 29651 | 52746 |
| FAM117B | 6557 | 29652 | 52747 |
| FAM118A | 6558 | 29653 | 52748 |
| FAM118B | 6559 | 29654 | 52749 |
| FAM120A | 6560 | 29655 | 52750 |
| FAM120A | 6561 | 29656 | 52751 |
| FAM120A | 6562 | 29657 | 52752 |
| FAM120AOS | 6563 | 29658 | 52753 |
| FAM120B | 6564 | 29659 | 52754 |
| FAM120C | 6565 | 29660 | 52755 |
| FAM120C | 6566 | 29661 | 52756 |
| FAM120C | 6567 | 29662 | 52757 |
| FAM122A | 6568 | 29663 | 52758 |
| FAM122B | 6569 | 29664 | 52759 |
| FAM122B | 6570 | 29665 | 52760 |
| FAM122C | 6571 | 29666 | 52761 |
| FAM122C | 6572 | 29667 | 52762 |
| FAM122C | 6573 | 29668 | 52763 |
| FAM122C | 6574 | 29669 | 52764 |
| FAM122C | 6575 | 29670 | 52765 |
| FAM122C | 6576 | 29671 | 52766 |
| FAM124A | 6577 | 29672 | 52767 |
| FAM124A | 6578 | 29673 | 52768 |
| FAM124B | 6579 | 29674 | 52769 |
| FAM124B | 6580 | 29675 | 52770 |
| FAM126A | 6581 | 29676 | 52771 |
| FAM126B | 6582 | 29677 | 52772 |
| FAM129A | 6583 | 29678 | 52773 |
| FAM129B | 6584 | 29679 | 52774 |
| FAM129C | 6585 | 29680 | 52775 |
| FAM129C | 6586 | 29681 | 52776 |
| FAM131A | 6587 | 29682 | 52777 |
| FAM131B | 6588 | 29683 | 52778 |
| FAM131C | 6589 | 29684 | 52779 |
| FAM133A | 6590 | 29685 | 52780 |
| FAM133B | 6591 | 29686 | 52781 |
| FAM135A | 6592 | 29687 | 52782 |
| FAM135B | 6593 | 29688 | 52783 |
| FAM136A | 6594 | 29689 | 52784 |
| FAM13A | 6595 | 29690 | 52785 |
| FAM13B | 6596 | 29691 | 52786 |
| FAM13C | 6597 | 29692 | 52787 |
| FAM13C | 6598 | 29693 | 52788 |
| FAM149A | 6599 | 29694 | 52789 |
| FAM149B1 | 6600 | 29695 | 52790 |
| FAM151A | 6601 | 29696 | 52791 |
| FAM151B | 6602 | 29697 | 52792 |
| FAM153B | 6603 | 29698 | 52793 |
| FAM155A | 6604 | 29699 | 52794 |
| FAM155B | 6605 | 29700 | 52795 |
| FAM156B | 6606 | 29701 | 52796 |
| FAM159A | 6607 | 29702 | 52797 |
| FAM159B | 6608 | 29703 | 52798 |
| FAM160A1 | 6609 | 29704 | 52799 |
| FAM160A2 | 6610 | 29705 | 52800 |
| FAM160B1 | 6611 | 29706 | 52801 |
| FAM160B1 | 6612 | 29707 | 52802 |
| FAM160B2 | 6613 | 29708 | 52803 |
| FAM161A | 6614 | 29709 | 52804 |
| FAM161B | 6615 | 29710 | 52805 |
| FAM162A | 6616 | 29711 | 52806 |
| FAM162B | 6617 | 29712 | 52807 |
| FAM163A | 6618 | 29713 | 52808 |
| FAM163A | 6619 | 29714 | 52809 |
| FAM163B | 6620 | 29715 | 52810 |
| FAM166A | 6621 | 29716 | 52811 |
| FAM166B | 6622 | 29717 | 52812 |
| FAM166B | 6623 | 29718 | 52813 |
| FAM166B | 6624 | 29719 | 52814 |
| FAM167A | 6625 | 29720 | 52815 |
| FAM167B | 6626 | 29721 | 52816 |
| FAM168A | 6627 | 29722 | 52817 |
| FAM168B | 6628 | 29723 | 52818 |
| FAM169A | 6629 | 29724 | 52819 |
| FAM169B | 6630 | 29725 | 52820 |
| FAM170A | 6631 | 29726 | 52821 |
| FAM170B | 6632 | 29727 | 52822 |
| FAM171A1 | 6633 | 29728 | 52823 |
| FAM171A2 | 6634 | 29729 | 52824 |
| FAM171B | 6635 | 29730 | 52825 |
| FAM172A | 6636 | 29731 | 52826 |
| FAM173A | 6637 | 29732 | 52827 |
| FAM173B | 6638 | 29733 | 52828 |
| FAM173B | 6639 | 29734 | 52829 |
| FAM174A | 6640 | 29735 | 52830 |
| FAM174B | 6641 | 29736 | 52831 |
| FAM177A1 | 6642 | 29737 | 52832 |
| FAM177B | 6643 | 29738 | 52833 |
| FAM178B | 6644 | 29739 | 52834 |
| FAM180A | 6645 | 29740 | 52835 |
| FAM180B | 6646 | 29741 | 52836 |
| FAM181A | 6647 | 29742 | 52837 |
| FAM181B | 6648 | 29743 | 52838 |
| FAM183A | 6649 | 29744 | 52839 |
| FAM184A | 6650 | 29745 | 52840 |
| FAM184B | 6651 | 29746 | 52841 |
| FAM185A | 6652 | 29747 | 52842 |
| FAM186A | 6653 | 29748 | 52843 |
| FAM186B | 6654 | 29749 | 52844 |
| FAM187A | 6655 | 29750 | 52845 |
| FAM187B | 6656 | 29751 | 52846 |
| FAM189A1 | 6657 | 29752 | 52847 |
| FAM189A2 | 6658 | 29753 | 52848 |
| FAM189B | 6659 | 29754 | 52849 |
| FAM192A | 6660 | 29755 | 52850 |
| FAM193A | 6661 | 29756 | 52851 |
| FAM193A | 6662 | 29757 | 52852 |
| FAM193B | 6663 | 29758 | 52853 |
| FAM196A | 6664 | 29759 | 52854 |
| FAM196B | 6665 | 29760 | 52855 |
| FAM198A | 6666 | 29761 | 52856 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| FAM198B | 6667 | 29762 | 52857 |
| FAM199X | 6668 | 29763 | 52858 |
| FAM19A1 | 6669 | 29764 | 52859 |
| FAM19A2 | 6670 | 29765 | 52860 |
| FAM19A3 | 6671 | 29766 | 52861 |
| FAM19A3 | 6672 | 29767 | 52862 |
| FAM19A4 | 6673 | 29768 | 52863 |
| FAM19A5 | 6674 | 29769 | 52864 |
| FAM200A | 6675 | 29770 | 52865 |
| FAM200B | 6676 | 29771 | 52866 |
| FAM204A | 6677 | 29772 | 52867 |
| FAM205A | 6678 | 29773 | 52868 |
| FAM205C | 6679 | 29774 | 52869 |
| FAM206A | 6680 | 29775 | 52870 |
| FAM207A | 6681 | 29776 | 52871 |
| FAM208A | 6682 | 29777 | 52872 |
| FAM208A | 6683 | 29778 | 52873 |
| FAM208B | 6684 | 29779 | 52874 |
| FAM209B | 6685 | 29780 | 52875 |
| FAM20A | 6686 | 29781 | 52876 |
| FAM20B | 6687 | 29782 | 52877 |
| FAM20C | 6688 | 29783 | 52878 |
| FAM210A | 6689 | 29784 | 52879 |
| FAM210B | 6690 | 29785 | 52880 |
| FAM212A | 6691 | 29786 | 52881 |
| FAM212B | 6692 | 29787 | 52882 |
| FAM213A | 6693 | 29788 | 52883 |
| FAM213B | 6694 | 29789 | 52884 |
| FAM213B | 6695 | 29790 | 52885 |
| FAM214A | 6696 | 29791 | 52886 |
| FAM214B | 6697 | 29792 | 52887 |
| FAM216A | 6698 | 29793 | 52888 |
| FAM216B | 6699 | 29794 | 52889 |
| FAM217A | 6700 | 29795 | 52890 |
| FAM217B | 6701 | 29796 | 52891 |
| FAM218A | 6702 | 29797 | 52892 |
| FAM219A | 6703 | 29798 | 52893 |
| FAM219B | 6704 | 29799 | 52894 |
| FAM220A | 6705 | 29800 | 52895 |
| FAM221A | 6706 | 29801 | 52896 |
| FAM221B | 6707 | 29802 | 52897 |
| FAM222A | 6708 | 29803 | 52898 |
| FAM222B | 6709 | 29804 | 52899 |
| FAM227A | 6710 | 29805 | 52900 |
| FAM227B | 6711 | 29806 | 52901 |
| FAM227B | 6712 | 29807 | 52902 |
| FAM228A | 6713 | 29808 | 52903 |
| FAM228B | 6714 | 29809 | 52904 |
| FAM229A | 6715 | 29810 | 52905 |
| FAM229B | 6716 | 29811 | 52906 |
| FAM231B | 6717 | 29812 | 52907 |
| FAM231C | 6718 | 29813 | 52908 |
| FAM234A | 6719 | 29814 | 52909 |
| FAM234B | 6720 | 29815 | 52910 |
| FAM236D | 6721 | 29816 | 52911 |
| FAM237A | 6722 | 29817 | 52912 |
| FAM240A | 6723 | 29818 | 52913 |
| FAM241A | 6724 | 29819 | 52914 |
| FAM241B | 6725 | 29820 | 52915 |
| FAM24A | 6726 | 29821 | 52916 |
| FAM24B | 6727 | 29822 | 52917 |
| FAM25A | 6728 | 29823 | 52918 |
| FAM25C | 6729 | 29824 | 52919 |
| FAM25E | 6730 | 29825 | 52920 |
| FAM32A | 6731 | 29826 | 52921 |
| FAM35A | 6732 | 29827 | 52922 |
| FAM3A | 6733 | 29828 | 52923 |
| FAM3B | 6734 | 29829 | 52924 |
| FAM3C | 6735 | 29830 | 52925 |
| FAM3D | 6736 | 29831 | 52926 |
| FAM43A | 6737 | 29832 | 52927 |
| FAM43B | 6738 | 29833 | 52928 |
| FAM45A | 6739 | 29834 | 52929 |
| FAM46A | 6740 | 29835 | 52930 |
| FAM46B | 6741 | 29836 | 52931 |
| FAM46C | 6742 | 29837 | 52932 |
| FAM46D | 6743 | 29838 | 52933 |
| FAM47A | 6744 | 29839 | 52934 |
| FAM47B | 6745 | 29840 | 52935 |
| FAM47C | 6746 | 29841 | 52936 |
| FAM47E | 6747 | 29842 | 52937 |
| FAM47E-STBD1 | 6748 | 29843 | 52938 |
| FAM49A | 6749 | 29844 | 52939 |
| FAM49B | 6750 | 29845 | 52940 |
| FAM50A | 6751 | 29846 | 52941 |
| FAM50B | 6752 | 29847 | 52942 |
| FAM53A | 6753 | 29848 | 52943 |
| FAM53A | 6754 | 29849 | 52944 |
| FAM53B | 6755 | 29850 | 52945 |
| FAM53C | 6756 | 29851 | 52946 |
| FAM57A | 6757 | 29852 | 52947 |
| FAM57B | 6758 | 29853 | 52948 |
| FAM69A | 6759 | 29854 | 52949 |
| FAM69A | 6760 | 29855 | 52950 |
| FAM69B | 6761 | 29856 | 52951 |
| FAM69C | 6762 | 29857 | 52952 |
| FAM71A | 6763 | 29858 | 52953 |
| FAM71B | 6764 | 29859 | 52954 |
| FAM71C | 6765 | 29860 | 52955 |
| FAM71D | 6766 | 29861 | 52956 |
| FAM71E1 | 6767 | 29862 | 52957 |
| FAM71E2 | 6768 | 29863 | 52958 |
| FAM71F1 | 6769 | 29864 | 52959 |
| FAM71F2 | 6770 | 29865 | 52960 |
| FAM72C | 6771 | 29866 | 52961 |
| FAM72C | 6772 | 29867 | 52962 |
| FAM72C | 6773 | 29868 | 52963 |
| FAM76A | 6774 | 29869 | 52964 |
| FAM76B | 6775 | 29870 | 52965 |
| FAM78A | 6776 | 29871 | 52966 |
| FAM78B | 6777 | 29872 | 52967 |
| FAM78B | 6778 | 29873 | 52968 |
| FAM81A | 6779 | 29874 | 52969 |
| FAM81B | 6780 | 29875 | 52970 |
| FAM83A | 6781 | 29876 | 52971 |
| FAM83A | 6782 | 29877 | 52972 |
| FAM83A | 6783 | 29878 | 52973 |
| FAM83A | 6784 | 29879 | 52974 |
| FAM83B | 6785 | 29880 | 52975 |
| FAM83C | 6786 | 29881 | 52976 |
| FAM83D | 6787 | 29882 | 52977 |
| FAM83E | 6788 | 29883 | 52978 |
| FAM83F | 6789 | 29884 | 52979 |
| FAM83G | 6790 | 29885 | 52980 |
| FAM83H | 6791 | 29886 | 52981 |
| FAM84A | 6792 | 29887 | 52982 |
| FAM84B | 6793 | 29888 | 52983 |
| FAM86B2 | 6794 | 29889 | 52984 |
| FAM86C1 | 6795 | 29890 | 52985 |
| FAM89A | 6796 | 29891 | 52986 |
| FAM89B | 6797 | 29892 | 52987 |
| FAM8A1 | 6798 | 29893 | 52988 |
| FAM90A1 | 6799 | 29894 | 52989 |
| FAM91A1 | 6800 | 29895 | 52990 |
| FAM91A1 | 6801 | 29896 | 52991 |
| FAM92A | 6802 | 29897 | 52992 |
| FAM92B | 6803 | 29898 | 52993 |
| FAM96A | 6804 | 29899 | 52994 |
| FAM96A | 6805 | 29900 | 52995 |
| FAM96B | 6806 | 29901 | 52996 |
| FAM98A | 6807 | 29902 | 52997 |
| FAM98B | 6808 | 29903 | 52998 |
| FAM98C | 6809 | 29904 | 52999 |
| FAM9A | 6810 | 29905 | 53000 |
| FAM9B | 6811 | 29906 | 53001 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| FAM9C | 6812 | 29907 | 53002 |
| FAN1 | 6813 | 29908 | 53003 |
| FAN1 | 6814 | 29909 | 53004 |
| FANCA | 6815 | 29910 | 53005 |
| FANCA | 6816 | 29911 | 53006 |
| FANCA | 6817 | 29912 | 53007 |
| FANCB | 6818 | 29913 | 53008 |
| FANCC | 6819 | 29914 | 53009 |
| FANCC | 6820 | 29915 | 53010 |
| FANCD2 | 6821 | 29916 | 53011 |
| FANCD2 | 6822 | 29917 | 53012 |
| FANCD2OS | 6823 | 29918 | 53013 |
| FANCE | 6824 | 29919 | 53014 |
| FANCF | 6825 | 29920 | 53015 |
| FANCG | 6826 | 29921 | 53016 |
| FANCI | 6827 | 29922 | 53017 |
| FANCL | 6828 | 29923 | 53018 |
| FANCM | 6829 | 29924 | 53019 |
| FANCM | 6830 | 29925 | 53020 |
| FANK1 | 6831 | 29926 | 53021 |
| FAP | 6832 | 29927 | 53022 |
| FAR1 | 6833 | 29928 | 53023 |
| FAR2 | 6834 | 29929 | 53024 |
| FARP1 | 6835 | 29930 | 53025 |
| FARP1 | 6836 | 29931 | 53026 |
| FARP2 | 6837 | 29932 | 53027 |
| FARP2 | 6838 | 29933 | 53028 |
| FARP2 | 6839 | 29934 | 53029 |
| FARS2 | 6840 | 29935 | 53030 |
| FARSA | 6841 | 29936 | 53031 |
| FARSB | 6842 | 29937 | 53032 |
| FAS | 6843 | 29938 | 53033 |
| FAS | 6844 | 29939 | 53034 |
| FAS | 6845 | 29940 | 53035 |
| FASLG | 6846 | 29941 | 53036 |
| FASLG | 6847 | 29942 | 53037 |
| FASN | 6848 | 29943 | 53038 |
| FASTK | 6849 | 29944 | 53039 |
| FASTKD1 | 6850 | 29945 | 53040 |
| FASTKD2 | 6851 | 29946 | 53041 |
| FASTKD3 | 6852 | 29947 | 53042 |
| FASTKD5 | 6853 | 29948 | 53043 |
| FAT1 | 6854 | 29949 | 53044 |
| FAT2 | 6855 | 29950 | 53045 |
| FAT3 | 6856 | 29951 | 53046 |
| FAT4 | 6857 | 29952 | 53047 |
| FATE1 | 6858 | 29953 | 53048 |
| FAU | 6859 | 29954 | 53049 |
| FAXC | 6860 | 29955 | 53050 |
| FAXDC2 | 6861 | 29956 | 53051 |
| FBF1 | 6862 | 29957 | 53052 |
| FBL | 6863 | 29958 | 53053 |
| FBLIM1 | 6864 | 29959 | 53054 |
| FBLIM1 | 6865 | 29960 | 53055 |
| FBLN1 | 6866 | 29961 | 53056 |
| FBLN1 | 6867 | 29962 | 53057 |
| FBLN1 | 6868 | 29963 | 53058 |
| FBLN1 | 6869 | 29964 | 53059 |
| FBLN2 | 6870 | 29965 | 53060 |
| FBLN5 | 6871 | 29966 | 53061 |
| FBLN7 | 6872 | 29967 | 53062 |
| FBN1 | 6873 | 29968 | 53063 |
| FBN2 | 6874 | 29969 | 53064 |
| FBN3 | 6875 | 29970 | 53065 |
| FBP1 | 6876 | 29971 | 53066 |
| FBP2 | 6877 | 29972 | 53067 |
| FBRS | 6878 | 29973 | 53068 |
| FBRSL1 | 6879 | 29974 | 53069 |
| FBXL12 | 6880 | 29975 | 53070 |
| FBXL13 | 6881 | 29976 | 53071 |
| FBXL14 | 6882 | 29977 | 53072 |
| FBXL15 | 6883 | 29978 | 53073 |
| FBXL16 | 6884 | 29979 | 53074 |
| FBXL17 | 6885 | 29980 | 53075 |
| FBXL18 | 6886 | 29981 | 53076 |
| FBXL18 | 6887 | 29982 | 53077 |
| FBXL19 | 6888 | 29983 | 53078 |
| FBXL2 | 6889 | 29984 | 53079 |
| FBXL20 | 6890 | 29985 | 53080 |
| FBXL21 | 6891 | 29986 | 53081 |
| FBXL22 | 6892 | 29987 | 53082 |
| FBXL3 | 6893 | 29988 | 53083 |
| FBXL4 | 6894 | 29989 | 53084 |
| FBXL5 | 6895 | 29990 | 53085 |
| FBXL6 | 6896 | 29991 | 53086 |
| FBXL7 | 6897 | 29992 | 53087 |
| FBXL8 | 6898 | 29993 | 53088 |
| FBXO10 | 6899 | 29994 | 53089 |
| FBXO11 | 6900 | 29995 | 53090 |
| FBXO15 | 6901 | 29996 | 53091 |
| FBXO16 | 6902 | 29997 | 53092 |
| FBXO17 | 6903 | 29998 | 53093 |
| FBXO18 | 6904 | 29999 | 53094 |
| FBXO2 | 6905 | 30000 | 53095 |
| FBXO20 | 6906 | 30001 | 53096 |
| FBXO22 | 6907 | 30002 | 53097 |
| FBXO22 | 6908 | 30003 | 53098 |
| FBXO24 | 6909 | 30004 | 53099 |
| FBXO25 | 6910 | 30005 | 53100 |
| FBXO27 | 6911 | 30006 | 53101 |
| FBXO28 | 6912 | 30007 | 53102 |
| FBXO28 | 6913 | 30008 | 53103 |
| FBXO3 | 6914 | 30009 | 53104 |
| FBXO3 | 6915 | 30010 | 53105 |
| FBXO30 | 6916 | 30011 | 53106 |
| FBXO31 | 6917 | 30012 | 53107 |
| FBXO32 | 6918 | 30013 | 53108 |
| FBXO33 | 6919 | 30014 | 53109 |
| FBXO34 | 6920 | 30015 | 53110 |
| FBXO36 | 6921 | 30016 | 53111 |
| FBXO38 | 6922 | 30017 | 53112 |
| FBXO39 | 6923 | 30018 | 53113 |
| FBXO4 | 6924 | 30019 | 53114 |
| FBXO4 | 6925 | 30020 | 53115 |
| FBXO4 | 6926 | 30021 | 53116 |
| FBXO40 | 6927 | 30022 | 53117 |
| FBXO41 | 6928 | 30023 | 53118 |
| FBXO42 | 6929 | 30024 | 53119 |
| FBXO43 | 6930 | 30025 | 53120 |
| FBXO44 | 6931 | 30026 | 53121 |
| FBXO44 | 6932 | 30027 | 53122 |
| FBXO45 | 6933 | 30028 | 53123 |
| FBXO46 | 6934 | 30029 | 53124 |
| FBXO47 | 6935 | 30030 | 53125 |
| FBXO48 | 6936 | 30031 | 53126 |
| FBXO5 | 6937 | 30032 | 53127 |
| FBXO6 | 6938 | 30033 | 53128 |
| FBXO7 | 6939 | 30034 | 53129 |
| FBXO8 | 6940 | 30035 | 53130 |
| FBXO9 | 6941 | 30036 | 53131 |
| FBXW10 | 6942 | 30037 | 53132 |
| FBXW11 | 6943 | 30038 | 53133 |
| FBXW12 | 6944 | 30039 | 53134 |
| FBXW2 | 6945 | 30040 | 53135 |
| FBXW4 | 6946 | 30041 | 53136 |
| FBXW5 | 6947 | 30042 | 53137 |
| FBXW7 | 6948 | 30043 | 53138 |
| FBXW7 | 6949 | 30044 | 53139 |
| FBXW8 | 6950 | 30045 | 53140 |
| FBXW9 | 6951 | 30046 | 53141 |
| FCAMR | 6952 | 30047 | 53142 |
| FCAMR | 6953 | 30048 | 53143 |
| FCAR | 6954 | 30049 | 53144 |
| FCAR | 6955 | 30050 | 53145 |
| FCER1A | 6956 | 30051 | 53146 |
| FCER1G | 6957 | 30052 | 53147 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| FCER2 | 6958 | 30053 | 53148 |
| FCF1 | 6959 | 30054 | 53149 |
| FCGBP | 6960 | 30055 | 53150 |
| FCGR1A | 6961 | 30056 | 53151 |
| FCGR1B | 6962 | 30057 | 53152 |
| FCGR1B | 6963 | 30058 | 53153 |
| FCGR2A | 6964 | 30059 | 53154 |
| FCGR2B | 6965 | 30060 | 53155 |
| FCGR3A | 6966 | 30061 | 53156 |
| FCGR3B | 6967 | 30062 | 53157 |
| FCGRT | 6968 | 30063 | 53158 |
| FCHO1 | 6969 | 30064 | 53159 |
| FCHO2 | 6970 | 30065 | 53160 |
| FCHSD1 | 6971 | 30066 | 53161 |
| FCHSD2 | 6972 | 30067 | 53162 |
| FCMR | 6973 | 30068 | 53163 |
| FCMR | 6974 | 30069 | 53164 |
| FCN1 | 6975 | 30070 | 53165 |
| FCN2 | 6976 | 30071 | 53166 |
| FCN3 | 6977 | 30072 | 53167 |
| FCRL1 | 6978 | 30073 | 53168 |
| FCRL1 | 6979 | 30074 | 53169 |
| FCRL2 | 6980 | 30075 | 53170 |
| FCRL3 | 6981 | 30076 | 53171 |
| FCRL3 | 6982 | 30077 | 53172 |
| FCRL4 | 6983 | 30078 | 53173 |
| FCRL5 | 6984 | 30079 | 53174 |
| FCRL5 | 6985 | 30080 | 53175 |
| FCRL6 | 6986 | 30081 | 53176 |
| FCRL6 | 6987 | 30082 | 53177 |
| FCRLA | 6988 | 30083 | 53178 |
| FCRLB | 6989 | 30084 | 53179 |
| FCRLB | 6990 | 30085 | 53180 |
| FCRLB | 6991 | 30086 | 53181 |
| FDCSP | 6992 | 30087 | 53182 |
| FDFT1 | 6993 | 30088 | 53183 |
| FDPS | 6994 | 30089 | 53184 |
| FDX1 | 6995 | 30090 | 53185 |
| FDX1L | 6996 | 30091 | 53186 |
| FDXACB1 | 6997 | 30092 | 53187 |
| FDXR | 6998 | 30093 | 53188 |
| FECH | 6999 | 30094 | 53189 |
| FEM1A | 7000 | 30095 | 53190 |
| FEM1B | 7001 | 30096 | 53191 |
| FEM1C | 7002 | 30097 | 53192 |
| FEN1 | 7003 | 30098 | 53193 |
| FER | 7004 | 30099 | 53194 |
| FER | 7005 | 30100 | 53195 |
| FER1L5 | 7006 | 30101 | 53196 |
| FER1L6 | 7007 | 30102 | 53197 |
| FERD3L | 7008 | 30103 | 53198 |
| FERMT1 | 7009 | 30104 | 53199 |
| FERMT2 | 7010 | 30105 | 53200 |
| FERMT2 | 7011 | 30106 | 53201 |
| FERMT3 | 7012 | 30107 | 53202 |
| FES | 7013 | 30108 | 53203 |
| FETUB | 7014 | 30109 | 53204 |
| FEV | 7015 | 30110 | 53205 |
| FEZ1 | 7016 | 30111 | 53206 |
| FEZ1 | 7017 | 30112 | 53207 |
| FEZ2 | 7018 | 30113 | 53208 |
| FEZF1 | 7019 | 30114 | 53209 |
| FEZF2 | 7020 | 30115 | 53210 |
| FFAR1 | 7021 | 30116 | 53211 |
| FFAR2 | 7022 | 30117 | 53212 |
| FFAR3 | 7023 | 30118 | 53213 |
| FFAR4 | 7024 | 30119 | 53214 |
| FGA | 7025 | 30120 | 53215 |
| FGA | 7026 | 30121 | 53216 |
| FGB | 7027 | 30122 | 53217 |
| FGD1 | 7028 | 30123 | 53218 |
| FGD2 | 7029 | 30124 | 53219 |
| FGD3 | 7030 | 30125 | 53220 |
| FGD4 | 7031 | 30126 | 53221 |
| FGD4 | 7032 | 30127 | 53222 |
| FGD5 | 7033 | 30128 | 53223 |
| FGD6 | 7034 | 30129 | 53224 |
| FGF1 | 7035 | 30130 | 53225 |
| FGF10 | 7036 | 30131 | 53226 |
| FGF11 | 7037 | 30132 | 53227 |
| FGF12 | 7038 | 30133 | 53228 |
| FGF13 | 7039 | 30134 | 53229 |
| FGF14 | 7040 | 30135 | 53230 |
| FGF14 | 7041 | 30136 | 53231 |
| FGF16 | 7042 | 30137 | 53232 |
| FGF17 | 7043 | 30138 | 53233 |
| FGF18 | 7044 | 30139 | 53234 |
| FGF19 | 7045 | 30140 | 53235 |
| FGF2 | 7046 | 30141 | 53236 |
| FGF20 | 7047 | 30142 | 53237 |
| FGF21 | 7048 | 30143 | 53238 |
| FGF22 | 7049 | 30144 | 53239 |
| FGF22 | 7050 | 30145 | 53240 |
| FGF23 | 7051 | 30146 | 53241 |
| FGF3 | 7052 | 30147 | 53242 |
| FGF4 | 7053 | 30148 | 53243 |
| FGF5 | 7054 | 30149 | 53244 |
| FGF5 | 7055 | 30150 | 53245 |
| FGF6 | 7056 | 30151 | 53246 |
| FGF7 | 7057 | 30152 | 53247 |
| FGF8 | 7058 | 30153 | 53248 |
| FGF9 | 7059 | 30154 | 53249 |
| FGFBP1 | 7060 | 30155 | 53250 |
| FGFBP2 | 7061 | 30156 | 53251 |
| FGFBP3 | 7062 | 30157 | 53252 |
| FGFR1 | 7063 | 30158 | 53253 |
| FGFR1 | 7064 | 30159 | 53254 |
| FGFR1OP | 7065 | 30160 | 53255 |
| FGFR1OP | 7066 | 30161 | 53256 |
| FGFR1OP2 | 7067 | 30162 | 53257 |
| FGFR1OP2 | 7068 | 30163 | 53258 |
| FGFR2 | 7069 | 30164 | 53259 |
| FGFR2 | 7070 | 30165 | 53260 |
| FGFR2 | 7071 | 30166 | 53261 |
| FGFR3 | 7072 | 30167 | 53262 |
| FGFR4 | 7073 | 30168 | 53263 |
| FGFRL1 | 7074 | 30169 | 53264 |
| FGG | 7075 | 30170 | 53265 |
| FGG | 7076 | 30171 | 53266 |
| FGGY | 7077 | 30172 | 53267 |
| FGGY | 7078 | 30173 | 53268 |
| FGL1 | 7079 | 30174 | 53269 |
| FGL2 | 7080 | 30175 | 53270 |
| FGR | 7081 | 30176 | 53271 |
| FH | 7082 | 30177 | 53272 |
| FHAD1 | 7083 | 30178 | 53273 |
| FHDC1 | 7084 | 30179 | 53274 |
| FHIT | 7085 | 30180 | 53275 |
| FHIT | 7086 | 30181 | 53276 |
| FHL1 | 7087 | 30182 | 53277 |
| FHL1 | 7088 | 30183 | 53278 |
| FHL2 | 7089 | 30184 | 53279 |
| FHL2 | 7090 | 30185 | 53280 |
| FHL3 | 7091 | 30186 | 53281 |
| FHL5 | 7092 | 30187 | 53282 |
| FHOD1 | 7093 | 30188 | 53283 |
| FHOD3 | 7094 | 30189 | 53284 |
| FIBCD1 | 7095 | 30190 | 53285 |
| FIBIN | 7096 | 30191 | 53286 |
| FIBP | 7097 | 30192 | 53287 |
| FICD | 7098 | 30193 | 53288 |
| FIG4 | 7099 | 30194 | 53289 |
| FIGLA | 7100 | 30195 | 53290 |
| FIGN | 7101 | 30196 | 53291 |
| FIGNL1 | 7102 | 30197 | 53292 |
| FIGNL2 | 7103 | 30198 | 53293 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| FILIP1 | 7104 | 30199 | 53294 |
| FILIP1 | 7105 | 30200 | 53295 |
| FILIP1L | 7106 | 30201 | 53296 |
| FILIP1L | 7107 | 30202 | 53297 |
| FIP1L1 | 7108 | 30203 | 53298 |
| FIS1 | 7109 | 30204 | 53299 |
| FITM1 | 7110 | 30205 | 53300 |
| FITM2 | 7111 | 30206 | 53301 |
| FIZ1 | 7112 | 30207 | 53302 |
| FJX1 | 7113 | 30208 | 53303 |
| FKBP10 | 7114 | 30209 | 53304 |
| FKBP11 | 7115 | 30210 | 53305 |
| FKBP11 | 7116 | 30211 | 53306 |
| FKBP14 | 7117 | 30212 | 53307 |
| FKBP15 | 7118 | 30213 | 53308 |
| FKBP1A | 7119 | 30214 | 53309 |
| FKBP1A | 7120 | 30215 | 53310 |
| FKBP1B | 7121 | 30216 | 53311 |
| FKBP1B | 7122 | 30217 | 53312 |
| FKBP2 | 7123 | 30218 | 53313 |
| FKBP3 | 7124 | 30219 | 53314 |
| FKBP4 | 7125 | 30220 | 53315 |
| FKBP5 | 7126 | 30221 | 53316 |
| FKBP5 | 7127 | 30222 | 53317 |
| FKBP6 | 7128 | 30223 | 53318 |
| FKBP7 | 7129 | 30224 | 53319 |
| FKBP8 | 7130 | 30225 | 53320 |
| FKBP9 | 7131 | 30226 | 53321 |
| FKBPL | 7132 | 30227 | 53322 |
| FKRP | 7133 | 30228 | 53323 |
| FKTN | 7134 | 30229 | 53324 |
| FKTN | 7135 | 30230 | 53325 |
| FKTN | 7136 | 30231 | 53326 |
| FLAD1 | 7137 | 30232 | 53327 |
| FLAD1 | 7138 | 30233 | 53328 |
| FLAD1 | 7139 | 30234 | 53329 |
| FLCN | 7140 | 30235 | 53330 |
| FLCN | 7141 | 30236 | 53331 |
| FLG | 7142 | 30237 | 53332 |
| FLG2 | 7143 | 30238 | 53333 |
| FLI1 | 7144 | 30239 | 53334 |
| FLII | 7145 | 30240 | 53335 |
| FLJ44635 | 7146 | 30241 | 53336 |
| FLJ45513 | 7147 | 30242 | 53337 |
| FLNA | 7148 | 30243 | 53338 |
| FLNB | 7149 | 30244 | 53339 |
| FLNC | 7150 | 30245 | 53340 |
| FLOT1 | 7151 | 30246 | 53341 |
| FLOT2 | 7152 | 30247 | 53342 |
| FLRT1 | 7153 | 30248 | 53343 |
| FLRT2 | 7154 | 30249 | 53344 |
| FLRT3 | 7155 | 30250 | 53345 |
| FLT1 | 7156 | 30251 | 53346 |
| FLT1 | 7157 | 30252 | 53347 |
| FLT1 | 7158 | 30253 | 53348 |
| FLT1 | 7159 | 30254 | 53349 |
| FLT3 | 7160 | 30255 | 53350 |
| FLT3LG | 7161 | 30256 | 53351 |
| FLT3LG | 7162 | 30257 | 53352 |
| FLT4 | 7163 | 30258 | 53353 |
| FLT4 | 7164 | 30259 | 53354 |
| FLVCR1 | 7165 | 30260 | 53355 |
| FLVCR2 | 7166 | 30261 | 53356 |
| FLYWCH1 | 7167 | 30262 | 53357 |
| FLYWCH1 | 7168 | 30263 | 53358 |
| FLYWCH2 | 7169 | 30264 | 53359 |
| FMC1 | 7170 | 30265 | 53360 |
| FMN1 | 7171 | 30266 | 53361 |
| FMN1 | 7172 | 30267 | 53362 |
| FMN2 | 7173 | 30268 | 53363 |
| FMNL1 | 7174 | 30269 | 53364 |
| FMNL2 | 7175 | 30270 | 53365 |
| FMNL3 | 7176 | 30271 | 53366 |
| FMO1 | 7177 | 30272 | 53367 |
| FMO2 | 7178 | 30273 | 53368 |
| FMO3 | 7179 | 30274 | 53369 |
| FMO4 | 7180 | 30275 | 53370 |
| FMO5 | 7181 | 30276 | 53371 |
| FMO5 | 7182 | 30277 | 53372 |
| FMO5 | 7183 | 30278 | 53373 |
| FMOD | 7184 | 30279 | 53374 |
| FMR1 | 7185 | 30280 | 53375 |
| FMR1NB | 7186 | 30281 | 53376 |
| FN1 | 7187 | 30282 | 53377 |
| FN1 | 7188 | 30283 | 53378 |
| FN3K | 7189 | 30284 | 53379 |
| FN3KRP | 7190 | 30285 | 53380 |
| FNBP1 | 7191 | 30286 | 53381 |
| FNBP1L | 7192 | 30287 | 53382 |
| FNBP4 | 7193 | 30288 | 53383 |
| FNDC1 | 7194 | 30289 | 53384 |
| FNDC10 | 7195 | 30290 | 53385 |
| FNDC11 | 7196 | 30291 | 53386 |
| FNDC3A | 7197 | 30292 | 53387 |
| FNDC3B | 7198 | 30293 | 53388 |
| FNDC4 | 7199 | 30294 | 53389 |
| FNDC5 | 7200 | 30295 | 53390 |
| FNDC5 | 7201 | 30296 | 53391 |
| FNDC5 | 7202 | 30297 | 53392 |
| FNDC7 | 7203 | 30298 | 53393 |
| FNDC8 | 7204 | 30299 | 53394 |
| FNDC9 | 7205 | 30300 | 53395 |
| FNIP1 | 7206 | 30301 | 53396 |
| FNIP1 | 7207 | 30302 | 53397 |
| FNIP2 | 7208 | 30303 | 53398 |
| FNTA | 7209 | 30304 | 53399 |
| FOCAD | 7210 | 30305 | 53400 |
| FOLH1 | 7211 | 30306 | 53401 |
| FOLR1 | 7212 | 30307 | 53402 |
| FOLR2 | 7213 | 30308 | 53403 |
| FOLR3 | 7214 | 30309 | 53404 |
| FOLR3 | 7215 | 30310 | 53405 |
| FOPNL | 7216 | 30311 | 53406 |
| FOPNL | 7217 | 30312 | 53407 |
| FOS | 7218 | 30313 | 53408 |
| FOSB | 7219 | 30314 | 53409 |
| FOSL1 | 7220 | 30315 | 53410 |
| FOSL1 | 7221 | 30316 | 53411 |
| FOSL2 | 7222 | 30317 | 53412 |
| FOXA1 | 7223 | 30318 | 53413 |
| FOXA2 | 7224 | 30319 | 53414 |
| FOXA3 | 7225 | 30320 | 53415 |
| FOXB1 | 7226 | 30321 | 53416 |
| FOXB2 | 7227 | 30322 | 53417 |
| FOXC1 | 7228 | 30323 | 53418 |
| FOXC2 | 7229 | 30324 | 53419 |
| FOXD1 | 7230 | 30325 | 53420 |
| FOXD2 | 7231 | 30326 | 53421 |
| FOXD3 | 7232 | 30327 | 53422 |
| FOXD4 | 7233 | 30328 | 53423 |
| FOXD4L1 | 7234 | 30329 | 53424 |
| FOXD4L4 | 7235 | 30330 | 53425 |
| FOXD4L5 | 7236 | 30331 | 53426 |
| FOXD4L6 | 7237 | 30332 | 53427 |
| FOXE1 | 7238 | 30333 | 53428 |
| FOXE3 | 7239 | 30334 | 53429 |
| FOXF1 | 7240 | 30335 | 53430 |
| FOXF2 | 7241 | 30336 | 53431 |
| FOXG1 | 7242 | 30337 | 53432 |
| FOXH1 | 7243 | 30338 | 53433 |
| FOXI1 | 7244 | 30339 | 53434 |
| FOXI2 | 7245 | 30340 | 53435 |
| FOXI3 | 7246 | 30341 | 53436 |
| FOXJ1 | 7247 | 30342 | 53437 |
| FOXJ2 | 7248 | 30343 | 53438 |
| FOXJ3 | 7249 | 30344 | 53439 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| FOXK1 | 7250 | 30345 | 53440 |
| FOXK2 | 7251 | 30346 | 53441 |
| FOXL1 | 7252 | 30347 | 53442 |
| FOXL2 | 7253 | 30348 | 53443 |
| FOXL2NB | 7254 | 30349 | 53444 |
| FOXM1 | 7255 | 30350 | 53445 |
| FOXN1 | 7255 | 30351 | 53446 |
| FOXN2 | 7257 | 30352 | 53447 |
| FOXN3 | 7258 | 30353 | 53448 |
| FOXN4 | 7259 | 30354 | 53449 |
| FOXO1 | 7260 | 30355 | 53450 |
| FOXO3 | 7261 | 30356 | 53451 |
| FOXO4 | 7262 | 30357 | 53452 |
| FOXO6 | 7263 | 30358 | 53453 |
| FOXP1 | 7264 | 30359 | 53454 |
| FOXP1 | 7265 | 30360 | 53455 |
| FOXP2 | 7266 | 30361 | 53456 |
| FOXP2 | 7267 | 30362 | 53457 |
| FOXP3 | 7268 | 30363 | 53458 |
| FOXP4 | 7269 | 30364 | 53459 |
| FOXQ1 | 7270 | 30365 | 53460 |
| FOXR1 | 7271 | 30366 | 53461 |
| FOXR2 | 7272 | 30367 | 53462 |
| FOXRED1 | 7273 | 30368 | 53463 |
| FOXRED2 | 7274 | 30369 | 53464 |
| FOXS1 | 7275 | 30370 | 53465 |
| FPGS | 7276 | 30371 | 53456 |
| FPGT | 7277 | 30372 | 53467 |
| FPGT-TNNI3K | 7278 | 30373 | 53468 |
| FPR1 | 7279 | 30374 | 53469 |
| FPR2 | 7280 | 30375 | 53470 |
| FPR3 | 7281 | 30376 | 53471 |
| FRA10AC1 | 7282 | 30377 | 53472 |
| FRAS1 | 7283 | 30378 | 53473 |
| FRAS1 | 7284 | 30379 | 53474 |
| FRAT1 | 7285 | 30380 | 53475 |
| FRAT2 | 7286 | 30381 | 53476 |
| FREM1 | 7287 | 30382 | 53477 |
| FREM2 | 7288 | 30383 | 53478 |
| FREM3 | 7289 | 30384 | 53479 |
| FRG1 | 7290 | 30385 | 53480 |
| FRG2B | 7291 | 30386 | 53481 |
| FRG2C | 7292 | 30387 | 53482 |
| FRK | 7293 | 30388 | 53483 |
| FRMD1 | 7294 | 30389 | 53484 |
| FRMD3 | 7295 | 30390 | 53485 |
| FRMD3 | 7296 | 30391 | 53486 |
| FRMD4A | 7297 | 30392 | 53487 |
| FRMD4B | 7298 | 30393 | 53488 |
| FRMD5 | 7299 | 30394 | 53489 |
| FRMD5 | 7300 | 30395 | 53490 |
| FRMD5 | 7301 | 30396 | 53491 |
| FRMD6 | 7302 | 30397 | 53492 |
| FRMD7 | 7303 | 30398 | 53493 |
| FRMD8 | 7304 | 30399 | 53494 |
| FRMPD1 | 7305 | 30400 | 53495 |
| FRMPD2 | 7306 | 30401 | 53496 |
| FRMPD3 | 7307 | 30402 | 53497 |
| FRMPD4 | 7308 | 30403 | 53498 |
| FRRS1 | 7309 | 30404 | 53499 |
| FRRS1L | 7310 | 30405 | 53500 |
| FRS2 | 7311 | 30406 | 53501 |
| FRS3 | 7312 | 30407 | 53502 |
| FRY | 7313 | 30408 | 53503 |
| FRYL | 7314 | 30409 | 53504 |
| FRZB | 7315 | 30410 | 53505 |
| FSBP | 7316 | 30411 | 53506 |
| FSCB | 7317 | 30412 | 53507 |
| FSCN1 | 7318 | 30413 | 53508 |
| FSCN2 | 7319 | 30414 | 53509 |
| FSCN3 | 7320 | 30415 | 53510 |
| FSD1 | 7321 | 30416 | 53511 |
| FSD1 | 7322 | 30417 | 53512 |
| FSD1L | 7323 | 30418 | 53513 |
| FSD1L | 7324 | 30419 | 53514 |
| FSD2 | 7325 | 30420 | 53515 |
| FSHB | 7326 | 30421 | 53516 |
| FSHR | 7327 | 30422 | 53517 |
| FSIP1 | 7328 | 30423 | 53518 |
| FSIP2 | 7329 | 30424 | 53519 |
| FST | 7330 | 30425 | 53520 |
| FST | 7331 | 30426 | 53521 |
| FSTL1 | 7332 | 30427 | 53522 |
| FSTL3 | 7333 | 30428 | 53523 |
| FSTL4 | 7334 | 30429 | 53524 |
| FSTL5 | 7335 | 30430 | 53525 |
| FTCD | 7336 | 30431 | 53526 |
| FTCD | 7337 | 30432 | 53527 |
| FTCD | 7338 | 30433 | 53528 |
| FTCD-AS1 | 7339 | 30434 | 53529 |
| FTCDNL1 | 7340 | 30435 | 53530 |
| FTCDNL1 | 7341 | 30436 | 53531 |
| FTCDNL1 | 7342 | 30437 | 53532 |
| FTH1 | 7343 | 30438 | 53533 |
| FTH1P18 | 7344 | 30439 | 53534 |
| FTHL17 | 7345 | 30440 | 53535 |
| FTL | 7346 | 30441 | 53536 |
| FTMT | 7347 | 30442 | 53537 |
| FTO | 7348 | 30443 | 53538 |
| FTSJ1 | 7349 | 30444 | 53539 |
| FTSJ3 | 7350 | 30445 | 53540 |
| FUBP1 | 7351 | 30446 | 53541 |
| FUBP3 | 7352 | 30447 | 53542 |
| FUCA1 | 7353 | 30448 | 53543 |
| FUCA2 | 7354 | 30449 | 53544 |
| FUK | 7355 | 30450 | 53545 |
| FUNDC1 | 7356 | 30451 | 53546 |
| FUNDC2 | 7357 | 30452 | 53547 |
| FUOM | 7358 | 30453 | 53548 |
| FUOM | 7359 | 30454 | 53549 |
| FURIN | 7360 | 30455 | 53550 |
| FUS | 7361 | 30456 | 53551 |
| FUT1 | 7362 | 30457 | 53552 |
| FUT10 | 7363 | 30458 | 53553 |
| FUT11 | 7364 | 30459 | 53554 |
| FUT11 | 7365 | 30460 | 53555 |
| FUT2 | 7366 | 30461 | 53556 |
| FUT3 | 7367 | 30462 | 53557 |
| FUT4 | 7368 | 30463 | 53558 |
| FUT7 | 7369 | 30464 | 53559 |
| FUT8 | 7370 | 30465 | 53560 |
| FUT9 | 7371 | 30466 | 53561 |
| FUZ | 7372 | 30467 | 53562 |
| FXN | 7373 | 30468 | 53563 |
| FXN | 7374 | 30469 | 53564 |
| FXN | 7375 | 30470 | 53565 |
| FXR1 | 7376 | 30471 | 53566 |
| FXR1 | 7377 | 30472 | 53567 |
| FXR2 | 7378 | 30473 | 53568 |
| FXYD1 | 7379 | 30474 | 53569 |
| FXYD2 | 7380 | 30475 | 53570 |
| FXYD3 | 7381 | 30476 | 53571 |
| FXYD3 | 7382 | 30477 | 53572 |
| FXYD3 | 7383 | 30478 | 53573 |
| FXYD4 | 7384 | 30479 | 53574 |
| FXYD5 | 7385 | 30480 | 53575 |
| FXYD5 | 7386 | 30481 | 53576 |
| FXYD6 | 7387 | 30482 | 53577 |
| FXYD6 | 7388 | 30483 | 53578 |
| FXYD6-FXYD2 | 7389 | 30484 | 53579 |
| FXYD7 | 7390 | 30485 | 53580 |
| FYB1 | 7391 | 30486 | 53581 |
| FYB2 | 7392 | 30487 | 53582 |
| FYCO1 | 7393 | 30488 | 53583 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| FYN | 7394 | 30489 | 53584 |
| FYTTD1 | 7395 | 30490 | 53585 |
| FZD1 | 7396 | 30491 | 53586 |
| FZD10 | 7397 | 30492 | 53587 |
| FZD2 | 7398 | 30493 | 53588 |
| FZD3 | 7399 | 30494 | 53589 |
| FZD4 | 7400 | 30495 | 53590 |
| FZD5 | 7401 | 30496 | 53591 |
| FZD6 | 7402 | 30497 | 53592 |
| FZD7 | 7403 | 30498 | 53593 |
| FZD8 | 7404 | 30499 | 53594 |
| FZD9 | 7405 | 30500 | 53595 |
| FZR1 | 7406 | 30501 | 53596 |
| G0S2 | 7407 | 30502 | 53597 |
| G2E3 | 7408 | 30503 | 53598 |
| G3BP1 | 7409 | 30504 | 53599 |
| G3BP2 | 7410 | 30505 | 53600 |
| G6PC | 7411 | 30506 | 53601 |
| G6PC | 7412 | 30507 | 53602 |
| G6PC2 | 7413 | 30508 | 53603 |
| G6PC3 | 7414 | 30509 | 53604 |
| G6PC3 | 7415 | 30510 | 53605 |
| G6PD | 7416 | 30511 | 53606 |
| GAA | 7417 | 30512 | 53607 |
| GAB1 | 7418 | 30513 | 53608 |
| GAB2 | 7419 | 30514 | 53609 |
| GAB3 | 7420 | 30515 | 53610 |
| GAB4 | 7421 | 30516 | 53611 |
| GABARAP | 7422 | 30517 | 53612 |
| GABARAPL1 | 7423 | 30518 | 53613 |
| GABARAPL2 | 7424 | 30519 | 53614 |
| GABBR1 | 7425 | 30520 | 53615 |
| GABBR2 | 7426 | 30521 | 53616 |
| GABPA | 7427 | 30522 | 53617 |
| GABPB1 | 7428 | 30523 | 53618 |
| GABPB1 | 7429 | 30524 | 53619 |
| GABPB2 | 7430 | 30525 | 53620 |
| GABPB2 | 7431 | 30526 | 53621 |
| GABRA1 | 7432 | 30527 | 53622 |
| GABRA2 | 7433 | 30528 | 53623 |
| GABRA3 | 7434 | 30529 | 53624 |
| GABRA4 | 7435 | 30530 | 53625 |
| GABRA5 | 7436 | 30531 | 53626 |
| GABRA6 | 7437 | 30532 | 53627 |
| GABRB1 | 7438 | 30533 | 53628 |
| GABRB2 | 7439 | 30534 | 53629 |
| GABRB3 | 7440 | 30535 | 53630 |
| GABRD | 7441 | 30536 | 53631 |
| GABRE | 7442 | 30537 | 53632 |
| GABRG1 | 7443 | 30538 | 53633 |
| GABRG2 | 7444 | 30539 | 53634 |
| GABRG3 | 7445 | 30540 | 53635 |
| GABRG3 | 7446 | 30541 | 53636 |
| GABRP | 7447 | 30542 | 53637 |
| GABRP | 7448 | 30543 | 53638 |
| GABRQ | 7449 | 30544 | 53639 |
| GABRR1 | 7450 | 30545 | 53640 |
| GABRR2 | 7451 | 30546 | 53641 |
| GABRR3 | 7452 | 30547 | 53642 |
| GAD1 | 7453 | 30548 | 53643 |
| GAD1 | 7454 | 30549 | 53644 |
| GAD2 | 7455 | 30550 | 53645 |
| GADD45A | 7456 | 30551 | 53646 |
| GADD45A | 7457 | 30552 | 53647 |
| GADD45B | 7458 | 30553 | 53648 |
| GADD45G | 7459 | 30554 | 53649 |
| GADD45GIP1 | 7460 | 30555 | 53650 |
| GADL1 | 7461 | 30556 | 53651 |
| GAGE10 | 7462 | 30557 | 53652 |
| GAGE12E | 7463 | 30558 | 53653 |
| GAGE12G | 7464 | 30559 | 53654 |
| GAGE2E | 7465 | 30560 | 53655 |
| GAK | 7466 | 30561 | 53656 |
| GAL | 7467 | 30562 | 53657 |
| GAL3ST1 | 7468 | 30563 | 53658 |
| GAL3ST2 | 7469 | 30564 | 53659 |
| GAL3ST3 | 7470 | 30565 | 53660 |
| GAL3ST4 | 7471 | 30566 | 53661 |
| GALC | 7472 | 30567 | 53662 |
| GALE | 7473 | 30568 | 53663 |
| GALK1 | 7474 | 30569 | 53664 |
| GALK2 | 7475 | 30570 | 53665 |
| GALK2 | 7476 | 30571 | 53666 |
| GALM | 7477 | 30572 | 53667 |
| GALNS | 7478 | 30573 | 53668 |
| GALNT1 | 7479 | 30574 | 53669 |
| GALNT10 | 7480 | 30575 | 53670 |
| GALNT11 | 7481 | 30576 | 53671 |
| GALNT12 | 7482 | 30577 | 53672 |
| GALNT13 | 7483 | 30578 | 53673 |
| GALNT13 | 7484 | 30579 | 53674 |
| GALNT14 | 7485 | 30580 | 53675 |
| GALNT14 | 7486 | 30581 | 53676 |
| GALNT15 | 7487 | 30582 | 53677 |
| GALNT15 | 7488 | 30583 | 53678 |
| GALNT16 | 7489 | 30584 | 53679 |
| GALNT17 | 7490 | 30585 | 53680 |
| GALNT18 | 7491 | 30586 | 53681 |
| GALNT2 | 7492 | 30587 | 53682 |
| GALNT3 | 7493 | 30588 | 53683 |
| GALNT4 | 7494 | 30589 | 53684 |
| GALNT5 | 7495 | 30590 | 53685 |
| GALNT6 | 7496 | 30591 | 53686 |
| GALNT6 | 7497 | 30592 | 53687 |
| GALNT7 | 7498 | 30593 | 53688 |
| GALNT8 | 7499 | 30594 | 53689 |
| GALNT9 | 7500 | 30595 | 53690 |
| GALNTL5 | 7501 | 30596 | 53691 |
| GALNTL6 | 7502 | 30597 | 53692 |
| GALP | 7503 | 30598 | 53693 |
| GALR1 | 7504 | 30599 | 53694 |
| GALR2 | 7505 | 30600 | 53695 |
| GALR3 | 7506 | 30601 | 53696 |
| GALT | 7507 | 30602 | 53697 |
| GAMT | 7508 | 30603 | 53698 |
| GAMT | 7509 | 30604 | 53699 |
| GAN | 7510 | 30605 | 53700 |
| GANAB | 7511 | 30606 | 53701 |
| GANC | 7512 | 30607 | 53702 |
| GANC | 7513 | 30608 | 53703 |
| GANC | 7514 | 30609 | 53704 |
| GAP43 | 7515 | 30610 | 53705 |
| GAPDH | 7516 | 30611 | 53706 |
| GAPDHS | 7517 | 30612 | 53707 |
| GAPT | 7518 | 30613 | 53708 |
| GAPVD1 | 7519 | 30614 | 53709 |
| GAPVD1 | 7520 | 30615 | 53710 |
| GAR1 | 7521 | 30616 | 53711 |
| GAREM1 | 7522 | 30617 | 53712 |
| GAREM2 | 7523 | 30618 | 53713 |
| GARNL3 | 7524 | 30619 | 53714 |
| GARS | 7525 | 30620 | 53715 |
| GART | 7526 | 30621 | 53716 |
| GART | 7527 | 30622 | 53717 |
| GAS1 | 7528 | 30623 | 53718 |
| GAS2 | 7529 | 30624 | 53719 |
| GAS2 | 7530 | 30625 | 53720 |
| GAS2L1 | 7531 | 30626 | 53721 |
| GAS2L2 | 7532 | 30627 | 53722 |
| GAS2L3 | 7533 | 30628 | 53723 |
| GAS6 | 7534 | 30629 | 53724 |
| GAS7 | 7535 | 30630 | 53725 |
| GAS8 | 7536 | 30631 | 53726 |
| GAST | 7537 | 30632 | 53727 |
| GATA1 | 7538 | 30633 | 53728 |
| GATA2 | 7539 | 30634 | 53729 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| GATA3 | 7540 | 30635 | 53730 |
| GATA4 | 7541 | 30636 | 53731 |
| GATA5 | 7542 | 30637 | 53732 |
| GATA6 | 7543 | 30638 | 53733 |
| GATAD1 | 7544 | 30639 | 53734 |
| GATAD2A | 7545 | 30640 | 53735 |
| GATAD2B | 7546 | 30641 | 53736 |
| GATB | 7547 | 30642 | 53737 |
| GATC | 7548 | 30643 | 53738 |
| GATD1 | 7549 | 30644 | 53739 |
| GATD1 | 7550 | 30645 | 53740 |
| GATM | 7551 | 30646 | 53741 |
| GATS | 7552 | 30647 | 53742 |
| GBA | 7553 | 30648 | 53743 |
| GBA2 | 7554 | 30649 | 53744 |
| GBA2 | 7555 | 30650 | 53745 |
| GBA3 | 7556 | 30651 | 53746 |
| GBE1 | 7557 | 30652 | 53747 |
| GBF1 | 7558 | 30653 | 53748 |
| GBGT1 | 7559 | 30654 | 53749 |
| GBGT1 | 7560 | 30655 | 53750 |
| GBP1 | 7561 | 30656 | 53751 |
| GBP2 | 7562 | 30657 | 53752 |
| GBP3 | 7563 | 30658 | 53753 |
| GBP3 | 7564 | 30659 | 53754 |
| GBP4 | 7565 | 30660 | 53755 |
| GBP5 | 7566 | 30661 | 53756 |
| GBP6 | 7567 | 30662 | 53757 |
| GBP7 | 7568 | 30663 | 53758 |
| GBX1 | 7569 | 30664 | 53759 |
| GBX2 | 7570 | 30665 | 53760 |
| GBX2 | 7571 | 30666 | 53761 |
| GC | 7572 | 30667 | 53762 |
| GCA | 7573 | 30668 | 53763 |
| GCAT | 7574 | 30669 | 53764 |
| GCC1 | 7575 | 30670 | 53765 |
| GCC2 | 7576 | 30671 | 53766 |
| GCDH | 7577 | 30672 | 53767 |
| GCDH | 7578 | 30673 | 53768 |
| GCFC2 | 7579 | 30674 | 53769 |
| GCFC2 | 7580 | 30675 | 53770 |
| GCG | 7581 | 30676 | 53771 |
| GCGR | 7582 | 30677 | 53772 |
| GCH1 | 7583 | 30678 | 53773 |
| GCH1 | 7584 | 30679 | 53774 |
| GCH1 | 7585 | 30680 | 53775 |
| GCHFR | 7586 | 30681 | 53776 |
| GCK | 7587 | 30682 | 53777 |
| GCKR | 7588 | 30683 | 53778 |
| GCLC | 7589 | 30684 | 53779 |
| GCLM | 7590 | 30685 | 53780 |
| GCM1 | 7591 | 30686 | 53781 |
| GCM2 | 7592 | 30687 | 53782 |
| GCN1 | 7593 | 30688 | 53783 |
| GCNA | 7594 | 30689 | 53784 |
| GCNT1 | 7595 | 30690 | 53785 |
| GCNT2 | 7596 | 30691 | 53786 |
| GCNT3 | 7597 | 30692 | 53787 |
| GCNT4 | 7598 | 30693 | 53788 |
| GCNT7 | 7599 | 30694 | 53789 |
| GCOM1 | 7600 | 30695 | 53790 |
| GCSAM | 7601 | 30696 | 53791 |
| GCSAML | 7602 | 30697 | 53792 |
| GCSAML | 7603 | 30698 | 53793 |
| GCSH | 7604 | 30699 | 53794 |
| GDA | 7605 | 30700 | 53795 |
| GDA | 7606 | 30701 | 53796 |
| GDA | 7607 | 30702 | 53797 |
| GDAP1 | 7608 | 30703 | 53798 |
| GDAP1L1 | 7609 | 30704 | 53799 |
| GDAP2 | 7610 | 30705 | 53800 |
| GDAP2 | 7611 | 30706 | 53801 |
| GDE1 | 7612 | 30707 | 53802 |
| GDF10 | 7613 | 30708 | 53803 |
| GDF11 | 7614 | 30709 | 53804 |
| GDF15 | 7615 | 30710 | 53805 |
| GDF2 | 7616 | 30711 | 53806 |
| GDF3 | 7617 | 30712 | 53807 |
| GDF5 | 7618 | 30713 | 53808 |
| GDF5OS | 7619 | 30714 | 53809 |
| GDF6 | 7620 | 30715 | 53810 |
| GDF7 | 7621 | 30716 | 53811 |
| GDF9 | 7622 | 30717 | 53812 |
| GDI1 | 7623 | 30718 | 53813 |
| GDI2 | 7624 | 30719 | 53814 |
| GDNF | 7625 | 30720 | 53815 |
| GDPD1 | 7626 | 30721 | 53816 |
| GDPD1 | 7627 | 30722 | 53817 |
| GDPD1 | 7628 | 30723 | 53818 |
| GDPD2 | 7629 | 30724 | 53819 |
| GDPD3 | 7630 | 30725 | 53820 |
| GDPD4 | 7631 | 30726 | 53821 |
| GDPD5 | 7632 | 30727 | 53822 |
| GDPGP1 | 7633 | 30728 | 53823 |
| GEM | 7634 | 30729 | 53824 |
| GEMIN2 | 7635 | 30730 | 53825 |
| GEMIN2 | 7636 | 30731 | 53826 |
| GEMIN4 | 7637 | 30732 | 53827 |
| GEMIN5 | 7638 | 30733 | 53828 |
| GEMIN6 | 7639 | 30734 | 53829 |
| GEMIN7 | 7640 | 30735 | 53830 |
| GEMIN8 | 7641 | 30736 | 53831 |
| GEN1 | 7642 | 30737 | 53832 |
| GET4 | 7643 | 30738 | 53833 |
| GFAP | 7644 | 30739 | 53834 |
| GFAP | 7645 | 30740 | 53835 |
| GFAP | 7646 | 30741 | 53836 |
| GFER | 7647 | 30742 | 53837 |
| GFI1 | 7648 | 30743 | 53838 |
| GFI1B | 7649 | 30744 | 53839 |
| GFM1 | 7650 | 30745 | 53840 |
| GFM1 | 7651 | 30746 | 53841 |
| GFM2 | 7652 | 30747 | 53842 |
| GFM2 | 7653 | 30748 | 53843 |
| GFOD1 | 7654 | 30749 | 53844 |
| GFOD1 | 7655 | 30750 | 53845 |
| GFOD2 | 7656 | 30751 | 53846 |
| GFOD2 | 7657 | 30752 | 53847 |
| GFPT1 | 7658 | 30753 | 53848 |
| GFPT2 | 7659 | 30754 | 53849 |
| GFRA1 | 7660 | 30755 | 53850 |
| GFRA2 | 7661 | 30756 | 53851 |
| GFRA3 | 7662 | 30757 | 53852 |
| GFRA4 | 7663 | 30758 | 53853 |
| GFRAL | 7664 | 30759 | 53854 |
| GFY | 7665 | 30760 | 53855 |
| GGA1 | 7666 | 30761 | 53856 |
| GGA2 | 7667 | 30762 | 53857 |
| GGA3 | 7668 | 30763 | 53858 |
| GGA3 | 7669 | 30764 | 53859 |
| GGACT | 7670 | 30765 | 53860 |
| GGCT | 7671 | 30766 | 53861 |
| GGCT | 7672 | 30767 | 53862 |
| GGCX | 7673 | 30768 | 53863 |
| GGCX | 7674 | 30769 | 53864 |
| GGH | 7675 | 30770 | 53865 |
| GGN | 7676 | 30771 | 53866 |
| GGNBP2 | 7677 | 30772 | 53867 |
| GGPS1 | 7678 | 30773 | 53868 |
| GGT1 | 7679 | 30774 | 53869 |
| GGT5 | 7680 | 30775 | 53870 |
| GGT5 | 7681 | 30776 | 53871 |
| GGT6 | 7682 | 30777 | 53872 |
| GGT6 | 7683 | 30778 | 53873 |
| GGT7 | 7684 | 30779 | 53874 |
| GGT7 | 7685 | 30780 | 53875 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| GGTLC1 | 7686 | 30781 | 53876 |
| GH2 | 7687 | 30782 | 53877 |
| GH2 | 7688 | 30783 | 53878 |
| GH2 | 7689 | 30784 | 53879 |
| GHDC | 7690 | 30785 | 53880 |
| GHDC | 7691 | 30786 | 53881 |
| GHITM | 7692 | 30787 | 53882 |
| GHR | 7693 | 30788 | 53883 |
| GHR | 7694 | 30789 | 53884 |
| GHRH | 7695 | 30790 | 53885 |
| GHRHR | 7696 | 30791 | 53886 |
| GHRL | 7697 | 30792 | 53887 |
| GHSR | 7698 | 30793 | 53888 |
| GHSR | 7699 | 30794 | 53889 |
| GID4 | 7700 | 30795 | 53890 |
| GID8 | 7701 | 30796 | 53891 |
| GIF | 7702 | 30797 | 53892 |
| GIGYF1 | 7703 | 30798 | 53893 |
| GIGYF2 | 7704 | 30799 | 53894 |
| GIMAP1 | 7705 | 30800 | 53895 |
| GIMAP1-GIMAP5 | 7706 | 30801 | 53896 |
| GIMAP2 | 7707 | 30802 | 53897 |
| GIMAP4 | 7708 | 30803 | 53898 |
| GIMAP6 | 7709 | 30804 | 53899 |
| GIMAP7 | 7710 | 30805 | 53900 |
| GIMAP8 | 7711 | 30806 | 53901 |
| GIMD1 | 7712 | 30807 | 53902 |
| GIN1 | 7713 | 30808 | 53903 |
| GINM1 | 7714 | 30809 | 53904 |
| GINS1 | 7715 | 30810 | 53905 |
| GINS2 | 7716 | 30811 | 53906 |
| GINS3 | 7717 | 30812 | 53907 |
| GINS4 | 7718 | 30813 | 53908 |
| GIP | 7719 | 30814 | 53909 |
| GIPC1 | 7720 | 30815 | 53910 |
| GIPC2 | 7721 | 30816 | 53911 |
| GIPC3 | 7722 | 30817 | 53912 |
| GIPR | 7723 | 30818 | 53913 |
| GIT1 | 7724 | 30819 | 53914 |
| GIT2 | 7725 | 30820 | 53915 |
| GIT2 | 7726 | 30821 | 53916 |
| GIT2 | 7727 | 30822 | 53917 |
| GJA1 | 7728 | 30823 | 53918 |
| GJA10 | 7729 | 30824 | 53919 |
| GJA3 | 7730 | 30825 | 53920 |
| GJA4 | 7731 | 30826 | 53921 |
| GJA5 | 7732 | 30827 | 53922 |
| GJA8 | 7733 | 30828 | 53923 |
| GJA9 | 7734 | 30829 | 53924 |
| GJB1 | 7735 | 30830 | 53925 |
| GJB2 | 7736 | 30831 | 53926 |
| GJB3 | 7737 | 30832 | 53927 |
| GJB4 | 7738 | 30833 | 53928 |
| GJB5 | 7739 | 30834 | 53929 |
| GJB6 | 7740 | 30835 | 53930 |
| GJB7 | 7741 | 30836 | 53931 |
| GJC1 | 7742 | 30837 | 53932 |
| GJC2 | 7743 | 30838 | 53933 |
| GJC3 | 7744 | 30839 | 53934 |
| GJD2 | 7745 | 30840 | 53935 |
| GJD3 | 7746 | 30841 | 53936 |
| GJD4 | 7747 | 30842 | 53937 |
| GK | 7748 | 30843 | 53938 |
| GK | 7749 | 30844 | 53939 |
| GK2 | 7750 | 30845 | 53940 |
| GK5 | 7751 | 30846 | 53941 |
| GKAP1 | 7752 | 30847 | 53942 |
| GKN1 | 7753 | 30848 | 53943 |
| GKN2 | 7754 | 30849 | 53944 |
| GLA | 7755 | 30850 | 53945 |
| GLB1 | 7756 | 30851 | 53946 |
| GLB1L | 7757 | 30852 | 53947 |
| GLB1L2 | 7758 | 30853 | 53948 |
| GLB1L3 | 7759 | 30854 | 53949 |
| GLCCI1 | 7760 | 30855 | 53950 |
| GLCE | 7761 | 30856 | 53951 |
| GLCE | 7762 | 30857 | 53952 |
| GLDC | 7763 | 30858 | 53953 |
| GLDN | 7764 | 30859 | 53954 |
| GLE1 | 7765 | 30860 | 53955 |
| GLE1 | 7766 | 30861 | 53956 |
| GLG1 | 7767 | 30862 | 53957 |
| GLG1 | 7768 | 30863 | 53958 |
| GLI1 | 7769 | 30864 | 53959 |
| GLI2 | 7770 | 30865 | 53960 |
| GLI3 | 7771 | 30866 | 53961 |
| GLI4 | 7772 | 30867 | 53962 |
| GLIPR1 | 7773 | 30868 | 53963 |
| GLIPR1L1 | 7774 | 30869 | 53964 |
| GLIPR1L2 | 7775 | 30870 | 53965 |
| GLIPR1L2 | 7776 | 30871 | 53966 |
| GLIPR2 | 7777 | 30872 | 53967 |
| GLIPR2 | 7778 | 30873 | 53968 |
| GLIS1 | 7779 | 30874 | 53969 |
| GLIS2 | 7780 | 30875 | 53970 |
| GLIS3 | 7781 | 30876 | 53971 |
| GLMN | 7782 | 30877 | 53972 |
| GLMP | 7783 | 30878 | 53973 |
| GLMP | 7784 | 30879 | 53974 |
| GLO1 | 7785 | 30880 | 53975 |
| GLOD4 | 7786 | 30881 | 53976 |
| GLOD5 | 7787 | 30882 | 53977 |
| GLP1R | 7788 | 30883 | 53978 |
| GLP2R | 7789 | 30884 | 53979 |
| GLRA1 | 7790 | 30885 | 53980 |
| GLRA2 | 7791 | 30886 | 53981 |
| GLRA3 | 7792 | 30887 | 53982 |
| GLRA4 | 7793 | 30888 | 53983 |
| GLRA4 | 7794 | 30889 | 53984 |
| GLRB | 7795 | 30890 | 53985 |
| GLRB | 7796 | 30891 | 53986 |
| GLRX | 7797 | 30892 | 53987 |
| GLRX2 | 7798 | 30893 | 53988 |
| GLRX3 | 7799 | 30894 | 53989 |
| GLRX5 | 7800 | 30895 | 53990 |
| GLS | 7801 | 30896 | 53991 |
| GLS | 7802 | 30897 | 53992 |
| GLS2 | 7803 | 30898 | 53993 |
| GLS2 | 7804 | 30899 | 53994 |
| GLT1D1 | 7805 | 30900 | 53995 |
| GLT6D1 | 7806 | 30901 | 53996 |
| GLT8D1 | 7807 | 30902 | 53997 |
| GLT8D2 | 7808 | 30903 | 53998 |
| GLTP | 7809 | 30904 | 53999 |
| GLTPD2 | 7810 | 30905 | 54000 |
| GLUD1 | 7811 | 30906 | 54001 |
| GLUL | 7812 | 30907 | 54002 |
| GLYAT | 7813 | 30908 | 54003 |
| GLYAT | 7814 | 30909 | 54004 |
| GLYATL1 | 7815 | 30910 | 54005 |
| GLYATL2 | 7816 | 30911 | 54006 |
| GLYATL3 | 7817 | 30912 | 54007 |
| GLYCTK | 7818 | 30913 | 54008 |
| GLYCTK | 7819 | 30914 | 54009 |
| GLYR1 | 7820 | 30915 | 54010 |
| GM2A | 7821 | 30916 | 54011 |
| GM2A | 7822 | 30917 | 54012 |
| GMCL1 | 7823 | 30918 | 54013 |
| GMDS | 7824 | 30919 | 54014 |
| GMEB1 | 7825 | 30920 | 54015 |
| GMEB2 | 7826 | 30921 | 54016 |
| GMFB | 7827 | 30922 | 54017 |
| GMFG | 7828 | 30923 | 54018 |
| GMIP | 7829 | 30924 | 54019 |
| GML | 7830 | 30925 | 54020 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| GMNC | 7831 | 30926 | 54021 |
| GMNN | 7832 | 30927 | 54022 |
| GMPPA | 7833 | 30928 | 54023 |
| GMPPB | 7834 | 30929 | 54024 |
| GMPR | 7835 | 30930 | 54025 |
| GMPR2 | 7836 | 30931 | 54026 |
| GMPS | 7837 | 30932 | 54027 |
| GNA11 | 7838 | 30933 | 54028 |
| GNA12 | 7839 | 30934 | 54029 |
| GNA13 | 7840 | 30935 | 54030 |
| GNA14 | 7841 | 30936 | 54031 |
| GNA15 | 7842 | 30937 | 54032 |
| GNAI1 | 7843 | 30938 | 54033 |
| GNAI2 | 7844 | 30939 | 54034 |
| GNAI3 | 7845 | 30940 | 54035 |
| GNAL | 7846 | 30941 | 54036 |
| GNAO1 | 7847 | 30942 | 54037 |
| GNAO1 | 7848 | 30943 | 54038 |
| GNAQ | 7849 | 30944 | 54039 |
| GNAS | 7850 | 30945 | 54040 |
| GNAS | 7851 | 30946 | 54041 |
| GNAS | 7852 | 30947 | 54042 |
| GNAT1 | 7853 | 30948 | 54043 |
| GNAT2 | 7854 | 30949 | 54044 |
| GNAT3 | 7855 | 30950 | 54045 |
| GNAZ | 7856 | 30951 | 54046 |
| GNB1 | 7857 | 30952 | 54047 |
| GNB1L | 7858 | 30953 | 54048 |
| GNB2 | 7859 | 30954 | 54049 |
| GNB3 | 7860 | 30955 | 54050 |
| GNB4 | 7861 | 30956 | 54051 |
| GNB5 | 7862 | 30957 | 54052 |
| GNE | 7863 | 30958 | 54053 |
| GNG10 | 7864 | 30959 | 54054 |
| GNG11 | 7865 | 30960 | 54055 |
| GNG12 | 7866 | 30961 | 54056 |
| GNG13 | 7867 | 30962 | 54057 |
| GNG14 | 7868 | 30963 | 54058 |
| GNG2 | 7869 | 30964 | 54059 |
| GNG3 | 7870 | 30965 | 54060 |
| GNG4 | 7871 | 30966 | 54061 |
| GNG5 | 7872 | 30967 | 54062 |
| GNG7 | 7873 | 30968 | 54063 |
| GNG8 | 7874 | 30969 | 54064 |
| GNGT1 | 7875 | 30970 | 54065 |
| GNGT2 | 7876 | 30971 | 54066 |
| GNL1 | 7877 | 30972 | 54067 |
| GNL2 | 7878 | 30973 | 54068 |
| GNL3 | 7879 | 30974 | 54069 |
| GNL3L | 7880 | 30975 | 54070 |
| GNLY | 7881 | 30976 | 54071 |
| GNMT | 7882 | 30977 | 54072 |
| GNPAT | 7883 | 30978 | 54073 |
| GNPDA1 | 7884 | 30979 | 54074 |
| GNPDA2 | 7885 | 30980 | 54075 |
| GNPNAT1 | 7886 | 30981 | 54076 |
| GNPTAB | 7887 | 30982 | 54077 |
| GNPTG | 7888 | 30983 | 54078 |
| GNRH1 | 7889 | 30984 | 54079 |
| GNRH2 | 7890 | 30985 | 54080 |
| GNRHR | 7891 | 30986 | 54081 |
| GNRHR | 7892 | 30987 | 54082 |
| GNS | 7893 | 30988 | 54083 |
| GOLGA1 | 7894 | 30989 | 54084 |
| GOLGA2 | 7895 | 30990 | 54085 |
| GOLGA3 | 7896 | 30991 | 54086 |
| GOLGA3 | 7897 | 30992 | 54087 |
| GOLGA4 | 7898 | 30993 | 54088 |
| GOLGA4 | 7899 | 30994 | 54089 |
| GOLGA5 | 7900 | 30995 | 54090 |
| GOLGA6C | 7901 | 30996 | 54091 |
| GOLGA6L2 | 7902 | 30997 | 54092 |
| GOLGA6L22 | 7903 | 30998 | 54093 |
| GOLGA6L6 | 7904 | 30999 | 54094 |
| GOLGA6L9 | 7905 | 31000 | 54095 |
| GOLGA7 | 7906 | 31001 | 54096 |
| GOLGA7 | 7907 | 31002 | 54097 |
| GOLGA7B | 7908 | 31003 | 54098 |
| GOLGA8A | 7909 | 31004 | 54099 |
| GOLGA8G | 7910 | 31005 | 54100 |
| GOLGA8H | 7911 | 31006 | 54101 |
| GOLGA8J | 7912 | 31007 | 54102 |
| GOLGA8O | 7913 | 31008 | 54103 |
| GOLGB1 | 7914 | 31009 | 54104 |
| GOLIM4 | 7915 | 31010 | 54105 |
| GOLM1 | 7916 | 31011 | 54106 |
| GOLPH3 | 7917 | 31012 | 54107 |
| GOLPH3L | 7918 | 31013 | 54108 |
| GOLT1A | 7919 | 31014 | 54109 |
| GOLT1B | 7920 | 31015 | 54110 |
| GON4L | 7921 | 31016 | 54111 |
| GON4L | 7922 | 31017 | 54112 |
| GON7 | 7923 | 31018 | 54113 |
| GOPC | 7924 | 31019 | 54114 |
| GORAB | 7925 | 31020 | 54115 |
| GORAB | 7926 | 31021 | 54116 |
| GORASP1 | 7927 | 31022 | 54117 |
| GORASP2 | 7928 | 31023 | 54118 |
| GOSR1 | 7929 | 31024 | 54119 |
| GOSR2 | 7930 | 31025 | 54120 |
| GOSR2 | 7931 | 31026 | 54121 |
| GOSR2 | 7932 | 31027 | 54122 |
| GOSR2 | 7933 | 31028 | 54123 |
| GOT1 | 7934 | 31029 | 54124 |
| GOT1L1 | 7935 | 31030 | 54125 |
| GOT2 | 7936 | 31031 | 54126 |
| GP1BA | 7937 | 31032 | 54127 |
| GP1BB | 7938 | 31033 | 54128 |
| GP2 | 7939 | 31034 | 54129 |
| GP5 | 7940 | 31035 | 54130 |
| GP6 | 7941 | 31036 | 54131 |
| GP9 | 7942 | 31037 | 54132 |
| GPA33 | 7943 | 31038 | 54133 |
| GPAA1 | 7944 | 31039 | 54134 |
| GPALPP1 | 7945 | 31040 | 54135 |
| GPAM | 7946 | 31041 | 54136 |
| GPANK1 | 7947 | 31042 | 54137 |
| GPAT2 | 7948 | 31043 | 54138 |
| GPAT2 | 7949 | 31044 | 54139 |
| GPAT3 | 7950 | 31045 | 54140 |
| GPAT4 | 7951 | 31046 | 54141 |
| GPATCH1 | 7952 | 31047 | 54142 |
| GPATCH11 | 7953 | 31048 | 54143 |
| GPATCH2 | 7954 | 31049 | 54144 |
| GPATCH2 | 7955 | 31050 | 54145 |
| GPATCH2L | 7956 | 31051 | 54146 |
| GPATCH2L | 7957 | 31052 | 54147 |
| GPATCH2L | 7958 | 31053 | 54148 |
| GPATCH2L | 7959 | 31054 | 54149 |
| GPATCH2L | 7960 | 31055 | 54150 |
| GPATCH2L | 7961 | 31056 | 54151 |
| GPATCH2L | 7962 | 31057 | 54152 |
| GPATCH3 | 7963 | 31058 | 54153 |
| GPATCH4 | 7964 | 31059 | 54154 |
| GPATCH8 | 7965 | 31060 | 54155 |
| GPBAR1 | 7966 | 31061 | 54156 |
| GPBP1 | 7967 | 31062 | 54157 |
| GPBP1L1 | 7968 | 31063 | 54158 |
| GPC1 | 7969 | 31064 | 54159 |
| GPC2 | 7970 | 31065 | 54160 |
| GPC3 | 7971 | 31066 | 54161 |
| GPC4 | 7972 | 31067 | 54162 |
| GPC5 | 7973 | 31068 | 54163 |
| GPC6 | 7974 | 31069 | 54164 |
| GPCPD1 | 7975 | 31070 | 54165 |
| GPD1 | 7976 | 31071 | 54166 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| GPD1L | 7977 | 31072 | 54167 |
| GPD2 | 7978 | 31073 | 54168 |
| GPER1 | 7979 | 31074 | 54169 |
| GPHA2 | 7980 | 31075 | 54170 |
| GPHB5 | 7981 | 31076 | 54171 |
| GPHN | 7982 | 31077 | 54172 |
| GPI | 7983 | 31078 | 54173 |
| GPIHBP1 | 7984 | 31079 | 54174 |
| GPIHBP1 | 7985 | 31080 | 54175 |
| GPKOW | 7986 | 31081 | 54176 |
| GPLD1 | 7987 | 31082 | 54177 |
| GPM6A | 7988 | 31083 | 54178 |
| GPM6B | 7989 | 31084 | 54179 |
| GPM6B | 7990 | 31085 | 54180 |
| GPN1 | 7991 | 31086 | 54181 |
| GPN2 | 7992 | 31087 | 54182 |
| GPN3 | 7993 | 31088 | 54183 |
| GPNMB | 7994 | 31089 | 54184 |
| GPR1 | 7995 | 31090 | 54185 |
| GPR101 | 7996 | 31091 | 54186 |
| GPR107 | 7997 | 31092 | 54187 |
| GPR107 | 7998 | 31093 | 54188 |
| GPR108 | 7999 | 31094 | 54189 |
| GPR119 | 8000 | 31095 | 54190 |
| GPR12 | 8001 | 31096 | 54191 |
| GPR132 | 8002 | 31097 | 54192 |
| GPR135 | 8003 | 31098 | 54193 |
| GPR137 | 8004 | 31099 | 54194 |
| GPR137 | 8005 | 31100 | 54195 |
| GPR137 | 8006 | 31101 | 54196 |
| GPR137B | 8007 | 31102 | 54197 |
| GPR137C | 8008 | 31103 | 54198 |
| GPR139 | 8009 | 31104 | 54199 |
| GPR141 | 8010 | 31105 | 54200 |
| GPR142 | 8011 | 31106 | 54201 |
| GPR143 | 8012 | 31107 | 54202 |
| GPR146 | 8013 | 31108 | 54203 |
| GPR148 | 8014 | 31109 | 54204 |
| GPR149 | 8015 | 31110 | 54205 |
| GPR15 | 8016 | 31111 | 54206 |
| GPR150 | 8017 | 31112 | 54207 |
| GPR151 | 8018 | 31113 | 54208 |
| GPR152 | 8019 | 31114 | 54209 |
| GPR153 | 8020 | 31115 | 54210 |
| GPR155 | 8021 | 31116 | 54211 |
| GPR156 | 8022 | 31117 | 54212 |
| GPR157 | 8023 | 31118 | 54213 |
| GPR158 | 8024 | 31119 | 54214 |
| GPR160 | 8025 | 31120 | 54215 |
| GPR161 | 8026 | 31121 | 54216 |
| GPR162 | 8027 | 31122 | 54217 |
| GPR17 | 8028 | 31123 | 54218 |
| GPR171 | 8029 | 31124 | 54219 |
| GPR173 | 8030 | 31125 | 54220 |
| GPR174 | 8031 | 31126 | 54221 |
| GPR176 | 8032 | 31127 | 54222 |
| GPR179 | 8033 | 31128 | 54223 |
| GPR18 | 8034 | 31129 | 54224 |
| GPR180 | 8035 | 31130 | 54225 |
| GPR182 | 8036 | 31131 | 54226 |
| GPR183 | 8037 | 31132 | 54227 |
| GPR19 | 8038 | 31133 | 54228 |
| GPR20 | 8039 | 31134 | 54229 |
| GPR21 | 8040 | 31135 | 54230 |
| GPR22 | 8041 | 31136 | 54231 |
| GPR25 | 8042 | 31137 | 54232 |
| GPR26 | 8043 | 31138 | 54233 |
| GPR27 | 8044 | 31139 | 54234 |
| GPR3 | 8045 | 31140 | 54235 |
| GPR31 | 8046 | 31141 | 54236 |
| GPR32 | 8047 | 31142 | 54237 |
| GPR33 | 8048 | 31143 | 54238 |
| GPR34 | 8049 | 31144 | 54239 |
| GPR35 | 8050 | 31145 | 54240 |
| GPR37 | 8051 | 31146 | 54241 |
| GPR37L1 | 8052 | 31147 | 54242 |
| GPR39 | 8053 | 31148 | 54243 |
| GPR4 | 8054 | 31149 | 54244 |
| GPR42 | 8055 | 31150 | 54245 |
| GPR45 | 8056 | 31151 | 54246 |
| GPR50 | 8057 | 31152 | 54247 |
| GPR52 | 8058 | 31153 | 54248 |
| GPR55 | 8059 | 31154 | 54249 |
| GPR6 | 8060 | 31155 | 54250 |
| GPR61 | 8061 | 31156 | 54251 |
| GPR62 | 8062 | 31157 | 54252 |
| GPR63 | 8063 | 31158 | 54253 |
| GPR65 | 8064 | 31159 | 54254 |
| GPR68 | 8065 | 31160 | 54255 |
| GPR75 | 8066 | 31161 | 54256 |
| GPR78 | 8067 | 31162 | 54257 |
| GPR82 | 8068 | 31163 | 54258 |
| GPR83 | 8069 | 31164 | 54259 |
| GPR84 | 8070 | 31165 | 54260 |
| GPR85 | 8071 | 31166 | 54261 |
| GPR87 | 8072 | 31167 | 54262 |
| GPR88 | 8073 | 31168 | 54263 |
| GPR89A | 8074 | 31169 | 54264 |
| GPRASP1 | 8075 | 31170 | 54265 |
| GPRASP2 | 8076 | 31171 | 54266 |
| GPRC5A | 8077 | 31172 | 54267 |
| GPRC5B | 8078 | 31173 | 54268 |
| GPRC5C | 8079 | 31174 | 54269 |
| GPRC5D | 8080 | 31175 | 54270 |
| GPRC6A | 8081 | 31176 | 54271 |
| GPRIN1 | 8082 | 31177 | 54272 |
| GPRIN2 | 8083 | 31178 | 54273 |
| GPRIN3 | 8084 | 31179 | 54274 |
| GPS1 | 8085 | 31180 | 54275 |
| GPS2 | 8086 | 31181 | 54276 |
| GPSM1 | 8087 | 31182 | 54277 |
| GPSM1 | 8088 | 31183 | 54278 |
| GPSM1 | 8089 | 31184 | 54279 |
| GPSM2 | 8090 | 31185 | 54280 |
| GPSM3 | 8091 | 31186 | 54281 |
| GPT | 8092 | 31187 | 54282 |
| GPT2 | 8093 | 31188 | 54283 |
| GPX1 | 8094 | 31189 | 54284 |
| GPX1 | 8095 | 31190 | 54285 |
| GPX2 | 8096 | 31191 | 54286 |
| GPX3 | 8097 | 31192 | 54287 |
| GPX4 | 8098 | 31193 | 54288 |
| GPX4 | 8099 | 31194 | 54289 |
| GPX4 | 8100 | 31195 | 54290 |
| GPX5 | 8101 | 31196 | 54291 |
| GPX5 | 8102 | 31197 | 54292 |
| GPX6 | 8103 | 31198 | 54293 |
| GPX7 | 8104 | 31199 | 54294 |
| GPX8 | 8105 | 31200 | 54295 |
| GPX8 | 8106 | 31201 | 54296 |
| GRAMD1A | 8107 | 31202 | 54297 |
| GRAMD1B | 8108 | 31203 | 54298 |
| GRAMD1C | 8109 | 31204 | 54299 |
| GRAMD2A | 8110 | 31205 | 54300 |
| GRAMD2B | 8111 | 31206 | 54301 |
| GRAMD4 | 8112 | 31207 | 54302 |
| GRAP | 8113 | 31208 | 54303 |
| GRAP | 8114 | 31209 | 54304 |
| GRAP2 | 8115 | 31210 | 54305 |
| GRAPL | 8116 | 31211 | 54306 |
| GRASP | 8117 | 31212 | 54307 |
| GRB10 | 8118 | 31213 | 54308 |
| GRB14 | 8119 | 31214 | 54309 |
| GRB2 | 8120 | 31215 | 54310 |
| GRB7 | 8121 | 31216 | 54311 |
| GRB7 | 8122 | 31217 | 54312 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| GREB1 | 8123 | 31218 | 54313 |
| GREB1 | 8124 | 31219 | 54314 |
| GREB1 | 8125 | 31220 | 54315 |
| GREB1L | 8126 | 31221 | 54316 |
| GREM1 | 8127 | 31222 | 54317 |
| GREM2 | 8128 | 31223 | 54318 |
| GRHL1 | 8129 | 31224 | 54319 |
| GRHL2 | 8130 | 31225 | 54320 |
| GRHL3 | 8131 | 31226 | 54321 |
| GRHL3 | 8132 | 31227 | 54322 |
| GRHPR | 8133 | 31228 | 54323 |
| GRIA1 | 8134 | 31229 | 54324 |
| GRIA2 | 8135 | 31230 | 54325 |
| GRIA3 | 8136 | 31231 | 54326 |
| GRIA3 | 8137 | 31232 | 54327 |
| GRIA4 | 8138 | 31233 | 54328 |
| GRIA4 | 8139 | 31234 | 54329 |
| GRIA4 | 8140 | 31235 | 54330 |
| GRID1 | 8141 | 31236 | 54331 |
| GRID2 | 8142 | 31237 | 54332 |
| GRID2IP | 8143 | 31238 | 54333 |
| GRIFIN | 8144 | 31239 | 54334 |
| GRIK1 | 8145 | 31240 | 54335 |
| GRIK1 | 8146 | 31241 | 54336 |
| GRIK1 | 8147 | 31242 | 54337 |
| GRIK2 | 8148 | 31243 | 54338 |
| GRIK2 | 8149 | 31244 | 54339 |
| GRIK2 | 8150 | 31245 | 54340 |
| GRIK3 | 8151 | 31246 | 54341 |
| GRIK4 | 8152 | 31247 | 54342 |
| GRIK4 | 8153 | 31248 | 54343 |
| GRIK5 | 8154 | 31249 | 54344 |
| GRIK5 | 8155 | 31250 | 54345 |
| GRIN1 | 8156 | 31251 | 54346 |
| GRIN1 | 8157 | 31252 | 54347 |
| GRIN2A | 8158 | 31253 | 54348 |
| GRIN2A | 8159 | 31254 | 54349 |
| GRIN2B | 8160 | 31255 | 54350 |
| GRIN2C | 8161 | 31256 | 54351 |
| GRIN2C | 8162 | 31257 | 54352 |
| GRIN2D | 8163 | 31258 | 54353 |
| GRIN3A | 8164 | 31259 | 54354 |
| GRIN3B | 8165 | 31260 | 54355 |
| GRINA | 8166 | 31261 | 54356 |
| GRIP1 | 8167 | 31262 | 54357 |
| GRIP2 | 8168 | 31263 | 54358 |
| GRIPAP1 | 8169 | 31264 | 54359 |
| GRK1 | 8170 | 31265 | 54360 |
| GRK2 | 8171 | 31266 | 54361 |
| GRK3 | 8172 | 31267 | 54362 |
| GRK4 | 8173 | 31268 | 54363 |
| GRK5 | 8174 | 31269 | 54364 |
| GRK6 | 8175 | 31270 | 54365 |
| GRK6 | 8176 | 31271 | 54366 |
| GRK6 | 8177 | 31272 | 54367 |
| GRK7 | 8178 | 31273 | 54368 |
| GRM1 | 8179 | 31274 | 54369 |
| GRM1 | 8180 | 31275 | 54370 |
| GRM1 | 8181 | 31276 | 54371 |
| GRM2 | 8182 | 31277 | 54372 |
| GRM3 | 8183 | 31278 | 54373 |
| GRM4 | 8184 | 31279 | 54374 |
| GRM5 | 8185 | 31280 | 54375 |
| GRM6 | 8186 | 31281 | 54376 |
| GRM7 | 8187 | 31282 | 54377 |
| GRM7 | 8188 | 31283 | 54378 |
| GRM8 | 8189 | 31284 | 54379 |
| GRM8 | 8190 | 31285 | 54380 |
| GRN | 8191 | 31286 | 54381 |
| GRP | 8192 | 31287 | 54382 |
| GRP | 8193 | 31288 | 54383 |
| GRPEL1 | 8194 | 31289 | 54384 |
| GRPEL2 | 8195 | 31290 | 54385 |
| GRPR | 8196 | 31291 | 54386 |
| GRSF1 | 8197 | 31292 | 54387 |
| GRTP1 | 8198 | 31293 | 54388 |
| GRTP1 | 8199 | 31294 | 54389 |
| GRTP1 | 8200 | 31295 | 54390 |
| GRWD1 | 8201 | 31296 | 54391 |
| GRXCR1 | 8202 | 31297 | 54392 |
| GRXCR2 | 8203 | 31298 | 54393 |
| GSAP | 8204 | 31299 | 54394 |
| GSAP | 8205 | 31300 | 54395 |
| GSC | 8206 | 31301 | 54396 |
| GSC2 | 8207 | 31302 | 54397 |
| GSDMA | 8208 | 31303 | 54398 |
| GSDMB | 8209 | 31304 | 54399 |
| GSDMC | 8210 | 31305 | 54400 |
| GSDMD | 8211 | 31306 | 54401 |
| GSE1 | 8212 | 31307 | 54402 |
| GSG1 | 8213 | 31308 | 54403 |
| GSG1 | 8214 | 31309 | 54404 |
| GSG1L | 8215 | 31310 | 54405 |
| GSG1L | 8216 | 31311 | 54406 |
| GSG1L2 | 8217 | 31312 | 54407 |
| GSK3A | 8218 | 31313 | 54408 |
| GSK3B | 8219 | 31314 | 54409 |
| GSKIP | 8220 | 31315 | 54410 |
| GSN | 8221 | 31316 | 54411 |
| GSPT1 | 8222 | 31317 | 54412 |
| GSPT2 | 8223 | 31318 | 54413 |
| GSR | 8224 | 31319 | 54414 |
| GSS | 8225 | 31320 | 54415 |
| GSTA1 | 8226 | 31321 | 54416 |
| GSTA2 | 8227 | 31322 | 54417 |
| GSTA3 | 8228 | 31323 | 54418 |
| GSTA4 | 8229 | 31324 | 54419 |
| GSTCD | 8230 | 31325 | 54420 |
| GSTK1 | 8231 | 31326 | 54421 |
| GSTM1 | 8232 | 31327 | 54422 |
| GSTM2 | 8233 | 31328 | 54423 |
| GSTM3 | 8234 | 31329 | 54424 |
| GSTM4 | 8235 | 31330 | 54425 |
| GSTM4 | 8236 | 31331 | 54426 |
| GSTM5 | 8237 | 31332 | 54427 |
| GSTO1 | 8238 | 31333 | 54428 |
| GSTO2 | 8239 | 31334 | 54429 |
| GSTP1 | 8240 | 31335 | 54430 |
| GSTT2 | 8241 | 31336 | 54431 |
| GSTZ1 | 8242 | 31337 | 54432 |
| GSX1 | 8243 | 31338 | 54433 |
| GSX2 | 8244 | 31339 | 54434 |
| GTDC1 | 8245 | 31340 | 54435 |
| GTDC1 | 8246 | 31341 | 54436 |
| GTDC1 | 8247 | 31342 | 54437 |
| GTF2A1 | 8248 | 31343 | 54438 |
| GTF2A2 | 8249 | 31344 | 54439 |
| GTF2B | 8250 | 31345 | 54440 |
| GTF2E1 | 8251 | 31346 | 54441 |
| GTF2E2 | 8252 | 31347 | 54442 |
| GTF2E2 | 8253 | 31348 | 54443 |
| GTF2F1 | 8254 | 31349 | 54444 |
| GTF2F2 | 8255 | 31350 | 54445 |
| GTF2H1 | 8256 | 31351 | 54446 |
| GTF2H2C_2 | 8257 | 31352 | 54447 |
| GTF2H3 | 8258 | 31353 | 54448 |
| GTF2H4 | 8259 | 31354 | 54449 |
| GTF2H5 | 8260 | 31355 | 54450 |
| GTF2I | 8261 | 31356 | 54451 |
| GTF2I | 8262 | 31357 | 54452 |
| GTF2IRD1 | 8263 | 31358 | 54453 |
| GTF2IRD2 | 8264 | 31359 | 54454 |
| GTF2IRD2B | 8265 | 31360 | 54455 |
| GTF3A | 8266 | 31361 | 54456 |
| GTF3C1 | 8267 | 31362 | 54457 |
| GTF3C2 | 8268 | 31363 | 54458 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| GTF3C3 | 8269 | 31364 | 54459 |
| GTF3C3 | 8270 | 31365 | 54460 |
| GTF3C4 | 8271 | 31366 | 54461 |
| GTF3C5 | 8272 | 31367 | 54462 |
| GTF3C6 | 8273 | 31368 | 54463 |
| GTPBP1 | 8274 | 31369 | 54464 |
| GTPBP10 | 8275 | 31370 | 54465 |
| GTPBP2 | 8276 | 31371 | 54466 |
| GTPBP3 | 8277 | 31372 | 54467 |
| GTPBP4 | 8278 | 31373 | 54468 |
| GTPBP6 | 8279 | 31374 | 54469 |
| GTPBP8 | 8280 | 31375 | 54470 |
| GTSCR1 | 8281 | 31376 | 54471 |
| GTSE1 | 8282 | 31377 | 54472 |
| GTSF1 | 8283 | 31378 | 54473 |
| GTSF1L | 8284 | 31379 | 54474 |
| GUCA1A | 8285 | 31380 | 54475 |
| GUCA1B | 8286 | 31381 | 54476 |
| GUCA1C | 8287 | 31382 | 54477 |
| GUCA2A | 8288 | 31383 | 54478 |
| GUCA2B | 8289 | 31384 | 54479 |
| GUCD1 | 8290 | 31385 | 54480 |
| GUCD1 | 8291 | 31386 | 54481 |
| GUCY1A2 | 8292 | 31387 | 54482 |
| GUCY1A3 | 8293 | 31388 | 54483 |
| GUCY1A3 | 8294 | 31389 | 54484 |
| GUCY1B3 | 8295 | 31390 | 54485 |
| GUCY2C | 8296 | 31391 | 54486 |
| GUCY2D | 8297 | 31392 | 54487 |
| GUCY2F | 8298 | 31393 | 54488 |
| GUF1 | 8299 | 31394 | 54489 |
| GUK1 | 8300 | 31395 | 54490 |
| GUK1 | 8301 | 31396 | 54491 |
| GULP1 | 8302 | 31397 | 54492 |
| GULP1 | 8303 | 31398 | 54493 |
| GUSB | 8304 | 31399 | 54494 |
| GVQW2 | 8305 | 31400 | 54495 |
| GXYLT1 | 8306 | 31401 | 54496 |
| GXYLT2 | 8307 | 31402 | 54497 |
| GYG1 | 8308 | 31403 | 54498 |
| GYG1 | 8309 | 31404 | 54499 |
| GYG2 | 8310 | 31405 | 54500 |
| GYPA | 8311 | 31406 | 54501 |
| GYPB | 8312 | 31407 | 54502 |
| GYPC | 8313 | 31408 | 54503 |
| GYPC | 8314 | 31409 | 54504 |
| GYPE | 8315 | 31410 | 54505 |
| GYS1 | 8316 | 31411 | 54506 |
| GYS2 | 8317 | 31412 | 54507 |
| GZF1 | 8318 | 31413 | 54508 |
| GZF1 | 8319 | 31414 | 54509 |
| GZMA | 8320 | 31415 | 54510 |
| GZMB | 8321 | 31416 | 54511 |
| GZMH | 8322 | 31417 | 54512 |
| GZMK | 8323 | 31418 | 54513 |
| GZMM | 8324 | 31419 | 54514 |
| H2AFX | 8325 | 31420 | 54515 |
| H2AFZ | 8326 | 31421 | 54516 |
| H6PD | 8327 | 31422 | 54517 |
| HAAO | 8328 | 31423 | 54518 |
| HABP2 | 8329 | 31424 | 54519 |
| HABP4 | 8330 | 31425 | 54520 |
| HACD1 | 8331 | 31426 | 54521 |
| HACD2 | 8332 | 31427 | 54522 |
| HACD3 | 8333 | 31428 | 54523 |
| HACD4 | 8334 | 31429 | 54524 |
| HACE1 | 8335 | 31430 | 54525 |
| HACL1 | 8336 | 31431 | 54526 |
| HADH | 8337 | 31432 | 54527 |
| HADHA | 8338 | 31433 | 54528 |
| HADHB | 8339 | 31434 | 54529 |
| HAGH | 8340 | 31435 | 54530 |
| HAGH | 8341 | 31436 | 54531 |
| HAGHL | 8342 | 31437 | 54532 |
| HAGHL | 8343 | 31438 | 54533 |
| HAL | 8344 | 31439 | 54534 |
| HAL | 8345 | 31440 | 54535 |
| HAMP | 8346 | 31441 | 54536 |
| HAND1 | 8347 | 31442 | 54537 |
| HAND2 | 8348 | 31443 | 54538 |
| HAO1 | 8349 | 31444 | 54539 |
| HAO2 | 8350 | 31445 | 54540 |
| HAP1 | 8351 | 31446 | 54541 |
| HAPLN1 | 8352 | 31447 | 54542 |
| HAPLN2 | 8353 | 31448 | 54543 |
| HAPLN3 | 8354 | 31449 | 54544 |
| HAPLN4 | 8355 | 31450 | 54545 |
| HARBI1 | 8356 | 31451 | 54546 |
| HARS | 8357 | 31452 | 54547 |
| HARS2 | 8358 | 31453 | 54548 |
| HAS1 | 8359 | 31454 | 54549 |
| HAS2 | 8360 | 31455 | 54550 |
| HAS3 | 8361 | 31456 | 54551 |
| HAS3 | 8362 | 31457 | 54552 |
| HASPIN | 8363 | 31458 | 54553 |
| HAT1 | 8364 | 31459 | 54554 |
| HAUS1 | 8365 | 31460 | 54555 |
| HAUS2 | 8366 | 31461 | 54556 |
| HAUS2 | 8367 | 31462 | 54557 |
| HAUS3 | 8368 | 31463 | 54558 |
| HAUS4 | 8369 | 31464 | 54559 |
| HAUS5 | 8370 | 31465 | 54560 |
| HAUS6 | 8371 | 31466 | 54561 |
| HAUS7 | 8372 | 31467 | 54562 |
| HAUS8 | 8373 | 31468 | 54563 |
| HAVCR1 | 8374 | 31469 | 54564 |
| HAVCR1 | 8375 | 31470 | 54565 |
| HAVCR2 | 8376 | 31471 | 54566 |
| HAX1 | 8377 | 31472 | 54567 |
| HBA1 | 8378 | 31473 | 54568 |
| HBB | 8379 | 31474 | 54569 |
| HBD | 8380 | 31475 | 54570 |
| HBE1 | 8381 | 31476 | 54571 |
| HBEGF | 8382 | 31477 | 54572 |
| HBG1 | 8383 | 31478 | 54573 |
| HBM | 8384 | 31479 | 54574 |
| HBP1 | 8385 | 31480 | 54575 |
| HBQ1 | 8386 | 31481 | 54576 |
| HBS1L | 8387 | 31482 | 54577 |
| HBS1L | 8388 | 31483 | 54578 |
| HBZ | 8389 | 31484 | 54579 |
| HCAR1 | 8390 | 31485 | 54580 |
| HCAR2 | 8391 | 31486 | 54581 |
| HCAR3 | 8392 | 31487 | 54582 |
| HCCS | 8393 | 31488 | 54583 |
| HCFC1 | 8394 | 31489 | 54584 |
| HCFC1R1 | 8395 | 31490 | 54585 |
| HCFC2 | 8396 | 31491 | 54586 |
| HCG22 | 8397 | 31492 | 54587 |
| HCK | 8398 | 31493 | 54588 |
| HCLS1 | 8399 | 31494 | 54589 |
| HCN1 | 8400 | 31495 | 54590 |
| HCN2 | 8401 | 31496 | 54591 |
| HCN3 | 8402 | 31497 | 54592 |
| HCN4 | 8403 | 31498 | 54593 |
| HCRT | 8404 | 31499 | 54594 |
| HCRTR1 | 8405 | 31500 | 54595 |
| HCRTR2 | 8406 | 31501 | 54596 |
| HCST | 8407 | 31502 | 54597 |
| HDAC1 | 8408 | 31503 | 54598 |
| HDAC10 | 8409 | 31504 | 54599 |
| HDAC11 | 8410 | 31505 | 54600 |
| HDAC2 | 8411 | 31506 | 54601 |
| HDAC3 | 8412 | 31507 | 54602 |
| HDAC4 | 8413 | 31508 | 54603 |
| HDAC5 | 8414 | 31509 | 54604 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| HDAC6 | 8415 | 31510 | 54605 |
| HDAC6 | 8416 | 31511 | 54606 |
| HDAC7 | 8417 | 31512 | 54607 |
| HDAC8 | 8418 | 31513 | 54608 |
| HDAC8 | 8419 | 31514 | 54609 |
| HDAC8 | 8420 | 31515 | 54610 |
| HDAC8 | 8421 | 31516 | 54611 |
| HDAC9 | 8422 | 31517 | 54612 |
| HDAC9 | 8423 | 31518 | 54613 |
| HDAC9 | 8424 | 31519 | 54614 |
| HDAC9 | 8425 | 31520 | 54615 |
| HDC | 8426 | 31521 | 54616 |
| HDDC2 | 8427 | 31522 | 54617 |
| HDDC3 | 8428 | 31523 | 54618 |
| HDDC3 | 8429 | 31524 | 54619 |
| HDGF | 8430 | 31525 | 54620 |
| HDGFL1 | 8431 | 31526 | 54621 |
| HDGFL2 | 8432 | 31527 | 54622 |
| HDGFL3 | 8433 | 31528 | 54623 |
| HDHD2 | 8434 | 31529 | 54624 |
| HDHD3 | 8435 | 31530 | 54625 |
| HDHD5 | 8436 | 31531 | 54626 |
| HDLBP | 8437 | 31532 | 54627 |
| HDLBP | 8438 | 31533 | 54628 |
| HDX | 8439 | 31534 | 54629 |
| HEATR1 | 8440 | 31535 | 54630 |
| HEATR3 | 8441 | 31536 | 54631 |
| HEATR4 | 8442 | 31537 | 54632 |
| HEATR5A | 8443 | 31538 | 54633 |
| HEATR5B | 8444 | 31539 | 54634 |
| HEATR6 | 8445 | 31540 | 54635 |
| HEATR9 | 8446 | 31541 | 54636 |
| HEBP1 | 8447 | 31542 | 54637 |
| HEBP2 | 8448 | 31543 | 54638 |
| HEBP2 | 8449 | 31544 | 54639 |
| HECA | 8450 | 31545 | 54640 |
| HECTD1 | 8451 | 31546 | 54641 |
| HECTD2 | 8452 | 31547 | 54642 |
| HECTD2 | 8453 | 31548 | 54643 |
| HECTD3 | 8454 | 31549 | 54644 |
| HECTD4 | 8455 | 31550 | 54645 |
| HECW1 | 8456 | 31551 | 54646 |
| HECW2 | 8457 | 31552 | 54647 |
| HEG1 | 8458 | 31553 | 54648 |
| HELB | 8459 | 31554 | 54649 |
| HELLS | 8460 | 31555 | 54650 |
| HELQ | 8461 | 31556 | 54651 |
| HELQ | 8462 | 31557 | 54652 |
| HELT | 8463 | 31558 | 54653 |
| HELZ | 8464 | 31559 | 54654 |
| HELZ2 | 8465 | 31560 | 54655 |
| HEMGN | 8466 | 31561 | 54656 |
| HEMK1 | 8467 | 31562 | 54657 |
| HENMT1 | 8468 | 31563 | 54658 |
| HEPACAM | 8469 | 31564 | 54659 |
| HEPACAM2 | 8470 | 31565 | 54660 |
| HEPH | 8471 | 31566 | 54661 |
| HEPHL1 | 8472 | 31567 | 54662 |
| HEPN1 | 8473 | 31568 | 54663 |
| HERC1 | 8474 | 31569 | 54664 |
| HERC2 | 8475 | 31570 | 54665 |
| HERC3 | 8476 | 31571 | 54666 |
| HERC3 | 8477 | 31572 | 54667 |
| HERC4 | 8478 | 31573 | 54668 |
| HERC4 | 8479 | 31574 | 54669 |
| HERC5 | 8480 | 31575 | 54670 |
| HERC6 | 8481 | 31576 | 54671 |
| HERPUD1 | 8482 | 31577 | 54672 |
| HERPUD1 | 8483 | 31578 | 54673 |
| HERPUD2 | 8484 | 31579 | 54674 |
| HES1 | 8485 | 31580 | 54675 |
| HES2 | 8486 | 31581 | 54676 |
| HES3 | 8487 | 31582 | 54677 |
| HES4 | 8488 | 31583 | 54678 |
| HES5 | 8489 | 31584 | 54679 |
| HES6 | 8490 | 31585 | 54680 |
| HES7 | 8491 | 31586 | 54681 |
| HESX1 | 8492 | 31587 | 54682 |
| HEXA | 8493 | 31588 | 54683 |
| HEXB | 8494 | 31589 | 54684 |
| HEXDC | 8495 | 31590 | 54685 |
| HEXDC | 8496 | 31591 | 54686 |
| HEXIM1 | 8497 | 31592 | 54687 |
| HEXIM2 | 8498 | 31593 | 54688 |
| HEY1 | 8499 | 31594 | 54689 |
| HEY2 | 8500 | 31595 | 54690 |
| HEYL | 8501 | 31596 | 54691 |
| HFE | 8502 | 31597 | 54692 |
| HFE | 8503 | 31598 | 54693 |
| HFE | 8504 | 31599 | 54694 |
| HFE2 | 8505 | 31600 | 54695 |
| HFM1 | 8506 | 31601 | 54696 |
| HGC6.3 | 8507 | 31602 | 54697 |
| HGD | 8508 | 31603 | 54698 |
| HGF | 8509 | 31604 | 54699 |
| HGF | 8510 | 31605 | 54700 |
| HGF | 8511 | 31606 | 54701 |
| HGFAC | 8512 | 31607 | 54702 |
| HGH1 | 8513 | 31608 | 54703 |
| HGS | 8514 | 31609 | 54704 |
| HGSNAT | 8515 | 31610 | 54705 |
| HHAT | 8516 | 31611 | 54706 |
| HHATL | 8517 | 31612 | 54707 |
| HHEX | 8518 | 31613 | 54708 |
| HHIP | 8519 | 31614 | 54709 |
| HHIPL1 | 8520 | 31615 | 54710 |
| HHIPL1 | 8521 | 31616 | 54711 |
| HHIPL2 | 8522 | 31617 | 54712 |
| HHLA1 | 8523 | 31618 | 54713 |
| HHLA2 | 8524 | 31619 | 54714 |
| HHLA3 | 8525 | 31620 | 54715 |
| HHLA3 | 8526 | 31621 | 54716 |
| HIBADH | 8527 | 31622 | 54717 |
| HIBCH | 8528 | 31623 | 54718 |
| HIBCH | 8529 | 31624 | 54719 |
| HIC1 | 8530 | 31625 | 54720 |
| HIC2 | 8531 | 31626 | 54721 |
| HID1 | 8532 | 31627 | 54722 |
| HIF1A | 8533 | 31628 | 54723 |
| HIF1A | 8534 | 31629 | 54724 |
| HIF1AN | 8535 | 31630 | 54725 |
| HIF3A | 8536 | 31631 | 54726 |
| HIF3A | 8537 | 31632 | 54727 |
| HIGD1A | 8538 | 31633 | 54728 |
| HIGD1B | 8539 | 31634 | 54729 |
| HIGD1C | 8540 | 31635 | 54730 |
| HIGD2A | 8541 | 31636 | 54731 |
| HIGD2B | 8542 | 31637 | 54732 |
| HIKESHI | 8543 | 31638 | 54733 |
| HILPDA | 8544 | 31639 | 54734 |
| HINFP | 8545 | 31640 | 54735 |
| HINFP | 8546 | 31641 | 54736 |
| HINT1 | 8547 | 31642 | 54737 |
| HINT2 | 8548 | 31643 | 54738 |
| HINT3 | 8549 | 31644 | 54739 |
| HIP1 | 8550 | 31645 | 54740 |
| HIP1R | 8551 | 31646 | 54741 |
| HIP1R | 8552 | 31647 | 54742 |
| HIPK1 | 8553 | 31648 | 54743 |
| HIPK1 | 8554 | 31649 | 54744 |
| HIPK2 | 8555 | 31650 | 54745 |
| HIPK3 | 8556 | 31651 | 54746 |
| HIPK4 | 8557 | 31652 | 54747 |
| HIRA | 8558 | 31653 | 54748 |
| HIRIP3 | 8559 | 31654 | 54749 |
| HIST1H1C | 8560 | 31655 | 54750 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| HIST1H1E | 8561 | 31656 | 54751 |
| HIST1H2AM | 8562 | 31657 | 54752 |
| HIST1H2BN | 8563 | 31658 | 54753 |
| HIST1H3F | 8564 | 31659 | 54754 |
| HIST1H3H | 8565 | 31660 | 54755 |
| HIST1H4C | 8566 | 31661 | 54756 |
| HIST1H4D | 8567 | 31662 | 54757 |
| HIST1H4H | 8568 | 31663 | 54758 |
| HIST1H4J | 8569 | 31664 | 54759 |
| HIST2H2AA3 | 8570 | 31665 | 54760 |
| HIST2H3C | 8571 | 31666 | 54761 |
| HIST2H4B | 8572 | 31667 | 54762 |
| HIST3H2A | 8573 | 31668 | 54763 |
| HIST3H2BB | 8574 | 31669 | 54764 |
| HIVEP1 | 8575 | 31670 | 54765 |
| HIVEP2 | 8576 | 31671 | 54766 |
| HIVEP3 | 8577 | 31672 | 54767 |
| HJURP | 8578 | 31673 | 54768 |
| HK1 | 8579 | 31674 | 54769 |
| HK2 | 8580 | 31675 | 54770 |
| HK3 | 8581 | 31676 | 54771 |
| HKDC1 | 8582 | 31677 | 54772 |
| HKR1 | 8583 | 31678 | 54773 |
| HKR1 | 8584 | 31679 | 54774 |
| HLA-C | 8585 | 31680 | 54775 |
| HLA-DMA | 8586 | 31681 | 54776 |
| HLA-DMB | 8587 | 31682 | 54777 |
| HLA-DOA | 8588 | 31683 | 54778 |
| HLA-DOB | 8589 | 31684 | 54779 |
| HLA-DPA1 | 8590 | 31685 | 54780 |
| HLA-DPB1 | 8591 | 31686 | 54781 |
| HLA-DQA1 | 8592 | 31687 | 54782 |
| HLA-DQA2 | 8593 | 31688 | 54783 |
| HLA-DQB1 | 8594 | 31689 | 54784 |
| HLA-DQB1 | 8595 | 31690 | 54785 |
| HLA-DQB1 | 8596 | 31691 | 54786 |
| HLA-DQB2 | 8597 | 31692 | 54787 |
| HLA-DRA | 8598 | 31693 | 54788 |
| HLA-DRB1 | 8599 | 31694 | 54789 |
| HLA-DRB1 | 8600 | 31695 | 54790 |
| HLA-DRB4 | 8601 | 31696 | 54791 |
| HLA-DRB5 | 8602 | 31697 | 54792 |
| HLA-E | 8603 | 31698 | 54793 |
| HLA-F | 8604 | 31699 | 54794 |
| HLA-F | 8605 | 31700 | 54795 |
| HLA-G | 8606 | 31701 | 54796 |
| HLCS | 8607 | 31702 | 54797 |
| HLF | 8608 | 31703 | 54798 |
| HLTF | 8609 | 31704 | 54799 |
| HLX | 8610 | 31705 | 54800 |
| HM13 | 8611 | 31706 | 54801 |
| HM13 | 8612 | 31707 | 54802 |
| HM13 | 8613 | 31708 | 54803 |
| HMBOX1 | 8614 | 31709 | 54804 |
| HMBOX1 | 8615 | 31710 | 54805 |
| HMBOX1 | 8616 | 31711 | 54806 |
| HMBS | 8617 | 31712 | 54807 |
| HMCES | 8618 | 31713 | 54808 |
| HMCN1 | 8619 | 31714 | 54809 |
| HMCN2 | 8620 | 31715 | 54810 |
| HMG20A | 8621 | 31716 | 54811 |
| HMG20B | 8622 | 31717 | 54812 |
| HMGA1 | 8623 | 31718 | 54813 |
| HMGA2 | 8624 | 31719 | 54814 |
| HMGA2 | 8625 | 31720 | 54815 |
| HMGA2 | 8626 | 31721 | 54816 |
| HMGA2 | 8627 | 31722 | 54817 |
| HMGB1 | 8628 | 31723 | 54818 |
| HMGB2 | 8629 | 31724 | 54819 |
| HMGB3 | 8630 | 31725 | 54820 |
| HMGB4 | 8631 | 31726 | 54821 |
| HMGCL | 8632 | 31727 | 54822 |
| HMGCLL1 | 8633 | 31728 | 54823 |
| HMGCR | 8634 | 31729 | 54824 |
| HMGCS1 | 8635 | 31730 | 54825 |
| HMGCS2 | 8636 | 31731 | 54826 |
| HMGN1 | 8637 | 31732 | 54827 |
| HMGN2 | 8638 | 31733 | 54828 |
| HMGN3 | 8639 | 31734 | 54829 |
| HMGN3 | 8640 | 31735 | 54830 |
| HMGN3 | 8641 | 31736 | 54831 |
| HMGN3 | 8642 | 31737 | 54832 |
| HMGN4 | 8643 | 31738 | 54833 |
| HMGN5 | 8644 | 31739 | 54834 |
| HMGXB3 | 8645 | 31740 | 54835 |
| HMGXB4 | 8646 | 31741 | 54836 |
| HMHB1 | 8647 | 31742 | 54837 |
| HMMR | 8648 | 31743 | 54838 |
| HMOX1 | 8649 | 31744 | 54839 |
| HMOX2 | 8650 | 31745 | 54840 |
| HMSD | 8651 | 31746 | 54841 |
| HMX1 | 8652 | 31747 | 54842 |
| HMX1 | 8653 | 31748 | 54843 |
| HMX2 | 8654 | 31749 | 54844 |
| HMX3 | 8655 | 31750 | 54845 |
| HNF1A | 8656 | 31751 | 54846 |
| HNF1B | 8657 | 31752 | 54847 |
| HNF1B | 8658 | 31753 | 54848 |
| HNF4A | 8659 | 31754 | 54849 |
| HNF4A | 8660 | 31755 | 54850 |
| HNF4G | 8661 | 31756 | 54851 |
| HNMT | 8662 | 31757 | 54852 |
| HNMT | 8663 | 31758 | 54853 |
| HNMT | 8664 | 31759 | 54854 |
| HNRNPAO | 8665 | 31760 | 54855 |
| HNRNPA1 | 8666 | 31761 | 54856 |
| HNRNPA2B1 | 8667 | 31762 | 54857 |
| HNRNPA3 | 8668 | 31763 | 54858 |
| HNRNPAB | 8669 | 31764 | 54859 |
| HNRNPC | 8670 | 31765 | 54860 |
| HNRNPCL2 | 8671 | 31766 | 54861 |
| HNRNPD | 8672 | 31767 | 54862 |
| HNRNPDL | 8673 | 31768 | 54863 |
| HNRNPF | 8674 | 31769 | 54864 |
| HNRNPH1 | 8675 | 31770 | 54865 |
| HNRNPH2 | 8676 | 31771 | 54866 |
| HNRNPH3 | 8677 | 31772 | 54867 |
| HNRNPK | 8678 | 31773 | 54868 |
| HNRNPK | 8679 | 31774 | 54869 |
| HNRNPL | 8680 | 31775 | 54870 |
| HNRNPLL | 8681 | 31776 | 54871 |
| HNRNPM | 8682 | 31777 | 54872 |
| HNRNPR | 8683 | 31778 | 54873 |
| HNRNPU | 8684 | 31779 | 54874 |
| HNRNPUL1 | 8685 | 31780 | 54875 |
| HNRNPUL2 | 8686 | 31781 | 54876 |
| HOGA1 | 8687 | 31782 | 54877 |
| HOMER1 | 8688 | 31783 | 54878 |
| HOMER1 | 8689 | 31784 | 54879 |
| HOMER2 | 8690 | 31785 | 54880 |
| HOMER3 | 8691 | 31786 | 54881 |
| HOMEZ | 8692 | 31787 | 54882 |
| HOOK1 | 8693 | 31788 | 54883 |
| HOOK2 | 8694 | 31789 | 54884 |
| HOOK3 | 8695 | 31790 | 54885 |
| HOPX | 8696 | 31791 | 54886 |
| HOPX | 8697 | 31792 | 54887 |
| HORMAD1 | 8698 | 31793 | 54888 |
| HORMAD2 | 8699 | 31794 | 54889 |
| HOTS | 8700 | 31795 | 54890 |
| HOXA1 | 8701 | 31796 | 54891 |
| HOXA1 | 8702 | 31797 | 54892 |
| HOXA10 | 8703 | 31798 | 54893 |
| HOXA11 | 8704 | 31799 | 54894 |
| HOXA13 | 8705 | 31800 | 54895 |
| HOXA2 | 8706 | 31801 | 54896 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| HOXA3 | 8707 | 31802 | 54897 |
| HOXA4 | 8708 | 31803 | 54898 |
| HOXA5 | 8709 | 31804 | 54899 |
| HOXA6 | 8710 | 31805 | 54900 |
| HOXA7 | 8711 | 31806 | 54901 |
| HOXA9 | 8712 | 31807 | 54902 |
| HOXB1 | 8713 | 31808 | 54903 |
| HOXB13 | 8714 | 31809 | 54904 |
| HOXB2 | 8715 | 31810 | 54905 |
| HOXB3 | 8716 | 31811 | 54906 |
| HOXB4 | 8717 | 31812 | 54907 |
| HOXB5 | 8718 | 31813 | 54908 |
| HOXB6 | 8719 | 31814 | 54909 |
| HOXB7 | 8720 | 31815 | 54910 |
| HOXB8 | 8721 | 31816 | 54911 |
| HOXB9 | 8722 | 31817 | 54912 |
| HOXC10 | 8723 | 31818 | 54913 |
| HOXC11 | 8724 | 31819 | 54914 |
| HOXC12 | 8725 | 31820 | 54915 |
| HOXC13 | 8726 | 31821 | 54916 |
| HOXC4 | 8727 | 31822 | 54917 |
| HOXC5 | 8728 | 31823 | 54918 |
| HOXC6 | 8729 | 31824 | 54919 |
| HOXC8 | 8730 | 31825 | 54920 |
| HOXC9 | 8731 | 31826 | 54921 |
| HOXD1 | 8732 | 31827 | 54922 |
| HOXD10 | 8733 | 31828 | 54923 |
| HOXD11 | 8734 | 31829 | 54924 |
| HOXD12 | 8735 | 31830 | 54925 |
| HOXD13 | 8736 | 31831 | 54926 |
| HOXD3 | 8737 | 31832 | 54927 |
| HOXD4 | 8738 | 31833 | 54928 |
| HOXD8 | 8739 | 31834 | 54929 |
| HOXD9 | 8740 | 31835 | 54930 |
| HP | 8741 | 31836 | 54931 |
| HP1BP3 | 8742 | 31837 | 54932 |
| HPCA | 8743 | 31838 | 54933 |
| HPCAL1 | 8744 | 31839 | 54934 |
| HPCAL4 | 8745 | 31840 | 54935 |
| HPD | 8746 | 31841 | 54936 |
| HPDL | 8747 | 31842 | 54937 |
| HPF1 | 8748 | 31843 | 54938 |
| HPGD | 8749 | 31844 | 54939 |
| HPGDS | 8750 | 31845 | 54940 |
| HPN | 8751 | 31846 | 54941 |
| HPRT1 | 8752 | 31847 | 54942 |
| HPS1 | 8753 | 31848 | 54943 |
| HPS1 | 8754 | 31849 | 54944 |
| HPS1 | 8755 | 31850 | 54945 |
| HPS3 | 8756 | 31851 | 54946 |
| HPS4 | 8757 | 31852 | 54947 |
| HPS4 | 8758 | 31853 | 54948 |
| HPS4 | 8759 | 31854 | 54949 |
| HPS5 | 8760 | 31855 | 54950 |
| HPS6 | 8761 | 31856 | 54951 |
| HPSE | 8762 | 31857 | 54952 |
| HPSE2 | 8763 | 31858 | 54953 |
| HPSE2 | 8764 | 31859 | 54954 |
| HPX | 8765 | 31860 | 54955 |
| HR | 8766 | 31861 | 54956 |
| HRAS | 8767 | 31862 | 54957 |
| HRAS | 8768 | 31863 | 54958 |
| HRASLS | 8769 | 31864 | 54959 |
| HRASLS2 | 8770 | 31865 | 54960 |
| HRASLS5 | 8771 | 31866 | 54961 |
| HRASLS5 | 8772 | 31867 | 54962 |
| HRC | 8773 | 31868 | 54963 |
| HRCT1 | 8774 | 31869 | 54964 |
| HRG | 8775 | 31870 | 54965 |
| HRH1 | 8776 | 31871 | 54966 |
| HRH2 | 8777 | 31872 | 54967 |
| HRH2 | 8778 | 31873 | 54968 |
| HRH3 | 8779 | 31874 | 54969 |
| HRH4 | 8780 | 31875 | 54970 |
| HRK | 8781 | 31876 | 54971 |
| HRNR | 8782 | 31877 | 54972 |
| HS1BP3 | 8783 | 31878 | 54973 |
| HS2ST1 | 8784 | 31879 | 54974 |
| HS2ST1 | 8785 | 31880 | 54975 |
| HS3ST1 | 8786 | 31881 | 54976 |
| HS3ST2 | 8787 | 31882 | 54977 |
| HS3ST3A1 | 8788 | 31883 | 54978 |
| HS3ST3B1 | 8789 | 31884 | 54979 |
| HS3ST4 | 8790 | 31885 | 54980 |
| HS3ST5 | 8791 | 31886 | 54981 |
| HS3ST6 | 8792 | 31887 | 54982 |
| HS6ST1 | 8793 | 31888 | 54983 |
| HS6ST2 | 8794 | 31889 | 54984 |
| HS6ST3 | 8795 | 31890 | 54985 |
| HSBP1 | 8796 | 31891 | 54986 |
| HSBP1L1 | 8797 | 31892 | 54987 |
| HSCB | 8798 | 31893 | 54988 |
| HSCB | 8799 | 31894 | 54989 |
| HSD11B1 | 8800 | 31895 | 54990 |
| HSD11B1L | 8801 | 31896 | 54991 |
| HSD11B1L | 8802 | 31897 | 54992 |
| HSD11B1L | 8803 | 31898 | 54993 |
| HSD11B2 | 8804 | 31899 | 54994 |
| HSD17B1 | 8805 | 31900 | 54995 |
| HSD17B10 | 8806 | 31901 | 54996 |
| HSD17B11 | 8807 | 31902 | 54997 |
| HSD17B12 | 8808 | 31903 | 54998 |
| HSD17B13 | 8809 | 31904 | 54999 |
| HSD17B14 | 8810 | 31905 | 55000 |
| HSD17B2 | 8811 | 31906 | 55001 |
| HSD17B3 | 8812 | 31907 | 55002 |
| HSD17B4 | 8813 | 31908 | 55003 |
| HSD17B6 | 8814 | 31909 | 55004 |
| HSD17B7 | 8815 | 31910 | 55005 |
| HSD17B7 | 8816 | 31911 | 55006 |
| HSD17B7 | 8817 | 31912 | 55007 |
| HSD17B8 | 8818 | 31913 | 55008 |
| HSD3B2 | 8819 | 31914 | 55009 |
| HSD3B7 | 8820 | 31915 | 55010 |
| HSD3B7 | 8821 | 31916 | 55011 |
| HSDL1 | 8822 | 31917 | 55012 |
| HSDL2 | 8823 | 31918 | 55013 |
| HSF1 | 8824 | 31919 | 55014 |
| HSF2 | 8825 | 31920 | 55015 |
| HSF2 | 8826 | 31921 | 55016 |
| HSF2BP | 8827 | 31922 | 55017 |
| HSF4 | 8828 | 31923 | 55018 |
| HSF5 | 8829 | 31924 | 55019 |
| HSFX2 | 8830 | 31925 | 55020 |
| HSFX3 | 8831 | 31926 | 55021 |
| HSFX4 | 8832 | 31927 | 55022 |
| HSFY1 | 8833 | 31928 | 55023 |
| HSFY2 | 8834 | 31929 | 55024 |
| HSH2D | 8835 | 31930 | 55025 |
| HSH2D | 8836 | 31931 | 55026 |
| HSP90AA1 | 8837 | 31932 | 55027 |
| HSP90AB1 | 8838 | 31933 | 55028 |
| HSP90B1 | 8839 | 31934 | 55029 |
| HSPA12A | 8840 | 31935 | 55030 |
| HSPA12B | 8841 | 31936 | 55031 |
| HSPA13 | 8842 | 31937 | 55032 |
| HSPA14 | 8843 | 31938 | 55033 |
| HSPA14 | 8844 | 31939 | 55034 |
| HSPA1A | 8845 | 31940 | 55035 |
| HSPA1B | 8846 | 31941 | 55036 |
| HSPA1L | 8847 | 31942 | 55037 |
| HSPA2 | 8848 | 31943 | 55038 |
| HSPA4 | 8849 | 31944 | 55039 |
| HSPA4L | 8850 | 31945 | 55040 |
| HSPA5 | 8851 | 31946 | 55041 |
| HSPA6 | 8852 | 31947 | 55042 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| HSPA8 | 8853 | 31948 | 55043 |
| HSPA9 | 8854 | 31949 | 55044 |
| HSPB1 | 8855 | 31950 | 55045 |
| HSPB11 | 8856 | 31951 | 55046 |
| HSPB2 | 8857 | 31952 | 55047 |
| HSPB3 | 8858 | 31953 | 55048 |
| HSPB6 | 8859 | 31954 | 55049 |
| HSPB7 | 8860 | 31955 | 55050 |
| HSPB8 | 8861 | 31956 | 55051 |
| HSPB9 | 8862 | 31957 | 55052 |
| HSPBAP1 | 8863 | 31958 | 55053 |
| HSPBP1 | 8864 | 31959 | 55054 |
| HSPD1 | 8865 | 31960 | 55055 |
| HSPE1 | 8866 | 31961 | 55056 |
| HSPG2 | 8867 | 31962 | 55057 |
| HSPH1 | 8868 | 31963 | 55058 |
| HSPH1 | 8869 | 31964 | 55059 |
| HTATIP2 | 8870 | 31965 | 55060 |
| HTATIP2 | 8871 | 31966 | 55061 |
| HTATSF1 | 8872 | 31967 | 55062 |
| HTN1 | 8873 | 31968 | 55063 |
| HTN3 | 8874 | 31969 | 55064 |
| HTR1A | 8875 | 31970 | 55065 |
| HTR1B | 8876 | 31971 | 55066 |
| HTR1D | 8877 | 31972 | 55067 |
| HTR1E | 8878 | 31973 | 55068 |
| HTR1F | 8879 | 31974 | 55069 |
| HTR2A | 8880 | 31975 | 55070 |
| HTR2B | 8881 | 31976 | 55071 |
| HTR2C | 8882 | 31977 | 55072 |
| HTR3A | 8883 | 31978 | 55073 |
| HTR3B | 8884 | 31979 | 55074 |
| HTR3C | 8885 | 31980 | 55075 |
| HTR3D | 8886 | 31981 | 55076 |
| HTR4 | 8887 | 31982 | 55077 |
| HTR4 | 8888 | 31983 | 55078 |
| HTR4 | 8889 | 31984 | 55079 |
| HTR4 | 8890 | 31985 | 55080 |
| HTR4 | 8891 | 31986 | 55081 |
| HTR5A | 8892 | 31987 | 55082 |
| HTR6 | 8893 | 31988 | 55083 |
| HTR7 | 8894 | 31989 | 55084 |
| HTR7 | 8895 | 31990 | 55085 |
| HTRA1 | 8896 | 31991 | 55086 |
| HTRA2 | 8897 | 31992 | 55087 |
| HTRA3 | 8898 | 31993 | 55088 |
| HTRA3 | 8899 | 31994 | 55089 |
| HTRA4 | 8900 | 31995 | 55090 |
| HTT | 8901 | 31996 | 55091 |
| HUNK | 8902 | 31997 | 55092 |
| HUS1 | 8903 | 31998 | 55093 |
| HUS1B | 8904 | 31999 | 55094 |
| HUWE1 | 8905 | 32000 | 55095 |
| HVCN1 | 8906 | 32001 | 55096 |
| HYAL1 | 8907 | 32002 | 55097 |
| HYAL2 | 8908 | 32003 | 55098 |
| HYAL3 | 8909 | 32004 | 55099 |
| HYAL4 | 8910 | 32005 | 55100 |
| HYDIN | 8911 | 32006 | 55101 |
| HYDIN | 8912 | 32007 | 55102 |
| HYDIN | 8913 | 32008 | 55103 |
| HYI | 8914 | 32009 | 55104 |
| HYI | 8915 | 32010 | 55105 |
| HYKK | 8916 | 32011 | 55106 |
| HYKK | 8917 | 32012 | 55107 |
| HYLS1 | 8918 | 32013 | 55108 |
| HYOU1 | 8919 | 32014 | 55109 |
| HYPK | 8920 | 32015 | 55110 |
| HYPM | 8921 | 32016 | 55111 |
| IAH1 | 8922 | 32017 | 55112 |
| IAPP | 8923 | 32018 | 55113 |
| IARS | 8924 | 32019 | 55114 |
| IARS2 | 8925 | 32020 | 55115 |
| IBA57 | 8926 | 32021 | 55116 |
| IBSP | 8927 | 32022 | 55117 |
| IBTK | 8928 | 32023 | 55118 |
| ICA1 | 8929 | 32024 | 55119 |
| ICA1L | 8930 | 32025 | 55120 |
| ICA1L | 8931 | 32026 | 55121 |
| ICAM1 | 8932 | 32027 | 55122 |
| ICAM2 | 8933 | 32028 | 55123 |
| ICAM3 | 8934 | 32029 | 55124 |
| ICAM4 | 8935 | 32030 | 55125 |
| ICAM4 | 8936 | 32031 | 55126 |
| ICAM5 | 8937 | 32032 | 55127 |
| ICE1 | 8938 | 32033 | 55128 |
| ICE2 | 8939 | 32034 | 55129 |
| ICE2 | 8940 | 32035 | 55130 |
| ICK | 8941 | 32036 | 55131 |
| ICMT | 8942 | 32037 | 55132 |
| ICOS | 8943 | 32038 | 55133 |
| ICOSLG | 8944 | 32039 | 55134 |
| ICOSLG | 8945 | 32040 | 55135 |
| ID1 | 8946 | 32041 | 55136 |
| ID1 | 8947 | 32042 | 55137 |
| ID2 | 8948 | 32043 | 55138 |
| ID3 | 8949 | 32044 | 55139 |
| ID4 | 8950 | 32045 | 55140 |
| IDE | 8951 | 32046 | 55141 |
| IDH1 | 8952 | 32047 | 55142 |
| IDH2 | 8953 | 32048 | 55143 |
| IDH3A | 8954 | 32049 | 55144 |
| IDH3B | 8955 | 32050 | 55145 |
| IDH3B | 8956 | 32051 | 55146 |
| IDH3B | 8957 | 32052 | 55147 |
| IDH3B | 8958 | 32053 | 55148 |
| IDH3G | 8959 | 32054 | 55149 |
| IDH3G | 8960 | 32055 | 55150 |
| IDI1 | 8961 | 32056 | 55151 |
| IDI2 | 8962 | 32057 | 55152 |
| IDNK | 8963 | 32058 | 55153 |
| IDO1 | 8964 | 32059 | 55154 |
| IDO2 | 8965 | 32060 | 55155 |
| IDS | 8966 | 32061 | 55156 |
| IDS | 8967 | 32062 | 55157 |
| IDUA | 8968 | 32063 | 55158 |
| IER2 | 8969 | 32064 | 55159 |
| IER3 | 8970 | 32065 | 55160 |
| IER3IP1 | 8971 | 32066 | 55161 |
| IER5 | 8972 | 32067 | 55162 |
| IER5L | 8973 | 32068 | 55163 |
| IFFO1 | 8974 | 32069 | 55164 |
| IFFO2 | 8975 | 32070 | 55165 |
| IFI16 | 8976 | 32071 | 55166 |
| IFI27 | 8977 | 32072 | 55167 |
| IFI27 | 8978 | 32073 | 55168 |
| IFI27L1 | 8979 | 32074 | 55169 |
| IFI27L2 | 8980 | 32075 | 55170 |
| IFI30 | 8981 | 32076 | 55171 |
| IFI35 | 8982 | 32077 | 55172 |
| IFI44 | 8983 | 32078 | 55173 |
| IFI44L | 8984 | 32079 | 55174 |
| IFI6 | 8985 | 32080 | 55175 |
| IFIH1 | 8986 | 32081 | 55176 |
| IFIT1 | 8987 | 32082 | 55177 |
| IFIT1B | 8988 | 32083 | 55178 |
| IFIT2 | 8989 | 32084 | 55179 |
| IFIT3 | 8990 | 32085 | 55180 |
| IFIT5 | 8991 | 32086 | 55181 |
| IFITM1 | 8992 | 32087 | 55182 |
| IFITM10 | 8993 | 32088 | 55183 |
| IFITM2 | 8994 | 32089 | 55184 |
| IFITM3 | 8995 | 32090 | 55185 |
| IFITM5 | 8996 | 32091 | 55186 |
| IFNA1 | 8997 | 32092 | 55187 |
| IFNA16 | 8998 | 32093 | 55188 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| IFNA21 | 8999 | 32094 | 55189 |
| IFNA4 | 9000 | 32095 | 55190 |
| IFNA6 | 9001 | 32096 | 55191 |
| IFNA8 | 9002 | 32097 | 55192 |
| IFNAR1 | 9003 | 32098 | 55193 |
| IFNAR2 | 9004 | 32099 | 55194 |
| IFNAR2 | 9005 | 32100 | 55195 |
| IFNAR2 | 9006 | 32101 | 55196 |
| IFNB1 | 9007 | 32102 | 55197 |
| IFNE | 9008 | 32103 | 55198 |
| IFNG | 9009 | 32104 | 55199 |
| IFNGR1 | 9010 | 32105 | 55200 |
| IFNGR2 | 9011 | 32106 | 55201 |
| IFNK | 9012 | 32107 | 55202 |
| IFNL1 | 9013 | 32108 | 55203 |
| IFNL2 | 9014 | 32109 | 55204 |
| IFNL3 | 9015 | 32110 | 55205 |
| IFNL4 | 9016 | 32111 | 55206 |
| IFNLR1 | 9017 | 32112 | 55207 |
| IFNW1 | 9018 | 32113 | 55208 |
| IFRD1 | 9019 | 32114 | 55209 |
| IFRD2 | 9020 | 32115 | 55210 |
| IFT122 | 9021 | 32116 | 55211 |
| IFT140 | 9022 | 32117 | 55212 |
| IFT172 | 9023 | 32118 | 55213 |
| IFT20 | 9024 | 32119 | 55214 |
| IFT20 | 9025 | 32120 | 55215 |
| IFT22 | 9026 | 32121 | 55216 |
| IFT27 | 9027 | 32122 | 55217 |
| IFT43 | 9028 | 32123 | 55218 |
| IFT43 | 9029 | 32124 | 55219 |
| IFT46 | 9030 | 32125 | 55220 |
| IFT52 | 9031 | 32126 | 55221 |
| IFT52 | 9032 | 32127 | 55222 |
| IFT52 | 9033 | 32128 | 55223 |
| IFT57 | 9034 | 32129 | 55224 |
| IFT74 | 9035 | 32130 | 55225 |
| IFT74 | 9036 | 32131 | 55226 |
| IFT74 | 9037 | 32132 | 55227 |
| IFT80 | 9038 | 32133 | 55228 |
| IFT81 | 9039 | 32134 | 55229 |
| IFT81 | 9040 | 32135 | 55230 |
| IFT88 | 9041 | 32136 | 55231 |
| IFT88 | 9042 | 32137 | 55232 |
| IGBP1 | 9043 | 32138 | 55233 |
| IGDCC3 | 9044 | 32139 | 55234 |
| IGDCC4 | 9045 | 32140 | 55235 |
| IGF1 | 9046 | 32141 | 55236 |
| IGF1 | 9047 | 32142 | 55237 |
| IGF1 | 9048 | 32143 | 55238 |
| IGF1R | 9049 | 32144 | 55239 |
| IGF2 | 9050 | 32145 | 55240 |
| IGF2BP1 | 9051 | 32146 | 55241 |
| IGF2BP2 | 9052 | 32147 | 55242 |
| IGF2BP3 | 9053 | 32148 | 55243 |
| IGF2R | 9054 | 32149 | 55244 |
| IGFALS | 9055 | 32150 | 55245 |
| IGFBP1 | 9056 | 32151 | 55246 |
| IGFBP2 | 9057 | 32152 | 55247 |
| IGFBP3 | 9058 | 32153 | 55248 |
| IGFBP4 | 9059 | 32154 | 55249 |
| IGFBP5 | 9060 | 32155 | 55250 |
| IGFBP6 | 9061 | 32156 | 55251 |
| IGFBP7 | 9062 | 32157 | 55252 |
| IGFBP7 | 9063 | 32158 | 55253 |
| IGFBPL1 | 9064 | 32159 | 55254 |
| IGFL1 | 9065 | 32160 | 55255 |
| IGFL2 | 9066 | 32161 | 55256 |
| IGFL3 | 9067 | 32162 | 55257 |
| IGFL4 | 9068 | 32163 | 55258 |
| IGFLR1 | 9069 | 32164 | 55259 |
| IGFLR1 | 9070 | 32165 | 55260 |
| IGFN1 | 9071 | 32166 | 55261 |
| IGHMBP2 | 9072 | 32167 | 55262 |
| IGIP | 9073 | 32168 | 55263 |
| IGLL1 | 9074 | 32169 | 55264 |
| IGLL1 | 9075 | 32170 | 55265 |
| IGLL5 | 9076 | 32171 | 55266 |
| IGLON5 | 9077 | 32172 | 55267 |
| IGSF1 | 9078 | 32173 | 55268 |
| IGSF1 | 9079 | 32174 | 55269 |
| IGSF10 | 9080 | 32175 | 55270 |
| IGSF11 | 9081 | 32176 | 55271 |
| IGSF21 | 9082 | 32177 | 55272 |
| IGSF22 | 9083 | 32178 | 55273 |
| IGSF23 | 9084 | 32179 | 55274 |
| IGSF3 | 9085 | 32180 | 55275 |
| IGSF5 | 9086 | 32181 | 55276 |
| IGSF6 | 9087 | 32182 | 55277 |
| IGSF8 | 9088 | 32183 | 55278 |
| IGSF9 | 9089 | 32184 | 55279 |
| IGSF9B | 9090 | 32185 | 55280 |
| IHH | 9091 | 32186 | 55281 |
| IK | 9092 | 32187 | 55282 |
| IKBIP | 9093 | 32188 | 55283 |
| IKBIP | 9094 | 32189 | 55284 |
| IKBKB | 9095 | 32190 | 55285 |
| IKBKE | 9096 | 32191 | 55286 |
| IKBKE | 9097 | 32192 | 55287 |
| IKBKG | 9098 | 32193 | 55288 |
| IKZF1 | 9099 | 32194 | 55289 |
| IKZF1 | 9100 | 32195 | 55290 |
| IKZF1 | 9101 | 32196 | 55291 |
| IKZF2 | 9102 | 32197 | 55292 |
| IKZF3 | 9103 | 32198 | 55293 |
| IKZF3 | 9104 | 32199 | 55294 |
| IKZF4 | 9105 | 32200 | 55295 |
| IKZF5 | 9106 | 32201 | 55296 |
| IL10 | 9107 | 32202 | 55297 |
| IL10RA | 9108 | 32203 | 55298 |
| IL10RB | 9109 | 32204 | 55299 |
| IL11 | 9110 | 32205 | 55300 |
| IL11RA | 9111 | 32206 | 55301 |
| IL12A | 9112 | 32207 | 55302 |
| IL12B | 9113 | 32208 | 55303 |
| IL12RB1 | 9114 | 32209 | 55304 |
| IL12RB1 | 9115 | 32210 | 55305 |
| IL12RB1 | 9116 | 32211 | 55306 |
| IL12RB2 | 9117 | 32212 | 55307 |
| IL12RB2 | 9118 | 32213 | 55308 |
| IL12RB2 | 9119 | 32214 | 55309 |
| IL13 | 9120 | 32215 | 55310 |
| IL13RA1 | 9121 | 32216 | 55311 |
| IL13RA2 | 9122 | 32217 | 55312 |
| IL15 | 9123 | 32218 | 55313 |
| IL15RA | 9124 | 32219 | 55314 |
| IL15RA | 9125 | 32220 | 55315 |
| IL16 | 9126 | 32221 | 55316 |
| IL17A | 9127 | 32222 | 55317 |
| IL17B | 9128 | 32223 | 55318 |
| IL17C | 9129 | 32224 | 55319 |
| IL17D | 9130 | 32225 | 55320 |
| IL17F | 9131 | 32226 | 55321 |
| IL17RA | 9132 | 32227 | 55322 |
| IL17RB | 9133 | 32228 | 55323 |
| IL17RC | 9134 | 32229 | 55324 |
| IL17RD | 9135 | 32230 | 55325 |
| IL17RE | 9136 | 32231 | 55326 |
| IL17RE | 9137 | 32232 | 55327 |
| IL17REL | 9138 | 32233 | 55328 |
| IL18 | 9139 | 32234 | 55329 |
| IL18BP | 9140 | 32235 | 55330 |
| IL18BP | 9141 | 32236 | 55331 |
| IL18BP | 9142 | 32237 | 55332 |
| IL18R1 | 9143 | 32238 | 55333 |
| IL18RAP | 9144 | 32239 | 55334 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| IL19 | 9145 | 32240 | 55335 |
| IL1A | 9146 | 32241 | 55336 |
| IL1B | 9147 | 32242 | 55337 |
| IL1F10 | 9148 | 32243 | 55338 |
| IL1R1 | 9149 | 32244 | 55339 |
| IL1R1 | 9150 | 32245 | 55340 |
| IL1R2 | 9151 | 32246 | 55341 |
| IL1R2 | 9152 | 32247 | 55342 |
| IL1RAP | 9153 | 32248 | 55343 |
| IL1RAP | 9154 | 32249 | 55344 |
| IL1RAP | 9155 | 32250 | 55345 |
| IL1RAPL1 | 9156 | 32251 | 55346 |
| IL1RAPL2 | 9157 | 32252 | 55347 |
| IL1RL1 | 9158 | 32253 | 55348 |
| IL1RL1 | 9159 | 32254 | 55349 |
| IL1RL2 | 9160 | 32255 | 55350 |
| IL1RN | 9161 | 32256 | 55351 |
| IL2 | 9162 | 32257 | 55352 |
| IL20 | 9163 | 32258 | 55353 |
| IL20RA | 9164 | 32259 | 55354 |
| IL20RB | 9165 | 32260 | 55355 |
| IL21 | 9166 | 32261 | 55356 |
| IL21 | 9167 | 32262 | 55357 |
| IL21R | 9168 | 32263 | 55358 |
| IL22 | 9169 | 32264 | 55359 |
| IL22RA1 | 9170 | 32265 | 55360 |
| IL22RA2 | 9171 | 32266 | 55361 |
| IL22RA2 | 9172 | 32267 | 55362 |
| IL23A | 9173 | 32268 | 55363 |
| IL23R | 9174 | 32269 | 55364 |
| IL24 | 9175 | 32270 | 55365 |
| IL24 | 9176 | 32271 | 55366 |
| IL25 | 9177 | 32272 | 55367 |
| IL26 | 9178 | 32273 | 55368 |
| IL27 | 9179 | 32274 | 55369 |
| IL27RA | 9180 | 32275 | 55370 |
| IL2RA | 9181 | 32276 | 55371 |
| IL2RB | 9182 | 32277 | 55372 |
| IL2RG | 9183 | 32278 | 55373 |
| IL3 | 9184 | 32279 | 55374 |
| IL31 | 9185 | 32280 | 55375 |
| IL31RA | 9186 | 32281 | 55376 |
| IL31RA | 9187 | 32282 | 55377 |
| IL31RA | 9188 | 32283 | 55378 |
| IL32 | 9189 | 32284 | 55379 |
| IL33 | 9190 | 32285 | 55380 |
| IL34 | 9191 | 32286 | 55381 |
| IL36A | 9192 | 32287 | 55382 |
| IL36B | 9193 | 32288 | 55383 |
| IL36B | 9194 | 32289 | 55384 |
| IL36G | 9195 | 32290 | 55385 |
| IL36RN | 9196 | 32291 | 55386 |
| IL37 | 9197 | 32292 | 55387 |
| IL3RA | 9198 | 32293 | 55388 |
| IL4 | 9199 | 32294 | 55389 |
| IL4I1 | 9200 | 32295 | 55390 |
| IL4R | 9201 | 32296 | 55391 |
| IL5 | 9202 | 32297 | 55392 |
| IL5RA | 9203 | 32298 | 55393 |
| IL5RA | 9204 | 32299 | 55394 |
| IL5RA | 9205 | 32300 | 55395 |
| IL6 | 9206 | 32301 | 55396 |
| IL6R | 9207 | 32302 | 55397 |
| IL6R | 9208 | 32303 | 55398 |
| IL6R | 9209 | 32304 | 55399 |
| IL6ST | 9210 | 32305 | 55400 |
| IL7 | 9211 | 32306 | 55401 |
| IL7 | 9212 | 32307 | 55402 |
| IL7 | 9213 | 32308 | 55403 |
| IL7R | 9214 | 32309 | 55404 |
| IL9 | 9215 | 32310 | 55405 |
| IL9R | 9216 | 32311 | 55406 |
| IL9R | 9217 | 32312 | 55407 |
| ILDR1 | 9218 | 32313 | 55408 |
| ILDR2 | 9219 | 32314 | 55409 |
| ILF2 | 9220 | 32315 | 55410 |
| ILF3 | 9221 | 32316 | 55411 |
| ILF3 | 9222 | 32317 | 55412 |
| ILF3 | 9223 | 32318 | 55413 |
| ILK | 9224 | 32319 | 55414 |
| ILKAP | 9225 | 32320 | 55415 |
| ILVBL | 9226 | 32321 | 55416 |
| IMMP1L | 9227 | 32322 | 55417 |
| IMMP2L | 9228 | 32323 | 55418 |
| IMMP2L | 9229 | 32324 | 55419 |
| IMMP2L | 9230 | 32325 | 55420 |
| IMMP2L | 9231 | 32326 | 55421 |
| IMMT | 9232 | 32327 | 55422 |
| IMP3 | 9233 | 32328 | 55423 |
| IMP4 | 9234 | 32329 | 55424 |
| IMPA1 | 9235 | 32330 | 55425 |
| IMPA1 | 9236 | 32331 | 55426 |
| IMPA2 | 9237 | 32332 | 55427 |
| IMPACT | 9238 | 32333 | 55428 |
| IMPAD1 | 9239 | 32334 | 55429 |
| IMPDH1 | 9240 | 32335 | 55430 |
| IMPDH2 | 9241 | 32336 | 55431 |
| IMPG1 | 9242 | 32337 | 55432 |
| IMPG2 | 9243 | 32338 | 55433 |
| INA | 9244 | 32339 | 55434 |
| INAFM1 | 9245 | 32340 | 55435 |
| INAFM2 | 9246 | 32341 | 55436 |
| INCA1 | 9247 | 32342 | 55437 |
| INCENP | 9248 | 32343 | 55438 |
| INF2 | 9249 | 32344 | 55439 |
| INF2 | 9250 | 32345 | 55440 |
| INF2 | 9251 | 32346 | 55441 |
| ING1 | 9252 | 32347 | 55442 |
| ING2 | 9253 | 32348 | 55443 |
| ING3 | 9254 | 32349 | 55444 |
| ING3 | 9255 | 32350 | 55445 |
| ING4 | 9256 | 32351 | 55446 |
| ING4 | 9257 | 32352 | 55447 |
| ING5 | 9258 | 32353 | 55448 |
| ING5 | 9259 | 32354 | 55449 |
| ING5 | 9260 | 32355 | 55450 |
| INHA | 9261 | 32356 | 55451 |
| INHBA | 9262 | 32357 | 55452 |
| INHBB | 9263 | 32358 | 55453 |
| INHBC | 9264 | 32359 | 55454 |
| INHBE | 9265 | 32360 | 55455 |
| INIP | 9266 | 32361 | 55456 |
| INIP | 9267 | 32362 | 55457 |
| INMT | 9268 | 32363 | 55458 |
| INO80 | 9269 | 32364 | 55459 |
| INO80B | 9270 | 32365 | 55460 |
| INO80C | 9271 | 32366 | 55461 |
| INO80D | 9272 | 32367 | 55462 |
| INO80E | 9273 | 32368 | 55463 |
| INO80E | 9274 | 32369 | 55464 |
| INPP1 | 9275 | 32370 | 55465 |
| INPP4A | 9276 | 32371 | 55466 |
| INPP4A | 9277 | 32372 | 55467 |
| INPP4B | 9278 | 32373 | 55468 |
| INPP4B | 9279 | 32374 | 55469 |
| INPP5A | 9280 | 32375 | 55470 |
| INPP5B | 9281 | 32376 | 55471 |
| INPP5D | 9282 | 32377 | 55472 |
| INPP5E | 9283 | 32378 | 55473 |
| INPP5F | 9284 | 32379 | 55474 |
| INPP5F | 9285 | 32380 | 55475 |
| INPP5J | 9286 | 32381 | 55476 |
| INPP5K | 9287 | 32382 | 55477 |
| INPPL1 | 9288 | 32383 | 55478 |
| INS | 9289 | 32384 | 55479 |
| INS-IGF2 | 9290 | 32385 | 55480 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| INSC | 9291 | 32386 | 55481 |
| INSC | 9292 | 32387 | 55482 |
| INSIG1 | 9293 | 32388 | 55483 |
| INSIG1 | 9294 | 32389 | 55484 |
| INSIG1 | 9295 | 32390 | 55485 |
| INSIG2 | 9296 | 32391 | 55486 |
| INSIG2 | 9297 | 32392 | 55487 |
| INSL3 | 9298 | 32393 | 55488 |
| INSL3 | 9299 | 32394 | 55489 |
| INSL4 | 9300 | 32395 | 55490 |
| INSL5 | 9301 | 32396 | 55491 |
| INSL6 | 9302 | 32397 | 55492 |
| INSM1 | 9303 | 32398 | 55493 |
| INSM2 | 9304 | 32399 | 55494 |
| INSR | 9305 | 32400 | 55495 |
| INSRR | 9306 | 32401 | 55496 |
| INTS1 | 9307 | 32402 | 55497 |
| INTS10 | 9308 | 32403 | 55498 |
| INTS11 | 9309 | 32404 | 55499 |
| INTS12 | 9310 | 32405 | 55500 |
| INTS13 | 9311 | 32406 | 55501 |
| INTS14 | 9312 | 32407 | 55502 |
| INTS2 | 9313 | 32408 | 55503 |
| INTS3 | 9314 | 32409 | 55504 |
| INTS4 | 9315 | 32410 | 55505 |
| INTS5 | 9316 | 32411 | 55506 |
| INTS6 | 9317 | 32412 | 55507 |
| INTS6 | 9318 | 32413 | 55508 |
| INTS6L | 9319 | 32414 | 55509 |
| INTS6L | 9320 | 32415 | 55510 |
| INTS7 | 9321 | 32416 | 55511 |
| INTS8 | 9322 | 32417 | 55512 |
| INTS9 | 9323 | 32418 | 55513 |
| INTU | 9324 | 32419 | 55514 |
| INVS | 9325 | 32420 | 55515 |
| IP6K1 | 9326 | 32421 | 55516 |
| IP6K2 | 9327 | 32422 | 55517 |
| IP6K2 | 9328 | 32423 | 55518 |
| IP6K2 | 9329 | 32424 | 55519 |
| IP6K2 | 9330 | 32425 | 55520 |
| IP6K3 | 9331 | 32426 | 55521 |
| IPCEF1 | 9332 | 32427 | 55522 |
| IPMK | 9333 | 32428 | 55523 |
| IPO11 | 9334 | 32429 | 55524 |
| IPO13 | 9335 | 32430 | 55525 |
| IPO4 | 9336 | 32431 | 55526 |
| IPO5 | 9337 | 32432 | 55527 |
| IPO7 | 9338 | 32433 | 55528 |
| IPO8 | 9339 | 32434 | 55529 |
| IPO9 | 9340 | 32435 | 55530 |
| IPP | 9341 | 32436 | 55531 |
| IPP | 9342 | 32437 | 55532 |
| IPPK | 9343 | 32438 | 55533 |
| IQCA1 | 9344 | 32439 | 55534 |
| IQCA1L | 9345 | 32440 | 55535 |
| IQCB1 | 9346 | 32441 | 55536 |
| IQCC | 9347 | 32442 | 55537 |
| IQCD | 9348 | 32443 | 55538 |
| IQCE | 9349 | 32444 | 55539 |
| IQCE | 9350 | 32445 | 55540 |
| IQCF1 | 9351 | 32446 | 55541 |
| IQCF2 | 9352 | 32447 | 55542 |
| IQCF3 | 9353 | 32448 | 55543 |
| IQCF5 | 9354 | 32449 | 55544 |
| IQCF6 | 9355 | 32450 | 55545 |
| IQCG | 9356 | 32451 | 55546 |
| IQCG | 9357 | 32452 | 55547 |
| IQCH | 9358 | 32453 | 55548 |
| IQCH | 9359 | 32454 | 55549 |
| IQCH | 9360 | 32455 | 55550 |
| IQCH | 9361 | 32456 | 55551 |
| IQCJ | 9362 | 32457 | 55552 |
| IQCJ | 9363 | 32458 | 55553 |
| IQCK | 9364 | 32459 | 55554 |
| IQCK | 9365 | 32460 | 55555 |
| IQGAP1 | 9366 | 32461 | 55556 |
| IQGAP2 | 9367 | 32462 | 55557 |
| IQGAP3 | 9368 | 32463 | 55558 |
| IQSEC1 | 9369 | 32464 | 55559 |
| IQSEC1 | 9370 | 32465 | 55560 |
| IQSEC1 | 9371 | 32466 | 55561 |
| IQSEC2 | 9372 | 32467 | 55562 |
| IQSEC2 | 9373 | 32468 | 55563 |
| IQSEC2 | 9374 | 32469 | 55564 |
| IQSEC3 | 9375 | 32470 | 55565 |
| IQSEC3 | 9376 | 32471 | 55566 |
| IQUB | 9377 | 32472 | 55567 |
| IRAKI | 9378 | 32473 | 55568 |
| IRAK1BP1 | 9379 | 32474 | 55569 |
| IRAK2 | 9380 | 32475 | 55570 |
| IRAK3 | 9381 | 32476 | 55571 |
| IRAK4 | 9382 | 32477 | 55572 |
| IREB2 | 9383 | 32478 | 55573 |
| IREB2 | 9384 | 32479 | 55574 |
| IRF1 | 9385 | 32480 | 55575 |
| IRF2 | 9386 | 32481 | 55576 |
| IRF2BP1 | 9387 | 32482 | 55577 |
| IRF2BP2 | 9388 | 32483 | 55578 |
| IRF2BPL | 9389 | 32484 | 55579 |
| IRF3 | 9390 | 32485 | 55580 |
| IRF3 | 9391 | 32486 | 55581 |
| IRF4 | 9392 | 32487 | 55582 |
| IRF5 | 9393 | 32488 | 55583 |
| IRF6 | 9394 | 32489 | 55584 |
| IRF7 | 9395 | 32490 | 55585 |
| IRF8 | 9396 | 32491 | 55586 |
| IRF9 | 9397 | 32492 | 55587 |
| IRGC | 9398 | 32493 | 55588 |
| IRGM | 9399 | 32494 | 55589 |
| IRGM | 9400 | 32495 | 55590 |
| IRGQ | 9401 | 32496 | 55591 |
| IRS1 | 9402 | 32497 | 55592 |
| IRS2 | 9403 | 32498 | 55593 |
| IRS4 | 9404 | 32499 | 55594 |
| IRX1 | 9405 | 32500 | 55595 |
| IRX2 | 9406 | 32501 | 55596 |
| IRX3 | 9407 | 32502 | 55597 |
| IRX4 | 9408 | 32503 | 55598 |
| IRX5 | 9409 | 32504 | 55599 |
| IRX6 | 9410 | 32505 | 55600 |
| ISCA1 | 9411 | 32506 | 55601 |
| ISCA2 | 9412 | 32507 | 55602 |
| ISCA2 | 9413 | 32508 | 55603 |
| ISCU | 9414 | 32509 | 55604 |
| ISCU | 9415 | 32510 | 55605 |
| ISCU | 9416 | 32511 | 55606 |
| ISG15 | 9417 | 32512 | 55607 |
| ISG20 | 9418 | 32513 | 55608 |
| ISG20L2 | 9419 | 32514 | 55609 |
| ISL1 | 9420 | 32515 | 55610 |
| ISL2 | 9421 | 32516 | 55611 |
| ISLR | 9422 | 32517 | 55612 |
| ISLR2 | 9423 | 32518 | 55613 |
| ISM1 | 9424 | 32519 | 55614 |
| ISM2 | 9425 | 32520 | 55615 |
| ISM2 | 9426 | 32521 | 55616 |
| ISOC1 | 9427 | 32522 | 55617 |
| ISOC2 | 9428 | 32523 | 55618 |
| ISPD | 9429 | 32524 | 55619 |
| IST1 | 9430 | 32525 | 55620 |
| ISX | 9431 | 32526 | 55621 |
| ISY1 | 9432 | 32527 | 55622 |
| ISY1-RAB43 | 9433 | 32528 | 55623 |
| ISYNA1 | 9434 | 32529 | 55624 |
| ITCH | 9435 | 32530 | 55625 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ITFG1 | 9436 | 32531 | 55626 |
| ITFG1 | 9437 | 32532 | 55627 |
| ITFG2 | 9438 | 32533 | 55628 |
| ITGA1 | 9439 | 32534 | 55629 |
| ITGA10 | 9440 | 32535 | 55630 |
| ITGA11 | 9441 | 32536 | 55631 |
| ITGA2 | 9442 | 32537 | 55632 |
| ITGA2B | 9443 | 32538 | 55633 |
| ITGA3 | 9444 | 32539 | 55634 |
| ITGA4 | 9445 | 32540 | 55635 |
| ITGA4 | 9446 | 32541 | 55636 |
| ITGA5 | 9447 | 32542 | 55637 |
| ITGA6 | 9448 | 32543 | 55638 |
| ITGA6 | 9449 | 32544 | 55639 |
| ITGA7 | 9450 | 32545 | 55640 |
| ITGA8 | 9451 | 32546 | 55641 |
| ITGA9 | 9452 | 32547 | 55642 |
| ITGAD | 9453 | 32548 | 55643 |
| ITGAE | 9454 | 32549 | 55644 |
| ITGAL | 9455 | 32550 | 55645 |
| ITGAM | 9456 | 32551 | 55646 |
| ITGAV | 9457 | 32552 | 55647 |
| ITGAX | 9458 | 32553 | 55648 |
| ITGAX | 9459 | 32554 | 55649 |
| ITGB1 | 9460 | 32555 | 55650 |
| ITGB1 | 9461 | 32556 | 55651 |
| ITGB1BP1 | 9462 | 32557 | 55652 |
| ITGB1BP2 | 9463 | 32558 | 55653 |
| ITGB2 | 9464 | 32559 | 55654 |
| ITGB3 | 9465 | 32560 | 55655 |
| ITGB3BP | 9466 | 32561 | 55656 |
| ITGB3BP | 9467 | 32562 | 55657 |
| ITGB4 | 9468 | 32563 | 55658 |
| ITGB5 | 9469 | 32564 | 55659 |
| ITGB6 | 9470 | 32565 | 55660 |
| ITGB7 | 9471 | 32566 | 55661 |
| ITGB8 | 9472 | 32567 | 55662 |
| ITGBL1 | 9473 | 32568 | 55663 |
| ITIH1 | 9474 | 32569 | 55664 |
| ITIH2 | 9475 | 32570 | 55665 |
| ITIH3 | 9476 | 32571 | 55666 |
| ITIH4 | 9477 | 32572 | 55667 |
| ITIH5 | 9478 | 32573 | 55668 |
| ITIH5 | 9479 | 32574 | 55669 |
| ITIH6 | 9480 | 32575 | 55670 |
| ITK | 9481 | 32576 | 55671 |
| ITLN1 | 9482 | 32577 | 55672 |
| ITLN2 | 9483 | 32578 | 55673 |
| ITM2A | 9484 | 32579 | 55674 |
| ITM2B | 9485 | 32580 | 55675 |
| ITM2C | 9486 | 32581 | 55676 |
| ITPA | 9487 | 32582 | 55677 |
| ITPA | 9488 | 32583 | 55678 |
| ITPA | 9489 | 32584 | 55679 |
| ITPK1 | 9490 | 32585 | 55680 |
| ITPK1 | 9491 | 32586 | 55681 |
| ITPKA | 9492 | 32587 | 55682 |
| ITPKB | 9493 | 32588 | 55683 |
| ITPKC | 9494 | 32589 | 55684 |
| ITPR1 | 9495 | 32590 | 55685 |
| ITPR2 | 9496 | 32591 | 55686 |
| ITPR3 | 9497 | 32592 | 55687 |
| ITPRIP | 9498 | 32593 | 55688 |
| ITPRIPL1 | 9499 | 32594 | 55689 |
| ITPRIPL2 | 9500 | 32595 | 55690 |
| ITSN1 | 9501 | 32596 | 55691 |
| ITSN1 | 9502 | 32597 | 55692 |
| ITSN2 | 9503 | 32598 | 55693 |
| ITSN2 | 9504 | 32599 | 55694 |
| ITSN2 | 9505 | 32600 | 55695 |
| IVD | 9506 | 32601 | 55696 |
| IVL | 9507 | 32602 | 55697 |
| IVNS1ABP | 9508 | 32603 | 55698 |
| IWS1 | 9509 | 32604 | 55699 |
| IYD | 9510 | 32605 | 55700 |
| IYD | 9511 | 32606 | 55701 |
| IYD | 9512 | 32607 | 55702 |
| IZUMO1 | 9513 | 32608 | 55703 |
| IZUMO1 | 9514 | 32609 | 55704 |
| IZUMO1R | 9515 | 32610 | 55705 |
| IZUMO2 | 9516 | 32611 | 55706 |
| IZUMO2 | 9517 | 32612 | 55707 |
| IZUMO3 | 9518 | 32613 | 55708 |
| IZUMO4 | 9519 | 32614 | 55709 |
| JADE1 | 9520 | 32615 | 55710 |
| JADE1 | 9521 | 32616 | 55711 |
| JADE2 | 9522 | 32617 | 55712 |
| JADE3 | 9523 | 32618 | 55713 |
| JAG1 | 9524 | 32619 | 55714 |
| JAG2 | 9525 | 32620 | 55715 |
| JAGN1 | 9526 | 32621 | 55716 |
| JAK1 | 9527 | 32622 | 55717 |
| JAK2 | 9528 | 32623 | 55718 |
| JAK3 | 9529 | 32624 | 55719 |
| JAKMIP1 | 9530 | 32625 | 55720 |
| JAKMIP1 | 9531 | 32626 | 55721 |
| JAKMIP2 | 9532 | 32627 | 55722 |
| JAKMIP2 | 9533 | 32628 | 55723 |
| JAKMIP3 | 9534 | 32629 | 55724 |
| JAKMIP3 | 9535 | 32630 | 55725 |
| JAM2 | 9536 | 32631 | 55726 |
| JAM2 | 9537 | 32632 | 55727 |
| JAM3 | 9538 | 32633 | 55728 |
| JAML | 9539 | 32634 | 55729 |
| JARID2 | 9540 | 32635 | 55730 |
| JAZF1 | 9541 | 32636 | 55731 |
| JCAD | 9542 | 32637 | 55732 |
| JCHAIN | 9543 | 32638 | 55733 |
| JDP2 | 9544 | 32639 | 55734 |
| JKAMP | 9545 | 32640 | 55735 |
| JKAMP | 9546 | 32641 | 55736 |
| JMJD1C | 9547 | 32642 | 55737 |
| JMJD4 | 9548 | 32643 | 55738 |
| JMJD6 | 9549 | 32644 | 55739 |
| JMJD6 | 9550 | 32645 | 55740 |
| JMJD7 | 9551 | 32646 | 55741 |
| JMJD7-PLA2G4B | 9552 | 32647 | 55742 |
| JMJD7-PLA2G4B | 9553 | 32648 | 55743 |
| JMJD8 | 9554 | 32649 | 55744 |
| JMJD8 | 9555 | 32650 | 55745 |
| JMY | 9556 | 32651 | 55746 |
| JOSD1 | 9557 | 32652 | 55747 |
| JOSD2 | 9558 | 32653 | 55748 |
| JPH1 | 9559 | 32654 | 55749 |
| JPH2 | 9560 | 32655 | 55750 |
| JPH2 | 9561 | 32656 | 55751 |
| JPH3 | 9562 | 32657 | 55752 |
| JPH3 | 9563 | 32658 | 55753 |
| JPH3 | 9564 | 32659 | 55754 |
| JPH4 | 9565 | 32660 | 55755 |
| JPT1 | 9566 | 32661 | 55756 |
| JPT1 | 9567 | 32662 | 55757 |
| JPT1 | 9568 | 32663 | 55758 |
| JPT1 | 9569 | 32664 | 55759 |
| JPT2 | 9570 | 32665 | 55760 |
| JRK | 9571 | 32666 | 55761 |
| JRK | 9572 | 32667 | 55762 |
| JRKL | 9573 | 32668 | 55763 |
| JSRP1 | 9574 | 32669 | 55764 |
| JTB | 9575 | 32670 | 55765 |
| JUN | 9576 | 32671 | 55766 |
| JUNB | 9577 | 32672 | 55767 |
| JUND | 9578 | 32673 | 55768 |
| JUP | 9579 | 32674 | 55769 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| KAAG1 | 9580 | 32675 | 55770 |
| KALRN | 9581 | 32676 | 55771 |
| KALRN | 9582 | 32677 | 55772 |
| KALRN | 9583 | 32678 | 55773 |
| KANK1 | 9584 | 32679 | 55774 |
| KANK2 | 9585 | 32680 | 55775 |
| KANK3 | 9586 | 32681 | 55776 |
| KANK4 | 9587 | 32682 | 55777 |
| KANSL1 | 9588 | 32683 | 55778 |
| KANSL1L | 9589 | 32684 | 55779 |
| KANSL2 | 9590 | 32685 | 55780 |
| KANSL3 | 9591 | 32686 | 55781 |
| KANSL3 | 9592 | 32687 | 55782 |
| KARS | 9593 | 32688 | 55783 |
| KAT14 | 9594 | 32689 | 55784 |
| KAT2A | 9595 | 32690 | 55785 |
| KAT2B | 9596 | 32691 | 55786 |
| KAT5 | 9597 | 32692 | 55787 |
| KAT6A | 9598 | 32693 | 55788 |
| KAT6A | 9599 | 32694 | 55789 |
| KAT6B | 9600 | 32695 | 55790 |
| KAT7 | 9601 | 32696 | 55791 |
| KAT8 | 9602 | 32697 | 55792 |
| KAT8 | 9603 | 32698 | 55793 |
| KATNA1 | 9604 | 32699 | 55794 |
| KATNA1 | 9605 | 32700 | 55795 |
| KATNAL1 | 9606 | 32701 | 55796 |
| KATNAL2 | 9607 | 32702 | 55797 |
| KATNAL2 | 9608 | 32703 | 55798 |
| KATNAL2 | 9609 | 32704 | 55799 |
| KATNAL2 | 9610 | 32705 | 55800 |
| KATNB1 | 9611 | 32706 | 55801 |
| KATNBL1 | 9612 | 32707 | 55802 |
| KAZALD1 | 9613 | 32708 | 55803 |
| KAZALD1 | 9614 | 32709 | 55804 |
| KAZN | 9615 | 32710 | 55805 |
| KAZN | 9616 | 32711 | 55806 |
| KBTBD11 | 9617 | 32712 | 55807 |
| KBTBD12 | 9618 | 32713 | 55808 |
| KBTBD13 | 9619 | 32714 | 55809 |
| KBTBD2 | 9620 | 32715 | 55810 |
| KBTBD3 | 9621 | 32716 | 55811 |
| KBTBD4 | 9622 | 32717 | 55812 |
| KBTBD6 | 9623 | 32718 | 55813 |
| KBTBD7 | 9624 | 32719 | 55814 |
| KBTBD8 | 9625 | 32720 | 55815 |
| KCMF1 | 9626 | 32721 | 55816 |
| KCNA1 | 9627 | 32722 | 55817 |
| KCNA10 | 9628 | 32723 | 55818 |
| KCNA2 | 9629 | 32724 | 55819 |
| KCNA2 | 9630 | 32725 | 55820 |
| KCNA3 | 9631 | 32726 | 55821 |
| KCNA4 | 9632 | 32727 | 55822 |
| KCNA5 | 9633 | 32728 | 55823 |
| KCNA6 | 9634 | 32729 | 55824 |
| KCNA7 | 9635 | 32730 | 55825 |
| KCNAB1 | 9636 | 32731 | 55826 |
| KCNAB2 | 9637 | 32732 | 55827 |
| KCNAB3 | 9638 | 32733 | 55828 |
| KCNB1 | 9639 | 32734 | 55829 |
| KCNB2 | 9640 | 32735 | 55830 |
| KCNC1 | 9641 | 32736 | 55831 |
| KCNC1 | 9642 | 32737 | 55832 |
| KCNC2 | 9643 | 32738 | 55833 |
| KCNC2 | 9644 | 32739 | 55834 |
| KCNC2 | 9645 | 32740 | 55835 |
| KCNC2 | 9646 | 32741 | 55836 |
| KCNC3 | 9647 | 32742 | 55837 |
| KCNC4 | 9648 | 32743 | 55838 |
| KCNC4 | 9649 | 32744 | 55839 |
| KCND1 | 9650 | 32745 | 55840 |
| KCND2 | 9651 | 32746 | 55841 |
| KCND3 | 9652 | 32747 | 55842 |
| KCNE1 | 9653 | 32748 | 55843 |
| KCNE2 | 9654 | 32749 | 55844 |
| KCNE3 | 9655 | 32750 | 55845 |
| KCNE4 | 9656 | 32751 | 55846 |
| KCNE5 | 9657 | 32752 | 55847 |
| KCNF1 | 9658 | 32753 | 55848 |
| KCNG1 | 9659 | 32754 | 55849 |
| KCNG2 | 9660 | 32755 | 55850 |
| KCNG3 | 9661 | 32756 | 55851 |
| KCNG4 | 9662 | 32757 | 55852 |
| KCNH1 | 9663 | 32758 | 55853 |
| KCNH2 | 9664 | 32759 | 55854 |
| KCNH2 | 9665 | 32760 | 55855 |
| KCNH3 | 9666 | 32761 | 55856 |
| KCNH4 | 9667 | 32762 | 55857 |
| KCNH5 | 9668 | 32763 | 55858 |
| KCNH5 | 9669 | 32764 | 55859 |
| KCNH6 | 9670 | 32765 | 55860 |
| KCNH7 | 9671 | 32766 | 55861 |
| KCNH7 | 9672 | 32767 | 55862 |
| KCNH8 | 9673 | 32768 | 55863 |
| KCNIP1 | 9674 | 32769 | 55864 |
| KCNIP2 | 9675 | 32770 | 55865 |
| KCNIP2 | 9676 | 32771 | 55866 |
| KCNIP3 | 9677 | 32772 | 55867 |
| KCNIP4 | 9678 | 32773 | 55868 |
| KCNJ1 | 9679 | 32774 | 55869 |
| KCNJ10 | 9680 | 32775 | 55870 |
| KCNJ11 | 9681 | 32776 | 55871 |
| KCNJ12 | 9682 | 32777 | 55872 |
| KCNJ13 | 9683 | 32778 | 55873 |
| KCNJ14 | 9684 | 32779 | 55874 |
| KCNJ15 | 9685 | 32780 | 55875 |
| KCNJ16 | 9686 | 32781 | 55876 |
| KCNJ18 | 9687 | 32782 | 55877 |
| KCNJ2 | 9688 | 32783 | 55878 |
| KCNJ3 | 9689 | 32784 | 55879 |
| KCNJ3 | 9690 | 32785 | 55880 |
| KCNJ3 | 9691 | 32786 | 55881 |
| KCNJ3 | 9692 | 32787 | 55882 |
| KCNJ4 | 9693 | 32788 | 55883 |
| KCNJ5 | 9694 | 32789 | 55884 |
| KCNJ6 | 9695 | 32790 | 55885 |
| KCNJ8 | 9696 | 32791 | 55886 |
| KCNJ9 | 9697 | 32792 | 55887 |
| KCNK1 | 9698 | 32793 | 55888 |
| KCNK10 | 9699 | 32794 | 55889 |
| KCNK12 | 9700 | 32795 | 55890 |
| KCNK13 | 9701 | 32796 | 55891 |
| KCNK15 | 9702 | 32797 | 55892 |
| KCNK16 | 9703 | 32798 | 55893 |
| KCNK16 | 9704 | 32799 | 55894 |
| KCNK16 | 9705 | 32800 | 55895 |
| KCNK17 | 9706 | 32801 | 55896 |
| KCNK17 | 9707 | 32802 | 55897 |
| KCNK18 | 9708 | 32803 | 55898 |
| KCNK2 | 9709 | 32804 | 55899 |
| KCNK3 | 9710 | 32805 | 55900 |
| KCNK4 | 9711 | 32806 | 55901 |
| KCNK5 | 9712 | 32807 | 55902 |
| KCNK6 | 9713 | 32808 | 55903 |
| KCNK7 | 9714 | 32809 | 55904 |
| KCNK7 | 9715 | 32810 | 55905 |
| KCNK7 | 9716 | 32811 | 55906 |
| KCNK9 | 9717 | 32812 | 55907 |
| KCNMA1 | 9718 | 32813 | 55908 |
| KCNMA1 | 9719 | 32814 | 55909 |
| KCNMA1 | 9720 | 32815 | 55910 |
| KCNMA1 | 9721 | 32816 | 55911 |
| KCNMA1 | 9722 | 32817 | 55912 |
| KCNMA1 | 9723 | 32818 | 55913 |
| KCNMB1 | 9724 | 32819 | 55914 |
| KCNMB2 | 9725 | 32820 | 55915 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| KCNMB3 | 9726 | 32821 | 55916 |
| KCNMB3 | 9727 | 32822 | 55917 |
| KCNMB4 | 9728 | 32823 | 55918 |
| KCNN1 | 9729 | 32824 | 55919 |
| KCNN2 | 9730 | 32825 | 55920 |
| KCNN3 | 9731 | 32826 | 55921 |
| KCNN4 | 9732 | 32827 | 55922 |
| KCNQ1 | 9733 | 32828 | 55923 |
| KCNQ2 | 9734 | 32829 | 55924 |
| KCNQ2 | 9735 | 32830 | 55925 |
| KCNQ3 | 9736 | 32831 | 55926 |
| KCNQ4 | 9737 | 32832 | 55927 |
| KCNQ5 | 9738 | 32833 | 55928 |
| KCNRG | 9739 | 32834 | 55929 |
| KCNRG | 9740 | 32835 | 55930 |
| KCNS1 | 9741 | 32836 | 55931 |
| KCNS2 | 9742 | 32837 | 55932 |
| KCNS3 | 9743 | 32838 | 55933 |
| KCNT1 | 9744 | 32839 | 55934 |
| KCNT2 | 9745 | 32840 | 55935 |
| KCNU1 | 9746 | 32841 | 55936 |
| KCNV1 | 9747 | 32842 | 55937 |
| KCNV2 | 9748 | 32843 | 55938 |
| KCP | 9749 | 32844 | 55939 |
| KCP | 9750 | 32845 | 55940 |
| KCTD1 | 9751 | 32846 | 55941 |
| KCTD10 | 9752 | 32847 | 55942 |
| KCTD11 | 9753 | 32848 | 55943 |
| KCTD12 | 9754 | 32849 | 55944 |
| KCTD13 | 9755 | 32850 | 55945 |
| KCTD15 | 9756 | 32851 | 55946 |
| KCTD15 | 9757 | 32852 | 55947 |
| KCTD16 | 9758 | 32853 | 55948 |
| KCTD17 | 9759 | 32854 | 55949 |
| KCTD17 | 9760 | 32855 | 55950 |
| KCTD17 | 9761 | 32856 | 55951 |
| KCTD18 | 9762 | 32857 | 55952 |
| KCTD19 | 9763 | 32858 | 55953 |
| KCTD2 | 9764 | 32859 | 55954 |
| KCTD20 | 9765 | 32860 | 55955 |
| KCTD21 | 9766 | 32861 | 55956 |
| KCTD3 | 9767 | 32862 | 55957 |
| KCTD4 | 9768 | 32863 | 55958 |
| KCTD5 | 9769 | 32864 | 55959 |
| KCTD6 | 9770 | 32865 | 55960 |
| KCTD7 | 9771 | 32866 | 55961 |
| KCTD7 | 9772 | 32867 | 55962 |
| KCTD8 | 9773 | 32868 | 55963 |
| KCTD9 | 9774 | 32869 | 55964 |
| KDELC1 | 9775 | 32870 | 55965 |
| KDELC2 | 9776 | 32871 | 55966 |
| KDELR1 | 9777 | 32872 | 55967 |
| KDELR2 | 9778 | 32873 | 55968 |
| KDELR2 | 9779 | 32874 | 55969 |
| KDELR3 | 9780 | 32875 | 55970 |
| KDELR3 | 9781 | 32876 | 55971 |
| KDF1 | 9782 | 32877 | 55972 |
| KDM1A | 9783 | 32878 | 55973 |
| KDM1B | 9784 | 32879 | 55974 |
| KDM2A | 9785 | 32880 | 55975 |
| KDM2B | 9786 | 32881 | 55976 |
| KDM2B | 9787 | 32882 | 55977 |
| KDM3A | 9788 | 32883 | 55978 |
| KDM3B | 9789 | 32884 | 55979 |
| KDM4A | 9790 | 32885 | 55980 |
| KDM4B | 9791 | 32886 | 55981 |
| KDM4C | 9792 | 32887 | 55982 |
| KDM4C | 9793 | 32888 | 55983 |
| KDM4C | 9794 | 32889 | 55984 |
| KDM4C | 9795 | 32890 | 55985 |
| KDM4D | 9796 | 32891 | 55986 |
| KDM4E | 9797 | 32892 | 55987 |
| KDM5A | 9798 | 32893 | 55988 |
| KDM5B | 9799 | 32894 | 55989 |
| KDM5C | 9800 | 32895 | 55990 |
| KDM5C | 9801 | 32896 | 55991 |
| KDM5C | 9802 | 32897 | 55992 |
| KDM5C | 9803 | 32898 | 55993 |
| KDM5D | 9804 | 32899 | 55994 |
| KDM6A | 9805 | 32900 | 55995 |
| KDM6B | 9806 | 32901 | 55996 |
| KDM7A | 9807 | 32902 | 55997 |
| KDM8 | 9808 | 32903 | 55998 |
| KDR | 9809 | 32904 | 55999 |
| KDSR | 9810 | 32905 | 56000 |
| KEAP1 | 9811 | 32906 | 56001 |
| KEL | 9812 | 32907 | 56002 |
| KERA | 9813 | 32908 | 56003 |
| KHDC1 | 9814 | 32909 | 56004 |
| KHDC1L | 9815 | 32910 | 56005 |
| KHDC3L | 9816 | 32911 | 56006 |
| KHDRBS1 | 9817 | 32912 | 56007 |
| KHDRBS2 | 9818 | 32913 | 56008 |
| KHDRBS3 | 9819 | 32914 | 56009 |
| KHK | 9820 | 32915 | 56010 |
| KHNYN | 9821 | 32916 | 56011 |
| KHSRP | 9822 | 32917 | 56012 |
| KIAA0040 | 9823 | 32918 | 56013 |
| KIAA0100 | 9824 | 32919 | 56014 |
| KIAA0100 | 9825 | 32920 | 56015 |
| KIAA0141 | 9826 | 32921 | 56016 |
| KIAA0141 | 9827 | 32922 | 56017 |
| KIAA0232 | 9828 | 32923 | 56018 |
| KIAA0319 | 9829 | 32924 | 56019 |
| KIAA0319 | 9830 | 32925 | 56020 |
| KIAA0319L | 9831 | 32926 | 56021 |
| KIAA0355 | 9832 | 32927 | 56022 |
| KIAA0368 | 9833 | 32928 | 56023 |
| KIAA0391 | 9834 | 32929 | 56024 |
| KIAA0408 | 9835 | 32930 | 56025 |
| KIAA0513 | 9836 | 32931 | 56026 |
| KIAA0513 | 9837 | 32932 | 56027 |
| KIAA0556 | 9838 | 32933 | 56028 |
| KIAA0586 | 9839 | 32934 | 56029 |
| KIAA0586 | 9840 | 32935 | 56030 |
| KIAA0586 | 9841 | 32936 | 56031 |
| KIAA0753 | 9842 | 32937 | 56032 |
| KIAA0754 | 9843 | 32938 | 56033 |
| KIAA0825 | 9844 | 32939 | 56034 |
| KIAA0825 | 9845 | 32940 | 56035 |
| KIAA0895 | 9846 | 32941 | 56036 |
| KIAA0895L | 9847 | 32942 | 56037 |
| KIAA0907 | 9848 | 32943 | 56038 |
| KIAA0930 | 9849 | 32944 | 56039 |
| KIAA1024 | 9850 | 32945 | 56040 |
| KIAA1024L | 9851 | 32946 | 56041 |
| KIAA1107 | 9852 | 32947 | 56042 |
| KIAA1109 | 9853 | 32948 | 56043 |
| KIAA1143 | 9854 | 32949 | 56044 |
| KIAA1143 | 9855 | 32950 | 56045 |
| KIAA1147 | 9856 | 32951 | 56046 |
| KIAA1191 | 9857 | 32952 | 56047 |
| KIAA1210 | 9858 | 32953 | 56048 |
| KIAA1211 | 9859 | 32954 | 56049 |
| KIAA1211L | 9860 | 32955 | 56050 |
| KIAA1217 | 9861 | 32956 | 56051 |
| KIAA1217 | 9862 | 32957 | 56052 |
| KIAA1257 | 9863 | 32958 | 56053 |
| KIAA1257 | 9864 | 32959 | 56054 |
| KIAA1324 | 9865 | 32960 | 56055 |
| KIAA1324 | 9866 | 32961 | 56056 |
| KIAA1324L | 9867 | 32962 | 56057 |
| KIAA1328 | 9868 | 32963 | 56058 |
| KIAA1456 | 9869 | 32964 | 56059 |
| KIAA1468 | 9870 | 32965 | 56060 |
| KIAA1468 | 9871 | 32966 | 56061 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| KIAA1522 | 9872 | 32967 | 56062 |
| KIAA1522 | 9873 | 32968 | 56063 |
| KIAA1549 | 9874 | 32969 | 56064 |
| KIAA1549L | 9875 | 32970 | 56065 |
| KIAA1551 | 9876 | 32971 | 56066 |
| KIAA1586 | 9877 | 32972 | 56067 |
| KIAA1614 | 9878 | 32973 | 56068 |
| KIAA1644 | 9879 | 32974 | 56069 |
| KIAA1671 | 9880 | 32975 | 56070 |
| KIAA1683 | 9881 | 32976 | 56071 |
| KIAA1755 | 9882 | 32977 | 56072 |
| KIAA1841 | 9883 | 32978 | 56073 |
| KIAA1841 | 9884 | 32979 | 56074 |
| KIAA1958 | 9885 | 32980 | 56075 |
| KIAA1958 | 9886 | 32981 | 56076 |
| KIAA2012 | 9887 | 32982 | 56077 |
| KIAA2013 | 9888 | 32983 | 56078 |
| KIAA2026 | 9889 | 32984 | 56079 |
| KIDINS220 | 9890 | 32985 | 56080 |
| KIDINS220 | 9891 | 32986 | 56081 |
| KIDINS220 | 9892 | 32987 | 56082 |
| KIF11 | 9893 | 32988 | 56083 |
| KIF12 | 9894 | 32989 | 56084 |
| KIF13A | 9895 | 32990 | 56085 |
| KIF13A | 9896 | 32991 | 56086 |
| KIF13A | 9897 | 32992 | 56087 |
| KIF13B | 9898 | 32993 | 56088 |
| KIF14 | 9899 | 32994 | 56089 |
| KIF15 | 9900 | 32995 | 56090 |
| KIF16B | 9901 | 32996 | 56091 |
| KIF16B | 9902 | 32997 | 56092 |
| KIF17 | 9903 | 32998 | 56093 |
| KIF18A | 9904 | 32999 | 56094 |
| KIF18B | 9905 | 33000 | 56095 |
| KIF18B | 9906 | 33001 | 56096 |
| KIF19 | 9907 | 33002 | 56097 |
| KIF1A | 9908 | 33003 | 56098 |
| KIF1B | 9909 | 33004 | 56099 |
| KIF1B | 9910 | 33005 | 56100 |
| KIF1BP | 9911 | 33006 | 56101 |
| KIF1C | 9912 | 33007 | 56102 |
| KIF20A | 9913 | 33008 | 56103 |
| KIF20B | 9914 | 33009 | 56104 |
| KIF21A | 9915 | 33010 | 56105 |
| KIF21B | 9916 | 33011 | 56106 |
| KIF21B | 9917 | 33012 | 56107 |
| KIF22 | 9918 | 33013 | 56108 |
| KIF23 | 9919 | 33014 | 56109 |
| KIF24 | 9920 | 33015 | 56110 |
| KIF25 | 9921 | 33016 | 56111 |
| KIF26A | 9922 | 33017 | 56112 |
| KIF26B | 9923 | 33018 | 56113 |
| KIF27 | 9924 | 33019 | 56114 |
| KIF2A | 9925 | 33020 | 56115 |
| KIF2B | 9926 | 33021 | 56116 |
| KIF2C | 9927 | 33022 | 56117 |
| KIF3A | 9928 | 33023 | 56118 |
| KIF3B | 9929 | 33024 | 56119 |
| KIF3C | 9930 | 33025 | 56120 |
| KIF4A | 9931 | 33026 | 56121 |
| KIF5A | 9932 | 33027 | 56122 |
| KIF5B | 9933 | 33028 | 56123 |
| KIF5C | 9934 | 33029 | 56124 |
| KIF6 | 9935 | 33030 | 56125 |
| KIF6 | 9936 | 33031 | 56126 |
| KIF6 | 9937 | 33032 | 56127 |
| KIF7 | 9938 | 33033 | 56128 |
| KIF9 | 9939 | 33034 | 56129 |
| KIFAP3 | 9940 | 33035 | 56130 |
| KIFC1 | 9941 | 33036 | 56131 |
| KIFC2 | 9942 | 33037 | 56132 |
| KIFC3 | 9943 | 33038 | 56133 |
| KIFC3 | 9944 | 33039 | 56134 |
| KIN | 9945 | 33040 | 56135 |
| KIR2DL3 | 9946 | 33041 | 56136 |
| KIR2DL4 | 9947 | 33042 | 56137 |
| KIR2DL4 | 9948 | 33043 | 56138 |
| KIR2DS2 | 9949 | 33044 | 56139 |
| KIR2DS2 | 9950 | 33045 | 56140 |
| KIR2DS4*003 allele | 9951 | 33046 | 56141 |
| KIR3DL2 | 9952 | 33047 | 56142 |
| KIR3DL3 | 9953 | 33048 | 56143 |
| KIR3DS1 | 9954 | 33049 | 56144 |
| KIRREL1 | 9955 | 33050 | 56145 |
| KIRREL2 | 9956 | 33051 | 56146 |
| KIRREL2 | 9957 | 33052 | 56147 |
| KIRREL3 | 9958 | 33053 | 56148 |
| KIRREL3 | 9959 | 33054 | 56149 |
| KISS1 | 9960 | 33055 | 56150 |
| KISS1R | 9961 | 33056 | 56151 |
| KIT | 9962 | 33057 | 56152 |
| KITLG | 9963 | 33058 | 56153 |
| KIZ | 9964 | 33059 | 56154 |
| KL | 9965 | 33060 | 56155 |
| KLB | 9966 | 33061 | 56156 |
| KLC1 | 9967 | 33062 | 56157 |
| KLC1 | 9968 | 33063 | 56158 |
| KLC2 | 9969 | 33064 | 56159 |
| KLC3 | 9970 | 33065 | 56160 |
| KLC4 | 9971 | 33066 | 56161 |
| KLC4 | 9972 | 33067 | 56162 |
| KLF1 | 9973 | 33068 | 56163 |
| KLF10 | 9974 | 33069 | 56164 |
| KLF11 | 9975 | 33070 | 56165 |
| KLF12 | 9976 | 33071 | 56166 |
| KLF13 | 9977 | 33072 | 56167 |
| KLF13 | 9978 | 33073 | 56168 |
| KLF14 | 9979 | 33074 | 56169 |
| KLF15 | 9980 | 33075 | 56170 |
| KLF16 | 9981 | 33076 | 56171 |
| KLF17 | 9982 | 33077 | 56172 |
| KLF2 | 9983 | 33078 | 56173 |
| KLF3 | 9984 | 33079 | 56174 |
| KLF4 | 9985 | 33080 | 56175 |
| KLF5 | 9986 | 33081 | 56176 |
| KLF6 | 9987 | 33082 | 56177 |
| KLF6 | 9988 | 33083 | 56178 |
| KLF7 | 9989 | 33084 | 56179 |
| KLF8 | 9990 | 33085 | 56180 |
| KLF8 | 9991 | 33086 | 56181 |
| KLF9 | 9992 | 33087 | 56182 |
| KLHDC1 | 9993 | 33088 | 56183 |
| KLHDC10 | 9994 | 33089 | 56184 |
| KLHDC2 | 9995 | 33090 | 56185 |
| KLHDC3 | 9996 | 33091 | 56186 |
| KLHDC4 | 9997 | 33092 | 56187 |
| KLHDC7A | 9998 | 33093 | 56188 |
| KLHDC7B | 9999 | 33094 | 56189 |
| KLHDC8A | 10000 | 33095 | 56190 |
| KLHDC8B | 10001 | 33096 | 56191 |
| KLHDC9 | 10002 | 33097 | 56192 |
| KLHDC9 | 10003 | 33098 | 56193 |
| KLHL1 | 10004 | 33099 | 56194 |
| KLHL10 | 10005 | 33100 | 56195 |
| KLHL11 | 10006 | 33101 | 56196 |
| KLHL12 | 10007 | 33102 | 56197 |
| KLHL13 | 10008 | 33103 | 56198 |
| KLHL14 | 10009 | 33104 | 56199 |
| KLHL15 | 10010 | 33105 | 56200 |
| KLHL17 | 10011 | 33106 | 56201 |
| KLHL18 | 10012 | 33107 | 56202 |
| KLHL2 | 10013 | 33108 | 56203 |
| KLHL20 | 10014 | 33109 | 56204 |
| KLHL21 | 10015 | 33110 | 56205 |
| KLHL21 | 10016 | 33111 | 56206 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| KLHL22 | 10017 | 33112 | 56207 |
| KLHL23 | 10018 | 33113 | 56208 |
| KLHL24 | 10019 | 33114 | 56209 |
| KLHL25 | 10020 | 33115 | 56210 |
| KLHL26 | 10021 | 33116 | 56211 |
| KLHL26 | 10022 | 33117 | 56212 |
| KLHL26 | 10023 | 33118 | 56213 |
| KLHL28 | 10024 | 33119 | 56214 |
| KLHL29 | 10025 | 33120 | 56215 |
| KLHL3 | 10026 | 33121 | 56216 |
| KLHL30 | 10027 | 33122 | 56217 |
| KLHL31 | 10028 | 33123 | 56218 |
| KLHL32 | 10029 | 33124 | 56219 |
| KLHL32 | 10030 | 33125 | 56220 |
| KLHL32 | 10031 | 33126 | 56221 |
| KLHL33 | 10032 | 33127 | 56222 |
| KLHL34 | 10033 | 33128 | 56223 |
| KLHL35 | 10034 | 33129 | 56224 |
| KLHL36 | 10035 | 33130 | 56225 |
| KLHL38 | 10036 | 33131 | 56226 |
| KLHL4 | 10037 | 33132 | 56227 |
| KLHL4 | 10038 | 33133 | 56228 |
| KLHL40 | 10039 | 33134 | 56229 |
| KLHL41 | 10040 | 33135 | 56230 |
| KLHL42 | 10041 | 33136 | 56231 |
| KLHL5 | 10042 | 33137 | 56232 |
| KLHL6 | 10043 | 33138 | 56233 |
| KLHL7 | 10044 | 33139 | 56234 |
| KLHL7 | 10045 | 33140 | 56235 |
| KLHL8 | 10046 | 33141 | 56236 |
| KLHL9 | 10047 | 33142 | 56237 |
| KLK1 | 10048 | 33143 | 56238 |
| KLK10 | 10049 | 33144 | 56239 |
| KLK11 | 10050 | 33145 | 56240 |
| KLK12 | 10051 | 33146 | 56241 |
| KLK12 | 10052 | 33147 | 56242 |
| KLK13 | 10053 | 33148 | 56243 |
| KLK13 | 10054 | 33149 | 56244 |
| KLK14 | 10055 | 33150 | 56245 |
| KLK15 | 10056 | 33151 | 56246 |
| KLK15 | 10057 | 33152 | 56247 |
| KLK2 | 10058 | 33153 | 56248 |
| KLK2 | 10059 | 33154 | 56249 |
| KLK3 | 10060 | 33155 | 56250 |
| KLK3 | 10061 | 33156 | 56251 |
| KLK4 | 10062 | 33157 | 56252 |
| KLK4 | 10063 | 33158 | 56253 |
| KLK5 | 10064 | 33159 | 56254 |
| KLK6 | 10065 | 33160 | 56255 |
| KLK6 | 10066 | 33161 | 56256 |
| KLK7 | 10067 | 33162 | 56257 |
| KLK8 | 10068 | 33163 | 56258 |
| KLK8 | 10069 | 33164 | 56259 |
| KLK9 | 10070 | 33165 | 56260 |
| KLKB1 | 10071 | 33166 | 56261 |
| KLKB1 | 10072 | 33167 | 56262 |
| KLLN | 10073 | 33168 | 56263 |
| KLRB1 | 10074 | 33169 | 56264 |
| KLRC1 | 10075 | 33170 | 56265 |
| KLRC2 | 10076 | 33171 | 56266 |
| KLRC3 | 10077 | 33172 | 56267 |
| KLRC4 | 10078 | 33173 | 56268 |
| KLRD1 | 10079 | 33174 | 56269 |
| KLRF1 | 10080 | 33175 | 56270 |
| KLRF1 | 10081 | 33176 | 56271 |
| KLRF2 | 10082 | 33177 | 56272 |
| KLRG1 | 10083 | 33178 | 56273 |
| KLRG1 | 10084 | 33179 | 56274 |
| KLRG2 | 10085 | 33180 | 56275 |
| KLRK1 | 10086 | 33181 | 56276 |
| KMO | 10087 | 33182 | 56277 |
| KMT2A | 10088 | 33183 | 56278 |
| KMT2B | 10089 | 33184 | 56279 |
| KMT2C | 10090 | 33185 | 56280 |
| KMT2D | 10091 | 33186 | 56281 |
| KMT2E | 10092 | 33187 | 56282 |
| KMT5A | 10093 | 33188 | 56283 |
| KMT5B | 10094 | 33189 | 56284 |
| KMT5B | 10095 | 33190 | 56285 |
| KMT5C | 10096 | 33191 | 56286 |
| KNCN | 10097 | 33192 | 56287 |
| KNDC1 | 10098 | 33193 | 56288 |
| KNDC1 | 10099 | 33194 | 56289 |
| KNDC1 | 10100 | 33195 | 56290 |
| KNDC1 | 10101 | 33196 | 56291 |
| KNG1 | 10102 | 33197 | 56292 |
| KNG1 | 10103 | 33198 | 56293 |
| KNL1 | 10104 | 33199 | 56294 |
| KNOP1 | 10105 | 33200 | 56295 |
| KNSTRN | 10106 | 33201 | 56296 |
| KNSTRN | 10107 | 33202 | 56297 |
| KNSTRN | 10108 | 33203 | 56298 |
| KNTC1 | 10109 | 33204 | 56299 |
| KPNA1 | 10110 | 33205 | 56300 |
| KPNA2 | 10111 | 33206 | 56301 |
| KPNA3 | 10112 | 33207 | 56302 |
| KPNA4 | 10113 | 33208 | 56303 |
| KPNA5 | 10114 | 33209 | 56304 |
| KPNA6 | 10115 | 33210 | 56305 |
| KPNA7 | 10116 | 33211 | 56306 |
| KPNB1 | 10117 | 33212 | 56307 |
| KPRP | 10118 | 33213 | 56308 |
| KPTN | 10119 | 33214 | 56309 |
| KRAS | 10120 | 33215 | 56310 |
| KRAS | 10121 | 33216 | 56311 |
| KRBA1 | 10122 | 33217 | 56312 |
| KRBA2 | 10123 | 33218 | 56313 |
| KRBOX1 | 10124 | 33219 | 56314 |
| KRBOX4 | 10125 | 33220 | 56315 |
| KRBOX4 | 10126 | 33221 | 56316 |
| KRCC1 | 10127 | 33222 | 56317 |
| KREMEN1 | 10128 | 33223 | 56318 |
| KREMEN1 | 10129 | 33224 | 56319 |
| KREMEN2 | 10130 | 33225 | 56320 |
| KREMEN2 | 10131 | 33226 | 56321 |
| KRI1 | 10132 | 33227 | 56322 |
| KRIT1 | 10133 | 33228 | 56323 |
| KRR1 | 10134 | 33229 | 56324 |
| KRT1 | 10135 | 33230 | 56325 |
| KRT10 | 10136 | 33231 | 56326 |
| KRT12 | 10137 | 33232 | 56327 |
| KRT13 | 10138 | 33233 | 56328 |
| KRT13 | 10139 | 33234 | 56329 |
| KRT14 | 10140 | 33235 | 56330 |
| KRT15 | 10141 | 33236 | 56331 |
| KRT16 | 10142 | 33237 | 56332 |
| KRT17 | 10143 | 33238 | 56333 |
| KRT18 | 10144 | 33239 | 56334 |
| KRT19 | 10145 | 33240 | 56335 |
| KRT2 | 10146 | 33241 | 56336 |
| KRT20 | 10147 | 33242 | 56337 |
| KRT222 | 10148 | 33243 | 56338 |
| KRT23 | 10149 | 33244 | 56339 |
| KRT24 | 10150 | 33245 | 56340 |
| KRT25 | 10151 | 33246 | 56341 |
| KRT26 | 10152 | 33247 | 56342 |
| KRT27 | 10153 | 33248 | 56343 |
| KRT28 | 10154 | 33249 | 56344 |
| KRT3 | 10155 | 33250 | 56345 |
| KRT31 | 10156 | 33251 | 56346 |
| KRT32 | 10157 | 33252 | 56347 |
| KRT33A | 10158 | 33253 | 56348 |
| KRT33B | 10159 | 33254 | 56349 |
| KRT34 | 10160 | 33255 | 56350 |
| KRT35 | 10161 | 33256 | 56351 |
| KRT36 | 10162 | 33257 | 56352 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| KRT37 | 10163 | 33258 | 56353 |
| KRT38 | 10164 | 33259 | 56354 |
| KRT39 | 10165 | 33260 | 56355 |
| KRT4 | 10166 | 33261 | 56356 |
| KRT40 | 10167 | 33262 | 56357 |
| KRT5 | 10168 | 33263 | 56358 |
| KRT6A | 10169 | 33264 | 56359 |
| KRT6B | 10170 | 33265 | 56360 |
| KRT7 | 10171 | 33266 | 56361 |
| KRT71 | 10172 | 33267 | 56362 |
| KRT72 | 10173 | 33268 | 56363 |
| KRT73 | 10174 | 33269 | 56364 |
| KRT74 | 10175 | 33270 | 56365 |
| KRT75 | 10176 | 33271 | 56366 |
| KRT76 | 10177 | 33272 | 56367 |
| KRT77 | 10178 | 33273 | 56368 |
| KRT78 | 10179 | 33274 | 56369 |
| KRT79 | 10180 | 33275 | 56370 |
| KRT8 | 10181 | 33276 | 56371 |
| KRT80 | 10182 | 33277 | 56372 |
| KRT80 | 10183 | 33278 | 56373 |
| KRT81 | 10184 | 33279 | 56374 |
| KRT82 | 10185 | 33280 | 56375 |
| KRT83 | 10186 | 33281 | 56376 |
| KRT84 | 10187 | 33282 | 56377 |
| KRT85 | 10188 | 33283 | 56378 |
| KRT86 | 10189 | 33284 | 56379 |
| KRT9 | 10190 | 33285 | 56380 |
| KRTAP1-1 | 10191 | 33286 | 56381 |
| KRTAP1-3 | 10192 | 33287 | 56382 |
| KRTAP1-4 | 10193 | 33288 | 56383 |
| KRTAP1-5 | 10194 | 33289 | 56384 |
| KRTAP10-11 | 10195 | 33290 | 56385 |
| KRTAP10-2 | 10196 | 33291 | 56386 |
| KRTAP10-3 | 10197 | 33292 | 56387 |
| KRTAP10-4 | 10198 | 33293 | 56388 |
| KRTAP10-5 | 10199 | 33294 | 56389 |
| KRTAP10-6 | 10200 | 33295 | 56390 |
| KRTAP10-7 | 10201 | 33296 | 56391 |
| KRTAP10-9 | 10202 | 33297 | 56392 |
| KRTAP11-1 | 10203 | 33298 | 56393 |
| KRTAP12-1 | 10204 | 33299 | 56394 |
| KRTAP12-3 | 10205 | 33300 | 56395 |
| KRTAP12-4 | 10206 | 33301 | 56396 |
| KRTAP13-1 | 10207 | 33302 | 56397 |
| KRTAP13-2 | 10208 | 33303 | 56398 |
| KRTAP13-3 | 10209 | 33304 | 56399 |
| KRTAP13-4 | 10210 | 33305 | 56400 |
| KRTAP15-1 | 10211 | 33306 | 56401 |
| KRTAP16-1 | 10212 | 33307 | 56402 |
| KRTAP17-1 | 10213 | 33308 | 56403 |
| KRTAP19-1 | 10214 | 33309 | 56404 |
| KRTAP19-2 | 10215 | 33310 | 56405 |
| KRTAP19-3 | 10216 | 33311 | 56406 |
| KRTAP19-4 | 10217 | 33312 | 56407 |
| KRTAP19-5 | 10218 | 33313 | 56408 |
| KRTAP19-6 | 10219 | 33314 | 56409 |
| KRTAP19-7 | 10220 | 33315 | 56410 |
| KRTAP19-8 | 10221 | 33316 | 56411 |
| KRTAP2-2 | 10222 | 33317 | 56412 |
| KRTAP2-3 | 10223 | 33318 | 56413 |
| KRTAP2-4 | 10224 | 33319 | 56414 |
| KRTAP20-1 | 10225 | 33320 | 56415 |
| KRTAP20-2 | 10226 | 33321 | 56416 |
| KRTAP20-3 | 10227 | 33322 | 56417 |
| KRTAP20-4 | 10228 | 33323 | 56418 |
| KRTAP21-1 | 10229 | 33324 | 56419 |
| KRTAP21-2 | 10230 | 33325 | 56420 |
| KRTAP21-3 | 10231 | 33326 | 56421 |
| KRTAP22-1 | 10232 | 33327 | 56422 |
| KRTAP22-2 | 10233 | 33328 | 56423 |
| KRTAP23-1 | 10234 | 33329 | 56424 |
| KRTAP24-1 | 10235 | 33330 | 56425 |
| KRTAP25-1 | 10236 | 33331 | 56426 |
| KRTAP26-1 | 10237 | 33332 | 56427 |
| KRTAP27-1 | 10238 | 33333 | 56428 |
| KRTAP29-1 | 10239 | 33334 | 56429 |
| KRTAP3-1 | 10240 | 33335 | 56430 |
| KRTAP3-2 | 10241 | 33336 | 56431 |
| KRTAP3-3 | 10242 | 33337 | 56432 |
| KRTAP4-1 | 10243 | 33338 | 56433 |
| KRTAP4-12 | 10244 | 33339 | 56434 |
| KRTAP4-2 | 10245 | 33340 | 56435 |
| KRTAP4-3 | 10246 | 33341 | 56436 |
| KRTAP4-4 | 10247 | 33342 | 56437 |
| KRTAP4-5 | 10248 | 33343 | 56438 |
| KRTAP4-6 | 10249 | 33344 | 56439 |
| KRTAP4-8 | 10250 | 33345 | 56440 |
| KRTAP5-1 | 10251 | 33346 | 56441 |
| KRTAP5-4 | 10252 | 33347 | 56442 |
| KRTAP5-6 | 10253 | 33348 | 56443 |
| KRTAP5-8 | 10254 | 33349 | 56444 |
| KRTAP5-9 | 10255 | 33350 | 56445 |
| KRTAP6-1 | 10256 | 33351 | 56446 |
| KRTAP6-2 | 10257 | 33352 | 56447 |
| KRTAP6-3 | 10258 | 33353 | 56448 |
| KRTAP7-1 | 10259 | 33354 | 56449 |
| KRTAP8-1 | 10260 | 33355 | 56450 |
| KRTAP9-1 | 10261 | 33356 | 56451 |
| KRTAP9-3 | 10262 | 33357 | 56452 |
| KRTAP9-4 | 10263 | 33358 | 56453 |
| KRTAP9-6 | 10264 | 33359 | 56454 |
| KRTAP9-7 | 10265 | 33360 | 56455 |
| KRTAP9-8 | 10266 | 33361 | 56456 |
| KRTAP9-9 | 10267 | 33362 | 56457 |
| KRTCAP2 | 10268 | 33363 | 56458 |
| KRTCAP3 | 10269 | 33364 | 56459 |
| KRTDAP | 10270 | 33365 | 56460 |
| KSR1 | 10271 | 33366 | 56461 |
| KSR2 | 10272 | 33367 | 56462 |
| KTI12 | 10273 | 33368 | 56463 |
| KTN1 | 10274 | 33369 | 56464 |
| KXD1 | 10275 | 33370 | 56465 |
| KY | 10276 | 33371 | 56466 |
| KY | 10277 | 33372 | 56467 |
| KYAT1 | 10278 | 33373 | 56468 |
| KYAT3 | 10279 | 33374 | 56469 |
| KYNU | 10280 | 33375 | 56470 |
| KYNU | 10281 | 33376 | 56471 |
| L1CAM | 10282 | 33377 | 56472 |
| L1TD1 | 10283 | 33378 | 56473 |
| L2HGDH | 10284 | 33379 | 56474 |
| L3HYPDH | 10285 | 33380 | 56475 |
| L3HYPDH | 10286 | 33381 | 56476 |
| L3HYPDH | 10287 | 33382 | 56477 |
| L3MBTL1 | 10288 | 33383 | 56478 |
| L3MBTL2 | 10289 | 33384 | 56479 |
| L3MBTL3 | 10290 | 33385 | 56480 |
| L3MBTL4 | 10291 | 33386 | 56481 |
| LACC1 | 10292 | 33387 | 56482 |
| LACC1 | 10293 | 33388 | 56483 |
| LACRT | 10294 | 33389 | 56484 |
| LACTB | 10295 | 33390 | 56485 |
| LACTB | 10296 | 33391 | 56486 |
| LACTB | 10297 | 33392 | 56487 |
| LACTB2 | 10298 | 33393 | 56488 |
| LACTBL1 | 10299 | 33394 | 56489 |
| LAD1 | 10300 | 33395 | 56490 |
| LAG3 | 10301 | 33396 | 56491 |
| LAGE3 | 10302 | 33397 | 56492 |
| LAIR1 | 10303 | 33398 | 56493 |
| LAIR2 | 10304 | 33399 | 56494 |
| LALBA | 10305 | 33400 | 56495 |
| LAMA1 | 10306 | 33401 | 56496 |
| LAMA2 | 10307 | 33402 | 56497 |
| LAMA3 | 10308 | 33403 | 56498 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| LAMA3 | 10309 | 33404 | 56499 |
| LAMA4 | 10310 | 33405 | 56500 |
| LAMA4 | 10311 | 33406 | 56501 |
| LAMA5 | 10312 | 33407 | 56502 |
| LAMB1 | 10313 | 33408 | 56503 |
| LAMB2 | 10314 | 33409 | 56504 |
| LAMB3 | 10315 | 33410 | 56505 |
| LAMB4 | 10316 | 33411 | 56506 |
| LAMB4 | 10317 | 33412 | 56507 |
| LAMB4 | 10318 | 33413 | 56508 |
| LAMC1 | 10319 | 33414 | 56509 |
| LAMC2 | 10320 | 33415 | 56510 |
| LAMC2 | 10321 | 33416 | 56511 |
| LAMC3 | 10322 | 33417 | 56512 |
| LAMP1 | 10323 | 33418 | 56513 |
| LAMP2 | 10324 | 33419 | 56514 |
| LAMP2 | 10325 | 33420 | 56515 |
| LAMP2 | 10326 | 33421 | 56516 |
| LAMP3 | 10327 | 33422 | 56517 |
| LAMP5 | 10328 | 33423 | 56518 |
| LAMTOR1 | 10329 | 33424 | 56519 |
| LAMTOR2 | 10330 | 33425 | 56520 |
| LAMTOR3 | 10331 | 33426 | 56521 |
| LAMTOR4 | 10332 | 33427 | 56522 |
| LAMTOR4 | 10333 | 33428 | 56523 |
| LAMTOR5 | 10334 | 33429 | 56524 |
| LANCL1 | 10335 | 33430 | 56525 |
| LANCL2 | 10336 | 33431 | 56526 |
| LANCL3 | 10337 | 33432 | 56527 |
| LANCL3 | 10338 | 33433 | 56528 |
| LAP3 | 10339 | 33434 | 56529 |
| LAPTM4A | 10340 | 33435 | 56530 |
| LAPTM4B | 10341 | 33436 | 56531 |
| LAPTM5 | 10342 | 33437 | 56532 |
| LARGE1 | 10343 | 33438 | 56533 |
| LARGE2 | 10344 | 33439 | 56534 |
| LARP1 | 10345 | 33440 | 56535 |
| LARP1B | 10346 | 33441 | 56536 |
| LARP1B | 10347 | 33442 | 56537 |
| LARP1B | 10348 | 33443 | 56538 |
| LARP1B | 10349 | 33444 | 56539 |
| LARP4 | 10350 | 33445 | 56540 |
| LARP4 | 10351 | 33446 | 56541 |
| LARP4 | 10352 | 33447 | 56542 |
| LARP4 | 10353 | 33448 | 56543 |
| LARP4B | 10354 | 33449 | 56544 |
| LARP6 | 10355 | 33450 | 56545 |
| LARP6 | 10356 | 33451 | 56546 |
| LARP7 | 10357 | 33452 | 56547 |
| LARS | 10358 | 33453 | 56548 |
| LARS2 | 10359 | 33454 | 56549 |
| LAS1L | 10360 | 33455 | 56550 |
| LASP1 | 10361 | 33456 | 56551 |
| LAT | 10362 | 33457 | 56552 |
| LAT2 | 10363 | 33458 | 56553 |
| LATS1 | 10364 | 33459 | 56554 |
| LATS1 | 10365 | 33460 | 56555 |
| LATS2 | 10366 | 33461 | 56556 |
| LAX1 | 10367 | 33462 | 56557 |
| LAYN | 10368 | 33463 | 56558 |
| LBH | 10369 | 33464 | 56559 |
| LBHD1 | 10370 | 33465 | 56560 |
| LBP | 10371 | 33466 | 56561 |
| LBR | 10372 | 33467 | 56562 |
| LBX1 | 10373 | 33468 | 56563 |
| LBX2 | 10374 | 33469 | 56564 |
| LCA5 | 10375 | 33470 | 56565 |
| LCA5L | 10376 | 33471 | 56566 |
| LCAT | 10377 | 33472 | 56567 |
| LCE1B | 10378 | 33473 | 56568 |
| LCE1C | 10379 | 33474 | 56569 |
| LCE2A | 10380 | 33475 | 56570 |
| LCE2C | 10381 | 33476 | 56571 |
| LCE3A | 10382 | 33477 | 56572 |
| LCE3B | 10383 | 33478 | 56573 |
| LCE3E | 10384 | 33479 | 56574 |
| LCE4A | 10385 | 33480 | 56575 |
| LCE5A | 10386 | 33481 | 56576 |
| LCE6A | 10387 | 33482 | 56577 |
| LCK | 10388 | 33483 | 56578 |
| LCLAT1 | 10389 | 33484 | 56579 |
| LCMT1 | 10390 | 33485 | 56580 |
| LCMT2 | 10391 | 33486 | 56581 |
| LCN1 | 10392 | 33487 | 56582 |
| LCN1 | 10393 | 33488 | 56583 |
| LCN10 | 10394 | 33489 | 56584 |
| LCN12 | 10395 | 33490 | 56585 |
| LCN15 | 10396 | 33491 | 56586 |
| LCN2 | 10397 | 33492 | 56587 |
| LCN6 | 10398 | 33493 | 56588 |
| LCN8 | 10399 | 33494 | 56589 |
| LCN9 | 10400 | 33495 | 56590 |
| LCNL1 | 10401 | 33496 | 56591 |
| LCOR | 10402 | 33497 | 56592 |
| LCOR | 10403 | 33498 | 56593 |
| LCOR | 10404 | 33499 | 56594 |
| LCORL | 10405 | 33500 | 56595 |
| LCORL | 10406 | 33501 | 56596 |
| LCP1 | 10407 | 33502 | 56597 |
| LCP2 | 10408 | 33503 | 56598 |
| LCT | 10409 | 33504 | 56599 |
| LCTL | 10410 | 33505 | 56600 |
| LDAH | 10411 | 33506 | 56601 |
| LDAH | 10412 | 33507 | 56602 |
| LDB1 | 10413 | 33508 | 56603 |
| LDB2 | 10414 | 33509 | 56604 |
| LDB2 | 10415 | 33510 | 56605 |
| LDB2 | 10416 | 33511 | 56606 |
| LDB3 | 10417 | 33512 | 56607 |
| LDB3 | 10418 | 33513 | 56608 |
| LDHA | 10419 | 33514 | 56609 |
| LDHA | 10420 | 33515 | 56610 |
| LDHA | 10421 | 33516 | 56611 |
| LDHAL6A | 10422 | 33517 | 56612 |
| LDHAL6B | 10423 | 33518 | 56613 |
| LDHB | 10424 | 33519 | 56614 |
| LDHC | 10425 | 33520 | 56615 |
| LDHD | 10426 | 33521 | 56616 |
| LDLR | 10427 | 33522 | 56617 |
| LDLRAD1 | 10428 | 33523 | 56618 |
| LDLRAD1 | 10429 | 33524 | 56619 |
| LDLRAD2 | 10430 | 33525 | 56620 |
| LDLRAD3 | 10431 | 33526 | 56621 |
| LDLRAD4 | 10432 | 33527 | 56622 |
| LDLRAP1 | 10433 | 33528 | 56623 |
| LDOC1 | 10434 | 33529 | 56624 |
| LEAP2 | 10435 | 33530 | 56625 |
| LECT2 | 10436 | 33531 | 56626 |
| LEF1 | 10437 | 33532 | 56627 |
| LEF1 | 10438 | 33533 | 56628 |
| LEFTY1 | 10439 | 33534 | 56629 |
| LEFTY2 | 10440 | 33535 | 56630 |
| LEKR1 | 10441 | 33536 | 56631 |
| LEKR1 | 10442 | 33537 | 56632 |
| LELP1 | 10443 | 33538 | 56633 |
| LEMD1 | 10444 | 33539 | 56634 |
| LEMD1 | 10445 | 33540 | 56635 |
| LEMD2 | 10446 | 33541 | 56636 |
| LEMD3 | 10447 | 33542 | 56637 |
| LENEP | 10448 | 33543 | 56638 |
| LENG1 | 10449 | 33544 | 56639 |
| LENG8 | 10450 | 33545 | 56640 |
| LENG9 | 10451 | 33546 | 56641 |
| LEO1 | 10452 | 33547 | 56642 |
| LEO1 | 10453 | 33548 | 56643 |
| LEP | 10454 | 33549 | 56644 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| LEPR | 10455 | 33550 | 56645 |
| LEPR | 10456 | 33551 | 56646 |
| LEPR | 10457 | 33552 | 56647 |
| LEPR | 10458 | 33553 | 56648 |
| LEPROT | 10459 | 33554 | 56649 |
| LEPROT | 10460 | 33555 | 56650 |
| LEPROTL1 | 10461 | 33556 | 56651 |
| LEPROTL1 | 10462 | 33557 | 56652 |
| LETM1 | 10463 | 33558 | 56653 |
| LETM2 | 10464 | 33559 | 56654 |
| LETM2 | 10465 | 33560 | 56655 |
| LETMD1 | 10466 | 33561 | 56656 |
| LETMD1 | 10467 | 33562 | 56657 |
| LETMD1 | 10468 | 33563 | 56658 |
| LEUTX | 10469 | 33564 | 56659 |
| LEXM | 10470 | 33565 | 56660 |
| LEXM | 10471 | 33566 | 56661 |
| LFNG | 10472 | 33567 | 56662 |
| LFNG | 10473 | 33568 | 56663 |
| LGALS1 | 10474 | 33569 | 56664 |
| LGALS12 | 10475 | 33570 | 56665 |
| LGALS13 | 10476 | 33571 | 56666 |
| LGALS14 | 10477 | 33572 | 56667 |
| LGALS16 | 10478 | 33573 | 56668 |
| LGALS2 | 10479 | 33574 | 56669 |
| LGALS3 | 10480 | 33575 | 56670 |
| LGALS3 | 10481 | 33576 | 56671 |
| LGALS3BP | 10482 | 33577 | 56672 |
| LGALS4 | 10483 | 33578 | 56673 |
| LGALS7B | 10484 | 33579 | 56674 |
| LGALS8 | 10485 | 33580 | 56675 |
| LGALS9 | 10486 | 33581 | 56676 |
| LGALS9 | 10487 | 33582 | 56677 |
| LGALS9B | 10488 | 33583 | 56678 |
| LGALSL | 10489 | 33584 | 56679 |
| LGI1 | 10490 | 33585 | 56680 |
| LGI1 | 10491 | 33586 | 56681 |
| LGI2 | 10492 | 33587 | 56682 |
| LGI3 | 10493 | 33588 | 56683 |
| LGI4 | 10494 | 33589 | 56684 |
| LGMN | 10495 | 33590 | 56685 |
| LGR4 | 10496 | 33591 | 56686 |
| LGR5 | 10497 | 33592 | 56687 |
| LGR6 | 10498 | 33593 | 56688 |
| LGSN | 10499 | 33594 | 56689 |
| LGSN | 10500 | 33595 | 56690 |
| LHB | 10501 | 33596 | 56691 |
| LHCGR | 10502 | 33597 | 56692 |
| LHFPL1 | 10503 | 33598 | 56693 |
| LHFPL2 | 10504 | 33599 | 56694 |
| LHFPL3 | 10505 | 33600 | 56695 |
| LHFPL4 | 10506 | 33601 | 56696 |
| LHFPL5 | 10507 | 33602 | 56697 |
| LHFPL6 | 10508 | 33603 | 56698 |
| LHPP | 10509 | 33604 | 56699 |
| LHPP | 10510 | 33605 | 56700 |
| LHPP | 10511 | 33606 | 56701 |
| LHX1 | 10512 | 33607 | 56702 |
| LHX2 | 10513 | 33608 | 56703 |
| LHX3 | 10514 | 33609 | 56704 |
| LHX4 | 10515 | 33610 | 56705 |
| LHX5 | 10516 | 33611 | 56706 |
| LHX6 | 10517 | 33612 | 56707 |
| LHX6 | 10518 | 33613 | 56708 |
| LHX8 | 10519 | 33614 | 56709 |
| LHX9 | 10520 | 33615 | 56710 |
| LIAS | 10521 | 33616 | 56711 |
| LIAS | 10522 | 33617 | 56712 |
| LIAS | 10523 | 33618 | 56713 |
| LIAS | 10524 | 33619 | 56714 |
| LIF | 10525 | 33620 | 56715 |
| LIF | 10526 | 33621 | 56716 |
| LIFR | 10527 | 33622 | 56717 |
| LIG1 | 10528 | 33623 | 56718 |
| LIG3 | 10529 | 33624 | 56719 |
| LIG3 | 10530 | 33625 | 56720 |
| LIG4 | 10531 | 33626 | 56721 |
| LILRA1 | 10532 | 33627 | 56722 |
| LILRA1 | 10533 | 33628 | 56723 |
| LILRA2 | 10534 | 33629 | 56724 |
| LILRA2 | 10535 | 33630 | 56725 |
| LILRA3 | 10536 | 33631 | 56726 |
| LILRA4 | 10537 | 33632 | 56727 |
| LILRA5 | 10538 | 33633 | 56728 |
| LILRA5 | 10539 | 33634 | 56729 |
| LILRA6 | 10540 | 33635 | 56730 |
| LILRB1 | 10541 | 33636 | 56731 |
| LILRB1 | 10542 | 33637 | 56732 |
| LILRB2 | 10543 | 33638 | 56733 |
| LILRB2 | 10544 | 33639 | 56734 |
| LILRB2 | 10545 | 33640 | 56735 |
| LILRB3 | 10546 | 33641 | 56736 |
| LILRB4 | 10547 | 33642 | 56737 |
| LILRB4 | 10548 | 33643 | 56738 |
| LILRB5 | 10549 | 33644 | 56739 |
| LIM2 | 10550 | 33645 | 56740 |
| LIMA1 | 10551 | 33646 | 56741 |
| LIMCH1 | 10552 | 33647 | 56742 |
| LIMD1 | 10553 | 33648 | 56743 |
| LIMD2 | 10554 | 33649 | 56744 |
| LIME1 | 10555 | 33650 | 56745 |
| LIME1 | 10556 | 33651 | 56746 |
| LIMK1 | 10557 | 33652 | 56747 |
| LIMK2 | 10558 | 33653 | 56748 |
| LIMK2 | 10559 | 33654 | 56749 |
| LIMS1 | 10560 | 33655 | 56750 |
| LIMS2 | 10561 | 33656 | 56751 |
| LIMS4 | 10562 | 33657 | 56752 |
| LIN28A | 10563 | 33658 | 56753 |
| LIN28B | 10564 | 33659 | 56754 |
| LIN37 | 10565 | 33660 | 56755 |
| LIN52 | 10566 | 33661 | 56756 |
| LIN54 | 10567 | 33662 | 56757 |
| LIN7A | 10568 | 33663 | 56758 |
| LIN7B | 10569 | 33664 | 56759 |
| LIN7C | 10570 | 33665 | 56760 |
| LIN9 | 10571 | 33666 | 56761 |
| LINC00452 | 10572 | 33667 | 56762 |
| LINC00694 | 10573 | 33668 | 56763 |
| LINC00890 | 10574 | 33669 | 56764 |
| LINC01125 | 10575 | 33670 | 56765 |
| LINC01638 | 10576 | 33671 | 56766 |
| LINC01835 | 10577 | 33672 | 56767 |
| LINC02054 | 10578 | 33673 | 56768 |
| LINC02210-CRHR1 | 10579 | 33674 | 56769 |
| LINGO1 | 10580 | 33675 | 56770 |
| LINGO2 | 10581 | 33676 | 56771 |
| LINGO3 | 10582 | 33677 | 56772 |
| LINGO4 | 10583 | 33678 | 56773 |
| LINS1 | 10584 | 33679 | 56774 |
| LIPA | 10585 | 33680 | 56775 |
| LIPC | 10586 | 33681 | 56776 |
| LIPE | 10587 | 33682 | 56777 |
| LIPF | 10588 | 33683 | 56778 |
| LIPG | 10589 | 33684 | 56779 |
| LIPH | 10590 | 33685 | 56780 |
| LIPI | 10591 | 33686 | 56781 |
| LIPI | 10592 | 33687 | 56782 |
| LIPJ | 10593 | 33688 | 56783 |
| LIPK | 10594 | 33689 | 56784 |
| LIPM | 10595 | 33690 | 56785 |
| LIPN | 10596 | 33691 | 56786 |
| LIPT1 | 10597 | 33692 | 56787 |
| LIPT2 | 10598 | 33693 | 56788 |
| LIPT2 | 10599 | 33694 | 56789 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| LITAF | 10600 | 33695 | 56790 |
| LITAF | 10601 | 33696 | 56791 |
| LIX1 | 10602 | 33697 | 56792 |
| LIX1L | 10603 | 33698 | 56793 |
| LKAAEAR1 | 10604 | 33699 | 56794 |
| LKAAEAR1 | 10605 | 33700 | 56795 |
| LLCFC1 | 10606 | 33701 | 56796 |
| LLGL1 | 10607 | 33702 | 56797 |
| LLGL2 | 10608 | 33703 | 56798 |
| LLGL2 | 10609 | 33704 | 56799 |
| LLGL2 | 10610 | 33705 | 56800 |
| LLPH | 10611 | 33706 | 56801 |
| LMAN1 | 10612 | 33707 | 56802 |
| LMAN1L | 10613 | 33708 | 56803 |
| LMAN2 | 10614 | 33709 | 56804 |
| LMAN2L | 10615 | 33710 | 56805 |
| LMBR1 | 10616 | 33711 | 56806 |
| LMBR1L | 10617 | 33712 | 56807 |
| LMBRD1 | 10618 | 33713 | 56808 |
| LMBRD2 | 10619 | 33714 | 56809 |
| LMCD1 | 10620 | 33715 | 56810 |
| LMCD1 | 10621 | 33716 | 56811 |
| LMF1 | 10622 | 33717 | 56812 |
| LMF1 | 10623 | 33718 | 56813 |
| LMF2 | 10624 | 33719 | 56814 |
| LMLN | 10625 | 33720 | 56815 |
| LMNA | 10626 | 33721 | 56816 |
| LMNA | 10627 | 33722 | 56817 |
| LMNA | 10628 | 33723 | 56818 |
| LMNB1 | 10629 | 33724 | 56819 |
| LMNB2 | 10630 | 33725 | 56820 |
| LMNTD1 | 10631 | 33726 | 56821 |
| LMNTD2 | 10632 | 33727 | 56822 |
| LMO1 | 10633 | 33728 | 56823 |
| LMO2 | 10634 | 33729 | 56824 |
| LMO3 | 10635 | 33730 | 56825 |
| LMO4 | 10636 | 33731 | 56826 |
| LMO7 | 10637 | 33732 | 56827 |
| LMO7 | 10638 | 33733 | 56828 |
| LMO7DN | 10639 | 33734 | 56829 |
| LMOD1 | 10640 | 33735 | 56830 |
| LMOD2 | 10641 | 33736 | 56831 |
| LMOD3 | 10642 | 33737 | 56832 |
| LMTK2 | 10643 | 33738 | 56833 |
| LMTK3 | 10644 | 33739 | 56834 |
| LMX1A | 10645 | 33740 | 56835 |
| LMX1B | 10646 | 33741 | 56836 |
| LNP1 | 10647 | 33742 | 56837 |
| LNPEP | 10648 | 33743 | 56838 |
| LNPK | 10649 | 33744 | 56839 |
| LNX1 | 10650 | 33745 | 56840 |
| LNX2 | 10651 | 33746 | 56841 |
| LOC100128108 | 10652 | 33747 | 56842 |
| LOC100129083 | 10653 | 33748 | 56843 |
| LOC100129307 | 10654 | 33749 | 56844 |
| LOC100129697 | 10655 | 33750 | 56845 |
| LOC100129940 | 10656 | 33751 | 56846 |
| LOC100130357 | 10657 | 33752 | 56847 |
| LOC100130370 | 10658 | 33753 | 56848 |
| LOC100130451 | 10659 | 33754 | 56849 |
| LOC100130520 | 10660 | 33755 | 56850 |
| LOC100130705 | 10661 | 33756 | 56851 |
| LOC100130880 | 10662 | 33757 | 56852 |
| LOC100131107 | 10663 | 33758 | 56853 |
| LOC100131303 | 10664 | 33759 | 56854 |
| LOC100132813 | 10665 | 33760 | 56855 |
| LOC100134391 | 10666 | 33761 | 56856 |
| LOC100287036 | 10667 | 33762 | 56857 |
| LOC100287896 | 10668 | 33763 | 56858 |
| LOC100288966 | 10669 | 33764 | 56859 |
| LOC100289561 | 10670 | 33765 | 56860 |
| LOC100505549 | 10671 | 33766 | 56861 |
| LOC100505841 | 10672 | 33767 | 56862 |
| LOC100506127 | 10673 | 33768 | 56863 |
| LOC100506127 | 10674 | 33769 | 56864 |
| LOC100506127 | 10675 | 33770 | 56865 |
| LOC100506127 | 10676 | 33771 | 56866 |
| LOC100506388 | 10677 | 33772 | 56867 |
| LOC100506422 | 10678 | 33773 | 56868 |
| LOC100507507 | 10679 | 33774 | 56869 |
| LOC100996693 | 10680 | 33775 | 56870 |
| LOC100996842 | 10681 | 33776 | 56871 |
| LOC101927322 | 10682 | 33777 | 56872 |
| LOC101927503 | 10683 | 33778 | 56873 |
| LOC101927572 | 10684 | 33779 | 56874 |
| LOC101927572 | 10685 | 33780 | 56875 |
| LOC101927844 | 10686 | 33781 | 56876 |
| LOC101928120 | 10687 | 33782 | 56877 |
| LOC101928436 | 10688 | 33783 | 56878 |
| LOC101928436 | 10689 | 33784 | 56879 |
| LOC101928841 | 10690 | 33785 | 56880 |
| LOC101929372 | 10691 | 33786 | 56881 |
| LOC102723383 | 10692 | 33787 | 56882 |
| LOC102724219 | 10693 | 33788 | 56883 |
| LOC102724265 | 10694 | 33789 | 56884 |
| LOC102724652 | 10695 | 33790 | 56885 |
| LOC102724957 | 10696 | 33791 | 56886 |
| LOC105372977 | 10697 | 33792 | 56887 |
| LOC105375787 | 10698 | 33793 | 56888 |
| LOC105376731 | 10699 | 33794 | 56889 |
| LOC105377372 | 10700 | 33795 | 56890 |
| LOC107984640 | 10701 | 33796 | 56891 |
| LOC107984974 | 10702 | 33797 | 56892 |
| LOC107984974 | 10703 | 33798 | 56893 |
| LOC107984974 | 10704 | 33799 | 56894 |
| LOC110117498 | 10705 | 33800 | 56895 |
| LOC149373 | 10706 | 33801 | 56896 |
| LOC150051 | 10707 | 33802 | 56897 |
| LOC283710 | 10708 | 33803 | 56898 |
| LOC284898 | 10709 | 33804 | 56899 |
| LOC285556 | 10710 | 33805 | 56900 |
| LOC339862 | 10711 | 33806 | 56901 |
| LOC388282 | 10712 | 33807 | 56902 |
| LOC388692 | 10713 | 33808 | 56903 |
| LOC388780 | 10714 | 33809 | 56904 |
| LOC388813 | 10715 | 33810 | 56905 |
| LOC389199 | 10716 | 33811 | 56906 |
| LOC389602 | 10717 | 33812 | 56907 |
| LOC389831 | 10718 | 33813 | 56908 |
| LOC389895 | 10719 | 33814 | 56909 |
| LOC390877 | 10720 | 33815 | 56910 |
| LOC391322 | 10721 | 33816 | 56911 |
| LOC391322 | 10722 | 33817 | 56912 |
| LOC403312 | 10723 | 33818 | 56913 |
| LOC441155 | 10724 | 33819 | 56914 |
| LOC643802 | 10725 | 33820 | 56915 |
| LOC645177 | 10726 | 33821 | 56916 |
| LOC645188 | 10727 | 33822 | 56917 |
| LOC728392 | 10728 | 33823 | 56918 |
| LOC728485 | 10729 | 33824 | 56919 |
| LOC729159 | 10730 | 33825 | 56920 |
| LOC730098 | 10731 | 33826 | 56921 |
| LOC730183 | 10732 | 33827 | 56922 |
| LOC79999 | 10733 | 33828 | 56923 |
| LONP1 | 10734 | 33829 | 56924 |
| LONP2 | 10735 | 33830 | 56925 |
| LONRF1 | 10736 | 33831 | 56926 |
| LONRF2 | 10737 | 33832 | 56927 |
| LONRF3 | 10738 | 33833 | 56928 |
| LOR | 10739 | 33834 | 56929 |
| LOX | 10740 | 33835 | 56930 |
| LOXHD1 | 10741 | 33836 | 56931 |
| LOXHD1 | 10742 | 33837 | 56932 |
| LOXHD1 | 10743 | 33838 | 56933 |
| LOXL1 | 10744 | 33839 | 56934 |
| LOXL2 | 10745 | 33840 | 56935 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| LOXL3 | 10746 | 33841 | 56936 |
| LOXL4 | 10747 | 33842 | 56937 |
| LPA | 10748 | 33843 | 56938 |
| LPAR1 | 10749 | 33844 | 56939 |
| LPAR2 | 10750 | 33845 | 56940 |
| LPAR3 | 10751 | 33846 | 56941 |
| LPAR4 | 10752 | 33847 | 56942 |
| LPAR5 | 10753 | 33848 | 56943 |
| LPAR6 | 10754 | 33849 | 56944 |
| LPCAT1 | 10755 | 33850 | 56945 |
| LPCAT2 | 10756 | 33851 | 56946 |
| LPCAT3 | 10757 | 33852 | 56947 |
| LPCAT4 | 10758 | 33853 | 56948 |
| LPGAT1 | 10759 | 33854 | 56949 |
| LPIN1 | 10760 | 33855 | 56950 |
| LPIN2 | 10761 | 33856 | 56951 |
| LPIN3 | 10762 | 33857 | 56952 |
| LPL | 10763 | 33858 | 56953 |
| LPO | 10764 | 33859 | 56954 |
| LPP | 10765 | 33860 | 56955 |
| LPXN | 10766 | 33861 | 56956 |
| LRAT | 10767 | 33862 | 56957 |
| LRBA | 10768 | 33863 | 56958 |
| LRCH1 | 10769 | 33864 | 56959 |
| LRCH1 | 10770 | 33865 | 56960 |
| LRCH2 | 10771 | 33866 | 56961 |
| LRCH3 | 10772 | 33867 | 56962 |
| LRCH4 | 10773 | 33868 | 56963 |
| LRCH4 | 10774 | 33869 | 56964 |
| LRCOL1 | 10775 | 33870 | 56965 |
| LRFN1 | 10776 | 33871 | 56966 |
| LRFN2 | 10777 | 33872 | 56967 |
| LRFN3 | 10778 | 33873 | 56968 |
| LRFN4 | 10779 | 33874 | 56969 |
| LRFN5 | 10780 | 33875 | 56970 |
| LRFN5 | 10781 | 33876 | 56971 |
| LRG1 | 10782 | 33877 | 56972 |
| LRGUK | 10783 | 33878 | 56973 |
| LRIF1 | 10784 | 33879 | 56974 |
| LRIG1 | 10785 | 33880 | 56975 |
| LRIG2 | 10786 | 33881 | 56976 |
| LRIG3 | 10787 | 33882 | 56977 |
| LRIT1 | 10788 | 33883 | 56978 |
| LRIT2 | 10789 | 33884 | 56979 |
| LRIT3 | 10790 | 33885 | 56980 |
| LRMDA | 10791 | 33886 | 56981 |
| LRMP | 10792 | 33887 | 56982 |
| LRP1 | 10793 | 33888 | 56983 |
| LRP10 | 10794 | 33889 | 56984 |
| LRP10 | 10795 | 33890 | 56985 |
| LRP11 | 10796 | 33891 | 56986 |
| LRP12 | 10797 | 33892 | 56987 |
| LRP1B | 10798 | 33893 | 56988 |
| LRP2 | 10799 | 33894 | 56989 |
| LRP2BP | 10800 | 33895 | 56990 |
| LRP3 | 10801 | 33896 | 56991 |
| LRP4 | 10802 | 33897 | 56992 |
| LRP5 | 10803 | 33898 | 56993 |
| LRP5L | 10804 | 33899 | 56994 |
| LRP6 | 10805 | 33900 | 56995 |
| LRP8 | 10806 | 33901 | 56996 |
| LRPAP1 | 10807 | 33902 | 56997 |
| LRPPRC | 10808 | 33903 | 56998 |
| LRR1 | 10809 | 33904 | 56999 |
| LRRC1 | 10810 | 33905 | 57000 |
| LRRC10 | 10811 | 33906 | 57001 |
| LRRC10B | 10812 | 33907 | 57002 |
| LRRC14 | 10813 | 33908 | 57003 |
| LRRC14B | 10814 | 33909 | 57004 |
| LRRC15 | 10815 | 33910 | 57005 |
| LRRC17 | 10816 | 33911 | 57006 |
| LRRC17 | 10817 | 33912 | 57007 |
| LRRC18 | 10818 | 33913 | 57008 |
| LRRC19 | 10819 | 33914 | 57009 |
| LRRC2 | 10820 | 33915 | 57010 |
| LRRC20 | 10821 | 33916 | 57011 |
| LRRC20 | 10822 | 33917 | 57012 |
| LRRC23 | 10823 | 33918 | 57013 |
| LRRC23 | 10824 | 33919 | 57014 |
| LRRC24 | 10825 | 33920 | 57015 |
| LRRC25 | 10826 | 33921 | 57016 |
| LRRC26 | 10827 | 33922 | 57017 |
| LRRC27 | 10828 | 33923 | 57018 |
| LRRC27 | 10829 | 33924 | 57019 |
| LRRC27 | 10830 | 33925 | 57020 |
| LRRC27 | 10831 | 33926 | 57021 |
| LRRC28 | 10832 | 33927 | 57022 |
| LRRC29 | 10833 | 33928 | 57023 |
| LRRC3 | 10834 | 33929 | 57024 |
| LRRC30 | 10835 | 33930 | 57025 |
| LRRC31 | 10836 | 33931 | 57026 |
| LRRC31 | 10837 | 33932 | 57027 |
| LRRC32 | 10838 | 33933 | 57028 |
| LRRC34 | 10839 | 33934 | 57029 |
| LRRC34 | 10840 | 33935 | 57030 |
| LRRC36 | 10841 | 33936 | 57031 |
| LRRC37A | 10842 | 33937 | 57032 |
| LRRC37B | 10843 | 33938 | 57033 |
| LRRC38 | 10844 | 33939 | 57034 |
| LRRC39 | 10845 | 33940 | 57035 |
| LRRC39 | 10846 | 33941 | 57036 |
| LRRC3B | 10847 | 33942 | 57037 |
| LRRC3C | 10848 | 33943 | 57038 |
| LRRC4 | 10849 | 33944 | 57039 |
| LRRC40 | 10850 | 33945 | 57040 |
| LRRC41 | 10851 | 33946 | 57041 |
| LRRC42 | 10852 | 33947 | 57042 |
| LRRC43 | 10853 | 33948 | 57043 |
| LRRC45 | 10854 | 33949 | 57044 |
| LRRC46 | 10855 | 33950 | 57045 |
| LRRC47 | 10856 | 33951 | 57046 |
| LRRC49 | 10857 | 33952 | 57047 |
| LRRC4B | 10858 | 33953 | 57048 |
| LRRC4C | 10859 | 33954 | 57049 |
| LRRC52 | 10860 | 33955 | 57050 |
| LRRC55 | 10861 | 33956 | 57051 |
| LRRC56 | 10862 | 33957 | 57052 |
| LRRC57 | 10863 | 33958 | 57053 |
| LRRC58 | 10864 | 33959 | 57054 |
| LRRC59 | 10865 | 33960 | 57055 |
| LRRC6 | 10866 | 33961 | 57056 |
| LRRC61 | 10867 | 33962 | 57057 |
| LRRC63 | 10868 | 33963 | 57058 |
| LRRC66 | 10869 | 33964 | 57059 |
| LRRC69 | 10870 | 33965 | 57060 |
| LRRC7 | 10871 | 33966 | 57061 |
| LRRC7 | 10872 | 33967 | 57062 |
| LRRC70 | 10873 | 33968 | 57063 |
| LRRC71 | 10874 | 33969 | 57064 |
| LRRC72 | 10875 | 33970 | 57065 |
| LRRC73 | 10876 | 33971 | 57066 |
| LRRC74A | 10877 | 33972 | 57067 |
| LRRC74B | 10878 | 33973 | 57068 |
| LRRC75A | 10879 | 33974 | 57069 |
| LRRC75A | 10880 | 33975 | 57070 |
| LRRC75B | 10881 | 33976 | 57071 |
| LRRC8A | 10882 | 33977 | 57072 |
| LRRC8B | 10883 | 33978 | 57073 |
| LRRC8C | 10884 | 33979 | 57074 |
| LRRC8D | 10885 | 33980 | 57075 |
| LRRC8E | 10886 | 33981 | 57076 |
| LRRCC1 | 10887 | 33982 | 57077 |
| LRRD1 | 10888 | 33983 | 57078 |
| LRRFIP1 | 10889 | 33984 | 57079 |
| LRRFIP1 | 10890 | 33985 | 57080 |
| LRRFIP2 | 10891 | 33986 | 57081 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| LRRIQ1 | 10892 | 33987 | 57082 |
| LRRIQ3 | 10893 | 33988 | 57083 |
| LRRIQ3 | 10894 | 33989 | 57084 |
| LRRIQ4 | 10895 | 33990 | 57085 |
| LRRK1 | 10896 | 33991 | 57086 |
| LRRK2 | 10897 | 33992 | 57087 |
| LRRN1 | 10898 | 33993 | 57088 |
| LRRN2 | 10899 | 33994 | 57089 |
| LRRN3 | 10900 | 33995 | 57090 |
| LRRN4 | 10901 | 33996 | 57091 |
| LRRN4CL | 10902 | 33997 | 57092 |
| LRRTM1 | 10903 | 33998 | 57093 |
| LRRTM2 | 10904 | 33999 | 57094 |
| LRRTM3 | 10905 | 34000 | 57095 |
| LRRTM4 | 10906 | 34001 | 57096 |
| LRRTM4 | 10907 | 34002 | 57097 |
| LRSAM1 | 10908 | 34003 | 57098 |
| LRTM1 | 10909 | 34004 | 57099 |
| LRTM2 | 10910 | 34005 | 57100 |
| LRTOMT | 10911 | 34006 | 57101 |
| LRTOMT | 10912 | 34007 | 57102 |
| LRTOMT | 10913 | 34008 | 57103 |
| LRTOMT | 10914 | 34009 | 57104 |
| LRWD1 | 10915 | 34010 | 57105 |
| LSAMP | 10916 | 34011 | 57106 |
| LSG1 | 10917 | 34012 | 57107 |
| LSM1 | 10918 | 34013 | 57108 |
| LSM1 | 10919 | 34014 | 57109 |
| LSM1 | 10920 | 34015 | 57110 |
| LSM10 | 10921 | 34016 | 57111 |
| LSM11 | 10922 | 34017 | 57112 |
| LSM12 | 10923 | 34018 | 57113 |
| LSM14A | 10924 | 34019 | 57114 |
| LSM14A | 10925 | 34020 | 57115 |
| LSM14B | 10926 | 34021 | 57116 |
| LSM2 | 10927 | 34022 | 57117 |
| LSM3 | 10928 | 34023 | 57118 |
| LSM4 | 10929 | 34024 | 57119 |
| LSM5 | 10930 | 34025 | 57120 |
| LSM5 | 10931 | 34026 | 57121 |
| LSM6 | 10932 | 34027 | 57122 |
| LSM7 | 10933 | 34028 | 57123 |
| LSM8 | 10934 | 34029 | 57124 |
| LSMEM1 | 10935 | 34030 | 57125 |
| LSMEM2 | 10936 | 34031 | 57126 |
| LSP1 | 10937 | 34032 | 57127 |
| LSR | 10938 | 34033 | 57128 |
| LSS | 10939 | 34034 | 57129 |
| LST1 | 10940 | 34035 | 57130 |
| LST1 | 10941 | 34036 | 57131 |
| LTA | 10942 | 34037 | 57132 |
| LTA4H | 10943 | 34038 | 57133 |
| LTA4H | 10944 | 34039 | 57134 |
| LTB | 10945 | 34040 | 57135 |
| LTB | 10946 | 34041 | 57136 |
| LTB4R | 10947 | 34042 | 57137 |
| LTB4R2 | 10948 | 34043 | 57138 |
| LTBP1 | 10949 | 34044 | 57139 |
| LTBP2 | 10950 | 34045 | 57140 |
| LTBP3 | 10951 | 34046 | 57141 |
| LTBP4 | 10952 | 34047 | 57142 |
| LTBR | 10953 | 34048 | 57143 |
| LTC4S | 10954 | 34049 | 57144 |
| LTF | 10955 | 34050 | 57145 |
| LTK | 10956 | 34051 | 57146 |
| LTN1 | 10957 | 34052 | 57147 |
| LTV1 | 10958 | 34053 | 57148 |
| LUC7L | 10959 | 34054 | 57149 |
| LUC7L | 10960 | 34055 | 57150 |
| LUC7L2 | 10961 | 34056 | 57151 |
| LUC7L3 | 10962 | 34057 | 57152 |
| LUC7L3 | 10963 | 34058 | 57153 |
| LUM | 10964 | 34059 | 57154 |
| LURAP1 | 10965 | 34060 | 57155 |
| LURAP1L | 10966 | 34061 | 57156 |
| LUZP1 | 10967 | 34062 | 57157 |
| LUZP2 | 10968 | 34063 | 57158 |
| LUZP4 | 10969 | 34064 | 57159 |
| LUZP6 | 10970 | 34065 | 57160 |
| LVRN | 10971 | 34066 | 57161 |
| LXN | 10972 | 34067 | 57162 |
| LY6D | 10973 | 34068 | 57163 |
| LY6E | 10974 | 34069 | 57164 |
| LY6G5B | 10975 | 34070 | 57165 |
| LY6G5C | 10976 | 34071 | 57166 |
| LY6G6C | 10977 | 34072 | 57167 |
| LY6G6D | 10978 | 34073 | 57168 |
| LY6G6F | 10979 | 34074 | 57169 |
| LY6G6F-LY6G6D | 10980 | 34075 | 57170 |
| LY6H | 10981 | 34076 | 57171 |
| LY6K | 10982 | 34077 | 57172 |
| LY6K | 10983 | 34078 | 57173 |
| LY6K | 10984 | 34079 | 57174 |
| LY75 | 10985 | 34080 | 57175 |
| LY86 | 10986 | 34081 | 57176 |
| LY9 | 10987 | 34082 | 57177 |
| LY9 | 10988 | 34083 | 57178 |
| LY96 | 10989 | 34084 | 57179 |
| LYAR | 10990 | 34085 | 57180 |
| LYG1 | 10991 | 34086 | 57181 |
| LYG2 | 10992 | 34087 | 57182 |
| LYL1 | 10993 | 34088 | 57183 |
| LYN | 10994 | 34089 | 57184 |
| LYNX1 | 10995 | 34090 | 57185 |
| LYNX1 | 10996 | 34091 | 57186 |
| LYPD1 | 10997 | 34092 | 57187 |
| LYPD1 | 10998 | 34093 | 57188 |
| LYPD1 | 10999 | 34094 | 57189 |
| LYPD2 | 11000 | 34095 | 57190 |
| LYPD3 | 11001 | 34096 | 57191 |
| LYPD4 | 11002 | 34097 | 57192 |
| LYPD5 | 11003 | 34098 | 57193 |
| LYPD6 | 11004 | 34099 | 57194 |
| LYPD6B | 11005 | 34100 | 57195 |
| LYPD8 | 11006 | 34101 | 57196 |
| LYPLA1 | 11007 | 34102 | 57197 |
| LYPLA2 | 11008 | 34103 | 57198 |
| LYPLAL1 | 11009 | 34104 | 57199 |
| LYRM1 | 11010 | 34105 | 57200 |
| LYRM2 | 11011 | 34106 | 57201 |
| LYRM4 | 11012 | 34107 | 57202 |
| LYRM4 | 11013 | 34108 | 57203 |
| LYRM4 | 11014 | 34109 | 57204 |
| LYRM4 | 11015 | 34110 | 57205 |
| LYRM4 | 11016 | 34111 | 57206 |
| LYRM7 | 11017 | 34112 | 57207 |
| LYRM7 | 11018 | 34113 | 57208 |
| LYRM9 | 11019 | 34114 | 57209 |
| LYSMD1 | 11020 | 34115 | 57210 |
| LYSMD2 | 11021 | 34116 | 57211 |
| LYSMD3 | 11022 | 34117 | 57212 |
| LYSMD3 | 11023 | 34118 | 57213 |
| LYSMD4 | 11024 | 34119 | 57214 |
| LYST | 11025 | 34120 | 57215 |
| LYVE1 | 11026 | 34121 | 57216 |
| LYZ | 11027 | 34122 | 57217 |
| LYZL1 | 11028 | 34123 | 57218 |
| LYZL2 | 11029 | 34124 | 57219 |
| LYZL4 | 11030 | 34125 | 57220 |
| LYZL6 | 11031 | 34126 | 57221 |
| LZIC | 11032 | 34127 | 57222 |
| LZIC | 11033 | 34128 | 57223 |
| LZTFL1 | 11034 | 34129 | 57224 |
| LZTFL1 | 11035 | 34130 | 57225 |
| LZTR1 | 11036 | 34131 | 57226 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| LZTS1 | 11037 | 34132 | 57227 |
| LZTS2 | 11038 | 34133 | 57228 |
| LZTS3 | 11039 | 34134 | 57229 |
| M1AP | 11040 | 34135 | 57230 |
| M1AP | 11041 | 34136 | 57231 |
| M6PR | 11042 | 34137 | 57232 |
| MAATS1 | 11043 | 34138 | 57233 |
| MAB21L1 | 11044 | 34139 | 57234 |
| MAB21L2 | 11045 | 34140 | 57235 |
| MAB21L3 | 11046 | 34141 | 57236 |
| MACC1 | 11047 | 34142 | 57237 |
| MACF1 | 11048 | 34143 | 57238 |
| MACROD1 | 11049 | 34144 | 57239 |
| MACROD2 | 11050 | 34145 | 57240 |
| MAD1L1 | 11051 | 34146 | 57241 |
| MAD2L1 | 11052 | 34147 | 57242 |
| MAD2L1BP | 11053 | 34148 | 57243 |
| MAD2L2 | 11054 | 34149 | 57244 |
| MADCAM1 | 11055 | 34150 | 57245 |
| MADD | 11056 | 34151 | 57246 |
| MADD | 11057 | 34152 | 57247 |
| MAEA | 11058 | 34153 | 57248 |
| MAEL | 11059 | 34154 | 57249 |
| MAF | 11060 | 34155 | 57250 |
| MAF | 11061 | 34156 | 57251 |
| MAF1 | 11062 | 34157 | 57252 |
| MAFA | 11063 | 34158 | 57253 |
| MAFB | 11064 | 34159 | 57254 |
| MAFF | 11065 | 34160 | 57255 |
| MAFG | 11066 | 34161 | 57256 |
| MAFK | 11067 | 34162 | 57257 |
| MAG | 11068 | 34163 | 57258 |
| MAG | 11069 | 34164 | 57259 |
| MAGEA1 | 11070 | 34165 | 57260 |
| MAGEA10 | 11071 | 34166 | 57261 |
| MAGEA11 | 11072 | 34167 | 57262 |
| MAGEA12 | 11073 | 34168 | 57263 |
| MAGEA2B | 11074 | 34169 | 57264 |
| MAGEA3 | 11075 | 34170 | 57265 |
| MAGEA4 | 11076 | 34171 | 57266 |
| MAGEA5 | 11077 | 34172 | 57267 |
| MAGEA6 | 11078 | 34173 | 57268 |
| MAGEA8 | 11079 | 34174 | 57269 |
| MAGEA9B | 11080 | 34175 | 57270 |
| MAGEB1 | 11081 | 34176 | 57271 |
| MAGEB10 | 11082 | 34177 | 57272 |
| MAGEB16 | 11083 | 34178 | 57273 |
| MAGEB17 | 11084 | 34179 | 57274 |
| MAGEB18 | 11085 | 34180 | 57275 |
| MAGEB2 | 11086 | 34181 | 57276 |
| MAGEB3 | 11087 | 34182 | 57277 |
| MAGEB4 | 11088 | 34183 | 57278 |
| MAGEB5 | 11089 | 34184 | 57279 |
| MAGEB6 | 11090 | 34185 | 57280 |
| MAGEC1 | 11091 | 34186 | 57281 |
| MAGEC2 | 11092 | 34187 | 57282 |
| MAGEC3 | 11093 | 34188 | 57283 |
| MAGEC3 | 11094 | 34189 | 57284 |
| MAGED1 | 11095 | 34190 | 57285 |
| MAGED2 | 11096 | 34191 | 57286 |
| MAGED4 | 11097 | 34192 | 57287 |
| MAGED4 | 11098 | 34193 | 57288 |
| MAGEE1 | 11099 | 34194 | 57289 |
| MAGEE2 | 11100 | 34195 | 57290 |
| MAGEF1 | 11101 | 34196 | 57291 |
| MAGEH1 | 11102 | 34197 | 57292 |
| MAGEL2 | 11103 | 34198 | 57293 |
| MAGI1 | 11104 | 34199 | 57294 |
| MAGI1 | 11105 | 34200 | 57295 |
| MAGI1 | 11106 | 34201 | 57296 |
| MAGI2 | 11107 | 34202 | 57297 |
| MAGI3 | 11108 | 34203 | 57298 |
| MAGI3 | 11109 | 34204 | 57299 |
| MAGIX | 11110 | 34205 | 57300 |
| MAGOH | 11111 | 34206 | 57301 |
| MAGOHB | 11112 | 34207 | 57302 |
| MAGT1 | 11113 | 34208 | 57303 |
| MAIP1 | 11114 | 34209 | 57304 |
| MAJIN | 11115 | 34210 | 57305 |
| MAJIN | 11116 | 34211 | 57306 |
| MAK | 11117 | 34212 | 57307 |
| MAK 16 | 11118 | 34213 | 57308 |
| MAL | 11119 | 34214 | 57309 |
| MAL | 11120 | 34215 | 57310 |
| MAL2 | 11121 | 34216 | 57311 |
| MALL | 11122 | 34217 | 57312 |
| MALRD1 | 11123 | 34218 | 57313 |
| MALSU1 | 11124 | 34219 | 57314 |
| MALT1 | 11125 | 34220 | 57315 |
| MAMDC2 | 11126 | 34221 | 57316 |
| MAMDC2 | 11127 | 34222 | 57317 |
| MAMDC4 | 11128 | 34223 | 57318 |
| MAML1 | 11129 | 34224 | 57319 |
| MAML2 | 11130 | 34225 | 57320 |
| MAML3 | 11131 | 34226 | 57321 |
| MAMLD1 | 11132 | 34227 | 57322 |
| MAMLD1 | 11133 | 34228 | 57323 |
| MAMSTR | 11134 | 34229 | 57324 |
| MAN1A1 | 11135 | 34230 | 57325 |
| MAN1A2 | 11136 | 34231 | 57326 |
| MAN1B1 | 11137 | 34232 | 57327 |
| MAN1C1 | 11138 | 34233 | 57328 |
| MAN1C1 | 11139 | 34234 | 57329 |
| MAN2A1 | 11140 | 34235 | 57330 |
| MAN2A2 | 11141 | 34236 | 57331 |
| MAN2B1 | 11142 | 34237 | 57332 |
| MAN2B2 | 11143 | 34238 | 57333 |
| MAN2C1 | 11144 | 34239 | 57334 |
| MANBA | 11145 | 34240 | 57335 |
| MANBAL | 11146 | 34241 | 57336 |
| MANEA | 11147 | 34242 | 57337 |
| MANEAL | 11148 | 34243 | 57338 |
| MANEAL | 11149 | 34244 | 57339 |
| MANF | 11150 | 34245 | 57340 |
| MANSC1 | 11151 | 34246 | 57341 |
| MANSC4 | 11152 | 34247 | 57342 |
| MAOA | 11153 | 34248 | 57343 |
| MAOA | 11154 | 34249 | 57344 |
| MAOB | 11155 | 34250 | 57345 |
| MAP10 | 11156 | 34251 | 57346 |
| MAP1A | 11157 | 34252 | 57347 |
| MAP1B | 11158 | 34253 | 57348 |
| MAP1LC3A | 11159 | 34254 | 57349 |
| MAP1LC3B | 11160 | 34255 | 57350 |
| MAP1LC3B2 | 11161 | 34256 | 57351 |
| MAP1LC3C | 11162 | 34257 | 57352 |
| MAP1S | 11163 | 34258 | 57353 |
| MAP2 | 11164 | 34259 | 57354 |
| MAP2K1 | 11165 | 34260 | 57355 |
| MAP2K2 | 11166 | 34261 | 57356 |
| MAP2K3 | 11167 | 34262 | 57357 |
| MAP2K4 | 11168 | 34263 | 57358 |
| MAP2K5 | 11169 | 34264 | 57359 |
| MAP2K6 | 11170 | 34265 | 57360 |
| MAP2K7 | 11171 | 34266 | 57361 |
| MAP3K1 | 11172 | 34267 | 57362 |
| MAP3K10 | 11173 | 34268 | 57363 |
| MAP3K11 | 11174 | 34269 | 57364 |
| MAP3K12 | 11175 | 34270 | 57365 |
| MAP3K13 | 11176 | 34271 | 57366 |
| MAP3K14 | 11177 | 34272 | 57367 |
| MAP3K15 | 11178 | 34273 | 57368 |
| MAP3K19 | 11179 | 34274 | 57369 |
| MAP3K19 | 11180 | 34275 | 57370 |
| MAP3K2 | 11181 | 34276 | 57371 |
| MAP3K20 | 11182 | 34277 | 57372 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MAP3K20 | 11183 | 34278 | 57373 |
| MAP3K21 | 11184 | 34279 | 57374 |
| MAP3K3 | 11185 | 34280 | 57375 |
| MAP3K4 | 11186 | 34281 | 57376 |
| MAP3K5 | 11187 | 34282 | 57377 |
| MAP3K6 | 11188 | 34283 | 57378 |
| MAP3K7 | 11189 | 34284 | 57379 |
| MAP3K7 | 11190 | 34285 | 57380 |
| MAP3K7CL | 11191 | 34286 | 57381 |
| MAP3K7CL | 11192 | 34287 | 57382 |
| MAP3K7CL | 11193 | 34288 | 57383 |
| MAP3K8 | 11194 | 34289 | 57384 |
| MAP3K9 | 11195 | 34290 | 57385 |
| MAP4 | 11196 | 34291 | 57386 |
| MAP4 | 11197 | 34292 | 57387 |
| MAP4 | 11198 | 34293 | 57388 |
| MAP4K1 | 11199 | 34294 | 57389 |
| MAP4K1 | 11200 | 34295 | 57390 |
| MAP4K2 | 11201 | 34296 | 57391 |
| MAP4K3 | 11202 | 34297 | 57392 |
| MAP4K4 | 11203 | 34298 | 57393 |
| MAP4K5 | 11204 | 34299 | 57394 |
| MAP6 | 11205 | 34300 | 57395 |
| MAP6 | 11206 | 34301 | 57396 |
| MAP6D1 | 11207 | 34302 | 57397 |
| MAP7 | 11208 | 34303 | 57398 |
| MAP7D1 | 11209 | 34304 | 57399 |
| MAP7D2 | 11210 | 34305 | 57400 |
| MAP7D3 | 11211 | 34306 | 57401 |
| MAP9 | 11212 | 34307 | 57402 |
| MAPK1 | 11213 | 34308 | 57403 |
| MAPK10 | 11214 | 34309 | 57404 |
| MAPK10 | 11215 | 34310 | 57405 |
| MAPK11 | 11216 | 34311 | 57406 |
| MAPK12 | 11217 | 34312 | 57407 |
| MAPK13 | 11218 | 34313 | 57408 |
| MAPK14 | 11219 | 34314 | 57409 |
| MAPK14 | 11220 | 34315 | 57410 |
| MAPK14 | 11221 | 34316 | 57411 |
| MAPK15 | 11222 | 34317 | 57412 |
| MAPK1IP1L | 11223 | 34318 | 57413 |
| MAPK3 | 11224 | 34319 | 57414 |
| MAPK3 | 11225 | 34320 | 57415 |
| MAPK4 | 11226 | 34321 | 57416 |
| MAPK4 | 11227 | 34322 | 57417 |
| MAPK6 | 11228 | 34323 | 57418 |
| MAPK7 | 11229 | 34324 | 57419 |
| MAPK8 | 11230 | 34325 | 57420 |
| MAPK8 | 11231 | 34326 | 57421 |
| MAPK8IP1 | 11232 | 34327 | 57422 |
| MAPK8IP2 | 11233 | 34328 | 57423 |
| MAPK8IP3 | 11234 | 34329 | 57424 |
| MAPK9 | 11235 | 34330 | 57425 |
| MAPK9 | 11236 | 34331 | 57426 |
| MAPK9 | 11237 | 34332 | 57427 |
| MAPK9 | 11238 | 34333 | 57428 |
| MAPKAP1 | 11239 | 34334 | 57429 |
| MAPKAP1 | 11240 | 34335 | 57430 |
| MAPKAPK2 | 11241 | 34336 | 57431 |
| MAPKAPK2 | 11242 | 34337 | 57432 |
| MAPKAPK3 | 11243 | 34338 | 57433 |
| MAPKAPK5 | 11244 | 34339 | 57434 |
| MAPKBP1 | 11245 | 34340 | 57435 |
| MAPRE1 | 11246 | 34341 | 57436 |
| MAPRE2 | 11247 | 34342 | 57437 |
| MAPRE3 | 11248 | 34343 | 57438 |
| MAPT | 11249 | 34344 | 57439 |
| MARC1 | 11250 | 34345 | 57440 |
| MARC2 | 11251 | 34346 | 57441 |
| MARC2 | 11252 | 34347 | 57442 |
| MARCH1 | 11253 | 34348 | 57443 |
| MARCH10 | 11254 | 34349 | 57444 |
| MARCH10 | 11255 | 34350 | 57445 |
| MARCH11 | 11256 | 34351 | 57446 |
| MARCH2 | 11257 | 34352 | 57447 |
| MARCH3 | 11258 | 34353 | 57448 |
| MARCH4 | 11259 | 34354 | 57449 |
| MARCH5 | 11260 | 34355 | 57450 |
| MARCH6 | 11261 | 34356 | 57451 |
| MARCH7 | 11262 | 34357 | 57452 |
| MARCH8 | 11263 | 34358 | 57453 |
| MARCH9 | 11264 | 34359 | 57454 |
| MARCKS | 11265 | 34360 | 57455 |
| MARCKSL1 | 11266 | 34361 | 57456 |
| MARCO | 11267 | 34362 | 57457 |
| MARF1 | 11268 | 34363 | 57458 |
| MARK1 | 11269 | 34364 | 57459 |
| MARK1 | 11270 | 34365 | 57460 |
| MARK2 | 11271 | 34366 | 57461 |
| MARK3 | 11272 | 34367 | 57462 |
| MARK4 | 11273 | 34368 | 57463 |
| MARK4 | 11274 | 34369 | 57464 |
| MARS | 11275 | 34370 | 57465 |
| MARS2 | 11276 | 34371 | 57466 |
| MARVELD1 | 11277 | 34372 | 57467 |
| MARVELD2 | 11278 | 34373 | 57468 |
| MARVELD3 | 11279 | 34374 | 57469 |
| MARVELD3 | 11280 | 34375 | 57470 |
| MAS1 | 11281 | 34376 | 57471 |
| MAS1L | 11282 | 34377 | 57472 |
| MASP1 | 11283 | 34378 | 57473 |
| MASP1 | 11284 | 34379 | 57474 |
| MASP1 | 11285 | 34380 | 57475 |
| MASP2 | 11286 | 34381 | 57476 |
| MASP2 | 11287 | 34382 | 57477 |
| MAST1 | 11288 | 34383 | 57478 |
| MAST2 | 11289 | 34384 | 57479 |
| MAST3 | 11290 | 34385 | 57480 |
| MAST4 | 11291 | 34386 | 57481 |
| MAST4 | 11292 | 34387 | 57482 |
| MASTL | 11293 | 34388 | 57483 |
| MAT1A | 11294 | 34389 | 57484 |
| MAT2A | 11295 | 34390 | 57485 |
| MAT2B | 11296 | 34391 | 57486 |
| MATK | 11297 | 34392 | 57487 |
| MATN1 | 11298 | 34393 | 57488 |
| MATN2 | 11299 | 34394 | 57489 |
| MATN3 | 11300 | 34395 | 57490 |
| MATN4 | 11301 | 34396 | 57491 |
| MATR3 | 11302 | 34397 | 57492 |
| MAU2 | 11303 | 34398 | 57493 |
| MAVS | 11304 | 34399 | 57494 |
| MAX | 11305 | 34400 | 57495 |
| MAX | 11306 | 34401 | 57496 |
| MAX | 11307 | 34402 | 57497 |
| MAX | 11308 | 34403 | 57498 |
| MAZ | 11309 | 34404 | 57499 |
| MAZ | 11310 | 34405 | 57500 |
| MB | 11311 | 34406 | 57501 |
| MB21D1 | 11312 | 34407 | 57502 |
| MB21D2 | 11313 | 34408 | 57503 |
| MBD1 | 11314 | 34409 | 57504 |
| MBD1 | 11315 | 34410 | 57505 |
| MBD1 | 11316 | 34411 | 57506 |
| MBD1 | 11317 | 34412 | 57507 |
| MBD1 | 11318 | 34413 | 57508 |
| MBD2 | 11319 | 34414 | 57509 |
| MBD2 | 11320 | 34415 | 57510 |
| MBD3 | 11321 | 34416 | 57511 |
| MBD3L1 | 11322 | 34417 | 57512 |
| MBD3L2 | 11323 | 34418 | 57513 |
| MBD3L4 | 11324 | 34419 | 57514 |
| MBD3L5 | 11325 | 34420 | 57515 |
| MBD4 | 11326 | 34421 | 57516 |
| MBD4 | 11327 | 34422 | 57517 |
| MBD4 | 11328 | 34423 | 57518 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MBD5 | 11329 | 34424 | 57519 |
| MBD6 | 11330 | 34425 | 57520 |
| MBIP | 11331 | 34426 | 57521 |
| MBIP | 11332 | 34427 | 57522 |
| MBL2 | 11333 | 34428 | 57523 |
| MBLAC1 | 11334 | 34429 | 57524 |
| MBLAC2 | 11335 | 34430 | 57525 |
| MBNL1 | 11336 | 34431 | 57526 |
| MBNL1 | 11337 | 34432 | 57527 |
| MBNL2 | 11338 | 34433 | 57528 |
| MBNL2 | 11339 | 34434 | 57529 |
| MBNL3 | 11340 | 34435 | 57530 |
| MBOAT1 | 11341 | 34436 | 57531 |
| MBOAT2 | 11342 | 34437 | 57532 |
| MBOAT4 | 11343 | 34438 | 57533 |
| MBOAT7 | 11344 | 34439 | 57534 |
| MBOAT7 | 11345 | 34440 | 57535 |
| MBP | 11346 | 34441 | 57536 |
| MBP | 11347 | 34442 | 57537 |
| MBTD1 | 11348 | 34443 | 57538 |
| MBTPS1 | 11349 | 34444 | 57539 |
| MBTPS2 | 11350 | 34445 | 57540 |
| MC1R | 11351 | 34446 | 57541 |
| MC2R | 11352 | 34447 | 57542 |
| MC3R | 11353 | 34448 | 57543 |
| MC4R | 11354 | 34449 | 57544 |
| MC5R | 11355 | 34450 | 57545 |
| MCAM | 11356 | 34451 | 57546 |
| MCAT | 11357 | 34452 | 57547 |
| MCAT | 11358 | 34453 | 57548 |
| MCC | 11359 | 34454 | 57549 |
| MCCC1 | 11360 | 34455 | 57550 |
| MCCC2 | 11361 | 34456 | 57551 |
| MCCD1 | 11362 | 34457 | 57552 |
| MCEE | 11363 | 34458 | 57553 |
| MCEMP1 | 11364 | 34459 | 57554 |
| MCF2 | 11365 | 34460 | 57555 |
| MCF2L | 11366 | 34461 | 57556 |
| MCF2L | 11367 | 34462 | 57557 |
| MCF2L2 | 11368 | 34463 | 57558 |
| MCFD2 | 11369 | 34464 | 57559 |
| MCFD2 | 11370 | 34465 | 57560 |
| MCHR1 | 11371 | 34466 | 57561 |
| MCHR2 | 11372 | 34467 | 57562 |
| MCIDAS | 11373 | 34468 | 57563 |
| MCL1 | 11374 | 34469 | 57564 |
| MCM10 | 11375 | 34470 | 57565 |
| MCM2 | 11376 | 34471 | 57566 |
| MCM3 | 11377 | 34472 | 57567 |
| MCM3AP | 11378 | 34473 | 57568 |
| MCM4 | 11379 | 34474 | 57569 |
| MCM5 | 11380 | 34475 | 57570 |
| MCM6 | 11381 | 34476 | 57571 |
| MCM7 | 11382 | 34477 | 57572 |
| MCM8 | 11383 | 34478 | 57573 |
| MCM9 | 11384 | 34479 | 57574 |
| MCM9 | 11385 | 34480 | 57575 |
| MCMBP | 11386 | 34481 | 57576 |
| MCMDC2 | 11387 | 34482 | 57577 |
| MCMDC2 | 11388 | 34483 | 57578 |
| MCMDC2 | 11389 | 34484 | 57579 |
| MCOLN1 | 11390 | 34485 | 57580 |
| MCOLN2 | 11391 | 34486 | 57581 |
| MCOLN3 | 11392 | 34487 | 57582 |
| MCPH1 | 11393 | 34488 | 57583 |
| MCPH1 | 11394 | 34489 | 57584 |
| MCPH1 | 11395 | 34490 | 57585 |
| MCRIP1 | 11396 | 34491 | 57586 |
| MCRIP2 | 11397 | 34492 | 57587 |
| MCRS1 | 11398 | 34493 | 57588 |
| MCTP1 | 11399 | 34494 | 57589 |
| MCTP2 | 11400 | 34495 | 57590 |
| MCTP2 | 11401 | 34496 | 57591 |
| MCTS1 | 11402 | 34497 | 57592 |
| MCU | 11403 | 34498 | 57593 |
| MCUB | 11404 | 34499 | 57594 |
| MCUR1 | 11405 | 34500 | 57595 |
| MDC1 | 11406 | 34501 | 57596 |
| MDFI | 11407 | 34502 | 57597 |
| MDFIC | 11408 | 34503 | 57598 |
| MDFIC | 11409 | 34504 | 57599 |
| MDGA1 | 11410 | 34505 | 57600 |
| MDGA2 | 11411 | 34506 | 57601 |
| MDH1 | 11412 | 34507 | 57602 |
| MDH1B | 11413 | 34508 | 57603 |
| MDH2 | 11414 | 34509 | 57604 |
| MDK | 11415 | 34510 | 57605 |
| MDM1 | 11416 | 34511 | 57606 |
| MDM1 | 11417 | 34512 | 57607 |
| MDM1 | 11418 | 34513 | 57608 |
| MDM2 | 11419 | 34514 | 57609 |
| MDM4 | 11420 | 34515 | 57610 |
| MDM4 | 11421 | 34516 | 57611 |
| MDM4 | 11422 | 34517 | 57612 |
| MDN1 | 11423 | 34518 | 57613 |
| MDP1 | 11424 | 34519 | 57614 |
| MDP1 | 11425 | 34520 | 57615 |
| MDP1 | 11426 | 34521 | 57616 |
| MDS2 | 11427 | 34522 | 57617 |
| ME1 | 11428 | 34523 | 57618 |
| ME2 | 11429 | 34524 | 57619 |
| ME2 | 11430 | 34525 | 57620 |
| ME3 | 11431 | 34526 | 57621 |
| MEA1 | 11432 | 34527 | 57622 |
| MEAF6 | 11433 | 34528 | 57623 |
| MEAF6 | 11434 | 34529 | 57624 |
| MEAF6 | 11435 | 34530 | 57625 |
| MECOM | 11436 | 34531 | 57626 |
| MECP2 | 11437 | 34532 | 57627 |
| MECR | 11438 | 34533 | 57628 |
| MED1 | 11439 | 34534 | 57629 |
| MED10 | 11440 | 34535 | 57630 |
| MED11 | 11441 | 34536 | 57631 |
| MED11 | 11442 | 34537 | 57632 |
| MED12 | 11443 | 34538 | 57633 |
| MED12L | 11444 | 34539 | 57634 |
| MED13 | 11445 | 34540 | 57635 |
| MED13L | 11446 | 34541 | 57636 |
| MED14 | 11447 | 34542 | 57637 |
| MED14OS | 11448 | 34543 | 57638 |
| MED15 | 11449 | 34544 | 57639 |
| MED16 | 11450 | 34545 | 57640 |
| MED17 | 11451 | 34546 | 57641 |
| MED18 | 11452 | 34547 | 57642 |
| MED19 | 11453 | 34548 | 57643 |
| MED19 | 11454 | 34549 | 57644 |
| MED20 | 11455 | 34550 | 57645 |
| MED20 | 11456 | 34551 | 57646 |
| MED21 | 11457 | 34552 | 57647 |
| MED22 | 11458 | 34553 | 57648 |
| MED22 | 11459 | 34554 | 57649 |
| MED23 | 11460 | 34555 | 57650 |
| MED23 | 11461 | 34556 | 57651 |
| MED23 | 11462 | 34557 | 57652 |
| MED24 | 11463 | 34558 | 57653 |
| MED25 | 11464 | 34559 | 57654 |
| MED26 | 11465 | 34560 | 57655 |
| MED27 | 11466 | 34561 | 57656 |
| MED27 | 11467 | 34562 | 57657 |
| MED28 | 11468 | 34563 | 57658 |
| MED29 | 11469 | 34564 | 57659 |
| MED29 | 11470 | 34565 | 57660 |
| MED30 | 11471 | 34566 | 57661 |
| MED31 | 11472 | 34567 | 57662 |
| MED4 | 11473 | 34568 | 57663 |
| MED6 | 11474 | 34569 | 57664 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MED6 | 11475 | 34570 | 57665 |
| MED7 | 11476 | 34571 | 57666 |
| MED8 | 11477 | 34572 | 57667 |
| MED8 | 11478 | 34573 | 57668 |
| MED9 | 11479 | 34574 | 57669 |
| MEDAG | 11480 | 34575 | 57670 |
| MEF2A | 11481 | 34576 | 57671 |
| MEF2B | 11482 | 34577 | 57672 |
| MEF2C | 11483 | 34578 | 57673 |
| MEF2D | 11484 | 34579 | 57674 |
| MEFV | 11485 | 34580 | 57675 |
| MEFV | 11486 | 34581 | 57676 |
| MEGF10 | 11487 | 34582 | 57677 |
| MEGF10 | 11488 | 34583 | 57678 |
| MEGF11 | 11489 | 34584 | 57679 |
| MEGF6 | 11490 | 34585 | 57680 |
| MEGF8 | 11491 | 34586 | 57681 |
| MEGF9 | 11492 | 34587 | 57682 |
| MEI1 | 11493 | 34588 | 57683 |
| MEI4 | 11494 | 34589 | 57684 |
| MEIG1 | 11495 | 34590 | 57685 |
| MEIKIN | 11496 | 34591 | 57686 |
| MEIOB | 11497 | 34592 | 57687 |
| MEIOC | 11498 | 34593 | 57688 |
| MEIS1 | 11499 | 34594 | 57689 |
| MEIS2 | 11500 | 34595 | 57690 |
| MEIS2 | 11501 | 34596 | 57691 |
| MEIS3 | 11502 | 34597 | 57692 |
| MELK | 11503 | 34598 | 57693 |
| MELTF | 11504 | 34599 | 57694 |
| MELTF | 11505 | 34600 | 57695 |
| MEMO1 | 11506 | 34601 | 57696 |
| MEN1 | 11507 | 34602 | 57697 |
| MEOX1 | 11508 | 34603 | 57698 |
| MEOX1 | 11509 | 34604 | 57699 |
| MEOX2 | 11510 | 34605 | 57700 |
| MEP1A | 11511 | 34606 | 57701 |
| MEP1B | 11512 | 34607 | 57702 |
| MEPCE | 11513 | 34608 | 57703 |
| MEPE | 11514 | 34609 | 57704 |
| MERTK | 11515 | 34610 | 57705 |
| MESD | 11516 | 34611 | 57706 |
| MESP1 | 11517 | 34612 | 57707 |
| MESP2 | 11518 | 34613 | 57708 |
| MEST | 11519 | 34614 | 57709 |
| MET | 11520 | 34615 | 57710 |
| MET | 11521 | 34616 | 57711 |
| METAP1 | 11522 | 34617 | 57712 |
| METAP1D | 11523 | 34618 | 57713 |
| METAP2 | 11524 | 34619 | 57714 |
| METRN | 11525 | 34620 | 57715 |
| METRNL | 11526 | 34621 | 57716 |
| METTL1 | 11527 | 34622 | 57717 |
| METTL1 | 11528 | 34623 | 57718 |
| METTL11B | 11529 | 34624 | 57719 |
| METTL12 | 11530 | 34625 | 57720 |
| METTL13 | 11531 | 34626 | 57721 |
| METTL14 | 11532 | 34627 | 57722 |
| METTL15 | 11533 | 34628 | 57723 |
| METTL15 | 11534 | 34629 | 57724 |
| METTL15 | 11535 | 34630 | 57725 |
| METTL16 | 11536 | 34631 | 57726 |
| METTL17 | 11537 | 34632 | 57727 |
| METTL17 | 11538 | 34633 | 57728 |
| METTL18 | 11539 | 34634 | 57729 |
| METTL21A | 11540 | 34635 | 57730 |
| METTL21A | 11541 | 34636 | 57731 |
| METTL21A | 11542 | 34637 | 57732 |
| METTL21C | 11543 | 34638 | 57733 |
| METTL22 | 11544 | 34639 | 57734 |
| METTL23 | 11545 | 34640 | 57735 |
| METTL24 | 11546 | 34641 | 57736 |
| METTL25 | 11547 | 34642 | 57737 |
| METTL26 | 11548 | 34643 | 57738 |
| METTL26 | 11549 | 34644 | 57739 |
| METTL27 | 11550 | 34645 | 57740 |
| METTL2A | 11551 | 34646 | 57741 |
| METTL2B | 11552 | 34647 | 57742 |
| METTL3 | 11553 | 34648 | 57743 |
| METTL4 | 11554 | 34649 | 57744 |
| METTL4 | 11555 | 34650 | 57745 |
| METTL5 | 11556 | 34651 | 57746 |
| METTL6 | 11557 | 34652 | 57747 |
| METTL6 | 11558 | 34653 | 57748 |
| METTL6 | 11559 | 34654 | 57749 |
| METTL6 | 11560 | 34655 | 57750 |
| METTL7A | 11561 | 34656 | 57751 |
| METTL7B | 11562 | 34657 | 57752 |
| METTL8 | 11563 | 34658 | 57753 |
| METTL8 | 11564 | 34659 | 57754 |
| METTL9 | 11565 | 34660 | 57755 |
| MEX3A | 11566 | 34661 | 57756 |
| MEX3B | 11567 | 34662 | 57757 |
| MEX3C | 11568 | 34663 | 57758 |
| MEX3D | 11569 | 34664 | 57759 |
| MEX3D | 11570 | 34665 | 57760 |
| MFAP1 | 11571 | 34666 | 57761 |
| MFAP2 | 11572 | 34667 | 57762 |
| MFAP3 | 11573 | 34668 | 57763 |
| MFAP3L | 11574 | 34669 | 57764 |
| MFAP4 | 11575 | 34670 | 57765 |
| MFAP5 | 11576 | 34671 | 57766 |
| MFF | 11577 | 34672 | 57767 |
| MFGE8 | 11578 | 34673 | 57768 |
| MFHAS1 | 11579 | 34674 | 57769 |
| MFN1 | 11580 | 34675 | 57770 |
| MFN2 | 11581 | 34676 | 57771 |
| MFNG | 11582 | 34677 | 57772 |
| MFSD1 | 11583 | 34678 | 57773 |
| MFSD10 | 11584 | 34679 | 57774 |
| MFSD11 | 11585 | 34680 | 57775 |
| MFSD12 | 11586 | 34681 | 57776 |
| MFSD13A | 11587 | 34682 | 57777 |
| MFSD14A | 11588 | 34683 | 57778 |
| MFSD14B | 11589 | 34684 | 57779 |
| MFSD2A | 11590 | 34685 | 57780 |
| MFSD2B | 11591 | 34686 | 57781 |
| MFSD3 | 11592 | 34687 | 57782 |
| MFSD4A | 11593 | 34688 | 57783 |
| MFSD4B | 11594 | 34689 | 57784 |
| MFSD5 | 11595 | 34690 | 57785 |
| MFSD6 | 11596 | 34691 | 57786 |
| MFSD6L | 11597 | 34692 | 57787 |
| MFSD7 | 11598 | 34693 | 57788 |
| MFSD8 | 11599 | 34694 | 57789 |
| MFSD9 | 11600 | 34695 | 57790 |
| MGA | 11601 | 34696 | 57791 |
| MGAM | 11602 | 34697 | 57792 |
| MGAM2 | 11603 | 34698 | 57793 |
| MGARP | 11604 | 34699 | 57794 |
| MGAT1 | 11605 | 34700 | 57795 |
| MGAT2 | 11606 | 34701 | 57796 |
| MGAT3 | 11607 | 34702 | 57797 |
| MGAT4A | 11608 | 34703 | 57798 |
| MGAT4A | 11609 | 34704 | 57799 |
| MGAT4B | 11610 | 34705 | 57800 |
| MGAT4C | 11611 | 34706 | 57801 |
| MGAT4D | 11612 | 34707 | 57802 |
| MGAT5 | 11613 | 34708 | 57803 |
| MGAT5B | 11614 | 34709 | 57804 |
| MGEA5 | 11615 | 34710 | 57805 |
| MGLL | 11616 | 34711 | 57806 |
| MGME1 | 11617 | 34712 | 57807 |
| MGME1 | 11618 | 34713 | 57808 |
| MGMT | 11619 | 34714 | 57809 |
| MGP | 11620 | 34715 | 57810 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MGRN1 | 11621 | 34716 | 57811 |
| MGRN1 | 11622 | 34717 | 57812 |
| MGST1 | 11623 | 34718 | 57813 |
| MGST1 | 11624 | 34719 | 57814 |
| MGST1 | 11625 | 34720 | 57815 |
| MGST2 | 11626 | 34721 | 57816 |
| MGST2 | 11627 | 34722 | 57817 |
| MGST3 | 11628 | 34723 | 57818 |
| MIA | 11629 | 34724 | 57819 |
| MIA2 | 11630 | 34725 | 57820 |
| MIA2 | 11631 | 34726 | 57821 |
| MIA2 | 11632 | 34727 | 57822 |
| MIA3 | 11633 | 34728 | 57823 |
| MIB1 | 11634 | 34729 | 57824 |
| MIB2 | 11635 | 34730 | 57825 |
| MIB2 | 11636 | 34731 | 57826 |
| MICA | 11637 | 34732 | 57827 |
| MICA | 11638 | 34733 | 57828 |
| MICAL1 | 11639 | 34734 | 57829 |
| MICAL2 | 11640 | 34735 | 57830 |
| MICAL2 | 11641 | 34736 | 57831 |
| MICAL2 | 11642 | 34737 | 57832 |
| MICAL3 | 11643 | 34738 | 57833 |
| MICAL3 | 11644 | 34739 | 57834 |
| MICAL3 | 11645 | 34740 | 57835 |
| MICALCL | 11646 | 34741 | 57836 |
| MICALL1 | 11647 | 34742 | 57837 |
| MICALL2 | 11648 | 34743 | 57838 |
| MICB | 11649 | 34744 | 57839 |
| MICU1 | 11650 | 34745 | 57840 |
| MICU2 | 11651 | 34746 | 57841 |
| MICU3 | 11652 | 34747 | 57842 |
| MID1 | 11653 | 34748 | 57843 |
| MID1 | 11654 | 34749 | 57844 |
| MID1 | 11655 | 34750 | 57845 |
| MID1IP1 | 11656 | 34751 | 57846 |
| MID2 | 11657 | 34752 | 57847 |
| MIDN | 11658 | 34753 | 57848 |
| MIEF1 | 11659 | 34754 | 57849 |
| MIEF1 | 11660 | 34755 | 57850 |
| MIEF2 | 11661 | 34756 | 57851 |
| MIEF2 | 11662 | 34757 | 57852 |
| MIEN1 | 11663 | 34758 | 57853 |
| MIEN1 | 11664 | 34759 | 57854 |
| MIER1 | 11665 | 34760 | 57855 |
| MIER1 | 11666 | 34761 | 57856 |
| MIER1 | 11667 | 34762 | 57857 |
| MIER2 | 11668 | 34763 | 57858 |
| MIER3 | 11669 | 34764 | 57859 |
| MIF | 11670 | 34765 | 57860 |
| MIF4GD | 11671 | 34766 | 57861 |
| MIGA1 | 11672 | 34767 | 57862 |
| MIGA2 | 11673 | 34768 | 57863 |
| MIIP | 11674 | 34769 | 57864 |
| MILR1 | 11675 | 34770 | 57865 |
| MINDY1 | 11676 | 34771 | 57866 |
| MINDY2 | 11677 | 34772 | 57867 |
| MINDY3 | 11678 | 34773 | 57868 |
| MINDY4 | 11679 | 34774 | 57869 |
| MINDY4B | 11680 | 34775 | 57870 |
| MINK1 | 11681 | 34776 | 57871 |
| MINOS1 | 11682 | 34777 | 57872 |
| MINOS1 | 11683 | 34778 | 57873 |
| MINOS1 | 11684 | 34779 | 57874 |
| MINPP1 | 11685 | 34780 | 57875 |
| MINPP1 | 11686 | 34781 | 57876 |
| MIOS | 11687 | 34782 | 57877 |
| MIOX | 11688 | 34783 | 57878 |
| MIP | 11689 | 34784 | 57879 |
| MIPEP | 11690 | 34785 | 57880 |
| MIPOL1 | 11691 | 34786 | 57881 |
| MIR1-1HG | 11692 | 34787 | 57882 |
| MIS12 | 11693 | 34788 | 57883 |
| MIS18A | 11694 | 34789 | 57884 |
| MIS18BP1 | 11695 | 34790 | 57885 |
| MISP | 11696 | 34791 | 57886 |
| MISP3 | 11697 | 34792 | 57887 |
| MITD1 | 11698 | 34793 | 57888 |
| MITD1 | 11699 | 34794 | 57889 |
| MITF | 11700 | 34795 | 57890 |
| MITF | 11701 | 34796 | 57891 |
| MIXL1 | 11702 | 34797 | 57892 |
| MKI67 | 11703 | 34798 | 57893 |
| MKKS | 11704 | 34799 | 57894 |
| MKL1 | 11705 | 34800 | 57895 |
| MKL1 | 11706 | 34801 | 57896 |
| MKL2 | 11707 | 34802 | 57897 |
| MKLN1 | 11708 | 34803 | 57898 |
| MKNK1 | 11709 | 34804 | 57899 |
| MKNK1 | 11710 | 34805 | 57900 |
| MKNK2 | 11711 | 34806 | 57901 |
| MKNK2 | 11712 | 34807 | 57902 |
| MKRN1 | 11713 | 34808 | 57903 |
| MKRN1 | 11714 | 34809 | 57904 |
| MKRN2 | 11715 | 34810 | 57905 |
| MKRN2OS | 11716 | 34811 | 57906 |
| MKRN3 | 11717 | 34812 | 57907 |
| MKS1 | 11718 | 34813 | 57908 |
| MKS1 | 11719 | 34814 | 57909 |
| MKS1 | 11720 | 34815 | 57910 |
| MKX | 11721 | 34816 | 57911 |
| MLANA | 11722 | 34817 | 57912 |
| MLC1 | 11723 | 34818 | 57913 |
| MLEC | 11724 | 34819 | 57914 |
| MLF1 | 11725 | 34820 | 57915 |
| MLF2 | 11726 | 34821 | 57916 |
| MLH1 | 11727 | 34822 | 57917 |
| MLH3 | 11728 | 34823 | 57918 |
| MLIP | 11729 | 34824 | 57919 |
| MLIP | 11730 | 34825 | 57920 |
| MLKL | 11731 | 34826 | 57921 |
| MLLT1 | 11732 | 34827 | 57922 |
| MLLT10 | 11733 | 34828 | 57923 |
| MLLT10 | 11734 | 34829 | 57924 |
| MLLT10 | 11735 | 34830 | 57925 |
| MLLT11 | 11736 | 34831 | 57926 |
| MLLT3 | 11737 | 34832 | 57927 |
| MLLT6 | 11738 | 34833 | 57928 |
| MLN | 11739 | 34834 | 57929 |
| MLNR | 11740 | 34835 | 57930 |
| MLPH | 11741 | 34836 | 57931 |
| MLST8 | 11742 | 34837 | 57932 |
| MLX | 11743 | 34838 | 57933 |
| MLXIP | 11744 | 34839 | 57934 |
| MLXIPL | 11745 | 34840 | 57935 |
| MLYCD | 11746 | 34841 | 57936 |
| MMAA | 11747 | 34842 | 57937 |
| MMAB | 11748 | 34843 | 57938 |
| MMACHC | 11749 | 34844 | 57939 |
| MMADHC | 11750 | 34845 | 57940 |
| MMD | 11751 | 34846 | 57941 |
| MMD2 | 11752 | 34847 | 57942 |
| MMD2 | 11753 | 34848 | 57943 |
| MME | 11754 | 34849 | 57944 |
| MMEL1 | 11755 | 34850 | 57945 |
| MMGT1 | 11756 | 34851 | 57946 |
| MMP1 | 11757 | 34852 | 57947 |
| MMP10 | 11758 | 34853 | 57948 |
| MMP11 | 11759 | 34854 | 57949 |
| MMP12 | 11760 | 34855 | 57950 |
| MMP13 | 11761 | 34856 | 57951 |
| MMP14 | 11762 | 34857 | 57952 |
| MMP15 | 11763 | 34858 | 57953 |
| MMP16 | 11764 | 34859 | 57954 |
| MMP17 | 11765 | 34860 | 57955 |
| MMP19 | 11766 | 34861 | 57956 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MMP19 | 11767 | 34862 | 57957 |
| MMP2 | 11768 | 34863 | 57958 |
| MMP20 | 11769 | 34864 | 57959 |
| MMP21 | 11770 | 34865 | 57960 |
| MMP23B | 11771 | 34866 | 57961 |
| MMP24 | 11772 | 34867 | 57962 |
| MMP25 | 11773 | 34868 | 57963 |
| MMP26 | 11774 | 34869 | 57964 |
| MMP27 | 11775 | 34870 | 57965 |
| MMP28 | 11776 | 34871 | 57966 |
| MMP28 | 11777 | 34872 | 57967 |
| MMP28 | 11778 | 34873 | 57968 |
| MMP3 | 11779 | 34874 | 57969 |
| MMP7 | 11780 | 34875 | 57970 |
| MMP8 | 11781 | 34876 | 57971 |
| MMP9 | 11782 | 34877 | 57972 |
| MMRN1 | 11783 | 34878 | 57973 |
| MMRN2 | 11784 | 34879 | 57974 |
| MMS19 | 11785 | 34880 | 57975 |
| MMS22L | 11786 | 34881 | 57976 |
| MN1 | 11787 | 34882 | 57977 |
| MNAT1 | 11788 | 34883 | 57978 |
| MND1 | 11789 | 34884 | 57979 |
| MND1 | 11790 | 34885 | 57980 |
| MNDA | 11791 | 34886 | 57981 |
| MNS1 | 11792 | 34887 | 57982 |
| MNT | 11793 | 34888 | 57983 |
| MNX1 | 11794 | 34889 | 57984 |
| MOAP1 | 11795 | 34890 | 57985 |
| MOB1A | 11796 | 34891 | 57986 |
| MOB1A | 11797 | 34892 | 57987 |
| MOB1B | 11798 | 34893 | 57988 |
| MOB1B | 11799 | 34894 | 57989 |
| MOB2 | 11800 | 34895 | 57990 |
| MOB2 | 11801 | 34896 | 57991 |
| MOB3A | 11802 | 34897 | 57992 |
| MOB3B | 11803 | 34898 | 57993 |
| MOB3C | 11804 | 34899 | 57994 |
| MOB4 | 11805 | 34900 | 57995 |
| MOBP | 11805 | 34901 | 57996 |
| MOBP | 11807 | 34902 | 57997 |
| MOBP | 11808 | 34903 | 57998 |
| MOCOS | 11809 | 34904 | 57999 |
| MOCS1 | 11810 | 34905 | 58000 |
| MOCS2 | 11811 | 34906 | 58001 |
| MOCS3 | 11812 | 34907 | 58002 |
| MOG | 11813 | 34908 | 58003 |
| MOG | 11814 | 34909 | 58004 |
| MOG | 11815 | 34910 | 58005 |
| MOGAT1 | 11816 | 34911 | 58006 |
| MOGAT2 | 11817 | 34912 | 58007 |
| MOGAT3 | 11818 | 34913 | 58008 |
| MOGAT3 | 11819 | 34914 | 58009 |
| MOGS | 11820 | 34915 | 58010 |
| MOK | 11821 | 34916 | 58011 |
| MON1A | 11822 | 34917 | 58012 |
| MON1B | 11823 | 34918 | 58013 |
| MON2 | 11824 | 34919 | 58014 |
| MON2 | 11825 | 34920 | 58015 |
| MORC1 | 11826 | 34921 | 58016 |
| MORC2 | 11827 | 34922 | 58017 |
| MORC3 | 11828 | 34923 | 58018 |
| MORC4 | 11829 | 34924 | 58019 |
| MORC4 | 11830 | 34925 | 58020 |
| MORF4L1 | 11831 | 34926 | 58021 |
| MORF4L2 | 11832 | 34927 | 58022 |
| MORN1 | 11833 | 34928 | 58023 |
| MORN1 | 11834 | 34929 | 58024 |
| MORN2 | 11835 | 34930 | 58025 |
| MORN3 | 11836 | 34931 | 58026 |
| MORN4 | 11837 | 34932 | 58027 |
| MORN5 | 11838 | 34933 | 58028 |
| MORN5 | 11839 | 34934 | 58029 |
| MOS | 11840 | 34935 | 58030 |
| MOSPD1 | 11841 | 34936 | 58031 |
| MOSPD2 | 11842 | 34937 | 58032 |
| MOSPD2 | 11843 | 34938 | 58033 |
| MOSPD3 | 11844 | 34939 | 58034 |
| MOV10 | 11845 | 34940 | 58035 |
| MOV10L1 | 11846 | 34941 | 58036 |
| MOV10L1 | 11847 | 34942 | 58037 |
| MOXD1 | 11848 | 34943 | 58038 |
| MPC1 | 11849 | 34944 | 58039 |
| MPC1L | 11850 | 34945 | 58040 |
| MPC2 | 11851 | 34946 | 58041 |
| MPDU1 | 11852 | 34947 | 58042 |
| MPDU1 | 11853 | 34948 | 58043 |
| MPDZ | 11854 | 34949 | 58044 |
| MPEG1 | 11855 | 34950 | 58045 |
| MPG | 11856 | 34951 | 58046 |
| MPHOSPH10 | 11857 | 34952 | 58047 |
| MPHOSPH6 | 11858 | 34953 | 58048 |
| MPHOSPH8 | 11859 | 34954 | 58049 |
| MPHOSPH9 | 11860 | 34955 | 58050 |
| MPI | 11861 | 34956 | 58051 |
| MPI | 11862 | 34957 | 58052 |
| MPIG6B | 11863 | 34958 | 58053 |
| MPIG6B | 11864 | 34959 | 58054 |
| MPIG6B | 11865 | 34960 | 58055 |
| MPL | 11866 | 34961 | 58056 |
| MPLKIP | 11867 | 34962 | 58057 |
| MPND | 11868 | 34963 | 58058 |
| MPO | 11869 | 34964 | 58059 |
| MPP1 | 11870 | 34965 | 58060 |
| MPP2 | 11871 | 34966 | 58061 |
| MPP3 | 11872 | 34967 | 58062 |
| MPP4 | 11873 | 34968 | 58063 |
| MPP5 | 11874 | 34969 | 58064 |
| MPP6 | 11875 | 34970 | 58065 |
| MPP7 | 11876 | 34971 | 58066 |
| MPPE1 | 11877 | 34972 | 58067 |
| MPPED1 | 11878 | 34973 | 58068 |
| MPPED2 | 11879 | 34974 | 58069 |
| MPPED2 | 11880 | 34975 | 58070 |
| MPRIP | 11881 | 34976 | 58071 |
| MPRIP | 11882 | 34977 | 58072 |
| MPST | 11883 | 34978 | 58073 |
| MPV17 | 11884 | 34979 | 58074 |
| MPV17L | 11885 | 34980 | 58075 |
| MPV17L | 11886 | 34981 | 58076 |
| MPV17L2 | 11887 | 34982 | 58077 |
| MPZ | 11888 | 34983 | 58078 |
| MPZL1 | 11889 | 34984 | 58079 |
| MPZL1 | 11890 | 34985 | 58080 |
| MPZL1 | 11891 | 34986 | 58081 |
| MPZL2 | 11892 | 34987 | 58082 |
| MPZL3 | 11893 | 34988 | 58083 |
| MR1 | 11894 | 34989 | 58084 |
| MRAP | 11895 | 34990 | 58085 |
| MRAP | 11896 | 34991 | 58086 |
| MRAP2 | 11897 | 34992 | 58087 |
| MRAS | 11898 | 34993 | 58088 |
| MRC1 | 11899 | 34994 | 58089 |
| MRC2 | 11900 | 34995 | 58090 |
| MRE11 | 11901 | 34996 | 58091 |
| MREG | 11902 | 34997 | 58092 |
| MRFAP1 | 11903 | 34998 | 58093 |
| MRFAP1 | 11904 | 34999 | 58094 |
| MRFAP1L1 | 11905 | 35000 | 58095 |
| MRGBP | 11906 | 35001 | 58096 |
| MRGPRD | 11907 | 35002 | 58097 |
| MRGPRE | 11908 | 35003 | 58098 |
| MRGPRF | 11909 | 35004 | 58099 |
| MRGPRG | 11910 | 35005 | 58100 |
| MRGPRX2 | 11911 | 35006 | 58101 |
| MRGPRX3 | 11912 | 35007 | 58102 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MRGPRX4 | 11913 | 35008 | 58103 |
| MRI1 | 11914 | 35009 | 58104 |
| MRLN | 11915 | 35010 | 58105 |
| MRLN | 11916 | 35011 | 58106 |
| MRM1 | 11917 | 35012 | 58107 |
| MRM2 | 11918 | 35013 | 58108 |
| MRM3 | 11919 | 35014 | 58109 |
| MRNIP | 11920 | 35015 | 58110 |
| MRO | 11921 | 35016 | 58111 |
| MROH1 | 11922 | 35017 | 58112 |
| MROH1 | 11923 | 35018 | 58113 |
| MROH2A | 11924 | 35019 | 58114 |
| MROH2B | 11925 | 35020 | 58115 |
| MROH5 | 11926 | 35021 | 58116 |
| MROH6 | 11927 | 35022 | 58117 |
| MROH7 | 11928 | 35023 | 58118 |
| MROH8 | 11929 | 35024 | 58119 |
| MROH8 | 11930 | 35025 | 58120 |
| MROH9 | 11931 | 35026 | 58121 |
| MROH9 | 11932 | 35027 | 58122 |
| MRPL1 | 11933 | 35028 | 58123 |
| MRPL10 | 11934 | 35029 | 58124 |
| MRPL11 | 11935 | 35030 | 58125 |
| MRPL11 | 11936 | 35031 | 58126 |
| MRPL12 | 11937 | 35032 | 58127 |
| MRPL13 | 11938 | 35033 | 58128 |
| MRPL14 | 11939 | 35034 | 58129 |
| MRPL15 | 11940 | 35035 | 58130 |
| MRPL16 | 11941 | 35036 | 58131 |
| MRPL17 | 11942 | 35037 | 58132 |
| MRPL18 | 11943 | 35038 | 58133 |
| MRPL19 | 11944 | 35039 | 58134 |
| MRPL2 | 11945 | 35040 | 58135 |
| MRPL2 | 11946 | 35041 | 58136 |
| MRPL20 | 11947 | 35042 | 58137 |
| MRPL20 | 11948 | 35043 | 58138 |
| MRPL21 | 11949 | 35044 | 58139 |
| MRPL22 | 11950 | 35045 | 58140 |
| MRPL23 | 11951 | 35046 | 58141 |
| MRPL24 | 11952 | 35047 | 58142 |
| MRPL27 | 11953 | 35048 | 58143 |
| MRPL28 | 11954 | 35049 | 58144 |
| MRPL3 | 11955 | 35050 | 58145 |
| MRPL30 | 11956 | 35051 | 58146 |
| MRPL32 | 11957 | 35052 | 58147 |
| MRPL33 | 11958 | 35053 | 58148 |
| MRPL33 | 11959 | 35054 | 58149 |
| MRPL34 | 11960 | 35055 | 58150 |
| MRPL35 | 11961 | 35056 | 58151 |
| MRPL35 | 11962 | 35057 | 58152 |
| MRPL36 | 11963 | 35058 | 58153 |
| MRPL37 | 11964 | 35059 | 58154 |
| MRPL37 | 11965 | 35060 | 58155 |
| MRPL38 | 11966 | 35061 | 58156 |
| MRPL39 | 11967 | 35062 | 58157 |
| MRPL39 | 11968 | 35063 | 58158 |
| MRPL4 | 11969 | 35064 | 58159 |
| MRPL4 | 11970 | 35065 | 58160 |
| MRPL40 | 11971 | 35066 | 58161 |
| MRPL41 | 11972 | 35067 | 58162 |
| MRPL42 | 11973 | 35068 | 58163 |
| MRPL43 | 11974 | 35069 | 58164 |
| MRPL43 | 11975 | 35070 | 58165 |
| MRPL43 | 11976 | 35071 | 58166 |
| MRPL43 | 11977 | 35072 | 58167 |
| MRPL43 | 11978 | 35073 | 58168 |
| MRPL44 | 11979 | 35074 | 58169 |
| MRPL45 | 11980 | 35075 | 58170 |
| MRPL46 | 11981 | 35076 | 58171 |
| MRPL47 | 11982 | 35077 | 58172 |
| MRPL48 | 11983 | 35078 | 58173 |
| MRPL49 | 11984 | 35079 | 58174 |
| MRPL50 | 11985 | 35080 | 58175 |
| MRPL51 | 11986 | 35081 | 58176 |
| MRPL52 | 11987 | 35082 | 58177 |
| MRPL52 | 11988 | 35083 | 58178 |
| MRPL53 | 11989 | 35084 | 58179 |
| MRPL54 | 11990 | 35085 | 58180 |
| MRPL55 | 11991 | 35086 | 58181 |
| MRPL57 | 11992 | 35087 | 58182 |
| MRPL58 | 11993 | 35088 | 58183 |
| MRPL58 | 11994 | 35089 | 58184 |
| MRPL9 | 11995 | 35090 | 58185 |
| MRPS10 | 11996 | 35091 | 58186 |
| MRPS11 | 11997 | 35092 | 58187 |
| MRPS11 | 11998 | 35093 | 58188 |
| MRPS11 | 11999 | 35094 | 58189 |
| MRPS12 | 12000 | 35095 | 58190 |
| MRPS14 | 12001 | 35096 | 58191 |
| MRPS15 | 12002 | 35097 | 58192 |
| MRPS16 | 12003 | 35098 | 58193 |
| MRPS17 | 12004 | 35099 | 58194 |
| MRPS18A | 12005 | 35100 | 58195 |
| MRPS18A | 12006 | 35101 | 58196 |
| MRPS18B | 12007 | 35102 | 58197 |
| MRPS18C | 12008 | 35103 | 58198 |
| MRPS18C | 12009 | 35104 | 58199 |
| MRPS18C | 12010 | 35105 | 58200 |
| MRPS2 | 12011 | 35106 | 58201 |
| MRPS21 | 12012 | 35107 | 58202 |
| MRPS22 | 12013 | 35108 | 58203 |
| MRPS23 | 12014 | 35109 | 58204 |
| MRPS25 | 12015 | 35110 | 58205 |
| MRPS26 | 12016 | 35111 | 58206 |
| MRPS27 | 12017 | 35112 | 58207 |
| MRPS28 | 12018 | 35113 | 58208 |
| MRPS30 | 12019 | 35114 | 58209 |
| MRPS31 | 12020 | 35115 | 58210 |
| MRPS33 | 12021 | 35116 | 58211 |
| MRPS34 | 12022 | 35117 | 58212 |
| MRPS35 | 12023 | 35118 | 58213 |
| MRPS35 | 12024 | 35119 | 58214 |
| MRPS36 | 12025 | 35120 | 58215 |
| MRPS5 | 12026 | 35121 | 58216 |
| MRPS6 | 12027 | 35122 | 58217 |
| MRPS7 | 12028 | 35123 | 58218 |
| MRPS9 | 12029 | 35124 | 58219 |
| MRRF | 12030 | 35125 | 58220 |
| MRRF | 12031 | 35126 | 58221 |
| MRRF | 12032 | 35127 | 58222 |
| MRS2 | 12033 | 35128 | 58223 |
| MRS2 | 12034 | 35129 | 58224 |
| MRTO4 | 12035 | 35130 | 58225 |
| MRVI1 | 12036 | 35131 | 58226 |
| MS4A1 | 12037 | 35132 | 58227 |
| MS4A10 | 12038 | 35133 | 58228 |
| MS4A12 | 12039 | 35134 | 58229 |
| MS4A13 | 12040 | 35135 | 58230 |
| MS4A14 | 12041 | 35136 | 58231 |
| MS4A15 | 12042 | 35137 | 58232 |
| MS4A15 | 12043 | 35138 | 58233 |
| MS4A18 | 12044 | 35139 | 58234 |
| MS4A2 | 12045 | 35140 | 58235 |
| MS4A3 | 12046 | 35141 | 58236 |
| MS4A4A | 12047 | 35142 | 58237 |
| MS4A4E | 12048 | 35143 | 58238 |
| MS4A5 | 12049 | 35144 | 58239 |
| MS4A6A | 12050 | 35145 | 58240 |
| MS4A6A | 12051 | 35146 | 58241 |
| MS4A6A | 12052 | 35147 | 58242 |
| MS4A6E | 12053 | 35148 | 58243 |
| MS4A7 | 12054 | 35149 | 58244 |
| MS4A8 | 12055 | 35150 | 58245 |
| MSANTD1 | 12056 | 35151 | 58246 |
| MSANTD2 | 12057 | 35152 | 58247 |
| MSANTD3 | 12058 | 35153 | 58248 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MSANTD3 | 12059 | 35154 | 58249 |
| MSANTD4 | 12060 | 35155 | 58250 |
| MSC | 12061 | 35156 | 58251 |
| MSGN1 | 12062 | 35157 | 58252 |
| MSH2 | 12063 | 35158 | 58253 |
| MSH3 | 12064 | 35159 | 58254 |
| MSH4 | 12065 | 35160 | 58255 |
| MSH5 | 12066 | 35161 | 58256 |
| MSH6 | 12067 | 35162 | 58257 |
| MSI1 | 12068 | 35163 | 58258 |
| MSI2 | 12069 | 35164 | 58259 |
| MSI2 | 12070 | 35165 | 58260 |
| MSL1 | 12071 | 35166 | 58261 |
| MSL2 | 12072 | 35167 | 58262 |
| MSL3 | 12073 | 35168 | 58263 |
| MSL3 | 12074 | 35169 | 58264 |
| MSLN | 12075 | 35170 | 58265 |
| MSMB | 12076 | 35171 | 58266 |
| MSMO1 | 12077 | 35172 | 58267 |
| MSMP | 12078 | 35173 | 58268 |
| MSN | 12079 | 35174 | 58269 |
| MSR1 | 12080 | 35175 | 58270 |
| MSR1 | 12081 | 35176 | 58271 |
| MSRA | 12082 | 35177 | 58272 |
| MSRB1 | 12083 | 35178 | 58273 |
| MSRB2 | 12084 | 35179 | 58274 |
| MSRB3 | 12085 | 35180 | 58275 |
| MSS51 | 12086 | 35181 | 58276 |
| MST1L | 12087 | 35182 | 58277 |
| MST1R | 12088 | 35183 | 58278 |
| MSTN | 12089 | 35184 | 58279 |
| MSTO1 | 12090 | 35185 | 58280 |
| MSTO1 | 12091 | 35186 | 58281 |
| MSX1 | 12092 | 35187 | 58282 |
| MSX2 | 12093 | 35188 | 58283 |
| MT1A | 12094 | 35189 | 58284 |
| MT1B | 12095 | 35190 | 58285 |
| MT1E | 12096 | 35191 | 58286 |
| MT1F | 12097 | 35192 | 58287 |
| MT1F | 12098 | 35193 | 58288 |
| MT1G | 12099 | 35194 | 58289 |
| MT1HL1 | 12100 | 35195 | 58290 |
| MT1M | 12101 | 35196 | 58291 |
| MT1X | 12102 | 35197 | 58292 |
| MT2A | 12103 | 35198 | 58293 |
| MT3 | 12104 | 35199 | 58294 |
| MT4 | 12105 | 35200 | 58295 |
| MTA1 | 12106 | 35201 | 58296 |
| MTA1 | 12107 | 35202 | 58297 |
| MTA2 | 12108 | 35203 | 58298 |
| MTA3 | 12109 | 35204 | 58299 |
| MTA3 | 12110 | 35205 | 58300 |
| MTAP | 12111 | 35206 | 58301 |
| MTBP | 12112 | 35207 | 58302 |
| MTCH1 | 12113 | 35208 | 58303 |
| MTCH2 | 12114 | 35209 | 58304 |
| MTCL1 | 12115 | 35210 | 58305 |
| MTCP1 | 12116 | 35211 | 58306 |
| MTDH | 12117 | 35212 | 58307 |
| MTERF1 | 12118 | 35213 | 58308 |
| MTERF2 | 12119 | 35214 | 58309 |
| MTERF3 | 12120 | 35215 | 58310 |
| MTERF3 | 12121 | 35216 | 58311 |
| MTERF4 | 12122 | 35217 | 58312 |
| MTERF4 | 12123 | 35218 | 58313 |
| MTF1 | 12124 | 35219 | 58314 |
| MTF2 | 12125 | 35220 | 58315 |
| MTFMT | 12126 | 35221 | 58316 |
| MTFP1 | 12127 | 35222 | 58317 |
| MTFP1 | 12128 | 35223 | 58318 |
| MTFR1 | 12129 | 35224 | 58319 |
| MTFR1 | 12130 | 35225 | 58320 |
| MTFR1L | 12131 | 35226 | 58321 |
| MTFR1L | 12132 | 35227 | 58322 |
| MTFR2 | 12133 | 35228 | 58323 |
| MTG1 | 12134 | 35229 | 58324 |
| MTG2 | 12135 | 35230 | 58325 |
| MTHFD1 | 12136 | 35231 | 58326 |
| MTHFD1L | 12137 | 35232 | 58327 |
| MTHFD1L | 12138 | 35233 | 58328 |
| MTHFD2 | 12139 | 35234 | 58329 |
| MTHFD2L | 12140 | 35235 | 58330 |
| MTHFD2L | 12141 | 35236 | 58331 |
| MTHFD2L | 12142 | 35237 | 58332 |
| MTHFD2L | 12143 | 35238 | 58333 |
| MTHFR | 12144 | 35239 | 58334 |
| MTHFSD | 12145 | 35240 | 58335 |
| MTIF2 | 12146 | 35241 | 58336 |
| MTIF3 | 12147 | 35242 | 58337 |
| MTM1 | 12148 | 35243 | 58338 |
| MTMR1 | 12149 | 35244 | 58339 |
| MTMR1 | 12150 | 35245 | 58340 |
| MTMR10 | 12151 | 35246 | 58341 |
| MTMR11 | 12152 | 35247 | 58342 |
| MTMR11 | 12153 | 35248 | 58343 |
| MTMR12 | 12154 | 35249 | 58344 |
| MTMR14 | 12155 | 35250 | 58345 |
| MTMR2 | 12156 | 35251 | 58346 |
| MTMR3 | 12157 | 35252 | 58347 |
| MTMR4 | 12158 | 35253 | 58348 |
| MTMR6 | 12159 | 35254 | 58349 |
| MTMR7 | 12160 | 35255 | 58350 |
| MTMR8 | 12161 | 35256 | 58351 |
| MTMR9 | 12162 | 35257 | 58352 |
| MTNR1A | 12163 | 35258 | 58353 |
| MTNR1B | 12164 | 35259 | 58354 |
| MTO1 | 12165 | 35260 | 58355 |
| MTOR | 12166 | 35261 | 58356 |
| MTPAP | 12167 | 35262 | 58357 |
| MTR | 12168 | 35263 | 58358 |
| MTRF1 | 12169 | 35264 | 58359 |
| MTRF1L | 12170 | 35265 | 58360 |
| MTRF1L | 12171 | 35266 | 58361 |
| MTRF1L | 12172 | 35267 | 58362 |
| MTRNR2L1 | 12173 | 35268 | 58363 |
| MTRNR2L10 | 12174 | 35269 | 58364 |
| MTRNR2L2 | 12175 | 35270 | 58365 |
| MTRNR2L3 | 12176 | 35271 | 58366 |
| MTRNR2L4 | 12177 | 35272 | 58367 |
| MTRNR2L5 | 12178 | 35273 | 58368 |
| MTRNR2L6 | 12179 | 35274 | 58369 |
| MTRNR2L7 | 12180 | 35275 | 58370 |
| MTRNR2L8 | 12181 | 35276 | 58371 |
| MTRNR2L9 | 12182 | 35277 | 58372 |
| MTRR | 12183 | 35278 | 58373 |
| MTSS1 | 12184 | 35279 | 58374 |
| MTSS1L | 12185 | 35280 | 58375 |
| MTTP | 12186 | 35281 | 58376 |
| MTURN | 12187 | 35282 | 58377 |
| MTUS1 | 12188 | 35283 | 58378 |
| MTUS2 | 12189 | 35284 | 58379 |
| MTX1 | 12190 | 35285 | 58380 |
| MTX2 | 12191 | 35286 | 58381 |
| MTX2 | 12192 | 35287 | 58382 |
| MTX3 | 12193 | 35288 | 58383 |
| MTX3 | 12194 | 35289 | 58384 |
| MUC1 | 12195 | 35290 | 58385 |
| MUC1 | 12196 | 35291 | 58386 |
| MUC12 | 12197 | 35292 | 58387 |
| MUC13 | 12198 | 35293 | 58388 |
| MUC15 | 12199 | 35294 | 58389 |
| MUC16 | 12200 | 35295 | 58390 |
| MUC17 | 12201 | 35296 | 58391 |
| MUC19 | 12202 | 35297 | 58392 |
| MUC2 | 12203 | 35298 | 58393 |
| MUC20 | 12204 | 35299 | 58394 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MUC21 | 12205 | 35300 | 58395 |
| MUC22 | 12206 | 35301 | 58396 |
| MUC3A | 12207 | 35302 | 58397 |
| MUC4 | 12208 | 35303 | 58398 |
| MUC5AC | 12209 | 35304 | 58399 |
| MUC5B | 12210 | 35305 | 58400 |
| MUC6 | 12211 | 35306 | 58401 |
| MUC7 | 12212 | 35307 | 58402 |
| MUCL1 | 12213 | 35308 | 58403 |
| MUL1 | 12214 | 35309 | 58404 |
| MUM1 | 12215 | 35310 | 58405 |
| MUM1L1 | 12216 | 35311 | 58406 |
| MUS81 | 12217 | 35312 | 58407 |
| MUSK | 12218 | 35313 | 58408 |
| MUSTN1 | 12219 | 35314 | 58409 |
| MUT | 12220 | 35315 | 58410 |
| MUTYH | 12221 | 35316 | 58411 |
| MVB12A | 12222 | 35317 | 58412 |
| MVB12B | 12223 | 35318 | 58413 |
| MVB12B | 12224 | 35319 | 58414 |
| MVD | 12225 | 35320 | 58415 |
| MVK | 12226 | 35321 | 58416 |
| MVP | 12227 | 35322 | 58417 |
| MX1 | 12228 | 35323 | 58418 |
| MX1 | 12229 | 35324 | 58419 |
| MX2 | 12230 | 35325 | 58420 |
| MXD1 | 12231 | 35326 | 58421 |
| MXD3 | 12232 | 35327 | 58422 |
| MXD3 | 12233 | 35328 | 58423 |
| MXD4 | 12234 | 35329 | 58424 |
| MXI1 | 12235 | 35330 | 58425 |
| MXRA5 | 12236 | 35331 | 58426 |
| MXRA7 | 12237 | 35332 | 58427 |
| MXRA7 | 12238 | 35333 | 58428 |
| MXRA7 | 12239 | 35334 | 58429 |
| MXRA8 | 12240 | 35335 | 58430 |
| MXRA8 | 12241 | 35336 | 58431 |
| MYADM | 12242 | 35337 | 58432 |
| MYADML2 | 12243 | 35338 | 58433 |
| MYB | 12244 | 35339 | 58434 |
| MYBBP1A | 12245 | 35340 | 58435 |
| MYBBP1A | 12246 | 35341 | 58436 |
| MYBL1 | 12247 | 35342 | 58437 |
| MYBL2 | 12248 | 35343 | 58438 |
| MYBPC1 | 12249 | 35344 | 58439 |
| MYBPC1 | 12250 | 35345 | 58440 |
| MYBPC1 | 12251 | 35346 | 58441 |
| MYBPC1 | 12252 | 35347 | 58442 |
| MYBPC2 | 12253 | 35348 | 58443 |
| MYBPC3 | 12254 | 35349 | 58444 |
| MYBPH | 12255 | 35350 | 58445 |
| MYBPHL | 12256 | 35351 | 58446 |
| MYC | 12257 | 35352 | 58447 |
| MYCBP | 12258 | 35353 | 58448 |
| MYCBP2 | 12259 | 35354 | 58449 |
| MYCBPAP | 12260 | 35355 | 58450 |
| MYCL | 12261 | 35356 | 58451 |
| MYCL | 12262 | 35357 | 58452 |
| MYCN | 12263 | 35358 | 58453 |
| MYCNOS | 12264 | 35359 | 58454 |
| MYCT1 | 12265 | 35360 | 58455 |
| MYD88 | 12266 | 35361 | 58456 |
| MYD88 | 12267 | 35362 | 58457 |
| MYDGF | 12268 | 35363 | 58458 |
| MYEF2 | 12269 | 35364 | 58459 |
| MYEOV | 12270 | 35365 | 58460 |
| MYF5 | 12271 | 35366 | 58461 |
| MYF6 | 12272 | 35367 | 58462 |
| MYH1 | 12273 | 35368 | 58463 |
| MYH10 | 12274 | 35369 | 58464 |
| MYH11 | 12275 | 35370 | 58465 |
| MYH11 | 12276 | 35371 | 58466 |
| MYH13 | 12277 | 35372 | 58467 |
| MYH14 | 12278 | 35373 | 58468 |
| MYH15 | 12279 | 35374 | 58469 |
| MYH2 | 12280 | 35375 | 58470 |
| MYH3 | 12281 | 35376 | 58471 |
| MYH4 | 12282 | 35377 | 58472 |
| MYH6 | 12283 | 35378 | 58473 |
| MYH7 | 12284 | 35379 | 58474 |
| MYH7B | 12285 | 35380 | 58475 |
| MYH8 | 12286 | 35381 | 58476 |
| MYH9 | 12287 | 35382 | 58477 |
| MYL1 | 12288 | 35383 | 58478 |
| MYL10 | 12289 | 35384 | 58479 |
| MYL12A | 12290 | 35385 | 58480 |
| MYL2 | 12291 | 35386 | 58481 |
| MYL3 | 12292 | 35387 | 58482 |
| MYL4 | 12293 | 35388 | 58483 |
| MYL5 | 12294 | 35389 | 58484 |
| MYL6 | 12295 | 35390 | 58485 |
| MYL6 | 12296 | 35391 | 58486 |
| MYL6B | 12297 | 35392 | 58487 |
| MYL7 | 12298 | 35393 | 58488 |
| MYL9 | 12299 | 35394 | 58489 |
| MYL9 | 12300 | 35395 | 58490 |
| MYLIP | 12301 | 35396 | 58491 |
| MYLK | 12302 | 35397 | 58492 |
| MYLK2 | 12303 | 35398 | 58493 |
| MYLK3 | 12304 | 35399 | 58494 |
| MYLK4 | 12305 | 35400 | 58495 |
| MYLPF | 12306 | 35401 | 58496 |
| MYMK | 12307 | 35402 | 58497 |
| MYMX | 12308 | 35403 | 58498 |
| MYNN | 12309 | 35404 | 58499 |
| MYO10 | 12310 | 35405 | 58500 |
| MYO15A | 12311 | 35406 | 58501 |
| MYO15B | 12312 | 35407 | 58502 |
| MYO16 | 12313 | 35408 | 58503 |
| MYO18A | 12314 | 35409 | 58504 |
| MYO18B | 12315 | 35410 | 58505 |
| MYO19 | 12316 | 35411 | 58506 |
| MYO19 | 12317 | 35412 | 58507 |
| MYO1A | 12318 | 35413 | 58508 |
| MYO1B | 12319 | 35414 | 58509 |
| MYO1C | 12320 | 35415 | 58510 |
| MYO1D | 12321 | 35416 | 58511 |
| MYO1D | 12322 | 35417 | 58512 |
| MYO1D | 12323 | 35418 | 58513 |
| MYO1E | 12324 | 35419 | 58514 |
| MYO1F | 12325 | 35420 | 58515 |
| MYO1G | 12326 | 35421 | 58516 |
| MYO1H | 12327 | 35422 | 58517 |
| MYO3A | 12328 | 35423 | 58518 |
| MYO3B | 12329 | 35424 | 58519 |
| MYO5A | 12330 | 35425 | 58520 |
| MYO5B | 12331 | 35426 | 58521 |
| MYO5C | 12332 | 35427 | 58522 |
| MYO6 | 12333 | 35428 | 58523 |
| MYO7A | 12334 | 35429 | 58524 |
| MYO7A | 12335 | 35430 | 58525 |
| MYO7B | 12336 | 35431 | 58526 |
| MYO9A | 12337 | 35432 | 58527 |
| MYO9B | 12338 | 35433 | 58528 |
| MYO9B | 12339 | 35434 | 58529 |
| MYOC | 12340 | 35435 | 58530 |
| MYOCD | 12341 | 35436 | 58531 |
| MYOD1 | 12342 | 35437 | 58532 |
| MYOF | 12343 | 35438 | 58533 |
| MYOG | 12344 | 35439 | 58534 |
| MYOM1 | 12345 | 35440 | 58535 |
| MYOM2 | 12346 | 35441 | 58536 |
| MYOM3 | 12347 | 35442 | 58537 |
| MYORG | 12348 | 35443 | 58538 |
| MYOT | 12349 | 35444 | 58539 |
| MYOZ1 | 12350 | 35445 | 58540 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| MYOZ2 | 12351 | 35446 | 58541 |
| MYOZ3 | 12352 | 35447 | 58542 |
| MYPN | 12353 | 35448 | 58543 |
| MYPOP | 12354 | 35449 | 58544 |
| MYRF | 12355 | 35450 | 58545 |
| MYRFL | 12356 | 35451 | 58546 |
| MYRIP | 12357 | 35452 | 58547 |
| MYSM1 | 12358 | 35453 | 58548 |
| MYT1 | 12359 | 35454 | 58549 |
| MYT1L | 12360 | 35455 | 58550 |
| MYT1L | 12361 | 35456 | 58551 |
| MYT1L | 12362 | 35457 | 58552 |
| MYZAP | 12363 | 35458 | 58553 |
| MZB1 | 12364 | 35459 | 58554 |
| MZF1 | 12365 | 35460 | 58555 |
| MZF1 | 12366 | 35461 | 58556 |
| MZT1 | 12367 | 35462 | 58557 |
| MZT2A | 12368 | 35463 | 58558 |
| MZT2B | 12369 | 35464 | 58559 |
| MZT2B | 12370 | 35465 | 58560 |
| N4BP1 | 12371 | 35466 | 58561 |
| N4BP2 | 12372 | 35467 | 58562 |
| N4BP2L1 | 12373 | 35468 | 58563 |
| N4BP2L1 | 12374 | 35469 | 58564 |
| N4BP2L1 | 12375 | 35470 | 58565 |
| N4BP2L1 | 12376 | 35471 | 58566 |
| N4BP2L1 | 12377 | 35472 | 58567 |
| N4BP2L2 | 12378 | 35473 | 58568 |
| N4BP2L2 | 12379 | 35474 | 58569 |
| N4BP3 | 12380 | 35475 | 58570 |
| N6AMT1 | 12381 | 35476 | 58571 |
| NAA10 | 12382 | 35477 | 58572 |
| NAA11 | 12383 | 35478 | 58573 |
| NAA15 | 12384 | 35479 | 58574 |
| NAA16 | 12385 | 35480 | 58575 |
| NAA16 | 12386 | 35481 | 58576 |
| NAA16 | 12387 | 35482 | 58577 |
| NAA20 | 12388 | 35483 | 58578 |
| NAA20 | 12389 | 35484 | 58579 |
| NAA25 | 12390 | 35485 | 58580 |
| NAA30 | 12391 | 35486 | 58581 |
| NAA35 | 12392 | 35487 | 58582 |
| NAA38 | 12393 | 35488 | 58583 |
| NAA40 | 12394 | 35489 | 58584 |
| NAA50 | 12395 | 35490 | 58585 |
| NAA60 | 12396 | 35491 | 58586 |
| NAA60 | 12397 | 35492 | 58587 |
| NAA60 | 12398 | 35493 | 58588 |
| NAAA | 12399 | 35494 | 58589 |
| NAAA | 12400 | 35495 | 58590 |
| NAALAD2 | 12401 | 35496 | 58591 |
| NAALADL1 | 12402 | 35497 | 58592 |
| NAALADL2 | 12403 | 35498 | 58593 |
| NAB1 | 12404 | 35499 | 58594 |
| NAB2 | 12405 | 35500 | 58595 |
| NABP1 | 12406 | 35501 | 58596 |
| NABP2 | 12407 | 35502 | 58597 |
| NACA | 12408 | 35503 | 58598 |
| NACA | 12409 | 35504 | 58599 |
| NACA2 | 12410 | 35505 | 58600 |
| NACAD | 12411 | 35506 | 58601 |
| NACC1 | 12412 | 35507 | 58602 |
| NACC2 | 12413 | 35508 | 58603 |
| NADK | 12414 | 35509 | 58604 |
| NADK2 | 12415 | 35510 | 58605 |
| NADSYN1 | 12416 | 35511 | 58606 |
| NAE1 | 12417 | 35512 | 58607 |
| NAF1 | 12418 | 35513 | 58608 |
| NAF1 | 12419 | 35514 | 58609 |
| NAGA | 12420 | 35515 | 58610 |
| NAGK | 12421 | 35516 | 58611 |
| NAGLU | 12422 | 35517 | 58612 |
| NAGPA | 12423 | 35518 | 58613 |
| NAGS | 12424 | 35519 | 58614 |
| NAIF1 | 12425 | 35520 | 58615 |
| NAIP | 12426 | 35521 | 58616 |
| NALCN | 12427 | 35522 | 58617 |
| NAMPT | 12428 | 35523 | 58618 |
| NANOG | 12429 | 35524 | 58619 |
| NANOGNB | 12430 | 35525 | 58620 |
| NANOS1 | 12431 | 35526 | 58621 |
| NANOS2 | 12432 | 35527 | 58622 |
| NANOS3 | 12433 | 35528 | 58623 |
| NANP | 12434 | 35529 | 58624 |
| NANS | 12435 | 35530 | 58625 |
| NAP1L1 | 12436 | 35531 | 58626 |
| NAP1L1 | 12437 | 35532 | 58627 |
| NAP1L2 | 12438 | 35533 | 58628 |
| NAP1L3 | 12439 | 35534 | 58629 |
| NAP1L4 | 12440 | 35535 | 58630 |
| NAP1L5 | 12441 | 35536 | 58631 |
| NAPA | 12442 | 35537 | 58632 |
| NAPB | 12443 | 35538 | 58633 |
| NAPEPLD | 12444 | 35539 | 58634 |
| NAPG | 12445 | 35540 | 58635 |
| NAPRT | 12446 | 35541 | 58636 |
| NAPSA | 12447 | 35542 | 58637 |
| NARF | 12448 | 35543 | 58638 |
| NARFL | 12449 | 35544 | 58639 |
| NARS | 12450 | 35545 | 58640 |
| NARS2 | 12451 | 35546 | 58641 |
| NASP | 12452 | 35547 | 58642 |
| NAT1 | 12453 | 35548 | 58643 |
| NAT10 | 12454 | 35549 | 58644 |
| NAT14 | 12455 | 35550 | 58645 |
| NAT16 | 12456 | 35551 | 58646 |
| NAT2 | 12457 | 35552 | 58647 |
| NAT6 | 12458 | 35553 | 58648 |
| NAT8 | 12459 | 35554 | 58649 |
| NAT8B | 12460 | 35555 | 58650 |
| NAT8L | 12461 | 35556 | 58651 |
| NAT9 | 12462 | 35557 | 58652 |
| NAT9 | 12463 | 35558 | 58653 |
| NATD1 | 12464 | 35559 | 58654 |
| NAV1 | 12465 | 35560 | 58655 |
| NAV2 | 12466 | 35561 | 58656 |
| NAV3 | 12467 | 35562 | 58657 |
| NAXD | 12468 | 35563 | 58658 |
| NAXE | 12469 | 35564 | 58659 |
| NBAS | 12470 | 35565 | 58660 |
| NBDY | 12471 | 35566 | 58661 |
| NBEA | 12472 | 35567 | 58662 |
| NBEAL1 | 12473 | 35568 | 58663 |
| NBEAL2 | 12474 | 35569 | 58664 |
| NBL1 | 12475 | 35570 | 58665 |
| NBN | 12476 | 35571 | 58666 |
| NBPF1 | 12477 | 35572 | 58667 |
| NBPF10 | 12478 | 35573 | 58668 |
| NBPF11 | 12479 | 35574 | 58669 |
| NBPF14 | 12480 | 35575 | 58670 |
| NBPF15 | 12481 | 35576 | 58671 |
| NBPF19 | 12482 | 35577 | 58672 |
| NBPF20 | 12483 | 35578 | 58673 |
| NBPF3 | 12484 | 35579 | 58674 |
| NBPF4 | 12485 | 35580 | 58675 |
| NBPF6 | 12486 | 35581 | 58676 |
| NBPF7 | 12487 | 35582 | 58677 |
| NBPF9 | 12488 | 35583 | 58678 |
| NBR1 | 12489 | 35584 | 58679 |
| NBR1 | 12490 | 35585 | 58680 |
| NBR1 | 12491 | 35586 | 58681 |
| NCALD | 12492 | 35587 | 58682 |
| NCAM1 | 12493 | 35588 | 58683 |
| NCAM1 | 12494 | 35589 | 58684 |
| NCAM2 | 12495 | 35590 | 58685 |
| NCAM2 | 12496 | 35591 | 58686 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| NCAM2 | 12497 | 35592 | 58687 |
| NCAM2 | 12498 | 35593 | 58688 |
| NCAM2 | 12499 | 35594 | 58689 |
| NCAN | 12500 | 35595 | 58690 |
| NCAPD2 | 12501 | 35596 | 58691 |
| NCAPD3 | 12502 | 35597 | 58692 |
| NCAPG | 12503 | 35598 | 58693 |
| NCAPG2 | 12504 | 35599 | 58694 |
| NCAPG2 | 12505 | 35600 | 58695 |
| NCAPH | 12506 | 35601 | 58696 |
| NCAPH2 | 12507 | 35602 | 58697 |
| NCAPH2 | 12508 | 35603 | 58698 |
| NCBP1 | 12509 | 35604 | 58699 |
| NCBP2 | 12510 | 35605 | 58700 |
| NCBP2L | 12511 | 35606 | 58701 |
| NCBP3 | 12512 | 35607 | 58702 |
| NCCRP1 | 12513 | 35608 | 58703 |
| NCDN | 12514 | 35609 | 58704 |
| NCEH1 | 12515 | 35610 | 58705 |
| NCF1 | 12516 | 35611 | 58706 |
| NCF2 | 12517 | 35612 | 58707 |
| NCF4 | 12518 | 35613 | 58708 |
| NCF4 | 12519 | 35614 | 58709 |
| NCK1 | 12520 | 35615 | 58710 |
| NCK2 | 12521 | 35616 | 58711 |
| NCK2 | 12522 | 35617 | 58712 |
| NCKAP1 | 12523 | 35618 | 58713 |
| NCKAP1L | 12524 | 35619 | 58714 |
| NCKAP5 | 12525 | 35620 | 58715 |
| NCKAP5L | 12526 | 35621 | 58716 |
| NCKIPSD | 12527 | 35622 | 58717 |
| NCL | 12528 | 35623 | 58718 |
| NCLN | 12529 | 35624 | 58719 |
| NCMAP | 12530 | 35625 | 58720 |
| NCOA1 | 12531 | 35626 | 58721 |
| NCOA1 | 12532 | 35627 | 58722 |
| NCOA2 | 12533 | 35628 | 58723 |
| NCOA3 | 12534 | 35629 | 58724 |
| NCOA4 | 12535 | 35630 | 58725 |
| NCOA4 | 12536 | 35631 | 58726 |
| NCOA5 | 12537 | 35632 | 58727 |
| NCOA5 | 12538 | 35633 | 58728 |
| NCOA6 | 12539 | 35634 | 58729 |
| NCOA7 | 12540 | 35635 | 58730 |
| NCOR1 | 12541 | 35636 | 58731 |
| NCOR1 | 12542 | 35637 | 58732 |
| NCOR2 | 12543 | 35638 | 58733 |
| NCR1 | 12544 | 35639 | 58734 |
| NCR2 | 12545 | 35640 | 58735 |
| NCR2 | 12546 | 35641 | 58736 |
| NCR3 | 12547 | 35642 | 58737 |
| NCR3 | 12548 | 35643 | 58738 |
| NCR3 | 12549 | 35644 | 58739 |
| NCR3LG1 | 12550 | 35645 | 58740 |
| NCS1 | 12551 | 35646 | 58741 |
| NCSTN | 12552 | 35647 | 58742 |
| NDC1 | 12553 | 35648 | 58743 |
| NDC80 | 12554 | 35649 | 58744 |
| NDE1 | 12555 | 35650 | 58745 |
| NDEL1 | 12556 | 35651 | 58746 |
| NDEL1 | 12557 | 35652 | 58747 |
| NDEL1 | 12558 | 35653 | 58748 |
| NDFIP1 | 12559 | 35654 | 58749 |
| NDFIP2 | 12560 | 35655 | 58750 |
| NDN | 12561 | 35656 | 58751 |
| NDNF | 12562 | 35657 | 58752 |
| NDOR1 | 12563 | 35658 | 58753 |
| NDOR1 | 12564 | 35659 | 58754 |
| NDP | 12565 | 35660 | 58755 |
| NDRG1 | 12566 | 35661 | 58756 |
| NDRG2 | 12567 | 35662 | 58757 |
| NDRG3 | 12568 | 35663 | 58758 |
| NDRG4 | 12569 | 35664 | 58759 |
| NDST1 | 12570 | 35665 | 58760 |
| NDST2 | 12571 | 35666 | 58761 |
| NDST2 | 12572 | 35667 | 58762 |
| NDST3 | 12573 | 35668 | 58763 |
| NDST4 | 12574 | 35669 | 58764 |
| NDUFA1 | 12575 | 35670 | 58765 |
| NDUFA10 | 12576 | 35671 | 58766 |
| NDUFA10 | 12577 | 35672 | 58767 |
| NDUFA10 | 12578 | 35673 | 58768 |
| NDUFA11 | 12579 | 35674 | 58769 |
| NDUFA11 | 12580 | 35675 | 58770 |
| NDUFA12 | 12581 | 35676 | 58771 |
| NDUFA12 | 12582 | 35677 | 58772 |
| NDUFA13 | 12583 | 35678 | 58773 |
| NDUFA2 | 12584 | 35679 | 58774 |
| NDUFA2 | 12585 | 35680 | 58775 |
| NDUFA3 | 12586 | 35681 | 58776 |
| NDUFA4 | 12587 | 35682 | 58777 |
| NDUFA4L2 | 12588 | 35683 | 58778 |
| NDUFA5 | 12589 | 35684 | 58779 |
| NDUFA6 | 12590 | 35685 | 58780 |
| NDUFA7 | 12591 | 35686 | 58781 |
| NDUFA8 | 12592 | 35687 | 58782 |
| NDUFA8 | 12593 | 35688 | 58783 |
| NDUFA9 | 12594 | 35689 | 58784 |
| NDUFAB1 | 12595 | 35690 | 58785 |
| NDUFAF1 | 12596 | 35691 | 58786 |
| NDUFAF2 | 12597 | 35692 | 58787 |
| NDUFAF3 | 12598 | 35693 | 58788 |
| NDUFAF4 | 12599 | 35694 | 58789 |
| NDUFAF5 | 12600 | 35695 | 58790 |
| NDUFAF5 | 12601 | 35696 | 58791 |
| NDUFAF6 | 12602 | 35697 | 58792 |
| NDUFAF7 | 12603 | 35698 | 58793 |
| NDUFAF8 | 12604 | 35699 | 58794 |
| NDUFAF8 | 12605 | 35700 | 58795 |
| NDUFAF8 | 12606 | 35701 | 58796 |
| NDUFB1 | 12607 | 35702 | 58797 |
| NDUFB10 | 12608 | 35703 | 58798 |
| NDUFB11 | 12609 | 35704 | 58799 |
| NDUFB2 | 12610 | 35705 | 58800 |
| NDUFB3 | 12611 | 35706 | 58801 |
| NDUFB4 | 12612 | 35707 | 58802 |
| NDUFB4 | 12613 | 35708 | 58803 |
| NDUFB5 | 12614 | 35709 | 58804 |
| NDUFB5 | 12615 | 35710 | 58805 |
| NDUFB6 | 12616 | 35711 | 58806 |
| NDUFB7 | 12617 | 35712 | 58807 |
| NDUFB8 | 12618 | 35713 | 58808 |
| NDUFB8 | 12619 | 35714 | 58809 |
| NDUFB9 | 12620 | 35715 | 58810 |
| NDUFC1 | 12621 | 35716 | 58811 |
| NDUFC1 | 12622 | 35717 | 58812 |
| NDUFC2 | 12623 | 35718 | 58813 |
| NDUFC2 | 12624 | 35719 | 58814 |
| NDUFC2-KCTD14 | 12625 | 35720 | 58815 |
| NDUFS1 | 12626 | 35721 | 58816 |
| NDUFS2 | 12627 | 35722 | 58817 |
| NDUFS2 | 12628 | 35723 | 58818 |
| NDUFS3 | 12629 | 35724 | 58819 |
| NDUFS4 | 12630 | 35725 | 58820 |
| NDUFS4 | 12631 | 35726 | 58821 |
| NDUFS5 | 12632 | 35727 | 58822 |
| NDUFS6 | 12633 | 35728 | 58823 |
| NDUFS7 | 12634 | 35729 | 58824 |
| NDUFS8 | 12635 | 35730 | 58825 |
| NDUFV1 | 12636 | 35731 | 58826 |
| NDUFV2 | 12637 | 35732 | 58827 |
| NDUFV3 | 12638 | 35733 | 58828 |
| NEB | 12639 | 35734 | 58829 |
| NEBL | 12640 | 35735 | 58830 |
| NEBL | 12641 | 35736 | 58831 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| NECAB1 | 12642 | 35737 | 58832 |
| NECAB2 | 12643 | 35738 | 58833 |
| NECAB3 | 12644 | 35739 | 58834 |
| NECAP1 | 12645 | 35740 | 58835 |
| NECAP2 | 12646 | 35741 | 58836 |
| NECAP2 | 12647 | 35742 | 58837 |
| NECTIN1 | 12648 | 35743 | 58838 |
| NECTIN1 | 12649 | 35744 | 58839 |
| NECTIN1 | 12650 | 35745 | 58840 |
| NECTIN2 | 12651 | 35746 | 58841 |
| NECTIN2 | 12652 | 35747 | 58842 |
| NECTIN3 | 12653 | 35748 | 58843 |
| NECTIN3 | 12654 | 35749 | 58844 |
| NECTIN3 | 12655 | 35750 | 58845 |
| NECTIN4 | 12656 | 35751 | 58846 |
| NEDD1 | 12657 | 35752 | 58847 |
| NEDD4 | 12658 | 35753 | 58848 |
| NEDD4L | 12659 | 35754 | 58849 |
| NEDD8 | 12660 | 35755 | 58850 |
| NEDD9 | 12661 | 35756 | 58851 |
| NEDD9 | 12662 | 35757 | 58852 |
| NEFH | 12663 | 35758 | 58853 |
| NEFL | 12664 | 35759 | 58854 |
| NEFM | 12665 | 35760 | 58855 |
| NEGR1 | 12666 | 35761 | 58856 |
| NEIL1 | 12667 | 35762 | 58857 |
| NEIL1 | 12668 | 35763 | 58858 |
| NEIL2 | 12669 | 35764 | 58859 |
| NEIL3 | 12670 | 35765 | 58860 |
| NEK1 | 12671 | 35766 | 58861 |
| NEK10 | 12672 | 35767 | 58862 |
| NEK10 | 12673 | 35768 | 58863 |
| NEK11 | 12674 | 35769 | 58864 |
| NEK11 | 12675 | 35770 | 58865 |
| NEK11 | 12676 | 35771 | 58866 |
| NEK11 | 12677 | 35772 | 58867 |
| NEK2 | 12678 | 35773 | 58868 |
| NEK2 | 12679 | 35774 | 58869 |
| NEK2 | 12680 | 35775 | 58870 |
| NEK3 | 12681 | 35776 | 58871 |
| NEK4 | 12682 | 35777 | 58872 |
| NEK4 | 12683 | 35778 | 58873 |
| NEK5 | 12684 | 35779 | 58874 |
| NEK6 | 12685 | 35780 | 58875 |
| NEK7 | 12686 | 35781 | 58876 |
| NEK8 | 12687 | 35782 | 58877 |
| NEK9 | 12688 | 35783 | 58878 |
| NELFA | 12689 | 35784 | 58879 |
| NELFB | 12690 | 35785 | 58880 |
| NELFCD | 12691 | 35786 | 58881 |
| NELFE | 12692 | 35787 | 58882 |
| NELL1 | 12693 | 35788 | 58883 |
| NELL2 | 12694 | 35789 | 58884 |
| NEMF | 12695 | 35790 | 58885 |
| NEMP1 | 12696 | 35791 | 58886 |
| NEMP2 | 12697 | 35792 | 58887 |
| NENF | 12698 | 35793 | 58888 |
| NEO1 | 12699 | 35794 | 58889 |
| NEPRO | 12700 | 35795 | 58890 |
| NES | 12701 | 35796 | 58891 |
| NET1 | 12702 | 35797 | 58892 |
| NETO1 | 12703 | 35798 | 58893 |
| NETO1 | 12704 | 35799 | 58894 |
| NETO2 | 12705 | 35800 | 58895 |
| NEU1 | 12706 | 35801 | 58896 |
| NEU2 | 12707 | 35802 | 58897 |
| NEU3 | 12708 | 35803 | 58898 |
| NEU4 | 12709 | 35804 | 58899 |
| NEURL1 | 12710 | 35805 | 58900 |
| NEURL1B | 12711 | 35806 | 58901 |
| NEURL2 | 12712 | 35807 | 58902 |
| NEURL2 | 12713 | 35808 | 58903 |
| NEURL3 | 12714 | 35809 | 58904 |
| NEURL3 | 12715 | 35810 | 58905 |
| NEURL4 | 12716 | 35811 | 58906 |
| NEUROD1 | 12717 | 35812 | 58907 |
| NEUROD2 | 12718 | 35813 | 58908 |
| NEUROD4 | 12719 | 35814 | 58909 |
| NEUROD6 | 12720 | 35815 | 58910 |
| NEUROG1 | 12721 | 35816 | 58911 |
| NEUROG2 | 12722 | 35817 | 58912 |
| NEUROG3 | 12723 | 35818 | 58913 |
| NEXMIF | 12724 | 35819 | 58914 |
| NEXN | 12725 | 35820 | 58915 |
| NF1 | 12726 | 35821 | 58916 |
| NF1 | 12727 | 35822 | 58917 |
| NF2 | 12728 | 35823 | 58918 |
| NF2 | 12729 | 35824 | 58919 |
| NFAM1 | 12730 | 35825 | 58920 |
| NFASC | 12731 | 35826 | 58921 |
| NFASC | 12732 | 35827 | 58922 |
| NFAT5 | 12733 | 35828 | 58923 |
| NFATC1 | 12734 | 35829 | 58924 |
| NFATC1 | 12735 | 35830 | 58925 |
| NFATC1 | 12736 | 35831 | 58926 |
| NFATC2 | 12737 | 35832 | 58927 |
| NFATC2 | 12738 | 35833 | 58928 |
| NFATC2IP | 12739 | 35834 | 58929 |
| NFATC3 | 12740 | 35835 | 58930 |
| NFATC3 | 12741 | 35836 | 58931 |
| NFATC3 | 12742 | 35837 | 58932 |
| NFATC4 | 12743 | 35838 | 58933 |
| NFATC4 | 12744 | 35839 | 58934 |
| NFE2 | 12745 | 35840 | 58935 |
| NFE2L1 | 12746 | 35841 | 58936 |
| NFE2L2 | 12747 | 35842 | 58937 |
| NFE2L3 | 12748 | 35843 | 58938 |
| NFE4 | 12749 | 35844 | 58939 |
| NFIA | 12750 | 35845 | 58940 |
| NFIA | 12751 | 35846 | 58941 |
| NFIB | 12752 | 35847 | 58942 |
| NFIB | 12753 | 35848 | 58943 |
| NFIC | 12754 | 35849 | 58944 |
| NFIC | 12755 | 35850 | 58945 |
| NFIL3 | 12756 | 35851 | 58946 |
| NFIX | 12757 | 35852 | 58947 |
| NFIX | 12758 | 35853 | 58948 |
| NFKB1 | 12759 | 35854 | 58949 |
| NFKB2 | 12760 | 35855 | 58950 |
| NFKBIA | 12761 | 35856 | 58951 |
| NFKBIB | 12762 | 35857 | 58952 |
| NFKBID | 12763 | 35858 | 58953 |
| NFKBIE | 12764 | 35859 | 58954 |
| NFKBIL1 | 12765 | 35860 | 58955 |
| NFKBIZ | 12766 | 35861 | 58956 |
| NFRKB | 12767 | 35862 | 58957 |
| NFS1 | 12768 | 35863 | 58958 |
| NFU1 | 12769 | 35864 | 58959 |
| NFX1 | 12770 | 35865 | 58960 |
| NFX1 | 12771 | 35866 | 58961 |
| NFXL1 | 12772 | 35867 | 58962 |
| NFYA | 12773 | 35868 | 58963 |
| NFYB | 12774 | 35869 | 58964 |
| NFYC | 12775 | 35870 | 58965 |
| NGB | 12776 | 35871 | 58966 |
| NGDN | 12777 | 35872 | 58967 |
| NGEF | 12778 | 35873 | 58968 |
| NGF | 12779 | 35874 | 58969 |
| NGFR | 12780 | 35875 | 58970 |
| NGLY1 | 12781 | 35876 | 58971 |
| NGLY1 | 12782 | 35877 | 58972 |
| NGRN | 12783 | 35878 | 58973 |
| NHEJ1 | 12784 | 35879 | 58974 |
| NHLH1 | 12785 | 35880 | 58975 |
| NHLH2 | 12786 | 35881 | 58976 |
| NHLRC1 | 12787 | 35882 | 58977 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| NHLRC2 | 12788 | 35883 | 58978 |
| NHLRC3 | 12789 | 35884 | 58979 |
| NHLRC4 | 12790 | 35885 | 58980 |
| NHP2 | 12791 | 35886 | 58981 |
| NHP2 | 12792 | 35887 | 58982 |
| NHS | 12793 | 35888 | 58983 |
| NHSL1 | 12794 | 35889 | 58984 |
| NHSL2 | 12795 | 35890 | 58985 |
| NICN1 | 12796 | 35891 | 58986 |
| NID1 | 12797 | 35892 | 58987 |
| NID2 | 12798 | 35893 | 58988 |
| NIF3L1 | 12799 | 35894 | 58989 |
| NIF3L1 | 12800 | 35895 | 58990 |
| NIFK | 12801 | 35896 | 58991 |
| NIM1K | 12802 | 35897 | 58992 |
| NIN | 12803 | 35898 | 58993 |
| NIN | 12804 | 35899 | 58994 |
| NIN | 12805 | 35900 | 58995 |
| NINJ1 | 12806 | 35901 | 58996 |
| NINJ2 | 12807 | 35902 | 58997 |
| NINL | 12808 | 35903 | 58998 |
| NIP7 | 12809 | 35904 | 58999 |
| NIPA1 | 12810 | 35905 | 59000 |
| NIPA2 | 12811 | 35906 | 59001 |
| NIPAL1 | 12812 | 35907 | 59002 |
| NIPAL2 | 12813 | 35908 | 59003 |
| NIPAL2 | 12814 | 35909 | 59004 |
| NIPAL3 | 12815 | 35910 | 59005 |
| NIPAL3 | 12816 | 35911 | 59006 |
| NIPAL3 | 12817 | 35912 | 59007 |
| NIPAL4 | 12818 | 35913 | 59008 |
| NIPBL | 12819 | 35914 | 59009 |
| NIPBL | 12820 | 35915 | 59010 |
| NIPSNAP1 | 12821 | 35916 | 59011 |
| NIPSNAP2 | 12822 | 35917 | 59012 |
| NIPSNAP3A | 12823 | 35918 | 59013 |
| NIPSNAP3B | 12824 | 35919 | 59014 |
| NISCH | 12825 | 35920 | 59015 |
| NISCH | 12826 | 35921 | 59016 |
| NISCH | 12827 | 35922 | 59017 |
| NIT1 | 12828 | 35923 | 59018 |
| NIT1 | 12829 | 35924 | 59019 |
| NIT2 | 12830 | 35925 | 59020 |
| NKAIN1 | 12831 | 35926 | 59021 |
| NKAIN2 | 12832 | 35927 | 59022 |
| NKAIN3 | 12833 | 35928 | 59023 |
| NKAIN4 | 12834 | 35929 | 59024 |
| NKAP | 12835 | 35930 | 59025 |
| NKAPL | 12836 | 35931 | 59026 |
| NKD1 | 12837 | 35932 | 59027 |
| NKD2 | 12838 | 35933 | 59028 |
| NKD2 | 12839 | 35934 | 59029 |
| NKG7 | 12840 | 35935 | 59030 |
| NKIRAS1 | 12841 | 35936 | 59031 |
| NKIRAS2 | 12842 | 35937 | 59032 |
| NKIRAS2 | 12843 | 35938 | 59033 |
| NKPD1 | 12844 | 35939 | 59034 |
| NKRF | 12845 | 35940 | 59035 |
| NKTR | 12846 | 35941 | 59036 |
| NKX1-1 | 12847 | 35942 | 59037 |
| NKX1-2 | 12848 | 35943 | 59038 |
| NKX2-1 | 12849 | 35944 | 59039 |
| NKX2-2 | 12850 | 35945 | 59040 |
| NKX2-3 | 12851 | 35946 | 59041 |
| NKX2-4 | 12852 | 35947 | 59042 |
| NKX2-5 | 12853 | 35948 | 59043 |
| NKX2-5 | 12854 | 35949 | 59044 |
| NKX2-5 | 12855 | 35950 | 59045 |
| NKX2-6 | 12856 | 35951 | 59046 |
| NKX2-8 | 12857 | 35952 | 59047 |
| NKX3-1 | 12858 | 35953 | 59048 |
| NKX3-2 | 12859 | 35954 | 59049 |
| NKX6-1 | 12860 | 35955 | 59050 |
| NKX6-2 | 12861 | 35956 | 59051 |
| NKX6-3 | 12862 | 35957 | 59052 |
| NLE1 | 12863 | 35958 | 59053 |
| NLGN1 | 12864 | 35959 | 59054 |
| NLGN2 | 12865 | 35960 | 59055 |
| NLGN3 | 12866 | 35961 | 59056 |
| NLGN4X | 12867 | 35962 | 59057 |
| NLGN4Y | 12868 | 35963 | 59058 |
| NLGN4Y | 12869 | 35964 | 59059 |
| NLK | 12870 | 35965 | 59060 |
| NLN | 12871 | 35966 | 59061 |
| NLRC3 | 12872 | 35967 | 59062 |
| NLRC4 | 12873 | 35968 | 59063 |
| NLRC5 | 12874 | 35969 | 59064 |
| NLRP1 | 12875 | 35970 | 59065 |
| NLRP1 | 12876 | 35971 | 59066 |
| NLRP10 | 12877 | 35972 | 59067 |
| NLRP11 | 12878 | 35973 | 59068 |
| NLRP12 | 12879 | 35974 | 59069 |
| NLRP13 | 12880 | 35975 | 59070 |
| NLRP13 | 12881 | 35976 | 59071 |
| NLRP14 | 12882 | 35977 | 59072 |
| NLRP2 | 12883 | 35978 | 59073 |
| NLRP2B | 12884 | 35979 | 59074 |
| NLRP3 | 12885 | 35980 | 59075 |
| NLRP4 | 12886 | 35981 | 59076 |
| NLRP5 | 12887 | 35982 | 59077 |
| NLRP6 | 12888 | 35983 | 59078 |
| NLRP7 | 12889 | 35984 | 59079 |
| NLRP8 | 12890 | 35985 | 59080 |
| NLRP9 | 12891 | 35986 | 59081 |
| NLRX1 | 12892 | 35987 | 59082 |
| NMB | 12893 | 35988 | 59083 |
| NMB | 12894 | 35989 | 59084 |
| NMBR | 12895 | 35990 | 59085 |
| NMD3 | 12896 | 35991 | 59086 |
| NMD3 | 12897 | 35992 | 59087 |
| NME1 | 12898 | 35993 | 59088 |
| NME1- NME2 | 12899 | 35994 | 59089 |
| NME2 | 12900 | 35995 | 59090 |
| NME3 | 12901 | 35996 | 59091 |
| NME4 | 12902 | 35997 | 59092 |
| NME4 | 12903 | 35998 | 59093 |
| NME4 | 12904 | 35999 | 59094 |
| NME5 | 12905 | 36000 | 59095 |
| NME6 | 12906 | 36001 | 59096 |
| NME6 | 12907 | 36002 | 59097 |
| NME7 | 12908 | 36003 | 59098 |
| NME8 | 12909 | 36004 | 59099 |
| NME9 | 12910 | 36005 | 59100 |
| NME9 | 12911 | 36006 | 59101 |
| NMI | 12912 | 36007 | 59102 |
| NMNAT1 | 12913 | 36008 | 59103 |
| NMNAT1 | 12914 | 36009 | 59104 |
| NMNAT2 | 12915 | 36010 | 59105 |
| NMNAT3 | 12916 | 36011 | 59106 |
| NMRAL1 | 12917 | 36012 | 59107 |
| NMRAL1 | 12918 | 36013 | 59108 |
| NMRK1 | 12919 | 36014 | 59109 |
| NMRK2 | 12920 | 36015 | 59110 |
| NMS | 12921 | 36016 | 59111 |
| NMT1 | 12922 | 36017 | 59112 |
| NMT2 | 12923 | 36018 | 59113 |
| NMU | 12924 | 36019 | 59114 |
| NMUR1 | 12925 | 36020 | 59115 |
| NMUR2 | 12926 | 36021 | 59116 |
| NNAT | 12927 | 36022 | 59117 |
| NNAT | 12928 | 36023 | 59118 |
| NNAT | 12929 | 36024 | 59119 |
| NNMT | 12930 | 36025 | 59120 |
| NNT | 12931 | 36026 | 59121 |
| NOA1 | 12932 | 36027 | 59122 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| NOB1 | 12933 | 36028 | 59123 |
| NOBOX | 12934 | 36029 | 59124 |
| NOC2L | 12935 | 36030 | 59125 |
| NOC3L | 12936 | 36031 | 59126 |
| NOC4L | 12937 | 36032 | 59127 |
| NOCT | 12938 | 36033 | 59128 |
| NOD1 | 12939 | 36034 | 59129 |
| NOD2 | 12940 | 36035 | 59130 |
| NODAL | 12941 | 36036 | 59131 |
| NOG | 12942 | 36037 | 59132 |
| NOL10 | 12943 | 36038 | 59133 |
| NOL11 | 12944 | 36039 | 59134 |
| NOL12 | 12945 | 36040 | 59135 |
| NOL3 | 12946 | 36041 | 59136 |
| NOL3 | 12947 | 36042 | 59137 |
| NOL4 | 12948 | 36043 | 59138 |
| NOL4 | 12949 | 36044 | 59139 |
| NOL4L | 12950 | 36045 | 59140 |
| NOL4L | 12951 | 36046 | 59141 |
| NOL6 | 12952 | 36047 | 59142 |
| NOL7 | 12953 | 36048 | 59143 |
| NOL8 | 12954 | 36049 | 59144 |
| NOL9 | 12955 | 36050 | 59145 |
| NOLC1 | 12956 | 36051 | 59146 |
| NOM1 | 12957 | 36052 | 59147 |
| NOMO1 | 12958 | 36053 | 59148 |
| NOMO2 | 12959 | 36054 | 59149 |
| NOMO2 | 12960 | 36055 | 59150 |
| NONO | 12961 | 36056 | 59151 |
| NOP10 | 12962 | 36057 | 59152 |
| NOP14 | 12963 | 36058 | 59153 |
| NOP14 | 12964 | 36059 | 59154 |
| NOP16 | 12965 | 36060 | 59155 |
| NOP16 | 12966 | 36061 | 59156 |
| NOP16 | 12967 | 36062 | 59157 |
| NOP2 | 12968 | 36063 | 59158 |
| NOP2 | 12969 | 36064 | 59159 |
| NOP53 | 12970 | 36065 | 59160 |
| NOP56 | 12971 | 36066 | 59161 |
| NOP58 | 12972 | 36067 | 59162 |
| NOP9 | 12973 | 36068 | 59163 |
| NOP9 | 12974 | 36069 | 59164 |
| NOS1 | 12975 | 36070 | 59155 |
| NOS1AP | 12976 | 36071 | 59155 |
| NOS2 | 12977 | 36072 | 59157 |
| NOS3 | 12978 | 36073 | 59158 |
| NOS3 | 12979 | 36074 | 59159 |
| NOS3 | 12980 | 36075 | 59170 |
| NOS3 | 12981 | 36076 | 59171 |
| NOSIP | 12982 | 36077 | 59172 |
| NOSTRIN | 12983 | 36078 | 59173 |
| NOTCH1 | 12984 | 36079 | 59174 |
| NOTCH2 | 12985 | 36080 | 59175 |
| NOTCH2 | 12986 | 36081 | 59175 |
| NOTCH2NL | 12987 | 36082 | 59177 |
| NOTCH3 | 12988 | 36083 | 59178 |
| NOTCH4 | 12989 | 36084 | 59179 |
| NOTO | 12990 | 36085 | 59180 |
| NOTUM | 12991 | 36086 | 59181 |
| NOV | 12992 | 36087 | 59182 |
| NOVA1 | 12993 | 36088 | 59183 |
| NOVA1 | 12994 | 36089 | 59184 |
| NOVA2 | 12995 | 36090 | 59185 |
| NOX1 | 12996 | 36091 | 59185 |
| NOX3 | 12997 | 36092 | 59187 |
| NOX4 | 12998 | 36093 | 59188 |
| NOX5 | 12999 | 36094 | 59189 |
| NOXA1 | 13000 | 36095 | 59190 |
| NOXO1 | 13001 | 36096 | 59191 |
| NOXRED1 | 13002 | 36097 | 59192 |
| NPAP1 | 13003 | 36098 | 59193 |
| NPAS1 | 13004 | 36099 | 59194 |
| NPAS1 | 13005 | 36100 | 59195 |
| NPAS2 | 13006 | 36101 | 59195 |
| NPAS3 | 13007 | 36102 | 59197 |
| NPAS4 | 13008 | 36103 | 59198 |
| NPAT | 13009 | 36104 | 59199 |
| NPB | 13010 | 36105 | 59200 |
| NPBWR1 | 13011 | 36106 | 59201 |
| NPBWR2 | 13012 | 36107 | 59202 |
| NPC1 | 13013 | 36108 | 59203 |
| NPC1L1 | 13014 | 36109 | 59204 |
| NPC1L1 | 13015 | 36110 | 59205 |
| NPC2 | 13016 | 36111 | 59205 |
| NPDC1 | 13017 | 36112 | 59207 |
| NPEPL1 | 13018 | 35113 | 59208 |
| NPEPPS | 13019 | 36114 | 59209 |
| NPFF | 13020 | 36115 | 59210 |
| NPFFR1 | 13021 | 36116 | 59211 |
| NPFFR2 | 13022 | 36117 | 59212 |
| NPHP1 | 13023 | 36118 | 59213 |
| NPHP3 | 13024 | 36119 | 59214 |
| NPHP4 | 13025 | 36120 | 59215 |
| NPHS1 | 13026 | 36121 | 59216 |
| NPHS2 | 13027 | 36122 | 59217 |
| NPIPA2 | 13028 | 36123 | 59218 |
| NPIPA5 | 13029 | 36124 | 59219 |
| NPIPA7 | 13030 | 36125 | 59220 |
| NPIPB11 | 13031 | 36126 | 59221 |
| NPIPB15 | 13032 | 36127 | 59222 |
| NPIPB3 | 13033 | 36128 | 59223 |
| NPIPB8 | 13034 | 36129 | 59224 |
| NPL | 13035 | 36130 | 59225 |
| NPL | 13036 | 35131 | 59226 |
| NPL | 13037 | 35132 | 59227 |
| NPLOC4 | 13038 | 35133 | 59228 |
| NPM1 | 13039 | 35134 | 59229 |
| NPM1 | 13040 | 35135 | 59230 |
| NPM2 | 13041 | 36136 | 59231 |
| NPM2 | 13042 | 36137 | 59232 |
| NPM3 | 13043 | 36138 | 59233 |
| NPNT | 13044 | 36139 | 59234 |
| NPPA | 13045 | 36140 | 59235 |
| NPPB | 13046 | 36141 | 59236 |
| NPPC | 13047 | 36142 | 59237 |
| NPR1 | 13048 | 36143 | 59238 |
| NPR2 | 13049 | 36144 | 59239 |
| NPR3 | 13050 | 36145 | 59240 |
| NPRL2 | 13051 | 36146 | 59241 |
| NPRL3 | 13052 | 36147 | 59242 |
| NPS | 13053 | 36148 | 59243 |
| NPSR1 | 13054 | 36149 | 59244 |
| NPSR1 | 13055 | 36150 | 59245 |
| NPSR1 | 13056 | 36151 | 59246 |
| NPTN | 13057 | 36152 | 59247 |
| NPTX1 | 13058 | 36153 | 59248 |
| NPTX2 | 13059 | 36154 | 59249 |
| NPTXR | 13060 | 36155 | 59250 |
| NPVF | 13061 | 36156 | 59251 |
| NPW | 13062 | 36157 | 59252 |
| NPY | 13063 | 36158 | 59253 |
| NPY1R | 13064 | 36159 | 59254 |
| NPY2R | 13065 | 36160 | 59255 |
| NPY4R2 | 13066 | 36161 | 59256 |
| NPY5R | 13067 | 36162 | 59257 |
| NQO1 | 13068 | 36163 | 59258 |
| NQO2 | 13069 | 36164 | 59259 |
| NR0B1 | 13070 | 36165 | 59260 |
| NR0B2 | 13071 | 36166 | 59261 |
| NR1D1 | 13072 | 36167 | 59262 |
| NR1D2 | 13073 | 36168 | 59263 |
| NR1H2 | 13074 | 36169 | 59264 |
| NR1H3 | 13075 | 36170 | 59265 |
| NR1H4 | 13076 | 36171 | 59266 |
| NR1I2 | 13077 | 36172 | 59267 |
| NR1I3 | 13078 | 36173 | 59268 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| NR1I3 | 13079 | 36174 | 59269 |
| NR2C1 | 13080 | 36175 | 59270 |
| NR2C1 | 13081 | 36176 | 59271 |
| NR2C1 | 13082 | 36177 | 59272 |
| NR2C2 | 13083 | 36178 | 59273 |
| NR2C2AP | 13084 | 36179 | 59274 |
| NR2C2AP | 13085 | 36180 | 59275 |
| NR2E1 | 13086 | 36181 | 59276 |
| NR2E3 | 13087 | 36182 | 59277 |
| NR2E3 | 13088 | 36183 | 59278 |
| NR2F1 | 13089 | 36184 | 59279 |
| NR2F2 | 13090 | 36185 | 59280 |
| NR2F6 | 13091 | 36186 | 59281 |
| NR3C1 | 13092 | 36187 | 59282 |
| NR3C1 | 13093 | 36188 | 59283 |
| NR3C1 | 13094 | 36189 | 59284 |
| NR3C2 | 13095 | 36190 | 59285 |
| NR4A1 | 13096 | 36191 | 59286 |
| NR4A2 | 13097 | 36192 | 59287 |
| NR4A3 | 13098 | 36193 | 59288 |
| NR4A3 | 13099 | 36194 | 59289 |
| NR5A1 | 13100 | 36195 | 59290 |
| NR5A2 | 13101 | 36196 | 59291 |
| NR6A1 | 13102 | 36197 | 59292 |
| NRAP | 13103 | 36198 | 59293 |
| NRARP | 13104 | 36199 | 59294 |
| NRAS | 13105 | 36200 | 59295 |
| NRBF2 | 13106 | 36201 | 59296 |
| NRBP1 | 13107 | 36202 | 59297 |
| NRBP2 | 13108 | 36203 | 59298 |
| NRCAM | 13109 | 36204 | 59299 |
| NRDC | 13110 | 36205 | 59300 |
| NRDE2 | 13111 | 36206 | 59301 |
| NREP | 13112 | 36207 | 59302 |
| NRF1 | 13113 | 36208 | 59303 |
| NRG1 | 13114 | 36209 | 59304 |
| NRG1 | 13115 | 36210 | 59305 |
| NRG1 | 13116 | 36211 | 59306 |
| NRG1 | 13117 | 36212 | 59307 |
| NRG1 | 13118 | 36213 | 59308 |
| NRG2 | 13119 | 36214 | 59309 |
| NRG3 | 13120 | 36215 | 59310 |
| NRG4 | 13121 | 36216 | 59311 |
| NRGN | 13122 | 36217 | 59312 |
| NRIP1 | 13123 | 36218 | 59313 |
| NRIP2 | 13124 | 36219 | 59314 |
| NRIP3 | 13125 | 36220 | 59315 |
| NRK | 13126 | 36221 | 59316 |
| NRL | 13127 | 36222 | 59317 |
| NRM | 13128 | 36223 | 59318 |
| NRM | 13129 | 36224 | 59319 |
| NRM | 13130 | 36225 | 59320 |
| NRN1 | 13131 | 36226 | 59321 |
| NRN1L | 13132 | 36227 | 59322 |
| NRN1L | 13133 | 36228 | 59323 |
| NRP1 | 13134 | 36229 | 59324 |
| NRP1 | 13135 | 36230 | 59325 |
| NRP2 | 13136 | 36231 | 59326 |
| NRP2 | 13137 | 36232 | 59327 |
| NRP2 | 13138 | 36233 | 59328 |
| NRROS | 13139 | 36234 | 59329 |
| NRSN1 | 13140 | 36235 | 59330 |
| NRSN2 | 13141 | 36236 | 59331 |
| NRTN | 13142 | 36237 | 59332 |
| NRXN1 | 13143 | 36238 | 59333 |
| NRXN1 | 13144 | 36239 | 59334 |
| NRXN1 | 13145 | 36240 | 59335 |
| NRXN1 | 13146 | 36241 | 59336 |
| NRXN2 | 13147 | 36242 | 59337 |
| NRXN3 | 13148 | 36243 | 59338 |
| NSA2 | 13149 | 36244 | 59339 |
| NSD1 | 13150 | 36245 | 59340 |
| NSD2 | 13151 | 36246 | 59341 |
| NSD2 | 13152 | 36247 | 59342 |
| NSD2 | 13153 | 36248 | 59343 |
| NSD3 | 13154 | 36249 | 59344 |
| NSD3 | 13155 | 36250 | 59345 |
| NSDHL | 13156 | 36251 | 59346 |
| NSF | 13157 | 36252 | 59347 |
| NSFL1C | 13158 | 36253 | 59348 |
| NSG1 | 13159 | 36254 | 59349 |
| NSG2 | 13160 | 36255 | 59350 |
| NSL1 | 13161 | 36256 | 59351 |
| NSL1 | 13162 | 36257 | 59352 |
| NSL1 | 13163 | 36258 | 59353 |
| NSL1 | 13164 | 36259 | 59354 |
| NSMAF | 13165 | 36260 | 59355 |
| NSMCE1 | 13166 | 36261 | 59356 |
| NSMCE2 | 13167 | 36262 | 59357 |
| NSMCE2 | 13168 | 36263 | 59358 |
| NSMCE3 | 13169 | 36264 | 59359 |
| NSMCE4A | 13170 | 36265 | 59360 |
| NSMF | 13171 | 36266 | 59361 |
| NSRP1 | 13172 | 36267 | 59362 |
| NSUN2 | 13173 | 36268 | 59363 |
| NSUN3 | 13174 | 36269 | 59364 |
| NSUN4 | 13175 | 36270 | 59365 |
| NSUN5 | 13176 | 36271 | 59366 |
| NSUN5 | 13177 | 36272 | 59367 |
| NSUN5 | 13178 | 36273 | 59368 |
| NSUN6 | 13179 | 36274 | 59369 |
| NSUN7 | 13180 | 36275 | 59370 |
| NSUN7 | 13181 | 36276 | 59371 |
| NT5C | 13182 | 36277 | 59372 |
| NT5C1A | 13183 | 36278 | 59373 |
| NT5C1B | 13184 | 36279 | 59374 |
| NT5C1B-RDH14 | 13185 | 36280 | 59375 |
| NT5C2 | 13186 | 36281 | 59376 |
| NT5C3A | 13187 | 36282 | 59377 |
| NT5C3B | 13188 | 36283 | 59378 |
| NT5DC1 | 13189 | 36284 | 59379 |
| NT5DC2 | 13190 | 36285 | 59380 |
| NT5DC3 | 13191 | 36286 | 59381 |
| NT5DC4 | 13192 | 36287 | 59382 |
| NT5E | 13193 | 36288 | 59383 |
| NT5M | 13194 | 36289 | 59384 |
| NTAN1 | 13195 | 36290 | 59385 |
| NTF3 | 13196 | 36291 | 59386 |
| NTF4 | 13197 | 36292 | 59387 |
| NTHL1 | 13198 | 36293 | 59388 |
| NTM | 13199 | 36294 | 59389 |
| NTM | 13200 | 36295 | 59390 |
| NTMT1 | 13201 | 36296 | 59391 |
| NTMT1 | 13202 | 36297 | 59392 |
| NTN1 | 13203 | 36298 | 59393 |
| NTN3 | 13204 | 36299 | 59394 |
| NTN4 | 13205 | 36300 | 59395 |
| NTN5 | 13206 | 36301 | 59396 |
| NTNG1 | 13207 | 36302 | 59397 |
| NTNG2 | 13208 | 36303 | 59398 |
| NTPCR | 13209 | 36304 | 59399 |
| NTPCR | 13210 | 36305 | 59400 |
| NTRK1 | 13211 | 36306 | 59401 |
| NTRK2 | 13212 | 36307 | 59402 |
| NTRK2 | 13213 | 36308 | 59403 |
| NTRK2 | 13214 | 36309 | 59404 |
| NTRK3 | 13215 | 36310 | 59405 |
| NTRK3 | 13216 | 36311 | 59406 |
| NTRK3 | 13217 | 36312 | 59407 |
| NTS | 13218 | 36313 | 59408 |
| NTSR1 | 13219 | 36314 | 59409 |
| NTSR2 | 13220 | 36315 | 59410 |
| NUAK1 | 13221 | 36316 | 59411 |
| NUAK2 | 13222 | 36317 | 59412 |
| NUB1 | 13223 | 36318 | 59413 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| NUBP1 | 13224 | 36319 | 59414 |
| NUBP1 | 13225 | 36320 | 59415 |
| NUBP2 | 13226 | 36321 | 59416 |
| NUBP2 | 13227 | 36322 | 59417 |
| NUBPL | 13228 | 36323 | 59418 |
| NUCB1 | 13229 | 36324 | 59419 |
| NUCB2 | 13230 | 36325 | 59420 |
| NUCKS1 | 13231 | 36326 | 59421 |
| NUDC | 13232 | 36327 | 59422 |
| NUDCD1 | 13233 | 36328 | 59423 |
| NUDCD2 | 13234 | 36329 | 59424 |
| NUDCD3 | 13235 | 36330 | 59425 |
| NUDT1 | 13236 | 36331 | 59426 |
| NUDT10 | 13237 | 36332 | 59427 |
| NUDT11 | 13238 | 36333 | 59428 |
| NUDT12 | 13239 | 36334 | 59429 |
| NUDT13 | 13240 | 36335 | 59430 |
| NUDT13 | 13241 | 36336 | 59431 |
| NUDT14 | 13242 | 36337 | 59432 |
| NUDT14 | 13243 | 36338 | 59433 |
| NUDT15 | 13244 | 36339 | 59434 |
| NUDT15 | 13245 | 36340 | 59435 |
| NUDT16 | 13246 | 36341 | 59436 |
| NUDT16 | 13247 | 36342 | 59437 |
| NUDT16 | 13248 | 36343 | 59438 |
| NUDT16L1 | 13249 | 36344 | 59439 |
| NUDT16L1 | 13250 | 36345 | 59440 |
| NUDT17 | 13251 | 36346 | 59441 |
| NUDT18 | 13252 | 36347 | 59442 |
| NUDT19 | 13253 | 36348 | 59443 |
| NUDT2 | 13254 | 36349 | 59444 |
| NUDT21 | 13255 | 36350 | 59445 |
| NUDT22 | 13256 | 36351 | 59446 |
| NUDT3 | 13257 | 36352 | 59447 |
| NUDT4 | 13258 | 36353 | 59448 |
| NUDT5 | 13259 | 36354 | 59449 |
| NUDT6 | 13260 | 36355 | 59450 |
| NUDT7 | 13261 | 36356 | 59451 |
| NUDT8 | 13262 | 36357 | 59452 |
| NUDT8 | 13263 | 36358 | 59453 |
| NUDT9 | 13264 | 36359 | 59454 |
| NUF2 | 13265 | 36360 | 59455 |
| NUFIP1 | 13266 | 36361 | 59456 |
| NUFIP2 | 13267 | 36362 | 59457 |
| NUGGC | 13268 | 36363 | 59458 |
| NUMA1 | 13269 | 36364 | 59459 |
| NUMB | 13270 | 36365 | 59460 |
| NUMBL | 13271 | 36366 | 59461 |
| NUP107 | 13272 | 36367 | 59462 |
| NUP133 | 13273 | 36368 | 59463 |
| NUP153 | 13274 | 36369 | 59464 |
| NUP155 | 13275 | 36370 | 59465 |
| NUP160 | 13276 | 36371 | 59466 |
| NUP160 | 13277 | 36372 | 59467 |
| NUP188 | 13278 | 36373 | 59468 |
| NUP205 | 13279 | 36374 | 59469 |
| NUP210 | 13280 | 36375 | 59470 |
| NUP210L | 13281 | 36376 | 59471 |
| NUP214 | 13282 | 36377 | 59472 |
| NUP35 | 13283 | 36378 | 59473 |
| NUP37 | 13284 | 36379 | 59474 |
| NUP43 | 13285 | 36380 | 59475 |
| NUP50 | 13286 | 36381 | 59476 |
| NUP54 | 13287 | 36382 | 59477 |
| NUP58 | 13288 | 36383 | 59478 |
| NUP62 | 13289 | 36384 | 59479 |
| NUP62CL | 13290 | 36385 | 59480 |
| NUP85 | 13291 | 36386 | 59481 |
| NUP88 | 13292 | 36387 | 59482 |
| NUP93 | 13293 | 36388 | 59483 |
| NUP98 | 13294 | 36389 | 59484 |
| NUP98 | 13295 | 36390 | 59485 |
| NUPL2 | 13296 | 36391 | 59486 |
| NUPR1 | 13297 | 36392 | 59487 |
| NUPR2 | 13298 | 36393 | 59488 |
| NUS1 | 13299 | 36394 | 59489 |
| NUSAP1 | 13300 | 36395 | 59490 |
| NUTF2 | 13301 | 36396 | 59491 |
| NUTM1 | 13302 | 36397 | 59492 |
| NUTM2B | 13303 | 36398 | 59493 |
| NUTM2D | 13304 | 36399 | 59494 |
| NUTM2G | 13305 | 36400 | 59495 |
| NUTM2G | 13306 | 36401 | 59496 |
| NVL | 13307 | 36402 | 59497 |
| NWD1 | 13308 | 36403 | 59498 |
| NWD1 | 13309 | 36404 | 59499 |
| NWD2 | 13310 | 36405 | 59500 |
| NXF1 | 13311 | 36406 | 59501 |
| NXF1 | 13312 | 36407 | 59502 |
| NXF2 | 13313 | 36408 | 59503 |
| NXF3 | 13314 | 36409 | 59504 |
| NXF5 | 13315 | 36410 | 59505 |
| NXN | 13316 | 36411 | 59506 |
| NXNL1 | 13317 | 36412 | 59507 |
| NXNL2 | 13318 | 36413 | 59508 |
| NXNL2 | 13319 | 36414 | 59509 |
| NXPE1 | 13320 | 36415 | 59510 |
| NXPE2 | 13321 | 36416 | 59511 |
| NXPE3 | 13322 | 36417 | 59512 |
| NXPE4 | 13323 | 36418 | 59513 |
| NXPH1 | 13324 | 36419 | 59514 |
| NXPH2 | 13325 | 36420 | 59515 |
| NXPH3 | 13326 | 36421 | 59516 |
| NXPH4 | 13327 | 36422 | 59517 |
| NXT1 | 13328 | 36423 | 59518 |
| NXT2 | 13329 | 36424 | 59519 |
| NYAP1 | 13330 | 36425 | 59520 |
| NYAP2 | 13331 | 36426 | 59521 |
| NYNRIN | 13332 | 36427 | 59522 |
| NYX | 13333 | 36428 | 59523 |
| OAF | 13334 | 36429 | 59524 |
| OARD1 | 13335 | 36430 | 59525 |
| OARD1 | 13336 | 36431 | 59526 |
| OARD1 | 13337 | 36432 | 59527 |
| OAS1 | 13338 | 36433 | 59528 |
| OAS1 | 13339 | 36434 | 59529 |
| OAS1 | 13340 | 36435 | 59530 |
| OAS1 | 13341 | 36436 | 59531 |
| OAS2 | 13342 | 36437 | 59532 |
| OAS2 | 13343 | 36438 | 59533 |
| OAS2 | 13344 | 36439 | 59534 |
| OAS3 | 13345 | 36440 | 59535 |
| OASL | 13346 | 36441 | 59536 |
| OASL | 13347 | 36442 | 59537 |
| OAT | 13348 | 36443 | 59538 |
| OAZ1 | 13349 | 36444 | 59539 |
| OAZ2 | 13350 | 36445 | 59540 |
| OAZ3 | 13351 | 36446 | 59541 |
| OBP2A | 13352 | 36447 | 59542 |
| OBP2A | 13353 | 36448 | 59543 |
| OBP2B | 13354 | 36449 | 59544 |
| OBSCN | 13355 | 36450 | 59545 |
| OBSCN | 13356 | 36451 | 59546 |
| OBSL1 | 13357 | 36452 | 59547 |
| OBSL1 | 13358 | 36453 | 59548 |
| OBSL1 | 13359 | 36454 | 59549 |
| OC90 | 13360 | 36455 | 59550 |
| OCA2 | 13361 | 36456 | 59551 |
| OCEL1 | 13362 | 36457 | 59552 |
| OCIAD1 | 13363 | 36458 | 59553 |
| OCIAD1 | 13364 | 36459 | 59554 |
| OCIAD1 | 13365 | 36460 | 59555 |
| OCIAD2 | 13366 | 36461 | 59556 |
| OCIAD2 | 13367 | 36462 | 59557 |
| OCLM | 13368 | 36463 | 59558 |
| OCLN | 13369 | 36464 | 59559 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| OCM2 | 13370 | 36465 | 59560 |
| OCRL | 13371 | 36466 | 59561 |
| OCSTAMP | 13372 | 36467 | 59562 |
| ODAM | 13373 | 36468 | 59563 |
| ODAPH | 13374 | 36469 | 59564 |
| ODC1 | 13375 | 36470 | 59565 |
| ODF1 | 13376 | 36471 | 59566 |
| ODF2 | 13377 | 36472 | 59567 |
| ODF2 | 13378 | 36473 | 59568 |
| ODF2L | 13379 | 36474 | 59569 |
| ODF2L | 13380 | 36475 | 59570 |
| ODF3 | 13381 | 36476 | 59571 |
| ODF3B | 13382 | 36477 | 59572 |
| ODF3L1 | 13383 | 36478 | 59573 |
| ODF3L2 | 13384 | 36479 | 59574 |
| ODF4 | 13385 | 36480 | 59575 |
| OFD1 | 13386 | 36481 | 59576 |
| OGDH | 13387 | 36482 | 59577 |
| OGDH | 13388 | 36483 | 59578 |
| OGDHL | 13389 | 36484 | 59579 |
| OGFOD1 | 13390 | 36485 | 59580 |
| OGFOD2 | 13391 | 36486 | 59581 |
| OGFOD3 | 13392 | 36487 | 59582 |
| OGFOD3 | 13393 | 36488 | 59583 |
| OGFR | 13394 | 36489 | 59584 |
| OGFRL1 | 13395 | 36490 | 59585 |
| OGG1 | 13396 | 36491 | 59586 |
| OGG1 | 13397 | 36492 | 59587 |
| OGG1 | 13398 | 36493 | 59588 |
| OGG1 | 13399 | 36494 | 59589 |
| OGG1 | 13400 | 36495 | 59590 |
| OGG1 | 13401 | 36496 | 59591 |
| OGN | 13402 | 36497 | 59592 |
| OGT | 13403 | 36498 | 59593 |
| OIP5 | 13404 | 36499 | 59594 |
| OIT3 | 13405 | 36500 | 59595 |
| OLA1 | 13406 | 36501 | 59596 |
| OLAH | 13407 | 36502 | 59597 |
| OLFM1 | 13408 | 36503 | 59598 |
| OLFM1 | 13409 | 36504 | 59599 |
| OLFM2 | 13410 | 36505 | 59600 |
| OLFM3 | 13411 | 36506 | 59601 |
| OLFM4 | 13412 | 36507 | 59602 |
| OLFML1 | 13413 | 36508 | 59603 |
| OLFML2A | 13414 | 36509 | 59604 |
| OLFML2B | 13415 | 36510 | 59605 |
| OLFML3 | 13416 | 36511 | 59606 |
| OLIG1 | 13417 | 36512 | 59607 |
| OLIG2 | 13418 | 36513 | 59608 |
| OLIG3 | 13419 | 36514 | 59609 |
| OLR1 | 13420 | 36515 | 59610 |
| OLR1 | 13421 | 36516 | 59611 |
| OLR1 | 13422 | 36517 | 59612 |
| OMA1 | 13423 | 36518 | 59613 |
| OMD | 13424 | 36519 | 59614 |
| OMG | 13425 | 36520 | 59615 |
| OMP | 13426 | 36521 | 59616 |
| ONECUT1 | 13427 | 36522 | 59617 |
| ONECUT2 | 13428 | 36523 | 59618 |
| ONECUT3 | 13429 | 36524 | 59619 |
| OOEP | 13430 | 36525 | 59620 |
| OOSP2 | 13431 | 36526 | 59621 |
| OPA1 | 13432 | 36527 | 59622 |
| OPA3 | 13433 | 36528 | 59623 |
| OPA3 | 13434 | 36529 | 59624 |
| OPALIN | 13435 | 36530 | 59625 |
| OPALIN | 13436 | 36531 | 59626 |
| OPCML | 13437 | 36532 | 59627 |
| OPHN1 | 13438 | 36533 | 59628 |
| OPLAH | 13439 | 36534 | 59629 |
| OPN1LW | 13440 | 36535 | 59630 |
| OPN1SW | 13441 | 36536 | 59631 |
| OPN3 | 13442 | 36537 | 59632 |
| OPN4 | 13443 | 36538 | 59633 |
| OPN5 | 13444 | 36539 | 59634 |
| OPRD1 | 13445 | 36540 | 59635 |
| OPRK1 | 13446 | 36541 | 59636 |
| OPRL1 | 13447 | 36542 | 59637 |
| OPRM1 | 13448 | 36543 | 59638 |
| OPRM1 | 13449 | 36544 | 59639 |
| OPRM1 | 13450 | 36545 | 59640 |
| OPRM1 | 13451 | 36546 | 59641 |
| OPRM1 | 13452 | 36547 | 59642 |
| OPRM1 | 13453 | 36548 | 59643 |
| OPRM1 | 13454 | 36549 | 59644 |
| OPRM1 | 13455 | 36550 | 59645 |
| OPRM1 | 13456 | 36551 | 59646 |
| OPRM1 | 13457 | 36552 | 59647 |
| OPRM1 | 13458 | 36553 | 59648 |
| OPRPN | 13459 | 36554 | 59649 |
| OPRPN | 13460 | 36555 | 59650 |
| OPTC | 13461 | 36556 | 59651 |
| OPTN | 13462 | 36557 | 59652 |
| OR10A2 | 13463 | 36558 | 59653 |
| OR10A3 | 13464 | 36559 | 59654 |
| OR10A4 | 13465 | 36560 | 59655 |
| OR10A6 | 13466 | 36561 | 59656 |
| OR10A7 | 13467 | 36562 | 59657 |
| OR10AC1 | 13468 | 36563 | 59658 |
| OR10AD1 | 13469 | 36564 | 59659 |
| OR10AG1 | 13470 | 36565 | 59660 |
| OR10C1 | 13471 | 36566 | 59661 |
| OR10G2 | 13472 | 36567 | 59662 |
| OR10G3 | 13473 | 36568 | 59663 |
| OR10G4 | 13474 | 36569 | 59664 |
| OR10G7 | 13475 | 36570 | 59665 |
| OR10G8 | 13476 | 36571 | 59666 |
| OR10G9 | 13477 | 36572 | 59667 |
| OR10H1 | 13478 | 36573 | 59668 |
| OR10H2 | 13479 | 36574 | 59669 |
| OR10H3 | 13480 | 36575 | 59670 |
| OR10H4 | 13481 | 36576 | 59671 |
| OR10H5 | 13482 | 36577 | 59672 |
| OR10J1 | 13483 | 36578 | 59673 |
| OR10J3 | 13484 | 36579 | 59674 |
| OR10J4 | 13485 | 36580 | 59675 |
| OR10J5 | 13486 | 36581 | 59676 |
| OR10K1 | 13487 | 36582 | 59677 |
| OR10K2 | 13488 | 36583 | 59678 |
| OR10P1 | 13489 | 36584 | 59679 |
| OR10Q1 | 13490 | 36585 | 59680 |
| OR10R2 | 13491 | 36586 | 59681 |
| OR10S1 | 13492 | 36587 | 59682 |
| OR10T2 | 13493 | 36588 | 59683 |
| OR10V1 | 13494 | 36589 | 59684 |
| OR10W1 | 13495 | 36590 | 59685 |
| OR10X1 | 13496 | 36591 | 59686 |
| OR10Z1 | 13497 | 36592 | 59687 |
| OR11A1 | 13498 | 36593 | 59688 |
| OR11G2 | 13499 | 36594 | 59689 |
| OR11H1 | 13500 | 36595 | 59690 |
| OR11H12 | 13501 | 36596 | 59691 |
| OR11H2 | 13502 | 36597 | 59692 |
| OR11H4 | 13503 | 36598 | 59693 |
| OR11H6 | 13504 | 36599 | 59694 |
| OR11H7 | 13505 | 36600 | 59695 |
| OR11L1 | 13506 | 36601 | 59696 |
| OR12D1 | 13507 | 36602 | 59697 |
| OR12D2 | 13508 | 36603 | 59698 |
| OR12D3 | 13509 | 36604 | 59699 |
| OR13A1 | 13510 | 36605 | 59700 |
| OR13C2 | 13511 | 36606 | 59701 |
| OR13C3 | 13512 | 36607 | 59702 |
| OR13C4 | 13513 | 36608 | 59703 |
| OR13C5 | 13514 | 36609 | 59704 |
| OR13C8 | 13515 | 36610 | 59705 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| OR13C9 | 13516 | 36611 | 59706 |
| OR13D1 | 13517 | 36612 | 59707 |
| OR13F1 | 13518 | 36613 | 59708 |
| OR13G1 | 13519 | 36614 | 59709 |
| OR13H1 | 13520 | 36615 | 59710 |
| OR13J1 | 13521 | 36616 | 59711 |
| OR14A16 | 13522 | 36617 | 59712 |
| OR14C36 | 13523 | 36618 | 59713 |
| OR14I1 | 13524 | 36619 | 59714 |
| OR14J1 | 13525 | 36620 | 59715 |
| OR1A1 | 13526 | 36621 | 59716 |
| OR1A2 | 13527 | 36622 | 59717 |
| OR1B1 | 13528 | 36623 | 59718 |
| OR1C1 | 13529 | 36624 | 59719 |
| OR1D2 | 13530 | 36625 | 59720 |
| OR1D5 | 13531 | 36626 | 59721 |
| OR1E1 | 13532 | 36627 | 59722 |
| OR1E2 | 13533 | 36628 | 59723 |
| OR1E3 | 13534 | 36629 | 59724 |
| OR1F1 | 13535 | 36630 | 59725 |
| OR1G1 | 13536 | 36631 | 59726 |
| OR1I1 | 13537 | 36632 | 59727 |
| OR1J1 | 13538 | 36633 | 59728 |
| OR1J2 | 13539 | 36634 | 59729 |
| OR1J4 | 13540 | 36635 | 59730 |
| OR1K1 | 13541 | 36636 | 59731 |
| OR1L1 | 13542 | 36637 | 59732 |
| OR1L3 | 13543 | 36638 | 59733 |
| OR1L4 | 13544 | 36639 | 59734 |
| OR1L6 | 13545 | 36640 | 59735 |
| OR1L8 | 13546 | 36641 | 59736 |
| OR1M1 | 13547 | 36642 | 59737 |
| OR1N1 | 13548 | 36643 | 59738 |
| OR1N2 | 13549 | 36644 | 59739 |
| OR1Q1 | 13550 | 36645 | 59740 |
| OR1S1 | 13551 | 36646 | 59741 |
| OR2A12 | 13552 | 36647 | 59742 |
| OR2A14 | 13553 | 36648 | 59743 |
| OR2A2 | 13554 | 36649 | 59744 |
| OR2A25 | 13555 | 36650 | 59745 |
| OR2A42 | 13556 | 36651 | 59746 |
| OR2A5 | 13557 | 36652 | 59747 |
| OR2A7 | 13558 | 36653 | 59748 |
| OR2AE1 | 13559 | 36654 | 59749 |
| OR2AG1 | 13560 | 36655 | 59750 |
| OR2AG2 | 13561 | 36656 | 59751 |
| OR2AK2 | 13562 | 36657 | 59752 |
| OR2AP1 | 13563 | 36658 | 59753 |
| OR2AT4 | 13564 | 36659 | 59754 |
| OR2B11 | 13565 | 36660 | 59755 |
| OR2B2 | 13566 | 36661 | 59756 |
| OR2B3 | 13567 | 36662 | 59757 |
| OR2B6 | 13568 | 36663 | 59758 |
| OR2C1 | 13569 | 36664 | 59759 |
| OR2C3 | 13570 | 36665 | 59760 |
| OR2D2 | 13571 | 36666 | 59761 |
| OR2D3 | 13572 | 36667 | 59762 |
| OR2F1 | 13573 | 36668 | 59763 |
| OR2F2 | 13574 | 36669 | 59764 |
| OR2G2 | 13575 | 36670 | 59765 |
| OR2G3 | 13576 | 36671 | 59766 |
| OR2G6 | 13577 | 36672 | 59767 |
| OR2H1 | 13578 | 36673 | 59768 |
| OR2H2 | 13579 | 36674 | 59769 |
| OR2J1 | 13580 | 36675 | 59770 |
| OR2J2 | 13581 | 36676 | 59771 |
| OR2J3 | 13582 | 36677 | 59772 |
| OR2K2 | 13583 | 36678 | 59773 |
| OR2L13 | 13584 | 36679 | 59774 |
| OR2L2 | 13585 | 36680 | 59775 |
| OR2L3 | 13586 | 36681 | 59776 |
| OR2L5 | 13587 | 36682 | 59777 |
| OR2L8 | 13588 | 36683 | 59778 |
| OR2M2 | 13589 | 36684 | 59779 |
| OR2M3 | 13590 | 36685 | 59780 |
| OR2M4 | 13591 | 36686 | 59781 |
| OR2M5 | 13592 | 36687 | 59782 |
| OR2S2 | 13593 | 36688 | 59783 |
| OR2T1 | 13594 | 36689 | 59784 |
| OR2T10 | 13595 | 36690 | 59785 |
| OR2T11 | 13596 | 36691 | 59786 |
| OR2T12 | 13597 | 36692 | 59787 |
| OR2T2 | 13598 | 36693 | 59788 |
| OR2T27 | 13599 | 36694 | 59789 |
| OR2T29 | 13600 | 36695 | 59790 |
| OR2T3 | 13601 | 36696 | 59791 |
| OR2T4 | 13602 | 36697 | 59792 |
| OR2T6 | 13603 | 36698 | 59793 |
| OR2T8 | 13604 | 36699 | 59794 |
| OR2V2 | 13605 | 36700 | 59795 |
| OR2W1 | 13606 | 36701 | 59796 |
| OR2W3 | 13607 | 36702 | 59797 |
| OR2W5 | 13608 | 36703 | 59798 |
| OR2Y1 | 13609 | 36704 | 59799 |
| OR2Z1 | 13610 | 36705 | 59800 |
| OR3A1 | 13611 | 36706 | 59801 |
| OR3A2 | 13612 | 36707 | 59802 |
| OR3A3 | 13613 | 36708 | 59803 |
| OR4A15 | 13614 | 36709 | 59804 |
| OR4A16 | 13615 | 36710 | 59805 |
| OR4A47 | 13616 | 36711 | 59806 |
| OR4A5 | 13617 | 36712 | 59807 |
| OR4B1 | 13618 | 36713 | 59808 |
| OR4C11 | 13619 | 36714 | 59809 |
| OR4C12 | 13620 | 36715 | 59810 |
| OR4C13 | 13621 | 36716 | 59811 |
| OR4C15 | 13622 | 36717 | 59812 |
| OR4C16 | 13623 | 36718 | 59813 |
| OR4C3 | 13624 | 36719 | 59814 |
| OR4C45 | 13625 | 36720 | 59815 |
| OR4C46 | 13626 | 36721 | 59816 |
| OR4C5 | 13627 | 36722 | 59817 |
| OR4C6 | 13628 | 36723 | 59818 |
| OR4D1 | 13629 | 36724 | 59819 |
| OR4D10 | 13630 | 36725 | 59820 |
| OR4D11 | 13631 | 36726 | 59821 |
| OR4D2 | 13632 | 36727 | 59822 |
| OR4D5 | 13633 | 36728 | 59823 |
| OR4D6 | 13634 | 36729 | 59824 |
| OR4D9 | 13635 | 36730 | 59825 |
| OR4E1 | 13636 | 36731 | 59826 |
| OR4E2 | 13637 | 36732 | 59827 |
| OR4F15 | 13638 | 36733 | 59828 |
| OR4F17 | 13639 | 36734 | 59829 |
| OR4F21 | 13640 | 36735 | 59830 |
| OR4F29 | 13641 | 36736 | 59831 |
| OR4F4 | 13642 | 36737 | 59832 |
| OR4F6 | 13643 | 36738 | 59833 |
| OR4K1 | 13644 | 36739 | 59834 |
| OR4K13 | 13645 | 36740 | 59835 |
| OR4K14 | 13646 | 36741 | 59836 |
| OR4K15 | 13647 | 36742 | 59837 |
| OR4K17 | 13648 | 36743 | 59838 |
| OR4K2 | 13649 | 36744 | 59839 |
| OR4K3 | 13650 | 36745 | 59840 |
| OR4K5 | 13651 | 36746 | 59841 |
| OR4L1 | 13652 | 36747 | 59842 |
| OR4M1 | 13653 | 36748 | 59843 |
| OR4M2 | 13654 | 36749 | 59844 |
| OR4N2 | 13655 | 36750 | 59845 |
| OR4N4 | 13656 | 36751 | 59846 |
| OR4N5 | 13657 | 36752 | 59847 |
| OR4P4 | 13658 | 36753 | 59848 |
| OR4Q2 | 13659 | 36754 | 59849 |
| OR4Q3 | 13660 | 36755 | 59850 |
| OR4S1 | 13661 | 36756 | 59851 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| OR4S2 | 13662 | 36757 | 59852 |
| OR4X1 | 13663 | 36758 | 59853 |
| OR4X2 | 13664 | 36759 | 59854 |
| OR51A2 | 13665 | 36760 | 59855 |
| OR51A4 | 13666 | 36761 | 59856 |
| OR51A7 | 13667 | 36762 | 59857 |
| OR51B2 | 13668 | 36763 | 59858 |
| OR51B4 | 13669 | 36764 | 59859 |
| OR51B5 | 13670 | 36765 | 59860 |
| OR51B6 | 13671 | 36766 | 59861 |
| OR51D1 | 13672 | 36767 | 59862 |
| OR51E1 | 13673 | 36768 | 59863 |
| OR51E2 | 13674 | 36769 | 59864 |
| OR51F1 | 13675 | 36770 | 59865 |
| OR51F2 | 13676 | 36771 | 59866 |
| OR51G1 | 13677 | 36772 | 59867 |
| OR51G2 | 13678 | 36773 | 59868 |
| OR51H1 | 13679 | 36774 | 59869 |
| OR51I1 | 13680 | 36775 | 59870 |
| OR51I2 | 13681 | 36776 | 59871 |
| OR51J1 | 13682 | 36777 | 59872 |
| OR51L1 | 13683 | 36778 | 59873 |
| OR51M1 | 13684 | 36779 | 59874 |
| OR51Q1 | 13685 | 36780 | 59875 |
| OR51S1 | 13686 | 36781 | 59876 |
| OR51T1 | 13687 | 36782 | 59877 |
| OR51V1 | 13688 | 36783 | 59878 |
| OR52A1 | 13689 | 36784 | 59879 |
| OR52A5 | 13690 | 36785 | 59880 |
| OR52B2 | 13691 | 36786 | 59881 |
| OR52B4 | 13692 | 36787 | 59882 |
| OR52B6 | 13693 | 36788 | 59883 |
| OR52D1 | 13694 | 36789 | 59884 |
| OR52E1 | 13695 | 36790 | 59885 |
| OR52E2 | 13696 | 36791 | 59886 |
| OR52E4 | 13697 | 36792 | 59887 |
| OR52E6 | 13698 | 36793 | 59888 |
| OR52E8 | 13699 | 36794 | 59889 |
| OR52H1 | 13700 | 36795 | 59890 |
| OR52I1 | 13701 | 36796 | 59891 |
| OR52I2 | 13702 | 36797 | 59892 |
| OR52J3 | 13703 | 36798 | 59893 |
| OR52K1 | 13704 | 36799 | 59894 |
| OR52K2 | 13705 | 36800 | 59895 |
| OR52L1 | 13706 | 36801 | 59896 |
| OR52M1 | 13707 | 36802 | 59897 |
| OR52N1 | 13708 | 36803 | 59898 |
| OR52N2 | 13709 | 36804 | 59899 |
| OR52N4 | 13710 | 36805 | 59900 |
| OR52N5 | 13711 | 36806 | 59901 |
| OR52R1 | 13712 | 36807 | 59902 |
| OR52W1 | 13713 | 36808 | 59903 |
| OR52Z1 | 13714 | 36809 | 59904 |
| OR56A1 | 13715 | 36810 | 59905 |
| OR56A3 | 13716 | 36811 | 59906 |
| OR56A4 | 13717 | 36812 | 59907 |
| OR56A5 | 13718 | 36813 | 59908 |
| OR56B1 | 13719 | 36814 | 59909 |
| OR56B4 | 13720 | 36815 | 59910 |
| OR5A1 | 13721 | 36816 | 59911 |
| OR5A2 | 13722 | 36817 | 59912 |
| OR5AC2 | 13723 | 36818 | 59913 |
| OR5AK2 | 13724 | 36819 | 59914 |
| OR5AL1 | 13725 | 36820 | 59915 |
| OR5AN1 | 13726 | 36821 | 59916 |
| OR5AP2 | 13727 | 36822 | 59917 |
| OR5AR1 | 13728 | 36823 | 59918 |
| OR5AS1 | 13729 | 36824 | 59919 |
| OR5AU1 | 13730 | 36825 | 59920 |
| OR5B12 | 13731 | 36826 | 59921 |
| OR5B17 | 13732 | 36827 | 59922 |
| OR5B2 | 13733 | 36828 | 59923 |
| OR5B21 | 13734 | 36829 | 59924 |
| OR5B3 | 13735 | 36830 | 59925 |
| OR5C1 | 13736 | 36831 | 59926 |
| OR5D13 | 13737 | 36832 | 59927 |
| OR5D14 | 13738 | 36833 | 59928 |
| OR5D16 | 13739 | 36834 | 59929 |
| OR5D18 | 13740 | 36835 | 59930 |
| OR5F1 | 13741 | 36836 | 59931 |
| OR5H15 | 13742 | 36837 | 59932 |
| OR5H2 | 13743 | 36838 | 59933 |
| OR5H6 | 13744 | 36839 | 59934 |
| OR5I1 | 13745 | 36840 | 59935 |
| OR5J2 | 13746 | 36841 | 59936 |
| OR5K1 | 13747 | 36842 | 59937 |
| OR5K2 | 13748 | 36843 | 59938 |
| OR5K3 | 13749 | 36844 | 59939 |
| OR5K4 | 13750 | 36845 | 59940 |
| OR5L1 | 13751 | 36846 | 59941 |
| OR5L2 | 13752 | 36847 | 59942 |
| OR5M1 | 13753 | 36848 | 59943 |
| OR5M10 | 13754 | 36849 | 59944 |
| OR5M11 | 13755 | 36850 | 59945 |
| OR5M3 | 13756 | 36851 | 59946 |
| OR5M8 | 13757 | 36852 | 59947 |
| OR5M9 | 13758 | 36853 | 59948 |
| OR5P2 | 13759 | 36854 | 59949 |
| OR5R1 | 13760 | 36855 | 59950 |
| OR5T1 | 13761 | 36856 | 59951 |
| OR5T2 | 13762 | 36857 | 59952 |
| OR5T3 | 13763 | 36858 | 59953 |
| OR5V1 | 13764 | 36859 | 59954 |
| OR5W2 | 13765 | 36860 | 59955 |
| OR6A2 | 13766 | 36861 | 59956 |
| OR6B1 | 13767 | 36862 | 59957 |
| OR6B2 | 13768 | 36863 | 59958 |
| OR6B3 | 13769 | 36864 | 59959 |
| OR6C1 | 13770 | 36865 | 59960 |
| OR6C2 | 13771 | 36866 | 59961 |
| OR6C3 | 13772 | 36867 | 59962 |
| OR6C4 | 13773 | 36868 | 59963 |
| OR6C6 | 13774 | 36869 | 59964 |
| OR6C65 | 13775 | 36870 | 59965 |
| OR6C68 | 13776 | 36871 | 59966 |
| OR6C70 | 13777 | 36872 | 59967 |
| OR6C74 | 13778 | 36873 | 59968 |
| OR6C75 | 13779 | 36874 | 59969 |
| OR6C76 | 13780 | 36875 | 59970 |
| OR6F1 | 13781 | 36876 | 59971 |
| OR6J1 | 13782 | 36877 | 59972 |
| OR6K2 | 13783 | 36878 | 59973 |
| OR6K3 | 13784 | 36879 | 59974 |
| OR6K6 | 13785 | 36880 | 59975 |
| OR6M1 | 13786 | 36881 | 59976 |
| OR6N1 | 13787 | 36882 | 59977 |
| OR6N2 | 13788 | 36883 | 59978 |
| OR6P1 | 13789 | 36884 | 59979 |
| OR6Q1 | 13790 | 36885 | 59980 |
| OR6S1 | 13791 | 36886 | 59981 |
| OR6T1 | 13792 | 36887 | 59982 |
| OR6V1 | 13793 | 36888 | 59983 |
| OR6X1 | 13794 | 36889 | 59984 |
| OR6Y1 | 13795 | 36890 | 59985 |
| OR7A10 | 13796 | 36891 | 59986 |
| OR7A17 | 13797 | 36892 | 59987 |
| OR7A5 | 13798 | 36893 | 59988 |
| OR7C1 | 13799 | 36894 | 59989 |
| OR7C2 | 13800 | 36895 | 59990 |
| OR7D2 | 13801 | 36896 | 59991 |
| OR7D4 | 13802 | 36897 | 59992 |
| OR7E24 | 13803 | 36898 | 59993 |
| OR7G1 | 13804 | 36899 | 59994 |
| OR7G2 | 13805 | 36900 | 59995 |
| OR7G3 | 13806 | 36901 | 59996 |
| OR8A1 | 13807 | 36902 | 59997 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| OR8B12 | 13808 | 36903 | 59998 |
| OR8B3 | 13809 | 36904 | 59999 |
| OR8B4 | 13810 | 36905 | 60000 |
| OR8B8 | 13811 | 36906 | 60001 |
| OR8D1 | 13812 | 36907 | 60002 |
| OR8D2 | 13813 | 36908 | 60003 |
| OR8D4 | 13814 | 36909 | 60004 |
| OR8G1 | 13815 | 36910 | 60005 |
| OR8G2P | 13816 | 36911 | 60006 |
| OR8G5 | 13817 | 36912 | 60007 |
| OR8H3 | 13818 | 36913 | 60008 |
| OR8I2 | 13819 | 36914 | 60009 |
| OR8J1 | 13820 | 36915 | 60010 |
| OR8J3 | 13821 | 36916 | 60011 |
| OR8K1 | 13822 | 36917 | 60012 |
| OR8K3 | 13823 | 36918 | 60013 |
| OR8K5 | 13824 | 36919 | 60014 |
| OR8S1 | 13825 | 36920 | 60015 |
| OR8U8 | 13826 | 36921 | 60016 |
| OR8U9 | 13827 | 36922 | 60017 |
| OR9A2 | 13828 | 36923 | 60018 |
| OR9A4 | 13829 | 36924 | 60019 |
| OR9G4 | 13830 | 36925 | 60020 |
| OR9G9 | 13831 | 36926 | 60021 |
| OR9I1 | 13832 | 36927 | 60022 |
| OR9K2 | 13833 | 36928 | 60023 |
| OR9Q1 | 13834 | 36929 | 60024 |
| OR9Q2 | 13835 | 36930 | 60025 |
| ORAI1 | 13836 | 36931 | 60026 |
| ORAI2 | 13837 | 36932 | 60027 |
| ORAI2 | 13838 | 36933 | 60028 |
| ORAI3 | 13839 | 36934 | 60029 |
| ORAOV1 | 13840 | 36935 | 60030 |
| ORC1 | 13841 | 36936 | 60031 |
| ORC2 | 13842 | 36937 | 60032 |
| ORC3 | 13843 | 36938 | 60033 |
| ORC4 | 13844 | 36939 | 60034 |
| ORC5 | 13845 | 36940 | 60035 |
| ORC5 | 13846 | 36941 | 60036 |
| ORC6 | 13847 | 36942 | 60037 |
| ORM2 | 13848 | 36943 | 60038 |
| ORMDL1 | 13849 | 36944 | 60039 |
| ORMDL2 | 13850 | 36945 | 60040 |
| ORMDL3 | 13851 | 36946 | 60041 |
| OS9 | 13852 | 36947 | 60042 |
| OSBP | 13853 | 36948 | 60043 |
| OSBP2 | 13854 | 36949 | 60044 |
| OSBPL10 | 13855 | 36950 | 60045 |
| OSBPL11 | 13856 | 36951 | 60046 |
| OSBPL1A | 13857 | 36952 | 60047 |
| OSBPL2 | 13858 | 36953 | 60048 |
| OSBPL2 | 13859 | 36954 | 60049 |
| OSBPL3 | 13860 | 36955 | 60050 |
| OSBPL5 | 13861 | 36956 | 60051 |
| OSBPL6 | 13862 | 36957 | 60052 |
| OSBPL7 | 13863 | 36958 | 60053 |
| OSBPL8 | 13864 | 36959 | 60054 |
| OSBPL9 | 13865 | 36960 | 60055 |
| OSCAR | 13866 | 36961 | 60056 |
| OSCAR | 13867 | 36962 | 60057 |
| OSCP1 | 13868 | 36963 | 60058 |
| OSCP1 | 13869 | 36964 | 60059 |
| OSER1 | 13870 | 36965 | 60060 |
| OSGEP | 13871 | 36966 | 60061 |
| OSGEPL1 | 13872 | 36967 | 60062 |
| OSGIN1 | 13873 | 36968 | 60063 |
| OSGIN2 | 13874 | 36969 | 60064 |
| OSM | 13875 | 36970 | 60065 |
| OSMR | 13876 | 36971 | 60066 |
| OSMR | 13877 | 36972 | 60067 |
| OSMR | 13878 | 36973 | 60068 |
| OSR1 | 13879 | 36974 | 60069 |
| OSR2 | 13880 | 36975 | 60070 |
| OSR2 | 13881 | 36976 | 60071 |
| OST4 | 13882 | 36977 | 60072 |
| OSTC | 13883 | 36978 | 60073 |
| OSTC | 13884 | 36979 | 60074 |
| OSTC | 13885 | 36980 | 60075 |
| OSTF1 | 13886 | 36981 | 60076 |
| OSTM1 | 13887 | 36982 | 60077 |
| OSTN | 13888 | 36983 | 60078 |
| OTC | 13889 | 36984 | 60079 |
| OTOA | 13890 | 36985 | 60080 |
| OTOF | 13891 | 36986 | 60081 |
| OTOF | 13892 | 36987 | 60082 |
| OTOG | 13893 | 36988 | 60083 |
| OTOGL | 13894 | 36989 | 60084 |
| OTOL1 | 13895 | 36990 | 60085 |
| OTOP1 | 13896 | 36991 | 60086 |
| OTOP2 | 13897 | 36992 | 60087 |
| OTOP3 | 13898 | 36993 | 60088 |
| OTOR | 13899 | 36994 | 60089 |
| OTOS | 13900 | 36995 | 60090 |
| OTP | 13901 | 36996 | 60091 |
| OTUB1 | 13902 | 36997 | 60092 |
| OTUB2 | 13903 | 36998 | 60093 |
| OTUD1 | 13904 | 36999 | 60094 |
| OTUD3 | 13905 | 37000 | 60095 |
| OTUD4 | 13906 | 37001 | 60096 |
| OTUD4 | 13907 | 37002 | 60097 |
| OTUD5 | 13908 | 37003 | 60098 |
| OTUD6A | 13909 | 37004 | 60099 |
| OTUD6B | 13910 | 37005 | 60100 |
| OTUD7A | 13911 | 37006 | 60101 |
| OTUD7A | 13912 | 37007 | 60102 |
| OTUD7B | 13913 | 37008 | 60103 |
| OTULIN | 13914 | 37009 | 60104 |
| OTX1 | 13915 | 37010 | 60105 |
| OTX2 | 13916 | 37011 | 60106 |
| OVCA2 | 13917 | 37012 | 60107 |
| OVCH1 | 13918 | 37013 | 60108 |
| OVCH2 | 13919 | 37014 | 60109 |
| OVGP1 | 13920 | 37015 | 60110 |
| OVOL1 | 13921 | 37016 | 60111 |
| OVOL2 | 13922 | 37017 | 60112 |
| OVOL3 | 13923 | 37018 | 60113 |
| OXA1L | 13924 | 37019 | 60114 |
| OXCT1 | 13925 | 37020 | 60115 |
| OXCT2 | 13926 | 37021 | 60116 |
| OXER1 | 13927 | 37022 | 60117 |
| OXGR1 | 13928 | 37023 | 60118 |
| OXLD1 | 13929 | 37024 | 60119 |
| OXLD1 | 13930 | 37025 | 60120 |
| OXNAD1 | 13931 | 37026 | 60121 |
| OXR1 | 13932 | 37027 | 60122 |
| OXSM | 13933 | 37028 | 60123 |
| OXSR1 | 13934 | 37029 | 60124 |
| OXT | 13935 | 37030 | 60125 |
| OXTR | 13936 | 37031 | 60126 |
| P2RX1 | 13937 | 37032 | 60127 |
| P2RX2 | 13938 | 37033 | 60128 |
| P2RX2 | 13939 | 37034 | 60129 |
| P2RX3 | 13940 | 37035 | 60130 |
| P2RX4 | 13941 | 37036 | 60131 |
| P2RX4 | 13942 | 37037 | 60132 |
| P2RX5 | 13943 | 37038 | 60133 |
| P2RX6 | 13944 | 37039 | 60134 |
| P2RX6 | 13945 | 37040 | 60135 |
| P2RX7 | 13946 | 37041 | 60136 |
| P2RY1 | 13947 | 37042 | 60137 |
| P2RY10 | 13948 | 37043 | 60138 |
| P2RY11 | 13949 | 37044 | 60139 |
| P2RY12 | 13950 | 37045 | 60140 |
| P2RY13 | 13951 | 37046 | 60141 |
| P2RY14 | 13952 | 37047 | 60142 |
| P2RY2 | 13953 | 37048 | 60143 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| P2RY4 | 13954 | 37049 | 60144 |
| P2RY6 | 13955 | 37050 | 60145 |
| P2RY8 | 13956 | 37051 | 60146 |
| P3H1 | 13957 | 37052 | 60147 |
| P3H1 | 13958 | 37053 | 60148 |
| P3H1 | 13959 | 37054 | 60149 |
| P3H2 | 13960 | 37055 | 60150 |
| P3H3 | 13961 | 37056 | 60151 |
| P3H4 | 13962 | 37057 | 60152 |
| P4HA1 | 13963 | 37058 | 60153 |
| P4HA2 | 13964 | 37059 | 60154 |
| P4HA3 | 13965 | 37060 | 60155 |
| P4HA3 | 13966 | 37061 | 60156 |
| P4HB | 13967 | 37062 | 60157 |
| P4HTM | 13968 | 37063 | 60158 |
| PA2G4 | 13969 | 37064 | 60159 |
| PAAF1 | 13970 | 37065 | 60160 |
| PABPC1 | 13971 | 37066 | 60161 |
| PABPC1L | 13972 | 37067 | 60162 |
| PABPC1L2A | 13973 | 37068 | 60163 |
| PABPC3 | 13974 | 37069 | 60164 |
| PABPC4 | 13975 | 37070 | 60165 |
| PABPC4L | 13976 | 37071 | 60166 |
| PABPC5 | 13977 | 37072 | 60167 |
| PABPN1 | 13978 | 37073 | 60168 |
| PABPN1L | 13979 | 37074 | 60169 |
| PABPN1L | 13980 | 37075 | 60170 |
| PACRG | 13981 | 37076 | 60171 |
| PACRGL | 13982 | 37077 | 60172 |
| PACRGL | 13983 | 37078 | 60173 |
| PACS1 | 13984 | 37079 | 60174 |
| PACS2 | 13985 | 37080 | 60175 |
| PACSIN1 | 13986 | 37081 | 60176 |
| PACSIN2 | 13987 | 37082 | 60177 |
| PACSIN3 | 13988 | 37083 | 60178 |
| PADI1 | 13989 | 37084 | 60179 |
| PADI2 | 13990 | 37085 | 60180 |
| PADI3 | 13991 | 37086 | 60181 |
| PADI4 | 13992 | 37087 | 60182 |
| PADI6 | 13993 | 37088 | 60183 |
| PAEP | 13994 | 37089 | 60184 |
| PAEP | 13995 | 37090 | 60185 |
| PAF1 | 13996 | 37091 | 60186 |
| PAF1 | 13997 | 37092 | 60187 |
| PAFAH1B1 | 13998 | 37093 | 60188 |
| PAFAH1B2 | 13999 | 37094 | 60189 |
| PAFAH1B2 | 14000 | 37095 | 60190 |
| PAFAH1B2 | 14001 | 37096 | 60191 |
| PAFAH1B2 | 14002 | 37097 | 60192 |
| PAFAH1B3 | 14003 | 37098 | 60193 |
| PAFAH2 | 14004 | 37099 | 60194 |
| PAG1 | 14005 | 37100 | 60195 |
| PAGE1 | 14006 | 37101 | 60196 |
| PAGE2 | 14007 | 37102 | 60197 |
| PAGE3 | 14008 | 37103 | 60198 |
| PAGE4 | 14009 | 37104 | 60199 |
| PAGE5 | 14010 | 37105 | 60200 |
| PAGR1 | 14011 | 37106 | 60201 |
| PAH | 14012 | 37107 | 60202 |
| PAICS | 14013 | 37108 | 60203 |
| PAIP1 | 14014 | 37109 | 60204 |
| PAIP2 | 14015 | 37110 | 60205 |
| PAIP2B | 14016 | 37111 | 60206 |
| PAK1 | 14017 | 37112 | 60207 |
| PAK1IP1 | 14018 | 37113 | 60208 |
| PAK2 | 14019 | 37114 | 60209 |
| PAK3 | 14020 | 37115 | 60210 |
| PAK4 | 14021 | 37116 | 60211 |
| PAK5 | 14022 | 37117 | 60212 |
| PAK6 | 14023 | 37118 | 60213 |
| PAK6 | 14024 | 37119 | 60214 |
| PALB2 | 14025 | 37120 | 60215 |
| PALD1 | 14026 | 37121 | 60216 |
| PALLD | 14027 | 37122 | 60217 |
| PALLD | 14028 | 37123 | 60218 |
| PALM | 14029 | 37124 | 60219 |
| PALM2 | 14030 | 37125 | 60220 |
| PALM2-AKAP2 | 14031 | 37126 | 60221 |
| PALM3 | 14032 | 37127 | 60222 |
| PALMD | 14033 | 37128 | 60223 |
| PAM | 14034 | 37129 | 60224 |
| PAM16 | 14035 | 37130 | 60225 |
| PAMR1 | 14036 | 37131 | 60226 |
| PAN2 | 14037 | 37132 | 60227 |
| PAN3 | 14038 | 37133 | 60228 |
| PANK1 | 14039 | 37134 | 60229 |
| PANK2 | 14040 | 37135 | 60230 |
| PANK2 | 14041 | 37136 | 60231 |
| PANK3 | 14042 | 37137 | 60232 |
| PANK4 | 14043 | 37138 | 60233 |
| PANO1 | 14044 | 37139 | 60234 |
| PANX1 | 14045 | 37140 | 60235 |
| PANX2 | 14046 | 37141 | 60236 |
| PANX2 | 14047 | 37142 | 60237 |
| PANX3 | 14048 | 37143 | 60238 |
| PAOX | 14049 | 37144 | 60239 |
| PAOX | 14050 | 37145 | 60240 |
| PAOX | 14051 | 37146 | 60241 |
| PAPD4 | 14052 | 37147 | 60242 |
| PAPD5 | 14053 | 37148 | 60243 |
| PAPD7 | 14054 | 37149 | 60244 |
| PAPLN | 14055 | 37150 | 60245 |
| PAPOLA | 14056 | 37151 | 60246 |
| PAPOLA | 14057 | 37152 | 60247 |
| PAPOLA | 14058 | 37153 | 60248 |
| PAPOLB | 14059 | 37154 | 60249 |
| PAPOLG | 14060 | 37155 | 60250 |
| PAPPA | 14061 | 37156 | 60251 |
| PAPPA2 | 14062 | 37157 | 60252 |
| PAPPA2 | 14063 | 37158 | 60253 |
| PAPSS1 | 14064 | 37159 | 60254 |
| PAPSS2 | 14065 | 37160 | 60255 |
| PAQR3 | 14066 | 37161 | 60256 |
| PAQR4 | 14067 | 37162 | 60257 |
| PAQR5 | 14068 | 37163 | 60258 |
| PAQR6 | 14069 | 37164 | 60259 |
| PAQR6 | 14070 | 37165 | 60260 |
| PAQR7 | 14071 | 37166 | 60261 |
| PAQR8 | 14072 | 37167 | 60262 |
| PAQR9 | 14073 | 37168 | 60263 |
| PARD3 | 14074 | 37169 | 60264 |
| PARD3 | 14075 | 37170 | 60265 |
| PARD3B | 14076 | 37171 | 60266 |
| PARD6A | 14077 | 37172 | 60267 |
| PARD6B | 14078 | 37173 | 60268 |
| PARD6G | 14079 | 37174 | 60269 |
| PARG | 14080 | 37175 | 60270 |
| PARK7 | 14081 | 37176 | 60271 |
| PARL | 14082 | 37177 | 60272 |
| PARL | 14083 | 37178 | 60273 |
| PARM1 | 14084 | 37179 | 60274 |
| PARN | 14085 | 37180 | 60275 |
| PARP1 | 14086 | 37181 | 60276 |
| PARP10 | 14087 | 37182 | 60277 |
| PARP11 | 14088 | 37183 | 60278 |
| PARP12 | 14089 | 37184 | 60279 |
| PARP14 | 14090 | 37185 | 60280 |
| PARP15 | 14091 | 37186 | 60281 |
| PARP16 | 14092 | 37187 | 60282 |
| PARP2 | 14093 | 37188 | 60283 |
| PARP3 | 14094 | 37189 | 60284 |
| PARP4 | 14095 | 37190 | 60285 |
| PARP6 | 14096 | 37191 | 60286 |
| PARP8 | 14097 | 37192 | 60287 |
| PARP9 | 14098 | 37193 | 60288 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PARP9 | 14099 | 37194 | 60289 |
| PARPBP | 14100 | 37195 | 60290 |
| PARPBP | 14101 | 37196 | 60291 |
| PARPBP | 14102 | 37197 | 60292 |
| PARS2 | 14103 | 37198 | 60293 |
| PARVA | 14104 | 37199 | 60294 |
| PARVB | 14105 | 37200 | 60295 |
| PARVG | 14106 | 37201 | 60296 |
| PASD1 | 14107 | 37202 | 60297 |
| PASK | 14108 | 37203 | 60298 |
| PASK | 14109 | 37204 | 60299 |
| PATE1 | 14110 | 37205 | 60300 |
| PATE2 | 14111 | 37206 | 60301 |
| PATE3 | 14112 | 37207 | 60302 |
| PATE4 | 14113 | 37208 | 60303 |
| PATJ | 14114 | 37209 | 60304 |
| PATJ | 14115 | 37210 | 60305 |
| PATL1 | 14116 | 37211 | 60306 |
| PATL2 | 14117 | 37212 | 60307 |
| PATZ1 | 14118 | 37213 | 60308 |
| PATZ1 | 14119 | 37214 | 60309 |
| PATZ1 | 14120 | 37215 | 60310 |
| PAWR | 14121 | 37216 | 60311 |
| PAX1 | 14122 | 37217 | 60312 |
| PAX1 | 14123 | 37218 | 60313 |
| PAX2 | 14124 | 37219 | 60314 |
| PAX2 | 14125 | 37220 | 60315 |
| PAX2 | 14126 | 37221 | 60316 |
| PAX3 | 14127 | 37222 | 60317 |
| PAX3 | 14128 | 37223 | 60318 |
| PAX3 | 14129 | 37224 | 60319 |
| PAX3 | 14130 | 37225 | 60320 |
| PAX3 | 14131 | 37226 | 60321 |
| PAX3 | 14132 | 37227 | 60322 |
| PAX4 | 14133 | 37228 | 60323 |
| PAX5 | 14134 | 37229 | 60324 |
| PAX5 | 14135 | 37230 | 60325 |
| PAX6 | 14136 | 37231 | 60326 |
| PAX6 | 14137 | 37232 | 60327 |
| PAX7 | 14138 | 37233 | 60328 |
| PAX7 | 14139 | 37234 | 60329 |
| PAX8 | 14140 | 37235 | 60330 |
| PAX8 | 14141 | 37236 | 60331 |
| PAX9 | 14142 | 37237 | 60332 |
| PAXBP1 | 14143 | 37238 | 60333 |
| PAXBP1 | 14144 | 37239 | 60334 |
| PAXIP1 | 14145 | 37240 | 60335 |
| PAXX | 14146 | 37241 | 60336 |
| PAXX | 14147 | 37242 | 60337 |
| PBDC1 | 14148 | 37243 | 60338 |
| PBDC1 | 14149 | 37244 | 60339 |
| PBK | 14150 | 37245 | 60340 |
| PBLD | 14151 | 37246 | 60341 |
| PBLD | 14152 | 37247 | 60342 |
| PBOV1 | 14153 | 37248 | 60343 |
| PBRM1 | 14154 | 37249 | 60344 |
| PBX1 | 14155 | 37250 | 60345 |
| PBX1 | 14156 | 37251 | 60346 |
| PBX1 | 14157 | 37252 | 60347 |
| PBX2 | 14158 | 37253 | 60348 |
| PBX3 | 14159 | 37254 | 60349 |
| PBX3 | 14160 | 37255 | 60350 |
| PBX4 | 14161 | 37256 | 60351 |
| PBXIP1 | 14162 | 37257 | 60352 |
| PC | 14163 | 37258 | 60353 |
| PCBD1 | 14164 | 37259 | 60354 |
| PCBD1 | 14165 | 37260 | 60355 |
| PCBD2 | 14166 | 37261 | 60356 |
| PCBP1 | 14167 | 37262 | 60357 |
| PCBP2 | 14168 | 37263 | 60358 |
| PCBP3 | 14169 | 37264 | 60359 |
| PCBP4 | 14170 | 37265 | 60360 |
| PCCA | 14171 | 37266 | 60361 |
| PCCA | 14172 | 37267 | 60362 |
| PCCB | 14173 | 37268 | 60363 |
| PCDH1 | 14174 | 37269 | 60364 |
| PCDH1 | 14175 | 37270 | 60365 |
| PCDH10 | 14176 | 37271 | 60366 |
| PCDH10 | 14177 | 37272 | 60367 |
| PCDH11X | 14178 | 37273 | 60368 |
| PCDH11X | 14179 | 37274 | 60369 |
| PCDH11Y | 14180 | 37275 | 60370 |
| PCDH11Y | 14181 | 37276 | 60371 |
| PCDH12 | 14182 | 37277 | 60372 |
| PCDH15 | 14183 | 37278 | 60373 |
| PCDH15 | 14184 | 37279 | 60374 |
| PCDH15 | 14185 | 37280 | 60375 |
| PCDH15 | 14186 | 37281 | 60376 |
| PCDH17 | 14187 | 37282 | 60377 |
| PCDH18 | 14188 | 37283 | 60378 |
| PCDH19 | 14189 | 37284 | 60379 |
| PCDH20 | 14190 | 37285 | 60380 |
| PCDH7 | 14191 | 37286 | 60381 |
| PCDH7 | 14192 | 37287 | 60382 |
| PCDH7 | 14193 | 37288 | 60383 |
| PCDH8 | 14194 | 37289 | 60384 |
| PCDH9 | 14195 | 37290 | 60385 |
| PCDH9 | 14196 | 37291 | 60386 |
| PCDHA1 | 14197 | 37292 | 60387 |
| PCDHA10 | 14198 | 37293 | 60388 |
| PCDHA11 | 14199 | 37294 | 60389 |
| PCDHA12 | 14200 | 37295 | 60390 |
| PCDHA13 | 14201 | 37296 | 60391 |
| PCDHA2 | 14202 | 37297 | 60392 |
| PCDHA2 | 14203 | 37298 | 60393 |
| PCDHA3 | 14204 | 37299 | 60394 |
| PCDHA4 | 14205 | 37300 | 60395 |
| PCDHA5 | 14206 | 37301 | 60396 |
| PCDHA6 | 14207 | 37302 | 60397 |
| PCDHA7 | 14208 | 37303 | 60398 |
| PCDHA8 | 14209 | 37304 | 60399 |
| PCDHA9 | 14210 | 37305 | 60400 |
| PCDHAC1 | 14211 | 37306 | 60401 |
| PCDHAC1 | 14212 | 37307 | 60402 |
| PCDHAC2 | 14213 | 37308 | 60403 |
| PCDHB1 | 14214 | 37309 | 60404 |
| PCDHB10 | 14215 | 37310 | 60405 |
| PCDHB11 | 14216 | 37311 | 60406 |
| PCDHB12 | 14217 | 37312 | 60407 |
| PCDHB13 | 14218 | 37313 | 60408 |
| PCDHB14 | 14219 | 37314 | 60409 |
| PCDHB15 | 14220 | 37315 | 60410 |
| PCDHB16 | 14221 | 37316 | 60411 |
| PCDHB3 | 14222 | 37317 | 60412 |
| PCDHB4 | 14223 | 37318 | 60413 |
| PCDHB5 | 14224 | 37319 | 60414 |
| PCDHB6 | 14225 | 37320 | 60415 |
| PCDHB7 | 14226 | 37321 | 60416 |
| PCDHB8 | 14227 | 37322 | 60417 |
| PCDHB9 | 14228 | 37323 | 60418 |
| PCDHGA1 | 14229 | 37324 | 60419 |
| PCDHGA10 | 14230 | 37325 | 60420 |
| PCDHGA11 | 14231 | 37326 | 60421 |
| PCDHGA12 | 14232 | 37327 | 60422 |
| PCDHGA2 | 14233 | 37328 | 60423 |
| PCDHGA3 | 14234 | 37329 | 60424 |
| PCDHGA3 | 14235 | 37330 | 60425 |
| PCDHGA4 | 14236 | 37331 | 60426 |
| PCDHGA5 | 14237 | 37332 | 60427 |
| PCDHGA6 | 14238 | 37333 | 60428 |
| PCDHGA7 | 14239 | 37334 | 60429 |
| PCDHGA8 | 14240 | 37335 | 60430 |
| PCDHGA9 | 14241 | 37336 | 60431 |
| PCDHGB1 | 14242 | 37337 | 60432 |
| PCDHGB2 | 14243 | 37338 | 60433 |
| PCDHGB3 | 14244 | 37339 | 60434 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PCDHGB4 | 14245 | 37340 | 60435 |
| PCDHGB5 | 14246 | 37341 | 60436 |
| PCDHGB6 | 14247 | 37342 | 60437 |
| PCDHGB7 | 14248 | 37343 | 60438 |
| PCDHGC3 | 14249 | 37344 | 60439 |
| PCDHGC4 | 14250 | 37345 | 60440 |
| PCDHGC5 | 14251 | 37346 | 60441 |
| PCED1A | 14252 | 37347 | 60442 |
| PCED1B | 14253 | 37348 | 60443 |
| PCF11 | 14254 | 37349 | 60444 |
| PCGF1 | 14255 | 37350 | 60445 |
| PCGF2 | 14256 | 37351 | 60446 |
| PCGF3 | 14257 | 37352 | 60447 |
| PCGF5 | 14258 | 37353 | 60448 |
| PCGF6 | 14259 | 37354 | 60449 |
| PCID2 | 14260 | 37355 | 60450 |
| PCID2 | 14261 | 37356 | 60451 |
| PCID2 | 14262 | 37357 | 60452 |
| PCIF1 | 14263 | 37358 | 60453 |
| PCK1 | 14264 | 37359 | 60454 |
| PCK2 | 14265 | 37360 | 60455 |
| PCK2 | 14266 | 37361 | 60456 |
| PCLAF | 14267 | 37362 | 60457 |
| PCLO | 14268 | 37363 | 60458 |
| PCLO | 14269 | 37364 | 60459 |
| PCM1 | 14270 | 37365 | 60460 |
| PCM1 | 14271 | 37366 | 60461 |
| PCM1 | 14272 | 37367 | 60462 |
| PCMT1 | 14273 | 37368 | 60463 |
| PCMT1 | 14274 | 37369 | 60464 |
| PCMTD1 | 14275 | 37370 | 60465 |
| PCMTD2 | 14276 | 37371 | 60466 |
| PCNA | 14277 | 37372 | 60467 |
| PCNP | 14278 | 37373 | 60468 |
| PCNP | 14279 | 37374 | 60469 |
| PCNT | 14280 | 37375 | 60470 |
| PCNX1 | 14281 | 37376 | 60471 |
| PCNX2 | 14282 | 37377 | 60472 |
| PCNX2 | 14283 | 37378 | 60473 |
| PCNX3 | 14284 | 37379 | 60474 |
| PCNX4 | 14285 | 37380 | 60475 |
| PCOLCE | 14286 | 37381 | 60476 |
| PCOLCE2 | 14287 | 37382 | 60477 |
| PCOTH | 14288 | 37383 | 60478 |
| PCP2 | 14289 | 37384 | 60479 |
| PCP4 | 14290 | 37385 | 60480 |
| PCP4L1 | 14291 | 37386 | 60481 |
| PCSK1 | 14292 | 37387 | 60482 |
| PCSK1N | 14293 | 37388 | 60483 |
| PCSK2 | 14294 | 37389 | 60484 |
| PCSK4 | 14295 | 37390 | 60485 |
| PCSK5 | 14296 | 37391 | 60486 |
| PCSK5 | 14297 | 37392 | 60487 |
| PCSK6 | 14298 | 37393 | 60488 |
| PCSK6 | 14299 | 37394 | 60489 |
| PCSK6 | 14300 | 37395 | 60490 |
| PCSK6 | 14301 | 37396 | 60491 |
| PCSK6 | 14302 | 37397 | 60492 |
| PCSK7 | 14303 | 37398 | 60493 |
| PCSK9 | 14304 | 37399 | 60494 |
| PCTP | 14305 | 37400 | 60495 |
| PCTP | 14306 | 37401 | 60496 |
| PCTP | 14307 | 37402 | 60497 |
| PCYOX1 | 14308 | 37403 | 60498 |
| PCYOX1L | 14309 | 37404 | 60499 |
| PCYT1A | 14310 | 37405 | 60500 |
| PCYT1B | 14311 | 37406 | 60501 |
| PCYT1B | 14312 | 37407 | 60502 |
| PCYT2 | 14313 | 37408 | 60503 |
| PDAP1 | 14314 | 37409 | 60504 |
| PDC | 14315 | 37410 | 60505 |
| PDCD1 | 14316 | 37411 | 60506 |
| PDCD10 | 14317 | 37412 | 60507 |
| PDCD11 | 14318 | 37413 | 60508 |
| PDCD1LG2 | 14319 | 37414 | 60509 |
| PDCD2 | 14320 | 37415 | 60510 |
| PDCD2 | 14321 | 37416 | 60511 |
| PDCD2 | 14322 | 37417 | 60512 |
| PDCD2L | 14323 | 37418 | 60513 |
| PDCD4 | 14324 | 37419 | 60514 |
| PDCD5 | 14325 | 37420 | 60515 |
| PDCD6 | 14326 | 37421 | 60516 |
| PDCD6 | 14327 | 37422 | 60517 |
| PDCD6IP | 14328 | 37423 | 60518 |
| PDCD6IP | 14329 | 37424 | 60519 |
| PDCD7 | 14330 | 37425 | 60520 |
| PDCL | 14331 | 37426 | 60521 |
| PDCL2 | 14332 | 37427 | 60522 |
| PDCL3 | 14333 | 37428 | 60523 |
| PDE10A | 14334 | 37429 | 60524 |
| PDE11A | 14335 | 37430 | 60525 |
| PDE12 | 14336 | 37431 | 60526 |
| PDE12 | 14337 | 37432 | 60527 |
| PDE12 | 14338 | 37433 | 60528 |
| PDE1A | 14339 | 37434 | 60529 |
| PDE1A | 14340 | 37435 | 60530 |
| PDE1B | 14341 | 37436 | 60531 |
| PDE1C | 14342 | 37437 | 60532 |
| PDE1C | 14343 | 37438 | 60533 |
| PDE2A | 14344 | 37439 | 60534 |
| PDE3A | 14345 | 37440 | 60535 |
| PDE3B | 14346 | 37441 | 60536 |
| PDE4A | 14347 | 37442 | 60537 |
| PDE4B | 14348 | 37443 | 60538 |
| PDE4C | 14349 | 37444 | 60539 |
| PDE4D | 14350 | 37445 | 60540 |
| PDE4DIP | 14351 | 37446 | 60541 |
| PDE4DIP | 14352 | 37447 | 60542 |
| PDE4DIP | 14353 | 37448 | 60543 |
| PDE4DIP | 14354 | 37449 | 60544 |
| PDE5A | 14355 | 37450 | 60545 |
| PDE6A | 14356 | 37451 | 60546 |
| PDE6B | 14357 | 37452 | 60547 |
| PDE6B | 14358 | 37453 | 60548 |
| PDE6C | 14359 | 37454 | 60549 |
| PDE6D | 14360 | 37455 | 60550 |
| PDE6D | 14361 | 37456 | 60551 |
| PDE6G | 14362 | 37457 | 60552 |
| PDE6H | 14363 | 37458 | 60553 |
| PDE7A | 14364 | 37459 | 60554 |
| PDE7B | 14365 | 37460 | 60555 |
| PDE8A | 14366 | 37461 | 60556 |
| PDE8B | 14367 | 37462 | 60557 |
| PDE8B | 14368 | 37463 | 60558 |
| PDE9A | 14369 | 37464 | 60559 |
| PDF | 14370 | 37465 | 60560 |
| PDGFA | 14371 | 37466 | 60561 |
| PDGFA | 14372 | 37467 | 60562 |
| PDGFB | 14373 | 37468 | 60563 |
| PDGFC | 14374 | 37469 | 60564 |
| PDGFD | 14375 | 37470 | 60565 |
| PDGFRA | 14376 | 37471 | 60566 |
| PDGFRA | 14377 | 37472 | 60567 |
| PDGFRB | 14378 | 37473 | 60568 |
| PDGFRL | 14379 | 37474 | 60569 |
| PDHA1 | 14380 | 37475 | 60570 |
| PDHA2 | 14381 | 37476 | 60571 |
| PDHB | 14382 | 37477 | 60572 |
| PDHX | 14383 | 37478 | 60573 |
| PDIA2 | 14384 | 37479 | 60574 |
| PDIA3 | 14385 | 37480 | 60575 |
| PDIA4 | 14386 | 37481 | 60576 |
| PDIA5 | 14387 | 37482 | 60577 |
| PDIA6 | 14388 | 37483 | 60578 |
| PDIK1L | 14389 | 37484 | 60579 |
| PDILT | 14390 | 37485 | 60580 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PDK1 | 14391 | 37486 | 60581 |
| PDK2 | 14392 | 37487 | 60582 |
| PDK2 | 14393 | 37488 | 60583 |
| PDK3 | 14394 | 37489 | 60584 |
| PDK4 | 14395 | 37490 | 60585 |
| PDLIM1 | 14396 | 37491 | 60586 |
| PDLIM2 | 14397 | 37492 | 60587 |
| PDLIM2 | 14398 | 37493 | 60588 |
| PDLIM2 | 14399 | 37494 | 60589 |
| PDLIM3 | 14400 | 37495 | 60590 |
| PDLIM4 | 14401 | 37496 | 60591 |
| PDLIM4 | 14402 | 37497 | 60592 |
| PDLIM5 | 14403 | 37498 | 60593 |
| PDLIM5 | 14404 | 37499 | 60594 |
| PDLIM5 | 14405 | 37500 | 60595 |
| PDLIM5 | 14406 | 37501 | 60596 |
| PDLIM7 | 14407 | 37502 | 60597 |
| PDLIM7 | 14408 | 37503 | 60598 |
| PDP1 | 14409 | 37504 | 60599 |
| PDP2 | 14410 | 37505 | 60600 |
| PDPK1 | 14411 | 37506 | 60601 |
| PDPK1 | 14412 | 37507 | 60602 |
| PDPN | 14413 | 37508 | 60603 |
| PDPR | 14414 | 37509 | 60604 |
| PDRG1 | 14415 | 37510 | 60605 |
| PDS5A | 14416 | 37511 | 60606 |
| PDS5A | 14417 | 37512 | 60607 |
| PDS5B | 14418 | 37513 | 60608 |
| PDSS1 | 14419 | 37514 | 60609 |
| PDSS1 | 14420 | 37515 | 60610 |
| PDSS2 | 14421 | 37516 | 60611 |
| PDX1 | 14422 | 37517 | 60612 |
| PDXDC1 | 14423 | 37518 | 60613 |
| PDXDC1 | 14424 | 37519 | 60614 |
| PDXDC1 | 14425 | 37520 | 60615 |
| PDXK | 14426 | 37521 | 60616 |
| PDXP | 14427 | 37522 | 60617 |
| PDYN | 14428 | 37523 | 60618 |
| PDZD11 | 14429 | 37524 | 60619 |
| PDZD2 | 14430 | 37525 | 60620 |
| PDZD3 | 14431 | 37526 | 60621 |
| PDZD4 | 14432 | 37527 | 60622 |
| PDZD7 | 14433 | 37528 | 60623 |
| PDZD7 | 14434 | 37529 | 60624 |
| PDZD7 | 14435 | 37530 | 60625 |
| PDZD8 | 14436 | 37531 | 60626 |
| PDZD9 | 14437 | 37532 | 60627 |
| PDZK1 | 14438 | 37533 | 60628 |
| PDZK1IP1 | 14439 | 37534 | 60629 |
| PDZRN3 | 14440 | 37535 | 60630 |
| PDZRN4 | 14441 | 37536 | 60631 |
| PEA15 | 14442 | 37537 | 60632 |
| PEAK1 | 14443 | 37538 | 60633 |
| PEAK3 | 14444 | 37539 | 60634 |
| PEAR1 | 14445 | 37540 | 60635 |
| PEBP1 | 14446 | 37541 | 60636 |
| PEBP4 | 14447 | 37542 | 60637 |
| PECAM1 | 14448 | 37543 | 60638 |
| PECR | 14449 | 37544 | 60639 |
| PEF1 | 14450 | 37545 | 60640 |
| PEG10 | 14451 | 37546 | 60641 |
| PEG10 | 14452 | 37547 | 60642 |
| PEG3 | 14453 | 37548 | 60643 |
| PELI1 | 14454 | 37549 | 60644 |
| PELI2 | 14455 | 37550 | 60645 |
| PELI3 | 14456 | 37551 | 60646 |
| PELO | 14457 | 37552 | 60647 |
| PELP1 | 14458 | 37553 | 60648 |
| PEMT | 14459 | 37554 | 60649 |
| PEMT | 14460 | 37555 | 60650 |
| PENK | 14461 | 37556 | 60651 |
| PEPD | 14462 | 37557 | 60652 |
| PER1 | 14463 | 37558 | 60653 |
| PER2 | 14464 | 37559 | 60654 |
| PER3 | 14465 | 37560 | 60655 |
| PERM1 | 14466 | 37561 | 60656 |
| PERP | 14467 | 37562 | 60657 |
| PES1 | 14468 | 37563 | 60658 |
| PET100 | 14469 | 37564 | 60659 |
| PET117 | 14470 | 37565 | 60660 |
| PEX1 | 14471 | 37566 | 60661 |
| PEX10 | 14472 | 37567 | 60662 |
| PEX11A | 14473 | 37568 | 60663 |
| PEX11B | 14474 | 37569 | 60664 |
| PEX11G | 14475 | 37570 | 60665 |
| PEX12 | 14476 | 37571 | 60666 |
| PEX13 | 14477 | 37572 | 60667 |
| PEX14 | 14478 | 37573 | 60668 |
| PEX16 | 14479 | 37574 | 60669 |
| PEX16 | 14480 | 37575 | 60670 |
| PEX19 | 14481 | 37576 | 60671 |
| PEX2 | 14482 | 37577 | 60672 |
| PEX26 | 14483 | 37578 | 60673 |
| PEX3 | 14484 | 37579 | 60674 |
| PEX5 | 14485 | 37580 | 60675 |
| PEX5L | 14486 | 37581 | 60676 |
| PEX6 | 14487 | 37582 | 60677 |
| PEX7 | 14488 | 37583 | 60678 |
| PF4 | 14489 | 37584 | 60679 |
| PF4V1 | 14490 | 37585 | 60680 |
| PFAS | 14491 | 37586 | 60681 |
| PFDN1 | 14492 | 37587 | 60682 |
| PFDN2 | 14493 | 37588 | 60683 |
| PFDN4 | 14494 | 37589 | 60684 |
| PFDN5 | 14495 | 37590 | 60685 |
| PFDN6 | 14496 | 37591 | 60686 |
| PFKFB1 | 14497 | 37592 | 60687 |
| PFKFB2 | 14498 | 37593 | 60688 |
| PFKFB2 | 14499 | 37594 | 60689 |
| PFKFB3 | 14500 | 37595 | 60690 |
| PFKFB3 | 14501 | 37596 | 60691 |
| PFKFB4 | 14502 | 37597 | 60692 |
| PFKL | 14503 | 37598 | 60693 |
| PFKM | 14504 | 37599 | 60694 |
| PFKP | 14505 | 37600 | 60695 |
| PFN1 | 14506 | 37601 | 60696 |
| PFN2 | 14507 | 37602 | 60697 |
| PFN2 | 14508 | 37603 | 60698 |
| PFN3 | 14509 | 37604 | 60699 |
| PFN4 | 14510 | 37605 | 60700 |
| PGA3 | 14511 | 37606 | 60701 |
| PGA5 | 14512 | 37607 | 60702 |
| PGAM1 | 14513 | 37608 | 60703 |
| PGAM2 | 14514 | 37609 | 60704 |
| PGAM5 | 14515 | 37610 | 60705 |
| PGAM5 | 14516 | 37611 | 60706 |
| PGAP1 | 14517 | 37612 | 60707 |
| PGAP2 | 14518 | 37613 | 60708 |
| PGAP2 | 14519 | 37614 | 60709 |
| PGAP3 | 14520 | 37615 | 60710 |
| PGAP3 | 14521 | 37616 | 60711 |
| PGBD1 | 14522 | 37617 | 60712 |
| PGBD2 | 14523 | 37618 | 60713 |
| PGBD3 | 14524 | 37619 | 60714 |
| PGBD4 | 14525 | 37620 | 60715 |
| PGBD5 | 14526 | 37621 | 60716 |
| PGC | 14527 | 37622 | 60717 |
| PGC | 14528 | 37623 | 60718 |
| PGD | 14529 | 37624 | 60719 |
| PGF | 14530 | 37625 | 60720 |
| PGGHG | 14531 | 37626 | 60721 |
| PGGT1B | 14532 | 37627 | 60722 |
| PGK1 | 14533 | 37628 | 60723 |
| PGK2 | 14534 | 37629 | 60724 |
| PGLS | 14535 | 37630 | 60725 |
| PGLYRP1 | 14536 | 37631 | 60726 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PGLYRP2 | 14537 | 37632 | 60727 |
| PGLYRP3 | 14538 | 37633 | 60728 |
| PGLYRP4 | 14539 | 37634 | 60729 |
| PGM1 | 14540 | 37635 | 60730 |
| PGM2 | 14541 | 37636 | 60731 |
| PGM2L1 | 14542 | 37637 | 60732 |
| PGM3 | 14543 | 37638 | 60733 |
| PGM3 | 14544 | 37639 | 60734 |
| PGM3 | 14545 | 37640 | 60735 |
| PGM5 | 14546 | 37641 | 60736 |
| PGP | 14547 | 37642 | 60737 |
| PGPEP1 | 14548 | 37643 | 60738 |
| PGPEP1 | 14549 | 37644 | 60739 |
| PGPEP1 | 14550 | 37645 | 60740 |
| PGPEP1 | 14551 | 37646 | 60741 |
| PGPEP1L | 14552 | 37647 | 60742 |
| PGR | 14553 | 37648 | 60743 |
| PGRMC1 | 14554 | 37649 | 60744 |
| PGRMC2 | 14555 | 37650 | 60745 |
| PGS1 | 14556 | 37651 | 60746 |
| PHACTR1 | 14557 | 37652 | 60747 |
| PHACTR2 | 14558 | 37653 | 60748 |
| PHACTR3 | 14559 | 37654 | 60749 |
| PHACTR4 | 14560 | 37655 | 60750 |
| PHAX | 14561 | 37656 | 60751 |
| PHB | 14562 | 37657 | 60752 |
| PHB2 | 14563 | 37658 | 60753 |
| PHC1 | 14564 | 37659 | 60754 |
| PHC2 | 14565 | 37660 | 60755 |
| PHC3 | 14566 | 37661 | 60756 |
| PHEX | 14567 | 37662 | 60757 |
| PHEX | 14568 | 37663 | 60758 |
| PHF1 | 14569 | 37664 | 60759 |
| PHF1 | 14570 | 37665 | 60760 |
| PHF10 | 14571 | 37666 | 60761 |
| PHF11 | 14572 | 37667 | 60762 |
| PHF12 | 14573 | 37668 | 60763 |
| PHF12 | 14574 | 37669 | 60764 |
| PHF12 | 14575 | 37670 | 60765 |
| PHF13 | 14576 | 37671 | 60766 |
| PHF14 | 14577 | 37672 | 60767 |
| PHF19 | 14578 | 37673 | 60768 |
| PHF19 | 14579 | 37674 | 60769 |
| PHF19 | 14580 | 37675 | 60770 |
| PHF2 | 14581 | 37676 | 60771 |
| PHF20 | 14582 | 37677 | 60772 |
| PHF20L1 | 14583 | 37678 | 60773 |
| PHF20L1 | 14584 | 37679 | 60774 |
| PHF21A | 14585 | 37680 | 60775 |
| PHF21B | 14586 | 37681 | 60776 |
| PHF23 | 14587 | 37682 | 60777 |
| PHF24 | 14588 | 37683 | 60778 |
| PHF3 | 14589 | 37684 | 60779 |
| PHF3 | 14590 | 37685 | 60780 |
| PHF5A | 14591 | 37686 | 60781 |
| PHF6 | 14592 | 37687 | 60782 |
| PHF6 | 14593 | 37688 | 60783 |
| PHF7 | 14594 | 37689 | 60784 |
| PHF8 | 14595 | 37690 | 60785 |
| PHF8 | 14596 | 37691 | 60786 |
| PHF8 | 14597 | 37692 | 60787 |
| PHGDH | 14598 | 37693 | 60788 |
| PHGR1 | 14599 | 37694 | 60789 |
| PHIP | 14600 | 37695 | 60790 |
| PHKA1 | 14601 | 37696 | 60791 |
| PHKA2 | 14602 | 37697 | 60792 |
| PHKB | 14603 | 37698 | 60793 |
| PHKG1 | 14604 | 37699 | 60794 |
| PHKG2 | 14605 | 37700 | 60795 |
| PHKG2 | 14606 | 37701 | 60796 |
| PHLDA1 | 14607 | 37702 | 60797 |
| PHLDA2 | 14608 | 37703 | 60798 |
| PHLDA3 | 14609 | 37704 | 60799 |
| PHLDB1 | 14610 | 37705 | 60800 |
| PHLDB2 | 14611 | 37706 | 60801 |
| PHLDB3 | 14612 | 37707 | 60802 |
| PHLPP1 | 14613 | 37708 | 60803 |
| PHLPP2 | 14614 | 37709 | 60804 |
| PHOSPHO1 | 14615 | 37710 | 60805 |
| PHOSPHO2 | 14616 | 37711 | 60806 |
| PHOX2A | 14617 | 37712 | 60807 |
| PHOX2B | 14618 | 37713 | 60808 |
| PHPT1 | 14619 | 37714 | 60809 |
| PHPT1 | 14620 | 37715 | 60810 |
| PHRF1 | 14621 | 37716 | 60811 |
| PHTF1 | 14622 | 37717 | 60812 |
| PHTF1 | 14623 | 37718 | 60813 |
| PHTF1 | 14624 | 37719 | 60814 |
| PHTF2 | 14625 | 37720 | 60815 |
| PHTF2 | 14626 | 37721 | 60816 |
| PHYH | 14627 | 37722 | 60817 |
| PHYHD1 | 14628 | 37723 | 60818 |
| PHYHD1 | 14629 | 37724 | 60819 |
| PHYHIP | 14630 | 37725 | 60820 |
| PHYHIPL | 14631 | 37726 | 60821 |
| PHYKPL | 14632 | 37727 | 60822 |
| PI15 | 14633 | 37728 | 60823 |
| PI16 | 14634 | 37729 | 60824 |
| PI3 | 14635 | 37730 | 60825 |
| PI4K2A | 14636 | 37731 | 60826 |
| PI4K2B | 14637 | 37732 | 60827 |
| PI4KA | 14638 | 37733 | 60828 |
| PI4KB | 14639 | 37734 | 60829 |
| PIANP | 14640 | 37735 | 60830 |
| PIANP | 14641 | 37736 | 60831 |
| PIAS1 | 14642 | 37737 | 60832 |
| PIAS2 | 14643 | 37738 | 60833 |
| PIAS2 | 14644 | 37739 | 60834 |
| PIAS2 | 14645 | 37740 | 60835 |
| PIAS2 | 14646 | 37741 | 60836 |
| PIAS2 | 14647 | 37742 | 60837 |
| PIAS3 | 14648 | 37743 | 60838 |
| PIAS4 | 14649 | 37744 | 60839 |
| PIBF1 | 14650 | 37745 | 60840 |
| PICALM | 14651 | 37746 | 60841 |
| PICK1 | 14652 | 37747 | 60842 |
| PID1 | 14653 | 37748 | 60843 |
| PIDD1 | 14654 | 37749 | 60844 |
| PIEZO1 | 14655 | 37750 | 60845 |
| PIEZO2 | 14656 | 37751 | 60846 |
| PIF1 | 14657 | 37752 | 60847 |
| PIF1 | 14658 | 37753 | 60848 |
| PIFO | 14659 | 37754 | 60849 |
| PIGA | 14660 | 37755 | 60850 |
| PIGB | 14661 | 37756 | 60851 |
| PIGBOS1 | 14662 | 37757 | 60852 |
| PIGC | 14663 | 37758 | 60853 |
| PIGF | 14664 | 37759 | 60854 |
| PIGF | 14665 | 37760 | 60855 |
| PIGG | 14666 | 37761 | 60856 |
| PIGG | 14667 | 37762 | 60857 |
| PIGG | 14668 | 37763 | 60858 |
| PIGG | 14669 | 37764 | 60859 |
| PIGG | 14670 | 37765 | 60860 |
| PIGH | 14671 | 37766 | 60861 |
| PIGK | 14672 | 37767 | 60862 |
| PIGL | 14673 | 37768 | 60863 |
| PIGM | 14674 | 37769 | 60864 |
| PIGN | 14675 | 37770 | 60865 |
| PIGO | 14676 | 37771 | 60866 |
| PIGP | 14677 | 37772 | 60867 |
| PIGQ | 14678 | 37773 | 60868 |
| PIGQ | 14679 | 37774 | 60869 |
| PIGR | 14680 | 37775 | 60870 |
| PIGS | 14681 | 37776 | 60871 |
| PIGT | 14682 | 37777 | 60872 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PIGU | 14683 | 37778 | 60873 |
| PIGV | 14684 | 37779 | 60874 |
| PIGW | 14685 | 37780 | 60875 |
| PIGX | 14686 | 37781 | 60876 |
| PIGY | 14687 | 37782 | 60877 |
| PIGZ | 14688 | 37783 | 60878 |
| PIH1D1 | 14689 | 37784 | 60879 |
| PIH1D2 | 14690 | 37785 | 60880 |
| PIH1D2 | 14691 | 37786 | 60881 |
| PIH1D3 | 14692 | 37787 | 60882 |
| PIK3AP1 | 14693 | 37788 | 60883 |
| PIK3C2A | 14694 | 37789 | 60884 |
| PIK3C2B | 14695 | 37790 | 60885 |
| PIK3C2G | 14696 | 37791 | 60886 |
| PIK3C3 | 14697 | 37792 | 60887 |
| PIK3CA | 14698 | 37793 | 60888 |
| PIK3CB | 14699 | 37794 | 60889 |
| PIK3CD | 14700 | 37795 | 60890 |
| PIK3CG | 14701 | 37796 | 60891 |
| PIK3IP1 | 14702 | 37797 | 60892 |
| PIK3IP1 | 14703 | 37798 | 60893 |
| PIK3R1 | 14704 | 37799 | 60894 |
| PIK3R2 | 14705 | 37800 | 60895 |
| PIK3R3 | 14706 | 37801 | 60896 |
| PIK3R4 | 14707 | 37802 | 60897 |
| PIK3R5 | 14708 | 37803 | 60898 |
| PIK3R6 | 14709 | 37804 | 60899 |
| PIKFYVE | 14710 | 37805 | 60900 |
| PIKFYVE | 14711 | 37806 | 60901 |
| PILRA | 14712 | 37807 | 60902 |
| PILRA | 14713 | 37808 | 60903 |
| PILRB | 14714 | 37809 | 60904 |
| PIM1 | 14715 | 37810 | 60905 |
| PIM2 | 14716 | 37811 | 60906 |
| PIM3 | 14717 | 37812 | 60907 |
| PIMREG | 14718 | 37813 | 60908 |
| PIMREG | 14719 | 37814 | 60909 |
| PIN1 | 14720 | 37815 | 60910 |
| PIN4 | 14721 | 37816 | 60911 |
| PIN4 | 14722 | 37817 | 60912 |
| PINK1 | 14723 | 37818 | 60913 |
| PINLYP | 14724 | 37819 | 60914 |
| PINX1 | 14725 | 37820 | 60915 |
| PINX1 | 14726 | 37821 | 60916 |
| PIP | 14727 | 37822 | 60917 |
| PIP4K2A | 14728 | 37823 | 60918 |
| PIP4K2B | 14729 | 37824 | 60919 |
| PIP4K2C | 14730 | 37825 | 60920 |
| PIP4P1 | 14731 | 37826 | 60921 |
| PIP4P2 | 14732 | 37827 | 60922 |
| PIP5K1A | 14733 | 37828 | 60923 |
| PIP5K1B | 14734 | 37829 | 60924 |
| PIP5K1B | 14735 | 37830 | 60925 |
| PIP5K1C | 14736 | 37831 | 60926 |
| PIP5K1C | 14737 | 37832 | 60927 |
| PIP5K1C | 14738 | 37833 | 60928 |
| PIP5KL1 | 14739 | 37834 | 60929 |
| PIPOX | 14740 | 37835 | 60930 |
| PIR | 14741 | 37836 | 60931 |
| PIRT | 14742 | 37837 | 60932 |
| PISD | 14743 | 37838 | 60933 |
| PISD | 14744 | 37839 | 60934 |
| PITHD1 | 14745 | 37840 | 60935 |
| PITPNA | 14746 | 37841 | 60936 |
| PITPNB | 14747 | 37842 | 60937 |
| PITPNB | 14748 | 37843 | 60938 |
| PITPNC1 | 14749 | 37844 | 60939 |
| PITPNC1 | 14750 | 37845 | 60940 |
| PITPNM1 | 14751 | 37846 | 60941 |
| PITPNM2 | 14752 | 37847 | 60942 |
| PITPNM3 | 14753 | 37848 | 60943 |
| PITRM1 | 14754 | 37849 | 60944 |
| PITX1 | 14755 | 37850 | 60945 |
| PITX2 | 14756 | 37851 | 60946 |
| PITX3 | 14757 | 37852 | 60947 |
| PIWIL1 | 14758 | 37853 | 60948 |
| PIWIL1 | 14759 | 37854 | 60949 |
| PIWIL2 | 14760 | 37855 | 60950 |
| PIWIL3 | 14761 | 37856 | 60951 |
| PIWIL4 | 14762 | 37857 | 60952 |
| PJA1 | 14763 | 37858 | 60953 |
| PJA2 | 14764 | 37859 | 60954 |
| PJVK | 14765 | 37860 | 60955 |
| PKD1 | 14766 | 37861 | 60956 |
| PKD1L1 | 14767 | 37862 | 60957 |
| PKD1L2 | 14768 | 37863 | 60958 |
| PKD1L2 | 14769 | 37864 | 60959 |
| PKD1L3 | 14770 | 37865 | 60960 |
| PKD2 | 14771 | 37866 | 60961 |
| PKD2L1 | 14772 | 37867 | 60962 |
| PKD2L2 | 14773 | 37868 | 60963 |
| PKD2L2 | 14774 | 37869 | 60964 |
| PKDCC | 14775 | 37870 | 60965 |
| PKDREJ | 14776 | 37871 | 60966 |
| PKHD1 | 14777 | 37872 | 60967 |
| PKHD1 | 14778 | 37873 | 60968 |
| PKHD1L1 | 14779 | 37874 | 60969 |
| PKIA | 14780 | 37875 | 60970 |
| PKIB | 14781 | 37876 | 60971 |
| PKIB | 14782 | 37877 | 60972 |
| PKIG | 14783 | 37878 | 60973 |
| PKLR | 14784 | 37879 | 60974 |
| PKM | 14785 | 37880 | 60975 |
| PKMYT1 | 14786 | 37881 | 60976 |
| PKMYT1 | 14787 | 37882 | 60977 |
| PKN1 | 14788 | 37883 | 60978 |
| PKN2 | 14789 | 37884 | 60979 |
| PKN3 | 14790 | 37885 | 60980 |
| PKN3 | 14791 | 37886 | 60981 |
| PKNOX1 | 14792 | 37887 | 60982 |
| PKNOX2 | 14793 | 37888 | 60983 |
| PKP1 | 14794 | 37889 | 60984 |
| PKP2 | 14795 | 37890 | 60985 |
| PKP3 | 14796 | 37891 | 60986 |
| PKP4 | 14797 | 37892 | 60987 |
| PKP4 | 14798 | 37893 | 60988 |
| PLA1A | 14799 | 37894 | 60989 |
| PLA2G10 | 14800 | 37895 | 60990 |
| PLA2G12A | 14801 | 37896 | 60991 |
| PLA2G12B | 14802 | 37897 | 60992 |
| PLA2G15 | 14803 | 37898 | 60993 |
| PLA2G16 | 14804 | 37899 | 60994 |
| PLA2G1B | 14805 | 37900 | 60995 |
| PLA2G2A | 14806 | 37901 | 60996 |
| PLA2G2C | 14807 | 37902 | 60997 |
| PLA2G2D | 14808 | 37903 | 60998 |
| PLA2G2D | 14809 | 37904 | 60999 |
| PLA2G2E | 14810 | 37905 | 61000 |
| PLA2G2F | 14811 | 37906 | 61001 |
| PLA2G3 | 14812 | 37907 | 61002 |
| PLA2G4A | 14813 | 37908 | 61003 |
| PLA2G4C | 14814 | 37909 | 61004 |
| PLA2G4C | 14815 | 37910 | 61005 |
| PLA2G4D | 14816 | 37911 | 61006 |
| PLA2G4E | 14817 | 37912 | 61007 |
| PLA2G4F | 14818 | 37913 | 61008 |
| PLA2G5 | 14819 | 37914 | 61009 |
| PLA2G6 | 14820 | 37915 | 61010 |
| PLA2G7 | 14821 | 37916 | 61011 |
| PLA2R1 | 14822 | 37917 | 61012 |
| PLA2R1 | 14823 | 37918 | 61013 |
| PLAA | 14824 | 37919 | 61014 |
| PLAC1 | 14825 | 37920 | 61015 |
| PLAC4 | 14826 | 37921 | 61016 |
| PLAC8 | 14827 | 37922 | 61017 |
| PLAC8L1 | 14828 | 37923 | 61018 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PLAC9 | 14829 | 37924 | 61019 |
| PLAC9 | 14830 | 37925 | 61020 |
| PLAG1 | 14831 | 37926 | 61021 |
| PLAGL1 | 14832 | 37927 | 61022 |
| PLAGL2 | 14833 | 37928 | 61023 |
| PLAT | 14834 | 37929 | 61024 |
| PLAU | 14835 | 37930 | 61025 |
| PLAUR | 14836 | 37931 | 61026 |
| PLAUR | 14837 | 37932 | 61027 |
| PLB1 | 14838 | 37933 | 61028 |
| PLBD1 | 14839 | 37934 | 61029 |
| PLBD2 | 14840 | 37935 | 61030 |
| PLCB1 | 14841 | 37936 | 61031 |
| PLCB1 | 14842 | 37937 | 61032 |
| PLCB2 | 14843 | 37938 | 61033 |
| PLCB2 | 14844 | 37939 | 61034 |
| PLCB3 | 14845 | 37940 | 61035 |
| PLCB4 | 14846 | 37941 | 61036 |
| PLCB4 | 14847 | 37942 | 61037 |
| PLCD1 | 14848 | 37943 | 61038 |
| PLCD3 | 14849 | 37944 | 61039 |
| PLCD4 | 14850 | 37945 | 61040 |
| PLCE1 | 14851 | 37946 | 61041 |
| PLCG1 | 14852 | 37947 | 61042 |
| PLCG2 | 14853 | 37948 | 61043 |
| PLCH1 | 14854 | 37949 | 61044 |
| PLCH1 | 14855 | 37950 | 61045 |
| PLCH2 | 14856 | 37951 | 61046 |
| PLCH2 | 14857 | 37952 | 61047 |
| PLCH2 | 14858 | 37953 | 61048 |
| PLCL1 | 14859 | 37954 | 61049 |
| PLCL2 | 14860 | 37955 | 61050 |
| PLCXD1 | 14861 | 37956 | 61051 |
| PLCXD2 | 14862 | 37957 | 61052 |
| PLCXD2 | 14863 | 37958 | 61053 |
| PLCXD3 | 14864 | 37959 | 61054 |
| PLCZ1 | 14865 | 37960 | 61055 |
| PLD1 | 14866 | 37961 | 61056 |
| PLD2 | 14867 | 37962 | 61057 |
| PLD3 | 14868 | 37963 | 61058 |
| PLD4 | 14869 | 37964 | 61059 |
| PLD5 | 14870 | 37965 | 61060 |
| PLD6 | 14871 | 37966 | 61061 |
| PLEC | 14872 | 37967 | 61062 |
| PLEK | 14873 | 37968 | 61063 |
| PLEK2 | 14874 | 37969 | 61064 |
| PLEKHA1 | 14875 | 37970 | 61065 |
| PLEKHA1 | 14876 | 37971 | 61066 |
| PLEKHA1 | 14877 | 37972 | 61067 |
| PLEKHA2 | 14878 | 37973 | 61068 |
| PLEKHA3 | 14879 | 37974 | 61069 |
| PLEKHA4 | 14880 | 37975 | 61070 |
| PLEKHA4 | 14881 | 37976 | 61071 |
| PLEKHA5 | 14882 | 37977 | 61072 |
| PLEKHA5 | 14883 | 37978 | 61073 |
| PLEKHA6 | 14884 | 37979 | 61074 |
| PLEKHA7 | 14885 | 37980 | 61075 |
| PLEKHA7 | 14886 | 37981 | 61076 |
| PLEKHA8 | 14887 | 37982 | 61077 |
| PLEKHA8 | 14888 | 37983 | 61078 |
| PLEKHA8 | 14889 | 37984 | 61079 |
| PLEKHA8 | 14890 | 37985 | 61080 |
| PLEKHA8 | 14891 | 37986 | 61081 |
| PLEKHB1 | 14892 | 37987 | 61082 |
| PLEKHB2 | 14893 | 37988 | 61083 |
| PLEKHB2 | 14894 | 37989 | 61084 |
| PLEKHD1 | 14895 | 37990 | 61085 |
| PLEKHF1 | 14896 | 37991 | 61086 |
| PLEKHF2 | 14897 | 37992 | 61087 |
| PLEKHG1 | 14898 | 37993 | 61088 |
| PLEKHG1 | 14899 | 37994 | 61089 |
| PLEKHG2 | 14900 | 37995 | 61090 |
| PLEKHG2 | 14901 | 37996 | 61091 |
| PLEKHG3 | 14902 | 37997 | 61092 |
| PLEKHG4 | 14903 | 37998 | 61093 |
| PLEKHG4B | 14904 | 37999 | 61094 |
| PLEKHG5 | 14905 | 38000 | 61095 |
| PLEKHG6 | 14906 | 38001 | 61096 |
| PLEKHG7 | 14907 | 38002 | 61097 |
| PLEKHH1 | 14908 | 38003 | 61098 |
| PLEKHH2 | 14909 | 38004 | 61099 |
| PLEKHH3 | 14910 | 38005 | 61100 |
| PLEKHJ1 | 14911 | 38006 | 61101 |
| PLEKHJ1 | 14912 | 38007 | 61102 |
| PLEKHM1 | 14913 | 38008 | 61103 |
| PLEKHM1 | 14914 | 38009 | 61104 |
| PLEKHM2 | 14915 | 38010 | 61105 |
| PLEKHM3 | 14916 | 38011 | 61106 |
| PLEKHN1 | 14917 | 38012 | 61107 |
| PLEKHO1 | 14918 | 38013 | 61108 |
| PLEKHO2 | 14919 | 38014 | 61109 |
| PLEKHS1 | 14920 | 38015 | 61110 |
| PLEKHS1 | 14921 | 38016 | 61111 |
| PLEKHS1 | 14922 | 38017 | 61112 |
| PLET1 | 14923 | 38018 | 61113 |
| PLG | 14924 | 38019 | 61114 |
| PLGLB2 | 14925 | 38020 | 61115 |
| PLGRKT | 14926 | 38021 | 61116 |
| PLIN1 | 14927 | 38022 | 61117 |
| PLIN2 | 14928 | 38023 | 61118 |
| PLIN3 | 14929 | 38024 | 61119 |
| PLIN4 | 14930 | 38025 | 61120 |
| PLIN5 | 14931 | 38026 | 61121 |
| PLK1 | 14932 | 38027 | 61122 |
| PLK2 | 14933 | 38028 | 61123 |
| PLK3 | 14934 | 38029 | 61124 |
| PLK4 | 14935 | 38030 | 61125 |
| PLK5 | 14936 | 38031 | 61126 |
| PLLP | 14937 | 38032 | 61127 |
| PLN | 14938 | 38033 | 61128 |
| PLOD1 | 14939 | 38034 | 61129 |
| PLOD2 | 14940 | 38035 | 61130 |
| PLOD3 | 14941 | 38036 | 61131 |
| PLP1 | 14942 | 38037 | 61132 |
| PLP2 | 14943 | 38038 | 61133 |
| PLPBP | 14944 | 38039 | 61134 |
| PLPBP | 14945 | 38040 | 61135 |
| PLPP1 | 14946 | 38041 | 61136 |
| PLPP2 | 14947 | 38042 | 61137 |
| PLPP3 | 14948 | 38043 | 61138 |
| PLPP4 | 14949 | 38044 | 61139 |
| PLPP4 | 14950 | 38045 | 61140 |
| PLPP4 | 14951 | 38046 | 61141 |
| PLPP4 | 14952 | 38047 | 61142 |
| PLPP5 | 14953 | 38048 | 61143 |
| PLPP5 | 14954 | 38049 | 61144 |
| PLPP5 | 14955 | 38050 | 61145 |
| PLPP5 | 14956 | 38051 | 61146 |
| PLPP5 | 14957 | 38052 | 61147 |
| PLPP6 | 14958 | 38053 | 61148 |
| PLPP7 | 14959 | 38054 | 61149 |
| PLPPR1 | 14960 | 38055 | 61150 |
| PLPPR2 | 14961 | 38056 | 61151 |
| PLPPR2 | 14962 | 38057 | 61152 |
| PLPPR3 | 14963 | 38058 | 61153 |
| PLPPR4 | 14964 | 38059 | 61154 |
| PLPPR5 | 14965 | 38060 | 61155 |
| PLRG1 | 14966 | 38061 | 61156 |
| PLS1 | 14967 | 38062 | 61157 |
| PLS3 | 14968 | 38063 | 61158 |
| PLSCR1 | 14969 | 38064 | 61159 |
| PLSCR2 | 14970 | 38065 | 61160 |
| PLSCR3 | 14971 | 38066 | 61161 |
| PLSCR4 | 14972 | 38067 | 61162 |
| PLSCR5 | 14973 | 38068 | 61163 |
| PLTP | 14974 | 38069 | 61164 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PLVAP | 14975 | 38070 | 61165 |
| PLXDC1 | 14976 | 38071 | 61166 |
| PLXDC2 | 14977 | 38072 | 61167 |
| PLXNA1 | 14978 | 38073 | 61168 |
| PLXNA2 | 14979 | 38074 | 61169 |
| PLXNA3 | 14980 | 38075 | 61170 |
| PLXNA4 | 14981 | 38076 | 61171 |
| PLXNA4 | 14982 | 38077 | 61172 |
| PLXNA4 | 14983 | 38078 | 61173 |
| PLXNB1 | 14984 | 38079 | 61174 |
| PLXNB2 | 14985 | 38080 | 61175 |
| PLXNB3 | 14986 | 38081 | 61176 |
| PLXNC1 | 14987 | 38082 | 61177 |
| PLXND1 | 14988 | 38083 | 61178 |
| PM20D1 | 14989 | 38084 | 61179 |
| PM20D2 | 14990 | 38085 | 61180 |
| PMAIP1 | 14991 | 38086 | 61181 |
| PMCH | 14992 | 38087 | 61182 |
| PMEL | 14993 | 38088 | 61183 |
| PMEPA1 | 14994 | 38089 | 61184 |
| PMF1 | 14995 | 38090 | 61185 |
| PMF1 | 14996 | 38091 | 61186 |
| PMF1-BGLAP | 14997 | 38092 | 61187 |
| PMF1-BGLAP | 14998 | 38093 | 61188 |
| PMFBP1 | 14999 | 38094 | 61189 |
| PML | 15000 | 38095 | 61190 |
| PML | 15001 | 38096 | 61191 |
| PML | 15002 | 38097 | 61192 |
| PML | 15003 | 38098 | 61193 |
| PML | 15004 | 38099 | 61194 |
| PML | 15005 | 38100 | 61195 |
| PML | 15006 | 38101 | 61196 |
| PMM1 | 15007 | 38102 | 61197 |
| PMM2 | 15008 | 38103 | 61198 |
| PMP2 | 15009 | 38104 | 61199 |
| PMP2 | 15010 | 38105 | 61200 |
| PMP22 | 15011 | 38106 | 61201 |
| PMP22 | 15012 | 38107 | 61202 |
| PMPCA | 15013 | 38108 | 61203 |
| PMPCB | 15014 | 38109 | 61204 |
| PMS1 | 15015 | 38110 | 61205 |
| PMS1 | 15016 | 38111 | 61206 |
| PMS1 | 15017 | 38112 | 61207 |
| PMS2 | 15018 | 38113 | 61208 |
| PMVK | 15019 | 38114 | 61209 |
| PNCK | 15020 | 38115 | 61210 |
| PNISR | 15021 | 38116 | 61211 |
| PNISR | 15022 | 38117 | 61212 |
| PNISR | 15023 | 38118 | 61213 |
| PNISR | 15024 | 38119 | 61214 |
| PNISR | 15025 | 38120 | 61215 |
| PNKD | 15026 | 38121 | 61216 |
| PNKD | 15027 | 38122 | 61217 |
| PNKP | 15028 | 38123 | 61218 |
| PNLDC1 | 15029 | 38124 | 61219 |
| PNLIP | 15030 | 38125 | 61220 |
| PNLIPRP1 | 15031 | 38126 | 61221 |
| PNLIPRP2 | 15032 | 38127 | 61222 |
| PNLIPRP3 | 15033 | 38128 | 61223 |
| PNMA1 | 15034 | 38129 | 61224 |
| PNMA2 | 15035 | 38130 | 61225 |
| PNMA3 | 15036 | 38131 | 61226 |
| PNMA3 | 15037 | 38132 | 61227 |
| PNMA5 | 15038 | 38133 | 61228 |
| PNMA6A | 15039 | 38134 | 61229 |
| PNMA6E | 15040 | 38135 | 61230 |
| PNMA8A | 15041 | 38136 | 61231 |
| PNMA8A | 15042 | 38137 | 61232 |
| PNMA8B | 15043 | 38138 | 61233 |
| PNMT | 15044 | 38139 | 61234 |
| PNN | 15045 | 38140 | 61235 |
| PNO1 | 15046 | 38141 | 61236 |
| PNO1 | 15047 | 38142 | 61237 |
| PNOC | 15048 | 38143 | 61238 |
| PNP | 15049 | 38144 | 61239 |
| PNPLA1 | 15050 | 38145 | 61240 |
| PNPLA2 | 15051 | 38146 | 61241 |
| PNPLA3 | 15052 | 38147 | 61242 |
| PNPLA4 | 15053 | 38148 | 61243 |
| PNPLA5 | 15054 | 38149 | 61244 |
| PNPLA6 | 15055 | 38150 | 61245 |
| PNPLA7 | 15056 | 38151 | 61246 |
| PNPLA8 | 15057 | 38152 | 61247 |
| PNPO | 15058 | 38153 | 61248 |
| PNPT1 | 15059 | 38154 | 61249 |
| PNRC1 | 15060 | 38155 | 61250 |
| PNRC2 | 15061 | 38156 | 61251 |
| POC1A | 15062 | 38157 | 61252 |
| POC1B | 15063 | 38158 | 61253 |
| POC5 | 15064 | 38159 | 61254 |
| PODN | 15065 | 38160 | 61255 |
| PODNL1 | 15066 | 38161 | 61256 |
| PODXL | 15067 | 38162 | 61257 |
| PODXL2 | 15068 | 38163 | 61258 |
| POF1B | 15069 | 38164 | 61259 |
| POF1B | 15070 | 38165 | 61260 |
| POFUT1 | 15071 | 38166 | 61261 |
| POFUT1 | 15072 | 38167 | 61262 |
| POFUT2 | 15073 | 38168 | 61263 |
| POFUT2 | 15074 | 38169 | 61264 |
| POGK | 15075 | 38170 | 61265 |
| POGLUT1 | 15076 | 38171 | 61266 |
| POGZ | 15077 | 38172 | 61267 |
| POLA1 | 15078 | 38173 | 61268 |
| POLA2 | 15079 | 38174 | 61269 |
| POLB | 15080 | 38175 | 61270 |
| POLD1 | 15081 | 38176 | 61271 |
| POLD2 | 15082 | 38177 | 61272 |
| POLD3 | 15083 | 38178 | 61273 |
| POLD4 | 15084 | 38179 | 61274 |
| POLD4 | 15085 | 38180 | 61275 |
| POLDIP2 | 15086 | 38181 | 61276 |
| POLDIP3 | 15087 | 38182 | 61277 |
| POLE | 15088 | 38183 | 61278 |
| POLE2 | 15089 | 38184 | 61279 |
| POLE2 | 15090 | 38185 | 61280 |
| POLE3 | 15091 | 38186 | 61281 |
| POLE4 | 15092 | 38187 | 61282 |
| POLG | 15093 | 38188 | 61283 |
| POLG2 | 15094 | 38189 | 61284 |
| POLH | 15095 | 38190 | 61285 |
| POLH | 15096 | 38191 | 61286 |
| POLI | 15097 | 38192 | 61287 |
| POLI | 15098 | 38193 | 61288 |
| POLK | 15099 | 38194 | 61289 |
| POLL | 15100 | 38195 | 61290 |
| POLM | 15101 | 38196 | 61291 |
| POLM | 15102 | 38197 | 61292 |
| POLN | 15103 | 38198 | 61293 |
| POLQ | 15104 | 38199 | 61294 |
| POLR1A | 15105 | 38200 | 61295 |
| POLR1B | 15106 | 38201 | 61296 |
| POLR1C | 15107 | 38202 | 61297 |
| POLR1C | 15108 | 38203 | 61298 |
| POLR1D | 15109 | 38204 | 61299 |
| POLR1D | 15110 | 38205 | 61300 |
| POLR1E | 15111 | 38206 | 61301 |
| POLR2A | 15112 | 38207 | 61302 |
| POLR2B | 15113 | 38208 | 61303 |
| POLR2C | 15114 | 38209 | 61304 |
| POLR2D | 15115 | 38210 | 61305 |
| POLR2E | 15116 | 38211 | 61306 |
| POLR2E | 15117 | 38212 | 61307 |
| POLR2F | 15118 | 38213 | 61308 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| POLR2F | 15119 | 38214 | 61309 |
| POLR2F | 15120 | 38215 | 61310 |
| POLR2G | 15121 | 38216 | 61311 |
| POLR2H | 15122 | 38217 | 61312 |
| POLR2H | 15123 | 38218 | 61313 |
| POLR2H | 15124 | 38219 | 61314 |
| POLR2H | 15125 | 38220 | 61315 |
| POLR2H | 15126 | 38221 | 61316 |
| POLR2I | 15127 | 38222 | 61317 |
| POLR2J | 15128 | 38223 | 61318 |
| POLR2J2 | 15129 | 38224 | 61319 |
| POLR2K | 15130 | 38225 | 61320 |
| POLR2L | 15131 | 38226 | 61321 |
| POLR2M | 15132 | 38227 | 61322 |
| POLR3A | 15133 | 38228 | 61323 |
| POLR3B | 15134 | 38229 | 61324 |
| POLR3C | 15135 | 38230 | 61325 |
| POLR3D | 15136 | 38231 | 61326 |
| POLR3E | 15137 | 38232 | 61327 |
| POLR3F | 15138 | 38233 | 61328 |
| POLR3G | 15139 | 38234 | 61329 |
| POLR3GL | 15140 | 38235 | 61330 |
| POLR3H | 15141 | 38236 | 61331 |
| POLR3K | 15142 | 38237 | 61332 |
| POLRMT | 15143 | 38238 | 61333 |
| POM121 | 15144 | 38239 | 61334 |
| POM121C | 15145 | 38240 | 61335 |
| POM121L12 | 15146 | 38241 | 61336 |
| POM121L2 | 15147 | 38242 | 61337 |
| POMC | 15148 | 38243 | 61338 |
| POMGNT1 | 15149 | 38244 | 61339 |
| POMGNT1 | 15150 | 38245 | 61340 |
| POMGNT2 | 15151 | 38246 | 61341 |
| POMK | 15152 | 38247 | 61342 |
| POMP | 15153 | 38248 | 61343 |
| POMT1 | 15154 | 38249 | 61344 |
| POMT2 | 15155 | 38250 | 61345 |
| POMZP3 | 15156 | 38251 | 61346 |
| POMZP3 | 15157 | 38252 | 61347 |
| PON1 | 15158 | 38253 | 61348 |
| PON2 | 15159 | 38254 | 61349 |
| PON3 | 15160 | 38255 | 61350 |
| POP1 | 15161 | 38256 | 61351 |
| POP3 | 15162 | 38257 | 61352 |
| POP4 | 15163 | 38258 | 61353 |
| POP5 | 15164 | 38259 | 61354 |
| POP7 | 15165 | 38260 | 61355 |
| POPDC2 | 15166 | 38261 | 61356 |
| POPDC2 | 15167 | 38262 | 61357 |
| POPDC3 | 15168 | 38263 | 61358 |
| POR | 15169 | 38264 | 61359 |
| PORCN | 15170 | 38265 | 61360 |
| POSTN | 15171 | 38266 | 61361 |
| POT1 | 15172 | 38267 | 61362 |
| POTEA | 15173 | 38268 | 61363 |
| POTEB3 | 15174 | 38269 | 61364 |
| POTEC | 15175 | 38270 | 61365 |
| POTEF | 15176 | 38271 | 61366 |
| POTEI | 15177 | 38272 | 61367 |
| POTEM | 15178 | 38273 | 61368 |
| POU1F1 | 15179 | 38274 | 61369 |
| POU2AF1 | 15180 | 38275 | 61370 |
| POU2F1 | 15181 | 38276 | 61371 |
| POU2F2 | 15182 | 38277 | 61372 |
| POU2F2 | 15183 | 38278 | 61373 |
| POU2F2 | 15184 | 38279 | 61374 |
| POU2F3 | 15185 | 38280 | 61375 |
| POU3F1 | 15186 | 38281 | 61376 |
| POU3F2 | 15187 | 38282 | 61377 |
| POU3F3 | 15188 | 38283 | 61378 |
| POU3F4 | 15189 | 38284 | 61379 |
| POU4F1 | 15190 | 38285 | 61380 |
| POU4F2 | 15191 | 38286 | 61381 |
| POU4F3 | 15192 | 38287 | 61382 |
| POU5F1 | 15193 | 38288 | 61383 |
| POU5F2 | 15194 | 38289 | 61384 |
| POU6F1 | 15195 | 38290 | 61385 |
| POU6F1 | 15196 | 38291 | 61386 |
| POU6F2 | 15197 | 38292 | 61387 |
| PP2D1 | 15198 | 38293 | 61388 |
| PPA1 | 15199 | 38294 | 61389 |
| PPA2 | 15200 | 38295 | 61390 |
| PPAN | 15201 | 38296 | 61391 |
| PPAN-P2RY11 | 15202 | 38297 | 61392 |
| PPARA | 15203 | 38298 | 61393 |
| PPARD | 15204 | 38299 | 61394 |
| PPARD | 15205 | 38300 | 61395 |
| PPARG | 15206 | 38301 | 61396 |
| PPARG | 15207 | 38302 | 61397 |
| PPARGC1A | 15208 | 38303 | 61398 |
| PPARGC1B | 15209 | 38304 | 61399 |
| PPAT | 15210 | 38305 | 61400 |
| PPBP | 15211 | 38306 | 61401 |
| PPCDC | 15212 | 38307 | 61402 |
| PPCDC | 15213 | 38308 | 61403 |
| PPCS | 15214 | 38309 | 61404 |
| PPCS | 15215 | 38310 | 61405 |
| PPCS | 15216 | 38311 | 61406 |
| PPDPF | 15217 | 38312 | 61407 |
| PPDPF | 15218 | 38313 | 61408 |
| PPDPFL | 15219 | 38314 | 61409 |
| PPDPFL | 15220 | 38315 | 61410 |
| PPEF1 | 15221 | 38316 | 61411 |
| PPEF2 | 15222 | 38317 | 61412 |
| PPFIA1 | 15223 | 38318 | 61413 |
| PPFIA1 | 15224 | 38319 | 61414 |
| PPFIA2 | 15225 | 38320 | 61415 |
| PPFIA2 | 15226 | 38321 | 61416 |
| PPFIA3 | 15227 | 38322 | 61417 |
| PPFIA4 | 15228 | 38323 | 61418 |
| PPFIBP1 | 15229 | 38324 | 61419 |
| PPFIBP2 | 15230 | 38325 | 61420 |
| PPFIBP2 | 15231 | 38326 | 61421 |
| PPFIBP2 | 15232 | 38327 | 61422 |
| PPHLN1 | 15233 | 38328 | 61423 |
| PPHLN1 | 15234 | 38329 | 61424 |
| PPHLN1 | 15235 | 38330 | 61425 |
| PPIA | 15236 | 38331 | 61426 |
| PPIAL4F | 15237 | 38332 | 61427 |
| PPIB | 15238 | 38333 | 61428 |
| PPIC | 15239 | 38334 | 61429 |
| PPID | 15240 | 38335 | 61430 |
| PPIE | 15241 | 38336 | 61431 |
| PPIE | 15242 | 38337 | 61432 |
| PPIE | 15243 | 38338 | 61433 |
| PPIF | 15244 | 38339 | 61434 |
| PPIG | 15245 | 38340 | 61435 |
| PPIH | 15246 | 38341 | 61436 |
| PPIL1 | 15247 | 38342 | 61437 |
| PPIL2 | 15248 | 38343 | 61438 |
| PPIL2 | 15249 | 38344 | 61439 |
| PPIL2 | 15250 | 38345 | 61440 |
| PPIL3 | 15251 | 38346 | 61441 |
| PPIL4 | 15252 | 38347 | 61442 |
| PPIL6 | 15253 | 38348 | 61443 |
| PPIL6 | 15254 | 38349 | 61444 |
| PPIP5K1 | 15255 | 38350 | 61445 |
| PPIP5K2 | 15256 | 38351 | 61446 |
| PPL | 15257 | 38352 | 61447 |
| PPM1A | 15258 | 38353 | 61448 |
| PPM1A | 15259 | 38354 | 61449 |
| PPM1B | 15260 | 38355 | 61450 |
| PPM1B | 15261 | 38356 | 61451 |
| PPM1B | 15262 | 38357 | 61452 |
| PPM1D | 15263 | 38358 | 61453 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PPM1E | 15264 | 38359 | 61454 |
| PPM1F | 15265 | 38360 | 61455 |
| PPM1G | 15266 | 38361 | 61456 |
| PPM1H | 15267 | 38362 | 61457 |
| PPM1J | 15268 | 38363 | 61458 |
| PPM1K | 15269 | 38364 | 61459 |
| PPM1L | 15270 | 38365 | 61460 |
| PPM1M | 15271 | 38366 | 61461 |
| PPM1N | 15272 | 38367 | 61462 |
| PPME1 | 15273 | 38368 | 61463 |
| PPOX | 15274 | 38369 | 61464 |
| PPP1CA | 15275 | 38370 | 61465 |
| PPP1CB | 15276 | 38371 | 61466 |
| PPP1CC | 15277 | 38372 | 61467 |
| PPP1CC | 15278 | 38373 | 61468 |
| PPP1R10 | 15279 | 38374 | 61469 |
| PPP1R11 | 15280 | 38375 | 61470 |
| PPP1R12A | 15281 | 38376 | 61471 |
| PPP1R12B | 15282 | 38377 | 61472 |
| PPP1R12B | 15283 | 38378 | 61473 |
| PPP1R12B | 15284 | 38379 | 61474 |
| PPP1R12B | 15285 | 38380 | 61475 |
| PPP1R12C | 15286 | 38381 | 61476 |
| PPP1R13B | 15287 | 38382 | 61477 |
| PPP1R13L | 15288 | 38383 | 61478 |
| PPP1R14A | 15289 | 38384 | 61479 |
| PPP1R14C | 15290 | 38385 | 61480 |
| PPP1R14D | 15291 | 38386 | 61481 |
| PPP1R14D | 15292 | 38387 | 61482 |
| PPP1R15A | 15293 | 38388 | 61483 |
| PPP1R15B | 15294 | 38389 | 61484 |
| PPP1R16A | 15295 | 38390 | 61485 |
| PPP1R16B | 15296 | 38391 | 61486 |
| PPP1R17 | 15297 | 38392 | 61487 |
| PPP1R18 | 15298 | 38393 | 61488 |
| PPP1R1A | 15299 | 38394 | 61489 |
| PPP1R1B | 15300 | 38395 | 61490 |
| PPP1R1C | 15301 | 38396 | 61491 |
| PPP1R1C | 15302 | 38397 | 61492 |
| PPP1R2 | 15303 | 38398 | 61493 |
| PPP1R21 | 15304 | 38399 | 61494 |
| PPP1R26 | 15305 | 38400 | 61495 |
| PPP1R27 | 15306 | 38401 | 61496 |
| PPP1R2P9 | 15307 | 38402 | 61497 |
| PPP1R32 | 15308 | 38403 | 61498 |
| PPP1R35 | 15309 | 38404 | 61499 |
| PPP1R35 | 15310 | 38405 | 61500 |
| PPP1R36 | 15311 | 38406 | 61501 |
| PPP1R37 | 15312 | 38407 | 61502 |
| PPP1R3A | 15313 | 38408 | 61503 |
| PPP1R3B | 15314 | 38409 | 61504 |
| PPP1R3C | 15315 | 38410 | 61505 |
| PPP1R3D | 15316 | 38411 | 61506 |
| PPP1R3E | 15317 | 38412 | 61507 |
| PPP1R3F | 15318 | 38413 | 61508 |
| PPP1R3G | 15319 | 38414 | 61509 |
| PPP1R42 | 15320 | 38415 | 61510 |
| PPP1R42 | 15321 | 38416 | 61511 |
| PPP1R7 | 15322 | 38417 | 61512 |
| PPP1R7 | 15323 | 38418 | 61513 |
| PPP1R8 | 15324 | 38419 | 61514 |
| PPP1R9A | 15325 | 38420 | 61515 |
| PPP1R9B | 15326 | 38421 | 61516 |
| PPP2CA | 15327 | 38422 | 61517 |
| PPP2CB | 15328 | 38423 | 61518 |
| PPP2R1A | 15329 | 38424 | 61519 |
| PPP2R1B | 15330 | 38425 | 61520 |
| PPP2R1B | 15331 | 38426 | 61521 |
| PPP2R2A | 15332 | 38427 | 61522 |
| PPP2R2B | 15333 | 38428 | 61523 |
| PPP2R2C | 15334 | 38429 | 61524 |
| PPP2R2D | 15335 | 38430 | 61525 |
| PPP2R3A | 15336 | 38431 | 61526 |
| PPP2R3B | 15337 | 38432 | 61527 |
| PPP2R3C | 15338 | 38433 | 61528 |
| PPP2R5A | 15339 | 38434 | 61529 |
| PPP2R5B | 15340 | 38435 | 61530 |
| PPP2R5C | 15341 | 38436 | 61531 |
| PPP2R5C | 15342 | 38437 | 61532 |
| PPP2R5D | 15343 | 38438 | 61533 |
| PPP2R5E | 15344 | 38439 | 61534 |
| PPP3CA | 15345 | 38440 | 61535 |
| PPP3CB | 15346 | 38441 | 61536 |
| PPP3CB | 15347 | 38442 | 61537 |
| PPP3CC | 15348 | 38443 | 61538 |
| PPP3R1 | 15349 | 38444 | 61539 |
| PPP3R2 | 15350 | 38445 | 61540 |
| PPP4C | 15351 | 38446 | 61541 |
| PPP4R1 | 15352 | 38447 | 61542 |
| PPP4R2 | 15353 | 38448 | 61543 |
| PPP4R2 | 15354 | 38449 | 61544 |
| PPP4R3A | 15355 | 38450 | 61545 |
| PPP4R3B | 15356 | 38451 | 61546 |
| PPP4R3CP | 15357 | 38452 | 61547 |
| PPP4R4 | 15358 | 38453 | 61548 |
| PPP4R4 | 15359 | 38454 | 61549 |
| PPP4R4 | 15360 | 38455 | 61550 |
| PPP5C | 15361 | 38456 | 61551 |
| PPP5D1 | 15362 | 38457 | 61552 |
| PPP6C | 15363 | 38458 | 61553 |
| PPP6R1 | 15364 | 38459 | 61554 |
| PPP6R2 | 15365 | 38460 | 61555 |
| PPP6R2 | 15366 | 38461 | 61556 |
| PPP6R3 | 15367 | 38462 | 61557 |
| PPP6R3 | 15368 | 38463 | 61558 |
| PPRC1 | 15369 | 38464 | 61559 |
| PPT1 | 15370 | 38465 | 61560 |
| PPT2 | 15371 | 38466 | 61561 |
| PPTC7 | 15372 | 38467 | 61562 |
| PPWD1 | 15373 | 38468 | 61563 |
| PPY | 15374 | 38469 | 61564 |
| PQBP1 | 15375 | 38470 | 61565 |
| PQLC1 | 15376 | 38471 | 61566 |
| PQLC1 | 15377 | 38472 | 61567 |
| PQLC2 | 15378 | 38473 | 61568 |
| PQLC2L | 15379 | 38474 | 61569 |
| PQLC2L | 15380 | 38475 | 61570 |
| PQLC2L | 15381 | 38476 | 61571 |
| PQLC2L | 15382 | 38477 | 61572 |
| PQLC3 | 15383 | 38478 | 61573 |
| PQLC3 | 15384 | 38479 | 61574 |
| PQLC3 | 15385 | 38480 | 61575 |
| PRAC1 | 15386 | 38481 | 61576 |
| PRAC2 | 15387 | 38482 | 61577 |
| PRADC1 | 15388 | 38483 | 61578 |
| PRAF2 | 15389 | 38484 | 61579 |
| PRAG1 | 15390 | 38485 | 61580 |
| PRAM1 | 15391 | 38486 | 61581 |
| FRAME | 15392 | 38487 | 61582 |
| PRAMEF1 | 15393 | 38488 | 61583 |
| PRAMEF10 | 15394 | 38489 | 61584 |
| PRAMEF12 | 15395 | 38490 | 61585 |
| PRAMEF17 | 15396 | 38491 | 61586 |
| PRAMEF18 | 15397 | 38492 | 61587 |
| PRAMEF19 | 15398 | 38493 | 61588 |
| PRAMEF20 | 15399 | 38494 | 61589 |
| PRAMEF22 | 15400 | 38495 | 61590 |
| PRAMEF25 | 15401 | 38496 | 61591 |
| PRAMEF5 | 15402 | 38497 | 61592 |
| PRAMEF8 | 15403 | 38498 | 61593 |
| PRAP1 | 15404 | 38499 | 61594 |
| PRB1 | 15405 | 38500 | 61595 |
| PRB3 | 15406 | 38501 | 61596 |
| PRB4 | 15407 | 38502 | 61597 |
| PRC1 | 15408 | 38503 | 61598 |
| PRC1 | 15409 | 38504 | 61599 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PRCC | 15410 | 38505 | 61600 |
| PRCD | 15411 | 38506 | 61601 |
| PRCP | 15412 | 38507 | 61602 |
| PRDM1 | 15413 | 38508 | 61603 |
| PRDM10 | 15414 | 38509 | 61604 |
| PRDM11 | 15415 | 38510 | 61605 |
| PRDM11 | 15416 | 38511 | 61606 |
| PRDM12 | 15417 | 38512 | 61607 |
| PRDM13 | 15418 | 38513 | 61608 |
| PRDM14 | 15419 | 38514 | 61609 |
| PRDM15 | 15420 | 38515 | 61610 |
| PRDM16 | 15421 | 38516 | 61611 |
| PRDM2 | 15422 | 38517 | 61612 |
| PRDM2 | 15423 | 38518 | 61613 |
| PRDM2 | 15424 | 38519 | 61614 |
| PRDM4 | 15425 | 38520 | 61615 |
| PRDM5 | 15426 | 38521 | 61616 |
| PRDM5 | 15427 | 38522 | 61617 |
| PRDM6 | 15428 | 38523 | 61618 |
| PRDM7 | 15429 | 38524 | 61619 |
| PRDM8 | 15430 | 38525 | 61620 |
| PRDM9 | 15431 | 38526 | 61621 |
| PRDX1 | 15432 | 38527 | 61622 |
| PRDX2 | 15433 | 38528 | 61623 |
| PRDX3 | 15434 | 38529 | 61624 |
| PRDX4 | 15435 | 38530 | 61625 |
| PRDX5 | 15436 | 38531 | 61626 |
| PRDX6 | 15437 | 38532 | 61627 |
| PREB | 15438 | 38533 | 61628 |
| PREB | 15439 | 38534 | 61629 |
| PRELID1 | 15440 | 38535 | 61630 |
| PRELID2 | 15441 | 38536 | 61631 |
| PRELID3A | 15442 | 38537 | 61632 |
| PRELID3B | 15443 | 38538 | 61633 |
| PRELP | 15444 | 38539 | 61634 |
| PREP | 15445 | 38540 | 61635 |
| PREPL | 15446 | 38541 | 61636 |
| PREX1 | 15447 | 38542 | 61637 |
| PREX2 | 15448 | 38543 | 61638 |
| PREX2 | 15449 | 38544 | 61639 |
| PRF1 | 15450 | 38545 | 61640 |
| PRG2 | 15451 | 38546 | 61641 |
| PRG3 | 15452 | 38547 | 61642 |
| PRG4 | 15453 | 38548 | 61643 |
| PRH2 | 15454 | 38549 | 61644 |
| PRICKLE1 | 15455 | 38550 | 61645 |
| PRICKLE2 | 15456 | 38551 | 61646 |
| PRICKLE3 | 15457 | 38552 | 61647 |
| PRICKLE4 | 15458 | 38553 | 61648 |
| PRIM1 | 15459 | 38554 | 61649 |
| PRIM2 | 15460 | 38555 | 61650 |
| PRIM2 | 15461 | 38556 | 61651 |
| PRIMA1 | 15462 | 38557 | 61652 |
| PRIMPOL | 15463 | 38558 | 61653 |
| PRKAA1 | 15464 | 38559 | 61654 |
| PRKAA2 | 15465 | 38560 | 61655 |
| PRKAB1 | 15466 | 38561 | 61656 |
| PRKAB2 | 15467 | 38562 | 61657 |
| PRKACA | 15468 | 38563 | 61658 |
| PRKACB | 15469 | 38564 | 61659 |
| PRKACB | 15470 | 38565 | 61660 |
| PRKAG1 | 15471 | 38566 | 61661 |
| PRKAG2 | 15472 | 38567 | 61662 |
| PRKAG3 | 15473 | 38568 | 61663 |
| PRKAR1A | 15474 | 38569 | 61664 |
| PRKAR1A | 15475 | 38570 | 61665 |
| PRKAR1B | 15476 | 38571 | 61666 |
| PRKAR2A | 15477 | 38572 | 61667 |
| PRKAR2A | 15478 | 38573 | 61668 |
| PRKAR2B | 15479 | 38574 | 61669 |
| PRKCA | 15480 | 38575 | 61670 |
| PRKCB | 15481 | 38576 | 61671 |
| PRKCB | 15482 | 38577 | 61672 |
| PRKCD | 15483 | 38578 | 61673 |
| PRKCE | 15484 | 38579 | 61674 |
| PRKCG | 15485 | 38580 | 61675 |
| PRKCG | 15486 | 38581 | 61676 |
| PRKCH | 15487 | 38582 | 61677 |
| PRKCI | 15488 | 38583 | 61678 |
| PRKCQ | 15489 | 38584 | 61679 |
| PRKCQ | 15490 | 38585 | 61680 |
| PRKCSH | 15491 | 38586 | 61681 |
| PRKCZ | 15492 | 38587 | 61682 |
| PRKD1 | 15493 | 38588 | 61683 |
| PRKD2 | 15494 | 38589 | 61684 |
| PRKD3 | 15495 | 38590 | 61685 |
| PRKDC | 15496 | 38591 | 61686 |
| PRKG1 | 15497 | 38592 | 61687 |
| PRKG2 | 15498 | 38593 | 61688 |
| PRKN | 15499 | 38594 | 61689 |
| PRKRA | 15500 | 38595 | 61690 |
| PRKRIP1 | 15501 | 38596 | 61691 |
| PRKX | 15502 | 38597 | 61692 |
| PRL | 15503 | 38598 | 61693 |
| PRLH | 15504 | 38599 | 61694 |
| PRLHR | 15505 | 38600 | 61695 |
| PRLR | 15506 | 38601 | 61696 |
| PRLR | 15507 | 38602 | 61697 |
| PRLR | 15508 | 38603 | 61698 |
| PRLR | 15509 | 38604 | 61699 |
| PRM1 | 15510 | 38605 | 61700 |
| PRM2 | 15511 | 38606 | 61701 |
| PRM2 | 15512 | 38607 | 61702 |
| PRM2 | 15513 | 38608 | 61703 |
| PRM2 | 15514 | 38609 | 61704 |
| PRM3 | 15515 | 38610 | 61705 |
| PRMT1 | 15516 | 38611 | 61706 |
| PRMT2 | 15517 | 38612 | 61707 |
| PRMT2 | 15518 | 38613 | 61708 |
| PRMT2 | 15519 | 38614 | 61709 |
| PRMT2 | 15520 | 38615 | 61710 |
| PRMT3 | 15521 | 38616 | 61711 |
| PRMT5 | 15522 | 38617 | 61712 |
| PRMT6 | 15523 | 38618 | 61713 |
| PRMT7 | 15524 | 38619 | 61714 |
| PRMT7 | 15525 | 38620 | 61715 |
| PRMT8 | 15526 | 38621 | 61716 |
| PRMT9 | 15527 | 38622 | 61717 |
| PRND | 15528 | 38623 | 61718 |
| PRNP | 15529 | 38624 | 61719 |
| PROB1 | 15530 | 38625 | 61720 |
| PROC | 15531 | 38626 | 61721 |
| PROCA1 | 15532 | 38627 | 61722 |
| PROCR | 15533 | 38628 | 61723 |
| PRODH | 15534 | 38629 | 61724 |
| PRODH2 | 15535 | 38630 | 61725 |
| PROK1 | 15536 | 38631 | 61726 |
| PROK2 | 15537 | 38632 | 61727 |
| PROKR1 | 15538 | 38633 | 61728 |
| PROKR2 | 15539 | 38634 | 61729 |
| PROM1 | 15540 | 38635 | 61730 |
| PROM2 | 15541 | 38636 | 61731 |
| PROP1 | 15542 | 38637 | 61732 |
| PRORY | 15543 | 38638 | 61733 |
| PROS1 | 15544 | 38639 | 61734 |
| PROSER1 | 15545 | 38640 | 61735 |
| PROSER2 | 15546 | 38641 | 61736 |
| PROSER3 | 15547 | 38642 | 61737 |
| PROX1 | 15548 | 38643 | 61738 |
| PROX2 | 15549 | 38644 | 61739 |
| PROZ | 15550 | 38645 | 61740 |
| PRPF18 | 15551 | 38646 | 61741 |
| PRPF19 | 15552 | 38647 | 61742 |
| PRPF3 | 15553 | 38648 | 61743 |
| PRPF3 | 15554 | 38649 | 61744 |
| PRPF3 | 15555 | 38650 | 61745 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PRPF3 | 15556 | 38651 | 61746 |
| PRPF31 | 15557 | 38652 | 61747 |
| PRPF38A | 15558 | 38653 | 61748 |
| PRPF38B | 15559 | 38654 | 61749 |
| PRPF39 | 15560 | 38655 | 61750 |
| PRPF4 | 15561 | 38656 | 61751 |
| PRPF4 | 15562 | 38657 | 61752 |
| PRPF40A | 15563 | 38658 | 61753 |
| PRPF40B | 15564 | 38659 | 61754 |
| PRPF4B | 15565 | 38660 | 61755 |
| PRPF6 | 15566 | 38661 | 61756 |
| PRPF8 | 15567 | 38662 | 61757 |
| PRPH | 15568 | 38663 | 61758 |
| PRPH2 | 15569 | 38664 | 61759 |
| PRPS1 | 15570 | 38665 | 61760 |
| PRPS1L1 | 15571 | 38666 | 61761 |
| PRPS2 | 15572 | 38667 | 61762 |
| PRPSAP1 | 15573 | 38668 | 61763 |
| PRPSAP2 | 15574 | 38669 | 61764 |
| PRR11 | 15575 | 38670 | 61765 |
| PRR12 | 15576 | 38671 | 61766 |
| PRR13 | 15577 | 38672 | 61767 |
| PRR14 | 15578 | 38673 | 61768 |
| PRR14L | 15579 | 38674 | 61769 |
| PRR15 | 15580 | 38675 | 61770 |
| PRR15L | 15581 | 38676 | 61771 |
| PRR16 | 15582 | 38677 | 61772 |
| PRR18 | 15583 | 38678 | 61773 |
| PRR19 | 15584 | 38679 | 61774 |
| PRR20E | 15585 | 38680 | 61775 |
| PRR22 | 15586 | 38681 | 61776 |
| PRR23A | 15587 | 38682 | 61777 |
| PRR23B | 15588 | 38683 | 61778 |
| PRR23C | 15589 | 38684 | 61779 |
| PRR23D2 | 15590 | 38685 | 61780 |
| PRR25 | 15591 | 38686 | 61781 |
| PRR27 | 15592 | 38687 | 61782 |
| PRR29 | 15593 | 38688 | 61783 |
| PRR29 | 15594 | 38689 | 61784 |
| PRR29 | 15595 | 38690 | 61785 |
| PRR3 | 15596 | 38691 | 61786 |
| PRR30 | 15597 | 38692 | 61787 |
| PRR31 | 15598 | 38693 | 61788 |
| PRR32 | 15599 | 38694 | 61789 |
| PRR34 | 15600 | 38695 | 61790 |
| PRR35 | 15601 | 38696 | 61791 |
| PRR36 | 15602 | 38697 | 61792 |
| PRR4 | 15603 | 38698 | 61793 |
| PRR4 | 15604 | 38699 | 61794 |
| PRR5 | 15605 | 38700 | 61795 |
| PRR5L | 15606 | 38701 | 61796 |
| PRR5L | 15607 | 38702 | 61797 |
| PRR7 | 15608 | 38703 | 61798 |
| PRR9 | 15609 | 38704 | 61799 |
| PRRC1 | 15610 | 38705 | 61800 |
| PRRC1 | 15611 | 38706 | 61801 |
| PRRC2A | 15612 | 38707 | 61802 |
| PRRC2B | 15613 | 38708 | 61803 |
| PRRC2C | 15614 | 38709 | 61804 |
| PRRG1 | 15615 | 38710 | 61805 |
| PRRG1 | 15616 | 38711 | 61806 |
| PRRG2 | 15617 | 38712 | 61807 |
| PRRG3 | 15618 | 38713 | 61808 |
| PRRG4 | 15619 | 38714 | 61809 |
| PRRT1 | 15620 | 38715 | 61810 |
| PRRT2 | 15621 | 38716 | 61811 |
| PRRT2 | 15622 | 38717 | 61812 |
| PRRT2 | 15623 | 38718 | 61813 |
| PRRT3 | 15624 | 38719 | 61814 |
| PRRT3 | 15625 | 38720 | 61815 |
| PRRT4 | 15626 | 38721 | 61816 |
| PRRT4 | 15627 | 38722 | 61817 |
| PRRX1 | 15628 | 38723 | 61818 |
| PRRX1 | 15629 | 38724 | 61819 |
| PRRX2 | 15630 | 38725 | 61820 |
| PRSS1 | 15631 | 38726 | 61821 |
| PRSS12 | 15632 | 38727 | 61822 |
| PRSS16 | 15633 | 38728 | 61823 |
| PRSS2 | 15634 | 38729 | 61824 |
| PRSS21 | 15635 | 38730 | 61825 |
| PRSS21 | 15636 | 38731 | 61826 |
| PRSS22 | 15637 | 38732 | 61827 |
| PRSS23 | 15638 | 38733 | 61828 |
| PRSS27 | 15639 | 38734 | 61829 |
| PRSS3 | 15640 | 38735 | 61830 |
| PRSS33 | 15641 | 38736 | 61831 |
| PRSS35 | 15642 | 38737 | 61832 |
| PRSS36 | 15643 | 38738 | 61833 |
| PRSS37 | 15644 | 38739 | 61834 |
| PRSS38 | 15645 | 38740 | 61835 |
| PRSS41 | 15646 | 38741 | 61836 |
| PRSS42 | 15647 | 38742 | 61837 |
| PRSS45 | 15648 | 38743 | 61838 |
| PRSS47 | 15649 | 38744 | 61839 |
| PRSS48 | 15650 | 38745 | 61840 |
| PRSS48 | 15651 | 38746 | 61841 |
| PRSS50 | 15652 | 38747 | 61842 |
| PRSS53 | 15653 | 38748 | 61843 |
| PRSS54 | 15654 | 38749 | 61844 |
| PRSS55 | 15655 | 38750 | 61845 |
| PRSS55 | 15656 | 38751 | 61846 |
| PRSS56 | 15657 | 38752 | 61847 |
| PRSS57 | 15658 | 38753 | 61848 |
| PRSS58 | 15659 | 38754 | 61849 |
| PRSS8 | 15660 | 38755 | 61850 |
| PRTFDC1 | 15661 | 38756 | 61851 |
| PRTFDC1 | 15662 | 38757 | 61852 |
| PRTG | 15663 | 38758 | 61853 |
| PRTN3 | 15664 | 38759 | 61854 |
| PRUNE1 | 15665 | 38760 | 61855 |
| PRUNE2 | 15666 | 38761 | 61856 |
| PRX | 15667 | 38762 | 61857 |
| PRY | 15668 | 38763 | 61858 |
| PSAP | 15669 | 38764 | 61859 |
| PSAPL1 | 15670 | 38765 | 61860 |
| PSAT1 | 15671 | 38766 | 61861 |
| PSCA | 15672 | 38767 | 61862 |
| PSD | 15673 | 38768 | 61863 |
| PSD2 | 15674 | 38769 | 61864 |
| PSD3 | 15675 | 38770 | 61865 |
| PSD4 | 15676 | 38771 | 61866 |
| PSEN1 | 15677 | 38772 | 61867 |
| PSEN2 | 15678 | 38773 | 61868 |
| PSENEN | 15679 | 38774 | 61869 |
| PSG1 | 15680 | 38775 | 61870 |
| PSG1 | 15681 | 38776 | 61871 |
| PSG1 | 15682 | 38777 | 61872 |
| PSG11 | 15683 | 38778 | 61873 |
| PSG2 | 15684 | 38779 | 61874 |
| PSG3 | 15685 | 38780 | 61875 |
| PSG4 | 15686 | 38781 | 61876 |
| PSG5 | 15687 | 38782 | 61877 |
| PSG6 | 15688 | 38783 | 61878 |
| PSG6 | 15689 | 38784 | 61879 |
| PSG7 | 15690 | 38785 | 61880 |
| PSG8 | 15691 | 38786 | 61881 |
| PSG8 | 15692 | 38787 | 61882 |
| PSG9 | 15693 | 38788 | 61883 |
| PSIP1 | 15694 | 38789 | 61884 |
| PSIP1 | 15695 | 38790 | 61885 |
| PSKH1 | 15696 | 38791 | 61886 |
| PSKH2 | 15697 | 38792 | 61887 |
| PSMA1 | 15698 | 38793 | 61888 |
| PSMA1 | 15699 | 38794 | 61889 |
| PSMA2 | 15700 | 38795 | 61890 |
| PSMA3 | 15701 | 38796 | 61891 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PSMA4 | 15702 | 38797 | 61892 |
| PSMA4 | 15703 | 38798 | 61893 |
| PSMA5 | 15704 | 38799 | 61894 |
| PSMA6 | 15705 | 38800 | 61895 |
| PSMA7 | 15706 | 38801 | 61896 |
| PSMA8 | 15707 | 38802 | 61897 |
| PSMB1 | 15708 | 38803 | 61898 |
| PSMB10 | 15709 | 38804 | 61899 |
| PSMB11 | 15710 | 38805 | 61900 |
| PSMB2 | 15711 | 38806 | 61901 |
| PSMB3 | 15712 | 38807 | 61902 |
| PSMB4 | 15713 | 38808 | 61903 |
| PSMB5 | 15714 | 38809 | 61904 |
| PSMB5 | 15715 | 38810 | 61905 |
| PSMB6 | 15716 | 38811 | 61906 |
| PSMB6 | 15717 | 38812 | 61907 |
| PSMB7 | 15718 | 38813 | 61908 |
| PSMB8 | 15719 | 38814 | 61909 |
| PSMB9 | 15720 | 38815 | 61910 |
| PSMC1 | 15721 | 38816 | 61911 |
| PSMC2 | 15722 | 38817 | 61912 |
| PSMC2 | 15723 | 38818 | 61913 |
| PSMC3 | 15724 | 38819 | 61914 |
| PSMC3IP | 15725 | 38820 | 61915 |
| PSMC4 | 15726 | 38821 | 61916 |
| PSMC5 | 15727 | 38822 | 61917 |
| PSMC6 | 15728 | 38823 | 61918 |
| PSMD1 | 15729 | 38824 | 61919 |
| PSMD10 | 15730 | 38825 | 61920 |
| PSMD10 | 15731 | 38826 | 61921 |
| PSMD11 | 15732 | 38827 | 61922 |
| PSMD11 | 15733 | 38828 | 61923 |
| PSMD12 | 15734 | 38829 | 61924 |
| PSMD13 | 15735 | 38830 | 61925 |
| PSMD14 | 15736 | 38831 | 61926 |
| PSMD2 | 15737 | 38832 | 61927 |
| PSMD3 | 15738 | 38833 | 61928 |
| PSMD4 | 15739 | 38834 | 61929 |
| PSMD5 | 15740 | 38835 | 61930 |
| PSMD6 | 15741 | 38836 | 61931 |
| PSMD7 | 15742 | 38837 | 61932 |
| PSMD8 | 15743 | 38838 | 61933 |
| PSMD9 | 15744 | 38839 | 61934 |
| PSME1 | 15745 | 38840 | 61935 |
| PSME1 | 15746 | 38841 | 61936 |
| PSME1 | 15747 | 38842 | 61937 |
| PSME2 | 15748 | 38843 | 61938 |
| PSME3 | 15749 | 38844 | 61939 |
| PSME4 | 15750 | 38845 | 61940 |
| PSMF1 | 15751 | 38846 | 61941 |
| PSMF1 | 15752 | 38847 | 61942 |
| PSMF1 | 15753 | 38848 | 61943 |
| PSMF1 | 15754 | 38849 | 61944 |
| PSMG1 | 15755 | 38850 | 61945 |
| PSMG2 | 15756 | 38851 | 61946 |
| PSMG3 | 15757 | 38852 | 61947 |
| PSMG4 | 15758 | 38853 | 61948 |
| PSMG4 | 15759 | 38854 | 61949 |
| PSORS1C1 | 15760 | 38855 | 61950 |
| PSORS1C2 | 15761 | 38856 | 61951 |
| PSPC1 | 15762 | 38857 | 61952 |
| PSPH | 15763 | 38858 | 61953 |
| PSPN | 15764 | 38859 | 61954 |
| PSRC1 | 15765 | 38860 | 61955 |
| PSTK | 15766 | 38861 | 61956 |
| PSTPIP1 | 15767 | 38862 | 61957 |
| PSTPIP2 | 15768 | 38863 | 61958 |
| PTAFR | 15769 | 38864 | 61959 |
| PTAR1 | 15770 | 38865 | 61960 |
| PTBP1 | 15771 | 38866 | 61961 |
| PTBP2 | 15772 | 38867 | 61962 |
| PTBP3 | 15773 | 38868 | 61963 |
| PTBP3 | 15774 | 38869 | 61964 |
| PTCD1 | 15775 | 38870 | 61965 |
| PTCD2 | 15776 | 38871 | 61966 |
| PTCD3 | 15777 | 38872 | 61967 |
| PTCH1 | 15778 | 38873 | 61968 |
| PTCH2 | 15779 | 38874 | 61969 |
| PTCH2 | 15780 | 38875 | 61970 |
| PTCHD1 | 15781 | 38876 | 61971 |
| PTCHD3 | 15782 | 38877 | 61972 |
| PTCHD4 | 15783 | 38878 | 61973 |
| PTCHD4 | 15784 | 38879 | 61974 |
| PTCRA | 15785 | 38880 | 61975 |
| PTDSS1 | 15786 | 38881 | 61976 |
| PTDSS2 | 15787 | 38882 | 61977 |
| PTEN | 15788 | 38883 | 61978 |
| PTER | 15789 | 38884 | 61979 |
| PTF1A | 15790 | 38885 | 61980 |
| PTGDR | 15791 | 38886 | 61981 |
| PTGDR | 15792 | 38887 | 61982 |
| PTGDR2 | 15793 | 38888 | 61983 |
| PTGDS | 15794 | 38889 | 61984 |
| PTGER1 | 15795 | 38890 | 61985 |
| PTGER2 | 15796 | 38891 | 61986 |
| PTGER3 | 15797 | 38892 | 61987 |
| PTGER3 | 15798 | 38893 | 61988 |
| PTGER3 | 15799 | 38894 | 61989 |
| PTGER3 | 15800 | 38895 | 61990 |
| PTGER3 | 15801 | 38896 | 61991 |
| PTGER4 | 15802 | 38897 | 61992 |
| PTGES | 15803 | 38898 | 61993 |
| PTGES2 | 15804 | 38899 | 61994 |
| PTGES3 | 15805 | 38900 | 61995 |
| PTGES3L | 15806 | 38901 | 61996 |
| PTGFR | 15807 | 38902 | 61997 |
| PTGFR | 15808 | 38903 | 61998 |
| PTGFRN | 15809 | 38904 | 61999 |
| PTGIR | 15810 | 38905 | 62000 |
| PTGIS | 15811 | 38906 | 62001 |
| PTGR1 | 15812 | 38907 | 62002 |
| PTGR1 | 15813 | 38908 | 62003 |
| PTGR2 | 15814 | 38909 | 62004 |
| PTGS1 | 15815 | 38910 | 62005 |
| PTGS2 | 15816 | 38911 | 62006 |
| PTH | 15817 | 38912 | 62007 |
| PTH1R | 15818 | 38913 | 62008 |
| PTH2 | 15819 | 38914 | 62009 |
| PTH2R | 15820 | 38915 | 62010 |
| PTHLH | 15821 | 38916 | 62011 |
| PTHLH | 15822 | 38917 | 62012 |
| PTK2 | 15823 | 38918 | 62013 |
| PTK2 | 15824 | 38919 | 62014 |
| PTK2B | 15825 | 38920 | 62015 |
| PTK6 | 15826 | 38921 | 62016 |
| PTK7 | 15827 | 38922 | 62017 |
| PTMA | 15828 | 38923 | 62018 |
| PTMS | 15829 | 38924 | 62019 |
| PTN | 15830 | 38925 | 62020 |
| PTOV1 | 15831 | 38926 | 62021 |
| PTOV1 | 15832 | 38927 | 62022 |
| PTP4A1 | 15833 | 38928 | 62023 |
| PTP4A2 | 15834 | 38929 | 62024 |
| PTP4A2 | 15835 | 38930 | 62025 |
| PTP4A3 | 15836 | 38931 | 62026 |
| PTPA | 15837 | 38932 | 62027 |
| PTPDC1 | 15838 | 38933 | 62028 |
| PTPMT1 | 15839 | 38934 | 62029 |
| PTPMT1 | 15840 | 38935 | 62030 |
| PTPN1 | 15841 | 38936 | 62031 |
| PTPN11 | 15842 | 38937 | 62032 |
| PTPN11 | 15843 | 38938 | 62033 |
| PTPN12 | 15844 | 38939 | 62034 |
| PTPN13 | 15845 | 38940 | 62035 |
| PTPN14 | 15846 | 38941 | 62036 |
| PTPN18 | 15847 | 38942 | 62037 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| PTPN2 | 15848 | 38943 | 62038 |
| PTPN2 | 15849 | 38944 | 62039 |
| PTPN20 | 15850 | 38945 | 62040 |
| PTPN20 | 15851 | 38946 | 62041 |
| PTPN20 | 15852 | 38947 | 62042 |
| PTPN20 | 15853 | 38948 | 62043 |
| PTPN20 | 15854 | 38949 | 62044 |
| PTPN21 | 15855 | 38950 | 62045 |
| PTPN22 | 15856 | 38951 | 62046 |
| PTPN23 | 15857 | 38952 | 62047 |
| PTPN3 | 15858 | 38953 | 62048 |
| PTPN4 | 15859 | 38954 | 62049 |
| PTPN5 | 15860 | 38955 | 62050 |
| PTPN6 | 15861 | 38956 | 62051 |
| PTPN6 | 15862 | 38957 | 62052 |
| PTPN7 | 15863 | 38958 | 62053 |
| PTPN9 | 15864 | 38959 | 62054 |
| PTPRA | 15865 | 38960 | 62055 |
| PTPRB | 15866 | 38961 | 62056 |
| PTPRC | 15867 | 38962 | 62057 |
| PTPRC | 15868 | 38963 | 62058 |
| PTPRCAP | 15869 | 38964 | 62059 |
| PTPRD | 15870 | 38965 | 62060 |
| PTPRE | 15871 | 38966 | 62061 |
| PTPRF | 15872 | 38967 | 62062 |
| PTPRG | 15873 | 38968 | 62063 |
| PTPRH | 15874 | 38969 | 62064 |
| PTPRJ | 15875 | 38970 | 62065 |
| PTPRJ | 15876 | 38971 | 62066 |
| PTPRK | 15877 | 38972 | 62067 |
| PTPRK | 15878 | 38973 | 62068 |
| PTPRM | 15879 | 38974 | 62069 |
| PTPRN | 15880 | 38975 | 62070 |
| PTPRN2 | 15881 | 38976 | 62071 |
| PTPRO | 15882 | 38977 | 62072 |
| PTPRQ | 15883 | 38978 | 62073 |
| PTPRR | 15884 | 38979 | 62074 |
| PTPRS | 15885 | 38980 | 62075 |
| PTPRT | 15886 | 38981 | 62076 |
| PTPRU | 15887 | 38982 | 62077 |
| PTPRZ1 | 15888 | 38983 | 62078 |
| PTRH1 | 15889 | 38984 | 62079 |
| PTRH1 | 15890 | 38985 | 62080 |
| PTRH2 | 15891 | 38986 | 62081 |
| PTRH2 | 15892 | 38987 | 62082 |
| PTRHD1 | 15893 | 38988 | 62083 |
| PTS | 15894 | 38989 | 62084 |
| PTTG1 | 15895 | 38990 | 62085 |
| PTTG1IP | 15896 | 38991 | 62086 |
| PTTG1IP | 15897 | 38992 | 62087 |
| PTTG2 | 15898 | 38993 | 62088 |
| PTX3 | 15899 | 38994 | 62089 |
| PTX4 | 15900 | 38995 | 62090 |
| PUDP | 15901 | 38996 | 62091 |
| PUDP | 15902 | 38997 | 62092 |
| PUF60 | 15903 | 38998 | 62093 |
| PUM1 | 15904 | 38999 | 62094 |
| PUM2 | 15905 | 39000 | 62095 |
| PUM3 | 15906 | 39001 | 62096 |
| PURA | 15907 | 39002 | 62097 |
| PURB | 15908 | 39003 | 62098 |
| PURG | 15909 | 39004 | 62099 |
| PURG | 15910 | 39005 | 62100 |
| PUS1 | 15911 | 39006 | 62101 |
| PUS10 | 15912 | 39007 | 62102 |
| PUS3 | 15913 | 39008 | 62103 |
| PUS7 | 15914 | 39009 | 62104 |
| PUS7L | 15915 | 39010 | 62105 |
| PUSL1 | 15916 | 39011 | 62106 |
| PVALB | 15917 | 39012 | 62107 |
| PVR | 15918 | 39013 | 62108 |
| PVR | 15919 | 39014 | 62109 |
| PVRIG | 15920 | 39015 | 62110 |
| PWP1 | 15921 | 39016 | 62111 |
| PWP2 | 15922 | 39017 | 62112 |
| PWWP2A | 15923 | 39018 | 62113 |
| PWWP2A | 15924 | 39019 | 62114 |
| PWWP2A | 15925 | 39020 | 62115 |
| PWWP2B | 15926 | 39021 | 62116 |
| PWWP2B | 15927 | 39022 | 62117 |
| PXDC1 | 15928 | 39023 | 62118 |
| PXDN | 15929 | 39024 | 62119 |
| PXDNL | 15930 | 39025 | 62120 |
| PXK | 15931 | 39026 | 62121 |
| PXK | 15932 | 39027 | 62122 |
| PXK | 15933 | 39028 | 62123 |
| PXK | 15934 | 39029 | 62124 |
| PXMP2 | 15935 | 39030 | 62125 |
| PXMP4 | 15936 | 39031 | 62126 |
| PXMP4 | 15937 | 39032 | 62127 |
| PXN | 15938 | 39033 | 62128 |
| PXT1 | 15939 | 39034 | 62129 |
| PXYLP1 | 15940 | 39035 | 62130 |
| PYCARD | 15941 | 39036 | 62131 |
| PYCR1 | 15942 | 39037 | 62132 |
| PYCR1 | 15943 | 39038 | 62133 |
| PYCR1 | 15944 | 39039 | 62134 |
| PYCR2 | 15945 | 39040 | 62135 |
| PYCR3 | 15946 | 39041 | 62136 |
| PYDC1 | 15947 | 39042 | 62137 |
| PYDC2 | 15948 | 39043 | 62138 |
| PYGB | 15949 | 39044 | 62139 |
| PYGL | 15950 | 39045 | 62140 |
| PYGM | 15951 | 39046 | 62141 |
| PYGO1 | 15952 | 39047 | 62142 |
| PYGO2 | 15953 | 39048 | 62143 |
| PYHIN1 | 15954 | 39049 | 62144 |
| PYHIN1 | 15955 | 39050 | 62145 |
| PYM1 | 15956 | 39051 | 62146 |
| PYROXD1 | 15957 | 39052 | 62147 |
| PYROXD2 | 15958 | 39053 | 62148 |
| PYY | 15959 | 39054 | 62149 |
| PZP | 15960 | 39055 | 62150 |
| QARS | 15961 | 39056 | 62151 |
| QDPR | 15962 | 39057 | 62152 |
| QKI | 15963 | 39058 | 62153 |
| QKI | 15964 | 39059 | 62154 |
| QKI | 15965 | 39060 | 62155 |
| QKI | 15966 | 39061 | 62156 |
| QPCT | 15967 | 39062 | 62157 |
| QPCTL | 15968 | 39063 | 62158 |
| QPRT | 15969 | 39064 | 62159 |
| QRFP | 15970 | 39065 | 62160 |
| QRFPR | 15971 | 39066 | 62161 |
| QRICH1 | 15972 | 39067 | 62162 |
| QRICH2 | 15973 | 39068 | 62163 |
| QRSL1 | 15974 | 39069 | 62164 |
| QSER1 | 15975 | 39070 | 62165 |
| QSOX1 | 15976 | 39071 | 62166 |
| QSOX1 | 15977 | 39072 | 62167 |
| QSOX2 | 15978 | 39073 | 62168 |
| QTRT1 | 15979 | 39074 | 62169 |
| QTRT2 | 15980 | 39075 | 62170 |
| R3HCC1 | 15981 | 39076 | 62171 |
| R3HCC1L | 15982 | 39077 | 62172 |
| R3HDM1 | 15983 | 39078 | 62173 |
| R3HDM2 | 15984 | 39079 | 62174 |
| R3HDM4 | 15985 | 39080 | 62175 |
| R3HDML | 15986 | 39081 | 62176 |
| RAB10 | 15987 | 39082 | 62177 |
| RAB11A | 15988 | 39083 | 62178 |
| RAB11A | 15989 | 39084 | 62179 |
| RAB11B | 15990 | 39085 | 62180 |
| RAB11FIP1 | 15991 | 39086 | 62181 |
| RAB11FIP2 | 15992 | 39087 | 62182 |
| RAB11FIP3 | 15993 | 39088 | 62183 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| RAB11FIP4 | 15994 | 39089 | 62184 |
| RAB11FIP5 | 15995 | 39090 | 62185 |
| RAB12 | 15996 | 39091 | 62186 |
| RAB13 | 15997 | 39092 | 62187 |
| RAB14 | 15998 | 39093 | 62188 |
| RAB15 | 15999 | 39094 | 62189 |
| RAB15 | 16000 | 39095 | 62190 |
| RAB17 | 16001 | 39096 | 62191 |
| RAB18 | 16002 | 39097 | 62192 |
| RAB18 | 16003 | 39098 | 62193 |
| RAB19 | 16004 | 39099 | 62194 |
| RAB1A | 16005 | 39100 | 62195 |
| RAB1B | 16006 | 39101 | 62196 |
| RAB20 | 16007 | 39102 | 62197 |
| RAB21 | 16008 | 39103 | 62198 |
| RAB22A | 16009 | 39104 | 62199 |
| RAB23 | 16010 | 39105 | 62200 |
| RAB24 | 16011 | 39106 | 62201 |
| RAB25 | 16012 | 39107 | 62202 |
| RAB26 | 16013 | 39108 | 62203 |
| RAB27A | 16014 | 39109 | 62204 |
| RAB27B | 16015 | 39110 | 62205 |
| RAB28 | 16016 | 39111 | 62206 |
| RAB28 | 16017 | 39112 | 62207 |
| RAB28 | 16018 | 39113 | 62208 |
| RAB29 | 16019 | 39114 | 62209 |
| RAB2A | 16020 | 39115 | 62210 |
| RAB2B | 16021 | 39116 | 62211 |
| RAB30 | 16022 | 39117 | 62212 |
| RAB31 | 16023 | 39118 | 62213 |
| RAB32 | 16024 | 39119 | 62214 |
| RAB33A | 16025 | 39120 | 62215 |
| RAB33B | 16026 | 39121 | 62216 |
| RAB34 | 16027 | 39122 | 62217 |
| RAB34 | 16028 | 39123 | 62218 |
| RAB35 | 16029 | 39124 | 62219 |
| RAB36 | 16030 | 39125 | 62220 |
| RAB36 | 16031 | 39126 | 62221 |
| RAB37 | 16032 | 39127 | 62222 |
| RAB38 | 16033 | 39128 | 62223 |
| RAB39A | 16034 | 39129 | 62224 |
| RAB39B | 16035 | 39130 | 62225 |
| RAB3A | 16036 | 39131 | 62226 |
| RAB3B | 16037 | 39132 | 62227 |
| RAB3C | 16038 | 39133 | 62228 |
| RAB3D | 16039 | 39134 | 62229 |
| RAB3GAP1 | 16040 | 39135 | 62230 |
| RAB3GAP2 | 16041 | 39136 | 62231 |
| RAB3IL1 | 16042 | 39137 | 62232 |
| RAB3IP | 16043 | 39138 | 62233 |
| RAB3IP | 16044 | 39139 | 62234 |
| RAB40B | 16045 | 39140 | 62235 |
| RAB40C | 16046 | 39141 | 62236 |
| RAB41 | 16047 | 39142 | 62237 |
| RAB42 | 16048 | 39143 | 62238 |
| RAB43 | 16049 | 39144 | 62239 |
| RAB43 | 16050 | 39145 | 62240 |
| RAB44 | 16051 | 39146 | 62241 |
| RAB4A | 16052 | 39147 | 62242 |
| RAB4B | 16053 | 39148 | 62243 |
| RAB5A | 16054 | 39149 | 62244 |
| RAB5B | 16055 | 39150 | 62245 |
| RAB5C | 16056 | 39151 | 62246 |
| RAB6A | 16057 | 39152 | 62247 |
| RAB6B | 16058 | 39153 | 62248 |
| RAB6C | 16059 | 39154 | 62249 |
| RAB7A | 16060 | 39155 | 62250 |
| RAB7B | 16061 | 39156 | 62251 |
| RAB8A | 16062 | 39157 | 62252 |
| RAB8B | 16063 | 39158 | 62253 |
| RAB9A | 16064 | 39159 | 62254 |
| RAB9B | 16065 | 39160 | 62255 |
| RABAC1 | 16066 | 39161 | 62256 |
| RABEP1 | 16067 | 39162 | 62257 |
| RABEP1 | 16068 | 39163 | 62258 |
| RABEP2 | 16069 | 39164 | 62259 |
| RABEPK | 16070 | 39165 | 62260 |
| RABGAP1 | 16071 | 39166 | 62261 |
| RABGAP1L | 16072 | 39167 | 62262 |
| RABGAP1L | 16073 | 39168 | 62263 |
| RABGEF1 | 16074 | 39169 | 62264 |
| RABGGTA | 16075 | 39170 | 62265 |
| RABGGTB | 16076 | 39171 | 62266 |
| RABIF | 16077 | 39172 | 62267 |
| RABL2A | 16078 | 39173 | 62268 |
| RABL2A | 16079 | 39174 | 62269 |
| RABL3 | 16080 | 39175 | 62270 |
| RABL6 | 16081 | 39176 | 62271 |
| RABL6 | 16082 | 39177 | 62272 |
| RAC1 | 16083 | 39178 | 62273 |
| RAC2 | 16084 | 39179 | 62274 |
| RAC3 | 16085 | 39180 | 62275 |
| RAC3 | 16086 | 39181 | 62276 |
| RACGAP1 | 16087 | 39182 | 62277 |
| RACK1 | 16088 | 39183 | 62278 |
| RAD1 | 16089 | 39184 | 62279 |
| RAD17 | 16090 | 39185 | 62280 |
| RAD18 | 16091 | 39186 | 62281 |
| RAD21 | 16092 | 39187 | 62282 |
| RAD21L1 | 16093 | 39188 | 62283 |
| RAD23A | 16094 | 39189 | 62284 |
| RAD23B | 16095 | 39190 | 62285 |
| RAD50 | 16096 | 39191 | 62286 |
| RAD51 | 16097 | 39192 | 62287 |
| RAD51 | 16098 | 39193 | 62288 |
| RAD51AP1 | 16099 | 39194 | 62289 |
| RAD51AP2 | 16100 | 39195 | 62290 |
| RAD51B | 16101 | 39196 | 62291 |
| RAD51B | 16102 | 39197 | 62292 |
| RAD51B | 16103 | 39198 | 62293 |
| RAD51B | 16104 | 39199 | 62294 |
| RAD51B | 16105 | 39200 | 62295 |
| RAD51B | 16106 | 39201 | 62296 |
| RAD51B | 16107 | 39202 | 62297 |
| RAD51B | 16108 | 39203 | 62298 |
| RAD51C | 16109 | 39204 | 62299 |
| RAD51C | 16110 | 39205 | 62300 |
| RAD51D | 16111 | 39206 | 62301 |
| RAD52 | 16112 | 39207 | 62302 |
| RAD52 | 16113 | 39208 | 62303 |
| RAD52 | 16114 | 39209 | 62304 |
| RAD54B | 16115 | 39210 | 62305 |
| RAD54L | 16116 | 39211 | 62306 |
| RAD54L2 | 16117 | 39212 | 62307 |
| RAD9A | 16118 | 39213 | 62308 |
| RAD9B | 16119 | 39214 | 62309 |
| RAD9B | 16120 | 39215 | 62310 |
| RAD9B | 16121 | 39216 | 62311 |
| RADIL | 16122 | 39217 | 62312 |
| RAE1 | 16123 | 39218 | 62313 |
| RAET1E | 16124 | 39219 | 62314 |
| RAET1E | 16125 | 39220 | 62315 |
| RAET1E | 16126 | 39221 | 62316 |
| RAET1G | 16127 | 39222 | 62317 |
| RAET1L | 16128 | 39223 | 62318 |
| RAF1 | 16129 | 39224 | 62319 |
| RAG1 | 16130 | 39225 | 62320 |
| RAG2 | 16131 | 39226 | 62321 |
| RAI1 | 16132 | 39227 | 62322 |
| RAI14 | 16133 | 39228 | 62323 |
| RAI2 | 16134 | 39229 | 62324 |
| RALA | 16135 | 39230 | 62325 |
| RALB | 16136 | 39231 | 62326 |
| RALBP1 | 16137 | 39232 | 62327 |
| RALGAPA1 | 16138 | 39233 | 62328 |
| RALGAPA1 | 16139 | 39234 | 62329 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| RALGAPA2 | 16140 | 39235 | 62330 |
| RALGAPB | 16141 | 39236 | 62331 |
| RALGDS | 16142 | 39237 | 62332 |
| RALGPS1 | 16143 | 39238 | 62333 |
| RALGPS1 | 16144 | 39239 | 62334 |
| RALGPS1 | 16145 | 39240 | 62335 |
| RALGPS2 | 16146 | 39241 | 62336 |
| RALY | 16147 | 39242 | 62337 |
| RALYL | 16148 | 39243 | 62338 |
| RAMP1 | 16149 | 39244 | 62339 |
| RAMP2 | 16150 | 39245 | 62340 |
| RAMP3 | 16151 | 39246 | 62341 |
| RAN | 16152 | 39247 | 62342 |
| RANBP1 | 16153 | 39248 | 62343 |
| RANBP10 | 16154 | 39249 | 62344 |
| RANBP17 | 16155 | 39250 | 62345 |
| RANBP2 | 16156 | 39251 | 62346 |
| RANBP3 | 16157 | 39252 | 62347 |
| RANBP3L | 16158 | 39253 | 62348 |
| RANBP3L | 16159 | 39254 | 62349 |
| RANBP3L | 16160 | 39255 | 62350 |
| RANBP6 | 16161 | 39256 | 62351 |
| RANBP9 | 16162 | 39257 | 62352 |
| RANGAP1 | 16163 | 39258 | 62353 |
| RANGRF | 16164 | 39259 | 62354 |
| RANGRF | 16165 | 39260 | 62355 |
| RANGRF | 16166 | 39261 | 62356 |
| RANGRF | 16167 | 39262 | 62357 |
| RAP1A | 16168 | 39263 | 62358 |
| RAP1B | 16169 | 39264 | 62359 |
| RAP1GAP | 16170 | 39265 | 62360 |
| RAP1GAP2 | 16171 | 39266 | 62361 |
| RAP1GDS1 | 16172 | 39267 | 62362 |
| RAP2A | 16173 | 39268 | 62363 |
| RAP2B | 16174 | 39269 | 62364 |
| RAP2C | 16175 | 39270 | 62365 |
| RAPGEF1 | 16176 | 39271 | 62366 |
| RAPGEF2 | 16177 | 39272 | 62367 |
| RAPGEF3 | 16178 | 39273 | 62368 |
| RAPGEF4 | 16179 | 39274 | 62369 |
| RAPGEF5 | 16180 | 39275 | 62370 |
| RAPGEF6 | 16181 | 39276 | 62371 |
| RAPGEF6 | 16182 | 39277 | 62372 |
| RAPGEF6 | 16183 | 39278 | 62373 |
| RAPGEF6 | 16184 | 39279 | 62374 |
| RAPGEFL1 | 16185 | 39280 | 62375 |
| RAPH1 | 16186 | 39281 | 62376 |
| RAPH1 | 16187 | 39282 | 62377 |
| RAPH1 | 16188 | 39283 | 62378 |
| RAPSN | 16189 | 39284 | 62379 |
| RARA | 16190 | 39285 | 62380 |
| RARB | 16191 | 39286 | 62381 |
| RARG | 16192 | 39287 | 62382 |
| RARRES1 | 16193 | 39288 | 62383 |
| RARRES1 | 16194 | 39289 | 62384 |
| RARRES2 | 16195 | 39290 | 62385 |
| RARRES3 | 16196 | 39291 | 62386 |
| RARS | 16197 | 39292 | 62387 |
| RARS2 | 16198 | 39293 | 62388 |
| RARS2 | 16199 | 39294 | 62389 |
| RASA1 | 16200 | 39295 | 62390 |
| RASA2 | 16201 | 39296 | 62391 |
| RASA3 | 16202 | 39297 | 62392 |
| RASA4 | 16203 | 39298 | 62393 |
| RASAL1 | 16204 | 39299 | 62394 |
| RASAL2 | 16205 | 39300 | 62395 |
| RASAL3 | 16206 | 39301 | 62396 |
| RASAL3 | 16207 | 39302 | 62397 |
| RASD1 | 16208 | 39303 | 62398 |
| RASD1 | 16209 | 39304 | 62399 |
| RASD2 | 16210 | 39305 | 62400 |
| RASEF | 16211 | 39306 | 62401 |
| RASGEF1A | 16212 | 39307 | 62402 |
| RASGEF1B | 16213 | 39308 | 62403 |
| RASGEF1C | 16214 | 39309 | 62404 |
| RASGRF1 | 16215 | 39310 | 62405 |
| RASGRF2 | 16216 | 39311 | 62406 |
| RASGRP1 | 16217 | 39312 | 62407 |
| RASGRP1 | 16218 | 39313 | 62408 |
| RASGRP2 | 16219 | 39314 | 62409 |
| RASGRP3 | 16220 | 39315 | 62410 |
| RASGRP4 | 16221 | 39316 | 62411 |
| RASIP1 | 16222 | 39317 | 62412 |
| RASL10A | 16223 | 39318 | 62413 |
| RASL10B | 16224 | 39319 | 62414 |
| RASL11A | 16225 | 39320 | 62415 |
| RASL11B | 16226 | 39321 | 62416 |
| RASL12 | 16227 | 39322 | 62417 |
| RASSF1 | 16228 | 39323 | 62418 |
| RASSF10 | 16229 | 39324 | 62419 |
| RASSF2 | 16230 | 39325 | 62420 |
| RASSF3 | 16231 | 39326 | 62421 |
| RASSF4 | 16232 | 39327 | 62422 |
| RASSF5 | 16233 | 39328 | 62423 |
| RASSF5 | 16234 | 39329 | 62424 |
| RASSF6 | 16235 | 39330 | 62425 |
| RASSF7 | 16236 | 39331 | 62426 |
| RASSF7 | 16237 | 39332 | 62427 |
| RASSF7 | 16238 | 39333 | 62428 |
| RASSF8 | 16239 | 39334 | 62429 |
| RASSF8 | 16240 | 39335 | 62430 |
| RASSF9 | 16241 | 39336 | 62431 |
| RAVER1 | 16242 | 39337 | 62432 |
| RAVER2 | 16243 | 39338 | 62433 |
| RAX | 16244 | 39339 | 62434 |
| RAX2 | 16245 | 39340 | 62435 |
| RB1 | 16246 | 39341 | 62436 |
| RB1CC1 | 16247 | 39342 | 62437 |
| RBAK | 16248 | 39343 | 62438 |
| RBAK-RBAKDN | 16249 | 39344 | 62439 |
| RBBP4 | 16250 | 39345 | 62440 |
| RBBP5 | 16251 | 39346 | 62441 |
| RBBP5 | 16252 | 39347 | 62442 |
| RBBP5 | 16253 | 39348 | 62443 |
| RBBP6 | 16254 | 39349 | 62444 |
| RBBP6 | 16255 | 39350 | 62445 |
| RBBP7 | 16256 | 39351 | 62446 |
| RBBP8 | 16257 | 39352 | 62447 |
| RBBP8NL | 16258 | 39353 | 62448 |
| RBBP9 | 16259 | 39354 | 62449 |
| RBCK1 | 16260 | 39355 | 62450 |
| RBCK1 | 16261 | 39356 | 62451 |
| RBFA | 16262 | 39357 | 62452 |
| RBFA | 16263 | 39358 | 62453 |
| RBFOX1 | 16264 | 39359 | 62454 |
| RBFOX1 | 16265 | 39360 | 62455 |
| RBFOX1 | 16266 | 39361 | 62456 |
| RBFOX2 | 16267 | 39362 | 62457 |
| RBFOX3 | 16268 | 39363 | 62458 |
| RBKS | 16269 | 39364 | 62459 |
| RBL1 | 16270 | 39365 | 62460 |
| RBL1 | 16271 | 39366 | 62461 |
| RBL2 | 16272 | 39367 | 62462 |
| RBL2 | 16273 | 39368 | 62463 |
| RBM10 | 16274 | 39369 | 62464 |
| RBM11 | 16275 | 39370 | 62465 |
| RBM12 | 16276 | 39371 | 62466 |
| RBM12B | 16277 | 39372 | 62467 |
| RBM14 | 16278 | 39373 | 62468 |
| RBM14 | 16279 | 39374 | 62469 |
| RBM14-RBM4 | 16280 | 39375 | 62470 |
| RBM15 | 16281 | 39376 | 62471 |
| RBM15 | 16282 | 39377 | 62472 |
| RBM15B | 16283 | 39378 | 62473 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| RBM17 | 16284 | 39379 | 62474 |
| RBM18 | 16285 | 39380 | 62475 |
| RBM19 | 16286 | 39381 | 62476 |
| RBM20 | 16287 | 39382 | 62477 |
| RBM22 | 16288 | 39383 | 62478 |
| RBM23 | 16289 | 39384 | 62479 |
| RBM24 | 16290 | 39385 | 62480 |
| RBM25 | 16291 | 39386 | 62481 |
| REM26 | 16292 | 39387 | 62482 |
| RBM27 | 16293 | 39388 | 62483 |
| RBM28 | 16294 | 39389 | 62484 |
| RBM3 | 16295 | 39390 | 62485 |
| RBM33 | 16296 | 39391 | 62486 |
| RBM34 | 16297 | 39392 | 62487 |
| RBM38 | 16298 | 39393 | 62488 |
| RBM38 | 16299 | 39394 | 62489 |
| RBM39 | 16300 | 39395 | 62490 |
| RBM4 | 16301 | 39396 | 62491 |
| RBM4 | 16302 | 39397 | 62492 |
| RBM4 | 16303 | 39398 | 62493 |
| RBM41 | 16304 | 39399 | 62494 |
| RBM41 | 16305 | 39400 | 62495 |
| RBM42 | 16306 | 39401 | 62496 |
| RBM43 | 16307 | 39402 | 62497 |
| RBM44 | 16308 | 39403 | 62498 |
| RBM45 | 16309 | 39404 | 62499 |
| RBM46 | 16310 | 39405 | 62500 |
| RBM46 | 16311 | 39406 | 62501 |
| RBM46 | 16312 | 39407 | 62502 |
| RBM47 | 16313 | 39408 | 62503 |
| RBM48 | 16314 | 39409 | 62504 |
| RBM4B | 16315 | 39410 | 62505 |
| RBM4B | 16316 | 39411 | 62506 |
| RBM5 | 16317 | 39412 | 62507 |
| RBM6 | 16318 | 39413 | 62508 |
| RBM7 | 16319 | 39414 | 62509 |
| RBM8A | 16320 | 39415 | 62510 |
| RBMS1 | 16321 | 39416 | 62511 |
| RBMS2 | 16322 | 39417 | 62512 |
| RBMS3 | 16323 | 39418 | 62513 |
| RBMS3 | 16324 | 39419 | 62514 |
| RBMX | 16325 | 39420 | 62515 |
| RBMX2 | 16326 | 39421 | 62516 |
| RBMXL1 | 16327 | 39422 | 62517 |
| RBMXL3 | 16328 | 39423 | 62518 |
| RBMY1F | 16329 | 39424 | 62519 |
| RBMY1J | 16330 | 39425 | 62520 |
| RBP1 | 16331 | 39426 | 62521 |
| RBP1 | 16332 | 39427 | 62522 |
| RBP1 | 16333 | 39428 | 62523 |
| RBP2 | 16334 | 39429 | 62524 |
| RBP3 | 16335 | 39430 | 62525 |
| RBP4 | 16336 | 39431 | 62526 |
| RBP5 | 16337 | 39432 | 62527 |
| RBP5 | 16338 | 39433 | 62528 |
| RBP7 | 16339 | 39434 | 62529 |
| RBPJ | 16340 | 39435 | 62530 |
| RBPJL | 16341 | 39436 | 62531 |
| RBPJL | 16342 | 39437 | 62532 |
| RBPMS | 16343 | 39438 | 62533 |
| RBPMS | 16344 | 39439 | 62534 |
| RBPMS | 16345 | 39440 | 62535 |
| RBPMS2 | 16346 | 39441 | 62536 |
| RBSN | 16347 | 39442 | 62537 |
| RBX1 | 16348 | 39443 | 62538 |
| RC3H1 | 16349 | 39444 | 62539 |
| RC3H2 | 16350 | 39445 | 62540 |
| RC3H2 | 16351 | 39446 | 62541 |
| RC3H2 | 16352 | 39447 | 62542 |
| RCAN1 | 16353 | 39448 | 62543 |
| RCAN1 | 16354 | 39449 | 62544 |
| RCAN2 | 16355 | 39450 | 62545 |
| RCAN3 | 16356 | 39451 | 62546 |
| RCAN3 | 16357 | 39452 | 62547 |
| RCBTB1 | 16358 | 39453 | 62548 |
| RCBTB1 | 16359 | 39454 | 62549 |
| RCBTB1 | 16360 | 39455 | 62550 |
| RCBTB2 | 16361 | 39456 | 62551 |
| RCBTB2 | 16362 | 39457 | 62552 |
| RCBTB2 | 16363 | 39458 | 62553 |
| RCC1 | 16364 | 39459 | 62554 |
| RCC1L | 16365 | 39460 | 62555 |
| RCC1L | 16366 | 39461 | 62556 |
| RCC1L | 16367 | 39462 | 62557 |
| RCC2 | 16368 | 39463 | 62558 |
| RCCD1 | 16369 | 39464 | 62559 |
| RCE1 | 16370 | 39465 | 62560 |
| RCHY1 | 16371 | 39466 | 62561 |
| RCL1 | 16372 | 39467 | 62562 |
| RCN1 | 16373 | 39468 | 62563 |
| RCN2 | 16374 | 39469 | 62564 |
| RCN3 | 16375 | 39470 | 62565 |
| RCOR1 | 16376 | 39471 | 62566 |
| RCOR2 | 16377 | 39472 | 62567 |
| RCOR3 | 16378 | 39473 | 62568 |
| RCOR3 | 16379 | 39474 | 62569 |
| RCOR3 | 16380 | 39475 | 62570 |
| RCSD1 | 16381 | 39476 | 62571 |
| RCVRN | 16382 | 39477 | 62572 |
| RD3 | 16383 | 39478 | 62573 |
| RD3L | 16384 | 39479 | 62574 |
| RDH10 | 16385 | 39480 | 62575 |
| RDH11 | 16386 | 39481 | 62576 |
| RDH12 | 16387 | 39482 | 62577 |
| RDH13 | 16388 | 39483 | 62578 |
| RDH14 | 16389 | 39484 | 62579 |
| RDH16 | 16390 | 39485 | 62580 |
| RDH5 | 16391 | 39486 | 62581 |
| RDH8 | 16392 | 39487 | 62582 |
| RDM1 | 16393 | 39488 | 62583 |
| RDM1 | 16394 | 39489 | 62584 |
| RDM1 | 16395 | 39490 | 62585 |
| RDX | 16396 | 39491 | 62586 |
| RDX | 16397 | 39492 | 62587 |
| REC114 | 16398 | 39493 | 62588 |
| REC8 | 16399 | 39494 | 62589 |
| RECK | 16400 | 39495 | 62590 |
| RECK | 16401 | 39496 | 62591 |
| RECK | 16402 | 39497 | 62592 |
| RECQL | 16403 | 39498 | 62593 |
| RECQL4 | 16404 | 39499 | 62594 |
| RECQL5 | 16405 | 39500 | 62595 |
| RECQL5 | 16406 | 39501 | 62596 |
| RECQL5 | 16407 | 39502 | 62597 |
| REEP1 | 16408 | 39503 | 62598 |
| REEP1 | 16409 | 39504 | 62599 |
| REEP2 | 16410 | 39505 | 62600 |
| REEP3 | 16411 | 39506 | 62601 |
| REEP4 | 16412 | 39507 | 62602 |
| REEP4 | 16413 | 39508 | 62603 |
| REEP4 | 16414 | 39509 | 62604 |
| REEP5 | 16415 | 39510 | 62605 |
| REEP6 | 16416 | 39511 | 62606 |
| REEP6 | 16417 | 39512 | 62607 |
| REG1A | 16418 | 39513 | 62608 |
| REG1B | 16419 | 39514 | 62609 |
| REG3A | 16420 | 39515 | 62610 |
| REG3G | 16421 | 39516 | 62611 |
| REG4 | 16422 | 39517 | 62612 |
| REG4 | 16423 | 39518 | 62613 |
| REL | 16424 | 39519 | 62614 |
| RELA | 16425 | 39520 | 62615 |
| RELB | 16426 | 39521 | 62616 |
| RELL1 | 16427 | 39522 | 62617 |
| RELL2 | 16428 | 39523 | 62618 |
| RELN | 16429 | 39524 | 62619 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| RELT | 16430 | 39525 | 62620 |
| REM1 | 16431 | 39526 | 62621 |
| REM2 | 16432 | 39527 | 62622 |
| REN | 16433 | 39528 | 62623 |
| RENBP | 16434 | 39529 | 62624 |
| REP15 | 16435 | 39530 | 62625 |
| REPIN1 | 16436 | 39531 | 62626 |
| REPS1 | 16437 | 39532 | 62627 |
| REPS2 | 16438 | 39533 | 62628 |
| RER1 | 16439 | 39534 | 62629 |
| RERE | 16440 | 39535 | 62630 |
| RERG | 16441 | 39536 | 62631 |
| RERGL | 16442 | 39537 | 62632 |
| RESP18 | 16443 | 39538 | 62633 |
| REST | 16444 | 39539 | 62634 |
| RET | 16445 | 39540 | 62635 |
| RET | 16446 | 39541 | 62636 |
| RETN | 16447 | 39542 | 62637 |
| RETNLB | 16448 | 39543 | 62638 |
| RETREG1 | 16449 | 39544 | 62639 |
| RETREG2 | 16450 | 39545 | 62640 |
| RETREG3 | 16451 | 39546 | 62641 |
| RETSAT | 16452 | 39547 | 62642 |
| REV1 | 16453 | 39548 | 62643 |
| REV3L | 16454 | 39549 | 62644 |
| REX1BD | 16455 | 39550 | 62645 |
| REXO1 | 16456 | 39551 | 62646 |
| REXO2 | 16457 | 39552 | 62647 |
| REXO4 | 16458 | 39553 | 62648 |
| REXO5 | 16459 | 39554 | 62649 |
| RFC1 | 16460 | 39555 | 62650 |
| RFC2 | 16461 | 39556 | 62651 |
| RFC3 | 16462 | 39557 | 62652 |
| RFC3 | 16463 | 39558 | 62653 |
| RFC4 | 16464 | 39559 | 62654 |
| RFC5 | 16465 | 39560 | 62655 |
| RFESD | 16466 | 39561 | 62656 |
| RFFL | 16467 | 39562 | 62657 |
| RFK | 16468 | 39563 | 62658 |
| RFLNB | 16469 | 39564 | 62659 |
| RFNG | 16470 | 39565 | 62660 |
| RFPL1 | 16471 | 39566 | 62661 |
| RFPL2 | 16472 | 39567 | 62662 |
| RFPL3 | 16473 | 39568 | 62663 |
| RFPL4AL1 | 16474 | 39569 | 62664 |
| RFPL4B | 16475 | 39570 | 62665 |
| RFT1 | 16476 | 39571 | 62666 |
| RFTN1 | 16477 | 39572 | 62667 |
| RFTN2 | 16478 | 39573 | 62668 |
| RFWD2 | 16479 | 39574 | 62669 |
| RFWD3 | 16480 | 39575 | 62670 |
| RFX1 | 16481 | 39576 | 62671 |
| RFX2 | 16482 | 39577 | 62672 |
| RFX3 | 16483 | 39578 | 62673 |
| RFX3 | 16484 | 39579 | 62674 |
| RFX3 | 16485 | 39580 | 62675 |
| RFX4 | 16486 | 39581 | 62676 |
| RFX5 | 16487 | 39582 | 62677 |
| RFX6 | 16488 | 39583 | 62678 |
| RFX7 | 16489 | 39584 | 62679 |
| RFX8 | 16490 | 39585 | 62680 |
| RFXANK | 16491 | 39586 | 62681 |
| RFXAP | 16492 | 39587 | 62682 |
| RGCC | 16493 | 39588 | 62683 |
| RGL1 | 16494 | 39589 | 62684 |
| RGL2 | 16495 | 39590 | 62685 |
| RGL3 | 16496 | 39591 | 62686 |
| RGL4 | 16497 | 39592 | 62687 |
| RGL4 | 16498 | 39593 | 62688 |
| RGMA | 16499 | 39594 | 62689 |
| RGMB | 16500 | 39595 | 62690 |
| RGN | 16501 | 39596 | 62691 |
| RGP1 | 16502 | 39597 | 62692 |
| RGPD2 | 16503 | 39598 | 62693 |
| RGPD6 | 16504 | 39599 | 62694 |
| RGPD6 | 16505 | 39600 | 62695 |
| RGPD8 | 16506 | 39601 | 62696 |
| RGR | 16507 | 39602 | 62697 |
| RGS1 | 16508 | 39603 | 62698 |
| RGS10 | 16509 | 39604 | 62699 |
| RGS11 | 16510 | 39605 | 62700 |
| RGS12 | 16511 | 39606 | 62701 |
| RGS12 | 16512 | 39607 | 62702 |
| RGS13 | 16513 | 39608 | 62703 |
| RGS14 | 16514 | 39609 | 62704 |
| RGS16 | 16515 | 39610 | 62705 |
| RGS17 | 16516 | 39611 | 62706 |
| RGS18 | 16517 | 39612 | 62707 |
| RGS19 | 16518 | 39613 | 62708 |
| RGS2 | 16519 | 39614 | 62709 |
| RGS20 | 16520 | 39615 | 62710 |
| RGS21 | 16521 | 39616 | 62711 |
| RGS22 | 16522 | 39617 | 62712 |
| RGS3 | 16523 | 39618 | 62713 |
| RGS3 | 16524 | 39619 | 62714 |
| RGS4 | 16525 | 39620 | 62715 |
| RGS4 | 16526 | 39621 | 62716 |
| RGS5 | 16527 | 39622 | 62717 |
| RGS5 | 16528 | 39623 | 62718 |
| RGS6 | 16529 | 39624 | 62719 |
| RGS6 | 16530 | 39625 | 62720 |
| RGS7 | 16531 | 39626 | 62721 |
| RGS7 | 16532 | 39627 | 62722 |
| RGS7BP | 16533 | 39628 | 62723 |
| RGS7BP | 16534 | 39629 | 62724 |
| RGS8 | 16535 | 39630 | 62725 |
| RGS9 | 16536 | 39631 | 62726 |
| RGS9 | 16537 | 39632 | 62727 |
| RGS9BP | 16538 | 39633 | 62728 |
| RGSL1 | 16539 | 39634 | 62729 |
| RHAG | 16540 | 39635 | 62730 |
| RHBDD1 | 16541 | 39636 | 62731 |
| RHBDD2 | 16542 | 39637 | 62732 |
| RHBDD3 | 16543 | 39638 | 62733 |
| RHBDF1 | 16544 | 39639 | 62734 |
| RHBDF2 | 16545 | 39640 | 62735 |
| RHBDL1 | 16546 | 39641 | 62736 |
| RHBDL2 | 16547 | 39642 | 62737 |
| RHBDL3 | 16548 | 39643 | 62738 |
| RHBG | 16549 | 39644 | 62739 |
| RHCE | 16550 | 39645 | 62740 |
| RHCE | 16551 | 39646 | 62741 |
| RHCG | 16552 | 39647 | 62742 |
| RHD | 16553 | 39648 | 62743 |
| RHD | 16554 | 39649 | 62744 |
| RHD | 16555 | 39650 | 62745 |
| RHEB | 16556 | 39651 | 62746 |
| RHEBL1 | 16557 | 39652 | 62747 |
| RHNO1 | 16558 | 39653 | 62748 |
| RHO | 16559 | 39654 | 62749 |
| RHOA | 16560 | 39655 | 62750 |
| RHOA | 16561 | 39656 | 62751 |
| RHOA | 16562 | 39657 | 62752 |
| RHOB | 16563 | 39658 | 62753 |
| RHOBTB1 | 16564 | 39659 | 62754 |
| RHOBTB2 | 16565 | 39660 | 62755 |
| RHOBTB3 | 16566 | 39661 | 62756 |
| RHOC | 16567 | 39662 | 62757 |
| RHOD | 16568 | 39663 | 62758 |
| RHOF | 16569 | 39664 | 62759 |
| RHOG | 16570 | 39665 | 62760 |
| RHOH | 16571 | 39666 | 62761 |
| RHOJ | 16572 | 39667 | 62762 |
| RHOQ | 16573 | 39668 | 62763 |
| RHOT1 | 16574 | 39669 | 62764 |
| RHOT2 | 16575 | 39670 | 62765 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| RHOU | 16576 | 39671 | 62766 |
| RHOV | 16577 | 39672 | 62767 |
| RHOXF1 | 16578 | 39673 | 62768 |
| RHOXF2B | 16579 | 39674 | 62769 |
| RHPN1 | 16580 | 39675 | 62770 |
| RHPN2 | 16581 | 39676 | 62771 |
| RIBC1 | 16582 | 39677 | 62772 |
| RIBC1 | 16583 | 39678 | 62773 |
| RIBC1 | 16584 | 39679 | 62774 |
| RIBC2 | 16585 | 39680 | 62775 |
| RIC1 | 16586 | 39681 | 62776 |
| RIC1 | 16587 | 39682 | 62777 |
| RIC3 | 16588 | 39683 | 62778 |
| RIC3 | 16589 | 39684 | 62779 |
| RIC8A | 16590 | 39685 | 62780 |
| RIC8B | 16591 | 39686 | 62781 |
| RIC8B | 16592 | 39687 | 62782 |
| RICTOR | 16593 | 39688 | 62783 |
| RIDA | 16594 | 39689 | 62784 |
| RIF1 | 16595 | 39690 | 62785 |
| RIIAD1 | 16596 | 39691 | 62786 |
| RILP | 16597 | 39692 | 62787 |
| RILPL1 | 16598 | 39693 | 62788 |
| RILPL1 | 16599 | 39694 | 62789 |
| RILPL2 | 16600 | 39695 | 62790 |
| RIMBP2 | 16601 | 39696 | 62791 |
| RIMBP2 | 16602 | 39697 | 62792 |
| RIMBP2 | 16603 | 39698 | 62793 |
| RIMBP2 | 16604 | 39699 | 62794 |
| RIMBP2 | 16605 | 39700 | 62795 |
| RIMBP3C | 16606 | 39701 | 62796 |
| RIMKLA | 16607 | 39702 | 62797 |
| RIMKLB | 16608 | 39703 | 62798 |
| RIMS1 | 16609 | 39704 | 62799 |
| RIMS1 | 16610 | 39705 | 62800 |
| RIMS1 | 16611 | 39706 | 62801 |
| RIMS2 | 16612 | 39707 | 62802 |
| RIMS3 | 16613 | 39708 | 62803 |
| RIMS4 | 16614 | 39709 | 62804 |
| RIN1 | 16615 | 39710 | 62805 |
| RIN2 | 16616 | 39711 | 62806 |
| RIN3 | 16617 | 39712 | 62807 |
| RING1 | 16618 | 39713 | 62808 |
| RINL | 16619 | 39714 | 62809 |
| RINT1 | 16620 | 39715 | 62810 |
| RIOK1 | 16621 | 39716 | 62811 |
| RIOK2 | 16622 | 39717 | 62812 |
| RIOK2 | 16623 | 39718 | 62813 |
| RIOK3 | 16624 | 39719 | 62814 |
| RIOX1 | 16625 | 39720 | 62815 |
| RIOX2 | 16626 | 39721 | 62816 |
| RIPK1 | 16627 | 39722 | 62817 |
| RIPK2 | 16628 | 39723 | 62818 |
| RIPK3 | 16629 | 39724 | 62819 |
| RIPK4 | 16630 | 39725 | 62820 |
| RIPOR1 | 16631 | 39726 | 62821 |
| RIPOR2 | 16632 | 39727 | 62822 |
| RIPOR2 | 16633 | 39728 | 62823 |
| RIPOR2 | 16634 | 39729 | 62824 |
| RIPOR3 | 16635 | 39730 | 62825 |
| RIPPLY1 | 16636 | 39731 | 62826 |
| RIPPLY2 | 16637 | 39732 | 62827 |
| RIPPLY3 | 16638 | 39733 | 62828 |
| RIPPLY3 | 16639 | 39734 | 62829 |
| RIT1 | 16640 | 39735 | 62830 |
| RIT2 | 16641 | 39736 | 62831 |
| RIT2 | 16642 | 39737 | 62832 |
| RITA1 | 16643 | 39738 | 62833 |
| RLBP1 | 16644 | 39739 | 62834 |
| RLF | 16645 | 39740 | 62835 |
| RLIM | 16646 | 39741 | 62836 |
| RLN1 | 16647 | 39742 | 62837 |
| RLN2 | 16648 | 39743 | 62838 |
| RLN2 | 16649 | 39744 | 62839 |
| RLN3 | 16650 | 39745 | 62840 |
| RLN3 | 16651 | 39746 | 62841 |
| RMDN1 | 16652 | 39747 | 62842 |
| RMDN1 | 16653 | 39748 | 62843 |
| RMDN2 | 16654 | 39749 | 62844 |
| RMDN3 | 16655 | 39750 | 62845 |
| RMI1 | 16656 | 39751 | 62846 |
| RMI2 | 16657 | 39752 | 62847 |
| RMND1 | 16658 | 39753 | 62848 |
| RMND5A | 16659 | 39754 | 62849 |
| RMND5B | 16660 | 39755 | 62850 |
| RNASE1 | 16661 | 39756 | 62851 |
| RNASE10 | 16662 | 39757 | 62852 |
| RNASE11 | 16663 | 39758 | 62853 |
| RNASE12 | 16664 | 39759 | 62854 |
| RNASE13 | 16665 | 39760 | 62855 |
| RNASE2 | 16666 | 39761 | 62856 |
| RNASE3 | 16667 | 39762 | 62857 |
| RNASE4 | 16668 | 39763 | 62858 |
| RNASE4 | 16669 | 39764 | 62859 |
| RNASE6 | 16670 | 39765 | 62860 |
| RNASE7 | 16671 | 39766 | 62861 |
| RNASE8 | 16672 | 39767 | 62862 |
| RNASE9 | 16673 | 39768 | 62863 |
| RNASEH1 | 16674 | 39769 | 62864 |
| RNASEH2A | 16675 | 39770 | 62865 |
| RNASEH2B | 16676 | 39771 | 62866 |
| RNASEH2B | 16677 | 39772 | 62867 |
| RNASEH2C | 16678 | 39773 | 62868 |
| RNASEK | 16679 | 39774 | 62869 |
| RNASEL | 16680 | 39775 | 62870 |
| RNASET2 | 16681 | 39776 | 62871 |
| RND1 | 16682 | 39777 | 62872 |
| RND2 | 16683 | 39778 | 62873 |
| RND3 | 16684 | 39779 | 62874 |
| RNF10 | 16685 | 39780 | 62875 |
| RNF103 | 16686 | 39781 | 62876 |
| RNF103 | 16687 | 39782 | 62877 |
| RNF11 | 16688 | 39783 | 62878 |
| RNF111 | 16689 | 39784 | 62879 |
| RNF112 | 16690 | 39785 | 62880 |
| RNF113A | 16691 | 39786 | 62881 |
| RNF113B | 16692 | 39787 | 62882 |
| RNF114 | 16693 | 39788 | 62883 |
| RNF115 | 16694 | 39789 | 62884 |
| RNF121 | 16695 | 39790 | 62885 |
| RNF121 | 16696 | 39791 | 62886 |
| RNF122 | 16697 | 39792 | 62887 |
| RNF123 | 16698 | 39793 | 62888 |
| RNF125 | 16699 | 39794 | 62889 |
| RNF126 | 16700 | 39795 | 62890 |
| RNF128 | 16701 | 39796 | 62891 |
| RNF13 | 16702 | 39797 | 62892 |
| RNF130 | 16703 | 39798 | 62893 |
| RNF130 | 16704 | 39799 | 62894 |
| RNF133 | 16705 | 39800 | 62895 |
| RNF135 | 16706 | 39801 | 62896 |
| RNF135 | 16707 | 39802 | 62897 |
| RNF138 | 16708 | 39803 | 62898 |
| RNF139 | 16709 | 39804 | 62899 |
| RNF14 | 16710 | 39805 | 62900 |
| RNF141 | 16711 | 39806 | 62901 |
| RNF144A | 16712 | 39807 | 62902 |
| RNF144A | 16713 | 39808 | 62903 |
| RNF144A | 16714 | 39809 | 62904 |
| RNF144B | 16715 | 39810 | 62905 |
| RNF145 | 16716 | 39811 | 62906 |
| RNF146 | 16717 | 39812 | 62907 |
| RNF148 | 16718 | 39813 | 62908 |
| RNF149 | 16719 | 39814 | 62909 |
| RNF150 | 16720 | 39815 | 62910 |
| RNF151 | 16721 | 39816 | 62911 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| RNF151 | 16722 | 39817 | 62912 |
| RNF152 | 16723 | 39818 | 62913 |
| RNF157 | 16724 | 39819 | 62914 |
| RNF165 | 16725 | 39820 | 62915 |
| RNF166 | 16726 | 39821 | 62916 |
| RNF167 | 16727 | 39822 | 62917 |
| RNF168 | 16728 | 39823 | 62918 |
| RNF169 | 16729 | 39824 | 62919 |
| RNF17 | 16730 | 39825 | 62920 |
| RNF170 | 16731 | 39826 | 62921 |
| RNF170 | 16732 | 39827 | 62922 |
| RNF175 | 16733 | 39828 | 62923 |
| RNF180 | 16734 | 39829 | 62924 |
| RNF180 | 16735 | 39830 | 62925 |
| RNF180 | 16736 | 39831 | 62926 |
| RNF180 | 16737 | 39832 | 62927 |
| RNF181 | 16738 | 39833 | 62928 |
| RNF182 | 16739 | 39834 | 62929 |
| RNF183 | 16740 | 39835 | 62930 |
| RNF185 | 16741 | 39836 | 62931 |
| RNF186 | 16742 | 39837 | 62932 |
| RNF187 | 16743 | 39838 | 62933 |
| RNF19A | 16744 | 39839 | 62934 |
| RNF19B | 16745 | 39840 | 62935 |
| RNF19B | 16746 | 39841 | 62936 |
| RNF2 | 16747 | 39842 | 62937 |
| RNF20 | 16748 | 39843 | 62938 |
| RNF207 | 16749 | 39844 | 62939 |
| RNF208 | 16750 | 39845 | 62940 |
| RNF212 | 16751 | 39846 | 62941 |
| RNF212 | 16752 | 39847 | 62942 |
| RNF212 | 16753 | 39848 | 62943 |
| RNF212B | 16754 | 39849 | 62944 |
| RNF213 | 16755 | 39850 | 62945 |
| RNF213 | 16756 | 39851 | 62946 |
| RNF214 | 16757 | 39852 | 62947 |
| RNF215 | 16758 | 39853 | 62948 |
| RNF216 | 16759 | 39854 | 62949 |
| RNF217 | 16760 | 39855 | 62950 |
| RNF217 | 16761 | 39856 | 62951 |
| RNF219 | 16762 | 39857 | 62952 |
| RNF220 | 16763 | 39858 | 62953 |
| RNF222 | 16764 | 39859 | 62954 |
| RNF223 | 16765 | 39860 | 62955 |
| RNF224 | 16766 | 39861 | 62956 |
| RNF225 | 16767 | 39862 | 62957 |
| RNF24 | 16768 | 39863 | 62958 |
| RNF25 | 16769 | 39864 | 62959 |
| RNF26 | 16770 | 39865 | 62960 |
| RNF31 | 16771 | 39866 | 62961 |
| RNF32 | 16772 | 39867 | 62962 |
| RNF32 | 16773 | 39868 | 62963 |
| RNF32 | 16774 | 39869 | 62964 |
| RNF34 | 16775 | 39870 | 62965 |
| RNF38 | 16776 | 39871 | 62966 |
| RNF39 | 16777 | 39872 | 62967 |
| RNF4 | 16778 | 39873 | 62968 |
| RNF4 | 16779 | 39874 | 62969 |
| RNF40 | 16780 | 39875 | 62970 |
| RNF41 | 16781 | 39876 | 62971 |
| RNF43 | 16782 | 39877 | 62972 |
| RNF44 | 16783 | 39878 | 62973 |
| RNF5 | 16784 | 39879 | 62974 |
| RNF6 | 16785 | 39880 | 62975 |
| RNF6 | 16786 | 39881 | 62976 |
| RNF7 | 16787 | 39882 | 62977 |
| RNF7 | 16788 | 39883 | 62978 |
| RNF8 | 16789 | 39884 | 62979 |
| RNF8 | 16790 | 39885 | 62980 |
| RNFT1 | 16791 | 39886 | 62981 |
| RNFT2 | 16792 | 39887 | 62982 |
| RNFT2 | 16793 | 39888 | 62983 |
| RNGTT | 16794 | 39889 | 62984 |
| RNH1 | 16795 | 39890 | 62985 |
| RNLS | 16796 | 39891 | 62986 |
| RNLS | 16797 | 39892 | 62987 |
| RNMT | 16798 | 39893 | 62988 |
| RNMT | 16799 | 39894 | 62989 |
| RNPC3 | 16800 | 39895 | 62990 |
| RNPEP | 16801 | 39896 | 62991 |
| RNPEPL1 | 16802 | 39897 | 62992 |
| RNPS1 | 16803 | 39898 | 62993 |
| RNPS1 | 16804 | 39899 | 62994 |
| ROBO1 | 16805 | 39900 | 62995 |
| ROBO2 | 16806 | 39901 | 62996 |
| ROBO3 | 16807 | 39902 | 62997 |
| ROBO4 | 16808 | 39903 | 62998 |
| ROCK1 | 16809 | 39904 | 62999 |
| ROCK2 | 16810 | 39905 | 63000 |
| ROGDI | 16811 | 39906 | 63001 |
| ROM1 | 16812 | 39907 | 63002 |
| ROMO1 | 16813 | 39908 | 63003 |
| ROPN1 | 16814 | 39909 | 63004 |
| ROPN1B | 16815 | 39910 | 63005 |
| ROPN1L | 16816 | 39911 | 63006 |
| ROR1 | 16817 | 39912 | 63007 |
| ROR1 | 16818 | 39913 | 63008 |
| ROR2 | 16819 | 39914 | 63009 |
| ROR2 | 16820 | 39915 | 63010 |
| RORA | 16821 | 39916 | 63011 |
| RORB | 16822 | 39917 | 63012 |
| RORC | 16823 | 39918 | 63013 |
| ROS1 | 16824 | 39919 | 63014 |
| RP1 | 16825 | 39920 | 63015 |
| RP1L1 | 16826 | 39921 | 63016 |
| RP2 | 16827 | 39922 | 63017 |
| RP9 | 16828 | 39923 | 63018 |
| RPA1 | 16829 | 39924 | 63019 |
| RPA2 | 16830 | 39925 | 63020 |
| RPA3 | 16831 | 39926 | 63021 |
| RPA4 | 16832 | 39927 | 63022 |
| RPAIN | 16833 | 39928 | 63023 |
| RPAIN | 16834 | 39929 | 63024 |
| RPAIN | 16835 | 39930 | 63025 |
| RPAIN | 16836 | 39931 | 63026 |
| RPAP1 | 16837 | 39932 | 63027 |
| RPAP2 | 16838 | 39933 | 63028 |
| RPAP3 | 16839 | 39934 | 63029 |
| RPE | 16840 | 39935 | 63030 |
| RPE | 16841 | 39936 | 63031 |
| RPE | 16842 | 39937 | 63032 |
| RPE | 16843 | 39938 | 63033 |
| RPE65 | 16844 | 39939 | 63034 |
| RPEL1 | 16845 | 39940 | 63035 |
| RPF1 | 16846 | 39941 | 63036 |
| RPF2 | 16847 | 39942 | 63037 |
| RPGR | 16848 | 39943 | 63038 |
| RPGR | 16849 | 39944 | 63039 |
| RPGRIP1 | 16850 | 39945 | 63040 |
| RPGRIP1L | 16851 | 39946 | 63041 |
| RPGRIP1L | 16852 | 39947 | 63042 |
| RPGRIP1L | 16853 | 39948 | 63043 |
| RPH3A | 16854 | 39949 | 63044 |
| RPH3AL | 16855 | 39950 | 63045 |
| RPIA | 16856 | 39951 | 63046 |
| RPL10 | 16857 | 39952 | 63047 |
| RPL10 | 16858 | 39953 | 63048 |
| RPL10 | 16859 | 39954 | 63049 |
| RPL10A | 16860 | 39955 | 63050 |
| RPL10L | 16861 | 39956 | 63051 |
| RPL11 | 16862 | 39957 | 63052 |
| RPL12 | 16863 | 39958 | 63053 |
| RPL13 | 16864 | 39959 | 63054 |
| RPL13A | 16865 | 39960 | 63055 |
| RPL14 | 16866 | 39961 | 63056 |
| RPL15 | 16867 | 39962 | 63057 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| RPL15 | 16868 | 39963 | 63058 |
| RPL17 | 16869 | 39964 | 63059 |
| RPL17-C18orf32 | 16870 | 39965 | 63060 |
| RPL18 | 16871 | 39966 | 63061 |
| RPL18A | 16872 | 39967 | 63062 |
| RPL19 | 16873 | 39968 | 63063 |
| RPL22 | 16874 | 39969 | 63064 |
| RPL22L1 | 16875 | 39970 | 63065 |
| RPL23 | 16876 | 39971 | 63066 |
| RPL23A | 16877 | 39972 | 63067 |
| RPL24 | 16878 | 39973 | 63068 |
| RPL26 | 16879 | 39974 | 63069 |
| RPL26L1 | 16880 | 39975 | 63070 |
| RPL27 | 16881 | 39976 | 63071 |
| RPL27A | 16882 | 39977 | 63072 |
| RPL28 | 16883 | 39978 | 63073 |
| RPL28 | 16884 | 39979 | 63074 |
| RPL28 | 16885 | 39980 | 63075 |
| RPL28 | 16886 | 39981 | 63076 |
| RPL28 | 16887 | 39982 | 63077 |
| RPL29 | 16888 | 39983 | 63078 |
| RPL3 | 16889 | 39984 | 63079 |
| RPL30 | 16890 | 39985 | 63080 |
| RPL31 | 16891 | 39986 | 63081 |
| RPL31 | 16892 | 39987 | 63082 |
| RPL32 | 16893 | 39988 | 63083 |
| RPL34 | 16894 | 39989 | 63084 |
| RPL35 | 16895 | 39990 | 63085 |
| RPL35A | 16896 | 39991 | 63086 |
| RPL36 | 16897 | 39992 | 63087 |
| RPL36A | 16898 | 39993 | 63088 |
| RPL36A | 16899 | 39994 | 63089 |
| RPL36AL | 16900 | 39995 | 63090 |
| RPL37 | 16901 | 39996 | 63091 |
| RPL37A | 16902 | 39997 | 63092 |
| RPL38 | 16903 | 39998 | 63093 |
| RPL39 | 16904 | 39999 | 63094 |
| RPL39L | 16905 | 40000 | 63095 |
| RPL3L | 16906 | 40001 | 63096 |
| RPL4 | 16907 | 40002 | 63097 |
| RPL41 | 16908 | 40003 | 63098 |
| RPL5 | 16909 | 40004 | 63099 |
| RPL6 | 16910 | 40005 | 63100 |
| RPL7 | 16911 | 40006 | 63101 |
| RPL7A | 16912 | 40007 | 63102 |
| RPL7L1 | 16913 | 40008 | 63103 |
| RPL8 | 16914 | 40009 | 63104 |
| RPL9 | 16915 | 40010 | 63105 |
| RPLP0 | 16916 | 40011 | 63106 |
| RPLP1 | 16917 | 40012 | 63107 |
| RPLP2 | 16918 | 40013 | 63108 |
| RPN1 | 16919 | 40014 | 63109 |
| RPN2 | 16920 | 40015 | 63110 |
| RPN2 | 16921 | 40016 | 63111 |
| RPP14 | 16922 | 40017 | 63112 |
| RPP21 | 16923 | 40018 | 63113 |
| RPP21 | 16924 | 40019 | 63114 |
| RPP25 | 16925 | 40020 | 63115 |
| RPP25L | 16926 | 40021 | 63116 |
| RPP30 | 16927 | 40022 | 63117 |
| RPP30 | 16928 | 40023 | 63118 |
| RPP38 | 16929 | 40024 | 63119 |
| RPP40 | 16930 | 40025 | 63120 |
| RPRD1A | 16931 | 40026 | 63121 |
| RPRD1A | 16932 | 40027 | 63122 |
| RPRD1B | 16933 | 40028 | 63123 |
| RPRD2 | 16934 | 40029 | 63124 |
| RPRD2 | 16935 | 40030 | 63125 |
| RPRM | 16936 | 40031 | 63126 |
| RPRML | 16937 | 40032 | 63127 |
| RPS10 | 16938 | 40033 | 63128 |
| RPS11 | 16939 | 40034 | 63129 |
| RPS12 | 16940 | 40035 | 63130 |
| RPS13 | 16941 | 40036 | 63131 |
| RPS14 | 16942 | 40037 | 63132 |
| RPS15 | 16943 | 40038 | 63133 |
| RPS15A | 16944 | 40039 | 63134 |
| RPS16 | 16945 | 40040 | 63135 |
| RPS17 | 16946 | 40041 | 63136 |
| RPS18 | 16947 | 40042 | 63137 |
| RPS19 | 16948 | 40043 | 63138 |
| RPS19 | 16949 | 40044 | 63139 |
| RPS19BP1 | 16950 | 40045 | 63140 |
| RPS2 | 16951 | 40046 | 63141 |
| RPS20 | 16952 | 40047 | 63142 |
| RPS20 | 16953 | 40048 | 63143 |
| RPS21 | 16954 | 40049 | 63144 |
| RPS23 | 16955 | 40050 | 63145 |
| RPS24 | 16956 | 40051 | 63146 |
| RPS24 | 16957 | 40052 | 63147 |
| RPS24 | 16958 | 40053 | 63148 |
| RPS25 | 16959 | 40054 | 63149 |
| RPS26 | 16960 | 40055 | 63150 |
| RPS27 | 16961 | 40056 | 63151 |
| RPS27 | 16962 | 40057 | 63152 |
| RPS27A | 16963 | 40058 | 63153 |
| RPS27L | 16964 | 40059 | 63154 |
| RPS28 | 16965 | 40060 | 63155 |
| RPS29 | 16966 | 40061 | 63156 |
| RPS29 | 16967 | 40062 | 63157 |
| RPS3 | 16968 | 40063 | 63158 |
| RPS3 | 16969 | 40064 | 63159 |
| RPS3A | 16970 | 40065 | 63160 |
| RPS3A | 16971 | 40066 | 63161 |
| RPS4X | 16972 | 40067 | 63162 |
| RPS4Y1 | 16973 | 40068 | 63163 |
| RPS4Y2 | 16974 | 40069 | 63164 |
| RPS5 | 16975 | 40070 | 63165 |
| RPS6 | 16976 | 40071 | 63166 |
| RPS6KA1 | 16977 | 40072 | 63167 |
| RPS6KA2 | 16978 | 40073 | 63168 |
| RPS6KA3 | 16979 | 40074 | 63169 |
| RPS6KA4 | 16980 | 40075 | 63170 |
| RPS6KA5 | 16981 | 40076 | 63171 |
| RPS6KA5 | 16982 | 40077 | 63172 |
| RPS6KA6 | 16983 | 40078 | 63173 |
| RPS6KB1 | 16984 | 40079 | 63174 |
| RPS6KB1 | 16985 | 40080 | 63175 |
| RPS6KB2 | 16986 | 40081 | 63176 |
| RPS6KC1 | 16987 | 40082 | 63177 |
| RPS6KL1 | 16988 | 40083 | 63178 |
| RPS7 | 16989 | 40084 | 63179 |
| RPS8 | 16990 | 40085 | 63180 |
| RPS9 | 16991 | 40086 | 63181 |
| RPS9 | 16992 | 40087 | 63182 |
| RPSA | 16993 | 40088 | 63183 |
| RPTN | 16994 | 40089 | 63184 |
| RPTOR | 16995 | 40090 | 63185 |
| RPUSD1 | 16996 | 40091 | 63186 |
| RPUSD1 | 16997 | 40092 | 63187 |
| RPUSD2 | 16998 | 40093 | 63188 |
| RPUSD3 | 16999 | 40094 | 63189 |
| RPUSD3 | 17000 | 40095 | 63190 |
| RPUSD3 | 17001 | 40096 | 63191 |
| RPUSD4 | 17002 | 40097 | 63192 |
| RRAD | 17003 | 40098 | 63193 |
| RRAGA | 17004 | 40099 | 63194 |
| RRAGB | 17005 | 40100 | 63195 |
| RRAGC | 17006 | 40101 | 63196 |
| RRAGD | 17007 | 40102 | 63197 |
| RRAS | 17008 | 40103 | 63198 |
| RRAS2 | 17009 | 40104 | 63199 |
| RRBP1 | 17010 | 40105 | 63200 |
| RREB1 | 17011 | 40106 | 63201 |
| RRH | 17012 | 40107 | 63202 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| RRM1 | 17013 | 40108 | 63203 |
| RRM2 | 17014 | 40109 | 63204 |
| RRM2B | 17015 | 40110 | 63205 |
| RRN3 | 17016 | 40111 | 63206 |
| RRNAD1 | 17017 | 40112 | 63207 |
| RRNAD1 | 17018 | 40113 | 63208 |
| RRP1 | 17019 | 40114 | 63209 |
| RRP12 | 17020 | 40115 | 63210 |
| RRP15 | 17021 | 40116 | 63211 |
| RRP1B | 17022 | 40117 | 63212 |
| RRP36 | 17023 | 40118 | 63213 |
| RRP7A | 17024 | 40119 | 63214 |
| RRP8 | 17025 | 40120 | 63215 |
| RRP9 | 17026 | 40121 | 63216 |
| RRS1 | 17027 | 40122 | 63217 |
| RS1 | 17028 | 40123 | 63218 |
| RSAD1 | 17029 | 40124 | 63219 |
| RSAD2 | 17030 | 40125 | 63220 |
| RSBN1 | 17031 | 40126 | 63221 |
| RSBN1L | 17032 | 40127 | 63222 |
| RSC1A1 | 17033 | 40128 | 63223 |
| RSF1 | 17034 | 40129 | 63224 |
| RSG1 | 17035 | 40130 | 63225 |
| RSL1D1 | 17036 | 40131 | 63226 |
| RSL24D1 | 17037 | 40132 | 63227 |
| RSPH1 | 17038 | 40133 | 63228 |
| RSPH10B2 | 17039 | 40134 | 63229 |
| RSPH14 | 17040 | 40135 | 63230 |
| RSPH3 | 17041 | 40136 | 63231 |
| RSPH4A | 17042 | 40137 | 63232 |
| RSPH4A | 17043 | 40138 | 63233 |
| RSPH6A | 17044 | 40139 | 63234 |
| RSPH9 | 17045 | 40140 | 63235 |
| RSPH9 | 17046 | 40141 | 63236 |
| RSPO1 | 17047 | 40142 | 63237 |
| RSPO2 | 17048 | 40143 | 63238 |
| RSPO3 | 17049 | 40144 | 63239 |
| RSPO4 | 17050 | 40145 | 63240 |
| RSPRY1 | 17051 | 40146 | 63241 |
| RSPRY1 | 17052 | 40147 | 63242 |
| RSRC1 | 17053 | 40148 | 63243 |
| RSRC2 | 17054 | 40149 | 63244 |
| RSRP1 | 17055 | 40150 | 63245 |
| RSU1 | 17056 | 40151 | 63246 |
| RTBDN | 17057 | 40152 | 63247 |
| RTBDN | 17058 | 40153 | 63248 |
| RTCA | 17059 | 40154 | 63249 |
| RTCB | 17060 | 40155 | 63250 |
| RTEL1 | 17061 | 40156 | 63251 |
| RTEL1 | 17062 | 40157 | 63252 |
| RTF1 | 17063 | 40158 | 63253 |
| RTFDC1 | 17064 | 40159 | 63254 |
| RTFDC1 | 17065 | 40160 | 63255 |
| RTKN | 17066 | 40161 | 63256 |
| RTKN2 | 17067 | 40162 | 63257 |
| RTKN2 | 17068 | 40163 | 63258 |
| RTL1 | 17069 | 40164 | 63259 |
| RTL10 | 17070 | 40165 | 63260 |
| RTL3 | 17071 | 40166 | 63261 |
| RTL4 | 17072 | 40167 | 63262 |
| RTL5 | 17073 | 40168 | 63263 |
| RTL6 | 17074 | 40169 | 63264 |
| RTL8A | 17075 | 40170 | 63265 |
| RTL8A | 17076 | 40171 | 63266 |
| RTL8B | 17077 | 40172 | 63267 |
| RTL8C | 17078 | 40173 | 63268 |
| RTL9 | 17079 | 40174 | 63269 |
| RTN1 | 17080 | 40175 | 63270 |
| RTN2 | 17081 | 40176 | 63271 |
| RTN3 | 17082 | 40177 | 63272 |
| RTN3 | 17083 | 40178 | 63273 |
| RTN3 | 17084 | 40179 | 63274 |
| RTN4 | 17085 | 40180 | 63275 |
| RTN4IP1 | 17086 | 40181 | 63276 |
| RTN4R | 17087 | 40182 | 63277 |
| RTN4RL1 | 17088 | 40183 | 63278 |
| RTN4RL2 | 17089 | 40184 | 63279 |
| RTP1 | 17090 | 40185 | 63280 |
| RTP2 | 17091 | 40186 | 63281 |
| RTP3 | 17092 | 40187 | 63282 |
| RTP4 | 17093 | 40188 | 63283 |
| RTP5 | 17094 | 40189 | 63284 |
| RTTN | 17095 | 40190 | 63285 |
| RUBCN | 17096 | 40191 | 63286 |
| RUBCNL | 17097 | 40192 | 63287 |
| RUBCNL | 17098 | 40193 | 63288 |
| RUFY1 | 17099 | 40194 | 63289 |
| RUFY2 | 17100 | 40195 | 63290 |
| RUFY2 | 17101 | 40196 | 63291 |
| RUFY3 | 17102 | 40197 | 63292 |
| RUFY3 | 17103 | 40198 | 63293 |
| RUFY3 | 17104 | 40199 | 63294 |
| RUFY4 | 17105 | 40200 | 63295 |
| RUNDC1 | 17106 | 40201 | 63296 |
| RUNDC3A | 17107 | 40202 | 63297 |
| RUNDC3A | 17108 | 40203 | 63298 |
| RUNDC3B | 17109 | 40204 | 63299 |
| RUNX1 | 17110 | 40205 | 63300 |
| RUNX1 | 17111 | 40206 | 63301 |
| RUNX1T1 | 17112 | 40207 | 63302 |
| RUNX2 | 17113 | 40208 | 63303 |
| RUNX3 | 17114 | 40209 | 63304 |
| RUSC1 | 17115 | 40210 | 63305 |
| RUSC2 | 17116 | 40211 | 63306 |
| RUVBL1 | 17117 | 40212 | 63307 |
| RUVBL1 | 17118 | 40213 | 63308 |
| RUVBL1 | 17119 | 40214 | 63309 |
| RUVBL2 | 17120 | 40215 | 63310 |
| RWDD1 | 17121 | 40216 | 63311 |
| RWDD2A | 17122 | 40217 | 63312 |
| RWDD2B | 17123 | 40218 | 63313 |
| RWDD3 | 17124 | 40219 | 63314 |
| RWDD3 | 17125 | 40220 | 63315 |
| RWDD3 | 17126 | 40221 | 63316 |
| RWDD4 | 17127 | 40222 | 63317 |
| RXFP1 | 17128 | 40223 | 63318 |
| RXFP2 | 17129 | 40224 | 63319 |
| RXFP3 | 17130 | 40225 | 63320 |
| RXFP4 | 17131 | 40226 | 63321 |
| RXRA | 17132 | 40227 | 63322 |
| RXRB | 17133 | 40228 | 63323 |
| RXRG | 17134 | 40229 | 63324 |
| RYBP | 17135 | 40230 | 63325 |
| RYK | 17136 | 40231 | 63326 |
| RYR1 | 17137 | 40232 | 63327 |
| RYR2 | 17138 | 40233 | 63328 |
| RYR3 | 17139 | 40234 | 63329 |
| S100A1 | 17140 | 40235 | 63330 |
| S100A10 | 17141 | 40236 | 63331 |
| S100A11 | 17142 | 40237 | 63332 |
| S100A12 | 17143 | 40238 | 63333 |
| S100A13 | 17144 | 40239 | 63334 |
| S100A14 | 17145 | 40240 | 63335 |
| S100A16 | 17146 | 40241 | 63336 |
| S100A2 | 17147 | 40242 | 63337 |
| S100A3 | 17148 | 40243 | 63338 |
| S100A4 | 17149 | 40244 | 63339 |
| S100A5 | 17150 | 40245 | 63340 |
| S100A6 | 17151 | 40246 | 63341 |
| S100A7 | 17152 | 40247 | 63342 |
| S100A7A | 17153 | 40248 | 63343 |
| S100A7L2 | 17154 | 40249 | 63344 |
| S100A8 | 17155 | 40250 | 63345 |
| S100A9 | 17156 | 40251 | 63346 |
| S100B | 17157 | 40252 | 63347 |
| S100G | 17158 | 40253 | 63348 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| S100P | 17159 | 40254 | 63349 |
| S100PBP | 17160 | 40255 | 63350 |
| S100Z | 17161 | 40256 | 63351 |
| S1PR1 | 17162 | 40257 | 63352 |
| S1PR2 | 17163 | 40258 | 63353 |
| S1PR3 | 17164 | 40259 | 63354 |
| S1PR4 | 17165 | 40260 | 63355 |
| S1PR5 | 17166 | 40261 | 63356 |
| SAA1 | 17167 | 40262 | 63357 |
| SAA2 | 17168 | 40263 | 63358 |
| SAA4 | 17169 | 40264 | 63359 |
| SAAL1 | 17170 | 40265 | 63360 |
| SAC3D1 | 17171 | 40266 | 63361 |
| SACM1L | 17172 | 40267 | 63362 |
| SACS | 17173 | 40268 | 63363 |
| SAE1 | 17174 | 40269 | 63364 |
| SAE1 | 17175 | 40270 | 63365 |
| SAE1 | 17176 | 40271 | 63366 |
| SAFB | 17177 | 40272 | 63367 |
| SAFB2 | 17178 | 40273 | 63368 |
| SAG | 17179 | 40274 | 63369 |
| SAGE1 | 17180 | 40275 | 63370 |
| SALL1 | 17181 | 40276 | 63371 |
| SALL2 | 17182 | 40277 | 63372 |
| SALL2 | 17183 | 40278 | 63373 |
| SALL3 | 17184 | 40279 | 63374 |
| SALL4 | 17185 | 40280 | 63375 |
| SAMD1 | 17186 | 40281 | 63376 |
| SAMD10 | 17187 | 40282 | 63377 |
| SAMD11 | 17188 | 40283 | 63378 |
| SAMD12 | 17189 | 40284 | 63379 |
| SAMD12 | 17190 | 40285 | 63380 |
| SAMD13 | 17191 | 40286 | 63381 |
| SAMD14 | 17192 | 40287 | 63382 |
| SAMD15 | 17193 | 40288 | 63383 |
| SAMD3 | 17194 | 40289 | 63384 |
| SAMD4A | 17195 | 40290 | 63385 |
| SAMD4B | 17196 | 40291 | 63386 |
| SAMD4B | 17197 | 40292 | 63387 |
| SAMD5 | 17198 | 40293 | 63388 |
| SAMD7 | 17199 | 40294 | 63389 |
| SAMD8 | 17200 | 40295 | 63390 |
| SAMD8 | 17201 | 40296 | 63391 |
| SAMD9 | 17202 | 40297 | 63392 |
| SAMD9L | 17203 | 40298 | 63393 |
| SAMHD1 | 17204 | 40299 | 63394 |
| SAMM50 | 17205 | 40300 | 63395 |
| SAMSN1 | 17206 | 40301 | 63396 |
| SAP130 | 17207 | 40302 | 63397 |
| SAP18 | 17208 | 40303 | 63398 |
| SAP25 | 17209 | 40304 | 63399 |
| SAP30 | 17210 | 40305 | 63400 |
| SAP30BP | 17211 | 40306 | 63401 |
| SAP30L | 17212 | 40307 | 63402 |
| SAPCD1 | 17213 | 40308 | 63403 |
| SAPCD2 | 17214 | 40309 | 63404 |
| SAR1A | 17215 | 40310 | 63405 |
| SAR1B | 17216 | 40311 | 63406 |
| SARAF | 17217 | 40312 | 63407 |
| SARDH | 17218 | 40313 | 63408 |
| SARM1 | 17219 | 40314 | 63409 |
| SARNP | 17220 | 40315 | 63410 |
| SARS | 17221 | 40316 | 63411 |
| SARS2 | 17222 | 40317 | 63412 |
| SART1 | 17223 | 40318 | 63413 |
| SART3 | 17224 | 40319 | 63414 |
| SASH1 | 17225 | 40320 | 63415 |
| SASH3 | 17226 | 40321 | 63416 |
| SASS6 | 17227 | 40322 | 63417 |
| SAT1 | 17228 | 40323 | 63418 |
| SAT2 | 17229 | 40324 | 63419 |
| SATB1 | 17230 | 40325 | 63420 |
| SATB2 | 17231 | 40326 | 63421 |
| SATL1 | 17232 | 40327 | 63422 |
| SAV1 | 17233 | 40328 | 63423 |
| SAXO1 | 17234 | 40329 | 63424 |
| SAXO2 | 17235 | 40330 | 63425 |
| SAXO2 | 17236 | 40331 | 63426 |
| SAYSD1 | 17237 | 40332 | 63427 |
| SBDS | 17238 | 40333 | 63428 |
| SBF1 | 17239 | 40334 | 63429 |
| SBF2 | 17240 | 40335 | 63430 |
| SBK1 | 17241 | 40336 | 63431 |
| SBK2 | 17242 | 40337 | 63432 |
| SBK3 | 17243 | 40338 | 63433 |
| SBNO1 | 17244 | 40339 | 63434 |
| SBNO2 | 17245 | 40340 | 63435 |
| SBSN | 17246 | 40341 | 63436 |
| SBSPON | 17247 | 40342 | 63437 |
| SC5D | 17248 | 40343 | 63438 |
| SCAF1 | 17249 | 40344 | 63439 |
| SCAF11 | 17250 | 40345 | 63440 |
| SCAF4 | 17251 | 40346 | 63441 |
| SCAF8 | 17252 | 40347 | 63442 |
| SCAI | 17253 | 40348 | 63443 |
| SCAMP1 | 17254 | 40349 | 63444 |
| SCAMP2 | 17255 | 40350 | 63445 |
| SCAMP3 | 17256 | 40351 | 63446 |
| SCAMP4 | 17257 | 40352 | 63447 |
| SCAMP5 | 17258 | 40353 | 63448 |
| SCAND1 | 17259 | 40354 | 63449 |
| SCAP | 17260 | 40355 | 63450 |
| SCAPER | 17261 | 40356 | 63451 |
| SCARA3 | 17262 | 40357 | 63452 |
| SCARA3 | 17263 | 40358 | 63453 |
| SCARA5 | 17264 | 40359 | 63454 |
| SCARB1 | 17265 | 40360 | 63455 |
| SCARB1 | 17266 | 40361 | 63456 |
| SCARB2 | 17267 | 40362 | 63457 |
| SCARF1 | 17268 | 40363 | 63458 |
| SCARF1 | 17269 | 40364 | 63459 |
| SCARF2 | 17270 | 40365 | 63460 |
| SCCPDH | 17271 | 40366 | 63461 |
| SCD | 17272 | 40367 | 63462 |
| SCD5 | 17273 | 40368 | 63463 |
| SCD5 | 17274 | 40369 | 63464 |
| SCEL | 17275 | 40370 | 63465 |
| SCFD1 | 17276 | 40371 | 63466 |
| SCFD2 | 17277 | 40372 | 63467 |
| SCG2 | 17278 | 40373 | 63468 |
| SCG3 | 17279 | 40374 | 63469 |
| SCG5 | 17280 | 40375 | 63470 |
| SCGB1A1 | 17281 | 40376 | 63471 |
| SCGB1C1 | 17282 | 40377 | 63472 |
| SCGB1D1 | 17283 | 40378 | 63473 |
| SCGB1D2 | 17284 | 40379 | 63474 |
| SCGB1D4 | 17285 | 40380 | 63475 |
| SCGB2A1 | 17286 | 40381 | 63476 |
| SCGB2A2 | 17287 | 40382 | 63477 |
| SCGB2B2 | 17288 | 40383 | 63478 |
| SCGB3A1 | 17289 | 40384 | 63479 |
| SCGB3A2 | 17290 | 40385 | 63480 |
| SCGN | 17291 | 40386 | 63481 |
| SCHIP1 | 17292 | 40387 | 63482 |
| SCIMP | 17293 | 40388 | 63483 |
| SCIMP | 17294 | 40389 | 63484 |
| SCIN | 17295 | 40390 | 63485 |
| SCLT1 | 17296 | 40391 | 63486 |
| SCLT1 | 17297 | 40392 | 63487 |
| SCLT1 | 17298 | 40393 | 63488 |
| SCLY | 17299 | 40394 | 63489 |
| SCMH1 | 17300 | 40395 | 63490 |
| SCML1 | 17301 | 40396 | 63491 |
| SCML2 | 17302 | 40397 | 63492 |
| SCML4 | 17303 | 40398 | 63493 |
| SCN10A | 17304 | 40399 | 63494 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SCN11A | 17305 | 40400 | 63495 |
| SCN1A | 17306 | 40401 | 63496 |
| SCN1B | 17307 | 40402 | 63497 |
| SCN1B | 17308 | 40403 | 63498 |
| SCN2A | 17309 | 40404 | 63499 |
| SCN2B | 17310 | 40405 | 63500 |
| SCN3A | 17311 | 40406 | 63501 |
| SCN3B | 17312 | 40407 | 63502 |
| SCN4A | 17313 | 40408 | 63503 |
| SCN4B | 17314 | 40409 | 63504 |
| SCN4B | 17315 | 40410 | 63505 |
| SCN5A | 17316 | 40411 | 63506 |
| SCN7A | 17317 | 40412 | 63507 |
| SCN8A | 17318 | 40413 | 63508 |
| SCN9A | 17319 | 40414 | 63509 |
| SCNM1 | 17320 | 40415 | 63510 |
| SCNN1A | 17321 | 40416 | 63511 |
| SCNN1B | 17322 | 40417 | 63512 |
| SCNN1D | 17323 | 40418 | 63513 |
| SCNN1G | 17324 | 40419 | 63514 |
| SCO1 | 17325 | 40420 | 63515 |
| SCO2 | 17326 | 40421 | 63516 |
| SCOC | 17327 | 40422 | 63517 |
| SCP2 | 17328 | 40423 | 63518 |
| SCP2 | 17329 | 40424 | 63519 |
| SCP2 | 17330 | 40425 | 63520 |
| SCP2D1 | 17331 | 40426 | 63521 |
| SCPEP1 | 17332 | 40427 | 63522 |
| SCRG1 | 17333 | 40428 | 63523 |
| SCRIB | 17334 | 40429 | 63524 |
| SCRN1 | 17335 | 40430 | 63525 |
| SCRN2 | 17336 | 40431 | 63526 |
| SCRN2 | 17337 | 40432 | 63527 |
| SCRN3 | 17338 | 40433 | 63528 |
| SCRT1 | 17339 | 40434 | 63529 |
| SCRT2 | 17340 | 40435 | 63530 |
| SCT | 17341 | 40436 | 63531 |
| SCTR | 17342 | 40437 | 63532 |
| SCUBE1 | 17343 | 40438 | 63533 |
| SCUBE2 | 17344 | 40439 | 63534 |
| SCUBE3 | 17345 | 40440 | 63535 |
| SCX | 17346 | 40441 | 63536 |
| SCYL1 | 17347 | 40442 | 63537 |
| SCYL2 | 17348 | 40443 | 63538 |
| SCYL3 | 17349 | 40444 | 63539 |
| SDAD1 | 17350 | 40445 | 63540 |
| SDC1 | 17351 | 40446 | 63541 |
| SDC2 | 17352 | 40447 | 63542 |
| SDC3 | 17353 | 40448 | 63543 |
| SDC4 | 17354 | 40449 | 63544 |
| SDCBP | 17355 | 40450 | 63545 |
| SDCBP2 | 17356 | 40451 | 63546 |
| SDCCAG3 | 17357 | 40452 | 63547 |
| SDCCAG8 | 17358 | 40453 | 63548 |
| SDE2 | 17359 | 40454 | 63549 |
| SDF2 | 17360 | 40455 | 63550 |
| SDF2L1 | 17361 | 40456 | 63551 |
| SDF4 | 17362 | 40457 | 63552 |
| SDF4 | 17363 | 40458 | 63553 |
| SDHA | 17364 | 40459 | 63554 |
| SDHAF1 | 17365 | 40460 | 63555 |
| SDHAF2 | 17366 | 40461 | 63556 |
| SDHAF3 | 17367 | 40462 | 63557 |
| SDHAF4 | 17368 | 40463 | 63558 |
| SDHB | 17369 | 40464 | 63559 |
| SDHC | 17370 | 40465 | 63560 |
| SDHC | 17371 | 40466 | 63561 |
| SDHD | 17372 | 40467 | 63562 |
| SDHD | 17373 | 40468 | 63563 |
| SDK1 | 17374 | 40469 | 63564 |
| SDK1 | 17375 | 40470 | 63565 |
| SDK2 | 17376 | 40471 | 63566 |
| SDR16C5 | 17377 | 40472 | 63567 |
| SDR16C5 | 17378 | 40473 | 63568 |
| SDR39U1 | 17379 | 40474 | 63569 |
| SDR42E1 | 17380 | 40475 | 63570 |
| SDR9C7 | 17381 | 40476 | 63571 |
| SDS | 17382 | 40477 | 63572 |
| SDSL | 17383 | 40478 | 63573 |
| SEBOX | 17384 | 40479 | 63574 |
| SEC11A | 17385 | 40480 | 63575 |
| SEC11A | 17386 | 40481 | 63576 |
| SEC11A | 17387 | 40482 | 63577 |
| SEC11C | 17388 | 40483 | 63578 |
| SEC13 | 17389 | 40484 | 63579 |
| SEC13 | 17390 | 40485 | 63580 |
| SEC14L1 | 17391 | 40486 | 63581 |
| SEC14L1 | 17392 | 40487 | 63582 |
| SEC14L2 | 17393 | 40488 | 63583 |
| SEC14L2 | 17394 | 40489 | 63584 |
| SEC14L3 | 17395 | 40490 | 63585 |
| SEC14L4 | 17396 | 40491 | 63586 |
| SEC14L4 | 17397 | 40492 | 63587 |
| SEC14L5 | 17398 | 40493 | 63588 |
| SEC14L6 | 17399 | 40494 | 63589 |
| SEC14L6 | 17400 | 40495 | 63590 |
| SEC16A | 17401 | 40496 | 63591 |
| SEC16B | 17402 | 40497 | 63592 |
| SEC22A | 17403 | 40498 | 63593 |
| SEC22B | 17404 | 40499 | 63594 |
| SEC22C | 17405 | 40500 | 63595 |
| SEC22C | 17406 | 40501 | 63596 |
| SEC23A | 17407 | 40502 | 63597 |
| SEC23B | 17408 | 40503 | 63598 |
| SEC23IP | 17409 | 40504 | 63599 |
| SEC24A | 17410 | 40505 | 63600 |
| SEC24A | 17411 | 40506 | 63601 |
| SEC24B | 17412 | 40507 | 63602 |
| SEC24C | 17413 | 40508 | 63603 |
| SEC24D | 17414 | 40509 | 63604 |
| SEC31A | 17415 | 40510 | 63605 |
| SEC31B | 17416 | 40511 | 63606 |
| SEC61A1 | 17417 | 40512 | 63607 |
| SEC61A2 | 17418 | 40513 | 63608 |
| SEC61A2 | 17419 | 40514 | 63609 |
| SEC61B | 17420 | 40515 | 63610 |
| SEC61G | 17421 | 40516 | 63611 |
| SEC62 | 17422 | 40517 | 63612 |
| SEC63 | 17423 | 40518 | 63613 |
| SECISBP2 | 17424 | 40519 | 63614 |
| SECISBP2L | 17425 | 40520 | 63615 |
| SECTM1 | 17426 | 40521 | 63616 |
| SEH1L | 17427 | 40522 | 63617 |
| SEH1L | 17428 | 40523 | 63618 |
| SEL1L | 17429 | 40524 | 63619 |
| SEL1L | 17430 | 40525 | 63620 |
| SEL1L2 | 17431 | 40526 | 63621 |
| SEL1L3 | 17432 | 40527 | 63622 |
| SELE | 17433 | 40528 | 63623 |
| SELENBP1 | 17434 | 40529 | 63624 |
| SELENOF | 17435 | 40530 | 63625 |
| SELENOH | 17436 | 40531 | 63626 |
| SELENOI | 17437 | 40532 | 63627 |
| SELENOK | 17438 | 40533 | 63628 |
| SELENOM | 17439 | 40534 | 63629 |
| SELENON | 17440 | 40535 | 63630 |
| SELENOO | 17441 | 40536 | 63631 |
| SELENOP | 17442 | 40537 | 63632 |
| SELENOS | 17443 | 40538 | 63633 |
| SELENOT | 17444 | 40539 | 63634 |
| SELENOV | 17445 | 40540 | 63635 |
| SELENOW | 17446 | 40541 | 63636 |
| SELL | 17447 | 40542 | 63637 |
| SELP | 17448 | 40543 | 63638 |
| SELPLG | 17449 | 40544 | 63639 |
| SEM1 | 17450 | 40545 | 63640 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SEM1 | 17451 | 40546 | 63641 |
| SEMA3A | 17452 | 40547 | 63642 |
| SEMA3B | 17453 | 40548 | 63643 |
| SEMA3C | 17454 | 40549 | 63644 |
| SEMA3D | 17455 | 40550 | 63645 |
| SEMA3E | 17456 | 40551 | 63646 |
| SEMA3F | 17457 | 40552 | 63647 |
| SEMA3G | 17458 | 40553 | 63648 |
| SEMA4A | 17459 | 40554 | 63649 |
| SEMA4B | 17460 | 40555 | 63650 |
| SEMA4B | 17461 | 40556 | 63651 |
| SEMA4C | 17462 | 40557 | 63652 |
| SEMA4D | 17463 | 40558 | 63653 |
| SEMA4D | 17464 | 40559 | 63654 |
| SEMA4F | 17465 | 40560 | 63655 |
| SEMA4G | 17466 | 40561 | 63656 |
| SEMA4G | 17467 | 40562 | 63657 |
| SEMA5A | 17468 | 40563 | 63658 |
| SEMA5B | 17469 | 40564 | 63659 |
| SEMA6A | 17470 | 40565 | 63660 |
| SEMA6B | 17471 | 40566 | 63661 |
| SEMA6C | 17472 | 40567 | 63662 |
| SEMA6D | 17473 | 40568 | 63663 |
| SEMA6D | 17474 | 40569 | 63664 |
| SEMA6D | 17475 | 40570 | 63665 |
| SEMA7A | 17476 | 40571 | 63666 |
| SEMG1 | 17477 | 40572 | 63667 |
| SEMG2 | 17478 | 40573 | 63668 |
| SENP1 | 17479 | 40574 | 63669 |
| SENP2 | 17480 | 40575 | 63670 |
| SENP3 | 17481 | 40576 | 63671 |
| SENP5 | 17482 | 40577 | 63672 |
| SENP6 | 17483 | 40578 | 63673 |
| SENP6 | 17484 | 40579 | 63674 |
| SENP7 | 17485 | 40580 | 63675 |
| SENP7 | 17486 | 40581 | 63676 |
| SENP8 | 17487 | 40582 | 63677 |
| SEPHS1 | 17488 | 40583 | 63678 |
| SEPHS2 | 17489 | 40584 | 63679 |
| SEPSECS | 17490 | 40585 | 63680 |
| SEPT1 | 17491 | 40586 | 63681 |
| SEPT10 | 17492 | 40587 | 63682 |
| SEPT10 | 17493 | 40588 | 63683 |
| SEPT10 | 17494 | 40589 | 63684 |
| SEPT10 | 17495 | 40590 | 63685 |
| SEPT11 | 17496 | 40591 | 63686 |
| SEPT12 | 17497 | 40592 | 63687 |
| SEPT14 | 17498 | 40593 | 63688 |
| SEPT2 | 17499 | 40594 | 63689 |
| SEPT3 | 17500 | 40595 | 63690 |
| SEPT3 | 17501 | 40596 | 63691 |
| SEPT4 | 17502 | 40597 | 63692 |
| SEPT4 | 17503 | 40598 | 63693 |
| SEPT5 | 17504 | 40599 | 63694 |
| SEPT5 | 17505 | 40600 | 63695 |
| SEPT6 | 17506 | 40601 | 63696 |
| SEPT6 | 17507 | 40602 | 63697 |
| SEPT7 | 17508 | 40603 | 63698 |
| SEPT8 | 17509 | 40604 | 63699 |
| SEPT8 | 17510 | 40605 | 63700 |
| SEPT8 | 17511 | 40606 | 63701 |
| SEPT9 | 17512 | 40607 | 63702 |
| SERAC1 | 17513 | 40608 | 63703 |
| SERBP1 | 17514 | 40609 | 63704 |
| SERF1B | 17515 | 40610 | 63705 |
| SERF1B | 17516 | 40611 | 63706 |
| SERF2 | 17517 | 40612 | 63707 |
| SERGEF | 17518 | 40613 | 63708 |
| SERHL2 | 17519 | 40614 | 63709 |
| SERINC1 | 17520 | 40615 | 63710 |
| SERINC2 | 17521 | 40616 | 63711 |
| SERINC3 | 17522 | 40617 | 63712 |
| SERINC4 | 17523 | 40618 | 63713 |
| SERINC5 | 17524 | 40619 | 63714 |
| SERINC5 | 17525 | 40620 | 63715 |
| SERP1 | 17526 | 40621 | 63716 |
| SERP2 | 17527 | 40622 | 63717 |
| SERPINA1 | 17528 | 40623 | 63718 |
| SERPINA10 | 17529 | 40624 | 63719 |
| SERPINA11 | 17530 | 40625 | 63720 |
| SERPINA12 | 17531 | 40626 | 63721 |
| SERPINA2 | 17532 | 40627 | 63722 |
| SERPINA3 | 17533 | 40628 | 63723 |
| SERPINA4 | 17534 | 40629 | 63724 |
| SERPINA5 | 17535 | 40630 | 63725 |
| SERPINA6 | 17536 | 40631 | 63726 |
| SERPINA7 | 17537 | 40632 | 63727 |
| SERPINA9 | 17538 | 40633 | 63728 |
| SERPINB1 | 17539 | 40634 | 63729 |
| SERPINB10 | 17540 | 40635 | 63730 |
| SERPINB11 | 17541 | 40636 | 63731 |
| SERPINB12 | 17542 | 40637 | 63732 |
| SERPINB13 | 17543 | 40638 | 63733 |
| SERPINB2 | 17544 | 40639 | 63734 |
| SERPINB3 | 17545 | 40640 | 63735 |
| SERPINB4 | 17546 | 40641 | 63736 |
| SERPINB5 | 17547 | 40642 | 63737 |
| SERPINB6 | 17548 | 40643 | 63738 |
| SERPINB7 | 17549 | 40644 | 63739 |
| SERPINB8 | 17550 | 40645 | 63740 |
| SERPINB8 | 17551 | 40646 | 63741 |
| SERPINB8 | 17552 | 40647 | 63742 |
| SERPINB8 | 17553 | 40648 | 63743 |
| SERPINB9 | 17554 | 40649 | 63744 |
| SERPINC1 | 17555 | 40650 | 63745 |
| SERPIND1 | 17556 | 40651 | 63746 |
| SERPINE1 | 17557 | 40652 | 63747 |
| SERPINE2 | 17558 | 40653 | 63748 |
| SERPINE3 | 17559 | 40654 | 63749 |
| SERPINF1 | 17560 | 40655 | 63750 |
| SERPINF2 | 17561 | 40656 | 63751 |
| SERPING1 | 17562 | 40657 | 63752 |
| SERPINH1 | 17563 | 40658 | 63753 |
| SERPINI1 | 17564 | 40659 | 63754 |
| SERPINI2 | 17565 | 40660 | 63755 |
| SERTAD1 | 17566 | 40661 | 63756 |
| SERTAD2 | 17567 | 40662 | 63757 |
| SERTAD3 | 17568 | 40663 | 63758 |
| SERTAD4 | 17569 | 40664 | 63759 |
| SERTAD4 | 17570 | 40665 | 63760 |
| SERTM1 | 17571 | 40666 | 63761 |
| SESN1 | 17572 | 40667 | 63762 |
| SESN2 | 17573 | 40668 | 63763 |
| SESN3 | 17574 | 40669 | 63764 |
| SESTD1 | 17575 | 40670 | 63765 |
| SETBP1 | 17576 | 40671 | 63766 |
| SETBP1 | 17577 | 40672 | 63767 |
| SETD1A | 17578 | 40673 | 63768 |
| SETD1B | 17579 | 40674 | 63769 |
| SETD2 | 17580 | 40675 | 63770 |
| SETD3 | 17581 | 40676 | 63771 |
| SETD3 | 17582 | 40677 | 63772 |
| SETD4 | 17583 | 40678 | 63773 |
| SETD4 | 17584 | 40679 | 63774 |
| SETD5 | 17585 | 40680 | 63775 |
| SETD6 | 17586 | 40681 | 63776 |
| SETD7 | 17587 | 40682 | 63777 |
| SETD7 | 17588 | 40683 | 63778 |
| SETD7 | 17589 | 40684 | 63779 |
| SETD9 | 17590 | 40685 | 63780 |
| SETD9 | 17591 | 40686 | 63781 |
| SETD9 | 17592 | 40687 | 63782 |
| SETDB1 | 17593 | 40688 | 63783 |
| SETDB1 | 17594 | 40689 | 63784 |
| SETDB2 | 17595 | 40690 | 63785 |
| SETMAR | 17596 | 40691 | 63786 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SETMAR | 17597 | 40692 | 63787 |
| SETSIP | 17598 | 40693 | 63788 |
| SETX | 17599 | 40694 | 63789 |
| SEZ6 | 17600 | 40695 | 63790 |
| SEZ6 | 17601 | 40696 | 63791 |
| SEZ6L | 17602 | 40697 | 63792 |
| SEZ6L2 | 17603 | 40698 | 63793 |
| SF1 | 17604 | 40699 | 63794 |
| SF1 | 17605 | 40700 | 63795 |
| SF1 | 17606 | 40701 | 63796 |
| SF1 | 17607 | 40702 | 63797 |
| SF3A1 | 17608 | 40703 | 63798 |
| SF3A2 | 17609 | 40704 | 63799 |
| SF3A3 | 17610 | 40705 | 63800 |
| SF3B1 | 17611 | 40706 | 63801 |
| SF3B1 | 17612 | 40707 | 63802 |
| SF3B2 | 17613 | 40708 | 63803 |
| SF3B3 | 17614 | 40709 | 63804 |
| SF3B4 | 17615 | 40710 | 63805 |
| SF3B5 | 17616 | 40711 | 63806 |
| SF3B6 | 17617 | 40712 | 63807 |
| SFI1 | 17618 | 40713 | 63808 |
| SFMBT1 | 17619 | 40714 | 63809 |
| SFMBT2 | 17620 | 40715 | 63810 |
| SFN | 17621 | 40716 | 63811 |
| SFPQ | 17622 | 40717 | 63812 |
| SFR1 | 17623 | 40718 | 63813 |
| SFRP1 | 17624 | 40719 | 63814 |
| SFRP2 | 17625 | 40720 | 63815 |
| SFRP4 | 17626 | 40721 | 63816 |
| SFRP5 | 17627 | 40722 | 63817 |
| SFSWAP | 17628 | 40723 | 63818 |
| SFT2D1 | 17629 | 40724 | 63819 |
| SFT2D2 | 17630 | 40725 | 63820 |
| SFT2D3 | 17631 | 40726 | 63821 |
| SFTA2 | 17632 | 40727 | 63822 |
| SFTA3 | 17633 | 40728 | 63823 |
| SFTA3 | 17634 | 40729 | 63824 |
| SFTA3 | 17635 | 40730 | 63825 |
| SFTPA1 | 17636 | 40731 | 63826 |
| SFTPB | 17637 | 40732 | 63827 |
| SFTPC | 17638 | 40733 | 63828 |
| SFTPD | 17639 | 40734 | 63829 |
| SFXN1 | 17640 | 40735 | 63830 |
| SFXN1 | 17641 | 40736 | 63831 |
| SFXN1 | 17642 | 40737 | 63832 |
| SFXN2 | 17643 | 40738 | 63833 |
| SFXN3 | 17644 | 40739 | 63834 |
| SFXN4 | 17645 | 40740 | 63835 |
| SFXN5 | 17646 | 40741 | 63836 |
| SFXN5 | 17647 | 40742 | 63837 |
| SFXN5 | 17648 | 40743 | 63838 |
| SFXN5 | 17649 | 40744 | 63839 |
| SGCA | 17650 | 40745 | 63840 |
| SGCB | 17651 | 40746 | 63841 |
| SGCD | 17652 | 40747 | 63842 |
| SGCD | 17653 | 40748 | 63843 |
| SGCE | 17654 | 40749 | 63844 |
| SGCG | 17655 | 40750 | 63845 |
| SGCZ | 17656 | 40751 | 63846 |
| SGF29 | 17657 | 40752 | 63847 |
| SGIP1 | 17658 | 40753 | 63848 |
| SGK1 | 17659 | 40754 | 63849 |
| SGK2 | 17660 | 40755 | 63850 |
| SGK3 | 17661 | 40756 | 63851 |
| SGK494 | 17662 | 40757 | 63852 |
| SGMS1 | 17663 | 40758 | 63853 |
| SGMS2 | 17664 | 40759 | 63854 |
| SGO1 | 17665 | 40760 | 63855 |
| SGO1 | 17666 | 40761 | 63856 |
| SGO2 | 17667 | 40762 | 63857 |
| SGPL1 | 17668 | 40763 | 63858 |
| SGPP1 | 17669 | 40764 | 63859 |
| SGPP2 | 17670 | 40765 | 63860 |
| SGSH | 17671 | 40766 | 63861 |
| SGSH | 17672 | 40767 | 63862 |
| SGSH | 17673 | 40768 | 63863 |
| SGSM1 | 17674 | 40769 | 63864 |
| SGSM2 | 17675 | 40770 | 63865 |
| SGSM2 | 17676 | 40771 | 63866 |
| SGSM3 | 17677 | 40772 | 63867 |
| SGSM3 | 17678 | 40773 | 63868 |
| SGTA | 17679 | 40774 | 63869 |
| SGTB | 17680 | 40775 | 63870 |
| SH2B1 | 17681 | 40776 | 63871 |
| SH2B1 | 17682 | 40777 | 63872 |
| SH2B1 | 17683 | 40778 | 63873 |
| SH2B2 | 17684 | 40779 | 63874 |
| SH2B3 | 17685 | 40780 | 63875 |
| SH2D1A | 17686 | 40781 | 63876 |
| SH2D1B | 17687 | 40782 | 63877 |
| SH2D2A | 17688 | 40783 | 63878 |
| SH2D3A | 17689 | 40784 | 63879 |
| SH2D3C | 17690 | 40785 | 63880 |
| SH2D4A | 17691 | 40786 | 63881 |
| SH2D4B | 17692 | 40787 | 63882 |
| SH2D5 | 17693 | 40788 | 63883 |
| SH2D6 | 17694 | 40789 | 63884 |
| SH2D7 | 17695 | 40790 | 63885 |
| SH3BGR | 17696 | 40791 | 63886 |
| SH3BGRL | 17697 | 40792 | 63887 |
| SH3BGRL2 | 17698 | 40793 | 63888 |
| SH3BGRL3 | 17699 | 40794 | 63889 |
| SH3BP1 | 17700 | 40795 | 63890 |
| SH3BP1 | 17701 | 40796 | 63891 |
| SH3BP2 | 17702 | 40797 | 63892 |
| SH3BP4 | 17703 | 40798 | 63893 |
| SH3BP5 | 17704 | 40799 | 63894 |
| SH3BP5L | 17705 | 40800 | 63895 |
| SH3D19 | 17706 | 40801 | 63896 |
| SH3D21 | 17707 | 40802 | 63897 |
| SH3GL1 | 17708 | 40803 | 63898 |
| SH3GL2 | 17709 | 40804 | 63899 |
| SH3GL3 | 17710 | 40805 | 63900 |
| SH3GL3 | 17711 | 40806 | 63901 |
| SH3GLB1 | 17712 | 40807 | 63902 |
| SH3GLB2 | 17713 | 40808 | 63903 |
| SH3GLB2 | 17714 | 40809 | 63904 |
| SH3KBP1 | 17715 | 40810 | 63905 |
| SH3PXD2A | 17716 | 40811 | 63906 |
| SH3PXD2B | 17717 | 40812 | 63907 |
| SH3PXD2B | 17718 | 40813 | 63908 |
| SH3RF1 | 17719 | 40814 | 63909 |
| SH3RF2 | 17720 | 40815 | 63910 |
| SH3RF3 | 17721 | 40816 | 63911 |
| SH3TC1 | 17722 | 40817 | 63912 |
| SH3TC2 | 17723 | 40818 | 63913 |
| SH3YL1 | 17724 | 40819 | 63914 |
| SHANK1 | 17725 | 40820 | 63915 |
| SHANK2 | 17726 | 40821 | 63916 |
| SHANK3 | 17727 | 40822 | 63917 |
| SHARPIN | 17728 | 40823 | 63918 |
| SHB | 17729 | 40824 | 63919 |
| SHBG | 17730 | 40825 | 63920 |
| SHBG | 17731 | 40826 | 63921 |
| SHC1 | 17732 | 40827 | 63922 |
| SHC2 | 17733 | 40828 | 63923 |
| SHC3 | 17734 | 40829 | 63924 |
| SHC4 | 17735 | 40830 | 63925 |
| SHCBP1 | 17736 | 40831 | 63926 |
| SHCBP1L | 17737 | 40832 | 63927 |
| SHD | 17738 | 40833 | 63928 |
| SHE | 17739 | 40834 | 63929 |
| SHF | 17740 | 40835 | 63930 |
| SHF | 17741 | 40836 | 63931 |
| SHF | 17742 | 40837 | 63932 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SHH | 17743 | 40838 | 63933 |
| SHH | 17744 | 40839 | 63934 |
| SHISA2 | 17745 | 40840 | 63935 |
| SHISA3 | 17746 | 40841 | 63936 |
| SHISA4 | 17747 | 40842 | 63937 |
| SHISA5 | 17748 | 40843 | 63938 |
| SHISA5 | 17749 | 40844 | 63939 |
| SHISA5 | 17750 | 40845 | 63940 |
| SHISA6 | 17751 | 40846 | 63941 |
| SHISA7 | 17752 | 40847 | 63942 |
| SHISA8 | 17753 | 40848 | 63943 |
| SHISA9 | 17754 | 40849 | 63944 |
| SHISA9 | 17755 | 40850 | 63945 |
| SHKBP1 | 17756 | 40851 | 63946 |
| SHMT1 | 17757 | 40852 | 63947 |
| SHMT2 | 17758 | 40853 | 63948 |
| SHOC2 | 17759 | 40854 | 63949 |
| SHOX | 17760 | 40855 | 63950 |
| SHOX | 17761 | 40856 | 63951 |
| SHOX2 | 17762 | 40857 | 63952 |
| SHPK | 17763 | 40858 | 63953 |
| SHPRH | 17764 | 40859 | 63954 |
| SHPRH | 17765 | 40860 | 63955 |
| SHQ1 | 17766 | 40861 | 63956 |
| SHROOM1 | 17767 | 40862 | 63957 |
| SHROOM2 | 17768 | 40863 | 63958 |
| SHROOM3 | 17769 | 40864 | 63959 |
| SHROOM4 | 17770 | 40865 | 63960 |
| SHTN1 | 17771 | 40866 | 63961 |
| SHTN1 | 17772 | 40867 | 63962 |
| SHTN1 | 17773 | 40868 | 63963 |
| SI | 17774 | 40869 | 63964 |
| SIAE | 17775 | 40870 | 63965 |
| SIAH1 | 17776 | 40871 | 63966 |
| SIAH2 | 17777 | 40872 | 63967 |
| SIAH3 | 17778 | 40873 | 63968 |
| SIDT1 | 17779 | 40874 | 63969 |
| SIDT2 | 17780 | 40875 | 63970 |
| SIGIRR | 17781 | 40876 | 63971 |
| SIGLEC1 | 17782 | 40877 | 63972 |
| SIGLEC10 | 17783 | 40878 | 63973 |
| SIGLEC11 | 17784 | 40879 | 63974 |
| SIGLEC12 | 17785 | 40880 | 63975 |
| SIGLEC14 | 17786 | 40881 | 63976 |
| SIGLEC15 | 17787 | 40882 | 63977 |
| SIGLEC16 | 17788 | 40883 | 63978 |
| SIGLEC5 | 17789 | 40884 | 63979 |
| SIGLEC6 | 17790 | 40885 | 63980 |
| SIGLEC6 | 17791 | 40886 | 63981 |
| SIGLEC6 | 17792 | 40887 | 63982 |
| SIGLEC7 | 17793 | 40888 | 63983 |
| SIGLEC7 | 17794 | 40889 | 63984 |
| SIGLEC8 | 17795 | 40890 | 63985 |
| SIGLEC9 | 17796 | 40891 | 63986 |
| SIGLEC9 | 17797 | 40892 | 63987 |
| SIGLECL1 | 17798 | 40893 | 63988 |
| SIGMAR1 | 17799 | 40894 | 63989 |
| SIGMAR1 | 17800 | 40895 | 63990 |
| SIGMAR1 | 17801 | 40896 | 63991 |
| SIGMAR1 | 17802 | 40897 | 63992 |
| SIK1 | 17803 | 40898 | 63993 |
| SIK2 | 17804 | 40899 | 63994 |
| SIK3 | 17805 | 40900 | 63995 |
| SIKE1 | 17806 | 40901 | 63996 |
| SIL1 | 17807 | 40902 | 63997 |
| SIM1 | 17808 | 40903 | 63998 |
| SIM2 | 17809 | 40904 | 63999 |
| SIM2 | 17810 | 40905 | 64000 |
| SIMC1 | 17811 | 40906 | 64001 |
| SIN3A | 17812 | 40907 | 64002 |
| SIN3B | 17813 | 40908 | 64003 |
| SINHCAF | 17814 | 40909 | 64004 |
| SIPA1 | 17815 | 40910 | 64005 |
| SIPA1L1 | 17816 | 40911 | 64006 |
| SIPA1L2 | 17817 | 40912 | 64007 |
| SIPA1L3 | 17818 | 40913 | 64008 |
| SIRPA | 17819 | 40914 | 64009 |
| SIRPB1 | 17820 | 40915 | 64010 |
| SIRPB1 | 17821 | 40916 | 64011 |
| SIRPB2 | 17822 | 40917 | 64012 |
| SIRPD | 17823 | 40918 | 64013 |
| SIRPG | 17824 | 40919 | 64014 |
| SIRT1 | 17825 | 40920 | 64015 |
| SIRT2 | 17826 | 40921 | 64016 |
| SIRT2 | 17827 | 40922 | 64017 |
| SIRT3 | 17828 | 40923 | 64018 |
| SIRT4 | 17829 | 40924 | 64019 |
| SIRT5 | 17830 | 40925 | 64020 |
| SIRT5 | 17831 | 40926 | 64021 |
| SIRT6 | 17832 | 40927 | 64022 |
| SIRT6 | 17833 | 40928 | 64023 |
| SIRT7 | 17834 | 40929 | 64024 |
| SIT1 | 17835 | 40930 | 64025 |
| SIVA1 | 17836 | 40931 | 64026 |
| SIX1 | 17837 | 40932 | 64027 |
| SIX2 | 17838 | 40933 | 64028 |
| SIX3 | 17839 | 40934 | 64029 |
| SIX4 | 17840 | 40935 | 64030 |
| SIX5 | 17841 | 40936 | 64031 |
| SIX6 | 17842 | 40937 | 64032 |
| SKA1 | 17843 | 40938 | 64033 |
| SKA2 | 17844 | 40939 | 64034 |
| SKA2 | 17845 | 40940 | 64035 |
| SKA2 | 17846 | 40941 | 64036 |
| SKA3 | 17847 | 40942 | 64037 |
| SKA3 | 17848 | 40943 | 64038 |
| SKAP1 | 17849 | 40944 | 64039 |
| SKAP2 | 17850 | 40945 | 64040 |
| SKI | 17851 | 40946 | 64041 |
| SKIDA1 | 17852 | 40947 | 64042 |
| SKIL | 17853 | 40948 | 64043 |
| SKIV2L | 17854 | 40949 | 64044 |
| SKIV2L2 | 17855 | 40950 | 64045 |
| SKOR1 | 17856 | 40951 | 64046 |
| SKOR2 | 17857 | 40952 | 64047 |
| SKOR2 | 17858 | 40953 | 64048 |
| SKP1 | 17859 | 40954 | 64049 |
| SKP1 | 17860 | 40955 | 64050 |
| SKP2 | 17861 | 40956 | 64051 |
| SKP2 | 17862 | 40957 | 64052 |
| SLA | 17863 | 40958 | 64053 |
| SLA | 17864 | 40959 | 64054 |
| SLA2 | 17865 | 40960 | 64055 |
| SLA2 | 17866 | 40961 | 64056 |
| SLAIN1 | 17867 | 40962 | 64057 |
| SLAIN2 | 17868 | 40963 | 64058 |
| SLAMF1 | 17869 | 40964 | 64059 |
| SLAMF1 | 17870 | 40965 | 64060 |
| SLAMF6 | 17871 | 40966 | 64061 |
| SLAMF7 | 17872 | 40967 | 64062 |
| SLAMF8 | 17873 | 40968 | 64063 |
| SLAMF9 | 17874 | 40969 | 64064 |
| SLAMF9 | 17875 | 40970 | 64065 |
| SLBP | 17876 | 40971 | 64066 |
| SLBP | 17877 | 40972 | 64067 |
| SLC10A1 | 17878 | 40973 | 64068 |
| SLC10A2 | 17879 | 40974 | 64069 |
| SLC10A3 | 17880 | 40975 | 64070 |
| SLC10A4 | 17881 | 40976 | 64071 |
| SLC10A5 | 17882 | 40977 | 64072 |
| SLC10A6 | 17883 | 40978 | 64073 |
| SLC10A7 | 17884 | 40979 | 64074 |
| SLC10A7 | 17885 | 40980 | 64075 |
| SLC10A7 | 17886 | 40981 | 64076 |
| SLC10A7 | 17887 | 40982 | 64077 |
| SLC10A7 | 17888 | 40983 | 64078 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SLC11A1 | 17889 | 40984 | 64079 |
| SLC11A2 | 17890 | 40985 | 64080 |
| SLC11A2 | 17891 | 40986 | 64081 |
| SLC12A1 | 17892 | 40987 | 64082 |
| SLC12A2 | 17893 | 40988 | 64083 |
| SLC12A3 | 17894 | 40989 | 64084 |
| SLC12A4 | 17895 | 40990 | 64085 |
| SLC12A5 | 17896 | 40991 | 64086 |
| SLC12A6 | 17897 | 40992 | 64087 |
| SLC12A7 | 17898 | 40993 | 64088 |
| SLC12A8 | 17899 | 40994 | 64089 |
| SLC12A9 | 17900 | 40995 | 64090 |
| SLC12A9 | 17901 | 40996 | 64091 |
| SLC12A9 | 17902 | 40997 | 64092 |
| SLC13A1 | 17903 | 40998 | 64093 |
| SLC13A2 | 17904 | 40999 | 64094 |
| SLC13A3 | 17905 | 41000 | 64095 |
| SLC13A4 | 17906 | 41001 | 64096 |
| SLC13A5 | 17907 | 41002 | 64097 |
| SLC14A1 | 17908 | 41003 | 64098 |
| SLC14A2 | 17909 | 41004 | 64099 |
| SLC15A1 | 17910 | 41005 | 64100 |
| SLC15A2 | 17911 | 41006 | 64101 |
| SLC15A3 | 17912 | 41007 | 64102 |
| SLC15A4 | 17913 | 41008 | 64103 |
| SLC15A5 | 17914 | 41009 | 64104 |
| SLC16A1 | 17915 | 41010 | 64105 |
| SLC16A10 | 17916 | 41011 | 64106 |
| SLC16A11 | 17917 | 41012 | 64107 |
| SLC16A12 | 17918 | 41013 | 64108 |
| SLC16A13 | 17919 | 41014 | 64109 |
| SLC16A14 | 17920 | 41015 | 64110 |
| SLC16A2 | 17921 | 41016 | 64111 |
| SLC16A3 | 17922 | 41017 | 64112 |
| SLC16A4 | 17923 | 41018 | 64113 |
| SLC16A5 | 17924 | 41019 | 64114 |
| SLC16A6 | 17925 | 41020 | 64115 |
| SLC16A7 | 17926 | 41021 | 64116 |
| SLC16A8 | 17927 | 41022 | 64117 |
| SLC16A9 | 17928 | 41023 | 64118 |
| SLC17A1 | 17929 | 41024 | 64119 |
| SLC17A2 | 17930 | 41025 | 64120 |
| SLC17A2 | 17931 | 41026 | 64121 |
| SLC17A3 | 17932 | 41027 | 64122 |
| SLC17A4 | 17933 | 41028 | 64123 |
| SLC17A5 | 17934 | 41029 | 64124 |
| SLC17A6 | 17935 | 41030 | 64125 |
| SLC17A7 | 17936 | 41031 | 64126 |
| SLC17A8 | 17937 | 41032 | 64127 |
| SLC17A9 | 17938 | 41033 | 64128 |
| SLC18A1 | 17939 | 41034 | 64129 |
| SLC18A1 | 17940 | 41035 | 64130 |
| SLC18A2 | 17941 | 41036 | 64131 |
| SLC18A3 | 17942 | 41037 | 64132 |
| SLC18B1 | 17943 | 41038 | 64133 |
| SLC19A1 | 17944 | 41039 | 64134 |
| SLC19A1 | 17945 | 41040 | 64135 |
| SLC19A2 | 17946 | 41041 | 64136 |
| SLC19A3 | 17947 | 41042 | 64137 |
| SLC1A1 | 17948 | 41043 | 64138 |
| SLC1A2 | 17949 | 41044 | 64139 |
| SLC1A3 | 17950 | 41045 | 64140 |
| SLC1A3 | 17951 | 41046 | 64141 |
| SLC1A4 | 17952 | 41047 | 64142 |
| SLC1A5 | 17953 | 41048 | 64143 |
| SLC1A6 | 17954 | 41049 | 64144 |
| SLC1A6 | 17955 | 41050 | 64145 |
| SLC1A7 | 17956 | 41051 | 64146 |
| SLC1A7 | 17957 | 41052 | 64147 |
| SLC1A7 | 17958 | 41053 | 64148 |
| SLC20A1 | 17959 | 41054 | 64149 |
| SLC20A2 | 17960 | 41055 | 64150 |
| SLC22A1 | 17961 | 41056 | 64151 |
| SLC22A1 | 17962 | 41057 | 64152 |
| SLC22A10 | 17963 | 41058 | 64153 |
| SLC22A11 | 17964 | 41059 | 64154 |
| SLC22A12 | 17965 | 41060 | 64155 |
| SLC22A13 | 17966 | 41061 | 64156 |
| SLC22A14 | 17967 | 41062 | 64157 |
| SLC22A15 | 17968 | 41063 | 64158 |
| SLC22A16 | 17969 | 41064 | 64159 |
| SLC22A17 | 17970 | 41065 | 64160 |
| SLC22A18 | 17971 | 41066 | 64161 |
| SLC22A18AS | 17972 | 41067 | 64162 |
| SLC22A2 | 17973 | 41068 | 64163 |
| SLC22A20 | 17974 | 41069 | 64164 |
| SLC22A23 | 17975 | 41070 | 64165 |
| SLC22A23 | 17976 | 41071 | 64166 |
| SLC22A24 | 17977 | 41072 | 64167 |
| SLC22A24 | 17978 | 41073 | 64168 |
| SLC22A25 | 17979 | 41074 | 64169 |
| SLC22A3 | 17980 | 41075 | 64170 |
| SLC22A31 | 17981 | 41076 | 64171 |
| SLC22A4 | 17982 | 41077 | 64172 |
| SLC22A5 | 17983 | 41078 | 64173 |
| SLC22A6 | 17984 | 41079 | 64174 |
| SLC22A7 | 17985 | 41080 | 64175 |
| SLC22A8 | 17986 | 41081 | 64176 |
| SLC22A9 | 17987 | 41082 | 64177 |
| SLC23A1 | 17988 | 41083 | 64178 |
| SLC23A2 | 17989 | 41084 | 64179 |
| SLC23A3 | 17990 | 41085 | 64180 |
| SLC24A1 | 17991 | 41086 | 64181 |
| SLC24A1 | 17992 | 41087 | 64182 |
| SLC24A2 | 17993 | 41088 | 64183 |
| SLC24A3 | 17994 | 41089 | 64184 |
| SLC24A4 | 17995 | 41090 | 64185 |
| SLC24A5 | 17996 | 41091 | 64186 |
| SLC25A1 | 17997 | 41092 | 64187 |
| SLC25A10 | 17998 | 41093 | 64188 |
| SLC25A10 | 17999 | 41094 | 64189 |
| SLC25A11 | 18000 | 41095 | 64190 |
| SLC25A12 | 18001 | 41096 | 64191 |
| SLC25A13 | 18002 | 41097 | 64192 |
| SLC25A14 | 18003 | 41098 | 64193 |
| SLC25A15 | 18004 | 41099 | 64194 |
| SLC25A16 | 18005 | 41100 | 64195 |
| SLC25A16 | 18006 | 41101 | 64196 |
| SLC25A16 | 18007 | 41102 | 64197 |
| SLC25A17 | 18008 | 41103 | 64198 |
| SLC25A18 | 18009 | 41104 | 64199 |
| SLC25A19 | 18010 | 41105 | 64200 |
| SLC25A2 | 18011 | 41106 | 64201 |
| SLC25A20 | 18012 | 41107 | 64202 |
| SLC25A21 | 18013 | 41108 | 64203 |
| SLC25A21 | 18014 | 41109 | 64204 |
| SLC25A22 | 18015 | 41110 | 64205 |
| SLC25A23 | 18016 | 41111 | 64206 |
| SLC25A24 | 18017 | 41112 | 64207 |
| SLC25A25 | 18018 | 41113 | 64208 |
| SLC25A26 | 18019 | 41114 | 64209 |
| SLC25A27 | 18020 | 41115 | 64210 |
| SLC25A27 | 18021 | 41116 | 64211 |
| SLC25A27 | 18022 | 41117 | 64212 |
| SLC25A28 | 18023 | 41118 | 64213 |
| SLC25A29 | 18024 | 41119 | 64214 |
| SLC25A29 | 18025 | 41120 | 64215 |
| SLC25A3 | 18026 | 41121 | 64216 |
| SLC25A30 | 18027 | 41122 | 64217 |
| SLC25A31 | 18028 | 41123 | 64218 |
| SLC25A31 | 18029 | 41124 | 64219 |
| SLC25A32 | 18030 | 41125 | 64220 |
| SLC25A33 | 18031 | 41126 | 64221 |
| SLC25A34 | 18032 | 41127 | 64222 |
| SLC25A35 | 18033 | 41128 | 64223 |
| SLC25A35 | 18034 | 41129 | 64224 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SLC25A36 | 18035 | 41130 | 64225 |
| SLC25A37 | 18036 | 41131 | 64226 |
| SLC25A38 | 18037 | 41132 | 64227 |
| SLC25A39 | 18038 | 41133 | 64228 |
| SLC25A4 | 18039 | 41134 | 64229 |
| SLC25A40 | 18040 | 41135 | 64230 |
| SLC25A41 | 18041 | 41136 | 64231 |
| SLC25A41 | 18042 | 41137 | 64232 |
| SLC25A42 | 18043 | 41138 | 64233 |
| SLC25A43 | 18044 | 41139 | 64234 |
| SLC25A44 | 18045 | 41140 | 64235 |
| SLC25A45 | 18046 | 41141 | 64236 |
| SLC25A46 | 18047 | 41142 | 64237 |
| SLC25A47 | 18048 | 41143 | 64238 |
| SLC25A48 | 18049 | 41144 | 64239 |
| SLC25A48 | 18050 | 41145 | 64240 |
| SLC25A48 | 18051 | 41146 | 64241 |
| SLC25A5 | 18052 | 41147 | 64242 |
| SLC25A51 | 18053 | 41148 | 64243 |
| SLC25A53 | 18054 | 41149 | 64244 |
| SLC25A6 | 18055 | 41150 | 64245 |
| SLC26A1 | 18056 | 41151 | 64246 |
| SLC26A1 | 18057 | 41152 | 64247 |
| SLC26A10 | 18058 | 41153 | 64248 |
| SLC26A11 | 18059 | 41154 | 64249 |
| SLC26A2 | 18060 | 41155 | 64250 |
| SLC26A3 | 18061 | 41156 | 64251 |
| SLC26A4 | 18062 | 41157 | 64252 |
| SLC26A5 | 18063 | 41158 | 64253 |
| SLC26A5 | 18064 | 41159 | 64254 |
| SLC26A5 | 18065 | 41160 | 64255 |
| SLC26A6 | 18066 | 41161 | 64256 |
| SLC26A7 | 18067 | 41162 | 64257 |
| SLC26A7 | 18068 | 41163 | 64258 |
| SLC26A8 | 18069 | 41164 | 64259 |
| SLC26A9 | 18070 | 41165 | 64260 |
| SLC26A9 | 18071 | 41166 | 64261 |
| SLC27A1 | 18072 | 41167 | 64262 |
| SLC27A2 | 18073 | 41168 | 64263 |
| SLC27A3 | 18074 | 41169 | 64264 |
| SLC27A4 | 18075 | 41170 | 64265 |
| SLC27A5 | 18076 | 41171 | 64266 |
| SLC27A6 | 18077 | 41172 | 64267 |
| SLC28A1 | 18078 | 41173 | 64268 |
| SLC28A1 | 18079 | 41174 | 64269 |
| SLC28A1 | 18080 | 41175 | 64270 |
| SLC28A1 | 18081 | 41176 | 64271 |
| SLC28A2 | 18082 | 41177 | 64272 |
| SLC28A3 | 18083 | 41178 | 64273 |
| SLC29A1 | 18084 | 41179 | 64274 |
| SLC29A2 | 18085 | 41180 | 64275 |
| SLC29A2 | 18086 | 41181 | 64276 |
| SLC29A3 | 18087 | 41182 | 64277 |
| SLC29A3 | 18088 | 41183 | 64278 |
| SLC29A4 | 18089 | 41184 | 64279 |
| SLC2A1 | 18090 | 41185 | 64280 |
| SLC2A10 | 18091 | 41186 | 64281 |
| SLC2A11 | 18092 | 41187 | 64282 |
| SLC2A11 | 18093 | 41188 | 64283 |
| SLC2A12 | 18094 | 41189 | 64284 |
| SLC2A13 | 18095 | 41190 | 64285 |
| SLC2A14 | 18096 | 41191 | 64286 |
| SLC2A2 | 18097 | 41192 | 64287 |
| SLC2A3 | 18098 | 41193 | 64288 |
| SLC2A4 | 18099 | 41194 | 64289 |
| SLC2A4RG | 18100 | 41195 | 64290 |
| SLC2A5 | 18101 | 41196 | 64291 |
| SLC2A5 | 18102 | 41197 | 64292 |
| SLC2A6 | 18103 | 41198 | 64293 |
| SLC2A7 | 18104 | 41199 | 64294 |
| SLC2A8 | 18105 | 41200 | 64295 |
| SLC2A8 | 18106 | 41201 | 64296 |
| SLC2A9 | 18107 | 41202 | 64297 |
| SLC30A1 | 18108 | 41203 | 64298 |
| SLC30A10 | 18109 | 41204 | 64299 |
| SLC30A2 | 18110 | 41205 | 64300 |
| SLC30A3 | 18111 | 41206 | 64301 |
| SLC30A4 | 18112 | 41207 | 64302 |
| SLC30A4 | 18113 | 41208 | 64303 |
| SLC30A5 | 18114 | 41209 | 64304 |
| SLC30A5 | 18115 | 41210 | 64305 |
| SLC30A5 | 18116 | 41211 | 64306 |
| SLC30A6 | 18117 | 41212 | 64307 |
| SLC30A7 | 18118 | 41213 | 64308 |
| SLC30A8 | 18119 | 41214 | 64309 |
| SLC30A9 | 18120 | 41215 | 64310 |
| SLC31A1 | 18121 | 41216 | 64311 |
| SLC31A2 | 18122 | 41217 | 64312 |
| SLC32A1 | 18123 | 41218 | 64313 |
| SLC33A1 | 18124 | 41219 | 64314 |
| SLC34A1 | 18125 | 41220 | 64315 |
| SLC34A1 | 18126 | 41221 | 64316 |
| SLC34A2 | 18127 | 41222 | 64317 |
| SLC34A3 | 18128 | 41223 | 64318 |
| SLC35A1 | 18129 | 41224 | 64319 |
| SLC35A2 | 18130 | 41225 | 64320 |
| SLC35A2 | 18131 | 41226 | 64321 |
| SLC35A2 | 18132 | 41227 | 64322 |
| SLC35A2 | 18133 | 41228 | 64323 |
| SLC35A3 | 18134 | 41229 | 64324 |
| SLC35A3 | 18135 | 41230 | 64325 |
| SLC35A4 | 18136 | 41231 | 64326 |
| SLC35A5 | 18137 | 41232 | 64327 |
| SLC35A5 | 18138 | 41233 | 64328 |
| SLC35B1 | 18139 | 41234 | 64329 |
| SLC35B2 | 18140 | 41235 | 64330 |
| SLC35B3 | 18141 | 41236 | 64331 |
| SLC35B4 | 18142 | 41237 | 64332 |
| SLC35C1 | 18143 | 41238 | 64333 |
| SLC35C2 | 18144 | 41239 | 64334 |
| SLC35D1 | 18145 | 41240 | 64335 |
| SLC35D2 | 18146 | 41241 | 64336 |
| SLC35D3 | 18147 | 41242 | 64337 |
| SLC35E1 | 18148 | 41243 | 64338 |
| SLC35E2 | 18149 | 41244 | 64339 |
| SLC35E2 | 18150 | 41245 | 64340 |
| SLC35E2B | 18151 | 41246 | 64341 |
| SLC35E3 | 18152 | 41247 | 64342 |
| SLC35E4 | 18153 | 41248 | 64343 |
| SLC35E4 | 18154 | 41249 | 64344 |
| SLC35E4 | 18155 | 41250 | 64345 |
| SLC35F1 | 18156 | 41251 | 64346 |
| SLC35F2 | 18157 | 41252 | 64347 |
| SLC35F3 | 18158 | 41253 | 64348 |
| SLC35F4 | 18159 | 41254 | 64349 |
| SLC35F4 | 18160 | 41255 | 64350 |
| SLC35F4 | 18161 | 41256 | 64351 |
| SLC35F5 | 18162 | 41257 | 64352 |
| SLC35F5 | 18163 | 41258 | 64353 |
| SLC35F5 | 18164 | 41259 | 64354 |
| SLC35F6 | 18165 | 41260 | 64355 |
| SLC35G1 | 18166 | 41261 | 64356 |
| SLC35G2 | 18167 | 41262 | 64357 |
| SLC35G3 | 18168 | 41263 | 64358 |
| SLC35G4 | 18169 | 41264 | 64359 |
| SLC35G6 | 18170 | 41265 | 64360 |
| SLC36A1 | 18171 | 41266 | 64361 |
| SLC36A1 | 18172 | 41267 | 64362 |
| SLC36A1 | 18173 | 41268 | 64363 |
| SLC36A2 | 18174 | 41269 | 64364 |
| SLC36A3 | 18175 | 41270 | 64365 |
| SLC36A4 | 18176 | 41271 | 64366 |
| SLC37A1 | 18177 | 41272 | 64367 |
| SLC37A2 | 18178 | 41273 | 64368 |
| SLC37A2 | 18179 | 41274 | 64369 |
| SLC37A3 | 18180 | 41275 | 64370 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SLC37A3 | 18181 | 41276 | 64371 |
| SLC37A4 | 18182 | 41277 | 64372 |
| SLC38A1 | 18183 | 41278 | 64373 |
| SLC38A1 | 18184 | 41279 | 64374 |
| SLC38A10 | 18185 | 41280 | 64375 |
| SLC38A10 | 18186 | 41281 | 64376 |
| SLC38A11 | 18187 | 41282 | 64377 |
| SLC38A2 | 18188 | 41283 | 64378 |
| SLC38A3 | 18189 | 41284 | 64379 |
| SLC38A4 | 18190 | 41285 | 64380 |
| SLC38A5 | 18191 | 41286 | 64381 |
| SLC38A6 | 18192 | 41287 | 64382 |
| SLC38A6 | 18193 | 41288 | 64383 |
| SLC38A7 | 18194 | 41289 | 64384 |
| SLC38A7 | 18195 | 41290 | 64385 |
| SLC38A8 | 18196 | 41291 | 64386 |
| SLC38A9 | 18197 | 41292 | 64387 |
| SLC39A1 | 18198 | 41293 | 64388 |
| SLC39A10 | 18199 | 41294 | 64389 |
| SLC39A11 | 18200 | 41295 | 64390 |
| SLC39A12 | 18201 | 41296 | 64391 |
| SLC39A13 | 18202 | 41297 | 64392 |
| SLC39A13 | 18203 | 41298 | 64393 |
| SLC39A14 | 18204 | 41299 | 64394 |
| SLC39A14 | 18205 | 41300 | 64395 |
| SLC39A2 | 18206 | 41301 | 64396 |
| SLC39A3 | 18207 | 41302 | 64397 |
| SLC39A3 | 18208 | 41303 | 64398 |
| SLC39A4 | 18209 | 41304 | 64399 |
| SLC39A5 | 18210 | 41305 | 64400 |
| SLC39A6 | 18211 | 41306 | 64401 |
| SLC39A6 | 18212 | 41307 | 64402 |
| SLC39A7 | 18213 | 41308 | 64403 |
| SLC39A8 | 18214 | 41309 | 64404 |
| SLC39A8 | 18215 | 41310 | 64405 |
| SLC39A9 | 18216 | 41311 | 64406 |
| SLC39A9 | 18217 | 41312 | 64407 |
| SLC3A1 | 18218 | 41313 | 64408 |
| SLC3A2 | 18219 | 41314 | 64409 |
| SLC40A1 | 18220 | 41315 | 64410 |
| SLC41A1 | 18221 | 41316 | 64411 |
| SLC41A2 | 18222 | 41317 | 64412 |
| SLC41A3 | 18223 | 41318 | 64413 |
| SLC41A3 | 18224 | 41319 | 64414 |
| SLC43A1 | 18225 | 41320 | 64415 |
| SLC43A2 | 18226 | 41321 | 64416 |
| SLC43A3 | 18227 | 41322 | 64417 |
| SLC44A1 | 18228 | 41323 | 64418 |
| SLC44A1 | 18229 | 41324 | 64419 |
| SLC44A2 | 18230 | 41325 | 64420 |
| SLC44A3 | 18231 | 41326 | 64421 |
| SLC44A4 | 18232 | 41327 | 64422 |
| SLC44A5 | 18233 | 41328 | 64423 |
| SLC44A5 | 18234 | 41329 | 64424 |
| SLC45A1 | 18235 | 41330 | 64425 |
| SLC45A2 | 18236 | 41331 | 64426 |
| SLC45A2 | 18237 | 41332 | 64427 |
| SLC45A2 | 18238 | 41333 | 64428 |
| SLC45A3 | 18239 | 41334 | 64429 |
| SLC45A4 | 18240 | 41335 | 64430 |
| SLC45A4 | 18241 | 41336 | 64431 |
| SLC45A4 | 18242 | 41337 | 64432 |
| SLC46A1 | 18243 | 41338 | 64433 |
| SLC46A2 | 18244 | 41339 | 64434 |
| SLC46A3 | 18245 | 41340 | 64435 |
| SLC46A3 | 18246 | 41341 | 64436 |
| SLC47A1 | 18247 | 41342 | 64437 |
| SLC47A2 | 18248 | 41343 | 64438 |
| SLC48A1 | 18249 | 41344 | 64439 |
| SLC4A1 | 18250 | 41345 | 64440 |
| SLC4A10 | 18251 | 41346 | 64441 |
| SLC4A10 | 18252 | 41347 | 64442 |
| SLC4A11 | 18253 | 41348 | 64443 |
| SLC4A1AP | 18254 | 41349 | 64444 |
| SLC4A2 | 18255 | 41350 | 64445 |
| SLC4A3 | 18256 | 41351 | 64446 |
| SLC4A4 | 18257 | 41352 | 64447 |
| SLC4A4 | 18258 | 41353 | 64448 |
| SLC4A5 | 18259 | 41354 | 64449 |
| SLC4A7 | 18260 | 41355 | 64450 |
| SLC4A8 | 18261 | 41356 | 64451 |
| SLC4A8 | 18262 | 41357 | 64452 |
| SLC4A8 | 18263 | 41358 | 64453 |
| SLC4A9 | 18264 | 41359 | 64454 |
| SLC50A1 | 18265 | 41360 | 64455 |
| SLC50A1 | 18266 | 41361 | 64456 |
| SLC51A | 18267 | 41362 | 64457 |
| SLC51B | 18268 | 41363 | 64458 |
| SLC52A1 | 18269 | 41364 | 64459 |
| SLC52A2 | 18270 | 41365 | 64460 |
| SLC52A3 | 18271 | 41366 | 64461 |
| SLC5A1 | 18272 | 41367 | 64462 |
| SLC5A10 | 18273 | 41368 | 64463 |
| SLC5A11 | 18274 | 41369 | 64464 |
| SLC5A12 | 18275 | 41370 | 64465 |
| SLC5A2 | 18276 | 41371 | 64466 |
| SLC5A3 | 18277 | 41372 | 64467 |
| SLC5A4 | 18278 | 41373 | 64468 |
| SLC5A5 | 18279 | 41374 | 64469 |
| SLC5A6 | 18280 | 41375 | 64470 |
| SLC5A7 | 18281 | 41376 | 64471 |
| SLC5A8 | 18282 | 41377 | 64472 |
| SLC5A9 | 18283 | 41378 | 64473 |
| SLC6A1 | 18284 | 41379 | 64474 |
| SLC6A11 | 18285 | 41380 | 64475 |
| SLC6A11 | 18286 | 41381 | 64476 |
| SLC6A12 | 18287 | 41382 | 64477 |
| SLC6A13 | 18288 | 41383 | 64478 |
| SLC6A13 | 18289 | 41384 | 64479 |
| SLC6A14 | 18290 | 41385 | 64480 |
| SLC6A15 | 18291 | 41386 | 64481 |
| SLC6A15 | 18292 | 41387 | 64482 |
| SLC6A16 | 18293 | 41388 | 64483 |
| SLC6A17 | 18294 | 41389 | 64484 |
| SLC6A18 | 18295 | 41390 | 64485 |
| SLC6A19 | 18296 | 41391 | 64486 |
| SLC6A2 | 18297 | 41392 | 64487 |
| SLC6A2 | 18298 | 41393 | 64488 |
| SLC6A20 | 18299 | 41394 | 64489 |
| SLC6A3 | 18300 | 41395 | 64490 |
| SLC6A4 | 18301 | 41396 | 64491 |
| SLC6A5 | 18302 | 41397 | 64492 |
| SLC6A6 | 18303 | 41398 | 64493 |
| SLC6A6 | 18304 | 41399 | 64494 |
| SLC6A7 | 18305 | 41400 | 64495 |
| SLC6A8 | 18306 | 41401 | 64496 |
| SLC6A9 | 18307 | 41402 | 64497 |
| SLC7A1 | 18308 | 41403 | 64498 |
| SLC7A10 | 18309 | 41404 | 64499 |
| SLC7A11 | 18310 | 41405 | 64500 |
| SLC7A13 | 18311 | 41406 | 64501 |
| SLC7A14 | 18312 | 41407 | 64502 |
| SLC7A2 | 18313 | 41408 | 64503 |
| SLC7A3 | 18314 | 41409 | 64504 |
| SLC7A4 | 18315 | 41410 | 64505 |
| SLC7A5 | 18316 | 41411 | 64506 |
| SLC7A6 | 18317 | 41412 | 64507 |
| SLC7A6OS | 18318 | 41413 | 64508 |
| SLC7A7 | 18319 | 41414 | 64509 |
| SLC7A8 | 18320 | 41415 | 64510 |
| SLC7A9 | 18321 | 41416 | 64511 |
| SLC8A1 | 18322 | 41417 | 64512 |
| SLC8A2 | 18323 | 41418 | 64513 |
| SLC8A3 | 18324 | 41419 | 64514 |
| SLC8B1 | 18325 | 41420 | 64515 |
| SLC9A1 | 18326 | 41421 | 64516 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SLC9A2 | 18327 | 41422 | 64517 |
| SLC9A3 | 18328 | 41423 | 64518 |
| SLC9A3R1 | 18329 | 41424 | 64519 |
| SLC9A3R2 | 18330 | 41425 | 64520 |
| SLC9A4 | 18331 | 41426 | 64521 |
| SLC9A5 | 18332 | 41427 | 64522 |
| SLC9A5 | 18333 | 41428 | 64523 |
| SLC9A6 | 18334 | 41429 | 64524 |
| SLC9A7 | 18335 | 41430 | 64525 |
| SLC9A8 | 18336 | 41431 | 64526 |
| SLC9A9 | 18337 | 41432 | 64527 |
| SLC9B1 | 18338 | 41433 | 64528 |
| SLC9B1 | 18339 | 41434 | 64529 |
| SLC9B2 | 18340 | 41435 | 64530 |
| SLC9B2 | 18341 | 41436 | 64531 |
| SLC9C1 | 18342 | 41437 | 64532 |
| SLC9C2 | 18343 | 41438 | 64533 |
| SLCO1A2 | 18344 | 41439 | 64534 |
| SLCO1B1 | 18345 | 41440 | 64535 |
| SLCO1B3 | 18346 | 41441 | 64536 |
| SLCO1B7 | 18347 | 41442 | 64537 |
| SLCO1C1 | 18348 | 41443 | 64538 |
| SLCO1C1 | 18349 | 41444 | 64539 |
| SLCO2A1 | 18350 | 41445 | 64540 |
| SLCO2B1 | 18351 | 41446 | 64541 |
| SLCO3A1 | 18352 | 41447 | 64542 |
| SLCO3A1 | 18353 | 41448 | 64543 |
| SLCO4A1 | 18354 | 41449 | 64544 |
| SLCO4C1 | 18355 | 41450 | 64545 |
| SLCO5A1 | 18356 | 41451 | 64546 |
| SLCO5A1 | 18357 | 41452 | 64547 |
| SLCO6A1 | 18358 | 41453 | 64548 |
| SLF1 | 18359 | 41454 | 64549 |
| SLF2 | 18360 | 41455 | 64550 |
| SLF2 | 18361 | 41456 | 64551 |
| SLF2 | 18362 | 41457 | 64552 |
| SLFN11 | 18363 | 41458 | 64553 |
| SLFN12 | 18364 | 41459 | 64554 |
| SLFN12L | 18365 | 41460 | 64555 |
| SLFN13 | 18366 | 41461 | 64556 |
| SLFN14 | 18367 | 41462 | 64557 |
| SLFN5 | 18368 | 41463 | 64558 |
| SLFN5 | 18369 | 41464 | 64559 |
| SLFNL1 | 18370 | 41465 | 64560 |
| SLIRP | 18371 | 41466 | 64561 |
| SLIRP | 18372 | 41467 | 64562 |
| SLIT1 | 18373 | 41468 | 64563 |
| SLIT2 | 18374 | 41469 | 64564 |
| SLIT3 | 18375 | 41470 | 64565 |
| SLITRK1 | 18376 | 41471 | 64566 |
| SLITRK2 | 18377 | 41472 | 64567 |
| SLITRK3 | 18378 | 41473 | 64568 |
| SLITRK4 | 18379 | 41474 | 64569 |
| SLITRK5 | 18380 | 41475 | 64570 |
| SLITRK6 | 18381 | 41476 | 64571 |
| SLK | 18382 | 41477 | 64572 |
| SLMAP | 18383 | 41478 | 64573 |
| SLMAP | 18384 | 41479 | 64574 |
| SLMAP | 18385 | 41480 | 64575 |
| SLN | 18386 | 41481 | 64576 |
| SLPI | 18387 | 41482 | 64577 |
| SLTM | 18388 | 41483 | 64578 |
| SLU7 | 18389 | 41484 | 64579 |
| SLURP1 | 18390 | 41485 | 64580 |
| SLX1B | 18391 | 41486 | 64581 |
| SLX4 | 18392 | 41487 | 64582 |
| SLX4IP | 18393 | 41488 | 64583 |
| SMAD1 | 18394 | 41489 | 64584 |
| SMAD2 | 18395 | 41490 | 64585 |
| SMAD3 | 18396 | 41491 | 64586 |
| SMAD4 | 18397 | 41492 | 64587 |
| SMAD5 | 18398 | 41493 | 64588 |
| SMAD6 | 18399 | 41494 | 64589 |
| SMAD7 | 18400 | 41495 | 64590 |
| SMAD7 | 18401 | 41496 | 64591 |
| SMAD9 | 18402 | 41497 | 64592 |
| SMAGP | 18403 | 41498 | 64593 |
| SMAP1 | 18404 | 41499 | 64594 |
| SMAP1 | 18405 | 41500 | 64595 |
| SMAP2 | 18406 | 41501 | 64596 |
| SMARCA1 | 18407 | 41502 | 64597 |
| SMARCA1 | 18408 | 41503 | 64598 |
| SMARCA2 | 18409 | 41504 | 64599 |
| SMARCA4 | 18410 | 41505 | 64600 |
| SMARCA5 | 18411 | 41506 | 64601 |
| SMARCAD1 | 18412 | 41507 | 64602 |
| SMARCAL1 | 18413 | 41508 | 64603 |
| SMARCB1 | 18414 | 41509 | 64604 |
| SMARCC1 | 18415 | 41510 | 64605 |
| SMARCC2 | 18416 | 41511 | 64606 |
| SMARCD1 | 18417 | 41512 | 64607 |
| SMARCD2 | 18418 | 41513 | 64608 |
| SMARCD3 | 18419 | 41514 | 64609 |
| SMARCE1 | 18420 | 41515 | 64610 |
| SMC1A | 18421 | 41516 | 64611 |
| SMC1B | 18422 | 41517 | 64612 |
| SMC2 | 18423 | 41518 | 64613 |
| SMC3 | 18424 | 41519 | 64614 |
| SMC4 | 18425 | 41520 | 64615 |
| SMC5 | 18426 | 41521 | 64616 |
| SMC6 | 18427 | 41522 | 64617 |
| SMCHD1 | 18428 | 41523 | 64618 |
| SMCO1 | 18429 | 41524 | 64619 |
| SMCO2 | 18430 | 41525 | 64620 |
| SMCO3 | 18431 | 41526 | 64621 |
| SMCO4 | 18432 | 41527 | 64622 |
| SMCP | 18433 | 41528 | 64623 |
| SMCR8 | 18434 | 41529 | 64624 |
| SMDT1 | 18435 | 41530 | 64625 |
| SMG1 | 18436 | 41531 | 64626 |
| SMG1P1 | 18437 | 41532 | 64627 |
| SMG1P2 | 18438 | 41533 | 64628 |
| SMG1P6 | 18439 | 41534 | 64629 |
| SMG1P7 | 18440 | 41535 | 64630 |
| SMG5 | 18441 | 41536 | 64631 |
| SMG6 | 18442 | 41537 | 64632 |
| SMG7 | 18443 | 41538 | 64633 |
| SMG7 | 18444 | 41539 | 64634 |
| SMG8 | 18445 | 41540 | 64635 |
| SMG9 | 18446 | 41541 | 64636 |
| SMIM1 | 18447 | 41542 | 64637 |
| SMIM10 | 18448 | 41543 | 64638 |
| SMIM10L1 | 18449 | 41544 | 64639 |
| SMIM10L2A | 18450 | 41545 | 64640 |
| SMIM10L2B | 18451 | 41546 | 64641 |
| SMIM11B | 18452 | 41547 | 64642 |
| SMIM12 | 18453 | 41548 | 64643 |
| SMIM13 | 18454 | 41549 | 64644 |
| SMIM14 | 18455 | 41550 | 64645 |
| SMIM15 | 18456 | 41551 | 64646 |
| SMIM17 | 18457 | 41552 | 64647 |
| SMIM18 | 18458 | 41553 | 64648 |
| SMIM19 | 18459 | 41554 | 64649 |
| SMIM2 | 18460 | 41555 | 64650 |
| SMIM20 | 18461 | 41556 | 64651 |
| SMIM21 | 18462 | 41557 | 64652 |
| SMIM21 | 18463 | 41558 | 64653 |
| SMIM22 | 18464 | 41559 | 64654 |
| SMIM23 | 18465 | 41560 | 64655 |
| SMIM24 | 18466 | 41561 | 64656 |
| SMIM25 | 18467 | 41562 | 64657 |
| SMIM26 | 18468 | 41563 | 64658 |
| SMIM26 | 18469 | 41564 | 64659 |
| SMIM27 | 18470 | 41565 | 64660 |
| SMIM27 | 18471 | 41566 | 64661 |
| SMIM29 | 18472 | 41567 | 64662 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SMIM3 | 18473 | 41568 | 64663 |
| SMIM30 | 18474 | 41569 | 64664 |
| SMIM30 | 18475 | 41570 | 64665 |
| SMIM31 | 18476 | 41571 | 64666 |
| SMIM32 | 18477 | 41572 | 64667 |
| SMIM35 | 18478 | 41573 | 64668 |
| SMIM4 | 18479 | 41574 | 64669 |
| SMIM5 | 18480 | 41575 | 64670 |
| SMIM6 | 18481 | 41576 | 64671 |
| SMIM7 | 18482 | 41577 | 64672 |
| SMIM7 | 18483 | 41578 | 64673 |
| SMIM8 | 18484 | 41579 | 64674 |
| SMIM8 | 18485 | 41580 | 64675 |
| SMIM9 | 18486 | 41581 | 64676 |
| SMKR1 | 18487 | 41582 | 64677 |
| SMLR1 | 18488 | 41583 | 64678 |
| SMN2 | 18489 | 41584 | 64679 |
| SMNDC1 | 18490 | 41585 | 64680 |
| SMO | 18491 | 41586 | 64681 |
| SMOC1 | 18492 | 41587 | 64682 |
| SMOC2 | 18493 | 41588 | 64683 |
| SMOX | 18494 | 41589 | 64684 |
| SMPD1 | 18495 | 41590 | 64685 |
| SMPD1 | 18496 | 41591 | 64686 |
| SMPD1 | 18497 | 41592 | 64687 |
| SMPD2 | 18498 | 41593 | 64688 |
| SMPD3 | 18499 | 41594 | 64689 |
| SMPD4 | 18500 | 41595 | 64690 |
| SMPDL3A | 18501 | 41596 | 64691 |
| SMPDL3B | 18502 | 41597 | 64692 |
| SMPDL3B | 18503 | 41598 | 64693 |
| SMPX | 18504 | 41599 | 64694 |
| SMR3A | 18505 | 41600 | 64695 |
| SMR3B | 18506 | 41601 | 64696 |
| SMS | 18507 | 41602 | 64697 |
| SMTN | 18508 | 41603 | 64698 |
| SMTN | 18509 | 41604 | 64699 |
| SMTNL1 | 18510 | 41605 | 64700 |
| SMTNL2 | 18511 | 41606 | 64701 |
| SMU1 | 18512 | 41607 | 64702 |
| SMUG1 | 18513 | 41608 | 64703 |
| SMUG1 | 18514 | 41609 | 64704 |
| SMURF1 | 18515 | 41610 | 64705 |
| SMURF2 | 18516 | 41611 | 64706 |
| SMYD1 | 18517 | 41612 | 64707 |
| SMYD2 | 18518 | 41613 | 64708 |
| SMYD3 | 18519 | 41614 | 64709 |
| SMYD4 | 18520 | 41615 | 64710 |
| SMYD5 | 18521 | 41616 | 64711 |
| SNAI1 | 18522 | 41617 | 64712 |
| SNAI2 | 18523 | 41618 | 64713 |
| SNAI3 | 18524 | 41619 | 64714 |
| SNAP23 | 18525 | 41620 | 64715 |
| SNAP25 | 18526 | 41621 | 64716 |
| SNAP29 | 18527 | 41622 | 64717 |
| SNAP47 | 18528 | 41623 | 64718 |
| SNAP47 | 18529 | 41624 | 64719 |
| SNAP91 | 18530 | 41625 | 64720 |
| SNAPC1 | 18531 | 41626 | 64721 |
| SNAPC2 | 18532 | 41627 | 64722 |
| SNAPC3 | 18533 | 41628 | 64723 |
| SNAPC4 | 18534 | 41629 | 64724 |
| SNAPC5 | 18535 | 41630 | 64725 |
| SNAPC5 | 18536 | 41631 | 64726 |
| SNAPIN | 18537 | 41632 | 64727 |
| SNCA | 18538 | 41633 | 64728 |
| SNCA | 18539 | 41634 | 64729 |
| SNCAIP | 18540 | 41635 | 64730 |
| SNCAIP | 18541 | 41636 | 64731 |
| SNCB | 18542 | 41637 | 64732 |
| SNCB | 18543 | 41638 | 64733 |
| SNCG | 18544 | 41639 | 64734 |
| SNCG | 18545 | 41640 | 64735 |
| SND1 | 18546 | 41641 | 64736 |
| SNED1 | 18547 | 41642 | 64737 |
| SNF8 | 18548 | 41643 | 64738 |
| SNIP1 | 18549 | 41644 | 64739 |
| SNN | 18550 | 41645 | 64740 |
| SNPH | 18551 | 41646 | 64741 |
| SNRK | 18552 | 41647 | 64742 |
| SNRNP200 | 18553 | 41648 | 64743 |
| SNRNP25 | 18554 | 41649 | 64744 |
| SNRNP27 | 18555 | 41650 | 64745 |
| SNRNP35 | 18556 | 41651 | 64746 |
| SNRNP40 | 18557 | 41652 | 64747 |
| SNRNP48 | 18558 | 41653 | 64748 |
| SNRNP70 | 18559 | 41654 | 64749 |
| SNRPA | 18560 | 41655 | 64750 |
| SNRPA1 | 18561 | 41656 | 64751 |
| SNRPB | 18562 | 41657 | 64752 |
| SNRPB | 18563 | 41658 | 64753 |
| SNRPB2 | 18564 | 41659 | 64754 |
| SNRPC | 18565 | 41660 | 64755 |
| SNRPD1 | 18566 | 41661 | 64756 |
| SNRPD2 | 18567 | 41662 | 64757 |
| SNRPD3 | 18568 | 41663 | 64758 |
| SNRPE | 18569 | 41664 | 64759 |
| SNRPF | 18570 | 41665 | 64760 |
| SNRPG | 18571 | 41666 | 64761 |
| SNRPG | 18572 | 41667 | 64762 |
| SNRPN | 18573 | 41668 | 64763 |
| SNTA1 | 18574 | 41669 | 64764 |
| SNTB1 | 18575 | 41670 | 64765 |
| SNTB2 | 18576 | 41671 | 64766 |
| SNTG1 | 18577 | 41672 | 64767 |
| SNTG1 | 18578 | 41673 | 64768 |
| SNTG2 | 18579 | 41674 | 64769 |
| SNTN | 18580 | 41675 | 64770 |
| SNU13 | 18581 | 41676 | 64771 |
| SNUPN | 18582 | 41677 | 64772 |
| SNURF | 18583 | 41678 | 64773 |
| SNW1 | 18584 | 41679 | 64774 |
| SNW1 | 18585 | 41680 | 64775 |
| SNX1 | 18586 | 41681 | 64776 |
| SNX1 | 18587 | 41682 | 64777 |
| SNX10 | 18588 | 41683 | 64778 |
| SNX11 | 18589 | 41684 | 64779 |
| SNX12 | 18590 | 41685 | 64780 |
| SNX12 | 18591 | 41686 | 64781 |
| SNX13 | 18592 | 41687 | 64782 |
| SNX13 | 18593 | 41688 | 64783 |
| SNX13 | 18594 | 41689 | 64784 |
| SNX14 | 18595 | 41690 | 64785 |
| SNX15 | 18596 | 41691 | 64786 |
| SNX16 | 18597 | 41692 | 64787 |
| SNX17 | 18598 | 41693 | 64788 |
| SNX18 | 18599 | 41694 | 64789 |
| SNX18 | 18600 | 41695 | 64790 |
| SNX18 | 18601 | 41696 | 64791 |
| SNX19 | 18602 | 41697 | 64792 |
| SNX19 | 18603 | 41698 | 64793 |
| SNX19 | 18604 | 41699 | 64794 |
| SNX19 | 18605 | 41700 | 64795 |
| SNX2 | 18606 | 41701 | 64796 |
| SNX20 | 18607 | 41702 | 64797 |
| SNX20 | 18608 | 41703 | 64798 |
| SNX20 | 18609 | 41704 | 64799 |
| SNX21 | 18610 | 41705 | 64800 |
| SNX21 | 18611 | 41706 | 64801 |
| SNX22 | 18612 | 41707 | 64802 |
| SNX24 | 18613 | 41708 | 64803 |
| SNX25 | 18614 | 41709 | 64804 |
| SNX27 | 18615 | 41710 | 64805 |
| SNX27 | 18616 | 41711 | 64806 |
| SNX29 | 18617 | 41712 | 64807 |
| SNX3 | 18618 | 41713 | 64808 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SNX3 | 18619 | 41714 | 64809 |
| SNX30 | 18620 | 41715 | 64810 |
| SNX31 | 18621 | 41716 | 64811 |
| SNX32 | 18622 | 41717 | 64812 |
| SNX33 | 18623 | 41718 | 64813 |
| SNX4 | 18624 | 41719 | 64814 |
| SNX5 | 18625 | 41720 | 64815 |
| SNX6 | 18626 | 41721 | 64816 |
| SNX7 | 18627 | 41722 | 64817 |
| SNX8 | 18628 | 41723 | 64818 |
| SNX9 | 18629 | 41724 | 64819 |
| SOAT1 | 18630 | 41725 | 64820 |
| SOAT2 | 18631 | 41726 | 64821 |
| SOBP | 18632 | 41727 | 64822 |
| SOCS1 | 18633 | 41728 | 64823 |
| SOCS2 | 18634 | 41729 | 64824 |
| SOCS3 | 18635 | 41730 | 64825 |
| SOCS4 | 18636 | 41731 | 64826 |
| SOCS5 | 18637 | 41732 | 64827 |
| SOCS6 | 18638 | 41733 | 64828 |
| SOCS7 | 18639 | 41734 | 64829 |
| SOD1 | 18640 | 41735 | 64830 |
| SOD2 | 18641 | 41736 | 64831 |
| SOD2 | 18642 | 41737 | 64832 |
| SOD3 | 18643 | 41738 | 64833 |
| SOGA1 | 18644 | 41739 | 64834 |
| SOGA1 | 18645 | 41740 | 64835 |
| SOGA3 | 18646 | 41741 | 64836 |
| SOHLH1 | 18647 | 41742 | 64837 |
| SOHLH1 | 18648 | 41743 | 64838 |
| SOHLH2 | 18649 | 41744 | 64839 |
| SOHLH2 | 18650 | 41745 | 64840 |
| SON | 18651 | 41746 | 64841 |
| SON | 18652 | 41747 | 64842 |
| SON | 18653 | 41748 | 64843 |
| SORBS1 | 18654 | 41749 | 64844 |
| SORBS2 | 18655 | 41750 | 64845 |
| SORBS3 | 18656 | 41751 | 64846 |
| SORCS1 | 18657 | 41752 | 64847 |
| SORCS1 | 18658 | 41753 | 64848 |
| SORCS1 | 18659 | 41754 | 64849 |
| SORCS1 | 18660 | 41755 | 64850 |
| SORCS2 | 18661 | 41756 | 64851 |
| SORCS3 | 18662 | 41757 | 64852 |
| SORD | 18663 | 41758 | 64853 |
| SORL1 | 18664 | 41759 | 64854 |
| SORT1 | 18665 | 41760 | 64855 |
| SOS1 | 18666 | 41761 | 64856 |
| SOS2 | 18667 | 41762 | 64857 |
| SOST | 18668 | 41763 | 64858 |
| SOSTDC1 | 18669 | 41764 | 64859 |
| SOWAHA | 18670 | 41765 | 64860 |
| SOWAHB | 18671 | 41766 | 64861 |
| SOWAHC | 18672 | 41767 | 64862 |
| SOWAHD | 18673 | 41768 | 64863 |
| SOX1 | 18674 | 41769 | 64864 |
| SOX10 | 18675 | 41770 | 64865 |
| SOX11 | 18676 | 41771 | 64866 |
| SOX12 | 18677 | 41772 | 64867 |
| SOX13 | 18678 | 41773 | 64868 |
| SOX14 | 18679 | 41774 | 64869 |
| SOX15 | 18680 | 41775 | 64870 |
| SOX17 | 18681 | 41776 | 64871 |
| SOX18 | 18682 | 41777 | 64872 |
| SOX2 | 18683 | 41778 | 64873 |
| SOX21 | 18684 | 41779 | 64874 |
| SOX3 | 18685 | 41780 | 64875 |
| SOX30 | 18686 | 41781 | 64876 |
| SOX30 | 18687 | 41782 | 64877 |
| SOX4 | 18688 | 41783 | 64878 |
| SOX5 | 18689 | 41784 | 64879 |
| SOX6 | 18690 | 41785 | 64880 |
| SOX7 | 18691 | 41786 | 64881 |
| SOX8 | 18692 | 41787 | 64882 |
| SOX9 | 18693 | 41788 | 64883 |
| SP1 | 18694 | 41789 | 64884 |
| SP100 | 18695 | 41790 | 64885 |
| SP100 | 18696 | 41791 | 64886 |
| SP100 | 18697 | 41792 | 64887 |
| SP100 | 18698 | 41793 | 64888 |
| SP110 | 18699 | 41794 | 64889 |
| SP110 | 18700 | 41795 | 64890 |
| SP140 | 18701 | 41796 | 64891 |
| SP140 | 18702 | 41797 | 64892 |
| SP140L | 18703 | 41798 | 64893 |
| SP2 | 18704 | 41799 | 64894 |
| SP3 | 18705 | 41800 | 64895 |
| SP4 | 18706 | 41801 | 64896 |
| SP5 | 18707 | 41802 | 64897 |
| SP6 | 18708 | 41803 | 64898 |
| SP7 | 18709 | 41804 | 64899 |
| SP8 | 18710 | 41805 | 64900 |
| SP9 | 18711 | 41806 | 64901 |
| SPA17 | 18712 | 41807 | 64902 |
| SPAAR | 18713 | 41808 | 64903 |
| SPACA1 | 18714 | 41809 | 64904 |
| SPACA3 | 18715 | 41810 | 64905 |
| SPACA3 | 18716 | 41811 | 64906 |
| SPACA4 | 18717 | 41812 | 64907 |
| SPACA5B | 18718 | 41813 | 64908 |
| SPACA6 | 18719 | 41814 | 64909 |
| SPACA7 | 18720 | 41815 | 64910 |
| SPACA9 | 18721 | 41816 | 64911 |
| SPACA9 | 18722 | 41817 | 64912 |
| SPAG1 | 18723 | 41818 | 64913 |
| SPAG11A | 18724 | 41819 | 64914 |
| SPAG11B | 18725 | 41820 | 64915 |
| SPAG11B | 18726 | 41821 | 64916 |
| SPAG11B | 18727 | 41822 | 64917 |
| SPAG16 | 18728 | 41823 | 64918 |
| SPAG16 | 18729 | 41824 | 64919 |
| SPAG17 | 18730 | 41825 | 64920 |
| SPAG4 | 18731 | 41826 | 64921 |
| SPAG5 | 18732 | 41827 | 64922 |
| SPAG6 | 18733 | 41828 | 64923 |
| SPAG6 | 18734 | 41829 | 64924 |
| SPAG7 | 18735 | 41830 | 64925 |
| SPAG8 | 18736 | 41831 | 64926 |
| SPAG8 | 18737 | 41832 | 64927 |
| SPAG9 | 18738 | 41833 | 64928 |
| SPAM1 | 18739 | 41834 | 64929 |
| SPAM1 | 18740 | 41835 | 64930 |
| SPANXB1 | 18741 | 41836 | 64931 |
| SPANXC | 18742 | 41837 | 64932 |
| SPANXN2 | 18743 | 41838 | 64933 |
| SPANXN3 | 18744 | 41839 | 64934 |
| SPANXN4 | 18745 | 41840 | 64935 |
| SPANXN5 | 18746 | 41841 | 64936 |
| SPARC | 18747 | 41842 | 64937 |
| SPARC | 18748 | 41843 | 64938 |
| SPARCL1 | 18749 | 41844 | 54939 |
| SPART | 18750 | 41845 | 54940 |
| SPAST | 18751 | 41845 | 54941 |
| SPATA1 | 18752 | 41847 | 54942 |
| SPATA12 | 18753 | 41848 | 54943 |
| SPATA13 | 18754 | 41849 | 54944 |
| SPATA16 | 18755 | 41850 | 54945 |
| SPATA17 | 18756 | 41851 | 64946 |
| SPATA18 | 18757 | 41852 | 64947 |
| SPATA19 | 18758 | 41853 | 64948 |
| SPATA2 | 18759 | 41854 | 64949 |
| SPATA20 | 18760 | 41855 | 64950 |
| SPATA21 | 18761 | 41856 | 64951 |
| SPATA22 | 18762 | 41857 | 64952 |
| SPATA22 | 18763 | 41858 | 64953 |
| SPATA24 | 18764 | 41859 | 64954 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SPATA25 | 18765 | 41860 | 64955 |
| SPATA2L | 18766 | 41861 | 64956 |
| SPATA3 | 18767 | 41862 | 64957 |
| SPATA31A6 | 18768 | 41863 | 64958 |
| SPATA31C1 | 18769 | 41864 | 64959 |
| SPATA31C2 | 18770 | 41865 | 64960 |
| SPATA31D1 | 18771 | 41866 | 64961 |
| SPATA31D3 | 18772 | 41867 | 64962 |
| SPATA31E1 | 18773 | 41868 | 64963 |
| SPATA32 | 18774 | 41869 | 64964 |
| SPATA33 | 18775 | 41870 | 64965 |
| SPATA33 | 18776 | 41871 | 64966 |
| SPATA4 | 18777 | 41872 | 64967 |
| SPATA45 | 18778 | 41873 | 64968 |
| SPATA46 | 18779 | 41874 | 64969 |
| SPATA48 | 18780 | 41875 | 64970 |
| SPATA5 | 18781 | 41876 | 64971 |
| SPATA5 | 18782 | 41877 | 54972 |
| SPATA5L1 | 18783 | 41878 | 54973 |
| SPATA5L1 | 18784 | 41879 | 54974 |
| SPATA6 | 18785 | 41880 | 54975 |
| SPATA6L | 18786 | 41881 | 54976 |
| SPATA7 | 18787 | 41882 | 54977 |
| SPATA8 | 18788 | 41883 | 54978 |
| SPATA8 | 18789 | 41884 | 54979 |
| SPATA9 | 18790 | 41885 | 54980 |
| SPATC1 | 18791 | 41885 | 54981 |
| SPATC1 | 18792 | 41887 | 54982 |
| SPATC1L | 18793 | 41888 | 54983 |
| SPATS1 | 18794 | 41889 | 54984 |
| SPATS2 | 18795 | 41890 | 54985 |
| SPATS2L | 18796 | 41891 | 54986 |
| SPC24 | 18797 | 41892 | 54987 |
| SPC24 | 18798 | 41893 | 54988 |
| SPC24 | 18799 | 41894 | 54989 |
| SPC25 | 18800 | 41895 | 54990 |
| SPCS1 | 18801 | 41895 | 54991 |
| SPCS2 | 18802 | 41897 | 54992 |
| SPCS3 | 18803 | 41898 | 54993 |
| SPDEF | 18804 | 41899 | 54994 |
| SPDL1 | 18805 | 41900 | 54995 |
| SPDL1 | 18805 | 41901 | 54995 |
| SPDYA | 18807 | 41902 | 54997 |
| SPDYA | 18808 | 41903 | 54998 |
| SPDYC | 18809 | 41904 | 54999 |
| SPDYE1 | 18810 | 41905 | 55000 |
| SPDYE16 | 18811 | 41905 | 55001 |
| SPDYE17 | 18812 | 41907 | 55002 |
| SPDYE3 | 18813 | 41908 | 55003 |
| SPDYE4 | 18814 | 41909 | 55004 |
| SPECC1 | 18815 | 41910 | 55005 |
| SPECC1 | 18815 | 41911 | 55005 |
| SPECC1 | 18817 | 41912 | 55007 |
| SPECC1L | 18818 | 41913 | 55008 |
| SPEF1 | 18819 | 41914 | 55009 |
| SPEF2 | 18820 | 41915 | 55010 |
| SPEF2 | 18821 | 41915 | 55011 |
| SPEG | 18822 | 41917 | 55012 |
| SPEG | 18823 | 41918 | 55013 |
| SPEM1 | 18824 | 41919 | 55014 |
| SPEM2 | 18825 | 41920 | 55015 |
| SPEN | 18825 | 41921 | 55015 |
| SPERT | 18827 | 41922 | 55017 |
| SPESP1 | 18828 | 41923 | 55018 |
| SPG11 | 18829 | 41924 | 55019 |
| SPG21 | 18830 | 41925 | 55020 |
| SPG7 | 18831 | 41925 | 55021 |
| SPG7 | 18832 | 41927 | 55022 |
| SPHAR | 18833 | 41928 | 55023 |
| SPHK1 | 18834 | 41929 | 55024 |
| SPHK2 | 18835 | 41930 | 55025 |
| SPHKAP | 18836 | 41931 | 55025 |
| SPI1 | 18837 | 41932 | 55027 |
| SPIB | 18838 | 41933 | 65028 |
| SPIB | 18839 | 41934 | 65029 |
| SPIC | 18840 | 41935 | 65030 |
| SPICE1 | 18841 | 41936 | 65031 |
| SPIDR | 18842 | 41937 | 65032 |
| SPIDR | 18843 | 41938 | 65033 |
| SPIDR | 18844 | 41939 | 65034 |
| SPIDR | 18845 | 41940 | 65035 |
| SPIN1 | 18846 | 41941 | 65036 |
| SPIN2A | 18847 | 41942 | 65037 |
| SPIN3 | 18848 | 41943 | 65038 |
| SPIN4 | 18849 | 41944 | 65039 |
| SPINK1 | 18850 | 41945 | 65040 |
| SPINK13 | 18851 | 41946 | 65041 |
| SPINK14 | 18852 | 41947 | 65042 |
| SPINK2 | 18853 | 41948 | 65043 |
| SPINK2 | 18854 | 41949 | 65044 |
| SPINK2 | 18855 | 41950 | 65045 |
| SPINK4 | 18856 | 41951 | 65046 |
| SPINK5 | 18857 | 41952 | 65047 |
| SPINK5 | 18858 | 41953 | 65048 |
| SPINK6 | 18859 | 41954 | 65049 |
| SPINK7 | 18860 | 41955 | 65050 |
| SPINK8 | 18861 | 41956 | 65051 |
| SPINK9 | 18862 | 41957 | 65052 |
| SPINT1 | 18863 | 41958 | 65053 |
| SPINT2 | 18864 | 41959 | 65054 |
| SPINT3 | 18865 | 41960 | 65055 |
| SPINT4 | 18866 | 41961 | 65056 |
| SPIRE1 | 18867 | 41962 | 65057 |
| SPIRE2 | 18868 | 41963 | 65058 |
| SPN | 18869 | 41964 | 65059 |
| SPNS1 | 18870 | 41965 | 65060 |
| SPNS2 | 18871 | 41966 | 65061 |
| SPNS3 | 18872 | 41967 | 65062 |
| SPO11 | 18873 | 41968 | 65063 |
| SPOCD1 | 18874 | 41969 | 65064 |
| SPOCK1 | 18875 | 41970 | 65065 |
| SPOCK2 | 18876 | 41971 | 65066 |
| SPOCK2 | 18877 | 41972 | 65067 |
| SPOCK3 | 18878 | 41973 | 65068 |
| SPOCK3 | 18879 | 41974 | 65069 |
| SPON1 | 18880 | 41975 | 65070 |
| SPON2 | 18881 | 41976 | 65071 |
| SPOP | 18882 | 41977 | 65072 |
| SPOPL | 18883 | 41978 | 65073 |
| SPOUT1 | 18884 | 41979 | 65074 |
| SPP1 | 18885 | 41980 | 65075 |
| SPP2 | 18886 | 41981 | 65076 |
| SPPL2A | 18887 | 41982 | 65077 |
| SPPL2B | 18888 | 41983 | 65078 |
| SPPL2B | 18889 | 41984 | 65079 |
| SPPL2C | 18890 | 41985 | 65080 |
| SPPL3 | 18891 | 41986 | 65081 |
| SPR | 18892 | 41987 | 65082 |
| SPRED1 | 18893 | 41988 | 65083 |
| SPRED2 | 18894 | 41989 | 65084 |
| SPRED3 | 18895 | 41990 | 65085 |
| SPRN | 18896 | 41991 | 65086 |
| SPRR1B | 18897 | 41992 | 65087 |
| SPRR2B | 18898 | 41993 | 65088 |
| SPRR2E | 18899 | 41994 | 65089 |
| SPRR2G | 18900 | 41995 | 65090 |
| SPRR3 | 18901 | 41996 | 65091 |
| SPRR4 | 18902 | 41997 | 65092 |
| SPRTN | 18903 | 41998 | 65093 |
| SPRTN | 18904 | 41999 | 65094 |
| SPRY1 | 18905 | 42000 | 65095 |
| SPRY2 | 18906 | 42001 | 65096 |
| SPRY3 | 18907 | 42002 | 65097 |
| SPRY4 | 18908 | 42003 | 65098 |
| SPRYD3 | 18909 | 42004 | 65099 |
| SPRYD4 | 18910 | 42005 | 65100 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SPRYD7 | 18911 | 42006 | 65101 |
| SPSB1 | 18912 | 42007 | 65102 |
| SPSB2 | 18913 | 42008 | 65103 |
| SPSB3 | 18914 | 42009 | 65104 |
| SPSB4 | 18915 | 42010 | 65105 |
| SPTA1 | 18916 | 42011 | 65106 |
| SPTAN1 | 18917 | 42012 | 65107 |
| SPTB | 18918 | 42013 | 65108 |
| SPTB | 18919 | 42014 | 65109 |
| SPTBN1 | 18920 | 42015 | 65110 |
| SPTBN1 | 18921 | 42016 | 65111 |
| SPTBN2 | 18922 | 42017 | 65112 |
| SPTBN4 | 18923 | 42018 | 65113 |
| SPTBN4 | 18924 | 42019 | 65114 |
| SPTBN5 | 18925 | 42020 | 65115 |
| SPTLC1 | 18926 | 42021 | 65116 |
| SPTLC1 | 18927 | 42022 | 65117 |
| SPTLC1 | 18928 | 42023 | 65118 |
| SPTLC2 | 18929 | 42024 | 65119 |
| SPTLC3 | 18930 | 42025 | 65120 |
| SPTSSA | 18931 | 42026 | 65121 |
| SPTSSB | 18932 | 42027 | 65122 |
| SPTSSB | 18933 | 42028 | 65123 |
| SPTY2D1 | 18934 | 42029 | 65124 |
| SPX | 18935 | 42030 | 65125 |
| SPZ1 | 18936 | 42031 | 65126 |
| SQLE | 18937 | 42032 | 65127 |
| SQOR | 18938 | 42033 | 65128 |
| SQSTM1 | 18939 | 42034 | 65129 |
| SRA1 | 18940 | 42035 | 65130 |
| SRARP | 18941 | 42036 | 65131 |
| SRBD1 | 18942 | 42037 | 65132 |
| SRC | 18943 | 42038 | 65133 |
| SRCAP | 18944 | 42039 | 65134 |
| SRCIN1 | 18945 | 42040 | 65135 |
| SRD5A1 | 18946 | 42041 | 65136 |
| SRD5A1 | 18947 | 42042 | 65137 |
| SRD5A2 | 18948 | 42043 | 65138 |
| SRD5A3 | 18949 | 42044 | 65139 |
| SREBF1 | 18950 | 42045 | 65140 |
| SREBF2 | 18951 | 42046 | 65141 |
| SREK1 | 18952 | 42047 | 65142 |
| SREK1 | 18953 | 42048 | 65143 |
| SREK1IP1 | 18954 | 42049 | 65144 |
| SRF | 18955 | 42050 | 65145 |
| SRFBP1 | 18956 | 42051 | 65146 |
| SRGAP1 | 18957 | 42052 | 65147 |
| SRGAP2 | 18958 | 42053 | 65148 |
| SRGAP2 | 18959 | 42054 | 65149 |
| SRGAP2B | 18960 | 42055 | 65150 |
| SRGAP2C | 18961 | 42056 | 65151 |
| SRGAP3 | 18962 | 42057 | 65152 |
| SRGN | 18963 | 42058 | 65153 |
| SRI | 18964 | 42059 | 65154 |
| SRL | 18965 | 42060 | 65155 |
| SRL | 18966 | 42061 | 65156 |
| SRM | 18967 | 42062 | 65157 |
| SRMS | 18968 | 42063 | 65158 |
| SRP14 | 18969 | 42064 | 65159 |
| SRP19 | 18970 | 42065 | 65160 |
| SRP19 | 18971 | 42066 | 65161 |
| SRP19 | 18972 | 42067 | 65162 |
| SRP19 | 18973 | 42068 | 65163 |
| SRP54 | 18974 | 42069 | 65164 |
| SRP68 | 18975 | 42070 | 65165 |
| SRP72 | 18976 | 42071 | 65166 |
| SRP9 | 18977 | 42072 | 65167 |
| SRP9 | 18978 | 42073 | 65168 |
| SRPK1 | 18979 | 42074 | 65169 |
| SRPK2 | 18980 | 42075 | 65170 |
| SRPK2 | 18981 | 42076 | 65171 |
| SRPK3 | 18982 | 42077 | 65172 |
| SRPRA | 18983 | 42078 | 65173 |
| SRPRB | 18984 | 42079 | 65174 |
| SRPX | 18985 | 42080 | 65175 |
| SRPX | 18986 | 42081 | 65176 |
| SRPX2 | 18987 | 42082 | 65177 |
| SRR | 18988 | 42083 | 65178 |
| SRRD | 18989 | 42084 | 65179 |
| SRRM1 | 18990 | 42085 | 65180 |
| SRRM2 | 18991 | 42086 | 65181 |
| SRRM3 | 18992 | 42087 | 65182 |
| SRRM3 | 18993 | 42088 | 65183 |
| SRRM4 | 18994 | 42089 | 65184 |
| SRRM5 | 18995 | 42090 | 65185 |
| SRRT | 18996 | 42091 | 65186 |
| SRSF1 | 18997 | 42092 | 65187 |
| SRSF1 | 18998 | 42093 | 65188 |
| SRSF10 | 18999 | 42094 | 65189 |
| SRSF10 | 19000 | 42095 | 65190 |
| SRSF10 | 19001 | 42096 | 65191 |
| SRSF11 | 19002 | 42097 | 65192 |
| SRSF12 | 19003 | 42098 | 65193 |
| SRSF2 | 19004 | 42099 | 65194 |
| SRSF3 | 19005 | 42100 | 65195 |
| SRSF4 | 19006 | 42101 | 65196 |
| SRSF5 | 19007 | 42102 | 65197 |
| SRSF6 | 19008 | 42103 | 65198 |
| SRSF7 | 19009 | 42104 | 65199 |
| SRSF8 | 19010 | 42105 | 65200 |
| SRSF9 | 19011 | 42106 | 65201 |
| SRXN1 | 19012 | 42107 | 65202 |
| SRY | 19013 | 42108 | 65203 |
| SS18 | 19014 | 42109 | 65204 |
| SS18L1 | 19015 | 42110 | 65205 |
| SS18L2 | 19016 | 42111 | 65206 |
| SSB | 19017 | 42112 | 65207 |
| SSBP1 | 19018 | 42113 | 65208 |
| SSBP2 | 19019 | 42114 | 65209 |
| SSBP3 | 19020 | 42115 | 65210 |
| SSBP4 | 19021 | 42116 | 65211 |
| SSC4D | 19022 | 42117 | 65212 |
| SSC5D | 19023 | 42118 | 65213 |
| SSC5D | 19024 | 42119 | 65214 |
| SSFA2 | 19025 | 42120 | 65215 |
| SSFA2 | 19026 | 42121 | 65216 |
| SSFA2 | 19027 | 42122 | 65217 |
| SSH1 | 19028 | 42123 | 65218 |
| SSH1 | 19029 | 42124 | 65219 |
| SSH2 | 19030 | 42125 | 65220 |
| SSH2 | 19031 | 42126 | 65221 |
| SSH3 | 19032 | 42127 | 65222 |
| SSMEM1 | 19033 | 42128 | 65223 |
| SSNA1 | 19034 | 42129 | 65224 |
| SSPN | 19035 | 42130 | 65225 |
| SSPO | 19036 | 42131 | 65226 |
| SSR1 | 19037 | 42132 | 65227 |
| SSR2 | 19038 | 42133 | 65228 |
| SSR3 | 19039 | 42134 | 65229 |
| SSR4 | 19040 | 42135 | 65230 |
| SSRP1 | 19041 | 42136 | 65231 |
| SSSCA1 | 19042 | 42137 | 65232 |
| SST | 19043 | 42138 | 65233 |
| SSTR1 | 19044 | 42139 | 65234 |
| SSTR2 | 19045 | 42140 | 65235 |
| SSTR3 | 19046 | 42141 | 65236 |
| SSTR4 | 19047 | 42142 | 65237 |
| SSTR5 | 19048 | 42143 | 65238 |
| SSU72 | 19049 | 42144 | 65239 |
| SSUH2 | 19050 | 42145 | 65240 |
| SSX1 | 19051 | 42146 | 65241 |
| SSX2 | 19052 | 42147 | 65242 |
| SSX2IP | 19053 | 42148 | 65243 |
| SSX3 | 19054 | 42149 | 65244 |
| SSX4B | 19055 | 42150 | 65245 |
| SSX4B | 19056 | 42151 | 65246 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SSX5 | 19057 | 42152 | 65247 |
| SSX7 | 19058 | 42153 | 65248 |
| ST13 | 19059 | 42154 | 65249 |
| ST14 | 19060 | 42155 | 65250 |
| ST18 | 19061 | 42156 | 65251 |
| ST18 | 19062 | 42157 | 65252 |
| ST18 | 19063 | 42158 | 65253 |
| ST20 | 19064 | 42159 | 65254 |
| ST20-MTHFS | 19065 | 42160 | 65255 |
| ST3GAL1 | 19066 | 42161 | 65256 |
| ST3GAL2 | 19067 | 42162 | 65257 |
| ST3GAL3 | 19068 | 42163 | 65258 |
| ST3GAL3 | 19069 | 42164 | 65259 |
| ST3GAL3 | 19070 | 42165 | 65260 |
| ST3GAL3 | 19071 | 42166 | 65261 |
| ST3GAL4 | 19072 | 42167 | 65262 |
| ST3GAL4 | 19073 | 42168 | 65263 |
| ST3GAL5 | 19074 | 42169 | 65264 |
| ST3GAL6 | 19075 | 42170 | 65265 |
| ST5 | 19076 | 42171 | 65266 |
| ST6GAL1 | 19077 | 42172 | 65267 |
| ST6GAL2 | 19078 | 42173 | 65268 |
| ST6GAL2 | 19079 | 42174 | 65269 |
| ST6GALNAC1 | 19080 | 42175 | 65270 |
| ST6GALNAC2 | 19081 | 42176 | 65271 |
| ST6GALNAC3 | 19082 | 42177 | 65272 |
| ST6GALNAC3 | 19083 | 42178 | 65273 |
| ST6GALNAC3 | 19084 | 42179 | 65274 |
| ST6GALNAC3 | 19085 | 42180 | 65275 |
| ST6GALNAC4 | 19086 | 42181 | 65276 |
| ST6GALNAC5 | 19087 | 42182 | 65277 |
| ST6GALNAC5 | 19088 | 42183 | 65278 |
| ST6GALNAC5 | 19089 | 42184 | 65279 |
| ST6GALNAC6 | 19090 | 42185 | 65280 |
| ST6GALNAC6 | 19091 | 42186 | 65281 |
| ST6GALNAC6 | 19092 | 42187 | 65282 |
| ST7 | 19093 | 42188 | 65283 |
| ST7 | 19094 | 42189 | 65284 |
| ST7L | 19095 | 42190 | 65285 |
| ST7L | 19096 | 42191 | 65286 |
| ST8SIA1 | 19097 | 42192 | 65287 |
| ST8SIA2 | 19098 | 42193 | 65288 |
| ST8SIA3 | 19099 | 42194 | 65289 |
| ST8SIA4 | 19100 | 42195 | 65290 |
| ST8SIA4 | 19101 | 42196 | 65291 |
| ST8SIA5 | 19102 | 42197 | 65292 |
| ST8SIA6 | 19103 | 42198 | 65293 |
| STAB1 | 19104 | 42199 | 65294 |
| STAB2 | 19105 | 42200 | 65295 |
| STAC | 19106 | 42201 | 65296 |
| STAC2 | 19107 | 42202 | 65297 |
| STAC3 | 19108 | 42203 | 65298 |
| STAG1 | 19109 | 42204 | 65299 |
| STAG2 | 19110 | 42205 | 65300 |
| STAG3 | 19111 | 42206 | 65301 |
| STAM | 19112 | 42207 | 65302 |
| STAM2 | 19113 | 42208 | 65303 |
| STAMBP | 19114 | 42209 | 65304 |
| STAMBP | 19115 | 42210 | 65305 |
| STAMBPL1 | 19116 | 42211 | 65306 |
| STAP1 | 19117 | 42212 | 65307 |
| STAP2 | 19118 | 42213 | 65308 |
| STAR | 19119 | 42214 | 65309 |
| STARD10 | 19120 | 42215 | 65310 |
| STARD13 | 19121 | 42216 | 65311 |
| STARD13 | 19122 | 42217 | 65312 |
| STARD13 | 19123 | 42218 | 65313 |
| STARD3 | 19124 | 42219 | 65314 |
| STARD3NL | 19125 | 42220 | 65315 |
| STARD4 | 19126 | 42221 | 65316 |
| STARD4 | 19127 | 42222 | 65317 |
| STARD5 | 19128 | 42223 | 65318 |
| STARD6 | 19129 | 42224 | 65319 |
| STARD7 | 19130 | 42225 | 65320 |
| STARD8 | 19131 | 42226 | 65321 |
| STARD9 | 19132 | 42227 | 65322 |
| STAT1 | 19133 | 42228 | 65323 |
| STAT1 | 19134 | 42229 | 65324 |
| STAT2 | 19135 | 42230 | 65325 |
| STAT3 | 19136 | 42231 | 65326 |
| STAT3 | 19137 | 42232 | 65327 |
| STAT4 | 19138 | 42233 | 65328 |
| STAT5A | 19139 | 42234 | 65329 |
| STAT5B | 19140 | 42235 | 65330 |
| STAT6 | 19141 | 42236 | 65331 |
| STATH | 19142 | 42237 | 65332 |
| STAU1 | 19143 | 42238 | 65333 |
| STAU2 | 19144 | 42239 | 65334 |
| STAU2 | 19145 | 42240 | 65335 |
| STBD1 | 19146 | 42241 | 65336 |
| STC1 | 19147 | 42242 | 65337 |
| STC2 | 19148 | 42243 | 65338 |
| STEAP1 | 19149 | 42244 | 65339 |
| STEAP1B | 19150 | 42245 | 65340 |
| STEAP1B | 19151 | 42246 | 65341 |
| STEAP2 | 19152 | 42247 | 65342 |
| STEAP2 | 19153 | 42248 | 65343 |
| STEAP2 | 19154 | 42249 | 65344 |
| STEAP3 | 19155 | 42250 | 65345 |
| STEAP3 | 19156 | 42251 | 65346 |
| STEAP4 | 19157 | 42252 | 65347 |
| STH | 19158 | 42253 | 65348 |
| STIL | 19159 | 42254 | 65349 |
| STIM1 | 19160 | 42255 | 65350 |
| STIM1 | 19161 | 42256 | 65351 |
| STIM2 | 19162 | 42257 | 65352 |
| STIM2 | 19163 | 42258 | 65353 |
| STIP1 | 19164 | 42259 | 65354 |
| STK10 | 19165 | 42260 | 65355 |
| STK11 | 19166 | 42261 | 65356 |
| STK11IP | 19167 | 42262 | 65357 |
| STK16 | 19168 | 42263 | 65358 |
| STK17A | 19169 | 42264 | 65359 |
| STK17B | 19170 | 42265 | 65360 |
| STK19 | 19171 | 42266 | 65361 |
| STK24 | 19172 | 42267 | 65362 |
| STK25 | 19173 | 42268 | 65363 |
| STK26 | 19174 | 42269 | 65364 |
| STK3 | 19175 | 42270 | 65365 |
| STK31 | 19176 | 42271 | 65366 |
| STK32A | 19177 | 42272 | 65367 |
| STK32A | 19178 | 42273 | 65368 |
| STK32A | 19179 | 42274 | 65369 |
| STK32B | 19180 | 42275 | 65370 |
| STK32C | 19181 | 42276 | 65371 |
| STK32C | 19182 | 42277 | 65372 |
| STK32C | 19183 | 42278 | 65373 |
| STK32C | 19184 | 42279 | 65374 |
| STK32C | 19185 | 42280 | 65375 |
| STK33 | 19186 | 42281 | 65376 |
| STK33 | 19187 | 42282 | 65377 |
| STK35 | 19188 | 42283 | 65378 |
| STK36 | 19189 | 42284 | 65379 |
| STK38 | 19190 | 42285 | 65380 |
| STK38L | 19191 | 42286 | 65381 |
| STK39 | 19192 | 42287 | 65382 |
| STK4 | 19193 | 42288 | 65383 |
| STK4 | 19194 | 42289 | 65384 |
| STK40 | 19195 | 42290 | 65385 |
| STKLD1 | 19196 | 42291 | 65386 |
| STMN1 | 19197 | 42292 | 65387 |
| STMN1 | 19198 | 42293 | 65388 |
| STMN2 | 19199 | 42294 | 65389 |
| STMN2 | 19200 | 42295 | 65390 |
| STMN3 | 19201 | 42296 | 65391 |
| STMN4 | 19202 | 42297 | 65392 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| STMN4 | 19203 | 42298 | 65393 |
| STMND1 | 19204 | 42299 | 65394 |
| STMP1 | 19205 | 42300 | 65395 |
| STN1 | 19206 | 42301 | 65396 |
| STOM | 19207 | 42302 | 65397 |
| STOM | 19208 | 42303 | 65398 |
| STOM | 19209 | 42304 | 65399 |
| STOML1 | 19210 | 42305 | 65400 |
| STOML2 | 19211 | 42306 | 65401 |
| STOML3 | 19212 | 42307 | 65402 |
| STON1 | 19213 | 42308 | 65403 |
| STON1-GTF2A1L | 19214 | 42309 | 65404 |
| STON1-GTF2A1L | 19215 | 42310 | 65405 |
| STON2 | 19216 | 42311 | 65406 |
| STON2 | 19217 | 42312 | 65407 |
| STOX1 | 19218 | 42313 | 65408 |
| STOX1 | 19219 | 42314 | 65409 |
| STOX1 | 19220 | 42315 | 65410 |
| STOX2 | 19221 | 42316 | 65411 |
| STPG1 | 19222 | 42317 | 65412 |
| STPG2 | 19223 | 42318 | 65413 |
| STPG3 | 19224 | 42319 | 65414 |
| STPG3 | 19225 | 42320 | 65415 |
| STPG4 | 19226 | 42321 | 65416 |
| STPG4 | 19227 | 42322 | 65417 |
| STRA6 | 19228 | 42323 | 65418 |
| STRA6 | 19229 | 42324 | 65419 |
| STRA8 | 19230 | 42325 | 65420 |
| STRADA | 19231 | 42326 | 65421 |
| STRADA | 19232 | 42327 | 65422 |
| STRADA | 19233 | 42328 | 65423 |
| STRADB | 19234 | 42329 | 65424 |
| STRADB | 19235 | 42330 | 65425 |
| STRAP | 19236 | 42331 | 65426 |
| STRBP | 19237 | 42332 | 65427 |
| STRC | 19238 | 42333 | 65428 |
| STRIP1 | 19239 | 42334 | 65429 |
| STRIP2 | 19240 | 42335 | 65430 |
| STRIP2 | 19241 | 42336 | 65431 |
| STRN | 19242 | 42337 | 65432 |
| STRN3 | 19243 | 42338 | 65433 |
| STRN4 | 19244 | 42339 | 65434 |
| STS | 19245 | 42340 | 65435 |
| STT3A | 19246 | 42341 | 65436 |
| STT3B | 19247 | 42342 | 65437 |
| STUB1 | 19248 | 42343 | 65438 |
| STUM | 19249 | 42344 | 65439 |
| STX10 | 19250 | 42345 | 65440 |
| STX10 | 19251 | 42346 | 65441 |
| STX10 | 19252 | 42347 | 65442 |
| STX11 | 19253 | 42348 | 65443 |
| STX12 | 19254 | 42349 | 65444 |
| STX16 | 19255 | 42350 | 65445 |
| STX17 | 19256 | 42351 | 65446 |
| STX18 | 19257 | 42352 | 65447 |
| STX19 | 19258 | 42353 | 65448 |
| STX1A | 19259 | 42354 | 65449 |
| STX1A | 19260 | 42355 | 65450 |
| STX1B | 19261 | 42356 | 65451 |
| STX2 | 19262 | 42357 | 65452 |
| STX2 | 19263 | 42358 | 65453 |
| STX2 | 19264 | 42359 | 65454 |
| STX2 | 19265 | 42360 | 65455 |
| STX3 | 19266 | 42361 | 65456 |
| STX3 | 19267 | 42362 | 65457 |
| STX4 | 19268 | 42363 | 65458 |
| STX5 | 19269 | 42364 | 65459 |
| STX5 | 19270 | 42365 | 65460 |
| STX6 | 19271 | 42366 | 65461 |
| STX7 | 19272 | 42367 | 65462 |
| STX7 | 19273 | 42368 | 65463 |
| STX8 | 19274 | 42369 | 65464 |
| STXBP1 | 19275 | 42370 | 65465 |
| STXBP1 | 19276 | 42371 | 65466 |
| STXBP2 | 19277 | 42372 | 65467 |
| STXBP3 | 19278 | 42373 | 65468 |
| STXBP4 | 19279 | 42374 | 65469 |
| STXBP5 | 19280 | 42375 | 65470 |
| STXBP5L | 19281 | 42376 | 65471 |
| STXBP6 | 19282 | 42377 | 65472 |
| STYK1 | 19283 | 42378 | 65473 |
| STYX | 19284 | 42379 | 65474 |
| STYXL1 | 19285 | 42380 | 65475 |
| STYXL1 | 19286 | 42381 | 65476 |
| SUB1 | 19287 | 42382 | 65477 |
| SUCLA2 | 19288 | 42383 | 65478 |
| SUCLG1 | 19289 | 42384 | 65479 |
| SUCLG2 | 19290 | 42385 | 65480 |
| SUCLG2 | 19291 | 42386 | 65481 |
| SUCNR1 | 19292 | 42387 | 65482 |
| SUCO | 19293 | 42388 | 65483 |
| SUDS3 | 19294 | 42389 | 65484 |
| SUFU | 19295 | 42390 | 65485 |
| SUFU | 19296 | 42391 | 65486 |
| SUGCT | 19297 | 42392 | 65487 |
| SUGP1 | 19298 | 42393 | 65488 |
| SUGP2 | 19299 | 42394 | 65489 |
| SUGT1 | 19300 | 42395 | 65490 |
| SULF1 | 19301 | 42396 | 65491 |
| SULF2 | 19302 | 42397 | 65492 |
| SULT1A1 | 19303 | 42398 | 65493 |
| SULT1B1 | 19304 | 42399 | 65494 |
| SULT1C2 | 19305 | 42400 | 65495 |
| SULT1C3 | 19306 | 42401 | 65496 |
| SULT1C3 | 19307 | 42402 | 65497 |
| SULT1C4 | 19308 | 42403 | 65498 |
| SULT1E1 | 19309 | 42404 | 65499 |
| SULT2A1 | 19310 | 42405 | 65500 |
| SULT2B1 | 19311 | 42406 | 65501 |
| SULT4A1 | 19312 | 42407 | 65502 |
| SULT6B1 | 19313 | 42408 | 65503 |
| SUMF1 | 19314 | 42409 | 65504 |
| SUMF2 | 19315 | 42410 | 65505 |
| SUMF2 | 19316 | 42411 | 65506 |
| SUMO1 | 19317 | 42412 | 65507 |
| SUMO2 | 19318 | 42413 | 65508 |
| SUMO3 | 19319 | 42414 | 65509 |
| SUN1 | 19320 | 42415 | 65510 |
| SUN1 | 19321 | 42416 | 65511 |
| SUN2 | 19322 | 42417 | 65512 |
| SUN3 | 19323 | 42418 | 65513 |
| SUN5 | 19324 | 42419 | 65514 |
| SUOX | 19325 | 42420 | 65515 |
| SUPT16H | 19326 | 42421 | 65516 |
| SUPT20H | 19327 | 42422 | 65517 |
| SUPT20H | 19328 | 42423 | 65518 |
| SUPT20HL1 | 19329 | 42424 | 65519 |
| SUPT20HL2 | 19330 | 42425 | 65520 |
| SUPT3H | 19331 | 42426 | 65521 |
| SUPT3H | 19332 | 42427 | 65522 |
| SUPT4H1 | 19333 | 42428 | 65523 |
| SUPT5H | 19334 | 42429 | 65524 |
| SUPT6H | 19335 | 42430 | 65525 |
| SUPT7L | 19336 | 42431 | 65526 |
| SUPV3L1 | 19337 | 42432 | 65527 |
| SURF1 | 19338 | 42433 | 65528 |
| SURF2 | 19339 | 42434 | 65529 |
| SURF4 | 19340 | 42435 | 65530 |
| SURF4 | 19341 | 42436 | 65531 |
| SURF4 | 19342 | 42437 | 65532 |
| SURF6 | 19343 | 42438 | 65533 |
| SURF6 | 19344 | 42439 | 65534 |
| SUSD1 | 19345 | 42440 | 65535 |
| SUSD1 | 19346 | 42441 | 65536 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| SUSD2 | 19347 | 42442 | 65537 |
| SUSD3 | 19348 | 42443 | 65538 |
| SUSD4 | 19349 | 42444 | 65539 |
| SUSD4 | 19350 | 42445 | 65540 |
| SUSD5 | 19351 | 42446 | 65541 |
| SUSD6 | 19352 | 42447 | 65542 |
| SUV39H1 | 19353 | 42448 | 65543 |
| SUV39H2 | 19354 | 42449 | 65544 |
| SUZ12 | 19355 | 42450 | 65545 |
| SV2A | 19356 | 42451 | 65546 |
| SV2B | 19357 | 42452 | 65547 |
| SV2C | 19358 | 42453 | 65548 |
| SV2C | 19359 | 42454 | 65549 |
| SVBP | 19360 | 42455 | 65550 |
| SVEP1 | 19361 | 42456 | 65551 |
| SVIL | 19362 | 42457 | 65552 |
| SVIP | 19363 | 42458 | 65553 |
| SVIP | 19364 | 42459 | 65554 |
| SVOP | 19365 | 42460 | 65555 |
| SVOPL | 19366 | 42461 | 65556 |
| SWAP70 | 19367 | 42462 | 65557 |
| SWI5 | 19368 | 42463 | 65558 |
| SWSAP1 | 19369 | 42464 | 65559 |
| SWT1 | 19370 | 42465 | 65560 |
| SYAP1 | 19371 | 42466 | 65561 |
| SYBU | 19372 | 42467 | 65562 |
| SYCE1 | 19373 | 42468 | 65563 |
| SYCE1L | 19374 | 42469 | 65564 |
| SYCE2 | 19375 | 42470 | 65565 |
| SYCE3 | 19376 | 42471 | 65566 |
| SYCN | 19377 | 42472 | 65567 |
| SYCP1 | 19378 | 42473 | 65568 |
| SYCP2 | 19379 | 42474 | 65569 |
| SYCP2L | 19380 | 42475 | 65570 |
| SYCP3 | 19381 | 42476 | 65571 |
| SYDE1 | 19382 | 42477 | 65572 |
| SYDE2 | 19383 | 42478 | 65573 |
| SYF2 | 19384 | 42479 | 65574 |
| SYK | 19385 | 42480 | 65575 |
| SYMPK | 19386 | 42481 | 65576 |
| SYN1 | 19387 | 42482 | 65577 |
| SYN1 | 19388 | 42483 | 65578 |
| SYN2 | 19389 | 42484 | 65579 |
| SYN2 | 19390 | 42485 | 65580 |
| SYN3 | 19391 | 42486 | 65581 |
| SYN3 | 19392 | 42487 | 65582 |
| SYNC | 19393 | 42488 | 65583 |
| SYNC | 19394 | 42489 | 65584 |
| SYNCRIP | 19395 | 42490 | 65585 |
| SYNCRIP | 19396 | 42491 | 65586 |
| SYNDIG1 | 19397 | 42492 | 65587 |
| SYNDIG1L | 19398 | 42493 | 65588 |
| SYNE1 | 19399 | 42494 | 65589 |
| SYNE1 | 19400 | 42495 | 65590 |
| SYNE2 | 19401 | 42496 | 65591 |
| SYNE3 | 19402 | 42497 | 65592 |
| SYNE4 | 19403 | 42498 | 65593 |
| SYNGAP1 | 19404 | 42499 | 65594 |
| SYNGAP1 | 19405 | 42500 | 65595 |
| SYNGR1 | 19406 | 42501 | 65596 |
| SYNGR1 | 19407 | 42502 | 65597 |
| SYNGR2 | 19408 | 42503 | 65598 |
| SYNGR2 | 19409 | 42504 | 65599 |
| SYNGR3 | 19410 | 42505 | 65600 |
| SYNGR4 | 19411 | 42506 | 65601 |
| SYNJ1 | 19412 | 42507 | 65602 |
| SYNJ1 | 19413 | 42508 | 65603 |
| SYNJ2 | 19414 | 42509 | 65604 |
| SYNJ2BP | 19415 | 42510 | 65605 |
| SYNM | 19416 | 42511 | 65606 |
| SYNPO | 19417 | 42512 | 65607 |
| SYNPO | 19418 | 42513 | 65608 |
| SYNPO2 | 19419 | 42514 | 65609 |
| SYNPO2 | 19420 | 42515 | 65610 |
| SYNPO2 | 19421 | 42516 | 65611 |
| SYNPO2 | 19422 | 42517 | 65612 |
| SYNPO2L | 19423 | 42518 | 65613 |
| SYNPR | 19424 | 42519 | 65614 |
| SYNRG | 19425 | 42520 | 65615 |
| SYP | 19426 | 42521 | 65616 |
| SYPL1 | 19427 | 42522 | 65617 |
| SYPL2 | 19428 | 42523 | 65618 |
| SYS1 | 19429 | 42524 | 65619 |
| SYS1 | 19430 | 42525 | 65620 |
| SYT1 | 19431 | 42526 | 65621 |
| SYT10 | 19432 | 42527 | 65622 |
| SYT11 | 19433 | 42528 | 65623 |
| SYT12 | 19434 | 42529 | 65624 |
| SYT13 | 19435 | 42530 | 65625 |
| SYT14 | 19436 | 42531 | 65626 |
| SYT15 | 19437 | 42532 | 65627 |
| SYT15 | 19438 | 42533 | 65628 |
| SYT16 | 19439 | 42534 | 65629 |
| SYT17 | 19440 | 42535 | 65630 |
| SYT2 | 19441 | 42536 | 65631 |
| SYT3 | 19442 | 42537 | 65632 |
| SYT4 | 19443 | 42538 | 65633 |
| SYT5 | 19444 | 42539 | 65634 |
| SYT6 | 19445 | 42540 | 65635 |
| SYT7 | 19446 | 42541 | 65636 |
| SYT8 | 19447 | 42542 | 65637 |
| SYT9 | 19448 | 42543 | 65638 |
| SYTL1 | 19449 | 42544 | 65639 |
| SYTL2 | 19450 | 42545 | 65640 |
| SYTL3 | 19451 | 42546 | 65641 |
| SYTL4 | 19452 | 42547 | 65642 |
| SYTL5 | 19453 | 42548 | 65643 |
| SYVN1 | 19454 | 42549 | 65644 |
| SZRD1 | 19455 | 42550 | 65645 |
| SZT2 | 19456 | 42551 | 65646 |
| T | 19457 | 42552 | 65647 |
| TAAR1 | 19458 | 42553 | 65648 |
| TAAR2 | 19459 | 42554 | 65649 |
| TAAR5 | 19460 | 42555 | 65650 |
| TAAR6 | 19461 | 42556 | 65651 |
| TAAR8 | 19462 | 42557 | 65652 |
| TAAR9 | 19463 | 42558 | 65653 |
| TAB1 | 19464 | 42559 | 65654 |
| TAB1 | 19465 | 42560 | 65655 |
| TAB2 | 19466 | 42561 | 65656 |
| TAB3 | 19467 | 42562 | 65657 |
| TAC1 | 19468 | 42563 | 65658 |
| TAC1 | 19469 | 42564 | 65659 |
| TAC1 | 19470 | 42565 | 65660 |
| TAC3 | 19471 | 42566 | 65661 |
| TAC4 | 19472 | 42567 | 65662 |
| TAC4 | 19473 | 42568 | 65663 |
| TACC1 | 19474 | 42569 | 65664 |
| TACC1 | 19475 | 42570 | 65665 |
| TACC2 | 19476 | 42571 | 65666 |
| TACC3 | 19477 | 42572 | 65667 |
| TACO1 | 19478 | 42573 | 65668 |
| TACR1 | 19479 | 42574 | 65669 |
| TACR1 | 19480 | 42575 | 65670 |
| TACR2 | 19481 | 42576 | 65671 |
| TACR3 | 19482 | 42577 | 65672 |
| TACSTD2 | 19483 | 42578 | 65673 |
| TADA1 | 19484 | 42579 | 65674 |
| TADA2A | 19485 | 42580 | 65675 |
| TADA2A | 19486 | 42581 | 65676 |
| TADA2B | 19487 | 42582 | 65677 |
| TADA3 | 19488 | 42583 | 65678 |
| TADA3 | 19489 | 42584 | 65679 |
| TAF1 | 19490 | 42585 | 65680 |
| TAF10 | 19491 | 42586 | 65681 |
| TAF11 | 19492 | 42587 | 65682 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TAF11 | 19493 | 42588 | 65683 |
| TAF12 | 19494 | 42589 | 65684 |
| TAF13 | 19495 | 42590 | 65685 |
| TAF15 | 19496 | 42591 | 65686 |
| TAF1A | 19497 | 42592 | 65687 |
| TAF1B | 19498 | 42593 | 65688 |
| TAF1C | 19499 | 42594 | 65689 |
| TAF1D | 19500 | 42595 | 65690 |
| TAF1L | 19501 | 42596 | 65691 |
| TAF2 | 19502 | 42597 | 65692 |
| TAF3 | 19503 | 42598 | 65693 |
| TAF4 | 19504 | 42599 | 65694 |
| TAF4B | 19505 | 42600 | 65695 |
| TAF5 | 19506 | 42601 | 65696 |
| TAF5L | 19507 | 42602 | 65697 |
| TAF5L | 19508 | 42603 | 65698 |
| TAF6 | 19509 | 42604 | 65699 |
| TAF6L | 19510 | 42605 | 65700 |
| TAF7 | 19511 | 42606 | 65701 |
| TAF7L | 19512 | 42607 | 65702 |
| TAF8 | 19513 | 42608 | 65703 |
| TAF9 | 19514 | 42609 | 65704 |
| TAF9B | 19515 | 42610 | 65705 |
| TAGAP | 19516 | 42611 | 65706 |
| TAGAP | 19517 | 42612 | 65707 |
| TAGLN | 19518 | 42613 | 65708 |
| TAGLN2 | 19519 | 42614 | 65709 |
| TAGLN3 | 19520 | 42615 | 65710 |
| TAL1 | 19521 | 42616 | 65711 |
| TAL1 | 19522 | 42617 | 65712 |
| TAL2 | 19523 | 42618 | 65713 |
| TALDO1 | 19524 | 42619 | 65714 |
| TAMM41 | 19525 | 42620 | 65715 |
| TANC1 | 19526 | 42621 | 65716 |
| TANC1 | 19527 | 42622 | 65717 |
| TANC2 | 19528 | 42623 | 65718 |
| TANGO2 | 19529 | 42624 | 65719 |
| TANGO2 | 19530 | 42625 | 65720 |
| TANGO2 | 19531 | 42626 | 65721 |
| TANGO6 | 19532 | 42627 | 65722 |
| TANK | 19533 | 42628 | 65723 |
| TANK | 19534 | 42629 | 65724 |
| TAOK1 | 19535 | 42630 | 65725 |
| TAOK2 | 19536 | 42631 | 65726 |
| TAOK2 | 19537 | 42632 | 65727 |
| TAOK3 | 19538 | 42633 | 65728 |
| TAOK3 | 19539 | 42634 | 65729 |
| TAP1 | 19540 | 42635 | 65730 |
| TAP2 | 19541 | 42636 | 65731 |
| TAP2 | 19542 | 42637 | 65732 |
| TAP2 | 19543 | 42638 | 65733 |
| TAPBP | 19544 | 42639 | 65734 |
| TAPBP | 19545 | 42640 | 65735 |
| TAPBPL | 19546 | 42641 | 65736 |
| TAPT1 | 19547 | 42642 | 65737 |
| TARBP1 | 19548 | 42643 | 65738 |
| TARBP2 | 19549 | 42644 | 65739 |
| TARDBP | 19550 | 42645 | 65740 |
| TARM1 | 19551 | 42646 | 65741 |
| TARP | 19552 | 42647 | 65742 |
| TARS | 19553 | 42648 | 65743 |
| TARS2 | 19554 | 42649 | 65744 |
| TARSL2 | 19555 | 42650 | 65745 |
| TAS1R1 | 19556 | 42651 | 65746 |
| TAS1R2 | 19557 | 42652 | 65747 |
| TAS1R3 | 19558 | 42653 | 65748 |
| TAS2R1 | 19559 | 42654 | 65749 |
| TAS2R10 | 19560 | 42655 | 65750 |
| TAS2R13 | 19561 | 42656 | 65751 |
| TAS2R14 | 19562 | 42657 | 65752 |
| TAS2R16 | 19563 | 42658 | 65753 |
| TAS2R19 | 19564 | 42659 | 65754 |
| TAS2R20 | 19565 | 42660 | 65755 |
| TAS2R3 | 19566 | 42661 | 65756 |
| TAS2R30 | 19567 | 42662 | 65757 |
| TAS2R31 | 19568 | 42663 | 65758 |
| TAS2R38 | 19569 | 42664 | 65759 |
| TAS2R39 | 19570 | 42665 | 65760 |
| TAS2R4 | 19571 | 42666 | 65761 |
| TAS2R40 | 19572 | 42667 | 65762 |
| TAS2R41 | 19573 | 42668 | 65763 |
| TAS2R42 | 19574 | 42669 | 65764 |
| TAS2R43 | 19575 | 42670 | 65765 |
| TAS2R45 | 19576 | 42671 | 65766 |
| TAS2R46 | 19577 | 42672 | 65767 |
| TAS2R5 | 19578 | 42673 | 65768 |
| TAS2R50 | 19579 | 42674 | 65769 |
| TAS2R60 | 19580 | 42675 | 65770 |
| TAS2R7 | 19581 | 42676 | 65771 |
| TAS2R8 | 19582 | 42677 | 65772 |
| TAS2R9 | 19583 | 42678 | 65773 |
| TASP1 | 19584 | 42679 | 65774 |
| TAT | 19585 | 42680 | 65775 |
| TATDN1 | 19586 | 42681 | 65776 |
| TATDN2 | 19587 | 42682 | 65777 |
| TATDN3 | 19588 | 42683 | 65778 |
| TATDN3 | 19589 | 42684 | 65779 |
| TAX1BP1 | 19590 | 42685 | 65780 |
| TAX1BP3 | 19591 | 42686 | 65781 |
| TAZ | 19592 | 42687 | 65782 |
| TBATA | 19593 | 42688 | 65783 |
| TBC1D1 | 19594 | 42689 | 65784 |
| TBC1D10A | 19595 | 42690 | 65785 |
| TBC1D10B | 19596 | 42691 | 65786 |
| TBC1D10C | 19597 | 42692 | 65787 |
| TBC1D10C | 19598 | 42693 | 65788 |
| TBC1D12 | 19599 | 42694 | 65789 |
| TBC1D13 | 19600 | 42695 | 65790 |
| TBC1D14 | 19601 | 42696 | 65791 |
| TBC1D15 | 19602 | 42697 | 65792 |
| TBC1D16 | 19603 | 42698 | 65793 |
| TBC1D16 | 19604 | 42699 | 65794 |
| TBC1D17 | 19605 | 42700 | 65795 |
| TBC1D19 | 19606 | 42701 | 65796 |
| TBC1D2 | 19607 | 42702 | 65797 |
| TBC1D20 | 19608 | 42703 | 65798 |
| TBC1D21 | 19609 | 42704 | 65799 |
| TBC1D22A | 19610 | 42705 | 65800 |
| TBC1D22B | 19611 | 42706 | 65801 |
| TBC1D23 | 19612 | 42707 | 65802 |
| TBC1D24 | 19613 | 42708 | 65803 |
| TBC1D25 | 19614 | 42709 | 65804 |
| TBC1D26 | 19615 | 42710 | 65805 |
| TBC1D28 | 19616 | 42711 | 65806 |
| TBC1D29 | 19617 | 42712 | 65807 |
| TBC1D2B | 19618 | 42713 | 65808 |
| TBC1D2B | 19619 | 42714 | 65809 |
| TBC1D3 | 19620 | 42715 | 65810 |
| TBC1D30 | 19621 | 42716 | 65811 |
| TBC1D31 | 19622 | 42717 | 65812 |
| TBC1D32 | 19623 | 42718 | 65813 |
| TBC1D3B | 19624 | 42719 | 65814 |
| TBC1D3D | 19625 | 42720 | 65815 |
| TBC1D3E | 19626 | 42721 | 65816 |
| TBC1D3F | 19627 | 42722 | 65817 |
| TBC1D3L | 19628 | 42723 | 65818 |
| TBC1D4 | 19629 | 42724 | 65819 |
| TBC1D5 | 19630 | 42725 | 65820 |
| TBC1D7 | 19631 | 42726 | 65821 |
| TBC1D7 | 19632 | 42727 | 65822 |
| TBC1D8 | 19633 | 42728 | 65823 |
| TBC1D8B | 19634 | 42729 | 65824 |
| TBC1D8B | 19635 | 42730 | 65825 |
| TBC1D9 | 19636 | 42731 | 65826 |
| TBC1D9B | 19637 | 42732 | 65827 |
| TBCA | 19638 | 42733 | 65828 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TBCA | 19639 | 42734 | 65829 |
| TBCB | 19640 | 42735 | 65830 |
| TBCC | 19641 | 42736 | 65831 |
| TBCCD1 | 19642 | 42737 | 65832 |
| TBCD | 19643 | 42738 | 65833 |
| TBCE | 19644 | 42739 | 65834 |
| TBCEL | 19645 | 42740 | 65835 |
| TBCK | 19646 | 42741 | 65836 |
| TBK1 | 19647 | 42742 | 65837 |
| TBKBP1 | 19648 | 42743 | 65838 |
| TBL1X | 19649 | 42744 | 65839 |
| TBL1XR1 | 19650 | 42745 | 65840 |
| TBL1Y | 19651 | 42746 | 65841 |
| TBL2 | 19652 | 42747 | 65842 |
| TBL3 | 19653 | 42748 | 65843 |
| TBP | 19654 | 42749 | 65844 |
| TBPL1 | 19655 | 42750 | 65845 |
| TBPL2 | 19656 | 42751 | 65846 |
| TBR1 | 19657 | 42752 | 65847 |
| TBRG1 | 19658 | 42753 | 65848 |
| TBRG4 | 19659 | 42754 | 65849 |
| TBX1 | 19660 | 42755 | 65850 |
| TBX1 | 19661 | 42756 | 65851 |
| TBX1 | 19662 | 42757 | 65852 |
| TBX10 | 19663 | 42758 | 65853 |
| TBX15 | 19664 | 42759 | 65854 |
| TBX18 | 19665 | 42760 | 65855 |
| TBX19 | 19666 | 42761 | 65856 |
| TBX2 | 19667 | 42762 | 65857 |
| TBX20 | 19668 | 42763 | 65858 |
| TBX20 | 19669 | 42764 | 65859 |
| TBX21 | 19670 | 42765 | 65860 |
| TBX22 | 19671 | 42766 | 65861 |
| TBX3 | 19672 | 42767 | 65862 |
| TBX4 | 19673 | 42768 | 65863 |
| TBX5 | 19674 | 42769 | 65864 |
| TBX6 | 19675 | 42770 | 65865 |
| TBXA2R | 19676 | 42771 | 65866 |
| TBXA2R | 19677 | 42772 | 65867 |
| TBXAS1 | 19678 | 42773 | 65868 |
| TBXAS1 | 19679 | 42774 | 65869 |
| TC2N | 19680 | 42775 | 65870 |
| TCAF1 | 19681 | 42776 | 65871 |
| TCAF1 | 19682 | 42777 | 65872 |
| TCAF2 | 19683 | 42778 | 65873 |
| TCAF2 | 19684 | 42779 | 65874 |
| TCAIM | 19685 | 42780 | 65875 |
| TCAIM | 19686 | 42781 | 65876 |
| TCAP | 19687 | 42782 | 65877 |
| TCEA1 | 19688 | 42783 | 65878 |
| TCEA2 | 19689 | 42784 | 65879 |
| TCEA3 | 19690 | 42785 | 65880 |
| TCEAL1 | 19691 | 42786 | 65881 |
| TCEAL3 | 19692 | 42787 | 65882 |
| TCEAL4 | 19693 | 42788 | 65883 |
| TCEAL5 | 19694 | 42789 | 65884 |
| TCEAL6 | 19695 | 42790 | 65885 |
| TCEAL7 | 19696 | 42791 | 65886 |
| TCEAL8 | 19697 | 42792 | 65887 |
| TCEAL9 | 19698 | 42793 | 65888 |
| TCEANC | 19699 | 42794 | 65889 |
| TCEANC2 | 19700 | 42795 | 65890 |
| TCERG1 | 19701 | 42796 | 65891 |
| TCERG1L | 19702 | 42797 | 65892 |
| TCF12 | 19703 | 42798 | 65893 |
| TCF15 | 19704 | 42799 | 65894 |
| TCF19 | 19705 | 42800 | 65895 |
| TCF20 | 19706 | 42801 | 65896 |
| TCF20 | 19707 | 42802 | 65897 |
| TCF21 | 19708 | 42803 | 65898 |
| TCF21 | 19709 | 42804 | 65899 |
| TCF23 | 19710 | 42805 | 65900 |
| TCF24 | 19711 | 42806 | 65901 |
| TCF25 | 19712 | 42807 | 65902 |
| TCF3 | 19713 | 42808 | 65903 |
| TCF3 | 19714 | 42809 | 65904 |
| TCF4 | 19715 | 42810 | 65905 |
| TCF7 | 19716 | 42811 | 65906 |
| TCF7 | 19717 | 42812 | 65907 |
| TCF7 | 19718 | 42813 | 65908 |
| TCF7 | 19719 | 42814 | 65909 |
| TCF7L1 | 19720 | 42815 | 65910 |
| TCF7L2 | 19721 | 42816 | 65911 |
| TCF7L2 | 19722 | 42817 | 65912 |
| TCF7L2 | 19723 | 42818 | 65913 |
| TCF7L2 | 19724 | 42819 | 65914 |
| TCFL5 | 19725 | 42820 | 65915 |
| TCFL5 | 19726 | 42821 | 65916 |
| TCHH | 19727 | 42822 | 65917 |
| TCHHL1 | 19728 | 42823 | 65918 |
| TCHP | 19729 | 42824 | 65919 |
| TCIM | 19730 | 42825 | 65920 |
| TCIRG1 | 19731 | 42826 | 65921 |
| TCL1A | 19732 | 42827 | 65922 |
| TCL1B | 19733 | 42828 | 65923 |
| TCN1 | 19734 | 42829 | 65924 |
| TCN2 | 19735 | 42830 | 65925 |
| TCOF1 | 19736 | 42831 | 65926 |
| TCOF1 | 19737 | 42832 | 65927 |
| TCP1 | 19738 | 42833 | 65928 |
| TCP10L | 19739 | 42834 | 65929 |
| TCP10L2 | 19740 | 42835 | 65930 |
| TCP11 | 19741 | 42836 | 65931 |
| TCP11L1 | 19742 | 42837 | 65932 |
| TCP11L2 | 19743 | 42838 | 65933 |
| TCP11L2 | 19744 | 42839 | 65934 |
| TCP11X2 | 19745 | 42840 | 65935 |
| TCTA | 19746 | 42841 | 65936 |
| TCTE1 | 19747 | 42842 | 65937 |
| TCTE3 | 19748 | 42843 | 65938 |
| TCTEX1D1 | 19749 | 42844 | 65939 |
| TCTEX1D2 | 19750 | 42845 | 65940 |
| TCTEX1D4 | 19751 | 42846 | 65941 |
| TCTN1 | 19752 | 42847 | 65942 |
| TCTN1 | 19753 | 42848 | 65943 |
| TCTN2 | 19754 | 42849 | 65944 |
| TCTN3 | 19755 | 42850 | 65945 |
| TDG | 19756 | 42851 | 65946 |
| TDGF1 | 19757 | 42852 | 65947 |
| TDO2 | 19758 | 42853 | 65948 |
| TDP1 | 19759 | 42854 | 65949 |
| TDP1 | 19760 | 42855 | 65950 |
| TDP2 | 19761 | 42856 | 65951 |
| TDRD1 | 19762 | 42857 | 65952 |
| TDRD10 | 19763 | 42858 | 65953 |
| TDRD10 | 19764 | 42859 | 65954 |
| TDRD12 | 19765 | 42860 | 65955 |
| TDRD15 | 19766 | 42861 | 65956 |
| TDRD3 | 19767 | 42862 | 65957 |
| TDRD5 | 19768 | 42863 | 65958 |
| TDRD6 | 19769 | 42864 | 65959 |
| TDRD7 | 19770 | 42865 | 65960 |
| TDRD9 | 19771 | 42866 | 65961 |
| TDRKH | 19772 | 42867 | 65962 |
| TDRP | 19773 | 42868 | 65963 |
| TDRP | 19774 | 42869 | 65964 |
| TEAD1 | 19775 | 42870 | 65965 |
| TEAD2 | 19776 | 42871 | 65966 |
| TEAD3 | 19777 | 42872 | 65967 |
| TEAD4 | 19778 | 42873 | 65968 |
| TEC | 19779 | 42874 | 65969 |
| TECPR1 | 19780 | 42875 | 65970 |
| TECPR2 | 19781 | 42876 | 65971 |
| TECPR2 | 19782 | 42877 | 65972 |
| TECR | 19783 | 42878 | 65973 |
| TECRL | 19784 | 42879 | 65974 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TECTA | 19785 | 42880 | 65975 |
| TECTB | 19786 | 42881 | 65976 |
| TEDC1 | 19787 | 42882 | 65977 |
| TEDC2 | 19788 | 42883 | 65978 |
| TEDDM1 | 19789 | 42884 | 65979 |
| TEF | 19790 | 42885 | 65980 |
| TEFM | 19791 | 42886 | 65981 |
| TEK | 19792 | 42887 | 65982 |
| TEKT1 | 19793 | 42888 | 65983 |
| TEKT2 | 19794 | 42889 | 65984 |
| TEKT3 | 19795 | 42890 | 65985 |
| TEKT4 | 19796 | 42891 | 65986 |
| TEKT5 | 19797 | 42892 | 65987 |
| TELO2 | 19798 | 42893 | 65988 |
| TEN1 | 19799 | 42894 | 65989 |
| TENM1 | 19800 | 42895 | 65990 |
| TENM2 | 19801 | 42896 | 65991 |
| TENM3 | 19802 | 42897 | 65992 |
| TENM4 | 19803 | 42898 | 65993 |
| TEP1 | 19804 | 42899 | 65994 |
| TEPP | 19805 | 42900 | 65995 |
| TEPSIN | 19806 | 42901 | 65996 |
| TERB1 | 19807 | 42902 | 65997 |
| TERB2 | 19808 | 42903 | 65998 |
| TERF1 | 19809 | 42904 | 65999 |
| TERF2 | 19810 | 42905 | 66000 |
| TERF2IP | 19811 | 42906 | 66001 |
| TERT | 19812 | 42907 | 66002 |
| TES | 19813 | 42908 | 66003 |
| TESC | 19814 | 42909 | 66004 |
| TESK1 | 19815 | 42910 | 66005 |
| TESK2 | 19816 | 42911 | 66006 |
| TESMIN | 19817 | 42912 | 66007 |
| TESMIN | 19818 | 42913 | 66008 |
| TESPA1 | 19819 | 42914 | 66009 |
| TET1 | 19820 | 42915 | 66010 |
| TET2 | 19821 | 42916 | 66011 |
| TET2 | 19822 | 42917 | 66012 |
| TET3 | 19823 | 42918 | 66013 |
| TEX10 | 19824 | 42919 | 66014 |
| TEX101 | 19825 | 42920 | 66015 |
| TEX11 | 19826 | 42921 | 66016 |
| TEX12 | 19827 | 42922 | 66017 |
| TEX13A | 19828 | 42923 | 66018 |
| TEX13B | 19829 | 42924 | 66019 |
| TEX13C | 19830 | 42925 | 66020 |
| TEX14 | 19831 | 42926 | 66021 |
| TEX15 | 19832 | 42927 | 66022 |
| TEX19 | 19833 | 42928 | 66023 |
| TEX2 | 19834 | 42929 | 66024 |
| TEX22 | 19835 | 42930 | 66025 |
| TEX26 | 19836 | 42931 | 66026 |
| TEX261 | 19837 | 42932 | 66027 |
| TEX264 | 19838 | 42933 | 66028 |
| TEX28 | 19839 | 42934 | 66029 |
| TEX29 | 19840 | 42935 | 66030 |
| TEX30 | 19841 | 42936 | 66031 |
| TEX30 | 19842 | 42937 | 66032 |
| TEX33 | 19843 | 42938 | 66033 |
| TEX35 | 19844 | 42939 | 66034 |
| TEX35 | 19845 | 42940 | 66035 |
| TEX35 | 19846 | 42941 | 66036 |
| TEX36 | 19847 | 42942 | 66037 |
| TEX36 | 19848 | 42943 | 66038 |
| TEX37 | 19849 | 42944 | 66039 |
| TEX38 | 19850 | 42945 | 66040 |
| TEX43 | 19851 | 42946 | 66041 |
| TEX44 | 19852 | 42947 | 66042 |
| TEX45 | 19853 | 42948 | 66043 |
| TEX46 | 19854 | 42949 | 66044 |
| TEX47 | 19855 | 42950 | 66045 |
| TEX48 | 19856 | 42951 | 66046 |
| TEX49 | 19857 | 42952 | 66047 |
| TEX50 | 19858 | 42953 | 66048 |
| TEX51 | 19859 | 42954 | 66049 |
| TEX9 | 19860 | 42955 | 66050 |
| TF | 19861 | 42956 | 66051 |
| TFAM | 19862 | 42957 | 66052 |
| TFAP2A | 19863 | 42958 | 66053 |
| TFAP2B | 19864 | 42959 | 66054 |
| TFAP2C | 19865 | 42960 | 66055 |
| TFAP2D | 19866 | 42961 | 66056 |
| TFAP2E | 19867 | 42962 | 66057 |
| TFAP4 | 19868 | 42963 | 66058 |
| TFB1M | 19869 | 42964 | 66059 |
| TFB1M | 19870 | 42965 | 66060 |
| TFB2M | 19871 | 42966 | 66061 |
| TFCP2 | 19872 | 42967 | 66062 |
| TFCP2L1 | 19873 | 42968 | 66063 |
| TFDP1 | 19874 | 42969 | 66064 |
| TFDP2 | 19875 | 42970 | 66065 |
| TFDP3 | 19876 | 42971 | 66066 |
| TFE3 | 19877 | 42972 | 66067 |
| TFEB | 19878 | 42973 | 66068 |
| TFEC | 19879 | 42974 | 66069 |
| TFF1 | 19880 | 42975 | 66070 |
| TFF2 | 19881 | 42976 | 66071 |
| TFF3 | 19882 | 42977 | 66072 |
| TFG | 19883 | 42978 | 66073 |
| TFIP11 | 19884 | 42979 | 66074 |
| TFPI | 19885 | 42980 | 66075 |
| TFPI | 19886 | 42981 | 66076 |
| TFPI2 | 19887 | 42982 | 66077 |
| TFPI2 | 19888 | 42983 | 66078 |
| TFPT | 19889 | 42984 | 66079 |
| TFR2 | 19890 | 42985 | 66080 |
| TFRC | 19891 | 42986 | 66081 |
| TG | 19892 | 42987 | 66082 |
| TGDS | 19893 | 42988 | 66083 |
| TGFA | 19894 | 42989 | 66084 |
| TGFB1 | 19895 | 42990 | 66085 |
| TGFB1I1 | 19896 | 42991 | 66086 |
| TGFB2 | 19897 | 42992 | 66087 |
| TGFB3 | 19898 | 42993 | 66088 |
| TGFB3 | 19899 | 42994 | 66089 |
| TGFBI | 19900 | 42995 | 66090 |
| TGFBR1 | 19901 | 42996 | 66091 |
| TGFBR2 | 19902 | 42997 | 66092 |
| TGFBR3 | 19903 | 42998 | 66093 |
| TGFBR3L | 19904 | 42999 | 66094 |
| TGFBRAP1 | 19905 | 43000 | 66095 |
| TGFBRAP1 | 19906 | 43001 | 66096 |
| TGIF1 | 19907 | 43002 | 66097 |
| TGIF2 | 19908 | 43003 | 66098 |
| TGIF2LX | 19909 | 43004 | 66099 |
| TGIF2LY | 19910 | 43005 | 66100 |
| TGM1 | 19911 | 43006 | 66101 |
| TGM2 | 19912 | 43007 | 66102 |
| TGM2 | 19913 | 43008 | 66103 |
| TGM3 | 19914 | 43009 | 66104 |
| TGM4 | 19915 | 43010 | 66105 |
| TGM5 | 19916 | 43011 | 66106 |
| TGM6 | 19917 | 43012 | 66107 |
| TGM6 | 19918 | 43013 | 66108 |
| TGM7 | 19919 | 43014 | 66109 |
| TGOLN2 | 19920 | 43015 | 66110 |
| TGOLN2 | 19921 | 43016 | 66111 |
| TGOLN2 | 19922 | 43017 | 66112 |
| TGS1 | 19923 | 43018 | 66113 |
| TGS1 | 19924 | 43019 | 66114 |
| TH | 19925 | 43020 | 66115 |
| THADA | 19926 | 43021 | 66116 |
| THADA | 19927 | 43022 | 66117 |
| THADA | 19928 | 43023 | 66118 |
| THAP1 | 19929 | 43024 | 66119 |
| THAP10 | 19930 | 43025 | 66120 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| THAP11 | 19931 | 43026 | 66121 |
| THAP12 | 19932 | 43027 | 66122 |
| THAP2 | 19933 | 43028 | 66123 |
| THAP3 | 19934 | 43029 | 66124 |
| THAP3 | 19935 | 43030 | 66125 |
| THAP4 | 19936 | 43031 | 66126 |
| THAP5 | 19937 | 43032 | 66127 |
| THAP6 | 19938 | 43033 | 66128 |
| THAP7 | 19939 | 43034 | 66129 |
| THAP8 | 19940 | 43035 | 66130 |
| THAP9 | 19941 | 43036 | 66131 |
| THBD | 19942 | 43037 | 66132 |
| THBS1 | 19943 | 43038 | 66133 |
| THBS2 | 19944 | 43039 | 66134 |
| THBS3 | 19945 | 43040 | 66135 |
| THBS4 | 19946 | 43041 | 66136 |
| THEG | 19947 | 43042 | 66137 |
| THEG5 | 19948 | 43043 | 66138 |
| THEGL | 19949 | 43044 | 66139 |
| THEM4 | 19950 | 43045 | 66140 |
| THEM5 | 19951 | 43046 | 66141 |
| THEM6 | 19952 | 43047 | 66142 |
| THEMIS | 19953 | 43048 | 66143 |
| THEMIS2 | 19954 | 43049 | 66144 |
| THEMIS2 | 19955 | 43050 | 66145 |
| THG1L | 19956 | 43051 | 66146 |
| THNSL1 | 19957 | 43052 | 66147 |
| THNSL2 | 19958 | 43053 | 66148 |
| THNSL2 | 19959 | 43054 | 66149 |
| THNSL2 | 19960 | 43055 | 66150 |
| THOC1 | 19961 | 43056 | 66151 |
| THOC2 | 19962 | 43057 | 66152 |
| THOC3 | 19963 | 43058 | 66153 |
| THOC5 | 19964 | 43059 | 66154 |
| THOC6 | 19965 | 43060 | 66155 |
| THOC7 | 19966 | 43061 | 66156 |
| THOP1 | 19967 | 43062 | 66157 |
| THPO | 19968 | 43063 | 66158 |
| THPO | 19969 | 43064 | 66159 |
| THRA | 19970 | 43065 | 66160 |
| THRA | 19971 | 43066 | 66161 |
| THRAP3 | 19972 | 43067 | 66162 |
| THRB | 19973 | 43068 | 66163 |
| THRSP | 19974 | 43069 | 66164 |
| THSD1 | 19975 | 43070 | 66165 |
| THSD4 | 19976 | 43071 | 66166 |
| THSD7A | 19977 | 43072 | 66167 |
| THSD7B | 19978 | 43073 | 66168 |
| THTPA | 19979 | 43074 | 66169 |
| THTPA | 19980 | 43075 | 66170 |
| THUMPD1 | 19981 | 43076 | 66171 |
| THUMPD2 | 19982 | 43077 | 66172 |
| THUMPD2 | 19983 | 43078 | 66173 |
| THUMPD2 | 19984 | 43079 | 66174 |
| THUMPD2 | 19985 | 43080 | 66175 |
| THUMPD3 | 19986 | 43081 | 66176 |
| THY1 | 19987 | 43082 | 66177 |
| THYN1 | 19988 | 43083 | 66178 |
| THYN1 | 19989 | 43084 | 66179 |
| TIA1 | 19990 | 43085 | 66180 |
| TIA1 | 19991 | 43086 | 66181 |
| TIA1 | 19992 | 43087 | 66182 |
| TIA1 | 19993 | 43088 | 66183 |
| TIA1 | 19994 | 43089 | 66184 |
| TIA1 | 19995 | 43090 | 66185 |
| TIAF1 | 19996 | 43091 | 66186 |
| TIAL1 | 19997 | 43092 | 66187 |
| TIAM1 | 19998 | 43093 | 66188 |
| TIAM2 | 19999 | 43094 | 66189 |
| TICAM1 | 20000 | 43095 | 66190 |
| TICAM2 | 20001 | 43096 | 66191 |
| TICRR | 20002 | 43097 | 66192 |
| TIE1 | 20003 | 43098 | 66193 |
| TIFA | 20004 | 43099 | 66194 |
| TIFAB | 20005 | 43100 | 66195 |
| TIGAR | 20006 | 43101 | 66196 |
| TIGD1 | 20007 | 43102 | 66197 |
| TIGD2 | 20008 | 43103 | 66198 |
| TIGD3 | 20009 | 43104 | 66199 |
| TIGD4 | 20010 | 43105 | 66200 |
| TIGD5 | 20011 | 43106 | 66201 |
| TIGD6 | 20012 | 43107 | 66202 |
| TIGD7 | 20013 | 43108 | 66203 |
| TIGIT | 20014 | 43109 | 66204 |
| TIMD4 | 20015 | 43110 | 66205 |
| TIMELESS | 20016 | 43111 | 66206 |
| TIMM10 | 20017 | 43112 | 66207 |
| TIMM10B | 20018 | 43113 | 66208 |
| TIMM13 | 20019 | 43114 | 66209 |
| TIMM17A | 20020 | 43115 | 66210 |
| TIMM17B | 20021 | 43116 | 66211 |
| TIMM21 | 20022 | 43117 | 66212 |
| TIMM22 | 20023 | 43118 | 66213 |
| TIMM23 | 20024 | 43119 | 66214 |
| TIMM23B | 20025 | 43120 | 66215 |
| TIMM29 | 20026 | 43121 | 66216 |
| TIMM44 | 20027 | 43122 | 66217 |
| TIMM50 | 20028 | 43123 | 66218 |
| TIMM50 | 20029 | 43124 | 66219 |
| TIMM8A | 20030 | 43125 | 66220 |
| TIMM8A | 20031 | 43126 | 66221 |
| TIMM8B | 20032 | 43127 | 66222 |
| TIMM9 | 20033 | 43128 | 66223 |
| TIMMDC1 | 20034 | 43129 | 66224 |
| TIMP1 | 20035 | 43130 | 66225 |
| TIMP2 | 20036 | 43131 | 66226 |
| TIMP3 | 20037 | 43132 | 66227 |
| TIMP4 | 20038 | 43133 | 66228 |
| TINAG | 20039 | 43134 | 66229 |
| TINAGL1 | 20040 | 43135 | 66230 |
| TINF2 | 20041 | 43136 | 66231 |
| TINF2 | 20042 | 43137 | 66232 |
| TIPARP | 20043 | 43138 | 66233 |
| TIPIN | 20044 | 43139 | 66234 |
| TIPRL | 20045 | 43140 | 66235 |
| TIPRL | 20046 | 43141 | 66236 |
| TIRAP | 20047 | 43142 | 66237 |
| TIRAP | 20048 | 43143 | 66238 |
| TJAP1 | 20049 | 43144 | 66239 |
| TJP1 | 20050 | 43145 | 66240 |
| TJP2 | 20051 | 43146 | 66241 |
| TJP3 | 20052 | 43147 | 66242 |
| TK1 | 20053 | 43148 | 66243 |
| TK2 | 20054 | 43149 | 66244 |
| TK2 | 20055 | 43150 | 66245 |
| TKFC | 20056 | 43151 | 66246 |
| TKFC | 20057 | 43152 | 66247 |
| TKFC | 20058 | 43153 | 66248 |
| TKFC | 20059 | 43154 | 66249 |
| TKT | 20060 | 43155 | 66250 |
| TKTL1 | 20061 | 43156 | 66251 |
| TKTL2 | 20062 | 43157 | 66252 |
| TLCD1 | 20063 | 43158 | 66253 |
| TLCD2 | 20064 | 43159 | 66254 |
| TLDC1 | 20065 | 43160 | 66255 |
| TLDC2 | 20066 | 43161 | 66256 |
| TLE1 | 20067 | 43162 | 66257 |
| TLE2 | 20068 | 43163 | 66258 |
| TLE2 | 20069 | 43164 | 66259 |
| TLE3 | 20070 | 43165 | 66260 |
| TLE4 | 20071 | 43166 | 66261 |
| TLE6 | 20072 | 43167 | 66262 |
| TLK1 | 20073 | 43168 | 66263 |
| TLK2 | 20074 | 43169 | 66264 |
| TLL1 | 20075 | 43170 | 66265 |
| TLL1 | 20076 | 43171 | 66266 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TLL2 | 20077 | 43172 | 66267 |
| TLN1 | 20078 | 43173 | 66268 |
| TLN2 | 20079 | 43174 | 66269 |
| TLNRD1 | 20080 | 43175 | 66270 |
| TLR1 | 20081 | 43176 | 66271 |
| TLR10 | 20082 | 43177 | 66272 |
| TLR2 | 20083 | 43178 | 66273 |
| TLR3 | 20084 | 43179 | 66274 |
| TLR4 | 20085 | 43180 | 66275 |
| TLR5 | 20086 | 43181 | 66276 |
| TLR6 | 20087 | 43182 | 66277 |
| TLR7 | 20088 | 43183 | 66278 |
| TLR8 | 20089 | 43184 | 66279 |
| TLR9 | 20090 | 43185 | 66280 |
| TLX1 | 20091 | 43186 | 66281 |
| TLX1 | 20092 | 43187 | 66282 |
| TLX2 | 20093 | 43188 | 66283 |
| TLX3 | 20094 | 43189 | 66284 |
| TM2D1 | 20095 | 43190 | 66285 |
| TM2D2 | 20096 | 43191 | 66286 |
| TM2D3 | 20097 | 43192 | 66287 |
| TM2D3 | 20098 | 43193 | 66288 |
| TM4SF1 | 20099 | 43194 | 66289 |
| TM4SF18 | 20100 | 43195 | 66290 |
| TM4SF19 | 20101 | 43196 | 66291 |
| TM4SF19 | 20102 | 43197 | 66292 |
| TM4SF20 | 20103 | 43198 | 66293 |
| TM4SF4 | 20104 | 43199 | 66294 |
| TM4SF5 | 20105 | 43200 | 66295 |
| TM6SF1 | 20106 | 43201 | 66296 |
| TM6SF1 | 20107 | 43202 | 66297 |
| TM6SF1 | 20108 | 43203 | 66298 |
| TM6SF2 | 20109 | 43204 | 66299 |
| TM7SF2 | 20110 | 43205 | 66300 |
| TM7SF3 | 20111 | 43206 | 66301 |
| TM9SF1 | 20112 | 43207 | 66302 |
| TM9SF1 | 20113 | 43208 | 66303 |
| TM9SF2 | 20114 | 43209 | 66304 |
| TM9SF3 | 20115 | 43210 | 66305 |
| TM9SF4 | 20116 | 43211 | 66306 |
| TMA16 | 20117 | 43212 | 66307 |
| TMA7 | 20118 | 43213 | 66308 |
| TMA7 | 20119 | 43214 | 66309 |
| TMBIM1 | 20120 | 43215 | 66310 |
| TMBIM1 | 20121 | 43216 | 66311 |
| TMBIM4 | 20122 | 43217 | 66312 |
| TMBIM4 | 20123 | 43218 | 66313 |
| TMBIM6 | 20124 | 43219 | 66314 |
| TMC1 | 20125 | 43220 | 66315 |
| TMC2 | 20126 | 43221 | 66316 |
| TMC3 | 20127 | 43222 | 66317 |
| TMC4 | 20128 | 43223 | 66318 |
| TMC5 | 20129 | 43224 | 66319 |
| TMC6 | 20130 | 43225 | 66320 |
| TMC7 | 20131 | 43226 | 66321 |
| TMC7 | 20132 | 43227 | 66322 |
| TMC8 | 20133 | 43228 | 66323 |
| TMCC1 | 20134 | 43229 | 66324 |
| TMCC2 | 20135 | 43230 | 66325 |
| TMCC3 | 20136 | 43231 | 66326 |
| TMCO1 | 20137 | 43232 | 66327 |
| TMCO2 | 20138 | 43233 | 66328 |
| TMCO3 | 20139 | 43234 | 66329 |
| TMCO3 | 20140 | 43235 | 66330 |
| TMCO3 | 20141 | 43236 | 66331 |
| TMCO4 | 20142 | 43237 | 66332 |
| TMCO4 | 20143 | 43238 | 66333 |
| TMCO5A | 20144 | 43239 | 66334 |
| TMCO5A | 20145 | 43240 | 66335 |
| TMCO6 | 20146 | 43241 | 66336 |
| TMED1 | 20147 | 43242 | 66337 |
| TMED10 | 20148 | 43243 | 66338 |
| TMED2 | 20149 | 43244 | 66339 |
| TMED3 | 20150 | 43245 | 66340 |
| TMED3 | 20151 | 43246 | 66341 |
| TMED3 | 20152 | 43247 | 66342 |
| TMED4 | 20153 | 43248 | 66343 |
| TMED4 | 20154 | 43249 | 66344 |
| TMED4 | 20155 | 43250 | 66345 |
| TMED5 | 20156 | 43251 | 66346 |
| TMED5 | 20157 | 43252 | 66347 |
| TMED6 | 20158 | 43253 | 66348 |
| TMED7 | 20159 | 43254 | 66349 |
| TMED8 | 20160 | 43255 | 66350 |
| TMED9 | 20161 | 43256 | 66351 |
| TMEFF1 | 20162 | 43257 | 66352 |
| TMEFF2 | 20163 | 43258 | 66353 |
| TMEFF2 | 20164 | 43259 | 66354 |
| TMEFF2 | 20165 | 43260 | 66355 |
| TMEM100 | 20166 | 43261 | 66356 |
| TMEM101 | 20167 | 43262 | 66357 |
| TMEM102 | 20168 | 43263 | 66358 |
| TMEM104 | 20169 | 43264 | 66359 |
| TMEM104 | 20170 | 43265 | 66360 |
| TMEM105 | 20171 | 43266 | 66361 |
| TMEM106A | 20172 | 43267 | 66362 |
| TMEM106B | 20173 | 43268 | 66363 |
| TMEM106C | 20174 | 43269 | 66364 |
| TMEM107 | 20175 | 43270 | 66365 |
| TMEM108 | 20176 | 43271 | 66366 |
| TMEM109 | 20177 | 43272 | 66367 |
| TMEM11 | 20178 | 43273 | 66368 |
| TMEM110 | 20179 | 43274 | 66369 |
| TMEM114 | 20180 | 43275 | 66370 |
| TMEM114 | 20181 | 43276 | 66371 |
| TMEM115 | 20182 | 43277 | 66372 |
| TMEM116 | 20183 | 43278 | 66373 |
| TMEM117 | 20184 | 43279 | 66374 |
| TMEM117 | 20185 | 43280 | 66375 |
| TMEM119 | 20186 | 43281 | 66376 |
| TMEM120A | 20187 | 43282 | 66377 |
| TMEM120A | 20188 | 43283 | 66378 |
| TMEM120B | 20189 | 43284 | 66379 |
| TMEM121 | 20190 | 43285 | 66380 |
| TMEM121 | 20191 | 43286 | 66381 |
| TMEM121B | 20192 | 43287 | 66382 |
| TMEM123 | 20193 | 43288 | 66383 |
| TMEM125 | 20194 | 43289 | 66384 |
| TMEM126A | 20195 | 43290 | 66385 |
| TMEM126B | 20196 | 43291 | 66386 |
| TMEM126B | 20197 | 43292 | 66387 |
| TMEM127 | 20198 | 43293 | 66388 |
| TMEM128 | 20199 | 43294 | 66389 |
| TMEM129 | 20200 | 43295 | 66390 |
| TMEM129 | 20201 | 43296 | 66391 |
| TMEM130 | 20202 | 43297 | 66392 |
| TMEM131 | 20203 | 43298 | 66393 |
| TMEM131L | 20204 | 43299 | 66394 |
| TMEM132A | 20205 | 43300 | 66395 |
| TMEM132B | 20206 | 43301 | 66396 |
| TMEM132C | 20207 | 43302 | 66397 |
| TMEM132D | 20208 | 43303 | 66398 |
| TMEM132E | 20209 | 43304 | 66399 |
| TMEM134 | 20210 | 43305 | 66400 |
| TMEM135 | 20211 | 43306 | 66401 |
| TMEM136 | 20212 | 43307 | 66402 |
| TMEM138 | 20213 | 43308 | 66403 |
| TMEM138 | 20214 | 43309 | 66404 |
| TMEM139 | 20215 | 43310 | 66405 |
| TMEM140 | 20216 | 43311 | 66406 |
| TMEM141 | 20217 | 43312 | 66407 |
| TMEM143 | 20218 | 43313 | 66408 |
| TMEM144 | 20219 | 43314 | 66409 |
| TMEM145 | 20220 | 43315 | 66410 |
| TMEM147 | 20221 | 43316 | 66411 |
| TMEM14A | 20222 | 43317 | 66412 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TMEM14B | 20223 | 43318 | 66413 |
| TMEM14B | 20224 | 43319 | 66414 |
| TMEM14C | 20225 | 43320 | 66415 |
| TMEM150A | 20226 | 43321 | 66416 |
| TMEM150B | 20227 | 43322 | 66417 |
| TMEM150C | 20228 | 43323 | 66418 |
| TMEM151A | 20229 | 43324 | 66419 |
| TMEM151B | 20230 | 43325 | 66420 |
| TMEM154 | 20231 | 43326 | 66421 |
| TMEM155 | 20232 | 43327 | 66422 |
| TMEM155 | 20233 | 43328 | 66423 |
| TMEM156 | 20234 | 43329 | 66424 |
| TMEM158 | 20235 | 43330 | 66425 |
| TMEM159 | 20236 | 43331 | 66426 |
| TMEM159 | 20237 | 43332 | 66427 |
| TMEM160 | 20238 | 43333 | 66428 |
| TMEM161A | 20239 | 43334 | 66429 |
| TMEM161B | 20240 | 43335 | 66430 |
| TMEM161B | 20241 | 43336 | 66431 |
| TMEM161B | 20242 | 43337 | 66432 |
| TMEM163 | 20243 | 43338 | 66433 |
| TMEM164 | 20244 | 43339 | 66434 |
| TMEM164 | 20245 | 43340 | 66435 |
| TMEM165 | 20246 | 43341 | 66436 |
| TMEM167A | 20247 | 43342 | 66437 |
| TMEM167B | 20248 | 43343 | 66438 |
| TMEM167B | 20249 | 43344 | 66439 |
| TMEM168 | 20250 | 43345 | 66440 |
| TMEM169 | 20251 | 43346 | 66441 |
| TMEM17 | 20252 | 43347 | 66442 |
| TMEM170A | 20253 | 43348 | 66443 |
| TMEM170B | 20254 | 43349 | 66444 |
| TMEM171 | 20255 | 43350 | 66445 |
| TMEM173 | 20256 | 43351 | 66446 |
| TMEM173 | 20257 | 43352 | 66447 |
| TMEM174 | 20258 | 43353 | 66448 |
| TMEM175 | 20259 | 43354 | 66449 |
| TMEM176A | 20260 | 43355 | 66450 |
| TMEM176B | 20261 | 43356 | 66451 |
| TMEM177 | 20262 | 43357 | 66452 |
| TMEM178A | 20263 | 43358 | 66453 |
| TMEM178B | 20264 | 43359 | 66454 |
| TMEM179 | 20265 | 43360 | 66455 |
| TMEM179 | 20266 | 43361 | 66456 |
| TMEM179B | 20267 | 43362 | 66457 |
| TMEM18 | 20268 | 43363 | 66458 |
| TMEM181 | 20269 | 43364 | 66459 |
| TMEM182 | 20270 | 43365 | 66460 |
| TMEM183A | 20271 | 43366 | 66461 |
| TMEM183B | 20272 | 43367 | 66462 |
| TMEM184A | 20273 | 43368 | 66463 |
| TMEM184B | 20274 | 43369 | 66464 |
| TMEM184C | 20275 | 43370 | 66465 |
| TMEM185A | 20276 | 43371 | 66466 |
| TMEM185A | 20277 | 43372 | 66467 |
| TMEM185B | 20278 | 43373 | 66468 |
| TMEM186 | 20279 | 43374 | 66469 |
| TMEM187 | 20280 | 43375 | 66470 |
| TMEM189 | 20281 | 43376 | 66471 |
| TMEM19 | 20282 | 43377 | 66472 |
| TMEM190 | 20283 | 43378 | 66473 |
| TMEM191C | 20284 | 43379 | 66474 |
| TMEM192 | 20285 | 43380 | 66475 |
| TMEM196 | 20286 | 43381 | 66476 |
| TMEM198 | 20287 | 43382 | 66477 |
| TMEM199 | 20288 | 43383 | 66478 |
| TMEM2 | 20289 | 43384 | 66479 |
| TMEM200A | 20290 | 43385 | 66480 |
| TMEM200B | 20291 | 43386 | 66481 |
| TMEM200C | 20292 | 43387 | 66482 |
| TMEM201 | 20293 | 43388 | 66483 |
| TMEM201 | 20294 | 43389 | 66484 |
| TMEM202 | 20295 | 43390 | 66485 |
| TMEM203 | 20296 | 43391 | 66486 |
| TMEM204 | 20297 | 43392 | 66487 |
| TMEM205 | 20298 | 43393 | 66488 |
| TMEM206 | 20299 | 43394 | 66489 |
| TMEM207 | 20300 | 43395 | 66490 |
| TMEM208 | 20301 | 43396 | 66491 |
| TMEM209 | 20302 | 43397 | 66492 |
| TMEM210 | 20303 | 43398 | 66493 |
| TMEM211 | 20304 | 43399 | 66494 |
| TMEM212 | 20305 | 43400 | 66495 |
| TMEM213 | 20306 | 43401 | 66496 |
| TMEM214 | 20307 | 43402 | 66497 |
| TMEM215 | 20308 | 43403 | 66498 |
| TMEM216 | 20309 | 43404 | 66499 |
| TMEM216 | 20310 | 43405 | 66500 |
| TMEM217 | 20311 | 43406 | 66501 |
| TMEM217 | 20312 | 43407 | 66502 |
| TMEM217 | 20313 | 43408 | 66503 |
| TMEM218 | 20314 | 43409 | 66504 |
| TMEM219 | 20315 | 43410 | 66505 |
| TMEM220 | 20316 | 43411 | 66506 |
| TMEM221 | 20317 | 43412 | 66507 |
| TMEM222 | 20318 | 43413 | 66508 |
| TMEM223 | 20319 | 43414 | 66509 |
| TMEM225 | 20320 | 43415 | 66510 |
| TMEM225B | 20321 | 43416 | 66511 |
| TMEM229A | 20322 | 43417 | 66512 |
| TMEM229B | 20323 | 43418 | 66513 |
| TMEM230 | 20324 | 43419 | 66514 |
| TMEM230 | 20325 | 43420 | 66515 |
| TMEM231 | 20326 | 43421 | 66516 |
| TMEM232 | 20327 | 43422 | 66517 |
| TMEM233 | 20328 | 43423 | 66518 |
| TMEM234 | 20329 | 43424 | 66519 |
| TMEM235 | 20330 | 43425 | 66520 |
| TMEM235 | 20331 | 43426 | 66521 |
| TMEM236 | 20332 | 43427 | 66522 |
| TMEM237 | 20333 | 43428 | 66523 |
| TMEM238 | 20334 | 43429 | 66524 |
| TMEM239 | 20335 | 43430 | 66525 |
| TMEM240 | 20336 | 43431 | 66526 |
| TMEM241 | 20337 | 43432 | 66527 |
| TMEM242 | 20338 | 43433 | 66528 |
| TMEM243 | 20339 | 43434 | 66529 |
| TMEM244 | 20340 | 43435 | 66530 |
| TMEM245 | 20341 | 43436 | 66531 |
| TMEM246 | 20342 | 43437 | 66532 |
| TMEM247 | 20343 | 43438 | 66533 |
| TMEM248 | 20344 | 43439 | 66534 |
| TMEM249 | 20345 | 43440 | 66535 |
| TMEM249 | 20346 | 43441 | 66536 |
| TMEM25 | 20347 | 43442 | 66537 |
| TMEM25 | 20348 | 43443 | 66538 |
| TMEM25 | 20349 | 43444 | 66539 |
| TMEM250 | 20350 | 43445 | 66540 |
| TMEM251 | 20351 | 43446 | 66541 |
| TMEM252 | 20352 | 43447 | 66542 |
| TMEM253 | 20353 | 43448 | 66543 |
| TMEM254 | 20354 | 43449 | 66544 |
| TMEM254 | 20355 | 43450 | 66545 |
| TMEM254 | 20356 | 43451 | 66546 |
| TMEM255A | 20357 | 43452 | 66547 |
| TMEM255B | 20358 | 43453 | 66548 |
| TMEM256 | 20359 | 43454 | 66549 |
| TMEM258 | 20360 | 43455 | 66550 |
| TMEM259 | 20361 | 43456 | 66551 |
| TMEM259 | 20362 | 43457 | 66552 |
| TMEM26 | 20363 | 43458 | 66553 |
| TMEM260 | 20364 | 43459 | 66554 |
| TMEM262 | 20365 | 43460 | 66555 |
| TMEM262 | 20366 | 43461 | 66556 |
| TMEM263 | 20367 | 43462 | 66557 |
| TMEM265 | 20368 | 43463 | 66558 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TMEM266 | 20369 | 43464 | 66559 |
| TMEM267 | 20370 | 43465 | 66560 |
| TMEM268 | 20371 | 43466 | 66561 |
| TMEM269 | 20372 | 43467 | 66562 |
| TMEM27 | 20373 | 43468 | 66563 |
| TMEM270 | 20374 | 43469 | 66564 |
| TMEM272 | 20375 | 43470 | 66565 |
| TMEM272 | 20376 | 43471 | 66566 |
| TMEM30A | 20377 | 43472 | 66567 |
| TMEM30B | 20378 | 43473 | 66568 |
| TMEM31 | 20379 | 43474 | 66569 |
| TMEM33 | 20380 | 43475 | 66570 |
| TMEM35A | 20381 | 43476 | 66571 |
| TMEM35B | 20382 | 43477 | 66572 |
| TMEM37 | 20383 | 43478 | 66573 |
| TMEM38A | 20384 | 43479 | 66574 |
| TMEM38B | 20385 | 43480 | 66575 |
| TMEM39A | 20386 | 43481 | 66576 |
| TMEM39B | 20387 | 43482 | 66577 |
| TMEM40 | 20388 | 43483 | 66578 |
| TMEM41A | 20389 | 43484 | 66579 |
| TMEM41B | 20390 | 43485 | 66580 |
| TMEM41B | 20391 | 43486 | 66581 |
| TMEM42 | 20392 | 43487 | 66582 |
| TMEM43 | 20393 | 43488 | 66583 |
| TMEM44 | 20394 | 43489 | 66584 |
| TMEM44 | 20395 | 43490 | 66585 |
| TMEM45A | 20396 | 43491 | 66586 |
| TMEM45B | 20397 | 43492 | 66587 |
| TMEM47 | 20398 | 43493 | 66588 |
| TMEM5 | 20399 | 43494 | 66589 |
| TMEM50A | 20400 | 43495 | 66590 |
| TMEM50B | 20401 | 43496 | 66591 |
| TMEM51 | 20402 | 43497 | 66592 |
| TMEM51 | 20403 | 43498 | 66593 |
| TMEM52 | 20404 | 43499 | 66594 |
| TMEM52B | 20405 | 43500 | 66595 |
| TMEM53 | 20406 | 43501 | 66596 |
| TMEM54 | 20407 | 43502 | 66597 |
| TMEM56 | 20408 | 43503 | 66598 |
| TMEM56-RWDD3 | 20409 | 43504 | 66599 |
| TMEM57 | 20410 | 43505 | 66600 |
| TMEM59 | 20411 | 43506 | 66601 |
| TMEM59 | 20412 | 43507 | 66602 |
| TMEM59L | 20413 | 43508 | 66603 |
| TMEM60 | 20414 | 43509 | 66604 |
| TMEM61 | 20415 | 43510 | 66605 |
| TMEM62 | 20416 | 43511 | 66606 |
| TMEM63A | 20417 | 43512 | 66607 |
| TMEM63B | 20418 | 43513 | 66608 |
| TMEM63C | 20419 | 43514 | 66609 |
| TMEM64 | 20420 | 43515 | 66610 |
| TMEM65 | 20421 | 43516 | 66611 |
| TMEM67 | 20422 | 43517 | 66612 |
| TMEM68 | 20423 | 43518 | 66613 |
| TMEM68 | 20424 | 43519 | 66614 |
| TMEM68 | 20425 | 43520 | 66615 |
| TMEM69 | 20426 | 43521 | 66616 |
| TMEM70 | 20427 | 43522 | 66617 |
| TMEM70 | 20428 | 43523 | 66618 |
| TMEM71 | 20429 | 43524 | 66619 |
| TMEM72 | 20430 | 43525 | 66620 |
| TMEM74 | 20431 | 43526 | 66621 |
| TMEM74B | 20432 | 43527 | 66622 |
| TMEM79 | 20433 | 43528 | 66623 |
| TMEM80 | 20434 | 43529 | 66624 |
| TMEM80 | 20435 | 43530 | 66625 |
| TMEM80 | 20436 | 43531 | 66626 |
| TMEM81 | 20437 | 43532 | 66627 |
| TMEM82 | 20438 | 43533 | 66628 |
| TMEM86A | 20439 | 43534 | 66629 |
| TMEM86B | 20440 | 43535 | 66630 |
| TMEM87A | 20441 | 43536 | 66631 |
| TMEM87A | 20442 | 43537 | 66632 |
| TMEM87B | 20443 | 43538 | 66633 |
| TMEM88 | 20444 | 43539 | 66634 |
| TMEM88 | 20445 | 43540 | 66635 |
| TMEM88B | 20446 | 43541 | 66636 |
| TMEM89 | 20447 | 43542 | 66637 |
| TMEM8A | 20448 | 43543 | 66638 |
| TMEM8B | 20449 | 43544 | 66639 |
| TMEM8B | 20450 | 43545 | 66640 |
| TMEM9 | 20451 | 43546 | 66641 |
| TMEM91 | 20452 | 43547 | 66642 |
| TMEM91 | 20453 | 43548 | 66643 |
| TMEM91 | 20454 | 43549 | 66644 |
| TMEM91 | 20455 | 43550 | 66645 |
| TMEM92 | 20456 | 43551 | 66646 |
| TMEM94 | 20457 | 43552 | 66647 |
| TMEM95 | 20458 | 43553 | 66648 |
| TMEM95 | 20459 | 43554 | 66649 |
| TMEM97 | 20460 | 43555 | 66650 |
| TMEM98 | 20461 | 43556 | 66651 |
| TMEM99 | 20462 | 43557 | 66652 |
| TMEM9B | 20463 | 43558 | 66653 |
| TMF1 | 20464 | 43559 | 66654 |
| TMIE | 20465 | 43560 | 66655 |
| TMIGD1 | 20466 | 43561 | 66656 |
| TMIGD1 | 20467 | 43562 | 66657 |
| TMIGD2 | 20468 | 43563 | 66658 |
| TMIGD2 | 20469 | 43564 | 66659 |
| TMIGD3 | 20470 | 43565 | 66660 |
| TMLHE | 20471 | 43566 | 66661 |
| TMLHE | 20472 | 43567 | 66662 |
| TMOD1 | 20473 | 43568 | 66663 |
| TMOD2 | 20474 | 43569 | 66664 |
| TMOD3 | 20475 | 43570 | 66665 |
| TMOD4 | 20476 | 43571 | 66666 |
| TMPO | 20477 | 43572 | 66667 |
| TMPO | 20478 | 43573 | 66668 |
| TMPPE | 20479 | 43574 | 66669 |
| TMPRSS11A | 20480 | 43575 | 66670 |
| TMPRSS11B | 20481 | 43576 | 66671 |
| TMPRSS11D | 20482 | 43577 | 66672 |
| TMPRSS11E | 20483 | 43578 | 66673 |
| TMPRSS11F | 20484 | 43579 | 66674 |
| TMPRSS12 | 20485 | 43580 | 66675 |
| TMPRSS13 | 20486 | 43581 | 66676 |
| TMPRSS13 | 20487 | 43582 | 66677 |
| TMPRSS15 | 20488 | 43583 | 66678 |
| TMPRSS2 | 20489 | 43584 | 66679 |
| TMPRSS3 | 20490 | 43585 | 66680 |
| TMPRSS3 | 20491 | 43586 | 66681 |
| TMPRSS4 | 20492 | 43587 | 66682 |
| TMPRSS5 | 20493 | 43588 | 66683 |
| TMPRSS6 | 20494 | 43589 | 66684 |
| TMPRSS7 | 20495 | 43590 | 66685 |
| TMPRSS9 | 20496 | 43591 | 66686 |
| TMSB10 | 20497 | 43592 | 66687 |
| TMSB15A | 20498 | 43593 | 66688 |
| TMSB15B | 20499 | 43594 | 66689 |
| TMSB15B | 20500 | 43595 | 66690 |
| TMSB15B | 20501 | 43596 | 66691 |
| TMSB4X | 20502 | 43597 | 66692 |
| TMSB4Y | 20503 | 43598 | 66693 |
| TMTC1 | 20504 | 43599 | 66694 |
| TMTC2 | 20505 | 43600 | 66695 |
| TMTC2 | 20506 | 43601 | 66696 |
| TMTC3 | 20507 | 43602 | 66697 |
| TMTC4 | 20508 | 43603 | 66698 |
| TMUB1 | 20509 | 43604 | 66699 |
| TMUB2 | 20510 | 43605 | 66700 |
| TMUB2 | 20511 | 43606 | 66701 |
| TMX1 | 20512 | 43607 | 66702 |
| TMX2 | 20513 | 43608 | 66703 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TMX2 | 20514 | 43609 | 66704 |
| TMX3 | 20515 | 43610 | 66705 |
| TMX3 | 20516 | 43611 | 66706 |
| TMX3 | 20517 | 43612 | 66707 |
| TMX4 | 20518 | 43613 | 66708 |
| TNC | 20519 | 43614 | 66709 |
| TNF | 20520 | 43615 | 66710 |
| TNFAIP1 | 20521 | 43616 | 66711 |
| TNFAIP2 | 20522 | 43617 | 66712 |
| TNFAIP3 | 20523 | 43618 | 66713 |
| TNFAIP6 | 20524 | 43619 | 66714 |
| TNFAIP8 | 20525 | 43620 | 66715 |
| TNFAIP8L1 | 20526 | 43621 | 66716 |
| TNFAIP8L2 | 20527 | 43622 | 66717 |
| TNFAIP8L3 | 20528 | 43623 | 66718 |
| TNFRSF10A | 20529 | 43624 | 66719 |
| TNFRSF10B | 20530 | 43625 | 66720 |
| TNFRSF10C | 20531 | 43626 | 66721 |
| TNFRSF10D | 20532 | 43627 | 66722 |
| TNFRSF11A | 20533 | 43628 | 66723 |
| TNFRSF11A | 20534 | 43629 | 66724 |
| TNFRSF11B | 20535 | 43630 | 66725 |
| TNFRSF12A | 20536 | 43631 | 66726 |
| TNFRSF13B | 20537 | 43632 | 66727 |
| TNFRSF13C | 20538 | 43633 | 66728 |
| TNFRSF14 | 20539 | 43634 | 66729 |
| TNFRSF14 | 20540 | 43635 | 66730 |
| TNFRSF17 | 20541 | 43636 | 66731 |
| TNFRSF18 | 20542 | 43637 | 66732 |
| TNFRSF18 | 20543 | 43638 | 66733 |
| TNFRSF19 | 20544 | 43639 | 66734 |
| TNFRSF19 | 20545 | 43640 | 66735 |
| TNFRSF1A | 20546 | 43641 | 66736 |
| TNFRSF1B | 20547 | 43642 | 66737 |
| TNFRSF21 | 20548 | 43643 | 66738 |
| TNFRSF25 | 20549 | 43644 | 66739 |
| TNFRSF25 | 20550 | 43645 | 66740 |
| TNFRSF4 | 20551 | 43646 | 66741 |
| TNFRSF6B | 20552 | 43647 | 66742 |
| TNFRSF8 | 20553 | 43648 | 66743 |
| TNFRSF9 | 20554 | 43649 | 66744 |
| TNFSF10 | 20555 | 43650 | 66745 |
| TNFSF10 | 20556 | 43651 | 66746 |
| TNFSF10 | 20557 | 43652 | 66747 |
| TNFSF11 | 20558 | 43653 | 66748 |
| TNFSF12 | 20559 | 43654 | 66749 |
| TNFSF13 | 20560 | 43655 | 66750 |
| TNFSF13 | 20561 | 43656 | 66751 |
| TNFSF13B | 20562 | 43657 | 66752 |
| TNFSF14 | 20563 | 43658 | 66753 |
| TNFSF15 | 20564 | 43659 | 66754 |
| TNFSF18 | 20565 | 43660 | 66755 |
| TNFSF4 | 20566 | 43661 | 66756 |
| TNFSF8 | 20567 | 43662 | 66757 |
| TNFSF8 | 20568 | 43663 | 66758 |
| TNFSF9 | 20569 | 43664 | 66759 |
| TNIK | 20570 | 43665 | 66760 |
| TNIP1 | 20571 | 43666 | 66761 |
| TNIP1 | 20572 | 43667 | 66762 |
| TNIP1 | 20573 | 43668 | 66763 |
| TNIP1 | 20574 | 43669 | 66764 |
| TNIP2 | 20575 | 43670 | 66765 |
| TNIP3 | 20576 | 43671 | 66766 |
| TNIP3 | 20577 | 43672 | 66767 |
| TNK1 | 20578 | 43673 | 66768 |
| TNK2 | 20579 | 43674 | 66769 |
| TNKS | 20580 | 43675 | 66770 |
| TNKS1BP1 | 20581 | 43676 | 66771 |
| TNKS2 | 20582 | 43677 | 66772 |
| TNMD | 20583 | 43678 | 66773 |
| TNN | 20584 | 43679 | 66774 |
| TNNC1 | 20585 | 43680 | 66775 |
| TNNC2 | 20586 | 43681 | 66776 |
| TNNI1 | 20587 | 43682 | 66777 |
| TNNI2 | 20588 | 43683 | 66778 |
| TNNI3 | 20589 | 43684 | 66779 |
| TNNI3K | 20590 | 43685 | 66780 |
| TNNT1 | 20591 | 43686 | 66781 |
| TNNT2 | 20592 | 43687 | 66782 |
| TNNT3 | 20593 | 43688 | 66783 |
| TNP1 | 20594 | 43689 | 66784 |
| TNP2 | 20595 | 43690 | 66785 |
| TNPO1 | 20596 | 43691 | 66786 |
| TNPO2 | 20597 | 43692 | 66787 |
| TNPO3 | 20598 | 43693 | 66788 |
| TNR | 20599 | 43694 | 66789 |
| TNRC18 | 20600 | 43695 | 66790 |
| TNRC6A | 20601 | 43696 | 66791 |
| TNRC6B | 20602 | 43697 | 66792 |
| TNRC6C | 20603 | 43698 | 66793 |
| TNS1 | 20604 | 43699 | 66794 |
| TNS2 | 20605 | 43700 | 66795 |
| TNS3 | 20606 | 43701 | 66796 |
| TNS4 | 20607 | 43702 | 66797 |
| TNXB | 20608 | 43703 | 66798 |
| TOB1 | 20609 | 43704 | 66799 |
| TOB2 | 20610 | 43705 | 66800 |
| TOE1 | 20611 | 43706 | 66801 |
| TOGARAM1 | 20612 | 43707 | 66802 |
| TOGARAM2 | 20613 | 43708 | 66803 |
| TOLLIP | 20614 | 43709 | 66804 |
| TOLLIP | 20615 | 43710 | 66805 |
| TOM1 | 20616 | 43711 | 66806 |
| TOM1L1 | 20617 | 43712 | 66807 |
| TOM1L1 | 20618 | 43713 | 66808 |
| TOM1L2 | 20619 | 43714 | 66809 |
| TOMM20 | 20620 | 43715 | 66810 |
| TOMM20L | 20621 | 43716 | 66811 |
| TOMM22 | 20622 | 43717 | 66812 |
| TOMM34 | 20623 | 43718 | 66813 |
| TOMM40 | 20624 | 43719 | 66814 |
| TOMM40L | 20625 | 43720 | 66815 |
| TOMM5 | 20626 | 43721 | 66816 |
| TOMM5 | 20627 | 43722 | 66817 |
| TOMM5 | 20628 | 43723 | 66818 |
| TOMM6 | 20629 | 43724 | 66819 |
| TOMM7 | 20630 | 43725 | 66820 |
| TOMM70 | 20631 | 43726 | 66821 |
| TONSL | 20632 | 43727 | 66822 |
| TOP1 | 20633 | 43728 | 66823 |
| TOP1MT | 20634 | 43729 | 66824 |
| TOP2A | 20635 | 43730 | 66825 |
| TOP2B | 20636 | 43731 | 66826 |
| TOP3A | 20637 | 43732 | 66827 |
| TOP3B | 20638 | 43733 | 66828 |
| TOP3B | 20639 | 43734 | 66829 |
| TOPAZ1 | 20640 | 43735 | 66830 |
| TOPBP1 | 20641 | 43736 | 66831 |
| TOPORS | 20642 | 43737 | 66832 |
| TOR1A | 20643 | 43738 | 66833 |
| TOR1AIP1 | 20644 | 43739 | 66834 |
| TOR1AIP2 | 20645 | 43740 | 66835 |
| TOR1AIP2 | 20646 | 43741 | 66836 |
| TOR1B | 20647 | 43742 | 66837 |
| TOR1B | 20648 | 43743 | 66838 |
| TOR1B | 20649 | 43744 | 66839 |
| TOR2A | 20650 | 43745 | 66840 |
| TOR2A | 20651 | 43746 | 66841 |
| TOR2A | 20652 | 43747 | 66842 |
| TOR3A | 20653 | 43748 | 66843 |
| TOR4A | 20654 | 43749 | 66844 |
| TOX | 20655 | 43750 | 66845 |
| TOX2 | 20656 | 43751 | 66846 |
| TOX3 | 20657 | 43752 | 66847 |
| TOX4 | 20658 | 43753 | 66848 |
| TP53 | 20659 | 43754 | 66849 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TP53 | 20660 | 43755 | 66850 |
| TP53 | 20661 | 43756 | 66851 |
| TP53AIP1 | 20662 | 43757 | 66852 |
| TP53AIP1 | 20663 | 43758 | 66853 |
| TP53AIP1 | 20664 | 43759 | 66854 |
| TP53BP1 | 20665 | 43760 | 66855 |
| TP53BP2 | 20666 | 43761 | 66856 |
| TP53I11 | 20667 | 43762 | 66857 |
| TP53I11 | 20668 | 43763 | 66858 |
| TP53I11 | 20669 | 43764 | 66859 |
| TP53I13 | 20670 | 43765 | 66860 |
| TP53I3 | 20671 | 43766 | 66861 |
| TP53I3 | 20672 | 43767 | 66862 |
| TP53INP1 | 20673 | 43768 | 66863 |
| TP53INP1 | 20674 | 43769 | 66864 |
| TP53INP2 | 20675 | 43770 | 66865 |
| TP53RK | 20676 | 43771 | 66866 |
| TP53TG3E | 20677 | 43772 | 66867 |
| TP53TG5 | 20678 | 43773 | 66868 |
| TP63 | 20679 | 43774 | 66869 |
| TP63 | 20680 | 43775 | 66870 |
| TP63 | 20681 | 43776 | 66871 |
| TP63 | 20682 | 43777 | 66872 |
| TP73 | 20683 | 43778 | 66873 |
| TP73 | 20684 | 43779 | 66874 |
| TP73 | 20685 | 43780 | 66875 |
| TPBG | 20686 | 43781 | 66876 |
| TPBGL | 20687 | 43782 | 66877 |
| TPCN1 | 20688 | 43783 | 66878 |
| TPCN2 | 20689 | 43784 | 66879 |
| TPD52 | 20690 | 43785 | 66880 |
| TPD52 | 20691 | 43786 | 66881 |
| TPD52L1 | 20692 | 43787 | 66882 |
| TPD52L1 | 20693 | 43788 | 66883 |
| TPD52L1 | 20694 | 43789 | 66884 |
| TPD52L2 | 20695 | 43790 | 66885 |
| TPD52L2 | 20696 | 43791 | 66886 |
| TPD52L3 | 20697 | 43792 | 66887 |
| TPD52L3 | 20698 | 43793 | 66888 |
| TPD52L3 | 20699 | 43794 | 66889 |
| TPGS1 | 20700 | 43795 | 66890 |
| TPGS2 | 20701 | 43796 | 66891 |
| TPGS2 | 20702 | 43797 | 66892 |
| TPGS2 | 20703 | 43798 | 66893 |
| TPGS2 | 20704 | 43799 | 66894 |
| TPGS2 | 20705 | 43800 | 66895 |
| TPGS2 | 20706 | 43801 | 66896 |
| TPGS2 | 20707 | 43802 | 66897 |
| TPH1 | 20708 | 43803 | 66898 |
| TPH2 | 20709 | 43804 | 66899 |
| TPI1 | 20710 | 43805 | 66900 |
| TPK1 | 20711 | 43806 | 66901 |
| TPK1 | 20712 | 43807 | 66902 |
| TPM1 | 20713 | 43808 | 66903 |
| TPM1 | 20714 | 43809 | 66904 |
| TPM1 | 20715 | 43810 | 66905 |
| TPM1 | 20716 | 43811 | 66906 |
| TPM2 | 20717 | 43812 | 66907 |
| TPM2 | 20718 | 43813 | 66908 |
| TPM3 | 20719 | 43814 | 66909 |
| TPM3 | 20720 | 43815 | 66910 |
| TPM3 | 20721 | 43816 | 66911 |
| TPM4 | 20722 | 43817 | 66912 |
| TPMT | 20723 | 43818 | 66913 |
| TPMT | 20724 | 43819 | 66914 |
| TPO | 20725 | 43820 | 66915 |
| TPP1 | 20726 | 43821 | 66916 |
| TPP2 | 20727 | 43822 | 66917 |
| TPPP | 20728 | 43823 | 66918 |
| TPPP2 | 20729 | 43824 | 66919 |
| TPPP3 | 20730 | 43825 | 66920 |
| TPR | 20731 | 43826 | 66921 |
| TPRA1 | 20732 | 43827 | 66922 |
| TPRA1 | 20733 | 43828 | 66923 |
| TPRG1 | 20734 | 43829 | 66924 |
| TPRG1L | 20735 | 43830 | 66925 |
| TPRKB | 20736 | 43831 | 66926 |
| TPRN | 20737 | 43832 | 66927 |
| TPRX1 | 20738 | 43833 | 66928 |
| TPSAB1 | 20739 | 43834 | 66929 |
| TPSD1 | 20740 | 43835 | 66930 |
| TPSG1 | 20741 | 43836 | 66931 |
| TPST1 | 20742 | 43837 | 66932 |
| TPST2 | 20743 | 43838 | 66933 |
| TPT1 | 20744 | 43839 | 66934 |
| TPT1 | 20745 | 43840 | 66935 |
| TPTE | 20746 | 43841 | 66936 |
| TPTE2 | 20747 | 43842 | 66937 |
| TPX2 | 20748 | 43843 | 66938 |
| TRA2A | 20749 | 43844 | 66939 |
| TRA2B | 20750 | 43845 | 66940 |
| TRABD | 20751 | 43846 | 66941 |
| TRABD | 20752 | 43847 | 66942 |
| TRABD2A | 20753 | 43848 | 66943 |
| TRABD2A | 20754 | 43849 | 66944 |
| TRABD2B | 20755 | 43850 | 66945 |
| TRADD | 20756 | 43851 | 66946 |
| TRAF1 | 20757 | 43852 | 66947 |
| TRAF2 | 20758 | 43853 | 66948 |
| TRAF3 | 20759 | 43854 | 66949 |
| TRAF3IP1 | 20760 | 43855 | 66950 |
| TRAF3IP2 | 20761 | 43856 | 66951 |
| TRAF3IP3 | 20762 | 43857 | 66952 |
| TRAF3IP3 | 20763 | 43858 | 66953 |
| TRAF4 | 20764 | 43859 | 66954 |
| TRAF5 | 20765 | 43860 | 66955 |
| TRAF6 | 20766 | 43861 | 66956 |
| TRAF7 | 20767 | 43862 | 66957 |
| TRAFD1 | 20768 | 43863 | 66958 |
| TRAIP | 20769 | 43864 | 66959 |
| TRAK1 | 20770 | 43865 | 66960 |
| TRAK1 | 20771 | 43866 | 66961 |
| TRAK1 | 20772 | 43867 | 66962 |
| TRAK1 | 20773 | 43868 | 66963 |
| TRAK2 | 20774 | 43869 | 66964 |
| TRAM1 | 20775 | 43870 | 66965 |
| TRAM1L1 | 20776 | 43871 | 66966 |
| TRAM2 | 20777 | 43872 | 66967 |
| TRANK1 | 20778 | 43873 | 66968 |
| TRAP1 | 20779 | 43874 | 66969 |
| TRAPPC1 | 20780 | 43875 | 66970 |
| TRAPPC10 | 20781 | 43876 | 66971 |
| TRAPPC11 | 20782 | 43877 | 66972 |
| TRAPPC11 | 20783 | 43878 | 66973 |
| TRAPPC12 | 20784 | 43879 | 66974 |
| TRAPPC13 | 20785 | 43880 | 66975 |
| TRAPPC2 | 20786 | 43881 | 66976 |
| TRAPPC2L | 20787 | 43882 | 66977 |
| TRAPPC3 | 20788 | 43883 | 66978 |
| TRAPPC3L | 20789 | 43884 | 66979 |
| TRAPPC4 | 20790 | 43885 | 66980 |
| TRAPPC4 | 20791 | 43886 | 66981 |
| TRAPPC4 | 20792 | 43887 | 66982 |
| TRAPPC5 | 20793 | 43888 | 66983 |
| TRAPPC6A | 20794 | 43889 | 66984 |
| TRAPPC6A | 20795 | 43890 | 66985 |
| TRAPPC6B | 20796 | 43891 | 66986 |
| TRAPPC8 | 20797 | 43892 | 66987 |
| TRAPPC9 | 20798 | 43893 | 66988 |
| TRAT1 | 20799 | 43894 | 66989 |
| TRDMT1 | 20800 | 43895 | 66990 |
| TRDMT1 | 20801 | 43896 | 66991 |
| TRDN | 20802 | 43897 | 66992 |
| TRDN | 20803 | 43898 | 66993 |
| TRDN | 20804 | 43899 | 66994 |
| TRDN | 20805 | 43900 | 66995 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TRDN | 20806 | 43901 | 66996 |
| TREH | 20807 | 43902 | 66997 |
| TREM1 | 20808 | 43903 | 66998 |
| TREM1 | 20809 | 43904 | 66999 |
| TREM1 | 20810 | 43905 | 67000 |
| TREM2 | 20811 | 43906 | 67001 |
| TREM2 | 20812 | 43907 | 67002 |
| TREML1 | 20813 | 43908 | 67003 |
| TREML1 | 20814 | 43909 | 67004 |
| TREML2 | 20815 | 43910 | 67005 |
| TREML4 | 20816 | 43911 | 67006 |
| TRERF1 | 20817 | 43912 | 67007 |
| TREX1 | 20818 | 43913 | 67008 |
| TREX2 | 20819 | 43914 | 67009 |
| TRH | 20820 | 43915 | 67010 |
| TRHDE | 20821 | 43916 | 67011 |
| TRHR | 20822 | 43917 | 67012 |
| TRIAP1 | 20823 | 43918 | 67013 |
| TRIB1 | 20824 | 43919 | 67014 |
| TRIB2 | 20825 | 43920 | 67015 |
| TRIB3 | 20826 | 43921 | 67016 |
| TRIL | 20827 | 43922 | 67017 |
| TRIM10 | 20828 | 43923 | 67018 |
| TRIM10 | 20829 | 43924 | 67019 |
| TRIM11 | 20830 | 43925 | 67020 |
| TRIM13 | 20831 | 43926 | 67021 |
| TRIM14 | 20832 | 43927 | 67022 |
| TRIM15 | 20833 | 43928 | 67023 |
| TRIM16L | 20834 | 43929 | 67024 |
| TRIM16L | 20835 | 43930 | 67025 |
| TRIM16L | 20836 | 43931 | 67026 |
| TRIM17 | 20837 | 43932 | 67027 |
| TRIM17 | 20838 | 43933 | 67028 |
| TRIM2 | 20839 | 43934 | 67029 |
| TRIM2 | 20840 | 43935 | 67030 |
| TRIM21 | 20841 | 43936 | 67031 |
| TRIM22 | 20842 | 43937 | 67032 |
| TRIM23 | 20843 | 43938 | 67033 |
| TRIM23 | 20844 | 43939 | 67034 |
| TRIM23 | 20845 | 43940 | 67035 |
| TRIM24 | 20846 | 43941 | 67036 |
| TRIM25 | 20847 | 43942 | 67037 |
| TRIM26 | 20848 | 43943 | 67038 |
| TRIM27 | 20849 | 43944 | 67039 |
| TRIM28 | 20850 | 43945 | 67040 |
| TRIM29 | 20851 | 43946 | 67041 |
| TRIM3 | 20852 | 43947 | 67042 |
| TRIM31 | 20853 | 43948 | 67043 |
| TRIM32 | 20854 | 43949 | 67044 |
| TRIM33 | 20855 | 43950 | 67045 |
| TRIM34 | 20856 | 43951 | 67046 |
| TRIM35 | 20857 | 43952 | 67047 |
| TRIM35 | 20858 | 43953 | 67048 |
| TRIM36 | 20859 | 43954 | 67049 |
| TRIM36 | 20860 | 43955 | 67050 |
| TRIM37 | 20861 | 43956 | 67051 |
| TRIM38 | 20862 | 43957 | 67052 |
| TRIM39 | 20863 | 43958 | 67053 |
| TRIM4 | 20864 | 43959 | 67054 |
| TRIM40 | 20865 | 43960 | 67055 |
| TRIM41 | 20866 | 43961 | 67056 |
| TRIM41 | 20867 | 43962 | 67057 |
| TRIM42 | 20868 | 43963 | 67058 |
| TRIM43 | 20869 | 43964 | 67059 |
| TRIM44 | 20870 | 43965 | 67060 |
| TRIM45 | 20871 | 43966 | 67061 |
| TRIM46 | 20872 | 43967 | 67062 |
| TRIM46 | 20873 | 43968 | 67063 |
| TRIM47 | 20874 | 43969 | 67064 |
| TRIM48 | 20875 | 43970 | 67065 |
| TRIM49B | 20876 | 43971 | 67066 |
| TRIM49D1 | 20877 | 43972 | 67067 |
| TRIM5 | 20878 | 43973 | 67068 |
| TRIM5 | 20879 | 43974 | 67069 |
| TRIM5 | 20880 | 43975 | 67070 |
| TRIM50 | 20881 | 43976 | 67071 |
| TRIM51 | 20882 | 43977 | 67072 |
| TRIM52 | 20883 | 43978 | 67073 |
| TRIM52 | 20884 | 43979 | 67074 |
| TRIM52 | 20885 | 43980 | 67075 |
| TRIM52 | 20886 | 43981 | 67076 |
| TRIM52 | 20887 | 43982 | 67077 |
| TRIM54 | 20888 | 43983 | 67078 |
| TRIM55 | 20889 | 43984 | 67079 |
| TRIM55 | 20890 | 43985 | 67080 |
| TRIM56 | 20891 | 43986 | 67081 |
| TRIM58 | 20892 | 43987 | 67082 |
| TRIM59 | 20893 | 43988 | 67083 |
| TRIM6 | 20894 | 43989 | 67084 |
| TRIM6-TRIM34 | 20895 | 43990 | 67085 |
| TRIM60 | 20896 | 43991 | 67086 |
| TRIM61 | 20897 | 43992 | 67087 |
| TRIM62 | 20898 | 43993 | 67088 |
| TRIM63 | 20899 | 43994 | 67089 |
| TRIM64C | 20900 | 43995 | 67090 |
| TRIM65 | 20901 | 43996 | 67091 |
| TRIM66 | 20902 | 43997 | 67092 |
| TRIM67 | 20903 | 43998 | 67093 |
| TRIM68 | 20904 | 43999 | 67094 |
| TRIM69 | 20905 | 44000 | 67095 |
| TRIM7 | 20906 | 44001 | 67096 |
| TRIM7 | 20907 | 44002 | 67097 |
| TRIM71 | 20908 | 44003 | 67098 |
| TRIM72 | 20909 | 44004 | 67099 |
| TRIM74 | 20910 | 44005 | 67100 |
| TRIM77 | 20911 | 44006 | 67101 |
| TRIM8 | 20912 | 44007 | 67102 |
| TRIM9 | 20913 | 44008 | 67103 |
| TRIM9 | 20914 | 44009 | 67104 |
| TRIML1 | 20915 | 44010 | 67105 |
| TRIML2 | 20916 | 44011 | 67106 |
| TRIO | 20917 | 44012 | 67107 |
| TRIOBP | 20918 | 44013 | 67108 |
| TRIOBP | 20919 | 44014 | 67109 |
| TRIP10 | 20920 | 44015 | 67110 |
| TRIP10 | 20921 | 44016 | 67111 |
| TRIP11 | 20922 | 44017 | 67112 |
| TRIP12 | 20923 | 44018 | 67113 |
| TRIP12 | 20924 | 44019 | 67114 |
| TRIP13 | 20925 | 44020 | 67115 |
| TRIP13 | 20926 | 44021 | 67116 |
| TRIP4 | 20927 | 44022 | 67117 |
| TRIP6 | 20928 | 44023 | 67118 |
| TRIQK | 20929 | 44024 | 67119 |
| TRIR | 20930 | 44025 | 67120 |
| TRIR | 20931 | 44026 | 67121 |
| TRIT1 | 20932 | 44027 | 67122 |
| TRMO | 20933 | 44028 | 67123 |
| TRMT1 | 20934 | 44029 | 67124 |
| TRMT10A | 20935 | 44030 | 67125 |
| TRMT10B | 20936 | 44031 | 67126 |
| TRMT10C | 20937 | 44032 | 67127 |
| TRMT11 | 20938 | 44033 | 67128 |
| TRMT11 | 20939 | 44034 | 67129 |
| TRMT11 | 20940 | 44035 | 67130 |
| TRMT11 | 20941 | 44036 | 67131 |
| TRMT112 | 20942 | 44037 | 67132 |
| TRMT112 | 20943 | 44038 | 67133 |
| TRMT12 | 20944 | 44039 | 67134 |
| TRMT13 | 20945 | 44040 | 67135 |
| TRMT1L | 20946 | 44041 | 67136 |
| TRMT2A | 20947 | 44042 | 67137 |
| TRMT2A | 20948 | 44043 | 67138 |
| TRMT2B | 20949 | 44044 | 67139 |
| TRMT44 | 20950 | 44045 | 67140 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TRMT5 | 20951 | 44046 | 67141 |
| TRMT6 | 20952 | 44047 | 67142 |
| TRMT61A | 20953 | 44048 | 67143 |
| TRMT61B | 20954 | 44049 | 67144 |
| TRMU | 20955 | 44050 | 67145 |
| TRMU | 20956 | 44051 | 67146 |
| TRNAU1AP | 20957 | 44052 | 67147 |
| TRNP1 | 20958 | 44053 | 67148 |
| TRNT1 | 20959 | 44054 | 67149 |
| TRO | 20960 | 44055 | 67150 |
| TRO | 20961 | 44056 | 67151 |
| TROAP | 20962 | 44057 | 67152 |
| TROAP | 20963 | 44058 | 67153 |
| TROVE2 | 20964 | 44059 | 67154 |
| TROVE2 | 20965 | 44060 | 67155 |
| TRPA1 | 20966 | 44061 | 67156 |
| TRPC1 | 20967 | 44062 | 67157 |
| TRPC3 | 20968 | 44063 | 67158 |
| TRPC4 | 20969 | 44064 | 67159 |
| TRPC4AP | 20970 | 44065 | 67160 |
| TRPC5 | 20971 | 44066 | 67161 |
| TRPC5OS | 20972 | 44067 | 67162 |
| TRPC6 | 20973 | 44068 | 67163 |
| TRPC7 | 20974 | 44069 | 67164 |
| TRPM1 | 20975 | 44070 | 67165 |
| TRPM1 | 20976 | 44071 | 67166 |
| TRPM2 | 20977 | 44072 | 67167 |
| TRPM3 | 20978 | 44073 | 67168 |
| TRPM3 | 20979 | 44074 | 67169 |
| TRPM4 | 20980 | 44075 | 67170 |
| TRPM5 | 20981 | 44076 | 67171 |
| TRPM6 | 20982 | 44077 | 67172 |
| TRPM7 | 20983 | 44078 | 67173 |
| TRPM8 | 20984 | 44079 | 67174 |
| TRPS1 | 20985 | 44080 | 67175 |
| TRPT1 | 20986 | 44081 | 67176 |
| TRPV1 | 20987 | 44082 | 67177 |
| TRPV2 | 20988 | 44083 | 67178 |
| TRPV3 | 20989 | 44084 | 67179 |
| TRPV4 | 20990 | 44085 | 67180 |
| TRPV5 | 20991 | 44086 | 67181 |
| TRPV6 | 20992 | 44087 | 67182 |
| TRRAP | 20993 | 44088 | 67183 |
| TRUB1 | 20994 | 44089 | 67184 |
| TRUB2 | 20995 | 44090 | 67185 |
| TSACC | 20996 | 44091 | 67186 |
| TSACC | 20997 | 44092 | 67187 |
| TSC1 | 20998 | 44093 | 67188 |
| TSC2 | 20999 | 44094 | 67189 |
| TSC22D1 | 21000 | 44095 | 67190 |
| TSC22D1 | 21001 | 44096 | 67191 |
| TSC22D2 | 21002 | 44097 | 67192 |
| TSC22D3 | 21003 | 44098 | 67193 |
| TSC22D4 | 21004 | 44099 | 67194 |
| TSEN15 | 21005 | 44100 | 67195 |
| TSEN15 | 21006 | 44101 | 67196 |
| TSEN15 | 21007 | 44102 | 67197 |
| TSEN15 | 21008 | 44103 | 67198 |
| TSEN2 | 21009 | 44104 | 67199 |
| TSEN2 | 21010 | 44105 | 67200 |
| TSEN34 | 21011 | 44106 | 67201 |
| TSEN34 | 21012 | 44107 | 67202 |
| TSEN54 | 21013 | 44108 | 67203 |
| TSFM | 21014 | 44109 | 67204 |
| TSFM | 21015 | 44110 | 67205 |
| TSFM | 21016 | 44111 | 67206 |
| TSG101 | 21017 | 44112 | 67207 |
| TSGA10 | 21018 | 44113 | 67208 |
| TSGA10IP | 21019 | 44114 | 67209 |
| TSGA13 | 21020 | 44115 | 67210 |
| TSHB | 21021 | 44116 | 67211 |
| TSHR | 21022 | 44117 | 67212 |
| TSHR | 21023 | 44118 | 67213 |
| TSHZ1 | 21024 | 44119 | 67214 |
| TSHZ2 | 21025 | 44120 | 67215 |
| TSHZ3 | 21026 | 44121 | 67216 |
| TSKS | 21027 | 44122 | 67217 |
| TSKU | 21028 | 44123 | 67218 |
| TSLP | 21029 | 44124 | 67219 |
| TSN | 21030 | 44125 | 67220 |
| TSN | 21031 | 44126 | 67221 |
| TSNARE1 | 21032 | 44127 | 67222 |
| TSNARE1 | 21033 | 44128 | 67223 |
| TSNAX | 21034 | 44129 | 67224 |
| TSNAXIP1 | 21035 | 44130 | 67225 |
| TSPAN1 | 21036 | 44131 | 67226 |
| TSPAN10 | 21037 | 44132 | 67227 |
| TSPAN11 | 21038 | 44133 | 67228 |
| TSPAN12 | 21039 | 44134 | 67229 |
| TSPAN13 | 21040 | 44135 | 67230 |
| TSPAN14 | 21041 | 44136 | 67231 |
| TSPAN15 | 21042 | 44137 | 67232 |
| TSPAN16 | 21043 | 44138 | 67233 |
| TSPAN16 | 21044 | 44139 | 67234 |
| TSPAN17 | 21045 | 44140 | 67235 |
| TSPAN17 | 21046 | 44141 | 67236 |
| TSPAN18 | 21047 | 44142 | 67237 |
| TSPAN19 | 21048 | 44143 | 67238 |
| TSPAN2 | 21049 | 44144 | 67239 |
| TSPAN3 | 21050 | 44145 | 67240 |
| TSPAN31 | 21051 | 44146 | 67241 |
| TSPAN32 | 21052 | 44147 | 67242 |
| TSPAN33 | 21053 | 44148 | 67243 |
| TSPAN4 | 21054 | 44149 | 67244 |
| TSPAN5 | 21055 | 44150 | 67245 |
| TSPAN6 | 21056 | 44151 | 67246 |
| TSPAN6 | 21057 | 44152 | 67247 |
| TSPAN7 | 21058 | 44153 | 67248 |
| TSPAN8 | 21059 | 44154 | 67249 |
| TSPAN9 | 21060 | 44155 | 67250 |
| TSPEAR | 21061 | 44156 | 67251 |
| TSPO | 21062 | 44157 | 67252 |
| TSPO2 | 21063 | 44158 | 67253 |
| TSPOAP1 | 21064 | 44159 | 67254 |
| TSPY10 | 21065 | 44160 | 67255 |
| TSPY2 | 21066 | 44161 | 67256 |
| TSPYL1 | 21067 | 44162 | 67257 |
| TSPYL2 | 21068 | 44163 | 67258 |
| TSPYL4 | 21069 | 44164 | 67259 |
| TSPYL5 | 21070 | 44165 | 67260 |
| TSPYL6 | 21071 | 44166 | 67261 |
| TSR1 | 21072 | 44167 | 67262 |
| TSR2 | 21073 | 44168 | 67263 |
| TSR2 | 21074 | 44169 | 67264 |
| TSR3 | 21075 | 44170 | 67265 |
| TSSC4 | 21076 | 44171 | 67266 |
| TSSK1B | 21077 | 44172 | 67267 |
| TSSK2 | 21078 | 44173 | 67268 |
| TSSK3 | 21079 | 44174 | 67269 |
| TSSK4 | 21080 | 44175 | 67270 |
| TSSK6 | 21081 | 44176 | 67271 |
| TST | 21082 | 44177 | 67272 |
| TSTA3 | 21083 | 44178 | 67273 |
| TSTD1 | 21084 | 44179 | 67274 |
| TSTD1 | 21085 | 44180 | 67275 |
| TSTD2 | 21086 | 44181 | 67276 |
| TSTD3 | 21087 | 44182 | 67277 |
| TTBK1 | 21088 | 44183 | 67278 |
| TTBK2 | 21089 | 44184 | 67279 |
| TTC1 | 21090 | 44185 | 67280 |
| TTC12 | 21091 | 44186 | 67281 |
| TTC13 | 21092 | 44187 | 67282 |
| TTC14 | 21093 | 44188 | 67283 |
| TTC14 | 21094 | 44189 | 67284 |
| TTC14 | 21095 | 44190 | 67285 |
| TTC16 | 21096 | 44191 | 67286 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TTC17 | 21097 | 44192 | 67287 |
| TTC17 | 21098 | 44193 | 67288 |
| TTC19 | 21099 | 44194 | 67289 |
| TTC21A | 21100 | 44195 | 67290 |
| TTC21B | 21101 | 44196 | 67291 |
| TTC22 | 21102 | 44197 | 67292 |
| TTC22 | 21103 | 44198 | 67293 |
| TTC23 | 21104 | 44199 | 67294 |
| TTC23L | 21105 | 44200 | 67295 |
| TTC24 | 21106 | 44201 | 67296 |
| TTC25 | 21107 | 44202 | 67297 |
| TTC25 | 21108 | 44203 | 67298 |
| TTC26 | 21109 | 44204 | 67299 |
| TTC26 | 21110 | 44205 | 67300 |
| TTC26 | 21111 | 44206 | 67301 |
| TTC27 | 21112 | 44207 | 67302 |
| TTC28 | 21113 | 44208 | 67303 |
| TTC29 | 21114 | 44209 | 67304 |
| TTC3 | 21115 | 44210 | 67305 |
| TTC30A | 21116 | 44211 | 67306 |
| TTC30B | 21117 | 44212 | 67307 |
| TTC31 | 21118 | 44213 | 67308 |
| TTC32 | 21119 | 44214 | 67309 |
| TTC33 | 21120 | 44215 | 67310 |
| TTC34 | 21121 | 44216 | 67311 |
| TTC36 | 21122 | 44217 | 67312 |
| TTC37 | 21123 | 44218 | 67313 |
| TTC38 | 21124 | 44219 | 67314 |
| TTC39A | 21125 | 44220 | 67315 |
| TTC39A | 21126 | 44221 | 67316 |
| TTC39B | 21127 | 44222 | 67317 |
| TTC39C | 21128 | 44223 | 67318 |
| TTC39C | 21129 | 44224 | 67319 |
| TTC4 | 21130 | 44225 | 67320 |
| TTC5 | 21131 | 44226 | 67321 |
| TTC6 | 21132 | 44227 | 67322 |
| TTC7A | 21133 | 44228 | 67323 |
| TTC7B | 21134 | 44229 | 67324 |
| TTC8 | 21135 | 44230 | 67325 |
| TTC9 | 21136 | 44231 | 67326 |
| TTC9B | 21137 | 44232 | 67327 |
| TTC9C | 21138 | 44233 | 67328 |
| TTF1 | 21139 | 44234 | 67329 |
| TTF2 | 21140 | 44235 | 67330 |
| TTI1 | 21141 | 44236 | 67331 |
| TTI2 | 21142 | 44237 | 67332 |
| TTK | 21143 | 44238 | 67333 |
| TTL | 21144 | 44239 | 67334 |
| TTLL1 | 21145 | 44240 | 67335 |
| TTLL10 | 21146 | 44241 | 67336 |
| TTLL10 | 21147 | 44242 | 67337 |
| TTLL11 | 21148 | 44243 | 67338 |
| TTLL11 | 21149 | 44244 | 67339 |
| TTLL12 | 21150 | 44245 | 67340 |
| TTLL2 | 21151 | 44246 | 67341 |
| TTLL3 | 21152 | 44247 | 67342 |
| TTLL4 | 21153 | 44248 | 67343 |
| TTLL5 | 21154 | 44249 | 67344 |
| TTLL6 | 21155 | 44250 | 67345 |
| TTLL7 | 21156 | 44251 | 67346 |
| TTLL8 | 21157 | 44252 | 67347 |
| TTLL9 | 21158 | 44253 | 67348 |
| TTN | 21159 | 44254 | 67349 |
| TTN | 21160 | 44255 | 67350 |
| TTPA | 21161 | 44256 | 67351 |
| TTPAL | 21162 | 44257 | 67352 |
| TTR | 21163 | 44258 | 67353 |
| TTYH1 | 21164 | 44259 | 67354 |
| TTYH1 | 21165 | 44260 | 67355 |
| TTYH2 | 21166 | 44261 | 67356 |
| TTYH3 | 21167 | 44262 | 67357 |
| TUB | 21168 | 44263 | 67358 |
| TUBA1A | 21169 | 44264 | 67359 |
| TUBA1C | 21170 | 44265 | 67360 |
| TUBA3C | 21171 | 44266 | 67361 |
| TUBA3D | 21172 | 44267 | 67362 |
| TUBA4A | 21173 | 44268 | 67363 |
| TUBA8 | 21174 | 44269 | 67364 |
| TUBAL3 | 21175 | 44270 | 67365 |
| TUBB | 21176 | 44271 | 67366 |
| TUBB1 | 21177 | 44272 | 67367 |
| TUBB2B | 21178 | 44273 | 67368 |
| TUBB3 | 21179 | 44274 | 67369 |
| TUBB4A | 21180 | 44275 | 67370 |
| TUBB4B | 21181 | 44276 | 67371 |
| TUBB6 | 21182 | 44277 | 67372 |
| TUBB6 | 21183 | 44278 | 67373 |
| TUBB8 | 21184 | 44279 | 67374 |
| TUBD1 | 21185 | 44280 | 67375 |
| TUBE1 | 21186 | 44281 | 67376 |
| TUBG1 | 21187 | 44282 | 67377 |
| TUBG2 | 21188 | 44283 | 67378 |
| TUBGCP2 | 21189 | 44284 | 67379 |
| TUBGCP3 | 21190 | 44285 | 67380 |
| TUBGCP3 | 21191 | 44286 | 67381 |
| TUBGCP3 | 21192 | 44287 | 67382 |
| TUBGCP4 | 21193 | 44288 | 67383 |
| TUBGCP5 | 21194 | 44289 | 67384 |
| TUBGCP5 | 21195 | 44290 | 67385 |
| TUBGCP5 | 21196 | 44291 | 67386 |
| TUBGCP6 | 21197 | 44292 | 67387 |
| TUFM | 21198 | 44293 | 67388 |
| TUFT1 | 21199 | 44294 | 67389 |
| TULP1 | 21200 | 44295 | 67390 |
| TULP2 | 21201 | 44296 | 67391 |
| TULP3 | 21202 | 44297 | 67392 |
| TULP3 | 21203 | 44298 | 67393 |
| TULP4 | 21204 | 44299 | 67394 |
| TULP4 | 21205 | 44300 | 67395 |
| TUSC1 | 21206 | 44301 | 67396 |
| TUSC2 | 21207 | 44302 | 67397 |
| TUSC3 | 21208 | 44303 | 67398 |
| TUSC5 | 21209 | 44304 | 67399 |
| TUT1 | 21210 | 44305 | 67400 |
| TVP23A | 21211 | 44306 | 67401 |
| TVP23B | 21212 | 44307 | 67402 |
| TVP23B | 21213 | 44308 | 67403 |
| TVP23C | 21214 | 44309 | 67404 |
| TVP23C-CDRT4 | 21215 | 44310 | 67405 |
| TWF1 | 21216 | 44311 | 67406 |
| TWF2 | 21217 | 44312 | 67407 |
| TWIST1 | 21218 | 44313 | 67408 |
| TWIST2 | 21219 | 44314 | 67409 |
| TWISTNB | 21220 | 44315 | 67410 |
| TWNK | 21221 | 44316 | 67411 |
| TWNK | 21222 | 44317 | 67412 |
| TWSG1 | 21223 | 44318 | 67413 |
| TXK | 21224 | 44319 | 67414 |
| TXLNA | 21225 | 44320 | 67415 |
| TXLNB | 21226 | 44321 | 67416 |
| TXLNG | 21227 | 44322 | 67417 |
| TXN | 21228 | 44323 | 67418 |
| TXN2 | 21229 | 44324 | 67419 |
| TXNDC11 | 21230 | 44325 | 67420 |
| TXNDC12 | 21231 | 44326 | 67421 |
| TXNDC15 | 21232 | 44327 | 67422 |
| TXNDC16 | 21233 | 44328 | 67423 |
| TXNDC17 | 21234 | 44329 | 67424 |
| TXNDC2 | 21235 | 44330 | 67425 |
| TXNDC5 | 21236 | 44331 | 67426 |
| TXNDC8 | 21237 | 44332 | 67427 |
| TXNDC8 | 21238 | 44333 | 67428 |
| TXNDC9 | 21239 | 44334 | 67429 |
| TXNIP | 21240 | 44335 | 67430 |
| TXNL1 | 21241 | 44336 | 67431 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| TXNL4A | 21242 | 44337 | 67432 |
| TXNL4B | 21243 | 44338 | 67433 |
| TXNL4B | 21244 | 44339 | 67434 |
| TXNRD1 | 21245 | 44340 | 67435 |
| TXNRD2 | 21246 | 44341 | 67436 |
| TXNRD2 | 21247 | 44342 | 67437 |
| TXNRD3 | 21248 | 44343 | 67438 |
| TXNRD3NB | 21249 | 44344 | 67439 |
| TYK2 | 21250 | 44345 | 67440 |
| TYMP | 21251 | 44346 | 67441 |
| TYMS | 21252 | 44347 | 67442 |
| TYMSOS | 21253 | 44348 | 67443 |
| TYR | 21254 | 44349 | 67444 |
| TYRO3 | 21255 | 44350 | 67445 |
| TYROBP | 21256 | 44351 | 67446 |
| TYRP1 | 21257 | 44352 | 67447 |
| TYSND1 | 21258 | 44353 | 67448 |
| TYSND1 | 21259 | 44354 | 67449 |
| TYW1B | 21260 | 44355 | 67450 |
| TYW3 | 21261 | 44356 | 67451 |
| TYW5 | 21262 | 44357 | 67452 |
| U2AF1 | 21263 | 44358 | 67453 |
| U2AF1L4 | 21264 | 44359 | 67454 |
| U2AF1L4 | 21265 | 44360 | 67455 |
| U2AF2 | 21266 | 44361 | 67456 |
| U2SURP | 21267 | 44362 | 67457 |
| UACA | 21268 | 44363 | 67458 |
| UAP1 | 21269 | 44364 | 67459 |
| UAP1L1 | 21270 | 44365 | 67460 |
| UBA1 | 21271 | 44366 | 67461 |
| UBA2 | 21272 | 44367 | 67462 |
| UBA3 | 21273 | 44368 | 67463 |
| UBA5 | 21274 | 44369 | 67464 |
| UBA52 | 21275 | 44370 | 67465 |
| UBA52 | 21276 | 44371 | 67466 |
| UBA6 | 21277 | 44372 | 67467 |
| UBA7 | 21278 | 44373 | 67468 |
| UBAC1 | 21279 | 44374 | 67469 |
| UBAC2 | 21280 | 44375 | 67470 |
| UBALD1 | 21281 | 44376 | 67471 |
| UBALD2 | 21282 | 44377 | 67472 |
| UBAP1 | 21283 | 44378 | 67473 |
| UBAP1L | 21284 | 44379 | 67474 |
| UBAP2 | 21285 | 44380 | 67475 |
| UBAP2L | 21286 | 44381 | 67476 |
| UBAP2L | 21287 | 44382 | 67477 |
| UBAP2L | 21288 | 44383 | 67478 |
| UBASH3A | 21289 | 44384 | 67479 |
| UBASH3A | 21290 | 44385 | 67480 |
| UBASH3B | 21291 | 44386 | 67481 |
| UBB | 21292 | 44387 | 67482 |
| UBC | 21293 | 44388 | 67483 |
| UBD | 21294 | 44389 | 67484 |
| UBE2A | 21295 | 44390 | 67485 |
| UBE2B | 21296 | 44391 | 67486 |
| UBE2C | 21297 | 44392 | 67487 |
| UBE2C | 21298 | 44393 | 67488 |
| UBE2D1 | 21299 | 44394 | 67489 |
| UBE2D2 | 21300 | 44395 | 67490 |
| UBE2D3 | 21301 | 44396 | 67491 |
| UBE2D3 | 21302 | 44397 | 67492 |
| UBE2D4 | 21303 | 44398 | 67493 |
| UBE2E1 | 21304 | 44399 | 67494 |
| UBE2E2 | 21305 | 44400 | 67495 |
| UBE2F | 21306 | 44401 | 67496 |
| UBE2G1 | 21307 | 44402 | 67497 |
| UBE2G2 | 21308 | 44403 | 67498 |
| UBE2H | 21309 | 44404 | 67499 |
| UBE2I | 21310 | 44405 | 67500 |
| UBE2J1 | 21311 | 44406 | 67501 |
| UBE2J2 | 21312 | 44407 | 67502 |
| UBE2K | 21313 | 44408 | 67503 |
| UBE2L3 | 21314 | 44409 | 67504 |
| UBE2L6 | 21315 | 44410 | 67505 |
| UBE2M | 21316 | 44411 | 67506 |
| UBE2NL | 21317 | 44412 | 67507 |
| UBE2O | 21318 | 44413 | 67508 |
| UBE2Q1 | 21319 | 44414 | 67509 |
| UBE2Q2 | 21320 | 44415 | 67510 |
| UBE2Q2L | 21321 | 44416 | 67511 |
| UBE2QL1 | 21322 | 44417 | 67512 |
| UBE2R2 | 21323 | 44418 | 67513 |
| UBE2S | 21324 | 44419 | 67514 |
| UBE2T | 21325 | 44420 | 67515 |
| UBE2U | 21326 | 44421 | 67516 |
| UBE2V1 | 21327 | 44422 | 67517 |
| UBE2V1 | 21328 | 44423 | 67518 |
| UBE2V2 | 21329 | 44424 | 67519 |
| UBE2W | 21330 | 44425 | 67520 |
| UBE2Z | 21331 | 44426 | 67521 |
| UBE3A | 21332 | 44427 | 67522 |
| UBE3B | 21333 | 44428 | 67523 |
| UBE3B | 21334 | 44429 | 67524 |
| UBE3C | 21335 | 44430 | 67525 |
| UBE3D | 21336 | 44431 | 67526 |
| UBE4A | 21337 | 44432 | 67527 |
| UBE4B | 21338 | 44433 | 67528 |
| UBFD1 | 21339 | 44434 | 67529 |
| UBIAD1 | 21340 | 44435 | 67530 |
| UBIAD1 | 21341 | 44436 | 67531 |
| UBIAD1 | 21342 | 44437 | 67532 |
| UBL3 | 21343 | 44438 | 67533 |
| UBL4A | 21344 | 44439 | 67534 |
| UBL4B | 21345 | 44440 | 67535 |
| UBL5 | 21346 | 44441 | 67536 |
| UBL7 | 21347 | 44442 | 67537 |
| UBLCP1 | 21348 | 44443 | 67538 |
| UBN1 | 21349 | 44444 | 67539 |
| UBN2 | 21350 | 44445 | 67540 |
| UBOX5 | 21351 | 44446 | 67541 |
| UBOX5 | 21352 | 44447 | 67542 |
| UBP1 | 21353 | 44448 | 67543 |
| UBQLN1 | 21354 | 44449 | 67544 |
| UBQLN2 | 21355 | 44450 | 67545 |
| UBQLN3 | 21356 | 44451 | 67546 |
| UBQLN4 | 21357 | 44452 | 67547 |
| UBQLNL | 21358 | 44453 | 67548 |
| UBR1 | 21359 | 44454 | 67549 |
| UBR2 | 21360 | 44455 | 67550 |
| UBR2 | 21361 | 44456 | 67551 |
| UBR3 | 21362 | 44457 | 67552 |
| UBR4 | 21363 | 44458 | 67553 |
| UBR5 | 21364 | 44459 | 67554 |
| UBR7 | 21365 | 44460 | 67555 |
| UBTD1 | 21366 | 44461 | 67556 |
| UBTD2 | 21367 | 44462 | 67557 |
| UBTF | 21368 | 44463 | 67558 |
| UBTFL1 | 21369 | 44464 | 67559 |
| UBXN1 | 21370 | 44465 | 67560 |
| UBXN1 | 21371 | 44466 | 67561 |
| UBXN10 | 21372 | 44467 | 67562 |
| UBXN11 | 21373 | 44468 | 67563 |
| UBXN2A | 21374 | 44469 | 67564 |
| UBXN2B | 21375 | 44470 | 67565 |
| UBXN2B | 21376 | 44471 | 67566 |
| UBXN4 | 21377 | 44472 | 67567 |
| UBXN6 | 21378 | 44473 | 67568 |
| UBXN7 | 21379 | 44474 | 67569 |
| UBXN8 | 21380 | 44475 | 67570 |
| UCHL1 | 21381 | 44476 | 67571 |
| UCHL3 | 21382 | 44477 | 67572 |
| UCHL5 | 21383 | 44478 | 67573 |
| UCHL5 | 21384 | 44479 | 67574 |
| UCHL5 | 21385 | 44480 | 67575 |
| UCK1 | 21386 | 44481 | 67576 |
| UCK1 | 21387 | 44482 | 67577 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| UCK2 | 21388 | 44483 | 67578 |
| UCKL1 | 21389 | 44484 | 67579 |
| UCMA | 21390 | 44485 | 67580 |
| UCN | 21391 | 44486 | 67581 |
| UCN2 | 21392 | 44487 | 67582 |
| UCN3 | 21393 | 44488 | 67583 |
| UCP1 | 21394 | 44489 | 67584 |
| UCP2 | 21395 | 44490 | 67585 |
| UCP3 | 21396 | 44491 | 67586 |
| UCP3 | 21397 | 44492 | 67587 |
| UEVLD | 21398 | 44493 | 67588 |
| UEVLD | 21399 | 44494 | 67589 |
| UEVLD | 21400 | 44495 | 67590 |
| UEVLD | 21401 | 44496 | 67591 |
| UFC1 | 21402 | 44497 | 67592 |
| UFD1 | 21403 | 44498 | 67593 |
| UFD1 | 21404 | 44499 | 67594 |
| UFL1 | 21405 | 44500 | 67595 |
| UFM1 | 21406 | 44501 | 67596 |
| UFM1 | 21407 | 44502 | 67597 |
| UFSP1 | 21408 | 44503 | 67598 |
| UFSP2 | 21409 | 44504 | 67599 |
| UGCG | 21410 | 44505 | 67600 |
| UGDH | 21411 | 44506 | 67601 |
| UGGT1 | 21412 | 44507 | 67602 |
| UGGT2 | 21413 | 44508 | 67603 |
| UGP2 | 21414 | 44509 | 67604 |
| UGT1A1 | 21415 | 44510 | 67605 |
| UGT2A1 | 21416 | 44511 | 67606 |
| UGT2A3 | 21417 | 44512 | 67607 |
| UGT2B10 | 21418 | 44513 | 67608 |
| UGT2B11 | 21419 | 44514 | 67609 |
| UGT2B15 | 21420 | 44515 | 67610 |
| UGT2B17 | 21421 | 44516 | 67611 |
| UGT2B28 | 21422 | 44517 | 67612 |
| UGT2B4 | 21423 | 44518 | 67613 |
| UGT2B4 | 21424 | 44519 | 67614 |
| UGT2B7 | 21425 | 44520 | 67615 |
| UGT2B7 | 21426 | 44521 | 67616 |
| UGT3A1 | 21427 | 44522 | 67617 |
| UGT3A1 | 21428 | 44523 | 67618 |
| UGT3A2 | 21429 | 44524 | 67619 |
| UGT8 | 21430 | 44525 | 67620 |
| UHMK1 | 21431 | 44526 | 67621 |
| UHMK1 | 21432 | 44527 | 67622 |
| UHRF1 | 21433 | 44528 | 67623 |
| UHRF1BP1 | 21434 | 44529 | 67624 |
| UHRF1BP1L | 21435 | 44530 | 67625 |
| UHRF1BP1L | 21436 | 44531 | 67626 |
| UHRF2 | 21437 | 44532 | 67627 |
| UIMC1 | 21438 | 44533 | 67628 |
| ULBP1 | 21439 | 44534 | 67629 |
| ULBP1 | 21440 | 44535 | 67630 |
| ULBP2 | 21441 | 44536 | 67631 |
| ULBP3 | 21442 | 44537 | 67632 |
| ULK1 | 21443 | 44538 | 67633 |
| ULK2 | 21444 | 44539 | 67634 |
| ULK3 | 21445 | 44540 | 67635 |
| ULK4 | 21446 | 44541 | 67636 |
| ULK4 | 21447 | 44542 | 67637 |
| UMAD1 | 21448 | 44543 | 67638 |
| UMOD | 21449 | 44544 | 67639 |
| UMODL1 | 21450 | 44545 | 67640 |
| UMPS | 21451 | 44546 | 67641 |
| UNC119 | 21452 | 44547 | 67642 |
| UNC119 | 21453 | 44548 | 67643 |
| UNC119 | 21454 | 44549 | 67644 |
| UNC119B | 21455 | 44550 | 67645 |
| UNC13A | 21456 | 44551 | 67646 |
| UNC13B | 21457 | 44552 | 67647 |
| UNC13C | 21458 | 44553 | 67648 |
| UNC13D | 21459 | 44554 | 67649 |
| UNC45A | 21460 | 44555 | 67650 |
| UNC45B | 21461 | 44556 | 67651 |
| UNC50 | 21462 | 44557 | 67652 |
| UNC5A | 21463 | 44558 | 67653 |
| UNC5B | 21464 | 44559 | 67654 |
| UNC5C | 21465 | 44560 | 67655 |
| UNC5CL | 21466 | 44561 | 67656 |
| UNC5D | 21467 | 44562 | 67657 |
| UNC79 | 21468 | 44563 | 67658 |
| UNC80 | 21469 | 44564 | 67659 |
| UNC93A | 21470 | 44565 | 67660 |
| UNC93B1 | 21471 | 44566 | 67661 |
| UNCX | 21472 | 44567 | 67662 |
| UNG | 21473 | 44568 | 67663 |
| UNK | 21474 | 44569 | 67664 |
| UNKL | 21475 | 44570 | 67665 |
| UNKL | 21476 | 44571 | 67666 |
| UPB1 | 21477 | 44572 | 67667 |
| UPF1 | 21478 | 44573 | 67668 |
| UPF2 | 21479 | 44574 | 67669 |
| UPF3A | 21480 | 44575 | 67670 |
| UPF3A | 21481 | 44576 | 67671 |
| UPF3A | 21482 | 44577 | 67672 |
| UPF3A | 21483 | 44578 | 67673 |
| UPF3A | 21484 | 44579 | 67674 |
| UPF3A | 21485 | 44580 | 67675 |
| UPF3B | 21486 | 44581 | 67676 |
| UPK1A | 21487 | 44582 | 67677 |
| UPK1A | 21488 | 44583 | 67678 |
| UPK1B | 21489 | 44584 | 67679 |
| UPK2 | 21490 | 44585 | 67680 |
| UPK3A | 21491 | 44586 | 67681 |
| UPK3B | 21492 | 44587 | 67682 |
| UPK3B | 21493 | 44588 | 67683 |
| UPK3BL1 | 21494 | 44589 | 67684 |
| UPP1 | 21495 | 44590 | 67685 |
| UPP2 | 21496 | 44591 | 67686 |
| UPRT | 21497 | 44592 | 67687 |
| UPRT | 21498 | 44593 | 67688 |
| UQCC1 | 21499 | 44594 | 67689 |
| UQCC2 | 21500 | 44595 | 67690 |
| UQCC3 | 21501 | 44596 | 67691 |
| UQCR10 | 21502 | 44597 | 67692 |
| UQCR11 | 21503 | 44598 | 67693 |
| UQCRB | 21504 | 44599 | 67694 |
| UQCRB | 21505 | 44600 | 67695 |
| UQCRB | 21506 | 44601 | 67696 |
| UQCRC1 | 21507 | 44602 | 67697 |
| UQCRC2 | 21508 | 44603 | 67698 |
| UQCRFS1 | 21509 | 44604 | 67699 |
| UQCRH | 21510 | 44605 | 67700 |
| UQCRHL | 21511 | 44606 | 67701 |
| UQCRQ | 21512 | 44607 | 67702 |
| URAD | 21513 | 44608 | 67703 |
| URB1 | 21514 | 44609 | 67704 |
| URB2 | 21515 | 44610 | 67705 |
| URGCP | 21516 | 44611 | 67706 |
| URGCP-MRPS24 | 21517 | 44612 | 67707 |
| URI1 | 21518 | 44613 | 67708 |
| URI1 | 21519 | 44614 | 67709 |
| URM1 | 21520 | 44615 | 67710 |
| URM1 | 21521 | 44616 | 67711 |
| URM1 | 21522 | 44617 | 67712 |
| UROC1 | 21523 | 44618 | 67713 |
| UROD | 21524 | 44619 | 67714 |
| UROS | 21525 | 44620 | 67715 |
| UROS | 21526 | 44621 | 67716 |
| USB1 | 21527 | 44622 | 67717 |
| USB1 | 21528 | 44623 | 67718 |
| USB1 | 21529 | 44624 | 67719 |
| USE1 | 21530 | 44625 | 67720 |
| USF1 | 21531 | 44626 | 67721 |
| USF2 | 21532 | 44627 | 67722 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| USF3 | 21533 | 44628 | 67723 |
| USH1C | 21534 | 44629 | 67724 |
| USH1C | 21535 | 44630 | 67725 |
| USH1G | 21536 | 44631 | 67726 |
| USH2A | 21537 | 44632 | 67727 |
| USH2A | 21538 | 44633 | 67728 |
| USHBP1 | 21539 | 44634 | 67729 |
| USMG5 | 21540 | 44635 | 67730 |
| USO1 | 21541 | 44636 | 67731 |
| USP1 | 21542 | 44637 | 67732 |
| USP10 | 21543 | 44638 | 67733 |
| USP11 | 21544 | 44639 | 67734 |
| USP12 | 21545 | 44640 | 67735 |
| USP13 | 21546 | 44641 | 67736 |
| USP14 | 21547 | 44642 | 67737 |
| USP15 | 21548 | 44643 | 67738 |
| USP15 | 21549 | 44644 | 67739 |
| USP15 | 21550 | 44645 | 67740 |
| USP15 | 21551 | 44646 | 67741 |
| USP16 | 21552 | 44647 | 67742 |
| USP17L1 | 21553 | 44648 | 67743 |
| USP17L12 | 21554 | 44649 | 67744 |
| USP17L13 | 21555 | 44650 | 67745 |
| USP17L15 | 21556 | 44651 | 67746 |
| USP17L17 | 21557 | 44652 | 67747 |
| USP17L21 | 21558 | 44653 | 67748 |
| USP17L4 | 21559 | 44654 | 67749 |
| USP17L5 | 21560 | 44655 | 67750 |
| USP17L7 | 21561 | 44656 | 67751 |
| USP18 | 21562 | 44657 | 67752 |
| USP19 | 21563 | 44658 | 67753 |
| USP19 | 21564 | 44659 | 67754 |
| USP2 | 21565 | 44660 | 67755 |
| USP20 | 21566 | 44661 | 67756 |
| USP21 | 21567 | 44662 | 67757 |
| USP22 | 21568 | 44663 | 67758 |
| USP24 | 21569 | 44664 | 67759 |
| USP25 | 21570 | 44665 | 67760 |
| USP26 | 21571 | 44666 | 67761 |
| USP27X | 21572 | 44667 | 67762 |
| USP28 | 21573 | 44668 | 67763 |
| USP28 | 21574 | 44669 | 67764 |
| USP29 | 21575 | 44670 | 67765 |
| USP3 | 21576 | 44671 | 67766 |
| USP30 | 21577 | 44672 | 67767 |
| USP31 | 21578 | 44673 | 67768 |
| USP33 | 21579 | 44674 | 67769 |
| USP33 | 21580 | 44675 | 67770 |
| USP34 | 21581 | 44676 | 67771 |
| USP35 | 21582 | 44677 | 67772 |
| USP36 | 21583 | 44678 | 67773 |
| USP37 | 21584 | 44679 | 67774 |
| USP38 | 21585 | 44680 | 67775 |
| USP38 | 21586 | 44681 | 67776 |
| USP39 | 21587 | 44682 | 67777 |
| USP39 | 21588 | 44683 | 67778 |
| USP4 | 21589 | 44684 | 67779 |
| USP4 | 21590 | 44685 | 67780 |
| USP40 | 21591 | 44686 | 67781 |
| USP42 | 21592 | 44687 | 67782 |
| USP43 | 21593 | 44688 | 67783 |
| USP44 | 21594 | 44689 | 67784 |
| USP45 | 21595 | 44690 | 67785 |
| USP45 | 21596 | 44691 | 67786 |
| USP45 | 21597 | 44692 | 67787 |
| USP45 | 21598 | 44693 | 67788 |
| USP46 | 21599 | 44694 | 67789 |
| USP46 | 21600 | 44695 | 67790 |
| USP47 | 21601 | 44696 | 67791 |
| USP48 | 21602 | 44697 | 67792 |
| USP48 | 21603 | 44698 | 67793 |
| USP49 | 21604 | 44699 | 67794 |
| USP49 | 21605 | 44700 | 67795 |
| USP5 | 21606 | 44701 | 67796 |
| USP50 | 21607 | 44702 | 67797 |
| USP51 | 21608 | 44703 | 67798 |
| USP53 | 21609 | 44704 | 67799 |
| USP54 | 21610 | 44705 | 67800 |
| USP54 | 21611 | 44706 | 67801 |
| USP6 | 21612 | 44707 | 67802 |
| USP6NL | 21613 | 44708 | 67803 |
| USP7 | 21614 | 44709 | 67804 |
| USP8 | 21615 | 44710 | 67805 |
| USP9X | 21616 | 44711 | 67806 |
| USP9Y | 21617 | 44712 | 67807 |
| USPL1 | 21618 | 44713 | 67808 |
| UST | 21619 | 44714 | 67809 |
| UTF1 | 21620 | 44715 | 67810 |
| UTP11 | 21621 | 44716 | 67811 |
| UTP14A | 21622 | 44717 | 67812 |
| UTP14C | 21623 | 44718 | 67813 |
| UTP15 | 21624 | 44719 | 67814 |
| UTP18 | 21625 | 44720 | 67815 |
| UTP20 | 21626 | 44721 | 67816 |
| UTP23 | 21627 | 44722 | 67817 |
| UTP3 | 21628 | 44723 | 67818 |
| UTP4 | 21629 | 44724 | 67819 |
| UTP6 | 21630 | 44725 | 67820 |
| UTRN | 21631 | 44726 | 67821 |
| UTS2 | 21632 | 44727 | 67822 |
| UTS2B | 21633 | 44728 | 67823 |
| UTS2R | 21634 | 44729 | 67824 |
| UTY | 21635 | 44730 | 67825 |
| UTY | 21636 | 44731 | 67826 |
| UTY | 21637 | 44732 | 67827 |
| UTY | 21638 | 44733 | 67828 |
| UVRAG | 21639 | 44734 | 67829 |
| UVSSA | 21640 | 44735 | 67830 |
| UXS1 | 21641 | 44736 | 67831 |
| UXT | 21642 | 44737 | 67832 |
| VAC14 | 21643 | 44738 | 67833 |
| VAMP1 | 21644 | 44739 | 67834 |
| VAMP1 | 21645 | 44740 | 67835 |
| VAMP2 | 21646 | 44741 | 67836 |
| VAMP3 | 21647 | 44742 | 67837 |
| VAMP4 | 21648 | 44743 | 67838 |
| VAMP5 | 21649 | 44744 | 67839 |
| VAMP7 | 21650 | 44745 | 67840 |
| VAMP7 | 21651 | 44746 | 67841 |
| VAMP8 | 21652 | 44747 | 67842 |
| VANGL1 | 21653 | 44748 | 67843 |
| VANGL2 | 21654 | 44749 | 67844 |
| VAPA | 21655 | 44750 | 67845 |
| VAPB | 21656 | 44751 | 67846 |
| VAPB | 21657 | 44752 | 67847 |
| VARS | 21658 | 44753 | 67848 |
| VARS2 | 21659 | 44754 | 67849 |
| VASH1 | 21660 | 44755 | 67850 |
| VASH2 | 21661 | 44756 | 67851 |
| VASN | 21662 | 44757 | 67852 |
| VASP | 21663 | 44758 | 67853 |
| VAT1 | 21664 | 44759 | 67854 |
| VAT1L | 21665 | 44760 | 67855 |
| VAV1 | 21666 | 44761 | 67856 |
| VAV2 | 21667 | 44762 | 67857 |
| VAV3 | 21668 | 44763 | 67858 |
| VAX1 | 21669 | 44764 | 67859 |
| VAX1 | 21670 | 44765 | 67860 |
| VAX2 | 21671 | 44766 | 67861 |
| VBP1 | 21672 | 44767 | 67862 |
| VCAM1 | 21673 | 44768 | 67863 |
| VCAN | 21674 | 44769 | 67864 |
| VCL | 21675 | 44770 | 67865 |
| VCP | 21676 | 44771 | 67866 |
| VCPIP1 | 21677 | 44772 | 67867 |
| VCPKMT | 21678 | 44773 | 67868 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| VCX2 | 21679 | 44774 | 67869 |
| VCX3B | 21680 | 44775 | 67870 |
| VCY | 21681 | 44776 | 67871 |
| VDAC1 | 21682 | 44777 | 67872 |
| VDAC2 | 21683 | 44778 | 67873 |
| VDAC3 | 21684 | 44779 | 67874 |
| VDR | 21685 | 44780 | 67875 |
| VEGFA | 21686 | 44781 | 67876 |
| VEGFA | 21687 | 44782 | 67877 |
| VEGFA | 21688 | 44783 | 67878 |
| VEGFB | 21689 | 44784 | 67879 |
| VEGFB | 21690 | 44785 | 67880 |
| VEGFC | 21691 | 44786 | 67881 |
| VEGFD | 21692 | 44787 | 67882 |
| VENTX | 21693 | 44788 | 67883 |
| VEPH1 | 21694 | 44789 | 67884 |
| VEPH1 | 21695 | 44790 | 67885 |
| VEPH1 | 21696 | 44791 | 67886 |
| VEZF1 | 21697 | 44792 | 67887 |
| VEZT | 21698 | 44793 | 67888 |
| VEZT | 21699 | 44794 | 67889 |
| VEZT | 21700 | 44795 | 67890 |
| VGF | 21701 | 44796 | 67891 |
| VGLL1 | 21702 | 44797 | 67892 |
| VGLL2 | 21703 | 44798 | 67893 |
| VGLL3 | 21704 | 44799 | 67894 |
| VGLL3 | 21705 | 44800 | 67895 |
| VGLL4 | 21706 | 44801 | 67896 |
| VHL | 21707 | 44802 | 67897 |
| VHLL | 21708 | 44803 | 67898 |
| VIL1 | 21709 | 44804 | 67899 |
| VILL | 21710 | 44805 | 67900 |
| VIM | 21711 | 44806 | 67901 |
| VIP | 21712 | 44807 | 67902 |
| VIPAS39 | 21713 | 44808 | 67903 |
| VIPR1 | 21714 | 44809 | 67904 |
| VIPR2 | 21715 | 44810 | 67905 |
| VIRMA | 21716 | 44811 | 67906 |
| VIRMA | 21717 | 44812 | 67907 |
| VIT | 21718 | 44813 | 67908 |
| VIT | 21719 | 44814 | 67909 |
| VKORC1 | 21720 | 44815 | 67910 |
| VKORC1 | 21721 | 44816 | 67911 |
| VKORC1L1 | 21722 | 44817 | 67912 |
| VKORC1L1 | 21723 | 44818 | 67913 |
| VLDLR | 21724 | 44819 | 67914 |
| VMA21 | 21725 | 44820 | 67915 |
| VMAC | 21726 | 44821 | 67916 |
| VMO1 | 21727 | 44822 | 67917 |
| VMO1 | 21728 | 44823 | 67918 |
| VMO1 | 21729 | 44824 | 67919 |
| VMP1 | 21730 | 44825 | 67920 |
| VN1R1 | 21731 | 44826 | 67921 |
| VN1R2 | 21732 | 44827 | 67922 |
| VN1R3 | 21733 | 44828 | 67923 |
| VN1R4 | 21734 | 44829 | 67924 |
| VN1R5 | 21735 | 44830 | 67925 |
| VNN1 | 21736 | 44831 | 67926 |
| VNN2 | 21737 | 44832 | 67927 |
| VNN3 | 21738 | 44833 | 67928 |
| VNN3 | 21739 | 44834 | 67929 |
| VOPP1 | 21740 | 44835 | 67930 |
| VOPP1 | 21741 | 44836 | 67931 |
| VPREB1 | 21742 | 44837 | 67932 |
| VPREB3 | 21743 | 44838 | 67933 |
| VPS11 | 21744 | 44839 | 67934 |
| VPS13A | 21745 | 44840 | 67935 |
| VPS13A | 21746 | 44841 | 67936 |
| VPS13A | 21747 | 44842 | 67937 |
| VPS13B | 21748 | 44843 | 67938 |
| VPS13B | 21749 | 44844 | 67939 |
| VPS13B | 21750 | 44845 | 67940 |
| VPS13C | 21751 | 44846 | 67941 |
| VPS13C | 21752 | 44847 | 67942 |
| VPS13D | 21753 | 44848 | 67943 |
| VPS16 | 21754 | 44849 | 67944 |
| VPS18 | 21755 | 44850 | 67945 |
| VPS25 | 21756 | 44851 | 67946 |
| VPS26A | 21757 | 44852 | 67947 |
| VPS26A | 21758 | 44853 | 67948 |
| VPS26B | 21759 | 44854 | 67949 |
| VPS28 | 21760 | 44855 | 67950 |
| VPS28 | 21761 | 44856 | 67951 |
| VPS29 | 21762 | 44857 | 67952 |
| VPS33A | 21763 | 44858 | 67953 |
| VPS33A | 21764 | 44859 | 67954 |
| VPS33B | 21765 | 44860 | 67955 |
| VPS35 | 21766 | 44861 | 67956 |
| VPS36 | 21767 | 44862 | 67957 |
| VPS37A | 21768 | 44863 | 67958 |
| VPS37B | 21769 | 44864 | 67959 |
| VPS37C | 21770 | 44865 | 67960 |
| VPS37D | 21771 | 44866 | 67961 |
| VPS39 | 21772 | 44867 | 67962 |
| VPS41 | 21773 | 44868 | 67963 |
| VPS45 | 21774 | 44869 | 67964 |
| VPS45 | 21775 | 44870 | 67965 |
| VPS4A | 21776 | 44871 | 67966 |
| VPS4B | 21777 | 44872 | 67967 |
| VPS50 | 21778 | 44873 | 67968 |
| VPS50 | 21779 | 44874 | 67969 |
| VPS51 | 21780 | 44875 | 67970 |
| VPS52 | 21781 | 44876 | 67971 |
| VPS53 | 21782 | 44877 | 67972 |
| VPS53 | 21783 | 44878 | 67973 |
| VPS54 | 21784 | 44879 | 67974 |
| VPS72 | 21785 | 44880 | 67975 |
| VPS72 | 21786 | 44881 | 67976 |
| VPS8 | 21787 | 44882 | 67977 |
| VPS9D1 | 21788 | 44883 | 67978 |
| VRK1 | 21789 | 44884 | 67979 |
| VRK2 | 21790 | 44885 | 67980 |
| VRK2 | 21791 | 44886 | 67981 |
| VRK3 | 21792 | 44887 | 67982 |
| VRK3 | 21793 | 44888 | 67983 |
| VRTN | 21794 | 44889 | 67984 |
| VSIG1 | 21795 | 44890 | 67985 |
| VSIG10 | 21796 | 44891 | 67986 |
| VSIG10L | 21797 | 44892 | 67987 |
| VSIG2 | 21798 | 44893 | 67988 |
| VSIG2 | 21799 | 44894 | 67989 |
| VSIG4 | 21800 | 44895 | 67990 |
| VSIG4 | 21801 | 44896 | 67991 |
| VSIG4 | 21802 | 44897 | 67992 |
| VSIG8 | 21803 | 44898 | 67993 |
| VSIR | 21804 | 44899 | 67994 |
| VSNL1 | 21805 | 44900 | 67995 |
| VSTM1 | 21806 | 44901 | 67996 |
| VSTM2A | 21807 | 44902 | 67997 |
| VSTM2A | 21808 | 44903 | 67998 |
| VSTM2A | 21809 | 44904 | 67999 |
| VSTM2B | 21810 | 44905 | 68000 |
| VSTM2L | 21811 | 44906 | 68001 |
| VSTM4 | 21812 | 44907 | 68002 |
| VSTM4 | 21813 | 44908 | 68003 |
| VSTM5 | 21814 | 44909 | 68004 |
| VSX1 | 21815 | 44910 | 68005 |
| VSX1 | 21816 | 44911 | 68006 |
| VSX1 | 21817 | 44912 | 68007 |
| VSX1 | 21818 | 44913 | 68008 |
| VSX2 | 21819 | 44914 | 68009 |
| VTA1 | 21820 | 44915 | 68010 |
| VTCN1 | 21821 | 44916 | 68011 |
| VTI1A | 21822 | 44917 | 68012 |
| VTI1A | 21823 | 44918 | 68013 |
| VTI1B | 21824 | 44919 | 68014 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| VTN | 21825 | 44920 | 68015 |
| VWA1 | 21826 | 44921 | 68016 |
| VWA2 | 21827 | 44922 | 68017 |
| VWA3A | 21828 | 44923 | 68018 |
| VWA3B | 21829 | 44924 | 68019 |
| VWA5A | 21830 | 44925 | 68020 |
| VWA5A | 21831 | 44926 | 68021 |
| VWA5B1 | 21832 | 44927 | 68022 |
| VWA5B2 | 21833 | 44928 | 68023 |
| VWA7 | 21834 | 44929 | 68024 |
| VWA8 | 21835 | 44930 | 68025 |
| VWA8 | 21836 | 44931 | 68026 |
| VWC2 | 21837 | 44932 | 68027 |
| VWC2L | 21838 | 44933 | 68028 |
| VWC2L | 21839 | 44934 | 68029 |
| VWCE | 21840 | 44935 | 68030 |
| VWDE | 21841 | 44936 | 68031 |
| VWF | 21842 | 44937 | 68032 |
| WAC | 21843 | 44938 | 68033 |
| WAPL | 21844 | 44939 | 68034 |
| WARS | 21845 | 44940 | 68035 |
| WARS2 | 21846 | 44941 | 68036 |
| WARS2 | 21847 | 44942 | 68037 |
| WAS | 21848 | 44943 | 68038 |
| WASF1 | 21849 | 44944 | 68039 |
| WASF2 | 21850 | 44945 | 68040 |
| WASF2 | 21851 | 44946 | 68041 |
| WASF3 | 21852 | 44947 | 68042 |
| WASHC1 | 21853 | 44948 | 68043 |
| WASHC2A | 21854 | 44949 | 68044 |
| WASHC3 | 21855 | 44950 | 68045 |
| WASHC4 | 21856 | 44951 | 68046 |
| WASHC5 | 21857 | 44952 | 68047 |
| WASL | 21858 | 44953 | 68048 |
| WBP1 | 21859 | 44954 | 68049 |
| WBP11 | 21860 | 44955 | 68050 |
| WBP1L | 21861 | 44956 | 68051 |
| WBP2 | 21862 | 44957 | 68052 |
| WBP2NL | 21863 | 44958 | 68053 |
| WBP4 | 21864 | 44959 | 68054 |
| WDCP | 21865 | 44960 | 68055 |
| WDCP | 21866 | 44961 | 68056 |
| WDFY1 | 21867 | 44962 | 68057 |
| WDFY2 | 21868 | 44963 | 68058 |
| WDFY3 | 21869 | 44964 | 68059 |
| WDFY4 | 21870 | 44965 | 68060 |
| WDHD1 | 21871 | 44966 | 68061 |
| WDPCP | 21872 | 44967 | 68062 |
| WDPCP | 21873 | 44968 | 68063 |
| WDR1 | 21874 | 44969 | 68064 |
| WDR11 | 21875 | 44970 | 68065 |
| WDR12 | 21876 | 44971 | 68066 |
| WDR13 | 21877 | 44972 | 68067 |
| WDR17 | 21878 | 44973 | 68068 |
| WDR18 | 21879 | 44974 | 68069 |
| WDR19 | 21880 | 44975 | 68070 |
| WDR20 | 21881 | 44976 | 68071 |
| WDR20 | 21882 | 44977 | 68072 |
| WDR20 | 21883 | 44978 | 68073 |
| WDR20 | 21884 | 44979 | 68074 |
| WDR20 | 21885 | 44980 | 68075 |
| WDR24 | 21886 | 44981 | 68076 |
| WDR25 | 21887 | 44982 | 68077 |
| WDR26 | 21888 | 44983 | 68078 |
| WDR27 | 21889 | 44984 | 68079 |
| WDR27 | 21890 | 44985 | 68080 |
| WDR3 | 21891 | 44986 | 68081 |
| WDR31 | 21892 | 44987 | 68082 |
| WDR33 | 21893 | 44988 | 68083 |
| WDR33 | 21894 | 44989 | 68084 |
| WDR33 | 21895 | 44990 | 68085 |
| WDR34 | 21896 | 44991 | 68086 |
| WDR35 | 21897 | 44992 | 68087 |
| WDR36 | 21898 | 44993 | 68088 |
| WDR37 | 21899 | 44994 | 68089 |
| WDR38 | 21900 | 44995 | 68090 |
| WDR4 | 21901 | 44996 | 68091 |
| WDR41 | 21902 | 44997 | 68092 |
| WDR43 | 21903 | 44998 | 68093 |
| WDR44 | 21904 | 44999 | 68094 |
| WDR45 | 21905 | 45000 | 68095 |
| WDR45B | 21906 | 45001 | 68096 |
| WDR46 | 21907 | 45002 | 68097 |
| WDR47 | 21908 | 45003 | 68098 |
| WDR48 | 21909 | 45004 | 68099 |
| WDR49 | 21910 | 45005 | 68100 |
| WDR5 | 21911 | 45006 | 68101 |
| WDR53 | 21912 | 45007 | 68102 |
| WDR53 | 21913 | 45008 | 68103 |
| WDR54 | 21914 | 45009 | 68104 |
| WDR54 | 21915 | 45010 | 68105 |
| WDR55 | 21916 | 45011 | 68106 |
| WDR59 | 21917 | 45012 | 68107 |
| WDR59 | 21918 | 45013 | 68108 |
| WDR59 | 21919 | 45014 | 68109 |
| WDR5B | 21920 | 45015 | 68110 |
| WDR6 | 21921 | 45016 | 68111 |
| WDR60 | 21922 | 45017 | 68112 |
| WDR61 | 21923 | 45018 | 68113 |
| WDR62 | 21924 | 45019 | 68114 |
| WDR63 | 21925 | 45020 | 68115 |
| WDR64 | 21926 | 45021 | 68116 |
| WDR66 | 21927 | 45022 | 68117 |
| WDR66 | 21928 | 45023 | 68118 |
| WDR7 | 21929 | 45024 | 68119 |
| WDR70 | 21930 | 45025 | 68120 |
| WDR72 | 21931 | 45026 | 68121 |
| WDR72 | 21932 | 45027 | 68122 |
| WDR73 | 21933 | 45028 | 68123 |
| WDR74 | 21934 | 45029 | 68124 |
| WDR75 | 21935 | 45030 | 68125 |
| WDR76 | 21936 | 45031 | 68126 |
| WDR77 | 21937 | 45032 | 68127 |
| WDR78 | 21938 | 45033 | 68128 |
| WDR78 | 21939 | 45034 | 68129 |
| WDR81 | 21940 | 45035 | 68130 |
| WDR82 | 21941 | 45036 | 68131 |
| WDR83 | 21942 | 45037 | 68132 |
| WDR83OS | 21943 | 45038 | 68133 |
| WDR86 | 21944 | 45039 | 68134 |
| WDR86 | 21945 | 45040 | 68135 |
| WDR86 | 21946 | 45041 | 68136 |
| WDR87 | 21947 | 45042 | 68137 |
| WDR88 | 21948 | 45043 | 68138 |
| WDR89 | 21949 | 45044 | 68139 |
| WDR90 | 21950 | 45045 | 68140 |
| WDR91 | 21951 | 45046 | 68141 |
| WDR92 | 21952 | 45047 | 68142 |
| WDR92 | 21953 | 45048 | 68143 |
| WDR93 | 21954 | 45049 | 68144 |
| WDR93 | 21955 | 45050 | 68145 |
| WDR97 | 21956 | 45051 | 68146 |
| WDSUB1 | 21957 | 45052 | 68147 |
| WDTC1 | 21958 | 45053 | 68148 |
| WDYHV1 | 21959 | 45054 | 68149 |
| WEE1 | 21960 | 45055 | 68150 |
| WEE2 | 21961 | 45056 | 68151 |
| WFDC1 | 21962 | 45057 | 68152 |
| WFDC10A | 21963 | 45058 | 68153 |
| WFDC10B | 21964 | 45059 | 68154 |
| WFDC10B | 21965 | 45060 | 68155 |
| WFDC11 | 21966 | 45061 | 68156 |
| WFDC12 | 21967 | 45062 | 68157 |
| WFDC13 | 21968 | 45063 | 68158 |
| WFDC2 | 21969 | 45064 | 68159 |
| WFDC3 | 21970 | 45065 | 68160 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| WFDC5 | 21971 | 45066 | 68161 |
| WFDC6 | 21972 | 45067 | 68162 |
| WFDC8 | 21973 | 45068 | 68163 |
| WFDC8 | 21974 | 45069 | 68164 |
| WFDC9 | 21975 | 45070 | 68165 |
| WFIKKN1 | 21976 | 45071 | 68166 |
| WFIKKN2 | 21977 | 45072 | 68167 |
| WFS1 | 21978 | 45073 | 68168 |
| WHAMM | 21979 | 45074 | 68169 |
| WHRN | 21980 | 45075 | 68170 |
| WIF1 | 21981 | 45076 | 68171 |
| WIPF1 | 21982 | 45077 | 68172 |
| WIPF2 | 21983 | 45078 | 68173 |
| WIPF3 | 21984 | 45079 | 68174 |
| WIPI1 | 21985 | 45080 | 68175 |
| WIPI2 | 21986 | 45081 | 68176 |
| WISP1 | 21987 | 45082 | 68177 |
| WISP1 | 21988 | 45083 | 68178 |
| WISP2 | 21989 | 45084 | 68179 |
| WISP2 | 21990 | 45085 | 68180 |
| WISP3 | 21991 | 45086 | 68181 |
| WIZ | 21992 | 45087 | 68182 |
| WLS | 21993 | 45088 | 68183 |
| WLS | 21994 | 45089 | 68184 |
| WNK1 | 21995 | 45090 | 68185 |
| WNK2 | 21996 | 45091 | 68186 |
| WNK2 | 21997 | 45092 | 68187 |
| WNK3 | 21998 | 45093 | 68188 |
| WNK4 | 21999 | 45094 | 68189 |
| WNT1 | 22000 | 45095 | 68190 |
| WNT10A | 22001 | 45096 | 68191 |
| WNT10B | 22002 | 45097 | 68192 |
| WNT11 | 22003 | 45098 | 68193 |
| WNT16 | 22004 | 45099 | 68194 |
| WNT2 | 22005 | 45100 | 68195 |
| WNT2B | 22006 | 45101 | 68196 |
| WNT3 | 22007 | 45102 | 68197 |
| WNT3A | 22008 | 45103 | 68198 |
| WNT4 | 22009 | 45104 | 68199 |
| WNT5A | 22010 | 45105 | 68200 |
| WNT5B | 22011 | 45106 | 68201 |
| WNT6 | 22012 | 45107 | 68202 |
| WNT7A | 22013 | 45108 | 68203 |
| WNT7B | 22014 | 45109 | 68204 |
| WNT8A | 22015 | 45110 | 68205 |
| WNT8A | 22016 | 45111 | 68206 |
| WNT8B | 22017 | 45112 | 68207 |
| WNT9A | 22018 | 45113 | 68208 |
| WNT9B | 22019 | 45114 | 68209 |
| WNT9B | 22020 | 45115 | 68210 |
| WRAP53 | 22021 | 45116 | 68211 |
| WRAP73 | 22022 | 45117 | 68212 |
| WRB | 22023 | 45118 | 68213 |
| WRB-SH3BGR | 22024 | 45119 | 68214 |
| WRN | 22025 | 45120 | 68215 |
| WRNIP1 | 22026 | 45121 | 68216 |
| WSB1 | 22027 | 45122 | 68217 |
| WSB2 | 22028 | 45123 | 68218 |
| WSCD1 | 22029 | 45124 | 68219 |
| WSCD2 | 22030 | 45125 | 68220 |
| WT1 | 22031 | 45126 | 68221 |
| WTAP | 22032 | 45127 | 68222 |
| WTAP | 22033 | 45128 | 68223 |
| WTAP | 22034 | 45129 | 68224 |
| WTH3DI | 22035 | 45130 | 68225 |
| WTIP | 22036 | 45131 | 68226 |
| WWC1 | 22037 | 45132 | 68227 |
| WWC2 | 22038 | 45133 | 68228 |
| WWC3 | 22039 | 45134 | 68229 |
| WWOX | 22040 | 45135 | 68230 |
| WWOX | 22041 | 45136 | 68231 |
| WWP1 | 22042 | 45137 | 68232 |
| WWP2 | 22043 | 45138 | 68233 |
| WWP2 | 22044 | 45139 | 68234 |
| WWTR1 | 22045 | 45140 | 68235 |
| XAB2 | 22046 | 45141 | 68236 |
| XAF1 | 22047 | 45142 | 68237 |
| XAGE1B | 22048 | 45143 | 68238 |
| XAGE1E | 22049 | 45144 | 68239 |
| XAGE2 | 22050 | 45145 | 68240 |
| XAGE3 | 22051 | 45146 | 68241 |
| XAGE5 | 22052 | 45147 | 68242 |
| XBP1 | 22053 | 45148 | 68243 |
| XBP1 | 22054 | 45149 | 68244 |
| XCL1 | 22055 | 45150 | 68245 |
| XCL2 | 22056 | 45151 | 68246 |
| XCR1 | 22057 | 45152 | 68247 |
| XDH | 22058 | 45153 | 68248 |
| XG | 22059 | 45154 | 68249 |
| XIAP | 22060 | 45155 | 68250 |
| XIRP1 | 22061 | 45156 | 68251 |
| XIRP1 | 22062 | 45157 | 68252 |
| XIRP2 | 22063 | 45158 | 68253 |
| XIRP2 | 22064 | 45159 | 68254 |
| XK | 22065 | 45160 | 68255 |
| XKR3 | 22066 | 45161 | 68256 |
| XKR4 | 22067 | 45162 | 68257 |
| XKR5 | 22068 | 45163 | 68258 |
| XKR6 | 22069 | 45164 | 68259 |
| XKR7 | 22070 | 45165 | 68260 |
| XKR8 | 22071 | 45166 | 68261 |
| XKR9 | 22072 | 45167 | 68262 |
| XKRX | 22073 | 45168 | 68263 |
| XKRY | 22074 | 45169 | 68264 |
| XPA | 22075 | 45170 | 68265 |
| XPC | 22076 | 45171 | 68266 |
| XPNPEP1 | 22077 | 45172 | 68267 |
| XPNPEP1 | 22078 | 45173 | 68268 |
| XPNPEP2 | 22079 | 45174 | 68269 |
| XPNPEP3 | 22080 | 45175 | 68270 |
| XPNPEP3 | 22081 | 45176 | 68271 |
| XPO1 | 22082 | 45177 | 68272 |
| XPO4 | 22083 | 45178 | 68273 |
| XPO5 | 22084 | 45179 | 68274 |
| XPO6 | 22085 | 45180 | 68275 |
| XPO7 | 22086 | 45181 | 68276 |
| XPOT | 22087 | 45182 | 68277 |
| XPR1 | 22088 | 45183 | 68278 |
| XPR1 | 22089 | 45184 | 68279 |
| XRCC1 | 22090 | 45185 | 68280 |
| XRCC2 | 22091 | 45186 | 68281 |
| XRCC3 | 22092 | 45187 | 68282 |
| XRCC4 | 22093 | 45188 | 68283 |
| XRCC4 | 22094 | 45189 | 68284 |
| XRCC5 | 22095 | 45190 | 68285 |
| XRCC6 | 22096 | 45191 | 68286 |
| XRN1 | 22097 | 45192 | 68287 |
| XRN1 | 22098 | 45193 | 68288 |
| XRN2 | 22099 | 45194 | 68289 |
| XRRA1 | 22100 | 45195 | 68290 |
| XRRA1 | 22101 | 45196 | 68291 |
| XXYLT1 | 22102 | 45197 | 68292 |
| XYLB | 22103 | 45198 | 68293 |
| XYLB | 22104 | 45199 | 68294 |
| XYLB | 22105 | 45200 | 68295 |
| XYLT1 | 22106 | 45201 | 68296 |
| XYLT2 | 22107 | 45202 | 68297 |
| YAE1D1 | 22108 | 45203 | 68298 |
| YAE1D1 | 22109 | 45204 | 68299 |
| YAF2 | 22110 | 45205 | 68300 |
| YAF2 | 22111 | 45206 | 68301 |
| YAP1 | 22112 | 45207 | 68302 |
| YARS | 22113 | 45208 | 68303 |
| YARS2 | 22114 | 45209 | 68304 |
| YBEY | 22115 | 45210 | 68305 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| YBEY | 22116 | 45211 | 68306 |
| YBX1 | 22117 | 45212 | 68307 |
| YBX2 | 22118 | 45213 | 68308 |
| YBX3 | 22119 | 45214 | 68309 |
| YDJC | 22120 | 45215 | 68310 |
| YEATS2 | 22121 | 45216 | 68311 |
| YEATS2 | 22122 | 45217 | 68312 |
| YEATS4 | 22123 | 45218 | 68313 |
| YES1 | 22124 | 45219 | 68314 |
| YIF1A | 22125 | 45220 | 68315 |
| YIF1B | 22126 | 45221 | 68316 |
| YIF1B | 22127 | 45222 | 68317 |
| YIPF1 | 22128 | 45223 | 68318 |
| YIPF2 | 22129 | 45224 | 68319 |
| YIPF3 | 22130 | 45225 | 68320 |
| YIPF4 | 22131 | 45226 | 68321 |
| YIPF5 | 22132 | 45227 | 68322 |
| YIPF6 | 22133 | 45228 | 68323 |
| YIPF7 | 22134 | 45229 | 68324 |
| YJEFN3 | 22135 | 45230 | 68325 |
| YKT6 | 22136 | 45231 | 68326 |
| YLPM1 | 22137 | 45232 | 68327 |
| YME1L1 | 22138 | 45233 | 68328 |
| YOD1 | 22139 | 45234 | 68329 |
| YPEL1 | 22140 | 45235 | 68330 |
| YPEL2 | 22141 | 45236 | 68331 |
| YPEL3 | 22142 | 45237 | 68332 |
| YPEL4 | 22143 | 45238 | 68333 |
| YPEL5 | 22144 | 45239 | 68334 |
| YRDC | 22145 | 45240 | 68335 |
| YTHDC1 | 22146 | 45241 | 68336 |
| YTHDC2 | 22147 | 45242 | 68337 |
| YTHDF1 | 22148 | 45243 | 68338 |
| YTHDF2 | 22149 | 45244 | 68339 |
| YTHDF3 | 22150 | 45245 | 68340 |
| YWHAB | 22151 | 45246 | 68341 |
| YWHAE | 22152 | 45247 | 68342 |
| YWHAG | 22153 | 45248 | 68343 |
| YWHAH | 22154 | 45249 | 68344 |
| YWHAQ | 22155 | 45250 | 68345 |
| YWHAZ | 22156 | 45251 | 68346 |
| YY1 | 22157 | 45252 | 68347 |
| YY1AP1 | 22158 | 45253 | 68348 |
| YY1AP1 | 22159 | 45254 | 68349 |
| YY2 | 22160 | 45255 | 68350 |
| ZACN | 22161 | 45256 | 68351 |
| ZADH2 | 22162 | 45257 | 68352 |
| ZAN | 22163 | 45258 | 68353 |
| ZAP70 | 22164 | 45259 | 68354 |
| ZAR1 | 22165 | 45260 | 68355 |
| ZAR1L | 22166 | 45261 | 68356 |
| ZASP | 22167 | 45262 | 68357 |
| ZBBX | 22168 | 45263 | 68358 |
| ZBED1 | 22169 | 45264 | 68359 |
| ZBED2 | 22170 | 45265 | 68360 |
| ZBED3 | 22171 | 45266 | 68361 |
| ZBED4 | 22172 | 45267 | 68362 |
| ZBED5 | 22173 | 45268 | 68363 |
| ZBED6 | 22174 | 45269 | 68364 |
| ZBED6CL | 22175 | 45270 | 68365 |
| ZBED8 | 22176 | 45271 | 68366 |
| ZBED9 | 22177 | 45272 | 68367 |
| ZBP1 | 22178 | 45273 | 68368 |
| ZBP1 | 22179 | 45274 | 68369 |
| ZBTB1 | 22180 | 45275 | 68370 |
| ZBTB1 | 22181 | 45276 | 68371 |
| ZBTB10 | 22182 | 45277 | 68372 |
| ZBTB11 | 22183 | 45278 | 68373 |
| ZBTB12 | 22184 | 45279 | 68374 |
| ZBTB14 | 22185 | 45280 | 68375 |
| ZBTB16 | 22186 | 45281 | 68376 |
| ZBTB17 | 22187 | 45282 | 68377 |
| ZBTB18 | 22188 | 45283 | 68378 |
| ZBTB2 | 22189 | 45284 | 68379 |
| ZBTB20 | 22190 | 45285 | 68380 |
| ZBTB21 | 22191 | 45286 | 68381 |
| ZBTB22 | 22192 | 45287 | 68382 |
| ZBTB24 | 22193 | 45288 | 68383 |
| ZBTB24 | 22194 | 45289 | 68384 |
| ZBTB25 | 22195 | 45290 | 68385 |
| ZBTB25 | 22196 | 45291 | 68386 |
| ZBTB26 | 22197 | 45292 | 68387 |
| ZBTB3 | 22198 | 45293 | 68388 |
| ZBTB32 | 22199 | 45294 | 68389 |
| ZBTB33 | 22200 | 45295 | 68390 |
| ZBTB34 | 22201 | 45296 | 68391 |
| ZBTB37 | 22202 | 45297 | 68392 |
| ZBTB37 | 22203 | 45298 | 68393 |
| ZBTB37 | 22204 | 45299 | 68394 |
| ZBTB38 | 22205 | 45300 | 68395 |
| ZBTB39 | 22206 | 45301 | 68396 |
| ZBTB4 | 22207 | 45302 | 68397 |
| ZBTB40 | 22208 | 45303 | 68398 |
| ZBTB41 | 22209 | 45304 | 68399 |
| ZBTB42 | 22210 | 45305 | 68400 |
| ZBTB43 | 22211 | 45306 | 68401 |
| ZBTB44 | 22212 | 45307 | 68402 |
| ZBTB44 | 22213 | 45308 | 68403 |
| ZBTB44 | 22214 | 45309 | 68404 |
| ZBTB45 | 22215 | 45310 | 68405 |
| ZBTB46 | 22216 | 45311 | 68406 |
| ZBTB47 | 22217 | 45312 | 68407 |
| ZBTB48 | 22218 | 45313 | 68408 |
| ZBTB49 | 22219 | 45314 | 68409 |
| ZBTB5 | 22220 | 45315 | 68410 |
| ZBTB6 | 22221 | 45316 | 68411 |
| ZBTB7A | 22222 | 45317 | 68412 |
| ZBTB7B | 22223 | 45318 | 68413 |
| ZBTB7C | 22224 | 45319 | 68414 |
| ZBTB8A | 22225 | 45320 | 68415 |
| ZBTB8A | 22226 | 45321 | 68416 |
| ZBTB8B | 22227 | 45322 | 68417 |
| ZBTB8OS | 22228 | 45323 | 68418 |
| ZBTB8OS | 22229 | 45324 | 68419 |
| ZBTB9 | 22230 | 45325 | 68420 |
| ZC2HC1A | 22231 | 45326 | 68421 |
| ZC2HC1B | 22232 | 45327 | 68422 |
| ZC2HC1C | 22233 | 45328 | 68423 |
| ZC2HC1C | 22234 | 45329 | 68424 |
| ZC2HC1C | 22235 | 45330 | 68425 |
| ZC3H10 | 22236 | 45331 | 68426 |
| ZC3H11A | 22237 | 45332 | 68427 |
| ZC3H12A | 22238 | 45333 | 68428 |
| ZC3H12B | 22239 | 45334 | 68429 |
| ZC3H12C | 22240 | 45335 | 68430 |
| ZC3H12D | 22241 | 45336 | 68431 |
| ZC3H13 | 22242 | 45337 | 68432 |
| ZC3H13 | 22243 | 45338 | 68433 |
| ZC3H14 | 22244 | 45339 | 68434 |
| ZC3H15 | 22245 | 45340 | 68435 |
| ZC3H18 | 22246 | 45341 | 68436 |
| ZC3H3 | 22247 | 45342 | 68437 |
| ZC3H4 | 22248 | 45343 | 68438 |
| ZC3H6 | 22249 | 45344 | 68439 |
| ZC3H7A | 22250 | 45345 | 68440 |
| ZC3H7B | 22251 | 45346 | 68441 |
| ZC3H8 | 22252 | 45347 | 68442 |
| ZC3HAV1 | 22253 | 45348 | 68443 |
| ZC3HAV1 | 22254 | 45349 | 68444 |
| ZC3HAV1L | 22255 | 45350 | 68445 |
| ZC3HC1 | 22256 | 45351 | 68446 |
| ZC4H2 | 22257 | 45352 | 68447 |
| ZCCHC10 | 22258 | 45353 | 68448 |
| ZCCHC10 | 22259 | 45354 | 68449 |
| ZCCHC11 | 22260 | 45355 | 68450 |
| ZCCHC12 | 22261 | 45356 | 68451 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ZCCHC13 | 22262 | 45357 | 68452 |
| ZCCHC14 | 22263 | 45358 | 68453 |
| ZCCHC17 | 22264 | 45359 | 68454 |
| ZCCHC17 | 22265 | 45360 | 68455 |
| ZCCHC17 | 22266 | 45361 | 68456 |
| ZCCHC18 | 22267 | 45362 | 68457 |
| ZCCHC2 | 22268 | 45363 | 68458 |
| ZCCHC23 | 22269 | 45364 | 68459 |
| ZCCHC24 | 22270 | 45365 | 68460 |
| ZCCHC3 | 22271 | 45366 | 68461 |
| ZCCHC4 | 22272 | 45367 | 68462 |
| ZCCHC4 | 22273 | 45368 | 68463 |
| ZCCHC6 | 22274 | 45369 | 68464 |
| ZCCHC7 | 22275 | 45370 | 68465 |
| ZCCHC8 | 22276 | 45371 | 68466 |
| ZCCHC9 | 22277 | 45372 | 68467 |
| ZCRB1 | 22278 | 45373 | 68468 |
| ZCWPW1 | 22279 | 45374 | 68469 |
| ZCWPW1 | 22280 | 45375 | 68470 |
| ZCWPW2 | 22281 | 45376 | 68471 |
| ZDBF2 | 22282 | 45377 | 68472 |
| ZDHHC1 | 22283 | 45378 | 68473 |
| ZDHHC1 | 22284 | 45379 | 68474 |
| ZDHHC11 | 22285 | 45380 | 68475 |
| ZDHHC12 | 22286 | 45381 | 68476 |
| ZDHHC12 | 22287 | 45382 | 68477 |
| ZDHHC12 | 22288 | 45383 | 68478 |
| ZDHHC13 | 22289 | 45384 | 68479 |
| ZDHHC14 | 22290 | 45385 | 68480 |
| ZDHHC15 | 22291 | 45386 | 68481 |
| ZDHHC15 | 22292 | 45387 | 68482 |
| ZDHHC16 | 22293 | 45388 | 68483 |
| ZDHHC17 | 22294 | 45389 | 68484 |
| ZDHHC18 | 22295 | 45390 | 68485 |
| ZDHHC19 | 22296 | 45391 | 68486 |
| ZDHHC2 | 22297 | 45392 | 68487 |
| ZDHHC20 | 22298 | 45393 | 68488 |
| ZDHHC20 | 22299 | 45394 | 68489 |
| ZDHHC21 | 22300 | 45395 | 68490 |
| ZDHHC22 | 22301 | 45396 | 68491 |
| ZDHHC23 | 22302 | 45397 | 68492 |
| ZDHHC23 | 22303 | 45398 | 68493 |
| ZDHHC24 | 22304 | 45399 | 68494 |
| ZDHHC24 | 22305 | 45400 | 68495 |
| ZDHHC3 | 22306 | 45401 | 68496 |
| ZDHHC3 | 22307 | 45402 | 68497 |
| ZDHHC4 | 22308 | 45403 | 68498 |
| ZDHHC5 | 22309 | 45404 | 68499 |
| ZDHHC6 | 22310 | 45405 | 68500 |
| ZDHHC7 | 22311 | 45406 | 68501 |
| ZDHHC8 | 22312 | 45407 | 68502 |
| ZDHHC8 | 22313 | 45408 | 68503 |
| ZDHHC9 | 22314 | 45409 | 68504 |
| ZEB1 | 22315 | 45410 | 68505 |
| ZEB2 | 22316 | 45411 | 68506 |
| ZER1 | 22317 | 45412 | 68507 |
| ZFAND1 | 22318 | 45413 | 68508 |
| ZFAND1 | 22319 | 45414 | 68509 |
| ZFAND2A | 22320 | 45415 | 68510 |
| ZFAND2B | 22321 | 45416 | 68511 |
| ZFAND3 | 22322 | 45417 | 68512 |
| ZFAND4 | 22323 | 45418 | 68513 |
| ZFAND5 | 22324 | 45419 | 68514 |
| ZFAND6 | 22325 | 45420 | 68515 |
| ZFAT | 22326 | 45421 | 68516 |
| ZFC3H1 | 22327 | 45422 | 68517 |
| ZFHX2 | 22328 | 45423 | 68518 |
| ZFHX3 | 22329 | 45424 | 68519 |
| ZFHX4 | 22330 | 45425 | 68520 |
| ZFP1 | 22331 | 45426 | 68521 |
| ZFP14 | 22332 | 45427 | 68522 |
| ZFP2 | 22333 | 45428 | 68523 |
| ZFP28 | 22334 | 45429 | 68524 |
| ZFP28 | 22335 | 45430 | 68525 |
| ZFP3 | 22336 | 45431 | 68526 |
| ZFP30 | 22337 | 45432 | 68527 |
| ZFP36 | 22338 | 45433 | 68528 |
| ZFP36L1 | 22339 | 45434 | 68529 |
| ZFP36L2 | 22340 | 45435 | 68530 |
| ZFP37 | 22341 | 45436 | 68531 |
| ZFP41 | 22342 | 45437 | 68532 |
| ZFP42 | 22343 | 45438 | 68533 |
| ZFP57 | 22344 | 45439 | 68534 |
| ZFP62 | 22345 | 45440 | 68535 |
| ZFP64 | 22346 | 45441 | 68536 |
| ZFP64 | 22347 | 45442 | 68537 |
| ZFP69 | 22348 | 45443 | 68538 |
| ZFP69B | 22349 | 45444 | 68539 |
| ZFP82 | 22350 | 45445 | 68540 |
| ZFP82 | 22351 | 45446 | 68541 |
| ZFP82 | 22352 | 45447 | 68542 |
| ZFP90 | 22353 | 45448 | 68543 |
| ZFP90 | 22354 | 45449 | 68544 |
| ZFP91 | 22355 | 45450 | 68545 |
| ZFP92 | 22356 | 45451 | 68546 |
| ZFPL1 | 22357 | 45452 | 68547 |
| ZFPM1 | 22358 | 45453 | 68548 |
| ZFPM2 | 22359 | 45454 | 68549 |
| ZFR | 22360 | 45455 | 68550 |
| ZFR2 | 22361 | 45456 | 68551 |
| ZFR2 | 22362 | 45457 | 68552 |
| ZFX | 22363 | 45458 | 68553 |
| ZFX | 22364 | 45459 | 68554 |
| ZFY | 22365 | 45460 | 68555 |
| ZFYVE1 | 22366 | 45461 | 68556 |
| ZFYVE16 | 22367 | 45462 | 68557 |
| ZFYVE16 | 22368 | 45463 | 68558 |
| ZFYVE19 | 22369 | 45464 | 68559 |
| ZFYVE21 | 22370 | 45465 | 68560 |
| ZFYVE26 | 22371 | 45466 | 68561 |
| ZFYVE27 | 22372 | 45467 | 68562 |
| ZFYVE28 | 22373 | 45468 | 68563 |
| ZFYVE28 | 22374 | 45469 | 68564 |
| ZFYVE28 | 22375 | 45470 | 68565 |
| ZFYVE28 | 22376 | 45471 | 68566 |
| ZFYVE9 | 22377 | 45472 | 68567 |
| ZG16 | 22378 | 45473 | 68568 |
| ZG16B | 22379 | 45474 | 68569 |
| ZGLP1 | 22380 | 45475 | 68570 |
| ZGPAT | 22381 | 45476 | 68571 |
| ZGRF1 | 22382 | 45477 | 68572 |
| ZHX1 | 22383 | 45478 | 68573 |
| ZHX1-C8orf76 | 22384 | 45479 | 68574 |
| ZHX2 | 22385 | 45480 | 68575 |
| ZHX3 | 22386 | 45481 | 68576 |
| ZIC1 | 22387 | 45482 | 68577 |
| ZIC2 | 22388 | 45483 | 68578 |
| ZIC3 | 22389 | 45484 | 68579 |
| ZIC3 | 22390 | 45485 | 68580 |
| ZIC4 | 22391 | 45486 | 68581 |
| ZIC5 | 22392 | 45487 | 68582 |
| ZIK1 | 22393 | 45488 | 68583 |
| ZIM2 | 22394 | 45489 | 68584 |
| ZIM3 | 22395 | 45490 | 68585 |
| ZKSCAN1 | 22396 | 45491 | 68586 |
| ZKSCAN1 | 22397 | 45492 | 68587 |
| ZKSCAN2 | 22398 | 45493 | 68588 |
| ZKSCAN3 | 22399 | 45494 | 68589 |
| ZKSCAN4 | 22400 | 45495 | 68590 |
| ZKSCAN5 | 22401 | 45496 | 68591 |
| ZKSCAN7 | 22402 | 45497 | 68592 |
| ZKSCAN7 | 22403 | 45498 | 68593 |
| ZKSCAN7 | 22404 | 45499 | 68594 |
| ZKSCAN8 | 22405 | 45500 | 68595 |
| ZMAT1 | 22406 | 45501 | 68596 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ZMAT2 | 22407 | 45502 | 68597 |
| ZMAT3 | 22408 | 45503 | 68598 |
| ZMAT4 | 22409 | 45504 | 68599 |
| ZMAT5 | 22410 | 45505 | 68600 |
| ZMIZ1 | 22411 | 45506 | 68601 |
| ZMIZ2 | 22412 | 45507 | 68602 |
| ZMPSTE24 | 22413 | 45508 | 68603 |
| ZMYM1 | 22414 | 45509 | 68604 |
| ZMYM2 | 22415 | 45510 | 68605 |
| ZMYM2 | 22416 | 45511 | 68606 |
| ZMYM3 | 22417 | 45512 | 68607 |
| ZMYM3 | 22418 | 45513 | 68608 |
| ZMYM4 | 22419 | 45514 | 68609 |
| ZMYM5 | 22420 | 45515 | 68610 |
| ZMYM5 | 22421 | 45516 | 68611 |
| ZMYM5 | 22422 | 45517 | 68612 |
| ZMYM6 | 22423 | 45518 | 68613 |
| ZMYND10 | 22424 | 45519 | 68614 |
| ZMYND11 | 22425 | 45520 | 68615 |
| ZMYND11 | 22426 | 45521 | 68616 |
| ZMYND12 | 22427 | 45522 | 68617 |
| ZMYND15 | 22428 | 45523 | 68618 |
| ZMYND19 | 22429 | 45524 | 68619 |
| ZMYND8 | 22430 | 45525 | 68620 |
| ZMYND8 | 22431 | 45526 | 68621 |
| ZNF10 | 22432 | 45527 | 68622 |
| ZNF100 | 22433 | 45528 | 68623 |
| ZNF101 | 22434 | 45529 | 68624 |
| ZNF106 | 22435 | 45530 | 68625 |
| ZNF107 | 22436 | 45531 | 68626 |
| ZNF112 | 22437 | 45532 | 68627 |
| ZNF114 | 22438 | 45533 | 68628 |
| ZNF117 | 22439 | 45534 | 68629 |
| ZNF12 | 22440 | 45535 | 68630 |
| ZNF121 | 22441 | 45536 | 68631 |
| ZNF124 | 22442 | 45537 | 68632 |
| ZNF124 | 22443 | 45538 | 68633 |
| ZNF124 | 22444 | 45539 | 68634 |
| ZNF131 | 22445 | 45540 | 68635 |
| ZNF132 | 22446 | 45541 | 68636 |
| ZNF133 | 22447 | 45542 | 68637 |
| ZNF134 | 22448 | 45543 | 68638 |
| ZNF135 | 22449 | 45544 | 68639 |
| ZNF135 | 22450 | 45545 | 68640 |
| ZNF136 | 22451 | 45546 | 68641 |
| ZNF138 | 22452 | 45547 | 68642 |
| ZNF14 | 22453 | 45548 | 68643 |
| ZNF140 | 22454 | 45549 | 68644 |
| ZNF141 | 22455 | 45550 | 68645 |
| ZNF141 | 22456 | 45551 | 68646 |
| ZNF141 | 22457 | 45552 | 68647 |
| ZNF141 | 22458 | 45553 | 68648 |
| ZNF142 | 22459 | 45554 | 68649 |
| ZNF143 | 22460 | 45555 | 68650 |
| ZNF146 | 22461 | 45556 | 68651 |
| ZNF148 | 22462 | 45557 | 68652 |
| ZNF148 | 22463 | 45558 | 68653 |
| ZNF154 | 22464 | 45559 | 68654 |
| ZNF155 | 22465 | 45560 | 68655 |
| ZNF157 | 22466 | 45561 | 68656 |
| ZNF16 | 22467 | 45562 | 68657 |
| ZNF160 | 22468 | 45563 | 68658 |
| ZNF160 | 22469 | 45564 | 68659 |
| ZNF165 | 22470 | 45565 | 68660 |
| ZNF169 | 22471 | 45566 | 68661 |
| ZNF17 | 22472 | 45567 | 68662 |
| ZNF174 | 22473 | 45568 | 68663 |
| ZNF174 | 22474 | 45569 | 68664 |
| ZNF174 | 22475 | 45570 | 68665 |
| ZNF175 | 22476 | 45571 | 68666 |
| ZNF18 | 22477 | 45572 | 68667 |
| ZNF180 | 22478 | 45573 | 68668 |
| ZNF181 | 22479 | 45574 | 68669 |
| ZNF182 | 22480 | 45575 | 68670 |
| ZNF184 | 22481 | 45576 | 68671 |
| ZNF185 | 22482 | 45577 | 68672 |
| ZNF189 | 22483 | 45578 | 68673 |
| ZNF19 | 22484 | 45579 | 68674 |
| ZNF195 | 22485 | 45580 | 68675 |
| ZNF2 | 22486 | 45581 | 68676 |
| ZNF20 | 22487 | 45582 | 68677 |
| ZNF200 | 22488 | 45583 | 68678 |
| ZNF202 | 22489 | 45584 | 68679 |
| ZNF205 | 22490 | 45585 | 68680 |
| ZNF207 | 22491 | 45586 | 68681 |
| ZNF208 | 22492 | 45587 | 68682 |
| ZNF208 | 22493 | 45588 | 68683 |
| ZNF208 | 22494 | 45589 | 68684 |
| ZNF208 | 22495 | 45590 | 68685 |
| ZNF211 | 22496 | 45591 | 68686 |
| ZNF212 | 22497 | 45592 | 68687 |
| ZNF213 | 22498 | 45593 | 68688 |
| ZNF214 | 22499 | 45594 | 68689 |
| ZNF215 | 22500 | 45595 | 68690 |
| ZNF217 | 22501 | 45596 | 68691 |
| ZNF219 | 22502 | 45597 | 68692 |
| ZNF22 | 22503 | 45598 | 68693 |
| ZNF221 | 22504 | 45599 | 68694 |
| ZNF224 | 22505 | 45600 | 68695 |
| ZNF225 | 22506 | 45601 | 68696 |
| ZNF226 | 22507 | 45602 | 68697 |
| ZNF226 | 22508 | 45603 | 68698 |
| ZNF227 | 22509 | 45604 | 68699 |
| ZNF229 | 22510 | 45605 | 68700 |
| ZNF23 | 22511 | 45606 | 68701 |
| ZNF232 | 22512 | 45607 | 68702 |
| ZNF233 | 22513 | 45608 | 68703 |
| ZNF234 | 22514 | 45609 | 68704 |
| ZNF235 | 22515 | 45610 | 68705 |
| ZNF236 | 22516 | 45611 | 68706 |
| ZNF239 | 22517 | 45612 | 68707 |
| ZNF24 | 22518 | 45613 | 68708 |
| ZNF24 | 22519 | 45614 | 68709 |
| ZNF248 | 22520 | 45615 | 68710 |
| ZNF248 | 22521 | 45616 | 68711 |
| ZNF248 | 22522 | 45617 | 68712 |
| ZNF25 | 22523 | 45618 | 68713 |
| ZNF250 | 22524 | 45619 | 68714 |
| ZNF251 | 22525 | 45620 | 68715 |
| ZNF253 | 22526 | 45621 | 68716 |
| ZNF254 | 22527 | 45622 | 68717 |
| ZNF254 | 22528 | 45623 | 68718 |
| ZNF256 | 22529 | 45624 | 68719 |
| ZNF257 | 22530 | 45625 | 68720 |
| ZNF26 | 22531 | 45626 | 68721 |
| ZNF260 | 22532 | 45627 | 68722 |
| ZNF263 | 22533 | 45628 | 68723 |
| ZNF264 | 22534 | 45629 | 68724 |
| ZNF266 | 22535 | 45630 | 68725 |
| ZNF267 | 22536 | 45631 | 68726 |
| ZNF268 | 22537 | 45632 | 68727 |
| ZNF273 | 22538 | 45633 | 68728 |
| ZNF274 | 22539 | 45634 | 68729 |
| ZNF275 | 22540 | 45635 | 68730 |
| ZNF276 | 22541 | 45636 | 68731 |
| ZNF277 | 22542 | 45637 | 68732 |
| ZNF28 | 22543 | 45638 | 68733 |
| ZNF280A | 22544 | 45639 | 68734 |
| ZNF280B | 22545 | 45640 | 68735 |
| ZNF280C | 22546 | 45641 | 68736 |
| ZNF280D | 22547 | 45642 | 68737 |
| ZNF280D | 22548 | 45643 | 68738 |
| ZNF280D | 22549 | 45644 | 68739 |
| ZNF281 | 22550 | 45645 | 68740 |
| ZNF282 | 22551 | 45646 | 68741 |
| ZNF282 | 22552 | 45647 | 68742 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ZNF283 | 22553 | 45648 | 68743 |
| ZNF284 | 22554 | 45649 | 68744 |
| ZNF285 | 22555 | 45650 | 68745 |
| ZNF286A | 22556 | 45651 | 68746 |
| ZNF287 | 22557 | 45652 | 68747 |
| ZNF292 | 22558 | 45653 | 68748 |
| ZNF296 | 22559 | 45654 | 68749 |
| ZNF3 | 22560 | 45655 | 68750 |
| ZNF3 | 22561 | 45656 | 68751 |
| ZNF3 | 22562 | 45657 | 68752 |
| ZNF30 | 22563 | 45658 | 68753 |
| ZNF300 | 22564 | 45659 | 68754 |
| ZNF302 | 22565 | 45660 | 68755 |
| ZNF304 | 22566 | 45661 | 68756 |
| ZNF311 | 22567 | 45662 | 68757 |
| ZNF316 | 22568 | 45663 | 68758 |
| ZNF317 | 22569 | 45664 | 68759 |
| ZNF318 | 22570 | 45665 | 68760 |
| ZNF319 | 22571 | 45666 | 68761 |
| ZNF32 | 22572 | 45667 | 68762 |
| ZNF320 | 22573 | 45668 | 68763 |
| ZNF320 | 22574 | 45669 | 68764 |
| ZNF322 | 22575 | 45670 | 68765 |
| ZNF324 | 22576 | 45671 | 68766 |
| ZNF324B | 22577 | 45672 | 68767 |
| ZNF326 | 22578 | 45673 | 68768 |
| ZNF326 | 22579 | 45674 | 68769 |
| ZNF329 | 22580 | 45675 | 68770 |
| ZNF330 | 22581 | 45676 | 68771 |
| ZNF331 | 22582 | 45677 | 68772 |
| ZNF333 | 22583 | 45678 | 68773 |
| ZNF333 | 22584 | 45679 | 68774 |
| ZNF333 | 22585 | 45680 | 68775 |
| ZNF334 | 22586 | 45681 | 68776 |
| ZNF335 | 22587 | 45682 | 68777 |
| ZNF337 | 22588 | 45683 | 68778 |
| ZNF33A | 22589 | 45684 | 68779 |
| ZNF33B | 22590 | 45685 | 68780 |
| ZNF34 | 22591 | 45686 | 68781 |
| ZNF341 | 22592 | 45687 | 68782 |
| ZNF343 | 22593 | 45688 | 68783 |
| ZNF343 | 22594 | 45689 | 68784 |
| ZNF345 | 22595 | 45690 | 68785 |
| ZNF346 | 22596 | 45691 | 68786 |
| ZNF346 | 22597 | 45692 | 68787 |
| ZNF346 | 22598 | 45693 | 68788 |
| ZNF346 | 22599 | 45694 | 68789 |
| ZNF347 | 22600 | 45695 | 68790 |
| ZNF35 | 22601 | 45696 | 68791 |
| ZNF350 | 22602 | 45697 | 68792 |
| ZNF354A | 22603 | 45698 | 68793 |
| ZNF354B | 22604 | 45699 | 68794 |
| ZNF354C | 22605 | 45700 | 68795 |
| ZNF358 | 22606 | 45701 | 68796 |
| ZNF362 | 22607 | 45702 | 68797 |
| ZNF365 | 22608 | 45703 | 68798 |
| ZNF365 | 22609 | 45704 | 68799 |
| ZNF365 | 22610 | 45705 | 68800 |
| ZNF366 | 22611 | 45706 | 68801 |
| ZNF367 | 22612 | 45707 | 68802 |
| ZNF37A | 22613 | 45708 | 68803 |
| ZNF37A | 22614 | 45709 | 68804 |
| ZNF37A | 22615 | 45710 | 68805 |
| ZNF37A | 22616 | 45711 | 68806 |
| ZNF382 | 22617 | 45712 | 68807 |
| ZNF383 | 22618 | 45713 | 68808 |
| ZNF384 | 22619 | 45714 | 68809 |
| ZNF385A | 22620 | 45715 | 68810 |
| ZNF385B | 22621 | 45716 | 68811 |
| ZNF385C | 22622 | 45717 | 68812 |
| ZNF385D | 22623 | 45718 | 68813 |
| ZNF391 | 22624 | 45719 | 68814 |
| ZNF394 | 22625 | 45720 | 68815 |
| ZNF394 | 22626 | 45721 | 68816 |
| ZNF395 | 22627 | 45722 | 68817 |
| ZNF396 | 22628 | 45723 | 68818 |
| ZNF396 | 22629 | 45724 | 68819 |
| ZNF396 | 22630 | 45725 | 68820 |
| ZNF397 | 22631 | 45726 | 68821 |
| ZNF397 | 22632 | 45727 | 68822 |
| ZNF398 | 22633 | 45728 | 68823 |
| ZNF404 | 22634 | 45729 | 68824 |
| ZNF407 | 22635 | 45730 | 68825 |
| ZNF407 | 22636 | 45731 | 68826 |
| ZNF407 | 22637 | 45732 | 68827 |
| ZNF408 | 22638 | 45733 | 68828 |
| ZNF41 | 22639 | 45734 | 68829 |
| ZNF410 | 22640 | 45735 | 68830 |
| ZNF410 | 22641 | 45736 | 68831 |
| ZNF410 | 22642 | 45737 | 68832 |
| ZNF414 | 22643 | 45738 | 68833 |
| ZNF414 | 22644 | 45739 | 68834 |
| ZNF415 | 22645 | 45740 | 68835 |
| ZNF416 | 22646 | 45741 | 68836 |
| ZNF417 | 22647 | 45742 | 68837 |
| ZNF418 | 22648 | 45743 | 68838 |
| ZNF419 | 22649 | 45744 | 68839 |
| ZNF420 | 22650 | 45745 | 68840 |
| ZNF420 | 22651 | 45746 | 68841 |
| ZNF420 | 22652 | 45747 | 68842 |
| ZNF423 | 22653 | 45748 | 68843 |
| ZNF425 | 22654 | 45749 | 68844 |
| ZNF426 | 22655 | 45750 | 68845 |
| ZNF428 | 22656 | 45751 | 68846 |
| ZNF429 | 22657 | 45752 | 68847 |
| ZNF43 | 22658 | 45753 | 68848 |
| ZNF430 | 22659 | 45754 | 68849 |
| ZNF431 | 22660 | 45755 | 68850 |
| ZNF432 | 22661 | 45756 | 68851 |
| ZNF433 | 22662 | 45757 | 68852 |
| ZNF436 | 22663 | 45758 | 68853 |
| ZNF438 | 22664 | 45759 | 68854 |
| ZNF439 | 22665 | 45760 | 68855 |
| ZNF44 | 22666 | 45761 | 68856 |
| ZNF440 | 22667 | 45762 | 68857 |
| ZNF441 | 22568 | 45763 | 68858 |
| ZNF443 | 22669 | 45764 | 68859 |
| ZNF444 | 22670 | 45765 | 68860 |
| ZNF445 | 22671 | 45766 | 68861 |
| ZNF446 | 22672 | 45767 | 68862 |
| ZNF446 | 22673 | 45768 | 68863 |
| ZNF449 | 22674 | 45769 | 68864 |
| ZNF45 | 22675 | 45770 | 68865 |
| ZNF451 | 22676 | 45771 | 68866 |
| ZNF451 | 22677 | 45772 | 68867 |
| ZNF454 | 22678 | 45773 | 68868 |
| ZNF454 | 22679 | 45774 | 68869 |
| ZNF460 | 22680 | 45775 | 68870 |
| ZNF461 | 22681 | 45776 | 68871 |
| ZNF462 | 22682 | 45777 | 68872 |
| ZNF467 | 22683 | 45778 | 68873 |
| ZNF467 | 22684 | 45779 | 68874 |
| ZNF468 | 22685 | 45780 | 68875 |
| ZNF469 | 22686 | 45781 | 68876 |
| ZNF470 | 22687 | 45782 | 68877 |
| ZNF471 | 22688 | 45783 | 68878 |
| ZNF473 | 22689 | 45784 | 68879 |
| ZNF474 | 22690 | 45785 | 68880 |
| ZNF479 | 22691 | 45786 | 68881 |
| ZNF48 | 22692 | 45787 | 68882 |
| ZNF480 | 22693 | 45788 | 68883 |
| ZNF483 | 22694 | 45789 | 68884 |
| ZNF483 | 22695 | 45790 | 68885 |
| ZNF484 | 22696 | 45791 | 68886 |
| ZNF485 | 22697 | 45792 | 68887 |
| ZNF486 | 22698 | 45793 | 68888 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ZNF488 | 22699 | 45794 | 68889 |
| ZNF490 | 22700 | 45795 | 68890 |
| ZNF491 | 22701 | 45796 | 68891 |
| ZNF492 | 22702 | 45797 | 68892 |
| ZNF493 | 22703 | 45798 | 68893 |
| ZNF493 | 22704 | 45799 | 68894 |
| ZNF496 | 22705 | 45800 | 68895 |
| ZNF496 | 22706 | 45801 | 68896 |
| ZNF497 | 22707 | 45802 | 68897 |
| ZNF500 | 22708 | 45803 | 68898 |
| ZNF500 | 22709 | 45804 | 68899 |
| ZNF501 | 22710 | 45805 | 68900 |
| ZNF502 | 22711 | 45806 | 68901 |
| ZNF503 | 22712 | 45807 | 68902 |
| ZNF506 | 22713 | 45808 | 68903 |
| ZNF507 | 22714 | 45809 | 68904 |
| ZNF510 | 22715 | 45810 | 68905 |
| ZNF511 | 22716 | 45811 | 68906 |
| ZNF512 | 22717 | 45812 | 68907 |
| ZNF512B | 22718 | 45813 | 68908 |
| ZNF513 | 22719 | 45814 | 68909 |
| ZNF514 | 22720 | 45815 | 68910 |
| ZNF516 | 22721 | 45816 | 68911 |
| ZNF517 | 22722 | 45817 | 68912 |
| ZNF518A | 22723 | 45818 | 68913 |
| ZNF518B | 22724 | 45819 | 68914 |
| ZNF519 | 22725 | 45820 | 68915 |
| ZNF521 | 22726 | 45821 | 68916 |
| ZNF524 | 22727 | 45822 | 68917 |
| ZNF525 | 22728 | 45823 | 68918 |
| ZNF526 | 22729 | 45824 | 68919 |
| ZNF527 | 22730 | 45825 | 68920 |
| ZNF528 | 22731 | 45826 | 68921 |
| ZNF529 | 22732 | 45827 | 68922 |
| ZNF530 | 22733 | 45828 | 68923 |
| ZNF532 | 22734 | 45829 | 68924 |
| ZNF534 | 22735 | 45830 | 68925 |
| ZNF534 | 22736 | 45831 | 68926 |
| ZNF536 | 22737 | 45832 | 68927 |
| ZNF536 | 22738 | 45833 | 68928 |
| ZNF540 | 22739 | 45834 | 68929 |
| ZNF541 | 22740 | 45835 | 68930 |
| ZNF543 | 22741 | 45836 | 68931 |
| ZNF544 | 22742 | 45837 | 68932 |
| ZNF544 | 22743 | 45838 | 68933 |
| ZNF544 | 22744 | 45839 | 68934 |
| ZNF544 | 22745 | 45840 | 68935 |
| ZNF544 | 22746 | 45841 | 68936 |
| ZNF546 | 22747 | 45842 | 68937 |
| ZNF547 | 22748 | 45843 | 68938 |
| ZNF548 | 22749 | 45844 | 68939 |
| ZNF549 | 22750 | 45845 | 68940 |
| ZNF550 | 22751 | 45846 | 68941 |
| ZNF550 | 22752 | 45847 | 68942 |
| ZNF551 | 22753 | 45848 | 68943 |
| ZNF552 | 22754 | 45849 | 68944 |
| ZNF554 | 22755 | 45850 | 68945 |
| ZNF555 | 22756 | 45851 | 68946 |
| ZNF556 | 22757 | 45852 | 68947 |
| ZNF557 | 22758 | 45853 | 68948 |
| ZNF558 | 22759 | 45854 | 68949 |
| ZNF559 | 22760 | 45855 | 68950 |
| ZNF559-ZNF177 | 22761 | 45856 | 68951 |
| ZNF560 | 22762 | 45857 | 68952 |
| ZNF561 | 22763 | 45858 | 68953 |
| ZNF562 | 22764 | 45859 | 68954 |
| ZNF563 | 22765 | 45860 | 68955 |
| ZNF564 | 22766 | 45861 | 68956 |
| ZNF565 | 22767 | 45862 | 68957 |
| ZNF566 | 22768 | 45863 | 68958 |
| ZNF567 | 22769 | 45864 | 68959 |
| ZNF568 | 22770 | 45865 | 68960 |
| ZNF568 | 22771 | 45866 | 68961 |
| ZNF569 | 22772 | 45867 | 68962 |
| ZNF57 | 22773 | 45868 | 68963 |
| ZNF570 | 22774 | 45869 | 68964 |
| ZNF571 | 22775 | 45870 | 68965 |
| ZNF572 | 22776 | 45871 | 68966 |
| ZNF573 | 22777 | 45872 | 68967 |
| ZNF574 | 22778 | 45873 | 68968 |
| ZNF575 | 22779 | 45874 | 68969 |
| ZNF576 | 22780 | 45875 | 68970 |
| ZNF577 | 22781 | 45876 | 68971 |
| ZNF578 | 22782 | 45877 | 68972 |
| ZNF579 | 22783 | 45878 | 68973 |
| ZNF580 | 22784 | 45879 | 68974 |
| ZNF581 | 22785 | 45880 | 68975 |
| ZNF582 | 22786 | 45881 | 68976 |
| ZNF583 | 22787 | 45882 | 68977 |
| ZNF584 | 22788 | 45883 | 68978 |
| ZNF584 | 22789 | 45884 | 68979 |
| ZNF585A | 22790 | 45885 | 68980 |
| ZNF586 | 22791 | 45886 | 68981 |
| ZNF586 | 22792 | 45887 | 68982 |
| ZNF587B | 22793 | 45888 | 68983 |
| ZNF589 | 22794 | 45889 | 68984 |
| ZNF592 | 22795 | 45890 | 68985 |
| ZNF593 | 22796 | 45891 | 68986 |
| ZNF594 | 22797 | 45892 | 68987 |
| ZNF595 | 22798 | 45893 | 68988 |
| ZNF596 | 22799 | 45894 | 68989 |
| ZNF597 | 22800 | 45895 | 68990 |
| ZNF598 | 22801 | 45896 | 68991 |
| ZNF599 | 22802 | 45897 | 68992 |
| ZNF600 | 22803 | 45898 | 68993 |
| ZNF605 | 22804 | 45899 | 68994 |
| ZNF606 | 22805 | 45900 | 68995 |
| ZNF607 | 22806 | 45901 | 68996 |
| ZNF608 | 22807 | 45902 | 68997 |
| ZNF609 | 22808 | 45903 | 68998 |
| ZNF610 | 22809 | 45904 | 68999 |
| ZNF611 | 22810 | 45905 | 69000 |
| ZNF613 | 22811 | 45906 | 69001 |
| ZNF614 | 22812 | 45907 | 69002 |
| ZNF615 | 22813 | 45908 | 69003 |
| ZNF616 | 22814 | 45909 | 69004 |
| ZNF618 | 22815 | 45910 | 69005 |
| ZNF619 | 22816 | 45911 | 69006 |
| ZNF620 | 22817 | 45912 | 69007 |
| ZNF621 | 22818 | 45913 | 69008 |
| ZNF621 | 22819 | 45914 | 69009 |
| ZNF622 | 22820 | 45915 | 69010 |
| ZNF623 | 22821 | 45916 | 69011 |
| ZNF624 | 22822 | 45917 | 69012 |
| ZNF625 | 22823 | 45918 | 69013 |
| ZNF626 | 22824 | 45919 | 69014 |
| ZNF626 | 22825 | 45920 | 69015 |
| ZNF627 | 22826 | 45921 | 69016 |
| ZNF628 | 22827 | 45922 | 69017 |
| ZNF629 | 22828 | 45923 | 69018 |
| ZNF630 | 22829 | 45924 | 69019 |
| ZNF638 | 22830 | 45925 | 69020 |
| ZNF639 | 22831 | 45926 | 69021 |
| ZNF641 | 22832 | 45927 | 69022 |
| ZNF644 | 22833 | 45928 | 69023 |
| ZNF645 | 22834 | 45929 | 69024 |
| ZNF646 | 22835 | 45930 | 69025 |
| ZNF648 | 22836 | 45931 | 69026 |
| ZNF649 | 22837 | 45932 | 69027 |
| ZNF652 | 22838 | 45933 | 69028 |
| ZNF653 | 22839 | 45934 | 69029 |
| ZNF654 | 22840 | 45935 | 69030 |
| ZNF655 | 22841 | 45936 | 69031 |
| ZNF655 | 22842 | 45937 | 69032 |
| ZNF658 | 22843 | 45938 | 69033 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ZNF660 | 22844 | 45939 | 69034 |
| ZNF660-ZNF197 | 22845 | 45940 | 69035 |
| ZNF660-ZNF197 | 22846 | 45941 | 69036 |
| ZNF662 | 22847 | 45942 | 69037 |
| ZNF664 | 22848 | 45943 | 69038 |
| ZNF664-RFLNA | 22849 | 45944 | 69039 |
| ZNF665 | 22850 | 45945 | 69040 |
| ZNF667 | 22851 | 45946 | 69041 |
| ZNF668 | 22852 | 45947 | 69042 |
| ZNF669 | 22853 | 45948 | 69043 |
| ZNF670 | 22854 | 45949 | 69044 |
| ZNF671 | 22855 | 45950 | 69045 |
| ZNF672 | 22856 | 45951 | 69046 |
| ZNF674 | 22857 | 45952 | 69047 |
| ZNF675 | 22858 | 45953 | 69048 |
| ZNF676 | 22859 | 45954 | 69049 |
| ZNF677 | 22860 | 45955 | 69050 |
| ZNF678 | 22861 | 45956 | 69051 |
| ZNF679 | 22862 | 45957 | 69052 |
| ZNF680 | 22863 | 45958 | 69053 |
| ZNF680 | 22864 | 45959 | 69054 |
| ZNF681 | 22865 | 45960 | 69055 |
| ZNF682 | 22866 | 45961 | 69056 |
| ZNF683 | 22867 | 45962 | 69057 |
| ZNF684 | 22868 | 45963 | 69058 |
| ZNF687 | 22869 | 45964 | 69059 |
| ZNF688 | 22870 | 45965 | 69060 |
| ZNF689 | 22871 | 45966 | 69061 |
| ZNF69 | 22872 | 45967 | 69062 |
| ZNF691 | 22873 | 45968 | 69063 |
| ZNF692 | 22874 | 45969 | 69064 |
| ZNF695 | 22875 | 45970 | 69065 |
| ZNF695 | 22876 | 45971 | 69066 |
| ZNF696 | 22877 | 45972 | 69067 |
| ZNF697 | 22878 | 45973 | 69068 |
| ZNF699 | 22879 | 45974 | 69069 |
| ZNF7 | 22880 | 45975 | 69070 |
| ZNF7 | 22881 | 45976 | 69071 |
| ZNF70 | 22882 | 45977 | 69072 |
| ZNF700 | 22883 | 45978 | 69073 |
| ZNF701 | 22884 | 45979 | 69074 |
| ZNF703 | 22885 | 45980 | 69075 |
| ZNF704 | 22886 | 45981 | 69076 |
| ZNF705A | 22887 | 45982 | 69077 |
| ZNF705E | 22888 | 45983 | 69078 |
| ZNF705G | 22889 | 45984 | 69079 |
| ZNF706 | 22890 | 45985 | 69080 |
| ZNF707 | 22891 | 45986 | 69081 |
| ZNF708 | 22892 | 45987 | 69082 |
| ZNF709 | 22893 | 45988 | 69083 |
| ZNF71 | 22894 | 45989 | 69084 |
| ZNF710 | 22895 | 45990 | 69085 |
| ZNF711 | 22896 | 45991 | 69086 |
| ZNF713 | 22897 | 45992 | 69087 |
| ZNF714 | 22898 | 45993 | 69088 |
| ZNF716 | 22899 | 45994 | 69089 |
| ZNF717 | 22900 | 45995 | 69090 |
| ZNF717 | 22901 | 45996 | 69091 |
| ZNF717 | 22902 | 45997 | 69092 |
| ZNF718 | 22903 | 45998 | 69093 |
| ZNF720 | 22904 | 45999 | 69094 |
| ZNF721 | 22905 | 46000 | 69095 |
| ZNF723 | 22906 | 46001 | 69096 |
| ZNF726 | 22907 | 46002 | 69097 |
| ZNF726 | 22908 | 46003 | 69098 |
| ZNF726 | 22909 | 46004 | 69099 |
| ZNF726 | 22910 | 46005 | 69100 |
| ZNF727 | 22911 | 46006 | 69101 |
| ZNF728 | 22912 | 46007 | 69102 |
| ZNF729 | 22913 | 46008 | 69103 |
| ZNF730 | 22914 | 46009 | 69104 |
| ZNF732 | 22915 | 46010 | 69105 |
| ZNF735 | 22916 | 46011 | 69106 |
| ZNF736 | 22917 | 46012 | 69107 |
| ZNF736 | 22918 | 46013 | 69108 |
| ZNF737 | 22919 | 46014 | 69109 |
| ZNF74 | 22920 | 46015 | 69110 |
| ZNF740 | 22921 | 46016 | 69111 |
| ZNF746 | 22922 | 46017 | 69112 |
| ZNF747 | 22923 | 46018 | 69113 |
| ZNF747 | 22924 | 46019 | 69114 |
| ZNF749 | 22925 | 46020 | 69115 |
| ZNF750 | 22926 | 46021 | 69116 |
| ZNF75A | 22927 | 46022 | 69117 |
| ZNF75A | 22928 | 46023 | 69118 |
| ZNF75A | 22929 | 46024 | 69119 |
| ZNF75D | 22930 | 46025 | 69120 |
| ZNF76 | 22931 | 46026 | 69121 |
| ZNF761 | 22932 | 46027 | 69122 |
| ZNF761 | 22933 | 46028 | 69123 |
| ZNF763 | 22934 | 46029 | 69124 |
| ZNF764 | 22935 | 46030 | 69125 |
| ZNF765 | 22936 | 46031 | 69126 |
| ZNF766 | 22937 | 46032 | 69127 |
| ZNF768 | 22938 | 46033 | 69128 |
| ZNF77 | 22939 | 46034 | 69129 |
| ZNF770 | 22940 | 46035 | 69130 |
| ZNF771 | 22941 | 46036 | 69131 |
| ZNF772 | 22942 | 46037 | 69132 |
| ZNF773 | 22943 | 46038 | 69133 |
| ZNF773 | 22944 | 46039 | 69134 |
| ZNF774 | 22945 | 46040 | 69135 |
| ZNF775 | 22946 | 46041 | 69136 |
| ZNF776 | 22947 | 46042 | 69137 |
| ZNF776 | 22948 | 46043 | 69138 |
| ZNF777 | 22949 | 46044 | 69139 |
| ZNF778 | 22950 | 46045 | 69140 |
| ZNF780A | 22951 | 46046 | 69141 |
| ZNF780A | 22952 | 46047 | 69142 |
| ZNF780B | 22953 | 46048 | 69143 |
| ZNF781 | 22954 | 46049 | 69144 |
| ZNF782 | 22955 | 46050 | 69145 |
| ZNF783 | 22956 | 46051 | 69146 |
| ZNF784 | 22957 | 46052 | 69147 |
| ZNF785 | 22958 | 46053 | 69148 |
| ZNF786 | 22959 | 46054 | 69149 |
| ZNF787 | 22960 | 46055 | 69150 |
| ZNF787 | 22961 | 46056 | 69151 |
| ZNF788 | 22962 | 46057 | 69152 |
| ZNF789 | 22963 | 46058 | 69153 |
| ZNF789 | 22964 | 46059 | 69154 |
| ZNF789 | 22965 | 46060 | 69155 |
| ZNF79 | 22966 | 46061 | 69156 |
| ZNF790 | 22967 | 46062 | 69157 |
| ZNF791 | 22968 | 46063 | 69158 |
| ZNF792 | 22969 | 46064 | 69159 |
| ZNF793 | 22970 | 46065 | 69160 |
| ZNF799 | 22971 | 46066 | 69161 |
| ZNF8 | 22972 | 46067 | 69162 |
| ZNF80 | 22973 | 46068 | 69163 |
| ZNF800 | 22974 | 46069 | 69164 |
| ZNF804A | 22975 | 46070 | 69165 |
| ZNF804B | 22976 | 46071 | 69166 |
| ZNF808 | 22977 | 46072 | 69167 |
| ZNF81 | 22978 | 46073 | 69168 |
| ZNF814 | 22979 | 46074 | 69169 |
| ZNF816 | 22980 | 46075 | 69170 |
| ZNF816-ZNF321P | 22981 | 46076 | 69171 |
| ZNF821 | 22982 | 46077 | 69172 |
| ZNF823 | 22983 | 46078 | 69173 |
| ZNF827 | 22984 | 46079 | 69174 |
| ZNF827 | 22985 | 46080 | 69175 |

TABLE 2-continued

Target Genes (Each target gene name is followed by three SEQ ID NOs corresponding to the genomic target site, the adjacent sequence for mapping, and the oligonucleotide sequence used for generating a single guide RNA specific for the gene).

| Gene | SEQ ID | | |
|---|---|---|---|
| ZNF829 | 22986 | 46081 | 69176 |
| ZNF83 | 22987 | 46082 | 69177 |
| ZNF830 | 22988 | 46083 | 69178 |
| ZNF831 | 22989 | 46084 | 69179 |
| ZNF835 | 22990 | 46085 | 69180 |
| ZNF836 | 22991 | 46086 | 69181 |
| ZNF837 | 22992 | 46087 | 69182 |
| ZNF839 | 22993 | 46088 | 69183 |
| ZNF84 | 22994 | 46089 | 69184 |
| ZNF841 | 22995 | 46090 | 69185 |
| ZNF841 | 22996 | 46091 | 69186 |
| ZNF843 | 22997 | 46092 | 69187 |
| ZNF844 | 22998 | 46093 | 69188 |
| ZNF845 | 22999 | 46094 | 69189 |
| ZNF846 | 23000 | 46095 | 69190 |
| ZNF846 | 23001 | 46096 | 69191 |
| ZNF85 | 23002 | 46097 | 69192 |
| ZNF85 | 23003 | 46098 | 69193 |
| ZNF850 | 23004 | 46099 | 69194 |
| ZNF852 | 23005 | 46100 | 69195 |
| ZNF853 | 23006 | 46101 | 69196 |
| ZNF860 | 23007 | 46102 | 69197 |
| ZNF862 | 23008 | 46103 | 69198 |
| ZNF865 | 23009 | 46104 | 69199 |
| ZNF878 | 23010 | 46105 | 69200 |
| ZNF879 | 23011 | 46106 | 69201 |
| ZNF880 | 23012 | 46107 | 69202 |
| ZNF883 | 23013 | 46108 | 69203 |
| ZNF888 | 23014 | 46109 | 69204 |
| ZNF891 | 23015 | 46110 | 69205 |
| ZNF90 | 23016 | 46111 | 69206 |
| ZNF91 | 23017 | 46112 | 69207 |
| ZNF92 | 23018 | 46113 | 69208 |
| ZNF93 | 23019 | 46114 | 69209 |
| ZNF98 | 23020 | 46115 | 69210 |
| ZNF99 | 23021 | 46116 | 69211 |
| ZNFX1 | 23022 | 46117 | 69212 |
| ZNHIT1 | 23023 | 46118 | 69213 |
| ZNHIT2 | 23024 | 46119 | 69214 |
| ZNHIT3 | 23025 | 46120 | 69215 |
| ZNHIT3 | 23026 | 46121 | 69216 |
| ZNHIT3 | 23027 | 46122 | 69217 |
| ZNHIT6 | 23028 | 46123 | 69218 |
| ZNRD1 | 23029 | 46124 | 69219 |
| ZNRF1 | 23030 | 46125 | 69220 |
| ZNRF2 | 23031 | 46126 | 69221 |
| ZNRF3 | 23032 | 46127 | 69222 |
| ZNRF4 | 23033 | 46128 | 69223 |
| ZP1 | 23034 | 46129 | 69224 |
| ZP2 | 23035 | 46130 | 69225 |
| ZP3 | 23036 | 46131 | 69226 |
| ZP4 | 23037 | 46132 | 69227 |
| ZPBP | 23038 | 46133 | 69228 |
| ZPBP2 | 23039 | 46134 | 69229 |
| ZPLD1 | 23040 | 46135 | 69230 |
| ZPR1 | 23041 | 46136 | 69231 |
| ZRANB1 | 23042 | 46137 | 69232 |
| ZRANB2 | 23043 | 46138 | 69233 |
| ZRANB2 | 23044 | 46139 | 69234 |
| ZRANB3 | 23045 | 46140 | 69235 |
| ZRSR2 | 23046 | 46141 | 69236 |
| ZSCAN1 | 23047 | 46142 | 69237 |
| ZSCAN10 | 23048 | 46143 | 69238 |
| ZSCAN12 | 23049 | 46144 | 69239 |
| ZSCAN16 | 23050 | 46145 | 69240 |
| ZSCAN16 | 23051 | 46146 | 69241 |
| ZSCAN16 | 23052 | 46147 | 69242 |
| ZSCAN18 | 23053 | 46148 | 69243 |
| ZSCAN2 | 23054 | 46149 | 69244 |
| ZSCAN2 | 23055 | 46150 | 69245 |
| ZSCAN2 | 23056 | 46151 | 69246 |
| ZSCAN20 | 23057 | 46152 | 69247 |
| ZSCAN21 | 23058 | 46153 | 69248 |
| ZSCAN22 | 23059 | 46154 | 69249 |
| ZSCAN22 | 23060 | 46155 | 69250 |
| ZSCAN23 | 23061 | 46156 | 69251 |
| ZSCAN25 | 23062 | 46157 | 69252 |
| ZSCAN25 | 23063 | 46158 | 69253 |
| ZSCAN25 | 23064 | 46159 | 69254 |
| ZSCAN26 | 23065 | 46160 | 69255 |
| ZSCAN29 | 23066 | 46161 | 69256 |
| ZSCAN30 | 23067 | 46162 | 69257 |
| ZSCAN31 | 23068 | 46163 | 69258 |
| ZSCAN32 | 23069 | 46164 | 69259 |
| ZSCAN4 | 23070 | 46165 | 69260 |
| ZSCAN5A | 23071 | 46166 | 69261 |
| ZSCAN5B | 23072 | 46167 | 69262 |
| ZSCAN9 | 23073 | 46168 | 69263 |
| ZSWIM1 | 23074 | 46169 | 69264 |
| ZSWIM2 | 23075 | 46170 | 69265 |
| ZSWIM3 | 23076 | 46171 | 69266 |
| ZSWIM4 | 23077 | 46172 | 69267 |
| ZSWIM5 | 23078 | 46173 | 69268 |
| ZSWIM6 | 23079 | 46174 | 69269 |
| ZSWIM7 | 23080 | 46175 | 69270 |
| ZSWIM8 | 23081 | 46176 | 69271 |
| ZSWIM8 | 23082 | 46177 | 69272 |
| ZSWIM9 | 23083 | 46178 | 69273 |
| ZUFSP | 23084 | 46179 | 69274 |
| ZW10 | 23085 | 46180 | 69275 |
| ZWILCH | 23086 | 46181 | 69276 |
| ZWINT | 23087 | 46182 | 69277 |
| ZXDA | 23088 | 46183 | 69278 |
| ZXDC | 23089 | 46184 | 69279 |
| ZXDC | 23090 | 46185 | 69280 |
| ZYG11A | 23091 | 46186 | 69281 |
| ZYG11B | 23092 | 46187 | 69282 |
| ZYX | 23093 | 46188 | 69283 |
| ZZEF1 | 23094 | 46189 | 69284 |
| ZZZ3 | 23095 | 46190 | 69285 |

TABLE 3

| Pools of small molecules | | | | |
|---|---|---|---|---|
| Pool 1 | Pool 2 | Pool 3 | Pool 4 | Pool 5 |
| OSI-930 | RAF265 (CHIR-265) | L-H-Rhamnose Monohydrate | Akti-1/2 | GW788388 |
| KU-0063794 | AZD1480 | Lappaconitine | Coelenterazine | Milciclib (PHA-848125) |

TABLE 3-continued

| Pools of small molecules | | | | |
|---|---|---|---|---|
| 2-Methoxyestradiol (2-MeOE2) | PF-4708671 | Limonin | Smoothened Agonist (SAG) HCl | HER2-Inhibitor-1 |
| AG-1024 | PD128907 HCl | Luteolin | Combretastatin A4 | A1406 (SM-406) |
| Latrepirdine 2HCl | Givinostat (ITF2357) | Magnolol | SRT2104 (GSK2245840) | CUDC-907 |
| JNJ-7706621 | AG-14361 | (+)-Matrine | Purvalanol A | NVP-BVU972 |
| CHIR-99021 (CT99021) | SB743921 HCl | Methyl-Hesperidin | ORY-1001 (RG-6016) 2HCl | MK-2048 |
| PD173074 | AST-1306 | Morin Hydrate | GSK2879552 2HCl | 3-Methyladenine (3-MA) |
| WYE-354 | SB505124 | Myricetin | GNE-317 | Dovitinib (TKI-258) Dilactic Acid |
| BX-795 | Avasimibe | Myricitrin | A-1155463 | MK-5108 (VX-689) |
| BX-912 | Sapitinib (AZD8931) | Naringin | A-1331852 | Dalcetrapib (JTT-705, RO4607381) |
| Celastrol | GSK461364 | Neohesperidin Dihydrochalcone (Nhdc) | GSK503 | SB705498 |
| Epothilone A | R406 | Neohesperidin | FRAX486 | MK-2461 |
| Ki16425 | Lexibulin (CYT997) | Nobiletin | A17519 HCl | Nocodazole |
| Costunolide | A-966492 | Oleanolic Acid | MHY1485 | CPI-613 |
| Ginkgolide B | SGI-1776 free base | Oridonin | Itacitinib (INCB39110) | PF-5274857 |
| TG100-115 | Raf265 derivative | Osthole | AMG319 | GW842166X |
| Glesatinib? (MGCD265) | BMS-794833 | Oxymatrine | AI-10-49 | M344 |
| Ki8751 | NVP-BHG712 | Paeonol | MI-136 | RITA (NSC652287) |
| BMS-707035 | OSI-420 | (−)-Parthenolide | MI-463 | GW4064 |
| Pirarubicin | PIK-293 | Phloretin | MI-503 | Vistusertib (AZD2014) |
| Droxinostat | AZ 960 | Phlorizin | EPZ020411 2HCl | TAK-285 |
| Aurora A Inhibitor I | DAPT (GSI-IX) | Puerarin | Nazartinib (EGF816, NVS-816) | A-803467 |
| Tipifarnib | Torkinib (PP242) | Quercetin Dihydrate | 4-Hydroxytamoxifen | VU 0357121 |
| PHA-680632 | Momelotinib (CYT387) | Rotenone (Barbasco) | Licochalcone A | WP1066 |
| VX-745 | SB590885 | Rutaecarpine | SGC707 | AZD4547 |
| Thiazovivin | PF-3716556 | Salicin | OICR-9429 | Sirtinol |
| SP600125 | UK 383367 | Sclareol | Cyclo (-RGDfK) | CEP-33779 |
| AZD6482 | TAME | Sclareolide | I-BRD9 | Ipatasertib (GDC-0068) |
| Calcitriol | PIK-294 | Shikimic Acid | Endoxifen HCl | MPEP |
| GSK429286A | Belnacasan (VX-765) | Silymarin | BI-847325 | Sapanisertib (INK 128, MLN0128) |
| SB525334 | Telatinib | Sinomenine | Cyclo (RGDyK) | AT101 |
| MC1568 | Palomid 529 (P529) | Solanesol (Nonaisoprenol) | SirReal2 | Ciproxifan Maleate |
| HMN-214 | Tubacin | Synephrine | SGI-7079 | Tyrphostin AG 879 |
| AEE788 (NVP-AEE788) | Degrasyn (WP1130) | Tangeretin | BDA-366 | Torin 2 |
| PHA-793887 | AR-42 | Tanshinone I | AZD3264 | Tacedinaline (CI994) |
| PIK-93 | Buparlisib (BKM120, NVP-BKM120) | Tanshinone IIA | Brilanestrant (GDC-0810, ARN-810) | AM251 |
| Cefaclor | (−)-Epigallocatechin Gallate | Taxifolin (Dihydroquercetin) | 8-Bromo-cAMP | TAE226 (NVP-TAE226) |
| AT7519 | (+)-Usniacin | Tetrahydropapaverine HCl | SC79 | RG108 |
| Adavosertib (MK-1775) | 3-Indolebutyric acid (IBA) | Ursolic Acid | Oleuropein | 00000459 |
| LY2811376 | 4-Demethylepipodophyllotoxin (NSC-122819, VM-26) | Vanillylacetone | LJH685 | TPCA-1 |

TABLE 3-continued

| Pools of small molecules | | | | |
|---|---|---|---|---|
| Hesperadin | 4-Methylumbelliferone (4-MU) | Xanthone | LJI308 | ML133 HCl |
| BIX 02188 | Esculin | Aloin | NVP-CGM097 | JNJ-1661010 |
| BIX 02189 | Aloe-emodin | Biochanin A | ONO-4059 analogue | Epiandrosterone |
| AZD7762 | Amygdalin | Dioscin | BQ-123 | Apalutamide? (ARN-509) |
| R406 (free base) | Andrographolide | Diosmetin | AMI-1 | SAR131675 |
| Org 27569 | Apigenin | Gastrodin | SBI-0206965 | BI-D1870 |
| CP-673451 | Arbutin | Hematoxylin | CC-223 | Semaxanib (SU5416) |
| DMXAA (Vadimezan) | Asiatic Acid | Hordenine | Spautin-1 | Cathepsin Inhibitor 1 |
| AM1241 | Azomycin | Indirubin | Xanthohumol | SB269970 HCl |
| SB408124 | Baicalein | Lappaconite HBr | CC-115 | BRL-54443 |
| AZD8055 | Baicalin | Naringin Dihydrochalcone | Avadomide (CC-122) | BML-190 |
| PHT-427 | Bergenin | Polydatin | Sodium Tauroursodeoxy cholate (TUDC) | MRS 2578 |
| KRN 633 | Berberine chloride | Quercetin | GSK621 | SB 271046 hydrochloride |
| A17867 | Bilobalide | Sesamin | SW033291 | (−)-MK 801 maleate |
| BMS-777607 | Caffeic Acid | Naringenin | PFI-4 | StemRegenin 1 (SR1) |
| PD318088 | Chlorogenic Acid | Salidroside | Dp44mT | Golvatinib (E7050) |
| KU-60019 | Chrysin | Palmatine chloride | PD-1/PD-L1 inhibitor 1 | IEM 1754 2HBr |
| BS-181 HCl | Cinchonidine | Dihydromyricetin | BMS202 (PD-1/PD-L1 inhibitor 2) | CTEP (RO4956371) |
| Tie2 kinase inhibitor | Cinchonine (LA40221) | Sodium Danshensu | MCB-613 | VU 0364770 |
| H 89 2HCl | Cryptotanshinone | Isoliquiritigenin | Isoxazole 9 (ISX-9) | ML130 (Nodinitib-1) |
| TWS119 | Cytisine | Sophocarpine | B10-acetoxime | IMD 0354 |
| Lubiprostone | Daidzin | Chrysophanic Acid | Kenpaullone | VUF 10166 |
| Daidzein | Emodin | Curcumol | Bromodeoxyuridme (BrdU) | U-104 |
| Cyclocytidine HCl | Fisetin | Cephalomannine | DEL-22379 | WHI-P154 |
| PCI-34051 | Formononetin | 10-Deacetylbaccatin-III | Tiplaxtinin (PAI-039) | T0070907 |
| PF-573228 | Ferulic Acid | Paeoniflorin | SH5-07 (SH-5-07) | GW5074 |
| BMS-265246 | Genistin (Genistoside) | Geniposide | Bay K 8644 | (+)-MK 801 maleate |
| Suplatast Tosylate | Glycyrrhizin (Glycyrrhizic Acid) | Genipin | Lifirafenib (BGB-283) | IKK-16 (IKK Inhibitor VII) |
| ENMD-2076 L-(+)-Tartaric acid | gossypol-Acetic acid | Geniposidic acid | WZB117 | 4-Aminohippuric Acid |
| Ginkgolide A | Gramine | Astragaloside A | DASA-58 | Acesulfame Potassium |
| Cytidine | Gynostemma Extract | 20-Hydroxyecdysone | BEC HCl | A-205804 |
| Arbidol HCl | Hesperetin | (S)-10-Hydroxycamptothecin | Ixabepilone (BMS-247550) | PF-562271 |
| AZD8330 | Hesperidin | Apocynin | STF-31 | GW441756 |
| GSK1292263 | Honokiol | Rotundine | Indisulam | VU 0361737 |
| CGS 21680 HCl | Hyodeoxycholic acid (HDCA) | Synephrine HCl | Y-39983 HCl | SB742457 |
| LY2608204 | Icariin | Guanosine | KDO25 (SLx-2119) | Tyrphostin 9 |
| LY2886721 | Indole-3-carbinol | Gambogic Acid | Nemiralisib (GSK2269557) | ZM 323881 HCl |
| KW-2449 | Kaempferol | Forskolin | GSK2292767 | ZM 306416 |
| Almorexant HCl | Kinetin | Equol | Chetomin | MLN0905 |
| Pool 6 | Pool 7 | Pool 8 | Pool 9 | Pool 10 |
| GNF-2 | Euphorbiasteroid | TriacetonaMine | Maduramycin Ammonium | Tezacaftor? (VX-661) |
| CCG 50014 | Amentoflavone | Indole-3-carboxylic acid | SulfadiMethoxine sodium | PP1 |
| Lumiracoxib | Astaxanthin | Oxindole | 4-Aminophenylarsonic acid | Pinometostat (EPZ5676) |

TABLE 3-continued

| Pools of small molecules | | | | |
|---|---|---|---|---|
| PF-477736 | Loganin | 4-Hydroxyphenylacetic acid | Tabersonine hydrochloride | LY2090314 |
| JNJ-7777120 | 6-Gingerol | 2-Furoic acid | lutein | MK-8745 |
| Ki16198 | Echinocystic acid | Nicarbazin | Proanthocyanidins | GSK J4 HCl |
| Tempol | Carnosic acid | Propacetamol hydrochloride | Tylosin | (+)-Bicuculline |
| Go 6983 | 1-Deoxynojirimycin | Xanthinol Nicotinate | Ademetionine | NMDA (N-Methyl-D-aspartic acid) |
| WZ811 | Baohuoside I | Cefodizime Sodium | Safflower Yellow 7-Ethylcamptothecin | T0901317 |
| BAY 11-7082 | Eleutheroside B | Pyridoxal 5-phosphate monohydrate | | SGC 0946 |
| Dapivirine (TMC120) | Isoquercitrin | Cefazedone | alpha-Arbutin | RN486 |
| GW9662 | Madecassoside | Cephapirin Benzathine | Propyl gallate | IWR-1-endo |
| ML161 | Rosavin | Robenidine Hydrochoride | Hydroquinine | GSK2334470 |
| HC-030031 | Eupatilin | Calcium Dobesilate | Doramectin | UNC1215 |
| IOX2 | Panaxatriol | Resorantel | Olivetol | GSK923295 |
| PF-4981517 | Hydroxytyrosol Acetate | Lynestrenol | Abietic Acid | Zotarolimus (ABT-578) |
| Salubrinal | D-Galactose | Trans-Zeatin | Aleuritic Acid | SANT-1 |
| CHIR-99021 (CT99021) HCl | Glucosamine sulfate | Taurolidine | Spiculisporic Acid | IPA-3 |
| TDZD-8 | Camphor | Menbutone | Orsellinic acid ethyl ester | PF-3758309 |
| Apoptosis Activator 2 | Tetrahydropalmatine hydrochloride | Phenibut | Taurocholic acid sodium salt hydrate | KY02111 |
| TAK-715 | Ethyl ferulate | Cytosine | Casanthranol | HSP990 (NVP-HSP990) |
| Pifithrin-α (PFTα) HBr | Allantoin | D-Glucurone | Sodium erythorbate | PD123319 |
| Pifithrin-μ | 4-Hydroxybenzyl alcohol | Tenovin-6 | D(-)-Arabinose | (-)-Blebbistatin |
| PMSF | Lawsone | JNK-IN-8 | Hydroferulic acid | VE-822 |
| Piceatannol | Vanillyl Alcohol | QNZ (EVP4593) | Pyrithioxin | Taselisib (GDC0032) |
| Vanillin | Gallic acid trimethyl ether | JZL184 | D-(+)-Melezitose | AZD1208 |
| 2-Thiouracil | Methyl EudesMate | SC-514 | Citropten | AZD3463 |
| N6-methyladenosine (m6A) | Dulcitol | SN-38 | Neferine | Encorafenib (LGX818) |
| Catharanthine | Taurochenodeoxycholic acid | b-AP15 | Protoporphyrin IX | Pevonedistat (MLN4924) |
| Schisandrin B (Sch B) | Galanthamine | MNS (3,4-Methylenedioxy-β-nitrostyrene, MDBN) | 1,3,5-Trimethylpyrazole | (+)-JQ1 |
| Betulinic acid | (E)-Cardamoni Harmine | (R)-Nepicastat HCl Antiarol | Thymol Doxycycline | NLG919 Zebularine |
| Triptolide (PG490) | | | | |
| Borneol | Methyl protocatechuate | 4'-Hydroxychalcone | 4-Methoxysalicylic acid | NU6027 |
| Fangchinoline | D-Pinitol | Cedrol | Isovanillic acid | AMG-517 |
| Demethylzeylasteral (T-96) | Guaiacol | cis-Aconitic acid | 7-Methoxycoumarin | Go6976 |
| Berbamine (dihydrochloride) | Methyl 4-hydroxycinnamate | Maltol | Chlorotetracycline | MLN2480 |
| Cordycepin | Curcumenol | 4-Hydroxy-3,5-dimethoxybenzyl alcohol | Solvent Red 23 | XL888 |
| (+)-Fangchinoline | Alpinetin | Isovanillin | Benzoyleneurea | SC144 |
| Rosmarinic acid | Indigo | 2,3-Dihydroxybenzoic acid | Benzyl cinnamate | KPT-185 |
| Scoparone | Lysionotin | Fumaric acid | Anthraquinone | Marinopyrrole A (Maritoclax) |
| Dehydrocostus Lactone | Bavachinin | Usnic acid | 2,6-Dihydroxyanthraquinone | TIC10 Analogue |
| Asiaticoside | kaempferide | Glycocholic acid | Atrazine | PYR-41 |
| (20S)-Protopanaxatriol | Scopoletin | Skatole | Kojic acid | PR-619 |

TABLE 3-continued

| \multicolumn{5}{c}{Pools of small molecules} | | | | |
|---|---|---|---|---|
| Acetylspiramycin (ASPM) | Protopine | 3,4,5-Trimethoxycinnamic acid | (−)-Ambroxide | P5091 (P005091) |
| Diammonium Glycyrrhizinate | Jatrorrhizine | Purpurin | Diaveridine | P22077 |
| Quinolinic acid | Pyrogallol | Lactobionic acid | Acetylisovaleryltylosin Tartrate | IU1 |
| Tyramine | Quinic acid | Helecin | Quinocetone | LDN-57444 |
| Sesamol | L-Rhamnose monohydrate | 4-Methylesculetin | 4-Aminosalicylic acid | CGK 733 |
| Tryptamine | 3,4',5-Trimethoxy-trans-stilbene | Tropine | Imidazolidinyl Urea | BMS-833923 |
| BHQ | Arteether | Buparvaquone | Imidocarb dipropionate | CFTRinh-172 |
| Syringic acid | Leonurine | Iminostilbene | β-Estradiol 17-Acetate | TCID |
| Methyl Vanillate | Isopsoralen | Efonidipine | 2-Acetylphenothiazine (MLI71) | NSC697923 |
| Trichloroisocyanuric acid | Cycloastragenol | Azathramycin | NXY-059 (Disufenton sodium) | LGK-974 |
| Pyrrolidinedithioc arbamate ammonium | Sophoridine | Anamorelin | VX-702 | BMS-911543 |
| 6-Hydroxyflavone (6-HF) | (1R,2R)-trans-N-Boc-1,2-cyclohexanediamine | Cyclogalegenol | AP26113-analog (ALK-IN-1) | AZD1080 |
| Osalmid | (−)-Arctigenin | 2,2':5',2''-Terthiophene | AZD2932 | DMHI |
| Amitraz | Hydroxy Camptothecine | Sorbic acid | BAY-61-3606 | LDN-212854 |
| Sulfamonomethoxine | Hederagenin | Dimetghyl 4-Hydroxyisophthalate | PP2 | ML347 |
| Kitasamycin | Betulonic acid | Tiamulin fumarate | LCLI61 | NSC319726 |
| 4-Amino-5-imidazolecarboxamide | Astragaloside IV | AOA hemihydrochloride | GDC-0152 | C646 |
| 3-Nitropropionic acid | Ursonic acid | TBHQ | Merestinib (LY2801653) | 10058-F4 |
| Spermidine trihydrochloride | Lycorine | Methylcobalamin | VS-5584 (SB2343) | Glasdegib (PF-04449913) |
| Tauroursodeoxycholic Acid (TUDCA) | Isoimperatorin | Isoprinosine | CZC24832 | Mdivi-1 |
| Piribedil | Iso-Steviol | Indobufen | Stattic | Dyngo-4a |
| Promestriene | Astragalus polyphenols | Tilorone dihydrochloride | Embelin | UNCI999 |
| O6-Benzylguanine | Bulleyaconicine A | Etofylline | AZD246I | SSR128129E |
| Uniconazole | 4'-Demethylpodophyllotoxin | Melitracen hydrochloride | RG-7112 | Crenigacestat (LY3039478) |
| 2-Methoxy-1,4-naphthoquinone | Catalpol | Tiamulin | GSK2656157 | RO5126766 (CH5126766) |
| Trolox | 4,7-Dimethoxyisoflavone | Difloxacin hydrochloride | XL388 | GK1137831 |
| Ilaprazole | Veratramine | Benorylate | XL019 | ONX-0914 (PR-957) |
| Thymopentin | Cephalotaxine | Isoxepac | Wnt-C59 (C59) | Spebrutinib (CC-292, AVL-292) |
| Cefsulodin sodium | α-Hederin | Nomilin | Epoxomicin | Opaganib (ABC294640) |
| Levamlodipine | Gracillin | Clonixin | PD168393 | SKI II |
| Umbelliferone | Macranthoidin B | Methyl α-D-mannopyranoside | AZD3514 | PF-543 |
| Carbendazim | 4',7-Dimethoxy-5-Hydroxyflavone | Thiocolchicoside | CX-6258 HCl | JTE 013 |
| Cinnamic acid | Hederacoside C | Revaprazan Hydrochloride | Brefeldin A | AGI-5198 |
| PTP Inhibitor II | 7β-Hydroxylathyrol | Xipamide | Oprozomib (ONX 0912) | CID755673 |
| Flavanone | Lathyrol | Azamethiphos | AZ20 | I-BET-762 |
| NLRP3 Inflammasome Inhibitor I | (−)-epigallocatechin | Febantel | CGI1746 | PF-04620110 |
| Ethyl 3-Aminobenzoate methanesulfonate | Ginsenoside Rg1 | Rafoxanide | LY2874455 | 1-Azakenpaullone |

TABLE 3-continued

| Pools of small molecules | | | | |
|---|---|---|---|---|
| Pool 11 | Pool 12 | Pool 13 | Pool 14 | Pool 15 |
| ERK5-IN-1 | Fenbendazole | NSC12 | ZM241385 | Drospirenone |
| IPI-3063 | Alizarin | NCT-501 | NSC59984 | Ruxolitinib (INCB018424) |
| CW069 | Asaraldehyde | Bioymifi | GSK1016790A | Isotretinoin |
| SH-4-54 | L-Ascorbyl 6-palmitate | O4I1 | GSK591 | Lopinavir |
| AZ191 | Scopine | O4I2 | MS023 | Meropenem |
| AZD3965 | Daphnetin | KC7F2 | ICI-118551 Hydrochloride | Mianserin HCl |
| CH5138303 | Pioglitazone | PX-12 | GMX1778 (CH5828) | Mosapride Citrate |
| URMC-099 | Dehydroepiandrosterone (DHEA) | MR167307 HCl | RHPS 4 methosulfate | Nafamostat Mesylate |
| JSH-23 | Ribitol | MR168921 HCl | BMS-582949 | Naftopidil DiHCl |
| Bay 11-7085 | TAK-733 | Ochromycinone (STA-21) | Pamapimod (R-1503, Ro4402257) | Omeprazole |
| EPZ004777 | MG-132 | ETC-1002 | MK571 | Ondansetron HCl |
| ARQ 621 | AZD5438 | CP21R7 (CP21) | BAY 41-2272 | Oxcarbazepine |
| HS-173 | PP121 | EPI-001 | Salinomycin (from Streptomycesalbus) | Pelitinib (EKB-569) |
| PF-562271 HCl | Omecamtiv mecarbil (CK-1827452) | Lificiguat (YC-1) | Deguelin | Pizotifen Malate |
| K02288 | OSI-027 | SIS3 HCl | Resiquimod | Resveratrol |
| OTX015 | Rabusertib (LY2603618) | Larotrectinib (LOXO-101) sulfate | Sivelestat (ONO-5046) | Rocuronium Bromide |
| BRD7552 | Tubastatin A HCl | TIC10 | Capsazepine | Stavudine (d4T) |
| Atglistatin | PNU-120596 | PLX7904 | GNF-7 | Tenofovir Disoproxil Fumarate |
| AdipoRon | GW3965 HCl | AZD8835 | Cl-amidine | Tenofovir |
| LY2119620 | URB597 | P7C3 | Halofuginone | Tigecycline |
| GNE-0877 | BMS-378806 | AZD3759 | MS049 | Trilostane |
| GNE-9605 | NPS-2143 | L755507 | PD0166285 | Vecuronium Bromide |
| 4EGI-1 | Rebastinib (DCC-2036) | SBC-115076 | NSC348884 | Bimatoprost |
| 4E1RCat | CCT128930 | FG-2216 | RSL3 | Linezolid |
| PTC-209 | A66 | VPS34-IN1 | ARS-853 (ARS853) | Alfuzosin HCl |
| UNC669 | Fasiglifam? (TAK-875) | A-196 | GDC-0326 | Clopidogrel |
| AEBSF HCl | SNX-2112 (PF-04928473) | LDC4297 (LDC044297) | ON123300 | Ranolazine 2HCl |
| E-64 | PF-04929113 (SNX-5422) | SKF38393 HCl | GDC-0084 | Repaglinide |
| Leupeptin Hemisulfate | 5-hydroxymethyl Tolterodine (PNU 200577, 5-HMT, 5-HM) | SKF96365 | Cucurbitacin B | Rolipram |
| Pepstatin A | MK-0752 | Tenovin-1 | ONO-4059 (GS-4059) hydrochloride | Sildenafil Citrate |
| Phosphoramidon Disodium Salt | WYE-125132 (WYE-132) | GSK2636771 | AMG 337 | Sumatriptan Succinate |
| (−)-p-Bromotetramisole Oxalate | ICG-001 | PQ 401 | GSK481 | Tianeptine sodium |
| MG-101 (ALLN) | WAY-100635 Maleate | ZM 39923 HCl | Daprodustat (GSK1278863) | Tizanidine HCl |
| Z-FA-FMK | PF-3845 | SMI-4a | Ro 61-8048 | Topiramate |
| Loxistatin Acid (E-64C) | A-674563 | BIX 01294 | Verubecestat (MK-8931) Trifluoroacetat | Tranilast |
| Calpeptin | AS-252424 | VE-821 | VO-Ohpic trihydrate | Venlafaxine HCl |
| FLI-06 | PF-00562271 | AG-18 | BH3I-1 | Voriconazole |
| Anisomycin | A922500 | PRX-08066 Maleic acid | Wnt agonist 1 | Zileuton |
| Ascomycin (FK520) | BRL-15572 (dihydrochloride) | GW9508 | BI-7273 | Ziprasidone HCl |
| Caffeic Acid Phenethyl Ester | Flavopiridol HCl | CEP-32496 | PF-CBP1 HCl | Zonisamide |
| CA-074 methyl ester (CA-074 Me) | AS-604850 | Nirogacestat (PF-03084014, PF-3084014) | SBI-0640756 | Ispinesib (SB-715992) |

TABLE 3-continued

| \multicolumn{5}{|c|}{Pools of small molecules} |
|---|---|---|---|---|
| CGP 57380 | CAY10505 | AZD5363 | NSC87877 | Cilomilast |
| KN-62 | CHIR-124 | GW0742 | FPS-ZM1 | Zibotentan (ZD4054) |
| KN-93 Phosphate | KW-2478 | TCS 359 | BFH772 | Atazanavir Sulfate |
| PD 151746 | NVP-BSK805 2HCI | Tyrphostin AG 1296 | BAW2881 (NVP-BAW2881) | Moxifloxacin HCI |
| MI-2 (MALT1 inhibitor) | Mardepodect (PF-2545920) | GSK3787 | CPI-637 | Doxercalciferol |
| SB-3CT | R547 | Tariquidar | SUN11602 | Alfacalcidol |
| TAPI-1 | WAY-600 | WY-14643 (Pirinixic Acid) | Lanabecestat (AZD3293, LY3314814) | Calcifediol |
| AR-A014418 | ADX-47273 | NSC 23766 | umbralisib (TGR-1202) | Orantinib (TSU-68, SU6668) |
| NH125 | BMY 7378 Dihydrochloride | PRT062607 (P505-15, BIIB057) HCI | ML264 | Safinamide Mesylate |
| Sal003 | TG101209 | VU 0364439 | MK-4101 | Pimasertib (AS-703026) |
| ME0328 | Turofexorate Isopropyl (XL335) | Butein | BI-78D3 | Lomibuvir (VX-222, VCH-222) |
| WS3 | Nepicastat (SYN-117) HCI | Necrostatin-1 | PF-06447475 | Zosuquidar (LY335979) 3HCI |
| WS6 | Apitolisib (GDC-0980, RG7422) | UPF 1069 | Ivosidenib (AG-120) | Daclatasvir (BMS-790052) |
| AP-III-a4 (ENOblock) | A-769662 | PU-H71 | Hydroxyfasudil (HA-1100) HCI | Iloperidone |
| Pyridostatin Trifluoroacetate Salt | RS-127445 | GDC-0349 | HLCL-61 HCL | Naratriptan HCI |
| E3330 | CH5132799 | GW2580 | BAY 1217389 | Ponatinib (AP24534) |
| ZLN005 | KX2-391 | Scriptaid | PF-8380 | Fludarabine |
| CORM-3 | GSK1838705A | BMS-345541 | A51842856 | Pralatrexate |
| CR10044876 | Dibenzazepine (YO-01027) | Dynasore | Netarsudil (AR-13324) 2HCI | Betamethasone |
| FH1 (BRD-K4477) | Geldanamycin | ETP-46464 | N1157 | Mycophenolate Mofetil |
| FPH1 (BRD-6125) | LY411575 | ASP3026 | Ensartinib (X-396) | Dyphylline |
| FPH2 (BRD-9424) | CP-91149 | Lomeguatrib | RS-1 | Aztreonam |
| Osilodrostat (LCI699) | TAK-901 | P276-00 | MK-886 (L-663,536) | Alprostadil |
| XEN445 | AMG-900 | Sabutoclax | IC261 | Lactulose |
| VER-49009 | ZM 336372 | Nutlin-3b | SB366791 | Tadalafil |
| VER-50589 | JTC-801 | Chaetocin | SMER28 | Cyclosporine |
| BTB06584 | PH-797804 | UNC0638 | EAI045 | Pracinostat (SB939) |
| LDC000067 | AG-1478 (Tyrphostin AG-1478) | NSC 405020 | Etomoxir (Na salt) | Natamycin |
| PI-1840 | SB415286 | Optovin | Thiomyristoyl | Voxtalisib (SAR245409, XL765) Analogue |
| FTI 277 HCI | AZ 3146 | PluriSlin #1 (NSC 14613) | RK-33 | Quizartinib (AC220) |
| GGTI 298 TFA salt | PAC-1 | RI-1 | IQ-1 | Telaprevir (VX-950) |
| LB42708 | GSK1070916 | GlyH-101 | HPI-4 (Ciliobrevin A) | Saxagliptin |
| Triapine | PHA-767491 | Tubercidin | Necrosulfonamide | Selisistat (EX 527) |
| Nexturastat A | PF-04691502 | Mirin | CC1245737 | Febuxostat |
| MG149 | CHIR-98014 | C-DIM12 | FIN56 | Dapagliflozin |

TABLE 3-continued

| Pools of small molecules | | | | |
|---|---|---|---|---|
| EHT 1864 2HCI | AZ 628 | K03861 | GSK583 | Nebivolol HCI |
| DMOG | AMG-458 | CB-5083 | PRI-724 | Pimobendan |
| FH535 | Anacetrapib (MK-0859) | Z-VAD (OH)-FMK (Caspase Inhibitor VI) | GSK6853 | VX-809 (Lumacaftor) |
| MPI-0479605 | BG1226 (NVP-BGT226) | SCH58261 | CFSE | Pomalidomide |

REFERENCES AND NOTES

1 Yen, H. C., Xu, Q., Chou, D. M., Zhao, Z. & Elledge, S. J. Global protein stability profiling in mammalian cells. Science 322, 918-923, doi: 10.1126/science.1160489 (2008).

2 Lundberg, E. & Borner, G. H. H. Spatial proteomics: a powerful discovery tool for cell biology. Nat Rev Mol Cell Biol, doi: 10.1038/s41580-018-0094-y (2019).

3 Egelhofer, T. A. et al. An assessment of histone-modification antibody quality. Nat Struct Mol Biol 18, 91-93, doi: 10.1038/nsmb. 1972 (2011).

4 Meliopoulos, V. A. & Schultz-Cherry, S. Although it's painful: The importance of stringent antibody validation. PLOS Pathog 14, e1006701, doi: 10.1371/journal.ppat. 1006701 (2018).

5 Aebersold, R. & Mann, M. Mass-spectrometric exploration of proteome structure and function. Nature 537, 347-355, doi: 10.1038/nature19949 (2016).

6 Huh, W. K. et al. Global analysis of protein localization in budding yeast. Nature 425, 686-691, doi: 10.1038/nature02026 (2003).

7 Cohen, A. A. et al. Dynamic proteomics of individual cancer cells in response to a drug. Science 322, 1511-1516, doi: 10.1126/science. 1160165 (2008).

8 Dewari, P. S. et al. An efficient and scalable pipeline for epitope tagging in mammalian stem cells using Cas9 ribonucleoprotein. Elife 7, doi: 10.7554/eLife.35069 (2018).

9 Roberts, B. et al. Systematic gene tagging using CRISPR/Cas9 in human stem cells to illuminate cell organization. Mol Biol Cell 28, 2854-2874, doi: 10.1091/mbc.E17-03-0209 (2017).

10 Leonetti, M. D., Sekine, S., Kamiyama, D., Weissman, J. S. & Huang, B. A scalable strategy for high-throughput GFP tagging of endogenous human proteins. Proc Natl Acad Sci USA 113, E3501-3508, doi: 10.1073/pnas. 1606731113 (2016).

11 Sigal, A. et al. Generation of a fluorescently labeled endogenous protein library in living human cells. Nat Protoc 2, 1515-1527, doi: 10.1038/nprot.2007.197 (2007).

12 Schmid-Burgk, J. L., Honing, K., Ebert, T. S. & Hornung, V. CRISPaint allows modular base-specific gene tagging using a ligase-4-dependent mechanism. Nat Commun 7, 12338, doi: 10.1038/ncomms12338 (2016).

13 Tsai, S. Q. et al. GUIDE-seq enables genome-wide profiling of off-target cleavage by CRISPR-Cas nucleases. Nat Biotechnol 33, 187-197, doi: 10.1038/nbt.3117 (2015).

14 Palmer, E. & Freeman, T. Investigation into the use of C- and N-terminal GFP fusion proteins for subcellular localization studies using reverse transfection microarrays. Comp Funct Genomics 5, 342-353, doi: 10.1002/cfg.405 (2004).

15 Ishihama, Y. et al. Exponentially modified protein abundance index (emPAI) for estimation of absolute protein amount in proteomics by the number of sequenced peptides per protein. Mol Cell Proteomics 4, 1265-1272, doi: 10.1074/mcp.M500061-MCP200 (2005).

16 Sakaue-Sawano, A. et al. Visualizing spatiotemporal dynamics of multicellular cell-cycle progression. Cell 132, 487-498, doi: 10.1016/j.cell.2007.12.033 (2008).

17 Teicher, B. A., Ara, G., Herbst, R., Palombella, V. J. & Adams, J. The proteasome inhibitor PS-341 in cancer therapy. Clin Cancer Res 5, 2638-2645 (1999).

18 Kane, R. C., Bross, P. F., Farrell, A. T. & Pazdur, R. Velcade: U.S. FDA approval for the treatment of multiple myeloma progressing on prior therapy. Oncologist 8, 508-513 (2003).

19 Decaux, O. et al. Inhibition of mTORC1 activity by REDD1 induction in myeloma cells resistant to bortezomib cytotoxicity. Cancer Sci 101, 889-897, doi: 10.1111/j.1349-7006.2009.01467.x (2010).

20 Barakat, D. J. et al. C/EBPbeta regulates sensitivity to bortezomib in prostate cancer cells by inducing REDD1 and autophagosome-lysosome fusion. Cancer Lett 375, 152-161, doi: 10.1016/j.canlet.2016.03.005 (2016).

21 Sun, X. H., Copeland, N. G., Jenkins, N. A. & Baltimore, D. Id proteins Id1 and Id2 selectively inhibit DNA binding by one class of helix-loop-helix proteins. Mol Cell Biol 11, 5603-5611 (1991).

22 Bounpheng, M. A., Dimas, J. J., Dodds, S. G. & Christy, B. A. Degradation of Id proteins by the ubiquitin-proteasome pathway. FASEB J 13, 2257-2264 (1999).

23 Jariel-Encontre, I. et al. Ubiquitinylation is not an absolute requirement for degradation of c-Jun protein by the 26 S proteasome. J Biol Chem 270, 11623-11627 (1995).

24 Zengerle, M., Chan, K. H. & Ciulli, A. Selective Small Molecule Induced Degradation of the BET Bromodomain Protein BRD4. ACS Chem Biol 10, 1770-1777, doi: 10.1021/acschembio.5b00216 (2015).

25 Han, T. et al. Anticancer sulfonamides target splicing by inducing RBM39 degradation via recruitment to DCAF15. Science 356, doi: 10.1126/science.aal3755 (2017).

26 Birnboim, H. C., Motora, D. & Liteplo, R. G. Indomethacin shifts the peak of c-fos, egr-1, and c-myc gene expression in confluent fibroblasts induced by phorbol myristate acetate. Biochem Biophys Res Commun 161, 508-513 (1989).

27 Fisher, S. L. & Phillips, A. J. Targeted protein degradation and the enzymology of degraders. Curr Opin Chem Biol 44, 47-55, doi: 10.1016/j.cbpa.2018.05.004 (2018).

28 Feldman, D. et al. Pooled optical screens in human cells. bioRxiv, doi: 10.1101/383943 (2018).

29 Picelli, S. et al. Tn5 transposase and tagmentation procedures for massively scaled sequencing projects. Genome Res 24, 2033-2040, doi: 10.1101/gr.177881.114 (2014).

30 Schmid-Burgk, J. L. & Hornung, V. BrowserGenome.org: web-based RNA-seq data analysis and visualization. *Nat Methods* 12, 1001, doi: 10.1038/nmeth.3615 (2015).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

SEQUENCE LISTING

The patent contains a lengthy sequence listing. A copy of the sequence listing is available in electronic form from the USPTO web site (https://seqdata.uspto.gov/?pageRequest=docDetail&DocID=US12281301B2). An electronic copy of the sequence listing will also be available from the USPTO upon request and payment of the fee set forth in 37 CFR 1.19(b)(3).

What is claimed is:

1. A method of determining the distribution of protein levels in a population of cells, said method comprising:
    a) sorting a library of cells into at least two groups based on expression of the detectable marker in each cell; and
    b) nucleic acid sequencing of the cells in each group, wherein the tagged target genes in each group are determined;
    wherein the library of cells comprises a plurality of cells, wherein each cell comprises a polynucleotide sequence encoding a protein tag integrated into the genome of the cell in frame with a protein coding gene selected from a set of target genes, wherein the library comprises more than one cell tagged at each target gene;
    wherein the library of cells is treated with a perturbation prior to determining expression of proteins, wherein the perturbation comprises a small molecule, protein, RNAi, CRISPR system, TALE system, Zn finger system, meganuclease, pathogen, allergen, recombinant virus, temperature, salt, lipid, biomolecule, a pool of any perturbation thereof, or any combination thereof; and
    wherein the protein tag is a detectable marker and the cell library is for use in detecting the distribution of protein levels in single cells comprising a plurality of cells.

2. The method according to claim 1, wherein the sequencing comprises PCR amplification of the UMIs with primers specific to the polynucleotide sequence encoding a detectable marker; or
    wherein the sequencing comprises transcription of the tagged gene by T7 polymerase, cDNA production, and sequencing of the cDNA; or
    wherein the sequencing comprises tagmentation with Tn5, PCR amplification; and/or
    wherein the localization of proteins is determined by further sorting the cells based on cleavage of the cleavable marker by the protease localized to a cellular compartment; or wherein the localization of proteins is determined by comparing the distribution of protein levels of tagged genes between sorted cells and sorted nuclei obtained from the library.

3. The method of claim 1 for use in identifying cell cycle regulated proteins; or
    for use in identifying or confirming drug targets that are not regulated at the transcript level.

4. The method of claim 1, further comprising transferring the library to an in vivo model and recovering the cells before the step of sorting.

5. The method of claim 1, wherein the cell library is for use in detecting protein interactions between a protein of interest and a set of target proteins, wherein each cell comprises a first polynucleotide sequence encoding a first protein tag that is a complementary protein integrated into the genome of the cell in frame with the protein of interest or comprises a first polynucleotide sequence encoding a fusion protein of the first complementary protein and protein of interest, wherein each cell comprises a second polynucleotide sequence encoding a second protein tag that is a complementary protein integrated into the genome of the cell in frame with a protein coding gene selected from the set of target genes, wherein the library comprises more than one cell tagged at a target gene, whereby an interaction between the protein of interest and a target gene can be detected with a detectable marker.

6. The method of claim 5, wherein the second polynucleotide sequence further comprises a codon-neutral unique molecular identifier (UMI) sequence or a non-coding UMI after the detectable marker coding sequence.

7. The method of claim 6, wherein the library is sequence-verified, such that each UMI identifies a tagged target gene.

8. The method of claim 7, wherein:
    a) the first and second complementary proteins comprise protein complementary assay (PCA) fragments, preferably, wherein the PCA fragments comprise split fluorescent protein fragments or split TEV fragments; or
    b) one of the first or second complementary proteins comprises a permuted inactive reporter and the other complementary protein comprises TEV; or
    c) the first and second complementary proteins comprise a different epitope tag, whereby interaction may be detected by proximity ligation; or
    d) one of the first or second complementary proteins comprises one or more TEV cleavage sites followed by one or more epitopes and the other complementary protein comprises TEV.

9. The method of claim 6, wherein the second polynucleotide sequence comprises a selectable marker operably linked to a separate regulatory element; or wherein the polynucleotide sequence comprises an IRES or a 2A peptide, whereby the selectable marker is expressed as a separate protein; and/or
  wherein the second polynucleotide sequence comprises a T7 RNA polymerase promoter;
  and/or wherein each cell comprises a sequence encoding a guide sequence specific for the tagged target gene, whereby detection of the sequence indicates the tagged target gene; and/or
  wherein the library comprises eukaryotic cells; and/or
  wherein the cells of the library were generated from cells configured to express a CRISPR enzyme; or wherein the cells of the library were generated from cells obtained from a transgenic animal configured to express a CRISPR enzyme.

10. The method of claim 1, wherein the cell library is for use in detecting protein modifications comprising a plurality of cells, wherein each cell stably expresses a protein tag that is a fusion protein comprising a protein modification binding protein fused to a first complementary protein, wherein each cell comprises a polynucleotide sequence encoding a second protein tag that is a complementary protein integrated into the genome of the cell in frame with a protein coding gene selected from the set of target genes, wherein the library comprises more than one cell tagged at each target gene and wherein binding of a protein modification binding protein to a target gene protein can be detected with a detectable marker.

11. The method of claim 10, wherein the polynucleotide sequence further comprises a codon-neutral unique molecular identifier (UMI) sequence or a non-coding UMI after the detectable marker coding sequence.

12. The method of claim 10, wherein:
  a) the first and second complementary proteins comprise protein complementary assay (PCA) fragments, preferably, wherein the PCA fragments comprise split fluorescent protein fragments or split TEV fragments; or
  b) one of the first or second complementary proteins comprises a permuted inactive reporter and the other complementary protein comprises TEV; or
  c) the first and second complementary proteins comprise a different epitope tag, whereby protein modification may be detected by proximity ligation; or
  d) one of the first or second complementary proteins comprises one or more TEV cleavage sites followed by one or more epitopes and the other complementary protein comprises TEV.

13. The method of claim 10, wherein the polynucleotide sequence comprises a selectable marker operably linked to a separate regulatory element; and/or
  wherein the polynucleotide sequence comprises a T7 RNA polymerase promoter; and/or
  wherein each cell comprises a sequence encoding a guide sequence specific for the tagged target gene, whereby detection of the sequence indicates the tagged target gene; and/or
  wherein the library comprises eukaryotic cells; and/or
  wherein the cells of the library were generated from cells configured to express a CRISPR enzyme; or the cells of the library were generated from cells obtained from a transgenic animal configured to express a CRISPR enzyme.

14. The method according to claim 2, wherein the PCR amplification comprises a nested PCR and sequencing the PCR products.

15. The method according to claim 2, comprising linear amplification (LAM).

16. The method according to claim 2, wherein the PCR amplification comprises nested PCR and sequencing of the amplified DNA.

17. The method according to claim 2, wherein the nuclei are fixed.

* * * * *